United States Patent
Guo et al.

(10) Patent No.: US 11,420,968 B2
(45) Date of Patent: Aug. 23, 2022

(54) BCL-2 INHIBITORS

(71) Applicant: BEIGENE, LTD., Grand Cayman (KY)

(72) Inventors: Yunhang Guo, Beijing (CN); Hai Xue, Beijing (CN); Zhiwei Wang, Beijing (CN); Hanzi Sun, Beijing (CN)

(73) Assignee: BEIGENE, LTD., Grand Cayman (KY)

( * ) Notice: Subject to any disclaimer, the term of this patent is extended or adjusted under 35 U.S.C. 154(b) by 0 days.

(21) Appl. No.: 17/050,581

(22) PCT Filed: Apr. 29, 2019

(86) PCT No.: PCT/CN2019/085001
§ 371 (c)(1),
(2) Date: Oct. 26, 2020

(87) PCT Pub. No.: WO2019/210828
PCT Pub. Date: Nov. 7, 2019

(65) Prior Publication Data
US 2021/0269433 A1 Sep. 2, 2021

(30) Foreign Application Priority Data

Apr. 29, 2018 (WO) ................ PCT/CN2018/085217
Sep. 21, 2018 (WO) ................ PCT/CN2018/107134

(51) Int. Cl.
| C07D 401/04 | (2006.01) |
| A61K 31/437 | (2006.01) |
| C07D 471/04 | (2006.01) |
| A61P 35/00 | (2006.01) |
| C07D 403/12 | (2006.01) |
| C07D 405/14 | (2006.01) |
| C07D 471/14 | (2006.01) |
| C07D 519/00 | (2006.01) |

(52) U.S. Cl.
CPC .......... *C07D 471/04* (2013.01); *A61P 35/00* (2018.01); *C07D 403/12* (2013.01); *C07D 405/14* (2013.01); *C07D 471/14* (2013.01); *C07D 519/00* (2013.01)

(58) Field of Classification Search
CPC .. C07D 471/04; C07D 401/14; C07D 241/04; A61K 31/437; A61K 31/496; A61P 35/00; A61P 25/28
USPC ........... 546/16, 113; 544/362; 514/278, 300, 514/253.04
See application file for complete search history.

(56) References Cited

U.S. PATENT DOCUMENTS

2002/0055631 A1   5/2002   Augeri et al.

FOREIGN PATENT DOCUMENTS

| CN | 102448959 A | 5/2012 |
| CN | 102947283 A | 2/2013 |
| CN | 103237797 A | 8/2013 |
| CN | 103562202 A | 2/2014 |
| CN | 106749233 A | 5/2017 |
| WO | WO 2010138588 A2 | 12/2010 |
| WO | WO-2011149492 A1 | 12/2011 |
| WO | WO 2011150016 A1 | 12/2011 |
| WO | WO 2012103059 A2 | 8/2012 |
| WO | WO-2019210828 A1 | 11/2019 |
| WO | WO-2020140005 A2 | 7/2020 |

OTHER PUBLICATIONS

Adams, J. M., and Cory, S. (2007) The Bcl-2 apoptotic switch in cancer development and therapy. Oncogene 26, 1324-1337.
Anderson, M. A., Huang, D., and Roberts, A. (2014) Targeting BCL2 for the treatment of lymphoid malignancies. Semin Hematol 51, 219-227.
Czabotar, P. E., Lessene, G., Strasser, A., and Adams, J. M. (2014) Control of apoptosis by the BCL-2 protein family: implications for physiology and therapy. Nat Rev Mol Cell Biol 15, 49-63.
(Continued)

*Primary Examiner* — Charanjit Aulakh
(74) *Attorney, Agent, or Firm* — Cooley LLP

(57) ABSTRACT

Disclosed herein is a compound of Formula (I) for inhibiting Bcl-2 and treating disease associated with undesirable bcl-2 activity (Bcl-2 related diseases), a method of using the compounds disclosed herein for treating dysregulated apoptotic diseases including cancers and treating autoimmune disease, and a pharmaceutical composition comprising the same.

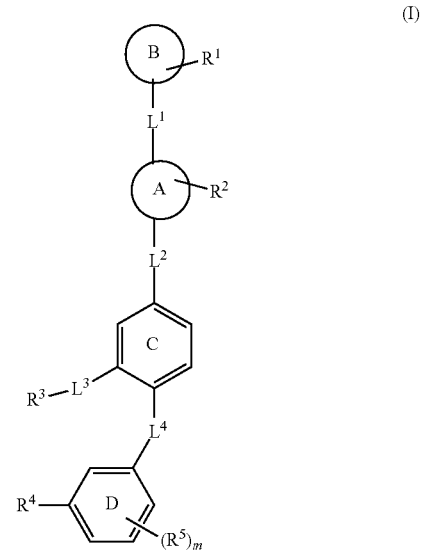

39 Claims, 2 Drawing Sheets

(56) References Cited

OTHER PUBLICATIONS

Egle, A., Harris, A. W., Bath, M. L., O'Reilly, L., and Cory, S. (2004) VavP-Bcl2 transgenic mice develop follicular lymphoma preceded by germinal center hyperplasia. Blood 103, 2276-2283.

International Search Report and Written Opinion for International Application No. PCT/CN2019/085001, dated Jul. 26, 2019, 12 pages.

Kondo, S., Oakes, M. G., and Sorenson, C. M. (2008) Rescue of renal hypoplasia and cystic dysplasia in Bcl-2 −/− mice expressing Bcl-2 in ureteric bud derived epithelia. Dev Dyn 237, 2450-2459.

Roberts, A. W. (2016) Targeting apoptotic pathways to treat lymphoid malignancies. Rinsho Ketsueki 57, 2054-2058.

Roberts, A. W., and Huang, D. (2017) Targeting BCL2 With BH3 Mimetics: Basic Science and Clinical Application of Venetoclax in Chronic Lymphocytic Leukemia and Related B Cell Malignancies. Clin Pharmacol Ther 101, 89-98.

Schenk, R. L., Strasser, A., and Dewson, G. (2017) BCL-2: Long and winding path from discovery to therapeutic target. Biochem Biophys Res Commun 482, 459-469.

Tausch, E., Close, W., Dolnik, A., Bloehdorn, J., Chyla, B., Bullinger, L., Dohner, H., Mertens, D., and Stilgenbauer, S. (2019) Venetoclax resistance and acquired BCL2 mutations in chronic lymphocytic leukemia. Haematologica 104, e434-e437.

Veis, D.J., Sorenson, C.M., Shutter, J.R. and Korsmeyer, S.J. (1993) Bcl-2-deficient mice demonstrate fulminant lymphoid apoptosis, polycystic kidneys, and hypopigmented hair. Cell, 75, 229-240.

Yamamura, K., Kamada, S., Ito, S., Nakagawa, K., Ichihashi, M., and Tsujimoto, Y. (1996) Accelerated disappearance of melanocytes in bcl-2-deficient mice. Cancer Res 56, 3546-3550.

Liu, X. et al., "Development of high potent and selective Bcl-2 inhibitors bearing the structural elements of natural product artemisinin," European Journal of Medicinal Chemistry, vol. 159 (2018) pp. 149-165.

Written Opinion for Singapore Application No. 11202009933W, dated Mar. 10, 2022, 7 pages.

BCL-2 INHIBITORS

CROSS-REFERENCE TO RELATED APPLICATIONS

This application is a U.S. National Stage Application under 35 U.S.C. § 371 of International Application No. PCT/CN2019/085001, filed Apr. 29, 2019, which claims the benefit of International Patent Application No. PCT/CN2018/085217, filed on Apr. 29, 2018, and PCT/CN2018/107134, filed on Sep. 21, 2018, the disclosures of which are hereby incorporated by reference in their entireties for all purposes.

FIELD OF THE INVENTION

Disclosed herein is a compound of Formula (I) for inhibiting Bcl-2 and treating disease associated with undesirable bcl-2 activity (Bcl-2 related diseases), a method of using the compounds disclosed herein for treating dysregulated apoptotic diseases including neurodegenerative conditions, e.g., Alzheimer's disease; and proliferative diseases, e.g., cancers, autoimmune diseases and pro-thrombotic conditions, and a pharmaceutical composition comprising the same.

BACKGROUND OF THE INVENTION

Programmed cell death or apoptosis occurs in multicellular organisms to dispose damaged or unwanted cells, which is critical for normal tissue homeostasis, (Br. J. Cancer 1972, 26, 239). However defective apoptotic processes have been implicated in a wide variety of diseases. Excessive apoptosis causes atrophy, whereas an insufficient amount results in uncontrolled cell proliferation, such as cancer (Cell 2011, 144, 646). Resistance to apoptotic ceil death is a hallmark of cancer and contributes to chemoresistance (Nat Med. 2004, 10, 789-799). Several key pathways controlling apoptosis are commonly altered in cancer. Some factors like Fas receptors and caspases promote apoptosis, while some members of the B-cell lymphoma 2 (Bcl-2) family of proteins inhibit apoptosis. Negative regulation of apoptosis inhibits cell death signaling pathways, helping tumors to evade cell death and developing drug resistance.

There are two distinct apoptosis pathways including the extrinsic pathway and the intrinsic pathway. The extrinsic pathway is activated in response to the binding of death-inducing ligands to cell-surface death receptors (Nat Rev Drag Discov. 2017 16, 273-284). The B cell lymphoma 2 (BCL-2) gene family, a group of proteins homologous to the Bcl-2 protein, encodes more than 20 proteins that regulate the intrinsic apoptosis pathway. Bcl-2 family proteins are characterized by containing at least one of four conserved Bcl-2 homology (BH) domains (BH1, BH2, BH3 and BH4) (Nat. Rev. Cancer 2008, 8, 121; Mol. Cell 2010, 37, 299; Nat. Rev. Mol. Cell Biol. 2014, 15, 49). Bcl-2 family proteins, consisting of pro-apoptotic and anti-apoptotic molecules, can be classified into the following three subfamilies according to sequence homology within four BH domains: (1) a subfamily shares sequence homology within all four BH domains, such as Bcl-2, Bcl-XL and Bcl-w which are anti-apoptotic; (2) a subfamily shares sequence homology within BH1, BH2 and BH4, such as Bax and Bale which are pro-apoptotic; (3) a subfamily shares sequence homology only within BH3, such as Bik, Bid and HRK which are pro-apoptotic. One of the unique features of Bcl-2 family proteins is heterodimerization between anti-apoptotic and pro-apoptotic proteins, which is considered to inhibit the biological activity of their partners. This heterodimerization is mediated by the insertion of a BH3 region of a pro-apoptotic protein into a hydrophobic cleft composed of BH1, BH2 and BH3 from an anti-apoptotic protein. In addition to the BH1 and BH2, the BH4 domain is required for anti-apoptotic activity. In contrast, BH3 domain is essential and, itself, sufficient for pro-apoptotic activity.

Similar to oncogene addiction, in which tumor cells rely on a single dominant gene for survival, tumor cells may also become dependent on Bcl-2 in order to survive. Bcl-2 overexpress is found frequently in acute myeloid leukemia (AML), acute lymphocytic leukemia (ALL), relapsed/refractory chronic lymphocytic leukemia (CLL), follicular lymphoma (FL), non-Hodgkin lymphoma (NHL) and solid tumors such as pancreatic, prostate, breast, and small cell and non-small cell lung cancers (Cancer 2001, 92, 1122-1129; Cancer Biol. 2003; 13:115-23; Curr. Cancer Drug Targets 2008, 8, 207-222: Cancers 2011, 3, 1527-1549). Dysregulated apoptotic pathways have also been implicated in the pathology of other significant diseases such as neurodegenerative conditions (up-regulated apoptosis), e.g., Alzheimer's disease; and proliferative diseases (down-regulated apoptosis), e.g., cancers, autoimmune diseases and pro-thrombotic conditions. Target to either Bcl-2 or Bcl-xL, a number of small-molecule BH3 mimetics have been reported in (Recent Patents on Anti-Cancer Drug Discovery, 2008, 3, 20-30; Bioorg. Med. Chem. Lett. 2016, 26, 2105-2114; Nature Reviews Drag Discovery 2017, 16, 273-284; WO2002024636; WO2005049593; WO2006127364; WO2006023778; WO2007040650; WO2008030836; WO2009152082; WO2009036051; WO2010065824; WO2010065865; WO2010083441; WO2010083442; WO2010067067; WO2011029842; WO2011068561; WO2011119345; WO2011149492; WO2011150016; WO2012058392; WO2012017251; WO2012162365; WO2012103059; WO2013053045; WO2013185202; WO2013096060; WO2013096059; WO2013096055; WO2013096051; WO2013096049; US2011312969; WO2014158528; WO2014113413; WO2018027097; WO2018041248; WO2018009444; CN106749233; CN106565706). Some of the Bcl-2 small molecule inhibitors have been investigated at various stages of drag development: the Bcl-2/Bcl-xL inhibitor ABT-263 (navitoclax, WO2009155386) has shown promising clinical activity in lymphoid malignancies such as chronic lymphocytic leukemia. However, its efficacy in these settings is limited by platelet death and attendant thrombocytopenia caused by Bcl-xL inhibition (Lancet Oncol. 2010, 11, 1149; J. Clin. Oncol. 2011, 29, 909; J. Clin. Oncol. 2012, 30, 488). The new generation of the BCL-2 selective inhibitor venetoclax (ABT-199/GDC-0199) was proceeded, which demonstrated robust activity in these cancers but also spared platelets (Journal of Hematology & Oncology 2015, 8, 129; Clinical Advances in Hematology & Oncology 2017, 15, 210). S55746 (also known as BCL201), APG-101, APG-1252 are being studied at clinical trial stage. Currently, Venetoclax (formerly ABT-199) is the only Bcl-2 selective inhibitor approved by FDA for the treatment of patients who have relapsed or refractory chronic lymphocytic leukemia (CLL) with the 17p deletion. Recently, however, a novel Gly101Val mutation in BCL2 was identified after the patients were treated with the Bcl-2 inhibitor venetoclax (ABT-199) for 19 to 42 months (Cancer Discov. 2019, 9, 342-353). This mutation dramatically reduced the binding affinity of Bcl-2 for Venetoclax (ABT-199) by about 180-fold in cell based assay.

Therefore, there is a need of new small molecules that selectively inhibit Bcl-2 proteins for the treatment of dys-regulated apoptotic diseases such as cancers, autoimmune diseases and pro-thrombotic conditions. Unexpectedly, the inventors of the present application found some compounds disclosed herein show not only much higher potency and selectivity but also much lower CYP2C9 inhibition, indicating potential better efficacy and lower potential risk of drag-drug interaction (DDI). Also, the inventors of the present application found that the compounds disclosed herein exhibit inhibitory activity against both Bcl-2 wild type and Bcl-2 G101V mutation type, suggesting a type of new potential Bcl-2 inhibitors without resistance concern.

SUMMARY OF THE INVENTION

Disclosed herein is a compound of Formula (I)

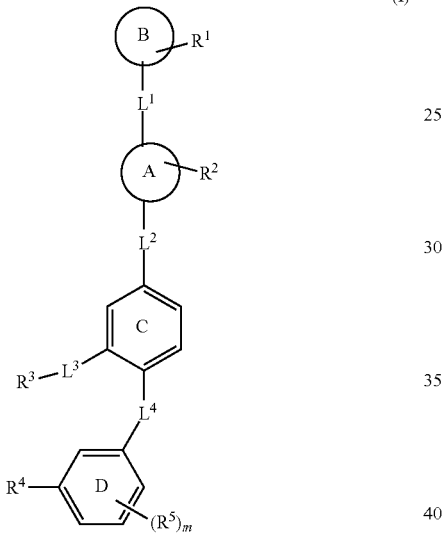

(I)

or a pharmaceutically acceptable salt thereof, or a stereoisomer thereof,
wherein
$L^1$, $L^2$, $L^3$ and $L^4$ are each independently a direct bond, —(CR$^a$R$^b$)$_t$—, —(CR$^a$R$^b$)$_{t-1}$—(CR$^c$=CR$^d$)—(CR$^a$R$^b$)$_{v-1}$—, —(CR$^a$R$^b$)$_{t-1}$—(C≡C)—(CR$^a$R$^b$)$_{v-1}$—, —O—, —S—, —S(O)—, —SO$_2$—, —C(O)—, C(O)O—, —OC(O)—, —NR$^a$—, —C(O)NR$^a$—, —NR$^a$C(O)—, —NR$^a$C(O)O—, —NR$^a$C(O)NR$^b$—, —SO$_2$NR$^a$—, —NR$^a$SO$_2$—, —NR$^a$S(O)$_2$NR$^b$—, —NR$^a$S(O)NR$^b$—, —C(O)NR$^a$SO$_2$—, —C(O)NR$^a$SO—, or —C(=NR$^a$)NR$^b$—, wherein t and v, at each occurrence, are independently a number of 1 to 7, and one or two CR$^a$R$^b$ moieties in —(CR$^a$R$^b$)$_t$—, —(CR$^a$R$^b$)$_{t-1}$—(CR$^c$=CR$^d$)—(CR$^a$R$^b$)$_{v-1}$—, —(CR$^a$R$^b$)$_{t-1}$—(C≡C)—(CR$^a$R$^b$)$_{v-1}$— are un-replaced or replaced with one or more moieties selected from O, S, SO, SO$_2$, C(O) and NR$^a$;
Ring A is cycloalkyl, cycloalkenyl, cycloalkynyl, aryl, heterocyclyl, or heteroaryl, each of which is optionally substituted with 1 to 4 substituents R$^2$;
R$^2$, at each occurrence, is independently selected from the group consisting of hydrogen, halogen, —C$_{1-8}$alkyl, —C$_{2-8}$alkenyl, C$_{2-8}$alkynyl, cycloalkyl, heterocyclyl, aryl, heteroaryl, oxo, —CN, —NO$_2$, —OR$^{2a}$, —SO$_2$R$^{2a}$, —COR$^{2a}$, —CO$_2$R$^{2a}$, —CONR$^{2a}$R$^{2b}$, —C(=NR$^{2a}$)NR$^{2b}$R$^{2c}$, —NR$^{2a}$R$^{2b}$, —NR$^{2a}$COR$^{2b}$, —NR$^{2a}$CONR$^{2b}$R$^{2c}$, —NR$^{2a}$CO$_2$R$^{2b}$, —NR$^{2a}$SONR$^{2b}$R$^{2c}$, —NR$^{2a}$SO$_2$NR$^{2b}$R$^{2c}$, or —NR$^{2a}$SO$_2$R$^{2b}$, each of said —C$_{1-8}$alkyl, —C$_{2-8}$alkenyl, —C$_{2-8}$alkynyl, cycloalkyl, heterocyclyl, aryl, or heteroaryl is optionally substituted with halogen, hydroxy, —C$_{1-8}$alkyoxy, cycloalkyl, heterocyclyl, aryl, or heteroaryl;
R$^{2a}$, R$^{2b}$, and R$^{2c}$, are each independently hydrogen, —C$_{1-8}$alkyl, —C$_{2-8}$alkenyl, —C$_{2-8}$alkynyl, cycloalkyl, heterocyclyl, aryl, or heteroaryl, each of said —C$_{1-8}$alkyl, —C$_{2-8}$alkenyl, —C$_{2-8}$alkynyl, cycloalkyl, heterocyclyl, aryl, or heteroaryl is optionally substituted with halogen, hydroxy or —C$_{1-8}$alkyoxy;
Ring B is cycloalkyl, cycloalkenyl, cycloalkynyl, aryl, heterocyclyl, or heteroaryl, each of which is optionally substituted with 1 to 4 substituents R$^1$;
R$^1$, at each occurrence, is independently selected from the group consisting of hydrogen, halogen, —C$_{1-8}$alkyl, —C$_{2-8}$alkenyl, —C$_{2-8}$alkynyl, cycloalkyl, heterocyclyl, aryl, heteroaryl, oxo, —CN, —NO$_2$, —OR$^{1a}$, —SO$_2$R$^{1a}$, —COR$^{1a}$, —CO$_2$R$^{1a}$, —CONR$^{1a}$R$^{1b}$, —C(=NR$^{1a}$)NR$^{1b}$R$^{1c}$, —NR$^{1a}$R$^{1b}$, —NR$^{1a}$COR$^{1b}$, —NR$^{1a}$CONR$^{1b}$R$^{1c}$, —NR$^{1a}$CO$_2$R$^{1b}$, —NR$^{1a}$SONR$^{1b}$R$^{1c}$, —NR$^{1a}$SO$_2$NR$^{1b}$R$^{1c}$, or NR$^{1a}$SO$_2$R$^{1b}$; wherein said —C$_{1-8}$alkyl, —C$_{2-8}$alkenyl, —C$_{2-8}$alkynyl, cycloalkyl, heterocyclyl, aryl or heteroaryl are each independently optionally substituted with 1 to 4 substituents R$^{1d}$;
R$^{1a}$, R$^{1b}$, and R$^{1c}$, are each independently hydrogen, —C$_{1-8}$alkyl, —C$_{2-8}$alkenyl, —C$_{2-8}$alkynyl, cycloalkyl, heterocyclyl, aryl, or heteroaryl, each of said —C$_{1-8}$alkyl, —C$_{2-8}$alkenyl, —C$_{2-8}$alkynyl, cycloalkyl, heterocyclyl, aryl, or heteroaryl is optionally substituted with halogen, hydroxy or —C$_{1-8}$alkyoxy;
R$^{1d}$, at each occurrence, is independently halogen, —C$_{1-8}$alkyl, —C$_{2-8}$alkenyl, —C$_{2-8}$alkynyl, cycloalkyl, heterocyclyl, aryl, heteroaryl, oxo, —CN, —NO$_2$, —OR$^{Ba}$, —SO$_2$R$^{Ba}$, —COR$^{Ba}$, CO$_2$R$^{Ba}$, —CONR$^{Ba}$R$^{Bb}$, —C(=NR$^{Ba}$)NR$^{Bb}$R$^{Bc}$, —NR$^{Ba}$R$^{Bb}$, —NR$^{Ba}$COR$^{Bb}$, —NR$^{Ba}$CONR$^{Bb}$R$^{Bc}$, —NR$^{Ba}$CO$_2$R$^{Bb}$, —NR$^{Ba}$SONR$^{Bb}$R$^{Bc}$, —NR$^{Ba}$SO$_2$NR$^{Bb}$R$^{Bc}$, or —NR$^{Ba}$SO$_2$R$^{Bb}$; wherein said —C$_{1-8}$alkyl, —C$_{2-8}$alkenyl, —C$_{2-8}$alkynyl, cycloalkyl, heterocyclyl, aryl or heteroaryl are each independently optionally substituted with 1 to 4 substituents R$^{Bd}$;
R$^{Ba}$, R$^{Bb}$, and R$^{Bc}$, are each independently hydrogen, —C$_{1-8}$alkyl, —C$_{2-8}$alkenyl, —C$_{2-8}$alkynyl, cycloalkyl, heterocyclyl, aryl, or heteroaryl, each of said —C$_{1-8}$alkyl, —C$_{2-8}$alkenyl, C$_{2-8}$alkynyl, cycloalkyl, heterocyclyl, aryl, or heteroaryl is optionally substituted with halogen, hydroxy, NH$_2$ or —N(C$_{1-6}$alkyl)$_2$, —C$_{1-8}$alkyoxy, cycloalkyl, heterocyclyl, aryl, or heteroaryl;
R$^{Bd}$, at each occurrence, is independently hydrogen, halogen, oxo, —CN, —NO$_2$, —C$_{1-8}$alkyl, —C$_{2-8}$alkenyl, —C$_{2-8}$alkynyl, cycloalkyl, heterocyclyl, aryl, or heteroaryl, each of said —C$_{1-8}$alkyl, —C$_{2-8}$alkenyl, —C$_{2-8}$alkynyl, cycloalkyl, heterocyclyl, aryl, or heteroaryl is optionally substituted with halogen, hydroxy, —$C_{1-8}$alkyoxy, cycloalkyl, heterocyclyl, aryl, or heteroaryl;

$R^3$ is hydrogen, halogen, $C_{1-8}$alkyl, $C_{2-8}$alkenyl, $C_{2-8}$alkynyl, cycloalkyl, aryl, heterocyclyl, or heteroaryl, each of said $C_{1-8}$alkyl, $C_{2-8}$alkenyl, $C_{2-8}$alkynyl, cycloalkyl, aryl, heterocyclyl, or heteroaryl is optionally substituted with 1 to 4 substituents $R^{3a}$;

$R^{3a}$, at each occurrence, is independently selected from halogen, cyano, —$NO_2$, —$OR^{3b}$, —$SR^{3b}$, —$NR^{3b}R^{3c}$, —$COR^{3b}$, —$SO_2R^{3b}$, —$C(=O)OR^{3b}$, —$C(=O)NR^{3b}R^{3c}$, —$C(=NR^{3b})NR^{3c}R^{3d}$, —$N(R^{3b})C(=O)R^{3c}$, —$N(R^{3b})C(=O)OR^{3c}$, —$N(R^{3b})C(O)NR^{3c}R^{3d}$, —$N(R^{3b})S(O)NR^{3c}R^{3d}$, —$N(R^{3b})S(O)_2NR^{3c}R^{3d}$, —$NR^{3b}SO_2R^{3c}$, —$C_{1-8}$alkyl, —$C_{2-8}$alkenyl, —$C_{2-8}$alkynyl, -cycloalkyl, heterocyclyl, aryl, or heteroaryl;

$R^{3b}$, $R^{3c}$, and $R^{3d}$ are independently hydrogen, —$C_{1-8}$ alkyl, —$C_{1-8}$alkenyl, —$C_{2-8}$alkynyl, cycloalkyl, heterocyclyl, aryl, or heteroaryl, each of said —$C_{1-8}$alkyl, —$C_{2-8}$alkenyl, —$C_{2-8}$alkynyl, cycloalkyl, heterocyclyl, aryl, or heteroaryl is optionally substituted with halogen, hydroxy or —$C_{1-8}$alkyoxy:

$R^4$ is hydrogen, halogen, cyano, $NO_2$, —$OR^{4a}$, —$SR^{4a}$, —$NR^{4a}R^{4b}$, —$COR^{4a}$, —$SO_2R^{4a}$, —$C(=O)OR^{4a}$, —$C(=O)NR^{4a}R^{4b}$, —$C(=NR^{4a})NR^{4b}R^{4c}$, —$N(R^{4a})C(=O)R^{4b}$, —$N(R^{4a})C(=O)OR^{4b}$, —$N(R^{4a})C(O)NR^{4b}R^{4c}$, —$N(R^{4a})S(O)NR^{4b}R^{4c}$, —$N(R^{4a})S(O)_2NR^{4b}R^{4c}$, —$NR^{4a}SO_2R^{4b}$, —$C_{1-8}$alkyl, —$C_{2-8}$alkenyl, —$C_{2-8}$alkynyl, -cycloalkyl, heterocyclyl, aryl, or heteroaryl, each of said —$C_{1-8}$alkyl, —$C_{2-8}$alkenyl, —$C_{2-8}$alkynyl, -cycloalkyl, heterocyclyl, aryl, or heteroaryl is independently and optionally substituted with one or two substituents $R^{4d}$;

$R^{4a}$, $R^{4b}$, and $R^{4c}$ are independently hydrogen, —$C_{1-8}$ alkyl, —$C_{2-8}$alkenyl, —$C_{2-8}$alkynyl, cycloalkyl, heterocyclyl, aryl, or heteroaryl, each of said —$C_{1-8}$ alkyl, —$C_{2-8}$alkenyl, —$C_{2-8}$alkynyl, cycloalkyl, heterocyclyl, aryl, or heteroaryl is optionally substituted with halogen, hydroxy or —$C_{1-8}$alkyoxy;

$R^{4d}$, at each occurrence, is independently hydrogen, oxo, —CN, —$NO_2$, halogen, —$C_{2-8}$alkyl, —$C_{2-8}$alkenyl, —$C_{1-8}$alkynyl, cycloalkyl, heterocyclyl, aryl, or heteroaryl, each of said —$C_{1-8}$alkyl, —$C_{2-8}$alkenyl, —$C_{2-8}$alkynyl, cycloalkyl, heterocyclyl, aryl, or heteroaryl is optionally substituted with halogen, hydroxy or —$C_{1-8}$alkyoxy;

m is an integer of 1-4;

$R^5$ is -$L^5$-CyC,

Wherein $L^5$ is a direct bond, —$(CR^aR^b)_t$—, —$(CR^aR^b)_{t-1}$—$(CR^c=CR^d)$—$(CR^aR^b)_{v-1}$—, —$(CR^aR^b)_{t-1}$—$(C\equiv C)$—$(CR^aR^b)_{v-1}$—, —O—, —S—, —S(O)—, —$SO_2$—, —C(O)—, C(O)O—, —OC(O)—, —$NR^a$—, —C(O)$NR^a$—, —$NR^aC(O)$—, —$NR^2C(O)O$—, —$NR^aC(O)NR^b$—, —$SO_2NR^3$—, —$NR^aSO_2$—, —$NR^aS(O)_2NR^b$—, —$NR^aS(O)NR^b$—, —C(O)$NR^aSO_2$—, —C(O)$NR^aSO$—, or —C(=$NR^a$)$NR^b$, wherein t and v, at each occurrence, are independently a number of 1 to 7, and one or two $CR^aR^b$ moieties in —$(CR^aR^b)_t$—, —$(CR^aR^b)_{t-1}$—$(CR^c=CR^d)$—$(CR^aR^b)_{v-1}$—, —$(CR^aR^b)_{t-1}$—$(C\equiv C)$—$(CR^aR^b)_{v-1}$— are un-replaced or replaced with one or more moieties selected from O, S, SO, $SO_2$, C(O) and $NR^a$;

CyC is cycloalkyl, heterocyclyl, aryl, or heteroaryl, each of which is optionally substituted with one or two substituents $R^{5a}$;

$R^{5a}$, at each occurrence, is independently selected from hydrogen, halogen, cyano, oxo, —$NO_2$, —$OR^{5b}$, —$SR^{5b}$, —$NR^{5b}R^{5c}$, —$COR^{5b}$, —$SO_2R^{5b}$, —$C(=O)OR^{5b}$, —$C(=O)NR^{5b}R^{5c}$, —$C(=NR^{5b})NR^{5c}R^{5d}$, —$N(R^{5b})C(=O)R^{5c}$, —$N(R^{5b})C(=O)OR^{5c}$, —$N(R^{5b})C(O)NR^{5c}R^{5d}$, —$N(R^{5b})S(O)NR^{5c}R^{5d}$, —$N(R^{5b})S(O)_2NR^{5c}R^{5d}$, —$NR^{5b}SO_2R^{5c}$, —$C_{1-8}$alkyl, —$C_{2-8}$alkenyl, —$C_{2-8}$alkynyl, -cycloalkyl, heterocyclyl, aryl, or heteroaryl, each of said —$C_{1-8}$alkyl, —$C_{2-8}$alkenyl, —$C_{2-8}$alkynyl, -cycloalkyl, heterocyclyl, aryl, or heteroaryl is optionally substituted with one or two substituents $R^{5e}$;

wherein $R^{5b}$, $R^{5c}$, and $R^{5d}$ are each independently hydrogen, —$C_{1-8}$alkyl, —$C_{2-8}$alkenyl, —$C_{2-8}$alkynyl, cycloalkyl, heterocyclyl, aryl, or heteroaryl, each of said —$C_{1-8}$alkyl, —$C_{2-8}$alkenyl, $C_{2-8}$alkynyl, -cycloalkyl, heterocyclyl, aryl, or heteroaryl is optionally substituted with one or two substituents $R^{5e}$;

$R^{5e}$, at each occurrence, is independently selected from hydrogen, halogen, cyano, oxo, —$NO_2$, —$OR^{5f}$, —$SR^{5f}$, —$NR^{5f}R^{5g}$, —$COR^{5f}$, —$SO_2R^{5f}$, —$C(=O)OR^{5f}$, —$C(=O)NR^{5f}R^{5g}$, —$C(=NR^{5f})NR^{5g}R^{5h}$, —$N(R^{5f})C(=O)R^{5g}$, —$N(R^{5f})C(=O)OR^{5g}$, —$N(R^{5f})C(O)NR^{5g}R^{5h}$, —$N(R^{5f})S(O)NR^{5g}R^{5h}$, —$N(R^{5f})S(O)_2NR^{5g}R^{5h}$, —$NR^5SO_2R^{5g}$, —$C_{1-8}$alkyl, —$C_{2-8}$alkenyl, —$C_{2-8}$ alkynyl, -cycloalkyl, heterocyclyl, aryl, or heteroaryl;

$R^{5f}$, $R^{5g}$, and $R^{5h}$ are each independently hydrogen, —$C_{1-8}$alkyl, —$C_{2-8}$alkenyl, —$C_{2-8}$alkynyl, cycloalkyl, heterocyclyl, aryl, or heteroaryl;

or, two adjacent $R^5$ on the phenyl ring together with the phenyl ring form a benzo ring, said ring is optionally substituted with halogen, oxo, cyano, —$NO_2$, —$OR^{5i}$, —$SR^{5i}$, —$NR^{5i}R^{5j}$, —$COR^{5i}$, —$SO_2R^{5i}$, —$C(=O)OR^{5i}$, —$C(=O)NR^{5i}R^{5j}$, —$C(=NR^{5i})NR^{5j}R^{5k}$, —$N(R^{5i})C(=O)R^{5j}$, —$N(R^{5i})C(=O)OR^{5j}$, —$N(R^{5i})C(O)NR^{5j}R^{5k}$, —$N(R^{5i})S(O)NR^{5j}R^{5k}$, —$N(R^{5i})S(O)_2NR^{5j}R^{5k}$, —$NR^{5i}SO_2R^{5k}$, —$C_{1-8}$alkyl, —$C_{2-8}$alkenyl, —$C_{2-8}$alkynyl, -cycloalkyl, heterocyclyl, aryl, or heteroaryl;

$R^{5i}$, $R^{5j}$, and $R^{5k}$ are independently hydrogen, —$C_{1-8}$ alkyl, —$C_{2-8}$alkenyl, —$C_{2-8}$alkynyl, cycloalkyl, heterocyclyl, aryl, or heteroaryl, each of said —$C_{1-8}$ alkyl, —$C_{2-8}$alkenyl, —$C_{2-8}$alkynyl, cycloalkyl, heterocyclyl, aryl, or heteroaryl is optionally substituted with halogen, hydroxy or —$C_{1-8}$alkyoxy;

$R^a$, $R^b$, $R^c$, and $R^d$ at each occurrence, are independently hydrogen, —$C_{1-8}$alkyl, —$C_{2-8}$alkenyl, —$C_{2-8}$alkynyl, cycloalkyl, heterocyclyl, aryl, or heteroaryl, said —$C_{1-8}$ alkyl, —$C_{2-8}$alkenyl, —$C_{2-8}$alkynyl, cycloalkyl, heterocyclyl, aryl, or heteroaryl are each independently substituted with —CN, halogen, —$NO_2$, —$NR^eR^f$, oxo, —$OR^e$, or —$SR^e$; and wherein $R^e$ and $R^f$ are each independently hydrogen, $C_{1-8}$alkyl, $C_{1-8}$alkoxy-$C_{1-8}$alkyl-, $C_{2-8}$alkenyl, $C_{2-8}$alkynyl, cycloalkyl, aryl, heterocyclyl, or heteroaryl.

In one embodiment, $R^a$, $R^b$, $R^c$ and $R^d$, at each occurrence, are independently hydrogen or $C_{1-6}$alkyl, preferably hydrogen or methyl.

In one embodiment, $L^1$ is a direct bond or —$(CR^aR^b)_t$—, wherein $R^a$, $R^b$ and t are defined as with Formula (I). In some embodiment, t is a number of 1 or 2. In a preferred embodiment, $L^1$ is a direct bond or —$(CR^aR^b)$—, wherein $R^a$ and $R^b$ are hydrogen or $C_{1-6}$alkyl, preferably hydrogen. In a most preferred embodiment, $L^1$ is a direct bond.

In one embodiment, $L^2$ is a direct bond, —$(CR^aR^b)_t$—, —$(CR^aR^b)_{t-1}$—$(CR^c$=$CR^d)$—$(CR^aR^b)_{v-1}$—, —$(CR^aR^b)_{t-1}$—(C≡C)—$(CR^aR^b)_{v-1}$—, —O— or —$NR^a$—, wherein $R^a$, $R^b$, $R^c$, t, and v are defined as with Formula (I). In some embodiment, t or v is a number of 1-4. In a preferred embodiment, $L^2$ is a direct bond, —$(CR^aR^b)_{1-5}$—, —$(CR^aR^b)_{1-3}$—(C≡C)—, —O— or —$NR^a$—, wherein $R^a$, $R^b$ and $R^c$, at each occurrence, are independently hydrogen or $C_{1-6}$alkyl, and one or two $CR^aR^b$ moieties in —$(CR^aR^b)_{1-5}$—, —$(CR^aR^b)_{1-3}$—(C≡C)— are replaced with one or two moieties from O, S, SO, $SO_2$, C(O) and $NR^a$. In an even preferred embodiment, $L^2$ is a direct bond, —$(CR^aR^b)_{1-5}$—, —$(CR^aR^b)_{1-3}$—(C≡C)—, or —$NR^a$— wherein $R^a$, $R^b$ and $R^c$, at each occurrence, are independently hydrogen or $C_{1-6}$alkyl, and one or two $CR^aR^b$ moieties in —$(CR^aR^b)_{1-5}$—, —$(CR^aR^b)$—(C≡C)— are replaced with one or two heteroatoms from O or $NR^a$, wherein $R^a$ is hydrogen or $C_{1-6}$alkyl, preferably hydrogen or $CH_3$. In another embodiment, $L^2$ is a direct bond, —$CH_2$—, —O—, —NH—,

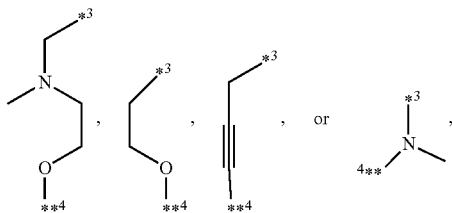

wherein *3 refers to the position attached to ring A, **4 refers to the position attached to the phenyl ring. In a most preferred embodiment, $L^2$ is a direct bond.

In a preferred embodiment, $L^1$ and $L^2$ are both direct bonds, or $L^1$ is —$CH_2$— or —$CH_2$—$CH_2$— and $L^2$ is a direct bond.

In one embodiment, $L^3$ is a direct bond, —$(CR^aR^b)_t$—, —O—, —S—, —S(O)—, —$SO_2$—, —C(O)—, C(O)O—, —OC(O)—, or —$NR^a$—, wherein $R^a$, $R^b$ and t are defined as with Formula (I). Preferably, $R^a$ and $R^b$ are independently hydrogen or $C_{1-6}$alkyl, and t is 1 or 2. In a preferred embodiment, $L^3$ is —O—, —$CH_2$—, a direct bond, or —C(O)—. More preferably, $L^3$ is —O—.

In one embodiment, $R^3$ is heteroaryl optionally substituted with one or two substituents $R^{3a}$ as defined with Formula (I). Preferably, $R^3$ is heteroaryl optionally substituted with one or two substituents $R^{3a}$ selected from halogen, —$C_{1-8}$alkyl, or —$NR^{3b}R^{3c}$, wherein $R^{3b}$ and $R^{3c}$ are independently hydrogen, or —$C_{1-8}$alkyl.

In one embodiment, $R^3$ is a 5 to 7-membered nitrogen-containing monocyclic heteroaryl optionally substituted with one or two substituents $R^{3a}$ selected from halogen, —$C_{1-8}$alkyl, or —$NR^{3b}R^{3c}$, wherein $R^{3b}$ and $R^{3c}$ are independently hydrogen, or —$C_{1-8}$alkyl. Preferably, $R^3$ is tetrazolyl, trizolyl, pyrazolyl, pyrrolyl, pyridinyl, pyrimidinyl, each of which optionally substituted with one or two substituents $R^{3a}$ selected from halogen, —$C_{1-8}$alkyl, or —$NR^{3b}R^{3c}$, wherein $R^{3b}$ and $R^{3c}$ are independently hydrogen, or —$C_{1-8}$alkyl.

In one embodiment, $R^3$ is a 8- to 12-membered bicyclic heteroaryl comprising 1 or 2 or 3 nitrogen atoms. Preferably, $R^3$ is indolyl, pyrrolopyridiny, or pyrazolopyridinyl, each of which optionally substituted with one or two substituents $R^{ja}$ selected from halogen, —$C_{1-8}$alkyl, or $NR^{3b}R^{3c}$, wherein $R^{3b}$ and $R^{3c}$ are independently hydrogen, or —$C_{1-8}$alkyl. More preferably, $R^3$ is indol-4-yl, pyrrolo[2,3-b]pyridin-5-yl, pyrazolo[4,3-b]pyridin-1-yl.

In one embodiment, $R^3$ is 11- to 14-membered tricyclic heteroaryl comprising 1 or 2 or 3 or 4 or 5 nitrogen atoms optionally substituted with one or two substituents $R^{ja}$ selected from halogen, —$C_{1-8}$alkyl, or —$NR^{3b}R^{3c}$, wherein $R^{3b}$ and $R^{3c}$ are independently hydrogen, or —$C_{1-8}$alkyl. Preferably, $R^3$ is pyrazolo[4,3-b]pyrrolo[3,2-e]pyridine-1-(5i)-yl.

In one embodiment, $L^3$ is —O—, and $R^3$ is pyrrolo[2,3-b]pyridin-5-yl.

In one embodiment, $L^4$ is —$C(O)NR^aSO_2$—, wherein $R^a$ is hydrogen and $C_{1-6}$alkyl; is preferably hydrogen. In a preferred embodiment, $L^4$ is *—$C(O)NR^aSO_2$—**, wherein $R^a$ is hydrogen and $C_{1-6}$alkyl; is preferably hydrogen, wherein * refers to the position attached to Ring C, and ** refers to the position attached to Ring D.

In one embodiment, $R^4$ is —$NO_2$, F, Cl, Br, cyano, or —$SO_2R^{4a}$, wherein $R^{4a}$ is defined as with Formula (I). In one embodiment, $R^4$ is —$NO_2$, F, Cl, Br, cyano, or —$SO_2R^{4a}$, wherein $R^{4a}$ is —$C_{1-8}$alkyl optionally substituted with halogen, preferably —$CF_3$. In a preferred embodiment, $R^4$ is —$NO_2$.

In one embodiment, ring A is cycloalkyl, cycloalkenyl, aryl, heterocyclyl, or heteroaryl, each of which is optionally substituted with 1 to 4 substituents $R^2$. Preferably, $R^2$ is hydrogen, halogen (e.g., F, Cl or Br) or $C_{1-6}$alkyl (e.g., methyl) optionally substituted with halogen (e.g., F, Cl or Br).

In a preferred embodiment, ring A is a phenyl ring, which is 1,2-phenylene, 1,3-phenylne, or 1,4-phenylene.

In a preferred embodiment, ring A is a cycloalkyl ring which is $C_{3-8}$-cycloalkyl. In a more preferred embodiment, ring A is selected from cyclobutyl, cyclopentyl, cyclohexyl, or cycloheptyl. Specifically, ring A is 1,2-cyclobutylene, 1,3-cyclobutylene, 1,2-cyclopentylene, 1,3-cyclopentylene, 1,2-cyclohexylene, 1,3-cyclohexylene, 1,4-cyclohexylene, 1,2-cycloheptylene, 1,3-cycloheptylene or 1,4-cycloheptylene.

In a preferred embodiment, ring A is $C_{3-8}$-cycloalkenyl. Preferably, ring A is cyclohexenyl. More preferably, ring A is cyclohex-3-enyl or cyclohex-2-enyl.

In a preferred embodiment, ring A is heteroaryl. Preferably, ring A is a monocyclic 5- or 6-membered heteroaryl comprising one or two or three or four heteroatoms selected from nitrogen, oxygen, and sulfur. Specifically, ring A is pyridine, pyrazole, thiophene, or pyrimidine. Preferably, ring A is 8- to 12-membered bicyclic heteroaryl ring. Specifically, ring A is pyrazolopyrimidine (e.g., pyrazolo[1,5-a]pyrimidine), benzothiophene (benzo[b]thiophene), or pyrazolopyridine (e.g., pyrazolo[1,5-a]pyridine) group.

In a preferred embodiment, ring A is heterocyclyl. Preferably, ring A is selected from
a) monocyclic 4 to 9-membered heterocyclyl groups containing one or two heteroatoms selected from nitrogen or oxygen or sulfur as ring member;
b) 5 to 12-membered spiro heterocyclyl comprising one or two heteroatoms selected from nitrogen, sulfur and oxygen as ring members;

c) 5 to 12-membered fused heterocyclyl comprising one or two heteroatoms selected from nitrogen, sulfur and oxygen as ring members; and
d) 5 to 12-membered bridged heterocyclyl comprising one or two heteroatoms selected from nitrogen, sulfur and oxygen as ring members.

In a more preferred embodiment, ring A is 5 to 12-membered spiro heterocyclyl comprising one or two heteroatoms selected from nitrogen, sulfur and oxygen as ring members. Specifically, ring A is 4-membered/4-membered, 3-membered/5-membered, 4-membered/5-membered, 4-membered/6-membered, 5-membered/5-membered, or 5-membered/6-membered mono-spiro heterocyclyl comprising one or two nitrogen or oxygen as ring members. Specifically, ring A is 4-membered/4-membered or 4-membered/6-membered mono-spiro heterocyclyl comprising one nitrogen as ring member. More specifically, ring A is

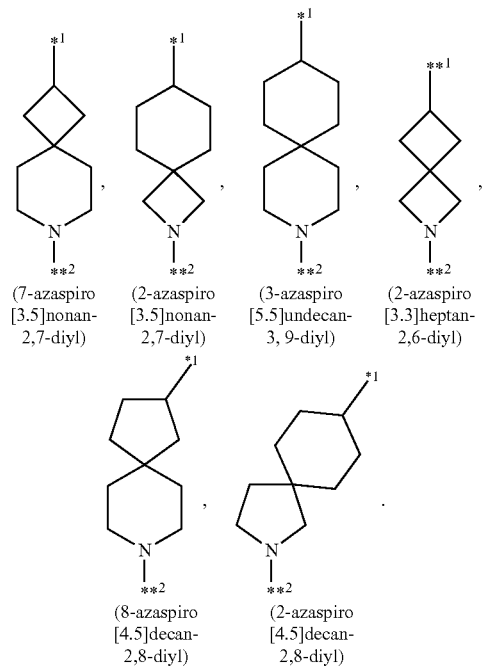

(7-azaspiro [3.5]nonan-2,7-diyl), (2-azaspiro [3.5]nonan-2,7-diyl), (3-azaspiro [5.5]undecan-3,9-diyl), (2-azaspiro [3.3]heptan-2,6-diyl), (8-azaspiro [4.5]decan-2,8-diyl), (2-azaspiro [4.5]decan-2,8-diyl).

Specifically, ring A is heterocyclic which is piperidine, pyrrolidine, and azetidine; 7-azaspiro[3.5]nonane, 2-azaspiro[3.5]nonane, 8-azabicyclo[3.2.1]octane; tetrahydrothienopyridine (e.g., 4,5,6,7-tetrahydrothieno[2,3-c]pyridine), tetrahydropyrrolopyrazine (e.g., 1,2,3,4-tetrahydropyrrolo[1,2-a]pyrazine), tetrahydropyrrolopyrazine (e.g., 1,2,3,4-tetrahydropyrrolo[1,2-a]pyrazine), hexahydroindolizine (e.g., 1,2,3,5,8,8a-hexahydroindolizine), dihydropyrrolothiazole (e.g., 5,6-dihydro-4H-pyrrolo[3,4-d]thiazole), or isoindoline.

In an even preferred embodiment, ring A is selected from the group consisting of:

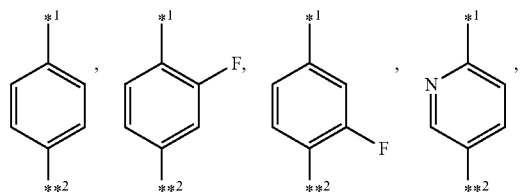

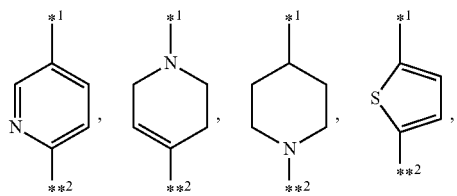

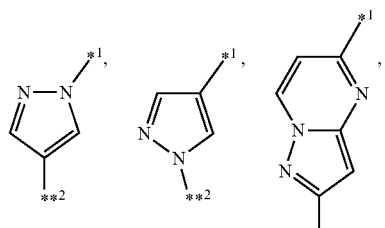

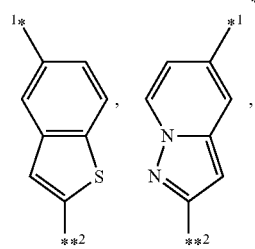

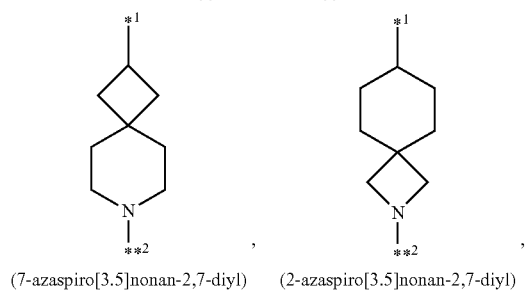

(7-azaspiro[3.5]nonan-2,7-diyl), (2-azaspiro[3.5]nonan-2,7-diyl)

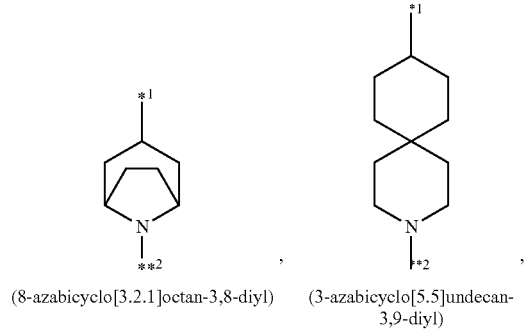

(8-azabicyclo[3.2.1]octan-3,8-diyl), (3-azabicyclo[5.5]undecan-3,9-diyl)

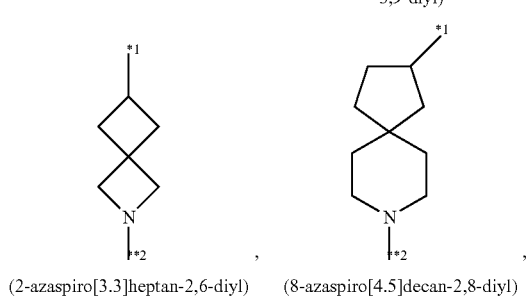

(2-azaspiro[3.3]heptan-2,6-diyl), (8-azaspiro[4.5]decan-2,8-diyl)

11

-continued

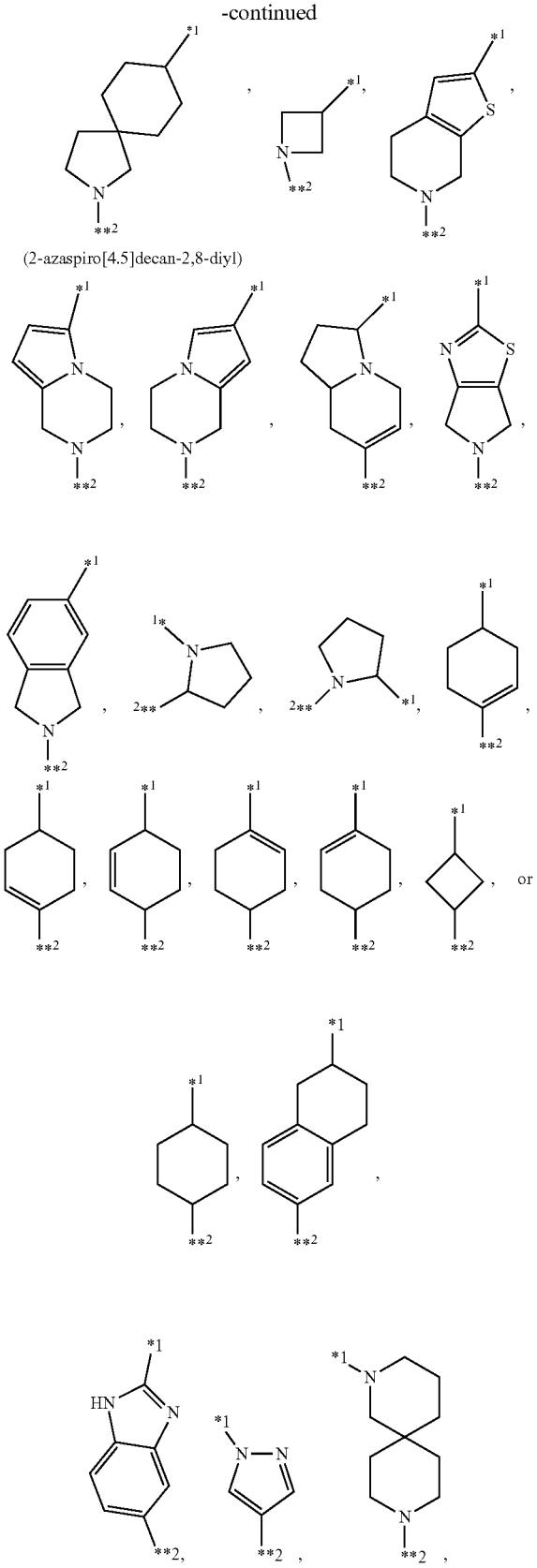

(2-azaspiro[4.5]decan-2,8-diyl)

wherein *1 refers to the position attached to L¹, and **2 refers to the position attached to L².

12

In a most preferred embodiment, ring A is

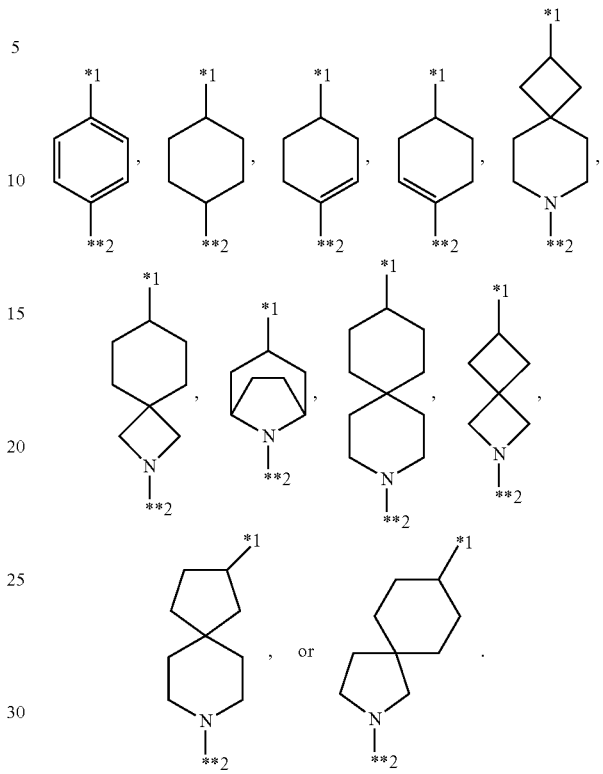

In one embodiment, Ring B is cycloalkyl, cycloalkenyl, aryl, or heterocyclyl, each of which is optionally substituted with 1 to 4 substituents $R^1$;

$R^1$, at each occurrence, is independently selected from the group consisting of halogen, $—C_{1-8}$alkyl, $—C_{2-8}$alkenyl, $—C_{2-8}$alkynyl, cycloalkyl, aryl, heteroaryl, oxo, —CN, or $—OR^{1a}$; wherein said $—C_{1-8}$alkyl, $—C_{2-8}$alkenyl, $—C_{2-8}$alkynyl, aryl or heteroaryl are each independently optionally substituted with 1 to 4 substituents $R^{1d}$;

$R^{1a}$ is hydrogen, or $—C_{1-8}$alkyl, said $—C_{1-8}$alkyl is optionally substituted with halogen, hydroxy or $—C_{1-8}$alkyoxy;

$R^{1d}$, at each occurrence, is independently halogen, $—C_{1-8}$alkyl, $—C_{2-8}$alkenyl, $—C_{2-8}$alkynyl, cycloalkyl, heterocyclyl, aryl, heteroaryl, —CN, $—OR^{Ba}$, $—SO_2R^{Ba}$, $—CONR^{Ba}R^{Bb}$, $—NR^{Ba}R^{Bb}$, $—NR^{Ba}COR^{Bd}$, or $—NR^{Ba}SO_2R^{Bb}$; wherein said $—C_{1-8}$alkyl, cycloalkyl, heterocyclyl, aryl or heteroaryl are each independently optionally substituted with 1 to 4 substituents $R^{Bd}$;

$R^{Ba}$ and $R^{Bb}$ are each independently hydrogen, $—C_{1-8}$ alkyl, cycloalkyl, or aryl, each of said $—C_{1-8}$ alkyl, cycloalkyl, or aryl is optionally substituted with halogen, hydroxy, $—C_{1-8}$alkyoxy, cycloalkyl, heterocyclyl, aryl, or heteroaryl; $R^{Bd}$, at each occurrence, is independently hydrogen, halogen, —CN, $—C_{1-8}$alkyl, $—C_{2-8}$alkynyl, cycloalkyl, or aryl, each of said $C_{1-8}$alkyl, $—C_{2-8}$alkynyl, or aryl is optionally substituted with halogen, hydroxy, $—C_{1-8}$alkyoxy, cycloalkyl, heterocyclyl, aryl, or heteroaryl.

In one embodiment, cycloalkyl as Ring B is monocyclic $C_{3-8}$-cycloalkyl, preferably cyclopentyl or cyclohexyl, substituted with $R^1$. In one embodiment, $R^1$ is an aryl group (e.g., phenyl) optionally substituted with $R^{1d}$ which is monocyclic $C_{3-8}$-cycloalkyl.

In one embodiment, cycloalkenyl as Ring B is monocyclic $C_{3-8}$-cycloalkenyl, preferably cyclopentenyl or cyclohexenyl, substituted with one or two or three $R^1$. In one embodiment, $R^1$ is $C_{1-8}$alkyl (e.g., $C_{1-6}$alkyl, preferably methyl), or an aryl group (e.g., phenyl) optionally substituted with $R^{id}$ which halogen.

In one embodiment, heterocyclyl as ring B is monocyclic 4 to 9-membered heterocyclyl, a 5 to 20-membered spiro heterocyclyl, a 5 to 20-membered fused heterocyclyl, or a 5 to 20-membered bridged heterocyclyl, each of which is optionally substituted with 1 to 4 substituents $R^1$.

In one embodiment, monocyclic heterocyclyl is a monocyclic 4 to 9-membered heterocyclyl comprising one or more heteroatoms selected from the group consisting of NH, O, S, SO or $SO_2$ heteroatoms as ring members.

In one embodiment, monocyclic heterocyclyl is a monocyclic 4 to 9-membered heterocyclyl comprising one nitrogen atom as the ring member. In a preferred embodiment, the monocyclic 4 to 9-membered heterocyclyl comprising one nitrogen atom as the ring member is C-linked or N-linked. In an even preferred embodiment, the monocyclic 4 to 9-membered heterocyclyl comprising one nitrogen atom as the ring member is saturated. Specifically, the saturated heterocyclyl is a N-linked saturated heterocyclyl, including, but not limited to aziridin-1-yl, azetidin-1-yl, pyrrolidin-1-yl, piperidin-1-yl, azepan-1-yl, and azocan-1-yl, preferably pyrrolidin-1-yl. Specifically, the saturated heterocyclyl is a C-linked saturated heterocyclyl, Including but not limited to aziridin-2-yl, azetidin-2-yl, azetidin-3-yl, pyrrolidin-2-yl, pyrrolidin-3-yl, piperidin-2-yl, piperidin-3-yl, piperidin-4-yl, azepan-2-yl, azepan-3-yl, azepan-4-yl, azocan-2-yl, azocan-3-yl, azocan-4-yl, and azocan-5-yl. In another even preferred embodiment, the monocyclic 4 to 9-membered heterocyclyl comprising one nitrogen atom as the ring member is unsaturated. In a yet even preferred embodiment, the monocyclic 4 to 9-membered heterocyclyl comprising one nitrogen atom as the ring member contains one carbon-carbon double bond. Specifically, the monocyclic 4 to 9-membered heterocyclyl comprising one nitrogen atom as the ring member is dihydropyrrolyl, e.g., 2,3-dihydro-1H-pyrrolyl and 2,5-dihydro-1H-pyrrolyl, or tetrahydropyridinyl.

In another embodiment, monocyclic heterocyclyl is a monocyclic 4 to 9-membered heterocyclyl comprising one nitrogen atom and one additional heteroatom selected from the group consisting of NH, O, S, SO or $SO_2$ heteroatoms as ring members. In a preferred embodiment, the monocyclic 4 to 9-membered heterocyclyl comprising one nitrogen atom and one additional heteroatom selected from the group consisting of NH, O, S, SO or $SO_2$ heteroatoms as ring members is C-linked or N-linked. In an even preferred embodiment, the monocyclic heterocyclyl is saturated. In a yet even preferred embodiment, the saturated monocyclic heterocyclyl is N-linked. In another yet even preferred embodiment, the saturated monocyclic heterocyclyl is C-linked.

In a preferred embodiment, ring B is pyrrolidin-1-yl substituted with 1 to 4 substituents $R^1$.

In one embodiment, $R^1$ is a phenyl group.

In a more preferred embodiment, ring B is aziridin-1-yl, azetidin-1-yl, pyrrolidin-1-yl, pyrrolidin-2-yl, piperidin-1-yl, azepan-1-yl, or azocan-1-yl, preferably pyrrolidin-1-yl which is substituted with a phenyl group at position 2 and further optionally substituted with 1 or 2 or 3 substituents $R^1$ on the pyrrolidinyl ring, and said phenyl group at position 2 is optionally substituted with $R^{1d}$ as defined with Formula (I).

In one aspect of this embodiment, $R^1$, at each occurrence, is independently selected from the group consisting of halogen, —$C_{1-8}$alkyl, —$C_{2-8}$alkenyl, —$C_{2-8}$alkynyl, cycloalkyl, aryl, heteroaryl, oxo, —CN, or $OR^{1a}$; wherein said —$C_{1-8}$alkyl, —$C_{2-8}$alkenyl, —$C_{2-8}$alkynyl, cycloalkyl, aryl, or heteroaryl is optionally substituted with 1 to 4 substituents $R^{id}$, wherein $R^{1a}$ is hydrogen or $C_{1-8}$alkyl, preferably methyl, and $R^{id}$ is halogen, —$C_{1-8}$alkyl, or —$OR^{Ba}$, wherein $R^{Ba}$ is hydrogen or —$C_{1-8}$alkyl. In another aspect, $R^1$ is heteroaryl, preferably furanyl, more preferably furan-3-yl. In some embodiment, $R^1$ is substituted at position 2 of the monocyclic heterocyclyl.

In one aspect of this embodiment, $R^{1d}$, when substituted on the phenyl group at position 2 of ring B (including the aziridin-1-yl, azetidin-1-yl, pyrrolidin-1-yl, pyrrolidin-2-yl, piperidin-1-yl, azepan-1-yl, or azocan-1-yl, preferably the pyrrolidin-1-yl group), is independently halogen, —$C_{1-8}$alkyl, —$C_{2-8}$alkenyl, —$C_{2-8}$alkynyl, cycloalkyl, heterocyclyl, aryl, heteroaryl, —CN, —$OR^{Ba}$, —$SO_2R^{Ba}$, —$CONR^{Ba}R^{Bb}$, —$NO_2$, —$NR^{Ba}R^{Bb}$, —$NR^{Ba}COR^{Bb}$, or —$NR^{Ba}SO_2R^{Bb}$; wherein said —$C_{1-8}$alkyl, —$C_{2-8}$alkenyl, —$C_{2-8}$alkynyl, cycloalkyl, heterocyclyl, aryl or heteroaryl are each independently optionally substituted with 1 to 4 substituents $R^{Bd}$ as defined with Formula (I), preferably 1 or 2 substituents $R^{Ba}$ as defined with Formula (I). In another aspect, one $R^{1a}$ is at position 2 of the phenyl ring at position 2 of ring B.

In one aspect, —$C_{1-8}$alkyl as $R^{1d}$ is further optionally substituted with 1 to 4 substituents $R^{Bd}$, which is halogen, phenyl, cycloalkyl (e.g., $C_{3-8}$-cycloalkyl, preferably cyclopropyl), heterocyclyl (e.g., piperazinyl, piperidinyl) optionally substituted with $C_{1-6}$alkyl, Specifically, $R^{1d}$ is —$C_{1-8}$alkyl selected from methyl, ethyl, isopropyl, propyl, tert-butyl, and isobutyl, optionally substituted with $R^{Bd}$. In another aspect, two methyl groups are at position 2 of the phenyl ring at position 2 of ring B.

In one aspect, cycloalkyl as $R^{1d}$ is further optionally substituted with 1 to 4 substituents $R^{Bd}$, which is halogen, cyano, $C_{2-8}$alkynyl (preferably ethynyl), or $C_{1-8}$alkyl optionally substituted with halogen (preferably $CF_3$). Specifically, $R^{1d}$ is $C_{3-8}$-cycloalkyl selected from cyclopropyl, cyclobutyl, cyclopentyl, or cyclohexyl, optionally substituted with $R^{Bd}$. In another aspect, one cyclopropyl is at position 2 of the phenyl ring at position 2 of ring B.

In one aspect, —$C_{2-8}$alkenyl as $R^{1d}$ is prop-1-en-2-yl.

In one aspect, —$C_{2-8}$alkynyl as $R^{1d}$ is ethynyl.

In one aspect, in the definition of —$OR^{Ba}$ as $R^{1d}$, $R^{Ba}$ is hydrogen, $C_{1-8}$alkyl (selected from methyl, ethyl, propyl, and isopropyl), $C_{3-8}$-cycloalkyl (preferably cyclopropyl or cyclohexyl), aryl (preferably phenyl), wherein $C_{1-8}$alkyl, $C_{3-8}$-cycloalkyl and aryl are each independently substituted with halogen, heterocyclyl (preferably monocyclic 4- to 9-membered heterocyclyl, more preferably morpholino), hydroxy, or —$C_{1-8}$alkoxyl (preferably methoxyl).

In one aspect, $R^{1d}$ is aryl which is phenyl.

In one aspect, $R^{1d}$ is heterocycle which is monocyclic 4 to 9-membered heterocyclyl groups containing one or two heteroatoms selected from nitrogen or oxygen or sulfur as ring member, preferably monocyclic 4 to 6-membered heterocyclyl comprising one oxygen atom as ring member or monocyclic 6-membered heterocyclyl comprising one or two nitrogen atoms as ring members.

In one aspect, $R^{1d}$ is heteroaryl, preferably thiophenyl or furanyl.

In one embodiment, ring B is pyrrolidin-1-yl substituted with a naphthyl group, preferably substituted with a naphthyl at position 2.

In one embodiment, ring B is pyrrolidin-1-yl substituted with a heteroaryl group, preferably substituted with a heteroaryl group at position 2. In one aspect, said heteroaryl is 5- to 6-membered heteroaryl comprising 1-4 heteroatoms selected from nitrogen, oxygen, and sulfur. Preferably, said heteroaryl is pyridinyl, furanyl, thiophenyl, or pyrazolyl. In another aspect, the heteroaryl is optionally substituted with halogen or $C_{3-8}$-cycloalkyl (preferably cyclopropyl).

In one embodiment, ring B is pyrrolidin-1-yl substituted with —$C_{1-8}$alkyl, —$C_{2-8}$alkenyl, or —$C_{2-8}$alkynyl, preferably substituted with —$C_{1-8}$alkyl, —$C_{2-8}$alkenyl, or —$C_{2-8}$alkynyl at position 2, each of said —$C_{1-8}$alkyl, —$C_{2-8}$alkenyl, or —$C_{2-8}$alkynyl is unsubstituted or substituted with a phenyl group, said phenyl group is optionally substituted with halogen or $C_{3-8}$-cycloalkyl (preferably cyclopropyl). In a preferred aspect, ring B is pyrrolidin-1-yl substituted with methyl, ethenyl, or ethynyl, each of which is optionally substituted with a phenyl group optionally substituted as above.

In a preferred embodiment, ring B is pyrrolidin-1-yl, optionally substituted with 1 to 4 substituents $R^1$ as defined with Formula (I).

In a preferred embodiment,

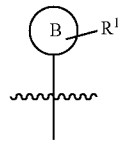

is selected from the group consisting of:

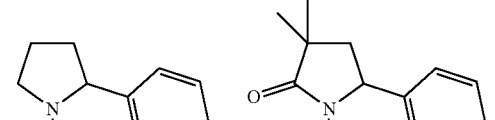

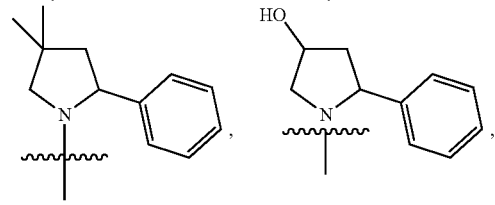

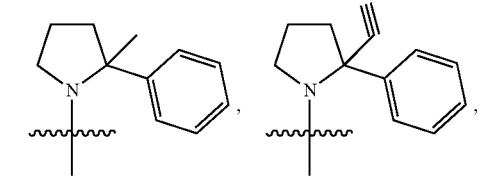

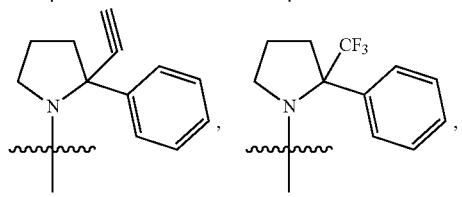

-continued

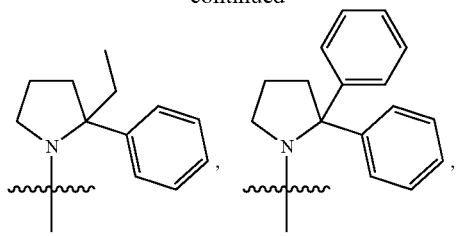

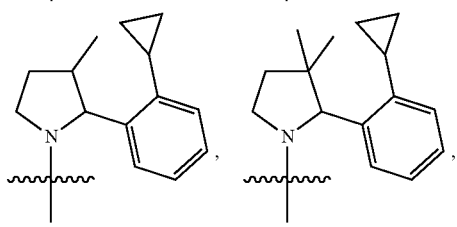

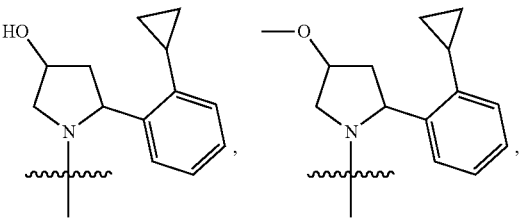

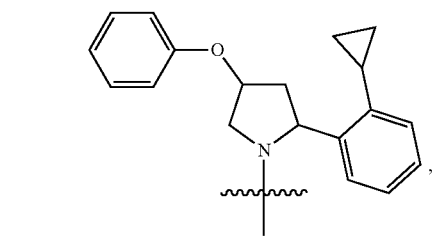

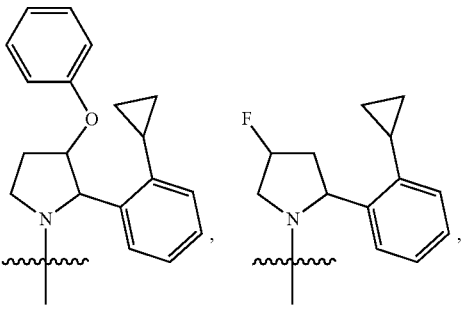

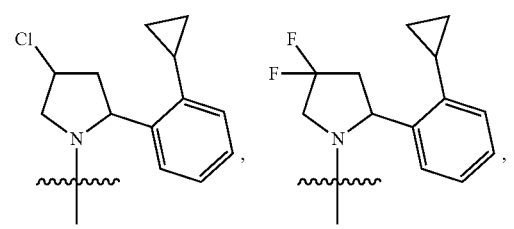

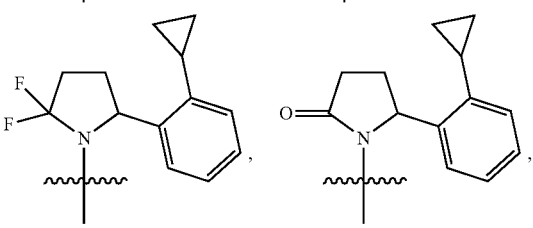

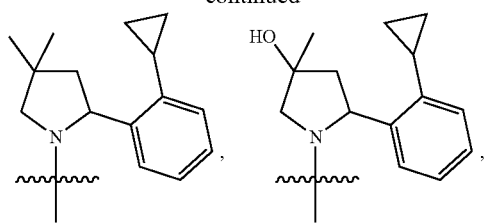
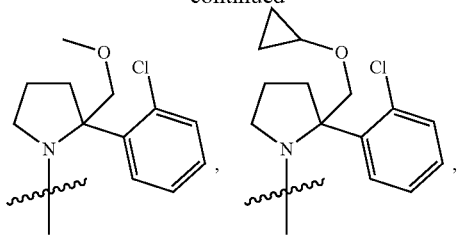
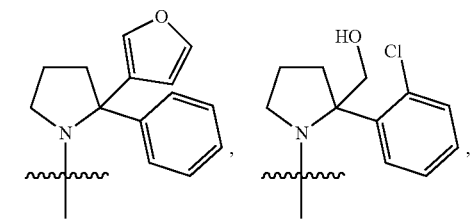
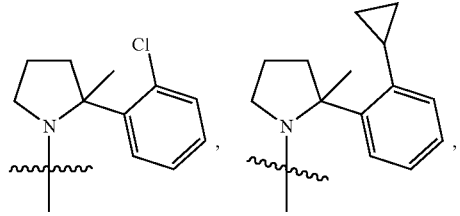
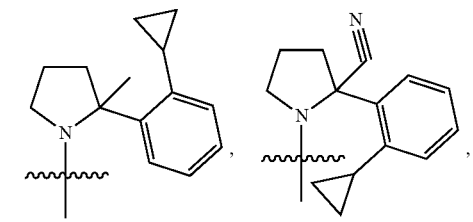
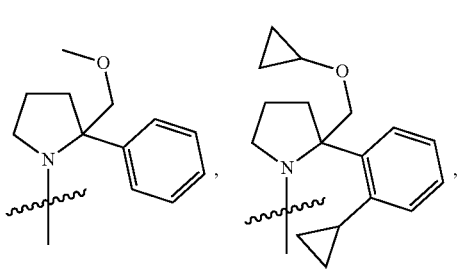
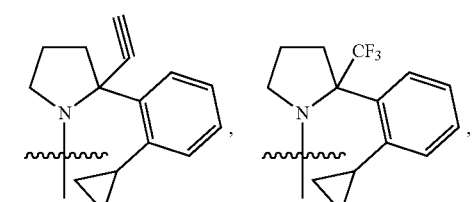
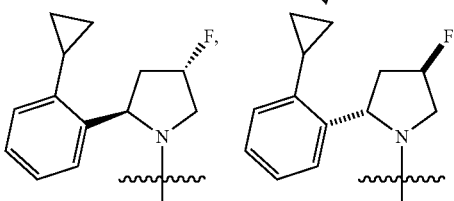
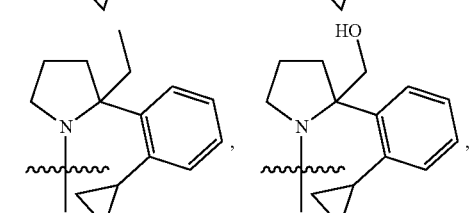
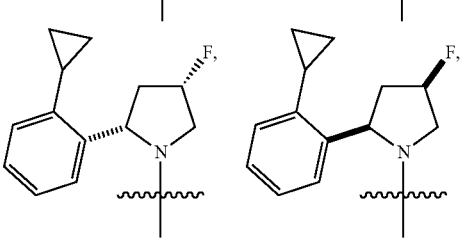
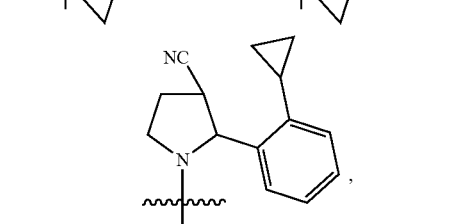
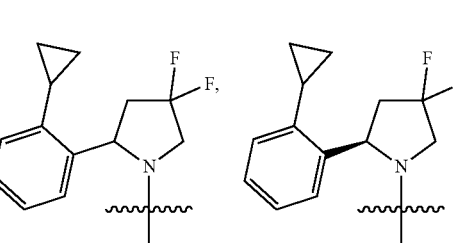
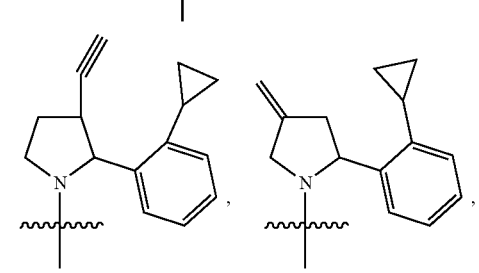
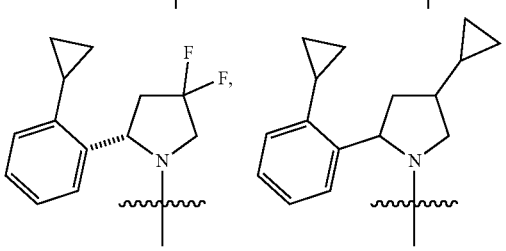

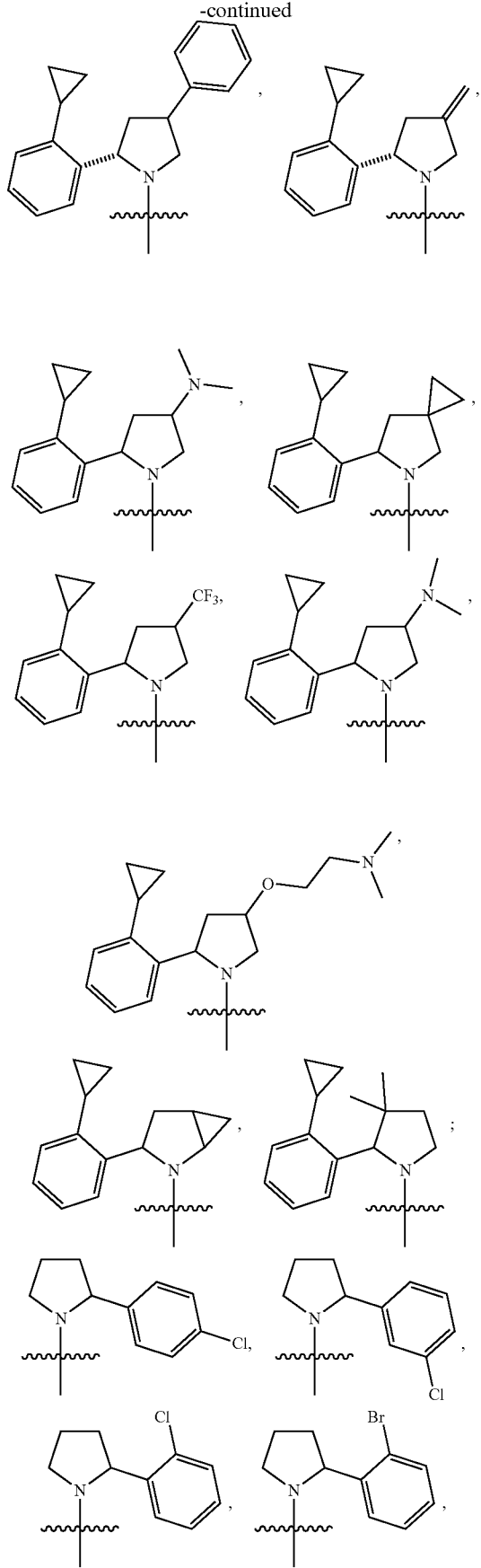
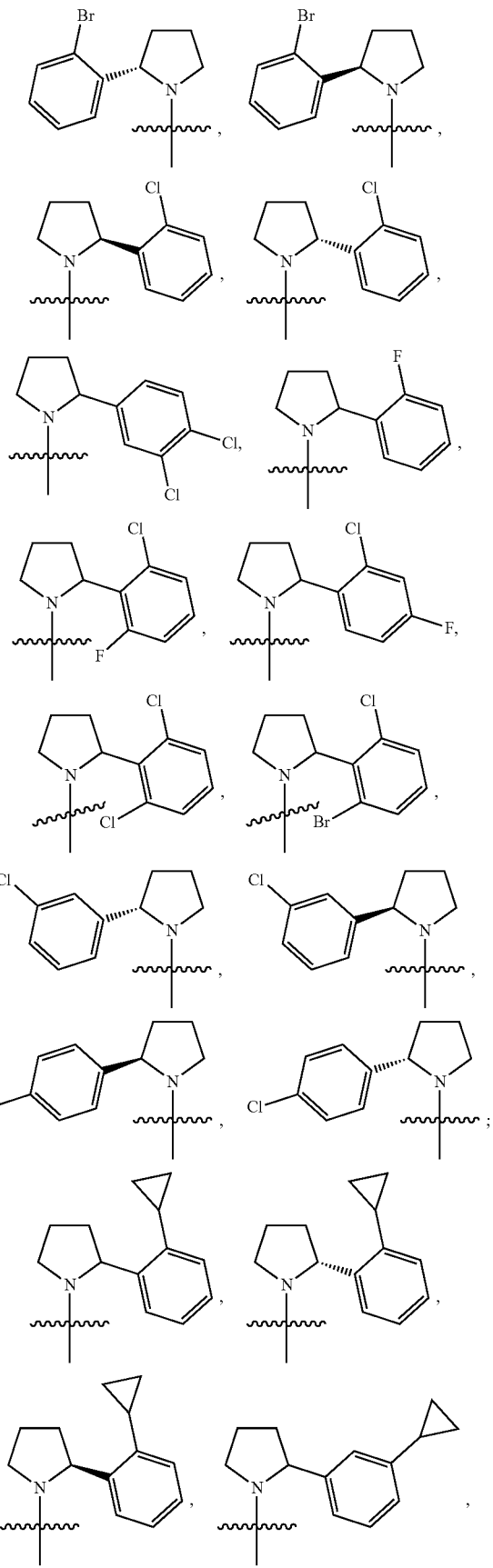

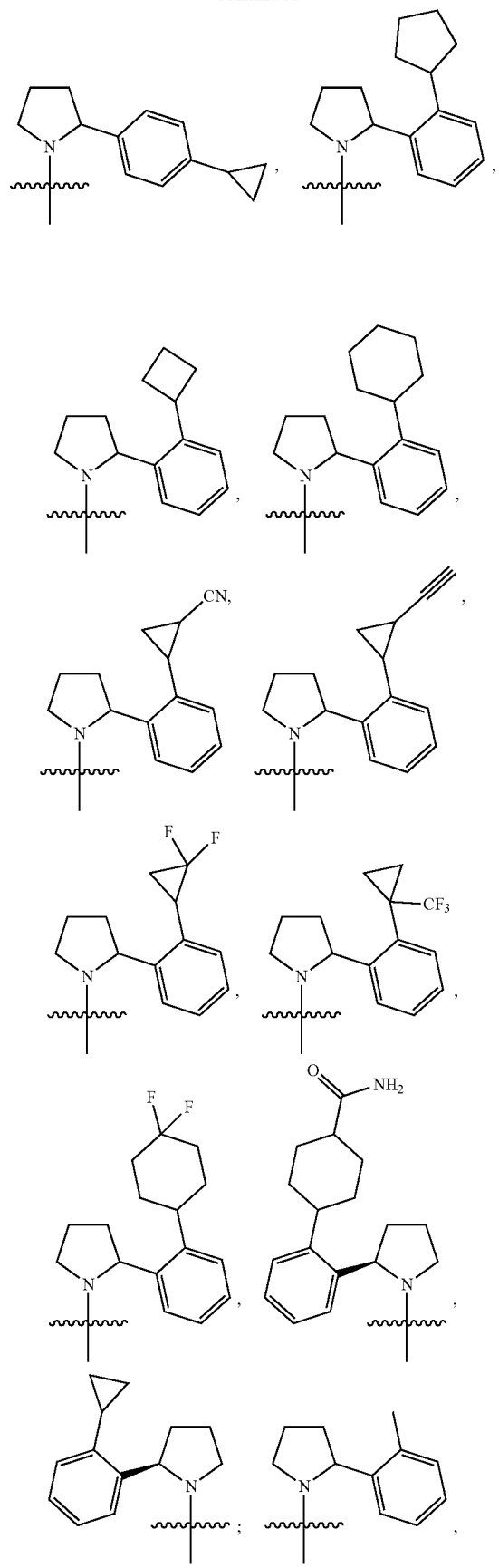
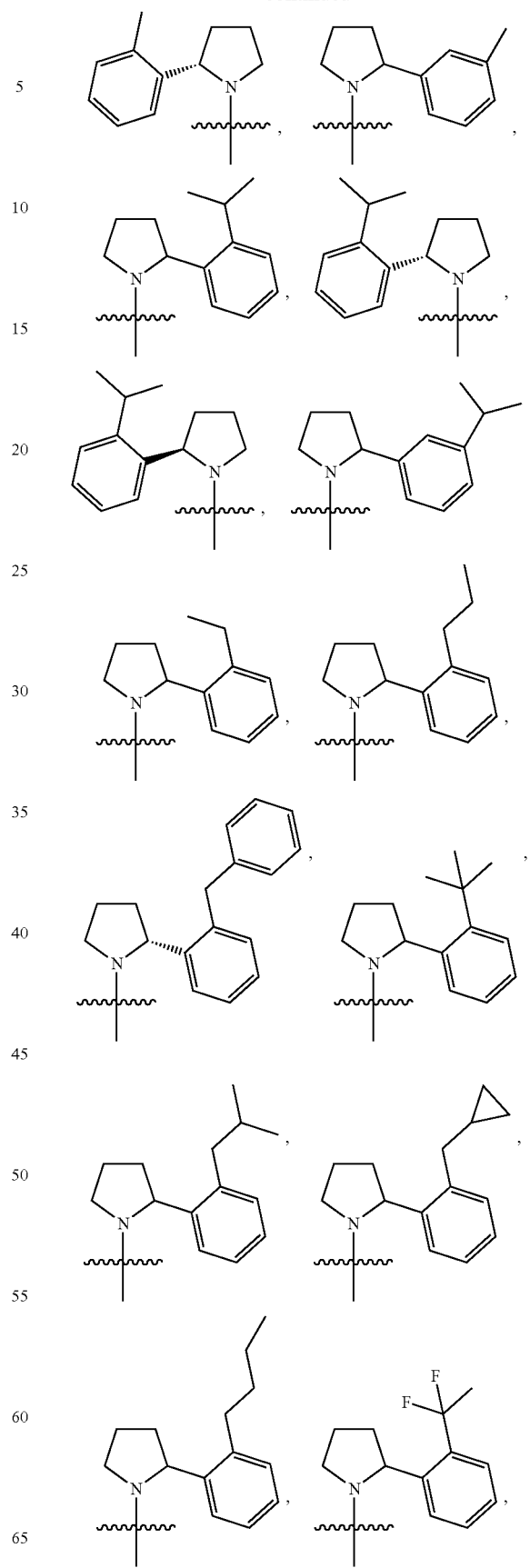

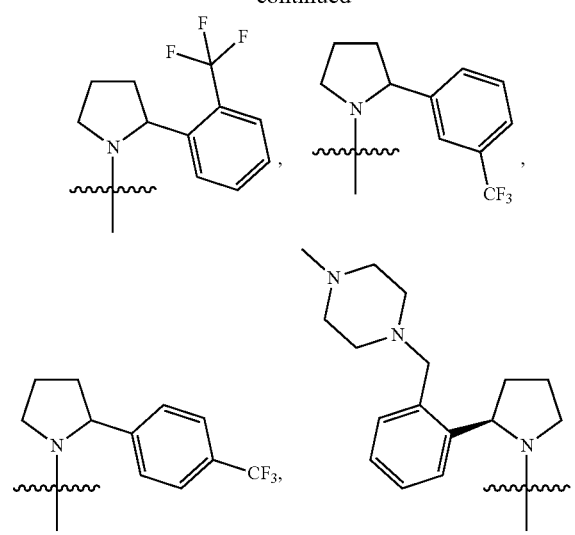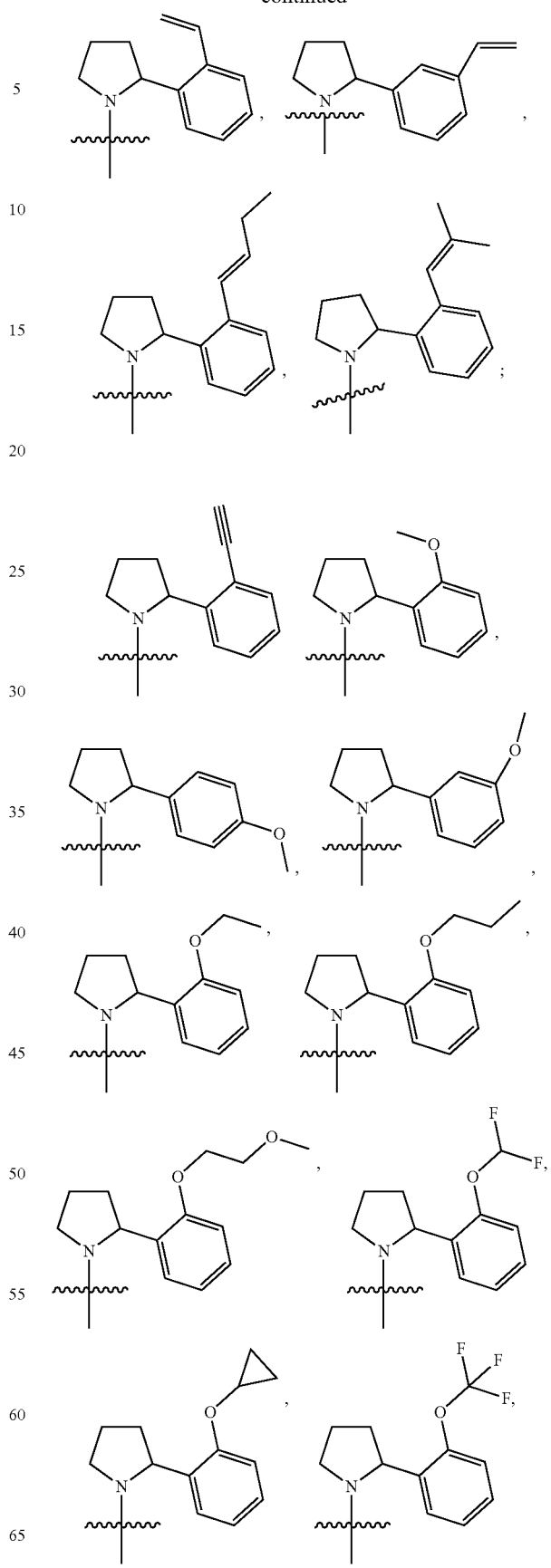

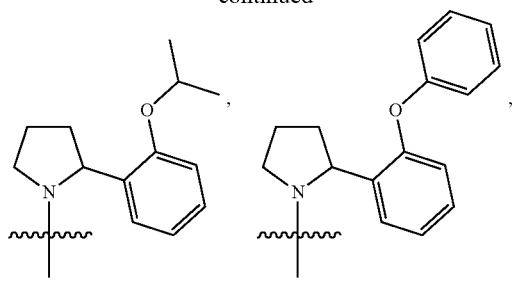
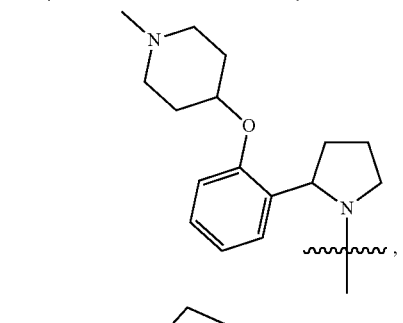
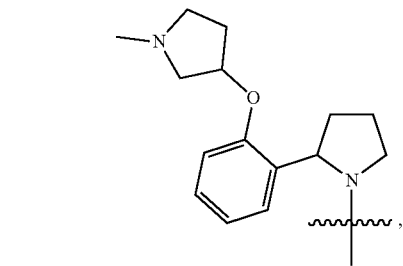
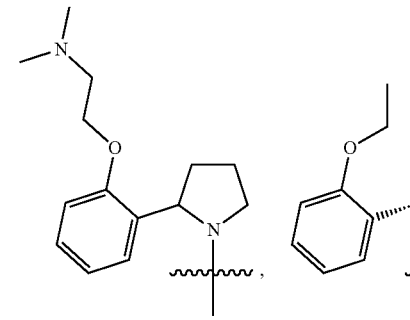
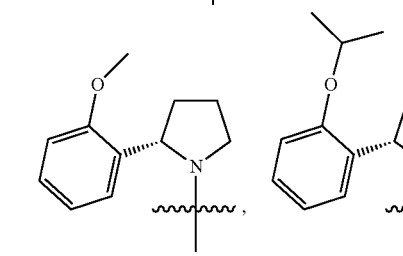
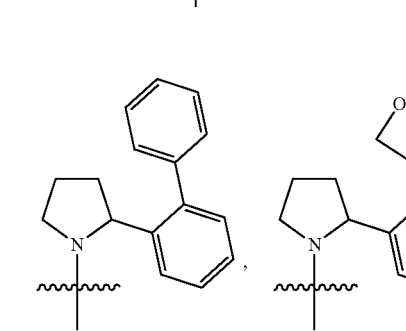
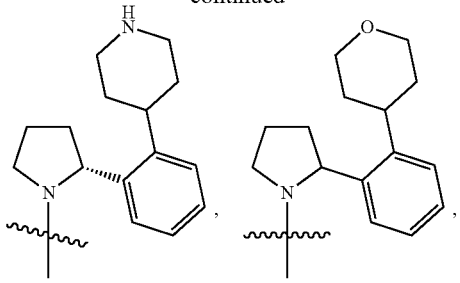
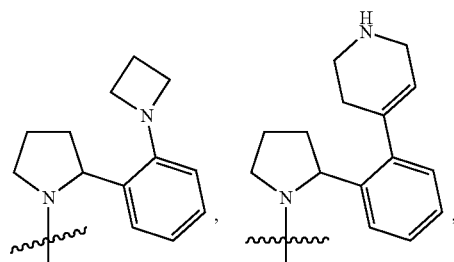
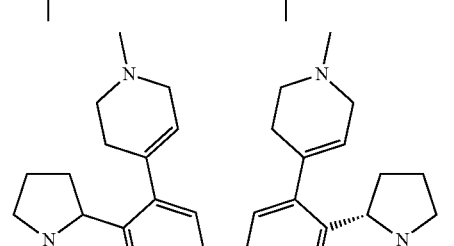
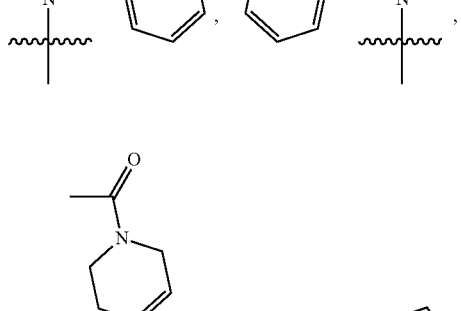
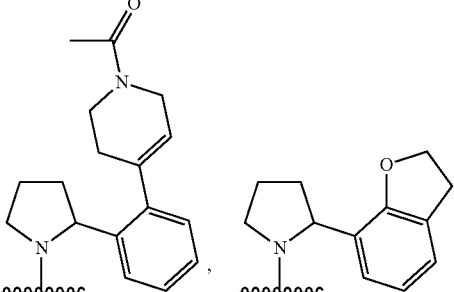
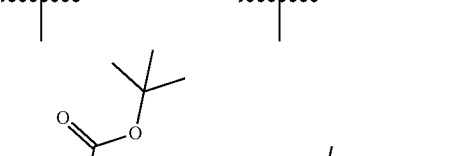
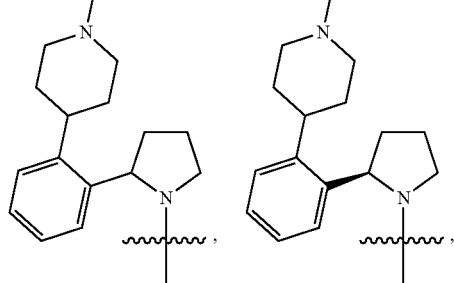

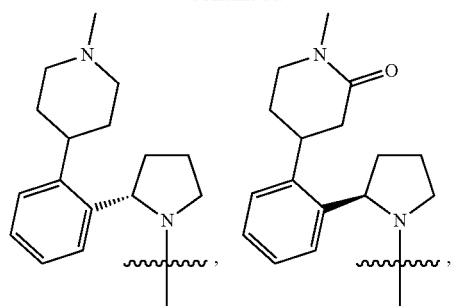
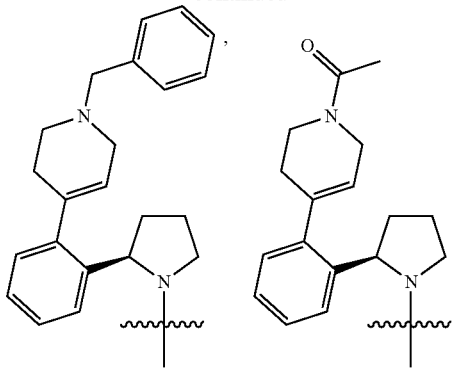
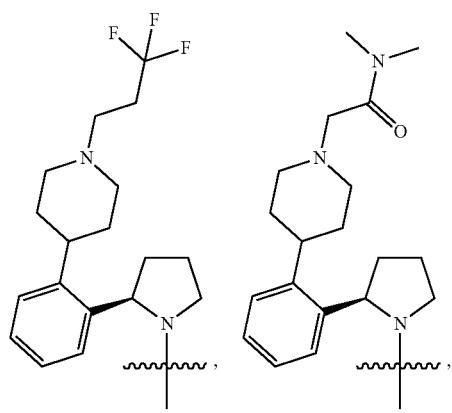
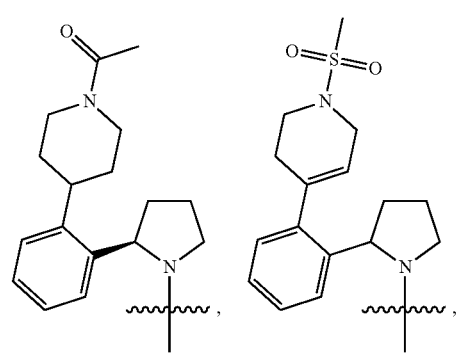
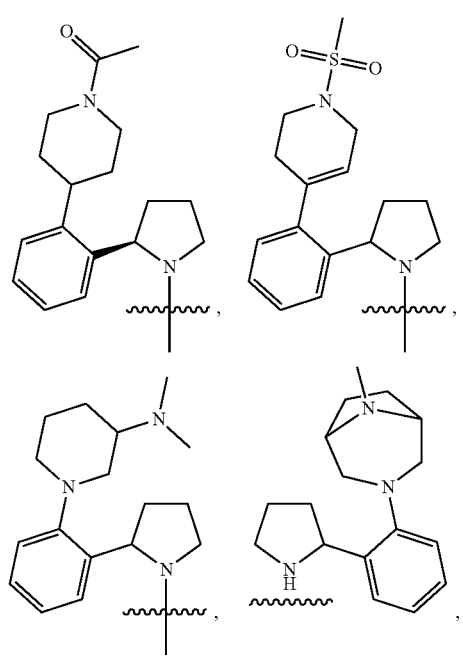
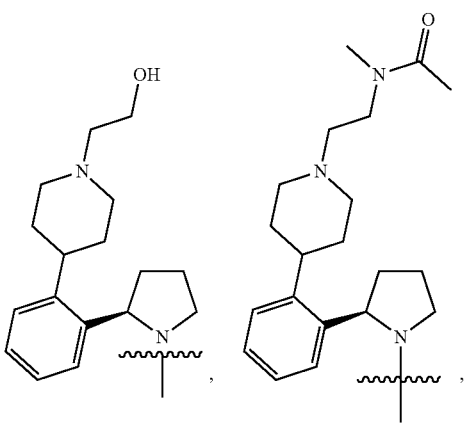
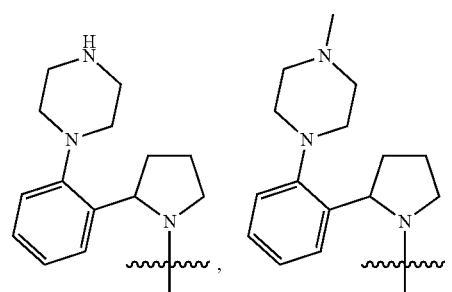
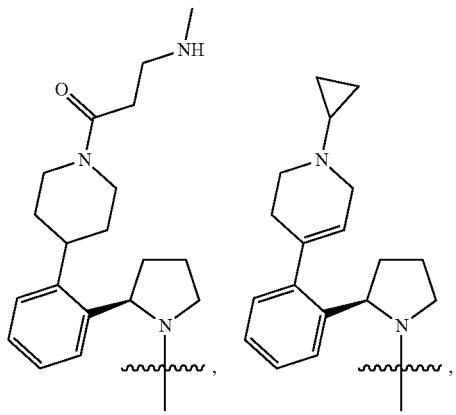
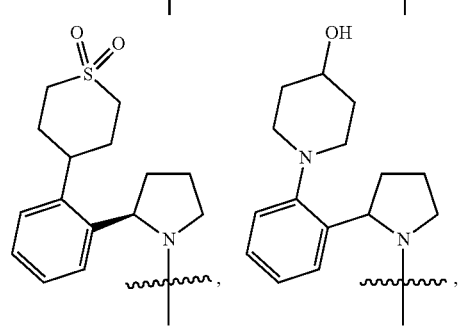

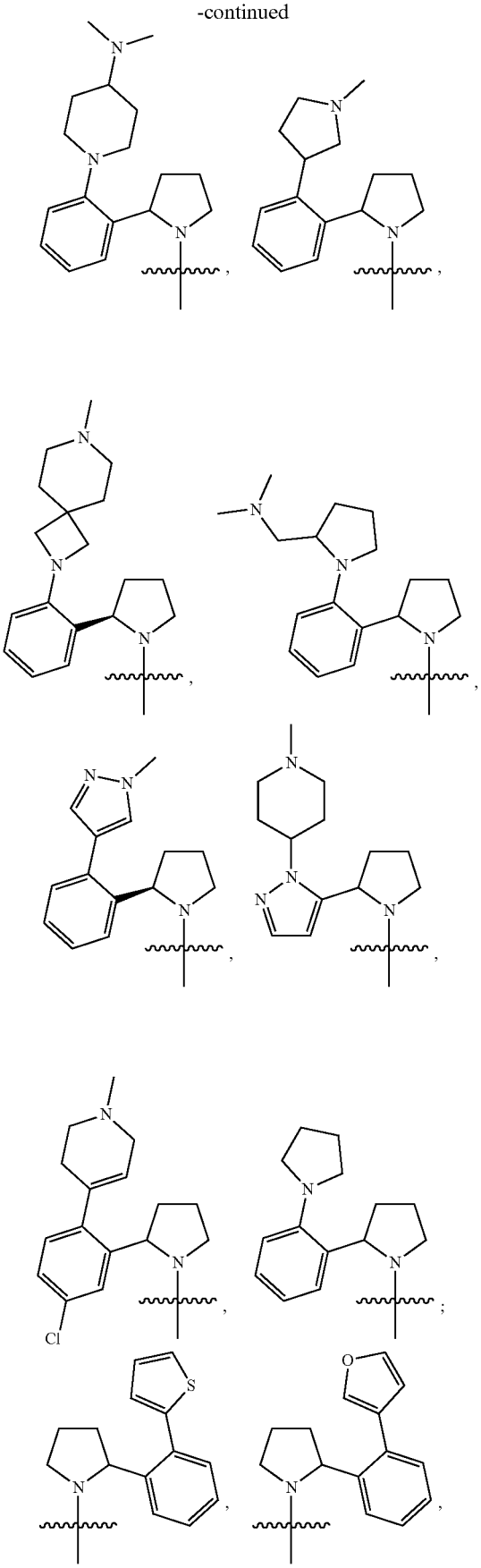
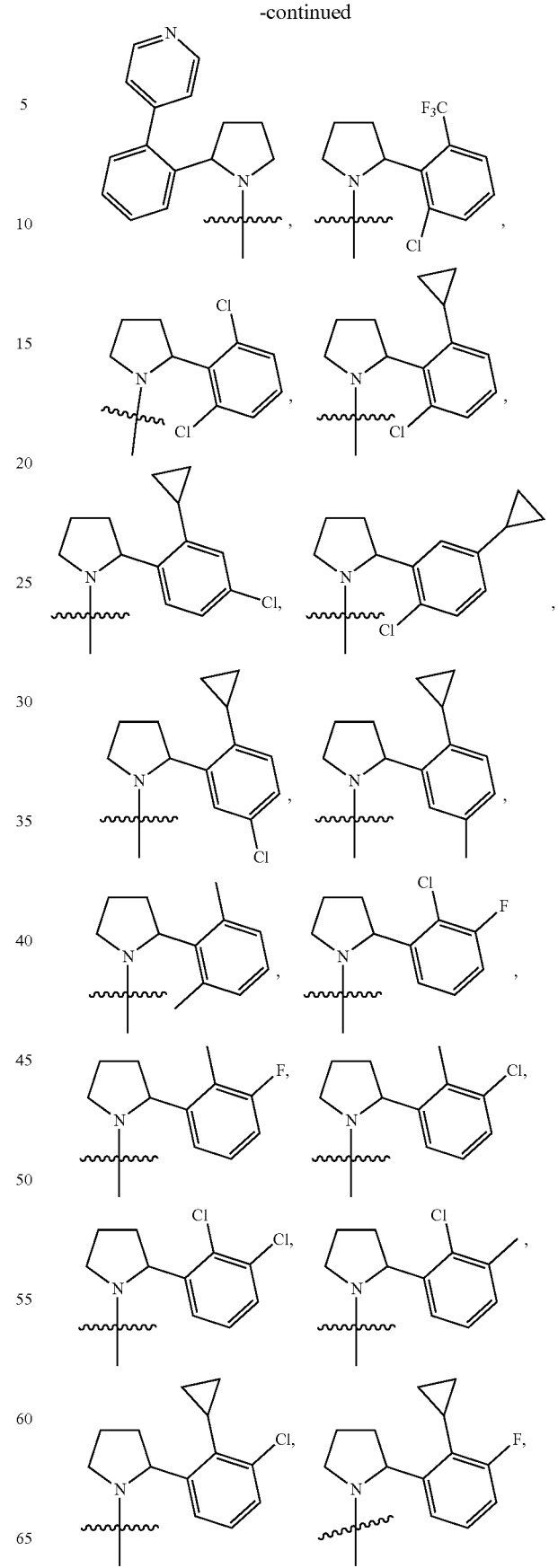

-continued

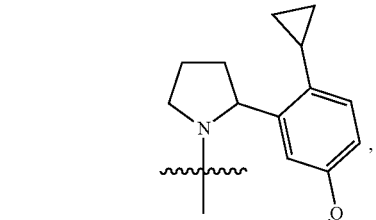
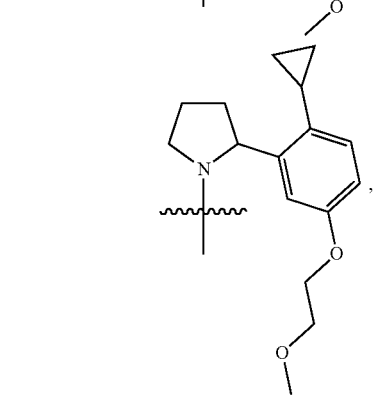
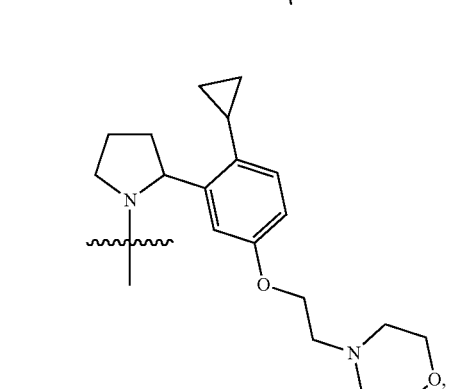
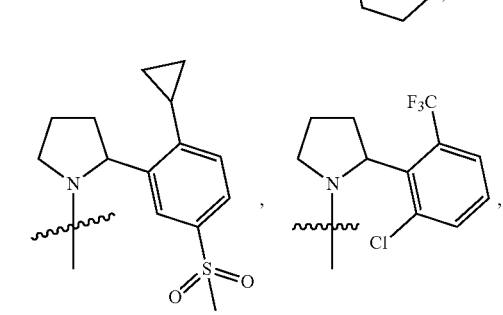
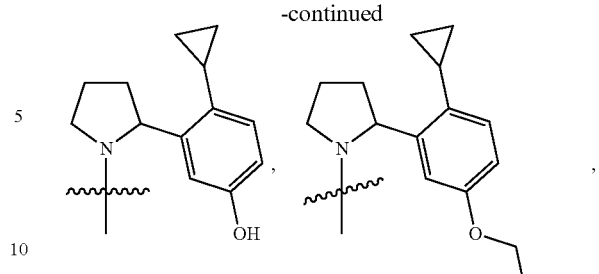
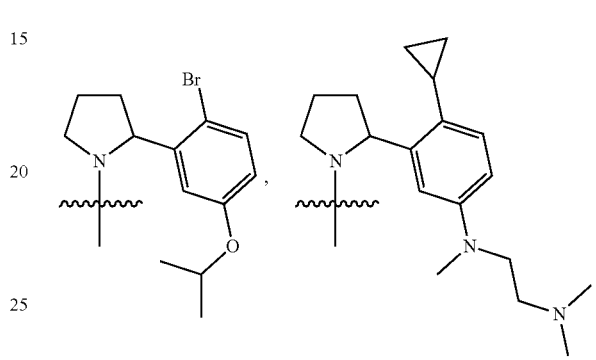
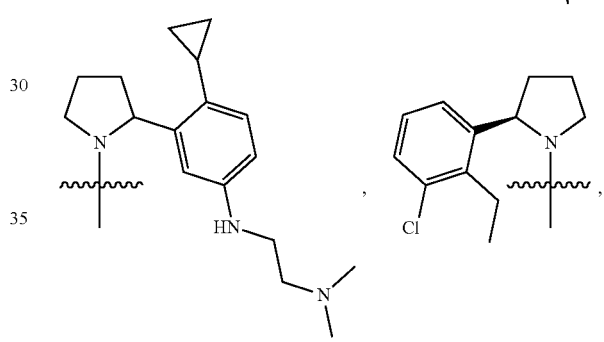
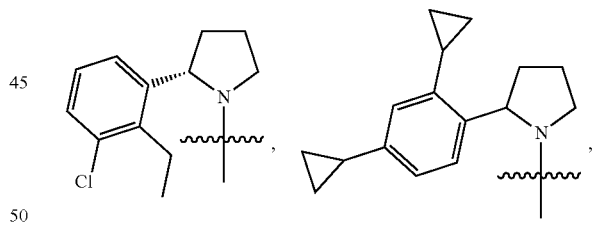
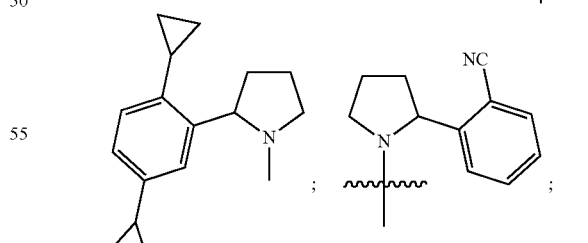
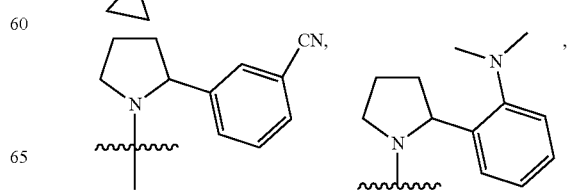

-continued
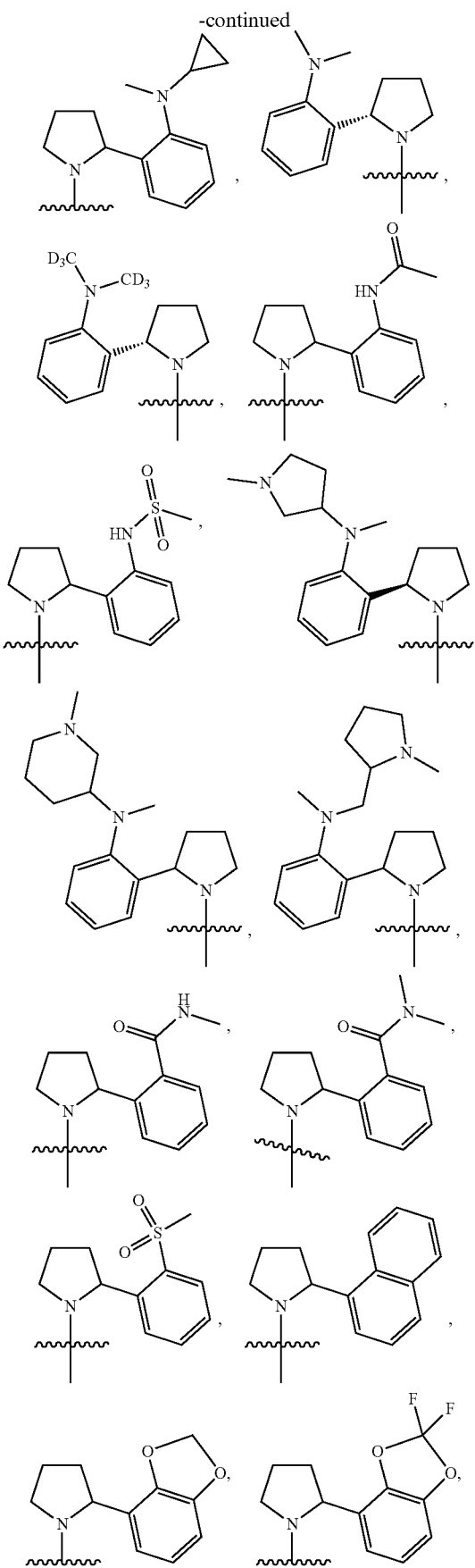
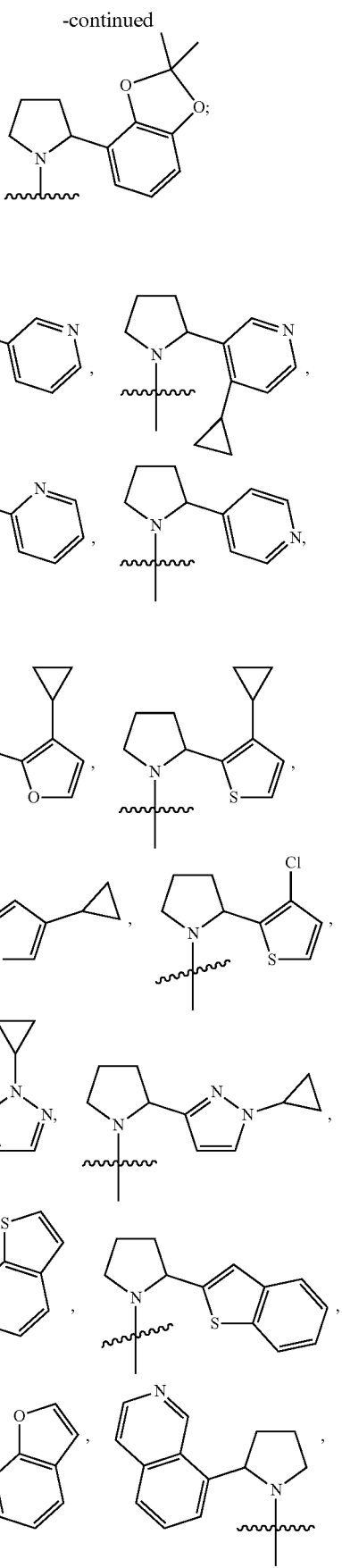

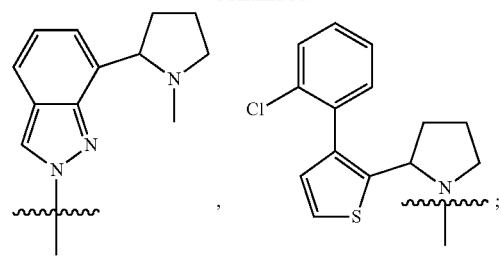
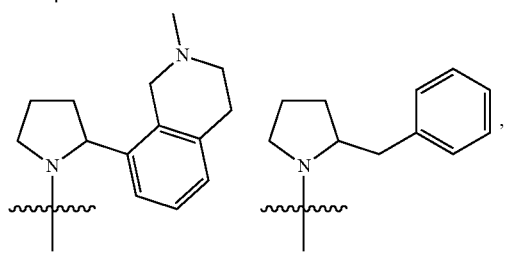
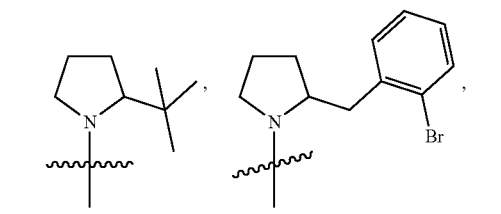
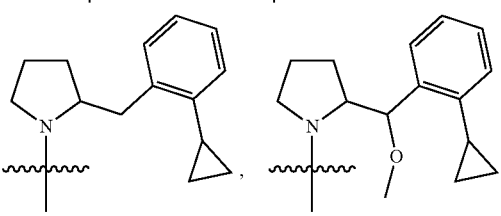
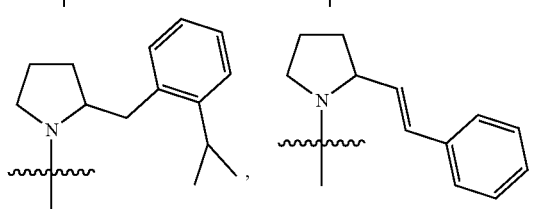
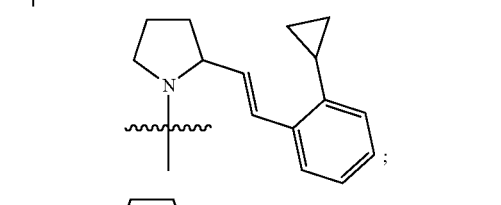
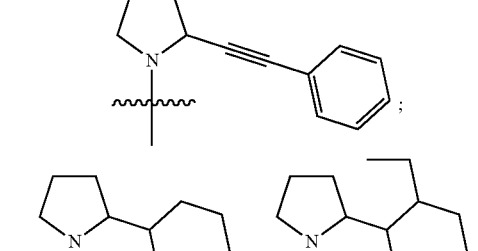
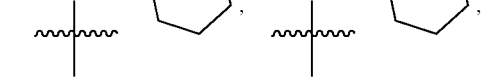
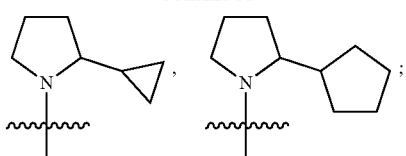
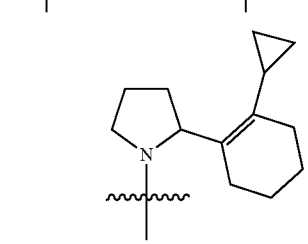
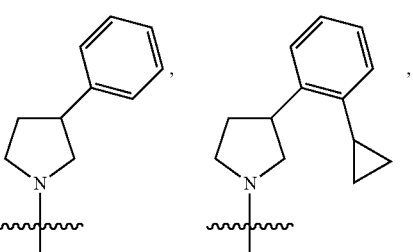
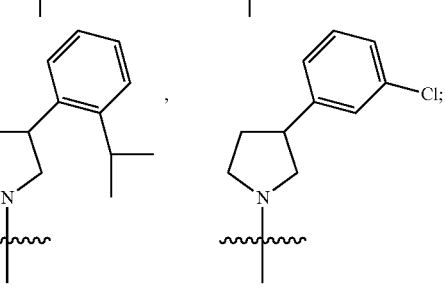
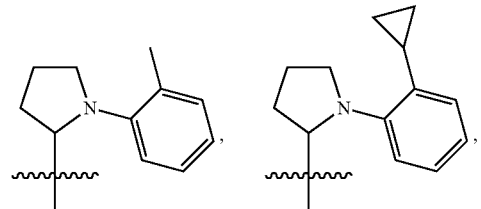
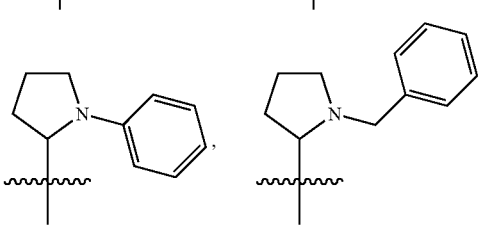
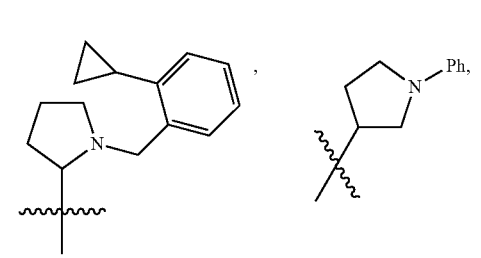

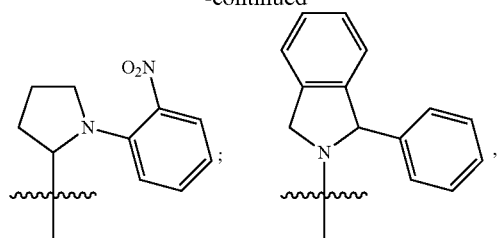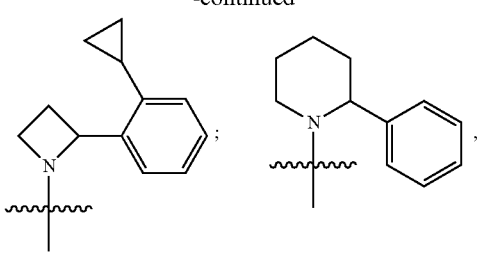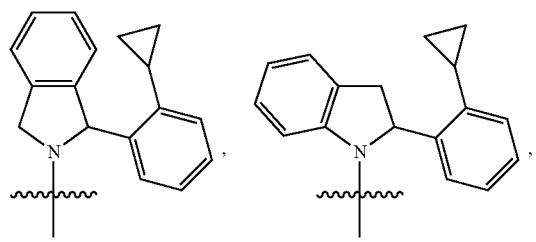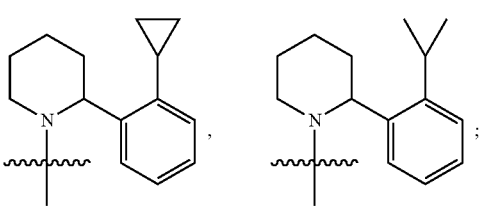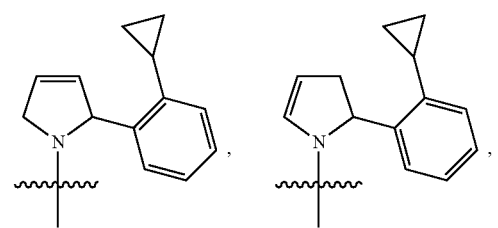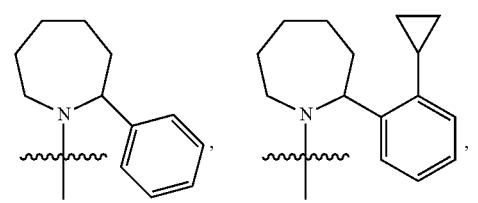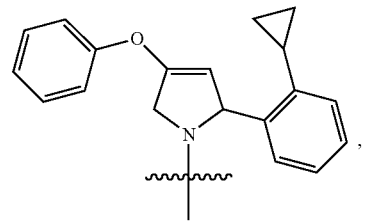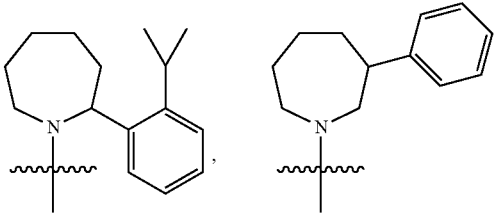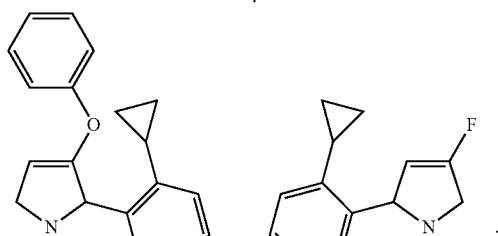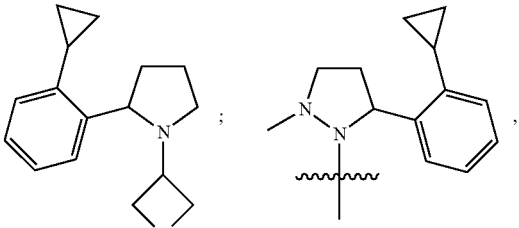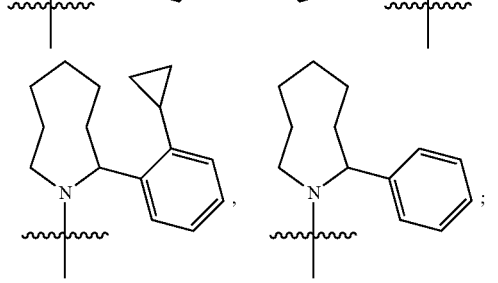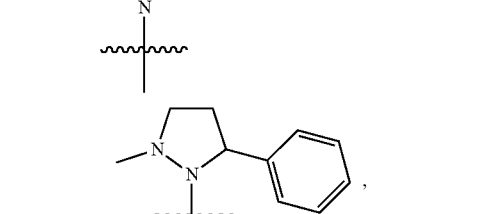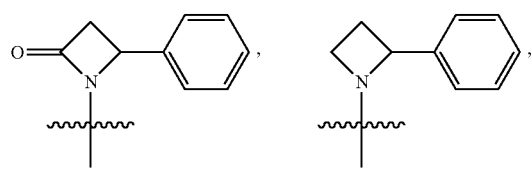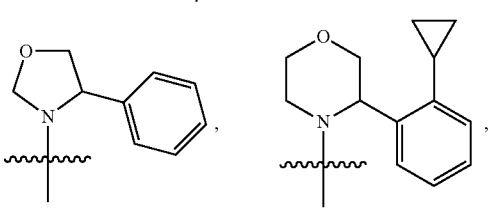

-continued
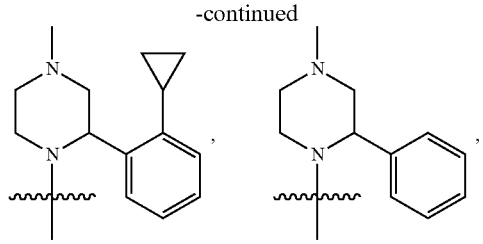
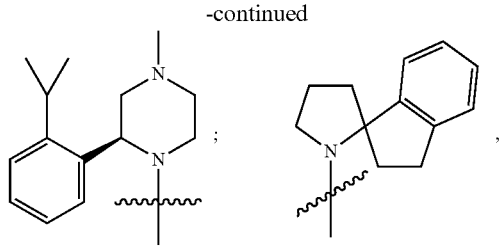
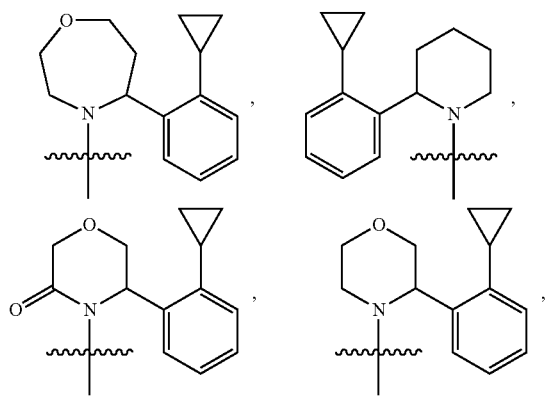
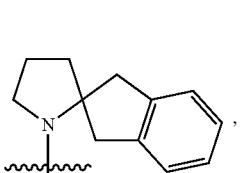
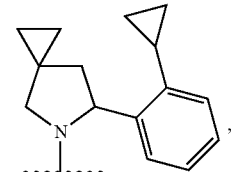
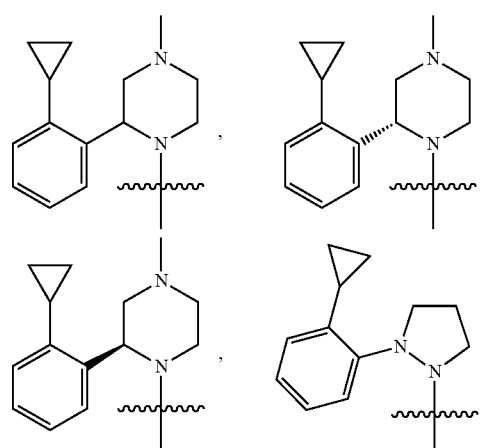
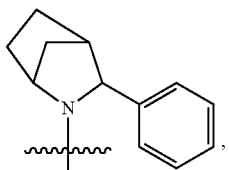
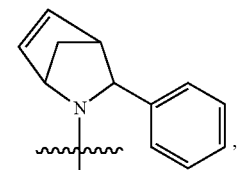
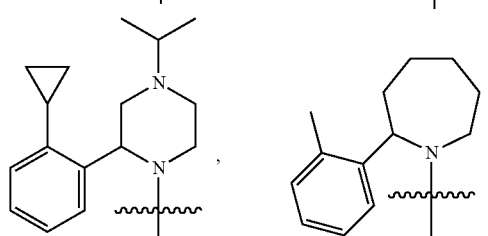
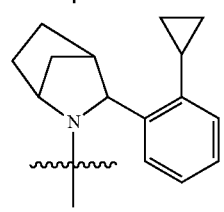
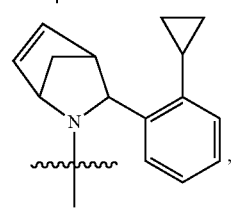
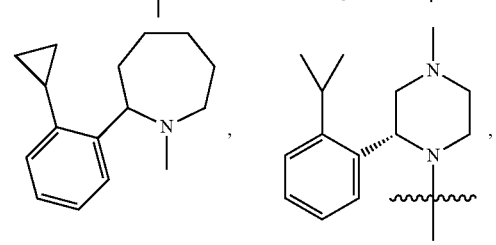

-continued

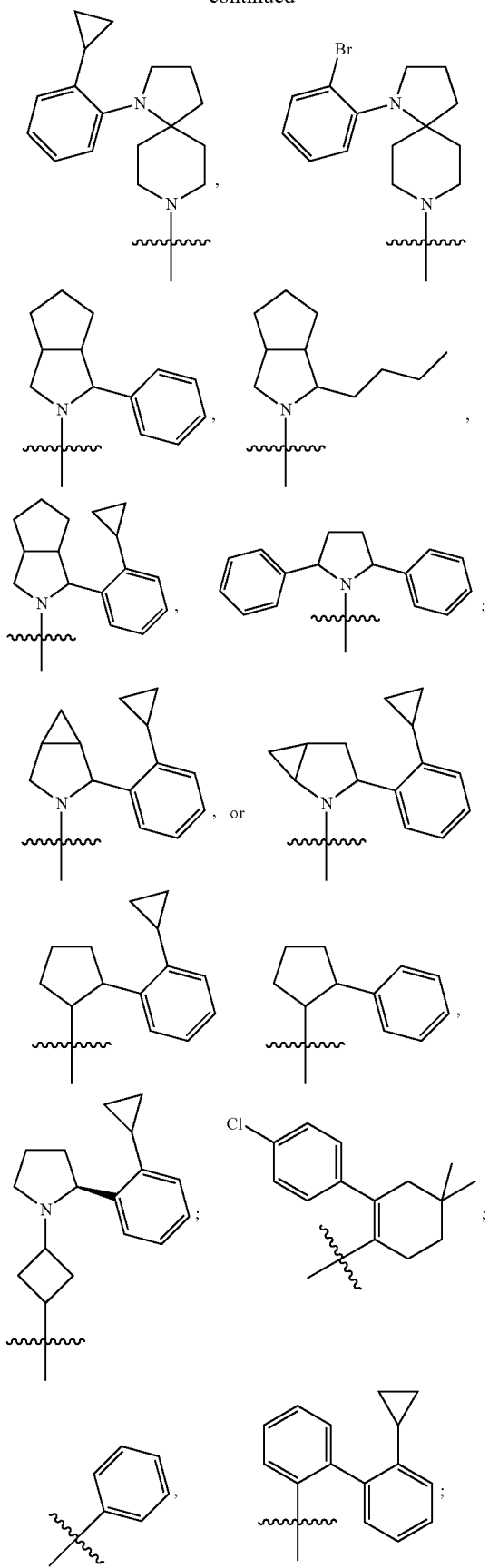

-continued

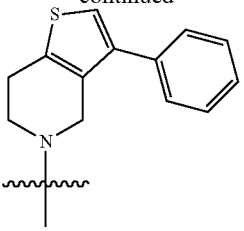

In one preferred embodiment, ring B is a 2-substituted pyrrolidin-1-yl group, $L_1$ is a direct bond, $L^2$ is a direct bond, ring A is a 1,4-phenylene ring, or 5 to 12-membered spiro heterocyclyl comprising one or two heteroatoms selected from nitrogen, sulfur and oxygen as ring members, preferably 5 to 12-membered spiro heterocyclyl comprising one or two nitrogens as ring member; more preferably a 4-membered/4-membered, 3-membered/5-membered, 4-membered/5-membered, 4-membered/6-membered, 5-membered/5-membered, or 5-membered/6-membered mono-spiro heterocyclyl comprising one or two nitrogen or oxygen as ring members; most preferably ring A is 7-azaspiro[3.5]nonan-2,7-diyl, 2-azaspiro[3.5]nonan-2,7-diyl, 3-azaspiro[5.5]undecan-3, 9-diyl, 2-azaspiro[3.3]heptan-2,6-diyl, 8-azaspiro[4.5]decan-2,8-diyl, or 2-azaspiro[4.5]decan-2,8-diyl. In a more preferred embodiment, ring B is a 2-(substituted phenyl)pyrrolidin-1-yl group, $L_1$ is a direct bond, $L^2$ is a direct bond, ring A is a 1,4-phenylene ring, or 5 to 12-membered spiro heterocyclyl comprising one or two heteroatoms selected from nitrogen, sulfur and oxygen as ring members, preferably 5 to 12-membered spiro heterocyclyl comprising one or two nitrogens as ring member; more preferably a 4-membered/4-membered, 3-membered/5-membered, 4-membered/5-membered, 4-membered/6-membered, 5-membered/5-membered, or 5-membered/6-membered mono-spiro heterocyclyl comprising one or two nitrogen or oxygen as ring members; most preferably ring A is 7-azaspiro[3.5]nonan-2,7-diyl, 2-azaspiro[3.5]nonan-2,7-diyl, 3-azaspiro[5.5]undecan-3, 9-diyl, 2-azaspiro[3.3]heptan-2,6-diyl, 8-azaspiro[4.5]decan-2,8-diyl, or 2-azaspiro[4.5]decan-2,8-diyl. In an even more preferred embodiment, ring B is a 2-(2-substituted phenyl)pyrrolidin-1-yl group or 2-(3-substituted phenyl)pyrrolidin-1-yl group, $L_1$ is a direct bond, $L^2$ is a direct bond, ring A is a 1,4-phenylene ring or 7-azaspiro[3.5]nonan-2,7-diyl, 2-azaspiro[3.5]nonan-2,7-diyl, 3-azaspiro[5.5]undecan-3, 9-diyl, 2-azaspiro[3.3]heptan-2,6-diyl, 8-azaspiro[4.5]decan-2,8-diyl, or 2-azaspiro[4.5]decan-2,8-diyl, wherein the phenyl group at position 2 of the pyrrolindin-1-yl is substituted with 1 to 4 substituents $R^{1d}$ as defined with Formula (I). In an alternative preferred embodiment, ring B is a 2-(2-substituted phenyl)pyrrolidin-1-yl group or 2-(3-substituted phenyl)pyrrolidin-1-yl group, $L_1$ is a direct bond, ring A is a 1,4-cyclohexylene ring or 1,4-cyclohex-3-enyl or 1,4-cyclohex-2-enyl or 1,4-cyclohex-1-enyl or 7-azaspiro[3.5]nonan-2,7-diyl, 2-azaspiro[3.5]nonan-2,7-diyl, 3-azaspiro[5.5]undecan-3, 9-diyl, 2-azaspiro[3.3]heptan-2,6-diyl, 8-azaspiro[4.5]decan-2,8-diyl, or 2-azaspiro[4.5]decan-2,8-diyl, $L^2$ is a direct bond, wherein the phenyl group at position 2 of the pyrrolindin-1-yl is substituted with 1 to 4 substituents $R^{1d}$ as defined with Formula (I). In one embodiment, one substituent $R^{1d}$ is substituted at position 2 of the phenyl group at position 2 of the pyrrolindin-1-yl.

In one embodiment, m is 1.

In one embodiment, $L^5$ is a direct bond, $(CR^aR^b)_t$— or —$NR^a$—, wherein t is a number of 1 to 7, and one or two CR$^a$R$^b$ moieties in —(CR$^a$R$^b$)$_t$— are un-replaced or replaced with one or more moieties selected from O and NR$^a$, wherein R$^a$ and R$^b$ are defined as with Formula (I).

In a preferred embodiment, L$^5$ is a direct bond, —(CR$^a$R$^b$)$_{1-4}$—, —O—(CR$^a$R$^b$)$_{1-3}$—, —NH—(CR$^a$R$^b$)$_{1-3}$, or —NH—, wherein R$^a$ and R$^b$ are defined as with Formula (I) so that the -L$^5$-CyC moiety is CyC, —(CR$^a$R$^b$)$_{1-4}$-CyC, —O—(CR$^a$R$^b$)$_{1-3}$-CyC, —NH—(CR$^a$R$^b$)$_{1-3}$-CyC, or —NH-CyC, respectively. More preferably, L$^5$ is a direct bond, —(CH$_2$)$_{1-4}$—, —O—(CH$_2$)$_{1-3}$—, —NH—(CR$^a$R$^b$)—(CH$_2$)$_2$—, or —NH—, wherein R$^a$ is hydrogen and R$^b$ is C$_{1-8}$alkyl optionally substituted with phenyl-S— so that the -L$^5$-CyC moiety is CyC, —(CH$_2$)$_{1-4}$-CyC, —O—(CH$_2$)$_{1-3}$-CyC, —NH—(CR$^a$R$^b$)—(CH$_2$)$_2$—CyC, or —NH-CyC, respectively. More preferably, L$^5$ is a direct bond, —CH$_2$—, —O—CH$_2$—, —NH—CH$_2$—, or —NH— so that the -L$^5$-CyC moiety is CyC, —CH$_2$—CyC, —O—CH$_2$—CyC, —NH—CH$_2$—CyC, or —NH-CyC, respectively.

In one embodiment, CyC is cycloalkyl, or heterocyclyl, each of which is optionally substituted with one or two substituents R$^{5a}$;

R$^{5a}$ is independently selected from hydrogen, halogen, cyano, oxo, —OR$^{5b}$, —NR$^{5b}$R$^{5c}$, —COR$^{5b}$, —SO$_2$R$^{5b}$, —C$_{1-8}$alkyl, C$_{2-8}$alkynyl, -cycloalkyl, or heterocyclyl, each of said C$_{1-8}$alkyl, and heterocyclyl is optionally substituted with one or two substituents R$^{5e}$ which is selected from hydrogen, halogen, cyano, —OR$^{5f}$, —C$_{1-8}$alkyl, -cycloalkyl, or heterocyclyl;

wherein R$^{5b}$, and R$^{5c}$ are each independently hydrogen, —C$_{1-8}$alkyl or heterocyclyl, said —C$_{1-8}$alkyl is optionally substituted with one or two substituents R$^{5e}$ which is hydrogen, —NR$^{5f}$R$^{5g}$, or -cycloalkyl;

R$^{5f}$ and R$^{5g}$ are each independently hydrogen or —C$_{1-8}$alkyl;

or, two adjacent R$^5$ on the phenyl ring together with the phenyl ring form a benzo ring, said ring is optionally substituted with heteroaryl.

In one embodiment. CyC is cycloalkyl selected from monocyclic C$_{3-8}$-cycloalkyl or bridged cycloalkyl

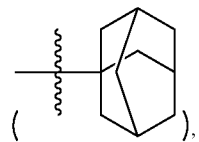

each of which is optionally substituted with one or two substituents R$^{5a}$. preferably, CyC is cyclopentyl or cyclohexyl, each of which is optionally substituted with one or two substituents R$^{5a}$.

In one embodiment, CyC is heterocyclyl selected from:
a) monocyclic 4 to 9-membered heterocyclyl groups containing one nitrogen or oxygen or sulfur heteroatom as ring member;
b) monocyclic 4 to 9-membered heterocyclyl groups containing two heteroatoms selected from oxygen, sulfur and nitrogen as ring members; and
c) 5 to 20-membered spiro heterocyclyl comprising one or two heteroatoms selected from nitrogen, sulfur and oxygen as ring members,
each of which is optionally substituted with one or two R$^{5a}$.

In a preferred embodiment, CyC is monocyclic 4 to 6-membered heterocyclyl groups containing one nitrogen or oxygen or sulfur heteroatom as ring member. More preferably, Cyc is selected from oxetanyl, tetrahydrofuranyl, tetrahydropyranyl, azetidinyl, pyrrolidinyl, and piperdinyl. Even more preferably, CyC is selected from, oxetan-2-yl, Oxetan-3-yl, tetrahydrofuran-4-yl, tetrahydrofuran-2-yl, tetrahydrofuran-3-yl, tetrahydropyran-2-yl, tetrahydropyran-3-yl, tetrahydropyran-4-yl, azetidin-3-yl, azetidin-2-yl, pyrrolidin-2-yl, pyrrolidin-3-yl, piperdin-4-yl, piperdin-2-yl, and piperdin-3-yl.

In a preferred embodiment, CyC is monocyclic 6-membered heterocyclyl group containing two heteroatoms selected from oxygen and nitrogen as ring members. More preferably, CyC is dioxanyl, morpholine, morpholinyl, or piperzinyl. Even more preferably 1,3-dioxan-2-yl, 1,3-dioxan-4-yl, 1,4-dioxan-2-yl, morpholin-1-yl, morpholin-2-yl, or morpholin-3-yl.

In a preferred embodiment, CyC is 4-membered/4-membered, 3-membered/5-membered, 4-membered/5-membered, 4-membered/6-membered, 5-membered/5-membered, or 5-membered/6-membered mono-spiro heterocyclyl comprising one or two nitrogen or oxygen as ring members. More preferably, CyC is

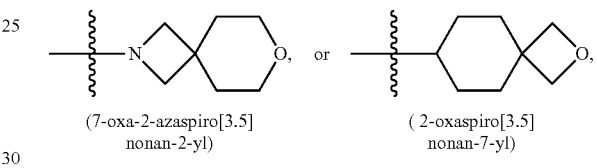

(7-oxa-2-azaspiro[3.5]
nonan-2-yl)    ( 2-oxaspiro[3.5]
nonan-7-yl)

In a preferred embodiment, R$^{5a}$ is independently selected from hydrogen, halogen, cyano, oxo, —OR$^{5b}$, —NR$^{5b}$R$^{5c}$, —COR$^{5b}$, —SO$_2$R$^{5b}$, —C$_{1-8}$alkyl, —C$_{2-8}$alkynyl, monocyclic C$_{3-8}$-cycloalkyl, or monocyclic 4 to 9-membered heterocyclyl group containing one or two heteroatoms selected from nitrogen or oxygen or sulfur heteroatom as ring members, each of said —C$_{1-8}$alkyl and monocyclic 4 to 9-membered heterocyclyl group is optionally substituted with one or two substituents R$^{5e}$. Preferably, cycloalkyl as R$^{5a}$ is C$_{3-6}$-cycloalkyl; more preferably cyclopropyl. Preferably, heterocyclyl as R$^{5a}$ is 4 to 6-membered heterocyclyl groups containing one or two heteroatoms selected from nitrogen or oxygen or sulfur heteroatom as ring members. More preferably, heterocyclyl as R$^{5a}$ is oxetanyl, tetrahydrofuranyl, tetrahydropyranyl, piperzinyl, or morpholinyl. Even more preferably, heterocyclyl as R$^{5a}$ is oxetan-3-yl, tetrahydrofuran-3-yl, tetrahydro-2H-pyran-4-yl, or morph in -4-yl.

In one embodiment, heterocyclyl as R$^{5e}$ is monocyclic 4 to 9-membered heterocyclyl group containing one or two heteroatoms selected from nitrogen or oxygen or sulfur heteroatom as ring members. Preferably, heterocyclyl as R$^{5e}$ is tetrahydro-pyran-4-yl.

In one embodiment, R$^{5a}$ is —NR$^{5b}$R$^{5c}$, wherein R$^{5b}$ is hydrogen, and R$^{5c}$ is heterocyclyl. In a more preferred embodiment, R$^{5a}$ is —NR$^{5b}$R$^{5c}$, wherein R$^{5b}$ is hydrogen, and R$^{5c}$ is tetrahydro-pyran-4-yl. In one embodiment, R$^{5a}$ is —NR$^{5b}$R$^{5c}$, wherein R$^{5b}$ and R$^{5c}$ are each independently hydrogen or —C$_{1-6}$alkyl substituted with cycloalkyl, preferably —C$_{1-6}$alkyl substituted with monocyclic C$_{3-8}$-cycloalkyl.

In one embodiment, R$^{5a}$ is —OR$^{5b}$ or —SO$_2$R$^{5b}$, wherein R$^{5b}$ is hydrogen or C$_{1-8}$alkyl, preferably methyl.

In one embodiment, R$^{5a}$ is —COR$^{5b}$, wherein R$^{5b}$ is hydrogen or C$^{1-8}$alkyl optionally-substituted with —NR$^{5f}$R$^{5g}$, wherein R$^{5f}$ and R$^{5g}$ are each independently hydrogen or C$_{1-8}$alkyl, preferably methyl.

In one embodiment, two adjacent R⁵ on the phenyl ring together with the phenyl ring form indazolyl which is substituted with tetrahydropyranyl.
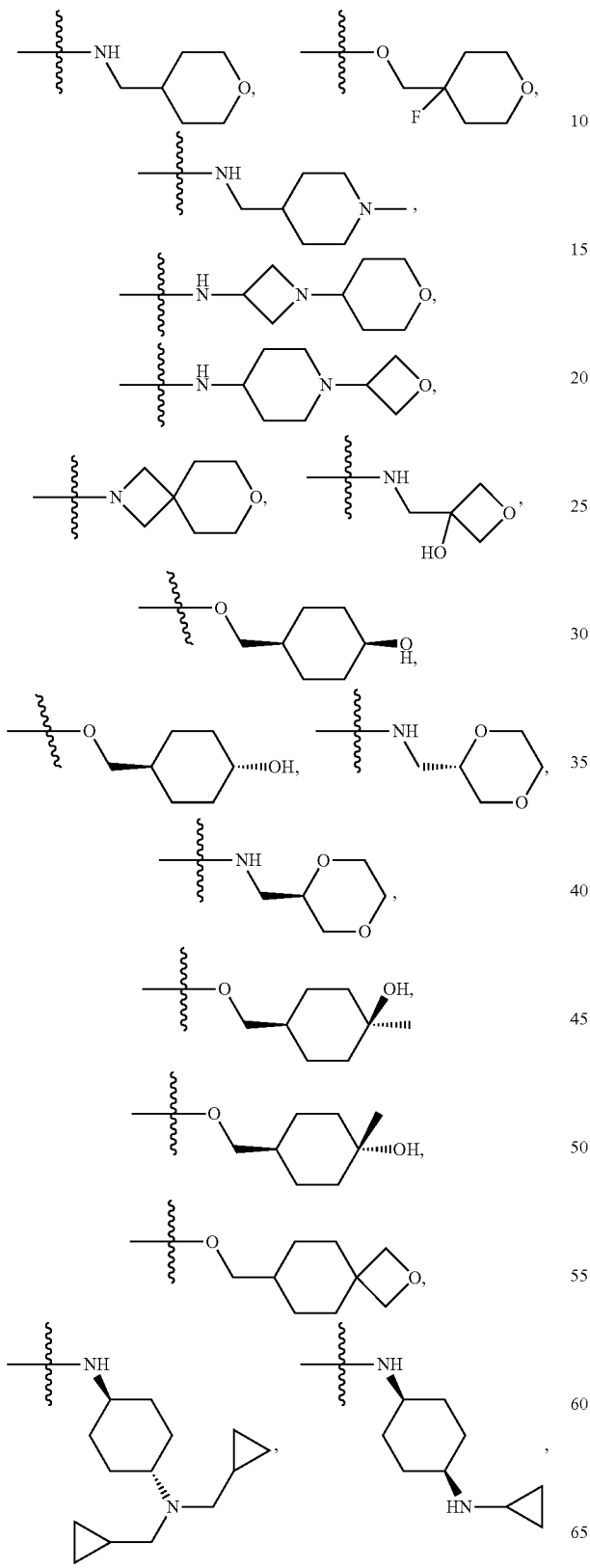
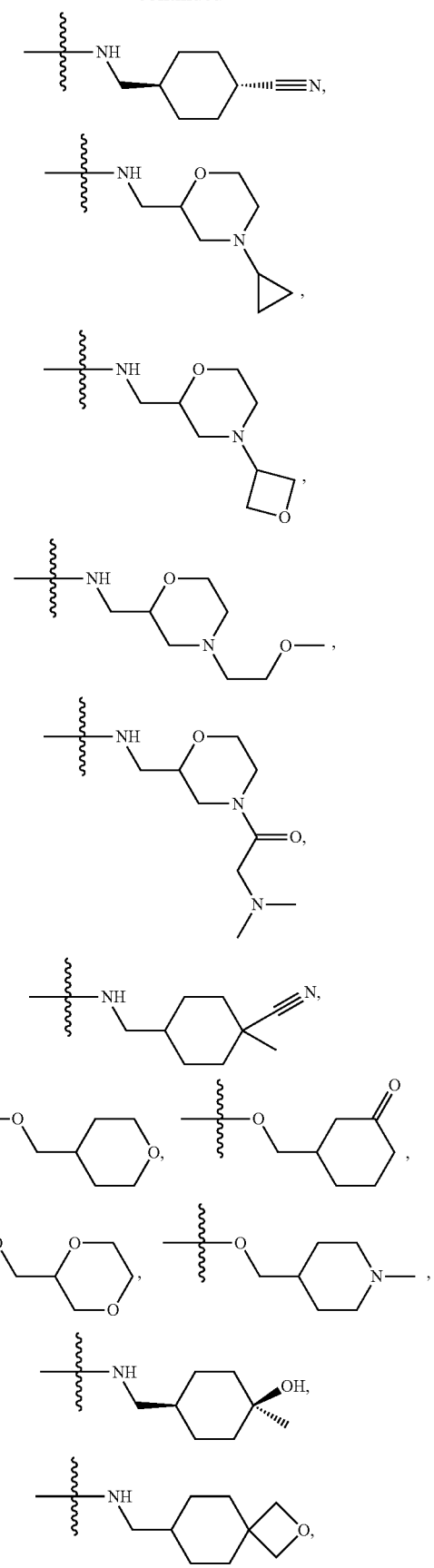

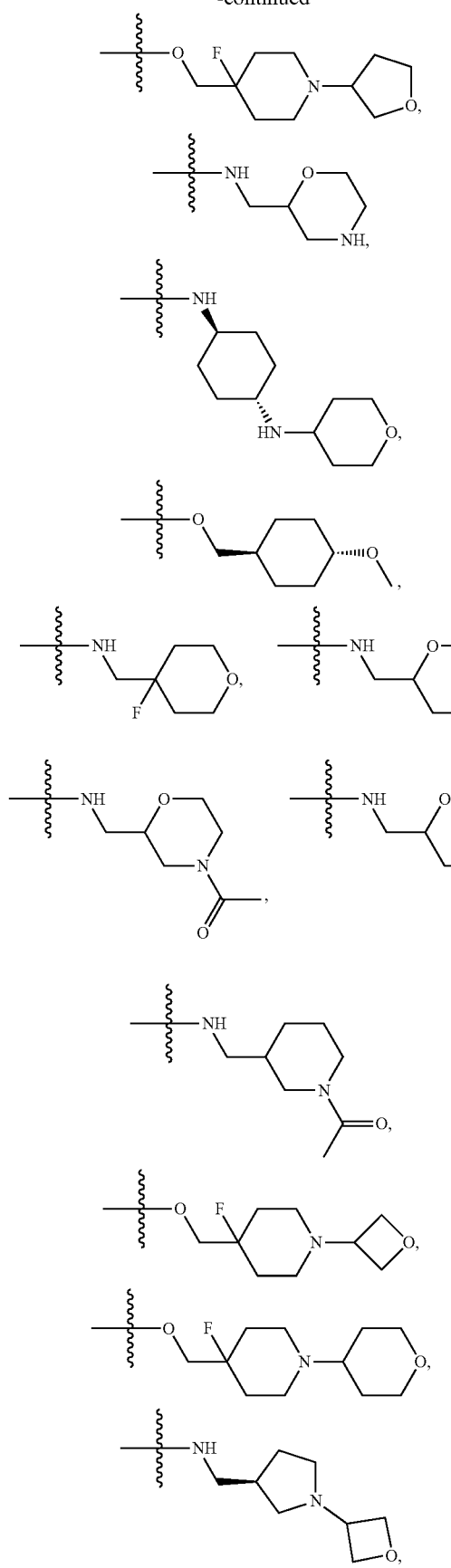
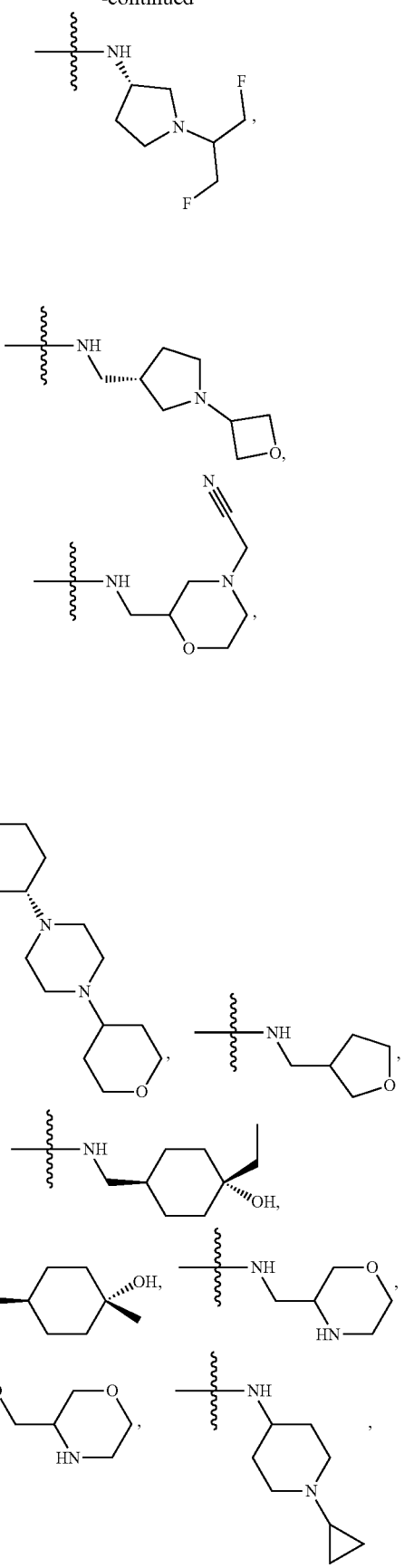

-continued
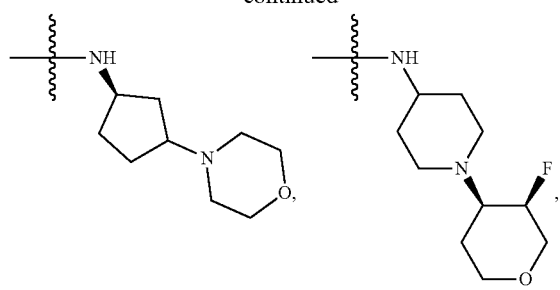
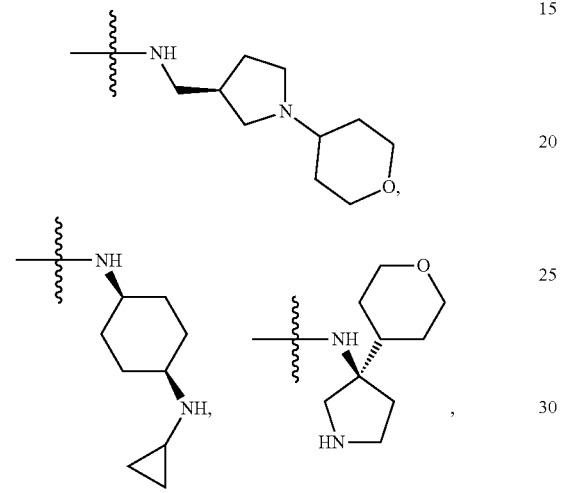
-continued
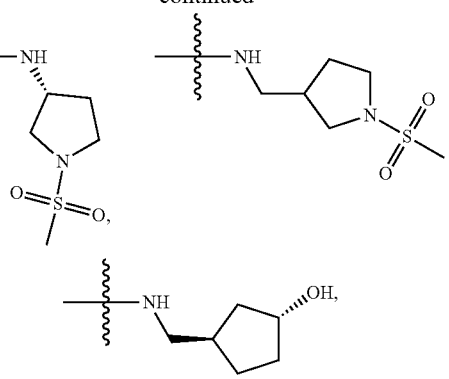
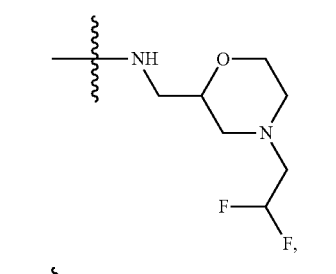
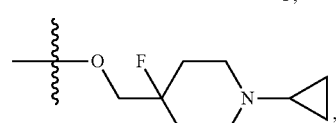
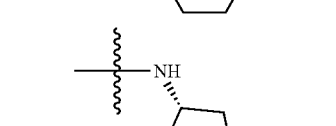
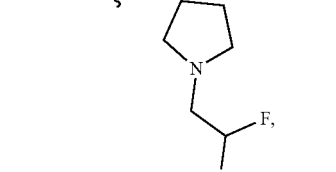

-continued
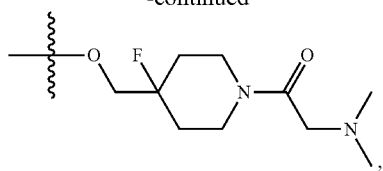
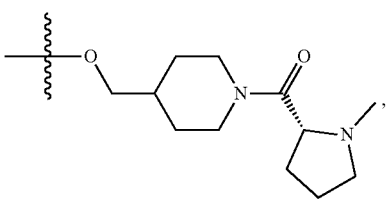
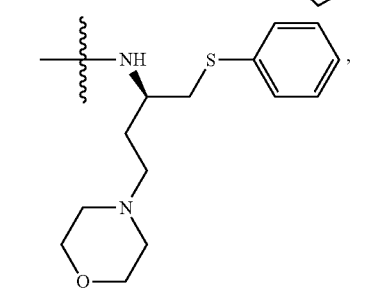
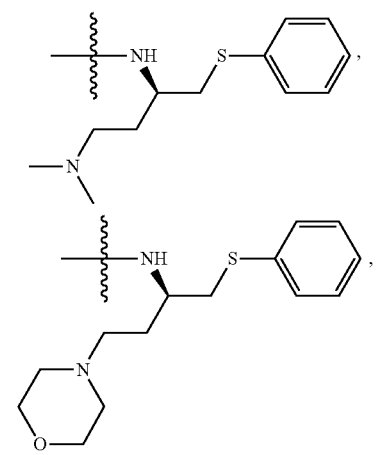
-continued
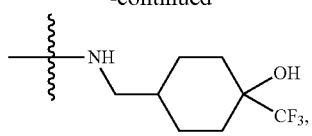
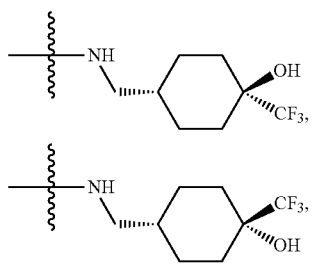
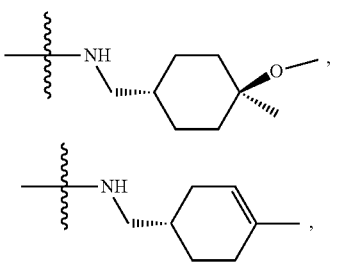
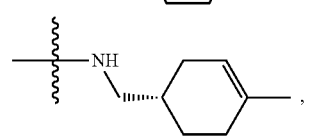
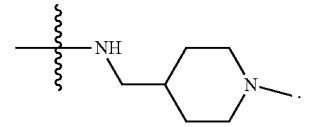

Also disclosed herein is a compound of Formula (II)

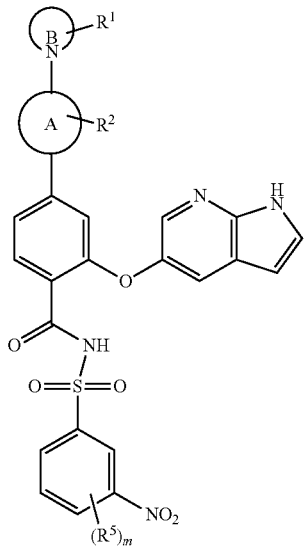

(II)

or a pharmaceutically acceptable salt thereof, or a stereoisomer thereof.
wherein
- Ring A is a phenyl ring, which is 1,4-phenylene; or 5 to 12-membered spiro heterocyclyl comprising one or two heteroatoms selected from nitrogen, sulfur and oxygen as ring members, each of which is optionally substituted with 1 to 4 substituents $R^2$;
- $R^2$, at each occurrence, is independently selected from the group consisting of hydrogen, halogen, or —$C_{1-8}$ alkyl optionally substituted with halogen:
- Ring B is a monocyclic 4 to 9-membered heterocyclyl comprising one nitrogen atom as the ring member or a monocyclic 4 to 9-membered heterocyclyl comprising one nitrogen atom and one additional heteroatom selected from the group consisting of NH, O, S, SO or $SO_2$ heteroatoms as ring members, said ring is N-linked;
- $R^1$, $R^5$ and m are defined with formula (I).

The compound of formula (II) corresponds to the compound of formula (I), wherein
- $L^1$ and $L^2$ are each independently a direct bond, and $L^4$ is —C(O)NHSO$_2$—;
- $L^3$ is —O—, and $R^3$ is pyrrolo[2,3-b]pyridin-5-yl;
- $R^4$ is NO$_2$.

In some embodiment, ring A is 1,4-phenylene. In some embodiment, ring A is 5 to 12-membered spiro heterocyclyl comprising one or two heteroatoms selected from nitrogen, sulfur and oxygen as ring members; preferably ring A is 4-membered/4-membered, 3-membered/5-membered, 4-membered/5-membered, 4-membered/6-membered, 5-membered/5-membered, or 5-membered/6-membered mono-spiro heterocyclyl comprising one or two nitrogen or oxygen as ring members; more preferably ring A is

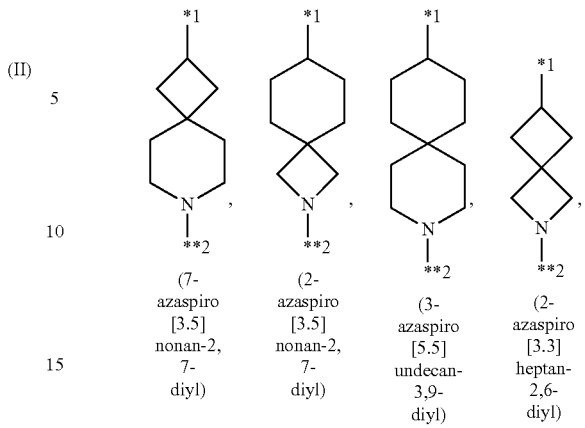

(7-azaspiro [3.5] nonan-2, 7-diyl)
(2-azaspiro [3.5] nonan-2, 7-diyl)
(3-azaspiro [5.5] undecan-3,9-diyl)
(2-azaspiro [3.3] heptan-2,6-diyl)

wherein *1 refers to the position attached to the pyrrolidinyl ring, and **2 refers to the position attached to the phenyl ring.

In some embodiment, ring B is aziridin-1-yl, azetidin-1-yl, pyrrolidin-1-yl, pyrrolidin-2-yl, piperidin-1-yl, azepan-1-yl, or azocan-1-yl, preferably pyrrolidin-1-yl, which is substituted with a phenyl group at position 2 and further optionally substituted with 1 or 2 or 3 substituents $R^1$ on the pyrrolidinyl ring, and said phenyl group at position 2 (i.e., ortho position) is optionally substituted with $R^{1d}$ as defined with Formula (I).

When ring B is pyrrolidin-1-yl, which is substituted with a phenyl group at position 2, and said phenyl group at position 2 (i.e., ortho position) is optionally substituted with $R^{1d}$ as defined with Formula (I), the compound has the following formula (III)

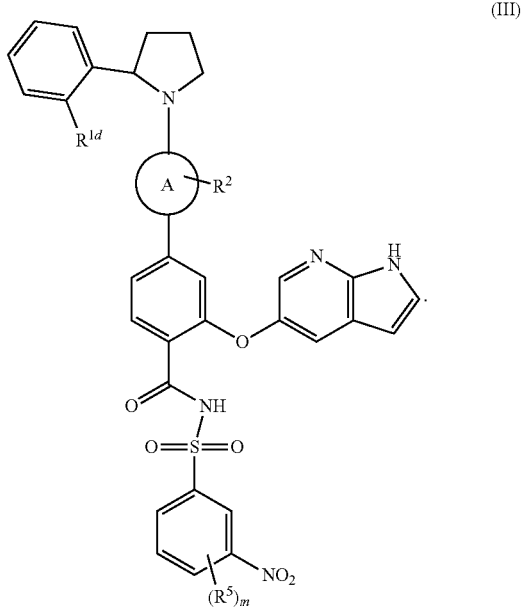

(III)

In one embodiment for formula (III), ring A is

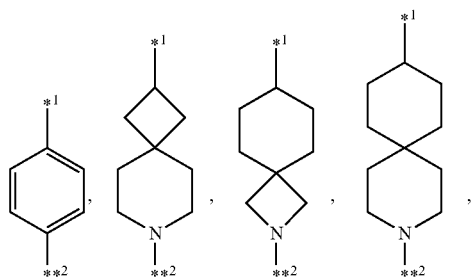

(7-azaspiro [3.5]nonan-2,7-diyl), (2-azaspiro [3.5]nonan-2,7-diyl), (3-azaspiro [5.5]undecan-3,9-diyl),

(2-azaspiro [3.3]heptan-2,6-diyl)

wherein *1 refers to the position attached to the pyrrolidinyl ring, and **2 refers to the position attached to the phenyl ring so that the compound of formula (III) may be represented by the following subgenus formulas (III-A), (III-B), (III-C), (III-D) or (III-E)

(III-A)

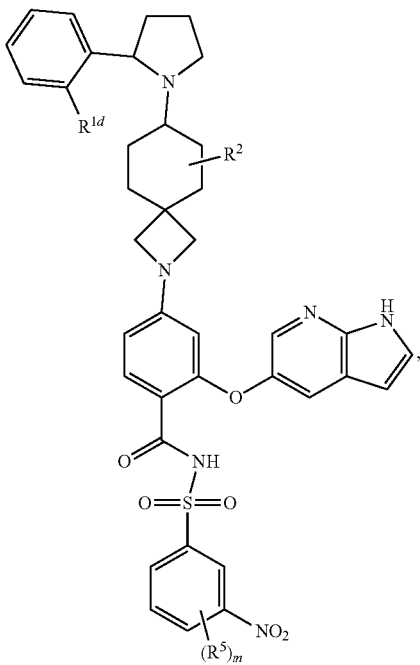

(III-B)

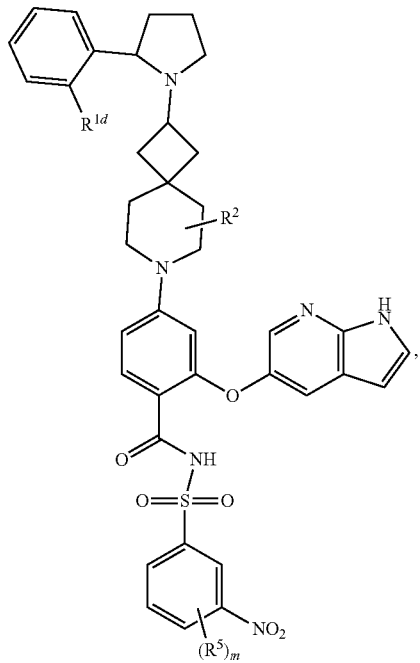

(III-C)

57

-continued

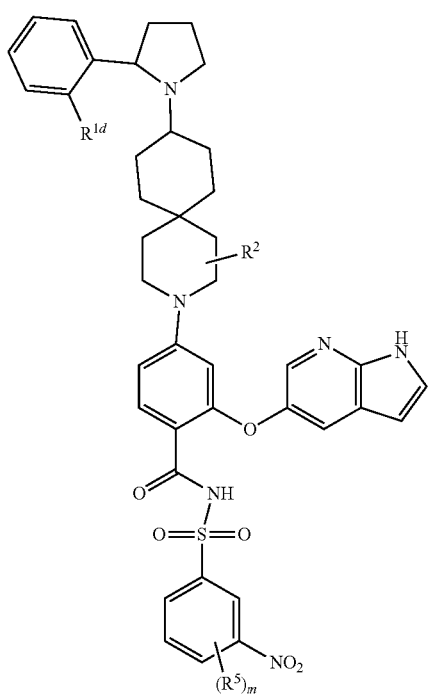
(III-D)

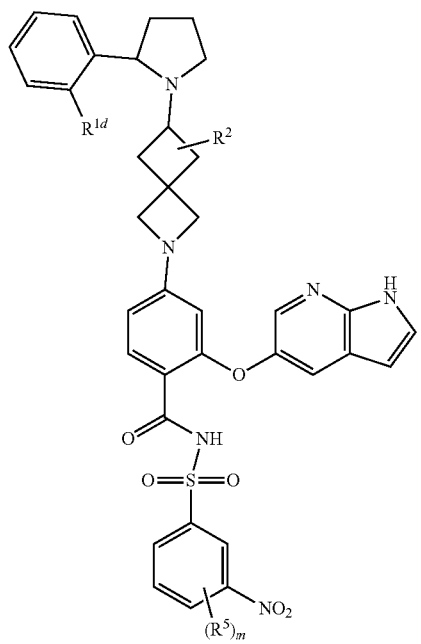
(III-E)

wherein the variables $R^{1d}$, $R^2$, $R^5$ and m are defined with formula (I).

In some embodiments for subgenus formulas (II), (III), (III-A), (III-B), (III-C), (III-D) or (III-E), wherein $R^2$ is hydrogen.

In some embodiments for subgenus formulas (II), (III), (III-A), (III-B), (III-C), (III-D) or (III-E), $R^{1d}$ is defined with formula (I), preferably, $R^{1d}$, when substituted on the phenyl group at position 2 of ring B (including the aziridin-1-yl, azetidin-1-yl, pyrrolidin-1-yl, pyrrolidin-2-yl, piperidin-1-yl, azepan-1-yl, or azocan-1-yl, preferably the pyrrolidin-1-yl group), is independently halogen, —$C_{1-8}$alkyl, —$C_{2-8}$alkenyl, —$C_{2-8}$alkynyl, cycloalkyl, heterocyclyl, aryl,

58 heteroaryl, —CN, —$OR^{Ba}$, —$SO_2R^{Ba}$, —$CONR^{Ba}R^{Bb}$, —$NO_2$, —$NR^{Ba}R^{Bb}$, —$NR^{Ba}COR^{Bb}$, or —$NR^{Ba}SO_2R^{Bb}$; wherein said —$C_{1-8}$alkyl, —$C_{2-8}$alkenyl, —$C_{2-8}$alkynyl, cycloalkyl, heterocyclyl, aryl or heteroaryl are each independently optionally substituted with 1 to 4 substituents $R^{Bd}$ as defined with Formula (I), preferably 1 or 2 substituents $R^{Bd}$ as defined with Formula (I). In another aspect, one $R^{1d}$ is at position 2 of the phenyl ring at position 2 of ring B.

In some preferred embodiments for subgenus formulas (II), (III), (III-A), (III-B), (III-C), (III-D) or (III-E), $R^{1a}$ is methyl, ethyl, isopropyl, propyl or methoxymethyl, or two methyl at position of the phenyl ring; or propenyl; or cyclopropyl, cyclobutyl, cyclopentyl, or cyclohexyl; or ethoxy or isopropoxy; or amino or dimethylamino.

In some preferred embodiments for subgenus formulas (III), (III-A), (III-B), (III-C), (III-D) or (III-E), the 2-(2-substituted phenyl)pyrrolidin-1-yl moiety as ring B is selected from the group consisting of:

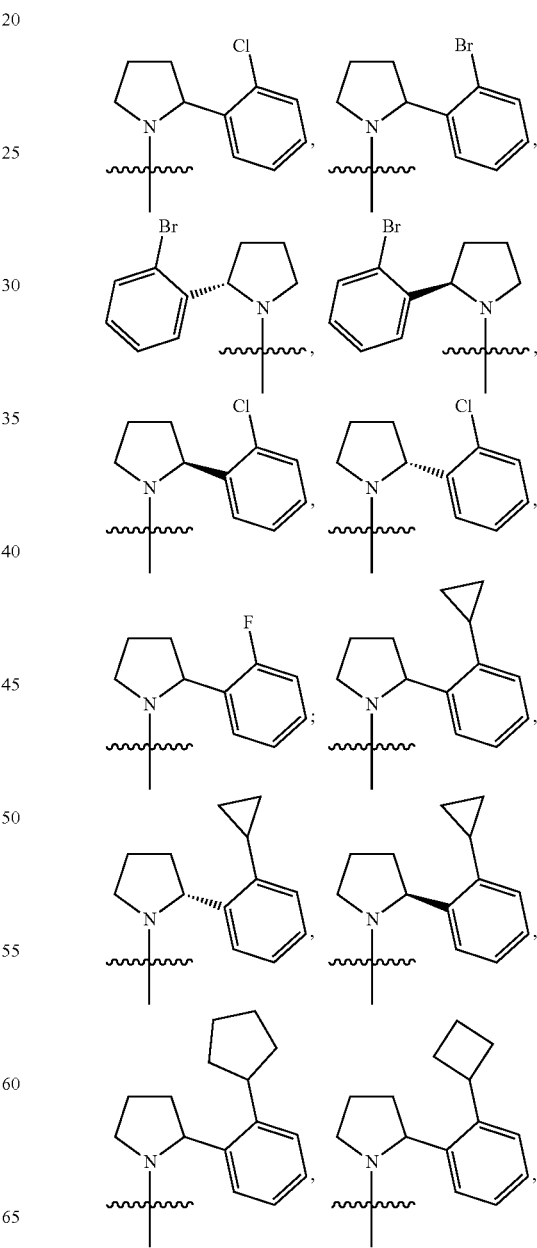

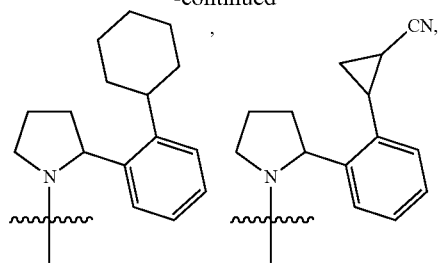
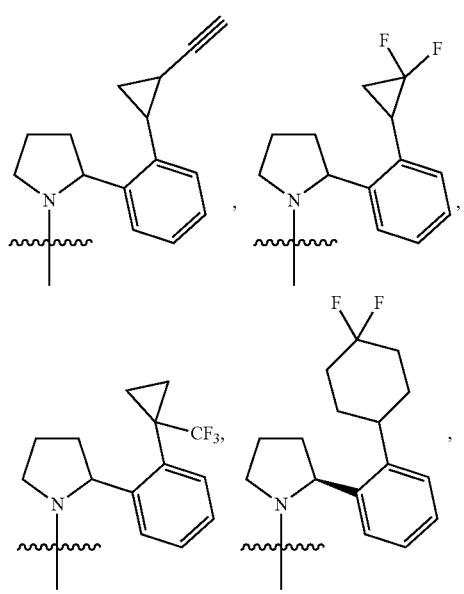
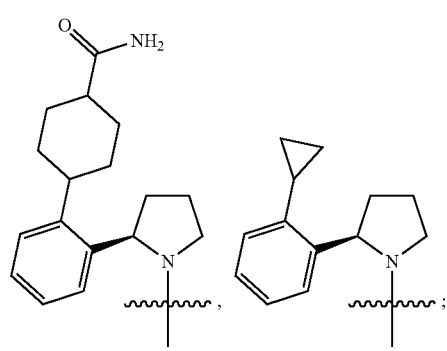
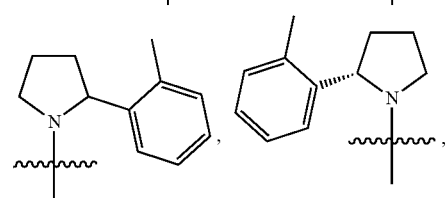
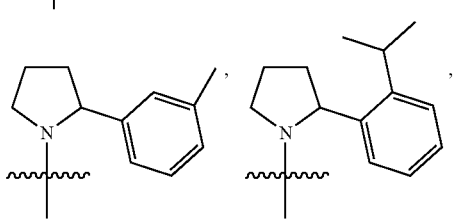
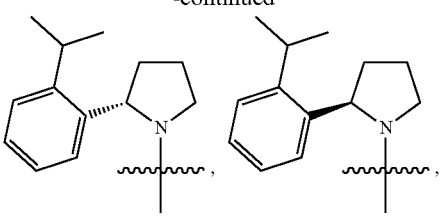
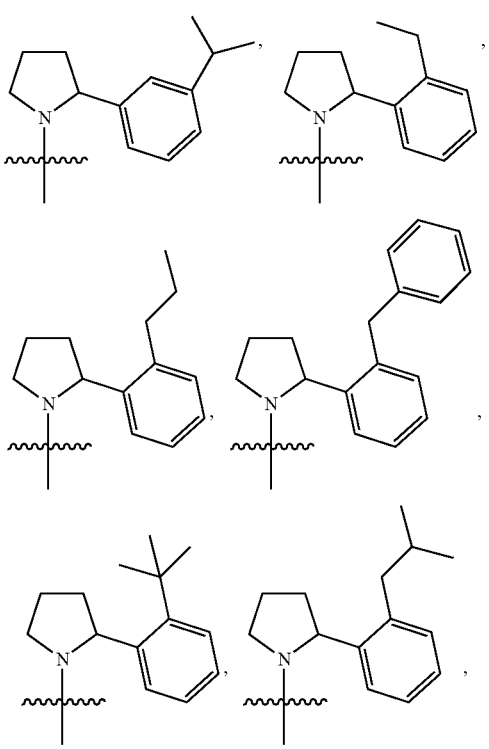
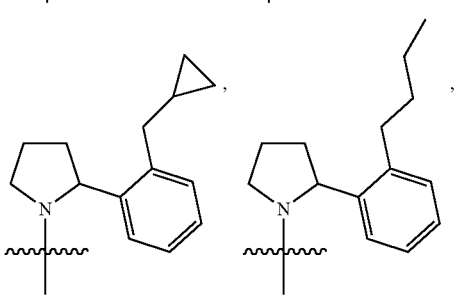
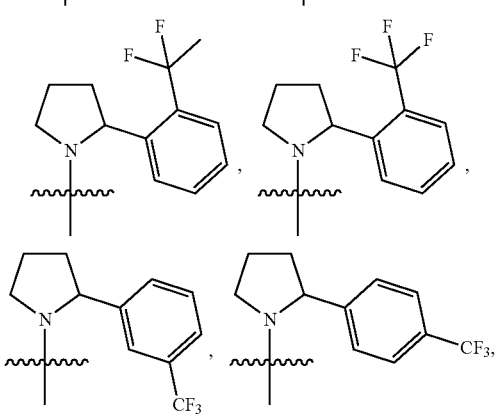

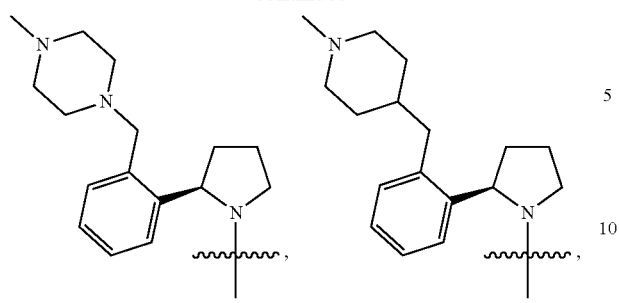
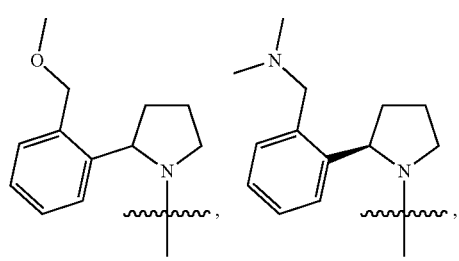
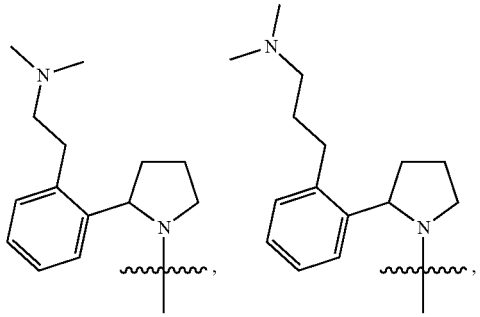
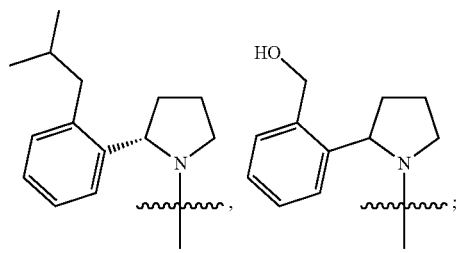
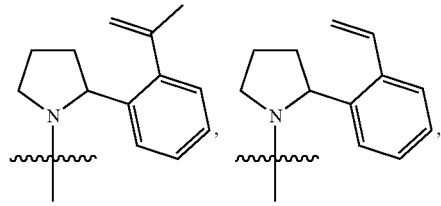
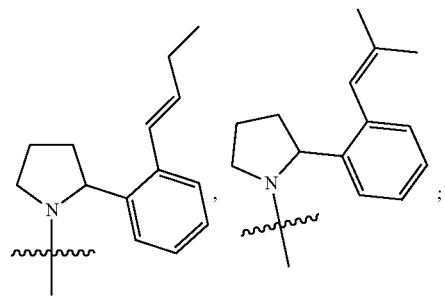
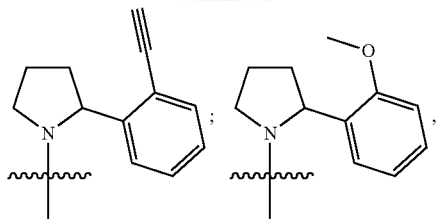
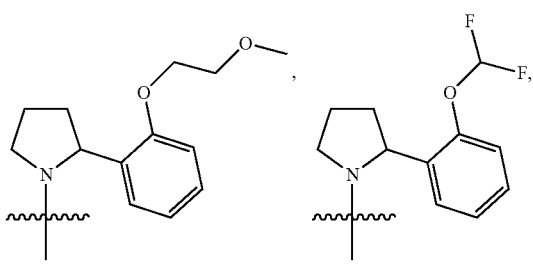
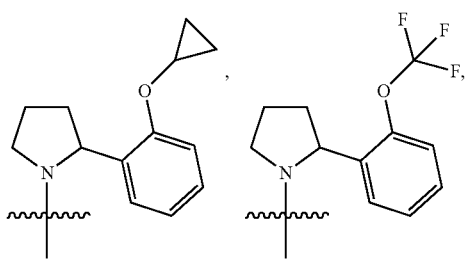
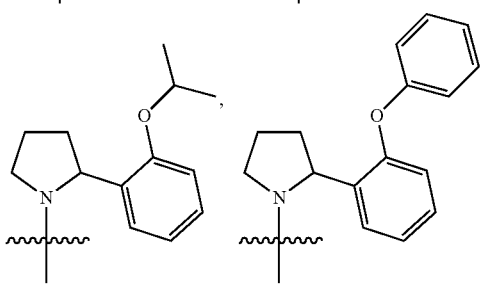
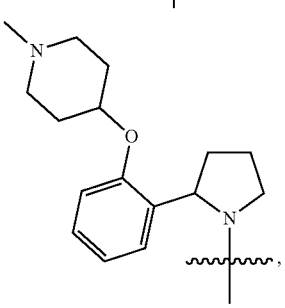

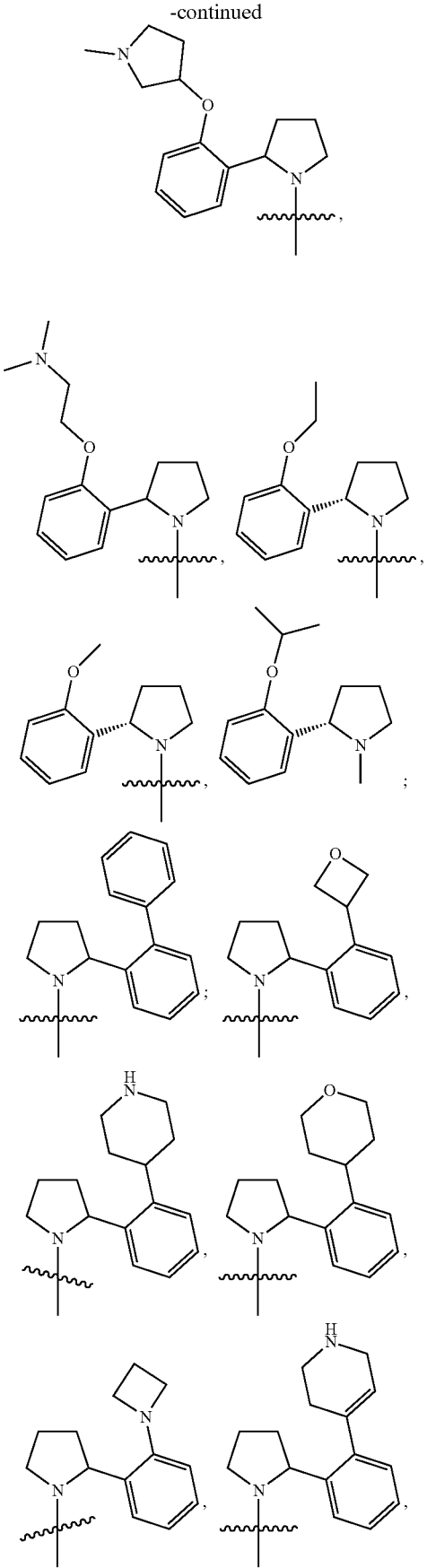
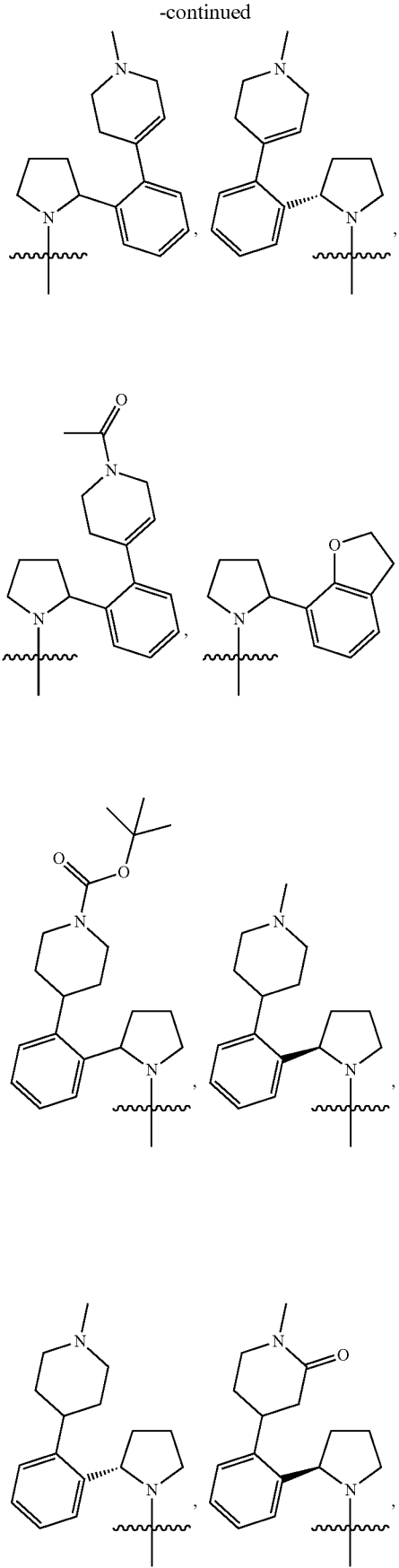

65
-continued
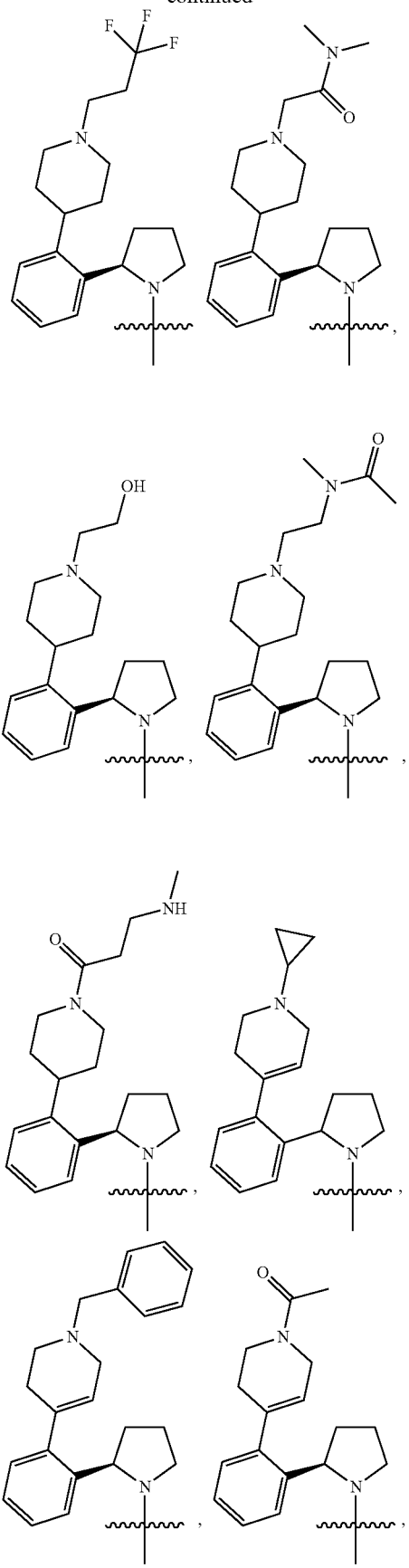
66
-continued
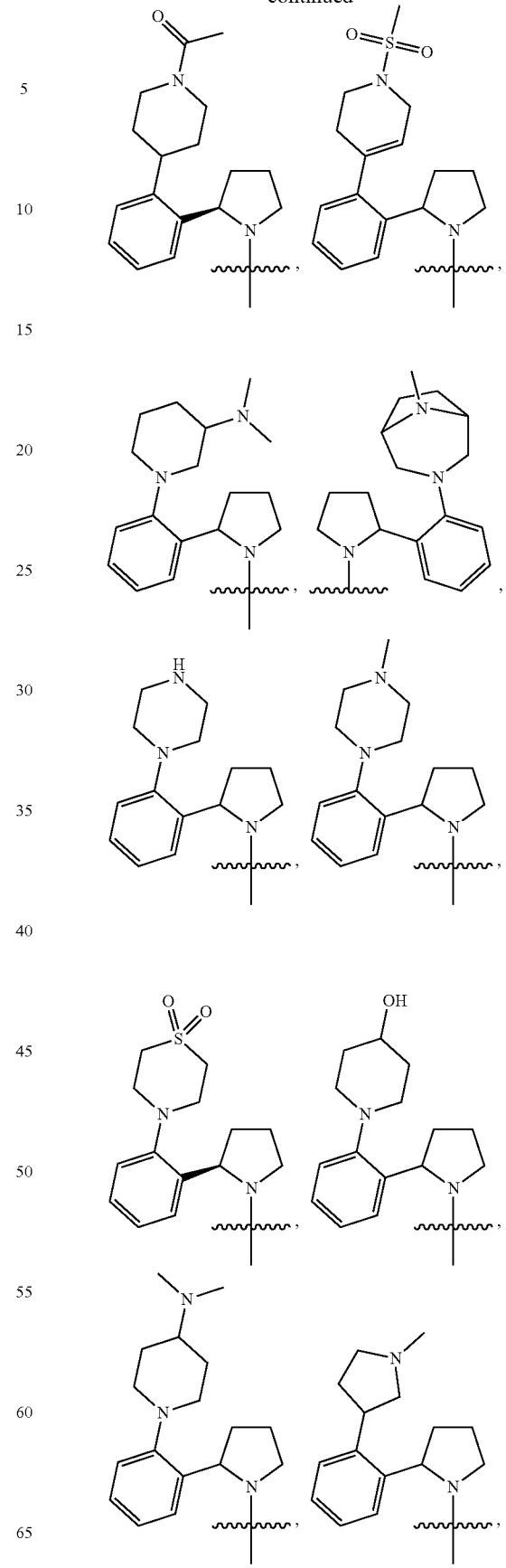

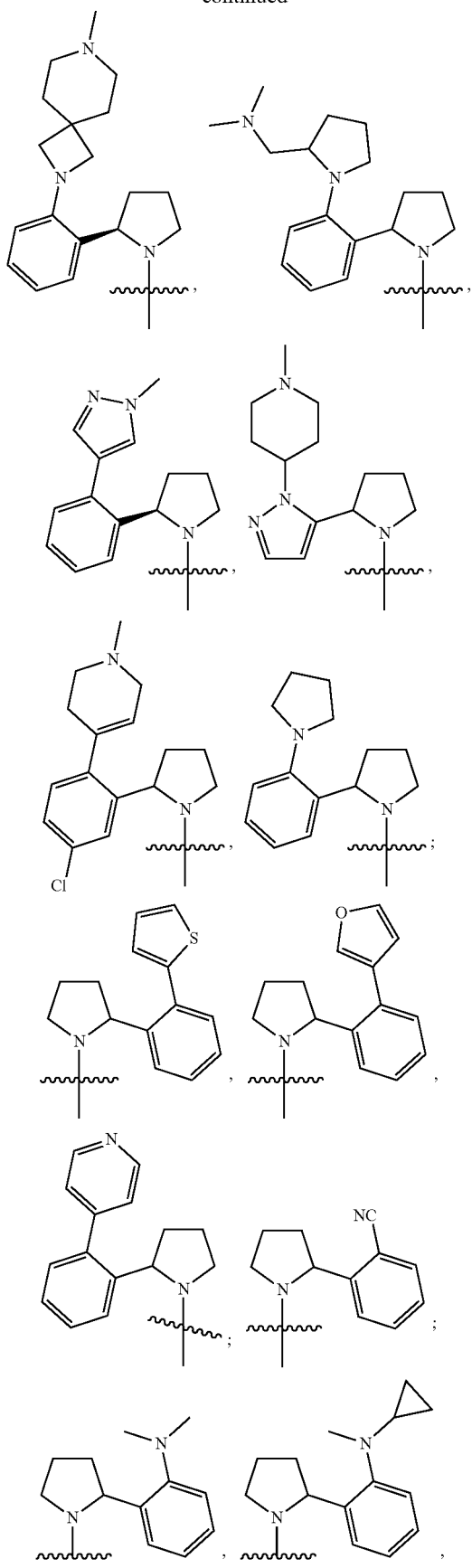
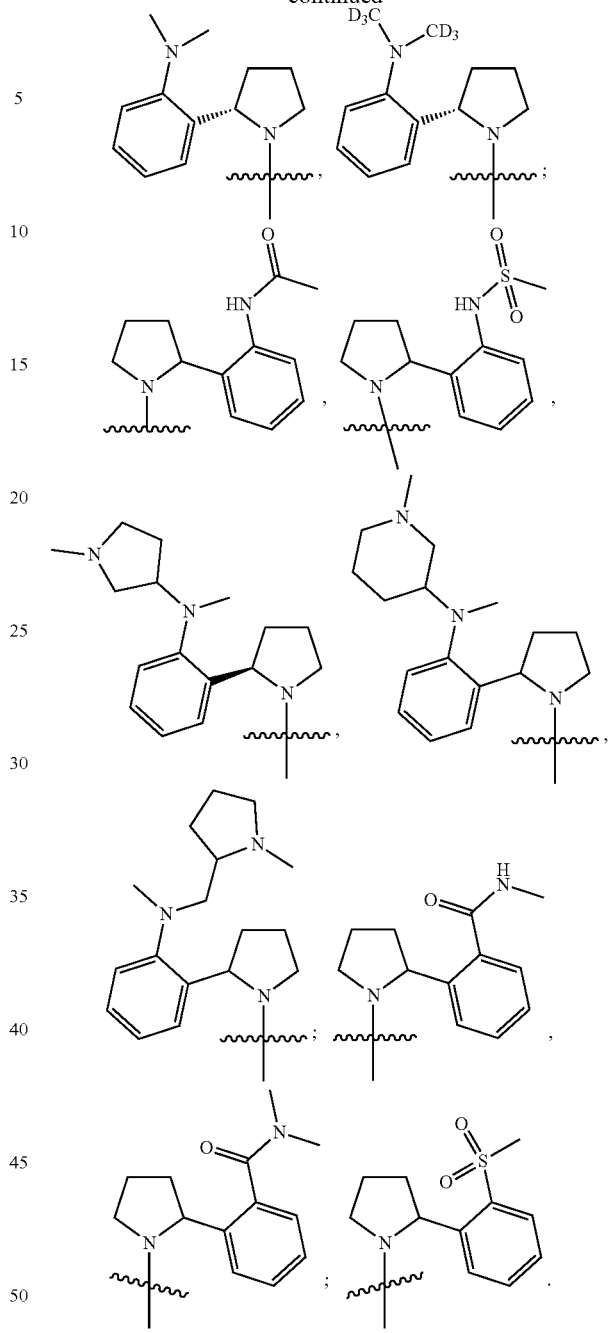

In some preferred embodiments for subgenus formulas (II), (III), (III-A), (III-B), (III-C), (III-D) or (III-E), m is 1; and $L^5$ is a direct bond, —$(CR^aR^b)_t$— or —$NR^a$, wherein t is a number of 1 to 7, and one or two $CR^aR^b$ moieties in —$(CR^aR^b)_t$— are un-replaced or replaced with one or more moieties selected from O and $NR^a$, wherein $R^a$ and $R^b$ are defined as with Formula (I).

In a preferred embodiment, $L^5$ is a direct bond, —$(CR^aR^b)_{1-4}$—, —O—$(CR^aR^b)_{1-3}$—, —NH—$(CR^aR^b)_{1-3}$, or —NH—, wherein $R^a$ and $R^b$ are defined as with Formula (I) so that the -$L^5$-CyC moiety is CyC, —$(CR^aR^b)_{1-4}$-CyC, —O—$(CR^aR^b)_{1-3}$-CyC, —NH—$(CR^aR^b)_{1-3}$-CyC, or —NH-CyC, respectively. More preferably, $L^5$ is a direct bond, —$(CH_2)_{1-4}$—, —O—$(CH_2)_{1-3}$—, —NH—$(CR^aR^b)$—

(CH$_2$)$_2$—, or —NH—, wherein R$^a$ is hydrogen and R$^b$ is C$_{1-8}$alkyl optionally substituted with phenyl-S— so that the 17-CyC moiety is CyC, —(CH$_2$)$_{1-4}$-CyC, —O—(CH$_2$)$_{1-3}$-CyC, —NH—(CR$^a$R$^b$)—(CH$_2$)$_2$—CyC, or —NH-CyC, respectively. More preferably, L$^5$ is a direct bond, —CH$_2$—, —O—CH$_2$—, —NH—CH$_2$—, or —NH— so that the -L$^5$-CyC moiety is CyC, —CH$_2$—CyC, —O—CH$_2$—CyC, —NH—CH$_2$—CyC, or —NH-CyC, respectively.

In one embodiment, CyC is cycloalkyl, or heterocyclyl, each of which is optionally substituted with one or two substituents R$^{5a}$;

R$^{5a}$ is independently selected from hydrogen, halogen, cyano, oxo, —OR$^{5b}$, —NR$^{5b}$R$^{5c}$, —COR$^{5b}$, —SO$_2$R$^{5b}$, —C$_{1-8}$alkyl, —C$_{2-8}$alkynyl, -cycloalkyl, or heterocyclyl, each of said —C$_{1-8}$alkyl, and heterocyclyl is optionally substituted with one or two substituents R$^{5e}$ which is selected from hydrogen, halogen, cyano, —OR$^{5f}$, —C$_{1-8}$alkyl, -cycloalkyl, or heterocyclyl;

wherein R$^{5b}$, and R$^{5c}$ are each independently hydrogen, —C$_{1-8}$alkyl or heterocyclyl, said —C$_{1-8}$alkyl is optionally substituted with one or two substituents R$^{5e}$ which is hydrogen, —NR$^{5f}$R$^{3g}$, or -cycloalkyl;

R$^{5f}$ and R$^{5g}$ are each independently hydrogen or —C$_{1-8}$alkyl;

or, two adjacent R$^5$ on the phenyl ring together with the phenyl ring form a benzo ring, said ring is optionally substituted with heteroaryl.

In one embodiment, CyC is cycloalkyl selected from monocyclic C$_{3-8}$-cycloalkyl or bridged cycloalkyl

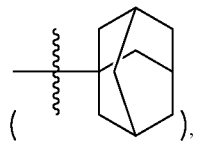

each of which is optionally substituted with one or two substituents R$^{5a}$. preferably, CyC is cyclopentyl or cyclohexyl, each of which is optionally substituted with one or two substituents R$^{5a}$.

In one embodiment, CyC Is heterocyclyl selected from:
a) monocyclic 4 to 9-membered heterocyclyl groups containing one nitrogen or oxygen or sulfur heteroatom as ring member;
b) monocyclic 4 to 9-membered heterocyclyl groups containing two heteroatoms selected from oxygen, sulfur and nitrogen as ring members; and
c) 5 to 20-membered spiro heterocyclyl comprising one or two heteroatoms selected from nitrogen, sulfur and oxygen as ring members,
each of which is optionally substituted with one or two R$^{5a}$.

In a preferred embodiment, CyC is monocyclic 4 to 6-membered heterocyclyl groups containing one nitrogen or oxygen or sulfur heteroatom as ring member. More preferably, Cyc is selected from oxetanyl, tetrahydrofuranyl, tetrahydropyranyl, azetidinyl, pyrrolidinyl, and piperidyl Even more preferably, CyC is selected from oxetan-2-yl, Oxetan-3-yl, tetrahydrofuran-4-yl, tetrahydrofuran-2-yl, tetrahydrofuran-3-yl, tetrahydropyran-2-yl, tetrahydropyran-3-yl, tetrahydropyran-4-yl, azetidin-3-yl, azetidin-2-yl, pyrrolidin-2-yl, pyrrolidin-3-yl, piperdin-4-yl, piperdin-2-yl, and piperdin-3-yl.

In a preferred embodiment, CyC is monocyclic 6-membered heterocyclyl group containing two heteroatoms selected from oxygen and nitrogen as ring members. More preferably, CyC is dioxanyl, morpholino, morpholinyl, or piperzinyl. Even more preferably 1,3-dioxan-2-yl, 1,3-dioxan-4-yl, 1,4-dioxan-2-yl, morpholin-1-yl, morpholin-2-yl, or morpholin-3-yl.

In a preferred embodiment, CyC is 4-membered/4-membered, 3-membered/5-membered, 4-membered/5-membered, 4-membered/6-membered, 5-membered/5-membered, or 5-membered/6-membered mono-spiro heterocyclyl comprising one or two nitrogen or oxygen as ring members. More preferably, CyC is

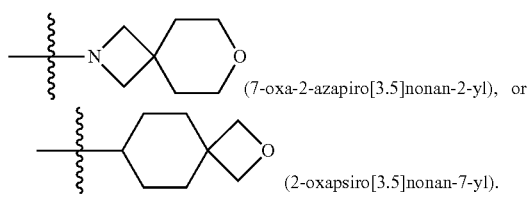

In a preferred embodiment, R$^{5a}$ is independently selected from hydrogen, halogen, cyano, oxo, —OR$^{5b}$, —NR$^{5b}$R$^{5c}$, —COR$^{5b}$, —SO$_2$R$^{5b}$, —C$_{1-8}$alkyl, —C$_{2-8}$alkynyl, monocyclic C$_{3-8}$-cycloalkyl, or monocyclic 4 to 9-membered heterocyclyl group containing one or two heteroatoms selected from nitrogen or oxygen or sulfur heteroatom as ring members, each of said —C$_{1-8}$alkyl and monocyclic 4 to 9-membered heterocyclyl group is optionally substituted with one or two substituents R$^{5e}$. Preferably, cycloalkyl as R$^{5a}$ is C$_{3-6}$-cycloalkyl; more preferably cyclopropyl. Preferably, heterocyclyl as R$^{5a}$ is 4 to 6-membered heterocyclyl groups containing one or two heteroatoms selected from nitrogen or oxygen or sulfur heteroatom as ring members. More preferably, heterocyclyl as R$^{5a}$ is oxetanyl, tetrahydrofuranyl, tetrahydropyranyl, piperzinyl, or morpholinyl. Even more preferably, heterocyclyl as R$^{5a}$ is oxetan-3-yl, tetrahydrofuran-3-yl tetrahydro-2H-pyran-4-yl, or morphin-4-yl.

In one embodiment, heterocyclyl as R$^{5e}$ is monocyclic 4 to 9-membered heterocyclyl group containing one or two heteroatoms selected from nitrogen or oxygen or sulfur heteroatom as ring members. Preferably, heterocyclyl as R$^{5e}$ is tetrahydro-pyran-4-yl.

In one embodiment, R$^{5a}$ is —NR$^{5b}$R$^{5c}$, wherein R$^{5b}$ is hydrogen, and R$^{5c}$ is heterocyclyl. In a more preferred embodiment, R$^{5a}$ is —NR$^{5b}$R$^{5c}$, wherein R$^{5b}$ is hydrogen, and R$^{5c}$ is tetrahydro-pyran-4-yl. In one embodiment, R$^{5a}$ is —NR$^{5b}$R$^{5c}$, wherein R$^{5b}$ and R$^{5c}$ are each independently hydrogen or —C$_{1-6}$alkyl substituted with cycloalkyl, preferably —C$_{1-6}$alkyl substituted with monocyclic C$_{3-8}$-cycloalkyl.

In one embodiment, R$^{5a}$ is —OR$^{5b}$ or —SO$_2$R$^{5b}$, wherein R$^{5b}$ is hydrogen or C$_{1-8}$alkyl, preferably methyl.

In one embodiment, R$^{5a}$ is —COR$^{5b}$, wherein R$^{5b}$ is hydrogen or C$^{1-8}$alkyl optionally substituted with —NR$^{5f}$R$^{5g}$, wherein R$^{5f}$ and R$^{5g}$ are each independently hydrogen or C$_{1-8}$alkyl, preferably methyl.

In one embodiment, two adjacent R$^5$ on the phenyl ring together with the phenyl ring form indazolyl which is substituted with tetrahydropyranyl.

In some embodiment, m is 1, and $R^5$ is -$L^5$-CyC selected, from the group consisting of:
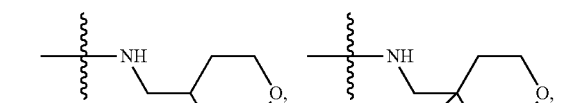
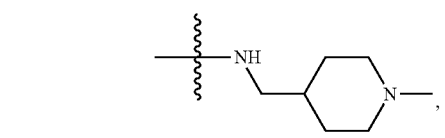
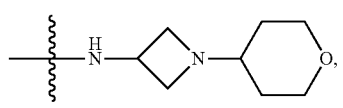
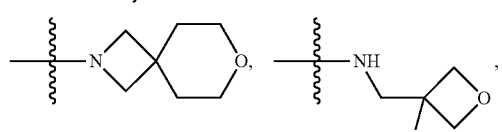
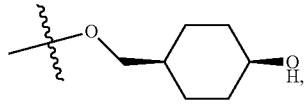
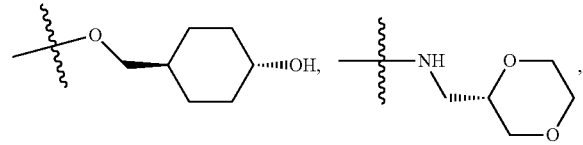
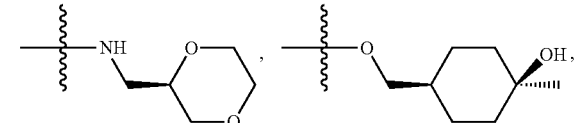
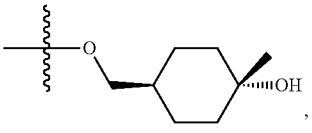
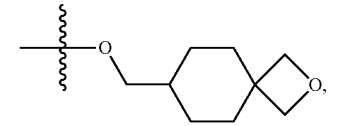
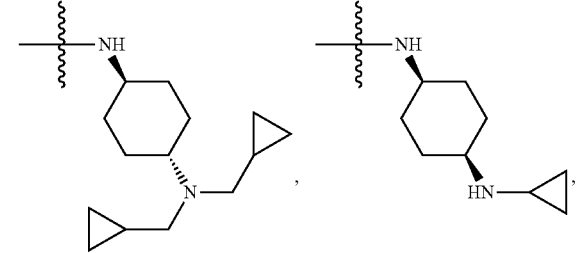
-continued
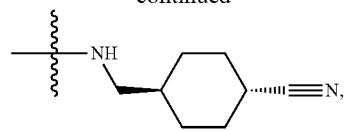
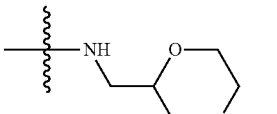
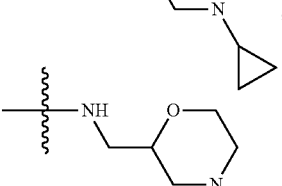
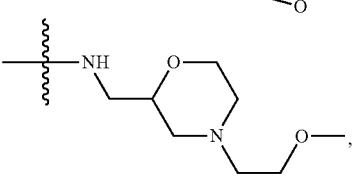
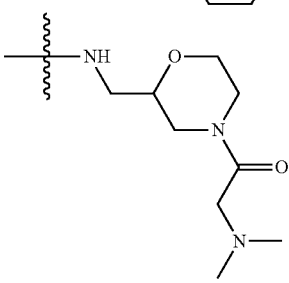
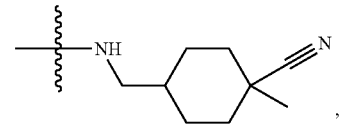
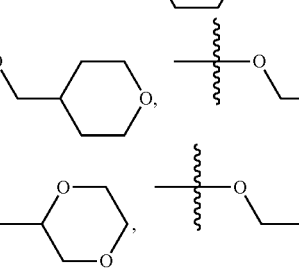
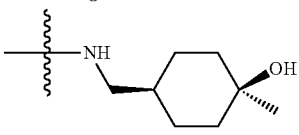
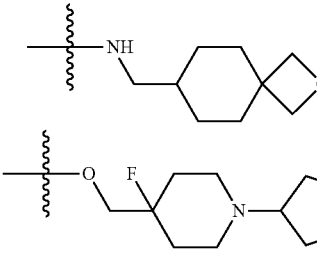

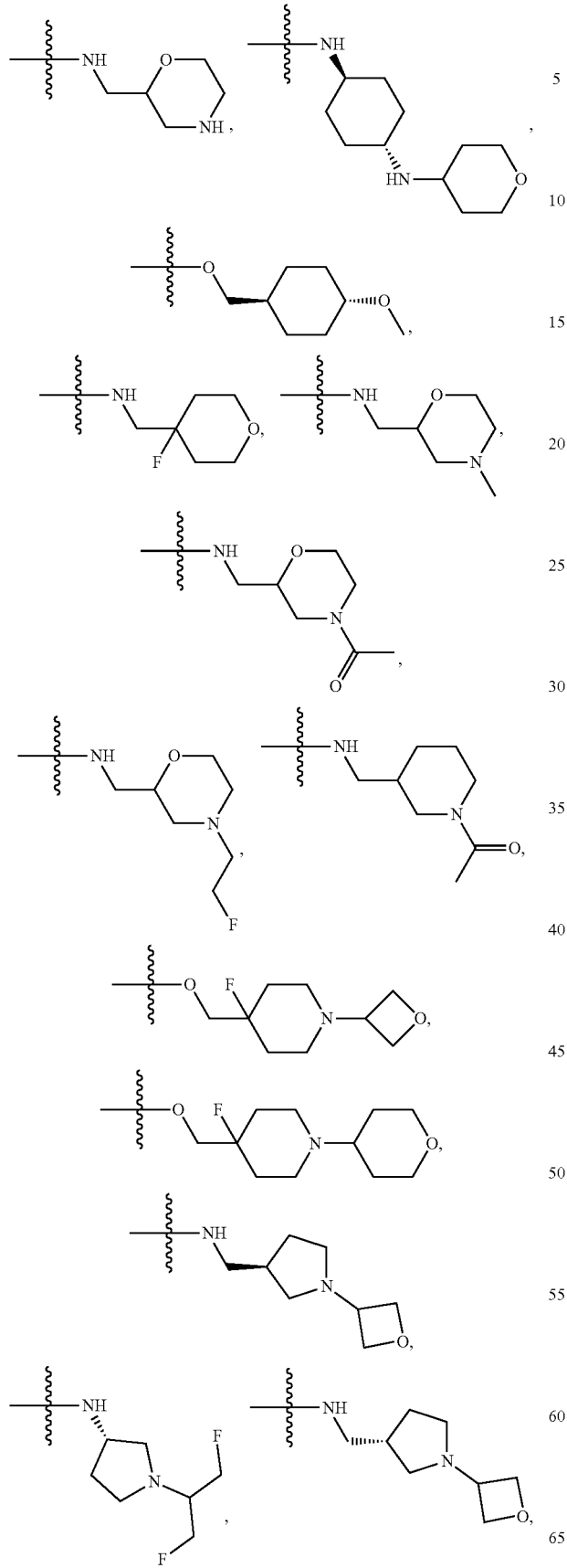
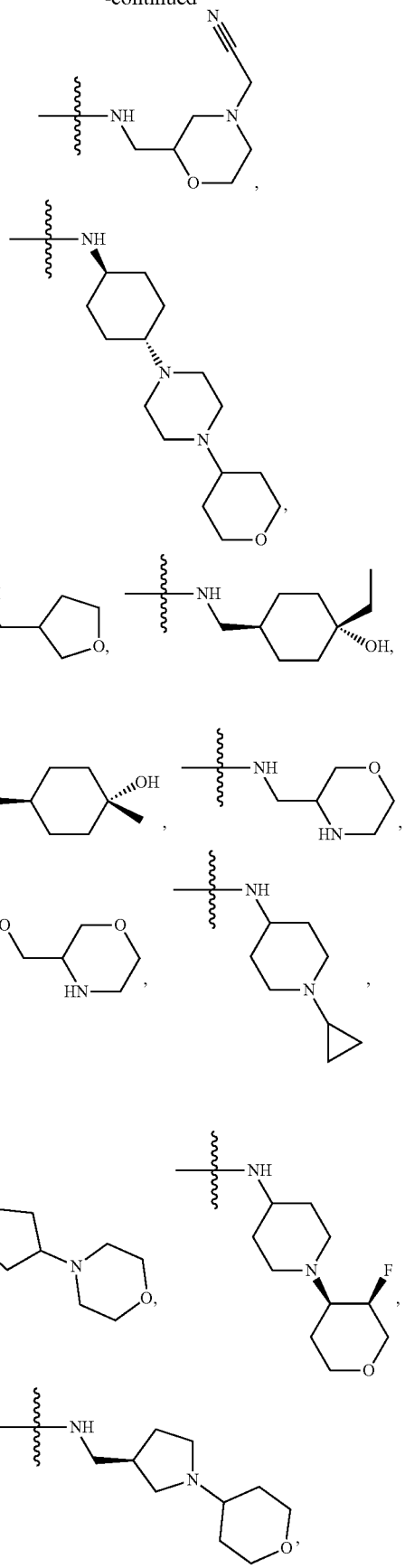

75
-continued
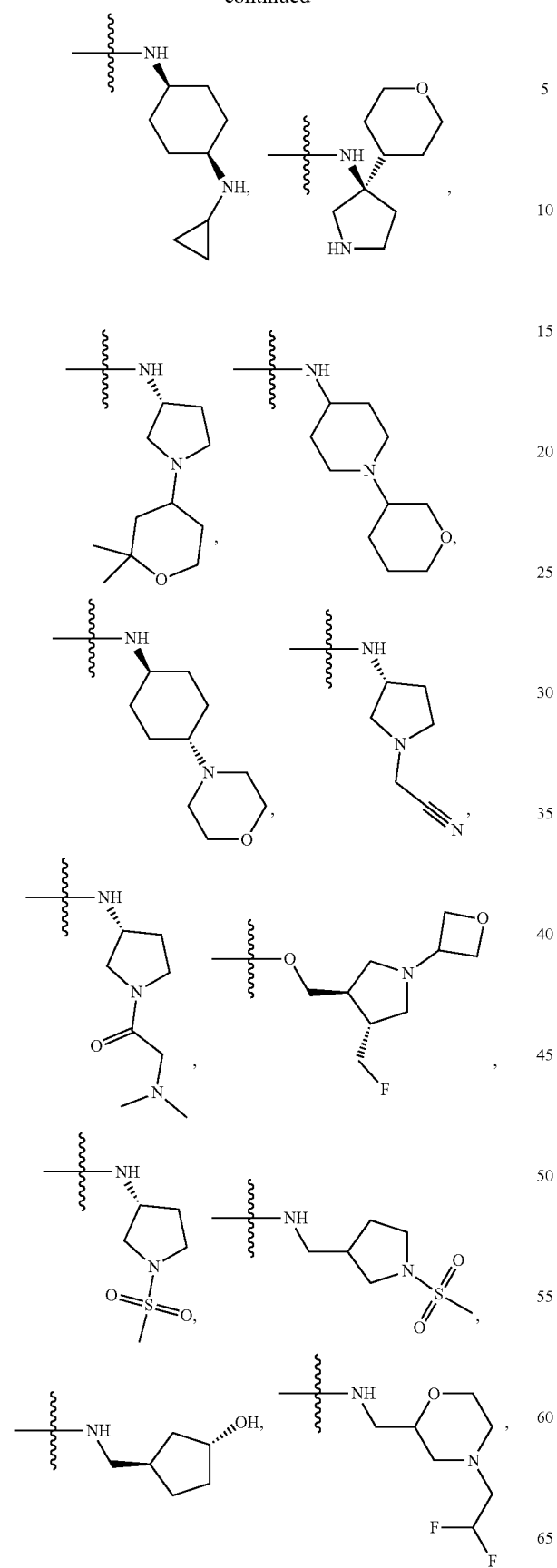
76
-continued
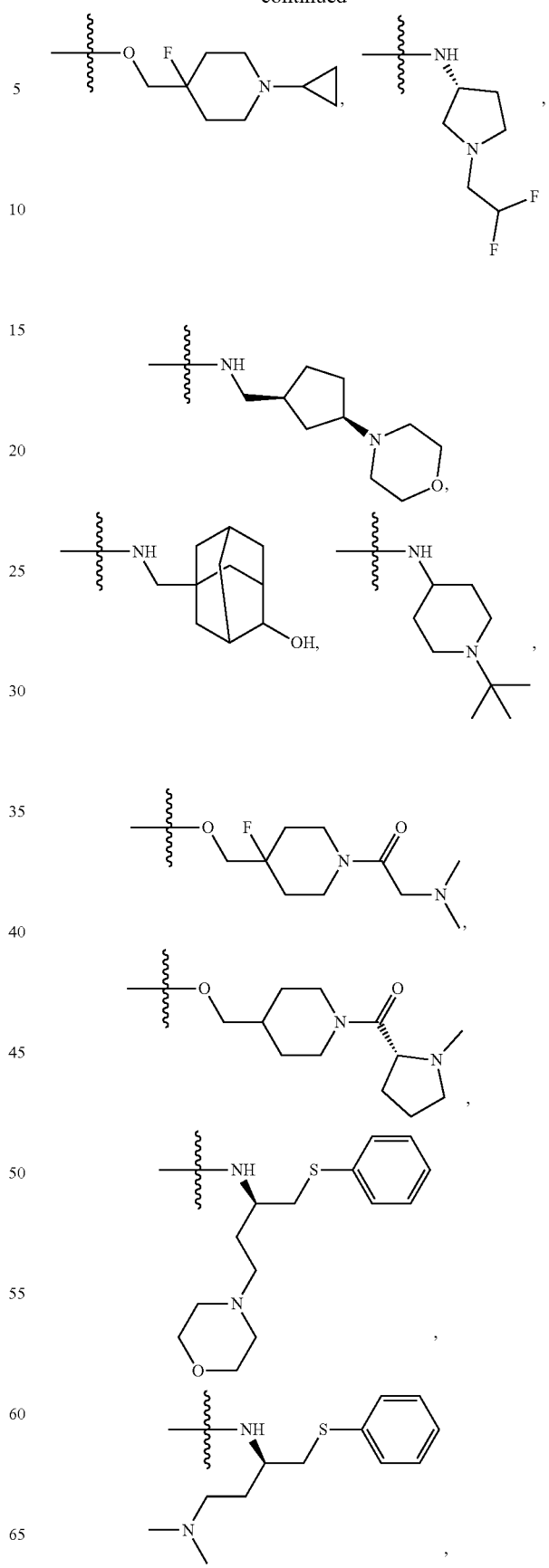

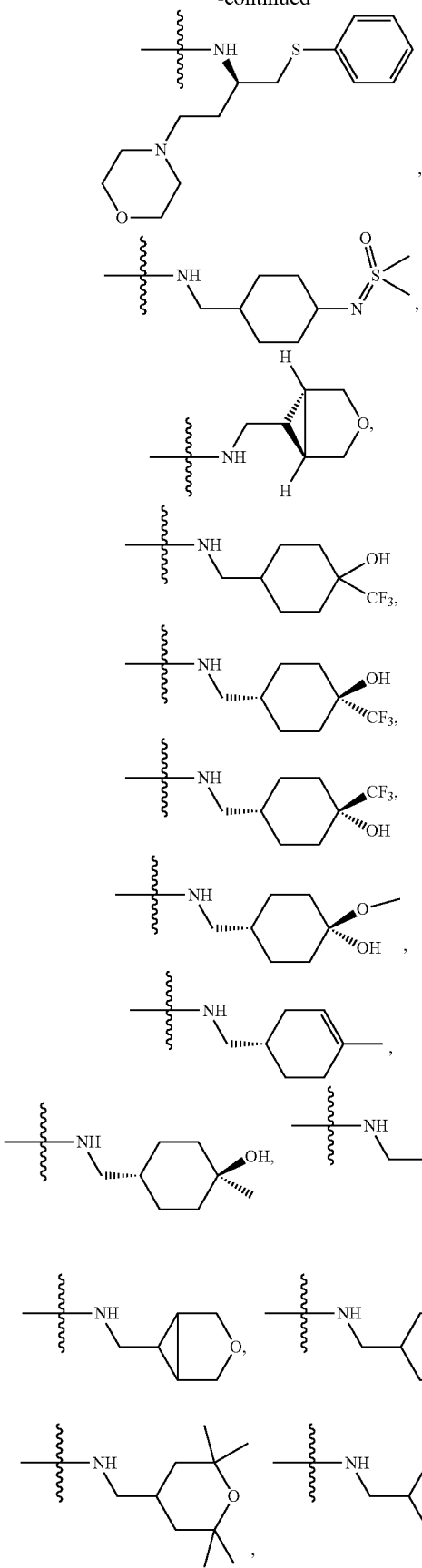
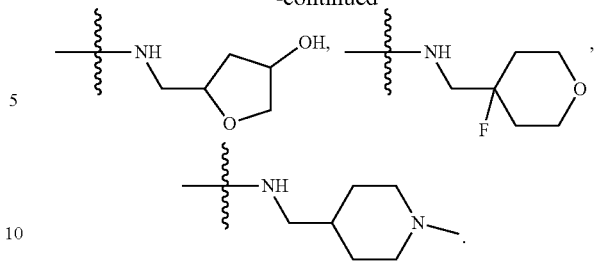
In a preferred embodiment, m is 1 and R⁵ is
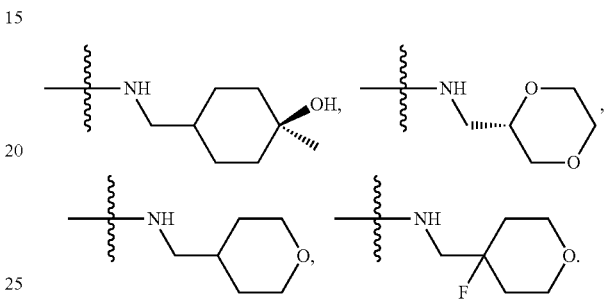
In some embodiment, the carbon atom at position 2 of the pyrrolidinyl ring, to which the phenyl ring in the subgenus formulas (III), (III-A), (III-B), (III-C), (III-D) or (III-E) is attached, is of (S)-configuration.
In some embodiment, compound of formula (I) has the formula (IV)
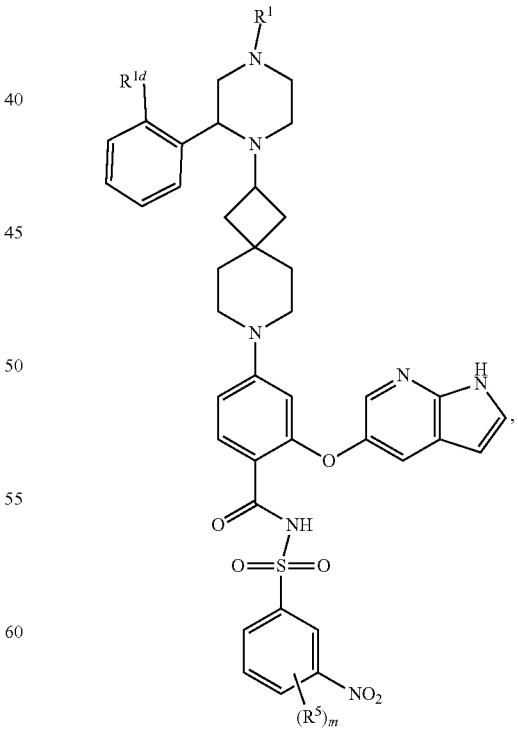
wherein the variable $R^1$, $R^{1d}$, $R^5$ and m are defined with Formula (I).

In some embodiment, the carbon atom at position 2 of the piperazinyl ring, to which the phenyl ring in the subgenus formula (IV) is attached, is of (S)- or (R)-configuration.

The inventors of the present application have found that the compounds of formula (III), including subgenus formulas (III-A), (III-B), (III-C), (III-D) or (III-E), and formula (IV) are more potent and highly selective due to the optimum combination of the spiro or phenylene moiety and substitution of a phenyl group at position of the nitrogen-linked heterocyclyl (in particular the 2-(2-substituted phenyl)pyrrolidin-1-yl moiety for formula (III) and 2-(2-substituted phenyl)piperazin-1-yl for formula (IV)) of the compounds disclosed herein.

Disclosed here are intermediate compounds selected from a compound selected from:

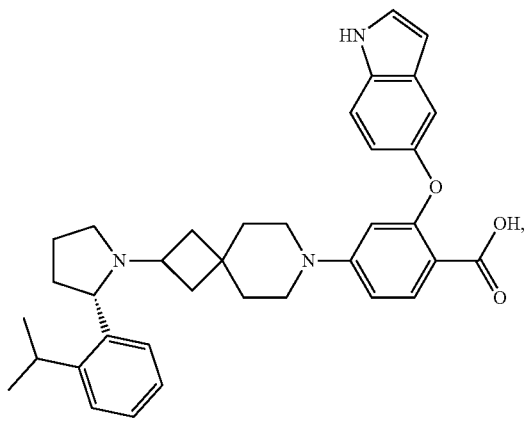

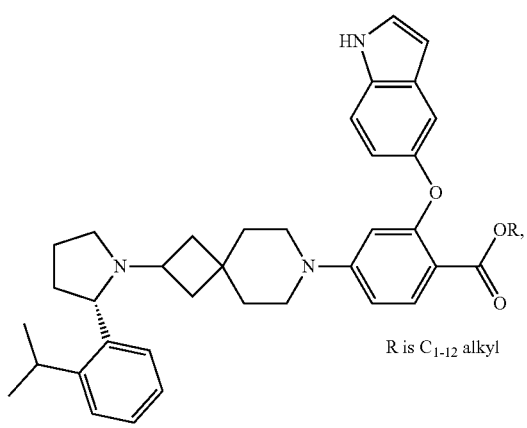

R is C$_{1-12}$ alkyl

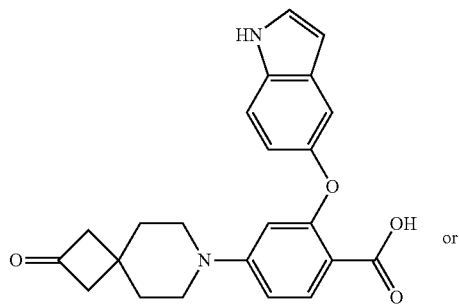

or

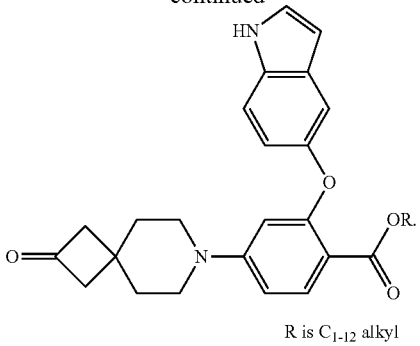

R is C$_{1-12}$ alkyl

Disclosed herein is a method for treating dysregulated apoptotic diseases, comprising administering a subject in need thereof a therapeutically effective amount of the compound disclosed herein, or a pharmaceutically acceptable salt thereof, or a stereoisomer thereof. In one embodiment, the dysregulated apoptotic disease is cancer, such as, bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer, spleen cancer published in WO 2005049593 and WO 2005049594.

In one embodiment, the dysregulated apoptotic disease is autoimmune disease, such as, Systemic Lupus Erythematosus (SLE).

Disclosed herein a pharmaceutical composition comprising the compound disclosed herein, or a pharmaceutically acceptable salt thereof, or a stereoisomer thereof, and a pharmaceutically acceptable carrier.

DETAILED DESCRIPTION OF THE INVENTION

Definitions

The following terms have the indicated meanings throughout the specification:

As used herein, including the appended claims, the singular forms of words such as "a", "an", and "the", include their corresponding plural references unless the context clearly dictates otherwise.

The term "or" is used to mean, and is used interchangeably with, the term "and/or" unless the context clearly dictates otherwise.

The term "alkyl" refers to a hydrocarbon group selected from linear and branched saturated hydrocarbon groups comprising from 1 to 18, such as from 1 to 12, further such as from 1 to 10, more further such as from 1 to 8, or from 1 to 6, or from 1 to 4, carbon atoms. Examples of alkyl groups comprising from 1 to 6 carbon atoms (i.e., C$_{1-6}$ alkyl) include, but not limited to, methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), 1,1-dimethylethyl or t-butyl ("t-Bu"), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl groups. The alkyl group can be optionallyenriched in deuterium, e.g., -CD$_3$, -CD$_2$CD$_3$ and the like.

The term "halogen" refers to fluoro (F), chloro (Cl), bromo (Br) and iodo (I).

The term "haloalkyl" refers to an alkyl group in which one or more hydrogen is/are replaced by one or more halogen atoms such as fluoro, chloro, bromo, and iodo. Examples of the haloalkyl include haloC$_{1-8}$alkyl, haloC$_{1-6}$alkyl or halo C$_{1-4}$alkyl, but not limited to —CF$_3$, —CH$_2$Cl, —CH$_2$CF$_3$, CCl$_2$, CF$_3$, and the like.

The term "alkenyl" refers to a hydrocarbon group selected from linear and branched hydrocarbon groups comprising at least one C=C double bond and from 2 to 18, such as from 2 to 8, further such as from 2 to 6, carbon atoms. Examples of the alkenyl group, e.g., C$_{2-6}$ alkenyl, include, but not limited to ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-dienyl, hex-1-enyl, hex-2-enyl, hex-3-enyl, hex-4-enyl, and hexa-1,3-dienyl groups.

The term "alkynyl" refers to a hydrocarbon group selected from linear and branched hydrocarbon group, comprising at least one C≡C triple bond and from 2 to 18, such as 2 to 8, further such as from 2 to 6, carbon atoms. Examples of the alkynyl group, e.g., C$_{2-6}$ alkynyl, include, but not limited to ethynyl, 1-propynyl, 2-propynyl (propargyl), 1-butynyl, 2-butynyl, and 3-butynyl groups.

The term "alkyloxy" or "alkoxy" refers to an alkyl group as defined above attached to the parent molecular moiety through an oxygen atom. Examples of an alkyloxy, e.g., C$_{1-6}$alkyloxy or C$_{1-4}$ alkyloxy includes, but not limited to, methoxy, ethoxy, isopropoxy, propoxy, n-butoxy, tert-butoxy, pentoxy and hexoxy and the like.

The term "cycloalkyl" refers to a hydrocarbon group selected from saturated cyclic hydrocarbon groups, comprising monocyclic and polycyclic (e.g., bicyclic and tricyclic) groups including fused, bridged or spiro cycloalkyl.

For example, the cycloalkyl group may comprise from 3 to 12, such as from 3 to 10, further such as 3 to 8, further such as 3 to 6, 3 to 5, or 3 to 4 carbon atoms. Even further for example, the cycloalkyl group may be selected from monocyclic group comprising from 3 to 12, such as from 3 to 10, further such as 3 to 8, 3 to 6 carbon atoms. Examples of the monocyclic cycloalkyl group include cyclopropyl, cyclobutyl, cyclopentyl, 1-cyclopent-1-enyl, cyclohexyl, cycloheptyl, cyclooctyl, cyclononyl, cyclodecyl, cycloundecyl, and cyclododecyl groups. In particular, Examples of the saturated monocyclic cycloalkyl group, e.g., C$_{3-8}$ cycloalkyl, include, but not limited to cyclopropyl, cyclobutyl, cyclopentyl, cyclohexyl, cycloheptyl, and cyclooctyl groups. In a preferred embedment, the cycloalkyl is a monocyclic ring comprising 3 to 6 carbon atoms (abbreviated as C$_{3-6}$-cycloalkyl), including but not limited to, cyclopropyl, cyclobutyl, cyclopentyl, and cyclohexyl. Examples of the bicyclic cycloalkyl groups include those having from 7 to 12 ring atoms arranged as a fused bicyclic ring selected from [4.4], [4,5], [5,5], [5,6] and [6,6] ring systems, or as a bridged bicyclic ring selected from bicyclo [2.2.1]heptane, bicyclo[2.2.2]octane, and bicyclo[3,2,2] nonane. Further Examples of the bicyclic cycloalkyl groups include those arranged as a bicyclic ring selected from [5,6] and [6,6] ring systems, such as

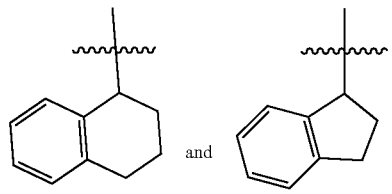 [SMILES: *C1CCCc2ccccc21 ; *C1CCc2ccccc21]

wherein the wavy lines indicate the points of attachment. The ring may be saturated or have at least one double bond (i.e. partially unsaturated), but is not fully conjugated, and is not aromatic, as aromatic is defined herein.

The term "spiro cycloalkyl" refers to a cyclic structure which contains carbon atoms and is formed by at least two rings sharing one atom. The term "7 to 10-membered spiro cycloalkyl" refers to a cyclic structure which contains 7 to 10 carbon atoms and is formed by at least two rings sharing one atom.

The term "fused cycloalkyl" refers to a fused ring which contains carbon atoms and is formed by two or more rings sharing two adjacent atoms. The term "4 to 10-membered fused cycloalkyl" refers to a fused ring which contains 4 to 10 ring carbon atoms and is formed by two or more rings sharing two adjacent atoms.

Examples include but are not limited to bicyclo[1.1.0] butyl, bicyclo[2.1.0]pentyl, bicyclo[3.1.0]hexyl, bicyclo [4.1.0]heptyl, bicyclo[3.3.0]octyl, bicyclo[4.2.0]octyl, decalin, as well as benzo 3 to 8-membered cycloalkyl, benzo C$_{4-6}$-cycloalkenyl, 2,3-dihydro-1H-indenyl, 1H-indenyl, 1,2,3,4-tetralyl, 1,4-dihydronaphthyl, etc. Preferred embodiments are 8 to 9 membered fused cyclyl, which refer to cyclic structures containing 8 to 9 ring atoms within the above examples.

The term "bridged cycloalkyl" refers to a cyclic structure which contains carbon atoms and is formed by two rings sharing two atoms which are not adjacent to each other. The term "7 to 10-membered bridged cycloalkyl" refers to a cyclic structure which contains 7 to 12 carbon atoms and is formed by two rings sharing two atoms which are not adjacent to each other.

The term "cycloalkenyl" refers to non-aromatic cyclic alkyl groups of from 3 to 10 carbon atoms having single or multiple rings and having at least one double bond and preferably from 1 to 2 double bonds. In one embodiment, the cycloalkenyl is cyclopentenyl or cyclohexenyl, preferably cyclohexenyl.

The term "cycloalkynyl" refers to non-aromatic cycloalkyl groups of from 5 to 10 carbon atoms having single or multiple rings and having at least one triple bond.

The term "aryl" used alone or in combination with other terms refers to a group selected from:
  a) 5- and 6-membered carbocyclic aromatic rings, e.g., phenyl;
  b) bicyclic ring systems such as 7 to 12-membered bicyclic ring systems, wherein at least one ring is carbocyclic and aromatic, e.g., naphthyl and indanyl; and,
  c) tricyclic ring systems such as 10 to 15-membered tricyclic ring systems wherein at least one ring is carbocyclic and aromatic, e.g., fluorenyl.

The terms "aromatic hydrocarbon ring" and "aryl" are used interchangeably throughout the disclosure herein. In some embodiments, a monocyclic or bicyclic aromatic hydrocarbon ring has 5 to 10 ring-forming carbon atoms (i.e., C$_{5-10}$ aryl). Examples of a monocyclic or bicyclic aromatic hydrocarbon ring includes, but not limited to, phenyl, naphth-1-yl, naphth-2-yl, anthracenyl, phenanthrenyl, and the like. In some embodiments, the aromatic hydrocarbon ring is a naphthalene ring (naphth-1-yl or naphth-2-yl) or phenyl ring. In some embodiments, the aromatic hydrocarbon ring is a phenyl ring.

The term "heteroaryl" refers to a group selected from:
a) 5-, 6- or 7-membered aromatic, monocyclic rings comprising at least one heteroatom, for example, from 1 to 4, or, in some embodiments, from 1 to 3, in some embodiments, from 1 to 2, heteroatoms, selected from nitrogen (N), sulfur (S) and oxygen (O), with the remaining ring atoms being carbon;
b) 8- to 12-membered bicyclic rings comprising at least one heteroatom, for example, from 1 to 4, or, in some embodiments, from 1 to 3, or, in other embodiments, 1 or 2, heteroatoms, selected from N, O, and S, with the remaining ring atoms being carbon and wherein at least one ring is aromatic and at least one heteroatom is present in the aromatic ring; and
c) 11- to 14-membered tricyclic rings comprising at least one heteroatom, for example, from 1 to 4, or in some embodiments, from 1 to 3, or, in other embodiments, 1 or 2, heteroatoms, selected from N, O, and S, with the remaining ring atoms being carbon and wherein at least one ring is aromatic and at least one heteroatom is present in an aromatic ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle Is not more than 1. When the heteroaryl group contains more than one heteroatom ring member, the heteroatoms may be the same or different. The nitrogen atoms in the ring(s) of the heteroaryl group can be oxidized to form N-oxides. The term "C-linked heteroaryl" as used herein means that the heteroaryl group is connected to the core molecule by a bond from a C-atom of the heteroaryl ring The terms "aromatic heterocyclic ring" and "heteroaryl" are used interchangeable throughout the disclosure herein. In some embodiments, a monocyclic or bicyclic aromatic heterocyclic ring has 5-, 6-, 7-, 8-, 9- or 10-ring forming members with 1, 2, 3, or 4 heteroatom ring members independently selected from nitrogen (N), sulfur (S) and oxygen (O) and the remaining ring members being carbon. In some embodiments, the monocyclic or bicyclic aromatic heterocyclic ring is a monocyclic or bicyclic ring comprising 1 or 2 heteroatom ring members independently selected from nitrogen (N), sulfur (S) and oxygen (O). In some embodiments, the monocyclic or bicyclic aromatic heterocyclic ring is a 5- to 6-membered heteroaryl ring, which is monocyclic and which has 1 or 2 heteroatom ring members independently selected from nitrogen (N), sulfur (S) and oxygen (O). In some embodiments, the monocyclic or bicyclic aromatic heterocyclic ring is a 8- to 10-membered heteroaryl ring, which is bicyclic and which has 1 or 2 heteroatom ring members independently selected from nitrogen, sulfur and oxygen.

Examples of the heteroaryl group or the monocyclic or bicyclic aromatic heterocyclic ring include, but are not limited to, (as numbered from the linkage position assigned priority 1) pyridyl (such as 2-pyridyl, 3-pyridyl, or 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl (such as 1,2,3-thiadiazolyl, 1,2,4-thiadiazolyl, or 1,3,4-thiadiazolyl), tetrazolyl, thienyl (such as thien-2-yl, thien-3-yl), triazinyl, benzothienyl, furyl or furanyl, benzofuryl, benzoimidazolyl, indolyl, isoindolyl, indolinyl, oxadiazolyl (such as 1,2,3-oxadiazolyl, 1,2,4-oxadiazolyl, or 1,3,4-oxadiazolyl), phthalazinyl, pyrazinyl, pyridazinyl, pyrrolyl, triazolyl (such as 1,2,3-triazolyl, 1,2,4-triazolyl, or 1,3,4-triazolyl), quinolinyl, isoquinolinyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzofuranyl, benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl (such as furazan-2-yl, furazan-3-yl), benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

"Heterocyclyl", "heterocycle" or "heterocyclic" are interchangeable and refer to a non-aromatic heterocyclyl group comprising one or more heteroatoms selected from the group consisting of NH, O, S, SO or $SO_2$ heteroatoms as ring members, with the remaining ring members being carbon, including monocyclic, fused, bridged, and spiro ring, i.e., containing monocyclic heterocyclyl, bridged heterocyclyl, spiro heterocyclyl, and fused heterocyclic groups.

The term "monocyclic heterocyclyl" refers to monocyclic groups in which at least one ring member is a heteroatom selected from the group consisting of NH, O, S, SO or $SO_2$. A heterocycle may be saturated or partially saturated.

Exemplary monocyclic 4 to 9-membered heterocyclyl groups include, but not limited to, (as numbered from the linkage position assigned priority 1) pyrrolidin-1-yl, pyrrolidin-2-yl, pyrrolidin-3-yl, imidazolidin-2-yl, imidazolidin-4-yl, pyrazolidin-2-yl, pyrazolidin-3-yl, piperidin-1-yl, piperidin-2-yl, piperidin-3-yl, piperidin-4-yl, 2,5-piperazinyl, pyranyl, morpholinyl, morpholino, morpholin-2-yl, morpholin-3-yl, oxiranyl, aziridin-1-yl, aziridin-2-yl, azocan-1-yl, azocan-2-yl, azocan-3-yl, azocan-4-yl, azocan-5-yl, thiiranyl, azetidin-1-yl, azetidin-2-yl, azetidin-3-yl, oxetanyl, thietanyl, 1,2-dithietanyl, 1,3-dithietanyl, dihydropyridinyl, tetrahydropyridinyl, thiomorpholinyl, thioxanyl, piperazinyl, homopiperazinyl, homopiperidinyl, azepan-1-yl, azepan-2-yl, azepan-3-yl, azepan-4-yl, oxepanyl, thiepanyl, 1,4-oxathianyl, 1,4-dioxepanyl, 1,4-oxathiepanyl, 1,4-oxaazepanyl, 1,4-dithiepanyl, 1,4-thiazepanyl and 1,4-diazepanyl, 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinyl, imidazolinyl, pyrimidinonyl, or 1,1-dioxo-thiomorpholinyl.

The term "spiro heterocyclyl" or "heterospirocyclyl" refers to a 5 to 20-membered polycyclic heterocyclyl with rings connected through one common carbon atom (called a spiro atom), comprising one or more heteroatoms selected from the group consisting of NH, O, S, SO or $SO_2$ heteroatoms as ring members, with the remaining ring members being carbon. One or more rings of a spiro heterocyclyl group may contain one or more double bonds, but none of the rings has a completely conjugated pi-electron system. Preferably a spiro heterocyclyl is 6 to 14-membered, and more preferably 7 to 10-membered. According to the number of common spiro atoms, a spiro heterocyclyl is divided into mono-spiro heterocyclyl, di-spiro heterocyclyl, or polyspiro heterocyclyl, and preferably refers to mono-spiro heterocyclyl or di-spiro heterocyclyl, and more preferably 4-membered/4-membered, 3-membered/5-membered, 4-membered/5-membered, 4-membered/6-membered, 5-membered/5-membered, or 5-membered/6-membered mono-spiro heterocyclyl. Representative examples of spiro heterocyclyls include, but not limited to the following groups: 2,3-dihydrospiro[indene-1,2'-pyrrolidine] (e.g., 2,3-dihydrospiro[indene-1,2'-pyrrolidine]-1'-yl), 1,3-dihydrospiro[indene-2,2'-pyrrolidine] (e.g., 1,3-dihydrospiro[indene-2,2'-pyrrolidine]-1'-yl), azaspiro[2.4]heptane (e.g., 5-azaspiro[2.4]heptane-5-yl), azaspiro[3.4]octane (e.g., 6-azaspiro[3.4]octane-6-yl), 2-oxa-6-azaspiro[3.4]octane (e.g., 2-oxa-6-azaspiro[3,4]octane-6-yl), azaspiro[3.4]octane (e.g., 6-azaspiro[3.4]octan-6-yl), azaspiro[3.4]octane (e.g., 6-azaspiro[3.4]octan-6-yl), 7-azaspiro[3.5]nonane (e.g., 7-azaspiro[3.5]nonan-7-yl), 2-azaspiro[3.5]nonane (e.g., 2-azaspiro[3.5]nonan-2-yl), 1,7-dioxaspiro[4.5]decane, 2-oxa-7-aza-spiro[4.4]nonane (e.g., 2-oxa-7-aza-spiro[4,4]non-7-yl), 7-oxaspiro[3.5]nonyl and 5-oxa-spiro[2.4]heptyl.

The term "fused heterocyclic group" refers to a 5 to 20-membered polycyclic heterocyclyl group, wherein each ring in the system shares an adjacent pair of atoms (carbon and carbon atoms or carbon and nitrogen atoms) with another ring, comprising one or more heteroatoms selected from the group consisting of NH, O, S, SO or $SO_2$ heteroatoms as ring members, with the remaining ring members being carbon. One or more rings of a fused heterocyclic group may contain one or more double bonds, but none of the rings has a completely conjugated pi-electron system. Preferably, a fused heterocyclyl is 6 to 14-membered, and more preferably 7 to 10-membered. According to the number of membered rings, a fused heterocyclyl is divided into bicyclic, tricyclic, tetracyclic, or polycyclic fused heterocyclyl, preferably refers to bicyclic or tricyclic fused heterocyclyl, and more preferably 5-membered/5-membered, or 5-membered/6-membered bicyclic fused heterocyclyl. Representative examples of fused heterocycles include, but not limited to, the following groups octahydrocyclopenta[c]pyrrole (e.g., octahydrocyclopenta[c]pyrrol-2-yl), octahydropyrrolo[3,4-c]pyrrolyl, octahydroisoindolyl, isoindolinyl (e.g., isoindoline-2-yl), octahydro-benzo[b][1,4]dioxin, dihydrobenzofuranyl, benzo[d][1,3]dioxolyl.

The term "bridged heterocyclyl" refers to a 5 to 14-membered polycyclic heterocyclic alkyl group, wherein every two rings in the system share two disconnected atoms, comprising one or more heteroatoms selected from the group consisting of NH, O, S, SO or $SO_2$ heteroatoms as ring members, with the remaining ring members being carbon. One or more rings of a bridged heterocyclyl group may contain one or more double bonds, but none of the rings has a completely conjugated pi-electron system. Preferably, a bridged heterocyclyl is 6 to 14-membered, and more preferably 7 to 10-membered. According to the number of membered rings, a bridged heterocyclyl is divided into bicyclic, tricyclic, tetracyclic or polycyclic bridged heterocyclyl, and preferably refers to bicyclic, tricyclic or tetracyclic bridged heterocyclyl, and more preferably bicyclic or tricyclic bridged heterocyclyl. Representative examples of bridged heterocyclyls include, but not limited to, the following groups: 2-azabicyclo[2.2.1]heptyl, azabicyclo[3.1.0]hexyl, 2-azabicyclo[2.2.2]octyl and 2-azabicyclo[3.3.2]decyl.

The heterocyclyl ring may be fused to aryl, heteroaryl or cycloalkyl ring, wherein the ring structure is connected to the parent heterocyclic group together.

"C-linked heterocyclyl" as used refers to a heterocyclyl group which is connected to the other part of the molecule by a direct bond from a carbon atom of the heterocyclyl ring.

"N-linked heterocyclyl" as used refers to a heterocyclyl group which is connected to the other part of the molecule by a direct bond from a nitrogen atom of the heterocyclyl ring.

Compounds disclosed herein may contain an asymmetric center and may thus exist as enantiomers. "Enantiomers" refer to two stereoisomers of a compound which are non-superimposable mirror images of one another. Where the compounds disclosed herein possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds disclosed herein and/or pharmaceutically acceptable salts thereof are intended to be included. Unless specifically mentioned otherwise, reference to one isomer applies to any of the possible isomers. Whenever the isomeric composition is unspecified, all possible isomers are included.

The term "substantially pure" as used herein means that the target stereoisomer contains no more than 35%, such as no more than 30%, further such as no more than 25%, even further such as no more than 20%, by weight of any other stereoisomer(s). In some embodiments, the term "substantially pure" means that the target stereoisomer contains no more than 10%, for example, no more than 5%, such as no more than 1%, by weight of any other stereoisomer(s).

When compounds disclosed herein contain olefinic double bonds, unless specified otherwise, such double bonds are meant to include both E and Z geometric isomers.

When compounds disclosed herein contain a di-substituted cyclohexyl or cyclobutyl group, substituents found on cyclohexyl or cyclobutyl ring may adopt cis and tram formations. Cis formation means that both substituents are found on the upper side of the 2 substituent placements on the carbon, while tram would mean that they were on opposing sides.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase exfraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

"Diastereomers" refers to stereoisomers of a compound with two or more chiral centers but which are not mirror images of one another, Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents (Eliel, E. and Wilen, S. *Stereochemistry of Organic Compounds*. New York: John Wiley & Sons, Inc., 1994; Lockmuller C. H., et al. "Chromatographic resolution of enantiomers: Selective review" *J. Chromatogr.*, 113(3) (1975): pp. 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Warner, Irving W, Ed. *Drug Stereochemistry: Analytical Methods and Pharmacology*. New York: Marcel Dekker, Inc., 1993.

"Pharmaceutically acceptable salts" refers to those salts which are, within the scope of sound medical judgment, suitable for use in contact with the tissues of humans and lower animals without undue toxicity, irritation, allergic response and the like, and are commensurate with a reasonable benefit/risk ratio, A pharmaceutically acceptable salt may be prepared in situ during the final isolation and purification of the compounds disclosed herein, or separately by reacting the tree base function with a suitable organic acid or by reacting the acidic group with a suitable base.

In addition, if a compound disclosed herein is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

As defined herein, "a pharmaceutically acceptable salt thereof" include salts of at least one compound of Formula (I), and salts of the stereoisomers of the compound of Formula (I), such as salts of enantiomers, and/or salts of diastereomers.

The terms "administration", "administering", "treating" and "treatment" herein, when applied to an animal, human, experimental subject, cell, tissue, organ, or biological fluid, mean contact of an exogenous pharmaceutical, therapeutic, diagnostic agent, or composition to the animal, human, subject, cell, tissue, organ, or biological fluid, Treatment of a cell encompasses contact of a reagent to the cell, as well as contact of a reagent to a fluid, where the fluid is in contact with the ceil. The term "administration" and "treatment" also means in vitro and ex vivo treatments, e.g., of a cell, by a reagent, diagnostic, binding compound, or by another cell. The term "subject" herein includes any organism, preferably an animal, more preferably a mammal (e.g., rat, mouse, dog, cat, rabbit) and most preferably a human.

The term "effective amount" or "therapeutically effective amount" refers to an amount of the active ingredient, such as compound that, when administered to a subject for treating a disease, or at least one of the clinical symptoms of a disease or disorder, is sufficient to affect such treatment for the disease, disorder, or symptom. The "therapeutically effective amount" can vary with the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be apparent to those skilled in the art or can be determined by routine experiments. In some embodiments, "therapeutically effective amount" is an amount of at least one compound and/or at least one stereoisomer thereof, and/or at least one pharmaceutically acceptable salt thereof disclosed herein effective to "treat" as defined above, a disease or disorder in a subject. In the case of combination therapy, the "therapeutically effective amount" refers to the total amount of the combination objects for the effective treatment of a disease, a disorder or a condition.

The pharmaceutical composition comprising the compound disclosed herein can be administrated via oral, inhalation, rectal, parenteral or topical administration to a subject in need thereof. For oral administration, the pharmaceutical composition may be a regular solid formulation such as tablets, powder, granule, capsules and the like, a liquid formulation such as water or oil suspension or other liquid formulation such as syrup, solution, suspension or the like; for parenteral administration, the pharmaceutical composition may be solution, water solution, oil suspension concentrate, lyophilized powder or the like. Preferably, the formulation of the pharmaceutical composition is selected from tablet, coated tablet, capsule, suppository, nasal spray or injection, more preferably tablet or capsule. The pharmaceutical composition can be a single unit administration with an accurate dosage. In addition, the pharmaceutical composition may further comprise additional active ingredients.

All formulations of the pharmaceutical composition disclosed herein can be produced by the conventional methods in the pharmaceutical field. For example, the active ingredient can be mixed with one or more excipients, then to make the desired formulation. The "pharmaceutically acceptable excipient" refers to conventional pharmaceutical carriers suitable for the desired pharmaceutical formulation, for example: a diluent, a vehicle such as water, various organic solvents, etc, a filler such as starch, sucrose, etc a binder such as cellulose derivatives, alginates, gelatin and polyvinylpyrrolidone (PVP); a wetting agent such as glycerol; a disintegrating agent such as agar, calcium carbonate and sodium bicarbonate; an absorption enhancer such as quaternary ammonium compound; a surfactant such as hexadecanol; an absorption carrier such as Kaolin and soap clay; a lubricant such as talc, calcium stearate, magnesium stearate, polyethylene glycol, etc. In addition, the pharmaceutical composition further comprises other pharmaceutically acceptable excipients such as a decentralized agent, a stabilizer, a thickener, a complexing agent, a buffering agent, a permeation enhancer, a polymer, aromatics, a sweetener, and a dye.

The term "disease" refers to any disease, discomfort, illness, symptoms or indications, and can be interchangeable with the term "disorder" or "condition".

Throughout this specification and the claims which follow, unless the context requires otherwise, the term "comprise", and variations such as "comprises" and "comprising" are intended to specify the presence of the features thereafter, but do not exclude the presence or addition of one or more other features. When used herein the term "comprising" can be substituted with the term "containing", "including" or sometimes "having".

Throughout this specification and the claims which follow, the term "$C_{n\text{-}m}$" indicates a range which includes the endpoints, wherein n and m are integers and indicate the number of carbons. Examples include $C_{1\text{-}8}$, $C_{1\text{-}6}$, and the like.

Unless specifically defined elsewhere in this document, all other technical and scientific terms used herein have the meaning commonly understood by one of ordinary skill in the art to which this invention belongs.

BRIEF DESCRIPTIONS OF THE DRAWINGS

FIG. 1 shows Co-crystal structure of A4a.

Figure 1:
Figure 2:
FIG. 2 show's ABT-199 analog (PDB code: 4MAN).
Figure 3:
FIG. 3 shows binding pose comparison of A4a with ABT-199 analog (PDB code: 4MAN) to Bcl2 protein.
Figure 4:
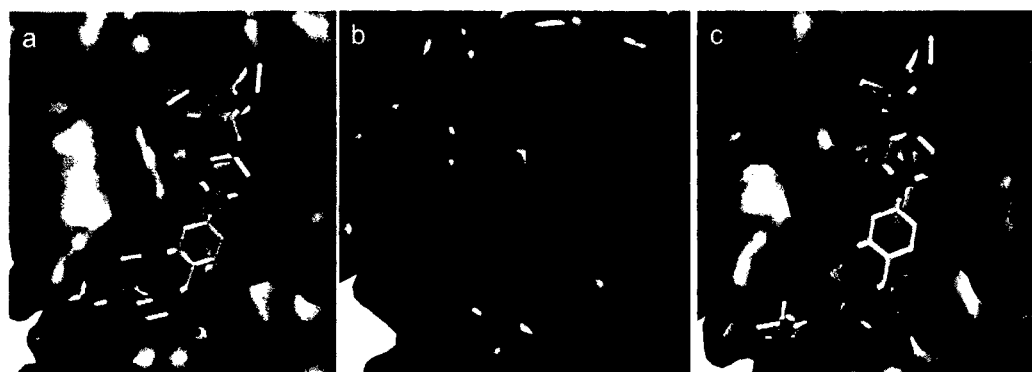

FIG. 4 shows a. Co-crystal structure of F22 with Bcl-2, b. Co-crystal structure of an ABT-199 analog with Bcl-2 (PDB code: 4MAN). c. Binding pose alignment between F22 and ABT-199 analog.

Figure 5:
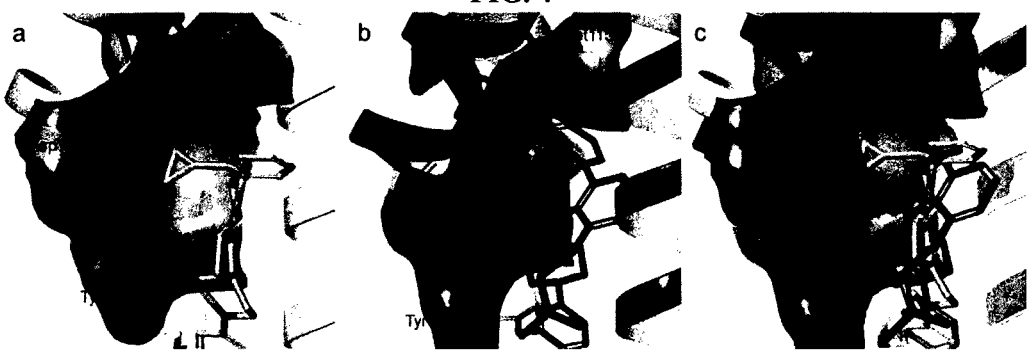

FIG. 5 show's a. Induced sub-pocket of Bcl-2 by cyclopropyl of F22 in crystal structure, b. No substituent in ABT-199 analog induces a similar sub-pocket at the same position (PDB code: 4MAN). c. Pocket surface alignment between F22 and ABT-199 analog.

Figure 6:
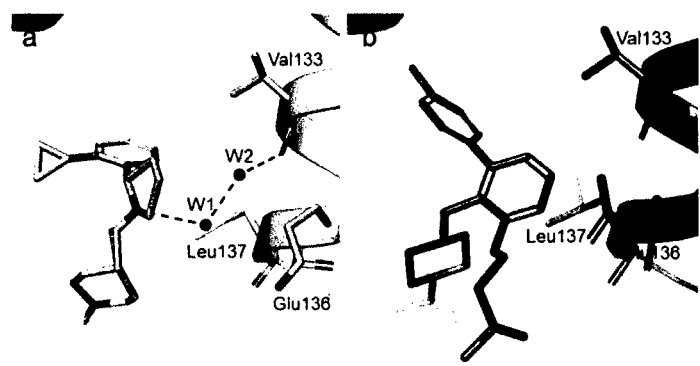

FIG. 6 shows a. Water bridge between F22 and Bcl-2 protein, b. No such water bridge can be observed between ABT-199 analog and Bcl-2.

Figure 7:
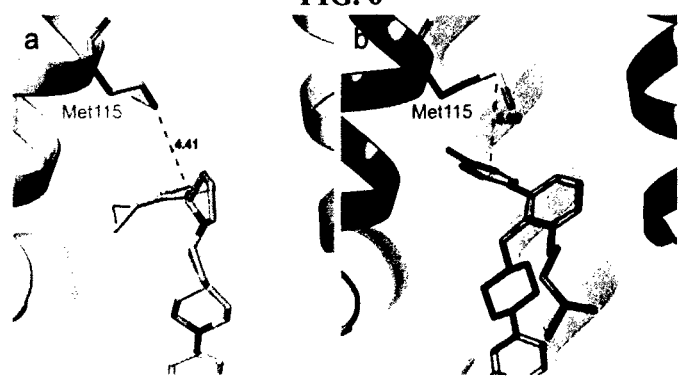

FIG. 7 show a. Sulfur-π interaction (4.41 Å) between Met115 and 2-cyclopropylphenyl of F22. b. Similar interaction (5.00 Å) between Met115 and 4-chlorophenyl of ABT-199 analog.

EXAMPLES

The examples below are intended to be purely exemplary and should not be considered to be limiting in any way. Efforts have been made to ensure accuracy with respect to numbers used (for example, amounts, temperature, etc.), but some experimental errors and deviations should be accounted for. Unless indicated otherwise, temperature is in degrees Centigrade. Reagents were purchased from commercial suppliers such as Sigma-Aldrich, Alfa Aesar, or TCI, and were used without further purification unless indicated otherwise.

Unless indicated otherwise, the reactions set forth below were performed under a positive pressure of nitrogen or argon or with a drying tube in anhydrous solvents; the reaction flasks were fitted with rubber septa for the introduction of substrates and reagents via syringe; and glassware was oven dried and/or heat dried.

$^1$H NMR spectra were recorded on a Agilent instrument operating at 400 MHz. $^1$H NMR spectra were obtained using $CDCl_3$, $CD_2Cl_2$, $CD_3OD$, $D_2O$, $d_6$-DMSO, $d_6$-acetone or $(CD_3)_2CO$ as solvent and tetramethylsilane (0.00 ppm) or residual solvent ($CDCl_3$: 7.25 ppm; $CD_3OD$: 3.31 ppm; $D_2O$: 4.79 ppm; $d_6$-DMSO: 2.50 ppm; d6-acetone: 2.05; $(CD_3)_2CO$: 2.05) as the reference standard. When peak multiplicities are reported, the following abbreviations are used: s (singlet), d (doublet), t (triplet), q (quartet), qn (quintuplet), sx (sextuplet), m (multiplet), hr (broadened), dd (doublet of doublets), dt (doublet of triplets). Coupling constants, when given, are reported in Hertz (Hz).

LC-MS spectrometer (Agilent 1260) Detector: MWD (190-400 nm), Mass detector: 6120 SQ Mobile phase: A: acetonitrile with 0.1% Formic acid, B: water with 0.1% Formic acid Column: Poroshell 120 EC-C18, 4.6×50 mm, 2.7 μm Gradient method: Flow: 1.8 mL/min

| Time (min) | A (%) | B (%) |
|---|---|---|
| 0.00 | 5 | 95 |
| 1.5 | 95 | 5 |
| 2.0 | 95 | 5 |
| 2.1 | 5 | 95 |
| 3.0 | 5 | 95 |

Preparative HPLC was conducted on a column (150×21.2 mm ID, 5 μm, Gemini NX-C18) at a different flow rate and injection volume, at room temperature and UV Detection at 214 nm and 254 nm.

In the following examples, the abbreviations below are used:
AcOH or HOAc Acetic acid
aq. aqueous
BINAP (2,2'-bis(diphenylphosphino)-1,1'-binaphthyl)
$BH_3$ Borane
Brine Saturated aqueous sodium chloride solution
$Boc_2O$ di(tert-butyl) carbonate
BSA Bovine serum albumin
DAST Diethylaminosulfur trifluoride
DBN 1,5-Diazabicyclo[4.3.0]non-5-ene
DBU 1,8-Diazabicyclo[5.4.0]undec-7-ene
DCE 1,2-Dichloroethane
DCM Dichloromethane
DMAP 4-Dimethylaminopyridine
$CH_3MgBr$ Methyl magnesium bromide
DIPEA N,N-Diisopropylethylamine
DMF N,N-Dimethylformamide
DMAC Dimethyl acetamide
DMSO Dimethyl sulfoxide
EA Ethyl acetate
EDCl 1-Ethyl-3-(3-dimethylaminopropyl)carbodiimide Hydrochloride
EDTA Ethylenediaminetetraacetic acid
EtOH Ethyl alcohol
h or hr hour
HATU 1-[Bis(dimethylamino)methylene]-1H-1,2,3-triazolo[4,5-b]pyridinium 3-oxide hexafluorophosphate
Hex Hexane
$^1$H NMR Proton Nuclear Magnetic Resonance
$H_2O_2$ Hydrogen peroxide
HOBt Hydroxybenzotriazole
IPA (i-PrOH) Isopropyl alcohol
KOAc Potassium Acetate
LAH Lithium aluminum hydride
LC-MS Liquid chromatography-mass spectrometry
LDA Lithium diisopropylamide
MeOH Methanol
MsOH Methanesulfonic acid
min minutes
MTBE Methyl tert-butyl ether
n-BuLi n-Butyl lithium
NaH Sodium hydride
$NaBH(OAc)_3$ Sodium triacetoxyborohydride NaBH₃CN Sodium cyanoborohydride
NH₄Cl Ammonium chloride
Pd/C Palladium on carbon powder
Pd(dppf)Cl₂ [1,1'Bis(diphenylphosphino)ferrocene]dichloropalladium(II)
Pd(PPh₃)₄ Tetrakis(triphenylphosphine)palladium(0)
Pd(OAc)₂ Palladium acetate
Pd(OH)₂/C Palladium hydroxide on carbon powder
PE Petroleum ether
pH -lg(hydrogen ion concentration)
Prep-HPLC Preparative high-pressure liquid chromatography
Prep-MPLC Preparative medium pressure liquid chromatography
Prep-SFC Preparative supercritical fluid chromatography
Pre-TLC Preparative thin layer chromatography
p-TsOH p-Toluenesulfonic acid
r.t. or RT room temperature
sat. Saturated
t-BuOK Potassium tert-butoxide
TBS tert-butyldimethylsilyl
THF Tetrahydrofuran
TEA Triethylamine
TFA Trifluoroacetic acid
TMSCF₃ Trimethyl(trifluoromethyl)silane

PREPARATION OF INTERMEDIATES

Intermediate 1-a: methyl 2-((1H-pyrrolo[2,3-b]pyridin-5-yl)oxy)-4-bromobenzoate

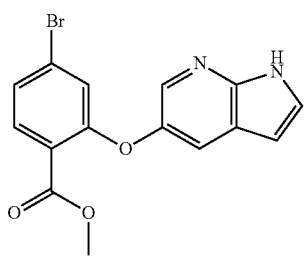 [SMILES: COC(=O)c1ccc(Br)cc1Oc1cnc2[nH]ccc2c1]

A mixture of methyl 4-bromo-2-fluorobenzoate (116.5 g, 0.5 mol), 1H-pyrrolo[2,3-b]pyridin-5-ol (67 g, 0.5 mol) and K₂CO₃ (138 g, 1.0 mol) in DMF (500 mL) was heated at 95° C. for about 16 h. The reaction mixture was cooled to ambient temperature, filtered and the filtrate was diluted with DCM (1 L). The resulting solution was washed with H₂O (500 mL×2) and concentrated. The residue was recrystallized from EA (200 mL) and PE (400 mL), the cake (68 g) was collected as the first batch. The filtrate was concentrated and dissolved in EA (500 mL). The solution was washed with H₂O (200 mL 2), concentrated, and slurried with EA (25 mL) and PE (25 mL) at reflux for 1 h, cooled to ambient temperature, filtered to give the product (38 g) as the second batch. The two batches of product were combined to afford the product (106 g, 61.3%) as a brown solid. MS (ESI, m/e) [M+1]⁺ 346.9, 348.9.

Intermediate 1-b: tert-butyl 2-((1H-pyrrolo[2,3-b]pyridin-5-yl)oxy)-4-bromobenzoate

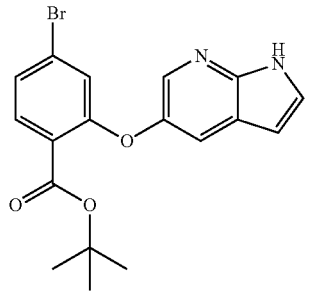 [SMILES: CC(C)(C)OC(=O)c1ccc(Br)cc1Oc1cnc2[nH]ccc2c1]

A mixture of tert-butyl 4-bromo-2-fluorobenzoate (238.5 g, 867.3 mmol), 1H-pyrrolo[2,3-b]pyridin-5-ol (116.2 g, 867.3 mmol) and K₂CO₃ (239.4 g, 1734.5 mmol) in DMF (1 L) was heated at 80° C. for about 16 h. Another batch of K₂CO₃ (100 g, 724.6 mmol) and 1H-pyrrolo[2,3-b]pyridin-5-ol (10 g, 74.6 mmol) were added into the reaction mixture, the reaction mixture was stirred at 100° C. for another 4 h. The reaction mixture was cooled to ambient temperature, filtered and the mother liquid was concentrated to remove about half volume of DMF. DCM (200 mL) and EA (200 mL) were added and stirred, the resulting mixture was filtered, the filtrate was concentrated, the residue was slurried in EA (200 mL) and PE (200 mL) at ambient temperature for 1 h. The precipitate was filtered and dried to afford the product (155 g, 46.1%) as a yellow solid. MS (ESI, m/e) [M+1]⁺ 389.0, 391.0.

Intermediate 1-c: tert-butyl 2-((1H-pyrrolo[2,3-b]pyridin-5-yl)oxy)-4-(4,4,5,5-tetramethyl-1,3,2-dioxaborolan-2-yl)benzoate

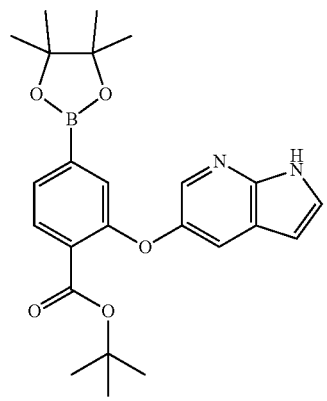 [SMILES: CC(C)(C)OC(=O)c1ccc(B2OC(C)(C)C(C)(C)O2)cc1Oc1cnc2[nH]ccc2c1]

To a mixture of tert-butyl 2-((1H-pyrrolo[2,3-b]pyridin-5-yl)oxy)-4-bromobenzoate (130 g, 334.2 mmol), 4,4,4',4',5,5,5',5'-octamethyl-2,2'-bi(1,3,2-dioxaborolane) (127 g, 501.3 mmol) and KOAc (98.3 g, 1002.3 mmol) in 1,4-dioxane (1.3 L) was added Pd(dppf)Cl₂ (24.5 g, 66.8 mmol), the mixture was stirred at 85° C. under N₂ for about 4 h. The reaction mixture was cooled to ambient temperature and concentrated, the residue was slurried in DCM (1 L), filtered, the mother liquid was concentrated, purified by chromatography column on silica (EA/DCM=1/1) to give the crude product. The crude product was recrystallized from EA (100 mL)/PE (100 mL) and dried to give the product as a brown powder (114.5 g, 78.6%). MS (ESI, m/e) [M+1]$^+$ 437.2, 355.1

Intermediate 1-d: methyl 2-((6-amino-5-chloropyridin-3-yl)oxy)-4-fluorobenzoate

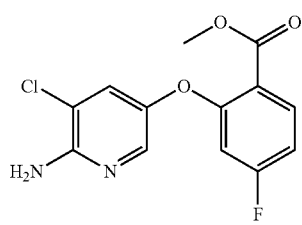 [SMILES: COC(=O)c1ccc(F)cc1Oc1cnc(N)c(Cl)c1]

Step 1: methyl 4-fluoro-2-((6-nitropyridin-3-yl)oxy)benzoate

A mixture of 5-chloro-2-nitropyridin (2.5 g, 15.75 mmol), methyl 4-fluoro-2-hydroxybenzoate (2.44 g, 14.38 mmol), K$_2$CO$_3$ (3.96 g, 28.65 mmol) in DMSO (30 mL) was stirred at 110° C. for 1 hour. TLC showed the reactant was consumed completely. The reaction mixture was cooled to room temperature and was poured into water and was then extracted with EA (40 mL×3), The combined organic layers were washed with brine (50 mL×2), dried over Na$_2$SO$_4$, filtered and concentrated to give a residue. The residue was purified by column chromatography on silica gel (eluent: PE/EA=50/1 to 1/1) to obtain methyl 4-fluoro-2-((6-nitropyridin-3-yl)oxy)benzoate (1.3 g), MS (ESI, m/e) [M+1]$^+$ 293.5.

Step 2: methyl 2-((6-aminopyridin-3-yl)oxy)-4-fluorobenzoate

The mixture of methyl 4-fluoro-2-((6-nitropyridin-3-yl)oxy)benzoate (50 g, 3.42 mmol) and Pd/C (0.8 g) in EtOH (20 mL) was stirred at 25° C. for 3 hours under H$_2$ (50 Psi). TLC showed the reactant was consumed completely. The mixture was filtered and concentrated to remove solvent. The residue was purified by prep-MPLC (eluent: PE/EA=20/1 to 5/1) to obtain methyl 2-((6-aminopyridin-3-yl)oxy)-4-fluorobenzoate (1.3 g, 4.96 mmol, yield: 72.49%). MS (ESI, m/e) [M+1]$^+$ 263.3.

Step 3: methyl 2-((6-amino-5-chloropyridin-3-yl)oxy)-4-fluorobenzoate

To the solution of methyl 2-((6-aminopyridin-3-yl)oxy)-4-fluorobenzoate (1 g, 38.14 umol) in DMF (10 mL) was added NCS (1 g, 76.28 umol). The mixture was stirred at 25° C. for 4 hours. TLC showed the reactant was consumed completely. The mixture was concentrated to remove solvent. The residue was purified by prep-MPLC (eluent: PE/EA=20/1 to 5/1) to obtain methyl 2-((6-amino-5-chloropyridin-3-yl)oxy)-4-fluorobenzoate (169 mg), fit NMR (400 MHz, CDCl$_3$) δ ppm: 7.84-7.98 (m, 2H), 7.77 (d, J=2.6 Hz, 1H), 7.26 (d, J=2.6 Hz, 1H), 6.77 (ddd, J=8.7, 7.6, 2.4 Hz, 1H), 6.48 (dd, J=10.0, 2.4 Hz, 1H), 4.88 (s, 2H), 3.81 (s, 3H). MS (ESI, m/e) [M+1]$^+$ 297.2.

Intermediate 2-a: 2-(2-cyclopropylphenyl)pyrrolidine

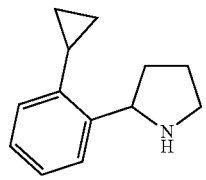 [SMILES: c1ccc(C2CCCN2)c(C2CC2)c1]

Step 1: tert-butyl 2-(2-bromophenyl)pyrrolidine-1-carboxylate

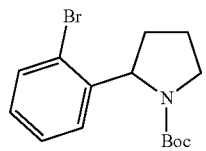 [SMILES: CC(C)(C)OC(=O)N1CCCC1c1ccccc1Br]

A mixture solution of 2-(2-bromophenyl)pyrrolidine (1.13 g, 5 mmol), Boc$_2$O (2.16 g, 10 mmol), TEA (1.01 g, 10 mmol) and DMAP (cat) in DCM (20 mL) was stirred at room temperature for 16 hrs. Then the mixture solution was concentrated, and the residue was purified by chromatography on silica-gel (eluting with 100% PE to PE/EA=5/1) to give the product (1.6 g, 98.1%) as a colorless oil. MS (ESI, m/e) [M+1]$^+$ 270.0, 272.0

Step 2: tert-butyl 2-(2-cyclopropylphenyl)pyrrolidine-1-carboxylate

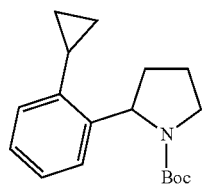 [SMILES: CC(C)(C)OC(=O)N1CCCC1c1ccccc1C1CC1]

Under a nitrogen atmosphere, a mixture of tert-butyl 2-(2-bromophenyl)pyrrolidine-1-carboxylate (1.56 g, 4.7 mmol), cyclopropyl boronic acid (1.23 g, 14.3 mmol), Pd(PPh$_3$)$_4$ (540 mg, 0.47 mmol) and K$_2$CO$_3$ (1.99 g, 14.3 mmol) in 1,4-dioxane/H$_2$O (9:1, 20 mL) was stirred at 90° C. for 16 hours. Then the reaction mixture was filtered and concentrated, the crude product (1.4 g) was used directly in next step without purification. MS (ESI, m/e) [M+1]$^+$ 232.1.

Step 3: 2-(2-cyclopropylphenyl)pyrrolidine

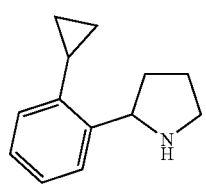 [SMILES: c1ccc(C2CCCN2)c(C2CC2)c1]

A mixture solution of tert-butyl 2-(2-cyclopropylphenyl)pyrrolidine-1-carboxylate (1.4 g) and TFA (5 mL) in DCM (50 mL) was stirred at room temperature for 16 hours. Then the mixture was concentrated to give a product (1.2 g, crude) as a yellow oil, MS (ESI, m/e) [M+1]⁺ 188.1.

Intermediate 2-b: 2-(2-isopropylphenyl)pyrrolidine

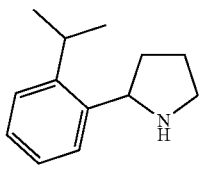

Step 1: tert-butyl 2-(2-(prop-1-en-2-yl)phenyl)pyrrolidine-1-carboxylate

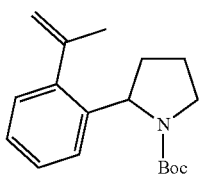 [SMILES: C=C(C)c1ccccc1C1CCCN1C(=O)OC(C)(C)C]

tert-butyl 2-(2-(prop-1-en-2-yl)phenyl)pyrrolidine-1-carboxylate was prepared using the similar procedure as tert-butyl 2-(2-cyclopropylphenyl)pyrrolidine-1-carboxylate. ¹H NMR (400 MHz, DMSO-d₆) δ ppm: 7.32-7.14 (m, 2H), 7.14-6.99 (m, 2H), 5.25 (s, 1H), 4.95-4.81 (m, 2H), 3.67-3.54 (m, 1H), 3.53-3.40 (m, 1H), 2.29-2.23 (m, 1H), 2.05 (s, 3H), 1.92-1.73 (m, 2H), 1.64 (s, 1H), 1.36 (s, 3H), 1.07 (s, 6H). MS (ESI, m/e) [M+1]⁺ 232.1.

Step 2: tert-butyl 2-(2-isopropylphenyl)pyrrolidine-1-carboxylate

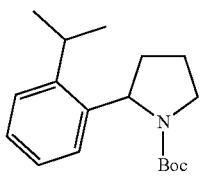 [SMILES: CC(C)c1ccccc1C1CCCN1C(=O)OC(C)(C)C]

A mixture of tert-butyl 2-(2-(prop-1-en-2-yl)phenyl)pyrrolidine-1-carboxylate (983 mg, 3.41 mmol) and Pd(OH)₂/C (100 mg) in MeOH (20 mL) was stirred overnight at room temperature under a balloon of H₂. Then the reaction mixture was filtered and concentrated to give the desired product as a colorless oil (803 mg, 81%) without further purification for the next deprotection step with TFA. ¹H NMR (400 MHz, DMSO-d₆) δ ppm: 7.27 (d, J=7.0 Hz, 1H), 7.15 (t, J=2.5, 7.0 Hz, 2H), 6.97 (d, J=7.0 Hz, 1H), 5.10-5.05 (m, 1H), 3.64-3.52 (m, 1H), 3.49-3.43 (m, 1H), 3.24-3.10 (m, 1H), 2.31-2.26 (m, 1H), 1.84-1.80 (m, 2H), 1.59-1.53 (m, 1H), 1.38 (s, 3H), 1.28-1.16 (m, 6H), 1.09 (s, 3H), 1.08 (s, 3H).

Step 3: 2-(2-isopropylphenyl)pyrrolidine

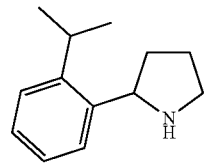

A solution of tert-butyl 2-(2-isopropylphenyl)pyrrolidine-1-carboxylate (803 mg, 2.77 mmol) in DCM (5 mL) and TFA (2 mL) was stirred at r.t. for 4 h. After solvents were removed, the resulted residue was dissolved with DCM (50 mL) and washed with aq. NaHCO₃ (30 mL×2). The organic layer was collected and dried over anhydrous Na₂SO₄, filtered and concentrated to give the desired product as a colorless oil (522 mg). ¹H NMR (400 MHz, DMSO-d₆) δ ppm: 7.52 (d, J=6.7 Hz, 1H), 7.24-7.22 (m, 1H), 7.19-7.05 (m, 2H), 4.29 (t, J=7.6 Hz, 1H), 3.30-3.23 (m, 1H), 3.27-3.02 (m, 1H), 2.91-2.82 (m, 1H), 2.14-2.06 (m, 1H), 1.79-1.71 (m, 2H), 1.41-1.32 (m, 1H), 1.19 (s, 3H), 1.17 (s, 3H), MS (ESI, m/e) [M+1]⁺ 190.1.

Intermediate 2-c: 2-(4-cyclopropylphenyl)pyrrolidine

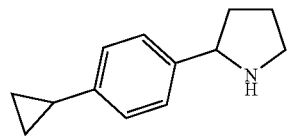 [SMILES: c1cc(C2CCCN2)ccc1C1CC1]

Step 1: tert-butyl 2-(4-bromophenyl)pyrrolidine-1-carboxylate

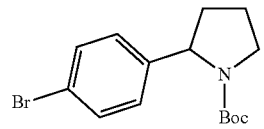 [SMILES: CC(C)(C)OC(=O)N1CCCC1c1ccc(Br)cc1]

A mixture of 2-(4-bromophenyl)pyrrolidine (2.0 g, 8.85 mmol), Boc₂O (2.9 g, 13.3 mmol), Et₃N (1.8 g, 17.7 mmol), DMAP (110 mg, 0.9 mmoL) in 20 mL of DCM was stirred for 16 hours at room temperature. The mixture was concentrated and purified by column chromatograph on silica gel using EA/PE (1/10) as an eluent to get 2.2 g (78.6%) of tert-butyl 2-(4-bromophenyl)pyrrolidine-1-carboxylate as a yellow oil. MS (ESI) m/e [M+1]⁺ 325.0, 327.0.

Step 2: tert-butyl 2-(4-cyclopropylphenyl)pyrrolidine-1-carboxylate

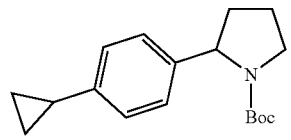 [SMILES: CC(C)(C)OC(=O)N1CCCC1c1ccc(C2CC2)cc1]

A mixture of tert-butyl 2-(4-bromophenyl)pyrrolidine-1-carboxylate (1.0 g, 3.07 mmol), cyclopropyl boronic acid (790 mg, 9.21 mmol), Pd(PPh$_3$)$_4$ (358 mg, 0.31 mmol) and K$_2$CO$_3$ (1.27 g, 9.21 mmol) in dioxane (10 mL) was heated to 100° C. for 16 hours under N$_2$. The mixture was filtrated and the filtrate was concentrated to get crude product and further purification by column chromatograph on silica gel using EA/PE (1/10, v/v) as eluent afforded 600 mg (68.1%) of tert-butyl 2-(4-cyclopropylphenyl)pyrrolidine-1-carboxylate as a yellow oil. MS (ESI) m/e [M+1–56]$^1$ 232.1.

Step 3: 2-(4-cyclopropylphenyl)pyrrolidine

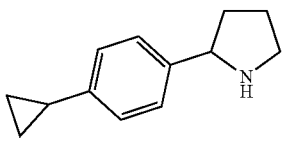 [SMILES: c1cc(C2CCCN2)ccc1C1CC1]

A solution of tert-butyl 2-(4-cyclopropylphenyl)pyrrolidine-1-carboxylate (1.2 g, 4.18 mmol) in TFA/DCM (2 mL/10 mL) was stirred at RT for 16 hr. The mixture was concentrated to remove solvent and the residue was partitioned between NaHCO$_3$ solution (10 mL) and DCM (10 mL). The organic layer was collected and dried over Na$_2$SO$_4$, concentrated to get 620 mg (79.2%) of 2-(4-cyclopropylphenyl)pyrrolidine. MS (ESI, m/e) [M+1]$^+$ 188.0.

Intermediate 2-d: 2-(2-methoxyphenyl)pyrrolidine

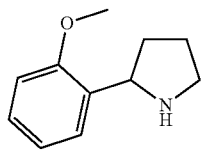

To a solution of 2-(2-bromophenyl)pyrrolidine (500 mg, 2.2 mmol) in MeOH (50 mL) was added Cuprous bromide (158.6 mg, 1.1 mmol) and sodium methanolate (358 mg, 6.6 mmol). The mixture was heated to reflux and stirred overnight. After cooled to room temperature, the mixture was filtered and concentrated, purified by chromatography column on silica (EA/PE=1/1) to give the product (300 mg, 76.6%) as a yellow oil. MS (ESI, m/e) [M+1]$^+$ 178.1.

Intermediate 2-e:
2-(2-chloro-6-fluorophenyl)pyrrolidine

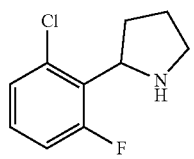 [SMILES: Fc1cccc(Cl)c1C1CCCN1]

Step 1: 3-(2-chloro-6-fluorobenzoyl)-1-vinylpyrrolidin-2-one

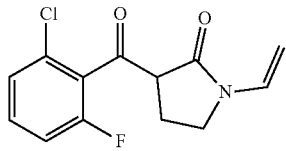 [SMILES: C=CN1CCC(C(=O)c2c(F)cccc2Cl)C1=O]

A dry, 100 mL three-necked, round-bottomed flask equipped with a mechanical stirrer, addition funnel, heating mantle, and reflux condenser, was charged with 60% sodium hydride (0.6 g, 15 mmol) and 25 mL of dry toluene. The stirred suspension was heated at reflux while a mixture of 1.1 g (10 mmol) of vinylpyrrolidin-2-one and 1.9 g (10 mmol) of methyl 2-chloro-6-fluorobenzoate was slowly added. Heating was continued for 10 hr. The reaction mixture was cooled to room temperature and the resultant thick slurry was carefully diluted with 25 mL of saturated aqueous ammonium chloride. The layers were separated, and the aqueous layer was extracted again with 25 mL of toluene. The combined organic layers were dried (MgSO$_4$) and concentrated under reduced pressure to afford 3-(2-chloro-6-fluorobenzoyl)-1-vinylpyrrolidin-2-one as a crude product. [M+1]$^+$ 268.0.

Step 2:
5-(2-chloro-6-fluorophenyl)-3,4-dihydro-2H-pyrrole

A mixture of 3-(2-chloro-6-fluorobenzoyl)-1-vinylpyrrolidin-2-one (1 g, crude) and HCl (6 M, 10 ml) was heated to reflux for 10 h. the mixture was cooled to r.t and basified to pH=10 and extracted with DCM. The organic layers were dried over anhydrous Na2SO4 and concentrated. The residue was used in next step without further purification (300 mg, crude). MS (ESI, m/e) [M+1]$^+$ 198.0

Step 3: 2-(2-chloro-6-fluorophenyl)pyrrolidine

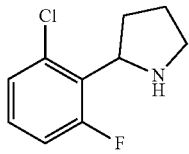 [SMILES: Fc1cccc(Cl)c1C1CCCN1]

To a solution of 5-(2-chloro-6-fluorophenyl)-3,4-dihydro-2H-pyrrole (300 mg, crude) in MeOH was added NaBH$_4$ (50 mg) and stirred at r.t for 1 h. then excess MeOH was removed under reduced pressure. The residue was added into water and extracted with DCM. The organic layers were concentrated to afford 2-(2-chloro-6-fluorophenyl)pyrrolidine, which was used in next step without further purification (100 mg, crude). MS (ESI, m/e) [M+1]⁺ 200.1.

Intermediate 2-f: 2-cyclohexylpyrrolidine

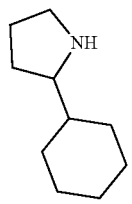 [SMILES: C1CCC(C2CCCN2)CC1]

A mixture of 2-phenylpyrrolidine (3.5 g, 23.77 mmol), PtO₂ (1.08 g, 4.75 mmol), AcOH (1.14 g, 19.02 mmol, 1.09 mL) in THF (60 mL) was degassed and purged with H₂ for 3 times, and then the mixture was stirred at 65° C. for 12 hr under H₂ atmosphere (50 psi). LC-MS showed the reaction was completed and one main peak with desired mass was detected. The reaction mixture was filtered and concentrated under reduced pressure to give a residue. The residue was purified by prep-HPLC (TFA condition) to give the product (4 g, TFA salt) as a yellow oil. The product (1 g, TFA salt) was freed by Amberlyst A-21 ion exchange resin in MeOH (60 mL), filtered and concentrated to give the product. The product was neutralized with sat. Na₂CO₃ (5 mL), extracted with DCM (80 mL), dried over Na₂SO₄, filtered and concentrated under reduced pressure to give the product (640 mg) as a yellow oil. ¹H NMR (400 MHz, CDCl₃) δ ppm: 4.37 (br s, 1H), 3.13-3.01 (m, 1H), 2.95-2.90 (m, 1H), 2.83-2.72 (m, 1H), 2.00-1.59 (m, 8H), 1.48-1.06 (m, 5H), 1.06-0.88 (m, 2H).

Intermediate 2-g:
2-(2-(trifluoromethyl)phenyl)pyrrolidine

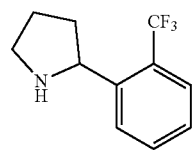 [SMILES: FC(F)(F)c1ccccc1C1CCCN1]

Step 1: tert-butyl (4-oxo-4-(2-(trifluoromethyl)phenyl)butyl)carbamate

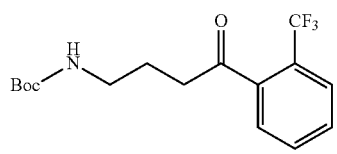 [SMILES: CC(C)(C)OC(=O)NCCCC(=O)c1ccccc1C(F)(F)F]

To a solution of 1-bromo-2-(trifluoromethyl)benzene (2 g, 8.89 mmol, 1.21 mL) in THF (15 mL) at −78° C. was added n-BuLi (2.5 M, 3.56 mL). The reaction was stirred at −78° C. for 15 minutes, then added to a solution of tert-butyl 2-oxopyrrolidine-1-carboxylate (1.65 g, 8.89 mmol, 1.51 mL) in THF (15 mL) at −78° C. After addition, the reaction mixture was warmed to 15° C. and stirred at 15° C. for 1 hr. TLC showed the reaction was ok. The mixture was quenched with sat. NH₄Cl (20 mL), extracted with EA (20 mL*2). The organic layer was separated, washed with brine, dried over with Na₂SO₄, filtered and concentrated. The residue was purified by silica gel (PE:EA=50:1 to 10:1) to afford tert-butyl (4-oxo-4-(2-(trifluoromethyl)phenyl)butyl)carbamate (2 g, 6.04 mmol, 67.91% yield) as yellow oil. ¹H NMR (400 MHz, CDCl₃) δ ppm: 7.72 (d, J=7.4 Hz, 1H), 7.64-7.53 (m, 2H), 7.44 (d, J=7.4 Hz, 1H), 4.63 (br s, 1H), 3.23 (q, J=6.4 Hz, 2H), 2.90 (t, J=7.0 Hz, 2H), 1.93 (quin, J=7.0 Hz, 2H), 1.44 (s, 9H).

Step 2:
4-amino-1-(2-(trifluoromethyl)phenyl)butan-1-one

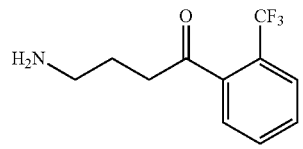 [SMILES: NCCCC(=O)c1ccccc1C(F)(F)F]

To the mixture solution of tert-butyl (4-oxo-4-(2-(trifluoromethyl)phenyl)butyl)carbamate (2.8 g, 8.45 mmol) in DCM (30 mL) was added TFA (30.80 g, 270.13 mmol, 20 mL). The mixture was stirred at 15° C. for 1 hr. The solvent was removed to afford 4-amino-1-(2-(trifluoromethyl)phenyl)butan-1-one (3.5 g, 7.24 mmol, 85.67%, TFA) as brown oil. ¹H NMR (400 MHz, CDCl₃) δ ppm: 9.14 (br s, 3H), 7.87-7.83 (m, 1H), 7.80-7.73 (m, 2H), 7.69-7.64 (m, 1H), 4.44-4.29 (m, 2H), 3.45 (t, J=7.9 Hz, 2H), 2.58-2.43 (m, 2H).

Step 3: 2-(2-(trifluoromethyl)phenyl)pyrrolidine

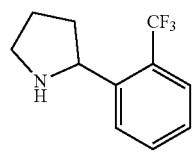 [SMILES: FC(F)(F)c1ccccc1C1CCCN1]

To the mixture solution of 4-amino-1-(2-(trifluoromethyl)phenyl)butan-1-one (3 g, 6.53 mmol, 2TFA) in EtOH (72 mL) and AcOH (8 mL) was added NaBH₃CN (697.85 mg, 11.10 mmol). The mixture was stirred at 15° C. for 12 hr. The reaction mixture was quenched with sat. NaHCO₃ solution in water (100 mL). The mixture was concentrated. The residue was dissolved with EA (100 mL). washed with water and brine, dried over with Na₂SO₄, filtered and concentrated to afford 2-(2-(trifluoromethyl)phenyl)pyrrolidine (0.71 g, 3.16 mmol, 48.33%) as yellow oil. ¹H NMR (400 MHz, CDCl₃) δ ppm: 7.83 (d, J=7.8 Hz, 1H), 7.63-7.52 (m, 2H), 7.38-7.29 (m, 1H), 4.54 (t, J=7.8 Hz, 1H), 3.27-3.25 (m, 1H), 3.18-3.03 (m, 2H), 2.27 (td, J=4.9, 7.8 Hz, 1H), 2.07-1.97 (m, 1H), 1.94-1.80 (m, 1H), 1.69-1.59 (m, 1H). MS (ESI, m/e; [M+1]⁺ 216.1/217.1.

Intermediate 2-h: 4,4-dimethyl-2-phenylpyrrolidine

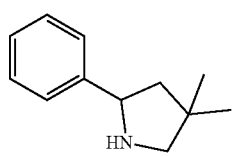

Step 1: 2,2-dimethyl-4-oxo-4-phenylbutanoic acid

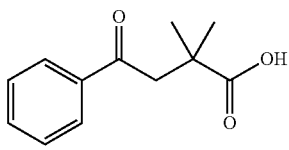

To a solution of 3,3-dimethyldihydrofuran-2,5-dione (15.3 g, 120 mmol) and AlCl$_3$ (31.92 g, 240 mmol) in DCM (200 mL) was added benzene (14.04 g, 180 mmol) dropwise with an ice-water bath. The mixture was warmed up to room temperature slowly and stirred overnight. I was poured into ice and diluted with DCM (400 mL) and conc. HCl acid (50 mL) was added and stirred until no precipitate. The organic layer was dried over anhydrous Na$_2$SO$_4$, filtered and concentrated. The residue was slurried with MTBE and PE to give the desired product as a white solid (22.52 g, 99%). $^1$H NMR (400 MHz, CDCl$_3$) δ ppm: 7.95 (d, J=8.0 Hz, 2H), 7.56 (t, J=8.0 Hz, 1H), 7.46 (t, J=8.0 Hz, 2H), 3.31 (s, 2H), 1.36 (s, 6H). MS (ESI, m/e) [M+1]$^+$ 205.1.

Step 2: N-(2,4-dimethoxybenzyl)-2,2-dimethyl-4-oxo-4-phenylbutanamide

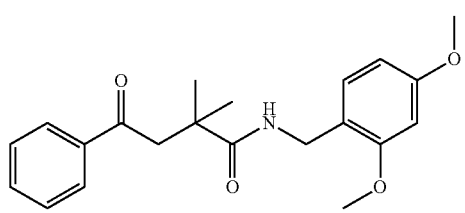 [SMILES: COc1ccc(CNC(=O)C(C)(C)CC(=O)c2ccccc2)c(OC)c1]

A solution of 2,2-dimethyl-4-oxo-4-phenylbutanoic acid (18.03 g, 87.5 mmol), (2,4-dimethoxyphenyl)methanamine (14.62 g, 87.5 mmol), HATU (33.25 g, 87.5 mmol) and Et$_3$N (13.3 g, 131.25 mmol), in DCM (200 mL) was stirred at room temperature overnight, DCM was removed. The residue was purified by column flash in silica gel eluted with EA/PE=1/4 to 1/1 (v/v) to give the desired product as a brown oil (30.2 g, 97%). MS (ESI, m/e) [M+1]$^+$ 356.1.

Step 3: 1-(2,4-dimethoxybenzyl)-3,3-dimethyl-5-phenyl-1,3-dihydro-2H-pyrrol-2-one

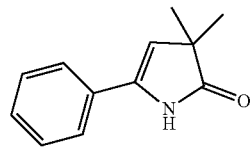

A solution of N-(2,4-dimethoxybenzyl)-2,2-dimethyl-4-oxo-4-phenylbutanamide (30.2 g, 85.1 mmol) in toluene (180 mL) and AcOH (10 mL) was refluxed overnight. It was cooled to r.t. and the solvent was removed. The residue was purified by column flash in silica gel eluted with EA/PE=1/10 to 1/1 (v/v) to give the crude product as a yellow oil (10 g, 30% yield). MS (ESI, m/e) [M+1]$^+$ 388.1.

Step 4: 3,3-dimethyl-5-phenyl-1,3-dihydro-2H-pyrrol-2-one

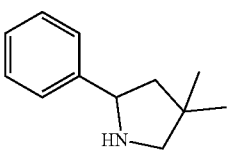

A solution of 1-(2,4-dimethoxybenzyl)-3,3-dimethyl-5-phenyl-1,3-dihydro-2H-pyrrol-2-one (9 g, 26.6 mmol) in TFA (50 mL) was stirred at 95° C. for 1 h. It was cooled to r.t. and TFA was removed. The residue was purified by column flash in silica gel eluted with EA/PE=1/1 to give the crude product as a brown oil (4.4 g, 88% yield). MS (ESI, m/e) [M+1]$^+$ 188.1.

Step 5: 4,4-dimethyl-2-phenylpyrrolidine

A solution of 1-(2,4-dimethoxybenzyl)-3,3-dimethyl-5-phenyl-1,3-dihydro-2H-pyrrol-2-one (2.4 g, 12.8 mmol) in THF (100 mL) and BH3-THF (64 mL, 1 mol/L) was refluxed for 2 h. It was cooled to r.t. and HCl acid (6 M, 20 mL) was added slowly. It was then refluxed for 30 min. The solvent was removed, and the residue was used for next step directly.

Intermediate 2-i: 1-phenylpyrrolidine-2-carbaldehyde

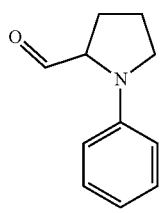 [SMILES: O=CC1CCCN1c1ccccc1]

Step 1: Phenylproline

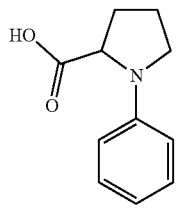 [SMILES: O=C(O)C1CCCN1c1ccccc1]

To a sealed tube flushed with nitrogen was added L-proline (11.5 g, 100 mmol), potassium carbonate (27.6 g, 200 mmol), copper (I) iodide (3.8 g, 20 mmol), iodobenzene (24.4 g, 120 mmol) and DMF (150 ml). The mixture was heated at 90° C. for 48 hours, then cooled to room temperature. Water was added, and the pH value was adjusted to <3 with concentrated HCl acid. The aqueous phase was extracted 4 times with ethyl acetate. The combined organic layers were washed with brine, dried over magnesium sulfate, filtered and concentrated in vacuo. Purification by silica gel chromatography (0 to 100% EtOAc/hexane gradient) afforded the crude product which was used directly in the next step. MS (ESI, m/e) [M+1]$^+$ 102.1

Step 2: (1-phenylpyrrolidin-2-yl)methanol

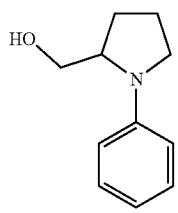 [SMILES: OCC1CCCN1c1ccccc1]

To a solution of phenylproline (1.5 g, 7.8 mmol) in THF (50 mL) was added BH$_3$-THF (1M, 15.6 mL). The reaction was refluxed for 1 hour. Then the reaction was cooled to r.t and quenched with MeOH (5 mL). Solvent was removed and the residue was purified by chromatography to give (1-phenylpyrrolidin-2-yl)methanol (1.3 g) as a colorless oil. MS (ESI, m/e) [M+1]$^+$ 192.1

Step 3: 1-phenylpyrrolidine-2-carbaldehyde

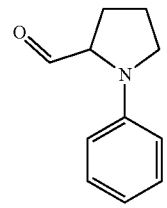 [SMILES: O=CC1CCCN1c1ccccc1]

To a solution of (1-phenylpyrrolidin-2-yl)methanol (531 mg, 3 mmol) in DCM (25 mL) was added Dess-Martin reagent (1.9 g, 4.5 mmol) in portions. The mixture was stirred overnight at r.t., then the mixture was washed with sat. NaHCO$_3$ solution and the organic layers were concentrated and purified by chromatography to give 1-phenylpyrrolidine-2-carbaldehyde (100 mg) as a colorless oil. MS (ESI, m/e) [M+1]$^+$ 176.1

Intermediate 2-j: 1-(4-bromophenyl)-2-methyl-2-phenylpyrrolidine

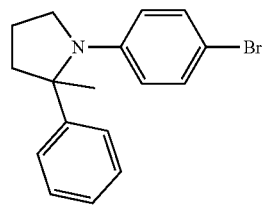 [SMILES: CC1(c2ccccc2)CCCN1c1ccc(Br)cc1]

Step 1: tert-butyl (4-oxo-4-phenylbutyl)carbamate

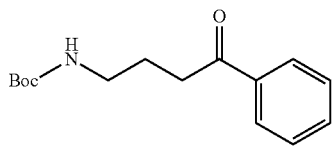 [SMILES: CC(C)(C)OC(=O)NCCCC(=O)c1ccccc1]

To a solution PhBr (8 g, 50.95 mmol, 5.37 mL) in THF (150 mL) was cooled to −78° C. and added n-BuLi (2.5 M, 26.50 mL). The mixture was stirred at −78° C. for 15 min. Then tert-butyl 2-oxopyrrolidine-1-carboxylate (10.38 g, 56.05 mmol, 9.52 mL) in THF (20 mL) was added at −78° C. The mixture was stirred at −78° C. for 15 min. TLC and LC-MS showed the reaction was completed and main peak was title product. H$_2$O (100 mL) was added. The mixture was extracted with EA (200 mL). The organic layer was washed with water and brine, dried over with Na$_2$SO$_4$, filtered and concentrated to afford tert-butyl (4-oxo-4-phenylbutyl)carbamate (14 g, crude) as yellow solid.

Step 2: 5-phenyl-3,4-dihydro-2H-pyrrole

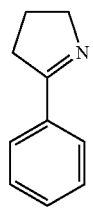 [SMILES: c1ccc(C2=NCCC2)cc1]

To a mixture of tert-butyl (4-oxo-4-phenylbutyl)carbamate (12.3 g, 46.71 mmol) in Toluene (61.5 mL) was added HCl (12 M, 8.56 mL), The mixture was stirred at 65° C. for 12 hr. TLC showed the reaction was completed. The reaction mixture was extracted with EA (50 mL). The aqueous layer was collected, adjusted to pH=10 by saturated NaHCO₃ solution, extracted with EA (50 mL). The organic layer was washed with brine, dried over with Na₂SO₄, filtered and concentrated. The residue was purified by silica gel (eluent: PE:EA=50:1 to 10:1) to afford 5-phenyl-3,4-dihydro-2H-pyrrole (3.5 g, 22.90 mmol, 49.03% yield) as light yellow solid. $^1$H NMR (400 MHz, CDCl₃) δ ppm: 7.89-7.81 (m, 2H), 7.44-7.41 (m, 2H), 4.08 (br t, J=7.4 Hz, 2H), 2.96 (br t, J=8.2 Hz, 2H), 2.05 (dd, J=7.4, 8.5 Hz, 2H).

Step 3: 2-methyl-2-phenylpyrrolidine

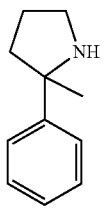

To a stirred solution of 5-phenyl-3,4-dihydro-2H-pyrrole (2 g, 13.77 mmol) in THF (60 mL) was added BF₃.Et₂O (7.82 g, 55.10 mmol, 6.80 mL) at −78° C. The mixture was stirred at −78° C. for 45 min. Then MeLi (1.6 M, 34.44 mL) was added at −78° C. The mixture was stirred at −78° C. for 2.5 hours, then warmed to 15° C. and stirred at 15° C. for 12 hr. TLC showed the reaction was completed. The mixture was poured into water (100 mL), adjusted to pH=12 by saturated NaOH solution, extracted with DCM (100 mL×2), The organic layer was washed with brine, dried over with Na₂SO₄, filtered and concentrated. The residue was purified by silica gel (eluent: PE:EA=100:1 to 20:1) to afford 2-methyl-2-phenylpyrrolidine (0.9 g, 5.30 mmol, 38.50% yield) as red oil. $^1$H NMR (400 MHz, CDCl₃) δ ppm: 7.52-7.46 (m, 2H), 7.36-7.29 (m, 2H), 7.2-7.18 (m, 1H), 3.17-3.09 (m, 1H), 3.04-2.96 (m, 1H), 2.14-2.05 (m, 1H), 1.94-1.85 (m, 2H), 1.80-1.70 (m, 2H), 1.45 (s, 3H).

Step 4: 1-(4-bromophenyl)-2-methyl-2-phenylpyrrolidine

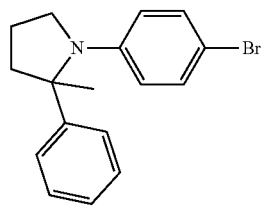 [SMILES: CC1(c2ccccc2)CCCN1c1ccc(Br)cc1]

The solution of 1-bromo-4-iodobenzene (4.21 g, 14.88 mmol), 2-methyl-2-phenylpyrrolidine (0.6 g, 3.72 mmol), Pd₂(dba)₃ (340.75 mg, 372.11 umol), BINAP (463.40 mg, 744.22 umol), t-BuOK (1.25 g, 11.16 mmol) in Toluene (40 mL) was stirred at 90° C. for 12 hr. After cooled to room temperature, the reaction mixture was filtered and concentrated. The residue was purified by prep-HPLC. After removal of mobile phase, the residue was dissolved with EA (20 mL), adjusted to pH=8 with saturated NaHCO₃ solution, separated and concentrated to afford 1-(4-bromophenyl)-2-methyl-2-phenylpyrrolidine (0.43 g, 33.31% yield) as brown oil. $^1$H NMR (400 MHz, CDCl₃) δ ppm: 7.34-7.29 (m, 2H), 7.27-7.22 (m, 3H), 7.14-7.12 (m, 2H), 6.31-6.26 (m, 2H), 3.64-3.55 (m, 2H), 2.15-2.10 (m, 2H), 2.01-1.96 (m, 2H), 1.77 (s, 3H), MS (ESI, m/e) [M+1]⁺ 316.1, 318.1.

Intermediate 2-k: 1-(azetidin-3-ylmethyl)-2-(2-cyclopropylphenyl)pyrrolidine

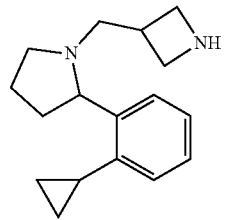 [SMILES: c1ccc(C2CCCN2CC2CNC2)c(C2CC2)c1]

Step 1: tert-butyl 3-((2-(2-cyclopropylphenyl)pyrrolidin-1-yl)methyl)azetidine-1-carboxylate 2-(2-cyclopropylphenyl)pyrrolidine (0.195 g, 647.19 umol) was dissolved in DCE (6 mL), tert-butyl 3-formylazetidine-1-carboxylate (359.62 mg, 1.94 mmol) and NaBH(OAc)₃ (274.33 mg, 1.29 mmol) were added. After stirring at 15° C. for 4 h, HOAc (116.59 mg, 1.94 mmol) was added. Stirring was continued at 15° C. for 24 h. Then the reaction mixture was poured into saturated aqueous NaHCO₃ (4 mL), The mixture was extracted three times with CH₂Cl₂ (3×5 mL), The combined organic phase extracts were washed with brine (5 mL), dried over Na₂SO₄, and concentrated. The residue was purified by column chromatography (SiO₂, Petroleum ether/Ethyl acetate=20/1 to 5/1). Tert-butyl 3-((2-(2-cyclopropylphenyl)pyrrolidin-1-yl)methyl)azetidine-1-carboxylate (0.18 g) was obtained as a yellow liquid.

Step 2: 1-(azetidin-3-ylmethyl)-2-(2-cyclopropylphenyl)pyrrolidine

To a solution of Tert-butyl 3-((2-(2-cyclopropylphenyl)pyrrolidin-1-yl)methyl)azetidine-1-carboxylate (0.7 g, 1.96 mmol) in CH$_2$Cl$_2$ (4.8 mL) was TFA (2.24 g, 19.64 mmol) at 0° C. under N$_2$. The mixture was stirred at 15° C. for 2 hours. The solution was concentrated under reduced pressure. The residue was adjusted to pH=14 with 1N NaOH solution and extracted with CH$_2$Cl$_2$ (3×5 mL). The combined organic layers were dried and concentrated under reduced pressure. 1-(azetidin-3-ylmethyl)-2-(2-cyclopropylphenyl)pyrrolidine (475 mg) was obtained as a yellow liquid.

Intermediate 2-l: 1-methyl-4-(2-(pyrrolidin-2-yl)phenyl)-1,2,3,6-tetrahydropyridine

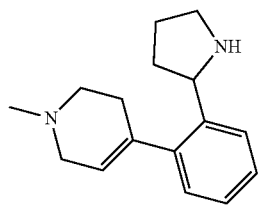 [SMILES: CN1CC=C(c2ccccc2C2CCCN2)CC1]

Step 1: 1-(2-(2-bromophenyl)pyrrolidin-1-yl)-2,2,2-trifluoroethan-1-one

Under inert N$_2$ atmosphere, to a solution of 2-(2-bromophenyl)pyrrolidine (4 g, 17.68 mmol) in DCM (100 mL) was added TEA (3.57 g, 35.36 mmol) at 0° C. and then trifluoroacetic anhydride (4.46 g, 21.22 mmol) dropwise. The mixture was stirred for overnight at room temperature. The reaction mixture was then poured into 100 mL of water, extracted with DCM (100 mL), washed with 50 mL of brine, dried over anhydrous Na$_2$SO$_4$. The solution was filtered and concentrated to give crude 1-(2-(2-bromophenyl)pyrrolidin-1-yl)-2,2,2-trifluoroethan-1-one (5.0 g) as a brown oil, which was used into next step without further purification.

Step 2: tert-butyl 4-(2-(1-(2,2,2-trifluoroacetyl)pyrrolidin-2-yl)phenyl)-3,6-dihydropyridine-1 (2H)-carboxylate To a solution of 1-(2-(2-bromophenyl)pyrrolidin-1-yl)-2,2,2-trifluoroethan-1-one (5 g, 15.5 mmol) in toluene (10 mL) was added tert-butyl 4-(4,4,5,5-tetramethyl-1,3,2-dioxaborolan-2-yl)-3,6-dihydropyridine-1(2H)-carboxylate (7.2 g, 23.25 mmol), Pd(OAc)$_2$ (350 mg, 1.55 mmol), Tricyclohexyl phosphine (870 mg, 3.1 mmol) and K$_3$PO$_4$ (11.5 g, 54.25 mmol). The suspension was stirred at 100° C. for 12 hours at N$_2$ atmosphere. The reaction mixture was filtered and the filtrate was concentrated under reduced pressure to give a residue. The residue was further purified by column chromatograph on silica gel (eluent: Petroleum ether/Ethyl acetate=50/1 to 10/1) to give tert-butyl 4-(2-(1-(2,2,2-trifluoroacetyl)pyrrolidin-2-yl)phenyl)-3,6-dihydropyridine-1(2H)-carboxylate (6.1 g) as yellow oil.

Step 3: 2,2,2-trifluoro-1-(2-(2-(1,2,3,6-tetrahydropyridin-4-yl)phenyl)pyrrolidin-1-yl)ethan-1-one To the solution of tert-butyl 4-(2-(1-(2,2,2-trifluoroacetyl)pyrrolidin-2-yl)phenyl)-3,6-dihydropyridine-1(2H)-carboxylate (6.1 g, 14.5 mmol) in DCM (100 mL) was added TFA (20 mL) at 0° C. and then the mixture was stirred at room temperature for 1 hour. The reaction mixture was adjusted pH to 8-9 using aq. Na$_2$CO$_3$, and then was extracted with DCM. The organic layer was dried, filtered and the filtrate was concentrated under reduced pressure to give 2,2,2-trifluoro-1-(2-(2-(1,2,3,6-tetrahydropyridin-4-yl)phenyl)pyrrolidin-1-yl)ethan-1-one (3.8 g) as a brown oil, which was used in next step without further purification.

Step 4: 2,2,2-trifluoro-1-(2-(2-(1-methyl-1,2,3,6-tetrahydropyridin-4-yl)phenyl)pyrrolidin-1-yl)ethan-1-one To the solution of 2,2,2-trifluoro-1-(2-(2-(1,2,3,6-tetrahydropyridin-4-yl)phenyl)pyrrolidin-1-yl)ethan-1-one (1 g, 3.08 mmol) in MeOH (50 mL) was added HCHO (37%, 1.5 g 18.49 mmol) and NaBH$_3$CN (774 mg, 12.32 mmol). The suspension was stirred at room temperature for 2 hours. The reaction mixture was concentrated under reduced pressure and then the residue was diluted water (15 mL) and EA (30 mL) under stirring. The organic layer was separated and washed with brine, and then dried, filtered and concentrated. The residue was purified by column chromatograph on silica gel (eluent: DCM/MeOH=20/1) to give 2,2,2-trifluoro-1-(2-(2-(1-methyl-1,2,3,6-tetrahydropyridin-4-yl)phenyl)pyrrolidin-1-yl)ethan-1-one (0.8 g) as a brown oil.

Step 5: 1-methyl-4-(2-(pyrrolidin-2-yl)phenyl)-1,2,3,6-tetrahydropyridine

To the solution of 2,2,2-trifluoro-1-(2-(2-(1-methyl-1,2,3,6-tetrahydropyridin-4-yl)phenyl)pyrrolidin-1-yl)ethan-1-one (0.8 g, 2.36 mmol) in MeOH (50 mL) and H$_2$O (50 mL) was added LiOH.H$_2$O (0.2 g, 4.73 mmol). After the addition, the mixture was heated to 60° C. and stirred for 2 hours. The reaction mixture was concentrated under reduced pressure and then the residue was diluted water (15 mL) and EA (30 mL) under stirring. The organic layer was separated and washed with brine, and then dried, filtered and concentrated. The residue was purified by column chromatograph on silica gel (eluent: DCM/MeOH=50/1) to give 1-methyl-4-(2-(pyrrolidin-2-yl)phenyl)-1,2,3,6-tetrahydropyridine (500 mg) as a brown oil. $^1$H NMR (400 MHz, CDCl$_3$) δ ppm: 7.51 (dd, J=0.98, 7.83 Hz, 1H), 7.24-7.29 (m, 1H), 7.18 (dt, J=1.34, 7.40 Hz, 1H), 7.08 (dd, J=1.22, 7.58 Hz, 1H), 5.55 (id, J=1.60, 3.27 Hz, 1H), 4.29 (t, J=7.83 Hz, 1H), 3.23 (ddd, J=5.14, 7.43, 9.93 Hz, 1H), 3.10 (q, J=2.81 Hz, 2H), 2.94-3.04 (m, 1H), 2.63-2.70 (m, 2H), 2.43 (s, 3H), 2.12 (dtd, J=4.89, 7.81, 12.50 Hz, 1H), 1.80-1.90 (m, 1H), 1.59-1.70 (m, 1H). MS (ESI, m/e) [M+1]$^+$ 243.1.

Intermediate 2-m: 2-(2-cyclopropylphenyl)-4-fluoropyrrolidine

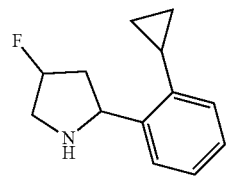

Step 1: tert-butyl 2-(2-bromophenyl)-4-fluoropyrrolidine-1-carboxylate

To a solution of tert-butyl 2-(2-bromophenyl)-4-hydroxypyrrolidine-1-carboxylate (2.5 g, 7.31 mmol) in DCM (30 mL) was added DAST (1.77 g, 10.96 mmol) dropwise. Then the solution was stirred at 20° C. for 12 hours. The reaction mixture was quenched with ice water (30 mL). The organic layer was separated, then washed with saturated NaHCO$_3$ solution (30 mL), brine (30 mL), dried over Na$_2$SO$_4$, and concentrated. The residue was purified by column chromatography on silica gel (eluent: PE/EA=20/1 to 10/1) to give tert-butyl 2-(2-bromophenyl)-4-fluoropyrrolidine-1-carboxylate (1.6 g) as a yellow oil.

Step 2: tert-butyl 2-(2-cyclopropylphenyl)-4-fluoropyrrolidine-1-carboxylate

To the solution of tert-butyl 2-(2-bromophenyl)-4-fluoropyrrolidine-1-carboxylate (1.5 g, 4.36 mmol) and cyclopropylboronic acid (1.1 g, 13.1 mmol) in toluene (20 mL) was added Pd(OAc)$_2$ (98 mg, 0.436 mmol), tricyclohexylphosphine (245 mg, 0.872 mmol), K$_3$PO$_4$ (3.2 g, 15.3 mmol) and H$_2$O (1 mL), The suspension was heated at 100° C. and stirred for 12 hours under N$_2$ atmosphere. To the reaction mixture was added water (20 mL) and EtOAc (20 mL). The organic layer was separated, washed with brine (20 mL), dried over Na$_2$SO$_4$ and concentrated. The residue was purified by column chromatography on silica gel (eluent: PE/EA=20/1) to give tert-butyl 2-(2-cyclopropylphenyl)-4-fluoropyrrolidine-1-carboxylate (1.1 g) as a brown oil.

Step 3: 2-(2-cyclopropylphenyl)-4-fluoropyrrolidine

A solution of tert-butyl 2-(2-cyclopropylphenyl)-4-fluoropyrrolidine-1-carboxylate (1.1 g, 3.6 mmol) in HCl solution (20 mL, 4M in EA) was stirred at room temperature for 2 hours. The reaction mixture was concentrated. To the residue was diluted with saturated Na$_2$CO$_3$ solution (20 mL) and EA (20 mL). The organic layer was separated, dried over anhydrous Na$_2$SO$_4$ and concentrated. The residue was purified by column chromatography on silica gel (eluent: PE/EA=4/1 to 1/1) to give 2-(2-cyclopropylphenyl)-4-fluoropyrrolidine (620 mg) as a yellow oil. $^1$H NMR (400 MHz, CDCl$_3$) δ ppm: 7.55 (dd, J=7.5, 1.4 Hz, 1H), 7.15-7.28 (m, 2H), 7.01-7.09 (m, 1H), 5.22-5.48 (m, 1H), 4.71-5.10 (m, 1H), 3.31-3.61 (m, 1H), 2.91-3.11 (m, 1H), 2.52-2.75 (m, 1H), 1.70-2.14 (m, 3H), 0.89-1.06 (m, 2H), 0.60-0.82 (m, 2H). MS (ESI, m/e) [M+1]$^+$ 206.1.

Intermediate 2-n:
2-chloro-N,N-dimethyl-6-(pyrrolidin-2-yl)aniline

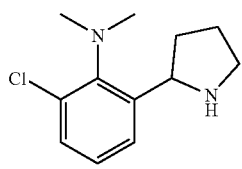

Step 1: tert-butyl (4-(3-chloro-2-(dimethylamino)phenyl)-4-oxobutyl)carbamate

To the solution of 2-bromo-6-chloro-N,N-dimethylaniline (3.5 g, 14.92 mmol) and tert-butyl 2-oxopyrrolidine-1-carboxylate (2.76 g, 14.92 mmol) in THF (50 mL) was added n-BuLi (6 mL, 2.5 M in hexane) at −70° C. and then stirred for 2 hours. The reaction mixture was added aq. NH$_4$Cl (50 mL) and extracted with EA (50 mL×3). The combined organic layers were dried over anhydrous Na$_2$SO$_4$ and concentrated under reduced pressure. The residue was purified by column chromatography on silica gel (eluent: PE/EA=5/1) to give tert-butyl (4-(3-chloro-2-(dimethylamino)phenyl)-4-oxobutyl)carbamate (1.8 g) as a yellow oil.

Step 2: 4-amino-1-(3-chloro-2-(dimethylamino)phenyl)butan-1-one

To the solution of tert-butyl (4-(3-chloro-2-(dimethylamino)phenyl)-4-oxobutyl)carbamate (1.7 g, 4.99 mmol) in DCM (10 mL) was added TFA (1 mL) and stirred at room temperature for 4 hours. The reaction mixture was concentrated under reduced pressure to give crude 4-amino-1-(3-chloro-2-(dimethylamino)phenyl)butan-1-one (1.2 g, crude) as a yellow oil.

Step 3:
2-chloro-N,N-dimethyl-6-(pyrrolidin-2-yl)aniline

To the solution of 4-amino-1-(3-chloro-2-(dimethylamino)phenyl)butan-1-one (1.2 g, 4.98 mmol) in EtOH (20 mL) was added NaBH$_3$CN (939.77 mg, 14.95 mmol) and HOAc (2 mL) and then stirred at room temperature for 36 hours. The reaction mixture was quenched with water (80 mL) and extracted with EA (50 mL×3). The combined organic layers were dried over anhydrous Na$_2$SO$_4$, filtered and concentrated under reduced pressure. The residue was purified by prep-HPLC (HCl). The solution of target peak was adjusted pH to 10 and extracted with DCM (30 mL×3). The organic phase was dried over Na$_2$SO$_4$ and concentrated to give 2-chloro-N,N-dimethyl-6-(pyrrolidin-2-yl)aniline (297 mg) as colorless oil. $^1$H NMR (400 MHz, CDCl$_3$) δ ppm: 7.40 (dd, J=1.3, 7.7 Hz, 1H), 7.19 (dd, J=1.5, 7.9 Hz, 1H), 7.12-7.05 (m, 1H), 4.56 (t, J=1.9 Hz, 1H), 3.19 (ddd, J=5.4, 7.4, 9.9 Hz, 1H), 3.09-2.99 (m, 1H), 2.85 (s, 6H), 2.24 (did, J=5.0, 7.7, 12.6 Hz, 1H), 1.95-1.80 (m, 2H), 1.58-1.45 (m, 1H). MS (ESI, m/e) [M+1]$^+$ 225.2.

Intermediate 2-o: 1-(4-bromophenyl)-2-(2-cyclopropylphenyl)-2-(trifluoromethyl)pyrrolidine

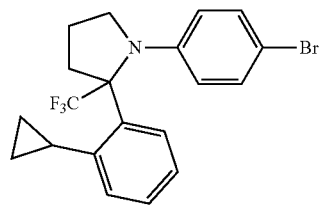 [SMILES: FC(F)(F)C1(c2ccccc2C2CC2)CCCN1c1ccc(Br)cc1]

Step 1: N-(4-bromophenyl)-1-(2-cyclopropylphenyl)-2,2,2-trifluoroethan-1-imine

The solution of N-(4-bromophenyl)-1,1,1-triphenyl-15-phosphanimine (1.8 g, 4.16 mmol) and 1-(2-cyclopropylphenyl)-2,2,2-trifluoroethan-1-one (891.83 mg, 4.16 mmol) in toluene (20 mL) was stirred at 110° C. for 12 hours. The reaction mixture was cooled down and concentrated under reduced pressure to remove solvent. The residue was purified by column chromatography on silica gel (eluent: PE/EA=50/1 to 10/1) to give N-(4-bromophenyl)-1-(2-cyclopropylphenyl)-2,2,2-trifluoroethan-1-imine (1.1 g, 2.99 mmol) as a yellow oil.

Step 2: 4-bromo-N-(2-(2-cyclopropylphenyl)-1,1,1-trifluoropent-4-en-2-yl)aniline To a solution of N-(4-bromophenyl)-1-(2-cyclopropylphenyl)-2,2,2-trifluoroethan-1-imine (1.1 g, 2.99 mmol) in DCM (10 mL) was added allylmagnesium bromide (1 M, 14.94 mL) at −20° C. and stirred for 2 hours. The reaction mixture was then quenched with aq. HN₄Cl (10 mL) and extracted EA (10 mL×3). The organic layer was dried over Na₂SO₄, filtered and concentrated. The residue was purified by column chromatography on silica gel (eluent: PE) to afford 4-bromo-N-(2-(2-cyclopropylphenyl)-1,1,1-trifluoropent-4-en-2-yl)aniline (1.20 g) as a white solid.

Step 3: 4-((4-bromophenyl)amino)-4-(2-cyclopropylphenyl)-5,5,5-trifluoropentan-1-ol To a solution of 4-bromo-N-(2-(2-cyclopropylphenyl)-1,1,1-trifluoropent-4-en-2-yl)aniline (1.20 g, 2.92 mmol) in THF (10 mL) was added BH3.THF (1 M, 14.62 mL) at 0° C. and stirred for 1 hour. Then NaOH (2.5 M, 2.92 mL) and H₂O₂ (1.49 g, 43.87 mmol) was added into the reaction mixture at 0° C. After addition, the mixture was further stirred for 1.5 hours at room temperature. The reaction mixture was then quenched with aq. HN₄Cl (10 mL) and extracted with EA (10 mL×3), The organic layer was dried over Na₂SO₄, filtered and concentrated. The residue was purified by column chromatography on silica gel (eluent: PE/EA=50/1 to 5/1) to afford 4-((4-bromophenyl)amino)-4-(2-cyclopropylphenyl)-5,5,5-trifluoropentan-1-ol (0.6 g) as a yellow oil.

Step 4: 1-(4-bromophenyl)-2-(2-cyclopropylphenyl)-2-(trifluoromethyl)pyrrolidine To a solution of 4-((4-bromophenyl)amino)-4-(2-cyclopropylphenyl)-5,5,5-trifluoropentan-1-ol (0.6 g, 1.55 mmol) in dioxane (10 mL) was added TEA (469.17 mg, 4.64 mmol) and MsCl (265.56 mg, 2.32 mmol) and the mixture was stirred at room temperature for 1.5 hours. Then the mixture was heated to 80° C. and stirred for 1 hour. The reaction mixture was then quenched with aq. NH₄Cl (10 mL) and extracted with DCM (10 mL×3), dried over Na₂SO₄, filtered and concentrated. The residue was purified by column chromatography on silica gel (eluent: PE/EA=10/1) to afford 1-(4-bromophenyl)-2-(2-cyclopropylphenyl)-2-(trifluoromethyl)pyrrolidine (306 mg) as a white solid. ¹H NMR (400 MHz, CDCl₃) δ ppm: 7.63 (td, J=2.6, 6.6 Hz, 1H), 7.26-7.22 (m, 2H), 7.06 (d, J=9.3 Hz, 2H), 6.88-6.83 (m, 1H), 6.32 (d, J=9.0 Hz, 2H), 3.73-3.56 (m, 2H), 2.94-2.68 (m, 2H), 2.44-2.31 (m, 1H), 2.27-2.16 (m, 1H), 1.63-1.58 (m, 1H), 0.96-0.85 (m, 1H), 0.60-0.47 (m, 3H). MS (ESI, m/e) [M+1]⁺ 410.0.

Intermediate 2-p:
2-(2-cyclopropylbenzyl)pyrrolidine

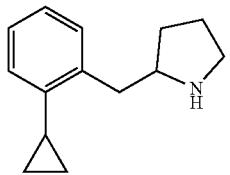 [SMILES: c1ccc(C2CC2)c(CC2CCCN2)c1]

Step 1: tert-butyl 2-((2-cyclopropylphenyl)(hydroxy)methyl)pyrrolidine-1-carboxylate A solution of 1-bromo-2-cyclopropylbenzene (4.50 g, 22.84 mmol) in THF (50 mL) was added n-BuLi (9.84 mL, 2.5M) at −70° C. under N₂ and stirred for 10 minutes, then tert-butyl 2-formylpyrrolidine-1-carboxylate (3.5 g, 17.57 mmol) was added into the mixture and further stirred for 2 hours. The mixture was quenched with saturated NH₄Cl solution (30 mL) and extracted with Ethyl acetate (50 mL×3). The organic phase was dried over Na₂SO₄, filtered, and concentrated. The residue was purified by column chromatography on silica gel (eluent: PE/EA=200/1 to 5/1) to give tert-butyl 2-((2-cyclopropylphenyl)(hydroxy)methyl)pyrrolidine-1-carboxylate (3.40 g, 10.72 mmol) as a yellow oil.

Step 2: tert-butyl 2-(((1H-imidazole-1-carbonothioyl)oxy)(2-cyclopropylphenyl)methyl)pyrrolidine-1-carboxylate A solution of tert-butyl 2-((2-cyclopropylphenyl)(hydroxy)methyl)pyrrolidine-1-carboxylate (3.40 g, 10.72 mmol), di(1H-imidazol-1-yl)methanethione (5.73 g, 32.16 mol) and DMAP (1.32 g, 1072 mmol) in DCM (30 mL) was stirred for 24 hours at room temperature. The mixture was poured into HCl acid (30 mL, 1M) and extracted with DCM (50 mL×3). The organic phase was dried over Na₂SO₄, filtered and concentrated. The residue was purified by column chromatography on silica gel (eluent: PE/EA=200/1 to 5/1) to give tert-butyl 2-(((1H-imidazole-1-carbonothioyl)oxy)(2-cyclopropylphenyl)methyl)pyrrolidine-1-carboxylate (3.0 g, 7.02 mmol) as a yellow oil.

Step 3: tert-butyl 2-(2-cyclopropylbenzyl)pyrrolidine-1-carboxylate

To a solution of tert-butyl 2-(((1H-imidazole-1-carbonothioyl)oxy)(2-cyclopropylphenyl)methyl)pyrrolidine-1-carboxylate (2.5 g, 5,852 mmol) in toluene (10 mL) was added tributyltin hydride (2.55 g, 8.778 mmol) and a catalytic amount of AIBN (192.06 g, 1.1704 mmol). The mixture was stirred at 100° C. for 2 hours. The mixture was washed with saturated aq. KF solution (50 mL) and extracted with EA (50 mL×3). The organic phase was dried over Na₂SO₄, filtered, and concentrated. The residue was purified by prep-HPLC (NaHCO₃) to give tert-butyl 2-(2-cyclopropylbenzyl)pyrrolidine-1-carboxylate (650 mg) as a yellow oil.

Step 4: 2-(2-cyclopropylbenzyl)pyrrolidine tert-butyl 2-(2-cyclopropylbenzyl)pyrrolidine-1-carboxylate (600.00 mg, 1.992 mmol) was added into a solution of MTBE/HCl (10 mL, 4M). The mixture was stirred for 2 hours at room temperature. The reaction mixture was concentrated and adjusted the pH to 10 with saturated Na₂CO₃ solution, then stirred for 15 mins, extracted with EA (30 mL×3). The organic phase was dried over Na₂SO₄ and filtered and concentrated to give 2-(2-cyclopropylbenzyl)pyrrolidine (302.00 mg) as a yellow oil. ¹H NMR (400 MHz, CDCl₃) δ ppm: 7.22-7.18 (m, 1H), 7.15-7.10 (m, 2H), 6.98-6.92 (m, 1H), 3.43-3.32 (m, 1H), 3.13-2.80 (m, 4H), 2.05-1.96 (m, 1H), 1.93-1.66 (m, 6H), 1.52-1.40 (m, 1H), 1.01-0.90 (m, 2H), 0.74-0.62 (m, 2H). MS (ESI, m/e) [M+1]⁺ 202.2.

Intermediate 2-q: 2-(2-(azetidin-1-yl)phenyl)-1-(4-bromophenyl)pyrrolidine

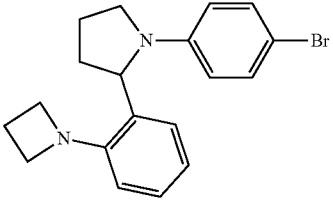 [SMILES: Brc1ccc(N2CCCC2c2ccccc2N2CCC2)cc1]

Step 1: 2-(azetidin-1-yl)benzaldehyde

To a solution of 2-fluorobenzaldehyde (10 g, 80.6 mmol) and azetidine (9.04 g, 96.7 mmol) in DMSO (50 mL) was added $K_2CO_3$ (33.4 g, 241.17 mmol) and stirred at 80° C. for 24 hours. The mixture was poured into water (300 mL) and was extracted with EA (100 mL×3). The combined organic phase was washed with brine (400 mL), dried with anhydrous $Na_2SO_4$, filtered and concentrated. The residue was purified by column chromatography on silica gel (eluent: PE/EA=100/1 to 20/1) to give 2-(azetidin-1-yl)benzaldehyde (9 g, crude) as yellow oil.

Step 2: 1-(2-(azetidin-1-yl)phenyl)-N-(4-bromophenyl)methanimine

To a mixture of 2-(azetidin-1-yl)benzaldehyde (4 g, 24.81 mmol) and 4-bromoaniline (4.27 g, 24.81 mmol) in toluene (40 mL) was added 4-methylbenzenesulfonic acid (854 mg, 4.96 mmol) and 4 Å molecular sieve (4 g). The mixture was stirred at 140° C. for 6 hours and was then concentrated in vacuum. The crude 1-(2-(azetidin-1-yl)phenyl)-N-(4-bromophenyl)methanimine (9 g) was obtained as yellow solid which was used I next step without further purification.

Step 3: N-(1-(2-(azetidin-1-yl)phenyl)but-3-en-1-yl)-4-bromoaniline

To a mixture of 1-(2-(azetidin-1-yl)phenyl)-N-(4-bromophenyl)methanimine (9 g, 28.55 mmol) in DCM (50 mL) was added allylmagnesium bromide (128.5 mL, 1M) at −20° C. under $N_2$. The mixture was stirred at room temperature for 2 hours. The mixture was then poured into sat. $NH_4Cl$ (200 mL) and was extracted with EA (200 mL×3). The combined organic phase was washed with brine (400 mL), dried with anhydrous $Na_2SO_4$, filtered and concentrated. The residue was purified by column chromatography on silica gel (PE/EA=20/1 to 1/1) to give N-(1-(2-(azetidin-1-yl)phenyl)but-3-en-1-yl)-4-bromoaniline (3 g) as yellow oil.

Step 4: 4-(2-(azetidin-1-yl)phenyl)-4-((4-bromophenyl)amino)butan-1-ol

To a solution of N-(1-(2-(azetidin-1-yl)phenyl)but-3-en-1-yl)-4-bromoaniline (3 g, 8.4 mmol) in THF (20 mL) was added BH3 THE (25 g, 25.19 mmol) at 0° C. under $N_2$ atmosphere. The mixture was stirred at 25° C. for 2 hours. NaOH (1.01 g, 25.19 mmol) and $H_2O_2$ (9.5 g, 83.97 mmol) at 0° C. was added, then the mixture was stirred for 3 hours. The mixture was poured into $H_2O$ (50 mL) and was extracted with EA (100 mL×3), The combined organic phase was washed with brine (200 mL), dried with anhydrous $Na_2SO_4$, filtered and concentrated. The residue was purified by column chromatography on silica gel (eluent: PE:EA=1/1 to 0/1) to give 4-(2-(azetidin-1-yl)phenyl)-4-((4-bromophenyl)amino)butan-1-ol (0.9 g) as yellow oil.

Step 5: 2-(2-(azetidin 1-yl)phenyl)-1-(4-bromophenyl)pyrrolidine

To a solution of 4-(2-(azetidin-1-yl)phenyl)-4-((4-bromophenyl)amino)butan-1-ol (0.9 g, 2.4 mmol) in THE (5 mL) was added TEA (960 mg, 9.59 mmol) and MsCl (329 mg, 2.88 umol) at 0° C. After stirred at 25° C. for 2 hours, the reaction mixture was concentrated in vacuum. The residue was purified by Pre-TLC (silica gel, eluent: PE/EA=1/1) to give 2-(2-(azetidin-1-yl)phenyl)-1-(4-bromophenyl)pyrrolidine (388.6 mg) as yellow oil. $^1$H NMR (400 MHz, $CDCl_3$) δ ppm: 7.24-7.18 (m, 2H), 7.17-7.11 (m, 1H), 6.94 (dd, J=1.4, 7.6 Hz, 1H), 6.74-6.66 (m, 1H), 6.55 (dd, J=0.8, 8.0 Hz, 1H), 6.39-6.31 (m, 2H), 4.80 (d, J=7.5 Hz, 1H), 4.11-3.91 (m, 4H), 3.69-3.57 (m, 1H), 3.36 (q, J=8.8 Hz, 1H), 2.38-2.21 (m, 3H), 2.17-1.89 (m, 4H). MS (ESI, m/e) $[M+1]^+$ 357.1.

Intermediate 2-r: 2-(2-(1,1-difluoroethyl)phenyl)pyrrolidine

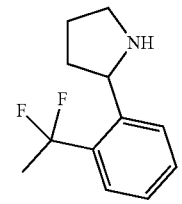

Step 1: 1-bromo-2-(1,1-difluoroethyl)benzene

To DAST (25 mL) was added 1-(2-bromophenyl)ethan-1-one (5 g, 25.120 mmol) in portions at room temperature. The resulting mixture was stirred for overnight at 50° C. under nitrogen atmosphere. The reaction mixture was diluted with $CH_2Cl_2$ (100 mL) and was then poured into ice/saturated aq. $NaHCO_3$ (250 mL) and was extracted with $CH_2Cl_2$ (2×100 mL). The combined organic layers were dried over anhydrous $Na_2SO_4$ and concentrated. The residue was purified by column chromatography on silica gel (eluent: PE/EA=50/1) to obtain 1-bromo-2-(1,1-difluoroethyl)benzene (3.5 g) as a yellow liquid.

Step 2: tert-butyl 2-(2-(1,1-difluoroethyl)phenyl)-1H-pyrrole-1-carboxylate To a stirred solution of 1-bromo-2-(1,1-difluoroethyl)benzene (1.5 g, 6.786 mmol) in THF (18 mL) and $H_2O$ (1.8 mL) were added [1-[(tert-butoxy)carbonyl]-1H-pyrrol-2-yl]boronic acid (1.44 g, 6.824 mmol), X-Phos (0.65 g, 1.363 mmol), $K_3PO_4$ (4.34 g, 20.446 mmol) and $Pd(OAc)_2$ (152.8 mg, 0.680 mmol). After stirred for 4.5 hours at 70° C. under nitrogen atmosphere, the reaction mixture was diluted with water (50 mL), and was extracted with EA (3×30 mL). The combined organic layers were washed with brine (50 mL), dried over anhydrous $Na_2SO_4$ and concentrated. The residue was purified by column chromatography on silica gel (eluent: PE/EA=50/1) to obtain tert-butyl 2-[2-(1,1-difluoroethyl)phenyl]-1H-pyrrole-1-carboxylate 2.2729 g (crude) as a dark yellow oil.

Step 3: tert-butyl 2-(2-(1,1-difluoroethyl)phenyl) pyrrolidine-1-carboxylate

To a stirred solution of tert-butyl 2-[2-(1,1-difluoroethyl)phenyl]-1H-pyrrole-1-carboxylate (2.2729 g, 7.395 mmol) in EtOH (45 mL) were added $PtO_2$ (1.1365 g, 5.005 mmol) and concentrated HCl acid (4 mL) in portions. The resulting mixture was stirred for 5 hours at room temperature under $H_2$ atmosphere (1 atm). After $PtO_2$ were filtered out, the filtrate was concentrated. The residue was diluted with saturated aq. $NaHCO_3$ (200 mL) at 0° C., then was extracted with EA (3×100 mL). The combined organic layers were washed with brine (100 mL), dried over anhydrous $Na_2SO_4$ and concentrated to afford tert-butyl 2-[2-(1,1-difluoroethyl)phenyl]pyrrolidine-1-carboxylate 1.7408 g (crude) as a dark yellow oil.

Step 4: 2-(2-(1,1-difluoroethyl)phenyl)pyrrolidine

To a solution of tert-butyl 2-[2-(1,1-difluoroethyl)phenyl]pyrrolidine-1-carboxylate (1.7408 g, 5.591 mmol) in DCM (35 mL) was added HCl solution (4 mL, 4 N in 1,4-dioxane) in portions. The resulting mixture was stirred for 4 h at room temperature under $N_2$ atmosphere. After adjusted PH value to 8 with saturated aq. $NaHCO_3$, the resulting mixture was extracted with DCM (3×50 mL). The combined organic layers were washed with brine (150 mL), dried over anhydrous $Na_2SO_4$ and concentrated. The residue was purified by reversed flash chromatography with the following conditions: column, C18 silica gel; mobile phase, $CH_3CN$ in water (0.05% $NH_4HCO_3$), 10% to 61% gradient in 25 min; detector, UV 220 nm. The resulting eluents was extracted with DCM (3×100 mL). Then the combined organic layers were concentrated to get (2-[2-(1,1-difluoroethyl)phenyl]pyrrolidine) (703.1 mg) as yellow oil. $^1$H NMR (400 MHz, Chloroform-d) δ ppm: 7.74 (d, J=7.9 Hz, 1H), 7.50-7.39 (m, 2H), 7.27 (t, J=7.7 Hz, 2H), 4.56 (t, J=7.8 Hz, 1H), 3.27 (ddd, J=9.8, 7.4, 5.1 Hz, 1H), 3.06 (dt, J=9.8, 7.4, I if). 2.23 (dtd, J=12.8, 7.8, 4.9 Hz, 1H), 2.05 (s, 1H), 2.03-1.94 (m, 5H), 1.94-1.81 (m, 1H), 1.78-1.58 (m, 1H). MS (ESI, m/e) [M+1]$^+$ 212.1.

Intermediate 2-s: 1-(4-bromophenyl)-2-(2-cyclopropylphenyl)piperidine

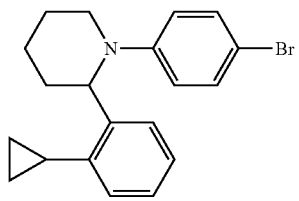 [SMILES: Brc1ccc(N2CCCCC2c2ccccc2C2CC2)cc1]

Step 1: 1-bromo-2-cyclopropylbenzene

To a stirred solution of 1-bromo-2-iodobenzene (40 g, 141.390 mmol) in dioxane (400 mL) were added $K_2CO_3$ (58.62 g, 424.151 mmol), cyclopropylboronic acid (36.44 g, 424.214 mmol) and Pd(dppf)$Cl_2$ (10.35 g, 14.14 mmol). The mixture was stirred for 48 hours at 70° C. under $N_2$ atmosphere. The mixture was diluted with water (1000 mL) and was extracted with EA (3×400 mL). The combined organic layers were washed with brine (400 mL), dried over anhydrous $Na_2SO_4$ and concentrated. The residue was purified by column chromatography on silica gel (eluent: PE/EA=100/1) to obtain 1-bromo-2-cyclopropylbenzene (22.0 g) as a colorless oil.

Step 2: 2-(2-cyclopropylphenyl)pyridine

To a stirred solution of 1-bromo-2-cyclopropylbenzene (12 g, 60.891 mmol) in dioxane (120 mL) were added 2-(tributylstannyl)pyridine (26.90 g, 73,069 mmol) and Pd(PPh$_3$)$_4$ (7.04 g, 6.089 mmol). The mixture was stirred for overnight at 100° C. under $N_2$ atmosphere. The reaction was quenched by the addition of water (100 mL). The resulting mixture was extracted with EA (3×50 mL). The combined organic layers were washed with 50 mL of brine, dried over anhydrous $Na_2SO_4$ and concentrated. The residue was purified by column chromatography on silica gel (eluent: PE/EA=70/1) to obtain 2-(2-cyclopropylphenyl)pyridine (5.80 g) as a light yellow oil.

Step 3: 2-(2-cyclopropylphenyl)piperidine

To a stirred solution of 2-(2-cyclopropylphenyl(pyridine (2.5 g, 12.820 mmol) in EtOH (100 mL) were added HCl acid (con., 3.5 mL) and $PtO_2$ (0,875 g, 3.846 mmol). The resulting mixture was stirred for 4 hours at room temperature under $H_2$ (1 atm) atmosphere. After $PtO_2$ was filtered out, the filtrate was concentrated. The residue was purified by reverse flash chromatography with the following conditions: column, $C_{1-8}$ silica gel, mobile phase, 0.05% TFA in water and $CH_3CN$, 0% to 10% gradient in 30 min; detector, UV 220 nm to afford 900 mg crude product, which was purified by Prep-HPLC with the following conditions (Column: XBridge Prep OBD C18 Column 30×150 mm 5 um; Mobile Phase A: Water (10 mMOL/L NH4HCO3), Mobile Phase B: $CH_3CN$; Flow rate: 60 mL/min; Gradient: 25% B to 37% B in 9 min; 254&220 nm; Rt: 7.92 min) to afford 2-(2-cyclopropylphenyl)piperidine (280 mg) as a yellow oil.

Step 4: 1-(4-bromophenyl)-2-(2-cyclopropylphenyl) piperidine

To a stirred mixture of 2-(2-cyclopropylphenyl)piperidine (2.50 g, 12.437 mmol), (4-bromophenyl)boronic acid (4.975 g, 24.874 mmol), Cu(OAc)$_2$ (5.627 g, 31.093 mmol) and activated 4 Å molecular sieves (2.0 g) in DCM (250 mL) was added DIPEA (4.011 g, 31.093 mmol) dropwise at room temperature. The resulting mixture was stirred for 3 hours at room temperature under $O_2$ atmosphere. The reaction mixture was filtered, and the filtrate was concentrated in vacuum. The residue was purified by Prep-HPLC with the following conditions (Column: XBridge Prep OBD C18 Column 30×150 mm Sum; Mobile Phase A: Water (0.05% TFA), Mobile Phase B: $CH_3CN$; Flow rate: 60 mL/min; Gradient: 43% B to 46% B in 9 min; 254&220 nm; Rt: 7.40 min) to obtain 1-(4-bromophenyl)-2-(2-cyclopropylphenyl) piperidine (310 mg) as a brown solid. $^1$H NMR (300 MHz, Methanol-d$_4$) δ ppm: 7.46 (s, 2H), 7.31 (d, J=8.5 Hz, 2H), 7.21-7.09 (m, 2H), 6.91 (d, J=7.3 Hz, 1H), 5.30 (s, 1H), 3.78 (s, 2H), 2.20 (s, 1H), 2.13 (s, 4H), 1.00 (d, J=8.4 Hz, 2H), 0.60 Cd, J=6.0 Hz, 1H), 0.50 (d, J=5.6 Hz, 1H). MS (ESI, m/e) [M+1]$^+$ 357.9.

Intermediate 2-t:
2-(2-cyclopropylphenyl)-4-methylpyrrolidine

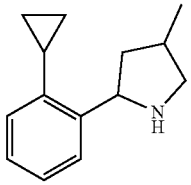

Step 1: methyl 3-methyl-4-nitrobutanoate

To a solution of (E)-methyl but-2-enoate (20 g, 199.77 mmol), CH$_3$NO$_2$ (48.78 g, 799.07 mmol) in MeOH (200 mL) was added DBN (4.60 mg, 39.95 mmol). The mixture was stirred at 60° C. for 6 hours under N$_2$ atmosphere. TLC indicated the reactant was consumed completely. The reaction mixture was added MTBE (700 mL), washed with 1 M HCl (500 mL) and H$_2$O (500 mL). The organic phase was concentrated under reduced pressure to give a residue. The residue was purified by column chromatography (Silica gel, Petroleum ether/Ethyl acetate=50/1). Methyl 3-methyl-4-nitrobutanoate (23 g, yield: 71.44%) was obtained as a yellow liquid. $^1$H NMR (400 MHz, CDCl$_3$) δ ppm: 4.27-4.49 (m, 2H), 3.66 (s, 3 H), 2.75 (m, 1H), 2.28-2.48 (m, 2H), 1.06 (d, J=6.84 Hz, 3H).

Step 2: 4-methylpyrrolidin-2-one

To a solution of methyl 3-methyl-4-nitrobutanoate (20 g, 124.10 mmol) in MeOH (200 mL) was added Raney Ni (728.41 mg, 12.41 mmol). The mixture was stirred at 50° C. for 4 hours under H$_2$ atmosphere. TLC indicated the reaction was complete. The reaction mixture was filtered and concentrated under reduced pressure to give 4-methylpyrrolidin-2-one (10 g) as a yellow solid, which was used in next step without further purification.

Step 3: tert-butyl 4-methyl-2-oxopyrrolidine-1-carboxylate

To a mixture of 4-methylpyrrolidin-2-one (10 g, 100.88 mmol), DMAP (6.16 g, 50.44 mmol), TEA (10.21 g, 100.88 mmol) in THF (100 mL) was added (Boc)$_2$O (44.03 g, 201.75 mmol). The mixture was stirred at 25° C. for 3 hours. TLC indicated the reaction was complete. The reaction mixture was filtered and concentrated under reduced pressure to give a residue. The residue was purified by column chromatography (Silica gel, Petroleum ether/Ethyl acetate=100/1 to 50/1). Tert-butyl 4-methyl-2-oxopyrrolidine-1-carboxylate (13 g, 64.68% yield) was obtained as a white solid. $^1$H NMR (400 MHz, CDCl$_3$) δ ppm: 3.87 (dd, J=10.7, 7.6 Hz, 1H), 3.29 (dd, J=10.7, 6.9 Hz, 1H), 2.64 (dd, J=17.0, 8.1 Hz, 1H), 2.39 (dd, J=14.6, 7.5 Hz, 1H) 2.16 (dd, J=17.0, 8.1 Hz, 1H), 1.53 (s, 9H), 1.14 (d, J=6.6 Hz, 3H).

Step 4: tert-butyl (4-(2-cyclopropylphenyl)-2-methyl-4-oxobutyl)carbamate

A mixture of 1-bromo-2-cyclopropylbenzene (3.5 g, 17.76 mmol) in THF (50 mL) was degassed and purged with N$_2$ for 3 times, and then n-BuLi (1.04 g, 16.28 mmol) was added dropwise into the mixture at −68° C. After stirred 10 min. Then tert-butyl 4-methyl-2-oxopyrrolidine-1-carboxylate (2.95 g, 14.80 mmol) in THF (10 mL) was added into the mixture. Then the mixture was stirred at −68° C. for 2 hours under N$_2$ atmosphere. TLC indicated the reaction was complete. The reaction was quenched with aqueous NH$_4$Cl (20 mL), extracted with EA (50 mL×3), The combined organic layer was washed with brine (20 mL), dried over Na$_2$SO$_4$, and concentrated under reduced pressure to give a residue. The residue was purified by column chromatography (Silica gel, Petroleum ether/Ethyl acetate=50/1 to 10/1). Tert-butyl (4-(2-cyclopropylphenyl)-2-methyl-4-oxobutyl) carbamate (3.6 g, 76.63% yield) was obtained as a yellow oil. $^1$H NMR (400 MHz, CDCl$_3$) δ ppm: 7.44 (dd, >7.7, 1.10 Hz, 1H), 7.32-7.38 (m, 1H), 7.17-7.24 (m, 1H), 7.03 (d, J=7.9 Hz, 1H), 4.68 (s, 1H), 3.12 (t, >6.3 Hz, 2H), 3.00 (dd, J=16.8, 5.51 Hz, 2H), 2.77 (dd, J=16.8, 7.72 Hz, 1H), 2.24-2.50 (m, 3H), 1.44 (s, 10H), 1.24-1.36 (m, 1H), 0.94-1.03 (m, 5H), 0.88-0.94 (m, 2H), 0.61-0.72 (m, 2H).

Step 5: 4-amino-1-(2-cyclopropylphenyl)-3-methylbutan-1-one

A solution of tert-butyl (4-(2-cyclopropylphenyl)-2-methyl-4-oxobutyl)carbamate (3.5 g, 11.03 mmol) in DCM (50 mL) was degassed and purged with N$_2$ for 3 times, and then TFA (12.57 g, 110.26 mmol) was added. The mixture was stirred at 20° C. for 1 hour under N$_2$ atmosphere. TLC indicated the reaction was complete. The reaction mixture was concentrated under reduced pressure to give a residue. The crude product (2.0 g) was used for next step without purification. $^1$H NMR (400 MHz, CDCl$_3$) δ ppm: 7.52 (d, J=7.7 Hz, 1H), 7.27-7.44 (m, 8H), 7.24 (d, J=1.1 Hz, 1H), 7.08-7.19 (m, 4H), 6.97 (d, J=7.7 Hz, 3H), 4.46 (t, J=7.2 Hz, 1H), 4.11-4.25 (m, 3H), 3.61-3.75 (m, 3H), 3.08-3.19 (m, 3H), 2.48-2.71 (m, 9H), 2.37 (d, J=5.5 Hz, 3H), 1.08-1.20 (m, 12H), 0.89-0.98 (m, 9H), 0.65-0.71 (m, 4H).

Step 6: 2-(2-cyclopropylphenyl)-4-methylpyrrolidine

A solution of 4-amino-1-(2-cyclopropylphenyl)-3-methylbutan-1-one (2.0 g, 9.20 mmol) in EtOH (20 mL) and HOAc (2 mL) was degassed and purged with N$_2$ for 3 times. Then NaBH$_3$CN (983.23 mg, 15.56 mmol) was added into the solution in portions. The mixture was stirred at 25° C. for 2 hours under N$_2$ atmosphere. LC/MS showed the reaction was completed. The reaction mixture was adjusted to pH=10 with aqueous Na$_2$CO$_3$ (1 N) and extracted with EA (20 mL×5). The combined organic layers were washed with brine (50 mL), dried over Na$_2$SO$_4$, concentrated under reduced pressure to give a residue. The residue was purified by prep-HPLC (TFA condition). 2-(2-cyclopropylphenyl)-4-methylpyrrolidine (421 mg) was obtained as a yellow oil. $^1$H NMR (400 MHz, CDCl$_3$) δ ppm: 7.48-7.59 (m, 1H), 7.11-7.25 (m, 2H), 7.01 (d, J=7.3 Hz, 1H), 4.82-4.91 (m, 1H), 3.39 (dd, J=9.9, 6.8 Hz, 1H), 3.24 (dd, J=10.1, 7.5 Hz, 1H), 2.77 (dd, J=10.2, 7.8 Hz, 1H), 2.29-2.51 (m, 2H), 2.00 (dd, J=8.3, 5.5 Hz, 1H), 1.35 (d, J=9.8 Hz, 1H), 1.08-1.15 (m, 3H), 0.88-0.98 (m, 2H), 0.61-0.71 (m, 2H). MS (ESI, m/e) [M+1]$^+$ 202.1.

119

Intermediate 2-u: (S)-2-(2-cyclopropylphenyl)-1-(7-(4,4,5,5-tetramethyl-1,3,2-dioxaborolan-2-yl)spiro[3.5]non-6-en-2-yl)pyrrolidine

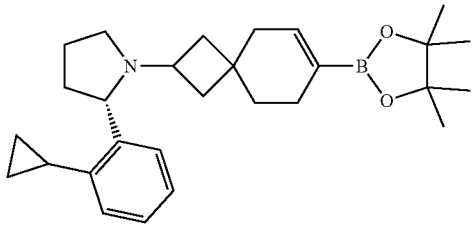 [SMILES: CC1(C)OB(C2=CCC3(CC2)CC(N2CCC[C@H]2c2ccccc2C2CC2)C3)OC1(C)C]

Step 1: (S)-2-(2-cyclopropylphenyl)-1-(8,11-dioxadispiro[3.2.4⁷.2⁴]tridecan-2-yl)pyrrolidine The solution of 8,11-dioxadispiro[3.2.4⁷.2⁴]tridecan-2-one (2.5 g, 13.35 mmol), (S)-2-(2-cyclopropylphenyl)pyrrolidine (2.36 g, 12.01 mmol) and HOAc (2.4 g, 40.05 mmol) in DCE (30 mL) was stirred at 15° C. for 2 h. Then Na(OAc)$_3$BH (5.6 g, 26.7 mmol) was added into the mixture and then stirred at 15° C. for 12 hours. TLC showed the reaction was completed. The mixture was adjusted to pH=10 with saturated aq. Na$_2$CO$_3$. The organic layer was washed with brine, dried over with Na$_2$SO$_4$, filtered and concentrated. The residue was purified by column chromatography on silica gel (eluent: PE/EA=20/1 to 7/1) to afford target product (2.5 g, erode) as yellow oil.

Step 2: (S)-2-(2-(2-cyclopropylphenyl)pyrrolidin-1-yl)spiro[3.5]nonan-7-one

The solution of (S)-2-(2-cyclopropylphenyl)-1-(8,11-dioxadispiro[3.2.4⁷.2⁴]tridecan-2-yl)pyrrolidine (2 g, 5.45 mmol) in acetone (27 mL) was added 1 N HCl acid (27 mL, 27.25 mmol). The mixture was stirred at 15° C. for 6 hours, TLC showed the reaction was completed. After removal of solvent, the residue was dissolved with EA (20 mL), adjusted to pH=9 with saturated aq. NaHCO$_3$. The organic layer was washed with water and brine, dried over with Na$_2$SO$_4$, filtered and concentrated to afford (S)-2-(2(2-cyclopropylphenyl)pyrrolidin-1-yl)spiro[3.5]nonan-7-one (1.7 g, crude) as yellow oil.

Step 3: (S)-2-(2-(2-cyclopropylphenyl)pyrrolidin-1-yl)spiro[3.5]non-6-en-7-yl trifluoromethanesulfonate The mixture solution of (S)-2-(2-(2-cyclopropylphenyl)pyrrolidin-1-yl)spiro[3.5]nonan-7-one (1.6 g, 4.95 mmol) and 1,1,1-trifluoro-N-phenyl-N-((trifluoromethyl)sulfonyl)methanesulfonamide (2.12 g, 5.94 mmol) in THF (20 mL) was cooled to −78° C. Then LDA (2.97 mL, 5.94 mmol) was added and stirred 2 hours. The mixture was warmed to 15° C. and stirred for 12 hours. TLC shows the reaction was completed. The mixture was poured into saturated aq. NH$_4$Cl, extracted with EA. The organic layer was washed with water and brine, dried over with Na$_2$SO$_4$, filtered and concentrated. The residue was purified by column chromatography on silica gel (eluent: PE/EA=50/1 to 5/1) to afford (S)-2-(2-(2-cyclopropylphenyl)pyrrolidin-1-yl)spiro[3.5]non-6-en-7-yl trifluoromethanesulfonate (2.4 g, crude) as yellow oil.

120

Step 4: (S)-2-(2-cyclopropylphenyl)-1-(7-(4,4,5,5-tetramethyl-1,3,2-dioxaborolan-2-yl)spiro[3.5]non-6-en-2-yl)pyrrolidine The mixture solution of (S)-2-(2-(2-cyclopropylphenyl)pyrrolidin-1-yl)spiro[3.5]non-6-en-7-yl trifluoromethanesulfonate (2.2 g, 4.83 mmol), B$_2$PIN$_2$ (1.84 g, 7.25 mmol), KOAc (1.42 g, 14.49 mmol) and Pd(dppf)Cl$_2$ (351 mg, 0.48 mmol) in dioxane (20 mL) was stirred at 85° C. for 3 hours. TLC showed the reaction was completed. The mixture was filtered and concentrated. The residue was purified by column chromatography on silica gel (eluent: PE/EA=10/1 to 5/1) to afford (S)-2-(2-cyclopropylphenyl)-1-(7-(4,4,5,5-tetramethyl-1,3,2-dioxaborolan-2-yl)spiro[3.5]non-6-en-2-yl)pyrrolidine (700 mg, 33% yield) as a yellow solid. $^1$H NMR (400 MHz, CDCl$_3$) δ ppm: 7.66 (t, J=6.1 Hz, 1H), 7.33-7.28 (m, 1H), 7.25-7.12 (m, 4H), 7.04-6.99 (m, 1H), 6.35 (s, 1H), 4.39 (s, 1H), 3.40 (s, 1H), 3.28-3.10 (m, 1H), 2.73 (s, 1H), 2.38-2.25 (m, 1H), 2.05 (s, 2H), 1.99-1.80 (m, 5H), 1.78-1.31 (m, 4H), 1.25 (s, 13H), 1.00-0.86 (m, 2H), 0.71-0.57 (m, 2H). MS (ESI, m/e) [M+1]$^+$ 434.1.

Intermediate 2-v: tert-butyl 4-(2-(1-(4-bromophenyl)pyrrolidin-2-yl)phenyl)piperazine-1-carboxylate

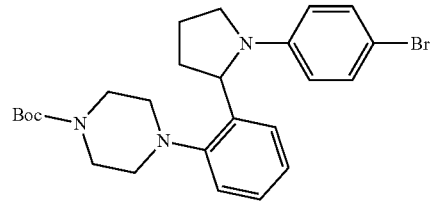 [SMILES: CC(C)(C)OC(=O)N1CCN(c2ccccc2C2CCCN2c2ccc(Br)cc2)CC1]

Step 1: tert-butyl 4-(2-formylphenyl)piperazine-1-carboxylate

To a solution of 2-fluorobenzaldehyde (13.33 g, 107.38 mmol) and tert-butyl piperazine-1-carboxylate (30.0 g, 161.07 mmol) in DMSO (150 mL) was added K$_2$CO$_3$ (44.52 g, 322.15 mmol). The mixture was stirred at 100° C. for 12 hr. TLC indicated the reactant was consumed completely. The reaction mixture was cooled to room temperature and poured into H$_2$O (150 mL) and extracted with EA (150 mL×3), dried over Na$_2$SO$_4$, filtered and concentrated. The residue was purified by column chromatography (Silica gel, PE/EA=100/1 to 30/1). Tert-butyl 4-(2-formylphenyl)piperazine-1-carboxylate (8.5 g) was obtained as a yellow solid. $^1$H NMR (400 MHz, CDCl$_3$) δ ppm: 1.50 (s, 9H), 3.02-3.08 (m, 4H), 3.61-3.66 (m, 4H), 7.11 (d, J=8.2 Hz, 1H), 7.17 (t, , J=7.5 Hz, 1H), 7.52-7.58 (m, 1H), 7.83 (dd, J=7.7, 1.8 Hz, 1H), 10.36 (s, 1H).

Step 2: (E)-tert-butyl 4-(2-(((4-bromophenyl)imino)methyl)phenyl)piperazine-1-carboxylate To a solution of tert-butyl 4-(2-formylphenyl)piperazine-1-carboxylate (8 g, 27.55 mmol) and 4-bromoaniline (4.74 g, 27.55 mmol) in toluene, (100 mL) was added 4 Å molecular sieve (5 g) and TsOH (474.45 mg, 2.76 mmol). The mixture was stirred at 120° C. for 12 hours. TLC indicated the reactant was consumed completely. The reaction mixture was concentrated under reduced pressure to remove solvent. (E)-tert-butyl 4-(2-(((4 bromophenyl)

imino)methyl)phenyl)piperazine-1-carboxylate (8 g, crude) was obtained as an brown oil. ¹H NMR (400 MHz, CDCl₃) δ ppm: 1.49 (s, 9H), 2.98 (br, 4H), 3.60 (br, 4H), 7.08-7.13 (m, 3H), 7.17-7.26 (m, 2H), 7.46 (td, J=7.7, 1.6 Hz, 1H), 7.50-7.54 (m, 2H), 8.83 (s, 1H).

Step 3: tert-butyl 4-(2-(1-((4-bromophenyl)amino) but-3-en-1-yl)phenyl)piperazine-1-carboxylate To a solution of (E)-tert-butyl-4-(2-(((4-bromophenyl) imino)methyl)phenyl)piperazine-1-carboxylate (8 g, 18.0 mmol) and in DCM (100 mL) was added allylmagnesium bromide (1 M, 18.0 mL) at −20° C. The mixture was stirred at −20° C. for 2 hr. TLC indicated Reactant was consumed completely. The reaction mixture was poured into aq. NH₄Cl (150 mL) and extracted with EA (150 mL×3), dried over Na₂SO₄, filtered and concentrated. The residue was purified by column chromatography (Silica gel, Petroleum ether), tert-butyl 4-(2-(1-((4-bromophenyl)amino)but-3-en-1-yl) phenyl)piperazine-1-carboxylate (6.0 g) was obtained as a yellow oil. ¹H NMR (400 MHz, CDCl₃) δ ppm: 1.51 (s, 9H), 2.47-2.66 (m, 2H), 2.83-2.98 (m, 5H), 3.48-3.75 (m, 3H), 4.23 (s, 1H), 4.89 (dd, J=8.1, 4.9 Hz, 1H), 5.10-5.21 (m, 2H), 5.79 (ddt, J=17.0, 10.1, 6.91 Hz, 1H), 6.40-6.44 (m, 2H), 7.10-7.20 (m, 4H), 7.24 (dd, J=7.2, 1.5 Hz, 1H), 7.34 (dd, >7.6, 1.5 Hz, 1H).

Step 4: tert-butyl 4-(2-(1-((4-bromophenyl)amino)-4-hydroxybutyl)phenyl)piperazine-1-carboxylate To a solution of tert-butyl 4-(2-(1-((4-bromophenyl) amino)but-3-en-1-yl)phenyl)piperazine-1-carboxylate (6 g, 12.33 mmol) in THF (100 mL) was added BH3.THF (1M, 185.02 mL) at 0° C. The mixture was stirred at 25° C. for 12 hr. And then NaOH (1.23 g, 30.84 mmol) and H₂O₂ (6.29 g, 185.02 mmol) was added into the mixture at 0° C. The mixture was stirred at 25° C. for 8 hr. TLC indicated Reactant 4 was consumed completely. The reaction mixture was poured into aq. NH₄Cl (150 mL) and extracted with EA (150 mL×3), dried over Na₂SO₄, filtered and concentrated. The residue was purified by column chromatography (Silica gel, PE/EA=100/1 to 30/1). tert-butyl 4-(2(1-((4-bromophenyl)amino)-4-hydroxybutyl)phenyl)piperazine-1-carboxylate (3.5 g) was obtained as a yellow sloid. ¹H NMR (400 MHz, CDCl₃) δ ppm: 1.50 (s, 10H), 1.56-1.80 (m, 3H), 1.83-1.99 (m, 2H), 2.80-2.94 (m, 4H), 3.38-3.76 (m, 5H), 4.88 (dd, J=7.9, 5.5 Hz, 1H), 6.46-6.51 (m, 2H), 7.11-7.18 (m, 4H), 7.21-7.24 (m, 1H), 7.31-7.34 (m, 1H).

Step 5: tert-butyl 4-(2-(1-(4-bromophenyl)pyrrolidin-2-yl)phenyl)piperazine-1-carboxylate To a solution of tert-butyl 4(2-(1-((4-bromophenyl) amino)-4-hydroxybutyl)phenyl)piperazine-1-carboxylate (3.5 g, 6.94 mmol) in DCM (50 mL) and TEA (3.51 g, 34.69 mmol) was added MsCl (715.29 mg, 6.24 mmol) at 0° C. and the mixture was stirred at 25° C. for 1.5 hr. LCMS showed the reactant was consumed completely and one main peak with desired MS was observed. The reaction mixture was poured into aq. NH₄Cl (150 mL) and extracted with EA (150 ml. 3), dried over Na₂SO₄, filtered and concentrated. The residue was purified by column chromatography (Silica gel, PE/EA=10/1). Tert-butyl 4-(2-(1-(4-bromophenyl)pyrrolidin-2-yl)phenyl)piperazine-1-carboxylate (3.0 g) was obtained as a white solid. ¹H NMR (400 MHz, CDCl₃) δ ppm: 1.47-1.54 (m, 9H), 1.90-1.98 (m, 1H), 1.98-2.17 (m, 2H), 2.40-2.52 (m, 1H), 2.86-3.02 (m, 4H), 3.35-3.43 (m, 1H), 3.55-3.67 (m, 3H), 3.67-3.75 (m, 1H), 5.07-5.12 (m, 1H), 6.27-6.34 (m, 2H), 7.01-7.07 (m, 1H), 7.08-7.12 (m, 1H), 7.15-7.26 (m, 4H). MS (ESI, m/e) [M+1]⁺ 486.1.

Intermediate 2-w: 6-(2-cyclopropylphenyl)-5-azaspiro[2.4]heptane

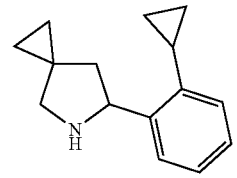 [SMILES: c1ccc(C2CC3(CC3)CN2)c(C2CC2)c1]

Step 1: tert-butyl 2-(2-cyclopropylphenyl)-4-hydroxypyrrolidine-1-carboxylate

To a solution of 5-(2-cyclopropylphenyl)pyrrolidin-3-ol (1.8 g, 8.9 mmol) and Et₃N (0.9 g, 8.9 mmol) in DCM (20 mL) was added Boc₂O (1.9 g, 8.9 mmol). Then the mixture was stirred at 20° C. for 12 hours. TLC showed the reaction was complete. The reaction mixture was washed with HCl acid (IN, 20 mL), saturated aq. NaHCO₃ solution (20 mL), brine (20 mL), dried over Na₂SO₄, and concentrated to give tert-butyl 2-(2-cyclopropylphenyl)-4-hydroxypyrrolidine-1-carboxylate (2.3 g, crude) as a yellow oil.

Step 2: tert-butyl 2-(2-cyclopropylphenyl)-4-oxopyrrolidine-1-carboxylate

To a solution of tert-butyl 2-(2-cyclopropylphenyl)-4-hydroxypyrrolidine-1-carboxylate (2.3 g, 7.6 mmol) in DCM (30 mL) was added NaHCO₃ (640 mg, 7.6 mmol) and Dess-Martin periodinane (3.2 g, 7.6 mmol). The mixture was stirred at 20° C. for 12 hours. TLC showed the reaction was complete. The reaction mixture was quenched with saturated aq. Na₂SO₃ solution (30 mL). The organic layer was washed with brine (30 mL), dried over Na₂SO₄, and concentrated to give tert-butyl 2-(2-cyclopropylphenyl)-4-oxopyrrolidine-1-carboxylate (2.1 g, crude) as a yellow oil.

Step 3: tert-butyl 2-(2-cyclopropylphenyl)-4-methylenepyrrolidine-1-carboxylate

To a mixture of Ph₃P⁺MeBr⁻ (5.5 g, 15.3 mmol) in THF (25 mL) was added t-BuOK (1.7 g, 15.3 mmol) in one portion. The mixture was stirred at 20° C. for 1 hour. Then tert-butyl 2-(2-cyclopropylphenyl)-4-oxopyrrolidine-1-carboxylate (2.3 g, 7.64 mmol) was added and the mixture was stirred at 20° C. for 12 hours. TLC showed the reaction was complete. The reaction mixture was quenched with saturated aq. NH₄Cl solution (25 mL), and then extracted with EA (25 mL). The organic layer was washed with brine (25 mL), dried over Na₂SO₄, and concentrated. The residue was purified by column chromatography on silica gel eluted with PE/EA=10/1 to give tert-butyl 2-(2-cyclopropylphenyl)-4-methylenepyrrolidine-1-carboxylate (1.3 g, yield: 56%).

Step 4: tert-butyl 6-(2-cyclopropylphenyl)-5-azaspiro[2.4]heptane-5-carboxylate

To a mixture of tert-butyl 2-(2-cyclopropylphenyl)-4-methylenepyrrolidine-1-carboxylate (1.3 g, 4.3 mmol) and Et₂Zn (1 M in toluene, 15 mL, 15 mmol) was added ClCH₂I (5.3 g, 30 mmol) at 0° C. Then the mixture was stirred at 20° C. for 12 hours. TLC showed a new spot was produced and no material remained. The reaction mixture was quenched with saturated aq. NH₄Cl solution (50 mL) and extracted with EA (50 mL). The organic layer was washed with brine (50 mL), dried over Na₂SO₄, and concentrated to give tert-butyl 6-(2-cyclopropylphenyl)-5-azaspiro[2.4]heptane-5-carboxylate (1 g, crude) as a yellow oil which was used in the next step directly.

Step 5: 6-(2-cyclopropylphenyl)-5-azaspiro[2.4]heptane

A solution of tert-butyl 6-(2-cyclopropylphenyl)-5-azaspiro[2.4]heptane-5-carboxylate (1 g, 3.2 mmol) in HCl/EA (10 mL, 4 M) was stirred at 20° C. for 2 h. LC/MS showed the reaction was complete. The mixture was concentrated. The residue was purified by prep-HPLC (0.1% TFA condition). The target eluent was basified with saturated aq. Na₂CO₃ solution to pH=10 and then extracted with EA (200 mL 4). The organic layers were combined, dried over Na₂SO₄, and concentrated to give 6-(2-cyclopropylphenyl)-5-azaspiro[2.4]heptane (293 mg) as a light yellow oil. ¹H NMR (400 MHz, CDCl₃) δ ppm: 7.60 (dd, J=7.6, 1.3 Hz, 1H), 7.13-7.25 (m, 2H), 7.01 (d, J=7.5 Hz, 1H), 4.97 (t, J=7.8 Hz, 1H), 3.02-3.13 (m, 2H), 2.34 (s, 1H), 2.14 (dd, J=12.3, 7.2 Hz, 1H), 2.04 (t, J=8.4, 1H), 1.81-1.90 (m, 1H), 0.87-1.02 (m, 2H), 0.53-0.76 (m, 6H). MS (ESI, m/e) [M+1]⁺ 214.1.

Intermediate 2-x: (R)-1-(2-(1-(4-bromophenyl)pyrrolidin-2-yl)benzyl)-4-methylpiperazine

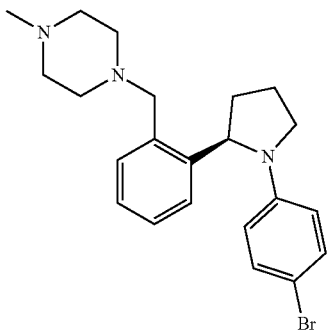 [SMILES: CN1CCN(Cc2ccccc2[C@H]2CCCN2c2ccc(Br)cc2)CC1]

Step 1: (R)-1-(2-(2-bromophenyl)pyrrolidin-1-yl)-2,2,2-trifluoroethanone

To a mixture of (R)-2-(2-bromophenyl)pyrrolidine (10 g, 44.23 mmol) and TFAA (18.58 g, 88.45 mmol) in DCM (100 mL) was added TEA (13.5 g, 132.69 mmol) dropwise at 0° C. The mixture was stirred at 20° C. for 10 hours. TLC indicated the reactant was consumed completely. The reaction mixture was washed with saturated aq. NH₄Cl (100 mL×2) and the organic phase was dried over Na₂SO₄, filtered and concentrated in vacuum. The residue was purified by column chromatography (Silica gel, PE/EA=100/1 to 50/1). (R)-1-(2-(2-bromophenyl)pyrrolidin-1-yl)-2,2,2-trifluoroethanone (13 g) was obtained as a yellow solid.

Step 2: (R)-2,2,2-trifluoro-1-(2-(2-vinylphenyl)pyrrolidin-1-yl)ethenone

To a mixture of (R)-1-(2-(2-bromophenyl)pyrrolidin-1-yl)-2,2,2-trifluoroethanone (5 g, 15.52 mmol), potassium trifluoro(vinyl)borate (2.91 g, 21.73 mmol) and Cs₂CO₃ (10.11 g, 31.04 mmol) in dioxane (120 mL), H₂O (12 mL) was added Pd(dppf)Cl₂ (567 mg, 776 umol) at 20° C. The mixture was purged with N₂ for three times and then heated to 100° C. for 5 hours. TLC and LC/MS indicated the reactant was consumed completely. The reaction mixture was concentrated in vacuum (30 mL). The residue was poured into ice-water (50 mL), The aqueous phase was extracted with EA (50 mL×3). The combined organic phases were dried with anhydrous Na₂SO₄, filtered and concentrated. The crude product was purified by column chromatography (Silica gel, PE/EA=100/1 to 50/1). (R)-2,2,2-trifluoro-1-(2-(2-vinylphenyl)pyrrolidin-1-yl)ethanone (3.4 g, 12.63 mmol, 81.34% yield) was obtained as a yellow oil. ¹H NMR (400 MHz, CDCl₃) δ ppm: 7.44-7.51 (m, 1H), 7.21-7.27 (m, 2H), 6.88-7.07 (m, 2H), 5.61-5.71 (m, 1H), 5.46-5.60 (m, 1H), 5.33-5.45 (m, 1H), 3.75-4.03 (m, 2H), 2.27-2.41 (m, 1H), 1.82-2.12 (m, 3H). MS (ESI, m/e) [M+1]⁺ 270.1.

Step 3: (R)-2-(1-(2,2,2-trifluoroacetyl)pyrrolidin-2-yl)benzaldehyde

To a mixture of (R)-2,2,2-trifluoro-1-(2-(2-vinylphenyl)pyrrolidin-1-yl)ethanone (3.4 g, 12.63 mmol) and K₂OsO₄·2H₂O (186 mg, 505.1 umol) in THF (60 mL), H₂O (60 mL) was added NaIO₄ (10.8 g, 50.51 mmol) in portions at 10° C. The mixture was stirred at 10° C. for 2 hr. TLC indicated the reactant was consumed completely. The reaction mixture was concentrated to remove THF. The aqueous phase was extracted with EA (50 mL×3). The combined organic phases were washed with brine, dried with anhydrous Na₂SO₄, filtered and concentrated. (R)-2-(1-(2,2,2-trifluoroacetyl)pyrrolidin-2-yl)benzaldehyde (3.4 g, crude) was obtained as a brown oil. MS (ESI, m/e) [M+1]⁺ 272.1.

Step 4: (R)-tert-butyl 4-(2-(1-(2,2,2-trifluoroacetyl)pyrrolidin-2-yl)benzyl)piperazine-1-carboxylate To a mixture of (R)-2-(1-(2,2,2-trifluoroacetyl)pyrrolidin-2-yl)benzaldehyde (3.4 g, 12.54 mmol) and tert-butyl piperazine-1-carboxylate (4.67 g, 25.07 mmol) in DCE (100 mL) was added NaBH(OAc)₃ (10.6 g, 50.16 mmol) in portions at 10° C. The mixture was stirred at 10° C. for 10 hours. TLC indicated the reactant was consumed completely. The reaction mixture was washed with NaHCO₃ (50 mL) and then the organic phase was separated. The organic phase was dried with anhydrous Na₂SO₄, filtered and concentrated. (R)-tert-butyl 4-(2-(1-(2,2,2-trifluoroacetyl)pyrrolidin-2-yl)benzyl)piperazine-1-carboxylate (3.5 g) was obtained as a yellow oil. MS (ESI, m/e) [M+1]⁺ 442.3.

Step 5: (R)-tert-butyl 4-(2-(pyrrolidin-2-yl)benzyl)piperazine-1-carboxylate

To a solution of (R)-tert-butyl 4-(2-(1-(2,2,2-trifluoroacetyl)pyrrolidin-2-yl)benzyl)piperazine-1-carboxylate (3.3 g, 7.47 mmol) in EtOH (50 mL) was added NaBH₄ (662.13 mg, 16.44 mmol) in portions at 20° C. The mixture was stirred at 20° C. for 4 hours. TLC indicated the reactant was consumed completely. The reaction mixture was concentrated to remove EtOH (10 mL), poured into ice-water (20 mL). The aqueous phase was extracted with EA (50 mL×3). The combined organic phases wore washed with brine, dried with anhydrous Na₂SO₄, filtered and concentrated, (R)-tertbutyl 4-(2-(pyrrolidin-2-yl)benzyl)piperazine-1-carboxylate (2.55 g, crude) was obtained as a yellow oil. MS (ESI, m/e) [M+1]+ 346.3.

Step 6: (R)-tert-butyl 4-(2(1-(4-bromophenyl)pyrrolidin-2-yl)benzyl)piperazine-1-carboxylate To a mixture of (R)-tert-butyl 4-(2-(pyrrolidin-2-yl)benzyl)piperazine-1-carboxylate (2.55 g, 7.38 mmol), 1-bromo-4-iodobenzene (3.13 g, 11.07 mmol), X-phos (703 mg, 1.48 mmol) and Cs$_2$CO$_3$ (4.81 g, 14.76 mmol) in toluene (100 mL) was added Pd(OAc)$_2$ (166 mg, 738 umol) at 20° C. The mixture was purged with N$_2$ for three times and then heated to 105° C. for 10 hours. TLC indicated the reactant was consumed completely. The reaction mixture was poured into ice-water (50 mL) and the organic phase was separated. The organic phase was dried with anhydrous Na$_2$SO$_4$, filtered and concentrated. (R)-tert-butyl 4-(2-(1-(4-bromophenyl)pyrrolidin-2-yl)benzyl)piperazine-1-carboxylate (1.25 g) was obtained as an orange solid. $^1$H NMR (400 MHz, CDCl3) δ ppm: 7.05-7.24 (m, 6H) 6.40 (d, J=8.9 Hz, 2H) 5.28-5.37 (m, 1H) 3.68-3.86 (m, 2H) 3.29-3.53 (m, 6H) 2.35-2.59 (m, 5H) 1.98-2.15 (m, 2H) 1.79-1.88 (m, 1H) 1.41-1.51 (m, 9H).

Step 7: (R)-1-(2-(1-(4-bromophenyl)pyrrolidin-2-yl)benzyl)piperazine

A solution of (R)-tert-butyl 4-(2-(1-(4-bromophenyl)pyrrolidin-2-yl)benzyl)piperazine-1-carboxylate (1.25 g, 2.50 mmol) in TFA (20 mL) and DCM (60 mL) was stirred at 20° C. for 12 hours, LC/MS indicated the reactant was consumed completely and desired compound was generated. The reaction solution was concentrated. The residue was diluted with EA (50 mL). The organic phase was washed with saturated aq, NaHCO$_3$ (50 mL) and the organic phase was separated. The organic phase was dried with anhydrous Na$_2$SO$_4$, filtered and concentrated. (R)-1-(2-(1-(4-bromophenyl)pyrrolidin-2-yl)benzyl)piperazine (1 g, crude) was obtained as a yellow oil. MS (ESI, m/e) [M+1]+ 400.2.

Step 8: (R)-1-(2-(1-(4-bromophenyl)pyrrolidin-2-yl)benzyl)-4-methylpiperazine

To a mixture of (R)-1-(2-(1-(4-bromophenyl)pyrrolidin-2-yl)benzyl)piperazine (1 g, 2.50 mmol) and HCHO (374.99 mg, 12.49 mmol) in DCE (50 mL) was added NaBH(OAc)$_3$ (2.1 g, 10 mmol) in portions at 20° C. The mixture was stirred at 20° C. for 1 hour. LC/MS indicated the reactant was consumed completely and desired compound was generated. The reaction mixture was filtered and the filtrate was concentrated. The crude was purified by prep-HPLC (Phenomenex tuna C18 250 mm*100 mm*10 um; mobile phase: [water (0.1% TAF)-ACN]). The purified solution was concentrated. The aqueous phase was based with saturated NaHCO$_3$ and then extracted with EA (50 mL×3). The combined organic phases were dried with anhydrous Na$_2$SO$_4$, filtered and concentrated. (R)-1-(2-(1-(4-bromophenyl)pyrrolidin-2-yl)benzyl)-4-methylpiperazine (440 mg) was obtained as a yellow solid. $^1$H NMR (400 MHz, CDCl$_3$) δ ppm: 7.01-7.24 (m, 6H), 6.36 (d, J=8.8 Hz, 2H), 5.22 (d, J=8.2 Hz, 1H), 3.88 (d, J=12.8 Hz, 1H), 3.72 (t, J=7.4 Hz, 1H), 3.33-3.50 (m, 2H), 2.34-3.14 (m, 12H), 2.06 (s, 2H), 1.84 (d, J=5.7 Hz, 1H). MS (ESI, m/e) [M+1]+ 414.2.

Intermediate 2-y: tert-butyl (R)-4-(2-(1-(4-bromophenyl)pyrrolidin-2-yl)benzyl)piperidine-1-carboxylate

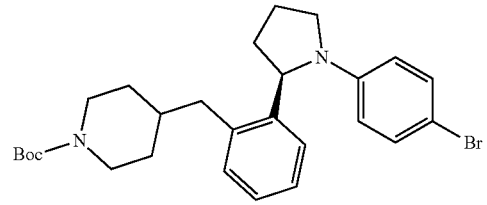 [SMILES: CC(C)(C)OC(=O)N1CCC(Cc2ccccc2[C@H]2CCCN2c2ccc(Br)cc2)CC1]

Step 1: (E)-tert-butyl 4-((2-tosylhydrazono)methyl)piperidine-1-carboxylate

A mixture of tert-butyl 4-formylpiperidine-1-carboxylate (1.75 g, 9.38 mmol) and 4-methylbenzenesulfonohydrazide (2.0 g, 9.38 mmol) in EtOH (30 mL) was stirred at 20° C. for 15 hours. TLC indicated the reactant was consumed completely. The reaction mixture was concentrated in vacuum. (E)-tert-butyl 4-((2-tosylhydrazono)methyl)piperidine-1-carboxylate (3.4 g, crude) was obtained as a colorless oil.

Step 2: (R)-tert-butyl 4-(2-(1-(2,2,2-trifluoroacetyl)pyrrolidin-2-yl)benzylidene (piperidine-1-carboxylate To a mixture of (R)-1-(2-(2-bromophenyl)pyrrolidin-1-yl)-2,2,2-trifluoroethanone (3 g, 9.31 mmol), (E)-tert-butyl 4-((2-tosylhydrazono)methyl)piperidine-1-carboxylate (5.33 g, 13.97 mmol) and t-BuOLi (2.98 g, 37.24 mmol) in dioxane (100 mL) was added Pd(PPh$_3$)$_2$Cl$_2$ (670.5 mg, 931 umol) at 20° C. The mixture was purged with N$_2$ for three times and then heated to 100° C. for 3 hours. TLC indicated the reactant was consumed completely. The reaction mixture was concentrated in vacuum (20 mL). The residue was poured into ice-water (30 mL) and was extracted with EA (50 mL×3). The combined organic phases were washed with brine (50 mL), dried with anhydrous Na$_2$SO$_4$, filtered and concentrated. The crude was purified by column chromatography (Silica gel, PE/EA=30/1 to 10/1). (R)-tert-butyl 4-(2-(1-(2,2,2-trifluoroacetyl)pyrrolidin-2-yl)benzylidene) piperidine-1-carboxylate (2.17 g, 4.95 mmol, 53.08% yield) was obtained as a red oil. $^1$H NMR (400 MHz, CDCl$_3$) δ ppm: 7.16-7.25 (m, 2H), 7.04-7.11 (m, 1H), 6.92-7.01 (m, 1H), 6.29-6.46 (m, 1H), 5.29-5.45 (m, 1H), 3.75-4.00 (m, 2H), 3.12-3.69 (m, 4H), 2.16-2.41 (m, 4H), 1.83-2.15 (m, 3H), 1.70-1.82 (m, 1H), 1.47 (s, 9H). MS (ESI, m/e) [M+1]+ 339.2.

Step 3: (R)-tert-butyl 4-(2-(1-(2,2,2-trifluoroacetyl)pyrrolidin-2-yl)benzyl)piperidine-1-carboxylate To a solution of (R)-tert-butyl 4-(2-(1-(2,2,2-trifluoroacetyl)pyrrolidin-2-yl)benzylidene)piperidine-1-carboxylate (2.3 g, 5.25 mmol) in MeOH (30 mL) was added Pd/C (300 mg, 10% wet). The mixture was purged with H$_2$ for three times and then stirred at 20° C. for 10 hours under 15 Psi H$_2$. LC/MS indicated Reactant was consumed completely and desired compound was formed. The reaction mixture was filtered with Celite, washed with MeOH. The filtrate was concentrated. (R)-tert-butyl 4-(2-(1-(2,2,2-trifluoroacetyl)pyrrolidin-2-yl)benzyl)piperidine-1-carboxylate (2.3 g, crude) was obtained as a brown solid. ¹H NMR (400 MHz, CDCL₃) δ ppm: 7.07-7.23 (m, 3H), 6.86-6.98 (m, 1H), 5.34-5.52 (m, 1H), 3.73-4.24 (m, 4H), 2.44-2.83 (m, 4H), 2.31-2.44 (m, 1H), 1.56-2.21 (m, 6H), 1.37-1.55 (m, 9H), 1.05-1.33 (m, 2H).

Step 4: (R)-tert-butyl 4-(2-(pyrrolidin-2-yl)benzyl) piperidine-1-carboxylate

To a solution of (R)-tert-butyl 4-(2-(1-(2,2,2-trifluoroacetyl)pyrrolidin-2-yl)benzyl)piperidine-1-carboxylate (2.3 g, 5.22 mmol) in MeOH (10 mL), H₂O (10 mL), THF (10 mL) was added LiOH.H₂O (438.5 mg, 10.44 mmol) at 20° C. The mixture was heated to 50° C. for 1 hour. TLC indicated the reactant was consumed completely. The reaction mixture was concentrated in vacuum to remove MeOH and THF. The aqueous phase was extracted with EA (30 mL×3). The combined organic phases were dried with anhydrous Na₂SO₄, filtered and concentrated. (R)-tert-butyl 4-(2-(pyrrolidin-2-yl)benzyl)piperidine-1-carboxylate (1.76 g, crude) was obtained as a yellow oil. MS (ESI, m/e) [M+1]⁺ 345.2.

Step 5: (R)-tert-butyl 4-(2-(1-(4-bromophenyl)pyrrolidin-2-yl)benzyl)piperidine-1-carboxylate To a mixture of (R)-tert-butyl 4-(2-(pyrrolidin-2-yl)benzyl)piperidine-1-carboxylate (1.4 g, 4.06 mmol), 1-bromo-4-iodobenzene (1.72 g, 6.10 mmol), X-phos (387 mg, 812 umol) and Cs₂CO₃ (2.64 g, 8.12 mmol) in toluene (50 mL) was added Pd(OAc)₂ (90 mg, 406 umol) at 20° C. The mixture was purged with N₂ for three times and then heated to 100° C. for 5 hours. TLC indicated the reactant was consumed completely. The reaction mixture was cooled to room temperature and poured into ice-water (30 mL) and then separated. The organic phase was washed with brine, dried with anhydrous Na₂SO₄, filtered and concentrated. The crude was purified by column chromatography (silica gel, eluent: PE/EA=100/1 to 50/1). (R)-tert-butyl 4-(2-(1-(4-bromophenyl)pyrrolidin-2-yl)benzyl)piperidine-1-carboxylate (720 mg) was obtained as a yellow solid. ¹H NMR (400 MHz, CDCl₃) δ ppm: 7.00-7.24 (m, 6H) 6.27 (d, 1-9.0 Hz, 2H) 4.80-4.92 (m, 1H) 4.02-4.27 (m, 2H) 3.65-3.78 (m, 1H) 3.35-3.47 (m, 1H) 2.57-2.83 (m, 4H) 2.36-2.51 (m, 1H) 1.97-2.12 (m, 2H) 1.80-1.95 (m, 2H) 1.71 (d, 3=12.1 Hz, 2H) 1.48 (s, 9H) 1.23-1.31 (m, 2H). MS (ESI, m/e) [M+1]⁺ 498.9.

Intermediate 2-z:
(S)—N,N-dimethyl-2-(pyrrolidin-2-yl)aniline

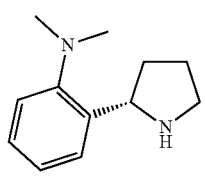

Step 1: (S)-tert-butyl 2-(2-((diphenylmethylene) amino)phenyl)pyrrolidine-1-carboxylate To a solution of (S)-tert-butyl 2-(2-bromophenyl)pyrrolidine-1-carboxylate (2.0 g, 6.13 mmol) in 1,4-dioxane (50 mL) was added diphenylmethanimine (1.67 g, 9.20 mmol), Cs₂CO₃ (3.99 g, 12.26 mmol), Pd₂(dba)₃ (561.4 mg, 6.13 mmol), and Xant-phos (1.06 g, 1.84 mmol). The mixture was stirred at 105° C. for 36 hours under N₂ protection. LC/MS showed (S)-tert-butyl 2-(2-bromophenyl)pyrrolidine-1-carboxylate was consumed completely and one main peak with desired mass signal. The mixture was evaporated in vacuum. The residue was used directly for next step. MS (ESI, m/e) [M−1]⁻ 427.2.

Step 2: (S)-tert-butyl 2-(2-aminophenyl)pyrrolidine-1-carboxylate

To a solution of (S)-tert-butyl 2-(2-((diphenylmethylene) amino)phenyl)pyrrolidine-1-carboxylate (262 mg, 613 umol, 1 eq) and In THF (5 mL) was added 0.5 N HCl acid 10 mL, The mixture was stirred at 20° C. for overnight. TLC showed (S)-tert-butyl 2-(2-((diphenylmethylene)amino)phenyl)pyrrolidine-1-carboxylate was consumed completely. The mixture was adjusted to PH ~8 with saturated aq. NaHCO₃, then was extracted with EA (20 ml). The organic phase was washed with brine, dried over Na₂SO₄, evaporated in vacuum. The residue was purified by column chromatography on silica gel (eluent: PE/EA=10/1 to 1/1) to give (S)-tert-butyl 2-(2-aminophenyl)pyrrolidine-1-carboxylate (50 mg). ¹H NMR (400 MHz, CDCl₃) δ ppm: 6.91-7.16 (m, 2H), 6.70-6.87 (m, 1H), 6.62-6.70 (m, 1H), 4.60-5.06 (m, 1H), 3.36-3.97 (m, 4H), 2.13-2.35 (m, 1H), 1.83-2.01 (m, 3H), 1.16-1.54 (m, 9H).

Step 3: (S)-tert-butyl 2-(2-(dimethylamino)phenyl) pyrrolidine-1-carboxylate

To a solution of (S)-tert-butyl 2-(2-aminophenyl)pyrrolidine-1-carboxylate (6.5 g, 22.87 mmol) in MeOH (200 mL) was added aq. HCHO (37%, 11.14 g, 137.22 mmol), and NaH₃CN (5.95 g, 114.35 mmol). The mixture was stirred at 20° C. for 14 hours, TLC showed (S)-tert-butyl 2-(2-aminophenyl)pyrrolidine-1-carboxylate was consumed completely. The mixture was evaporated in vacuum. The residue was dissolved with DCM (100 mL), washed with brine, dried over Na₂SO₄, concentrated. The residue was purified by column chromatography on silica gel (eluent: PE/EA=100/1 to 30/1) to give (S)-tert-butyl 2-(2-(dimethylamino)phenyl)pyrrolidine-1-carboxylate (5.9 g). ¹H NMR (400 MHz, CDCl₃) δ ppm: 6.93-7.15 (m, 4H), 5.12-5.37 (m, 1H), 3.36-3.69 (m, 2H), 2.60 (s, 6H), 2.20-2.37 (m, 1H), 1.64-1.87 (m, 3H), 1.39 (s, 2H), 1.10 (s, 6H).

Step 4:
(S)—N,N-dimethyl-2-(pyrrolidin-2-yl)aniline

To solution of (S)-tert-butyl 2-(2-(dimethylamino)phenyl) pyrrolidine-1-carboxylate (5.90 g, 20.32 mmol) in DCM (30 mL) was added TFA (30 mL). The mixture was stirred at 20° C. for 2 hours. TLC showed (S)-tert-butyl 2-(2-(dimethylamino)phenyl)pyrrolidine-1-carboxylate was consumed completely. The mixture was poured into water was then adjusted to pH ~10 with aq. NaOH (2N). The mixture was extracted with DCM (50 mL×3), washed with brine and water, dried with anhydrous Na₂SO₄. After filtration, the filtrate was concentrated in vacuum to give (S)—N,N-dimethyl-2-(pyrrolidin-2-yl)aniline (3.248 g). ¹H NMR (400 MHz, CDCl₃) δ ppm: 7.38-7.52 (m, 1H) 7.18-7.24 (m, 1H) 7.03-7.16 (m, 2H) 4.59 (1, J=7.9 Hz, 1H), 3.24 (ddd, J=10.0, 7.6, 5.1 Hz, 1H), 3.00 (dt, J=9.8, 7.7 Hz, 1H), 2.71 (br, 6H), 2.17-2.33 (m, 1H), 2.14 (s, 1H), 1.80-2.04 (m, 2H), 1.54-1.77 (m, 1H). MS (ESI, m/e) [M+1]⁺ 191.3.

Intermediate 2-z1: (S)—N,N-bis(methyl-d3)-2-(pyrrolidin-2-yl)aniline

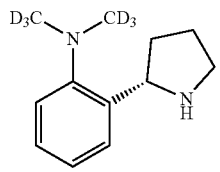 [SMILES: [2H]C([2H])([2H])N(c1ccccc1[C@@H]1CCCN1)C([2H])([2H])[2H]]

Step 1: (S)-tert-butyl 2-(2-(d6-dimethylamino)phenyl)pyrrolidine-1-carboxylate

To a solution of (S)-tert-butyl 2-(2-aminophenyl)pyrrolidine-1-carboxylate (6.5 g, 22.87 mmol) in DMF (20 mL) was added NaH (457.4 mg, 11.44 mmol), and CD₃I (2.21 g, 15.25 mmol) at 0° C., The mixture was stirred at 45° C. for 14 hours. TLC showed (S)-tert-butyl 2-(2-aminophenyl) pyrrolidine-1-carboxylate was consumed completely. The mixture was poured into water (50 mL), extracted with EA, concentrated in vacuum to give tert-butyl (S)-2-(2-(bis (methyl-d3)amino)phenyl)pyrrolidine-1-carboxylate (880 mg), which was used in next step without further purification. ¹H NMR (400 MHz, CDCl₃) δ ppm: 7.00-7.22 (m, 4H), 5.20-5.43 (m, 1H), 3.49-3.72 (m, 2H), 2.26-2.45 (m, 1H), 1.72-1.95 (m, 3H), 1.47 (s, 2H), 1.18 (s, 7 it). MS (ESI, m/e) [M+1]⁺ 297.4.

Step 2: (S)—N,N-bis(methyl-d3)-2-(pyrrolidin-2-yl) aniline

To solution of (S)-2-(2-(bis(methyl-d3)amino)phenyl) pyrrolidine-1-carboxylate (275 mg, 927.68 umol), in DCM (10 mL) was added TFA (5 mL), The mixture was stirred at 20° C. for 2 hours. TLC showed the reactant was consumed completely. The mixture was concentrated in vacuum to give a residue. The residue was dissolved with DCM (20 mL), washed with sat. aq, Na₂CO₃ (20 mL), dried with Na₂SO₄, concentrated in vacuum to give (S)—N,N-bis(methyl d3)-2-(pyrrolidin-2-yl)aniline (100 mg). ¹H NMR (400 MHz, CDCl₃) δ ppm: 7.42 (dd, J=1.1, 1.3 Hz, 1H), 7.19-7.26 (m, 1H), 7.07-7.18 (m, 2H), 4.63 (t, J=7.9 Hz, 1H), 3.24 (ddd, J=10.3, 7.4, 5.4 Hz, 1H), 3.04-3.11 (m, 1H), 2.18-2.30 (m, 1H), 1.87-2.06 (m, 2H), 1.66-1.77 (m, 1H), MS (ESI, m/e) [M+1]⁺ 197.3.

Intermediate 2-z2: 2-((1-(2-cyclopropylphenyl)pyrrolidin-2-yl)methyl)-2,6-diazaspiro[3.3]heptane

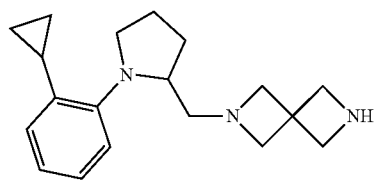 [SMILES: c1ccc(N2CCCC2CN2CC3(CNC3)C2)c(C2CC2)c1]

Step 1: (1-(2-cyclopropylphenyl)pyrrolidin-2-yl)methanol

To a solution of 2-(((tert-butyldimethylsilyl)oxy)methyl)-1-(2-cyclopropylphenyl)pyrrolidine (1.5 g, 4.52 mmol) in MeOH/HCl (20 mL) at 20° C. and the mixture was stirred for 1 hours. TLC indicated the reactant was consumed completely. The reaction mixture was concentrated to give (1-(2-cyclopropylphenyl)pyrrolidin-2-yl)methanol (0.8 g, crude). ¹H NMR (400 MHz, CDCl₃) δ ppm: 7.81 (d, J=7.7 Hz, 1H), 7.34-7.40 (m, 1H), 7.28-7.34 (m, 1H), 7.04 (dd, J=7.7, 1.2 Hz, 1H), 4.55 (br, 1H), 4.19 (s, 1H), 4.11 (d, J=13.9 Hz, 1H), 3.85-4.15 (m, 2H), 3.59-3.81 (m, 3H), 2.52-2.64 (m, 1H), 2.48 (s, 2H), 2.37 (s, 2H), 1.22-1.35 (m, 2H), 0.77-0.98 (m, 2H). MS (ESI, m/e) [M+1]⁺ 217.9.

Step 2: 1-(2-cyclopropylphenyl)pyrrolidine-2-carbaldehyde

To a solution of (COCl)₂ (700.9. m g, 5.52 mmol) in DCM (20 mL) was added DMSO (862.93 mg, 11.04 mmol) drop-wise at −65° C. The mixture was stirred at −65° C. for 0.5 hour. And then (1-(2-cyclopropylphenyl)pyrrolidin-2-yl) methanol (800.0 mg, 3.68) in DCM (2 mL) was added drop-wise at −65° C., The mixture was further stirred at −65° C. for 1 hour. TLC indicated the reactant was consumed completely. To the reaction mixture was added TEA (2.89 g, 29.45 mmol) and warmed to 20° C. for 0.5 hour. The reaction mixture was poured into water, extracted with DCM, dried over anhydrous Na₂SO₄ and concentrated In vacuum to obtain 1-(2-cyclopropylphenyl)pyrrolidine-2-carbaldehyde (1.2 g, crude). ¹H NMR (400 MHz, CDCl₃) δ ppm: 12.10 (s, 1H), 9.39 (d, J=3.8 Hz, 1H), 7.06-7.16 (m, 1H), 6.85-7.03 (m, 3H), 4.19 (td, J=7.1, 3.9 Hz, 1H), 3.86-3.96 (m, 1H), 3.05-3.16 (m, 6H), 2.62 (s, 1H), 2.12-2.26 (m, 2H), 2.00-2.12 (m, 2H), 1.90-2.00 (m, 1H), 1.42 (t, J=7.3 Hz, 9H), 1.00-1.10 (m, 1H), 0.75-0.94 (m, 2H), 0.59-0.67 (m, 1H).

Step 3: tert-butyl 6-((1-(2-cyclopropylphenyl)pyrrolidin-2-yl)methyl)-2,6-diazaspiro[3,3]heptane-2-carboxylate To a solution of 1-(2-cyclopropylphenyl)pyrrolidine-2-carbaldehyde (600 mg, 2.79 mmol) in DCM (10 mL) was added NaBH(OAc)₃ (1.18 g, 5.57 mmol) at 0° C. slowly. Then tert-butyl 2,6-diazaspiro[3.3]heptane-2-carboxylate oxalate (803.46 mg, 2.79 mmol) was added into the mixture at 0° C. The mixture was stirred at 20° C. for 1 hour. TLC indicated the reactant was consumed completely. The reaction mixture was poured into water, extracted with DCM (10 mL) and concentrated in vacuum to give a residue. The residue was purified by column chromatography (SiO₂, PE/EA=100/1 to 0/1). Tert-butyl 6-((1-(2-cyclopropylphenyl)pyrrolidin-2-yl)methyl)-2,6-diazaspiro[3.3]heptane-2-carboxylate (600 mg) was obtained. ¹H NMR. (400 MHz, CDCl₃) δ ppm: 7.07-7.14 (m, 1H), 7.01 (d, J=7.0 Hz, 1H), 6.90-6.97 (m, 1H), 6.83-6.88 (m, 1H), 3.95 (s, 4H), 3.61-3.75 (m, 2H), 3.16-3.43 (m, 4H), 2.86 (td, J=8.5, 5.1 Hz, 1H), 2.11-2.21 (m, 2H), 2.06 (s, 1H), 1.87-1.99 (m, 2H), 1.74-1.87 (m, 2H), 1.57-1.74 (m, 1H), 1.42 (s, 9H), 0.95-1.13 (m, 1H), 0.70-0.95 (m, 3H), 0.52-0.62 (m, 1H). MS (ESI, m/e) [M+1]⁺ 398.1.

Step 4: 2-((1-(2-cyclopropylphenyl)pyrrolidin-2-yl) methyl)-2,6-diazaspiro[3.3]heptane To a solution of tert-butyl 6-((1-(2-cyclopropylphenyl) pyrrolidin-2-yl)methyl)-2,6-diazaspiro[3.3]heptane-2-carboxylate (600 mg, 1.51 mmol) in DCM (8 mL) was added TFA (2 mL) at 20° C., The mixture was stirred at 20° C. for 1 hour. TLC indicated the reactant was consumed completely. The reaction mixture was concentrated to give 2-((1-(2-cyclopropylphenyl)pyrrolidin-2-yl)methyl)-2,6-diazaspiro[3.3]heptane (326 mg) as a yellow oil. $^1$H NMR (400 MHz, CDCl$_3$) δ ppm: 7.10 (t, J=7.3 Hz, 1H), 6.99-7.04 (m, 1H), 6.91 (s, 1H), 6.80-6.88 (m, 1H), 3.78 (br, 4H), 3.57-3.74 (m, 2H), 3.22-3.40 (m, 4H), 2.80-3.03 (m, 3H), 2.55 (d, J=12.6 Hz, 1H), 2.10-2.28 (m, 3H), 1.90 (s, 1H), 1.67-1.84 (m, 2H), 0.82-1.10 (m, 2H), 0.51-0.81 (m, 2H). MS (ESI, m/e) [M+1]$^+$ 298.2.

Intermediate 2-z3: (S)-4-(3-(2-(2-cyclopropylphenyl)pyrrolidin-1-yl)cyclobutyl)piperidine

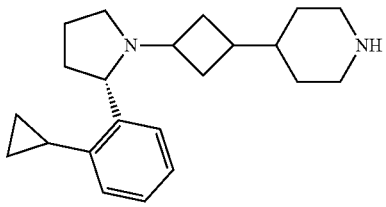 [SMILES: c1ccc([C@@H]2CCCN2C2CC(C3CCNCC3)C2)c(C2CC2)c1]

Step 1: tert-butyl 4-(2,2-dichloro-3-oxocyclobutyl)piperidine-1-carboxylate

To the mixture of Zn (4.64 g, 70.99 mmol) in dioxane (50 mL) under N$_2$ atmosphere was added tert-butyl 4-vinylpiperidine-1-carboxylate (5.0 g, 23.66 mmol) at 20° C. Then CCl$_3$COCl (6.45 g, 35.49 mmol) was added at 20° C. The mixture was stirred at 20° C. for 12 hours. To the reaction mixture was added aq. NaHCO$_3$ (50 mL) at 0° C. Then the mixture was extracted with EA (50 mL×5) and the combine organic phase was dried over anhydrous Na$_2$SO$_4$ and concentrated. The residue was purified by column chromatography (SiO$_2$, PE/EA=50/1 to 20/1). Tert-butyl 4-(2,2-dichloro-3-oxocyclobutyl)piperidine-1-carboxylate (3.0 g) was obtained. $^1$H NMR (400 MHz, CDCl$_3$) δ ppm: 4.05-4.21 (m, 2H) 3.04-3.27 (m, 2H) 2.77 (br, 2H) 2.60 (q, J=10.4 Hz, 1H) 2.03-2.10 (m, 1H) 1.84-1.97 (m, 1H) 1.52-1.63 (m, 1H) 1.46 (s, 9H) 1.16-1.41 (m, 3H).

Step 2: tert-butyl 4-(3-oxocyclobutyl)piperidine-1-carboxylate

To a mixture of Zn (1.22 g, 18.62 mmol) in HOAc (3.73 g, 62.07 mmol) under N$_2$ atmosphere was added tert-butyl 4-(2,2-dichloro-3-oxocyclobutyl)piperidine-1-carboxylate (2.0 g, 6.21 mmol) in Diox (15 mL) at 15° C., the mixture was stirred at 15° C. for 12 hours. The mixture was adjusted to pH ~9 with 33% aq. NaOH and was extracted with EA (50 mL×3). After dried and concentrated, the residue was purified by column chromatography (SiO$_2$, PE/EA=50/1 to 10/1). Tert-butyl 4-(3-oxocyclobutyl)piperidine-1-carboxylate (1.0 g, 3.95 mmol) was obtained. $^1$H NMR (400 MHz, CDCl$_3$) δ ppm: 4.14 (s, 2H) 3.02-3.17 (m, 2H) 2.64-2.83 (m, 4H) 2.05-2.18 (m, 1H) 1.72 (d, J=12.8 Hz, 2H) 1.35-1.36 (m, 1H) 1.47 (s, 8H) 1.15 (d, J=12.3, 4.3 Hz, 2H).

Step 3: (S)-tert-butyl 4-(3-(2-(2-cyclopropylphenyl)pyrrolidin-1-yl)cyclobutyl)piperidine-1-carboxylate To a solution of tert-butyl 4-(3-oxocyclobutyl)piperidine-1-carboxylate (0.7 g, 2.76 mmol, 1 eq) and (S)-2-(2-cyclopropylphenyl)pyrrolidine (569.23 mg, 3.04 mmol) in DCE (20 mL) was added AcOH (331.86 mg, 5.53 mmol) and NaBH(OAc)$_3$ (1.17 mg, 5.53 mmol). The mixture was stirred at 25° C. for 1 hour, TLC showed the reactant was consumed completely. The reaction mixture was quenched with aq. Na$_2$CO$_3$ (20 mL) and extracted EA (20 mL×3), dried over Na$_2$SO$_4$, filtered and concentrated. The residue was purified by prep-MPLC. (S)-tert-butyl 4-(3-(2-(2-cyclopropylphenyl)pyrrolidin-1-yl)cyclobutyl)piperidine-1-carboxylate (1.1 g) was obtained. MS (ESI, m/e) [M+1]$^+$ 425.3.

Step 4: (S)-4-(3-(2-(2-cyclopropylphenyl)pyrrolidin-1-yl)cyclobutyl)piperidine

A mixture of (S)-tert-butyl 4-(3-(2-(2-cyclopropylphenyl)pyrrolidin-1-yl)cyclobutyl)piperidine-1-carboxylate (0.9 g, 2.12 mmol) in DCM (5 mL) and TFA (5 mL) was stirred at 25° C. for 1 hour, LC/MS showed the reactant was consumed completely and one main peak with desired mass signal. The reaction mixture was concentrated in vacuum to remove solvent. The residue was diluted with H$_2$O (10 mL) and was adjusted to pH ~9 with saturated aq. Na$_2$CO$_3$. The mixture was extracted with EA (10 mL×3), dried over Na$_2$SO$_4$, filtered and concentrated. (S)-4-(3-(2-(2-cyclopropylphenyl)pyrrolidin-1-yl)cyclobutyl)piperidine (643 mg) was obtained. $^1$H NMR (400 MHz, CDCl$_3$) δ ppm: 7.66-7.56 (m, 1H), 7.21-7.08 (m, 2H), 6.97 (d, J=7.5 Hz, 1H), 6.34 (s, 1H), 3.96 (q, J=7.7 Hz, 1H), 3.30-2.83 (m, 4H), 2.75-2.60 (m, 2H), 2.46-2.31 (m, 1H), 2.29-2.14 (m, 1H), 2.06-1.44 (m, 10H), 1.40-1.03 (m, 4H), 0.98-0.85 (m, 2H), 0.74-0.55 (m, 2H). MS (ESI, m/e) [M+1]$^+$ 325.3.

Intermediate 2-z4: 4-(2-(1-(4-bromophenyl)pyrrolidin-2-yl)phenoxy)-1-methylpiperidine

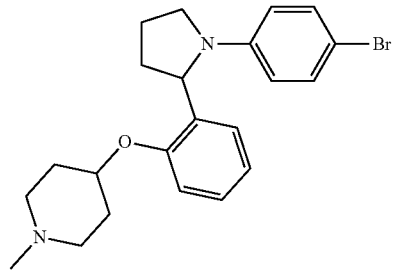 [SMILES: CN1CCC(Oc2ccccc2C2CCCN2c2ccc(Br)cc2)CC1]

Step 1: tert-butyl 4-(2-formylphenoxy)piperidine-1-carboxylate

To a solution of tert-butyl 4-hydroxypiperidine-1-carboxylate (5.0 g, 24.84 mmol) and 2-fluorobenzaldehyde (6.17 g, 49.69 mmol) in DMSO (150 mL) was added K$_2$CO$_3$ (10.15 g, 74.53 mmol). The mixture was stirred at 100° C. for 6 hours. TLC indicated the reactant was consumed completely. The reaction mixture was cooled to room temperature and was poured into H$_2$O (50 mL) and extracted with EA (50 mL×3), dried over Na$_2$SO$_4$, filtered and concentrated. The residue was purified by column chromatography (SiO$_2$, PE/EA=20/1 to 10/1) to obtain tert-butyl 4-(2-formylphenoxy)piperidine-1-carboxylate (6 g). MS (ESI, m/e) [M+1]$^+$ 306.1.

Step 2: (E)-tert-butyl 4-(2-(((4-bromophenyl)imino)methyl)phenoxy)piperidine-1-carboxylate A mixture of tert-butyl 4-(2-formylphenoxy)piperidine-1-carboxylate (4.30 g, 14.08 mmol), 4-bromoaniline (2.42 g, 14.08 mmol), TsOH (133.93 mg, 0.7 mmol) and 4 Å molecular sieve (2.15 g) in toluene (43 mL) was stirred at 140° C. for 12 hours. TLC indicated the reaction was completed. The reaction mixture was concentrated in vacuum to obtain the crude (E)-tert-butyl 4-(2-(((4-bromophenyl)imino) methyl)phenoxy)piperidine-1-carboxylate (7.5 g, crude), which was used directly for next step.

Step 3: tert-butyl 4-(2-(1-((4-bromophenyl)amino) but-3-en-1-yl)phenoxy)piperidine-1-carboxylate To a solution of (E)-tert-butyl 4-(2-(((4-bromophenyl)imino)methyl)phenoxy)piperidine-1-carboxylate (5.7 g) in DCM (50 mL) was added dropwise allylmagnesium bromide (49.63 mL, 1 M in THF) at 0° C. The mixture was stirred at 0-15° C. for 3 hours. TLC indicated the reaction was completed. The reaction mixture was poured into aq. HN$_4$Cl (50 mL) and extracted with and EA (50 mL×2). The combined organic layers were washed with brine (50 mL), dried over Na$_2$SO$_4$, filtered and concentrated in vacuum. The residue was purified by column chromatography on silica gel (eluent: PE/EA=50/1 to 20/1) to give tert-butyl 4-(2-(1-((4-bromophenyl)amino)but-3-en-1-yl)phenoxy)piperidine-1-carboxylate (4.2 g). MS (ESI, m/e) [M+1]$^+$ 502.2.

Step 4: tert-butyl 4-(2-(1-((4-bromophenyl)amino)-4-hydroxybutyl)phenoxy)piperidine-1-carboxylate To a solution of tert-butyl 4-(2-(1-((4-bromophenyl)amino)but-3-en-1-yl)phenoxy)piperidine-1-carboxylate (3.3 g, 6.58 mmol) in THF (50 mL) was added BH$_3$.THF (65.8 mL, 1M in THF) at 0° C. The mixture was stirred at 0° C. for 3 hours. And then H$_2$O$_2$ (6.58 mL, 65.81 mmol) was added in drops and stirred at 0° C. for 1 hour, Aq. NaOH (2.63 g, 65.81 mmol, 4M) was added in drops and stirred at 0-15° C. for 2 hours. TLC indicated the reaction was completed. The mixture was poured into saturated aq. Na$_2$S$_2$O$_3$ (50 mL) and stirred for 0.5 hour, extracted with EA (100 mL×2). The combined organic layers were washed with saturated aq, Na$_2$S$_2$O$_3$ (50 mL), aq. NaHCO$_3$ (50 mL) and brine (50 mL), dried over Na$_2$SO$_4$, filtered and concentrated in vacuum. The residue was purified by column chromatography (SiO$_2$, PE/EA=5/1 to 2/1) to give tert-butyl 4-(2-(1-((4-bromophenyl)amino)-4-hydroxybutyl)phenoxy)piperidine-1-carboxylate (2.4 g). MS (ESI, m/e) [M+1]$^+$ 520.3.

Step 5: tert-butyl 4-(2-(1-(4-bromophenyl)pyrrolidin-2-yl)phenoxy)piperidine-1-carboxylate To a mixture of tert-butyl 4-(2-(1-((4-bromophenyl)amino)-4-hydroxybutyl)phenoxy)piperidine-1-carboxylate (2.3 g, 4.43 mmol) and TEA (1.34 g, 13.28 mmol) in DCM (23 mL) was added MsCl (1.01 mg, 8.86 mmol) at 0° C. and the mixture was stirred at 25° C. for 5 hours. TLC showed the reaction was complete. The reaction mixture was poured into H$_2$O (20 mL), extracted with DCM (20 mL×2), The combined organic layers were washed with brine (20 mL), dried over Na$_2$SO$_4$, filtered and concentrated in vacuum. The residue was purified by column chromatography on silica gel (eluent: PE/EA=10/1 to 2/1) to obtain tert-butyl 4-(2-(1-(4-bromophenyl)pyrrolidin-2-yl)phenoxy)piperidine-1-carboxylate. MS (ESI, m/e) [M+1]$^+$ 502.2.

Step 6: 4-(2-(1-(4-bromophenyl)pyrrolidin-2-yl) phenoxy)piperidine

A mixture of tert-butyl 4-(2-(1-(4-bromophenyl)pyrrolidin-2-yl)phenoxy)piperidine-1-carboxylate (1.8 g, 3.59 mmol) in DCM (20 mL) was added TFA (7 mL) and was stirred at 15° C. for 3 hours, TLC indicated the reaction was completed. The mixture was concentrated in vacuum to obtain 4-(2-(1-(4-bromophenyl)pyrrolidin-2-yl)phenoxy)piperidine (1.8 g, TFA salt, crude). MS (ESI, m/e) [M+1]$^+$ 402.2.

Step 7: 4-(2-(1-(4-bromophenyl)pyrrolidin-2-yl) phenoxy)-1-methylpiperidine

To a solution of 4-(2-(1-(4-bromophenyl)pyrrolidin-2-yl)phenoxy)piperidine (1.0 g, 2.49 mmol) in MeOH (10 mL) was added aq, HCHO (37%, 1.01 g, 12.46 mmol) and NaBH$_3$CN (496.74 mg, 4.47 mmol) and stirred at 15° C. for 3 hours. TLC indicated the reaction was completed. The reaction mixture was concentrated in vacuum. The residue was poured into saturated aq. NaHCO$_3$ (20 mL), extracted with EA (30 mL×3). The combined organic layers were dried over Na$_2$SO$_4$, filtered and concentrated. The residue was purified by column chromatography on silica gel (eluent: PE/EA=1/1 to 1/10) to give 4-(2-(1-(4-bromophenyl)pyrrolidin-2-yl)phenoxy)-1-methylpiperidine. $^1$H NMR (400 MHz, CDCl$_3$) δ ppm: 7.15-7.24 (m, 3H) 6.99 (dd, J=7.5, 1.3 Hz, 1H) 6.88 (d, J=8.1 Hz, 1H) 6.79-6.85 (1H, m) 6.30 (2H, d, J=9.0 Hz) 4.96 (1H, d, J=7.9 Hz) 4.60 (1H, s) 3.63-3.70 (m, 1H) 3.32-3.41 (m, 1H) 2.64-2.87 (m, 4H) 2.46 (s, 3H) 2.29-2.40 (m, 1H) 2.14-2.24 (m, 2H) 1.92-2.10 (m, 5H). MS (ESI, m/e) [M+1]$^+$ 415.1.

Intermediate 2-z5: (S)-2-((2-(2-cyclopropylphenyl) pyrrolidin-1-yl)methyl)-7-azaspiro[3.5]nonane

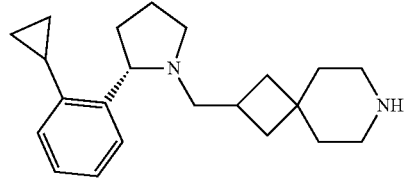 [SMILES: c1ccc([C@@H]2CCCN2CC2CC3(CCNCC3)C2)c(C2CC2)c1]

Step 1: tert-butyl 2-(methoxymethylene)-7-azaspiro [3.5]nonane-7-carboxylate

To a solution of (methoxymethyl)triphenylphosphonium chloride (3.72 g, 10.86 mmol) in toluene (30 mL) was added t-BuOK (1 M in THF, 10.86 mL, 10.86 mmol). The mixture was stirred at 25° C. for 20 minutes under N$_2$ protection. Then tert-butyl 2-oxo-7-azaspiro[3.5]nonane-7-carboxylate (2 g, 8.36 mmol) in toluene (20 mL) was added. The mixture was stirred at 70° C. for 4 hours. TLC showed the reactant was consumed completely. The reaction mixture was quenched by aq. HN$_4$Cl (30 mL) and extracted with EA (50 mL×3), dried over Na$_2$SO$_4$, filtered and concentrated. The residue was purified by prep-MPLC to obtain tert-butyl 2-(methoxymethylene)-7-azaspiro[3.5]nonane-7-carboxylate (1.2 g). MS (ESI, m/e) [M+1]$^+$ 268.3.

Step 2: tert-butyl 2-formyl-7-azaspiro[3,5]nonane-7-carboxylate

A mixture of tert-butyl 2-(methoxymethylene)-7-azaspiro [3,5]nonane-7-carboxylate (1 g, 3.74 mmol) in ACN (36 mL), H$_2$O (9 mL) and TFA (0.3 mL) was stirred at 25° C. for 4 hours, TLC showed the reactant was consumed completely. The reaction mixture was quenched by aq, NaHCO₃ (20 mL) and extracted with EA (20 mL×3), dried over Na₂SO₄, filtered and concentrated in vacuum. The residue was purified by prep-MPLC. Tert-butyl 2-formyl-7-azaspiro [3.5]nonane-7-carboxylate (390 mg) was obtained. ¹H NMR (400 MHz, CDCl₃) δ ppm: 9.76 (d, J=1.5 Hz, 1H), 3.39-3.32 (m, 2H), 3.31-3.25 (m, 2H), 3.20-3.10 (m, 1H), 2.11-1.95 (m, 4H), 1.64-1.56 (m, 2H), 1.44 (s, 9H).

Step 3: (S)-tert-butyl 2-((2-(2-cyclopropylphenyl) pyrrolidin-1-yl)methyl)-7-azaspiro[3.5]nonane-7-carboxylate To a solution of tert-butyl 2-formyl-7-azaspiro[3.5] nonane-7-carboxylate (0.3 g, 1.18 mmol) and (S)-2-(2-cyclopropylphenyl)pyrrolidine (184.81 mg, 986.83 umol) in DCE (5 mL) was added AcOH (118.52 mg, 1.97 mmol) and NaBH(OAc)₃ (418.30 mg, 1.97 mmol). The mixture was stirred at 25° C. for 2 hours. TLC showed the reactant was consumed completely. The reaction mixture was poured into aq. Na₂CO₃ (5 mL) and extracted EA (5 mL×3), dried over Na₂SO₄, filtered and concentrated. The residue was purified by prep-MPLC. (S)-tert-butyl 2-((2-(2-cyclopropylphenyl) pyrrolidin-1-yl)methyl)-7-azaspiro[3,5]nonane-7-carboxylate (300 mg, 0.7 mmol, 59.66% yield) was obtained. MS (ESI, m/e) [M+1]⁺ 425.3.

Step 4: (S)-2-((2-(2-cyclopropylphenyl)pyrrolidin-1-yl)methyl)-7-azaspiro[3.5]nonane A mixture of (S)-tert-butyl 2-((2-(2-cyclopropylphenyl) pyrrolidin-1-yl)methyl)-7-azaspiro[3.5]nonane-7-carboxylate (0.3 g, 0.7 mmol) in DCM (1.5 mL) and TFA (1.5 mL) was stirred at 25° C. for 1 hour. LC/MS showed the reactant was consumed completely and one main peak with desired mass signal. The reaction mixture was concentrated in vacuum to remove solvent. The residue was diluted with H₂O (10 mL), and adjusted to pH ~9 with Na₂CO₃. The mixture was extracted with EA (10 mL×3), dried over Na₂SO₄, filtered and concentrated. (S)-2-((2-(2-cyclopropylphenyl)pyrrolidin-1-yl)methyl)-7-azaspiro[3,5]nonane (180 mg) was obtained. ¹H NMR (400 MHz, CDCl₃) δ ppm: 7.58 (d, J=7.7 Hz, 1H), 7.23-7.17 (m, 1H), 7.17-7.11 (m, 1H), 7.00 (d, J=7.1 Hz, 1H), 3.81 (t, J=8.3 Hz, 1H), 3.27 (t, J=7.7 Hz, 1H), 2.95-2.84 (m, 2H), 2.83-2.72 (m, 2H), 2.58 (dd, J=8, 0, 11.8 Hz, 1H), 2.41 (td, J=7.8, 15.3 Hz, 1H), 2.30-2.15 (m, 2H), 2.13-1.98 (m, 2H), 1.97-1.87 (m, 3H), 1.83 (d, J=14.3 Hz, 1H), 1.74-1.64 (m, 2H), 1.63-1.53 (m, 1H), 1.53-1.45 (m, 2H), 1.44-1.31 (m, 2H), 0.98-0.85 (m, 2H), 0.77-0.67 (m, 1H), 0.66-0.55 (m, 1H). MS (ESI, m/e) [M+1]⁺ 325.3.

Intermediate 2-z6: 1-(2-cyclopropylphenyl)-1,9-diazaspiro[5.5]undecane

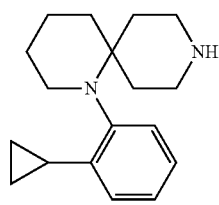 [SMILES: c1ccc(N2CCCCC23CCNCC3)c(C2CC2)c1]

Step 1: tert-butyl 4-(but-3-en-1-yl)-4-((2-cyclopropylphenyl)amino)piperidine-1-carboxylate To a solution of tert-butyl 4-((2-cyclopropylphenyl) imino)piperidine-1-carboxylate (5 g, 15.90 mmol) in DCM (50 mL) was added but-3-en-1-ylmagnesium bromide (0.5 M, 159 mL, 79.51 mmol) at −20° C. The mixture was stirred at −20° C. for 2 hours, TLC indicated the reactant was consumed completely. The reaction mixture was quenched by aq. HN₄Cl (100 mL) and extracted with DCM (100 mL×3), dried over Na₂SO₄, filtered and concentrated. After the residue was purified by prep-MPLC, tert-butyl 4-(but-3-en-1-yl)-4-((2-cyclopropylphenyl)amino)piperidine-1-carboxylate (2.5 g) was obtained as a yellow oil. MS (ESI, m/e) [M+1]⁺ 371.3.

Step 2: tert-butyl 4-((2-cyclopropylphenyl)amino)-4-(4-hydroxybutyl)piperidine-1-carboxylate To a solution of tert-butyl 4-(but-3-en-1-yl)-4-((2-cyclopropylphenyl)amino)piperidine-1-carboxylate (2.5 g, 6.75 mmol) in THF (25 mL) was added BH₃.THF (1M, 33.74 mL, 33.74 mmol) at 0° C. The mixture was stirred at 25° C. for 2 hours. Then to the mixture was added NaOH (2.5M, 6.75 mL, 6.75 mmol) and H₂O₂ (11.48 g, 101.21 mmol) at 0° C. The mixture was stirred at 25° C. for 2 hours. TLC indicated the reactant was consumed completely. The reaction mixture was poured into aq. Na₂SO₃ (100 mL) and extracted with EA (100 mL×3), dried over Na₂SO₄, filtered and concentrated. After the residue was purified by prep-MPLC, tert-butyl 4-((2-cyclopropylphenyl)amino)-4-(4-hydroxybutyl)piperidine-1-carboxylate (1.2 g) was obtained. ¹H NMR (400 MHz, CDCl₃) δ ppm: 7.09 (d, J=7.5 Hz, 1H), 7.07-7.01 (m, 1H), 6.74 (d, J=7.9 Hz, 1H), 6.61 (t, J=7.4 Hz, 1H), 3.95 (s, 1H), 3.77-3.67 (m, 1H), 3.63-3.50 (m, 1H), 3.11-2.93 (m, 2H), 2.55-2.41 (m, 1H), 2.00 (d, J=11.7 Hz, 1H), 1.92-1.70 (m, 4H), 1.66-1.56 (m, 1H), 1.46 (s, 9H), 1.36-1.29 (m, 1H), 0.98-0.86 (m, 5H), 0.67-0.57 (m, 2H).

Step 3: tert-butyl 1-(2-cyclopropylphenyl)-1,9-diazaspiro[5.5]undecane-9-carboxylate To a solution of tert-butyl 4-((2-cyclopropylphenyl) amino)-4-(4-hydroxybutyl)piperidine-1-carboxylate (1 g, 2.57 mmol) in DCM (10 mL) and TFA (520.87 mg, 5.51 mmol) was added MsCl (294.82 mg, 2.57 mmol) at 0° C. and the mixture was stirred at 25° C. for 2 hours. TLC indicated the reactant was consumed completely. The reaction mixture was quenched with aq. HN₄Cl (10 mL) and extracted with DCM (10 mL×3), dried over Na₂SO₄, filtered and concentrated. After the residue was purified by prep-MPLC, tert-butyl 1-(2-cyclopropylphenyl)-1,9-diazaspiro [5.5]undecane-9-carboxylate (0.7 g) was obtained as a yellow oil. MS (ESI, m/e) [M+1]⁺ 371.4.

Step 4: 1-(2-cyclopropylphenyl)-1,9-diazaspiro[5.5] undecane

A mixture of tert-butyl 1-(2-cyclopropylphenyl)-1,9-diazaspiro[5.5]undecane-9-carboxylate (0.7 g, 1.89 mmol) in DCM (4 mL) and TFA (4 mL) was stirred at 20° C. for 1 hour. LC/MS showed the reactant was consumed completely and one main peak with desired mass signal. The reaction mixture was concentrated in vacuum to remove solvent. The residue was diluted with H₂O (10 mL) and was adjusted to pH ~9 with Na₂CO₃. Then the mixture was extracted with EA (10 mL×3). The combined organic layers were washed with brine, dried over Na$_2$CO$_3$, filtered and concentrated to obtain 1-(2-cyclopropylphenyl)-1,9-diazaspiro[5.5]undecane (452 mg). TI NMR (400 MHz, CDCl$_3$) δ ppm: 7.25-7.20 (m, 1H), 7.11-7.04 (m, 2H), 6.73-6.66 (m, 1H), 3.40-3.27 (m, 2H), 3.04-2.92 (m, 2H), 2.81-2.58 (m, 3H), 2.48-2.42 (m, 1H), 2.33-2.22 (m, 1H), 1.82-1.67 (m, 2H), 1.67-1.54 (m, 2H), 1.22 (dt, J=4.0, 12.8 Hz, 1H), 1.11 (d, J=6.8 Hz, 3H), 0.94 (dd, J=1.8, 8.6 Hz, 2H), 0.75-0.66 (m, 1H), 0.61-0.54 (m, 1H). MS (ESI, m/e) [M+1]$^+$ 271.4.

Intermediate 2-z7:
5-(2-cyclopropylphenyl)-N,N-dimethylpyrrolidin-3-amine

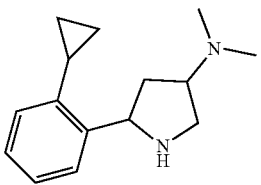 [SMILES: CN(C)C1CNC(c2ccccc2C2CC2)C1]

Step 1: 1-(tert-butylsulfonyl)-5-(2-cyclopropylphenyl)pyrrolidin-3-one

A mixture of 1-(tert-butylsulfonyl)-5-(2-cyclopropylphenyl)pyrrolidin-3-ol (5.0 g, 15.46 mmol), DMP (8.52 g, 20.1 mmol) and NaHCO$_3$ (1.43 g, 17.0 mmol) in DCM (50 mL), The mixture was stirred at 20° C. for 3 hours. TLC indicated the reaction was complete. The mixture was quenched with Na$_2$S$_2$O$_3$ (20 mL) and was adjusted to pH ~10 with aq. Na$_2$CO$_3$. After the mixture was extracted with DCM (50 mL×3), the combined organic layers were dried over Na$_2$SO$_4$, filtered and concentrated. After the residue was purified by column chromatography (SiO$_2$, PE/EA=50/1 to 15/1), 1-(tert-butylsulfonyl)-5-(2-cyclopropylphenyl)pyrrolidin-3-one (3.5 g) was obtained. $^1$H NMR (400 MHz, CDCl$_3$) δ ppm: 7.18-7.23 (m, 2H), 7.12-7.16 (m, 1H), 7.02-7.08 (m, 1H), 6.33 (d, J=8.8 Hz, 1H), 4.54 (d, J=18.7 Hz, 1H), 3.83 (d, J=18.7 Hz, 1H), 3.21 (dd, J=17.9, 10.03 Hz, 1H), 2.50 (d, J=17.9 Hz, 1H), 1.85-1.95 (m, 1H), 1.26 (s, 8H), 0.93-1.08 (m, 2H), 0.70-0.79 (m, 1H), 0.58-0.65 (m, 1H).

Step 2: 1-(tert-butylsulfonyl)-5-(2-cyclopropylphenyl)-N,N-dimethylpyrrolidin-3-amine To the mixture of 1-(tert-butylsulfonyl)-5-(2-cyclopropylphenyl)pyrrolidin-3-one (3.5 g, 10.89 mmol), dimethylamine hydrochloride (3.55 g, 43.55 mmol) in DCE (40 mL), was added NaBH(OAc)3 (6.92 g, 32.67 mmol). The mixture was stirred at 20° C. for 2 hours under N$_2$ atmosphere. TLC indicated the reaction was complete. The mixture was concentrated and purified by prep-HPLC (TFA condition). 1-(tert-butylsulfonyl)-5-(2-cyclopropylphenyl)-N,N-dimethylpyrrolidin-3-amine (2.2 g, 6.28 mmol, 57.64% yield) was obtained. MS (ESI, m/e) [M+1]$^+$ 351.3.

Step 3: 5-(2-cyclopropylphenyl)-N,N-dimethylpyrrolidin-3-amine

A mixture of 1-(tert-butylsulfonyl)-5-(2-cyclopropylphenyl)-N,N-dimethylpyrrolidin-3-amine (1.0 g, 2.85 mmol) in TFA (10 mL) was stirred at 70° C. for 12 hours. TLC showed the reaction was complete. The mixture was concentrated and was adjusted to pH -10 with saturated aq. Na$_2$CO$_3$ (10 mL). The mixture was extracted with EA (10 mL×5) and the combined organic layers were dried over anhydrous Na$_2$SO$_4$ and then concentrated. 5-(2-cyclopropylphenyl)-N,N-dimethylpyrrolidin-3-amine (170 mg) was obtained. $^1$H NMR (400 MHz, CDCl$_3$) δ ppm: 7.52-7.63 (m, 1H), 7.11-7.24 (m, 2H), 7.00 (d, J=7.5 Hz, 1H), 4.70-4.92 (m, 1H), 3.07-3.42 (m, 2H), 2.81-2.99 (m, 1H), 2.38-2.50 (m, 1H), 2.25-2.35 (m, 4H), 1.63 (dt, J=11.9, 9.8 Hz, 1H), 0.89-0.98 (m, 2H), 0.62-0.76 (m, 1H). MS (ESI, m/e) [M+1]$^+$ 231.3.

Intermediate 2-z8: tert-butyl (R)-4-(2-(1-(4-bromophenyl)pyrrolidin-2-yl)phenyl)piperidine-1-carboxylate

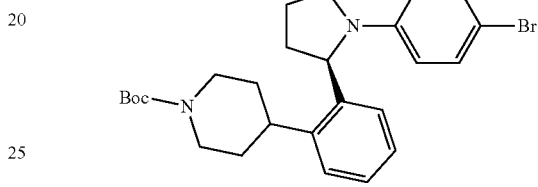

Step 1: (R)-tert-butyl 4-(2-(1-(2,2,2-trifluoroacetyl)pyrrolidin-2-yl)phenyl)-5,6-dihydropyridine-1(2H)-carboxylate A mixture of (R)-1-(2-(2-bromophenyl)pyrrolidin-1-yl)-2,2,2-trifluoroethanone (8 g, 24.8 mmol), tert-butyl 4-(4,4,5,5-tetramethyl-1,3,2-dioxaborolan-2-yl)-5,6-dihydropyridine-1(2H)-carboxylate (11.5 g, 37.2 mmol), Pd(OAc)$_2$ (560 mg, 2.48 mmol), tricyclohexyl phosphine (1.4 g, 4.96 mmol) and K$_3$PO$_4$ (15.8 g, 74.4 mmol, 3.0 eq) in toluene (100 ml) and H$_2$O (5 mL) was heated to 100° C. under N$_2$ protection and stirred for 5 hours. TLC showed the reaction was complete. The mixture was cooled to room temperature and diluted with EA (50 mL), washed with water (100 mL), brine (100 mL), dried over Na$_2$SO$_4$, and concentrated. The residue was purified by column chromatography on silica gel (eluent: PE/EA=5/1 to 2/1) to obtain (R)-tert-butyl 4-(2-(1-(2,2,2-trifluoroacetyl)pyrrolidin-2-yl)phenyl)-5,6-dihydropyridine-1(2H)-carboxylate (9 g, crude) as a brown solid. MS (ESI, m/e) [M+1]$^+$ 425.2.

Step 2: (R)-tert-butyl 4-(2-(1-(2,2,2-trifluoroacetyl)pyrrolidin-2-yl)phenyl)piperidine-1-carboxylate A mixture of (E)-tert-butyl 4-(2-(1-(2,2,2-trifluoroacetyl)pyrrolidin-2-yl)phenyl)-5,6-dihydropyridine-1(2H)-carboxylate (9 g, 21.2 mmol) and Pd/C (10%, 2 g) in CH$_3$OH (200 mL) was stirred at 20° C. under H$_2$ atmosphere (15 psi) for 12 hours. LC/MS showed the reaction was completed. The mixture was filtered and the filtrate was concentrated to give (R)-tert-butyl 4-(2-(1-(2,2,2-trifluoroacetyl)pyrrolidin-2-yl)phenyl)piperidine-1-carboxylate (7.5 g, crude) as an off-white solid. MS (ESI, m/e) [M+1]$^+$ 427.3.

Step 3: (R)-tert-butyl 4-(2-(pyrrolidin-2-yl)phenyl)piperidine-1-carboxylate

To a solution of (R)-tert-butyl 4-(2-(1-(2,2,2-trifluoroacetyl)pyrrolidin-2-yl)phenyl)piperidine-1-carboxylate (7.5 g, 17.6 mmol) in CH$_3$OH (50 mL) was added a solution of NaOH (2.8 g, 70.4 mmol) in H$_2$O (30 mL). Then the mixture was heated to 40° C. and stirred for 2 hours. TLC showed the reaction was complete. The mixture was concentrated in vacuum to remove the organic solvent and the remained water solution was extracted with EA (100 mL), The organic layer was washed with brine (100 mL), dried over Na$_2$SO$_4$, and concentrated to give (R)-tert-butyl 4-(2-(pyrrolidin-2-yl)phenyl)piperidine-1-carboxylate (6 g, crude). MS (ESI, m/e) [M+1]$^+$ 331.3.

Step 4: (R)-tert-butyl 4-(2-(1-(4-bromophenyl)pyrrolidin-2-yl)phenyl)piperidine-1-carboxylate A mixture of (R)-tert-butyl 4-(2-(pyrrolidin-2-yl)phenyl)piperidine-1-carboxylate (2 g, 6.1 mmol), 1-bromo-4-iodobenzene (3.5 g, 12.2 mmol), Pd$_2$(dba)$_3$ (559 mg, 0.61 mmol), BINAP (760 mg, 1.22 mmol) and t-BuOK (1.4 g, 12.2 mmol) in toluene (20 mL) was heated to 100° C. under N$_2$ protection and stirred for 12 hours. TLC showed the reaction was completed. The mixture was cooled to room temperature and diluted with EA (20 mL), washed with water (20 mL), brine (20 mL), dried over Na$_2$SO$_4$, and concentrated in vacuum. The residue was purified by column chromatography on silica gel (eluent: PE/EA=20/1 to 15/1) to give (R)-tert-butyl 4-(2-(1-(4-bromophenyl)pyrrolidin-2-yl)phenyl)piperidine-1-carboxylate (2 g), $^1$H NMR (400 MHz, CDCl$_3$) δ ppm: 7.29 (1H, s), 7.22-7.26 (1H, m), 7.18-7.22 (2H, m), 7.01-7.12 (2H, m), 6.23-6.31 (2H, m), 4.91 (1H, d, J=6.8 Hz), 4.31 (2H, s), 3.65-3.75 (1H, m), 3.35-3.47 (1H, m), 2.95-3.07 (1H, m), 2.82 (2H, s), 2.41-2.55 (1H, m), 1.97-2.10 (2H, m), 1.79-1.93 (3H, m), 1.61-1.74 (2H, m), 1.51 (9H, s). MS (ESI, m/e) [M+1]$^+$ 487.8.

Intermediate 2-z9: 1-(azetidin-3-yl)-2-(2-cyclopropylphenyl)pyrrolidine

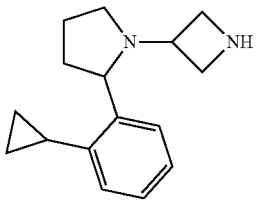 [SMILES: c1ccc(C2CCCN2C2CNC2)c(C2CC2)c1]

Step 1: tert-butyl 3-(2-(2-cyclopropylphenyl)pyrrolidin-1-yl)azetidine-1-carboxylate To a solution of 2-(2-cyclopropylphenyl)pyrrolidine (700 mg, 3.7 mmol) and tert-butyl 3-oxoazetidine-1-carboxylate (632 mg, 3.7 mmol) in DCM (10 mL) was added NaBH(OAc)$_3$ (600 mg, 3 mmol). The mixture was stirred at room temperature for 14 hours. Then saturated aq. NH$_4$Cl (30 mL) was added to the reaction mixture under stirring. The organic phase was separated and washed with brine (10 mL), dried over anhydrous Na$_2$SO$_4$, concentrated in vacuum to obtain 1 g crude product. MS (ESI, m/e) [M+1]$^+$ 343.0.

Step 2: 1-(azetidin-3-yl)-2-(2-cyclopropylphenyl)pyrrolidine

To a solution of tert-butyl 3-(2-(2-cyclopropylphenyl)pyrrolidin-1-yl)azetidine-1-carboxylate (680 mg, 2.0 mmol) in DCM (10 mL) was added TFA (2 mL). The mixture was stirred at room temperature for 4 hours. The solvent was removed to give 700 mg 1-(azetidin-3-yl)-2-(2-cyclopropylphenyl)pyrrolidine. MS (ESI, m/e) [M+1]$^+$ 243.0.

Intermediate 2-z10: 6-((2-(2-cyclopropylphenyl)pyrrolidin-1-yl)methyl)-2-azaspiro[3.3]heptane Step 1: tert-butyl 6-(methoxymethylene)-2-azaspiro[3.3]heptane-2-carboxylate To a solution of tert-butyl 6-oxo-2-azaspiro[3.3]heptane-2-carboxylate (3 g, 0.014 mol) in toluene (50 mL) was added t-BuOK (2.0 g, 0.018 mol). The mixture was stirred at 25° C. for 20 min at N$_2$ atmosphere. Then (methoxymethyl)triphenylphosphonium chloride (6.2 g, 0.018 mol) in toluene (20 mL) was added. The mixture was stirred at 70° C. for 4 hours. TLC indicated the reaction was complete. After removed the solvent, the residue was purified by column chromatograph on silica gel (eluent: PE/EA=20/1) to obtain tert-butyl 6-(methoxymethylene)-2-azaspiro[3.3]heptane-2-carboxylate (1 g). $^1$H NMR (400 MHz, CDCl$_3$) δ ppm: 5.81 (s, 1H), 3.86-4.00 (s, 4H), 3.55 (s, 3H), 2.86 (s, 2H), 2.79 (s, 2H), 1.43 (s, 9H).

Step 2: tert-butyl 6-formyl-2-azaspiro[3.3]heptane-2-carboxylate

To a solution of tert-butyl 6-(methoxymethylene)-2-azaspiro[3.3]heptane-2-carboxylate (1 g, 4.18 mmol) in CH$_3$CN (36 mL) and H$_2$O (9 mL) was added TFA (1 mL) and then the mixture was stirred at room temperature for 2 hours. TLC indicated the reaction was complete. The reaction mixture was adjusted to pH 8-9 with aq. Na$_2$CO$_3$ and was extracted with EA (20 mL×3). The combined organic layer was washed with brine, dried, filtered and concentrated to obtain tert-butyl 6-formyl-2-azaspiro[3.3]heptane-2-carboxylate (0.9 g), which was used into next step without further purification. $^1$H NMR (400 MHz, CDCl$_3$) δ ppm: 9.71 (d, J=1.7 Hz, 1H), 3.94 (s, 2H), 3.85-3.86 (m, 1H), 3.80-3.84 (m, 1H), 3.82 (s, 1H), 2.98-3.20 (m, 1H), 2.30-2.46 (m, 4H), 1.41 (s, 9H).

Step 3: tert-butyl 6-((2(2-cyclopropylphenyl)pyrrolidin-1-yl)methyl)-2-azaspiro[3.3]heptane-2-carboxylate To the solution of tert-butyl 6-formyl-2-azaspiro[3,3]heptane-2-carboxylate (0.9 g, 4.0 mmol) in DCE (30 mL) was added 2-(2-cyclopropylphenyl)pyrrolidine (0.68 g, 3.63 mmol) and HOAc (436 mg, 7.26 mmol). After the mixture was stirred at room temperature for 30 min, NaBH(OAc)$_3$ (1.54 g, 7.26 mmol) was added and then stirred for further 2 hours. LC/MS showed the reaction was complete. The reaction was quenched with aq. Na$_2$CO$_3$ (10 mL) and then extracted with EA (3×50 mL). The organic layer was dried, filtered and concentrated. The residue was purified by column chromatograph on silica gel (eluent: PE/EA=2/1) to obtain tert-butyl 6-((2-(2-cyclopropylphenyl)pyrrolidin-1-yl)methyl)-2-azaspiro[3.3]heptane-2-carboxylate (0.8 g). MS (ESI, m/e) [M+1]$^+$ 397.3.

Step 4: 6-((2-(2-cyclopropylphenyl)pyrrolidin-1-yl)methyl)-2-azaspiro[3.3]heptane To a solution of tert-butyl 6-((2-(2-cyclopropylphenyl)pyrrolidin-1-yl)methyl)-2-azaspiro[3.3]heptane-2-carboxylate (0.8 g, 2.0 mmol) in DCM (20 mL) was added TFA (10 mL) dropwise at 0° C. Then the mixture was stirred at room temperature for 2 hours. TLC indicated the reaction was complete. The reaction mixture was adjusted to pH 8-9 with aqueous $Na_2CO_3$ and then was extracted with DCM. The organic layer was dried, filtered and concentrated to obtain 6-((2-(2-cyclopropylphenyl)pyrrolidin-1-yl)methyl)-2-azaspiro[3.3]heptane (250 mg). $^1$H NMR (400 MHz, $CDCl_3$) δ ppm: 7.57 (d, J=7.4 Hz, 1H), 7.15-7.23 (m, 1H), 7.13 (dt, J=1.3, 7.4 Hz, 1H), 6.98 (d, J=7.4 Hz, 1H), 3.70-3.84 (m, 1H), 3.62 (d, J=1.7 Hz, 2H), 3.41 (s, 2H), 3.26 (t, J=8.3 Hz, 1H), 2.43-2.56 (m, 1H), 2.39 (s, 1H), 2.17-2.27 (m, 5H), 1.95-2.05 (m, 2H), 1.47-1.95 (m, 5H), 0.82-1.00 (m, 2H), 0.54-0.75 (m, 2H). MS (ESI, m/e) $[M+1]^+$ 297.3.

Intermediate 2-z11: 3-(2-cyclopropylphenyl)-2-azabicyclo[3.1.0]hexane

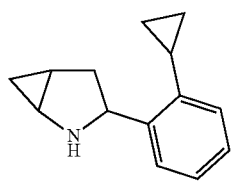 [SMILES: c1ccc(C2CC3CC3N2)c(C2CC2)c1]

Step 1: tert-butyl 2-(2-cyclopropylphenyl)-4-(tosyloxy)pyrrolidine-1-carboxylate To a solution of tert-butyl 2-(2-cyclopropylphenyl)-4-hydroxypyrrolidine-1-carboxylate (4.5 g, 14.8 mmol) in THF (50 mL) was added NaH (0.71 g, 17.8 mmol) and the mixture was stirred at 20° C. for 30 min. Then TosCl (3.4 g, 17.8 mmol) was added into the mixture and was further stirred at 20° C. for 12 hours. TLC showed the reaction was complete. The reaction mixture was quenched with water (100 mL), extracted with EA (100 mL), The organic layer was washed with brine (100 mL), dried over $Na_2SO_4$, and concentrated. The residue was purified by column chromatography on silica gel (eluent: PE/EA=10/1 to 5/1) to obtain tert-butyl 2-(2-cyclopropylphenyl)-4-(tosyloxy)pyrrolidine-1-carboxylate (2.9 g). MS (ESI, m/e) $[M+1]^+$ 458.2.

Step 2: tert-butyl 2-(2-cyclopropylphenyl)-2,3-dihydro-1H-pyrrole-1-carboxylate

To a solution of tert-butyl 2-(2-cyclopropylphenyl)-4-(tosyloxy)pyrrolidine-1-carboxylate (2.9 g, 6.3 mmol) in THF (50 mL) was added t-BuOK (1.4 g, 12.6 mmol) portion wise. After addition, the mixture was stirred at 20° C. for 12 hours. TLC showed the reaction was complete. The mixture was quenched with saturated aq. $NH_4Cl$ (50 mL) and was extracted with EA (50 mL). The organic layer was washed with brine (50 mL), dried over $Na_2SO_4$, and concentrated. The residue was purified by column chromatography on silica gel (eluent: PE/EA=100/1) to give tert-butyl 2-(2-cyclopropylphenyl)-2,3-dihydro-1H-pyrrole-1-carboxylate (900 mg). MS (ESI, m/e) $[M+1]^+$ 286.4.

Step 3: tert-butyl 3-(2-cyclopropylphenyl)-2-azabicyclo[3.1.0]hexane-2-carboxylate To a solution of tert-butyl 2-(2-cyclopropylphenyl)-2,3-dihydro-1H-pyrrole-1-carboxylate (900 mg, 3.2 mmol) in toluene (20 mL) at 0° C. was added $Et_2Zn$ (1 M in toluene, 15.8 mL, 15.8 mmol) and $ClCH_2I$ (5.56 g, 32 mmol). Then the mixture was stirred at 20° C. for 4 hours. TLC showed the reaction was complete. The reaction mixture was quenched with saturated aq. $NH_4Cl$ (20 mL) and was extracted with EA (30 mL×2). The organic layer was washed with brine (20 mL), dried over $Na_2SO_4$, and concentrated. The residue was purified by column chromatography on silica gel (eluent: PE/EA=30/1) to obtain tert-butyl 3-(2-cyclopropylphenyl)-2-azabicyclo[3.1.0]hexane-2-carboxylate (500 mg). MS (ESI, m/e) $[M+1]^+$ 300.2.

Step 4: 3-(2-cyclopropylphenyl)-2-azabicyclo[3.1.0]hexane

A solution of tert-butyl 3-(2-cyclopropylphenyl)-2-azabicyclo[3.1.0]hexane-2-carboxylate (500 mg, 1.7 mmol) in HCl in EA (4 M, 10 mL) was stirred at 20° C. for 2 hours. TLC showed the reaction was complete. The mixture was quenched with saturated aq. $Na_2CO_3$ (20 mL) and extracted with EA (20 mL×2). The organic layer was washed with brine (20 mL), dried over $Na_2SO_4$, and concentrated to obtain 3-(2-cyclopropytphenyl)-2-azabicyclo[3.1.0]hexane (293 mg). $^1$H NMR (400 MHz, $CDCl_3$) δ ppm: 7.63 (dd, J=7.7, 1.3 Hz, 1H), 7.18-7.23 (m, 1H), 7.11-7.16 (m, 1H), 6.98 (d, J=7.2 Hz, 1H), 4.54 (dd, J=10.0, 7.0 Hz, 1H), 3.00 (td, J=6.0, 2.6 Hz, 1H), 2.37 (dd, J=12.3, 7.0 Hz, 1H), 1.91-2.02 (m, 1H), 1.72-1.83 (m, 1H), 1.48-1.59 (m, 1H), 0.87-1.03 (m, 1H), 0.87-1.03 (m, 1H), 0.77-0.84 (m, 1H), 0.60-0.73 (m, 2H), 0.60-0.73 (m, 2H), 0.42 (dt, J=8.1, 5.9 Hz, 1H), 0.37-0.47 (m, 1H). MS (ESI, m/e) $[M+1]^+$ 200.2.

Intermediate 2-z12: 1-(2-cyclopropylphenyl)octahydrocyclopenta[c]pyrrole

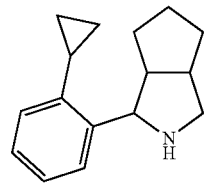 [SMILES: c1ccc(C2NCC3CCCC32)c(C2CC2)c1]

Step 1: 3-(2-cyclopropylphenyl)hexahydrocyclopenta[c]pyrrol-1(2H)-one

To the solution of 1-bromo-2-cyclopropylbenzene (8.5 g, 0.043 mol) in THF (20 mL) was added n-BuLi (21 mL, 0.052 mol, 2.5M in hexane) at −78° C. under $N_2$ atmosphere. Then the mixture was stirred at −78° C. for 1 hour. To the solution of tetrahydrocyclopenta[c]pyrrole-1,3(2H,3aH)-dione (4 g, 0.029 mol) in THF (20 mL) was added n-BuLi (13 mL, 0.035 mol, 2.5M in hexane) at −78° C. under $N_2$ atmosphere. Then the mixture was stirred at 0° C. for 1 hour. The solution formed from 1-bromo-2-cyclopropylbenzene was added dropwise to the solution formed from tetrahydrocyclopenta[c]pyrrole-1,3(2H,3aH)-dione at −78° C., The resulting mixture was stirred at room temperature for 3 hours, TLC showed tetrahydrocyclopenta[c]pyrrole-1,3(2H,3aH)-dione was consumed. $NaBH_3CN$ (2.2 g, 0.035 mol) was added to the mixture and then followed by addition of 6N HCl acid (20 mL) at 0° C., and further stirred at room temperature for 1 hour. $Na_2CO_3$ (50 mL) was added to the mixture to adjust the pH to 8-9. The mixture was then extracted with EA (50 mL×3), and the organic layer was washed with brine (50 mL×2). The combined organic layer was dried, filtered and concentrated. The residue was purified by column chromatograph on silica gel (eluent: PE/EA=10/1) to obtain 3-(2-cyclopropylphenyl)hexahydrocyclopenta[c]pyrrol-1(2H)-one (2.8 g). $^1$H NMR (400 MHz, CDCl$_3$) δ ppm: 7.19-7.23 (m, 1H), 7.11-7.16 (m, 2H), 6.95-7.01 (m, 1H), 6.20 (s, 1H), 5.44 (d, J=7.7 Hz, 1H), 3.08-3.24 (m, 1H), 2.93-3.04 (m, 1H), 2.73-2.87 (m, 1H), 1.91-2.06 (m, 1H), 1.73-1.83 (m, 2H), 1.51-1.64 (m, 1H), 1.40-1.49 (m, 2H), 1.33 (s, 1H), 1.10-1.20 (m, 1H), 0.52-0.73 (m, 2H). MS (ESI, m/e) [M+1]$^+$ 242.3.

Step 2: 1-(2-cyclopropylphenyl)octahydrocyclopenta[c]pyrrole

To the solution of 3-(2-cyclopropylphenyl)hexahydrocyclopenta[c]pyrrol-1 (2H)-one (1.0 g, 4.15 mmol, 1 eq) in THF (20 mL) was added BH$_3$.DMS (4.2 mL, 41.5 mmol, 10 eq, 10M in DMS) dropwise at 0° C., After the addition, the mixture was stirred at room temperature for 12 hr. TLC showed the reactant consumed completely. At 0° C., MeOH (2 mL) and 1N HCl (20 mL) were added into the reaction mixture carefully. The mixture was then stirred at room temperature for 1 hour. The reaction was quenched with aq. Na$_2$C0.3 (50 mL) and was adjusted to pH ~9. The mixture was extracted with EA (50 mL×3). The organic layer was washed with brine (50 mL×2), dried, filtered and concentrated. The residue was purified by column chromatograph on silica gel (eluent: PE/EA=5/1) to obtain target product (300 mg). $^1$H NMR (400 MHz, CDCl$_3$) δ ppm: 7.54-7.59 (m, 1H), 7.12-7.19 (m, 2H), 6.95-7.01 (m, 1H), 4.53 (d, J=6.97 Hz, 1H), 3.02-3.09 (m, 1H), 2.89-3.02 (m, 2H), 2.65 (quin, J=7.86 Hz, 1H), 1.91-2.03 (m, 2H), 1.55-1.64 (m, 1H), 1.24-1.39 (m, 1H), 1.18-1.39 (m, 1H), 1.18-1.20 (m, 1H), 1.11-1.21 (m, 1H), 0.87-0.99 (m, 3H), 0.61-0.78 (m, 2H). MS (ESI, m/e) [M+1]$^+$ 228.5.

Intermediate 2-z13: 2-((5-(2-cyclopropylphenyl) pyrrolidin-3-yl)oxy)-N,N-dimethylethan-1-amine

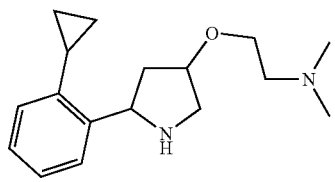 [SMILES: CN(C)CCOC1CNC(c2ccccc2C2CC2)C1]

Step 1: 2-((1-(tert-butylsulfonyl)-5-(2-cyclopropylphenyl)pyrrolidin-3-yl)oxy)-N,N-dimethylacetamide To a solution of 1-(tert-butylsulfonyl)-5-(2-cyclopropylphenyl)pyrrolidin-3-ol (10.5 g, 32.46 mmol) in DMF (250 mL) was added NaH (1.43 g, 35.71 mmol, 60%) in portions at 10° C. The mixture was stirred at 10° C. for 30 min, 2-chloro-N,N-dimethylacetamide (4.14 g, 34.09 mmol) was then added dropwise at 10° C., The mixture was stirred at 10° C. for 2 hour. TLC indicated the reactant was consumed completely. The reaction mixture was quenched by saturated aq.NH$_4$Cl (50 mL) and was extracted with EA (100 mL×3). The combined organic phases were washed with brine (50 mL×2), dried with anhydrous Na$_2$SO$_4$, filtered and concentrated. The residue was purified by column chromatography (SiO$_2$, PE/EA=5/1 to 0/1) and 2-((1-(tert-butyl sulfonyl)-5-(2-cyclopropylphenyl)pyrrolidin-3-yl)oxy)-N,N-dimethylacetamide (8.48 g) was obtained. MS (ESI, m/e) [M+1]$^+$ 410.1.

Step 2: 2-((5-(2-cyclopropylphenyl)pyrrolidin-3-yl) oxy)-N,N-dimethylacetamide

A solution of 2-((1-(tert-butylsulfonyl)-5-(2-cyclopropylphenyl)pyrrolidin-3-yl)oxy)-N,N-dimethylacetamide (8.4 g, 20.56 mmol) in TFA (100 mL) was stirred at 75° C. for 12 hours. LC/MS indicated the reactant was consumed completely and the desired mass signal. The reaction mixture was concentrated in vacuum to 20 mL and was poured into saturated aq. NaHCO$_3$ (50 mL) to adjust the pH -8. The aqueous phase was extracted with EA (100 mL×3), The combined organic phases were washed with brine (50 mL×2), dried with anhydrous Na$_2$SO$_4$, filtered and concentrated. 2-((5-(2-cyclopropylphenyl)pyrrolidin-3-yl)oxy)-N,N-dimethylacetamide (22 g, crude) was obtained. MS (ESI, m/e) [M+1]$^+$ 289.3.

Step 3: 2-((5-(2-cyclopropylphenyl)pyrrolidin-3-yl) oxy)-N,N-dimethylethanamine

A solution of 2-((5-(2-cyclopropylphenyl)pyrrolidin-3-yl) oxy)-N,N-dimethylacetamide (1.2 g, 4.16 mmol) in THF (50 mL) was added BH$_3$.DMS (8.32 mL, 83.2 mmol, 10N in DMS) dropwise at 20° C. The mixture was heated to 70° C. and stirred for 10 hours. LC/MS indicated the reactant was consumed completely. The reaction mixture was quenched with MeOH (10 mL) and was de-complexation by HCl/MeOH (4N, 20 mL) by reflux for 2 hours. LC/MS indicated the desired compound was generated. The reaction mixture was concentrated in vacuum. The residue was purified by prep-HPLC (Xtimate C18 10 u 250 mm*50 mm; mobile phase: [water (0.1% TFA)-ACN]). 2-((5-(2-cyclopropylphenyl)pyrrolidin-3-yl)oxy)-N,N-dimethylethanamine (1.4 g, TFA salt) was obtained. This salt was dissolved in CH$_3$CN (100 mL) and K$_2$CO$_3$ (560.9 mg, 4.07 mmol, 1.5 eq) was added into the solution in one portion and was then stirred at 20° C. for 2 hours. The mixture was filtered and the filtrate was concentrated to obtain 2-((5-(2-cyclopropylphenyl)pyrrolidin-3-yl)oxy)-N,N-dimethylethanamine (385 mg). $^1$H NMR (400 MHz, CDCl$_3$) δ ppm: 7.46-7.57 (m, 1H), 7.10-7.20 (m, 2H), 6.93-7.02 (m, 1H), 4.91 (t, J=8.0 Hz, 1H), 4.10-4.20 (m, 1H), 3.50-3.58 (m, 2H), 3.34 (dd, J=11.3, 5.1 Hz, 1H), 3.05-3.18 (m, 1H), 2.54 (t, J=5.8 Hz, 2H), 2.35-2.46 (m, 1H), 2.19-2.33 (m, 6H), 1.92-2.03 (m, 1H), 1.54-1.91 (m, 2H), 0.84-1.00 (m, 2H), 0.56-0.73 (m, 2H). MS (ESI, m/e) [M+1]$^+$ 275.1.

Intermediate 2-z14: (S)-2-(2-(2-ethoxyphenyl)pyrrolidin-1-yl)-7-azaspiro[3.5]nonane

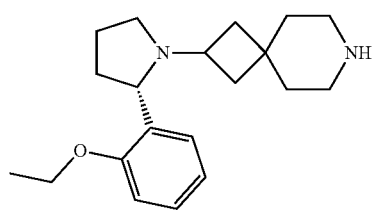 [SMILES: CCOc1ccccc1[C@@H]1CCCN1C1CC2(CCNCC2)C1]

Step 1: (S)-2-(2-ethoxyphenyl)pyrrolidine

To a mixture of (S)-2-(2-bromophenyl)pyrrolidine (1.5 g, 6.63 mmol) and EtONa (1.35 g, 19.90 mmol) in EtOH (15 mL) was added CuBr (475.81 mg, 3.32 mmol). Then the mixture was stirred at 90° C. for 12 hours. LC/MS showed the reaction was complete and the peak with desired mass signal. The mixture was cooled to room temperature and was adjusted to pH ~11 with aq. $Na_2CO_3$ and was then extracted with EA (20 mL×3). The combined organic layers were dried over $Na_2SO_4$, filtered and concentrated. The residue was purified by prep-HPLC (TFA condition). (S)-2-(2-ethoxyphenyl)pyrrolidine (0.7 g) was obtained. MS (ESI, m/e) [M+1]$^+$ 192.3.

Step 2: (S)-tert-butyl 2-(2-(2-ethoxyphenyl)pyrrolidin-1-yl)-7-azaspiro[3.5]nonane-7-carboxylate A mixture of (S)-2-(2-ethoxyphenyl)pyrrolidine (0.5 g, 2.61 mmol) and tert-butyl 2-oxo-7-azaspiro[3.5]nonane-7-carboxylate (568.71 mg, 2.38 mmol), HOAc (428.13 mg, 7.13 mmol) in DCE (5 mL) was stirred at 20° C. for 2 hours. NaBH(OAc)$_3$ (1.01 g, 4.75 mmol) was added into the mixture and was furthered stirred at 20° C. for 12 hours. TLC showed the reaction was complete. The mixture was adjusted to pH ~11 with aq. $Na_2CO_3$ and was then extracted with EA (20 mL×3). The combined organic layers were dried over $Na_2SO_4$, filtered and concentrated. The residue was purified by column chromatography on silica gel (eluent: PE/EA=20/1 to 10/1) and (S)-tert-butyl 2-(2-(2-ethoxyphenyl)pyrrolidin-1-yl)-7-azaspiro[3.5]nonane-7-carboxylate (0.6 g) was obtained. MS (ESI, m/e) [M+1]$^+$ 415.4.

Step 3: (S)-2-(2-(2-ethoxyphenyl)pyrrolidin-1-yl)-7-azaspiro[3.5]nonane

To the solution of (S)-tert-butyl 2-(2-(2-ethoxyphenyl)pyrrolidin-1-yl)-7-azaspiro[3.5]nonane-7-carboxylate (0.6 g, 1.45 mmol) in DCM (10 mL) was added TFA (1.65 g, 14.47 mmol). The mixture was stirred at 20° C. for 1 hour. TLC indicated one new spot formed. The reaction mixture was adjusted to pH 8-9 with aqueous $Na_2CO_3$ and then was extracted with DCM (10 mL×5). The combined organic layer was washed with brine, dried over $Na_2SO_4$ and concentrated. (S)-2-(2-(2-ethoxyphenyl)pyrrolidin-1-yl)-7-azaspiro[3.5]nonane (360 mg) was obtained. $^1$H NMR (400 MHz, CDCl$_3$) δ ppm: 7.49-7.58 (m, 1H), 7.13-7.21 (m, 1H), 6.93 (t, J=7.4 Hz, 1H), 6.82 (d, J=7.4 Hz, 1H), 4.04 (d, J=7.1 Hz, 2H), 3.91 (t, J=7.1 Hz, 1H), 3.07-3.21 (m, 2H), 2.72-2.90 (m, 4H), 2.40 (q, J=8.4 Hz, 1H), 2.14-2.26 (m, 1H), 1.73-1.94 (m, 5H), 1.47-1.73 (m, 8H), 1.41 (t, J=6.95 Hz, 3H). MS (ESI, m/e) [M+1]$^+$ 315.3.

Intermediate 2-z15: 2-(2'-cyclopropyl-[1,1'-biphenyl]-2-yl)-7-azaspiro[3.5]nonane

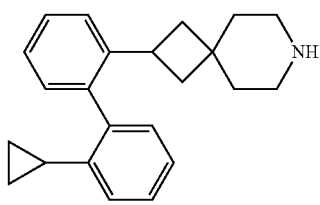 [SMILES: c1ccc(C2CC2)c(-c2ccccc2C2CC3(CCNCC3)C2)c1]

Step 1: tert-butyl 2-(2-tosylhydrazono)-7-azaspiro[3.5]nonane-7-carboxylate

A mixture of tert-butyl 2-oxo-7-azaspiro[3.5]nonane-7-carboxylate (10.00 g, 41.79 mmol) and 4-methylbenzenesulfonohydrazide (9.34 g, 50.14 mmol) in EtOH (100 mL) was stirred at 80° C. for 1 hour. TLC showed the reaction was completed. The mixture was cooled to room temperature and filtered. The filtrate was concentrated in vacuum to obtain tert-butyl 2-(2-tosylhydrazono)-7-azaspiro[3.5]nonane-7-carboxylate (8.0 g, crude). 1H NMR (400 MHz, CDCl$_3$) δ ppm: 7.84 (d, J=8.1 Hz, 2H), 7.39 (s, 1H), 7.33 (d, J=8.0 Hz, 2H), 3.22-3.39 (m, 5H), 2.64 (s, 2H), 2.49 (s, 2H), 2.44 (s, 3H), 1.54 (t, J=5.5 Hz, 4H), 1.45 (s, 10H).

Step 2: tert-butyl 2-(2-methoxyphenyl)-7-azaspiro[3.5]nonane-7-carboxylate

A mixture of tert-butyl 2-(2-tosylhydrazono)-7-azaspiro[3.5]nonane-7-carboxylate (8.0 g, 19.63 mmol) and (2-methoxyphenyl)boronic acid (8.95 g, 58.89 mmol), $Cs_2CO_3$ (19.19 g, 58.89 mmol) in dioxane (100 mL) was stirred at 110° C. for 4 hours. TLC showed the reaction was completed. The mixture was filtered and concentrated. The residue was purified by column chromatography on silica gel (eluent: PE). Tert-butyl 2-(2-methoxyphenyl)-7-azaspiro[3,5]nonane-7-carboxylate (3.0 g) was obtained. MS (ESI, m/e) [M+1]$^+$ 332.3.

Step 3: tert-butyl 2-(2-hydroxyphenyl)-7-azaspiro[3.5]nonane-7-carboxylate

To the solution of tert-butyl 2-(2-methoxyphenyl)-7-azaspiro[3.5]nonane-7-carboxylate (3.0 g, 9.05 mmol) in DCM (30 mL) under N$_2$ atmosphere was added BBr$_3$ (9.07 g, 36.20 mmol) at −78° C., After addition, the mixture was stirred at 20° C. for 6 hours. LC/MS indicated the reaction was complete. The mixture was quenched with aq. $Na_2CO_3$ and was extracted with DCM (20 mL×3). The combined organic phase was washed with brine, dried over $Na_2SO_4$ and concentrated. The residue was purified by column chromatography on silica gel (eluent: PE/EA=20/1). Tert-butyl 2-(2-hydroxyphenyl)-7-azaspiro[3.5]nonane-7-carboxylate (1.3 g) was obtained. MS (ESI, m/e) [M+1]$^+$ 318.4.

Step 4: tert-butyl 2-(2-(((trifluoromethyl)sulfonyl)oxy)phenyl)-7-azaspiro[3.5]nonane-7-carboxylate To the solution of tert-butyl 2-(2-hydroxyphenyl)-7-azaspiro[3.5]nonane-7-carboxylate (1.3 g, 4.10 mmol) and TEA (1.24 g, 6.14 mmol) in DCM (10 mL) was added Tf$_2$O (1.73 g, 12.29 mmol) under N$_2$ atmosphere at 0° C. The mixture was then stirred at 25° C. for 1 hour. TLC indicated the reaction was completed. The mixture was quenched with H$_2$O (10 mL) and NH$_4$Cl (10 mL) and extracted with DCM (10 mL×3). The organic phase was washed with brine, dried over $Na_2SO_4$ and concentrated in vacuum. The residue was purified by column chromatography on silica gel (eluent: PE/EA=40/1) to obtain ert-butyl 2-(2-(((trifluoromethyl)sulfonyl)oxy)phenyl)-7-azaspiro[3.5]nonane-7-carboxylate (1.84 g). MS (ESI, m/e) [M+1]$^+$ 450.2.

Step 5: tert-butyl 2-(2'-cyclopropyl-[1,1'-biphenyl]-2-yl)-7-azaspiro[3.5]nonane-7-carboxylate To the mixture of compound tert-butyl 2-(2-(((trifluoromethyl)sulfonyl)oxy)phenyl)-7-azaspiro[3.5]nonane-7-carboxylate (1.4 g, 3.11 mmol), 2-(2-cyclopropylphenyl)-4,4,5,5-tetramethyl-1,3,2-dioxaborolane (1.52 g, 6.23 mmol) and Cs$_2$CO$_3$ (3.04 g, 9.34 mmol) in dioxane (10 mL) was added Pd(dppf)Cl$_2$ (1.14 g, 1.56 mmol) under N$_2$ atmosphere. The mixture was stirred at 90° C. for 12 hours. TLC indicated the reactant was consumed completely and one new spot formed. The mixture was filtered and concentrated. The residue was purified by column chromatography on silica gel (eluent: PE/EA=50/1) to obtain tert-butyl 2-(2'-cyclopropyl-[1,1'-biphenyl]-2-yl)-7-azaspiro[3.5]nonane-7-carboxylate (0.6 mg). MS (ESI, m/e) [M+1]$^+$ 418.5.

Step 6: 2-(2'-cyclopropyl-[1,1'-biphenyl]-2-yl)-7-azaspiro[3.5]nonane

To the mixture of tert-butyl 2-(2'-cyclopropyl-[1,1'-biphenyl]-2-yl)-7-azaspiro[3.5]nonane-7-carboxylate (0.6 g, 1.44 mmol) in DCM (5 mL) was added TFA (1.39 g, 14.37 mmol). The mixture was stirred at 25° C. for 2 hours. LC/MS indicated the reaction was complete. The reaction mixture was adjusted to pH -10 with aq. Na$_2$CO$_3$ and then extracted with DCM (10 mL×3). The combined organic layer was washed with brine, dried over Na$_2$SO$_4$ and concentrated. 2-(2'-cyclopropyl-[1,1'-biphenyl]-2-yl)-7-azaspiro[3.5]nonane (340 mg) was obtained. $^1$H NMR (400 MHz, CDCl$_3$) δ ppm: 7.34-7.46 (m, 2H), 7.22-7.32 (m, 3H), 7.13-7.22 (m, 2H), 7.06 (d, J=7.5 Hz, 1H), 6.83 (d, J=7.7 Hz, 1H), 3.46 (m, J=9.15 Hz, 1H), 3.30 (s, 2 III 2.70-2.84 (m, 4H), 1.68-2.03 (m, 5H), 1.45-1.64 (m, 5H), 0.72-0.83 (m, 2H), 0.61-0.71 (m, 2H). MS (ESI, m/e) [M+1]$^+$ 318.1.

Intermediate 2-z16: 4-((2-(2-cyclopropylphenyl)pyrrolidin-1-yl)methyl)benzaldehyde

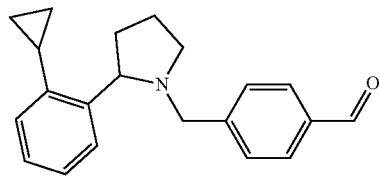 [SMILES: O=Cc1ccc(CN2CCCC2c2ccccc2C2CC2)cc1]

Step 1: methyl 4-((2-(2-cyclopropylphenyl)pyrrolidin-1-yl)methyl)benzoate

To a solution of 2-(2-cyclopropylphenyl)pyrrolidine (1.5 g, 8.01 mmol), methyl 4-formylbenzoate (1.14 g, 7.29 mmol) in DCE (20 mL) was added CH$_3$COOH (0.87 g, 14.58 mmol), NaBH(OAc)$_3$ (3.09 g, 14.58 mmol). The mixture was stirred at 25° C. for 4 hours. TLC showed the reactant was consumed completely. The reaction mixture was poured into H$_2$O (50 mL) and extracted with EA (20 mL×3). The combined organic layers were washed with brine (25 mL×2), dried over Na$_2$SO$_4$, filtered and concentrated under reduced pressure. The residue was purified by column chromatography on silica gel (eluent: PE/EA=50/1 to 1/1) to obtain methyl 4-((2-(2-cyclopropylphenyl)pyrrolidin-1-yl)methyl)benzoate (1.8 g). MS (ESI, m/e) [M+1]$^+$ 336.5.

Step 2: (4-((2-(2-cyclopropylphenyl)pyrrolidin-1-yl)methyl)phenyl(methanol

To a solution of methyl 4-((2-(2-cyclopropylphenyl)pyrrolidin-1-yl)methyl)benzoate (2 g, 6 mmol) in THE (30 mL) was added LiAlH$_4$ (46 g, 17.28 mmol) slowly at 0° C. The mixture was stirred at 0° C. for 30 min. TLC showed the reactant was consumed completely. The residue was quenched with saturated aq. NH4Cl (50 mL) and extracted with EA (50 mL). The organic phase was washed with brine, dried over Na$_2$SO$_4$ and concentrated to obtain (4-((2-(2-cyclopropylphenyl)pyrrolidin-1-yl)methyl)phenyl)methanol (1.5 g). MS (ESI, m/e) [M+1]$^+$ 308.3.

Step 3: 4-((2-(2-cyclopropylphenyl)pyrrolidin-1-yl)methyl)benzaldehyde

To the solution of (4-((2-(2-cyclopropylphenyl)pyrrolidin-1-yl)methyl)phenyl)methano (1.5 g, 4.89 mmol) in THE (20 mL) was added DMP (4.14 g, 9.78 mmol). The mixture was stirred at 25° C. for 4 hours. LC/MS showed the reactant was consumed completely and one main peak with desired mass signal. The reaction mixture was quenched by addition Na$_2$S$_2$O$_3$ (25 ml) and NaHCO$_3$ (15 ml) and extracted with EA (30 mL×3). The combined organic layers were washed with brine (30 mL×2), dried over Na$_2$SO$_4$ and concentrated to obtain 4-((2-(2-cyclopropylphenyl)pyrrolidin-1-yl)methyl)benzaldehyde (1.5 g). Mf NMR (400 MHz, CDCl$_3$) δ ppm: 9.91 (s, 1H), 7.74 (d, J=8.1 Hz, 2H), 7.68 (d, J=7.7 Hz, 1H), 7.43 (d, J=7.9 Hz, 2H), 7.14-7.18 (m, 1H), 7.09 (td, J=7.4, 1.2 Hz, 1H), 6.94 (d, J=7.5 Hz, 1H), 3.96 (t, J=8.2 Hz, 1H), 3.86 (d, J=13.8 Hz, 1H), 2.98-3.14 (m, 2H), 2.18-2.32 (m, 1H), 2.14 (q, J=8.8 Hz, 1H), 1.98 (d, J=7.7 Hz, 1H), 1.68-1.91 (m, 2H), 1.63 (dd, J=9.7, 2.4 Hz, 1H), 0.80-0.95 (m, 2H), 0.63-0.74 (m, 1H), 0.48-0.61 (m, 1H).

Intermediate 2-z17a and Intermediate 2-z17b: (S or R)-2-(3-chloro-2-cyclopropylphenyl)pyrrolidine: (R or S)-2-(3-chloro-2-cyclopropylphenyl)pyrrolidine

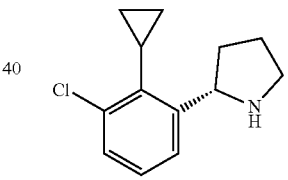 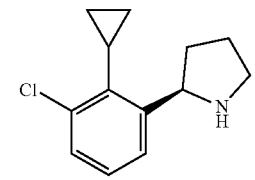

Step 1: 1-bromo-3-chloro-2-cyclopropylbenzene

The mixture of 1-bromo-3-chloro-2-iodobenzene (7 g, 22.1 mmol), cyclopropylboronic acid (3.8 g, 44.2 mmol), Pd(dppf)Cl$_2$ (1.6 g, 2.21 mmol) and K$_2$CO$_3$ (2 g, 7.3 mmol, 1.0 eq) in dioxane (100 mL) was heated at 70° C. for 12 hours under N$_2$ protection. TLC showed the reaction was complete and a new spot formed. The mixture was cooled to room temperature and was diluted with EtOAc (150 mL) and H$_2$O (50 mL), The organic phase was separated and washed with water (150 mL), brine (150 mL), dried over Na$_2$SO$_4$, and concentrated. The residue was purified by column chromatography on silica gel (eluent: PE) to give 1-bromo-3-chloro-2-cyclopropylbenzene (3 g, crude), which was used directly in next step.

Step 2: tert-butyl (4-(3-chloro-2-cyclopropylphenyl)-4-oxobutyl)carbamate

To a solution of 1-bromo-3-chloro-2-cyclopropylbenzene (3 g, 13 mmol) in THF (30 mL) was added n-BuLi (2.5 M, 5.7 mL, 14.3 mmol) dropwise at −70° C. After stirred at −70° C. for 30 min, a solution of tert-butyl 2-oxopyrrolidine-1-carboxylate (2.64 g, 14.3 mmol, 1.1 eq) in THF (5 mL) was added dropwise into the mixture at −70° C. The mixture was further stirred at −70° C. for 2 hours. TLC showed the reaction was complete. The mixture was quenched with water (50 mL) and extracted with EtOAc (50 mL). The organic layer was washed with brine (50 mL), dried over Na₂SO₄, and concentrated. The residue was purified by column chromatography on silica gel (eluent: PE/EA=5/1) to give tert-butyl (4-(3-chloro-2-cyclopropylphenyl)-4-oxobutyl) carbamate (1.3 g). ¹H NMR (400 MHz, CDCl₃) δ ppm: 7.35 (dd, J=7.6, 1.7 Hz, 1H), 7.06-7.15 (m, 2H), 4.56 (s, 1H), 3.14 (q, J=6.3 Hz, 2H), 2.89 (t, 1=7.2 Hz, 2H), 1.78-1.95 (m, 3H), 1.37 (s, 9H), 0.92-1.03 (m, 2H), 0.35-0.45 (m, 2H).

Step 3: 4-amino-1-(3-chloro-2-cyclopropylphenyl)butan-1-one

To a solution of tert-butyl (4-(3-chloro-2-cyclopropylphenyl)-4-oxobutyl)carbamate (1.3 g, 3.8 mmol) in DCM (20 mL) was added TFA (4.4 g, 38 mmol). Then the mixture was stirred at 20° C. for 2 hours. TLC showed the reaction was completed. The mixture was concentrated in vacuum to give 4-amino-1-(3-chloro-2-cyclopropylphenyl)butan-1-one (900 mg, crude). MS (ESI, m/e) [M+1]⁺ 237.9.

Step 4: 2-(3-chloro-2-cyclopropylphenyl)pyrrolidine

A solution of 4-amino-1-(3-chloro-2-cyclopropylphenyl)butan-1-one (900 mg, 3.8 mmol) and AcOH (0.5 mL) in EtOH (10 mL) was heated to 65° C. and stirred for 3 hours. Then the mixture was cooled to room temperature and NaBH₃CN (360 mg, 5.7 mmol, 1.5 eq) was added into it. The mixture was further stirred for 1 hour at room temperature. TLC showed the reaction was completed. The reaction mixture was quenched and adjusted to pH 10 with sat. aq. Na₂CO₃ and then extracted with EtOAc (20 mL×3). The organic layers were combined, dried over Na₂SO₄ and concentrated. The residue was purified by column chromatography on silica gel (eluent: EA/MeOH=10/0 to 10/1) to give the racemic 2-(3-chloro-2-cyclopropylphenyl)pyrrolidine.

The racemic product was purified by SFC (Instrument: Thar SFC350 preparative SFC; Column: Chiralpak AD, 250*50 mm i.d. 10 u; Mobile phase: A for C02 and B for MeOH (0.1% NH₃.H₂O); Gradient: B %=20%; Flow rate: 200 g/min; Wavelength: 220 nm; Column temperature: 40° C.; System back pressure: 100 bar) to give 2 isomers: the faster isomer (715 mg, retention time: 2.4 min) is (S or R)-2-(3-chloro-2-cyclopropylphenyl)pyrrolidine; the slower isomer (737 mg, retention time: 2.7 min) is (R or S)-2-(3-chloro-2-cyclopropylphenyl)pyrrolidine.

Intermediate 3-a: 3-nitro-4-(((tetrahydro-2H-pyran-4-yl)methyl)amino)benzenesulfonamide

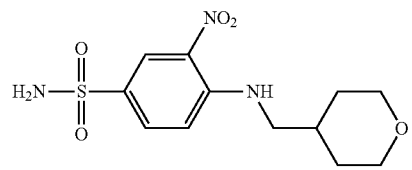 [SMILES: NS(=O)(=O)c1ccc(NCC2CCOCC2)c([N+](=O)[O-])c1]

To a solution of 4-fluoro-3-nitrobenzenesulfonamide (36.3 g, 0.165 mol) in THF (500 mL) were added (tetrahydro-2H-pyran-4-yl)methanamine (20.9 g, 0.182 mol) and TFA (20.0 g, 0.198 mol) at 0-5° C., the reaction was slowly warmed to r.t. stirred for about 16 hours, EA (1.5 L) was added to the reaction, the mixture was washed with sat. NaH₂PO₄ (100 mL) and saturated NaCl solution (100 mL), dried over anhydrous Na₂SO₄, filtered and concentrated to give the product (49.1 g, 95.0% yield) as yellow solid.

Intermediate 3-b: 4-((4-fluorotetrahydro-2H-pyran-4-yl)methoxy)-3-nitrobenzenesulfonamide

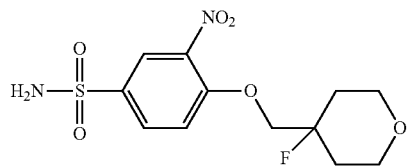 [SMILES: NS(=O)(=O)c1ccc(OCC2(F)CCOCC2)c([N+](=O)[O-])c1]

To a mixture of compound 4-fluoro-3-nitrobenzenesulfonamide (540 mg, 2.45 mmol) and Na₂CO₃ (155.97 mg, 1.47 mmol) in i-PrOH (1.5 mL) was added compound (4-fluorotetrahydro-2H-pyran-4-yl)methanol (489.89 mg, 3.68 mmol) at 20° C. under N₂, the mixture was stirred at 60° C. for 2 hours. The mixture was filtered and washed by water. Compound 4-((4-fluorotetrahydro-2H-pyran-4-yl)methoxy)-3-nitrobenzenesulfonamide (758 mg) was obtained as a yellow solid. ¹H NMR (400 MHz, DMSO-d₆) δ ppm: 8.58 (br t, J=6.0 Hz, 1H), 8.46 (d, J=6.0 Hz, 1H), 7.81 (dd, J=1.7, 9.3 Hz, 1H), 7.40 (br d, J=9.3 Hz, 1H), 7.30 (br s, 2H), 3.81-3.70 (m, 4H), 3.56-3.45 (m, 2H), 1.89-1.69 (m, 4H). MS (ESI, m/e) [M+1]⁺ 334.0.

Intermediate 3-c: 3-nitro-4-((1-(tetrahydro-2H-pyran-4-yl)azetidin-3-yl)amino)benzenesulfonamide

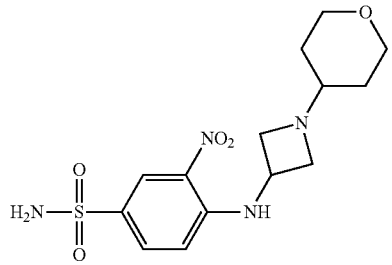 [SMILES: NS(=O)(=O)c1ccc(NC2CN(C3CCOCC3)C2)c([N+](=O)[O-])c1]

Step 1: tert-butyl n-(tetrahydro-2H-pyran-4-yl)azetidin-3-yl)carbamate

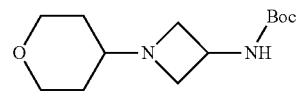 [SMILES: CC(C)(C)OC(=O)NC1CN(C2CCOCC2)C1]

To a solution of tetrahydro-4H-pyran-4-one (1.162 g, 11.6 mmol) in DCM (50 ml) was added tert-butyl azetidin-3-ylcarbamate (1 g, 5.8 mmol). The mixture was stirred at r.t.

for 2 hours. Then to the mixture was added NaBH(OAc)$_3$ (3.687 g, 17.4 mmol). The mixture was stirred at r.t. overnight. The mixture was diluted with DCM (200 ml), washed with brine (200 ml×2), dried over Na$_2$SO$_4$, concentrated. The residue was purified by chromatography column on silica with eluent of MeOH/DCM=1/20 (v/v) to give the product (800 mg) as a yellow oil. MS (ESI, m/e) [M+1]$^+$ 257.1.

Step 2: 1-(tetrahydro-2H-pyran-4-yl)azetidin-3-amine dihydrochloride

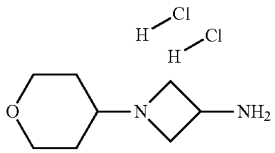

To a solution 4 N HCl (g) in dioxane (30 mL) was added tert-butyl (1-(tetrahydro-2H-pyran-4-yl)azetidin-3-yl)carbamate (300 mg, 1.17 mmol). The mixture was stirred at room temperature for 2 hours. The mixture was concentrated give the erode product (250 mg).

Step 3: 3-nitro-4-((1-(tetrahydro-2H-pyran-4-yl) azetidin-3-yl)amino)benzenesulfonamide

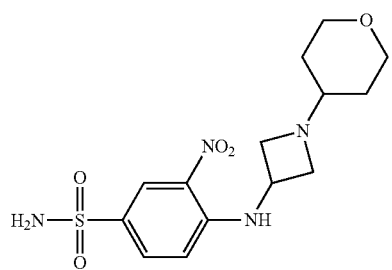 [SMILES: NS(=O)(=O)c1ccc(NC2CN(C3CCOCC3)C2)c([N+](=O)[O-])c1]

To a solution of 1-(tetrahydro-2H-pyran-4-yl)azetidin-3-amine dihydrochloride (206 mg, 0.899 mmol) and 4-fluoro-3-nitrobenzenesulfonamide (282 mg, 1.28 mmol) in THF (50 mL) was added triethylamine (540.4 mg, 5.35 mmol). The mixture was stirred at room temperature for 4 hours. The mixture was filtered to give the product (300 mg, 93.6%) as a yellow solid. $^1$H NMR (400 MHz, DMSO-d$_6$) δ ppm: 8.48 (s, 1H), 8.40 (s, 1H), 7.86 (d, J=9.0 Hz, 1H), 7.39 (s, 2H), 7.10 (d, J=9.0 Hz, 1H), 4.46-4.21 (m, 1H), 3.97-3.56 (m, 4H), 3.47-3.14 (m, 4H), 2.46-2.19 (m, 1H), 1.63 (d, J=10.4 Hz, 2H), 1.20-1.19 (m, 2H).

Intermediate 3-d: 4-(((1-methylpiperidin-4-yl) methyl)amino)-3-nitrobenzenesulfonamide

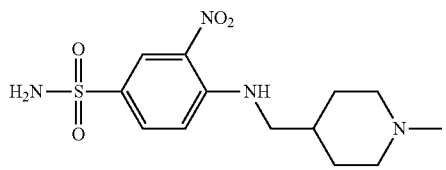

To a solution of 4-fluoro-3-nitrobenzenesulfonamide (1.15 g, 5.2 mmol) and (1-methylpiperidin-4-yl)methanamine (640 mg, 5 mmol) in THF (12 mL) v/as added TEA (1.01 g, 10 mmol). The mixture was stirred at room temperature for 3 hours. And some solid came out. The mixture was filtered. Collected the solid (550 mg) as a yellow solid. MS (ESI, m/e) [M+1]$^+$ 328.8.

Intermediate 3-e: 3-nitro-4-(7-oxa-2-azaspiro[3.5] nonan-2-yl)benzenesulfonamide

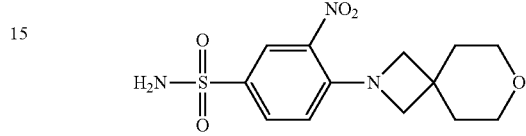

To a solution of 7-oxa-2-azaspiro[3,5]nonane hydrochloride (556 mg, 3.4 mmol) and 4-fluoro-3-nitrobenzenesulfonamide (500 mg, 2.27 mmol) in THF (50 mL) was added triethylamine (688 mg, 6.81 mmol). The mixture was stirred at room temperature for 4 hours. The reaction mixture was concentrated and purified by chromatography column on silica with the eluent of EA/PE=1/1 (v/v) to give the product (600 mg, 80.7% yield) as a yellow solid. $^1$H NMR (400 MHz, DMSO-d$_6$) δ ppm: 8.17 (d, J=2.0 Hz, 1H), 7.79 (dd, J=9.0, 2.0 Hz, 1H), 7.32 (s, 2H), 6.90 (d, J=9.0 Hz, 1H), 3.79 (s, 4H), 3.526 (t, J=5.0 Hz, 4H), 1.733 (t, J=5.0 Hz, 4H). MS (ESI, m/e) [M+1]$^+$ 328.

Intermediate 3-f: 3-nitro-4-((1-(oxetan-3-yl)piperidin-4-yl)amino)benzenesulfonamide

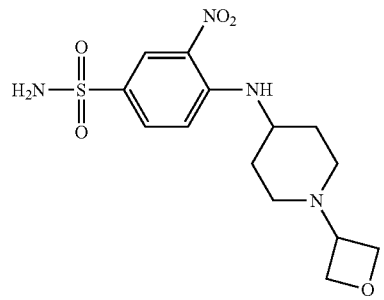 [SMILES: NS(=O)(=O)c1ccc(NC2CCN(C3COC3)CC2)c([N+](=O)[O-])c1]

Step 1: tert-butyl (1-(oxetan-3-yl)piperidin-4-yl)carbamate

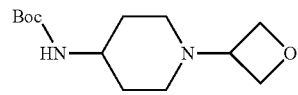 [SMILES: CC(C)(C)OC(=O)NC1CCN(C2COC2)CC1]

To a solution of tert-butyl piperidin-4-ylcarbamate (1 g, 5 mmol) in DCM (50 ml) was added oxetan-3-one (1.08 g, 15 mmol), HQ AC (0.2 ml). The mixture was stirred at room temperature for 2 hours. Then to the mixture was added NaBH(OAc)$_3$ (3.18 g, 15 mmol). The mixture was stirred at r.t, for overnight. The mixture was diluted with DCM (200 ml), washed with saturated aq. NaHCO₃ (100 ml), brine (200 ml×2), dried over Na₂SO₄, concentrated. The reaction residue was purified by chromatography column on silica (MeOH/DCM=1/20) to give the product (1 g, 78%) as a yellow oil. ¹H NMR (400 MHz, DMSO-d₆) δ ppm: 6.79 (d, J=6.3 Hz, 1H), 4.59-4.24 (m, 4H), 3.32-3.26 (m, 1H), 3.25-3.07 (m, 1H), 2.72-2.50 (m, 3H), 1.84-1.55 (m, 4H), 1.47-1.13 (m, 11H). MS (ESI, m/e) [M+1]⁺ 257.1.

Step: 2: 1-(oxetan-3-yl)piperidin-4-amine bis(2,2,2-trifluoroacetate)

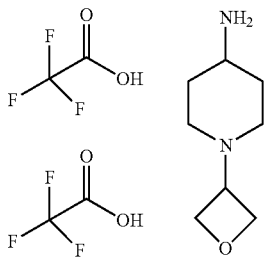

To a solution of tert-butyl (1-(oxetan-3-yl)piperidin-4-yl)carbamate (1 g, 3.9 mmol) in DCM (30 mL) was added TFA (5 ml). The mixture was stirred at room temperature for overnight. The mixture was concentrated to give the product (1.4 g, 93.4%) as a white solid. ¹H NMR (400 MHz, DMSO-d₆) δ ppm: 11.02 (s, 1H), 8.23 (s, 3H), 4.82-4.63 (m, 4H), 4.43-4.21 (m, 1H), 3.59-3.20 (m, 3H), 3.04-2.76 (m, 2H), 2.24-1.97 (m, 2H), 1.91-1.63 (m, 2H). MS (ESI, m/e) [M+1]⁺ 157.2.

Step: 3: 3-nitro-4-((1-(oxetan-3-yl)piperidin-4-yl)amino)benzenesulfonamide

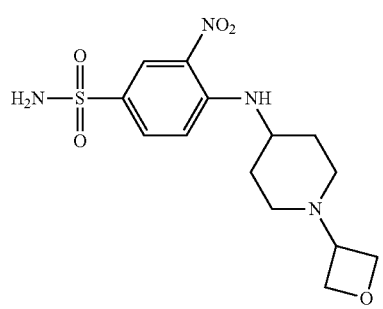 [SMILES: NS(=O)(=O)c1ccc(NC2CCN(C3COC3)CC2)c([N+](=O)[O-])c1]

To a solution of 1-(oxetan-3-yl)piperidin-4-amine bis(2,2,2-trifluoroacetate) (784 mg, 2.04 mmol) and 4-fluoro-3-nitrobenzenesulfonamide (471.6 mg, 2.142 mmol) in THF (50 mL) was added triethylamine (1.03 g, 10.2 mmol). The mixture was stirred at room temperature for 4 hours. The mixture was filtered to give the product (500 mg, 68.8%) as a yellow solid. MS (ESI, m/e) [M+1]⁺ 357.0

Intermediate 3-g: 4-(((3-((tert-butyldimethylsilyl)oxy)oxetan-3-yl)methyl)amino)-3-nitrobenzenesulfonamide

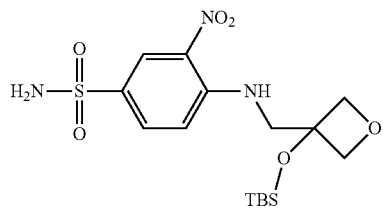

Step 1: (3-((tert-butyldimethylsilyl)oxy)oxetan-3-yl)methanamine

To a solution of 3-(aminomethyl)oxetan-3-ol (500 mg, 4.85 mmol) in DCM (50 ml) was added tert-butylchlorodimethylsilane (694 mg, 4.6 mmol), triethylamine (1.47 g, 14.55 mmol). The mixture was stirred at r.t, overnight. Then it was washed with saturated aq, NaHCO₃ (500 ml), brine (50 ml×2), dried over Na₂SO₄, concentrated to give the crude product, which was used directly for next step.

Step 2: 4-(((3-((tert-butyldimethylsilyl)oxy)oxetan-3-yl)methyl)amino)-3-nitrobenzenesulfonamide

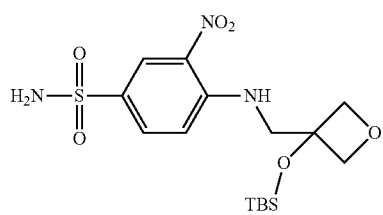

To a solution of (3-((tert-butyldimethylsilyl)oxy)oxetan-3-yl)methanamine (1.054 g, 4.85 mmol) in THF (50 mL) was added 4-fluoro-3-nitrobenzenesulfonamide (1.28 g, 5.82 mmol). The mixture was stirred at room temperature for 4 hours. The mixture was filtered to give the product (1.2 g, 59.3%) as a yellow solid. ¹H NMR (400 MHz, DMSO-d₆) δ ppm: 8.49 (d, J=2.2 Hz, 1H), 8.41 (t, J=4.8 Hz, 1H), 7.41-7.34 (m, 3H), 4.60 (d, J=7.0 Hz, 2H), 4.47 (d, J=7.0 Hz, 2H), 3.84 (d, J=5.1 Hz, 2H), 0.88 (s, 9H), 0.13 (s, 6H), MS (ESI, m/e) [M+1]⁺ 418.1

Intermediate 3-h: 4-((4-((tert-butyldimethylsilyl)oxy)cyclohexyl)methoxy)-3-nitrobenzenesulfonamide

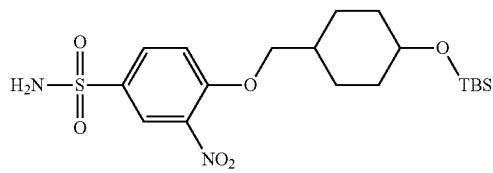

Step 1: ethyl 4-((tert-butyldimethylsilyl)oxy)cyclohexane-1-carboxylate

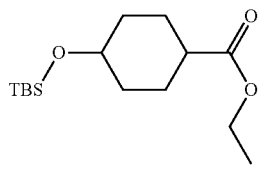

To a solution of ethyl 4-hydroxycyclohexane-1-carboxylate (2 g, 11.61 mmol) in DMF (50 ml) were added tert-butylchlorodimethylsilane (1.575 g, 10.4 mmol) and imidazole (1.58 g, 23.22 mmol). The mixture was stirred at r.t. for 2 days. The mixture was concentrated. The residue was dissolved with DCM (200 ml), washed with brine, dried over $Na_2SO_4$ and concentrated. The residue was purified by chromatography column on silica (eluent: EA/PE=1/40) to give the product (2.32 g, 69.8%).

Step 2: (4-((tert-butyldimethylsilyl)oxy)cyclohexyl)methanol

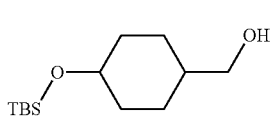

To a solution of ethyl 4-((tert-butyldimethylsilyl)oxy)cyclohexane-1-carboxylate (2.32 g, 8.1 mmol) in MTBE (50 mL) was added LAH (369 mg, 9.72 mmol). The mixture was stirred at reflux for 2 hours. The mixture was quenched with MeOH (10 ml) at 0° C. The mixture was concentrated. The residue was purified by chromatography column on silica (eluent: EA/PE=1/2) to give the product (1.5 g, 75.8%) as a yellow oil. MS (ESI, m/e) [M+1]$^+$ 245.1

Step 3: 4-((4-((tert-butyldimethylsilyl)oxy)cyclohexyl)methoxy)-3-nitrobenzenesulfonamide

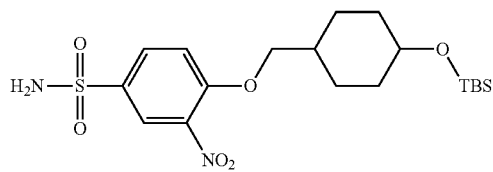

To a solution of (4-((tert-butyldimethylsilyl)oxy)cyclohexyl)methanole (587 mg, 2.4 mmol) in THF (50 ml) was added NaH (576 mg, 14.4 mmol). The mixture was stirred at room temperature for 0.5 hour. Then to the mixture was added 4-fluoro-3-nitrobenzenesulfonamide (370 mg, 1.68 mmol). The mixture was stirred overnight at room temperature. The mixture was poured into sat. $NaHCO_3$ water solution (200 mL), then adjusted pH=5~6 with HCl acid (1 M), then extracted with ethyl acetate (200 mL×3). The combined organic phase was washed with brine, dried over $Na_2SO_4$, concentrated. The residue was purified by chromatography column on silica (eluent: EA/PE=1/2) to give the product as a yellow solid. MS (ESI, m/e) [M+1]$^+$ 445.1.

Intermediate 3-i: 4-((4-fluoro-1-(tetrahydrofuran-3-yl)piperidin-4-yl)methoxy)-3-nitrobenzenesulfonamide

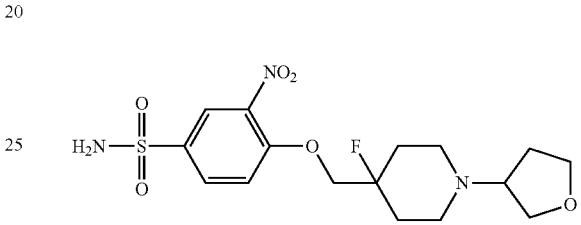

Step 1: tert-butyl 4-fluoro-4-((2-nitro-4-sulfamoylphenoxy)methyl)piperidine-1-carboxylate

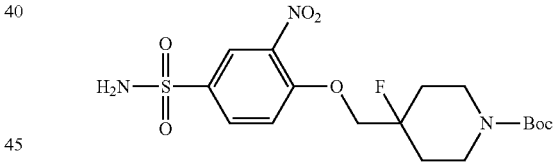

To a mixture of 4-fluoro-3-nitrobenzenesulfonamide (1 g, 4.54 mmol) and compound tert-butyl 4-fluoro-4-(hydroxymethyl)piperidine-1-carboxylate (1.06 g, 4.54 mmol) in THF (20 mL) was added NaH (726.61 mg, 18.17 mmol, 60% purity) in one portion at 0° C. under $N_2$, The mixture was stirred at 15° C. for 14 hours. TLC showed the reaction was completed. 20 mL saturated $NH_4Cl$ solution was added to the mixture, the aqueous phase was extracted with ethyl acetate (20 mL×3), The combined organic phase was washed with brine (50 mL), dried with anhydrous $Na_2SO_4$, filtered and concentrated in vacuum. The crude product was purified by re-crystallization in EtOAc (10 mL) to give tert-butyl 4-fluoro-4-((2-nitro-4-sulfamoylphenoxy)methyl) piperidine 1-carboxylate (1.17 g, 2.70 mmol, 59.4% yield) as yellow solid. $^1$H NMR (400 MHz, DMSO-$d_6$) δ ppm: 8.31 (br s, 1H), 8.06 (br d, J=8.6 Hz, 1H), 7.64-7.54 (m, 1H), 7.25 (br s, 2H), 4.48-4.33 (m, 2H), 3.84 (br d, J=11.9 Hz, 2H), 3.03 (br s, 2H), 1.97-1.84 (m, 2H), 1.82-1.61 (m, 2H), 1.41 (d, J=2.9 Hz, 9H).

Step 2: 4-((4-fluoropiperidin-4-yl)methoxy)-3-nitrobenzenesulfonamide

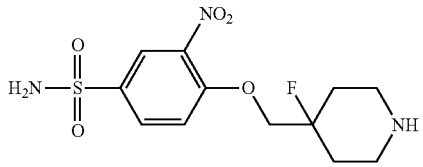 [SMILES: NS(=O)(=O)c1ccc(OCC2(F)CCNCC2)c([N+](=O)[O-])c1]

To a mixture of tert-butyl 4-fluoro-4-((2-nitro-4-sulfamoylphenoxy)methyl)piperidine-1-carboxylate (1.17 g, 2.70 mmol) in EA was added HCl acid (4 M, 78.00 mL) in one portion at 15° C. under $N_2$. The mixture was stirred at 15° C. for 12 hours. TLC showed the reaction was completed. The mixture was concentrated in vacuum to give 4-((4-fluoropiperidin-4-yl)methoxy)-3-nitrobenzenesulfonamide (1 g, crude, HCl salt) as yellow solid. It was used in next step directly. $^1$H NMR (400 MHz, METHANOL-$d_4$) δ ppm: 8.37 (d, J=2.3 Hz, 1H), 8.12 (dd, J=2.4, 8.9 Hz, 1H), 7.50 (d, J=8.9 Hz, 1H), 4.43 (d, J=10.0 Hz, 2H), 3.50-3.40 (m, 2H), 3.29-3.24 (m, 1H), 2.33 (br dd, J=10.0, 12.8 Hz, 2H), 2.23-2.10 (m, 2H).

Step 3: 4-((4-fluoro-1-(tetrahydrofuran-3-yl)piperidin-4-yl)methoxy)-3-nitrobenzenesulfonamide

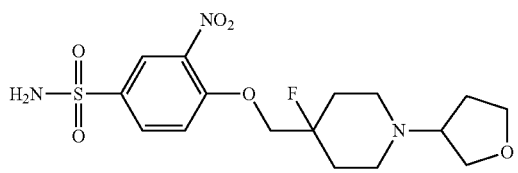 [SMILES: NS(=O)(=O)c1ccc(OCC2(F)CCN(C3CCOC3)CC2)c([N+](=O)[O-])c1]

To a mixture of 4-((4-fluoropiperidin-4-yl)methoxy)-3-nitrobenzenesulfonamide (1 g, 2.70 mmol, HCl) and dihydrofuran-3(2H)-one (698.40 mg, 8.11 mmol) in MeOH (20 mL) was added NaBH$_3$CN (509.81 mg, 8.11 mmol) in one portion at 0° C. under $N_2$. The mixture was stirred at 15° C. for 12 hours. LC-MS showed the reaction was completed. The mixture was poured into the sat. NaHCO$_3$ (20 mL) solution, the aqueous phase was extracted with ethyl acetate (20 mL×3). The combined organic phase was washed with brine (30 mL), dried with anhydrous Na$_2$SO$_4$, filtered and concentrated in vacuum. The mixture was dissolved in DCM, concentrated in vacuum to obtain a yellow solid. The crude product was purified by re-crystallization from MTBE (15 mL) to give 4-((4-fluoro-1-(tetrahydrofuran-3-yl)piperidin-4-yl)methoxy)-3-nitrobenzenesulfonamide (0.666 g, 1.65 mmol, 61.05% yield, 96.19% purity) as a yellow solid. $^1$H NMR (400 MHz. METHANOL-$d_6$) δ ppm: 8.34 (d, J=2.2 Hz, 1H), 8.09 (dd, J=2.2, 8.8 Hz, 1H), 7.47 (d, J=8.8 Hz, 1H), 4.31 (d, J=9.3 Hz, 2H), 4.00-3.88 (m, 2H), 3.83-3.72 (m, 1H), 3.66 (dd, J=7.0, 8.8 Hz, 1H), 3.07 (quin, J=7.2 Hz, 1H), 2.90 (d, J=11.0 Hz, 1H), 2.71 (d, J=11.8 Hz, 1H), 2.46 (q, J=11.8 Hz, 2H), 2.20-1.80 (m, 6H). MS (ESI, m/e) [M+1]$^+$ 404.1.

Intermediate 3-j: 3-nitro-4-(((4-(oxetan-3-yl)morpholin-2-yl)methyl)amino)benzenesulfonamide

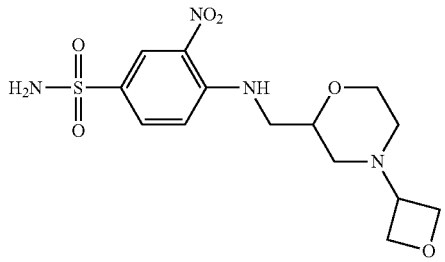 [SMILES: NS(=O)(=O)c1ccc(NCC2CN(C3COC3)CCO2)c([N+](=O)[O-])c1]

Step 1: tert-butyl 2-(((2-nitro-4-sulfamoylphenyl)amino)methyl)morpholine-4-carboxylate

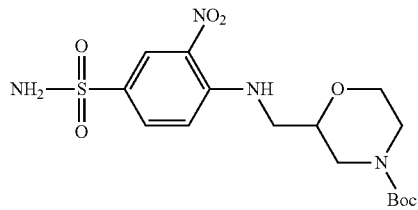 [SMILES: CC(C)(C)OC(=O)N1CCOC(CNc2ccc(S(N)(=O)=O)cc2[N+](=O)[O-])C1]

To a solution of 4-fluoro-3-nitrobenzenesulfonamide (2.55 g, 11.56 mmol) in IPA (90 mL) at 5560° C. were added Na$_2$CO$_3$ (735.09 mg, 6.94 mmol) and tert-butyl 2-(aminomethyl)morpholine-4-carboxylate (3 g, 13.87 mmol). The mixture was stirred at 5565° C. for 4 hr. TLC indicated 4-fluoro-3-nitrobenzenesulfonamide was consumed completely and one new spot formed. Concentrated and extracted with EtOAc (30 mL×3). The combined organic layers were washed with brine (30 mL), dried over Na$_2$SO$_4$, filtered and concentrated under reduced pressure to give a residue. Tert-butyl 2-(((2-nitro-4-sulfamoylphenyl)amino)methyl)morpholine-4-carboxylate (4.3 g, 10.33 mmol, 89.33% yield) was obtained as a yellow solid. The product was used in next step directly. $^1$H NMR (400 MHz, CDCl$_3$) δ ppm: 8.78 (d, J=2.2 Hz, 1H), 8.61 (br s, 1H), 7.92 (dd, J=2.1, 9.2 Hz, 1H), 6.98 id. J=9.0 Hz, 1H), 4.83 (s, 2H), 4.16-3.80 (m, 3H), 3.74 (t, J=3.4, 7.0, 10.5 Hz, 1H), 3.65-3.47 (m, 2H), 3.46-3.37 (m, 1H), 3.01 (br s, 1H), 2.80 (br s, 1H), 1.48 (s, 9H).

Step 2: 4-((morpholin-2-ylmethyl)amino)-3-nitrobenzenesulfonamide

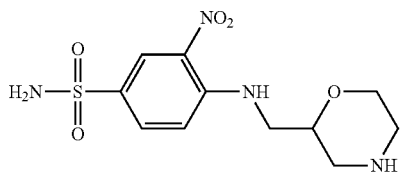 [SMILES: NS(=O)(=O)c1ccc(NCC2CNCCO2)c([N+](=O)[O-])c1]

A mixture of tert-butyl 2-(((2-nitro-4-sulfamoylphenyl)amino)methyl)morpholine-4-carboxylate (2.5 g, 6.00 mmol) in TFA (10 mL) and DCM (10 mL) was stirred at 25° C. for 1 hr, TLC indicated the reactant was consumed completely and one new spot formed. The reaction mixture was concentrated under reduced pressure to remove sol vent. 4-((morpholin-2-ylmethyl)amino)-3-nitrobenzenesulfonamide (2.5 g, crude) was obtained as a yellow oil, which was used directly in the next step. $^1$H NMR (400 MHz, DMSO-$d_6$) δ ppm 8.57 (br t, J=6.0 Hz, 1H), 8.48 (d, J=2.2 Hz, 1H), 7.85 (dd, J=2.1, 9.2 Hz, 1H), 7.36 (br s, 1H), 7.30 (d, J=9.2 Hz, 1H), 4.08-3.89 (m, 2H), 3.77-3.61 (m, 2H), 3.61-3.51 (m, 1H), 3.34 (br d, J=12.6 Hz, 1H), 3.20 (br d, J=12.6 Hz, 1H), 3.01 (br, 1H), 2.90 (m, 1H).

Step 3: 3-nitro-4-(((4-(oxetan-3-yl)morpholin-2-yl)methyl)amino)benzenesulfonamide

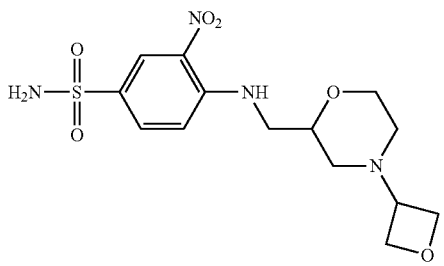

To a solution of 4-((morpholin-2-ylmethyl)amino)-3-nitrobenzenesulfonamide (600.00 mg, 1.90 mmol) and oxetan-3-one (410.05 mg, 5.69 mmol) in MeOH (60 mL) was added NaBH$_3$CN (357.58 mg, 5.69 mmol). The mixture was stirred at 15° C. for 14 hours. LC-MS showed 4-((morpholin-2-ylmethyl)amino)-3-nitrobenzenesulfonamide was consumed completely and one main peak with desired m/z. The reaction mixture was quenched by addition of H$_2$O (10 mL) and concentrated, then extracted with EtOAc (10 mL×3). The combined organic layers were washed with brine (10 mL), dried over Na$_2$SO$_4$, filtered and concentrated under reduced pressure to give a residue. The residue was washed with EA (5 mL). 3-nitro-4-(((4-(oxetan-3-yl)morpholin-2-yl)methyl) amino)benzenesulfonamide (580 mg, 1.49 mmol, 78.76% yield) was obtained as a yellow solid. $^1$H NMR (400 MHz, DMSO-$d_6$) δ ppm: 8.55 (br t, J=5.5 Hz, 1H), 8.47 (d, J=2.0 Hz, 1H), 7.84 (dd, J=2.0, 9.0 Hz, 1H), 7.34 (s, 2H), 7.27 (d, J=9.0 Hz, 1H), 4.59-4.51 (m, 2H), 4.49-4.41 (m, 2H), 3.86 (br d, J=11.0 Hz, 1H), 3.75 (br s, 1H), 3.62-3.52 (m, 1H), 3.50-3.39 (m, 2H), 2.75 (br d, J=11.0 Hz, 1H), 2.57 (br d, J=11.0 Hz, 1H), 1.96 (dt, J=2.9, 11.0 Hz, 1H), 1.80 (t, J=11.0 Hz, 1H). MS (ESI, m/e) [M+1]$^+$ 373.1.

Intermediate 3-k: 4-(((4-cyclopropylmorpholin-2-yl)methyl)amino)-3-nitrobenzenesulfonamide

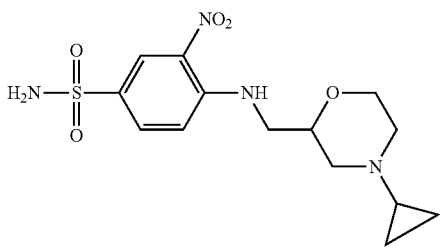 [SMILES: NS(=O)(=O)c1ccc(NCC2CN(C3CC3)CCO2)c([N+](=O)[O-])c1]

To a solution of 4-((morpholin-2-ylmethyl)amino)-3-nitrobenzenesulfonamide (1 g, 3.16 mmol) in MeOH (30 mL) were added 4 Å molecular sieve (0.5 g, 9.48 mmol), AcOH (1.33 g, 22.13 mmol, 1.27 mL), (1-ethoxycyclopropoxy)trimethylsilane (2.76 g, 15.81 mmol, 3.18 mL) and NaBH$_3$CN (595.97 mg, 9.48 mmol). The mixture was stirred at 70° C. for 5 hr. LC-MS showed 4-((morpholin-2-ylmethyl)amino)-3-nitrobenzenesulfonamide was consumed completely and one main peak with desired m/z. The reaction mixture was concentrated and diluted with H$_2$O (20 mL) and extracted with EtOAc (20 mL×3). The combined organic layers were washed with brine (20 mL) dried over Na$_2$SO$_4$, filtered and concentrated under reduced pressure to give a residue. The residue was purified by column chromatography (eluent: PE/EA=10:1 to EA), 4-(((4-cyclopropylmorpholin-2-yl)methyl)amino)-3-nitrobenzenesulfonamide (300 mg, 25.82% yield) was obtained as a yellow solid. $^1$H NMR (400 MHz, DMSO-$d_6$) δ ppm: 8.57 (br t, J=5.4 Hz, 1H), 8.47 (d, J=2.2 Hz, 1H), 7.84 (dd, J=2.2, 9.1 Hz, 1H), 7.35 (s, 2H), 7.28 (d, J=9.3 Hz, 1H), 3.83 (br d, J=11.4 Hz, 1H), 3.70-3.54 (m, 2H), 3.52-3.39 (m, 2H), 2.91 (br d, J=10.5 Hz, 1H), 2.73 (br d, J=11.4 Hz, 1H), 2.36-2.26 (m, 1H), 2.13 (t, J=10.5 Hz, 1H), 1.70-1.61 (m, 1H), 0.46-0.39 (m, 2H), 0.36-0.28 (m, 2H). MS (ESI, m/e) [M+1]$^+$ 357.1.

Intermediate 3-l: 3-nitro-4-(((1-(oxetan-3-yl)piperidin-4-yl)methyl)amino)benzenesulfonamide 2,2,2-trifluoroacetate

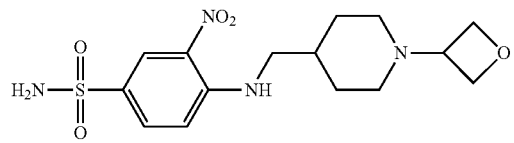 [SMILES: NS(=O)(=O)c1ccc(NCC2CCN(C3COC3)CC2)c([N+](=O)[O-])c1]

Step 1: tert-butyl ((1-(oxetan-3-yl)piperidin-4-yl)methyl)carbamate

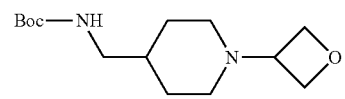 [SMILES: CC(C)(C)OC(=O)NCC1CCN(C2COC2)CC1]

To a solution of tert-butyl (piperidin-4-ylmethyl)carbamate (1 g, 4.67 mmol) in DCM (50 mL) was oxetan-3-one (1.01 g, 14 mmol) and HOAc (0.2 ml). The mixture was stirred at r.t. for 2 hours. Then to the mixture was added NaBH(OAc)$_3$ (2.967 g, 14 mmol). The mixture was stirred at r.t. for overnight. The mixture was diluted with DCM (200 ml), washed with sat. aq. NaHCO$_3$, brine (200 mL×2), dried over Na$_2$SO4, concentrated. The residue was purified by chromatography column on silica (eluent: MeOH/DCM=1/20) to give the product (1.2 g, 95%) as a yellow oil. MS (ESI, m/e) [M+1]$^+$ 271.1.

Step: 2: (1-(oxetan-3-yl)piperidin-4-yl)methanamine bis(2,2,2-trifluoroacetate)

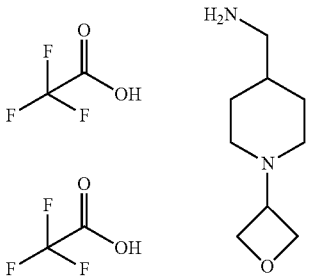 [SMILES: O=C(O)C(F)(F)F ; O=C(O)C(F)(F)F ; NCC1CCN(C2COC2)CC1]

To a solution of tert-butyl ((1-(oxetan-3-yl)piperidin-4-yl)methyl)carbamate (1.2 g 4.44 mmol) in DCM (50 mL) was added TFA (15 mL). The mixture was stirred at room temperature for overnight. The mixture was concentrated give the product. The crude product was used directly for next step.

Step: 3: 3-nitro-4-(((1-(oxetan-3-yl)piperidin-4-yl)methyl)amino)benzenesulfonamide 2,2,2-trifluoroacetate

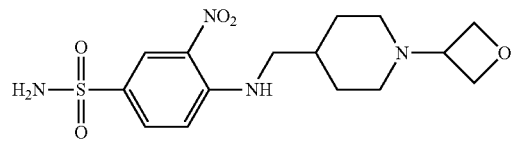 [SMILES: NS(=O)(=O)c1ccc(NCC2CCN(C3COC3)CC2)c([N+](=O)[O-])c1]

To a solution of (1-(oxetan-3-yl)piperidin-4-yl)methanamine bis(2,2,2-trifluoroacetate) (1.77 g, 4.44 mmol) and 4-fluoro-3-nitrobenzenesulfonamide (1.026 g, 4.66 mmol) in THF (50 mL) was added triethylamine (2.24 g, 22.2 mmol). The mixture was stirred at room temperature for overnight. The mixture was filtered to give the product (900 mg, 41.8%) as a yellow solid. MS (ESI, m/e) [M+1]$^+$ 371.1

Intermediate 3-m: (R)-4-(((1,4-dioxan-2-yl)methyl)amino)-3-nitrobenzenesulfonamide

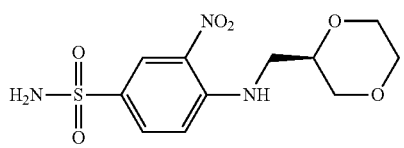 [SMILES: NS(=O)(=O)c1ccc(NC[C@@H]2COCCO2)c([N+](=O)[O-])c1]

To a solution of (R)-(1,4-dioxan-2-yl)methanamine (450 mg, 2.93 mmol) in THF (50 mL) was added 4-fluoro-3-nitrobenzenesulfonamide (709.5 mg, 3.22 mmol) and triethylamine (1.48 g, 14.65 mmol). The mixture was stirred at room temperature for 4 hours. Then the reaction mixture was filtered and the precipate was washed with petroleum to give the product (540 mg, 58%). MS (ESI, m/e) [M+1]$^+$ 318.0.

Intermediate 3-n: 4-(((tetrahydro-2H-pyran-4-yl)methyl)amino)-3-((trifluoromethyl)sulfonyl)benzenesulfonamide

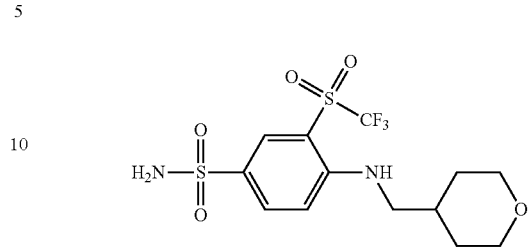

A solution of 4-fluoro-3-((trifluoromethyl)sulfonyl)benzenesulfonamide (469 mg, 1.53 mmol), (tetrahydro-2H-pyran-4-yl)methanamine (176 mg, 1.53 mmol) and Et$_3$N (232 mg, 2.3 mmol) was stirred at room temperature for 4 hours. After removal of solvent, the resulted residue was dissolved with EA (100 mL) and washed with brine (100 mL×4), dried over anhydrous Na$_2$SO$_4$, filtered and concentrated to give the crude product as a white solid (747 mg). MS (ESI, m/e) [M+1]+403.1.

Intermediate 3-o: 4-(((4-fluorotetrahydro-2H-pyran-4-yl)methyl)amino)-3-nitrobenzenesulfonamide

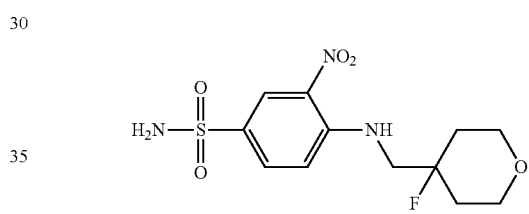

Step 1: 1,6-dioxaspiro[2.5]octane-2-carbonitrile

To a solution of oxan-4-one (100 g, 1 mol) in tert-Butanol (100 mL) was added 2-chloroacetonitrile (70 g, 0.93 mol). The resulting mixture was stirred for 30 min at 25° C. This was followed by the addition of a solution of t-BuOK (120 g, 1.07 mol) in tert-Butanol (1 L) dropwise with stirring at 25° C. in 40 min. The resulting mixture was stirred overnight at room temperature. After diluted with 200 mL of water and quenched with 40 mL of 10% hydrogen chloride, the resulting mixture was concentrated to one-third of its volume and then was extracted with 3×400 mL of ether. The combined organic layer was washed with 500 mL of brine, dried over anhydrous sodium sulfate and concentrated to afford 84.5 g (crude) of 1,6-dioxaspiro[2.5]octane-2-carbonitrile as yellow oil.

Step 2: 2-(4-fluorotetrahydro-2H-pyran-4-yl)-2-hydroxyacetonitrile

To a solution of 1,6-dioxaspiro[2.5]octane-2-carbonitrile (169 g, 1.22 mol) in 1 L of dichloromethane was added 70% HF/Py (148 mL) dropwise at 0° C. The resulting mixture was stirred overnight at room temperature. After diluted with 1000 mL of ethyl acetate, the reaction mixture was poured into NaHCO$_3$(sat.) and adjusted to PH ~7 with solid NaHCO$_3$ under stirring. The aqueous phase was extracted with 3×1000 mL of ethyl acetate and the organic layers was combined and then washed with 850 mL of 1% hydrogen chloride and 1×1000 mL of brine. Then it was dried over anhydrous sodium sulfate and concentrated to afford 139 g (crude) of 2-(4-fluorooxan-4-yl)-2-hydroxyacetonitrile as light yellow oil.

Step 3: (4-fluorotetrahydro-2H-pyran-4-yl)methanol

To a solution of 2-(4-fluorooxan-4-yl)-2-hydroxyacetonitrile (109 g, 685.5 mmol) in i-propanol/H$_2$O (800 mL/200 mL) was added NaBH$_4$ (39.1 g, 1028.3 mmol) in portions at 0° C. The resulting mixture was stirred 2 h at 0° C. and then quenched by the addition of 220 mL of acetone and stirred for another 1 h. The solids were filtered out and washed with 200 mL of ethyl acetate. The filtrate was concentrated and purified by silica gel column chromatography (eluent:ethyl acetate/petroleum ether=3/1) to afford 47.8 g (4-fluorooxan-4-yl)methanol as light yellow oil.

Step 4: (4-fluorotetrahydro-2H-pyran-4-yl)methyl methanesulfonate

To a solution of (4-fluorooxan-4-yl)methanol (57.8 g, 431.3 mmol) and TFA (65.5 g, 647.0 mmol) in 500 mL of dichloromethane was added MsCl (73.2 g, 647.0 mmol) dropwise at 0° C. The resulting mixture was stirred for 2 h at room temperature. After quenched with 500 mL of water, the resulting mixture was extracted with 2×500 mL of dichloromethane. The combined organic layer was dried over anhydrous sodium sulfate and concentrated to afford 105.8 g (crude) of (4-fluorooxan-4-yl)methyl methanesulfonate as yellow oil.

Step 5: 2-((4-fluorotetrahydro-2H-pyran-4-yl)methyl)isoindoline-1,3-dione

To a solution of (4-fluorooxan-4-yl)methyl methanesulfonate (105.8 g, 499.1 mmol) in 1 L of DMF was added potassium 1,3-dioxo-2,3-dihydro-1H-isoindol-2-ide (138.5 g, 748.6 mmol). The resulting mixture was stirred for overnight at 140° C. After cooled to room temperature. The reaction mixture was poured into 3 L of water and then filtered. The filter cake was dried under vacuum to afford 98 g (crude) of 2-((4-fluorotetrahydro-2H-pyran-4-yl) methyl) isoindoline-1,3-dione as off-white solid.

Step 6: (4-fluorotetrahydro-2H-pyran-4-yl)methanamine

To a solution of 2-((4-fluorotetrahydro-2H-pyran-4-yl) methyl)isoindoline-1,3-dione (98 g, 372.6 mmol) in 1 L of EtOH was added NH$_2$NH$_2$.H$_2$O (111.8 g, 2.24 mol). The resulting mixture was stirred for overnight at 70° C. After cooled to room temperature. The reaction mixture was concentrated and then diluted with 1 L of DCM After removal of the solid was by filtration, the filtrate was concentrated and purified by silica gel column chromatography (eluent: CH$_2$C$_{1-2}$/MeOH=100/1) to afford 30.2 g of (4-fluorooxan-4-yl)methanamine as light yellow oil.

Step 7: 4-(((4-fluorotetrahydro-2H-pyran-4-yl)methyl)amino)-3-nitrobenzenesulfonamide To a solution of (4-fluorotetrahydro-2H-pyran-4-yl)methanamine (30 g, 225.6 mmol) and 4-fluoro-3-nitrobenzene-1-sulfonamide (41.4 g, 188.0 mmol) in 500 mL of i-PrOH was added Na$_2$CO$_3$ (12.0 g, 112.8 mmol). The resulting mixture was stirred for 2 h at 60° C. and precipitation was formed. After filtration, the filter cake was washed by 3×100 mL of water and then dried under infrared light to afford 60.9 g of 4-[[(4-fluorooxan-4-yl)methyl]amino]-3-nitrobenzene-1-sulfonamide as a yellow solid.

Intermediate 3-p: 4-((((1r,4r)-4-hydroxy-4-methylcyclohexyl)methyl)amino)-3-nitrobenzenesulfonamide

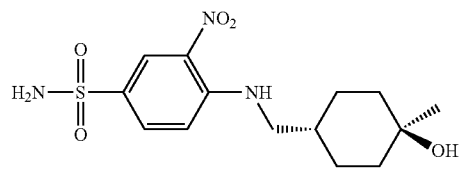 [SMILES: C[C@]1(O)CC[C@H](CNc2ccc(S(N)(=O)=O)cc2[N+](=O)[O-])CC1]

Step 1: 8-methyl-1,4-dioxaspiro[4.5]decan-8-ol

To a stirred solution of CH$_3$MgBr (344.0 ml, 1.032 mol, 3 M in Et$_2$O ) in dried toluene (2 L) was added 1,4-dioxaspiro[4.5]decan-8-one (70.0 g, 0.449 mol) solution in 350 ml dried toluene dropwise. The resulting mixture was stirred at 5-10° C. for 2 hours. The mixture was poured into saturated aq. NH$_4$Cl solution (3 L) and extracted with EtOAc (3×1 L). The combined organic phase was washed with brine (1.5 L), dried over Na$_2$SO$_4$ and concentrated to afford the 8-methyl-1,4-dioxaspiro[4.5]decan-8-ol (70.0 g, crude) as a white solid.

Step 2: 4-hydroxy-4-methylcyclohexan-1-one

To a stirred solution of 0.05 N HCl (1800 mL) was added 8-methyl-1,4-dioxaspiro[4.5]decan-8-ol (140.0 g, 0.814 mol). The mixture was stirred at 70° C. for 2.5 hours. The resulting mixture was cooled to room temperature and added NaCl solid to saturation, then extracted with EtOAc (5×700 mL), The combined organic phase was dried over Na$_2$SO$_4$ and concentrated to give the 4-hydroxy-4-methylcyclohexan-1-one (105.0 g, crude) as a yellow oil.

Step 3: (S)-1-methyl-4-(nitromethyl)cyclohex-3-en-1-ol

To a stirred solution of 4-hydroxy-4-methylcyclohexan-1-one (105.0 g, 0.820 mol) in CH$_3$NO$_2$ (600.0 mL) was added N$^1$,N$^1$-dimethylethane-1,2-diamine (7.216 g, 0.082 mol). The mixture was stirred for 2 hours at 100° C. under nitrogen atmosphere. After cooled to room temperature, the reaction mixture was concentrated and purified by silica gel column chromatography eluted with EA/PE=1/4 to afford the (S)-1-methyl-4-(nitromethyl)cyclohex-3-en-1-ol (96.0 g) as a yellow oil.

Step 4: (1r,4r)-1-methyl-4-(nitromethyl)cyclohexan-1-ol

To a stirred solution of (S)-1-methyl-4-(nitromethyl)cyclohex-3-en-1-ol (96.0 g, 0.561 mol) in DCM (1.5 L) was added Crabtree's catalyst (6.8 g, 0.008 mmol). The mixture was stirred at 50° C. for overnight under H$_2$ (30 atm) atmosphere. After cooled to room temperature, the reaction mixture was filtrated and concentrated to afford (1r,4r)-1-methyl-4-(nitromethyl)cyclohexan-1-ol (100.0 g, crude) as a yellow oil.

Step 5: (1r,4r)-4-(aminomethyl)-1-methylcyclohexan-1-ol

To a stirred solution of (1r,4r)-1-methyl-4-(nitromethyl)cyclohexan-1-ol (120.0 g, 0.694 mol) in MeOH (1.5 L) was added 10% wet Pd/C (30.0 g). The mixture was stirred for overnight at 85° C. under $H_2$ (30 atm) atmosphere. After cooled to room temperature, the reaction mixture was filtrated and concentrated to afford (1r,4r)-4-(aminomethyl)-1-methylcyclohexan-1-ol (95.0 g, crude) as a brown solid. $^1$H NMR (300 MHz, Methanol-$d_4$) δ ppm: 2.51 (d, J=6.7 Hz, 2H), 1.86-1.58 (m, 4H), 1.40-1.50 (s, 2H), 1.35-1.26 (m, 1H), 1.21 (s, 3H), 1.16-0.95 (m, 2H).

Step 6: 4-((((1r,4r)-4-hydroxy-4-methylcyclohexyl)methyl)amino)-3-nitrobenzenesulfonamide To a stirred solution of (1r,4r)-4-(aminomethyl)-1-methylcyclohexan-1-ol (100.0 g, 0.699 mol) in THF (1 L) was added 4-fluoro-3-nitrobenzenesulfonamide (107.6 g, 0.489 mol) and TFA (141.2 g, 1.389 mol). The mixture was stirred at room temperature for overnight. The resulting mixture was diluted with water (500 mL) and extracted with EtOAc (3×800 mL). The combined organic phase was washed with brine (1 L), dried over anhydrous $Na_2SO_4$ and concentrated. The residue was purified by slurry in EtOAc (800.0 mL) for three times to afford 4-((((1r,4r)-4-hydroxy-4-methylcyclohexyl)methyl)amino)-3-nitrobenzenesulfonamide (144.6 g) as a yellow solid. 1H NMR (300 MHz, DMSO-$d_6$) δ ppm: 8.52 (t, J=5.9 Hz, 1H), 8.45 (d, J=2.3 Hz, 1H), 7.80 (dd, J=9.2, 2.3 Hz, 1H), 7.42-7.11 (m, 3H), 4.24 (s, 1H), 3.31 (t, J=6.3 Hz, 2H), 1.66 (d, J=11.5 Hz, 3H), 1.53 (d, J=12.7 Hz, 2H), 1.31 (td, J=12.4, 3.4 Hz, 2H), 1.11-1.08 (m, 6H). MS (ESI, m/e) [M+1]$^+$ 343.9.

Intermediate 3-q1: (4-((((1 s,4s)-4-hydroxy-4-(trifluoromethyl)cyclohexyl)methyl)amino)-3-nitrobenzenesulfonamide

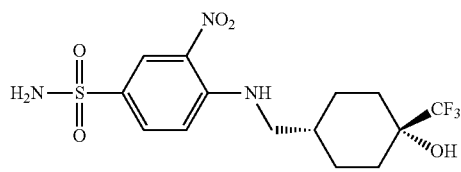 [SMILES: NS(=O)(=O)c1ccc(NC[C@H]2CC[C@](O)(C(F)(F)F)CC2)c([N+](=O)[O-])c1]

Intermediate 3-q2: 4-((((1r,4r)-4-hydroxy-4-(trifluoromethyl)cyclohexyl)methyl)amino)-3-nitrobenzenesulfonamide

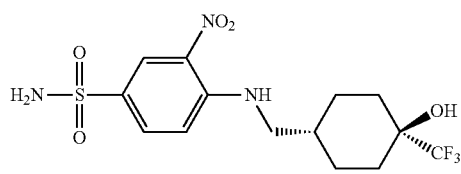 [SMILES: NS(=O)(=O)c1ccc(NC[C@H]2CC[C@@](O)(C(F)(F)F)CC2)c([N+](=O)[O-])c1]

Step 1: ethyl 4-(trifluoromethyl)-4-((trimethylsilyl)oxy)cyclohexanecarboxylate

To a solution of ethyl 4-oxocyclohexanecarboxylate (10 g, 58.75 mmol) in THF (100 mL) was added $TMSCF_3$ (12.53 g, 88.13 mmol) and CsF (8.92 g, 58.75 mmol). The mixture was stirred at 20° C. for 6 hours. TLC indicated the reactant was consumed completely. The reaction mixture was washed with saturated $NaHCO_3$ aqueous solution (50 mL×2) and extracted with ethyl acetate (50 mL×3). The combined organic phase was washed with brine (50 mL×2), dried with anhydrous $Na_2SO_4$, filtered and concentrated in vacuum. The residue was purified by column chromatography (silica gel, eluent: PE/EA=100/1 to 2/1). Ethyl 4-(trifluoromethyl)-4-((trimethylsilyl)oxy)cyclohexanecarboxylate (8.12 g) was obtained as yellow oil. 1H NMR (400 MHz, CDCl3) δ ppm: 4.15 (q, J=7.1 Hz, 2H), 2.20-2.66 (m, 1H), 1.98-2.08 (m, 1H), 1.63-1.95 (m, 6H), 1.53 (id, J=13.4, 4.2 Hz, 1H), 1.27 (t, J=7.1 Hz, 3H), 0.17 (d, J=4.5 Hz, 9H).

Step 2: (4-(trifluoromethyl)-4-((trimethylsilyl)oxy)cyclohexyl)methanol

To a solution of ethyl 4-(trifluoromethyl)-4-((trimethylsilyl)oxy)cyclohexanecarboxylate (8.10 g, 25.93 mmol) in THF (50 mL) was added LAH (1.97 g, 51.86 mmol) at 0° C., the mixture was stirred at 0° C. for 2 hours. TLC indicated the reactant was consumed completely. The reaction mixture was quenched by addition of water (15 mL), and then extracted with Ethyl acetate (50 mL×3). The combined organic layers were dried over $Na_2SO_4$, tittered and concentrated under reduced pressure. The crude product (6.2 g, crude) was used into the next step without further purification.

Step 3: (4-(trifluoromethyl)-4-((trimethylsilyl)oxy)cyclohexyl)methyl methanesulfonate To a solution of (4-(trifluoromethyl)-4-((trimethylsilyl)oxy)cyclohexyl)methanol (6.2 g, 22.93 mmol) and TFA (4.64 g, 45.86 mmol) in DCM (60 mL) was added MsCl (5.91 g, 51.60 mmol) at 0° C., the mixture was stirred at 0° C. for 2 hours. TLC indicated the reactant was consumed completely. The reaction mixture was washed with saturated $NaHCO_3$ aqueous solution (50 mL×2) and extracted with DCM (50 mL×2), The combined organic phase was washed with brine (50 mL×2), dried with anhydrous $Na_2SO_4$, filtered and concentrated in vacuum. The crude product (8.52 g, crude) was used into the next step without further purification.

Step 4: ((4-(azidomethyl)-1-(trifluoromethyl)cyclohexyl)oxy)trimethylsilane

To a solution of (4-(trifluoromethyl)-4-((trimethylsilyl)oxy)cyclohexyl)methyl methanesulfonate (8.51 g, 24.42 mmol) in DMF (150 mL) was added $NaN_3$ (7.94 g, 122.11 mmol) at 20° C., the mixture was stirred at 50° C. for 12 hours, TLC indicated the reactant was consumed completely. The mixture was diluted with water and extracted with MTBE (100 mL×3), dried over anhydrous $Na_2SO_4$ filtered. The combined organic layers were concentrated to obtain crude product, which was used for the next step directly.

Step 5: (4-(trifluoromethyl)-4-((trimethylsilyl)oxy)cyclohexyl)methanamine

A mixture of ((4-(azidomethyl)-1-(trifluoromethyl)cyclohexyl)oxy)trimethylsilane (7.21 g, theoretical yield) in CH₃OH (50 mL) was added Pd/C (2.5 g), the mixture was stirred at 30° C. for 16 hours under H₂ (30 psi), TLC indicated the reactant was consumed completely. The mixture was filtered and concentrated under reduced pressure. (4-(trifluoromethyl)-4-((trimethylsilyl)oxy)cyclohexyl)methanamine (4.67 g, crude) was obtained as yellow oil. The crude product was used into the next step without further purification.

Step 6: 4-(((4-hydroxy-4-(trifluoromethyl)cyclohexyl)methyl)amino)-3-nitrobenzenesulfonamide To a solution of 4-fluoro-3-nitrobenzenesulfonamide (2.50 g, 11.35 mmol) and (4-(trifluoromethyl)-4-((trimethylsilyl)oxy)cyclohexyl)methanamine (4.59 g, 17.04 mmol) in DMF (75 mL) was added DIPEA (2.94 g, 22.74 mmol), the mixture was stirred at 55° C. for 2 hours. TLC indicated the reactant was consumed completely. The reaction mixture was washed with water (200 mL) and extracted with EA (100 mL×3), The combined organic phase was washed with brine (50 mL×2), dried with anhydrous Na₂SO₄, filtered and concentrated in vacuum. The residue was washed with PE/EA=5/1 (30 mL) and filtered. The filter cake was purified by prep-HPLC (neutral). 4-((((1s,4s)-4-hydroxy-4-(trifluoromethyl)cyclohexyl)methyl)amino)-3-nitrobenzenesulfonamide (Intermediate 3-q1, retention time: 2.5 min) (1.04 g) was obtained as a yellow solid. ¹H NMR (400 MHz, methol-d₄) δ ppm: 8.65 (d, J=1.9 Hz, 1H), 8.49 (t, J=4.7 Hz, 1H), 7.91 (dd, J=9.1, 1.63 Hz, 1H), 7.17 (d, J=9.3 Hz, 1H), 3.46 (t, J=6.3 Hz, 2H), 2.06 (d, J=4.1 Hz, 1H), 1.84-2.00 (m, 4H), 1.52-1.70 (m, 4H). MS (ESI, m/e) [M+1]⁺ 396.0; 4-((((1r,4r)-4-hydroxy-4-(trifluoromethyl)cyclohexyl)methyl)amino)-3-nitrobenzenesulfonamide (Intermediate 3-q2, retention time: 2.6 min) (842 mg) was obtained as a yellow solid. ¹H NMR (400 MHz, methol-d₄) δ ppm: 8.65 (d, J=1.9 Hz, 1H), 8.54 (t, J=5.2 Hz, 1H), 7.90 (dd, J=9.1, 1.6 Hz, 1H), 7.17 (d, J=9.3 Hz, 1H), 3.33-3.41 (m, 2H), 1.24 (s, 1H), 1.87 (d, J=12.5 Hz, 2H), 1.71-1.82 (m, 3H), 1.42-1.69 (m, 4H). MS (ESI, m/e) [M+1]⁺ 396.0.

Intermediate 3-r: 4-(((3-oxabicyclo[3.1.0]hexan-6-yl)methyl)amino)-3-nitrobenzenesulfonamide

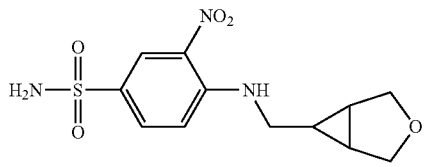 [SMILES: NS(=O)(=O)c1ccc(NCC2C3COCC23)c([N+](=O)[O-])c1]

Step 1: ethyl 3-oxabicyclo[3.1.0]hexane-6-carboxylate

To a solution of 2,5-dihydrofuran (10 g, 142.67 mmol) and ethyl 2-diazoacetate (32.56 g, 285.35 mmol) in DCM (250 mL) was added Rh(AcO)₂ (63.06 mg, 2.85 mmol). The mixture was stirred at 20° C. for 12 hours. TLC indicated the reactant was consumed completely. The reaction mixture was and concentrated in vacuum to give a residue. The residue was purified by prep-MPLC and ethyl 3-oxabicyclo[3.1.0]hexane-6-carboxylate (10.0 g) was obtained. ¹H NMR (400 MHz, CDCl₃) δ ppm: 4.08-4.16 (m, 2H), 3.92 (d, J=8.6 Hz, 2H), 3.74 (d, J=8.4 Hz, 2H), 2.13-2.17 (m, 2H), 1.59 (t, J=3.1 Hz, 1H), 1.23-1.28 (m, 3H).

Step 2: 3-oxabicyclo[3.1.0]hexan-6-ylmethanol

To a solution of ethyl 3-oxabicyclo[3.1.0]hexane-6-carboxylate (10 g, 64.03 mmol) in THF (50 mL) was added LiAlH₄ (2.43 g, 64.03 mmol) at 0° C., The mixture was stirred at 0° C. for 4 hours. TLC indicated the reactant was consumed completely. The reaction mixture was poured into H₂O (30 mL) and extracted with EA (30 mL×3), dried over Na₂SO₄, filtered and concentrated. 3-oxabicyclo[3.1.0]hexan-6-ylmethanol (7.0 g, crude) was obtained and used into the next step without further purification.

Step 3: 3-oxabicyclo[3.1.0]hexan-6-ylmethyl methanesulfonate

To a solution of 3-oxabicyclo[3.1.0]hexan-6-ylmethanol (7.0 g, 61.33 mmol) in DCM (100 mL) was added MsCl (21.08 g, 183.98 mmol) and TFA (24.82 g, 245.31 mmol). The mixture was stirred at 25° C. for 5 hours. TLC indicated the reactant was consumed completely. The reaction mixture was quenched with aq. NH₄Cl (30 mL) and extracted with EA (30 mL×3), dried over Na₂SO₄, filtered and concentrated. The residue was purified by column chromatography (SiO₂, PE/EA=100/1 to 30/1). 3-oxabicyclo[3.1.0]hexan-6-ylmethyl methanesulfonate (3.5 g) was obtained. ¹H NMR (400 MHz, CDCl₃) δ ppm: 4.15 (d, J=7.5 Hz, 2H), 3.90 (d, J=8.4 Hz, 2H), 3.71 (d, J=8.4 Hz, 2H), 3.03 (s, 3H), 1.69-1.72 (m, 2H), 1.21-1.29 (m, 1H).

Step 4: 6-(azidomethyl)-3-oxabicyclo[3.1.0]hexane

To a solution of 3-oxabicyclo[3.1.0]hexan-6-ylmethyl methanesulfonate (2 g, 10.4 mmol) in DMF (20 mL) was added NaN₃ (676.37 mg, 10.4 mmol). The mixture was stirred at 50° C. for 12 hours. TLC indicated the reactant was consumed completely. The reaction mixture was poured into H₂O (30 mL) and extracted with EA (30 mL×3), dried over Na₂SO₄, filtered and concentrated. The crude product was used in next step directly.

Step 5: 3-oxabicyclo[3.1.0]hexan-6-ylmethanamine

To a solution of 6-(azidomethyl)-3-oxabicyclo[3.1.0]hexane (1.4 g, 10.06 mmol) in DMF (15 mL) was added Pd/C (0.7 g, 1.006 mmol). The mixture was stirred at 25° C. for 2 hours under H₂ atmosphere (15 Psi). LC/MS showed the reactant was consumed completely and one main peak with desired mass signal. The reaction mixture was filtered and used next step directly. MS (ESI, m/e) [M+1]⁺ 114.0.

Step 6: 4-(((3-oxabicyclo[3.1.0]hexan-6-yl)methyl)amino)-3-nitrobenzenesulfonamide To a solution of 4-fluoro-3-nitrobenzenesulfonamide (1.5 g, 6.8 mmol) and 3-oxabicyclo[3.1.0]hexan-6-ylmethanamine (1 g, 8.84 mmol) in DMF (15 mL) was added DIEA (1.76 g, 13.6 mmol). The mixture was stirred at 60° C. for 2 hours. LC/MS showed 4-fluoro-3-nitrobenzenesulfonamide was consumed completely and one main peak with desired mass signal. The reaction mixture was cooled to room temperature and poured into H₂O (50 mL) under stirring. The precipitation was filtered and the cake was washed with MTBE (10 mL) and dried in vacuum. 4-((3-oxabicyclo[3.1.0]hexan-6-ylmethyl)amino)-3-nitrobenzenesulfonamide (758 mg) was obtained. ¹H NMR (400 MHz, DMSO-d₆) δ ppm: 8.59 (br, 1H), 8.47 (s, 1H), 7.84 (d, J=8.8 Hz, 1H), 7.37 (s, 2H), 7.28 (d, J=9.2 Hz, 1H), 3.72 (d, J=8.2 Hz, 2H), 3.55 (d, J=7.9 Hz, 2H), 3.36 (s, 2H), 1.71 (s, 2H), 1.05 (s, 1H), MS (ESI, m/e) [M+1]⁺ 314.0.

Example A1: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-phenylpyrrolidin-1-yl)-[1,1'-biphenyl]-4-carboxamide
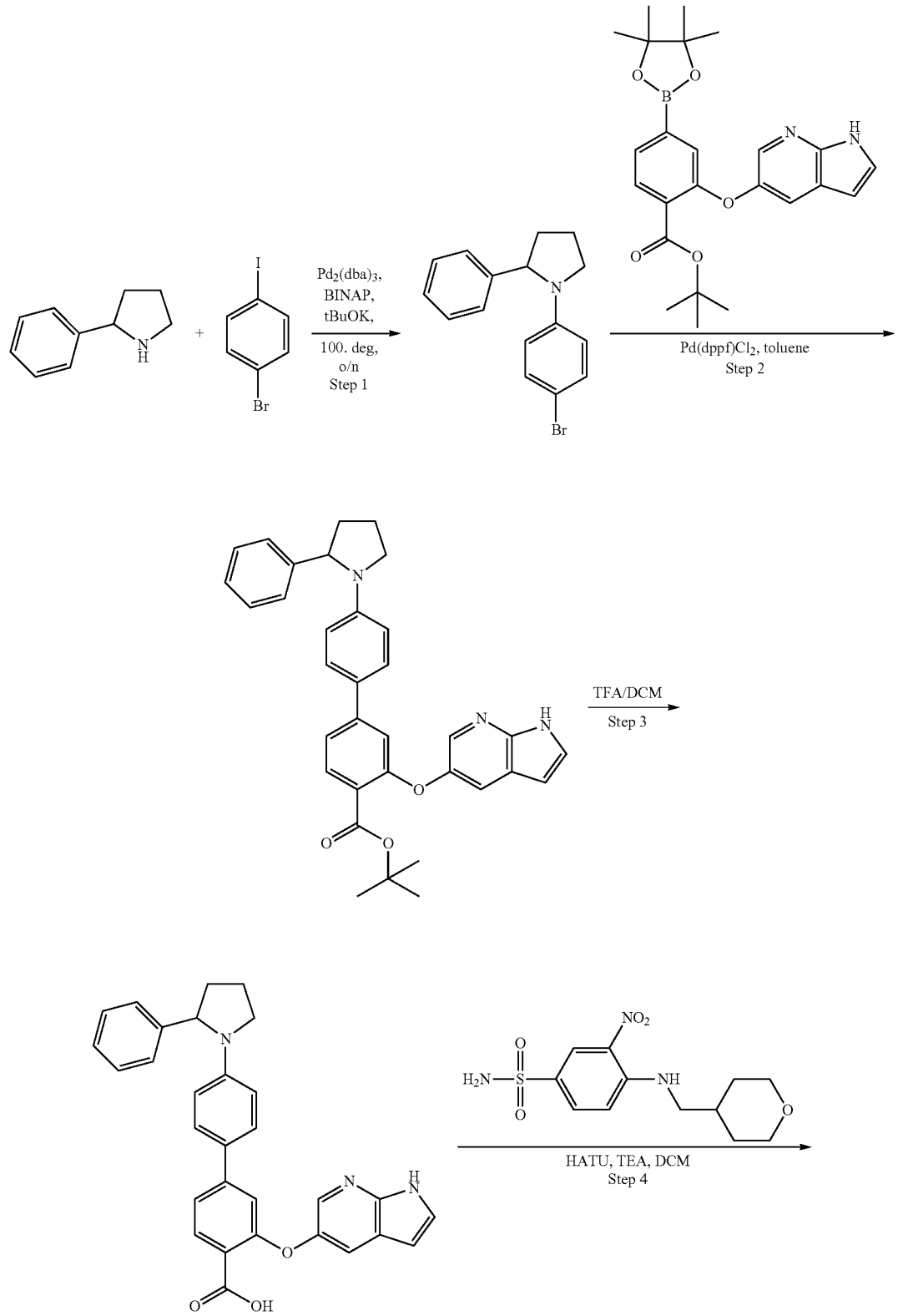

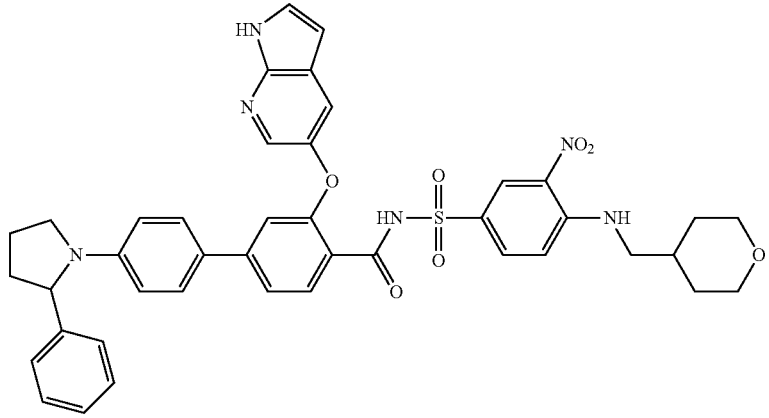

A1

Step 1: 1-(4-bromophenyl)-2-phenylpyrrolidine

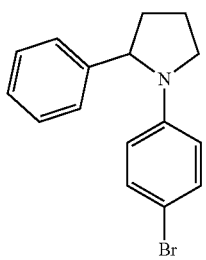 [SMILES: Brc1ccc(N2CCCC2c2ccccc2)cc1]

To a degassed solution of 2-phenylpyrrolidine (588 mg, 4 mmol), 1-bromo-4-iodobenzene (1.132 g, 16 mmol), BINAP (497 mg, 0.8 mmol) and K-OtBu (1.2 g, 12 mmol) in toluene (25 ml) was added $Pd_2(dba)_3$ (366 mg, 0.4 mmol). Nitrogen was bubbled through the mixture for 5 min, then heated to 90° C. and stirred overnight. After cooled to room temperature, the reaction mixture was washed with water and brine in sequence. The organic layer was dried over anhydrous $Na_2SO_4$, then filtered, concentrated and purified by column chromatography with 5%~20% EA/PE as eluent to give 1-(4-bromophenyl)-2-phenylpyrrolidine (750 mg, 62%) as a colorless oil. MS (ESI, m/e) $[M+1]^+$ 302.0, 304.1.

Step 2: tert-butyl-3-((1H-pyrrolo[2,3-b]pyridin-5-yl)oxy)-4'-(2-phenylpyrrolidin-1-yl)-[1,1'-biphenyl]-4-carboxylate

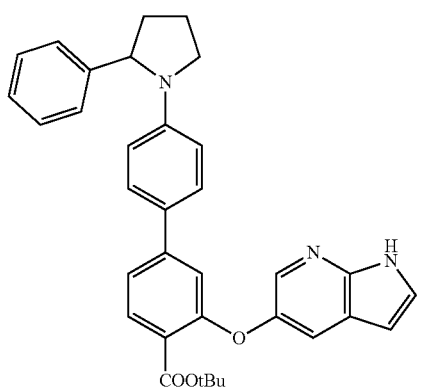

Under nitrogen atmosphere, a mixture of 1-(4-bromophenyl)-2-phenylpyrrolidine (525 mg, 1.74 mmol), tert-butyl 2-((1H-pyrrolo[2,3-b]pyridin-5-yl)oxy)-4-(4,4,5,5-tetramethyl-1,3,2-dioxaborolan-2-yl)benzoate (985 mg, 2.26 mmol), Pd(dppf)Cl$_2$ (128 mg, 0.174 mmol), and K$_2$CO$_3$ (480 mg, 3.48 mmol) in 1,4-dioxane/H$_2$O (50 mL/10 mL) was heated to 90° C. with stirring overnight. After cooled to room temperature, the reaction mixture was washed with water and brine in sequence. The organic layer was dried over anhydrous Na$_2$SO$_4$, then filtered, concentrated and purified by column chromatography with 10%~50% EA/PE as eluent to give tert-butyl-3-((1H-pyrrolo[2,3-b]pyridin-5-yl)oxy)-4'-(2-phenylpyrrolidin-1-yl)-[1,1'-biphenyl]-4-carboxylate (530 mg, 57.4%) as a white foam. MS (ESI, m/e) $[M+1]^+$ 532.3.

Step 3: 3-((1H-pyrrolo[2,3-b]pyridin-5-yl)oxy)-4'-(2-phenylpyrrolidin-1-yl)-[1,1'-biphenyl]-4-carboxylic acid

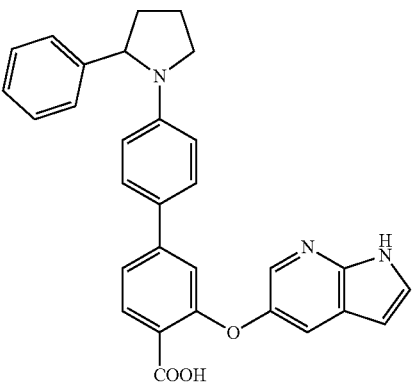 [SMILES: O=C(O)c1ccc(-c2ccc(N3CCCC3c3ccccc3)cc2)cc1Oc1cnc2[nH]ccc2c1]

To a solution of tert-butyl-3-((1H-pyrrolo[2,3-b]pyridin-5-yl)oxy)-4'-(2-phenylpyrrolidin-1-yl)-[1,1'-biphenyl]-4-carboxylate (531 mg, 1 mmol) in dichloromethane (25 mL) was added trifluoroacetic acid (5 mL). The reaction was stirred overnight at r.t. Then the solvent was removed under reduced pressure and the resulted residue was purified by column chromatography on silica gel with 5% methanol/dichloromethane to give 3-((1H-pyrrolo[2,3-b]pyridin-5-yl)oxy)-4'-(2-phenylpyrrolidin-1-yl)-[1,1'-biphenyl]-4-carboxylic acid (400 mg, 84.2%) as a white foam. MS (ESI, m/e) $[M+1]^+$ 476.2.

Step 4: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-phenylpyrrolidin-1-yl)-[1,1'-biphenyl]-4-carboxamide

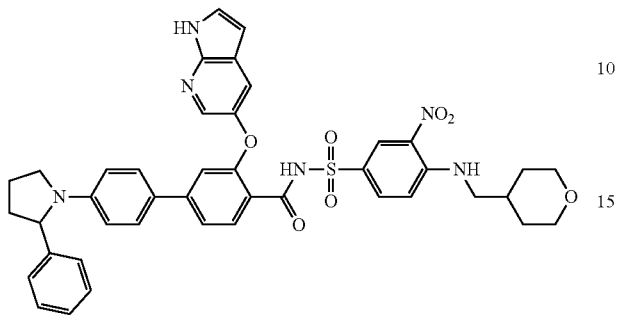

To a solution of 3-((1H-pyrrolo[2,3-b]pyridin-5-yl)oxy)-4'-(2-phenylpyrrolidin-1-yl)-[1,1'-biphenyl]-4-carboxylic acid (95 mg, 0.2 mmol) in dichloromethane (25 mL) were added HATU (114 mg, 0.3 mmol) and trimethylamine (0.2 mL). The mixture was stirred for 0.5 h at r.t. Then 3-nitro-4-(((tetrahydro-2H-pyran-4-yl)methyl)amino)benzenesulfonamide (126 mg, 0.4 mmol) was added. After stirred overnight at r.t, the reaction mixture was washed with water (10 mL), and the organic layers were dried over anhydrous $Na_2SO_4$, then concentrated in vacuum. The residue was further purified by prep-HPLC to give the desired compound.

$^1$H NMR (400 MHz, DMSO-$d_6$) δ ppm: 12.16 (s, 1H), 11.68 (s, 1H), 8.57 (s, 1H), 8.54 (s, 1H), 8.03 (s, 1H), 7.80 (d, J=8.6 Hz, 1H), 7.59-7.46 (m, 3H), 7.33-7.25 (m, 5H), 7.20-7.14 (m, 3H), 7.08 (d, J=8.1 Hz, 1H), 6.89 (s, 1H), 6.42 (d, J=8.5 Hz, 2H), 6.37 (s, 1H), 4.78 (d, J=7.4 Hz, 1H), 3.84 (d, J=8.4 Hz, 2H), 3.68 (s, 1H), 3.31-3.20 (m, 3H), 2.37-2.34 (m, 1H), 1.94-1.80 (m, 4H), 1.60 (d, J=12.0 Hz, 2H), 1.38-1.14 (m, 4H). MS (ESI, m/e) [M+1]$^+$ 773.3

Example A2: 3-((1H-pyrrolo[2,3-b]pyridin-5-yl)oxy)-4'-(2-(4-chlorophenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

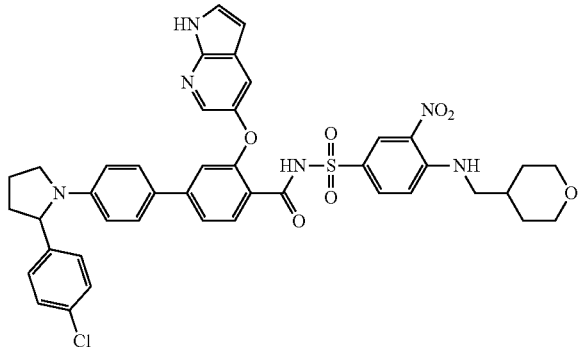 [SMILES: O=C(NS(=O)(=O)c1ccc(NCC2CCOCC2)c([N+](=O)[O-])c1)c1ccc(-c2ccc(N3CCCC3c3ccc(Cl)cc3)cc2)cc1Oc1cnc2[nH]ccc2c1]

The desired compound was synthesized starting from 2-(4-chlorophenyl)pyrrolidine and 1-bromo-4-iodobenzene following the procedures similar to those in Example A1. $^1$H NMR (400 MHz, DMSO-$d_6$) δ ppm: 12.16 (s, 1H), 11.70 (s, 1H), 8.60 (s, 1H), 8.56 (s, 1H), 8.05 (d, J=2.2 Hz, 1H), 7.82 (d, J=8.4 Hz, 1H), 7.59 (s, 1H), 7.57-7.48 (m, 2H), 7.34-7.28 (m, 5H), 7.18 (d, J=8.3 Hz, 2H), 7.12 (d, J=9.3 Hz, 1H), 6.89 (s, 1H), 6.41 (d, J=8.6 Hz, 2H), 6.38 (s, 1H), 4.78 (d, J=7.1 Hz, 1H), 3.84 (d, J=8.4 Hz, 2H), 3.67 (t, J=7.1 Hz, 1H), 3.30-3.18 (m, 4H), 2.37 (m, 1H), 2.00-1.69 (m, 4H), 1.60 (d, J=12.4 Hz, 2H), 1.34-1.13 (m, 3H). MS (ESI, m/e) [M+1]$^+$ 807.1

Example A3: 3-((1H-pyrrolo[2,3-b]pyridin-5-yl)oxy)-4'-(2-(3-chlorophenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

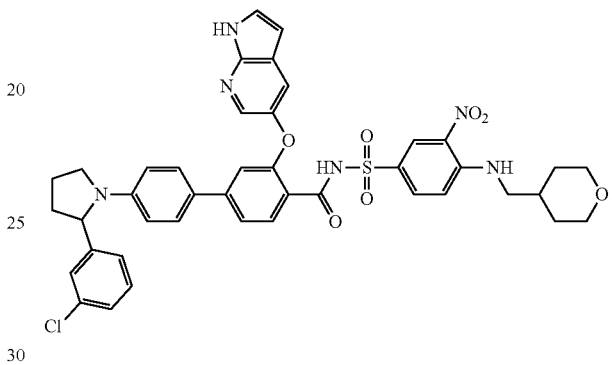

The desired compound was synthesized starting from 2-(3-chlorophenyl)pyrrolidine and 1-bromo-4-iodobenzene following the procedures similar to those in Example A1. $^1$H NMR (400 MHz, DMSO-$d_6$) δ ppm: 12.17 (s, 1H), 11.70 (s, 1H), 8.59 (s, 1H), 8.57 (s, 1H), 8.05 (s, 1H), 7.83 (d, J=9.0 Hz, 1H), 7.60 (s, 1H), 7.55-7.51 (m, 2H), 7.36-7.21 (m, 6H), 7.13 (d, J=8.4 Hz, 2H), 6.91 (s, 1H), 6.43 (d, J=8.4 Hz, 2H), 6.39 (s, 1H), 4.80 (d, J=7.7 Hz, 1H), 3.85 (d, J=9.9 Hz, 2H), 3.70 (s, 1H), 3.31-3.18 (m, 4H), 2.36-2.31 (m, 1H), 1.94-1.79 (m, 4H), 1.60 (d, J=12.5 Hz, 2H), 1.25 (m, 3H). MS (ESI, m/e) [M+1]$^+$ 807.1

Example A4: 3-((1H-pyrrolo[2,3-b]pyridin-5-yl)oxy)-4'-(2-(2-chlorophenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

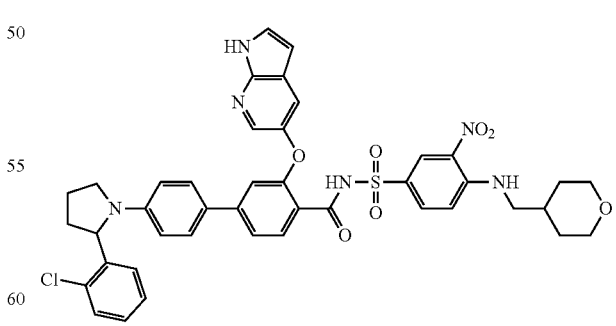

The desired compound was synthesized starting from 2-(2-chlorophenyl)pyrrolidine and 1-bromo-4-iodobenzene following the procedures similar to those in Example A1. $^1$H NMR (400 MHz, DMSO-$d_6$) δ ppm: 12.17 (s, 1H), 11.70 (s, 1H), 8.61 (s, 1H), 8.57 (s, 1H), 8.05 (s, 1H), 7.83 (d, J=9.4

Hz, 1H), 7.60-7.41 (m, 4H), 7.35-7.30 (m, 3H), 7.25-7.12 (m, 3H), 7.00 (d, J=7.7 Hz, 1H), 6.90 (s, 1H), 6.48-6.27 (m, 3H), 4.97 (d, J=7.4 Hz, 1H), 3.85 (d, J=11.3 Hz, 2H), 3.74 (s, 1H), 3.31-3.19 (m, 4H), 2.43-2.35 (m, 1H), 1.99-1.83 (m, 4H), 1.60 (d, J=12.5 Hz, 2H), 1.23 (s, 3H), MS (ESI, m/e) [M+1]$^+$ 807.1.

Example A4a: (S)-3-((1H-pyrrolo[2,3-b]pyridin-5-yl)oxy)-4'-(2-(2-chlorophenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide Example A4b: (R)-3-((1H-pyrrolo[2,3-b]pyridin-5-yl)oxy)-4'-(2-(2-chlorophenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

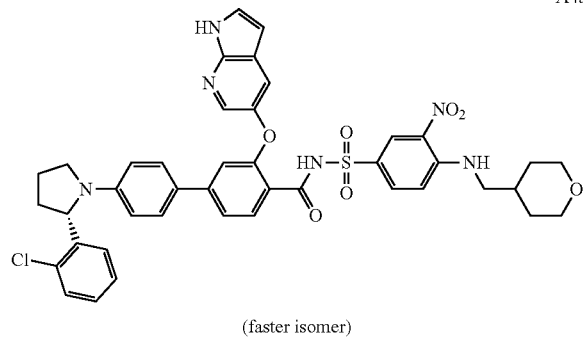

(faster isomer) A4a

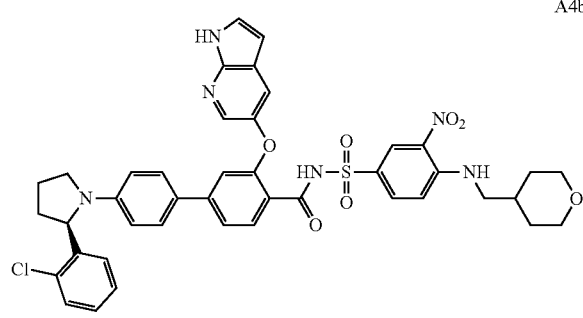

(slower isomer) A4b

Two enantiomers A4a (faster isomer) and A4b (slower isomer) were separated by chiral preparative HPLC. The chiral separation conditions are shown below. The faster enantiomer was eluted at retention time of 1.1 min to give 252 mg of product. The slower enantiomer was eluted at retention time of 1.8 min to give 238 mg of product. The absolute configuration of fast isomer was confirmed to be S by co-crystallization of Bcl2 with A4a, see the section "Protein purification and co-crystallization, of Bcl2 with A4a".

| Column | CHIRALPAK IG |
| --- | --- |
| Column size | 2 cm × 25 cm, 5 um |
| Injection | 4.8 mL |
| Mobile phase | CO$_2$:[DCM:EtOH(0.1% DEA) = 1:2] = 55:45 |
| Flow rate | 40 mL/min |

| Column | CHIRALPAK IG |
| --- | --- |
| Wave length | UV 220 nm |
| Temperature | 25° C. |
| Sample solution | 5.64 mg/mL in MeOH:DCM = 3:1 |
| Prep-SFC equipment | Prep-SFC-80 |

Example A5: 3-((1H-pyrrolo[2,3-b]pyridin-5-yl)oxy)-3'-chloro-4'-(2-(2-chlorophenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

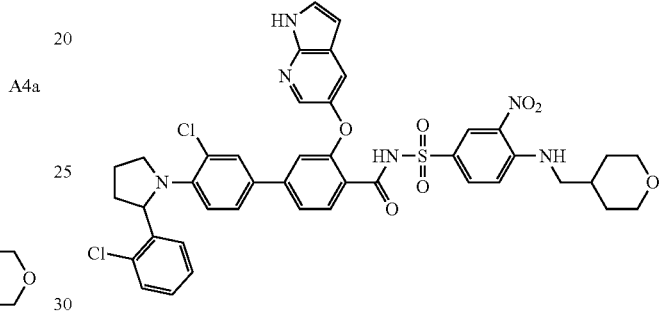

The desired compound was synthesized starting from 2-(2-chlorophenyl)pyrrolidine and 4-bromo-2-chloro-1-iodobenzene following the procedures similar to those in Example A1, $^1$H NMR (400 MHz, DMSO-d$_6$) δ ppm: 12.32 (s, 1H), 11.70 (s, 1H), 8.61 (t, J=5.7 Hz, 1H), 8.55 (d, J=2.0 Hz, 1H), 8.03 (d, J=2.4 Hz, 1H), 7.82 (d, J=7.6 Hz, 1H), 7.62-7.46 (m, 4H), 7.44-7.34 (m, 2H), 7.33-7.22 (m, 2H), 7.22-7.15 (m, 2H), 7.12 (d, J=9.4 Hz, 1H), 6.99 (s, 1H), 6.71 (d, J=8.8 Hz, 1H), 6.37 (s, 1H), 5.20 (t, J=7.6 Hz, 1H), 4.16 (m, 1H), 3.84 (d, J=8.4 Hz, 2H), 3.45-3.11 (m, 5H), 2.10-1.80 (m, 3H), 1.63 (m, 2H), 1.24 (m, 4H). MS (ESI, m/e) [M+1]$^+$ 841.1.

Example A6: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-phenylpyrrolidin-1-yl)-3'-(trifluoromethyl)-[1,1'-biphenyl]-4-carboxamide

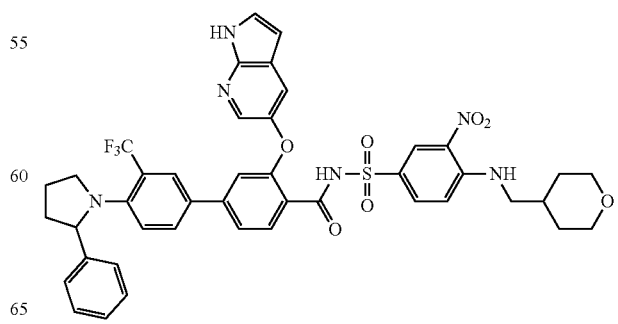

Step 1: 1-(4-bromo-2-(trifluoromethyl)phenyl)-2-phenylpyrrolidine

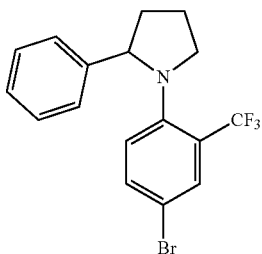 [SMILES: FC(F)(F)c1cc(Br)ccc1N1CCCC1c1ccccc1]

A mixture of 2-phenylpyrrolidine (1.46 g, 10 mmol), 4-bromo-1-fluoro-2-(trifluoromethyl)benzene (4.8 g, 20 mmol) and N,N-Diisopropylethylamine (2.5 g, 20 mmol) in Dimethyl sulfoxide (50 mL) was heated to 150° C. in a sealed tube with stirring overnight. The mixture was cooled and poured into water (100 mL). Then the mixture was extracted with EA (50 mL×3), the organic was washed with water, brine and dried over anhydrous $Na_2SO_4$. Solvent was removed in vacuum, the residue was purified by column chromatography with petroleum to give 1-(4-bromo-2-(trifluoromethyl)phenyl)-2-phenylpyrrolidine (180 mg, 4.9%) as a brown oil.

The desired compound was then synthesized from 1-(4-bromo-2-(trifluoromethyl)phenyl)-2-phenylpyrrolidine following the next procedures similar to those in Example A1.
$^1$H NMR (400 MHz, DMSO-$d_6$) δ ppm: 12.32 (s, 1H), 11.66 (s, 1H), 8.56-8.53 (m, 2H), 8.01 (s, 1H), 7.78 (s, 1H), 7.66 (s, 1H), 7.61-7.42 (m, 4H), 7.39 (d, J=8.0 Hz, 1H), 7.30 (d, J=7.2 Hz, 2H), 7.23 (t, J=7.2 Hz, 2H), 7.1-7.00 (m, 4H), 6.35 (s, 1H), 4.87 (d, J=9.4 Hz, 1H), 4.02-3.64 (m, 3H), 3.26-3.22 (m, 4H), 2.43-2.31 (m, 1H), 2.00-1.98 (m, 1H), 1.93-1.81 (m, 2H), 1.72-1.67 (m, 1H), 1.60 (d, J=12.0 Hz, 2H), 1.29-1.19 (m, 3H), MS (ESI, m/e) [M+1]$^+$ 841.1.

Example A7: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(3-(trifluoromethyl)phenyl)pyrrolidin-1-yl)-[1,1'-biphenyl]-4-carboxamide

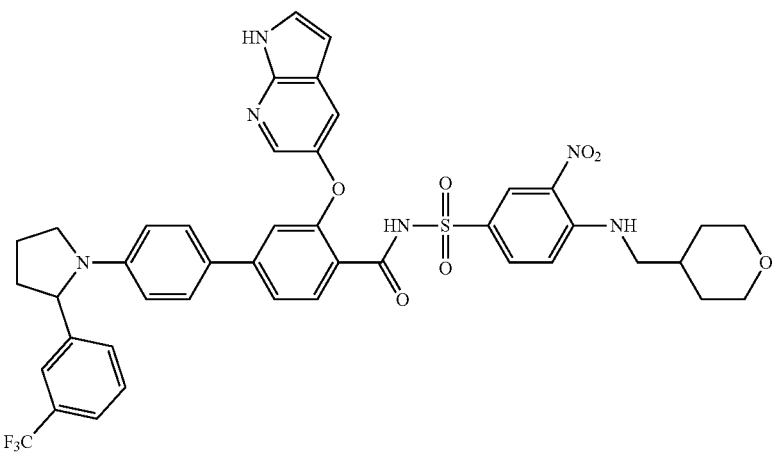 [SMILES: O=C(NS(=O)(=O)c1ccc(NCC2CCOCC2)c([N+](=O)[O-])c1)c1ccc(-c2ccc(N3CCCC3c3cccc(C(F)(F)F)c3)cc2)cc1Oc1cnc2[nH]ccc2c1]

The desired compound was synthesized starting from 2-(3-(trifluoromethyl)phenyl)pyrrolidine and 1-bromo-4-iodobenzene following the procedures similar to those in Example A1. $^1$H NMR (400 MHz, DMSO-d$_6$) δ ppm: 12.17 (s, 1H), 11.70 (s, 1H), 8.61 (s, 1H), 8.56 (s, 1H), 8.05 (d, J=2.0 Hz, 1H), 7.82 (d, J=9.2 Hz, 1H), 7.64-7.42 (m, 7H), 7.33 (dd, J=14.2, 8.5 Hz, 3H), 7.13 (d, J=9.2 Hz, 1H), 6.90 (s, 1H), 6.56-6.31 (m, 3H), 4.90 (d, J=7.4 Hz, 1H), 3.84 td, J=8.5 Hz, 2H), 3.73 (t, J=7.1 Hz, 1H), 3.31-3.22 (m, 5H), 2.05-1.77 (m, 5H), 1.60 td, J=12.1 Hz, 2H), 1.28 (s, 2H). MS (ESI, m/e) [M+1]$^+$ 841.1.

Example A8: 3-((1H-pyrrolo[2,3-b]pyridin-5-yl)oxy)-4'-(2-(2-cyclopropylphenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

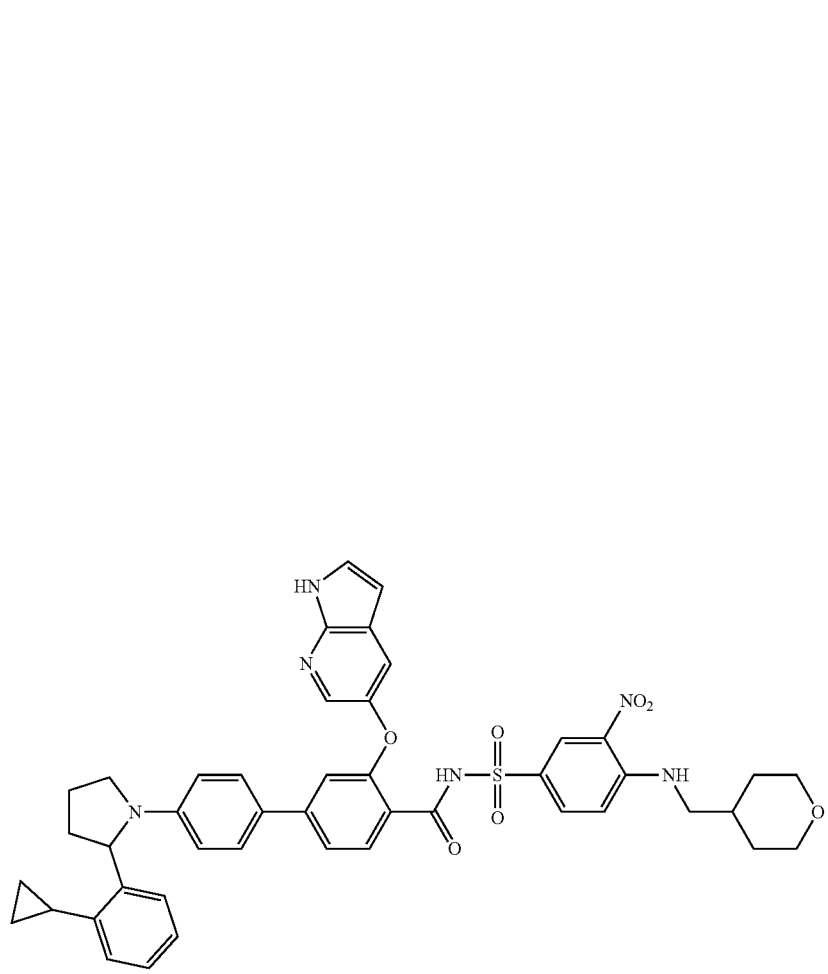

The desired compound was synthesized from 2-(2-cyclopropylphenyl)pyrrolidine and 1-bromo-4-iodobenzene following the next procedures similar to those in Example A1. $^1$H NMR (400 MHz, CDCl$_3$) δ ppm: 10.31 (s, 1H), 9.14 (s, 1H), 8.93 (d, J=2.0 Hz, 1 if). 8.54 (t, J=5.2 Hz, 1H), 8.24 (d, J=2.0 Hz, 1H), 8.19 (d, J=7.6 Hz, 1H), 8.09 (d, J=8.6 Hz, 1H), 7.71 (d, J=2.0 Hz, 1H), 7.45-7.41 (m, 1H), 7.29 (s, 1H), 7.20 (d, J=8.6 Hz, 2H), 7.12 (t, J=7.6 Hz, 1H), 7.04-6.98 (m, 2H), 6.93 (d, J=8.6 Hz, 2H), 6.81 (s, 1H), 6.53 (s, 1H), 6.36 (d, J=8.6 Hz, 2H), 5.20 (d, J=8.0 Hz, 1H), 4.03 (dd, J=11.0, 3.6 Hz, 2H), 3.70 (t, J=7.1 Hz, 1H), 3.50-3.41 (m, 3H), 3.27 (t, J=6.0 Hz, 2H), 2.47-2.37 (m, 1H), 2.04-1.90 (m, 7H), 1.76-1.71 (m, 2H), 1.63 (s, 4H), 1.50-1.36 (m, 2H), 1.04-0.94 (m, 2H), 0.84-0.80 (m, 1H), 0.72-0.68 (m, 1H). MS (ESI, m/e) [M+1]$^+$ 813.1.

Example A8a and Example A8b: (R or S)-3-((1H-pyrrolo[2,3-b]pyridin-5-yl)oxy)-4'-(2-(2-cyclopropylphenyl)pyrrolidin-1-yl)-N-((3-nitro-4-((((tetrahydro-2H-pyran-4-yl)methyl)amino)phenyl)sulfonyl)-[1,1'-biphenyl]-4-carboxamide, or (S or R)-3-((1H-pyrrolo[2,3-b]pyridin-5-yl)oxy)-4'-(2-(2-cyclopropylphenyl)pyrrolidin-1-yl)-N-((3-nitro-4-((((tetrahydro-2H-pyran-4-yl)methyl)amino)phenyl)sulfonyl)-[1,1'-biphenyl]-4-carboxamide

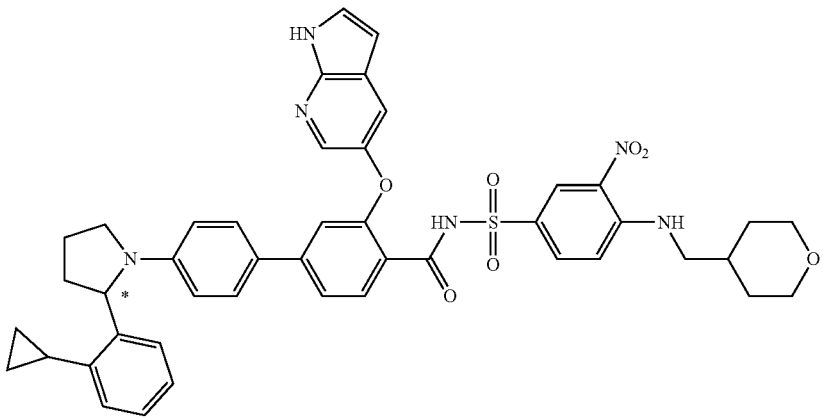

A8a (R or S)
faster isomer

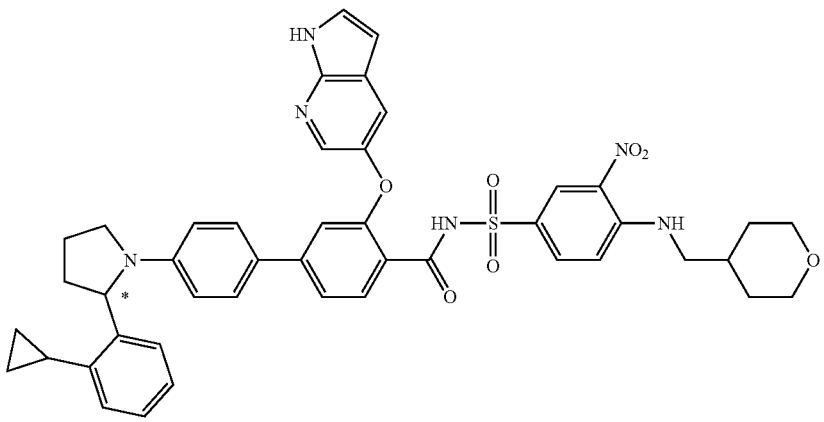 [SMILES: O=C(NS(=O)(=O)c1ccc(NCC2CCOCC2)c([N+](=O)[O-])c1)c1ccc(-c2ccc(N3CCCC3c3ccccc3C3CC3)cc2)cc1Oc1cnc2[nH]ccc2c1]

A8b (S or R)
slower isomer

Two enantiomers A8a (faster isomer) and A8b (slower isomer) were separated by chiral preparative HPLC, The chiral separation conditions are shown below. The faster enantiomer was eluted at retention time of 3.9 min to give 231 mg of product. The slower enantiomer was eluted at retention time of 4.7 min to give 219 mg of product,

| Column | CHIRAL ART Cellulose-SB |
| --- | --- |
| Column size | 2 cm × 25 cm, 5 um |
| Injection | 0.5 mL |
| Mobile phase | (Hex:DCM = 5:1)(0.1% FA):EtOH = 50:50 |
| Flow rate | 20 mL/min |
| Wave length | UV 220 nm |
| Temperature | 25° C. |
| Sample solution | 17.3 mg/mL in EtOH:DCM = 3:1 |
| Prep-HPLC equipment | Prep-HPLC-Gilson |

Example A9: 3-((1H-pyrrolo[2,3-b]pyridin-5-yl)oxy)-N-((3-nitro-4-((((tetrahydro-2H-pyran-4-yl)methyl)amino)phenyl)sulfonyl)-4'-(2-(4-(trifluoromethyl)phenyl)pyrrolidin-1-yl)-[1,1'-biphenyl]-4-carboxamide

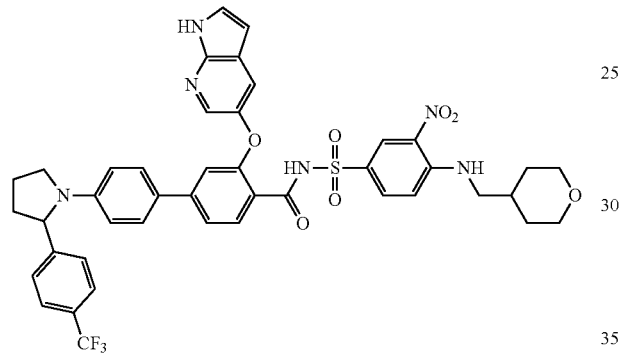

The desired compound was synthesized starting from 2-(4 (trifluoromethyl)phenyl)pyrrolidine and 1-bromo-4-iodobenzene following the procedures similar to those in Example A1. $^1$H NMR (400 MHz, DMSO-d$_6$) δ ppm: 12.17 (s, 1H), 11.70 (s, 1H), 8.60 (s, 1H), 8.56 (s, 1H), 8.04 (s, 1H), 7.82 (d, J=8.2 Hz, 1H), 7.64 (d, J=8.0 Hz, 2H), 7.58 (s, 1H), 7.53 (d, J=8.2 Hz, 1H), 7.50 (s, 1H), 7.39 (d, J=8.0 Hz, 2H), 7.33 (d, J=8.2 Hz, 1H), 7.30 (d, J=8.5 Hz, 2H), 7.12 (d, J=8.2 Hz, 1H), 6.89 (s, 1H), 6.43 (d, J=8.5 Hz, 2H), 6.38 (s, 1H), 4.89 (d, J=7.7 Hz, 1H), 3.84 (d, J=8.3 Hz, 2H), 3.71 (t, J=7.4 Hz, 1H), 3.43-3.19 (m, 5H), 2.46-2.35 (m, 1H), 2.05-1.76 (m, 4H), 1.60 (d, J=12.4 Hz, 2H), 1.29-1.20 (m, 2H). MS (ESI, m/e) [M+1]$^+$ 841.1.

Example A10: 3-((1H-pyrrolo[2,3-b]pyridin-5-yl)oxy)-4'-(2-(3-cyclopropylphenyl)pyrrolidin-1-yl)-N-((3-nitro-4-((((tetrahydro-2H-pyran-4-yl)methyl)amino)phenyl)sulfonyl)-[1,1'-biphenyl]-4-carboxamide

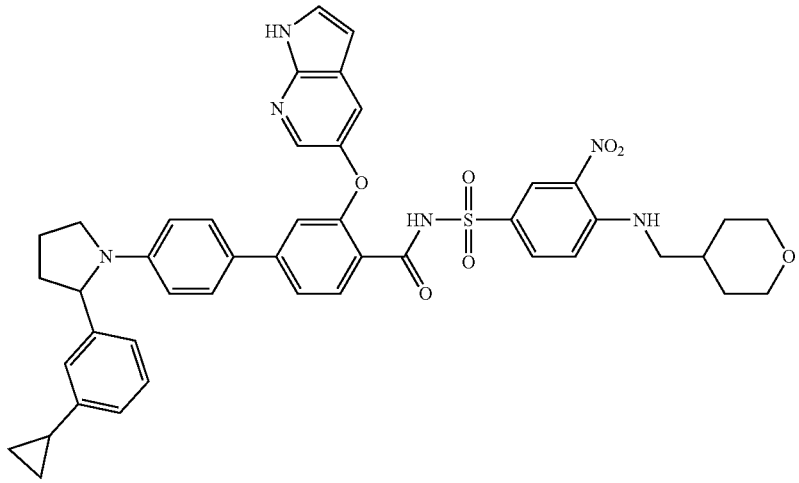 [SMILES: O=C(NS(=O)(=O)c1ccc(NCC2CCOCC2)c([N+](=O)[O-])c1)c1ccc(-c2ccc(N3CCCC3c3cccc(C4CC4)c3)cc2)cc1Oc1cnc2[nH]ccc2c1]

2-(3-cyclopropylphenyl)pyrrolidine was prepared by the similar procedure of 2-(2-cyclopropylphenyl)pyrrolidine. The desired compound was then synthesized from 2-(3-cyclopropylphenyl)pyrrolidine and 1-bromo-4-iodobenzene following the next procedures similar to those in Example A1. $^1$H NMR (400 MHz, DMSO-d$_6$) δ ppm: 11.55 (s, 1H), 8.39 (s, 1H), 8.34 (t, J=5.6 Hz, 1H), 7.95 (s, 1H), 7.64 (d, J=8.0 Hz, 1H), 7.57 (d, J=8.0 Hz, 1H), 7.41 (s, 1H), 7.34 (s, 1H), 7.30 (d, J=8.4 Hz, 2H), 7.25 (d, J=8.0 Hz, 1H), 7.13 (t, J=7.5 Hz, 1H), 6.95 (s, 1H), 6.93 (s, 1H), 6.89 (d, J=8.0 Hz, 1H), 6.85-6.77 (m, 2H), 6.42 (d, J=8.4 Hz, 2H), 6.29 (s, 1H), 4.72 (d, J=8.0 Hz, 1H), 3.83 (d, J=8.0 Hz, 2H), 3.67 (s, 1H), 3.25-3.23 (m, 3H), 2.41-2.27 (m, 1H), 1.93-1.78 (m, 6H), 1.60 (d, J=8.0 Hz, 2H), 1.29-1.17 (m, 3H), 0.89 (d, J=8.0 Hz, 2H), 0.64-0.57 (m, 2H). MS (ESI, m/e) [M+1]$^+$ 813.1.

Example A11: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(o-tolyl)pyrrolidin-1-yl)-[1,1'-biphenyl]-4-carboxamide

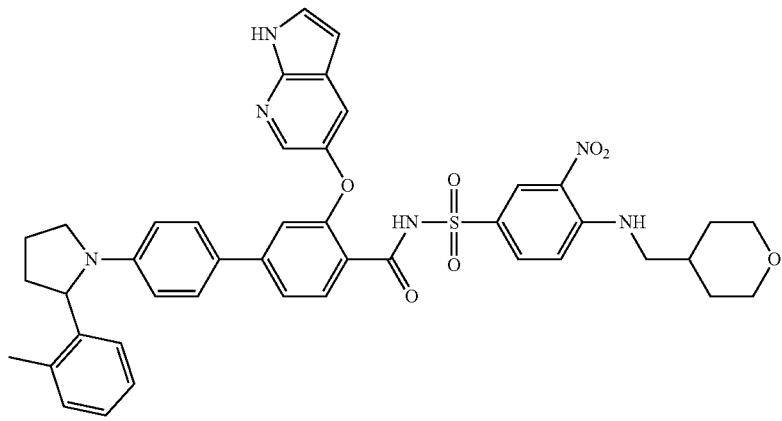 [SMILES: Cc1ccccc1C1CCCN1c1ccc(-c2ccc(C(=O)NS(=O)(=O)c3ccc(NCC4CCOCC4)c([N+](=O)[O-])c3)c(Oc3cnc4[nH]ccc4c3)c2)cc1]

The desired compound was synthesized starting from 2-(o-tolyl)pyrrolidine and 1-bromo-4-iodobenzene following the procedures similar to those in Example A1 $^1$H NMR. (400 MHz, DMSO-d6) δ ppm: 11.54 (s, 1H), 8.39 (s, 1H), 8.34 (t, J=5.5 Hz, 1H), 7.95 (d, J=2.1 Hz, 1H), 7.65 (d, J=9.1 Hz, 1H), 7.56 (d, J=8.0 Hz, 1H), 7.41 (s, 1H), 7.35 (d, J=2.1 Hz, 1H), 7.29 (d, J=8.5 Hz, 2H), 7.23 (d, J=8.0 Hz, 1H), 7.18 (d, J=8.0 Hz, 1H), 7.09 (t, J=7.3 Hz, 1H), 7.02 (t, J=7.3 Hz, 1H), 6.89 (s, 1H), 6.87 (d, J=8.0 Hz, 1H), 6.83 (d, J=9.1 Hz, 1H), 6.35 (d, J=8.5 Hz, 2H), 6.30 (d, J=2.1 Hz, 1H), 4.86 (d, J=8.0 Hz, 1H), 3.83 (d, J=8.0 Hz, 2H), 3.75-3.71 (m, 1H), 3.25-3.23 (m, 3H), 3.17 (s, 1H), 2.38 (s, 3H), 2.04-1.80 (m, 3H), 1.74-1.71 (m, 1H), 1.60 (d, J=12.0 Hz, 2H), 1.28-1.20 (m, 4H). MS (ESI, m/e) [M+1]$^+$ 787.1.

Example A12: 3-((1H-pyrrolo[2,3-b]pyridin-5-yl)oxy)-4'-(2-(2-isopropylphenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

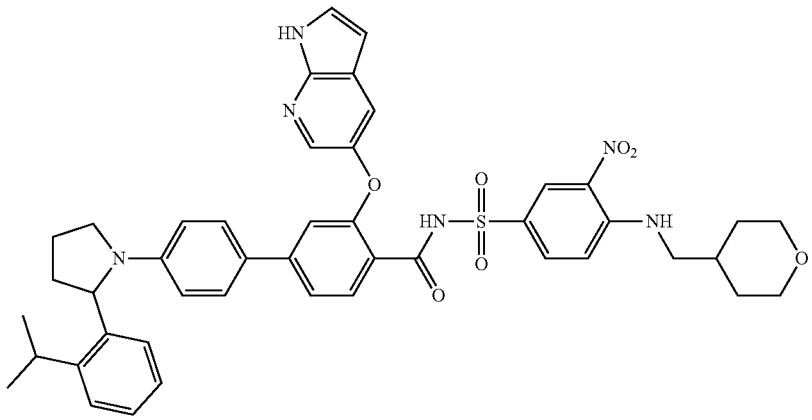

The desired compound was synthesized starting from 2-(2-isopropylphenyl)pyrrolidine and 1-bromo-4-iodobenzene following the next procedures similar to those in Example A1. $^1$H NMR (400 MHz, DMSO-d$_6$) δ ppm: 12.16 (s, 1H), 11.70 (s, 1H), 8.61 (s, 1H), 8.56 (s, 1H), 8.04 (s, 1H), 7.82 (d, J=8.5 Hz, 1H), 7.50-7.58 (m, 3H), 7.29-7.35 (m, 4H), 7.24-7.06 (m, 2H), 6.98 (t, J=7.3 Hz, 1H), 6.91 (s, 1H), 6.82 (d, J=7.6 Hz, 1H), 6.35-6.37 (m, 3H), 4.99 (d, J=7.9 Hz, 1H), 3.84 (d, J=8.5 Hz, 2H), 3.70 (t, J=7.9 Hz, 1H), 3.18-3.38 (m, 5H), 3.01 (s, 1H), 2.04-1.82 (m, 4H), 1.70 (s, 1H), 1.60 (d, J=12.2 Hz, 2H), 1.27-1.23 (m, 8H). MS (ESI, m/e) [M+1]$^+$ 815.2.

Example A13: 3-((1H-pyrrolo[2,3-b]pyridin-5-yl)oxy)-4'-(2-([1,1'-biphenyl]-2-yl)pyrrolidin-1-yl)-N-((3-nitro-4-(((tetrahydro-2H-pyran-4-yl)methyl)amino)phenyl)sulfonyl)-[1,1'-biphenyl]-4-carboxamide

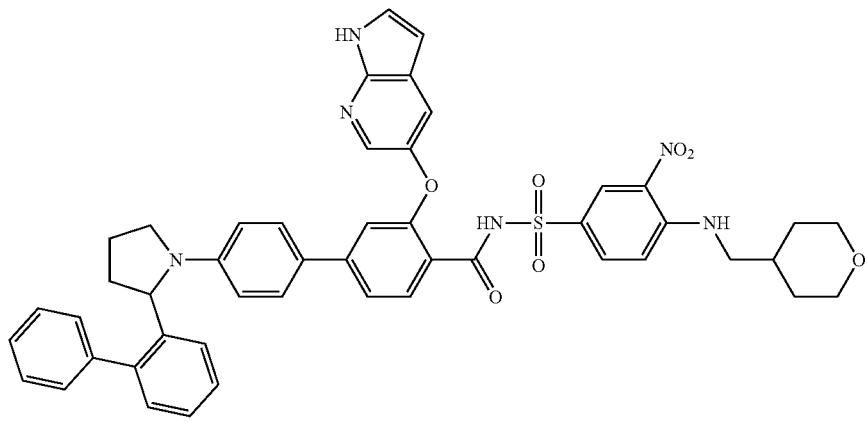 [SMILES: O=C(NS(=O)(=O)c1ccc(NCC2CCOCC2)c([N+](=O)[O-])c1)c1ccc(-c2ccc(N3CCCC3c3ccccc3-c3ccccc3)cc2)cc1Oc1cnc2[nH]ccc2c1]

The desired compound was synthesized starting from 2-([1,1'-biphenyl]-2-yl)pyrrolidine and 1-bromo-4-iodobenzene following the next procedures similar to those in Example A1. $^1$H NMR (400 MHz, DMSO-$d_6$) δ ppm: 12.16 (s, 1H), 11.62 (s, 1H), 8.48 (s, 2H), 8.00 (s, 1H), 7.73 (s, 1H), 7.62-7.35 (m, 8H), 7.35-7.13 (m, 7H), 7.10 (s, 1H), 6.90 (s, 1H), 6.33 (d, J=8.4 Hz, 3H), 4.61 (d, J=7.8 Hz, 1H), 3.84 (d, J=9.9 Hz, 2H), 3.70 (s, 1H), 3.26 (m, 4H), 2.98 (s, 1H), 2.19-2.07 (m, 1H), 1.97-2.02 (m, 2H), 1.78-1.89 (m, 3H), 1.60 (d, J=12.7 Hz, 2H), 1.28 (s, 1H). MS (ESI, m/e) [M+1]$^+$ 849.1.

Example A14: 3-((1H-pyrrolo[2,3-b]pyridin-5-yl)oxy)-4'-(2-(4-cyclopropylphenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

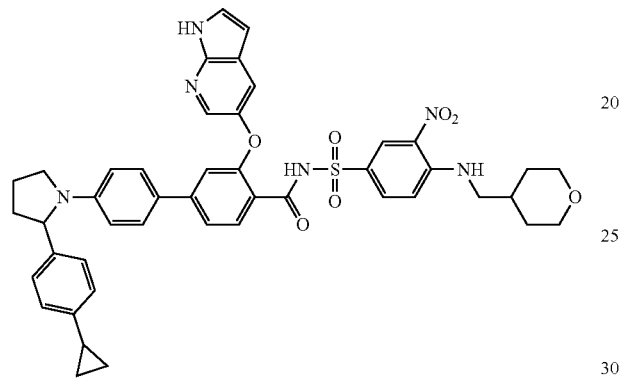

The desired compound was synthesized starting from 2-(4-cyclopropylphenyl)pyrrolidine and 1-bromo-4-iodobenzene following the procedures similar to those in Example A1. $^1$H NMR (400 MHz, DMSO-$d_6$) δ ppm: 12.16 (s, 1H), 11.72 (s, 1H), 8.63 (t, J=5.7 Hz, 1H), 8.57 (d, J=1.8 Hz, 1H), 8.05 (d, J=2.2 Hz, 1H), 7.83 (d, J=9.1 Hz, 1H), 7.60 (d, J=2.2 Hz, 1H), 7.55-7.50 (m, 2H), 7.35-7.25 (m, 3H), 7.14 (d, J=9.3 Hz, 1H), 7.05-6.95 (m, 4H), 6.89 (s, 1H), 6.45-6.35 (m, 3H), 4.72 (d, J=8.0 Hz, 2H), 3.90-3.80 (m, 2H), 3.70-3.60 (m, 2H), 3.40-3.15 (m, 3H), 2.35-2.26 (m, 2H), 2.02-1.68 (m, 4H), 1.65-1.55 (m, 2H), 1.30-1.15 (m, 2H), 0.92-0.86 (m, 2H), 0.62-0.55 (m, 2H), MS (ESI, m/e) [M+1]$^+$ 813.2.

Example A15: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-phenylazepan-1-yl)-[1,1'-biphenyl]-4-carboxamide

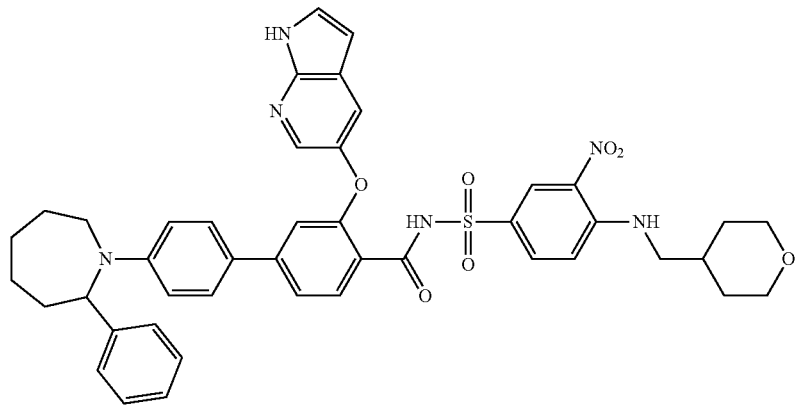 [SMILES: O=C(NS(=O)(=O)c1ccc(NCC2CCOCC2)c([N+](=O)[O-])c1)c1ccc(-c2ccc(N3CCCCCC3c3ccccc3)cc2)cc1Oc1cnc2[nH]ccc2c1]

The desired compound was synthesized starting from 2-phenylazepane and 1-bromo-4-iodobenzene following the procedures similar to those in Example. $^1$H NMR (400 MHz, DMSO-d$_6$) δ ppm: 12.15 (s, 1H), 11.72 (s, 1H), 8.68-8.63 (m, 1H), 8.58-8.52 (m, 1H), 8.06 (d, J=2.0 Hz, 1H), 7.84 (d, J=8.2 Hz, 1H), 7.61 (d, J=2.1 Hz, 1H), 7.53 (t, J=5.7 Hz, 3H), 7.40-7.23 (m, 6H), 7.20-7.13 (m, 5H), 6.87 (s, 1H), 6.57 (d, J=8.6 Hz, 2H), 6.39 (s, 1H), 4.65-4.55 (m, 1H), 3.88-3.75 (m, 2H), 3.58-3.43 (m, 1H), 3.30-3.20 (m, 3H), 2.42-2.30 (m, 1H), 1.95-1.87 (m, 2H), 1.82-1.67 (m, 3H), 1.65-1.52 (m, 4H), 1.29-1.23 (m, 2H). MS (ESI, m/e) [M+1]$^+$ 801.2.

Example A16: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-phenylpiperidin-1-yl)-[1,1'-biphenyl]-4-carboxamide

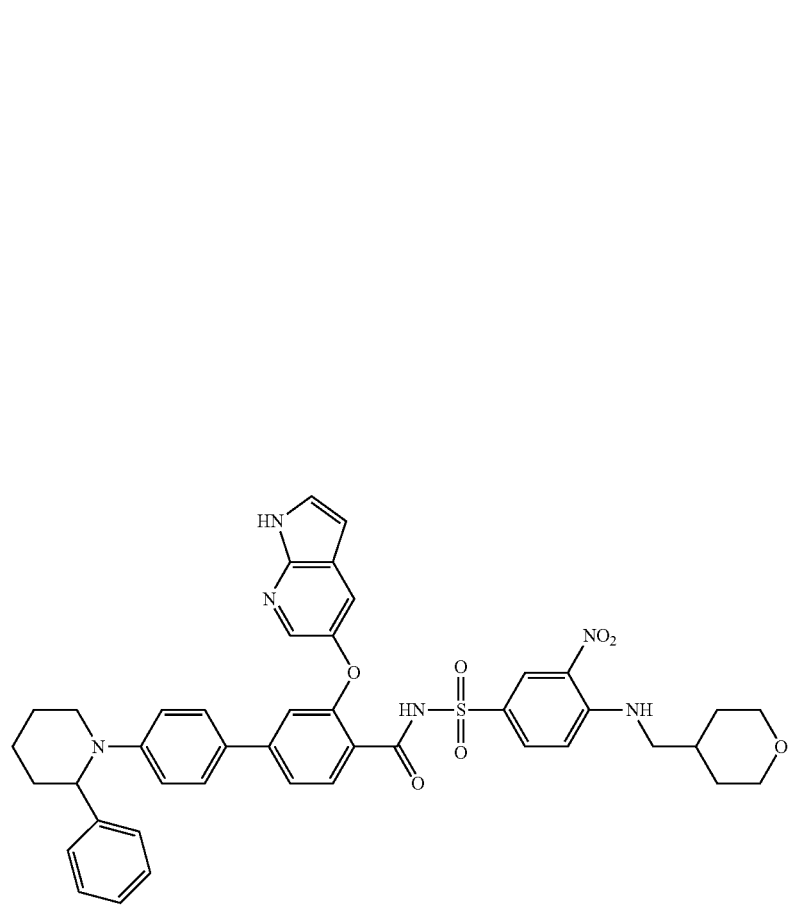 [SMILES: O=C(NS(=O)(=O)c1ccc(NCC2CCOCC2)c([N+](=O)[O-])c1)c1ccc(-c2ccc(N3CCCCC3c3ccccc3)cc2)cc1Oc1cnc2[nH]ccc2c1]

The desired compound was synthesized starting from 2-phenylpiperidine and 1-bromo-4-iodobenzene following the procedures similar to those in Example A1. ¹H NMR (400 MHz, DMSO-d₆) δ ppm: 12.21 (br, 1H), 11.63 (br, 1H), 8.48 (br, 2H), 8.01 (m, 1H), 7.76 (d, J=8.0 Hz, 1H), 7.56 (d, J=8.0 Hz, 1H), 7.54 (m, 2H), 7.32 (d, J=12.0 Hz, 2H), 7.25-7.21 (m, 4H), 7.13-7.11 (m, 1H), 6.91-6.86 (m, 4H), 6.35 (m, 1H), 4.79 (m, 1H), 3.75 (d, J=8.0 Hz, 2H), 3.45 (m, 1H), 3.32-3.23 (m, 5H), 1.92-1.70 (m, 4H), 1.62 (m, 2H), 1.48 (m, 2H), 1.25-1.20 (m, 3H). MS (ESI, m/e) [M+1]⁺ 787.1.

Example A17: 3-((1H-pyrrolo[2,3-b]pyridin-5-yl)oxy)-4'-(2-(3,4-dichlorophenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

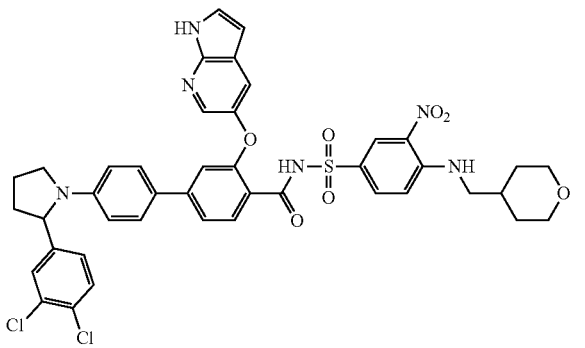 [SMILES: O=C(NS(=O)(=O)c1ccc(NCC2CCOCC2)c([N+](=O)[O-])c1)c1ccc(-c2ccc(N3CCCC3c3ccc(Cl)c(Cl)c3)cc2)cc1Oc1cnc2[nH]ccc2c1]

The desired compound was synthesized starting from 2-(3,4-dichlorophenyl)pyrrolidine and 1-bromo-4-iodobenzene following the procedures similar to those in Example A1. ¹H NMR (400 MHz, DMSO-d₆) δ ppm: 12.17 (s, 1H), 11.69 (s, 1H), 8.65-8.50 (m, 2H), 8.04 (s, 1H), 7.85-7.75 (m, 1H), 7.55-7.42 (m, 4H), 7.42-7.38 (m, 1H), 7.32-7.25 (m, 4H), 7.20-7.14 (m, 2H), 6.90 (s, 1H), 6.50-6.33 (m, 3H), 4.80 (d, J=7.8 Hz, 1H), 3.84 (d, J=8.1 Hz, 2H), 3.75-3.65 (m, 1H), 3.24-3.18 (m, 2H), 2.40-2.31 (m, 2H), 2.00-1.84 (m, 2H), 1.82-1.78 (m, 2H), 1.65-1.58 (m, 3H), 1.29-1.24 (m, 2H). MS (ESI, m/e) [M+1]⁺ 841.1.

Example A18: 3-((1H-pyrrolo[2,3-b]pyridin-5-yl)oxy)-4'-(2-(2-methoxyphenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

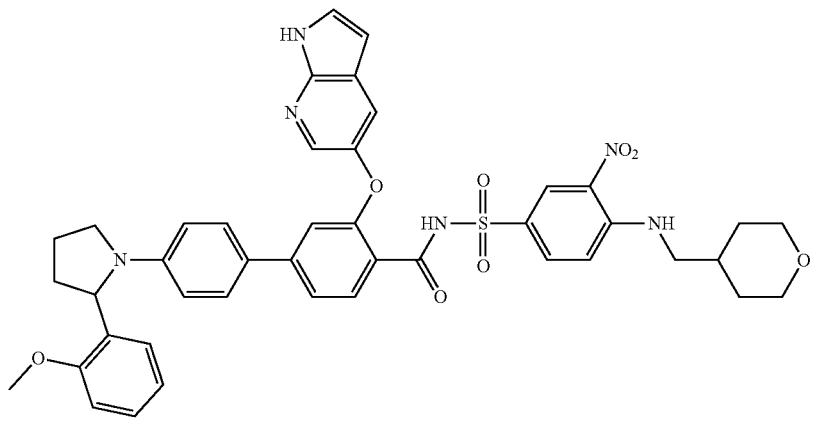 [SMILES: COc1ccccc1C1CCCN1c1ccc(-c2ccc(C(=O)NS(=O)(=O)c3ccc(NCC4CCOCC4)c([N+](=O)[O-])c3)c(Oc3cnc4[nH]ccc4c3)c2)cc1]

The desired compound was synthesized starting from 2-(2-methoxyphenyl)pyrrolidine and 1-bromo-4-iodobenzene following the procedures similar to those in Example A1. ¹H NMR (400 MHz, DMSO-d₆) δ ppm: 12.16 (s, 1H), 11.71 (s, 1H), 8.65-8.60 (m, 1H), 8.57 (d, J=2.6 Hz, 1H), 8.05 (d, J=2.6 Hz, 1H), 7.85-7.80 (m, 1H), 7.53 (d, J=8.2 Hz, 1H), 7.49-7.52 (m, 1H), 7.35-7.31 (m, 1H), 7.29 (d, J=8.7 Hz, 2H), 7.21-7.16 (m, 1H), 7.13 (d, J=9.2 Hz, 1H), 7.01 (d, J=8.1 Hz, 1H), 6.89 (d, J=1.3 Hz, 1H), 6.81-6.74 (m, 2H), 6.40-6.37 (m, 1H), 6.35 (d, J=8.6 Hz, 2H), 4.94 (d, J=8.0 Hz, 1H), 3.88-3.80 (m, 5H), 3.66 (t, J=7.9 Hz, 1H), 3.34-3.21 (m, 6H), 2.35-2.25 (m, 1H), 2.00-1.71 (s, 4H), 1.60 (d, J=12.1 Hz, 2H), 1.28-1.21 (m, 2H). MS (ESI, m/e) [M+1]⁺ 803.1

Example A19: 3-((1H-pyrrolo[2,3-b]pyridin-5-yl)oxy)-4'-(2-(4-methoxyphenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

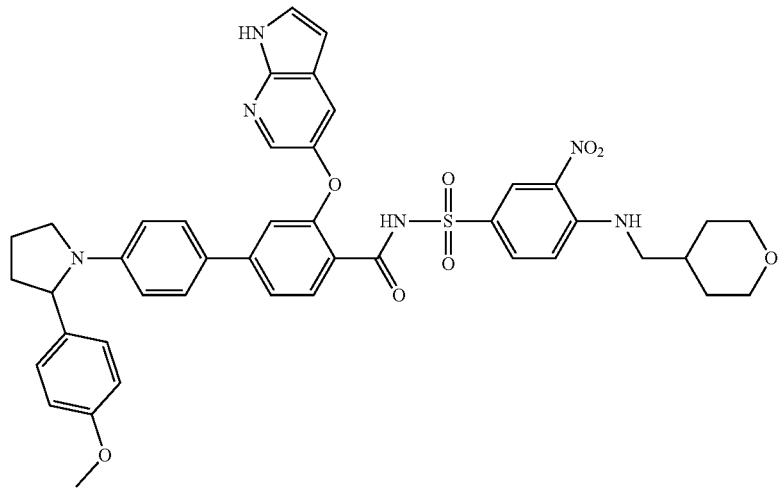 [SMILES: COc1ccc(C2CCCN2c2ccc(-c3ccc(C(=O)NS(=O)(=O)c4ccc(NCC5CCOCC5)c([N+](=O)[O-])c4)c(Oc4cnc5[nH]ccc5c4)c3)cc2)cc1]

The desired compound was synthesized starting from 2(4-methoxyphenyl)pyrrolidine and 1-bromo-4-iodobenzene following the procedures similar to those in Example A1. ¹H NMR (400 MHz, DMSO-d₆) δ ppm: 12.16 (s, 1H), 11.71 (s, 1H), 8.62 (t, J=5.5 Hz, 1H), 8.56 (d, J=1.8 Hz, 1H), 8.05 (d, J=2.4 Hz, 1H), 7.82 (d, J=7.8 Hz, 1H), 7.62-7.57 (m, 1H), 7.56-7.48 (m, 2H), 7.34 (d, J=8.1 Hz, 1H), 7.28 (d, J=8.6 Hz, 2H), 7.13 (d, J=9.2 Hz, 1H), 7.06 (d, J=8.5 Hz, 2H), 6.89 (s, 1H), 6.82 (d, J=8.5 Hz, 2H), 6.42 (d, J=8.0 Hz, 2H), 6.36-6.40 (m, 1H), 4.72 (d, J=8.0 Hz, 1H), 3.84 (dd, J=11.2, 3.0 Hz, 2H), 3.74-3.61 (m, 4H), 3.34-3.20 (m, 6H), 2.37-2.27 (m, 2H), 1.98-1.79 (m, 3H), 1.79-1.70 (m, 1H), 1.60 (d, J=12.0 Hz, 2H), 1.27-1.19 (m, 2H). MS (ESI, m/e) [M+1]⁺ 803.2

Example A20: 3-((1H-pyrrolo[2,3-b]pyridin-5-yl)oxy)-4'-(3,3-dimethyl-2-oxo-5-phenylpyrrolidin-1-yl)-N-((3-nitro-4-(((tetrahydro-2H-pyran-4-yl)methyl)amino)phenyl)sulfonyl)-[1,1'-biphenyl]-4-carboxamide

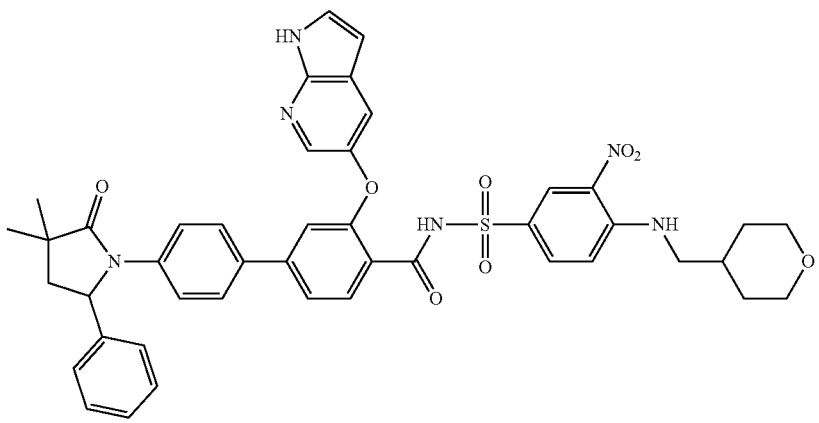 [SMILES: CC1(C)CC(c2ccccc2)N(c2ccc(-c3ccc(C(=O)NS(=O)(=O)c4ccc(NCC5CCOCC5)c([N+](=O)[O-])c4)c(Oc4cnc5[nH]ccc5c4)c3)cc2)C1=O]

Step 1: 2,2-dimethyl-4-oxo-4-phenylbutanoic acid

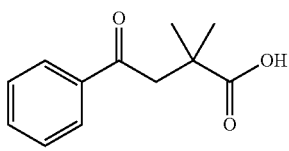

To a solution of 3,3-dimethyldihydrofuran-2,5-dione (15.3 g, 120 mmol) and AlCl$_3$ (31.92 g, 240 mmol) in DCM (200 mL) was added benzene (14.04 g, 180 mmol) dropwise with ice-water bath. It was warmed up to room temperature slowly and stirred overnight. The reaction mixture was poured into ice and diluted with DCM (400 mL) and conc. HCl acid (50 mL) was added and stirred until no precipitate. The organic layer was dried over anhydrous Na$_2$SO$_4$, filtered and concentrated. The residue was slurried with MTBE and PE to give the desired product as a white solid (22.52 g, 99%). $^1$H NMR (400 MHz, CDCl$_3$) δ ppm: 7.95 (d, J=7.7 Hz, 2H), 7.56 (t, J=7.7 Hz, 1H), 7.46 (t, J=7.7 Hz, 2H), 3.31 (s, 2H), 1.36 (s, 6H). MS (ESI, m/e) [M+1]$^+$ 205.1.

Step 2: N-(4-bromophenyl)-4-hydroxy-2,2-dimethyl-4-phenylbut-3-enamide

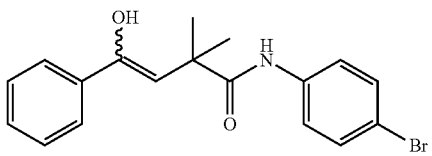 [SMILES: CC(C)(C=C(O)c1ccccc1)C(=O)Nc1ccc(Br)cc1]

A solution of 2,2-dimethyl-4-oxo-4-phenylbutanoic acid (2.06 g, 10 mmol), 4-bromoaniline (1.806 g, 10.5 mmol), HAITI (3.8 g, 10 mmol) and Et$_3$N (1.5 g, 15 mmol), in DCM (50 mL) was stirred at room temperature overnight. After DCM was removed, the residue was purified by column flash in silica gel eluted with EA/PE=1/5 to give the crude product as a brown oil (1.88 g). MS (ESI, m/e) [M+1]$^+$ 360.0.

Step 3: 1-(4-bromophenyl)-3,3-dimethyl-5-phenyl-1,3-dihydro-2H-pyrrol-2-one

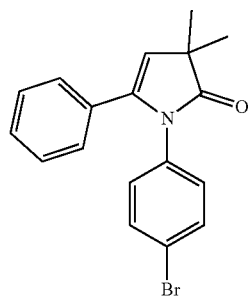 [SMILES: CC1(C)C=C(c2ccccc2)N(c2ccc(Br)cc2)C1=O]

A solution of N-(4-bromophenyl)-4-hydroxy-2,2-dimethyl-4-phenylbut-3-enamide (1.88 g, 5.22 mmol) and p-TsOH (50 mg, 0.26 mmol) in toluene (50 mL) was refluxed overnight. It was cooled to room temperature and toluene was removed. The residue was purified by flash column on silica gel eluted with EA/PE=1/17 to give the desired product as a yellow oil (1.24 g, 69%). $^1$H NMR (400 MHz, DMSO-d$_6$) δ 7.52 (d, J=8.0 Hz, 2H), 7.29 (s, 3H), 7.13 (s, 2H), 6.98 (d, J=8.0 Hz, 2H), 5.75 (s, 2H), 1.28 (s, 6H). MS (ESI, m/e) [M+1]$^+$342.0.

Step 4: tert-butyl 3-((1H-pyrrolo[2,3-b]pyridin-5-yl)oxy)-4'-(3,3-dimethyl-2-oxo-5-phenyl-2,3-dihydro-1H-pyrrol-1-yl)-[1,1'-biphenyl]-4-carboxylate

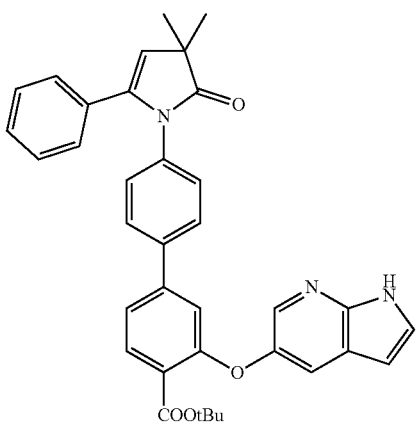

1-(4-bromophenyl)-3,3-dimethyl-5-phenyl-1,3-dihydro-2H-pyrrol-2-one (200 mg, 0.59 mmol), tert-butyl 2-((1H-pyrrolo[2,3-b]pyridin-5-yl)oxy)-4-(4,4,5,5-tetramethyl-1,3,2-dioxaborolan-2-yl)benzoate (256 mg, 0.59 mmol) and Pd(dppf)Cl$_2$ (43 mg, 0.059 mmol) in dioxane (20 mL) and sat. k$_2$CO$_3$ (2 mL) solution were stirred at 95° C. under N$_2$ overnight. After cooled to room temperature, the solvents were removed in vacuo. The residue was purified by pre-TLC (eluent: EA/PE=1/1) to give the desired product as a white solid (150 mg, 44%). $^1$H NMR (400 MHz, DMSO-d$_6$) δ 11.65 (s, 1H), 8.06 (d, J=2.3 Hz, 1H), 7.81 (d, J=8.4 Hz, 1H), 7.61 (d, J=8.4 Hz, 2H), 7.56 (d, J=8.4 Hz, 1H), 7.48 (s, 2H), 7.31-7.24 (m, 4H), 7.11 (d, J=5.7 Hz, 4H), 6.38 (s, 1H), 5.74 (s, 1H), 1.37 (s, 9H), 1.28 (s, 6H). MS (ESI, m/e) [M+1]$^+$ 572.2.

Step 5: tert-butyl 3-((1H-pyrrolo[2,3-b]pyridin-5-yl)oxy)-4'-(3,3-dimethyl-2-oxo-5-phenylpyrrolidin-1-yl)-[1,1'-biphenyl]-4-carboxylate

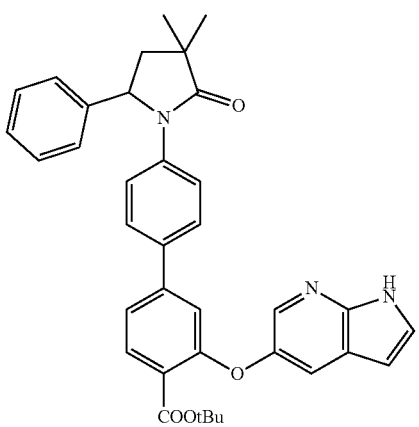

A mixture of tert-butyl 3-((1H-pyrrolo[2,3-b]pyridin-5-yl)oxy)-4'-(3,3-dimethyl-2-oxo-5-phenyl-2,3-dihydro-1H-pyrrol-1-yl)-[1,1'-biphenyl]-4-carboxylate (140 mg, 0.24 mmol) and Pd/C (30 mg) in MeOH (20 mL) was stirred at room temperature under a balloon of H₂ atmosphere. It was filtered, and the filtrate was concentrated to give the desired product was a white solid (134 mg, 97%). ¹H NMR (400 MHz, DMSO-d₆) δ ppm: 11.63 (s, 1H), 8.03 (d, J=2.2 Hz, 1H), 7.77 (d, J=8.1 Hz, 1H), 7.62-7.39 (m, 6H), 7.33-7.11 (m, 6H), 6.37 (s, 1H), 5.47 (t, J=7.6 Hz, 1H), 1.97-2.03 (m, 1H), 1.72-1.77 (m, 1H), 1.37 (s, 9H), 1.20 td, J=10.1 Hz, 6H). MS (ESI, m/e) [M+1]⁺ 574.2.

Step 6: 3-((1H-pyrrolo[2,3-b]pyridin-5-yl)oxy)-4'-(3,3-dimethyl-2-oxo-5-phenylpyrrolidin-1-yl)-[1,1'-biphenyl]-4-carboxylic acid

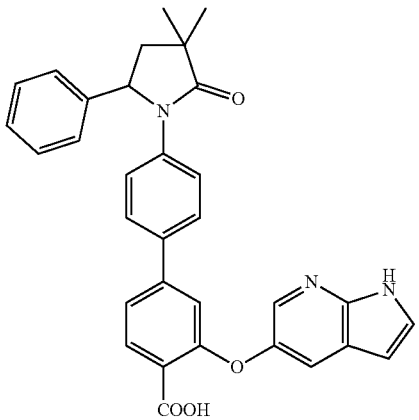 [SMILES: CC1(C)CC(c2ccccc2)N(c2ccc(-c3ccc(C(=O)O)c(Oc4cnc5[nH]ccc5c4)c3)cc2)C1=O]

A solution of tert-butyl 3-((1H-pyrrolo[2,3-b]pyridin-5-yl)oxy)-4'-(3,3-dimethyl-2-oxo-5-phenylpyrrolidin-1-yl)-[1,1'-biphenyl]-4-carboxylate (134 mg, 0.23 mmol) in DCM (6 mL) and TFA (4 mL) was stirred at room temperature for 4 hours. The solvents were removed to give the desired product as a white solid (125 mg). MS (ESI, m/e) [M+1]⁺ 518.1.

Then the desired compound in Example A20 was synthesized with 3-((1H-pyrrolo[2,3-b]pyridin-5-yl)oxy)-4'-(3,3-dimethyl-2-oxo-5-phenylpyrrolidin-1-yl)-[1,1'-biphenyl]-4-carboxylic acid and 3-nitro-4-(((tetrahydro-2H-pyran-4-yl)methyl)amino)benzenesulfonamide following the next procedures similar to those in Example A1. ¹H NMR (400 MHz, DMSO-d₆) δ ppm: 12.35 (s, 1H), 11.65 (s, 1H), 8.51 (s, 2H), 8.00 (s, 1H), 7.76 (s, 1H), 7.63-7.33 (m, 7H), 7.29-7.11 (m, 5H), 7.11-6.97 (m, 2H), 6.35 (s, 1H), 5.44 (t, J=7.7 Hz, 1H), 3.84 (d, J=8.5 Hz, 2H), 3.25-3.18 (m, 4H), 2.05-1.93 (m, 1H), 1.86 (s, 1H), 1.71-1.76 (m, 1H), 1.58-1.64 (m, 3H), 1.25-1.28 (m, 2H), 1.20 (s, 3H), 1.17 (s, 3H). MS (ESI, m/e) [M+1]⁺ 815.1.

Example A21: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-oxo-4-phenylazetidin-1-yl)-[1,1'-biphenyl]-4-carboxamide

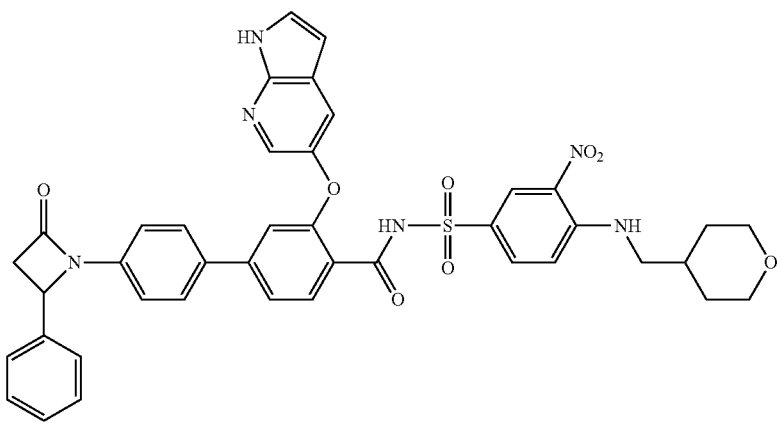 [SMILES: O=C(NS(=O)(=O)c1ccc(NCC2CCOCC2)c([N+](=O)[O-])c1)c1ccc(-c2ccc(N3C(=O)CC3c3ccccc3)cc2)cc1Oc1cnc2[nH]ccc2c1]

Step 1: 1-(4-bromophenyl)-4-phenylazetidin-2-one

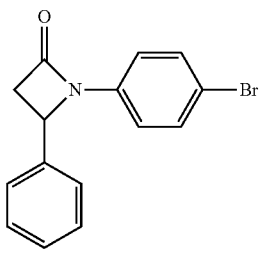 [SMILES: O=C1CC(c2ccccc2)N1c1ccc(Br)cc1]

A mixture of 4-phenylazetidin-2-one (500 mg, 3.40 mmol), (4-bromophenyl)boronic acid (2.05 g, 10.19 mmol), TFA (1.03 g, 10.19 mmol, 1.42 mL), 4 Å molecular sieve (300 mg) and Cu(OAC)$_2$ (617.07 mg, 3.40 mmol) in DCM (60 mL) was degassed and purged with O$_2$ for 3 times, and then the mixture was stirred at 40° C. for 16 hours under O$_2$ atmosphere. After cooled to room temperature, the reaction mixture was filtered and concentrated under reduced pressure to give a residue. The residue was purified by column chromatography (eluent: PE/EA=60:1 to 10:1). 1-(4-bromophenyl)-4-phenylazetidin-2-one (800 mg, 75.59% yield) was obtained as an off-white solid. $^1$H NMR (400 MHz, CDCl$_3$) δ ppm: 7.43-7.29 (m, 7H), 7.20-7.10 (m, 2H), 4.99 (dd, J=2.6, 5.7 Hz, 1H), 3.57 (dd, J=5.7, 15.2 Hz, 1H), 2.96 (dd, J=2.6, 15.2 Hz, 1H). MS (ESI, m/e) [M+1]$^+$ 302.0.

The desired compound was then synthesized with 1-(4-bromophenyl)-4-phenylazetidin-2-one and tert-butyl 2-((1H-pyrrolo[2,3-b]pyridin-5-yl)oxy)-4-(4,4,5,5-tetramethyl-1,3,2-dioxaborolan-2-yl)benzoate following the next procedures similar to those in Example A20. $^1$H NMR (DMSO-d$_6$) δ ppm: 12.33 (s, 1H), 11.69 (s, 1H), 8.62-8.56 (m, 2H), 8.03 (d, J=2.4 Hz, 1H), 7.83-7.80 (m, 1H), 7.62-7.57 (m, 2H), 7.50-7.48 (m, 3H), 7.41-7.28 (m, 6H), 7.23 (d, J=8.8 Hz, 2H), 7.11 (d, J=9.2 Hz, 1H), 7.01 (s, 1H), 6.37 (s, 1H), 5.22-5.19 (m, 1H), 3.86-3.82 (m, 2H), 3.63-3.58 (m, 1H), 3.28-3.22 (m, 4H), 2.91 (dd, J=2.4, 15.2 Hz, 1H), 1.93-1.90 (m, 1H), 1.60 (d, J=12.4 Hz, 2H), 1.29-1.20 (m, 2H). MS (ESI) m/e [M+1]$^+$: 773.1

Example A22: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(1-phenylpyrrolidin-2-yl)-[1,1'-biphenyl]-4-carboxamide

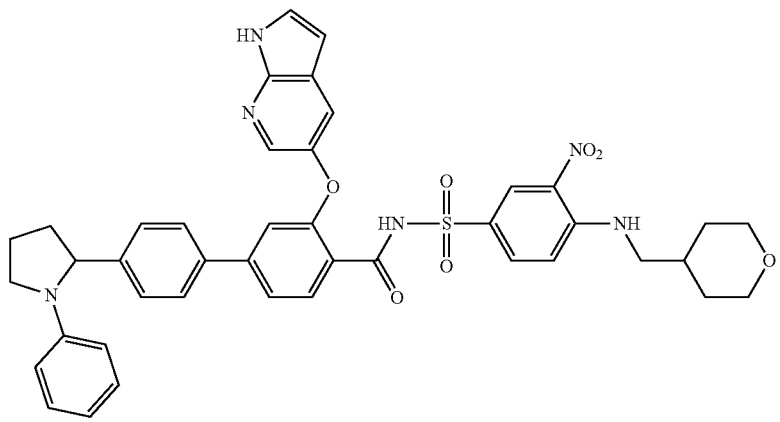 [SMILES: O=C(NS(=O)(=O)c1ccc(NCC2CCOCC2)c([N+](=O)[O-])c1)c1ccc(-c2ccc(C3CCCN3c3ccccc3)cc2)cc1Oc1cnc2[nH]ccc2c1]

Step 1: 2-(4-chlorophenyl)-1-phenylpyrrolidine

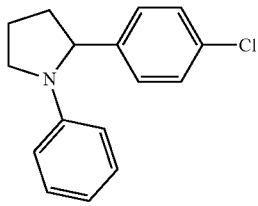 [SMILES: Clc1ccc(C2CCCN2c2ccccc2)cc1]

The mixture of 2-(4-chlorophenyl (pyrrolidine (545 mg, 3 mmol), iodobenzene (920 mg, 4.5 mmol), 2,2'-bis(diphenylphosphanyl)-1,1'-binaphthalene (374 mg, 0.60 mmol), tris(dibenzylideneacetone)dipalladium (275 mg, 0.3 mmol), t-BuOK (673 mg, 6 mmol) in toluene (50 mL) was heated to 90° C. overnight. The reaction was concentrated in vacuo and purified by chromatography column on silica (eluent: EA/PE=1/5) to give the product (582 mg, 75.3%) as a colorless oil. $^1$H NMR (400 MHz, DMSO-$d_6$) δ ppm: 7.36 (d, J=8.0 Hz, 2H), 7.24 (d, J=8.0 Hz, 2H), 7.07 (t, J=8.0 Hz, 2H), 6.54 (t, J=8.0 Hz, 1H), 6.41 (d, J=8.0 Hz, 2H), 4.75 (d, J=8.0 Hz, 1H), 3.70-3.65 (m, 1H), 3.36-3.29 (m, 1H), 2.39-2.33 (m, 1H), 1.96-1.88 (m, 2H), 1.79-1.75 (m, 1H). MS (ESI, m/e) [M+1]$^+$ 258.0.

Step 2: tert-butyl 3-((1H-pyrrolo[2,3-b]pyridin-5-yl)oxy)-4'-(1-phenylpyrrolidin-2-yl)-[1,1'-biphenyl]-4-carboxylate

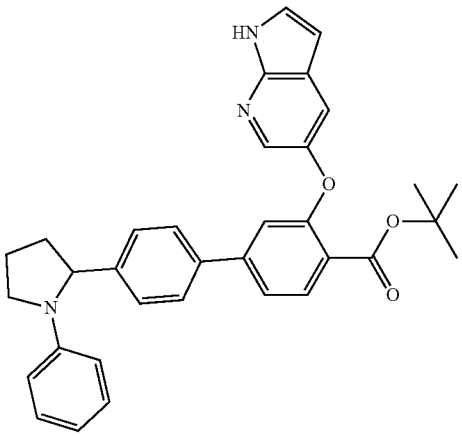 [SMILES: CC(C)(C)OC(=O)c1ccc(-c2ccc(C3CCCN3c3ccccc3)cc2)cc1Oc1cnc2[nH]ccc2c1]

The mixture of 2-(4-chlorophenyl)-1-phenylpyrrolidine (515 mg, 2 mmol), tert-butyl 2-((1H-pyrrolo[2,3-b]pyridin-5-yl)oxy)-4-(4,4,5,5-tetramethyl-1,3,2-dioxaborolan-2-yl)benzoate (959 mg, 2.2 mmol), 1,1'-bis(diphenylphosphino)ferrocene-palladium(II)dichloride dichloromethane complex (146 mg, 0.2 mmol), K$_2$CO$_3$ (691 mg, 5.0 mmol) in a solution of 1,4-dioxane (50 mL) and water (10 mL) was heated to 90° C. and stirred overnight. The reaction was concentrated in vacuo and purified by chromatography column on silica (eluent: EA/PE=1/1) to give the crude product (126 mg, 11.86%) as a brown oil. MS (ESI, m/e) [M+1]$^+$ 532.1.

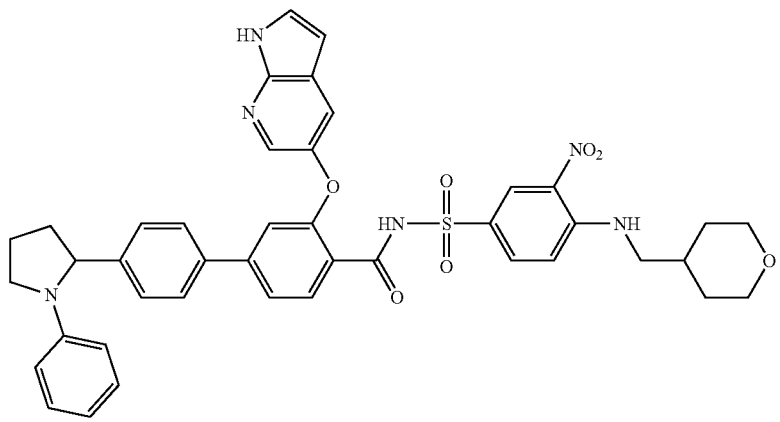 [SMILES: O=C(NS(=O)(=O)c1ccc(NCC2CCOCC2)c([N+](=O)[O-])c1)c1ccc(-c2ccc(C3CCCN3c3ccccc3)cc2)cc1Oc1cnc2[nH]ccc2c1]

The desired compound was then synthesized with tert-butyl 3-((1H-pyrrolo[2,3-b]pyridin-5-yl)oxy)-4'-(1-phenylpyrrolidin-2-yl)-[1,1'-biphenyl]-4-carboxylate following the procedures similar to those in Example A1. $^1$H NMR (400 MHz, DMSO-$d_6$) δ ppm: 12.37 (br, 1H), 11.73 (br, 1H), 8.64-8.61 (m, 1H), 8.58 (d, J=4.0 Hz, 1H), 8.07 (d, J=4.0 Hz, 1H), 7.86 (d, J=12.0 Hz, 1H), 7.63-7.59 (m, 2H), 7.52 (t, J=4.0 Hz, 1H), 7.46-7.42 (m, 3H), 7.24 (d, J=8.0 Hz, 2H), 7.15 (d, J=8.0 Hz, 1H), 7.04 (t, J=8.0 Hz, 2H), 6.99 (s, 1H), 6.51 (t, J=8.0 Hz, 1H), 6.39-6.37 (m, 4H), 4.74 (d, J=8.0 Hz, 1H), 3.85-3.83 (m, 2H), 3.65 (m, 1H), 3.28-3.23 (m, 4H), 2.35 (m, 1H), 1.93-1.76 (m, 4H), 1.61-1.58 (m, 2H), 1.28-1.23 (m, 3H). MS (ESI, m/e) [M+1]$^+$ 773.1.

Example A23: 3-((1H-pyrrolo[2,3-b]pyridin-5-yl)oxy)-4'-(1-benzylpyrrolidin-2-yl)-N-((3-nitro-4-(((tetrahydro-2H-pyran-4-yl)methyl)amino)phenyl)sulfonyl)-[1,1'-biphenyl]-4-carboxamide

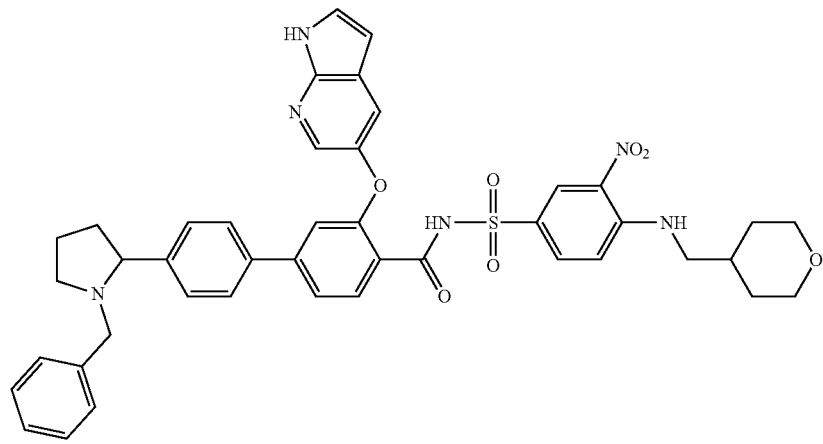 [SMILES: O=C(NS(=O)(=O)c1ccc(NCC2CCOCC2)c([N+](=O)[O-])c1)c1ccc(-c2ccc(C3CCCN3Cc3ccccc3)cc2)cc1Oc1cnc2[nH]ccc2c1]

Step 1: 1-benzyl-2-(4-chlorophenyl)pyrrolidine

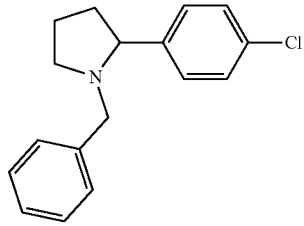 [SMILES: Clc1ccc(C2CCCN2Cc2ccccc2)cc1]

The mixture of 2-(4-chlorophenyl)pyrrolidine (546 mg, 3 mmol), (bromomethyl)benzene (770 mg, 4.5 mmol) and triethylamine (909 mg, 9 mmol) in THF (100 mL) was stirred at room temperature for overnight. The mixture was concentrated in vacuo and the residue was diluted with DCM. The organic layer was washed with brine (100 mL), dried over Na$_2$SO$_4$ and evaporated in vacuo, then the residue was purified by chromatography column on silica (eluent: PE/EA=2/1 to 1/1) to afford a crude product (1.2 g), as a brown oil. MS (ESI, m/e) [M+1]$^+$ 272.1.

Step 2: tert-butyl 3-((1H-pyrrolo[2,3-b]pyridin-5-yl)oxy)-4'-(1-benzylpyrrolidin-2-yl)-[1,1'-biphenyl]-4-carboxylate

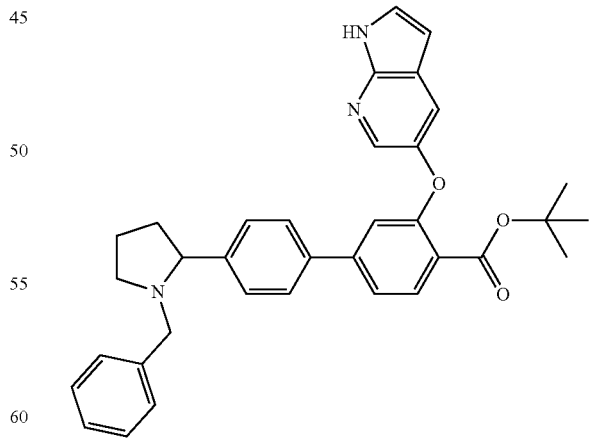

The mixture of 1-benzyl-2-(4-chlorophenyl)pyrrolidine (1.2 g, 4.4 mmol), tert-butyl 2-((1H-pyrrolo[2,3-b]pyridin-5-yl)oxy)-4-(4,4,5,5-tetramethyl-1,3,2-dioxaborolan-2-yl)benzoate (2.1 g, 4.8 mmol), 1,1'-Bis(diphenylphosphino)ferrocene-palladium(II)dichloride dichloromethane complex (322 mg, 0.44 mmol), K$_2$CO$_3$ (1.52 g, 11 mmol) in a solution of 1,4-dioxane (100 mL) and water (10 mL) was heated to 90° C. for overnight. The reaction was concentrated in vacuo and purified by chromatography column on silica (eluent: EA/PE=1/1) to give the crude product (512 mg, 21.35%) as a red oil. MS (ESI, m/e) [M+1]$^+$ 546.2.

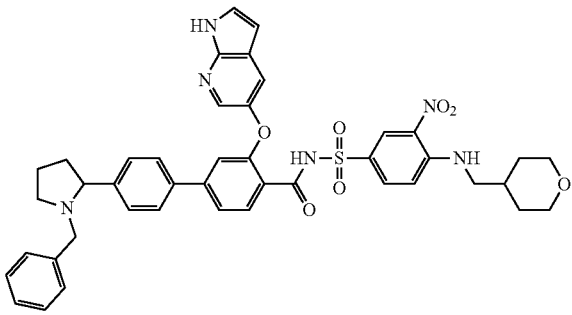 [SMILES: O=C(NS(=O)(=O)c1ccc(NCC2CCOCC2)c([N+](=O)[O-])c1)c1ccc(-c2ccc(C3CCCN3Cc3ccccc3)cc2)cc1Oc1cnc2[nH]ccc2c1]

The desired compound was then synthesized with tert-butyl 3-((1H-pyrrolo[2,3-b]pyridin-5-yl)oxy)-4'(1-benzylpyrrolidin-2-yl)-[1,1'-biphenyl]-4-carboxylate following the procedures similar to those in Example A1. $^1$H NMR (400 MHz, DMSO-d$_6$) δ ppm: 12.39 (br, 1H), 11.71 (br, 1H), 8.55 (m, 2H), 8.07 (d, J=4.0 Hz, 1H), 7.83 (d, J=8.0 Hz, 1H), 7.64-7.60 (m, 2H), 7.50-7.45 (m, 6H), 7.29 (m, 5H), 7.10 (d, J=8.0 Hz, 1H), 7.03 (s, 1H), 6.39 (m, 1H), 4.51-4.14 (m, 1H), 3.85-3.83 (m, 2H), 3.34-3.23 (m, 4H), 2.99 (m, 2H), 2.18 (m, 2H), 1.87 (m, 4H), 1.61-1.58 (m, 2H), 1.30-1.21 (m, 3H). MS (ESI, m/e) [M+1]$^+$ 787.2.

Example A24: 3-((1H-pyrrolo[2,3-b]pyridin-5-yl)oxy)-4'-(2-(2-ethylphenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

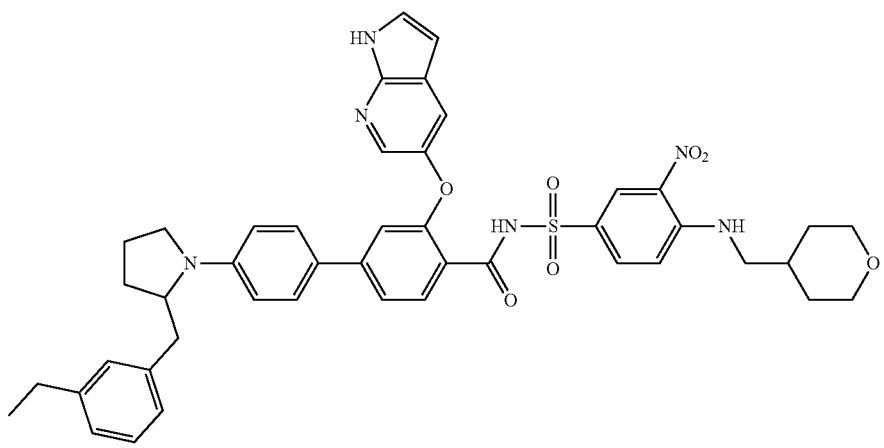 [SMILES: CCc1cccc(CC2CCCN2c2ccc(-c3ccc(C(=O)NS(=O)(=O)c4ccc(NCC5CCOCC5)c([N+](=O)[O-])c4)c(Oc4cnc5[nH]ccc5c4)c3)cc2)c1]

The desired compound was synthesized starting from 2-(2-ethylphenyl)pyrrolidine and 1-bromo-4-iodobenzene following the procedures similar to those in Example A1. $^1$H NMR (400 MHz, DMSO-d$_6$) δ 12.15 (s, 1H), 11.69 (s, 1H), 8.60 (s, 1H), 8.56 (s, 1H), 8.04 (d, J=2.0 Hz, 1H), 7.82 (d, J=8.7 Hz, 1H), 7.50-7.58 (m, 3H), 7.27-7.34 (m, 3H), 7.22 (d, J=7.4 Hz, 1H), 7.11-7.15 (m, 2H), 7.01 (t, J=7.4 Hz, 1H), 6.89 (s, 1H), 6.85 (d, J=7.4 Hz, 1H), 6.41-6.32 (m, 3H), 4.92 (d, J=8.0 Hz, 1H), 3.84 (d, J=7.9 Hz, 2H), 3.70 (t, J=7.9 Hz, 1H), 3.37 (d, J=7.9 Hz, 1H), 3.31-3.22 (m, 4H), 2.86-2.67 (m, 2H), 2.46-2.38 (m, 1H), 2.03-1.83 (m, 4H), 1.71 (s, 1H), 1.60 (d, J=12.2 Hz, 2H), 1.27-1.23 (m, 4H). MS (ESI, m/e) [M+1]$^+$ 801.2.

Example A25: 3-((1H-pyrrolo[2,3-b]pyridin-5-yl)oxy)-4'-(2-(2-cyclopentylphenyl)pyrrolidin-1-yl)-N-((3-nitro-4-((((tetrahydro-2H-pyran-4-yl)methyl)amino)phenyl)sulfonyl)-[1,1'-biphenyl]-4-carboxamide

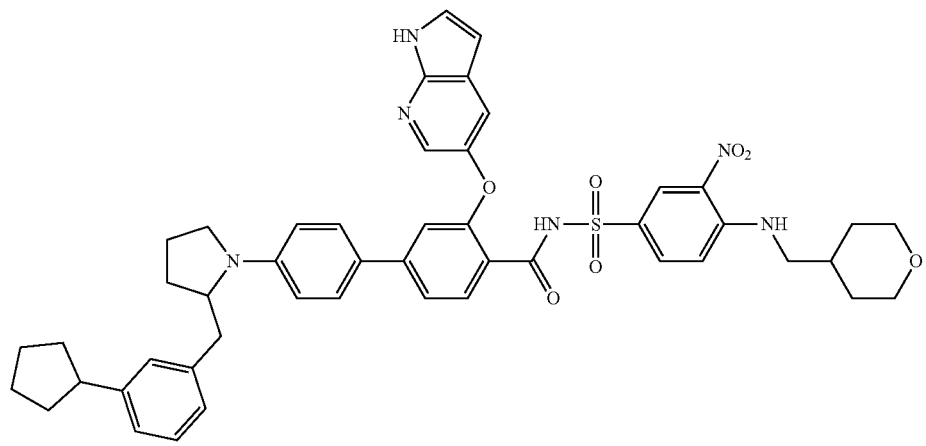 [SMILES: O=C(NS(=O)(=O)c1ccc(NCC2CCOCC2)c([N+](=O)[O-])c1)c1ccc(-c2ccc(N3CCCC3Cc3cccc(C4CCCC4)c3)cc2)cc1Oc1cnc2[nH]ccc2c1]

The desired compound was synthesized starting from 2-(2-cyclopentylphenyl)pyrrolidine and 1-bromo-4-iodobenzene following the procedures similar to those in Example A1. $^1$H NMR (400 MHz, DMSO-$d_6$) δ ppm: 12.16 (s, 1H), 11.70 (s, 1H), 8.61 (s, 1H), 8.56 (s, 1H), 8.05 (s, 1H), 7.82 (d, J=8.0 Hz, 1H), 7.58 (s, 1H), 7.53-7.51 (m, 2H), 7.34-7.31 (m, 3H), 7.29 (s, 1H), 7.17-7.11 (m, 2H), 6.98 (t, J=7.4 Hz, 1H), 6.91 (s, 1H), 6.82 (d, J=8.0 Hz, 1H), 6.37 (s, 2H), 6.35 (s, 1H), 5.02 (d, J=8.0 Hz, 1H), 3.84 (d, J=8.8 Hz, 2H), 3.72-3.68 (m, 1H), 3.25-3.23 (m, 2H), 2.45-2.42 (m, 1H), 2.19-2.13 (m, 1H), 2.01-1.81 (m, 8H), 1.72-1.65 (m, 4H), 1.62-1.56 (m, 3H), 1.29-1.20 (m, 4H). MS (ESI, m/e) [M+1]$^+$841.2.

Example A26: 3-((1H-pyrrolo[2,3-b]pyridin-5-yl)oxy)-4'-(2-(2-fluorophenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

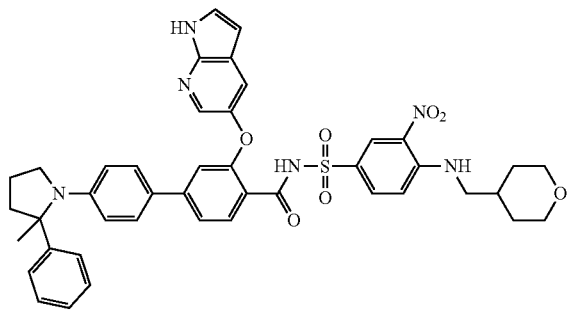 [SMILES: CC1(c2ccccc2)CCCN1c1ccc(-c2ccc(C(=O)NS(=O)(=O)c3ccc(NCC4CCOCC4)c([N+](=O)[O-])c3)c(Oc3cnc4[nH]ccc4c3)c2)cc1]

The desired compound was synthesized starting from 2-(2-fluorophenyl)pyrrolidine and 1-bromo-4-iodobenzene following the procedures similar to those in Example A1. $^1$H NMR (400 MHz, DMSO-$d_6$) δ ppm: 12.17 (s, 1H), 11.67 (s, 1H), 8.53 (s, 2H), 8.03 (s, 1H), 7.79 (d, J=8.0 Hz, 1H), 7.54 (d, J=7.8 Hz, 2H), 7.49 (s, 1H), 7.32 (d, J=7.8 Hz, 3H), 7.25-7.15 (m, 2H), 7.05 (t, J=7.2 Hz, 2H), 6.97 (t, J=12 Hz, 1H), 6.90 (s, 1H), 6.42 (d, J=8.0 Hz, 2H), 6.37 (s, 1H), 4.97 (d, J=8.0 Hz, 1H), 3.84 (d, J=8.8 Hz, 2H), 3.70-3.65 (m, 1H), 3.27 (d, J=8.0 Hz, 3H), 2.42-2.35 (m, 1H), 1.99-1.85 (m, 4H), 1.62-1.58 (m, 2H), 1.26-1.23 (m, 4H). MS (ESI, m/e) [M+1]$^+$ 791.1.

Example A27: 3-((1H-pyrrolo[2,3-b]pyridin-5-yl)oxy)-4'-(2-methyl-2-phenylpyrrolidin-1-yl)-N-((3-nitro-4-(((tetrahydro-2H-pyran-4-yl)methyl)amino)phenyl)sulfonyl)-[1,1'-biphenyl]-4-carboxamide

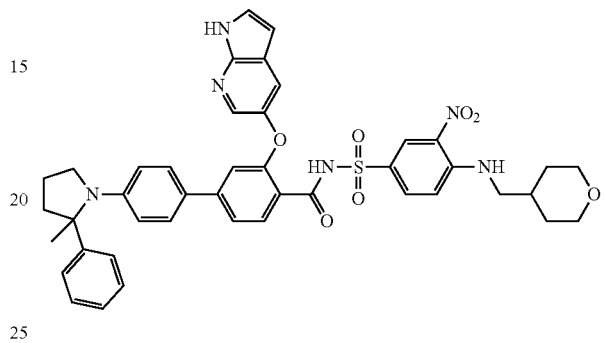

The desired compound was synthesized starting from 2-methyl-2-phenylpyrrolidine and 1-bromo-4-iodobenzene following the procedures similar to those in Example A1. $^1$H NMR (400 MHz, DMSO-$d_6$) δ ppm: 12.15 (s, 1H), 11.71 (s, 1H), 8.61 (t, J=6.0 Hz, 1H), 8.586-8.525 (m, 1H), 8.05 (d, J=2.3 Hz, 1H), 7.83 (d, J=8.6 Hz, 1H), 7.59 (d, J=2.0 Hz, 1H), 7.547-7.466 (m, 9H), 6.87 (s, 1H), 6.416-6.353 (m, 1H), 6.32 (d, J=8.8 Hz, 2H), 3.890-3.794 (m, 2H), 3.657-3.516 (m, 2H), 3.312-3.191 (m, 4H), 2.180-2.118 (m, 1H), 2.008-1.782 (m, 5H), 1.71 (s, 3H), 1.638-1.547 (m, 2H), 1.265-1.201 (m, 3H). MS (ESI, m/e) [M+1]$^+$787.1

Example A28: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(3-phenylpyrrolidin-1-yl)-[1,1'-biphenyl]-4-carboxamide

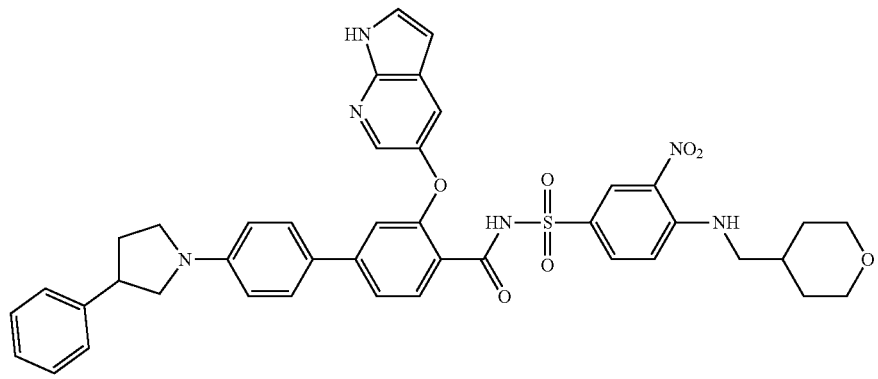 [SMILES: O=C(NS(=O)(=O)c1ccc(NCC2CCOCC2)c([N+](=O)[O-])c1)c1ccc(-c2ccc(N3CCC(c4ccccc4)C3)cc2)cc1Oc1cnc2[nH]ccc2c1]

The desired compound was synthesized starting from 3-phenylpyrrolidine and 1-bromo-4-iodobenzene following the procedures similar to those in Example A1. ¹H NMR (400 MHz, DMSO-d₆) δ ppm: 12.17 (s, 1H), 11.72 (s, 1H), 8.62 (s, 1H), 8.58 (d, J=2.2 Hz, 1H), 8.09 (d, J=2.5 Hz, 1H), 7.85 (d, J=9.3 Hz, 1H), 7.64 (d, J=2.3 Hz, 1H), 7.57 (d, J=8.1 Hz, 1H), 7.55-7.50 (m, 1H), 7.40 (1, J=8.3 Hz, 3H), 7.32 (d, J=4.4 Hz, 4H), 7.23 (dd, J=8.7, 4.5 Hz, 1H), 7.14 (d, J=9.4 Hz, 1H), 6.94 (s, 1H), 6.59 (d, J=8.9 Hz, 2H), 6.41 (s, 1H), 3.85 (d, J=7.3 Hz, 2H), 3.70 (t, J=8.6 Hz, 1H), 3.58-3.40 (m, 3H), 3.25-3.21 (m, 5H), 2.38-2.32 (m, 1H), 2.10-2.00 (m, 1H), 1.90-1.84 (m, 1H), 1.61 (d, J=11.3 Hz, 2H), 1.32-1.17 (m, 2H). MS (ESI, m/e) [M+1]⁺ 773.1

Example A29: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(pyridin-3-yl)pyrrolidin-1-yl)-[1,1'-biphenyl]-4-carboxamide

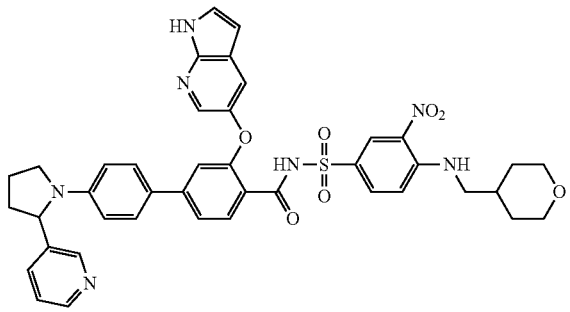 [SMILES: O=C(NS(=O)(=O)c1ccc(NCC2CCOCC2)c([N+](=O)[O-])c1)c1ccc(-c2ccc(N3CCCC3c3cccnc3)cc2)cc1Oc1cnc2[nH]ccc2c1]

The desired compound was synthesized starting from 3-(pyrrolidin-2-yl)pyridine and 1-bromo-4-iodobenzene following the procedures similar to those in Example A1. ¹H NMR (400 MHz, DMSO-d₆) δ ppm: 12.17 (s, 1H), 11.72 (s, 1H), 8.62 (s, 3H), 8.57 (m, 1H), 8.06 (m, 1H), 8.06-7.94 (m, 1H), 7.83 (d, J=9.2 Hz, 1H), 7.73-7.64 (m, 1H), 7.64-7.59 (m, 1H), 7.58-7.50 (m, 2H), 7.35-7.25 (m, 3H), 7.14 (d, J=9.2 Hz, 1H), 6.87 (s, 1H), 6.47 (d, J=8.5 Hz, 2H), 6.39 (s, 1H), 5.04-4.91 (m, 1H), 3.90-3.67 (m, 4H), 3.43-3.14 (m, 3H), 2.46-2.38 (m, 1H), 2.09-1.78 (m, 4H), 1.65-1.52 (m, 2H), 1.34-1.18 (m, 3H), MS (ESI) m/e [M+1]⁺ 774.2.

Example A30: 3-((1H-pyrrolo[2,3-b]pyridin-5-yl)oxy)-4'-(2-cyclohexylpyrrolidin-1-yl)-N-((3-nitro-4-(((tetrahydro-2H-pyran-4-yl)methyl)amino)phenyl)sulfonyl)-[1,1'-biphenyl]-4-carboxamide

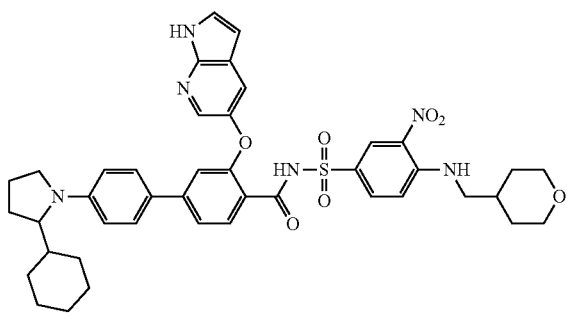 [SMILES: O=C(NS(=O)(=O)c1ccc(NCC2CCOCC2)c([N+](=O)[O-])c1)c1ccc(-c2ccc(N3CCCC3C3CCCCC3)cc2)cc1Oc1cnc2[nH]ccc2c1]

The desired compound was synthesized starting from 2-cyclohexylpyrrolidine and 1-bromo-4-iodobenzene following the procedures similar to those in Example A1. ¹H NMR (400 MHz, DMSO-d₆) δ ppm: 12.16 (s, 1H), 11.64 (s, 1H), 8.57-8.42 (m, 2H), 8.03 (s, 1H), 7.80-7.64 (m, 2H), 7.58 (d, J=8.0 Hz, 1H), 7.55-7.44 (m, 2H), 7.36-7.34 (m, 3H), 7.00 (s, 1H), 6.92 (s, 1H), 6.57 (d, J=8.0 Hz, 2H), 6.37 (s, 1H), 3.84 (d, J=8.5 Hz, 2H), 3.64-3.60 (m, 1H), 3.43-3.39 (m, 1H), 3.26-3.20 (m, 4H), 3.09-3.07 (m, 1H), 1.90-1.82 (m, 3H), 1.72-1.55 (m, 7H), 1.47-1.41 (m, 1H), 1.30-1.23 (m, 4H), 1.02-0.95 (m, 4H). MS (ESI, m/e) [M+1]⁺ 779.2.

Example A31: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(1-(o-tolyl)pyrrolidin-2-yl)-[1,1'-biphenyl]-4-carboxamide

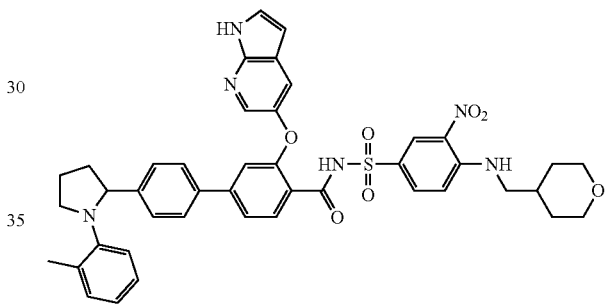

Step 1: 2-(4-bromophenyl)-1-(o-tolyl)pyrrolidine

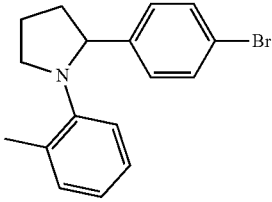 [SMILES: Cc1ccccc1N1CCCC1c1ccc(Br)cc1]

The mixture of 2-(4-bromophenyl)pyrrolidine (452 mg, 2 mmol), 1-iodo-2-methylbenzene (654 mg, 3 mmol), 2,2'-bis(diphenylphosphanyl)-1,1'-binaphthalene (249 mg, 0.4 mmol), Tris(dibenzylideneacetone)dipalladium (183 mg, 0.2 mmol), t-BuOK (449 mg, 4 mmol) in toluene (50 mL) was heated to 90° C. overnight. The reaction was concentrated in vacuo and purified by chromatography column on silica (eluent: EA/PE=1/5) to give the product (516 mg, 81.26%) as a colorless oil. ¹H NMR (400 MHz, CDCl₃) δ ppm: 7.33 (d, 8.0 Hz, 2H), 7.19 (d, J=8.0 Hz, 2H), 7.09 (d, J=4.0 Hz, 1H), 6.94 (t, J=8.0 Hz, 1H), 6.79 (t, J=8.0 Hz, 2H), 4.61 (dd, J=4.0, J=8.0 Hz, 1H), 3.88 (d, J=8.0 Hz, 1H), 2.93 (m, 1H), 2.39 (m, 1H), 2.33 (s, 3H), 2.05-1.76 (m, 3H). MS (ESI, m/e) [M+1]⁺ 258.0.

Step 2: tert-butyl 3-((1H-pyrrolo[2,3-b]pyridin-5-yl)oxy)-4'-(1-(o-tolyl)pyrrolidin-2-yl)-[1,1'-biphenyl]-4-carboxylate

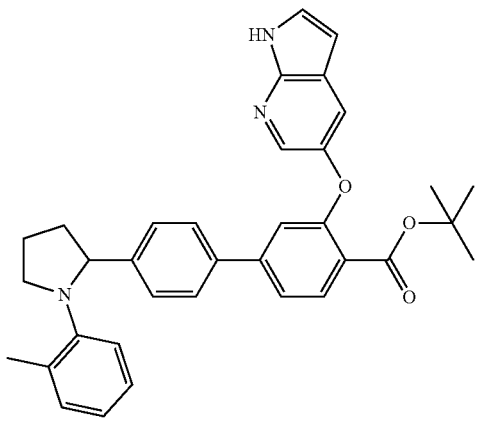 [SMILES: Cc1ccccc1N1CCCC1c1ccc(-c2ccc(C(=O)OC(C)(C)C)c(Oc3cnc4[nH]ccc4c3)c2)cc1]

The mixture of 2-(4-bromophenyl)-1-(o-tolyl)pyrrolidine (500 mg, 1.58 mmol), tert-butyl 2-((1H-pyrrolo[2,3-b]pyridin-5-yl)oxy)-4-(4,4,5,5-tetramethyl-1,3,2-dioxaborolan-2-yl)benzoate (760 mg, 1.74 mmol), 1,1'-Bis(diphenylphosphino)ferrocene-palladium(II)dichloride dichloromethane complex (117 mg, 0.16 mmol), K₂CO₃ (545 mg, 3.95 mmol) in a solution of 1,4-dioxane (50 mL) and water (2 mL) was heated to 90° C. for overnight. The reaction was concentrated in vacuo and purified by chromatography column on silica (eluent: EA/PE=1/1) to give the product (623 mg, 73.30%) as a grey solid. MS (ESI, m/e) [M+1]⁺ 546.1.

The desired compound was then synthesized with tert-butyl 3-((1H-pyrrolo[2,3-b]pyridin-5-yl)oxy)-4'-(1-(o-tolyl)pyrrolidin-2-yl)-[1,1'-biphenyl]-4-carboxylate following the procedures similar to those in Example A1. ¹H NMR (400 MHz, DMSO-d₆) δ ppm: 12.34 (br, 1H), 11.71 (br, 1H), 8.61 (1, J=4.0 Hz, 1H), 8.57 (d, J=4.0 Hz, 1H), 8.05 (d, J=4.0 Hz, 1H), 7.85 (d, J=8.0 Hz, 1H), 7.61 (d, J=4.0 Hz, 1H), 7.58 (d, J=8.0 Hz, 1H), 7.51 (t, J=8.0 Hz, 1H), 7.40-7.33 (m, 5H), 7.14 (d, J=8.0 Hz, 1H), 7.03 (d, J=8.0 Hz, 1H), 6.96 (s, 1H), 6.89-6.80 (m, 2H), 6.69 (t, J=8.0 Hz, 1H), 6.39-6.37 (m, 1H), 4.68 (m, 1H), 3.86-3.80 (m, 3H), 3.29-3.22 (m, 4H), 2.82 (m, 1H), 2.30 (m, 1H), 2.28 (s, 3H), 1.98-1.86 (m, 3H), 1.69-1.58 (m, 3H), 1.29 (m, 2H). MS (ESI, m/e) [M+1]⁺ 787.1.

Example A32: 3-((1H-pyrrolo[2,3-b]pyridin-5-yl)oxy)-4'-(2-(2-chloro-6-fluorophenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

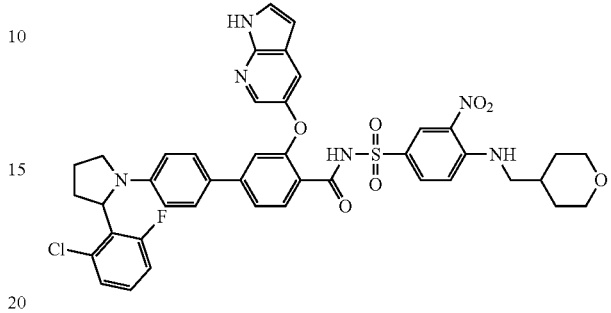

The desired compound was synthesized starting from 2-(2-chloro-6-fluorophenyl)pyrrolidine and 1-bromo-4-iodobenzene following the procedures similar to those in Example A1. ¹H NMR (400 MHz, DMSO-d6) δ ppm: 12.16 (s, 1H), 11.70 (s, 1H), 8.60 (d, J=5.6 Hz, 1H), 8.56 (d, J=2.0 Hz, 1H), 8.04 (d, J=2.4 Hz, 1H), 7.82 (d, J=9.2 Hz, 1H), 7.58 (d, J=2.5 Hz, 1H), 7.52 (s, 2H), 7.35-7.24 (m, 5H), 7.15-7.05 (m, 2H), 6.91 (s, 1H), 6.38 (s, 1H), 6.34 (d, J=8.7 Hz, 2H), 5.32 (t, J=4.8 Hz, 1H), 5.28-5.17 (m, 1H), 3.84 (d, J=11.7 Hz, 2H), 3.50-3.45 (m, 2H), 2.03-1.95 (m, 4H), 1.90-1.85 (m, 3H), 1.60 (d, J=12.8 Hz, 2H), 1.45 (s, 3H). MS (ESI, m/e) [M+1]⁺ 825.1.

Example A33: 3-((1H-pyrrolo[2,3-h]pyridin-5-yl)oxy)-3'-fluoro-N-((3-nitro-4-(((tetrahydro-2H-pyran-4-yl)methyl)amino)phenyl)sulfonyl)-4'-(2-phenylpyrrolidin-1-yl)-[1,1'-biphenyl]-4-carboxamide

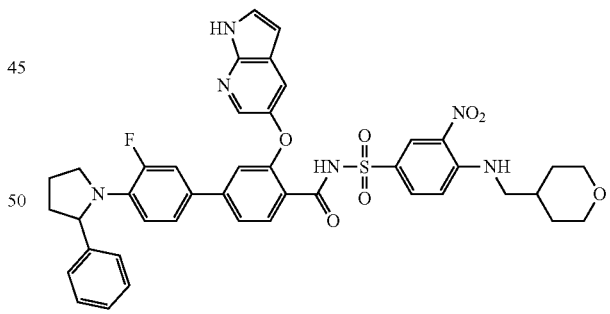

The desired compound was synthesized starting from 2-phenylpyrrolidine and 4-bromo-2-fluoro-1-iodobenzene following the procedures similar to those in Example A5. ¹H NMR (400 MHz, DMSO-d₆) δ ppm: 12.24 (s, 1H), 11.64 (s, 1H), 8.50-8.42 (m, 2H), 8.00 (s, 1H), 7.78-7.72 (m, 1H), 7.59-7.38 (m, 4H), 7.32-7.28 (m, 2H), 7.23-7.05 (m, 5H), 6.78 (s, 1H), 6.35 (s, 1H), 6.26 (d, J=8.7 Hz, 1H), 6.19 (m, 1H), 4.79 (d, J=6.8 Hz, 1H), 3.83 (d, J=8.3 Hz, 2H), 3.67 (s, 1H), 3.28-3.22 (m, 5H), 2.98 (s, 1H), 2.40-2.31 (m, 1H), 2.02-1.73 (m, 5H), 1.60 (d, J=11.8 Hz, 2H), MS (ESI, m/e) [M+1]⁺ 791.1.

Example A35: 3-((1H-pyrrolo[2,3-b]pyridin-5-yl)oxy)-4'-(2-(2-cyclobutylphenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

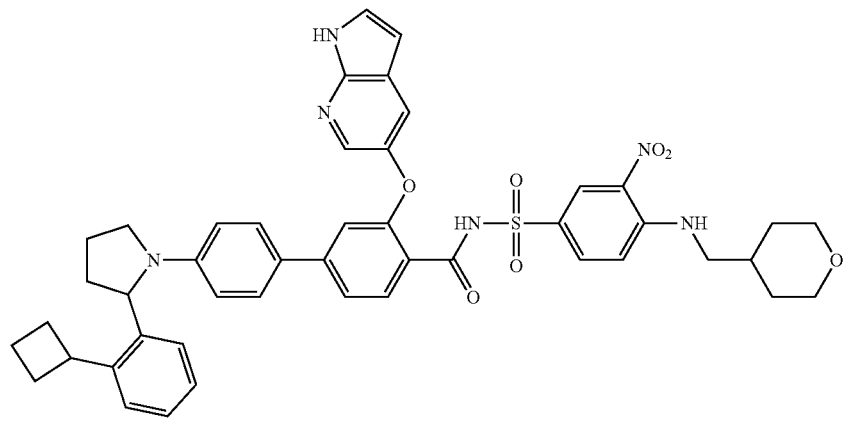 [SMILES: O=C(NS(=O)(=O)c1ccc(NCC2CCOCC2)c([N+](=O)[O-])c1)c1ccc(-c2ccc(N3CCCC3c3ccccc3C3CCC3)cc2)cc1Oc1cnc2[nH]ccc2c1]

The desired compound was synthesized starting from 2-(2-cyclobutylphenyl)pyrrolidine and 1-bromo-4-iodobenzene following the procedures similar to those in Example A1. $^1$H NMR (CDCl3-$d_6$) δ ppm: 10.24 (s, 1H), 9.53 (s, 1H), 8.92 (s, 1H), 8.60-8.45 (m, 1H), 8.28-7.97 (m, 3H), 7.79 (s, 1H), 7.56-7.31 (m, 4H), 7.22-7.12 (m, 3H), 7.06-6.89 (m, 3H), 6.77 (s, 1H), 6.60-6.51 (m, 1H), 6.34 (d, J=8.4 Hz, 2H), 4.86 (d, J=8.0 Hz, 1H), 4.09-3.96 (m, 2H), 3.82-3.63 (m, 2H), 3.42 (t, J=10.8 Hz, 2H), 3.31-3.21 (m, 2H), 2.38-2.21 (m, 4H), 2.05-1.88 (m, 8H), 1.78-1.70 (m, 2H), 1.50-1.39 (m, 2H). MS (ESI, m/e) [M+1]$^+$826.8.

Example A 37: 3-((1H-pyrrolo[2,3-b]pyridin-5-yl)oxy)-4'-(2-(2-cyclohexylphenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

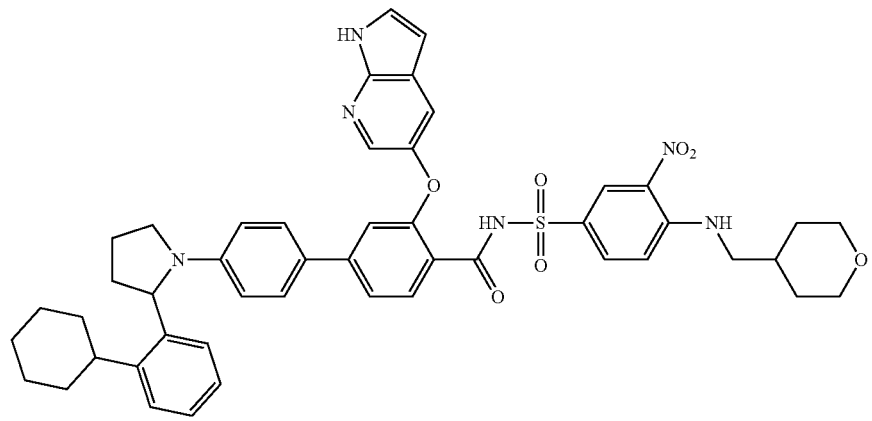 [SMILES: O=C(NS(=O)(=O)c1ccc(NCC2CCOCC2)c([N+](=O)[O-])c1)c1ccc(-c2ccc(N3CCCC3c3ccccc3C3CCCCC3)cc2)cc1Oc1cnc2[nH]ccc2c1]

The desired compound was synthesized starting from 2-(2-cyclohexylphenyl)pyrrolidine and 1-bromo-4-iodobenzene following the procedures similar to those in Example A1. $^1$H NMR (400 MHz, DMSO-d$_6$) δ ppm: $^1$H NMR (400 MHz, DMSO-d6) δ 12.14 (s, 1H), 11.68 (s, 1H), 8.9-8.55 (m, 2H), 8.04 (s, 1H), 7.81 (s, 1H), 7.62-7.44 (m, 2H), 7.35-7.28 (m, 5H), 7.14 (d, J=7.7 Hz, 2H), 6.98 (t, J=7.1 Hz, 1H), 6.91 (s, 1H), 6.82 (d, J=7.6 Hz, 1H), 6.40-6.31 (m, 3H), 4.97 (d, J=8.9 Hz, 1H), 3.84 (d, J=10.4 Hz, 2H), 3.75-3.71 (m, 1H), 3.35-3.21 (m, 5H), 3.03-2.83 (m, 3H), 2.01-1.95 (m, 2H), 1.88-1.75 (m, 4H), 1.74-1.67 (m, 2H), 1.62-1.55 (m, 4H), 1.48-1.38 (m, 3H), 1.30-1.25 (m, 2H). MS (ESI, m/e) [M+1]$^+$854.8.

Example A46: 3-((1H-pyrrolo[2,3-b]pyridin-5-yl)oxy)-4'-(4,4-dimethyl-2-phenylpyrrolidin-1-yl)-N-((3-nitro-4-(((tetrahydro-2H-pyran-4-yl)methyl)amino)phenyl)sulfonyl)-[1,1'-biphenyl]-4-carboxamide

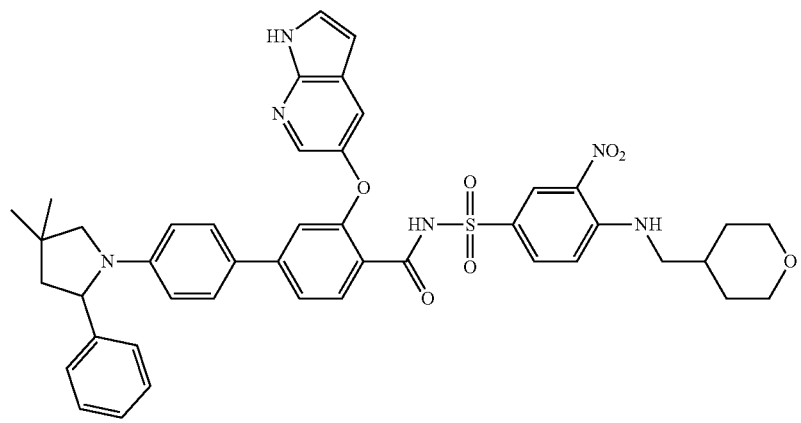 [SMILES: CC1(C)CC(c2ccccc2)N(c2ccc(-c3ccc(C(=O)NS(=O)(=O)c4ccc(NCC5CCOCC5)c([N+](=O)[O-])c4)c(Oc4cnc5[nH]ccc5c4)c3)cc2)C1]

The desired compound was synthesized starting from 4,4-dimethyl-2-phenylpyrrolidine and 1-bromo-4-iodobenzene following the procedures similar to those in Example A1. $^1$H NMR (400 MHz, DMSO-d$_6$) δ ppm: 12.15 (s, 1H), 11.70 (s, 1H), 8.62 (t, J=5.8 Hz, 1H), 8.57 (d, J=2.0 Hz, 1H), 8.04 (d, J=2.4 Hz, 1H), 7.83 td, J=7.5 Hz, 1H), 7.59 (d, J=2.3 Hz, 1H), 7.52 (d, J=8.0 Hz, 3H), 7.51-7.53 (m, 2H), 7.32 id., J=8.0 Hz, 1H), 7.12-7.28 (m, 8H), 6.87 (s, 1H), 6.39-6.42 (m, 3H), 4.78 (t, 7.8 Hz, 2H), 3.84 (d, J=8.2 Hz, 2H), 3.51 (d, J=9.6 Hz, 2H), 3.23-3.29 (m, 4H), 2.23-2.33 (m, 1H), 1.97-2.01 (m, 2H), 1.87 (s, 1H), 1.58-1.65 (m, 3H), 1.45 (s, 1H), 1.10 (s, 4H), 1.10 (s, 3H), 1.01 (s, 3H). MS (ESI, m/e) [M+1]$^+$ 801.1.

Example A47: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-phenylazetidin-1-yl)-[1,1'-biphenyl]-4-carboxamide

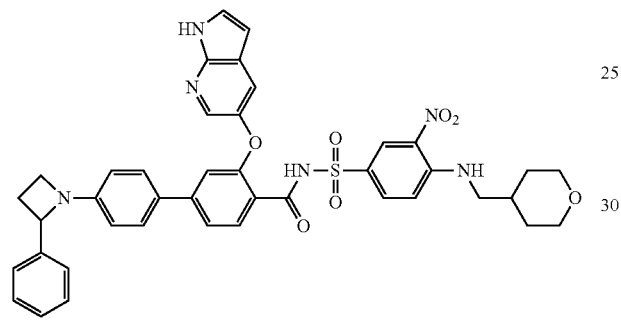

The desired compound was synthesized starting from 2-phenylazetidine and 1-bromo-4-iodobenzene following the procedures similar to those in Example A1. MS (ESI, m/e) [M+1]$^+$ 758.8.

Example A54: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-phenyl-2-(trifluoromethyl)pyrrolidin-1-yl)-[1,1'-biphenyl]-4-carboxamide

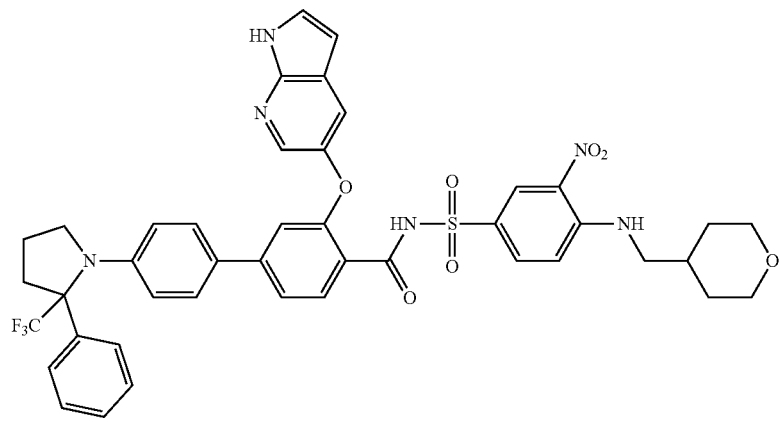 [SMILES: O=C(NS(=O)(=O)c1ccc(NCC2CCOCC2)c([N+](=O)[O-])c1)c1ccc(-c2ccc(N3CCCC3(c3ccccc3)C(F)(F)F)cc2)cc1Oc1cnc2[nH]ccc2c1]

The desired compound was synthesized from 1-(4-bromophenyl)-2-phenyl-2-(trifluoromethyl)pyrrolidine following the procedures similar to those in Example A1. $^1$H NMR (DMSO-d$_6$) δ ppm: 12.22 (s, 1H), 11.70 (s, 1H), 8.67-8.48 (m, 2H), 8.10-7.97 (m, 1H), 7.86-7.75 (m, 1H), 7.65-7.46 (m, 3H), 7.43-7.08 (m, 9H), 6.91 (s, 1H), 6.54-6.32 (m, 3H), 3.87-3.62 (m, 4H), 3.30-3.20 (m, 4H), 2.76-2.66 (m, 1H), 2.22-1.80 (m, 4H), 1.66-1.53 (m, 2H), 1.30-1.19 (m, 2H). MS (ESI, m/e) [M+1]$^+$ 840.7.

Example A55: 3-((1H-pyrrolo[2,3-b]pyridin-5-yl)oxy)-4'-(2-ethyl-2-phenylpyrrolidin-1-yl)-N-((3-nitro-4-(((tetrahydro-2H-pyran-4-yl)methyl)amino)phenyl)sulfonyl)-[1,1'-biphenyl]-4-carboxamide

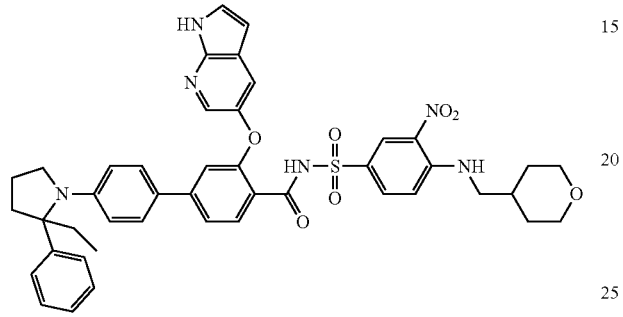

The desired compound was synthesized from 1-(4-bromophenyl)-2-ethyl-2-phenylpyrrolidine following the procedures similar to those in Example A1. $^1$H NMR (400 MHz, DMSO-d$_6$) δ ppm: 12.16 (s, 1H), 11.71 (s, 1H), 8.65-8.56 (m, 2H), 8.06 (d, J=2.4 Hz, 1H), 7.85 (d, J=8.8 Hz, 1H), 7.60 (s, 1H), 7.55-7.49 (m, 2H), 7.36-7.11 (m, 9H), 6.89 (s, 1H), 6.41-6.33 (m, 3H), 3.86 (d, J=8.4 Hz, 2H), 3.68-3.45 (m, 2H), 3.31-3.22 (m, 4H), 2.41-2.25 (m, 3H), 1.92-1.71 (m, 4H), 1.62 (d, J=12.4 Hz, 2H), 1.31-1.19 (m, 2H), 0.64 (t, J=12 Hz, 3H). MS (ESI, m/e) [M+1]$^+$ 800.7.

Example A56: 3-((1H-pyrrolo[2,3-b]pyridin-5-yl)oxy)-4'-(4-methyl-2-phenylpiperazin-1-yl)-N-((3-nitro-4-(((tetrahydro-2H-pyran-4-yl)methyl)amino)phenyl)sulfonyl)-[1,1'-biphenyl]-4-carboxamide

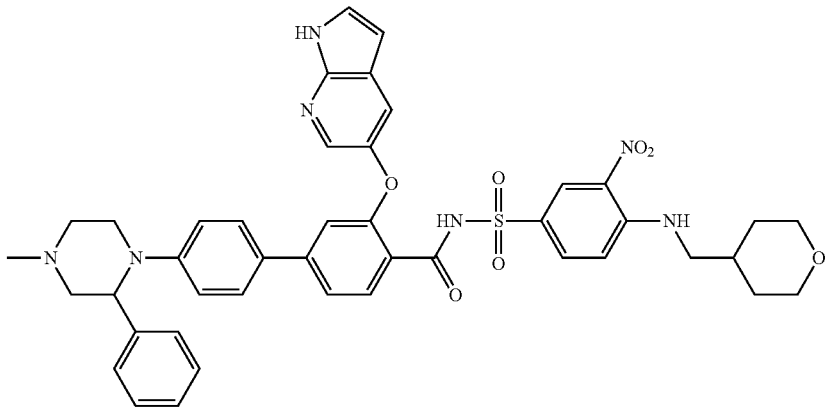 [SMILES: CN1CCN(c2ccc(-c3ccc(C(=O)NS(=O)(=O)c4ccc(NCC5CCOCC5)c([N+](=O)[O-])c4)c(Oc4cnc5[nH]ccc5c4)c3)cc2)C(c2ccccc2)C1]

The desired compound was synthesized starting from 1-methyl-3-phenylpiperazine and 1-bromo-4-iodobenzene following the procedures similar to those in Example A1. $^1$H NMR (400 MHz, DMSO-d$_6$) δ ppm: 11.66 (s, 1H), 8.51 (s, 1H), 8.02 (s, 1H), 7.78 (d, J=9.2 Hz, 1H), 7.60-7.48 (m, 4H), 7.35-7.28 (m, 6H), 7.25-7.21 (m, 2H), 7.16-7.13 (m, 1H), 7.04 (d, J=9.2 Hz, 1H), 6.97-6.90 (m, 3H), 6.36 (s, 1H), 4.73 (s, 1H), 3.84 (d, J=8.8 Hz, 2H), 3.57-3.45 (m, 3H), 3.28-3.22 (m, 4H), 3.15-2.90 (m, 5H), 2.05-1.79 (m, 2H), 1.59 (d, J=12.0 Hz, 2H), 1.26-1.23 (m, 2H). MS (ESI, m/e) [M+1]$^+$ 802.2.

Example A57: 3-((1H-pyrrolo[2,3-b]pyridin-5-yl)oxy)-4'-(2-(2-isopropylphenyl)piperidin-1-yl)-N-((3-nitro-4-(((tetrahydro-2H-pyran-4-yl)methyl)amino)phenyl)sulfonyl)-[1,1'-biphenyl]-4-carboxamide

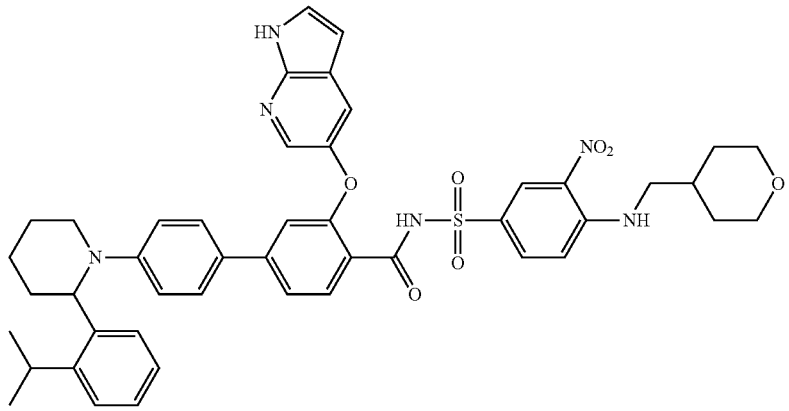 [SMILES: CC(C)c1ccccc1C1CCCCN1c1ccc(-c2ccc(C(=O)NS(=O)(=O)c3ccc(NCC4CCOCC4)c([N+](=O)[O-])c3)c(Oc3cnc4[nH]ccc4c3)c2)cc1]

The desired compound was synthesized from 1-(4-bromophenyl)-2-(2-isopropylphenyl)piperidine following the procedures similar to those in Example A1. $^1$H NMR (400 MHz, DMSO-d$_6$) δ ppm: 12.24 (s, 1H), 11.68 (s, 1H), 8.54 (s, 2H), 8.02 (s, 1H), 7.79 (s, 1H), 7.57-7.47 (m, 3H), 7.39-7.19 (m, 4H), 7.17-7.01 (m, 3H), 6.92 (s, 2H), 6.81 (d, J=8.2 Hz, 2H), 6.36 (s, 1H), 4.71 (s, 1H), 3.84 (d, J=9.7 Hz, 2H), 3.26-3.22 (m, 4H), 1.95-1.85 (m, 2H), 1.79-1.72 (m, 2H), 1.68-1.55 (m, 4H), 1.49-1.43 (m, 2H), 1.23-1.18 (m, 6H), 1.04 (d, J=5.2 Hz, 2H), 0.86-0.82 (m, 1H). MS (ESI, m/e) [M+1]$^+$ 828.8.

Example A 61: 3-((1H-pyrrolo[2,3-b]pyridin-5-yl)oxy)-4% 1-(2-cyclopropylphenyl)-5-oxopyrrolidin-2-yl)-N-((3-nitro-4-(((tetrahydro-2H-pyran-4-yl)methyl)amino)phenyl)sulfonyl)-[1,1'-biphenyl]-4-carboxamide

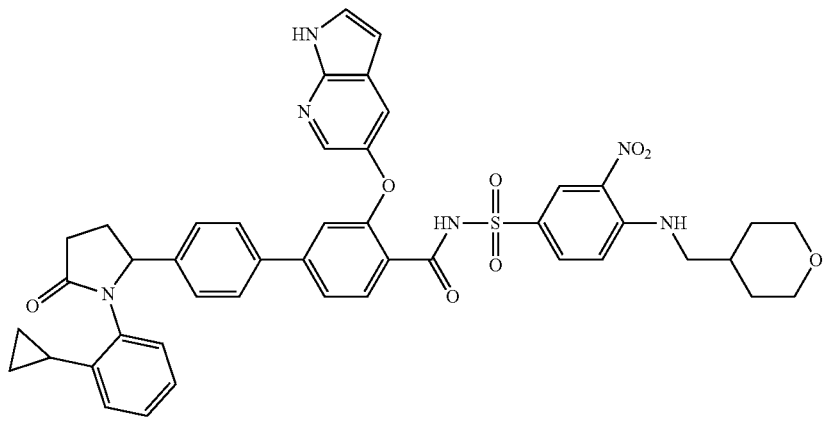

Step 1: 4-(4-bromophenyl)-4-oxobutanoic acid

Aids (26.7 g, 200 mmol) was added into a mixture of dihydrofuran-2,5-dione (10.0 g, 100 mmol) in bromobenzene (97 g) at about 0° C., the reaction temperature was maintained at about 0° C. for 1 h and then allowed to r. t. the mixture was stirred at r. t for 16 h. The reaction mixture was poured into ice water, HCl (1M) was added slowly until PH1. The mixture was extracted with EA (400 mL). The organic layer was dried over $Na_2SO_4$, concentrated, filtered and washed with PE (100 mL) to give the crude product as brown solid 14.5 g.

Step 2: methyl 4-(4-bromophenyl)-4-oxobutanoate

To a solution of 4-(4-bromophenyl)-4-oxobutanoic acid (14.5 g, 56.42 mmol) in $CH_3OH$ (200 mL) was added $SOCl_2$ (10 mL) slowly, the mixture was stirred at ambient temperature for 2 h. The solution was concentrated. The residue was partitioned between DCM (100 mL) and Sat. $NaHCO_3$ (300 mL). The organic layer was dried over $Na_2SO_4$ and concentrated to give the crude product as yellow oil. (15.0 g).

Step 3: methyl -4-(4-bromophenyl)-4-(hydroxyimino)butanoate

To a solution of methyl 4-(4-bromophenyl)-4-oxobutanoate (15 g, 55.35 mmol) in $CH_3OH$ (150 mL) was added hydroxylamine hydrochloride (9.2 g, 132.84 mmol), NaOAc (11.4 g, 138.38 mmol)/$H_2O$ (50 mL), the mixture was heated at reflux for about 1 h. Cooled to ambient temperature, concentrated to remove $CH_3OH$. The resulting mixture was partitioned between EA (300 mL) and Sat. $NaHCO_3$ (200 mL). The aqueous layer was extracted with EA (100 mL). The combined organic layers were washed with $H_2O$ (200 mL), concentrated and purified by column chromatograph on silica gel (100-200 mesh, eluent: EA:PE=1:10) to give the product as yellow oil. (11.2 g, 71.0%). $[M+1]^+$ 285.9, 287.9.

Step 4: 5-(4-bromophenyl)pyrrolidin-2-one

To a solution of methyl-4-(4-bromophenyl)-4-(hydroxyimino)butanoate (11.2 g, 39.16 mmol) in $CH_3OH$ (100 mL) was added Zn (powder, 5.2 g, 78.32 mmol), the mixture was stirred in a 80° C. oil bath under $N_2$ for about 16 h, Cooled to ambient temperature, filtered, the filtrate was concentrated. The residue was partitioned between DCM (500 mL) and Sat. $NaHCO_3$ (300 mL). The organic layer was separated, concentrated to give the crude product, which was slurry with PE (100 mL) to give the product as white solid. (6.5 g, 69.4%). $[M+1]^+$ 240.0, 241.9.

Step 5: tert-butyl 3-((1H-pyrrolo[2,3-b]pyridin-5-yl)oxy)-4'-(5-oxopyrrolidin-2-yl)-[1,1'-biphenyl]-4-carboxylate To a solution of tert-butyl 2-((1H-pyrrolo[2,3-b]pyridin-5-yl)oxy)-4-(4,4,5,5-tetramethyl-1,3,2-dioxaborolan-2-yl)benzoate (2.2 g, 5.00 mmol) in 1,4-dioxane (50 mL) was added 5-(4-bromophenyl)pyrrolidin-2-one (1.2 g, 5.00 mmol), Pd(dppf)$Cl_2$ (183 mg, 0.25 mmol) and 1 N $K_2CO_3$ (15 mL), the mixture was stirred in a 80° C. oil bath under $N_2$ for about 18 h. Cooled to r. t, extracted with DCM (50 mL×2). The combined organic layers were concentrated and purified by column chromatograph on silica gel (100-200 mesh, eluent: MeOH:DCM=1:10) to give the crude product as brown solid. (2.4 g), $[M+1]^+$ 469.8.

Step 6: tert-butyl 3-((1H-pyrrolo[2,3-b]pyridin-5-yl)oxy)-4'-(1-(2-bromophenyl)-5-oxopyrrolidin-2-yl)-[1,1'-biphenyl]-4-carboxylate To a solution of tert-butyl 3-((1H-pyrrolo[2,3-b]pyridin-5-yl)oxy)-4'-(5-oxopyrrolidin-2-yl)-[1,1'-biphenyl]-4-carboxylate (1.5 g, 3.20 mmol) in DCM (50 mL) was added (2-bromophenyl)boronic acid (640 mg, 3.20 mmol), Cu(OAc)$_2$ (920 mg, 4.80 mmol) and TFA (1.6 g, 15.99 mmol), the mixture was stirred at r, t in air for 3 h, (2-bromophenyl)boronic acid (640 mg, 3.20 mmol) was added, the mixture was stirred in air for 18 h. $H_2O$ (30 mL) was added, filtered, the organic layer was separated, concentrated and purified by column chromatograph on silica gel (100-200 mesh, eluent: MeOH:DCM=1:20) to give the product as brown solid. (1.0 g, 50.2%). $[M+1]^+$ 623.8.

Step 7: tert-butyl 3-((1H-pyrrolo[2,3-b]pyridin-5-yl)oxy)-4'-(1-(2-cyclopropylphenyl)-5-oxopyrrolidin-2-yl)-[1,1'-biphenyl]-4-carboxylate To a solution of tert-butyl 3-((1H-pyrrolo[2,3-b]pyridin-5-yl)oxy)-4'-(1-(2-bromophenyl)-5-oxopyrrolidin-2-yl)-[1,1'-biphenyl]-4-carboxylate (312 mg, 0.50 mmol) and cyclopropylboronic acid (172 mg, 2.00 mmol) in 1,4-dioxane (20 mL) was added 1N $K_2CO_3$ (2 mL) and Pd(dppf)$Cl_2$ (37 mg, 0.05 mmol), the mixture was stirred in a 80° C. oil bath under $N_2$ for 20 h. Cooled to r. t, diluted with DCM (30 mL), filtered, the filtrate was concentrated and purified by column chromatograph on silica gel (MeOH:DCM=1:20) to give the crude product, which was purified by pre-TLC (EA) to give the product as brown solid. (290 mg, 98.9%). $[M+1]^+$ 585.8

The desired compound was then synthesized with tert-butyl 3-((1H-pyrrolo[2,3-b]pyridin-5-yl)oxy)-4'-(1-(2-cyclopropylphenyl)-5-oxopyrrolidin-2-yl)-[1,1'-biphenyl]-4-carboxylate following the procedures similar to those in Example A1. $[M+1]^+$ 826.7.

Example A 62: 3-((1H-pyrrolo[2,3-b]pyridin-5-yl) oxy)-4'-(1-(2-cyclopropylphenyl)pyrrolidin-2-yl)-N-((3-nitro-4-(((tetrahydro-2H-pyran-4-yl)methyl) amino)phenyl)sulfonyl)-[1,1'-biphenyl]-4-carboxamide

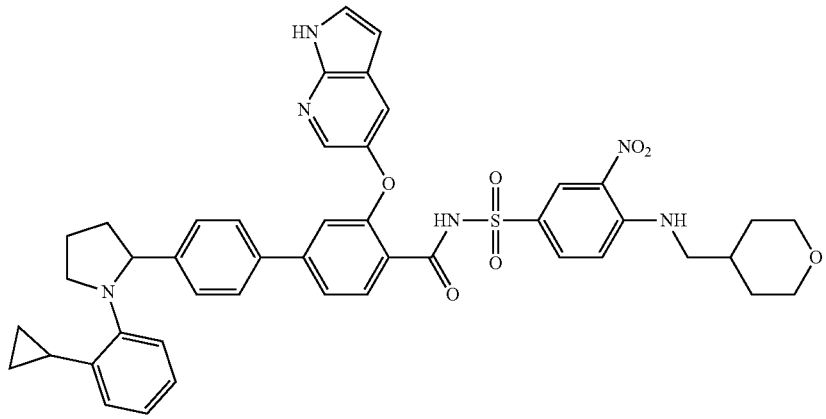

Step 1: 1-cyclopropyl-2-nitrobenzene

To a solution of 1-bromo-2-nitrobenzene (3.7 g, 18.32 mmol) and cyclopropylboronic acid (4.7 g, 54.95 mmol) in 1,4-dioxane (100 mL) was added K$_2$CO$_3$ (5.1 g, 36.64 mmol)/H$_2$O (20 mL) and Pd(dppf)Cl$_2$ (1.3 g, 1.83 mmol), the mixture was stirred at 90° C. under N$_2$ for 16 h. Cooled to ambient temperature, the organic layer was separated, concentrated and purified by column chromatograph on silica gel (100-200 mesh, eluent: EA:PE=1:4) to give the product as yellow oil. (2.6 g, 86.7%).

Step 2: 2-cyclopropylaniline

To a solution of 1-cyclopropyl-2-nitrobenzene (2.6 g, 15.95 mmol) in CH$_3$OH (50 mL) was added Sat. NH$_4$Cl (7.5 mL) and Zn (powder, 5.1 g, 79.75 mmol), the mixture was stirred at ambient temperature for 1 h. A filtration was formed, the filtrate was concentrated. The residue was partitioned between DCM (30 mL) and H$_2$O (20 mL). The organic layer was dried over Na$_2$SO$_4$ and concentrated to give the product as brown oil. (1.6 g, 75.4%). [M+1]$^+$ 134.2.

Step 3: 4-(4-bromophenyl)-N-(2-cyclopropylphenyl)-4-oxobutanamide

To a solution of 4-(4-bromophenyl)-4-oxobutanoic acid (3.7 g, 15.95 mmol) in DCM (50 mL) was added 2-cyclopropylaniline (1.6 g, 12.03 mmol), HATU (6.9 g, 18.04 mmol) and TFA (3.6 g, 36.10 mmol), the solution was stirred at ambient temperature for 17 h. The reaction solution was concentrated and purified by column chromatograph on silica gel (100-200 mesh, eluent: EA:DCM=1:2) to give the crude product, which was crystallized from EA/PE=1/3 (50 mL, 70° C.—r. t) to give the product as off-white solid. (1.9 g, 35.8%). [M+1]$^+$ 371.8, 373.8.

Step 4: 4-(4-bromophenyl)-N-(2-cyclopropylphenyl)-4-hydroxybutanamide

To a solution of 4-(4-bromophenyl)-N-(2-cyclopropylphenyl)-4-oxobutanamide (1.9 g, 5.12 mmol) in CH$_3$OH (60 mL) was added NaBH$_4$ (583 mg, 15.36 mmol) in portions, the solution was stirred at ambient temperature for 1 h. The reaction solution was concentrated. The residue was partitioned between DCM (50 mL) and Sat. NaCl (20 mL). The organic layer was separated, concentrated and purified by column chromatograph on silica gel (100-200 mesh, eluent: EA:DCM=1:1) to give the product as pink oil. (1.8 g, 94.7%). [M+1]$^+$ 373.8, 375.8.

Step 5: 5-(4-bromophenyl)-1-(2-cyclopropylphenyl)pyrrolidin-2-one

To a solution of 4-(4-bromophenyl)-N-(2-cyclopropylphenyl)-4-hydroxybutanamide (1.8 g, 4.83 mmol) in THF (50 mL) was added TosCl (1.2 g, 6.27 mmol) at −40° C., the solution was stirred at −40° C. for about 40 min, t-BuOK (1.08 g, 9.65 mmol) was then added, the mixture was stirred at −40° C. for 1 h. Warmed to r. t slowly, quenched by Sat. NaCl (10 mL). The organic layer was separated, concentrated and purified by column chromatograph on silica gel (100-200 mesh, eluent: EA:PE=1:1) to give the product as pink oil. (0.9 g, 52.5%), [M+1]$^+$ 355.8, 357.8.

Step 6: 5 2-(4-bromophenyl)-1-(2-cyclopropylphenyl)pyrrolidine

To a solution of 5-(4-bromophenyl)-1-(2-cyclopropylphenyl)pyrrolidin-2-one (900 mg, 2.53 mmol) in THF (20 mL) was added BH3/THF (0.9M, 10 mL, 9.0 mmol) slowly, the solution was stirred at 60° C. under N$_2$ for 3 h. Cooled to r. t, quenched by CH$_3$OH (2 mL), concentrated and purified by column chromatograph on silica gel (100-200 mesh, eluent: EA:PE=1:5) to give the product as yellow oil. (750 mg, 86.8%). [M+1]$^+$ 341.8, 343.8.

The desired compound was then synthesized with 2-(4-bromophenyl)-1-(2-cyclopropylphenyl)pyrrolidine following the procedures similar to those in Example A1, [M+1]+ 812.8.

Example A 63: 3-((1H-pyrrolo[2,3-b]pyridin-5-yl) oxy)-N-((3-nitro-4-(((tetrahydro-2H-pyran-4-yl) methyl)amino)phenyl)sulfonyl)-4'-(1-(2-nitrophenyl) pyrrolidin-2-yl)-[1,1'-biphenyl]-4-carboxamide

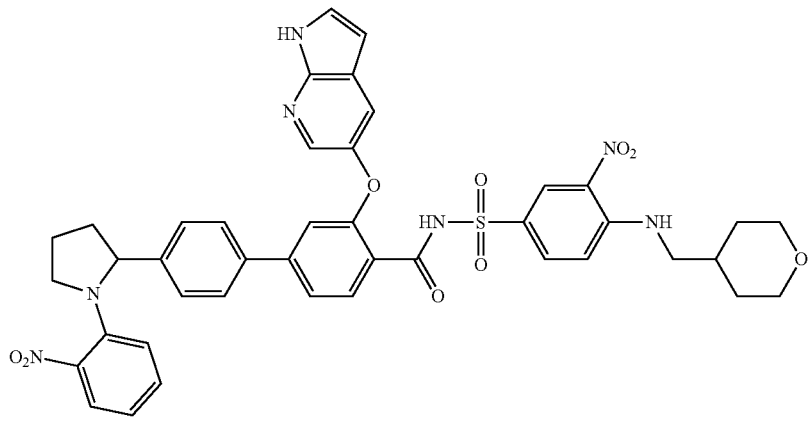 [SMILES: O=C(NS(=O)(=O)c1ccc(NCC2CCOCC2)c([N+](=O)[O-])c1)c1ccc(-c2ccc(C3CCCN3c3ccccc3[N+](=O)[O-])cc2)cc1Oc1cnc2[nH]ccc2c1]

To a solution of 3-((1H-pyrrolo[2,3-b]pyridin-5-yl)oxy)-N-((3-nitro-4-(((tetrahydro-2H-pyran-4-yl)methyl)amino) phenyl)sulfonyl)-4'-(pyrrolidin-2-yl)-[1,1'-biphenyl]-4-carboxamide (100 mg, 0.15 mmol) in $CH_3CN$ (10 mL) was added 1-fluoro-2-nitrobenzene (63 mg, 0.44 mmol) and TFA (149 mg, 1.47 mmol), the solution was stirred at 80° C. for 18 h. The reaction solution was concentrated and purified by pre-TLC (DCM:MeOH=25:1) to give the crude product, which was purified by pre-HPLC to give the product as yellow solid. (10 mg, 8.30%). $^1$H NMR (DMSO-$d_6$) δ ppm: 12.36 (s, 1H), 11.71 (s, 1H), 8.67-8.51 (m, 2H), 8.05 (d, J=2.4 Hz, 1H), 7.88-7.79 (m, 1H), 7.71-7.23 (m, 10H), 7.13 (d, J=9.6 Hz, 1H), 7.00 (s, 1H), 6.86-6.64 (m, 2H), 6.39 (s, 1H), 5.03-4.91 (m, 1H), 3.87-3.81 (m, 2H), 3.29-3.24 (m, 3H), 3.10-2.88 (m, 2H), 2.83-2.77 (m, 1H), 2.05-1.95 (m, 1H), 1.93-1.79 (m, 2H), 1.73-1.54 (m, 3H), 1.13-1.16 (m, 3H). MS (ESI, m/e) [M+1]$^+$ 817.7.

Example A 64: 3-((1H-pyrrolo[2,3-b]pyridin-5-yl) oxy)-4'-(2-(2-(tert-butyl)phenyl)pyrrolidin-1-yl)-N-((3-nitro-4-(((tetrahydro-2H-pyran-4-yl)methyl) amino)phenyl)sulfonyl)-[1,1'-biphenyl]-4-carboxamide

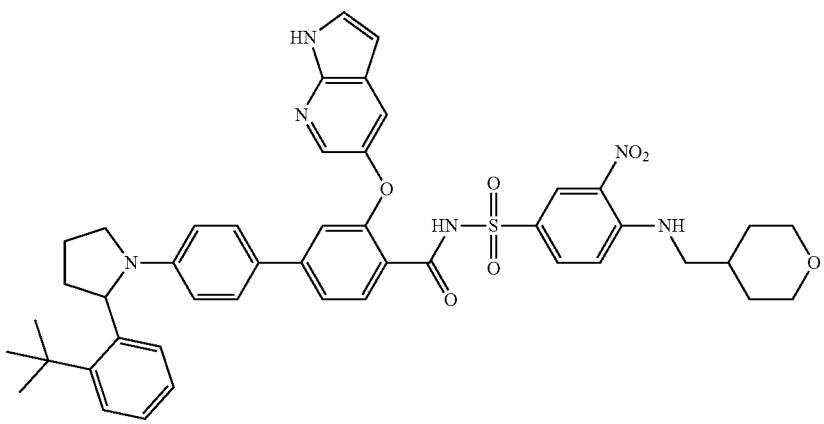 [SMILES: CC(C)(C)c1ccccc1C1CCCN1c1ccc(-c2ccc(C(=O)NS(=O)(=O)c3ccc(NCC4CCOCC4)c([N+](=O)[O-])c3)c(Oc3cnc4[nH]ccc4c3)c2)cc1]

The desired compound was synthesized starting from 2-(2-(tert-butyl)phenyl)pyrrolidine. $^1$H NMR. (400 MHz, DMSO-d6) δ 12.15 (s, 1H), 11.67 (s, 1H), 8.54 (s, 2H), 8.01 (s, 1H), 7.80 (s, 1H), 7.55-7.46 (m, 2H), 7.42 (d, J=8.1 Hz, 1H), 7.31 (s, 1H), 7.29-7.25 (m, 2H), 7.20 (s, 1H), 7.13 (s, 1H), 7.04 (s, 2H), 6.92 (s, 1H), 6.65 (s, 1H), 6.42-6.36 (m, 3H), 5.25 (d, J=7.8 Hz, 1H), 3.84 (d, J=9.2 Hz, 2H), 3.73 (s, 1H), 3.28-3.23 (m, 4H), 2.03-1.97 (m, 6H), 1.87 (s, 1H), 1.77 (s, 1H), 1.61-1.58 (m, 2H), 1.50 (s, 9H), 1.44 (s, 1H), 1.41 (s, 1H). MS (ESI, m/e) [M+1]$^+$ 828.8.

Example A65: 3-((1H-pyrrolo[2,3-b]pyridin-5-yl)oxy)-4'-(2-(2-(dimethylamino)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

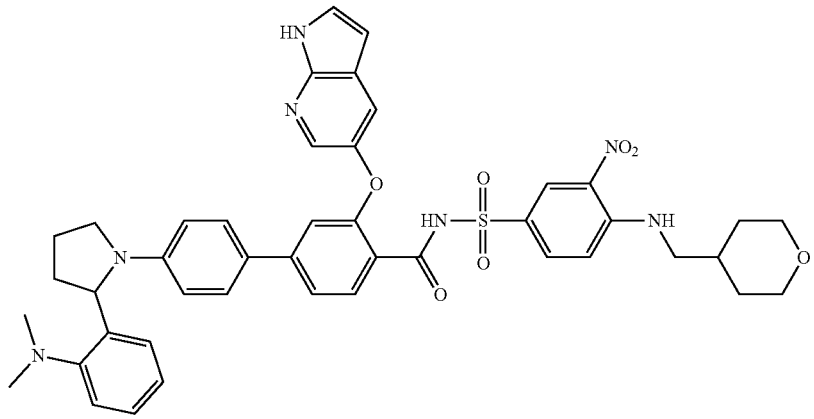

The desired compound was synthesized starting from N,N-dimethyl-2-(pyrrolidin-2-yl)aniline and 1-bromo-4-iodobenzene following the procedures similar to those in Example A1. $^1$H NMR (400 MHz, DMSO-d$_6$) δ ppm: 12.16 (s, 1H), 11.66 (s, 1H), 8.53 (s, 2H), 8.02 (s, 1H), 7.77 (s, 1H), 7.61-7.44 (m, 3H), 7.35-7.13 (m, 5H), 6.98-6.88 (m, 3H), 6.47-6.30 (m, 3H), 5.15-5.08 (m, 1H), 3.89-3.80 (m, 2H), 3.71 (s, 1H), 3.55-3.50 (m, 3H), 2.75-2.67 (m, 6H), 2.45-2.40 (m, 1H), 2.05-1.98 (m, 3H), 1.85 (s, 2H), 1.64-1.54 (m, 2H), 1.47-1.42 (m, 1H), 1.06-1.00 (m, 5H). MS (ESI) m/e [M+1]$^+$ 815.8.

Example A66: 3-((1H-pyrrolo[2,3-b]pyridin-5-yl)oxy)-4'-(2-(2-(azetidin-1-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

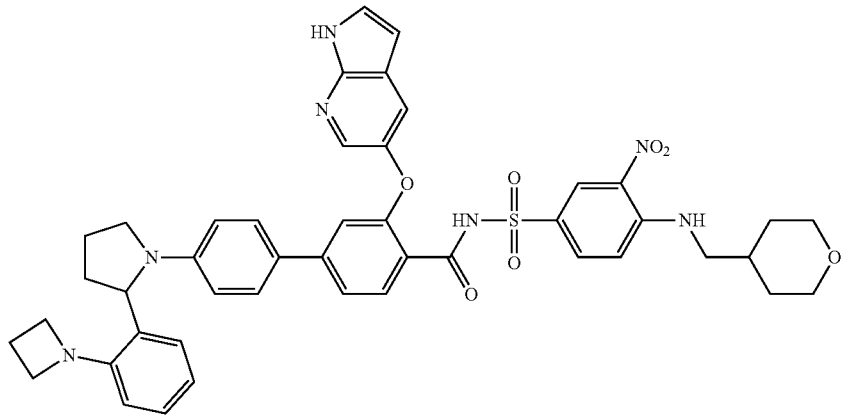 [SMILES: O=C(NS(=O)(=O)c1ccc(NCC2CCOCC2)c([N+](=O)[O-])c1)c1ccc(-c2ccc(N3CCCC3c3ccccc3N3CCC3)cc2)cc1Oc1cnc2[nH]ccc2c1]

The desired compound was synthesized from 2-(2-(azetidin-1-yl)phenyl)-1-(4-bromophenyl)pyrrolidine following the procedures similar to those in Example A1. $^1$H NMR (400 MHz, DMSO-$d_6$) δ ppm: 12.14 (s, 1H), 11.69 (s, 1H), 8.58 (t, J=6.0 Hz, 1H), 8.57 (d, J=2.4 Hz, 1H), 8.05 (d, J=2.4 Hz, 1H), 7.84 (d, J=8.8 Hz, 1H), 7.60 (d, J=2.4 Hz, 1H), 7.52-7.50 (m, 2H), 7.35-7.25 (m, 3H), 7.14 (d, J=9.2 Hz, 1H), 7.04 (t, J=6.4 Hz, 1H), 6.89 (s, 1H), 6.75 (d, J=7.6 Hz, 1H), 6.60 (t, J=7.6 Hz, 1H), 6.51 (d, J=7.6 Hz, 1H), 6.45-6.35 (m, 3H), 4.82 (d, J=8.0 Hz, 1H), 3.93 (t, J=7.4 Hz, 4H), 3.84-3.80 (m, 2H), 3.64 (t, J=8.0 Hz, 1H), 3.32-3.21 (m, 4H), 2.35-2.21 (m, 3H), 2.02-1.81 (m, 5H), 1.62 (d, J=12.8 Hz, 2H), 1.30-1.25 (m, 2H). MS (ESI, m/e) [M+1]$^+$ 827.8.

Example A67: 3-((1H-pyrrolo[2,3-b]pyridin-5-yl)oxy)-4'-(2-(2-(methylsulfonamido)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

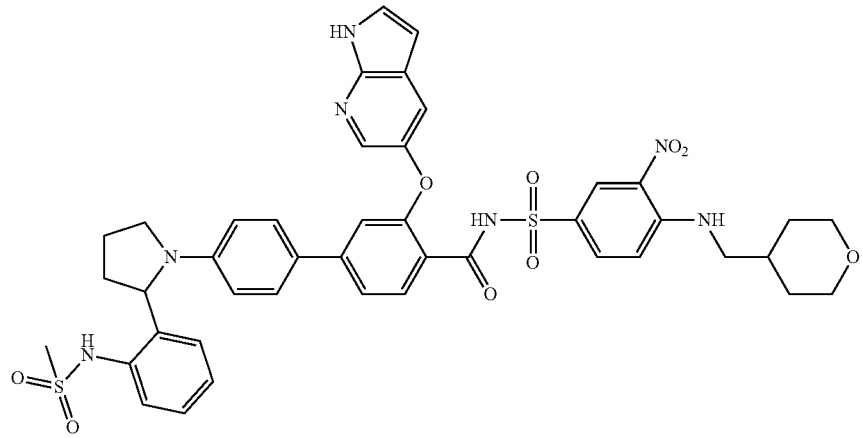 [SMILES: CS(=O)(=O)Nc1ccccc1C1CCCN1c1ccc(-c2ccc(C(=O)NS(=O)(=O)c3ccc(NCC4CCOCC4)c([N+](=O)[O-])c3)c(Oc3cnc4[nH]ccc4c3)c2)cc1]

The desired compound was synthesized starting from N-(2-(pyrrolidin-2-yl)phenyl)methanesulfonamide. $^1$H NMR (400 MHz, DMSO-$d_6$) δ ppm: 12.16 (s, 1H), 11.70 (s, 1H), 9.20 (s, 1H), 8.61-8.56 (m, 2H), 8.05 (s, 1H), 7.82 (d, J=8.0 Hz, 1H), 7.65-7.48 (m, 3H), 7.35-7.33 (m, 2H), 7.24-7.22 (m, 3H), 7.13 (t, J=7.2 Hz, 2H), 6.98-6.87 (m, 2H), 6.48 (d, J=8.6 Hz, 2H), 6.38 (s, 1H), 5.26 (d, J=7.9 Hz, 1H), 3.84 (d, J=8.6 Hz, 2H), 3.68 (s, 1H), 3.29-3.22 (m, 4H), 3.11 (s, 3H), 2.37-2.33 (m, 1H), 1.95 (s, 1H), 1.83-1.81 (m, 2H), 1.60 (d, J=12.5 Hz, 2H), 1.28-1.24 (m, 4H). MS (ESI, m/e) [M+1]$^+$ 865.7.

Example A68: 3-((1H-pyrrolo[2,3-b]pyridin-5-yl)oxy)-4'-(2-(2-(1-methyl-1,2,3,6-tetrahydropyridin-4-yl)phenyl)pyrrolidin-1-yl)-N-((3-nitro-4-((((tetrahydro-2H-pyran-4-yl)methyl)amino)phenyl)sulfonyl)-[1,1'-biphenyl]-4-carboxamide

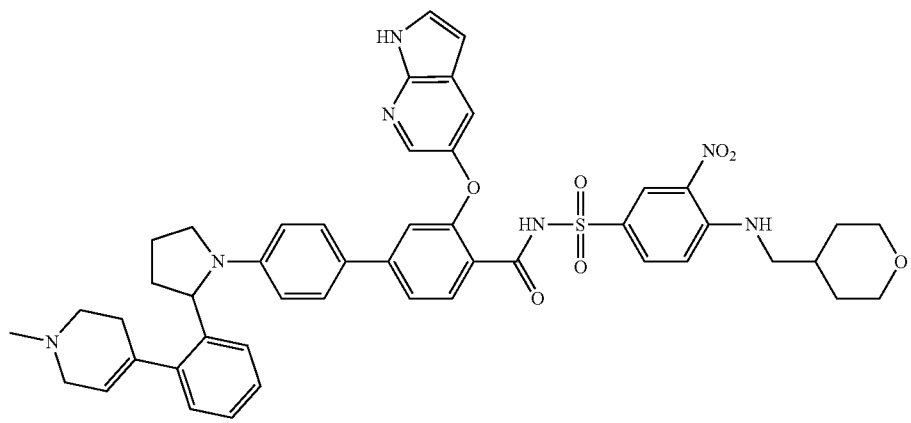 [SMILES: CN1CC=C(c2ccccc2C2CCCN2c2ccc(-c3ccc(C(=O)NS(=O)(=O)c4ccc(NCC5CCOCC5)c([N+](=O)[O-])c4)c(Oc4cnc5[nH]ccc5c4)c3)cc2)CC1]

The desired compound was synthesized starting from 1-methyl-4-(2-(pyrrolidin-2-yl)phenyl)-1,2,3,6-tetrahydropyridine and 1-bromo-4-iodobenzene following the procedures similar to those in Example A1. $^1$H NMR (400 MHz, DMSO-d$_6$) δ ppm: 11.56 (s, 1H), 8.41-8.37 (m, 2H), 7.96 (s, 1H), 7.68 (d, J=8.8 Hz, 1H), 7.57 (d, J=8.0 Hz, 1H), 7.43 (s, 1H), 7.37 (s, 1H), 7.30 (d, J=8.4 Hz, 2H), 7.33-7.12 (m, 4H), 7.04 (d, J=12 Hz, 1H), 6.91 (s, 1H), 6.87 (d, J=9.2 Hz, 1H), 6.38 (d, J=8.4 Hz, 1H), 6.30 (s, 1H), 5.70 (m, 1H), 4.85 (d, J=7.2 Hz, 1H), 3.84 (d, J=8.4 Hz, 2H), 3.79-3.55 (m, 3H), 3.28-3.12 (m, 7H), 2.79-2.56 (m, 5H), 2.42-2.31 (m, 1H), 2.09-1.71 (m, 5H), 1.61 (d, J=12.8 Hz, 2H), 1.50-1.32 (m, 2H). MS (ESI, m/e) [M+1]$^+$ 867.7.

Example A68-R: (R)-3-((1H-pyrrolo[2,3-b]pyridin-5-yl)oxy)-4'-(2-(2-(1-methyl-1,2,3,6-tetrahydropyridin-4-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

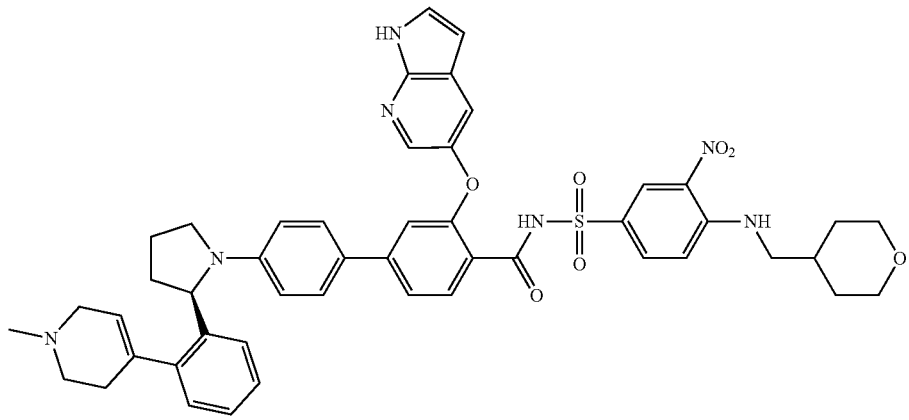 [SMILES: CN1CC=C(c2ccccc2[C@H]2CCCN2c2ccc(-c3ccc(C(=O)NS(=O)(=O)c4ccc(NCC5CCOCC5)c([N+](=O)[O-])c4)c(Oc4cnc5[nH]ccc5c4)c3)cc2)CC1]

Step 1: (R)-1-(2-(2-bromophenyl)pyrrolidin-1-yl)-2,2,2-trifluoroethan-1-one

To a solution of (R)-2-(2-bromophenyl)pyrrolidine (10 g, 44.22 mmol) in DCM (100 ml) was added triethylamine (6.699 g, 66.33 mmol), then added (CF$_3$CO)$_2$O (10.216 g, 48.65 mmol) at 0° C. After stirred at room temperature for 1 hour, the reaction mixture was concentrated. The resulted residue was dissolved with DCM (500 ml), and then washed with saturated aq. NaHCO$_3$ solution, brine. After dried over Na$_2$SO$_4$, the organic phase was concentrated to obtain the product (14 g) as a brown solid. MS (ESI, m/e) [M+1]$^+$ 321.8.

Step 2: tert-butyl (R)-4-(2-(1-(2,2,2-trifluoroacetyl)pyrrolidin-2-yl)phenyl)-3,6-dihydropyridine-1 (2H)-carboxylate To a solution of (R)-1-(2-(2-bromophenyl)pyrrolidin-1-yl)-2,2,2-trifluoroethan-1-one (5 g, 15.52 mmol) in toluene (100 ml) was added tert-butyl 4-(4,4,5,5-tetramethyl-1,3,2-dioxaborolan-2-yl)-3,6-dihydropyridine-1(2H)-carboxylate (7.189 g, 23.25 mmol), Pd(OAc)$_2$ (348 mg, 1.552 mmol), Tricyclohexyl phosphine (870 mg, 3.1 mmol) and K3PO4 (11.53 g, 54.32 mmol). The mixture was then stirred at 100° C. for 12 hours at N$_2$ atmosphere. After cooled to room temperature, the reaction mixture was washed with brine and dried over Na$_2$SO$_4$. After removal of solvent, the resulted residue was purified by chromatograph column on silica gel (eluent: PE/EA=50/1 to 10/1) to obtain the product (3.66 g) as yellow oil. MS (ESI, m/e) [M-55]$^+$ 368.8.

Step 3: (R)-2,2,2-trifluoro-1-(2-(2-(1,2,3,6-tetrahydropyridin-4-yl)phenyl)pyrrolidin-1-yl)ethan-1-one To a solution of tert-butyl (R)-4-(2-(1-(2,2,2-trifluoroacetyl)pyrrolidin-2-yl)phenyl)-3,6-dihydropyridine-1(2H)-carboxylate (3.66 g, 8.62 mmol) in DCM (100 ml) was added TFA (20 ml). The mixture was stirred at room temperature for 2 hours. After removal of solvent and TFA, the residue was dissolved with DCM (200 ml) and then washed with saturated aq. NaHCO$_3$ solution, brine, dried over Na$_2$SO$_4$, The DCM solution was concentrated to obtain the crude product (2.66 g) as a brown oil, which was used in next step without further purification.

Step 4: (R)-2,2,2-trifluoro-1-(2-(2-(1-methyl-1,2,3,6-tetrahydropyridin-4-yl)phenyl)pyrrolidin-1-yl)ethan-1-one To a solution of (R)-2,2,2-trifluoro-1-(2-(2-(1,2,3,6-tetrahydropyridin-4-yl)phenyl)pyrrolidin-1-yl)ethan-1-one (2.66 g, 8.2 mmol) in MeOH (100 mL) was added HCHO (37%, 3.99 g 49.18 mmol) and NaBH$_3$CN (2.058 g, 32.77 mmol). The mixture was stirred at room temperature for 2 hours. After removal of solvent, the residue was dissolved with EA (200 mi), washed with brine, and then dried over Na$_2$SO$_4$. The EA solution was concentrated to obtain the crude product (2.5 g) as a yellow solid, which was used in next step without further purification. MS (ESI, m/e) [M+1]+ 338.9.

Step 5: (R)-1-methyl-4-(2-(pyrrolidin-2-yl)phenyl)-1,2,3,6-tetrahydropyridine

To a solution of (R)-2,2,2-trifluoro-1-(2-(2-(1-methyl-1,2,3,6-tetrahydropyridin-4-yl)phenyl)pyrrolidin-1-yl)ethan-1-one (2.5 g, 7.39 mmol) in MeOH (50 mL) and H$_2$O (50 mL) was added LiOH.H$_2$O (3.1 g, 73.9 mmol). After stirred at 60° C. for 3 hours, the reaction mixture was extracted with DCM (200 mL×3). The combined organic phase was concentrated. The residue was purified by column chromatograph on silica gel (eluent: DCM/MeOH=10/1 (added 1% NH3.H2O)) to obtain the product (1.2 g). MS (ESI, m/e) [M+1]+ 243.0.

Step 6: (R)-4-(2-(1-(4-bromophenyl)pyrrolidin-2-yl)phenyl)-1-methyl-1,2,3,6-tetrahydropyridine To a solution of (R)-1-methyl-4-(2-(pyrrolidin-2-yl)phenyl)-1,2,3,6-tetrahydropyridine (500 mg, 2.07 mmol) in toluene (50 ml) was added 1-bromo-4-iodobenzene (1.165 g, 4.13 mmol), Pd$_2$(dba)$_3$ (189 mg, 0.207 mmol), BINAP (257.5 mg, 0.414 mmol) and t-BuOK (757.6 mg, 6.21 mmol). The mixture was stirred at 90° C. for 12 hours at N$_2$ atmosphere. After cooled to room temperature, the reaction mixture was washed with brine, dried over Na$_2$SO$_4$ and concentrated. The residue was purified by chromatograph column on silica gel (DCM/MeOH=50/1) to obtain the product (508 mg) as a yellow oil. MS (ESI, m/e) [M+1]+ 396.8.

Step 7: tert-butyl (R)-3-((1H-pyrrolo[2,3-b]pyridin-5-yl)oxy)-4'-(2-(2-(1-methyl-1,2,3,6-tetrahydropyridin-4-yl)phenyl)pyrrolidin-1-yl)-[1,1'-biphenyl]-4-carboxylate To a solution of (R)-4-(2-(1-(4-bromophenyl)pyrrolidin-2-yl)phenyl)-1-methyl-1,2,3,6-tetrahydropyridine (508 mg, 1.28 mmol) and tert-butyl 2-((1H-pyrrolo[2,3-b]pyridin-5-yl)oxy)-4-(3,3,4,4-tetramethylborolan-1-yl)benzoate (725.3 mg, 1.66 mmol) in 1,4-dioxane (50 mL) and H$_2$O (5 mL) was added Pd(ddpf)Cl$_2$ (93.6 mg, 0.128 mmol) and Cs$_2$CO$_3$ (1248 mg, 3.84 mmol). The mixture was stirred at 100° C. for 3 hours under N$_2$ protection. After cooled to room temperature, the reaction mixture was diluted with DCM (200 mL), then washed with brine (200 mL×2) and dried over Na2SO4. After concentration, the residue was purified by chromatography column on silica (eluent: DCM/MeOH=25/1) to obtain the product (367 mg) as a yellow solid. MS (ESI, m/e) [M+1]+ 626.9.

Step 8: (R)-3-((1H-pyrrolo[2,3-b]pyridin-5-yl)oxy)-4'-(2-(2-(1-methyl-1,2,3,6-tetrahydropyridin-4-yl)phenyl)pyrrolidin-1-yl)-[1,1'-biphenyl]-4-carboxylic acid To a solution of tert-butyl (R)-3-((1H-pyrrolo[2,3-b]pyridin-5-yl)oxy)-4'-(2-(2-(1-methyl-1,2,3,6-tetrahydropyridin-4-yl)phenyl)pyrrolidin-1-yl)-[1,1'-biphenyl]-4-carboxylate (367 mg, 0.585 mmol) in DCM (30 ml) was added TFA (15 ml). The mixture was stirred at room temperature for 2 hours. After removal of solvent and TFA, the crude product was obtained as a yellow solid, which was used in next step without further purification. MS (ESI, m/e) [M+1]+ 570.9.

The desired compound was then synthesized with 3-nitro-4-(((tetrahydro-2H-pyran-4-yl)methyl)amino)benzenesulfonamide and (R)-3-((1H-pyrrolo[2,3-b]pyridin-5-yl)oxy)-4'-(2-(2-(1-methyl-1,2,3,6-tetrahydropyridin-4-yl)phenyl)pyrrolidin-1-yl)-[1,1'-biphenyl]4-carboxylic acid following the procedure similar to those in Example A1. $^1$H NMR (400 MHz, DMSO-d$_6$) δ ppm: 12.34 (br, 1H), 11.71 (s, 1H), 8.69-8.46 (m, 2H), 8.12-7.95 (m, 1H), 7.87-7.74 (m, 1H), 7.65-7.45 (m, 3H), 7.40-6.94 (m, 8H), 6.89 (s, 1H), 6.53-6.23 (m, 3H), 5.71 (s, 1H), 4.78 (d, J=8.0 Hz, 1H), 4.04-3.45 (m, 6H), 3.41-3.36 (m, 2H), 3.32-3.19 (m, 6H), 2.92-2.81 (m, 3H), 2.44-2.33 (m, 1H), 2.06-1.67 (m, 4H), 1.67-1.51 (m, 2H), 1.32-1.16 (m, 2H). MS (ESI, m/e) [M+1]+ 868.5.

Example A68-S: (S)-3-((1H-pyrrolo[2,3-b]pyridin-5-yl)oxy)-4'-(2-(2-(1-methyl-1,2,3,6-tetrahydropyridin-4-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

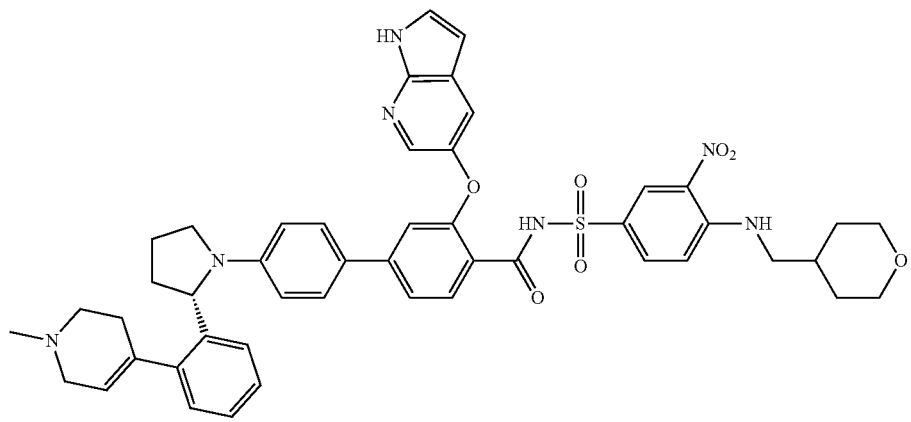 [SMILES: CN1CC=C(c2ccccc2[C@@H]2CCCN2c2ccc(-c3ccc(C(=O)NS(=O)(=O)c4ccc(NCC5CCOCC5)c([N+](=O)[O-])c4)c(Oc4cnc5[nH]ccc5c4)c3)cc2)CC1]

The desired compound was synthesized following the procedures similar to those in Example A68-R by replacing (R)-1-methyl-4-(2-(pyrrolidin-2-yl)phenyl)-1,2,3,6-tetrahydropyridine with (S)-1-methyl-4-(2-(pyrrolidin-2-yl)phenyl)-1,2,3,6-tetrahydropyridine. $^1$H NMR (400 MHz, DMSO-$d_6$) δ ppm: 11.55 (s, 1H), 8.39 (s, 1H), 8.36 (s, 1H), 7.96 (d, J=2.3 Hz, 1H), 7.66 (d, J=8.8 Hz, 1H), 7.56 (d, J=8.1 Hz, 1H), 7.42 (s, 1H), 7.35 (s, 1H), 7.29 (d, J=8.6 Hz, 2H), 7.27-7.09 (m, 4H), 7.03 (d, J=7.1 Hz, 1H), 6.91 (s, 1H), 6.85 (d, J=9.0 Hz, 1H), 6.37 (d, J=8.6 Hz, 2H), 6.30 (s, 1H), 5.69 (s, 1H), 4.84 (d, J=6.9 Hz, 1H), 3.83 (d, J=8.3 Hz, 2H), 3.74 (s, 1H), 3.30-3.21 (m, 6H), 3.08-2.91 (m, 3H), 2.40-2.29 (m, 3H), 2.10-1.70 (m, 6H), 1.60 (d, J=12.6 Hz, 2H), 1.30-1.18 (m, 3H). MS (ESI, m/e). [M+1]$^+$ 868.8.

Example A69: 3-((1H-pyrrolo[2,3-b]pyridin-5-yl)oxy)-4'-(2-(2-cyclopropylphenyl)pyrrolidin-1-yl)-3'-fluoro-N-((3-nitro-4-(((tetrahydro-2H-pyran-4-yl)methyl)amino)phenyl)sulfonyl)-[1,1'-biphenyl]-4-carboxamide

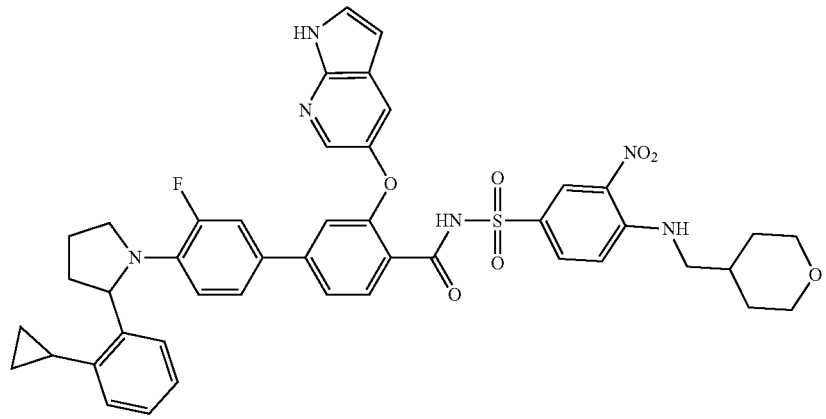 [SMILES: O=C(NS(=O)(=O)c1ccc(NCC2CCOCC2)c([N+](=O)[O-])c1)c1ccc(-c2ccc(N3CCCC3c3ccccc3C3CC3)c(F)c2)cc1Oc1cnc2[nH]ccc2c1]

The desired compound was synthesized from 1-(4-bromo-2-fluorophenyl)-2-(2-cyclopropylphenyl)pyrrolidine following the procedures similar to those in Example A1. $^1$H NMR (DMSO-$d_6$) δ ppm: 12.25 (s, 1H), 11.66 (s, 1H), 8.56-8.53 (m, 2H), 8.01 (s, 1H), 7.78 (d, J=8.8 Hz, 1H), 7.54-7.48 (m, 3H), 7.36 (d, J=8.1 Hz, 1H), 7.25 (d, J=15.8 Hz, 1H), 7.13 (d, J=8.1 Hz, 1H), 7.09-7.04 (m, 2H), 7.01-6.96 (m, 3H), 6.46 (t, J=8.8 Hz, 1H), 6.36 (s, 1H), 5.38 (s, 1H), 3.94 (s, 1H), 3.84 (d, J=8.7 Hz, 2H), 3.57-3.49 (m, 1H), 3.30-3.24 (m, 4H), 2.09-2.01 (m, 1H), 1.96-1.82 (m, 3H), 1.78-1.68 (m, 1H), 1.65-1.55 (m, 2H), 1.31-1.16 (m, 3H), 1.07-0.89 (m, 3H), 0.78-0.71 (m, 1H), 0.68-0.63 (d, J=3.6 Hz, 1H). MS (ESI, m/e) [M+1]$^+$ 830.8.

Example A70: 3-((1H-pyrrolo[2,3-b]pyridin-5-yl)oxy)-4'-(2-(2-cyclopropylphenyl)pyrrolidin-1-yl)-2'-fluoro-N-((3-nitro-4-(((tetrahydro-2H-pyran-4-yl)methyl)amino)phenyl)sulfonyl)-[1,1'-biphenyl]-4-carboxamide

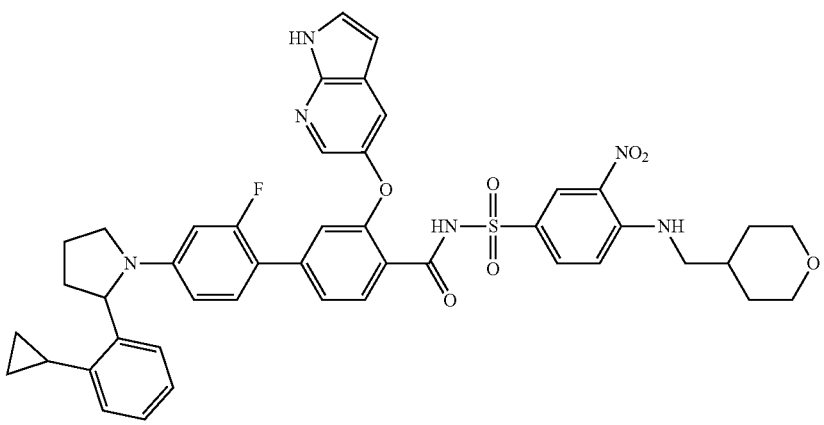

The desired compound was synthesized from 1-(4-bromo-3-fluorophenyl)-2-(2-cyclopropylphenyl)pyrrolidine following the procedures similar to those in Example A1. $^1$H NMR (DMSO-d$_6$) δ ppm: 12.24 (s, 1H), 11.72 (s, 1H), 8.68-8.52 (m, 2H), 8.05 (d, J=1.6 Hz, 1H), 7.85 (d, J=8.4 Hz, 1H), 7.63 (d, J=1.6 Hz, 1H), 7.57-7.48 (m, 2H), 7.22-6.99 (m, 6H), 6.86-6.75 (m, 2H), 6.40 (s, 1H), 6.22-6.06 (m, 2H), 5.24-5.12 (m, 1H), 3.87-3.80 (m, 2H), 3.74-3.65 (m, 1H), 3.29-3.23 (m, 3H), 2.47-2.35 (m, 1H), 2.07-1.82 (m, 5H), 1.65-1.52 (m, 2H), 1.29-1.21 (m, 2H), 1.08-0.93 (m, 4H), 0.81-0.62 (m, 2H). MS (ESI, m/e) [M+1]$^+$ 830.8.

Example A71: 3-((1H-pyrrolo[2,3-b]pyridin-5-yl)oxy)-4'-(2-(2-cyclopropylphenyl)-2-(trifluoromethyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

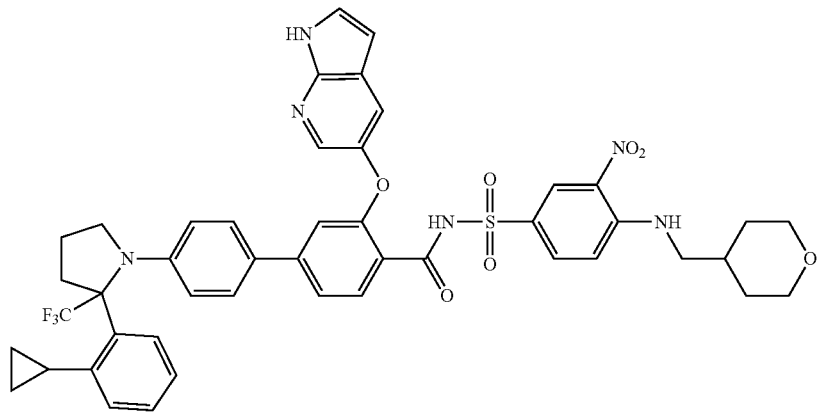 [SMILES: O=C(NS(=O)(=O)c1ccc(NCC2CCOCC2)c([N+](=O)[O-])c1)c1ccc(-c2ccc(N3CCCC3(c3ccccc3C3CC3)C(F)(F)F)cc2)cc1Oc1cnc2[nH]ccc2c1]

The desired compound was synthesized from 1-(4-bromophenyl)-2-(2-cyclopropylphenyl)-2-(trifluoromethyl)pyrrolidine following the procedures similar to those in Example A1. MS (ESI, m/e) [M+1]$^+$ 880.7.

Example A72: 3-((1H-pyrrolo[2,3-b]pyridin-5-yl)oxy)-4'-(2-(2-cyclopropylphenyl)piperidin-1-yl)-N-((3-nitro-4-(((tetrahydro-2H-pyran-4-yl)methyl)amino)phenyl)sulfonyl)-[1,1'-biphenyl]-4-carboxamide

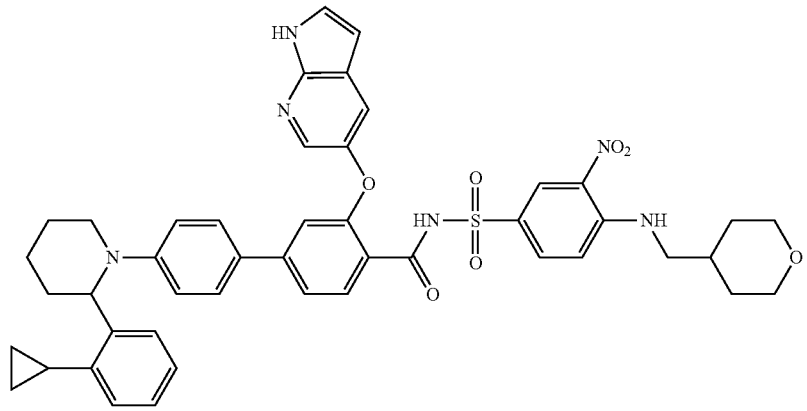 [SMILES: O=C(NS(=O)(=O)c1ccc(NCC2CCOCC2)c([N+](=O)[O-])c1)c1ccc(-c2ccc(N3CCCCC3c3ccccc3C3CC3)cc2)cc1Oc1cnc2[nH]ccc2c1]

The desired compound was synthesized from 1-(4-bromophenyl)-2-(2-cyclopropylphenyl)piperidine following the procedures similar to those in Example A1. MS (ESI, m/e) [M+1]⁺ 880.7.

Example A73: 3-((1H-pyrrolo[2,3-b]pyridin-5-yl)oxy)-4'-(2-(2-cyclopropylphenyl)-4-fluoropyrrolidin-1-yl)-N-((3-nitro-4-(((tetrahydro-2H-pyran-4-yl)methyl)amino)phenyl)sulfonyl)-[1,1'-biphenyl]-4-carboxamide

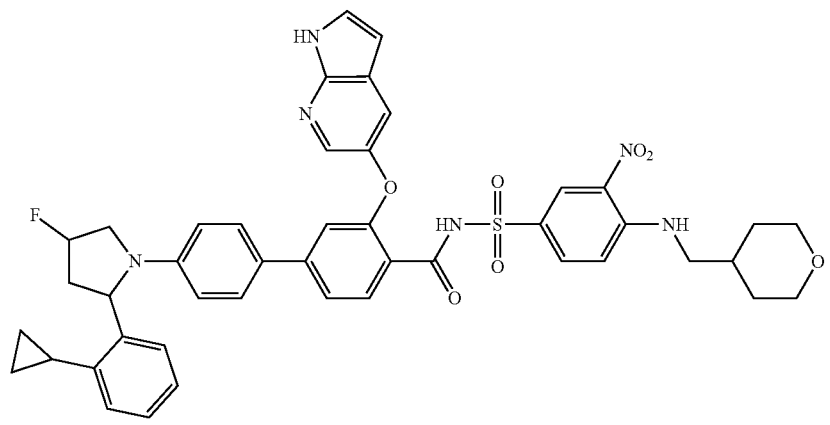 [SMILES: O=C(NS(=O)(=O)c1ccc(NCC2CCOCC2)c([N+](=O)[O-])c1)c1ccc(-c2ccc(N3CC(F)CC3c3ccccc3C3CC3)cc2)cc1Oc1cnc2[nH]ccc2c1]

The desired compound was synthesized starting from 2-(2-cyclopropylphenyl)-4-fluoropyrrolidine and 1-bromo-4-iodobenzene following the procedures similar to those in Example A1. ¹H NMR (CDCl3-d₆) δ ppm: 10.90-10.17 (m, 1H), 8.89 (s, 1H), 8.53 (s, 1H), 8.28-7.32 (m, 5H), 7.23-6.30 (m, 10H), 5.52-5.19 (m, 2H), 4.16-3.91 (m, 3H), 3.54-3.23 (m, 4H), 3.08-2.63 (m, 5H), 2.53-2.26 (m, 1H), 2.04-1.60 (m, 4H), 1.34-1.18 (m, 1H), 1.04-0.67 (m, 4H). MS (ESI, m/e) [M+1]+830.7.

Example A74: 3-((1H-pyrrolo[2,3-b]pyridin-5-yl)oxy)-4'-(4-chloro-2-(2-cyclopropylphenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

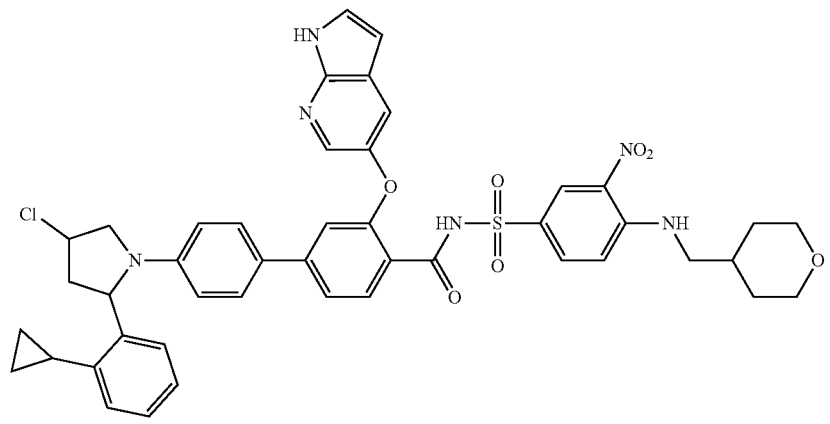 [SMILES: O=C(NS(=O)(=O)c1ccc(NCC2CCOCC2)c([N+](=O)[O-])c1)c1ccc(-c2ccc(N3CC(Cl)CC3c3ccccc3C3CC3)cc2)cc1Oc1cnc2[nH]ccc2c1]

The desired compound was synthesized starting from 4-chloro-2-(2-cyclopropylphenyl)pyrrolidine and 1-bromo-4-iodobenzene following the procedures similar to those in Example A1. ¹H NMR (DMSO-d₆) δ ppm: 12.19 (s, 1H), 11.70 (s, 1H), 8.66-8.51 (m, 2H), 8.05 (d, J=2.4 Hz, 1H), 7.83 (dd, J=8.8 Hz, 2.0 Hz, 1H), 7.62-7.48 (m, 3H), 7.37-7.27 (m, 3H), 7.21-7.06 (m, 3H), 7.01 (t, J=6.4 Hz, 2H), 6.91 (s, 1H), 6.46-6.34 (m, 3H), 5.26-5.16 (m, 1H), 4.90-4.80 (m, 1H), 3.96 (d, J=4.4 Hz, 2H), 3.87-3.80 (m, 2H), 3.29-3.17 (m, 4H), 2.18-2.09 (m, 1H), 2.04-1.96 (m, 1H), 1.92-1.82 (m, 1H), 1.63-1.55 (m, 2H), 1.30-1.21 (m, 4H), 1.01-0.91 (m, 2H), 0.80-0.66 (m, 2H). MS (ESI, m/e) [M+1]⁺ 846.7.

Example A75: 3-((1H-pyrrolo[2,3-b]pyridin-5-yl)oxy)-4'-(2-(2-cyclopropylphenyl)-4-methoxypyrrolidin-1-yl)-N-((3-nitro-4-(((tetrahydro-2H-pyran-4-yl)methyl)amino)phenyl)sulfonyl)-[1,1'-biphenyl]-4-carboxamide

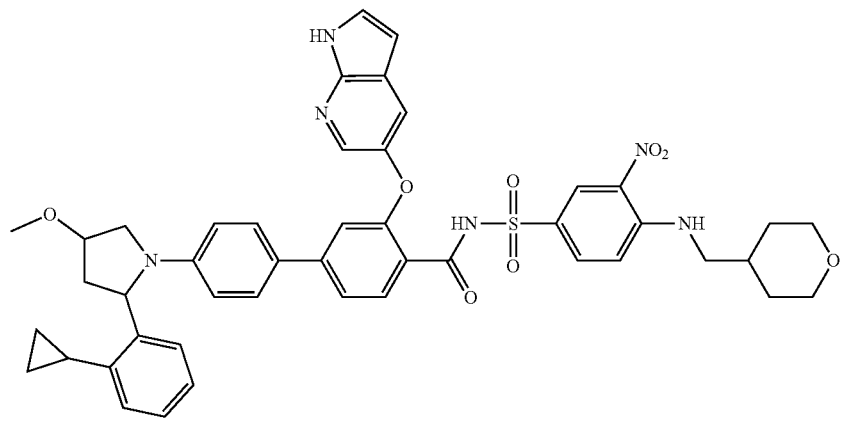 [SMILES: COC1CC(c2ccccc2C2CC2)N(c2ccc(-c3ccc(C(=O)NS(=O)(=O)c4ccc(NCC5CCOCC5)c([N+](=O)[O-])c4)c(Oc4cnc5[nH]ccc5c4)c3)cc2)C1]

The desired compound was synthesized starting from 2-(2-cyclopropylphenyl)-4-methoxypyrrolidine and 1-bromo-4-iodobenzene following the procedures similar to those in Example A1. ¹H NMR (DMSO-d₆) δ ppm: 12.16 (br, 1H), 11.68 (s, 1H), 8.62-8.55 (m, 2H), 8.03 (s, 1H), 7.83-7.79 (m, 1H), 7.57-7.47 (m, 3H), 7.34-7.27 (m, 3H), 7.14-6.96 (m, 5H), 6.90 (s, 1H), 6.42-6.35 (m, 3H), 4.17-4.08 (m, 1H), 3.98-3.83 (m, 1H), 3.84 (d, J=8.8 Hz, 2H), 3.47-3.42 (m, 1H), 3.25-3.16 (m, 6H), 3.06-2.93 (m, 1H), 2.67-2.51 (m, 1H), 2.09-1.95 (m, 4H), 1.92-1.81 (m, 1H), 1.61 (d, J=12.4 Hz, 2H), 1.50-1.43 (m, 1H), 0.95-0.84 (m, 2H), 0.68-0.45 (m, 2H). MS (ESI, m/e) [M+1]⁺ 842.8.

Example A76: 3-((1H-pyrrolo[2,3-b]pyridin-5-yl)oxy)-4'-(2-(2-cyclopropylphenyl)-3-methylpyrrolidin-1-yl)-N-((3-nitro-4-(((tetrahydro-2H-pyran-4-yl)methyl)amino)phenyl)sulfonyl)-[1,1'-biphenyl]-4-carboxamide

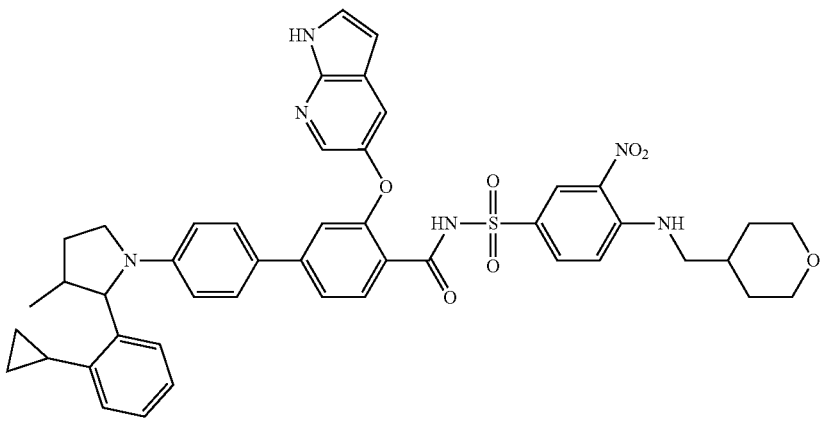 [SMILES: CC1CCN(c2ccc(-c3ccc(C(=O)NS(=O)(=O)c4ccc(NCC5CCOCC5)c([N+](=O)[O-])c4)c(Oc4cnc5[nH]ccc5c4)c3)cc2)C1c1ccccc1C1CC1]

The desired compound was synthesized starting from 2-(2-cyclopropylphenyl)-3-methylpyrrolidine and 1-bromo-4-iodobenzene following the procedures similar to those in Example A1. ¹H NMR (DMSO-d₆) δ ppm: 12.15 (s, 1H), 11.70 (s, 1H), 8.65-8.50 (m, 2H), 8.08-8.00 (m, 1H), 7.87-7.74 (m, 1H), 7.62-7.48 (m, 3H), 7.36-7.25 (m, 3H), 7.15-7.07 (m, 2H), 7.05-6.88 (m, 3H), 6.86-6.80 (m, 1H), 6.44-6.31 (m, 3H), 5.28 (d, J=8.0 Hz, 0.66H), 4.79 (s, 0.33H), 3.87-3.80 (m, 2H), 3.75-3.64 (m, 1H), 3.30-3.22 (m, 4H), 2.77-2.64 (m, 1H), 2.22-2.03 (m, 2H), 1.92-1.82 (m, 1H), 1.80-1.64 (m, 1H), 1.63-1.56 (m, 2H), 1.32-1.18 (m, 3H), 1.13 (d, J=6.8 Hz, 1H), 1.06-0.94 (m, 2H), 0.90-0.80 (m, 1H), 0.75-0.64 (m, 3H). MS (ESI, m/e) [M+1]⁺ 826.8.

Example A77: 3-((1H-pyrrolo[2,3-b]pyridin-5-yl)oxy)-4'-(2-(2-cyclopropylphenyl)-3,3-dimethylpyrrolidin-1-yl)-N-((3-nitro-4-(((tetrahydro-2H-pyran-4-yl)methyl)amino)phenyl)sulfonyl)-[1,1'-biphenyl]-4-carboxamide

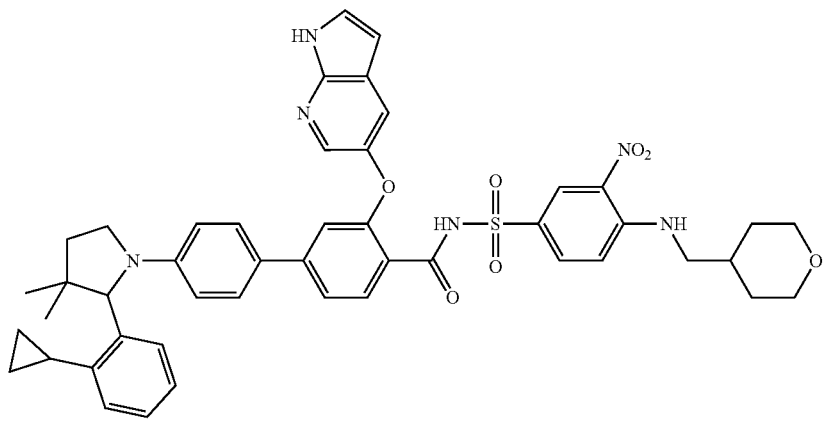 [SMILES: CC1(C)CCN(c2ccc(-c3ccc(C(=O)NS(=O)(=O)c4ccc(NCC5CCOCC5)c([N+](=O)[O-])c4)c(Oc4cnc5[nH]ccc5c4)c3)cc2)C1c1ccccc1C1CC1]

The desired compound was synthesized starting from 2-(2-cyclopropylphenyl)-3,3-dimethylpyrrolidine and 1-bromo-4-iodobenzene following the procedures similar to those in Example A1. ¹H NMR (DMSO-d₆) δ ppm: 12.15 (s, 1H), 11.69 (s, 1H), 8.60-8.55 (m, 2H), 8.03 (s, 1H), 7.81 (d, J=8.7 Hz, 1H), 7.62-7.45 (m, 3H), 7.33-7.27 (m, 3H), 7.10-7.04 (m, 2H), 7.02 (t, J=7.6 Hz, 1H), 6.95 (d, J=7.6 Hz, 1H), 6.92-6.83 (m, 2H), 6.37-6.35 (m, 2H), 4.87 (s, 1H), 3.84 (d, J=8.7 Hz, 2H), 3.70 (t, J=9.0 Hz, 1H), 3.51-3.43 (m, 1H), 3.29-3.22 (m, 3H), 2.09 (s, 1H), 2.04-1.95 (m, 2H), 1.87 (s, 1H), 1.74-1.71 (m, 1H), 1.60 (d, J=12.4 Hz, 2H), 1.45 (s, 1H), 1.18 (s, 3H), 1.08 (d, J=8.6 Hz, 1H), 0.98 (d, J=4.6 Hz, 1H), 0.95-0.82 (m, 2H), 0.70-0.68 (m, 4H). MS (ESI, m/e) [M+1]+840.8.

Example A78: 3-((1H-pyrrolo[2,3-b]pyridin-5-yl)oxy)-4'-(1-(2-cyclopropylphenyl)hexahydrocyclopenta[c]pyrrol-2(1H)-yl)-N-((3-nitro-4-(((tetrahydro-2H-pyran-4-yl)methyl)amino)phenyl)sulfonyl)-[1,1'-biphenyl]-4-carboxamide

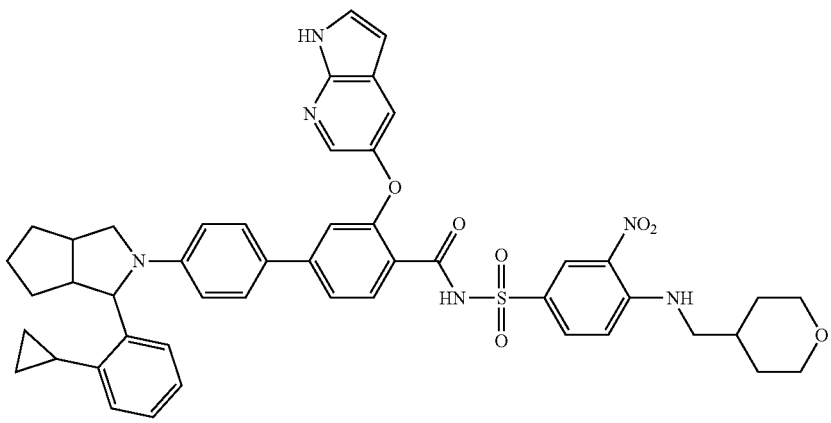 [SMILES: O=C(NS(=O)(=O)c1ccc(NCC2CCOCC2)c([N+](=O)[O-])c1)c1ccc(-c2ccc(N3CC4CCCC4C3c3ccccc3C3CC3)cc2)cc1Oc1cnc2[nH]ccc2c1]

The desired compound was synthesized starting from 1-(2-cyclopropylphenyl)octahydrocyclopenta[c]pyrrole and 1-bromo-4-iodobenzene following the procedures similar to those in Example A1. $^1$H NMR (DMSO-d$_6$) δ ppm: 11.54 (s, 1H), 8.40 (s, 1H), 8.36 (s, 1H), 7.95 (s, 1H), 7.66 (d, J=8.4 Hz, 1H), 7.54 (d, J=8.1 Hz, 1H), 7.42 (s, 1H), 7.35 (s, 1H), 7.30-7.21 (m, 3H), 7.12-6.98 (m, 3H), 6.93-6.77 (m, 3H), 6.36 (d, J=8.5 Hz, 2H), 6.30 (s, 1H), 5.34 (d, J=8.6 Hz, 1H), 3.83 (d, J=8.5 Hz, 2H), 3.72 (t, J=9.4 Hz, 1H), 3.49-3.38 (m, 1H), 3.30-3.19 (m, 6H), 2.10-1.98 (m, 2H), 1.90-1.76 (m, 2H), 1.66-1.35 (m, 6H), 1.08-0.90 (m, 3H), 0.90-0.71 (m, 2H), 0.71-0.59 (m, 1H). MS (ESI, m/e) [M+1]$^+$ 852.8.

Example A79: 3-((1H-pyrrolo[2,3-b]pyridin-5-yl)oxy)-4'-(2-cyclopropylpyrrolidin-1-yl)-N-((3-nitro-4-(((tetrahydro-2H-pyran-4-yl)methyl)amino)phenyl)sulfonyl)-[1,1'-biphenyl]-4-carboxamide

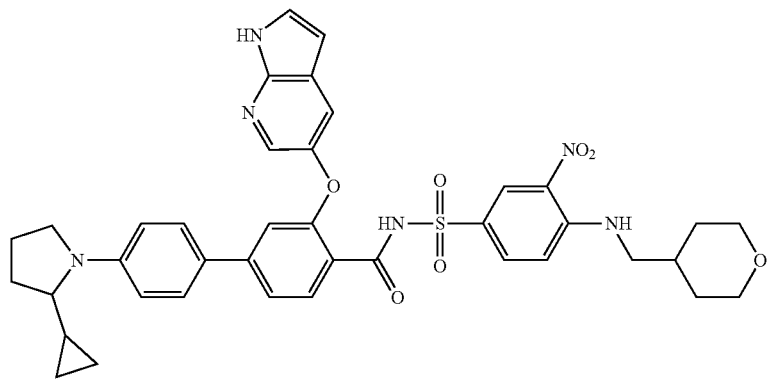 [SMILES: O=C(NS(=O)(=O)c1ccc(NCC2CCOCC2)c([N+](=O)[O-])c1)c1ccc(-c2ccc(N3CCCC3C3CC3)cc2)cc1Oc1cnc2[nH]ccc2c1]

The desired compound was synthesized starting from 2-cyclopropylpyrrolidine and 1-bromo-4-iodobenzene following the procedures similar to those in Example A1. MS (ESI, m/e) [M+1]$^+$ 736.8.

Example A80: 3-((1H-pyrrolo[2,3-b]pyridin-5-yl)oxy)-4'-(2-(2-ethylcyclohexyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

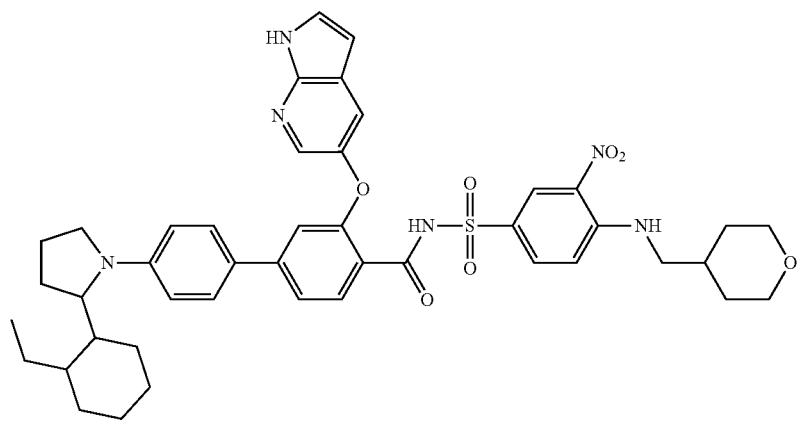 [SMILES: CCC1CCCCC1C1CCCN1c1ccc(-c2ccc(C(=O)NS(=O)(=O)c3ccc(NCC4CCOCC4)c([N+](=O)[O-])c3)c(Oc3cnc4[nH]ccc4c3)c2)cc1]

The desired compound was synthesized starting from 2-(2-ethylcyclohexyl)pyrrolidine and 1-bromo-4-iodobenzene following the procedures similar to those in Example A1. MS (ESI, m/e) [M+1]$^+$ 806.8.

Example A81: 3-((1H-pyrrolo[2,3-b]pyridin-5-yl)oxy)-4'-(2-(2-cyclopropylbenzyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

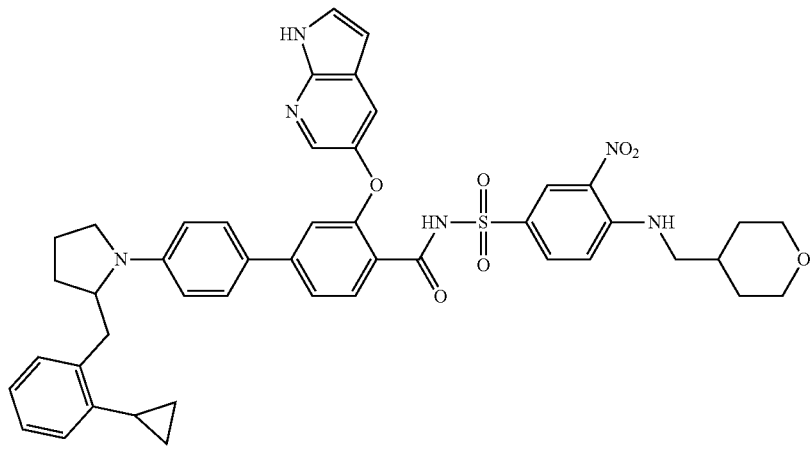 [SMILES: O=C(NS(=O)(=O)c1ccc(NCC2CCOCC2)c([N+](=O)[O-])c1)c1ccc(-c2ccc(N3CCCC3Cc3ccccc3C3CC3)cc2)cc1Oc1cnc2[nH]ccc2c1]

The desired compound was synthesized starting from 2-(2-cyclopropylbenzyl)pyrrolidine and 1-bromo-4-iodobenzene following the procedures similar to those in Example A1, MS (ESI, m/e) [M+1]$^+$ 826.8.

Example A82: 3-((1H-pyrrolo[2,3-b]pyridin-5-yl)oxy)-4'-(2-(4-cyclopropylpyridin-3-yl)pyrrolidin-1-yl)-N-((3-nitro-4-(((tetrahydro-2H-pyran-4-yl)methyl)amino)phenyl)sulfonyl)-[1,1'-biphenyl]-4-carboxamide

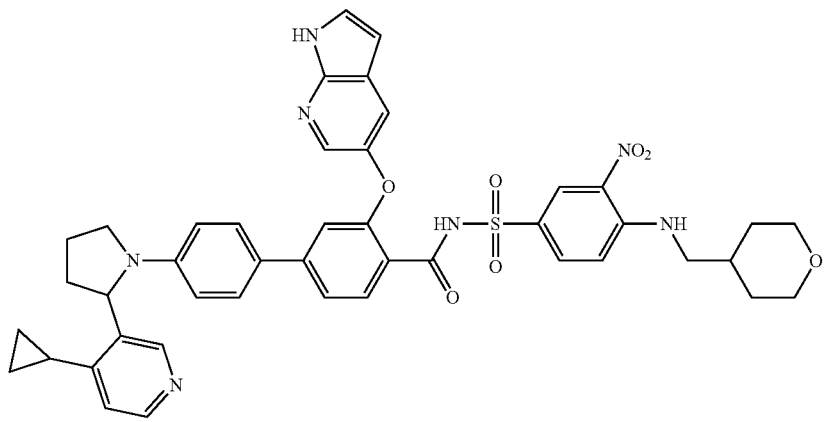 [SMILES: O=C(NS(=O)(=O)c1ccc(NCC2CCOCC2)c([N+](=O)[O-])c1)c1ccc(-c2ccc(N3CCCC3c3cnccc3C3CC3)cc2)cc1Oc1cnc2[nH]ccc2c1]

The desired compound was synthesized starting from 4-cyclopropyl-3-(pyrrolidin-2-yl)pyridine and 1-bromo-4-iodobenzene following the procedures similar to those in Example A1. $^1$H NMR (400 MHz, DMSO-d6) δ ppm: 12.16 (s, 1H), 11.70 (s, 1H), 8.61-8.57 (m, 2H), 8.41 (s, 1H), 8.05-8.02 (m, 2H), 7.83 (d, J=8.6 Hz, 1H), 7.61 (s, 1H), 7.57-7.49 (m, 2H), 7.36-7.32 (m, 3H), 7.24-7.11 (m, 2H), 6.89 (s, 1H), 6.65 (s, 2H), 6.42-6.39 (m, 3H), 5.23 (d, J=7.3 Hz, 1H), 3.84 (d, J=10.7 Hz, 2H), 3.28-3.22 (m, 4H), 2.02-1.99 (m, 6H), 1.91-1.89 (m, 1H), 1.61-1.58 (m, 2H), 1.45 (s, 3H), 0.85 (s, 4H). MS (ESI, m/e) [M+1]$^+$ 813.8.

Example A83: 3-((1H-pyrrolo[2,3-b]pyridin-5-yl)oxy)-4'-(2-(1-cyclopropyl-1H-pyrazol-5-yl)pyrrolidin-1-yl)-N-((3-nitro-4-(((tetrahydro-2H-pyran-4-yl)methyl)amino)phenyl)sulfonyl)-[1,1'-biphenyl]-4-carboxamide

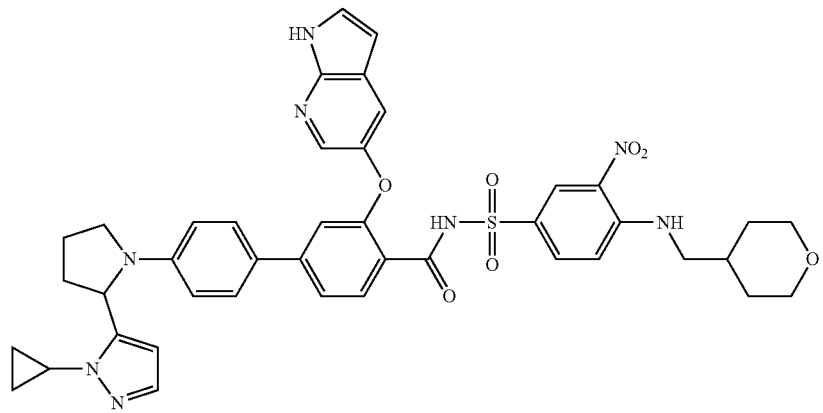 [SMILES: O=C(NS(=O)(=O)c1ccc(NCC2CCOCC2)c([N+](=O)[O-])c1)c1ccc(-c2ccc(N3CCCC3c3ccnn3C3CC3)cc2)cc1Oc1cnc2[nH]ccc2c1]

The desired compound was synthesized starting from 1-cyclopropyl-5-(pyrrolidin-2-yl)-1H-pyrazole and 1-bromo-4-iodobenzene following the procedures similar to those in Example A1. MS (ESI, m/e) [M+1]$^+$ 802.8

Example A84: 3-((1H-pyrrolo[2,3-b]pyridin-5-yl)oxy)-4'-(2-(3-chloro-2-cyclopropylphenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

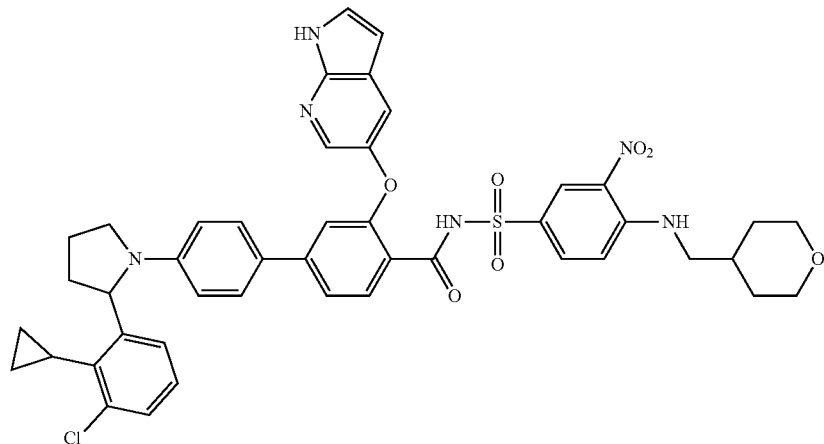 [SMILES: O=C(NS(=O)(=O)c1ccc(NCC2CCOCC2)c([N+](=O)[O-])c1)c1ccc(-c2ccc(N3CCCC3c3cccc(Cl)c3C3CC3)cc2)cc1Oc1cnc2[nH]ccc2c1]

The desired compound was synthesized starting from 2-(3-chloro-2-cyclopropylphenyl)pyrrolidine and 1-bromo-4-iodobenzene following the procedures similar to those in Example A1. MS (ESI, m/e) [M+1]+ 846.8

Example A85: 3-((1H-pyrrolo[2,3-b]pyridin-5-yl)oxy)-4'-(2-(2-cyclopropyl-5-methylphenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

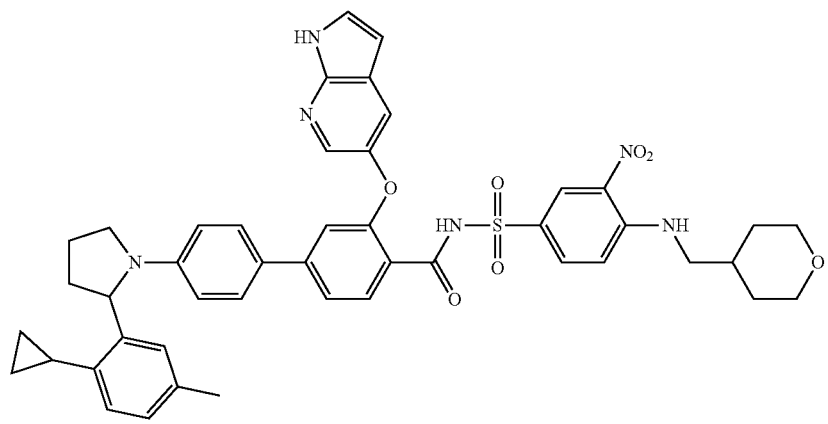 [SMILES: Cc1ccc(C2CC2)c(C2CCCN2c2ccc(-c3ccc(C(=O)NS(=O)(=O)c4ccc(NCC5CCOCC5)c([N+](=O)[O-])c4)c(Oc4cnc5[nH]ccc5c4)c3)cc2)c1]

The desired compound was synthesized starting from 2-(2-cyclopropyl-5-methylphenyl)pyrrolidine and 1-bromo-4-iodobenzene following the procedures similar to those in Example A1. $^1$H NMR (400 MHz, DMSO-d6) δ ppm: 12.15 (s, 1H), 11.68 (s, 1H), 8.55 (s, 2H), 8.04 (s, 1H), 7.80 (s, 1H), 7.58-7.50 (m, 3H), 7.36-7.30 (m, 2H), 7.14-7.08 (m, 1H), 6.91 (s, 2H), 6.79-6.63 (m, 3H), 6.40-6.30 (m, 3H), 5.16-5.10 (m, 1H), 3.8-3.80 (m, 3H), 3.73 (s, 1H), 2.99-2.86 (m, 5H), 2.10 (s, 2H), 2.05 (s, 1H), 1.97 (s, 3H), 1.66-1.58 (m, 2H), 1.30-1.20 (m, 2H), 0.95-0.89 (m, 2H), 0.74 (s, 1H), 0.64 (s, 1H). MS (ESI) m/e [M+1]+ 826.8.

Example A86: 3-((1H-pyrrolo[2,3-b]pyridin-5-yl)oxy)-4'-(2-(2,3-dihydrobenzofuran-7-yl)pyrrolidin-1-yl)-N-((3-nitro-4-(((tetrahydro-2H-pyran-4-yl)methyl)amino)phenyl)sulfonyl)-[1,1'-biphenyl]-4-carboxamide

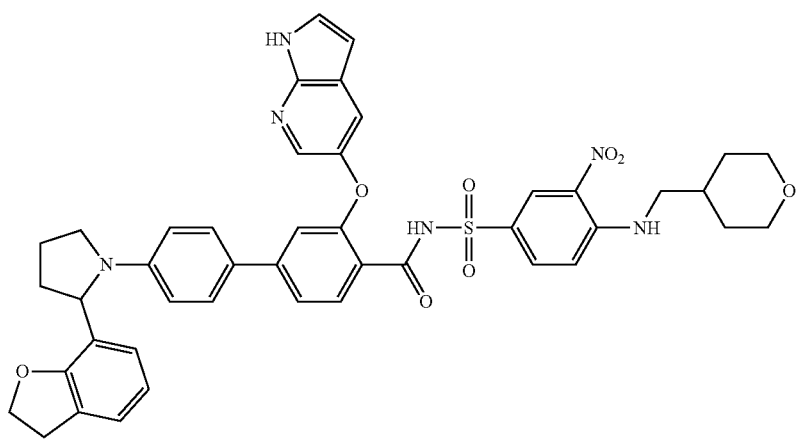 [SMILES: O=C(NS(=O)(=O)c1ccc(NCC2CCOCC2)c([N+](=O)[O-])c1)c1ccc(-c2ccc(N3CCCC3c3cccc4c3OCC4)cc2)cc1Oc1cnc2[nH]ccc2c1]

The desired compound was synthesized starting from 2-(2,3-dihydrobenzofuran-7-yl)pyrrolidine and 1-bromo-4-iodobenzene following the procedures similar to those in Example A1. MS (ESI) m/e [M+1]$^+$ 814.7.
Example A87: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(1-phenylhexahydrocyclopenta[c]pyrrol-2(1H)-yl)-[1,1'-biphenyl]-4-carboxamide
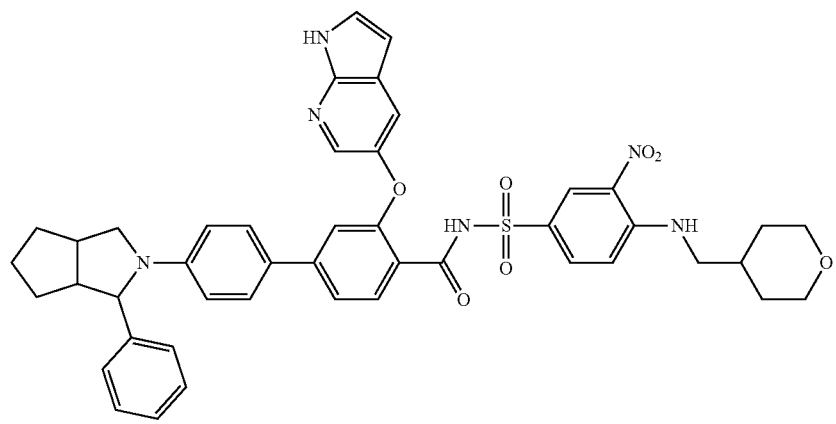 [SMILES: O=C(NS(=O)(=O)c1ccc(NCC2CCOCC2)c([N+](=O)[O-])c1)c1ccc(-c2ccc(N3CC4CCCC4C3c3ccccc3)cc2)cc1Oc1cnc2[nH]ccc2c1]

The desired compound was synthesized starting from 1-phenyloctahydrocyclopenta[c]pyrrole and 1-bromo-4-iodobenzene following the procedures similar to those in Example A1. $^1$H NMR (400 MHz, DMSO-d$_6$) δ ppm: 12.17 (br, 1H), 11.61 (s, 1H), 8.51-8.42 (m, 2H), 8.00 (d, J=2.4 Hz, 1H), 7.74 (d, J=8.0 Hz, 1H), 7.55 (d, J=8.4 Hz, 1H), 7.46 (s, 2H), 7.31-7.21 (m, 5H), 7.17-6.95 (m, 4H), 6.90 (s, 1H), 6.43 (d, J=8.8 Hz, 2H), 6.34 (s, 1H), 4.92 (d, J=8.4 Hz, 2H), 3.85 (d, J=8.4 Hz, 2H), 3.66 (t, J=9.2 Hz, 2H), 3.45-3.39 (m, 1H), 3.30-3.20 (m, 4H), 3.07-2.98 (m, 1H), 2.85-2.76 (m, 1H), 1.94-1.75 (m, 2H), 1.62 (d, J=12.8 Hz, 2H), 1.56-1.35 (m, 4H), 1.30-1.22 (m, 2H), 1.12-1.05 (m, 2H). MS (ESI, m/e) [M+1]$^+$ 812.8.

Example A88: 3-((1H-pyrrolo[2,3-b]pyridin-5-yl)oxy)-3'-(2-(2-cyclopropylphenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

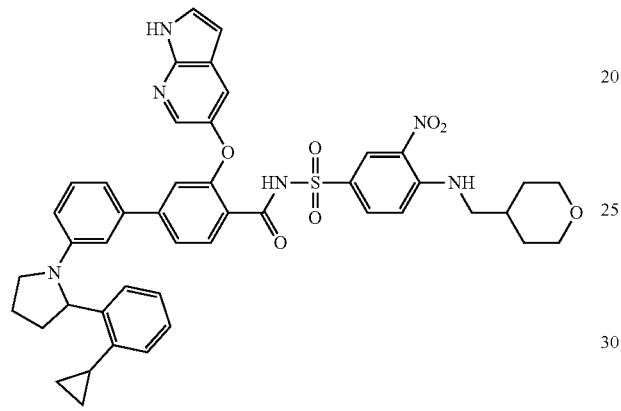

The desired compound was synthesized from 1-(3-bromophenyl)-2-(2-cyclopropylphenyl)pyrrolidine following the procedures similar to those in Example A1. $^1$H NMR (400 MHz, DMSO-d$_6$) δ ppm: 12.30 (s, 1H), 11.73 (s, 1H), 8.65-8.55 (m, 2H), 8.01 (s, 1H), 7.82 (d, J=8.9 Hz, 1H), 7.59-7.47 (m, 3H), 7.28-7.20 (m, 1H), 7.15-7.06 (m, 2H), 6.98-6.80 (m, 4H), 6.73 (s, 1H), 6.62 (d, J=7.4 Hz, 1H), 6.39 (s, 2H), 6.30 (s, 1H), 5.15 (d, J=7.4 Hz, 1H), 3.87-3.83 (m, 2H), 3.74-3.71 (m, 1H), 3.28-3.23 (m, 5H), 2.68 (s, 1H), 2.04-1.74 (m, 6H), 1.61-1.58 (m, 2H), 1.00-0.75 (m, 4H), 0.47-0.45 (m, 1H). MS (ESI) m/e [M+1]$^+$ 812.8.

Example A89: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(2-phenoxyphenyl)pyrrolidin-1-yl)-[1,1'-biphenyl]-4-carboxamide

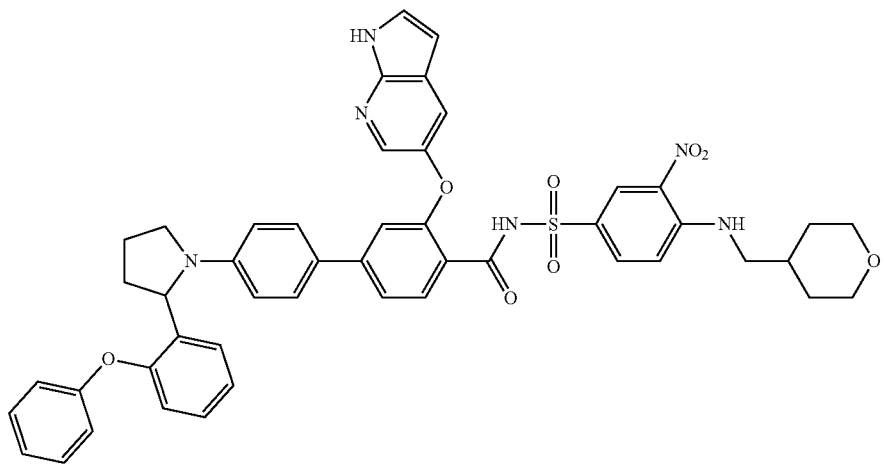 [SMILES: O=C(NS(=O)(=O)c1ccc(NCC2CCOCC2)c([N+](=O)[O-])c1)c1ccc(-c2ccc(N3CCCC3c3ccccc3Oc3ccccc3)cc2)cc1Oc1cnc2[nH]ccc2c1]

The desired compound was synthesized starting from 2-(2-phenoxyphenyl)pyrrolidine and 1-bromo-4-iodobenzene following the procedures similar to those in Example A1. MS (ESI) m/e [M+1]+ 864.7.

Example A90: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(2-(tetrahydro-2H-pyran-4-yl)phenyl)pyrrolidin-1-yl)-[1,1'-biphenyl]-4-carboxamide

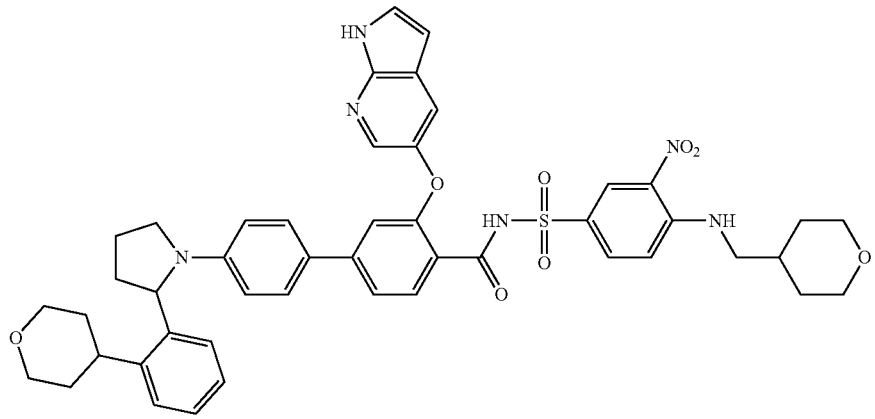 [SMILES: O=C(NS(=O)(=O)c1ccc(NCC2CCOCC2)c([N+](=O)[O-])c1)c1ccc(-c2ccc(N3CCCC3c3ccccc3C3CCOCC3)cc2)cc1Oc1cnc2[nH]ccc2c1]

The desired compound was synthesized starting from 2-(2-(tetrahydro-2H-pyran-4-yl)phenyl)pyrrolidine and 1-bromo-4-iodobenzene following the procedures similar to those in Example A1. $^1$H NMR (400 MHz, DMSO-d$_6$) δ ppm: 12.16 (s, 1H), 11.70 (s, 1H), 8.61 (d, J=5.6 Hz, 1H), 8.56 (d, J=1.8 Hz, 1H), 8.04 (d, J=2.3 Hz, 1H), 7.83 (d, J=7.9 Hz, 1H), 7.59 (d, J=1.9 Hz, 1H), 7.52 (d, J=8.1 Hz, 2H), 7.35-7.28 (m, 4H), 7.21-7.08 (m, 2H), 7.01 (t, J=7.4 Hz, 1H), 6.90 (s, 1H), 6.85 (d, J=7.6 Hz, 1H), 6.36 (d, J=9.3 Hz, 3H), 5.04 (d, J=7.9 Hz, 1H), 3.96 (t, J=9.9 Hz, 2H), 3.90-3.80 (m, 2H), 3.70 (t, J=7.9 Hz, 1H), 3.55-3.41 (m, 2H), 3.31-3.21 (m, 5H), 2.85 (s, 2H), 1.91-1.78 (m, 3H), 1.85-1.68 (m, 3H), 1.65-1.54 (m, 3H), 1.34-1.16 (m, 3H). MS (ESI, m/e) [M+1]+ 856.7.

Example A91: 3-((1H-pyrrolo[2,3-b]pyridin-5-yl)oxy)-4'-(2-(2-cyclopropylcyclohex-1-en-1-yl)pyrrolidin-1-yl)-N-((3-nitro-4-(((tetrahydro-2H-pyran-4-yl)methyl)amino)phenyl)sulfonyl)-[1,1'-biphenyl]-4-carboxamide

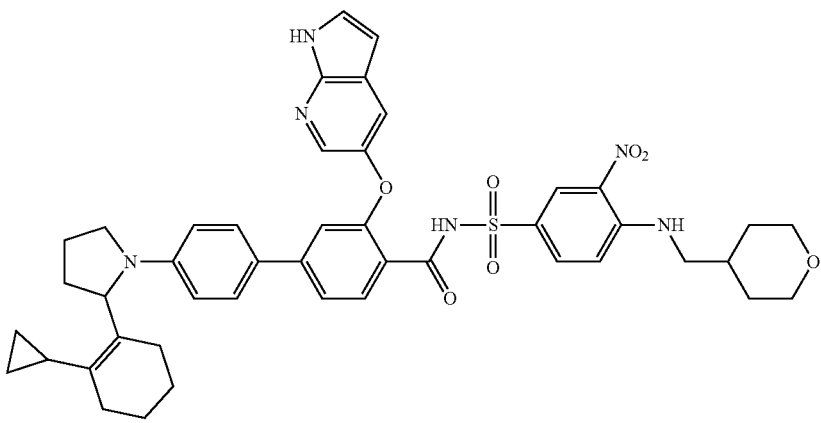 [SMILES: O=C(NS(=O)(=O)c1ccc(NCC2CCOCC2)c([N+](=O)[O-])c1)c1ccc(-c2ccc(N3CCCC3C3=C(C4CC4)CCCC3)cc2)cc1Oc1cnc2[nH]ccc2c1]

The desired compound was synthesized from 1-(4-bromophenyl)-2-(2-cyclopropylcyclohex-1-en-1-yl)pyrrolidine following the procedures similar to those in Example A1. $^1$H NMR (400 MHz, DMSO-$d_6$) δ ppm: 12.18 (s, 1H), 11.71 (s, 1H), 8.561-8.51 (m, 2H), 8.10-8.01 (m, 1H), 7.85-7.78 (m, 1H), 7.74-7.45 (m, 3H), 7.36 (d, J=8.6 Hz, 3H), 7.18-7.03 (m, 2H), 6.96 (s, 1H), 6.55-6.48 (m, 1H), 6.38 (s, 1H), 5.32 (s, 1H), 4.77 (s, 1H), 3.84 (d, J=9.4 Hz, 2H), 3.12-3.07 (m, 6H), 2.02-1.82 (m, 3H), 1.73 (s, 2H), 1.64-1.56 (m, 4H), 1.60-1.39 (m, 4H), 1.37-1.30 (m, 3H), 0.85-0.72 (m, 2H), 0.65-0.47 (m, 3H). MS (ESI, m/e) [M+1]$^+$ 816.8.

Example A92: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-phenylcyclopentyl)-[1,1'-biphenyl]-4-carboxamide

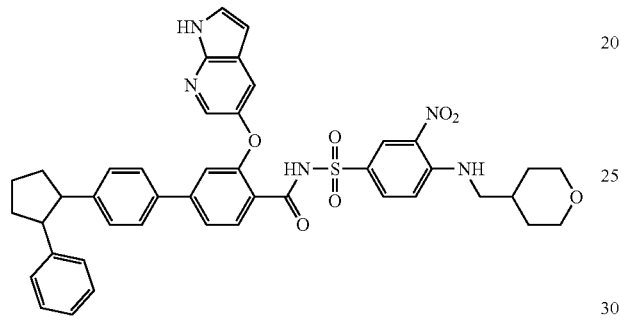

The desired compound was synthesized with 3-((1H-pyrrolo[2,3-b]pyridin-5-yl)oxy)-4'-(2-phenylcyclopentyl)-[1,1'-biphenyl]-4-carboxylic acid and 3-nitro-4-(((tetrahydro-2H-pyran-4-yl)methyl)amino)benzenesulfonamide following the procedure similar to those in Example A1. MS (ESI, m/e) [M+1]$^+$ 772.8.

Example A93: 3-((1H-pyrrolo[2,3-b]pyridin-5-yl)oxy)-4'-(2-(2-cyclopropylphenyl)pyrrolidin-1-yl)-N-(methyl(3-nitro-4-(((tetrahydro-2H-pyran-4-yl)methyl)amino)phenyl)(oxo)-16-sulfaneylidene)-[1,1'-biphenyl]-4-carboxamide

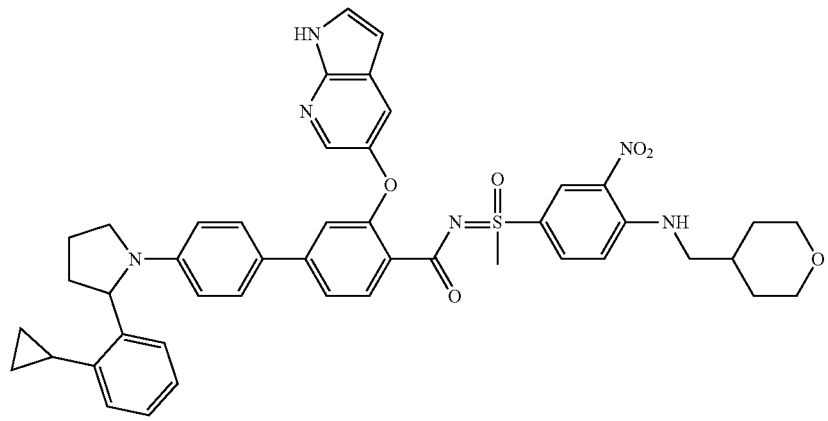 [SMILES: CS(=O)(=NC(=O)c1ccc(-c2ccc(N3CCCC3c3ccccc3C3CC3)cc2)cc1Oc1cnc2[nH]ccc2c1)c1ccc(NCC2CCOCC2)c([N+](=O)[O-])c1]

To a solution of 3-((1H-pyrrolo[2,3-b]pyridin-5-yl)oxy)-4'-(2-(2-cyclopropylphenyl)pyrrolidin-1-yl)-[1,1'-biphenyl]-4-carboxylic acid (100 mg, 0.194 mmol) in DCM (30 mL) was added EDCl (56 mg, 0.291 mmol) and DMAP (71 mg, 0,582 mmol). The mixture was stirred at room temperature for 0.5 hour. Then imino(methyl)(3-nitro-4-(((tetrahydro-2H-pyran-4-yl)methyl)amino)phenyl)-16-sulfanone (138 mg, 0.388 mmol) was added to the mixture. The mixture was stirred at room temperature for 2 days. The mixture was diluted with DCM (100 mL), then washed with saturated aq. NaHCO$_3$, brine, dried over Na$_2$SO$_4$, concentrated and purified by chromatography column on silica gel (eluent: DCM/EA=1/1 then MeOH/DCM=1/10) to give the crude product. The crude product was purified by prep-HPLC to give the desired compound (9 mg). $^1$H NMR (400 MHz, DMSO-d$_6$) δ ppm: 11.63 (s, 1H), 8.71-8.63 (m, 1H), 8.61-8.54 (m, 1H), 8.08-7.96 (m, 1H), 7.91-7.84 (m, 1H), 7.74-7.65 (m, 1H), 7.51-7.34 (s, 5H), 7.16-6.95 (m, 5H), 6.91-6.83 (m, 1H), 6.45-6.31 (m, 3H), 5.28-5.13 (m, 1H), 3.91-3.79 (m, 2H), 3.79-3.67 (m, 1H), 3.46-3.39 (m, 4H), 3.32-3.20 (m, 4H), 3.11-2.85 (m, 1H), 2.49-2.38 (m, 1H), 2.09-1.82 (m, 5H), 1.65-1.53 (m, 2H), 1.32-1.26 (m, 1H), 1.10-0.91 (m, 2H), 0.85-0.66 (m, 2H). MS (ESI, m/e) [M+1]$^+$ 810.8.

Example A94: 3-((1H-pyrrolo[2,3-b]pyridin-5-yl)oxy)-4'-(2-(2-(cyclopropylmethyl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

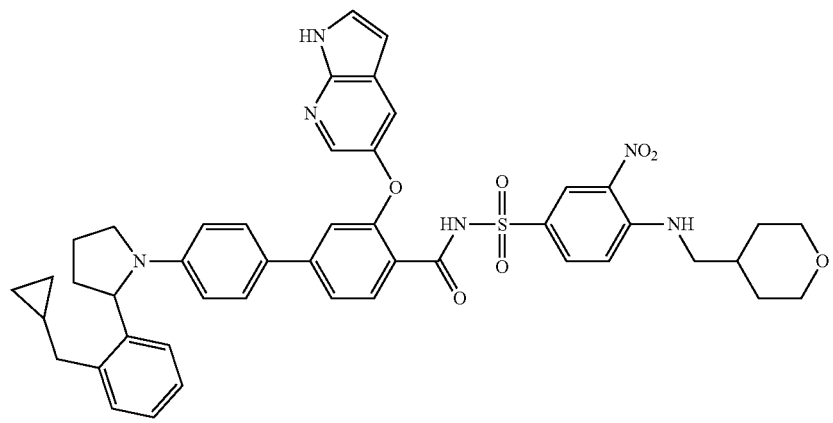 [SMILES: O=C(NS(=O)(=O)c1ccc(NCC2CCOCC2)c([N+](=O)[O-])c1)c1ccc(-c2ccc(N3CCCC3c3ccccc3CC3CC3)cc2)cc1Oc1cnc2[nH]ccc2c1]

The desired compound was synthesized starting from 2-(2-(cyclopropylmethyl)phenyl)pyrrolidine and 1-bromo-4-iodobenzene following the procedures similar to those in Example A1. $^1$H NMR (DMSO-d$_6$) δ ppm: 12.15 (s, 1H), 11.69 (s, 1H), 8.58 (m, 8.56-8.61, 2H), 8.04 (d, J=2.1 Hz, 1H), 7.82 (m, 1H), 7.58 (s, 1H), 7.55-7.47 (m, 2H), 7.39 (d, J=7.5 Hz, 1H), 7.31 (m, 3H), 7.16-7.11 (m, 2H), 7.05-7.01 (m, 1H), 6.89-6.84 (m, 2H), 6.38-6.35 (m, 3H), 4.92 (d, J=7.9 Hz, 1H), 3.84 (d, J=8.4 Hz, 2H), 3.71 (t, 3-7.7 Hz, 1H), 3.30-3.21 (m, 4H), 2.78-2.72 (m, 1H), 2.61-2.54 (m, 2H), 2.43-2.33 (m, 1H), 1.96-1.87 (m, 3H), 1.61-1.58 (m, 2H), 1.33-1.18 (m, 3H), 1.12-1.01 (m, 1H), 0.56 (d, J=7.7 Hz, 2H), 0.28 (d, J=2.1 Hz, 2H). MS (ESI, m/e) [M+1]$^+$ 826.8

Example A95: 3-((1H-pyrrolo[2,3-b]pyridin-5-yl)oxy)-2'-chloro-4'-(2-(2-cyclopropylphenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

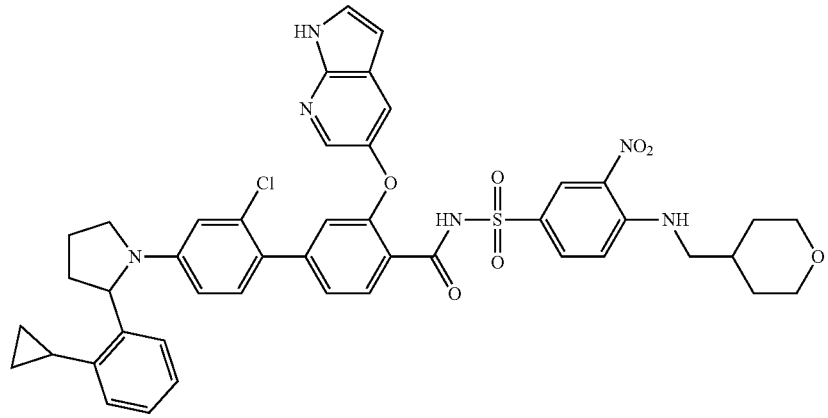 [SMILES: O=C(NS(=O)(=O)c1ccc(NCC2CCOCC2)c([N+](=O)[O-])c1)c1ccc(-c2ccc(N3CCCC3c3ccccc3C3CC3)cc2Cl)cc1Oc1cnc2[nH]ccc2c1]

The desired compound was synthesized starting from 2-(2-cyclopropylphenyl)pyrrolidine and 1-bromo-2-chloro-4-iodobenzene following the procedures similar to those in Example A1. $^1$H NMR (400 MHz, DMSO-d$_6$) δ ppm: 12.30 (s, 1H), 11.70 (s, 1H), 8.56 (s, 2H), 8.02 (s, 1H), 7.83 (d, J=8.8 Hz, 1H), 7.61 (s, 1H), 7.52 (d, J=8.2 Hz, 2H), 7.19-6.93 (m, 6H), 6.86 (d, J=7.5 Hz, 1H), 6.66 (s, 1H), 6.37 (s, 2H), 6.29 (d, J=8.3 Hz, 1H), 5.18 (d, J=7.9 Hz, 1H), 3.84 (d, J=8.5 Hz, 2H), 3.71 (t, J=7.7 Hz, 1H), 3.31-3.16 (m, 5H), 2.48-2.30 (m, 1H), 2.09-1.73 (m, 5H), 1.59 (d, J=12.4 Hz, 2H), 1.35-1.17 (m, 2H), 1.12-0.89 (m, 2H), 0.80 (dd, J=9.2, 4.2 Hz, 1H), 0.65 (dd, J=9.0, 3.8 Hz, 1H). MS (ESI, m/e) [M+1]$^+$ 846.7

Example A96: (R)-3-((1H-pyrrolo[2,3-b]pyridin-5-yl)oxy)-4'-(2-(2-(4,4-difluorocyclohexyl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

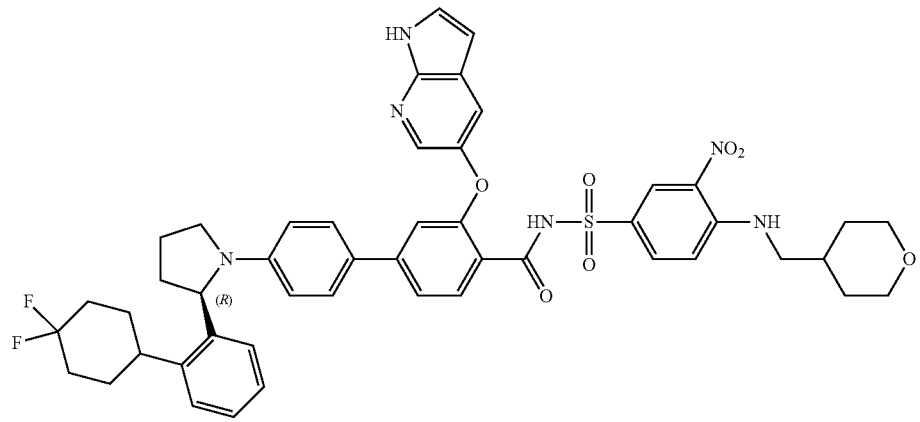

The desired compound was synthesized starting from (R)-2-(2-(4,4-difluorocyclohexyl)phenyl)pyrrolidine and 1-bromo-4-iodobenzene following the procedures similar to those in Example A1. MS (ESI, m/e) [M+1]$^+$ 890.8.

Example A97: 3-((1H-pyrrolo[2,3-b]pyridin-5-yl)oxy)-4'-((2R)-2-(2-(2-(dimethylamino)cyclopropyl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

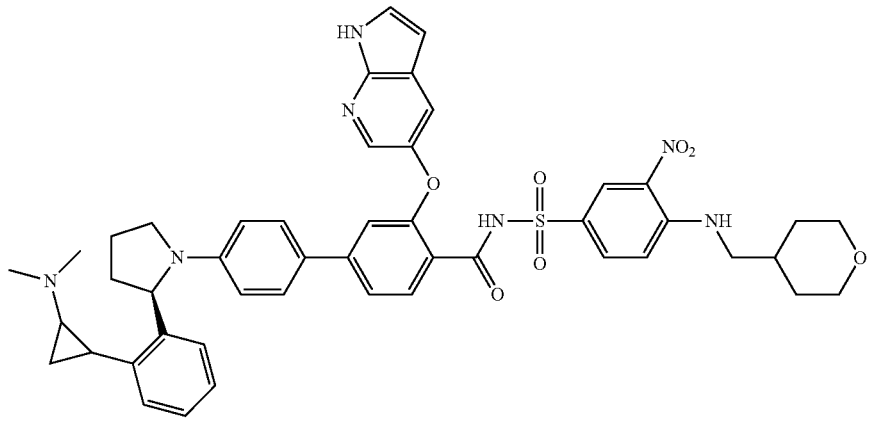 [SMILES: CN(C)C1CC1c1ccccc1[C@H]1CCCN1c1ccc(-c2ccc(C(=O)NS(=O)(=O)c3ccc(NCC4CCOCC4)c([N+](=O)[O-])c3)c(Oc3cnc4[nH]ccc4c3)c2)cc1]

The desired compound was synthesized starting from N,N-dimethyl-2-(2-((R)-pyrrolidin-2-yl)phenyl)cyclopropan-1-amine and 1-bromo-4-iodobenzene following the procedures similar to those in Example A1. $^1$H NMR (400 MHz, DMSO-d$_6$) δ ppm: 11.60 (s, 1H), 9.77 (s, 1H), 8.59-8.29 (m, 2H), 7.99 (s, 1H), 7.80-7.64 (m, 1H), 7.64-7.37 (m, 3H), 7.30-7.17 (m, 3H), 7.17-6.76 (m, 5H), 6.49-6.20 (m, 3H), 5.18-5.06 (m, 1H), 3.99-3.65 (m, 3H), 3.62-3.35 (m, 3H), 3.30-3.16 (m, 4H), 3.12-2.82 (m, 1H), 2.48-2.26 (m, 7H), 2.12-1.78 (m, 5H), 1.67-1.55 (m, 2H), 0.88-0.78 (m, 2H). MS (ESI, m/e) [M+1]$^+$ 855.8

Example A98: tert-butyl 4-(2-(1-(3'-((1H-pyrrolo[2,3-b]pyridin-5-yl)oxy)-4'-(((3-nitro-4-(((tetrahydro-2H-pyran-4-yl)methyl)amino)phenyl)sulfonyl)carbamoyl)-[1,1'-biphenyl]-4-yl)pyrrolidin-2-yl)phenyl)piperidine-1-carboxylate

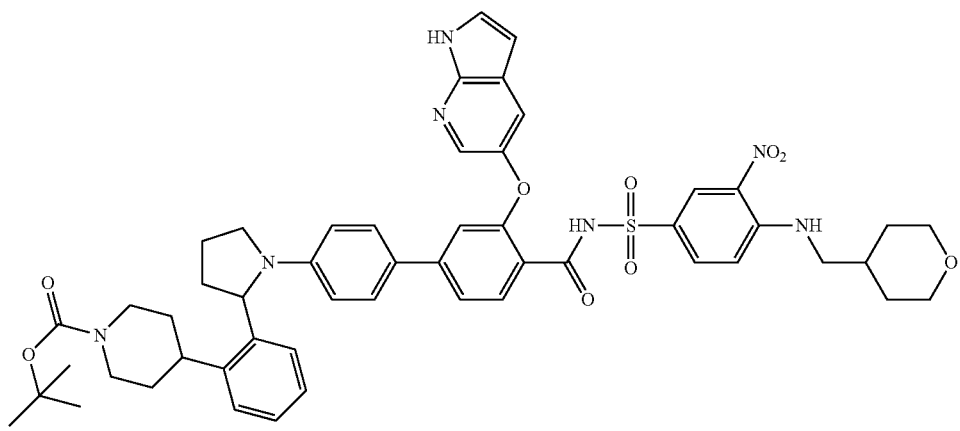 [SMILES: CC(C)(C)OC(=O)N1CCC(c2ccccc2C2CCCN2c2ccc(-c3ccc(C(=O)NS(=O)(=O)c4ccc(NCC5CCOCC5)c([N+](=O)[O-])c4)c(Oc4cnc5[nH]ccc5c4)c3)cc2)CC1]

The desired compound was synthesized starting from tert-butyl 4-(2-(pyrrolidin-2-yl)phenyl)piperidine-1-carboxylate and 1-bromo-4-iodobenzene following the procedures similar to those in Example A1. $^1$H NMR (400 MHz, DMSO-$d_6$): δ ppm: 12.16 (s, 1H), 11.70 (s, 1H), 8.62-8.56 (m, 2H), 8.04 (s, 1H), 7.82 (d, J=9.2 Hz, 1H), 7.61-7.49 (m, 3H), 7.35-7.28 (m, 4H), 7.19-7.11 (m, 2H), 7.01 (t, J=7.3 Hz, 1H), 6.90 (s, 1H), 6.84 (d, J=7.6 Hz, 1H), 6.67 (s, 1H), 6.37-6.35 (m, 3H), 5.03 (d, J=7.6 Hz, 1H), 4.10 (s, 2H), 3.84 (d, J=8.0 Hz, 2H), 3.71 (t, J=4 Hz, 1H), 3.39-3.33 (s, 2H), 3.27-3.17 (m, 4H), 3.06 (s, 1H), 2.99 (s. 1H), 2.02-1.97 (m, 3H), 1.85 (s, 2H), 1.74-1.56 (m, 5H), 1.43 (s, 10H), 1.27 (s, 2H). MS (ESI, m/e) [M+1]$^+$ 955.8.

Example A99: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(2-(piperidin-4-yl)phenyl)pyrrolidin-1-yl)-[1,1'-biphenyl]-4-carboxamide

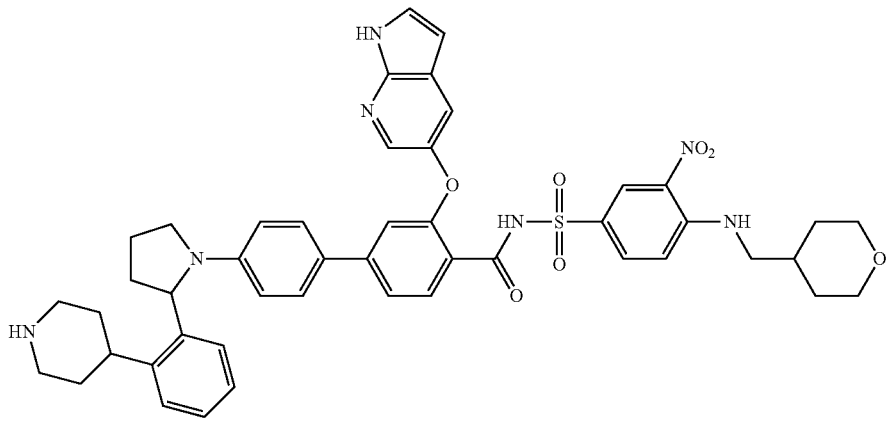 [SMILES: O=C(NS(=O)(=O)c1ccc(NCC2CCOCC2)c([N+](=O)[O-])c1)c1ccc(-c2ccc(N3CCCC3c3ccccc3C3CCNCC3)cc2)cc1Oc1cnc2[nH]ccc2c1]

The desired compound was synthesized by Boc deprotection of A98 in TFA/DCM. $^1$H NMR (400 MHz, DMSO-$d_6$) δ ppm: 12.16 (s, 1H), 11.70 (s, 1H), 8.58-8.56 (m, 2H), 8.04 (s, 1H), 7.81 (s, 1H), 7.59-7.50 (m, 3H), 7.30-7.22 (m, 5H), 7.14-7.11 (m, 1H), 7.05 (t, J=7.3 Hz, 1H), 6.88-6.86 (m, 2H), 6.67 (s, 1H), 6.38-6.36 (m, 2H), 5.05 (d, J=7.3 Hz, 1H), 3.84 (d, J=9.3 Hz, 2H), 3.72 (s, 1H), 3.40-3.38 (m, 2H), 3.29-3.23 (m, 5H), 3.06-2.96 (m, 3H), 2.0-1.96 (m, 4H), 1.88-1.82 (m, 3H), 1.69 (s, 1H), 1.60 (d, J=12.4 Hz, 2H), 1.45 (s, 1H), 1.28 (s, 2H). MS (ESI, m/e) [M+1]$^+$ 856.2.

Example A100: (R)-3-((1H-pyrrolo[2,3-b]pyridin-5-yl)oxy)-4'-(2-(2-(1-methylpiperidin-4-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

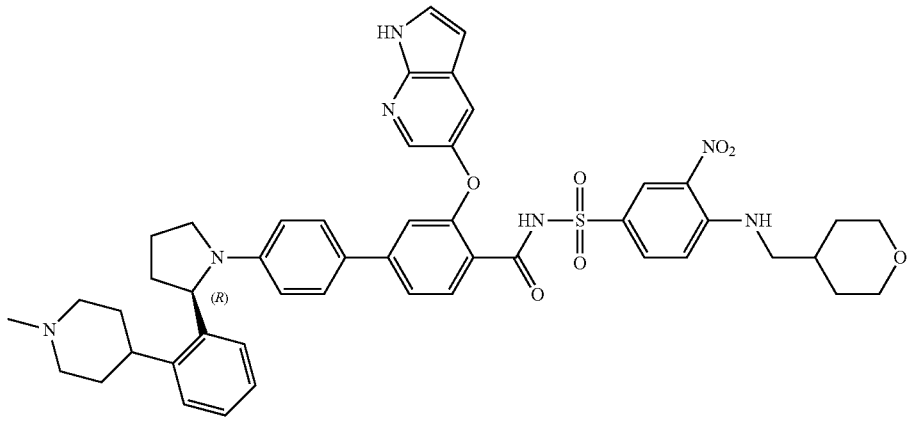

Step 1: tert-butyl (R)-2-(2-(1-methyl-1,2,3,6-tetrahydropyridin-4-yl)phenyl)pyrrolidine-1-carboxylate To a solution of tert-butyl (R)-2-(2-bromophenyl)pyrrolidine-1-carboxylate (14.6 g, 44.8 mmol) in dioxane/$H_2O$ (TOO mL/20 mL) were added 1-methyl-4-(4,4,5,5-tetramethyl-1,3,2-dioxaborolan-2-yl)-1,2,3,6-tetrahydropyridine (10 g, 44.8 mmol), Pd(dppf)$Cl_2$ (3.3 mg, 4.48 mmol) and $Cs_2CO_3$ (29 g, 90 mmol). The mixture was stirred at 90° C. for 12 hours under $N_2$ atmosphere. The reaction mixture was cooled to room temperature and then washed with brine, dried over $Na_2SO_4$, concentrated. The residue was purified by chromatograph column on silica gel (eluent: EA/$CH_3OH$=50/1 to 10/1) to give the product (4 g) as yellow oil. MS (ESI, m/e) [M+1]$^+$ 343.0.

Step 2: (R)-1-methyl-4-(2-(pyrrolidin-2-yl)phenyl)-1,2,3,6-tetrahydropyridine To a solution of tert-butyl (R)-2-(2-(1-methyl-1,2,3,6-tetrahydropyridin-4-yl)phenyl (pyrrolidine-1-carboxylate (4 g, 11.7 mmol) in DCM (100 mL) was added TFA (20 mL). The mixture was stirred at room temperature for 2 hours. After removal of solvent, the residue was dissolved with DCM (200 mL), washed with saturated aq, $NaHCO_3$, brine, dried over $Na_2SO_4$, and then concentrated to give the product (2 g) as a brown oil. $^1$H NMR (400 MHz, CDCl$_3$) δ ppm: 7.51 (d, J=7.8 Hz, 1H), 7.30-7.22 (m, 1H), 7.17 (td, J=7.4, 1.2 Hz, 1H), 7.07 (dd, J=7.6, 1.2 Hz, 1H), 5.57-5.51 (m, 1H), 4.27 (t, J=7.9 Hz, 1H), 3.25-3.21 (m, 1H), 3.08 (dd, J=5.7, 2.8 Hz, 2H), 2.99-2.94 (m, 1H), 2.65 (dd, J=8.3, 3.6 Hz, 2H), 2.46-2.38 (m, 5H), 2.12-2.07 (m, 2H), 1.95-1.92 (m, 1H), 1.90-1.77 (m, 1H), 1.68-1.55 (m, 1H). MS (ESI, m/e) [M+1]$^+$ 243.0. The residue was used into next step without further purification.

Step 3: (R)-1-methyl-4-(2-(pyrrolidin-2-yl)phenyl)piperidine

To a solution of (R)-1-methyl-4-(2-(pyrrolidin-2-yl)phenyl)-1,2,3,6-tetrahydropyridine (2 g, 8.2 mmol) in MeOH (100 mL) was added Pd(OH)$_2$ (0.5 g) under $H_2$ atmosphere. The mixture was stirred at 90° C. for 14 hours. The mixture was filtered. The filtrate was concentrated to give (R)-1-methyl-4-(2-(pyrrolidin-2-yl)phenyl)piperidine as a colorless oil, which was used in next step without further purification. $^1$H NMR (400 MHz, DMSO-d$_6$) ppm: δ 7.58-7.51 (m, 1H), 7.24-7.20 (m, 1H), 7.16-7.09 (m, 2H), 4.29 (t, J=7.7 Hz, 1H), 3.08-3.01 (m, 1H), 2.92-2.83 (m, 2H), 2.76-2.72 (m, 2H), 2.63-2.60 (m, 1H), 2.19 (s, 3H), 2.15-2.08 (m, 1H), 1.99-1.96 (m, 2H), 175-1.66 (m, 6H), 1.39-1.32 (m, 1H). MS (ESI, m/e) [M+1]$^+$ 245.0.

Step 4: (R)-4-(2-(1-(4-bromophenyl)pyrrolidin-2-yl)phenyl)-1-methylpiperidine To a solution of (R)-1-methyl-4-(2-(pyrrolidin-2-yl)phenyl)piperidine 2 g, 8 mmol) in toluene (100 mL) was added 1-bromo-4-iodobenzene (4.6 g, 16 mmol), Pd$_2$(dba)$_3$ (732 mg, 0.8 mmol), BINAP (1 mg, 1.6 mmol) and t-BuOK (2.7 g, 24 mmol). The mixture was stirred at 90° C. for 12 hours at $N_2$ atmosphere. The reaction mixture was washed with brine, dried over $Na_2SO_4$, concentrated. The residue was purified by chromatograph column on silica gel (eluent: DCM/MeOH=50/1) to give the title product (2 g). MS (ESI, m/e) [M+1]$^+$ 398.6, 400.6.

Step 5: tert-butyl-(R)-3-((1H-pyrrolo[2,3-b]pyridin-5-yl)oxy)-4'-(2-(2-(1-methylpiperidin-4-yl)phenyl)pyrrolidin-1-yl)-[1,1'-biphenyl]-4-carboxylate To a solution of (R)-4-(2-(1-(4-bromophenyl)pyrrolidin-2-yl)phenyl)-1-methylpiperidine (2 g, 5 mmol) and tert-butyl 2-((1H-pyrrolo[2,3-b]pyridin-5-yl)oxy)-4-(3,3,4,4-tetramethylborolan-1-yl)benzoate (2.18 g, 5 mmol) in 1,4-dioxane (50 mL) and $H_2O$ (5 mL) were added Pd(ddpf)$Cl_2$ (365 mg, 0.5 mmol) and $Cs_2CO_3$ (4.9 g, 15 mmol). The mixture was stirred at 90° C. overnight under nitrogen protection. The mixture was cooled to room temperature and then diluted with DCM (200 mL), washed with brine (200 mi. 2), dried over $Na_2SO_4$. After concentrated, the residue was purified by chromatography column on silica gel (eluent: DCM/MeOH=25/1) to give tert-butyl (R)-3-((1H-pyrrolo[2,3-b]pyridin-5-yl)oxy)-4'(2-(2-(1-methylpiperidin-4-yl)phenyl)pyrrolidin-1-yl)-[1,1'-biphenyl]-4-carboxylate (2 g) as a brown oil. MS (ESI, m/e) [M+1]$^+$ 629.0

Step 6: (R)-3-((1H-pyrrolo[2,3-b]pyridin-5-yl)oxy)-4'-(2-(2-(1-methylpiperidin-4-yl)phenyl)pyrrolidin-1-yl)-[1,1'-biphenyl]-4-carboxylic acid To a solution of tert-butyl (R)-3-((1H-pyrrolo[2,3-b]pyridin-5-yl)oxy)-4'-(2-(2-(1-methylpiperidin-4-yl)phenyl)pyrrolidin-1-yl)-[1,1'-biphenyl]-4-carboxylate (2 g, crude) in DCM (50 mL) was added TFA (15 mL). The mixture was stirred at room temperature for 2 hours. The mixture was concentrated to give the crude product as a yellow solid, which was used in next step without further purification. MS (ESI, m/e) [M+1]$^+$ 573.0.

The desired compound was then synthesized with (R)-3-((1H-pyrrolo[2,3-b]pyridin-5-yl)oxy)-4'-(2-(2-(1-methylpiperidin-4-yl)phenyl)pyrrolidin-1-yl)-[1,1'-biphenyl]-4-carboxylic acid and 3-nitro-4-(((tetrahydro-2H-pyran-4-yl)methyl)amino)benzenesulfonamide following the procedures similar to those in Example A1. $^1$H NMR (400 MHz, DMSO-d$_6$) δ ppm: 12.16 (s, 1H), 11.71 (s, 1H), 8.61 (s, 1H), 8.56 (s, 1H), 8.05 (d, J=2.2 Hz, 1H), 7.82 (d, J=8.7 Hz, 1H), 7.59 (s, 1H), 7.57-7.49 (m, 2H), 7.37-7.18 (m, 4H), 7.17-7.02 (m, 2H), 6.87 (d, J=7.7 Hz, 2H), 6.37 (d, J=8.5 Hz, 3H), 5.04 (d, J=7.6 Hz, 1H), 3.88-3.82 (m, 2H), 3.75-3.71 (m, 1H), 3.51 (s, 2H), 3.47-3.39 (m, 1H), 3.30-3.22 (m, 4H), 3.19-3.13 (m, 3H), 2.99-2.93 (m, 1H), 2.85-2.78 (m, 3H), 2.15-1.79 (m, 7H), 1.75-1.69 (m, 1H), 1.65-1.61 (m, 2H), 1.28-1.21 (m, 3H). MS (ESI, m/e) [M+1]$^+$ 869.8.

Example A101: 3-((1H-pyrrolo[2,3-b]pyridin-5-yl)oxy)-4'-((2R)-2-(2-(1-methyl-2-oxopiperidin-4-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

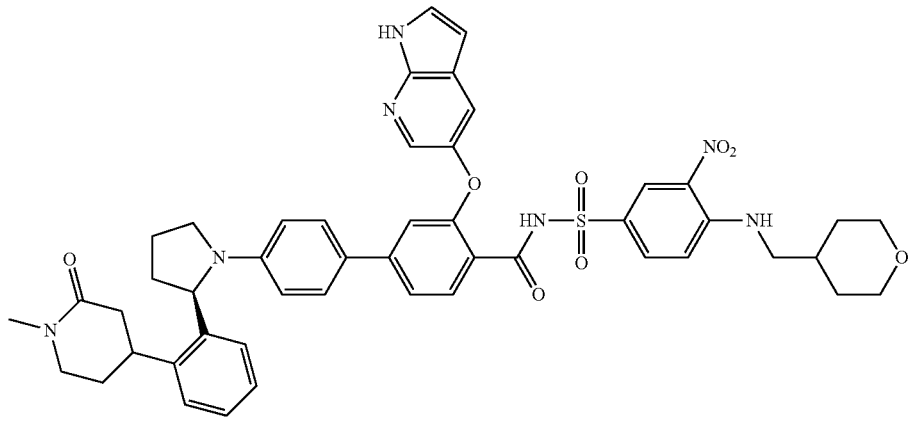 [SMILES: CN1CCC(c2ccccc2[C@H]2CCCN2c2ccc(-c3ccc(C(=O)NS(=O)(=O)c4ccc(NCC5CCOCC5)c([N+](=O)[O-])c4)c(Oc4cnc5[nH]ccc5c4)c3)cc2)CC1=O]

The desired compound was synthesized starting from 1-methyl-4-(2-((R)-pyrrolidin-2-yl)phenyl)piperidin-2-one and 1-bromo-4-iodobenzene following the procedures similar to those in Example A100. $^1$H NMR (400 MHz, DMSO-$d_6$) δ ppm: 12.16 (s, 1H), 11.70 (s, 1H), 8.72-8.44 (M, 2H), 8.05 (s, 1H), 7.90-7.67 (m, 1H), 7.66-7.44 (m, 3H), 7.44-7.24 (m, 4H), 7.24-6.98 (m, 3H), 6.96-6.78 (m, 2H), 6.43-6.25 (m, 3H), 5.15-4.95 (m, 1H), 3.96-3.76 (m, 2H), 3.76-3.63 (m, 1H), 3.59-3.38 (m, 3H), 3.31-3.13 (m, 5H), 2.87 (s, 3H), 2.42-2.27 (m, 2H), 2.15-1.44 (m, 9H), 0.91-0.71 (m, 2H). MS (ESI, m/e) [M+1]$^+$ 883.8.

Example A102: (R)-3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(2-(1-(3,3,3-trifluoropropyl)piperidin-4-yl)phenyl)pyrrolidin-1-yl)-[1,1'-biphenyl]-4-carboxamide

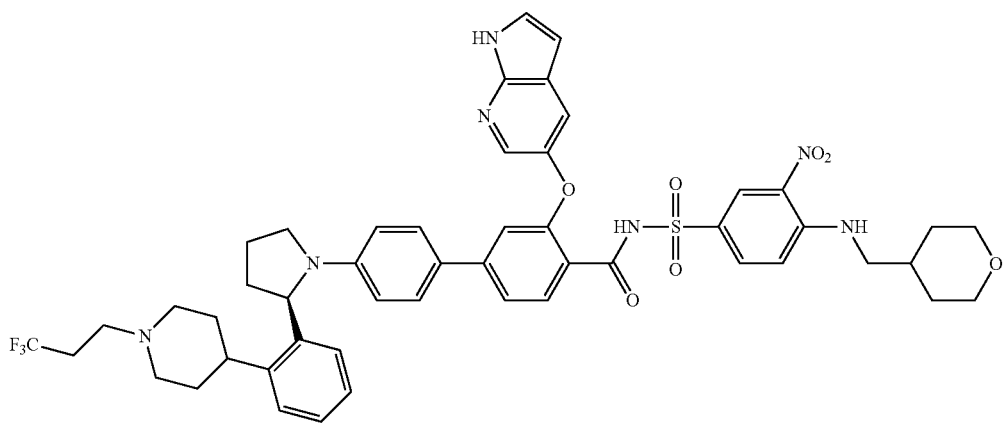 [SMILES: O=C(NS(=O)(=O)c1ccc(NCC2CCOCC2)c([N+](=O)[O-])c1)c1ccc(-c2ccc(N3CCC[C@@H]3c3ccccc3C3CCN(CCO)CC3)cc2)cc1Oc1cnc2[nH]ccc2c1]

The desired compound was synthesized starting from (R)-4-(2-(pyrrolidin-2-yl)phenyl)-1-(3,3,3-trifluoropropyl)piperidine and 1-bromo-4-iodobenzene following the procedures similar to those in Example A100. ¹H NMR (400 MHz, DMSO-d₆) δ ppm: 11.61 (s, 1H), 9.67 (s, 1H), 8.64-8.34 (m, 2H), 7.99 (s, 1H), 7.82-7.63 (m, 1H), 7.63-7.13 (m, 8H), 7.13-6.80 (m, 4H), 6.46-6.25 (m, 3H), 5.09-4.87 (m, 1H), 3.89-3.78 (m, 2H), 3.77-3.65 (m, 1H), 3.44-3.36 (m, 2H), 3.31-3.18 (m, 4H), 3.15-3.01 (m, 2H), 2.97-2.85 (m, 1H), 2.75-2.56 (m, 3H), 2.49-2.39 (m, 1H), 2.28-2.10 (m, 1H), 2.05-1.80 (m, 5H), 1.75-1.57 (m, 4H), 1.32-1.19 (m, 4H), MS (ESI, m/e) [M+1]⁺ 951.8.

Example A103: (R)-3-((1H-pyrrolo[2,3-b]pyridin-5-yl)oxy)-4'-(2-(2-(1-(2-hydroxyethyl)piperidin-4-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

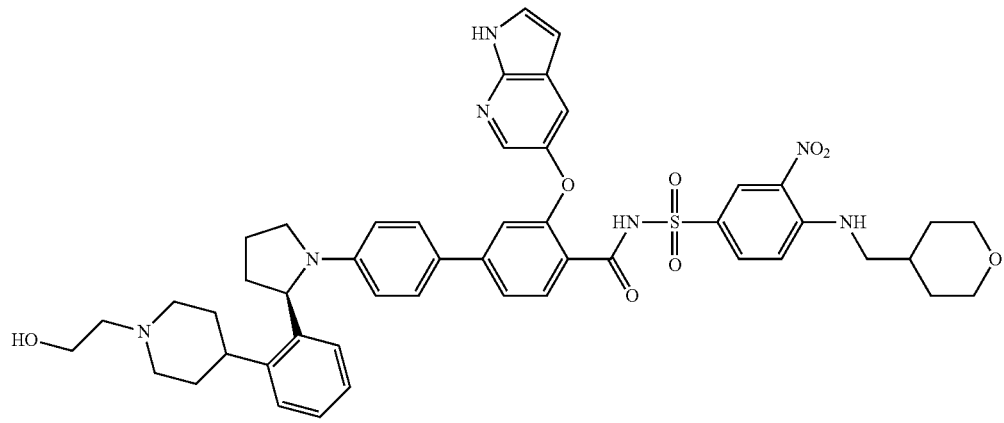

The desired compound was synthesized starting from (R)-2-(4-(2-(pyrrolidin-2-yl)phenyl)piperidin-1-yl)ethan-1-ol and 1-bromo-4-iodobenzene following the procedures similar to those in Example A100. ¹H NMR (400 MHz, DMSO-d₆) δ ppm: 11.55 (s, 1H), 9.32-9.05 (m, 1H), 8.46-8.26 (m, 2H), 7.96 (s, 1H), 7.72-7.62 (m, 1H), 7.59-7.51 (m, 1H), 7.45-7.16 (m, 7H), 7.11-7.00 (m, 1H), 6.95-6.79 (m, 3H), 6.45-6.20 (m, 3H), 5.10-4.94 (m, 1H), 3.90-3.79 (m, 2H), 3.79-3.64 (m, 3H), 3.59-3.35 (m, 4H), 3.30-3.19 (m, 5H), 3.17-2.79 (m, 4H), 2.18-1.65 (m, 9H), 1.65-1.55 (m, 2H), 1.33-1.26 (m, 2H). MS (ESI, m/e) [M+1]⁺ 899.9.

Example A104: (R)-3-((1H-pyrrolo[2,3-b]pyridin-5-yl)oxy)-4'-(2-(2-(1-(2-(dimethylamino)-2-oxoethyl)piperidin-4-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

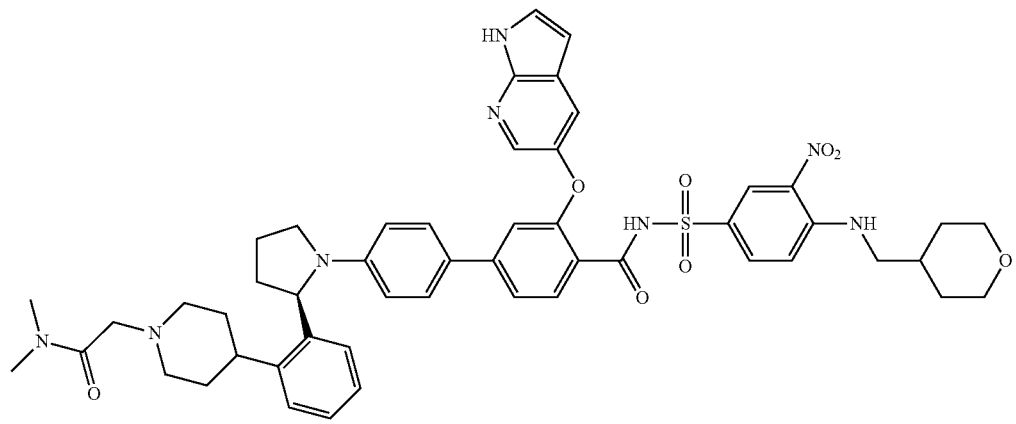 [SMILES: CN(C)C(=O)CN1CCC(c2ccccc2[C@H]2CCCN2c2ccc(-c3ccc(C(=O)NS(=O)(=O)c4ccc(NCC5CCOCC5)c([N+](=O)[O-])c4)c(Oc4cnc5[nH]ccc5c4)c3)cc2)CC1]

The desired compound was synthesized starting from (R)—N,N-dimethyl-2-(4-(2-(pyrrolidin-2-yl)phenyl)piperidin-1-yl)acetamide and 1-bromo-4-iodobenzene following the procedures similar to those in Example A100. $^1$H NMR (400 MHz, DMSO-d$_6$) δ ppm: 11.57 (s, 1H), 9.61 (s, 1H), 8.42 (s, 2H), 7.97 (s, 1H), 7.72-7.69 (m, 1H), 7.58-7.53 (m, 1H), 7.46-7.38 (m, 2H), 7.34-7.16 (m, 5H), 7.05 (s, 1H), 6.90 (s, 3H), 6.41-6.28 (m, 3H), 5.02 (s, 1H), 3.88-3.76 (m, 2H), 3.71 (s, 1H), 3.40-3.38 (m, 1H), 3.29-3.21 (m, 5H), 3.01 (s, 4H), 2.89 (s, 3H), 1.99-1.80 (m, 7H), 1.78-1.51 (m, 5H), 1.23 (s, 6H), MS (ESI) m/e [M+1]$^+$ 940.8.

Example A105: (R)-3-((1H-pyrrolo[2,3-b]pyridin-5-yl)oxy)-4'-(2-(2-(1-(2-(N-methylacetamido)ethyl)piperidin-4-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

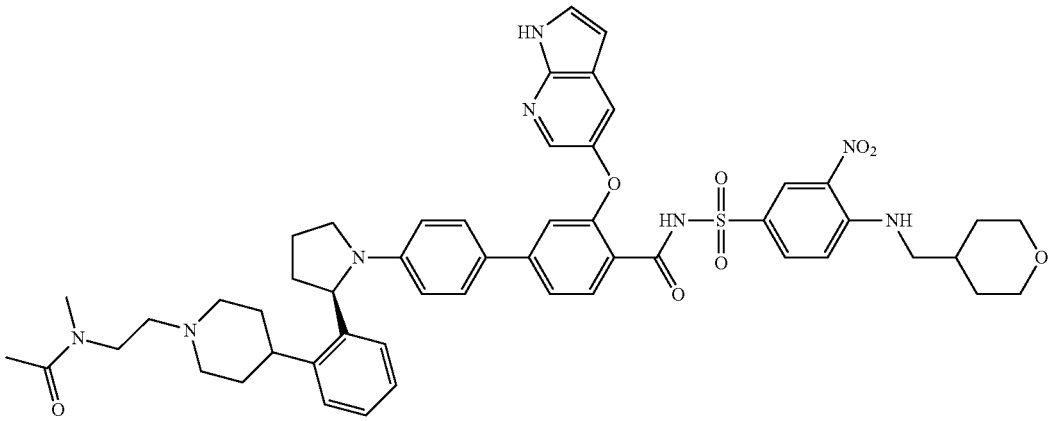 [SMILES: CC(=O)N(C)CCN1CCC(c2ccccc2[C@H]2CCCN2c2ccc(-c3ccc(C(=O)NS(=O)(=O)c4ccc(NCC5CCOCC5)c([N+](=O)[O-])c4)c(Oc4cnc5[nH]ccc5c4)c3)cc2)CC1]

The desired compound was synthesized starting from (R)—N-methyl-N-(2-(4-(2-(pyrrolidin-2-yl)phenyl)piperidin-1-yl)ethyl)acetamide and 1-bromo-4-iodobenzene following the procedures similar to those in Example A100. $^1$H NMR (400 MHz, DMSO-d$_6$) δ ppm: 11.60 (s, 1H), 8.56-8.22 (m, 2H), 7.99 (s, 1H), 7.83-7.66 (m, 1H), 7.60-7.39 (m, 3H), 7.38-7.13 (m, 5H), 7.12-6.78 (m, 4H), 6.46-6.25 (m, 3H), 5.10-4.93 (m, 1H), 3.91-3.77 (m, 2H), 3.77-3.66 (m, 1H), 3.66-3.33 (m, 6H), 3.32-3.17 (m, 4H), 3.16-2.90 (m, 4H), 2.88-2.67 (m, 2H), 2.48-2.38 (m, 1H), 2.11-1.66 (m, 10H), 1.65-1.53 (m, 2H), 1.53-1.23 (m, 3H). MS (ESI, m/e) [M+1]$^+$ 954.9.

Example A106: (R)-3-((1H-pyrrolo[2,3-b]pyridin-5-yl)oxy)-4'-(2-(2-(1-(3-(methyl amino)propanoyl)piperidin-4-yl)phenyl)pyrrolidin-1-yl)-N -((3-nitro-4-(((tetrahydro-2H-pyran-4-yl)methyl)amino)phenyl)sulfonyl)-[1,1'-biphenyl]-4-carboxamide

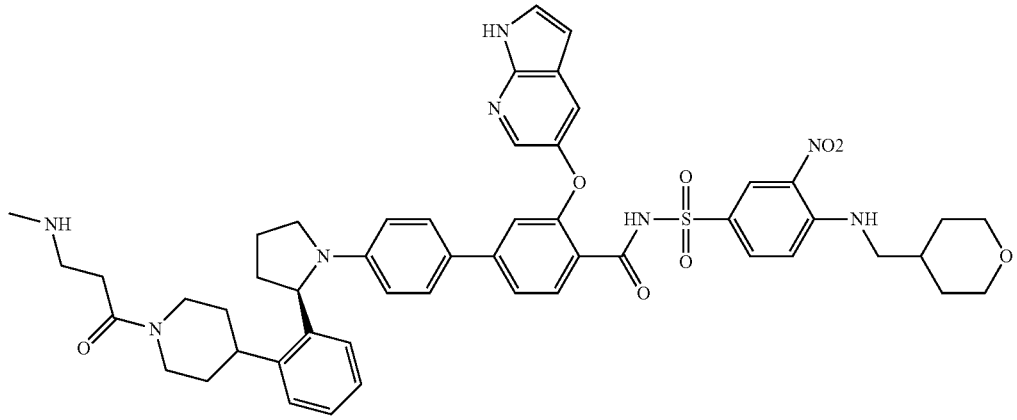 [SMILES: CNCCC(=O)N1CCC(c2ccccc2[C@H]2CCCN2c2ccc(-c3ccc(C(=O)NS(=O)(=O)c4ccc(NCC5CCOCC5)c([N+](=O)[O-])c4)c(Oc4cnc5[nH]ccc5c4)c3)cc2)CC1]

The desired compound A106 was synthesized by Boc-deprotection in TFA/DCM of tert-butyl (R)-(3-(4-(2-(1-(3'-((1H-pyrrolo[2,3-b]pyridin-5-yl)oxy)-4'-(((3-nitro-4-(((tetrahydro-2H-pyran-4-yl)methyl)amino)phenyl)sulfonyl)carbamoyl)-[1,1'-biphenyl]-4-yl)pyrrolidin-2-yl)phenyl)piperidin-1-yl)-3-oxopropyl)(methyl)carbamate, which was synthesized starting from tert-butyl (R)-methyl(3-oxo-3-(4-(2-(pyrrolidin-2-yl)phenyl)piperidin-1-yl)propyl)carbamate and 1-bromo-4-iodobenzene following the procedures similar to those in Example A100. $^1$H NMR (DMSO-d$_6$) δ ppm: 11.52 (s, 1H), 8.38 (s, 1H), 8.33 (s, 1H), 8.18 (s, 1H), 7.94 (s, 1H), 7.64 (d, J=8.6 Hz, 1H), 7.54 (d, J=7.9 Hz, 1H), 7.40 (s, 1H), 7.35-7.12 (m, 6H), 7.04-7.01 (m, 1H), 6.89 (s, 2H), 6.82 (d, J=9.0 Hz, 1H), 6.36 (d, J=7.8 Hz, 2H), 6.28 (s, 1H), 5.04 (s, 1H), 4.56 (s, 1H), 3.83-3.80 (m, 4H), 3.22-3.20 (m, 3H), 3.12 (s, 2H), 2.72-2.70 (m, 3H), 2.58 (s, 3H), 1.94-1.90 (m, 5H), 1.69 (s, 2H), 1.59-1.57 (m, 3H), 1.22 (s, 8H). MS (ESI) m/e [M+1]$^+$ 940.9.

Example A107: 3-((1H-pyrrolo[2,3-b]pyridin-5-yl)oxy)-4'-(2-(2-(1-cyclopropyl-1,2,3,6-tetrahydropyridin-4-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

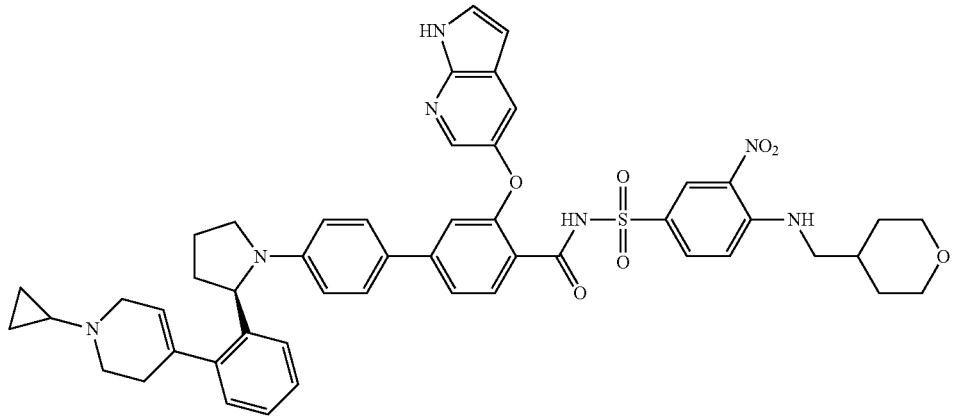 [SMILES: O=C(NS(=O)(=O)c1ccc(NCC2CCOCC2)c([N+](=O)[O-])c1)c1ccc(-c2ccc(N3CCC[C@@H]3c3ccccc3C3=CCN(C4CC4)CC3)cc2)cc1Oc1cnc2[nH]ccc2c1]

The desired compound was synthesized starting from 1-cyclopropyl-4-(2-(pyrrolidin-2-yl)phenyl)-1,2,3,6-tetrahydropyridine and 1-bromo-4-iodobenzene following the procedures similar to those in Example A68-R. $^1$H NMR (DMSO-d$_6$) δ ppm: 11.66 (s, 1H), 8.56-8.52 (m, 2H), 8.02 (s, 1H), 7.78 (d, J=8.9 Hz, 1H), 7.57-7.46 (m, 3H), 7.37-7.23 (m, 3H), 7.22-6.95 (m, 5H), 6.91 (s, 1H), 6.36-6.34 (m, 3H), 5.67 (s, 1H), 4.84-4.82 (m, 1H), 3.85-3.83 (m, 2H), 3.72 (s, 1H), 3.46-3.43 (m, 2H), 3.30-3.26 (m, 4H), 3.10-3.08 (m, 2H), 2.44-2.32 (m, 1H), 2.01-1.99 (m, 3H), 1.87 (s, 1H), 1.76-1.60 (m, 3H), 1.23 (s, 6H), 0.85-0.83 (m, 1H), 0.59 (s, 3H), MS (ESI) m/e [M+1]$^+$ 893.9.

Example A108: (R)-3-((1H-pyrrolo[2,3-b]pyridin-5-yl)oxy)-4'-(2-(2-(1-benzyl-1,2,3,6-tetrahydropyridin-4-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

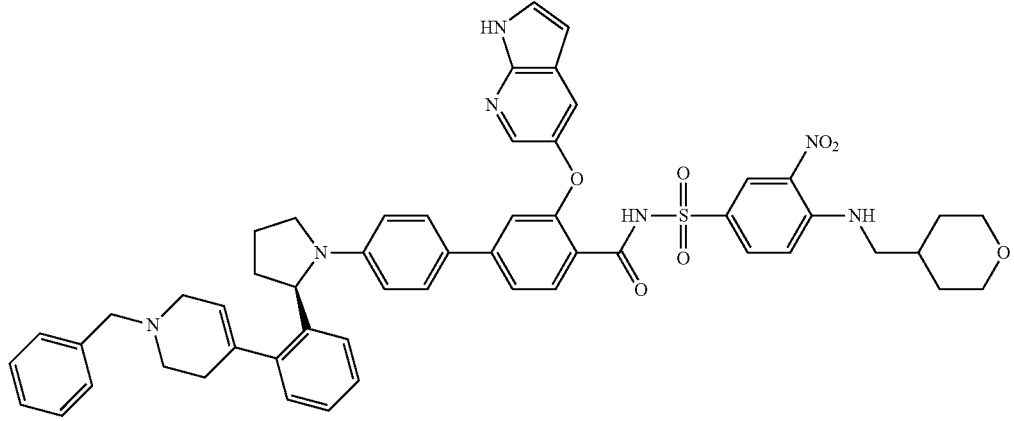 [SMILES: O=C(NS(=O)(=O)c1ccc(NCC2CCOCC2)c([N+](=O)[O-])c1)c1ccc(-c2ccc(N3CCC[C@@H]3c3ccccc3C3=CCN(Cc4ccccc4)CC3)cc2)cc1Oc1cnc2[nH]ccc2c1]

The desired compound was synthesized starting from (R)-1-benzyl-4-(2-(pyrrolidin-2-yl)phenyl)-1,2,3,6tetrahydropyridine and 1-bromo-4-iodobenzene following the procedures similar to those in Example A68-R. $^1$H NMR (DMSO-d$_6$) δ ppm: 11.60 (s, 1H), 8.46 (s, 2H), 7.98 (s, 1H), 7.74-7.69 (m, 1H), 7.54 (d, J=8.0 Hz, 1H), 7.53-7.38 (m, 7H), 7.33-7.27 (m, 4H), 7.18-7.10 (m, 3H), 7.00 (d, J=7.5 Hz, 1H), 6.98-6.91 (m, 1H), 6.91 (s, 1H), 6.39-6.27 (m, 3H), 5.67 (s, 1H), 4.83 (d, J=6.1 Hz, 1H), 3.84 (d, J=7.7 Hz, 3H), 3.73 (s, 2H), 3.31-3.21 (m, 6H), 3.28-3.19 (m, 3H), 2.41-2.33 (m, 1H), 2.01-1.77 (m, 5H), 1.63-1.59 (m, 2H), 1.26-1.21 (m, 3H). MS (ESI, m/e) [M+1]$^+$ 943.8.

Example A109: (R)-3-((1H-pyrrolo[2,3-b]pyridin-5-yl)oxy)-4'-(2-(2-(1-acetyl-1,2,3,6-tetrahydropyridin-4-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

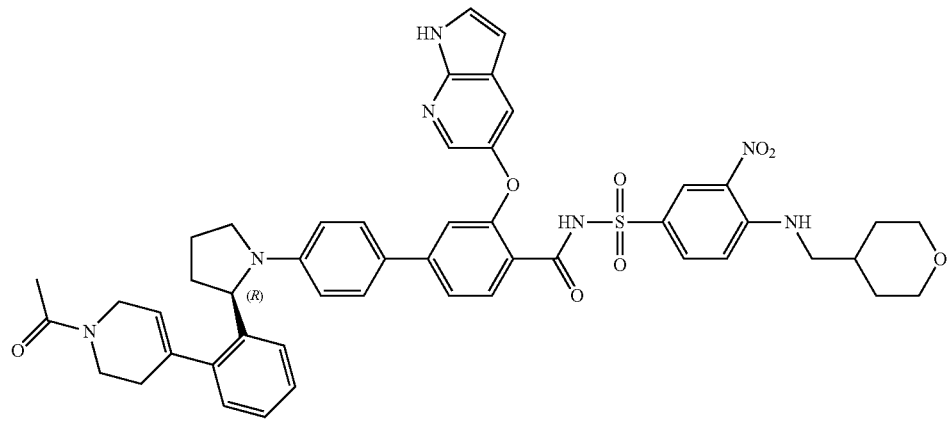

The desired compound was synthesized starting from (R)-1-(4-(2-(pyrrolidin-2-yl)phenyl)-3,6-dihydropyridin-1(2H)-yl)ethan-1-one and 1-bromo-4-iodobenzene following the procedures similar to those in Example A68-R. $^1$H NMR (DMSO-d$_6$) δ ppm: 12.16 (s, 1H), 11.70 (s, 1H), 8.67-8.43 (m, 2H), 8.10-7.99 (m, 1H), 7.87-7.76 (m, 1H), 7.62-7.46 (m, 3H), 7.42-7.25 (m, 3H), 7.25-7.05 (m, 4H), 7.05-6.94 (m, 1H), 6.93-6.84 (m, 1H), 6.42-6.29 (m, 3H), 5.71 (s, 1H), 4.87-4.76 (m, 1H), 4.17-4.02 (m, 2H), 3.92-3.78 (m, 2H), 3.81-3.59 (m, 3H), 3.39-3.35 (m, 1H), 3.31-3.17 (m, 4H), 2.48-2.44 (m, 1H), 2.43-2.26 (m, 2H), 2.13-2.01 (m, 3H), 2.01-1.92 (m, 2H), 1.92-1.83 (m, 1H), 1.80-1.70 (m, 1H), 1.64-1.54 (m, 2H), 1.33-1.18 (m, 2H). [M+1]$^+$ 895.8.

Example A110: (R)-3-((1H-pyrrolo[2,3-b]pyridin-5-yl)oxy)-4'-(2-(2-(1-acetylpiperidin-4-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

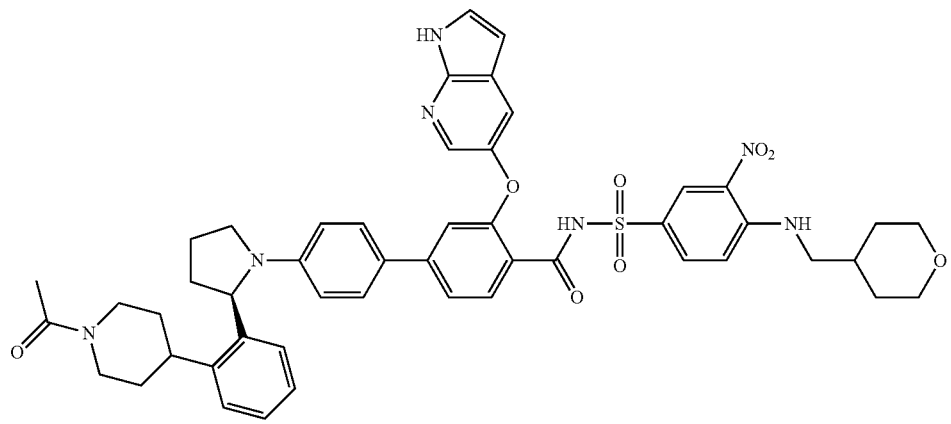 [SMILES: CC(=O)N1CCC(c2ccccc2[C@H]2CCCN2c2ccc(-c3ccc(C(=O)NS(=O)(=O)c4ccc(NCC5CCOCC5)c([N+](=O)[O-])c4)c(Oc4cnc5[nH]ccc5c4)c3)cc2)CC1]

The desired compound was synthesized starting from (R)-1-(4-(2-(pyrrolidin-2-yl)phenyl)piperidin-1-yl)ethan-1-one and 1-bromo-4-iodobenzene following the procedures similar to those in Example A100. $^1$H NMR (DMSO-d$_6$) δ ppm: 12.14 (s, 1H), 11.70 (s, 1H), 8.57-8.55 (m, 2H), 8.05 (d, J=2.5 Hz, 1H), 7.83 (d, J=9.4 Hz, 1H), 7.59 (s, 1H), 7.54-7.49 (m, 2H), 7.36-7.30 (m, 4H), 7.17-7.08 (m, 2H), 7.03-7.00 (m, 1H), 6.90 (s, 1H), 6.86-6.8 (m, 1H), 6.38-6.36 (m, 3H), 5.06 (s, 1H), 4.55 (s, 1H), 4.24 (s, 1H), 3.93 (s, 1H), 3.71 (s, 1H), 3.39-3.38 (m, 1H), 3.26-3.23 (m, 3H), 3.18-3.16 (m, 2H), 2.70-2.60 (m, 2H), 2.04 (s, 3H), 1.97 (s, 1H), 1.86 (s, 2H), 1.69-1.65 (m, 4H), 1.56-1.53 (m, 2H), 1.33-1.30 (m, 2H), 1.15-1.00 (m, 5H). MS (ESI) m/e [M+1]$^+$ 925.8.

Example A111: 3-((1H-pyrrolo[2,3-b]pyridin-5-yl)oxy)-4'-(2-(2-(1-(methylsulfonyl)-1,2,3,6-tetrahydropyridin-4-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

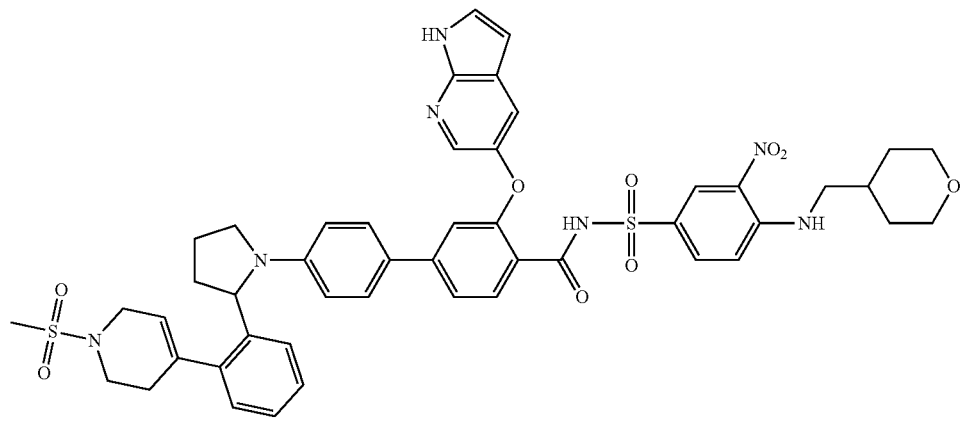 [SMILES: CS(=O)(=O)N1CC=C(c2ccccc2C2CCCN2c2ccc(-c3ccc(C(=O)NS(=O)(=O)c4ccc(NCC5CCOCC5)c([N+](=O)[O-])c4)c(Oc4cnc5[nH]ccc5c4)c3)cc2)CC1]

The desired compound was synthesized starting from 1-(methylsulfonyl)-4-(2-(pyrrolidin-2-yl)phenyl)-1,2,3,6-tetrahydropyridine and 1-bromo-4-iodobenzene following the procedures similar to those in Example A68-R. $^1$H NMR (DMSO-d$_6$) δ ppm: 12.17 (s, 1H), 11.70 (s, 1H), 8.70-8.51 (m, 2H), 8.08-7.98 (m, 1H), 7.86-7.74 (m, 1H), 7.63-7.46 (m, 3H), 7.39-7.25 (m, 3H), 7.25-7.04 (m, 4H), 7.04-6.95 (m, 1H), 6.91 (s, 1H), 6.46-6.25 (m, 3H), 5.75 (s, 1H), 4.88-4.75 (m, 1H), 3.91-3.80 (m, 4H), 3.77-3.66 (m, 1H), 3.45-3.38 (m, 2H), 3.31-3.21 (m, 5H), 2.95 (s, 3H), 2.87-2.82 (m, 1H), 2.42-2.28 (m, 1H), 2.03-1.70 (m, 4H), 1.65-1.54 (m, 2H), 1.34-1.18 (m, 3H), MS (ESI, m/e) [M+1]$^+$ 931.7.

Example A112: (R)-3-((1H-pyrrolo[2,3-b]pyridin-5-yl)oxy)-4'-(2-(2-((1-methylpiperidin-4-yl)methyl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

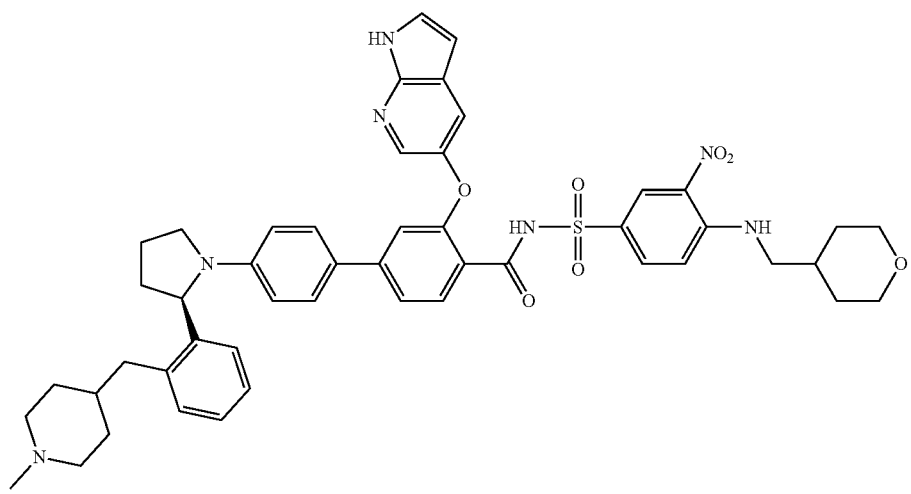

The desired compound was synthesized starting from (R)-1-methyl-4-(2-(pyrrolidin-2-yl)benzyl)piperidine and 1-bromo-4-iodobenzene following the procedures similar to those in Example A100. $^1$H NMR (DMSO-d$_6$) δ ppm: 12.15 (s, 1H), 11.64 (s, 1H), 9.09 (s, 1H), 8.51 (s, 2H), 8.01 (s, 1H), 7.76 (s, 1H), 7.59-7.43 (m, 3H), 7.30 (d, J=7.9 Hz, 3H), 7.22-6.97 (m, 4H), 6.91 (s, 2H), 6.35 (s, 3H), 4.90 (s, 1H), 3.84 (d, J=10.2 Hz, 2H), 3.72 (s, 1H), 3.39 (s, 3H), 3.30-3.21 (m, 4H), 2.89 (s, 2H), 2.75-2.65 (m, 4H), 1.99-1.92 (m, 7H), 1.70 (s, 1H), 1.68-1.57 (m, 4H), 1.45 (s, 2H), 1.24 (s, 7H), MS (ESI) m/e [M+1]$^+$ 883.9.

Example A113: 3-((1H-pyrrolo[2,3-b]pyridin-5-yl)oxy)-4'-(2-(2-((1-methylpiperidin-4-yl)oxy)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

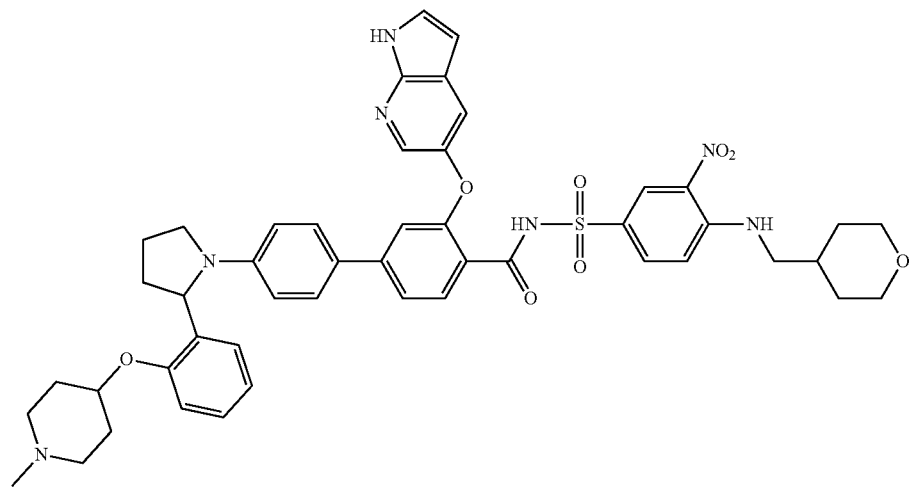 [SMILES: CN1CCC(Oc2ccccc2C2CCCN2c2ccc(-c3ccc(C(=O)NS(=O)(=O)c4ccc(NCC5CCOCC5)c([N+](=O)[O-])c4)c(Oc4cnc5[nH]ccc5c4)c3)cc2)CC1]

The desired compound was synthesized starting from 1-methyl-4-(2-(pyrrolidin-2-yl)phenoxy)piperidine and 1-bromo-4-iodobenzene following the procedures similar to those in Example A100. $^1$H NMR (DMSO-$d_6$) δ ppm: 11.55 (s, 1H), 9.60 (s, 1H), 8.39-8.36 (m, 2H), 7.96 (s, 1H), 7.66 (d, J=8.9 Hz, 1H), 7.56 (d, J=7.8 Hz, 1H), 7.42 (s, 1H), 7.38-7.22 (m, 5H), 7.16-7.14 (m, 1H), 7.06-7.04 (m, 1H), 6.91 (s, 1H), 6.85 (s, 2H), 6.79-6.76 (m, 1H), 6.38-6.35 (m, 2H), 6.30 (s, 1H), 4.99 (s, 1H), 4.66 (s, 1H), 3.83-3.81 (m, 2H), 3.68 (s, 1H), 3.27-3.25 (m, 4H), 2.94 (s, 2H), 2.33 (s, 2H), 2.10-1.77 (m, 11H), 1.62-1.60 (m, 2H), 1.23 (s, 5H). MS (ESI) m/e [M+1]$^+$ 885.8.

Example A114: (R)-3-((1H-pyrrolo[2,3-b]pyridin-5-yl)oxy)-4'-(2-(2-((4-methylpiperazin-1-yl)methyl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

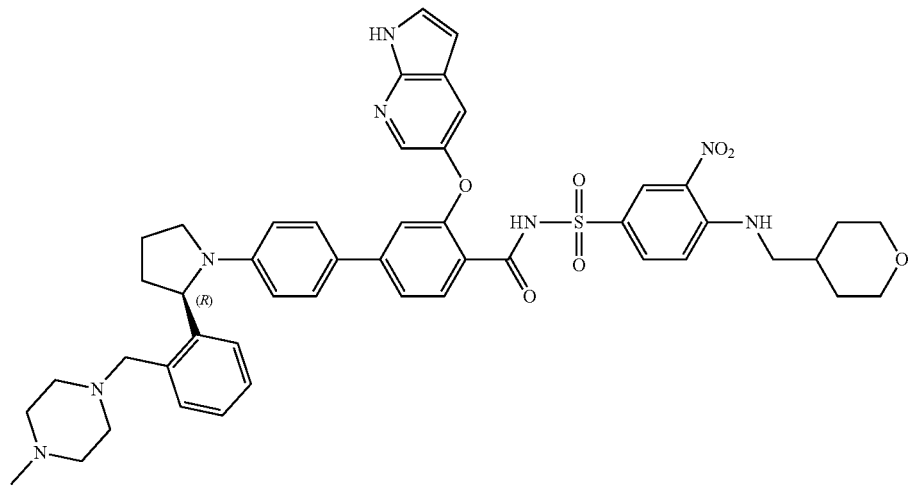

The desired compound was synthesized starting from (R)-1-methyl-4-(2-(pyrrolidin-2-yl)benzyl)piperazine and 1-bromo-4-iodobenzene following the procedures similar to those in Example A100. $^1$H NMR (DMSO-$d_6$) δ ppm: δ 11.56 (s, 1H), 9.91-9.17 (m, 1H), 8.44-8.37 (m, 2H), 7.97 (d, J=2.2 Hz, 1H), 7.68 (d, J=9.0 Hz, 1H), 7.58-7.55 (m, 1H), 7.48-7.40 (m, 2H), 7.33-7.18 (m, 4H), 7.18-7.07 (m, 2H), 6.99-6.92 (m, 1H), 6.89-6.83 (m, 2H), 6.46 (d, J=8.4 Hz, 2H), 6.31 (s, 1H), 5.26 (d, J=8.0 Hz, 1H), 3.92-3.69 (m, 4H), 3.45-3.34 (m, 2H), 3.28-3.21 (m, 5H), 3.12-2.58 (m, 6H), 1.97-1.70 (m, 6H), 1.61-1.58 (m, 3H), 1.28-1.21 (m, 4H). MS (ESI, m/e) [M+1]$^+$ 884.8.

Example A115: (R)-3-((1H-pyrrolo[2,3-b]pyridin-5-yl)oxy)-4'-(2-(2-(4-carbamoylcyclohexyl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

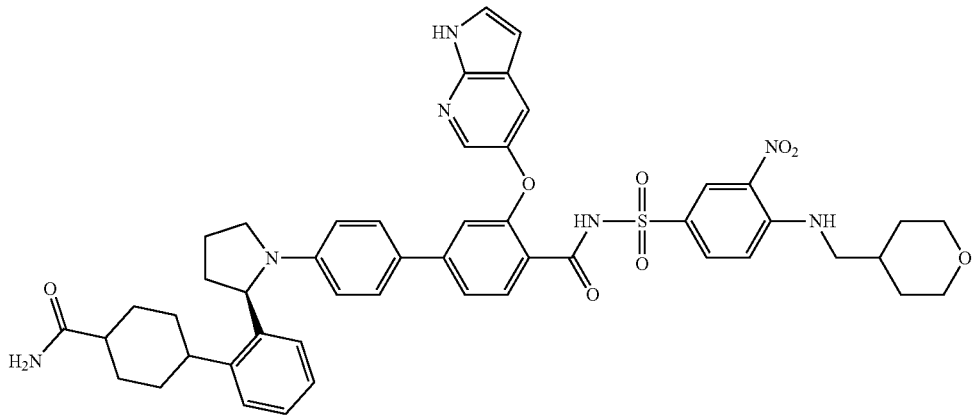 [SMILES: NC(=O)C1CCC(c2ccccc2[C@H]2CCCN2c2ccc(-c3ccc(C(=O)NS(=O)(=O)c4ccc(NCC5CCOCC5)c([N+](=O)[O-])c4)c(Oc4cnc5[nH]ccc5c4)c3)cc2)CC1]

The desired compound was synthesized starting from (R)-4-(2-(pyrrolidin-2-yl)phenyl)cyclohexane-1-carboxamide and 1-bromo-4-iodobenzene following the procedures similar to those in Example A100. ¹H NMR (DMSO-d₆) δ ppm: 12.16 (s, 0.5H), 11.60 (s, 1H), 9.67 (s, 0.5H), 8.68-8.19 (m, 2H), 7.99 (s, 1H), 7.81-7.63 (m, 1H), 7.58-7.11 (m, 9H), 7.07-6.79 (m, 4H), 6.79-6.60 (m, 1H), 6.41-6.25 (m, 3H), 5.04-4.89 (m, 1H), 3.90-3.774 On, 2H), 3.77-3.63 (m, 1H), 3.60-3.36 (m, 2H), 3.30-3.18 (m, 4H), 2.91-2.80 (m, 1H), 2.27-2.13 (m, 1H), 2.04-1.79 (m, 8H), 1.80-1.37 (m, 9H). MS (ESI, m/e) [M+1]⁺ 897.8.

Example A116: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(2-(pyridin-4-yl)phenyl)pyrrolidin-1-yl)-[1,1'-biphenyl]-4-carboxamide

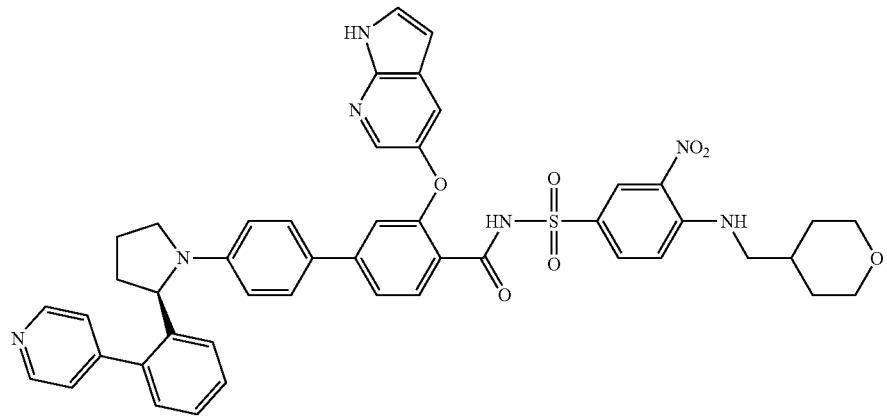 [SMILES: O=C(NS(=O)(=O)c1ccc(NCC2CCOCC2)c([N+](=O)[O-])c1)c1ccc(-c2ccc(N3CCC[C@@H]3c3ccccc3-c3ccncc3)cc2)cc1Oc1cnc2[nH]ccc2c1]

The desired compound was synthesized starting from 4-(2-(pyrrolidin-2-yl)phenyl)pyridine and 1-bromo-4-iodobenzene following the procedures similar to those in Example A1. 12.18 (s, 1H), 11.71 (s, 1H), 8.67 (d, J=5.3 Hz, 2H), 8.60-8.55 (m, 2H), 8.05 (d, J=2.3 Hz, 1H), 7.83 (d, J=9.1 Hz, 1H), 7.59 (s, 1H), 7.55-7.44 (m, 4H), 7.38-7.24 (m, 5H), 7.25-7.18 (m, 1H), 7.15-7.10 (m, 2H), 6.89 (s, 1H), 6.41-6.29 (m, 3H), 4.60 (d, J=6.6 Hz, 1H), 3.86-3.82 (m, 2H), 3.68 (s, 1H), 3.30-3.22 (m, 5H), 2.16-2.13 (m, 1H), 1.94-1.90 (m, 3H), 1.79-1.77 (m, 1H), 1.62-1.58 (m, 2H), 1.30-1.24 (m, 3H). MS (ESI) m/e [M+1]⁺ 849.8.

Example A117a and Example A117b: 3-((1H-pyrrolo[2,3-b]pyridin-5-yl)oxy)-4'-(2-(2-(1-methylpiperidin-3-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

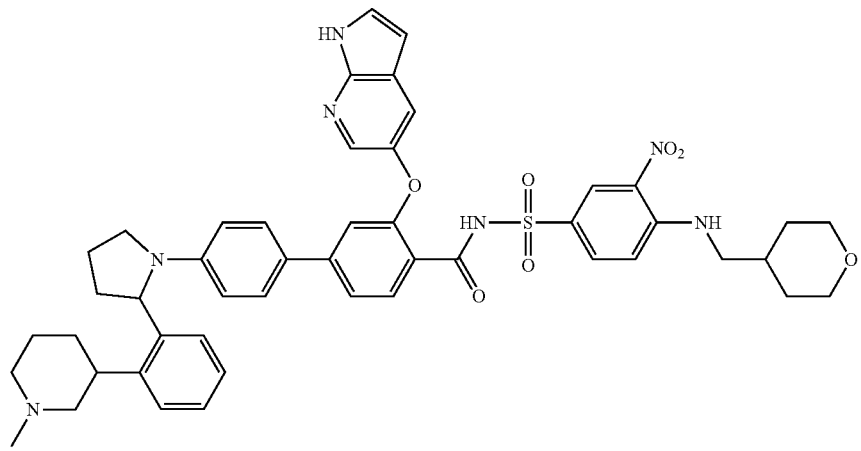 [SMILES: CN1CCCC(c2ccccc2C2CCCN2c2ccc(-c3ccc(C(=O)NS(=O)(=O)c4ccc(NCC5CCOCC5)c([N+](=O)[O-])c4)c(Oc4cnc5[nH]ccc5c4)c3)cc2)C1]

The desired compound was synthesized starting from 1-methyl-3-(2-(pyrrolidin-2-yl)phenyl)piperidine and 1-bromo-4-iodobenzene following the procedures similar to those in Example A1. The crude product was separated and purified by prep-HPLC to afford 2 isomers. The isomer as faster peak of HPLC (retention time: 6.28 minute) was obtained as Example A117a $^1$H NMR (400 MHz, DMSO-d$_6$): δ 11.55 (s, 1H), 8.41 (s, 1H), 8.36 (s, 1H), 7.96 (s, 1H), 7.67 (d, J=9.6 Hz, 1H), 7.56 (d, J=7.9 Hz, 1H), 7.42 (s, 1H), 7.39-7.27 (m, 4H), 7.25-7.20 (m, 3H), 7.13-7.08 (m, 1H), 6.93-6.87 (m, 3H), 6.38-6.34 (m, 2H), 6.30 (s, 1H), 4.98 (s, 1H), 3.83 (d, J=11.2 Hz, 2H), 3.78-3.71 (m, 1H), 3.45-3.41 (m, 1H), 3.28-3.20 (m, 5H), 2.01-1.69 (m, 10H), 1.63-1.59 (m, 4H), 1.26-1.23 (m, 5H), 0.88-0.81 (m, 1H). MS (ESI, m/e) [M+1]$^+$ 869.9; The isomer as slower peak of HPLC (retention time: 6.42 minute) was obtained as Example A117b. $^1$H NMR (400 MHz, DMSO-d$_6$): 11.55 (s, 1H), 8.41 (s, 1H), 8.36 (s, 1H), 7.96 (s, 1H), 7.67 (d, J=9.6 Hz, 1H), 7.56 (d, J=7.9 Hz, 1H), 7.42 (s, 1H), 7.39-7.27 (m, 4H), 7.25-7.20 (m, 3H), 7.13-7.08 (m, 1H), 6.93-6.87 (m, 3H), 6.38-6.34 (m, 2H), 6.30 (s, 1H), 4.98 (s, 1H), 3.83 (d, J=11.2 Hz, 2H), 3.78-3.71 (m, 1H), 3.47-3.41 (m, 1H), 3.28-3.21 (m, 5H), 2.00-1.70 (m, 10H), 1.65-1.60 (m, 4H), 1.25-1.23 (m, 5H), 0.86-0.80 (m, 1H). MS (ESI, m/e) [M+1]$^+$ 869.9. MS (ESI, m/e) [M+1]$^+$ 869.9.

Example A118a and Example A118b: 3-((1H-pyrrolo[2,3-b]pyridin-5-yl)oxy)-4'-(2-(2-(3-(dimethylamino)piperidin-1-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

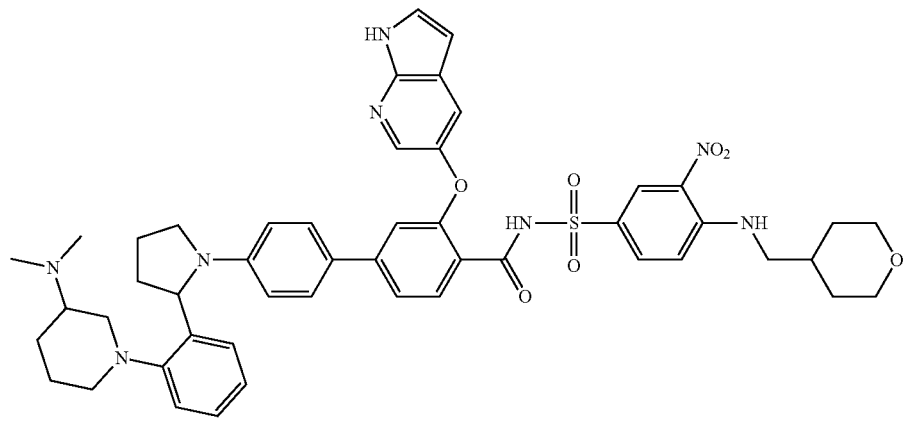 [SMILES: CN(C)C1CCCN(c2ccccc2C2CCCN2c2ccc(-c3ccc(C(=O)NS(=O)(=O)c4ccc(NCC5CCOCC5)c([N+](=O)[O-])c4)c(Oc4cnc5[nH]ccc5c4)c3)cc2)C1]

The desired compound was synthesized starting from N,N-dimethyl-1-(2-(pyrrolidin-2-yl)phenyl)piperidin-3-amine following the procedures similar to those in Example A100. After separation by prep-HPLC, two products had been obtained. Faster peak as Example A118a. $^1$H NMR (400 MHz, DMSO-d$_6$) δ ppm: 11.71 (s, 1H), 9.82 (br, 1H), 8.42-8.35 (m, 2H), 7.95 (s, 1H), 7.66 (d, J=8.8 Hz, 1H), 7.56 (d, J=8.0 Hz, 1H), 7.42-7.15 (m, 7H), 7.03-6.84 (m, 4H), 6.38 (d, J=8.0 Hz, 1H), 6.35-6.28 (m, 2H), 5.09 (d, J=4.4 Hz, 1H), 3.85 (d, J=8.4 Hz, 2H), 3.73-3.61 (m, 1H), 3.33-3.20 (m, 5H), 2.95-2.49 (m, 9H), 2.47-2.31 (m, 1H), 2.13-1.26 (m, 14H). MS (ESI, m/e) [M+1]$^+$ 898.9. slower peak as Example A118b. $^1$H NMR (400 MHz, DMSO-d$_6$) δ ppm: 11.56 (s, 1H), 10.58 (br, 1H), 8.41-8.35 (m, 2H), 7.96 (s, 1H), 7.69 (d, J=8.8 Hz, 1H), 7.60 (d, J=8.0 Hz, 1H), 7.43-7.15 (m, 7H), 7.03-6.84 (m, 5H), 6.41 (d, J=8.0 Hz, 1H), 6.35-6.28 (m, 2H), 5.04 (d, J=4.4 Hz, 1H), 3.85 (d, J=8.4 Hz, 2H), 3.73-3.61 (m, 1H), 3.33-3.20 (m, 5H), 2.90-2.52 (m, 9H), 2.47-2.31 (m, 1H), 2.13-1.18 (m, 14H). MS (ESI, m/e) [M+1]$^+$ 898.9.

Example A119: 3-((1H-pyrrolo[2,3-b]pyridin-5-yl)oxy)-4'(2-(2-(8-methyl-3,8-diazabicyclo[3.2.1]octan-3-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

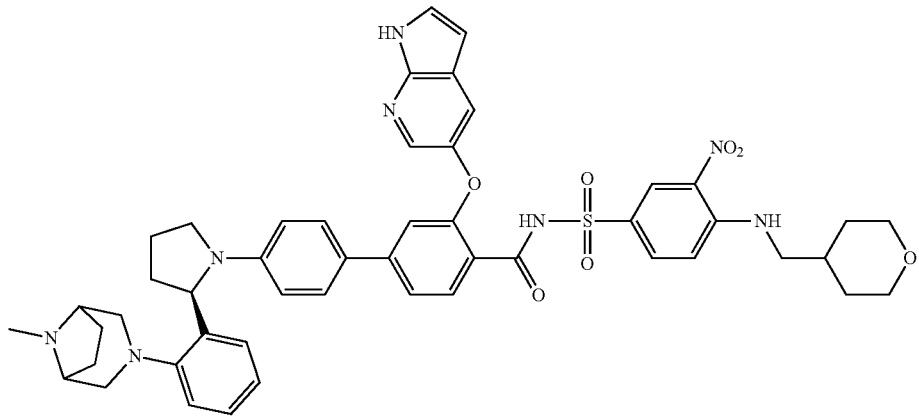 [SMILES: CN1C2CCC1CN(c1ccccc1[C@H]1CCCN1c1ccc(-c3ccc(C(=O)NS(=O)(=O)c4ccc(NCC5CCOCC5)c([N+](=O)[O-])c4)c(Oc4cnc5[nH]ccc5c4)c3)cc1)C2]

The desired compound was synthesized starting from 8-methyl-3-(2-(pyrrolidin-2-yl)phenyl)-3,8-diazabicyclo[3.2.1]octane and 1-bromo-4-iodobenzene following the procedures similar to those in Example A100. $^1$H NMR (400 MHz, CDCl$_3$) δ 11.62 (s, 1H), 9.85 (s, 1H), 8.53-8.35 (m, 2H), 8.07-7.97 (m, 1H), 7.78-7.69 (m, 1H), 7.68-7.58 (m, 1H), 7.54-7.22 (m, 7H), 7.17-7.00 (m, 2H), 7.00-6.85 (m, 2H), 6.49-6.25 (m, 3H), 5.22-5.07 (m, 1H), 4.14-3.71 (m, 5H), 3.36-3.21 (m, 5H), 3.18-2.91 (m, 3H), 2.91-2.69 (m, 3H), 2.32-2.12 (m, 4H), 2.13-1.77 (m, 5H), 1.78-1.59 (m, 2H), 1.57-1.43 (m, 1H), 1.42-1.36 (m, 1H), 0.95-0.80 (m, 2H). MS (ESI, m/e) [M+1]$^+$ 896.9.

Example A120: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(2-(piperazin-1-yl)phenyl)pyrrolidin-1-yl)-[1,1'-biphenyl]-4-carboxamide

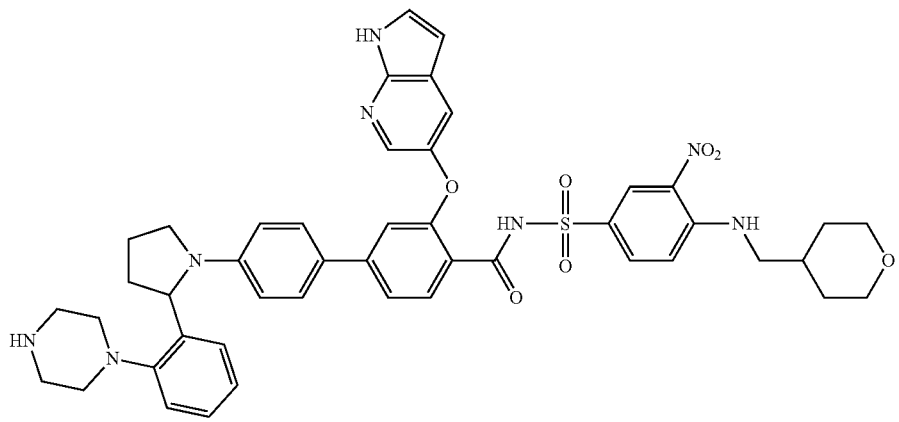 [SMILES: O=C(NS(=O)(=O)c1ccc(NCC2CCOCC2)c([N+](=O)[O-])c1)c1ccc(-c2ccc(N3CCCC3c3ccccc3N3CCNCC3)cc2)cc1Oc1cnc2[nH]ccc2c1]

The desired compound A120 was synthesized by Boc-deprotection in TFA/DCM of tert-butyl 4-(2-(i-(3'-((1H-pyrrolo[2,3-b]pyridin-5-yl)oxy)-4'-(((3-nitro-4-(((tetrahydro-2H-pyran-4-yl)methyl)amino)phenyl)sulfonyl)carbamoyl)-[1,1'-biphenyl]-4-yl)pyrrolidin-2-yl)phenyl)piperazine-1-carboxylate, which was synthesized starting from tert-butyl 4-(2-(pyrrolidin-2-yl)phenyl)piperazine-1-carboxylate and 1-bromo-4-iodobenzene following the procedures similar to those in Example A100. $^1$H NMR (400 MHz, DMSO-d$_6$) δ ppm: 11.54 (s, 1H), 8.42-8.31 (m, 2H), 7.67-7.61 (m, 1H), 7.59-7.52 (s, 1H), 7.43-7.38 (m, 1H), 7.34-7.26 (m, 4H), 7.25-7.16 (m, 3H), 7.05-6.98 (m, 2H), 6.90 (s, 1H), 6.85-6.78 (m, 1H), 6.41-6.35 (m, 2H), 6.31-6.27 (m, 1H), 5.11-5.08 (m, 1H), 3.89-3.77 (m, 3H), 3.76-3.68 (m, 1H), 3.28-3.21 (m, 5H), 3.18-3.08 (m, 4H), 3.04-2.95 (m, 4H), 2.02-1.97 (m, 2H), 1.88-1.78 (m, 3H), 1.63-1.57 (m, 4H). MS (ESI, m/e) [M+1]$^+$ 856.8.

Example A121: 3-((1H-pyrrolo[2,3-b]pyridin-5-yl)oxy)-4'-(2-(2-(4-methylpiperazin-1-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

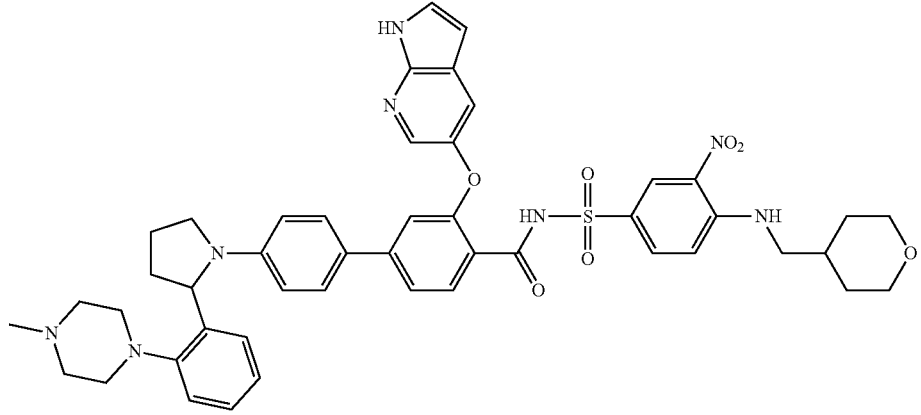 [SMILES: CN1CCN(c2ccccc2C2CCCN2c2ccc(-c3ccc(C(=O)NS(=O)(=O)c4ccc(NCC5CCOCC5)c([N+](=O)[O-])c4)c(Oc4cnc5[nH]ccc5c4)c3)cc2)CC1]

The desired compound was synthesized starting from 1-methyl-4-(2-(pyrrolidin-2-yl)phenyl)piperazine and 1-bromo-4-iodobenzene following the procedures similar to those in Example A100. $^1$H NMR (400 MHz, DMSO-d$_6$) δ ppm: 11.58 (s, 1H), 10.34 (s, 1H), 8.51-8.27 (m, 2H), 7.97 (s, 1H), 7.74-7.65 (m, 1H), 7.59-7.51 (m, 1H), 7.47-7.34 (m, 2H), 7.33-7.13 (m, 5H), 7.08-6.96 (m, 2H), 6.95-6.85 (m, 2H), 6.45-6.25 (m, 3H), 5.15-4.98 (m, 1H), 3.88-3.79 (m, 2H), 3.9-3.67 (m, 1H), 3.41-3.36 (m, 1H), 3.32-3.19 (m, 2H), 3.13-2.77 (m, 8H), 2.67-2.53 (m, 3H), 2.47-2.38 (m, 1H), 2.07-1.94 (m, 3H), 1.93-1.73 (m, 2H), 1.66-1.52 (m, 2H). MS (ESI, m/e) [M+1]$^+$ 870.8.

Example A122: 3-((1H-pyrrolo[2,3-b]pyridin-5-yl)oxy)-4'-(2-(2-morpholinophenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

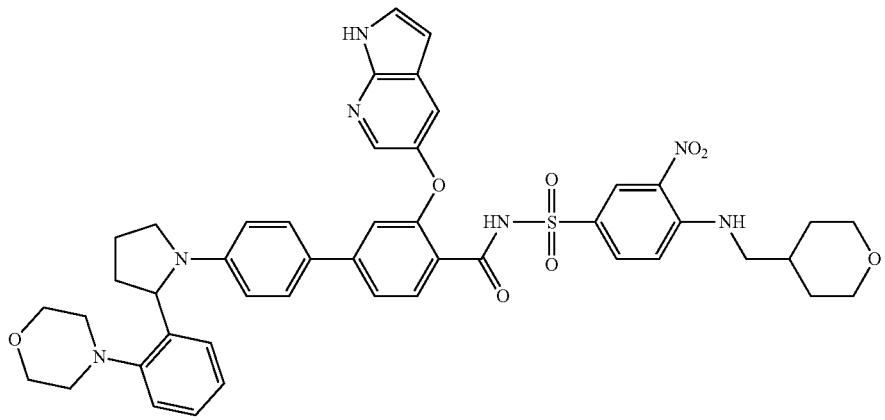 [SMILES: O=C(NS(=O)(=O)c1ccc(NCC2CCOCC2)c([N+](=O)[O-])c1)c1ccc(-c2ccc(N3CCCC3c3ccccc3N3CCOCC3)cc2)cc1Oc1cnc2[nH]ccc2c1]

The desired compound was synthesized starting from 4-(2-(pyrrolidin-2-yl)phenyl)morpholine and 1-bromo-4-iodobenzene following the procedures similar to those in Example A100. $^1$H NMR (400 MHz, DMSO-d$_6$) δ ppm: 12.15 (s, 1H), 11.69 (s, 1H), 8.63-8.55 (m, 2H), 7.56 (s, 1H), 7.34 (s, 1H), 7.33-7.20 (m, 3H), 7.19-7.13 (m, 7H), 7.00 (s, 2H), 6.90 (s, 1H), 6.43-6.37 (m, 3H), 5.16-5.13 (m, 1H), 3.86-3.75 (m, 8H), 3.33-3.25 (m, 5H), 3.10-2.95 (m, 4H), 1.84 (s, 3H), 1.60-1.57 (m, 4H). MS (ESI) m/e [M+1]$^+$ 857.8.

Example A123: (R)-3-((1H-pyrrolo[2,3-b]pyridin-5-yl)oxy)-4'-(2-(2-(1,1-dioxidotetrahydro-2H-thiopyran-4-yl)phenyl)pyrrolidin-1-yl)-N-((3-nitro-4-((((tetrahydro-2H-pyran-4-yl)methyl)amino)phenyl)sulfonyl)-[1,1'-biphenyl]-4-carboxamide

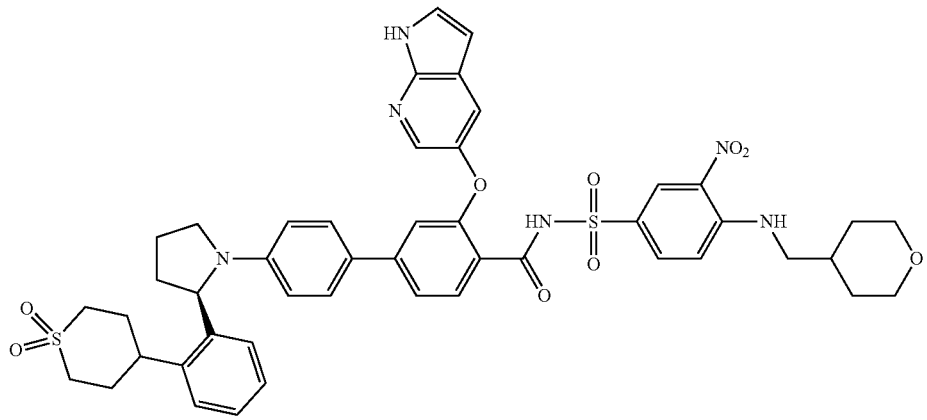 [SMILES: O=C(NS(=O)(=O)c1ccc(NCC2CCOCC2)c([N+](=O)[O-])c1)c1ccc(-c2ccc(N3CCC[C@@H]3c3ccccc3C3CCS(=O)(=O)CC3)cc2)cc1Oc1cnc2[nH]ccc2c1]

The desired compound was synthesized starting from (R)-2-(2-(tetrahydro-2H-thiopyran-4-yl)phenyl)pyrrolidine and 1-bromo-4-iodobenzene following the procedures similar to those in Example A100. $^1$H NMR (400 MHz, DMSO-d$_6$) δ ppm: 12.16 (s, 1H), 11.71 (s, 1H), 8.62-8.58 (m, 2H), 8.05 (s, 1H), 7.83 (d, J=8.8 Hz, 1H), 7.64-7.48 (m, 3H), 7.38-7.24 (m, 4H), 7.15-7.10 (m, 3H), 6.94-6.81 (m, 2H), 6.37-6.35 (m, 3H), 5.05-5.04 (m, 1H), 3.85-3.83 (m, 1H), 3.67 (s, 1H), 3.52-3.37 (m, 3H), 3.29-3.21 (m, 1H), 3.14 (s, 2H), 2.28-2.26 (m, 1H), 2.13-2.10 (m, 2H), 2.01-1.99 (m, 2H), 1.87 (s, 2H), 1.73-1.54 (m, 3H), 1.24 (s, 5H). MS (ESI) m/e [M+1]$^+$ 904.7.

Example A124: 3-((1H-pyrrolo[2,3-b]pyridin-5-yl)oxy)-4'-(2-(2-(4-hydroxypiperidin-1-yl)phenyl)pyrrolidin-1-yl)-N-((3-nitro-4-((((tetrahydro-2H-pyran-4-yl)methyl)amino)phenyl)sulfonyl)-[1,1'-biphenyl]-4-carboxamide

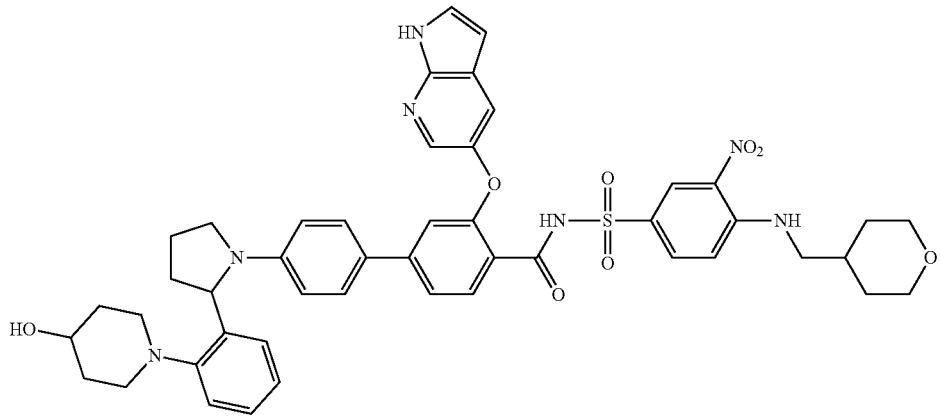 [SMILES: O=C(NS(=O)(=O)c1ccc(NCC2CCOCC2)c([N+](=O)[O-])c1)c1ccc(-c2ccc(N3CCCC3c3ccccc3N3CCC(O)CC3)cc2)cc1Oc1cnc2[nH]ccc2c1]

The desired compound was synthesized starting from 1-(2-(pyrrolidin-2-yl)phenyl)piperidin-4-ol and 1-bromo-4-iodobenzene following the procedures similar to those in Example A100. $^1$H NMR (DMSO-d$_6$) δ ppm: 12.15 (s, 1H), 11.67 (s, 1H), 8.53 (s, 2H), 8.02 (s, 1H), 7.79 (s, 1H), 7.58-7.46 (m, 3H), 7.35-7.28 (m, 3H), 7.21-7.04 (m, 3H), 6.96-6.88 (m, 3H), 6.44-6.31 (m, 3H), 5.06-5.04 (m, 1H), 4.68-4.65 (m, 1H), 3.89-3.85 (m, 2H), 3.68-3.63 (m, 2H), 3.30-3.21 (m, 4H), 3.10-2.95 (m, 4H), 2.79-2.74 (m, 2H), 1.99 (s, 3H), 1.86-1.82 (m, 4H), 1.62-1.58 (m, 4H), 1.25-1.21 (m, 2H). MS (ESI) m/e [M+1]$^+$ 871.8.

Example A125: 3-((1H-pyrrolo[2,3-b]pyridin-5-yl)oxy)-4'-(2-(2-(4-(dimethylamino)piperidin-1-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

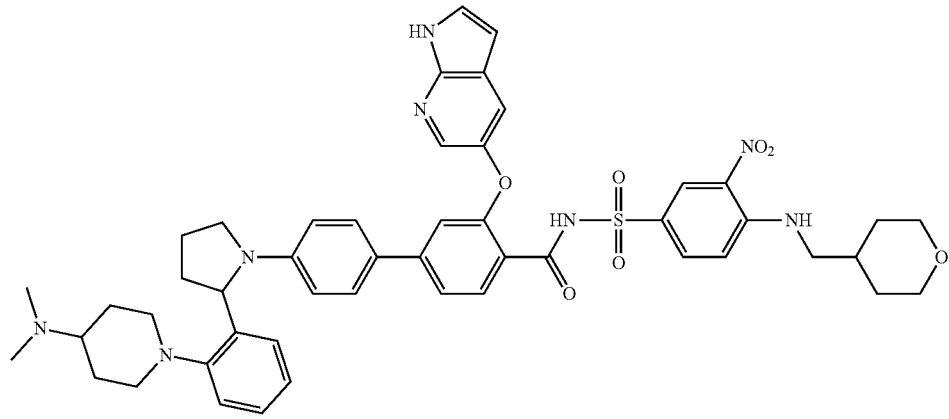 [SMILES: CN(C)C1CCN(c2ccccc2C2CCCN2c2ccc(-c3ccc(C(=O)NS(=O)(=O)c4ccc(NCC5CCOCC5)c([N+](=O)[O-])c4)c(Oc4cnc5[nH]ccc5c4)c3)cc2)CC1]

The desired compound was synthesized starting from N,N-dimethyl-1-(2-(pyrrolidin-2-yl)phenyl)piperidin-4-amine and 1-bromo-4-iodobenzene following the procedures similar to those in Example A100. $^1$H NMR (DMSO-d$_6$) δ ppm: 11.67 (s, 1H), 8.62-8.42 (m, 2H), 8.02 (s, 1H), 7.78 (d, J=9.2 Hz, 1H), 7.60-7.42 (m, 3H), 7.36-7.24 (m, 3H), 7.23-7.14 (m, 2H), 7.10-6.96 (m, 3H), 6.91 (s, 1H), 6.48-6.30 (m, 3H), 5.06 (d, J=7.6 Hz, 1H), 3.84 (d, J=8.0 Hz, 2H), 3.76-3.67 (m, 1H), 3.30-3.18 (m, 6H), 3.10-3.00 (m, 1H), 2.87 it, J=11.6 Hz, 1H), 2.77 (s, 6H), 2.47-2.39 (m, 1H), 2.16-1.95 (m, 4H), 1.90-1.74 (m, 4H), 1.60 (d, J=12.4 Hz, 2H), 1.30-1.18 (m, 1H). MS (ESI, m/e) [M+1]$^+$ 898.8.

Example A126: 3-((1H-pyrrolo[2,3-b]pyridin-5-yl)oxy)-4'-(2-(2-(1-methylpyrrolidin-3-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

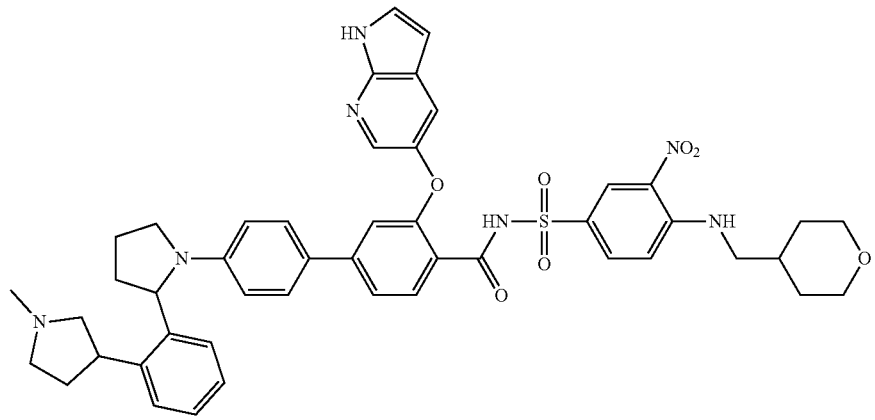 [SMILES: CN1CCC(c2ccccc2C2CCCN2c2ccc(-c3ccc(C(=O)NS(=O)(=O)c4ccc(NCC5CCOCC5)c([N+](=O)[O-])c4)c(Oc4cnc5[nH]ccc5c4)c3)cc2)C1]

The desired compound was synthesized starting from 1-methyl-3-(2-(pyrrolidin-2-yl)phenyl)pyrrolidine and 1-bromo-4-iodobenzene following the procedures similar to those in Example A100. $^1$H NMR (DMSO-d$_6$) δ ppm: 12.37-11.97 (m, 0.4H), 11.66 (s, 1H), 10.39-9.79 (m, 0.6H), 8.61-8.36 (m, 2H), 8.02 (s, 1H), 7.85-7.68 (m, 1H), 7.63-7.41 (m, 4H), 7.36-7.17 (m, 4H), 7.14-6.97 (m, 2H), 6.95-6.82 (m, 2H), 6.43-6.26 (m, 2H), 5.10-4.89 (m, 1H), 3.88-3.66 (m, 4H), 3.43-3.36 (m, 1H), 3.30-3.18 (m, 5H), 2.92 (s, 3H), 2.45-2.36 (m, 2H), 2.05-1.79 (m, 5H), 1.78-1.41 (m, 5H), 0.87-0.81 (m, 2H). MS (ESI, m/e) [M+1]$^+$ 855.9.

Example A127: 3-((1H-pyrrolo[2,3-b]pyridin-5-yl)oxy)-4'-(2-(2-(2-(dimethylamino)ethoxy)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

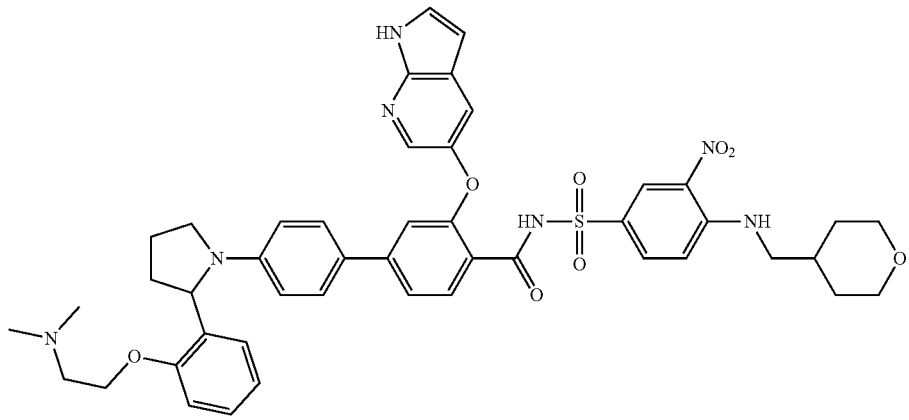 [SMILES: CN(C)CCOc1ccccc1C1CCCN1c1ccc(-c2ccc(C(=O)NS(=O)(=O)c3ccc(NCC4CCOCC4)c([N+](=O)[O-])c3)c(Oc3cnc4[nH]ccc4c3)c2)cc1]

The desired compound was synthesized starting from N,N-dimethyl-2-(2-(pyrrolidin-2-yl)phenoxy)ethan-1-amine and 1-bromo-4-iodobenzene following the procedures similar to those in Example A100. $^1$H NMR (DMSO-d$_6$) δ ppm: 11.56 (s, 1H), 8.44-8.32 (m, 2H), 7.96 (s, 1H), 7.71-7.64 (m, 2H), 7.58-7.52 (m, 1H), 7.46-7.35 (m, 2H), 7.32-7.22 (m, 3H), 7.21-7.16 (m, 1H), 7.07-7.01 (m, 1H), 6.97-6.71 (m, 5H), 6.40-6.34 (m, 2H), 6.31-6.27 (m, 1H), 5.33 (s, 1H), 5.06-4.99 (m, 1H), 4.38-4.22 (m, 2H), 3.88-3.79 (m, 2H), 3.70-3.65 (m, 1H), 3.30-3.19 (m, 5H), 2.71-2.59 (m, 6H), 2.05-1.92 (m, 3H), 1.88-1.78 (m, 3H), 1.65-1.55 (m, 3H). MS (ESI, m/e) [M+1]$^+$ 859.8.

Example A128: 3-((1H-pyrrolo[2,3-b]pyridin-5-yl)oxy)-4'-(2-(2-(methoxymethyl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

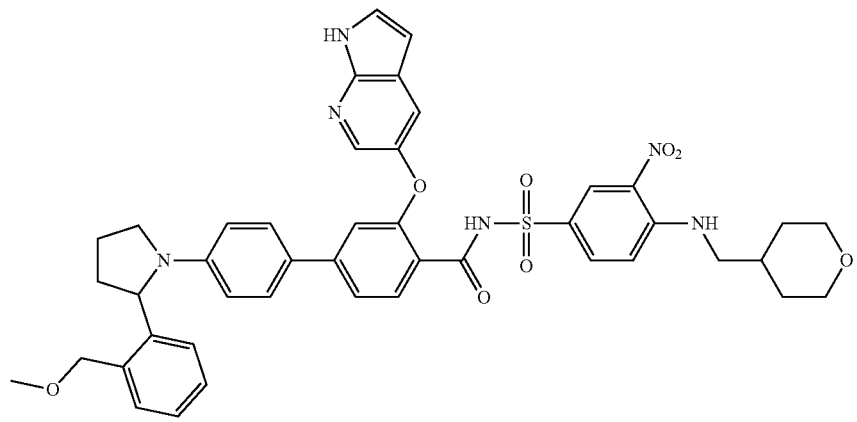 [SMILES: COCc1ccccc1C1CCCN1c1ccc(-c2ccc(C(=O)NS(=O)(=O)c3ccc(NCC4CCOCC4)c([N+](=O)[O-])c3)c(Oc3cnc4[nH]ccc4c3)c2)cc1]

The desired compound was synthesized starting from 2-(2-(methoxymethyl)phenyl)pyrrolidine and 1-bromo-4-iodobenzene following the procedures similar to those in Example A1. $^1$H NMR (DMSO-$d_6$) δ ppm: 12.17 (s, 1H), 11.70 (s, 1H), 8.71-8.49 (m, 2H), 8.04 (s, 1H), 7.81 (d, J=8.7 Hz, 1H), 7.60-7.47 (m, 3H), 7.38-7.25 (m, 4H), 7.22-7.10 (m, 3H), 6.92-6.88 (m, 2H), 6.49-6.33 (m, 3H), 4.99 (d, J=7.7 Hz, 1H), 4.69-4.60 (m, 1H), 4.55-4.46 (m, 1H), 3.91-3.78 (m, 2H), 3.72 (s, 1H), 3.34 (s, 3H), 3.29-3.25 (m, 2H), 3.24-3.18 (m, 1H), 3.06-2.98 (m, 1H), 2.39 (s, 1H), 2.07-1.82 (m, 4H), 1.76 (s, 1H), 1.68-1.54 (m, 2H), 1.26 (s, 2H). MS (ESI, m/e) [M+1]$^+$ 816.8.

Example A129: (R)-3-((1H-pyrrolo[2,3-b]pyridin-5-yl)oxy)-4'-(2-(2-(((dimethylamino)methyl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

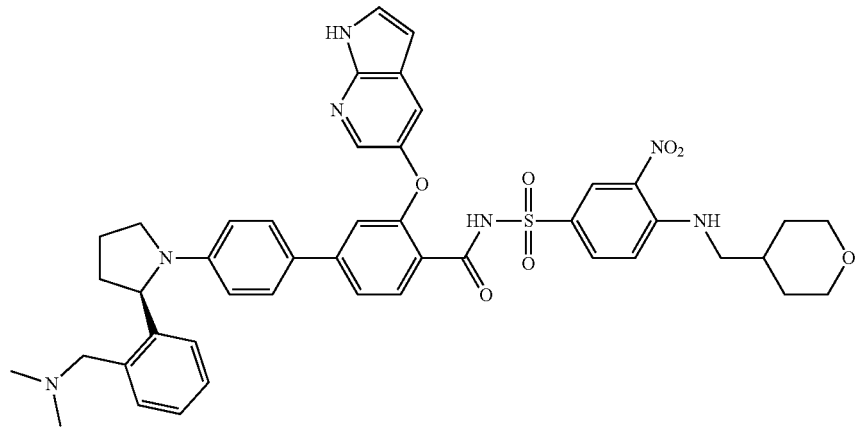 [SMILES: CN(C)Cc1ccccc1[C@H]1CCCN1c1ccc(-c2ccc(C(=O)NS(=O)(=O)c3ccc(NCC4CCOCC4)c([N+](=O)[O-])c3)c(Oc3cnc4[nH]ccc4c3)c2)cc1]

The desired compound was synthesized starting from (R)—N,N-dimethyl-1-(2-(pyrrolidin-2-yl)phenyl)methanamine and 1-bromo-4-iodobenzene following the procedures similar to those in Example A1. $^1$H NMR (400 MHz, DMSO-$d_6$) δ ppm: 11.64 (s, 1H), 8.60-8.40 (m, 2H), 8.01 (s, 1H), 7.80-7.75 (m, 1H), 7.60-7.40 (m, 4H), 7.39-7.13 (m, 5H), 7.10-6.85 (m, 3H), 6.49-6.26 (m, 3H), 5.25-5.15 (m, 1H), 3.75-3.88 (m, 2H), 3.75-3.65 (m, 1H), 3.35-3.25 (m, 5H), 3.15-3.06 (m, 1H), 2.45-2.30 (m, 2H), 2.07-1.80 (m, 4H), 1.70-1.65 (m, 1H), 1.64-1.60 (m, 2H), 1.35-1.15 (m, 6H). MS (ESI, m/e) [M+1]$^+$ 829.8.

Example A130: 3-((1H-pyrrolo[2,3-b]pyridin-5-yl)oxy)-4'-(2-(2-(2-(dimethylamino)ethyl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

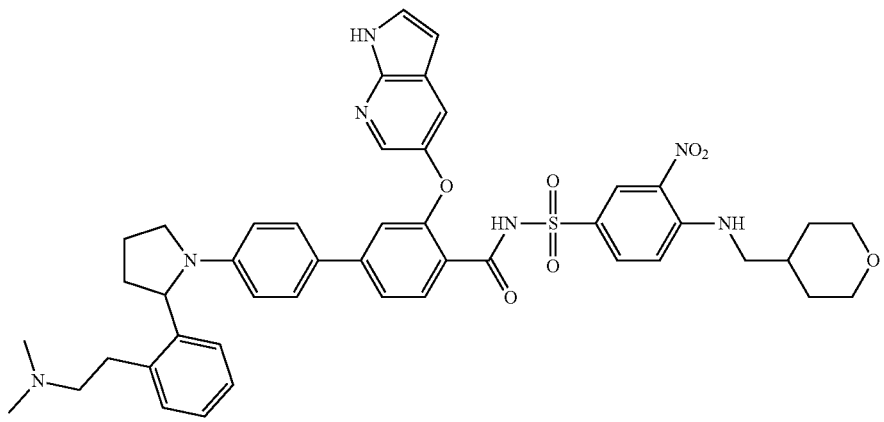 [SMILES: CN(C)CCc1ccccc1C1CCCN1c1ccc(-c2ccc(C(=O)NS(=O)(=O)c3ccc(NCC4CCOCC4)c([N+](=O)[O-])c3)c(Oc3cnc4[nH]ccc4c3)c2)cc1]

The desired compound was synthesized starting from N,N-dimethyl-2-(2-(pyrrolidin-2-yl)phenyl)ethan-1-amine and 1-bromo-4-iodobenzene following the procedures similar to those in Example A100. $^1$H NMR (DMSO-$d_6$) δ ppm: 11.54 (s, 1H), 9.75 (br, 1H), 8.41-8.33 (m, 2H), 7.96 (s, 1H), 7.55 (d, J=8.8 Hz, 1H), 7.48 (d, J=8.0 Hz, 1H), 7.37-7.07 (m, 7H), 7.03-6.84 (m, 4H), 6.41 (d, J=8.0 Hz, 2H), 6.30 (s, 1H), 4.94 (d, J=4.4 Hz, 1H), 3.85 (d, J=8.4 Hz, 2H), 3.73-3.61 (m, 1H), 3.33-3.20 (m, 6H), 3.05-2.92 (m, 4H), 2.80 (s, 6H), 2.07-1.26 (m, 8H). MS (ESI, m/e) [M+1]$^+$ 843.9.

Example A131: 3-((1H-pyrrolo[2,3-b]pyridin-5-yl)oxy)-4'-(2-(2-(3-(dimethylamino)propyl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

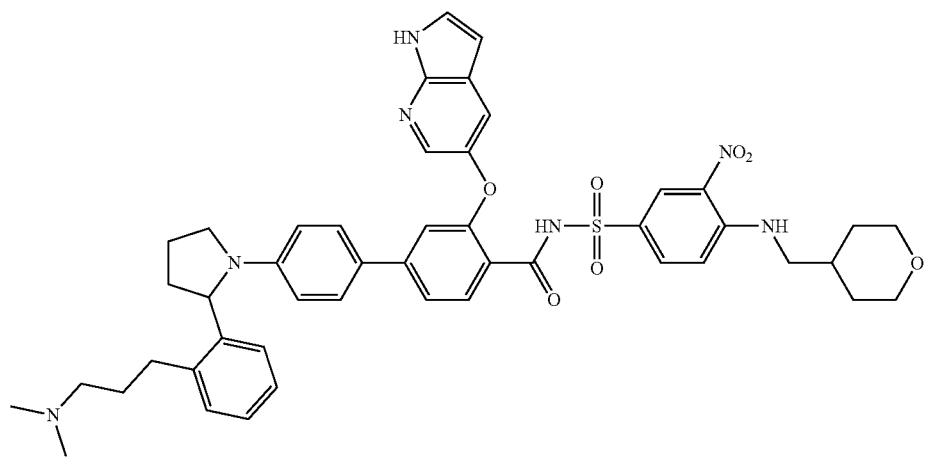 [SMILES: CN(C)CCCc1ccccc1C1CCCN1c1ccc(-c2ccc(C(=O)NS(=O)(=O)c3ccc(NCC4CCOCC4)c([N+](=O)[O-])c3)c(Oc3cnc4[nH]ccc4c3)c2)cc1]

The desired compound was synthesized starting from N,N-dimethyl-3-(2-(pyrrolidin-2-yl)phenyl)propan-1-amine and 1-bromo-4-iodobenzene following the procedures similar to those in Example A100. $^1$H NMR (DMSO-$d_6$) δ ppm: 11.58 (s, 1H), 8.43 (s, 2H), 7.98 (s, 1H), 7.69 (d, J=8.0 Hz, 1H), 7.56 (d, J=7.8 Hz, 1H), 7.43 (d, J=12.8 Hz, 2H), 7.33-7.12 (m, 6H), 7.08-7.07 (m, 1H), 6.96-6.84 (m, 3H), 6.41-6.28 (m, 3H), 3.88-3.82 (m, 2H), 3.73 (s, 1H), 3.39-3.37 (m, 1H), 3.27-3.23 (m, 4H), 3.13 (s, 2H), 2.86-2.62 (m, 9H), 1.96-1.90 (m, 6H), 1.71 (s, 1H), 1.62-1.58 (m, 2H), 1.24 (s, 5H). MS (ESI) m/e [M+1]$^+$ 857.9.

Example A132: 3-((1H-pyrrolo[2,3-b]pyridin-5-yl)oxy)-4'-(2-(2-((1-methylpyrrolidin-3-yl)oxy)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

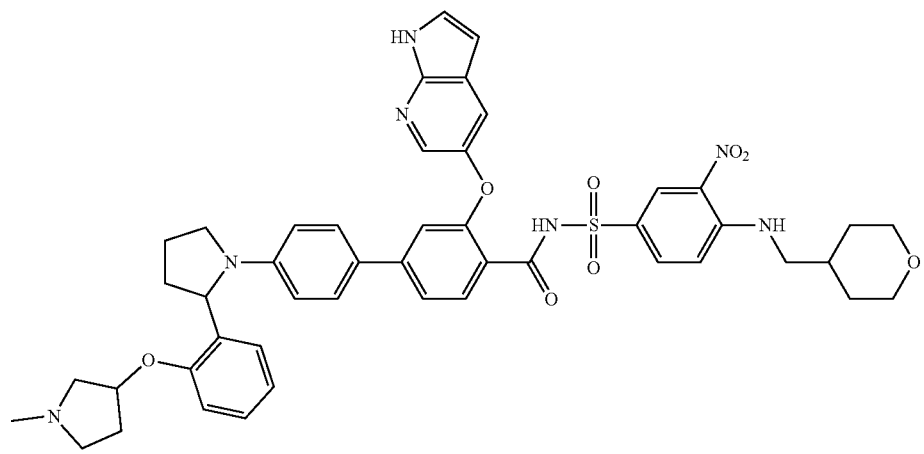 [SMILES: CN1CCC(Oc2ccccc2C2CCCN2c2ccc(-c3ccc(C(=O)NS(=O)(=O)c4ccc(NCC5CCOCC5)c([N+](=O)[O-])c4)c(Oc4cnc5[nH]ccc5c4)c3)cc2)C1]

The desired compound was synthesized starting from 1-methyl-3-(2-(pyrrolidin-2-yl)phenoxy)pyrrolidine and 1-bromo-4-iodobenzene following the procedures similar to those in Example A100. ¹H NMR (DMSO-d₆) δ ppm: 11.57 (s, 1H), 10.58 (br, 1H), 8.47-8.45 (m, 2H), 7.97 (s, 1H), 7.70 (d, J=8.8 Hz, 1H), 7.55 (d, J=8.0 Hz, 1H), 7.43-7.15 (m, 6H), 7.03-6.84 (m, 5H), 6.41-6.28 (m, 3H), 5.15 (d, J=24.4 Hz, 2H), 3.85 (d, J=8.4 Hz, 2H), 3.73-3.71 (m, 1H), 3.33-3.00 (m, 6H), 2.70 (s, 3H), 2.90-2.52 (m, 8H), 2.17-2.72 (m, 6H), 1.75 (d, J=8.4 Hz, 2H). MS (ESI, m/e) [M+1]⁺ 871.9.

Example A133: 3-((1H-pyrrolo[2,3-b]pyridin-5-yl)oxy)-4'-((2R)-2-(2-(methyl(1-methylpyrrolidin-3-yl)amino)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

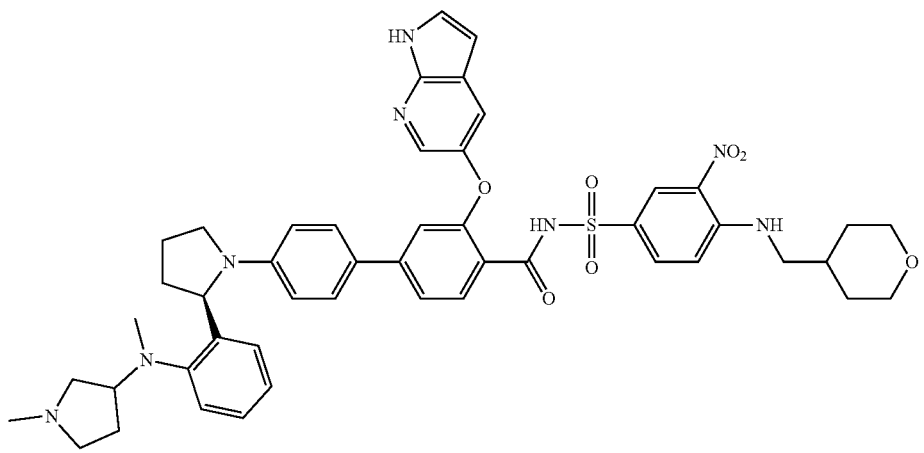

The desired compound was synthesized starting from N,1-dimethyl-N-(2-((R)-pyrrolidin-2-yl)phenyl)pyrrolidin-3-amine and 1-bromo-4-iodobenzene following the procedures similar to those In Example A100. ¹H NMR (DMSO-d₆) δ ppm: 11.55 (s, 1H), 9.80 (s, 1H), 8.45-8.28 (m, 2H), 7.95 (s, 1H), 7.74-7.61 (m, 1H), 7.60-7.52 (m, 1H), 7.42 (s, 1H), 7.39-7.31 (m, 1H), 7.31-7.12 (m, 5H), 7.06-6.94 (m, 2H), 6.94-6.77 (m, 2H), 6.44-6.23 (m, 3H), 5.18-4.98 (m, 1H), 3.93-3.64 (m, 4H), 3.31-3.12 (m, 5H), 3.10-2.75 (m, 3H), 2.70-2.53 (m, 6H), 2.45-2.36 (m, 2H), 2.19-1.93 (m, 3H), 1.90-1.72 (m, 3H), 1.66-1.53 (m, 2H), 1.26-1.21 (m, 2H). MS (ESI, m/e) [M+1]⁺ 884.9.

Example A134: 3-((1H-pyrrolo[2,3-b]pyridin-5-yl)oxy)-4'-(2-(2-(methyl(1-methylpiperidin-3-yl)amino)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

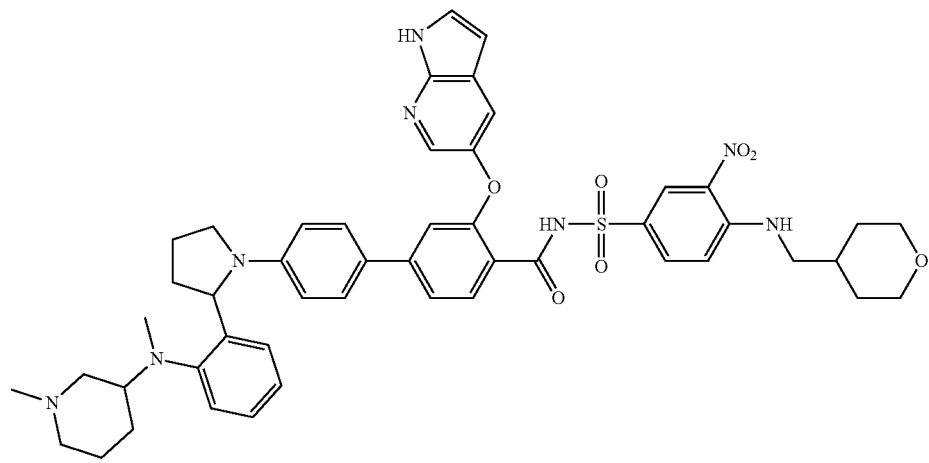 [SMILES: CN1CCCC(N(C)c2ccccc2C2CCCN2c2ccc(-c3ccc(C(=O)NS(=O)(=O)c4ccc(NCC5CCOCC5)c([N+](=O)[O-])c4)c(Oc4cnc5[nH]ccc5c4)c3)cc2)C1]

The desired compound was synthesized starting from N,1-dimethyl-N-(2-(pyrrolidin-2-yl)phenyl)piperidin-3-amine and 1-bromo-4-iodobenzene following the procedures similar to those in Example A100. ¹H NMR (DMSO-d₆) δ ppm: 11.56 (s, 1H), 8.41-8.37 (m, 2H), 7.96 (s, 1H), 7.68 (d, J=8.6 Hz, 1H), 7.56 (d, J=8.0 Hz, 1H), 7.43-7.38 (m, 2H), 7.28-7.24 (m, 6H), 6.99 (s, 2H), 6.89 (s, 2H), 6.42-6.26 (m, 3H), 5.01 (s, 1H), 3.85-3.81 (m, 2H), 3.71 (s, 1H), 3.37 (s, 1H), 3.27-3.23 (m, 6H), 3.09 (s, 3H), 2.69 (s, 5H), 2.42 (s, 1H), 2.01-1.98 (m, 4H), 1.86 (s, 4H), 1.63-1.58 (m, 5H). MS (ESI) m/e [M+1]⁺ 898.8.

Example A135: 3-((1H-pyrrolo[2,3-b]pyridin-5-yl)oxy)-4'-(2-(2-(methyl((1-methylpyrrolidin-2-yl)methyl)amino)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

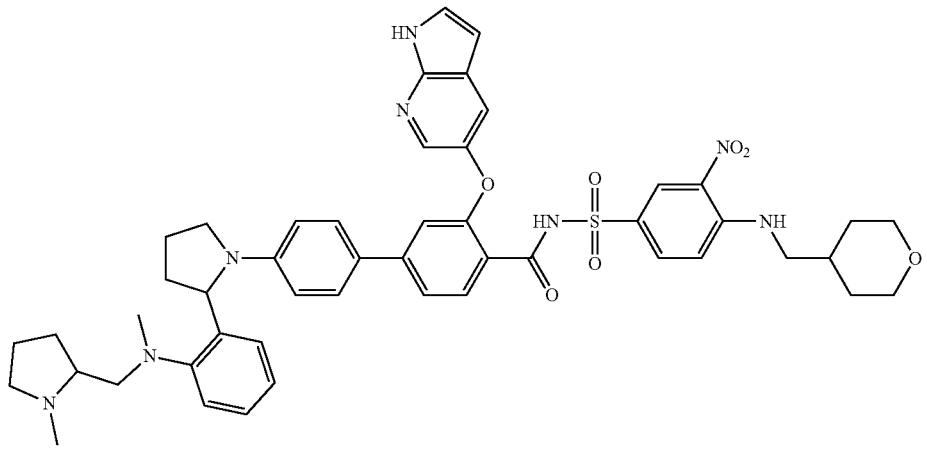 [SMILES: CN(CC1CCCN1C)c1ccccc1C1CCCN1c1ccc(-c2ccc(C(=O)NS(=O)(=O)c3ccc(NCC4CCOCC4)c([N+](=O)[O-])c3)c(Oc3cnc4[nH]ccc4c3)c2)cc1]

The desired compound was synthesized starting from N-methyl-N-((1-methylpyrrolidin-2-yl)methyl)-2-(pyrrolidin-2-yl)aniline and 1-bromo-4-iodobenzene following the procedures similar to those in Example A100. ¹H NMR (DMSO-d₆) δ ppm: 12.16 (s, 1H), 11.70 (s, 1H), 8.65-8.45 (m, 2H), 8.04 (d, J=2.0 Hz, 1H), 7.81 (d, J=8.8 Hz, 1H), 7.64-7.45 (m, 3H), 7.36-7.20 (m, 5H), 7.15-6.94 (m, 3H), 6.87 (s, 1H), 6.42-6.28 (m, 3H), 5.11-4.99 (m, 1H), 3.84 (d, J=8.0 Hz, 2H), 3.74-3.68 (m, 1H), 3.62-3.46 (m, 2H), 3.30-3.20 (m, 4H), 3.17-2.93 (m, 5H), 2.72-2.64 (m, 3H), 2.45-2.22 (m, 2H), 2.02-1.74 (m, 7H), 1.60 (d, J=12.0 Hz, 2H), 1.34-1.16 (m, 4H). MS (ESI, m/e) [M+1]⁺ 898.8.

Example A136: (R)-3-((1H-pyrrolo[2,3-b]pyridin-5-yl)oxy)-4'-(2-(2-(7-methyl-2,7-diazaspiro[3,5]nonan-2-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

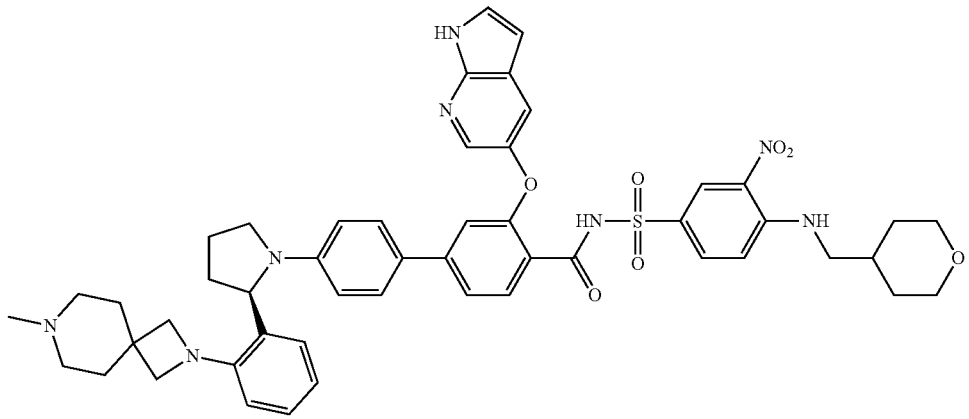 [SMILES: CN1CCC2(CC1)CN(c1ccccc1[C@H]1CCCN1c1ccc(-c3ccc(C(=O)NS(=O)(=O)c4ccc(NCC5CCOCC5)c([N+](=O)[O-])c4)c(Oc4cnc5[nH]ccc5c4)c3)cc1)C2]

The desired compound was synthesized starting from (R)-7-methyl-2-(2-(pyrrolidin-2-yl)phenyl)-2,7-diazaspiro[3.5]nonane and 1-bromo-4-iodobenzene following the procedures similar to those in Example A100. ¹H NMR (DMSO-d₆) δ ppm: 11.55 (s, 1H), 9.44 (s, 1H), 8.51-8.27 (m, 2H), 8.01-7.92 (m, 1H), 7.74-7.60 (m, 1H), 7.60-7.47 (m, 1H), 7.47-7.16 (m, 5H), 7.13-6.99 (m, 1H), 6.94-6.73 (m, 3H), 6.68-6.56 (m, 1H), 6.56-6.36 (m, 3H), 6.31 (s, 1H), 4.92-4.66 (m, 1H), 3.90-3.55 (m, 6H), 3.30-3.18 (m, 4H), 3.12-2.74 (m, 4H), 2.68-2.52 (m, 3H), 2.30-2.19 (m, 1H), 2.06-1.70 (m, 7H), 1.67-1.52 (m, 2H), 1.36-1.08 (m, 4H). MS (ESI, m/e) [M+1]⁺ 910.9.

Example A137: 3-((1H-pyrrolo[2,3-b]pyridin-5-yl)oxy)-4'-(2-(2-(2-((dimethylamino)methyl)pyrrolidin-1-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

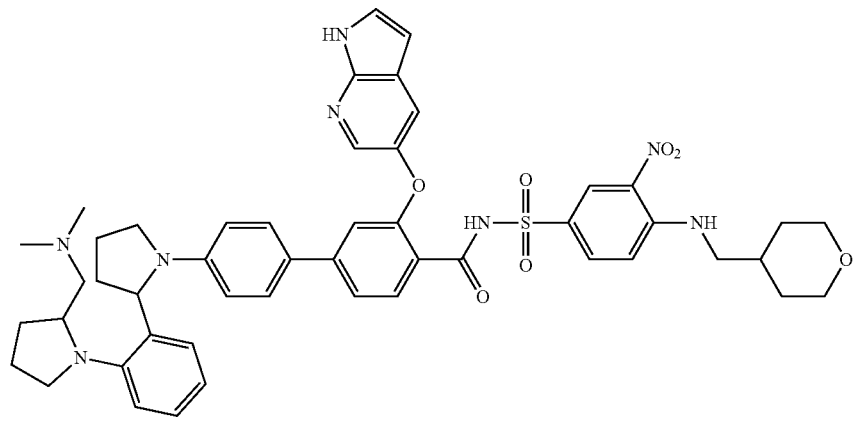 [SMILES: CN(C)CC1CCCN1c1ccccc1C1CCCN1c1ccc(-c2ccc(C(=O)NS(=O)(=O)c3ccc(NCC4CCOCC4)c([N+](=O)[O-])c3)c(Oc3cnc4[nH]ccc4c3)c2)cc1]

The desired compound was synthesized starting from N,N-dimethyl-1-(1-(2-(pyrrolidin-2-yl)phenyl)pyrrolidin-2-yl)methanamine and 1-bromo-4-iodobenzene following the procedures similar to those in Example A100. ¹H NMR (DMSO-d₆) δ ppm: 11.56 (s, 1H), 9.62 (s, 1H), 8.47-8.28 (m, 2H), 7.97 (s, 1H), 7.76-7.63 (m, 1H), 7.61-7.50 (m, 1H), 7.47-7.14 (m, 7H), 6.96-6.80 (m, 4H), 6.47-6.24 (m, 3H), 5.05-4.85 (m, 1H), 3.97-3.76 (m, 3H), 3.70-3.54 (m, 2H), 3.40-3.33 (m, 3H), 3.31-3.19 (m, 4H), 3.07-2.93 (m, 1H), 2.87-2.80 (m, 1H), 2.37-2.20 (m, 4H), 2.04-1.65 (m, 9H), 1.62-1.54 (m, 2H), 1.37-1.23 (m, 3H). MS (ESI, m/e) [M+1]⁺ 899.0.

Example A138: (R)-3-((1H-pyrrolo[2,3-b]pyridin-5-yl)oxy)-4'-(2-(2-(1-methyl-1H-pyrazol-4-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

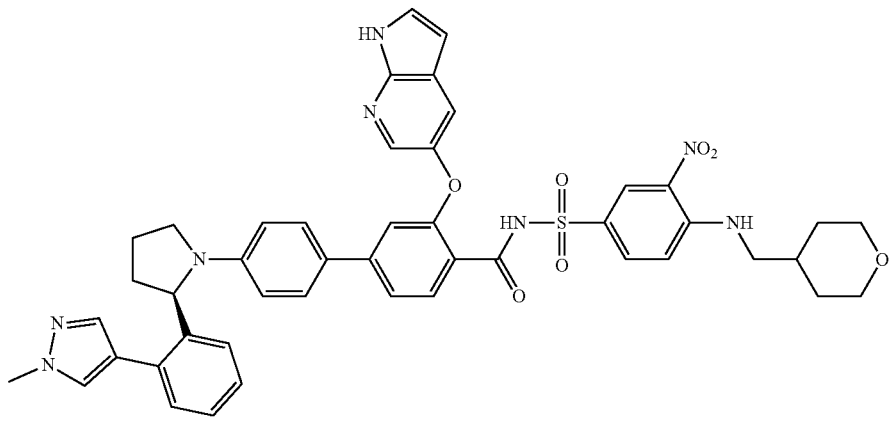 [SMILES: Cn1cc(-c2ccccc2[C@H]2CCCN2c2ccc(-c3ccc(C(=O)NS(=O)(=O)c4ccc(NCC5CCOCC5)c([N+](=O)[O-])c4)c(Oc4cnc5[nH]ccc5c4)c3)cc2)cn1]

The desired compound was synthesized starting from (R)-1-methyl-4-(2-(pyrrolidin-2-yl)phenyl)-1H-pyrazole and 1-bromo-4-iodobenzene following the procedures similar to those in Example A100. $^1$H NMR (DMSO-d$_6$) δ ppm: 12.15 (s, 1H), 11.70 (s, 1H), 8.66-8.53 (m, 2H), 8.04 (d, J=2.8 Hz, 1H), 7.94 (s, 1H), 7.82 (dd, J=1.6 Hz, 9.2 Hz, 1H), 7.66 (s, 1H), 7.58 (d, J=2.4 Hz, 1H), 7.54-7.48 (m, 2H), 7.39-7.10 (m, 7H), 7.05-7.00 (m, 1H), 6.88 (s, 1H), 6.41-6.35 (m, 1H), 6.26 (d, J=8.4 Hz, 1H), 4.86 (d, J=7.2 Hz, 1H), 3.90 (s, 3H), 3.84 (dd, J=2.8 Hz, 11.2 Hz, 2H), 3.77-3.68 (m, 1H), 3.29-3.25 (m, 2H), 3.14-3.06 (m, 1H), 2.46-2.32 (m, 1H), 2.06-1.94 (m, 2H), 1.92-1.74 (m, 2H), 1.60 (d, J=12.4 Hz, 2H), 1.28-1.22 (m, 2H), 1.18 (t, J=7.6 Hz, 2H). MS (ESI, m/e) [M+1]$^+$ 852.8.

Example A139: 3-((1H-pyrrolo[2,3-h]pyridin-5-yl)oxy)-4'-(2-(1-(1-methylpiperidin-4-yl)-1H-pyrazol-5-yl)pyrrolidin-1-yl)-N-((3-nitro-4-((((tetrahydro-2H-pyran-4-yl)methyl)amino)phenyl)sulfonyl)-[1,1'-biphenyl]-4-carboxamide

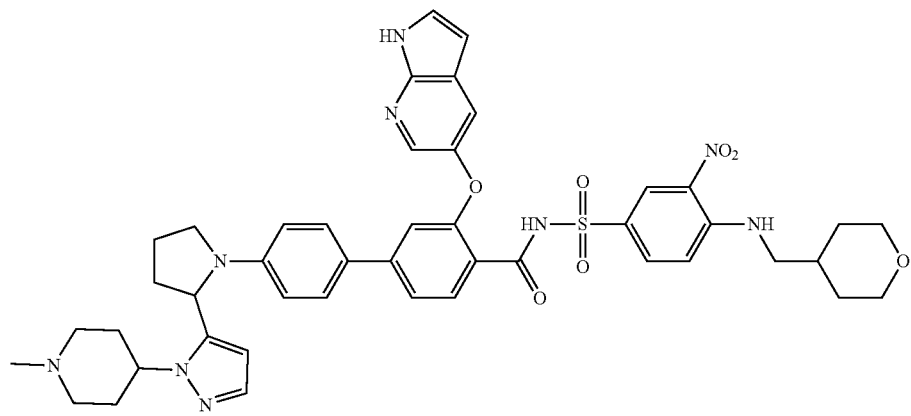 [SMILES: CN1CCC(n2nccc2C2CCCN2c2ccc(-c3ccc(C(=O)NS(=O)(=O)c4ccc(NCC5CCOCC5)c([N+](=O)[O-])c4)c(Oc4cnc5[nH]ccc5c4)c3)cc2)CC1]

The desired compound was synthesized starting from 1-methyl-4-(5-(pyrrolidin-2-yl)-1H-pyrazol-1-yl)piperidine and 1-bromo-4-iodobenzene following the procedures similar to those in Example A100. $^1$H NMR (DMSO-d$_6$) δ ppm: 11.56 (s, 1H), 9.74 (s, 1H), 8.56-8.25 (m, 2H), 8.04-7.89 (m, 1H), 7.74-7.51 (m, 2H), 7.49-7.18 (m, 6H), 6.97-6.77 (m, 2H), 6.51-6.37 (m, 2H), 6.31 (s, 1H), 5.76 (s, 1H), 5.15-4.93 (m, 1H), 4.60-4.29 (m, 1H), 3.94-3.75 (m, 2H), 3.68-3.55 (m, 1H), 3.39-3.32 (m, 2H), 3.30-3.16 (m, 5H), 3.01-2.72 (m, 2H), 2.72-2.56 (m, 3H), 2.42-1.73 (m, 9H), 1.67-1.53 (m, 2H), 1.29-1.19 (m, 2H). MS (ESI, m/e) [M+1]$^+$ 859.9.

Example A140: 3-((1H-pyrrolo[2,3-b]pyridin-5-yl)oxy)-4'-(2-(5-chloro-2-(1-methyl-1,2,3,6-tetrahydropyridin-4-yl)phenyl)pyrrolidin-1-yl)-N-((3-nitro-4-((((tetrahydro-2H-pyran-4-yl)methyl)amino)phenyl)sulfonyl)-[1,1'-biphenyl]-4-carboxamide

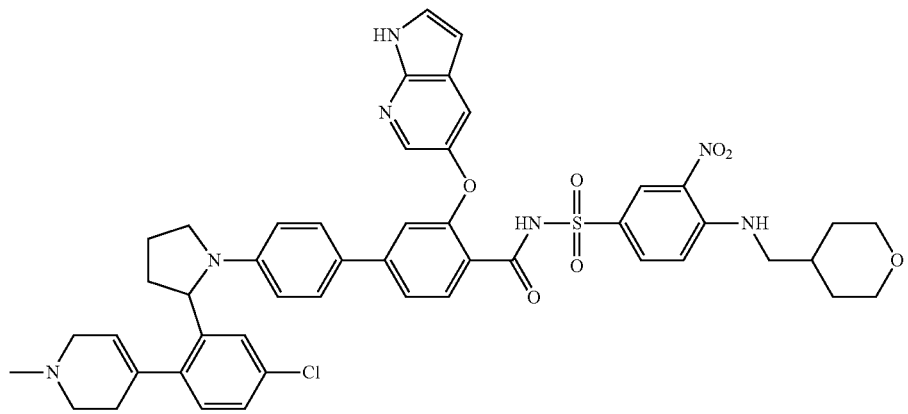 [SMILES: CN1CC=C(c2ccc(Cl)cc2C2CCCN2c2ccc(-c3ccc(C(=O)NS(=O)(=O)c4ccc(NCC5CCOCC5)c([N+](=O)[O-])c4)c(Oc4cnc5[nH]ccc5c4)c3)cc2)CC1]

The desired compound was synthesized starting from 4-(4-chloro-2-(pyrrolidin-2-yl)phenyl)-1-methyl-1,2,3,6-tetrahydropyridine and 1-bromo-4-iodobenzene following the procedures similar to those in Example A68-R. ¹H NMR (DMSO-d₆) δ ppm: 11.55 (s, 1H), 9.62 (s, 1H), 8.46-8.29 (m, 2H), 7.96 (s, 1H), 7.73-7.51 (m, 2H), 7.48-7.10 (m, 7H), 7.04 (s, 1H), 6.93 (s, 1H), 6.89-6.78 (m, 1H), 6.46-6.26 (m, 3H), 5.71 (s, 1H), 4.85-4.68 (m, 1H), 3.92-3.72 (m, 3H), 3.31-3.19 (m, 5H), 3.18-2.81 (m, 3H), 2.39-2.23 (m, 2H), 2.07-1.92 (m, 3H), 1.92-1.73 (m, 2H), 1.70-1.52 (m, 2H), 1.34-1.22 (m, 6H). MS (ESI, m/e) [M+1]⁺ 901.9.

Example A141: 3-((1H-pyrrolo[2,3-b]pyridin-5-yl)oxy)-4'-(2-(isoquinolin-8-yl)pyrrolidin-1-yl)-N-((3-nitro-4-(((tetrahydro-2H-pyran-4-yl)methyl)amino)phenyl)sulfonyl)-[1,1'-biphenyl]-4-carboxamide

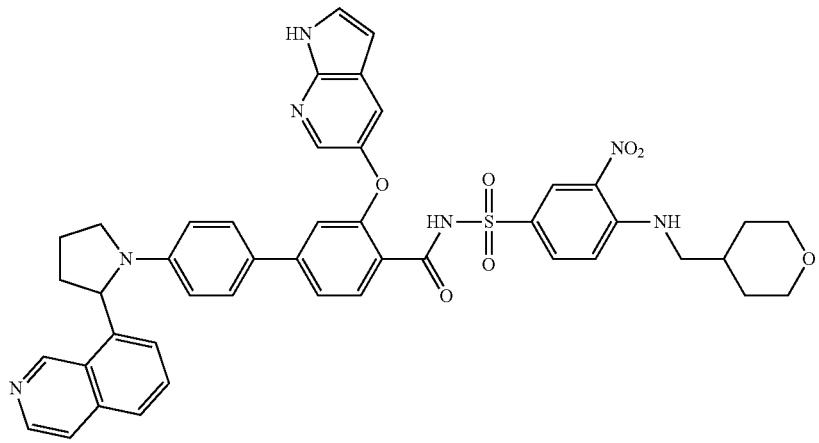 [SMILES: O=C(NS(=O)(=O)c1ccc(NCC2CCOCC2)c([N+](=O)[O-])c1)c1ccc(-c2ccc(N3CCCC3c3cccc4ccncc34)cc2)cc1Oc1cnc2[nH]ccc2c1]

The desired compound was synthesized starting from 8-(pyrrolidin-2-yl)isoquinoline and 1-bromo-4-iodobenzene following the procedures similar to those in Example A1. ¹H NMR (DMSO-d₆) δ ppm: 12.15 (s, 1H), 11.68 (s, 1H), 9.71 (s, 1H), 8.58-8.52 (m, 3H), 8.04 (s, 1H), 7.65-7.53 (m, 3H), 7.57-7.46 (m, 4H), 7.37-7.23 (m, 3H), 7.22-6.95 (m, 2H), 6.87 (s, 1H), 6.36-6.34 (m, 3H), 5.73 (s, 1H), 3.85-3.83 (m, 3H), 3.46-3.43 (m, 1H), 3.30-3.26 (m, 4H), 3.10-3.08 (m, 2H), 2.65-2.58 (m, 1H), 1.95-1.85 (m, 4H), 1.66-1.50 (m, 2H), 1.23 (s, 3H). MS (ESI) m/e [M+1]⁺ 823.8.

Example A142: 3-((1H-pyrrolo[2,3-b]pyridin-5-yl)oxy)-4'-(2-(2-methyl-2H-indazol-7-yl)pyrrolidin-1-yl)-N-((3-nitro-4-(((tetrahydro-2H-pyran-4-yl)methyl)amino)phenyl)sulfonyl)-[1,1'-biphenyl]-4-carboxamide

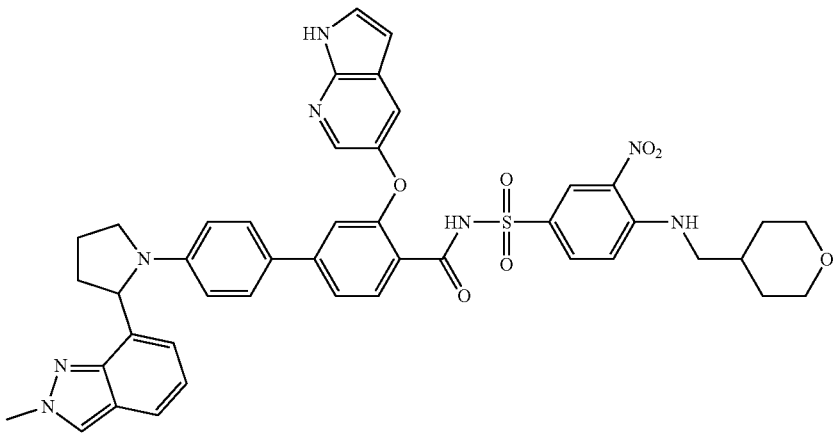 [SMILES: Cn1cc2cccc(C3CCCN3c3ccc(-c4ccc(C(=O)NS(=O)(=O)c5ccc(NCC6CCOCC6)c([N+](=O)[O-])c5)c(Oc5cnc6[nH]ccc6c5)c4)cc3)c2n1]

The desired compound was synthesized starting from 2-methyl-7-(pyrrolidin-2-yl)-2H-indazole and 1-bromo-4-iodobenzene following the procedures similar to those in Example A1. $^1$H NMR (DMSO-d$_6$) δ ppm: 11.58 (s, 1H), 10.34 (s, 1H), 8.51-8.27 (m, 2H), 7.97 (s, 1H), 7.74-7.65 (m, 1H), 7.59-7.51 (m, 1H), 7.47-7.34 (m, 2H), 7.33-7.13 (m, 5H), 7.08-6.96 (m, 2H), 6.95-6.85 (m, 2H), 6.45-6.25 (m, 3H), 5.15-4.98 (m, 1H), 3.88-3.79 (m, 2H), 3.9-3.67 (m, 1H), 3.41-3.36 (m, 1H), 3.32-3.19 (m, 2H), 3.13-2.77 (m, 8H), 2.67-2.53 (m, 3H), 2.47-2.38 (m, 1H), 2.07-1.94 (m, 3H), 1.93-1.73 (m, 2H), 1.66-1.52 (m, 2H). MS (ESI, m/e) [M+1]$^+$ 870.8.

Example A143: 3-((1H-pyrrolo[2,3-b]pyridin-5-yl)oxy)-4'-(2-(2-methyl-1,2,3,4-tetrahydroisoquinolin-8-yl)pyrrolidin-1-yl)-N-((3-nitro-4-((((tetrahydro-2H-pyran-4-yl)methyl)amino)phenyl)sulfonyl)-[1,1'-biphenyl]-4-carboxamide

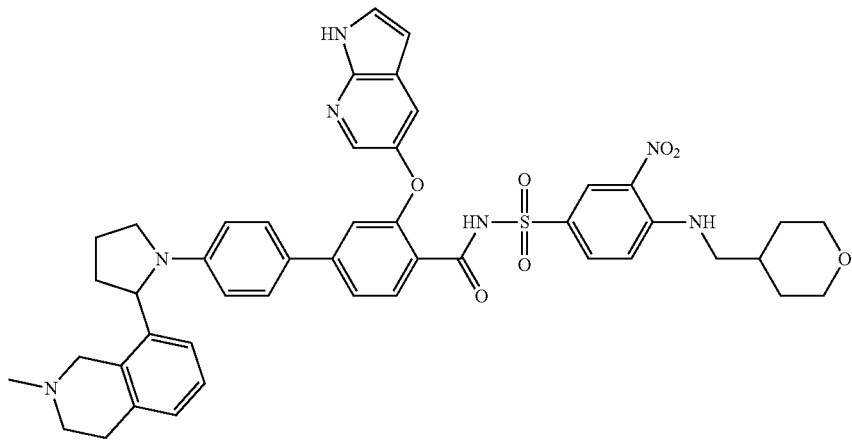 [SMILES: CN1CCc2cccc(C3CCCN3c3ccc(-c4ccc(C(=O)NS(=O)(=O)c5ccc(NCC6CCOCC6)c([N+](=O)[O-])c5)c(Oc5cnc6[nH]ccc6c5)c4)cc3)c2C1]

The desired compound was synthesized starting from 2-methyl-8-(pyrrolidin-2-yl)-1,2,3,4-tetrahydroisoquinoline and 1-bromo-4-iodobenzene following the procedures similar to those in Example A100. $^1$H NMR (DMSO-d$_6$) δ ppm: 11.60 (s, 1H), 10.54 (s, 1H), 8.53-8.33 (m, 2H), 8.04-7.92 (m, 1H), 7.78-7.63 (m, 1H), 7.60-7.38 (m, 3H), 7.33-7.15 (m, 3H), 7.15-7.01 (m, 2H), 6.99-6.71 (m, 3H), 6.46-6.22 (m, 3H), 4.87-4.67 (m, 1H), 4.60-4.31 (m, 1H), 4.19-3.92 (m, 1H), 3.92-3.79 (m, 2H), 3.77-3.60 (m, 1H), 3.40-3.34 (m, 1H), 3.29-3.17 (m, 5H), 3.10-2.95 (m, 2H), 2.89-2.75 (m, 2H), 2.41-2.24 (m, 1H), 2.02-1.76 (m, 3H), 1.76-1.50 (m, 3H), 1.33-1.13 (m, 3H), MS (ESI, m/e) [M+1]$^+$ 841.8.

Example A144: 3-((1H-pyrrolo[2,3-b]pyridin-5-yl)oxy)-4'-(2-(2-(2-cyclopropylphenyl)propan-2-yl)pyrrolidin-1-yl)-N-((3-nitro-4-((((tetrahydro-2H-pyran-4-yl)methyl)amino)phenyl)sulfonyl)-[1,1'-biphenyl]-4-carboxamide

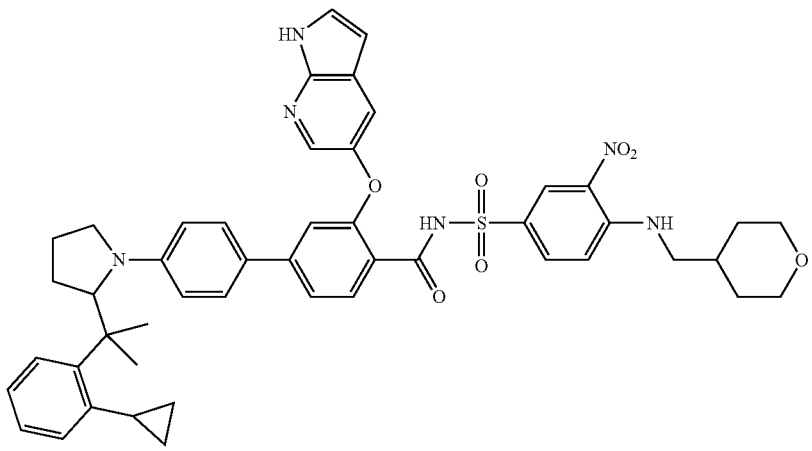 [SMILES: CC(C)(c1ccccc1C1CC1)C1CCCN1c1ccc(-c2ccc(C(=O)NS(=O)(=O)c3ccc(NCC4CCOCC4)c([N+](=O)[O-])c3)c(Oc3cnc4[nH]ccc4c3)c2)cc1]

The desired compound was synthesized starting from 2-(2-(2-cyclopropylphenyl)propan-2-yl)pyrrolidine and 1-bromo-4-iodobenzene following the procedures similar to those in Example A1. ¹H NMR (DMSO-d₆) δ ppm: 12.17 (s, 1H), 11.74 (s, 1H), 8.63-8.58 (m, 2H), 8.09 (s, 1H), 7.85 (d, J=8.1 Hz, 1H), 7.59-7.53 (m, 3H), 7.36-7.30 (m, 4H), 7.19-7.00 (m, 3H), 6.90 (s, 2H), 6.73-6.69 (m, 2H), 6.41 (s, 1H), 4.85 (s, 1H), 3.87-3.83 (m, 2H), 3.49 (s, 1H), 3.28-3.15 (m, 3H), 2.02-1.84 (m, 2H), 1.72-1.58 (m, 5H), 1.40 (s, 6H), 1.24 (s, 4H), 0.98-0.92 (m, 4H), 0.61 (s, 1H). MS (ESI) m/e [M+1]⁺ 854.8.

Example A145a and Example A145b: 3-((1H-pyrrolo[2,3-b]pyridin-5-yl)oxy)-4'-((2R,4S) or (2S,4R)-2-(2-cyclopropylphenyl)-4-fluoropyrrolidin-1-yl)-N-((3-nitro-4-(((tetrahydro-2H-pyran-4-yl)methyl)amino)phenyl)sulfonyl)-[1,1'-biphenyl]-4-carboxamide; and 3-((1H-pyrrolo[2,3-b]pyridin-5-yl)oxy)-4'-((2S,4R) or (2R,4S)-2-(2-cyclopropylphenyl)-4-fluoropyrrolidin-1-yl)-N-((3-nitro-4-(((tetrahydro-2H-pyran-4-yl)methyl)amino)phenyl)sulfonyl)-[1,1'-biphenyl]-4-carboxamide

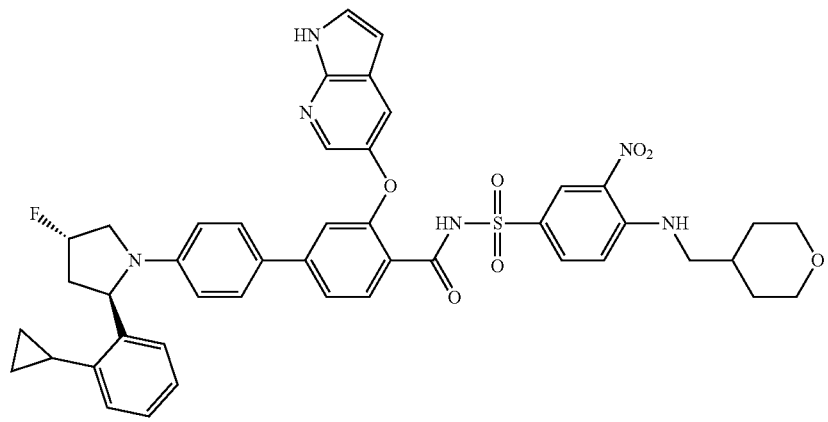

or

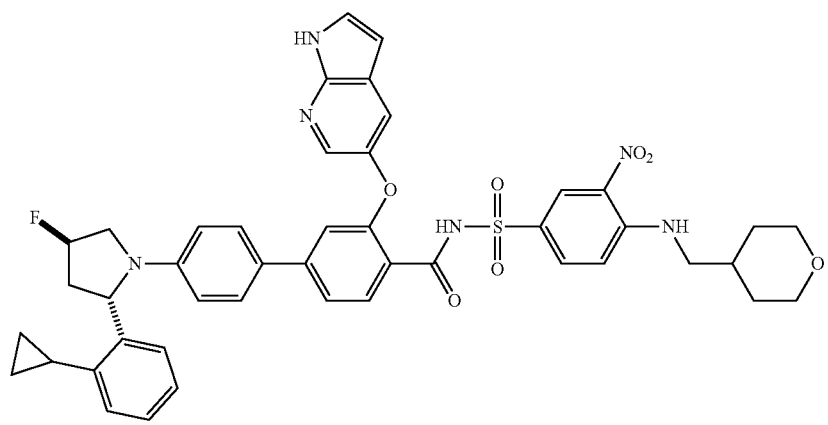

Step 1: (E)-N-(2-cyclopropylbenzylidene)-2-methylpropane-2-sulfinamide

To a solution of 2-cyclopropylbenzaldehyde (126.95 g, 868.39 mmol) and 2-methylpropane-2-sulfinamide (210.89 g, 1.74 mol) in THF (1300 mL) was added Ti(OEt)$_4$ (396.91 g, 1.74 mol). The mixture was stirred at 80° C. for 12 hours. TLC indicated the reactant was consumed completely. The reaction mixture was poured into water (500 mL) and filtered. The filtrate was extracted with Ethyl acetate (300 mL×3). The combined organic phase was washed with brine (50 mL×2), dried with anhydrous Na$_2$SO$_4$, filtered and concentrated in vacuum. The residue was purified by column chromatography on silica gel (eluent: PE/EA=200/1 to 50/1). (E)-N-(2-cyclopropylbenzylidene)-2-methylpropane-2-sulfinamide (190.13 g) was obtained as yellow solid.

Step 2: N-(1-(2-cyclopropylphenyl)but-3-en-1-yl)-2-methylpropane-2-sulfonamide To a solution of (E)-N-(2-cyclopropylbenzylidene)-2-methylpropane-2-sulfinamide (190 g, 761.92 mmol) in DCM (1.50 L) was added allylmagnesium bromide (2.28 L, 2.28 mol, 1M) at −10° C. to 0° C., the mixture was stirred at 0° C. for 1 hours. LC/MS showed that the reaction was completely. The reaction mixture was quenched by saturated NH$_4$Cl aqueous solution, and then extracted with DCM (200 mL×3). The combined organic layers were dried over Na$_2$SO$_4$, filtered and concentrated under reduced pressure. The residue was washed with MTBE (200 mL) and filtered. N-(1-(2-cyclopropylphenyl)but-3-en-1-yl)-2-methylpropane-2-sulfonamide (130.12 g) was obtained as white solid. $^1$H NMR (400 MHz, CDCl$_3$) δ ppm: 0.59-0.84 (m, 2H) 0.89-1.08 (m, 2H) 1.20 (s, 9H) 1.95-2.09 (m, 1H) 2.49 (dt, J=14.03, 8.45 Hz, 1H) 2.59-2.71 (m, 1H) 3.69 (br s, 1H) 5.11-5.26 (m, 3H) 5.70-5.86 (m, 1H) 7.03-7.12 (m, 1H) 7.15-7.25 (m, 2H) 7.32-7.41 (m, 1H).

Step 3: N-(1-(2-cyclopropylphenyl)-2-(oxiran-2-yl)ethyl)-2-methylpropane-2-sulfon amide To a solution of N-(1-(2-cyclopropylphenyl)but-3-en-1-yl)-2-methylpropane-2-sulfonamide (30 g, 102.93 mmol) in DCM (300 mL) was added m-CPBA (71.05 g, 411.73 mmol) at 0° C., the mixture was stirred at 20° C. for 12 hours. TLC indicated the reactant was consumed completely. The reaction mixture was washed with saturated Na$_2$CO$_3$ aqueous solution (100 mL) and extracted with DCM (100 mL×3). The combined organic phase was washed with brine (100 mL×2), dried with anhydrous Na$_2$SO$_4$, filtered and concentrated in vacuum. The residue was purified by column chromatography on silica gel (eluent: PE/EA=1/0 to 2/1). N-(1-(2-cyclopropylphenyl)-2-(oxiran-2-yl)ethyl)-2-methylpropane-2-sulfonamide (24.75 g) was obtained as yellow solid. $^1$H NMR (400 MHz, CDCl$_3$) δ ppm: 0.55-0.86 (m, 2H) 0.88-1.09 (m, 2H) 1.25 (s, 2H) 1.28 (d, J=0.73 Hz, 6H) 1.86-1.96 (m, 1H) 2.11-2.25 (m, 1H) 2.40-2.64 (m, 1H) 2.73-2.87 (m, 1H) 2.94-3.12 (m, 1H) 4.66-5.15 (m, 1H) 5.37-5.54 (m, 1H) 6.98-7.10 (m, 1H) 7.16-7.26 (m, 2H) 7.30-7.64 (m, 1H) 7.94-8.12 (m, 1H).

Step 4: 1-(tert-butylsulfonyl)-5-(2-cyclopropylphenyl)pyrrolidin-3-ol

To a solution of N-(1-(2-cyclopropylphenyl)-2-(oxiran-2-yl)ethyl)-2-methylpropane-2-sulfonamide (24.75 g, 76.52 mmol) in DMF (300 mL) was added K$_2$CO$_3$ (31.73 g, 229.56 mmol) and KI (12.70 g, 76.52 mmol), the mixture was stirred at 100° C. for 12 hours. TLC indicated the reactant was consumed completely. The mixture was cooled to room temperature and then poured into ice/water and extracted with EA (300 mL×3), dried with Na$_2$SO$_4$, filtered and concentrated under reduced pressure. The residue was purified by column chromatography on silica gel (eluent: PE/EA=200/1 to 2/1). 1-(tert-butylsulfonyl)-5-(2-cyclopropylphenyl)pyrrolidin-3-ol (20.63 g) was obtained as yellow oil. $^1$H NMR (400 MHz, CDCl3) δ ppm: 0.50-0.84 (m, 2H) 0.89-1.02 (m, 2H) 1.23 (d, J=5.29 Hz, 9H) 1.84-2.02 (m, 2H) 2.28 (d, J=4.85 Hz, 1H) 2.75 (br dd, J=7.17, 5.84 Hz, 1H) 3.38 (dd, J=11.47, 6.39 Hz, 1H) 4.03 (br d, J=12.35 Hz, 1H) 4.27 (dd, J=11.36, 6.50 Hz, 1H) 4.46-4.61 (m, 1H) 5.85-6.12 (m, 1H) 7.05 (d, J=7.72 Hz, 1H) 7.11-7.26 (m, 2H) 7.47 (d, J=7.72 Hz, 1H).

Step 5: 1-(tert-butylsulfonyl)-2-(2-cyclopropylphenyl)-4-fluoropyrrolidine

DAST (23.47 g, 145.62 mmol) A was added into the solution of 1-(tert-butylsulfonyl)-5-(2-cyclopropylphenyl)pyrrolidin-3-oi (15.70 g, 48.54 mmol) in DCM (200 mL) at 0° C. The mixture was stirred at 30° C. for 12 hours. TLC indicated the reactant was consumed completely. The reaction mixture was washed with saturated Na$_2$CO$_3$ aqueous solution (100 mL) and extracted with DCM (150 mL×3). The combined organic phase was washed with brine (100 mL×2), dried with anhydrous Na$_2$SO$_4$, filtered and concentrated in vacuum. The residue was purified by column chromatography on silica gel (eluent: PE/EA=I/O to 2/1). 1-(tert-butylsulfonyl)-2-(2-cyclopropylphenyl)-4-fluoropyrrolidine (10.21 g) was obtained as yellow solid.

Step 6: 2-(2-cyclopropylphenyl)-4-fluoropyrrolidine

A mixture of 1-(tert-butylsulfonyl)-2-(2-cyclopropylphenyl)-4-fluoropyrrolidine (10.21 g, 31.37 mmol) in TFA (80 mL) was stirred at 60° C. for 2 hours. TLC indicated the reactant was consumed completely. The reaction mixture was concentrated to remove the TFA in vacuum. The residue was adjusted to Ph ~10 with saturated Na$_2$CO$_3$ aqueous solution and extracted with EA (150 mL×3). The combined organic phase was washed with brine (100 mL×2), dried with anhydrous Na$_2$SO$_4$, filtered and concentrated in vacuum. 2-(2-cyclopropylphenyl)-4-fluoropyrrolidine (5.23 g) was obtained as yellow oil. The crude product was used into the next step without further purification. $^1$H NMR (400 MHz, CDCl3) δ ppm: 0.59-0.81 (m, 2H) 0.89-1.03 (m, 2H) 1.66-2.13 (m, 4H) 2.50-2.74 (m, 1H) 3.27-3.61 (m, 2H) 4.61-5.12 (m, 1H) 5.20-5.45 (m, 1H) 6.95-7.09 (m, 1H) 7.14-7.25 (m, 2H) 7.53 (d, J=7.02 Hz, 1H).

Step 7: 1-(4-bromophenyl)-2-(2-cyclopropylphenyl)-4-fluoropyrrolidine

To a solution of 2-(2-cyclopropylphenyl)-4-fluoropyrrolidine (1.6 g, 7.8 mmol) and 1-bromo-4-iodobenzene (6.6 g, 23.4 mmol) in toluene (20 mL) were added t-BuOK (2.62 g, 23.4 mmol), BINAP (968 mg, 1.56 mmol), Pd$_2$(dba)$_3$ (712 g, 780 umol). The mixture was stirred at 100° C. for 4 hours. TLC indicated the reactant was consumed completely. The reaction mixture was concentrated in vacuum. The residue was purified by prep-TLC (eluent: PE/EA=10/1) to give faster isomer as 1-(4-bromophenyl)-2-(2-cyclopropylphenyl)-4-trans-fluoropyrrolidine, and then give slower isomer as 1-(4-bromophenyl)-2-(2-cyclopropylphenyl)-4-cis-fluoropyrrolidine.

1-(4-bromophenyl)-2-(2-cyclopropylphenyl)-4-trans-fluoropyrrolidine was then separated by SFC (Instrument: Thar SFC350 preparative SFC; Column: Chiralpak AD, 250×50 mm i.d. 10 u; Mobile phase: A for $CO_2$ and B for MeOH; Gradient: B %=30%; Flow rate: 200 g/min; Wavelength: 220 nm; Column temperature: 40° C.; System backpressure: 100 bar) to obtain two isomers.

With the faster isomer in SFC (retention time: 1.0 min) as starting material, 3-((1H-pyrrolo[2,3-b]pyridin-5-yl)oxy)-4'-((2R,4S) or (2S,4R)-2-(2-cyclopropylphenyl)-4-fluoropyrrolidin-1-yl)-N-((3-nitro-4-(((tetrahydro-2H-pyran-4-yl)methyl)amino)phenyl)sulfonyl)-[1,1'-biphenyl]-4-carboxamide as example A145a was synthesized following the similar procedures with example A1. $^1$H NMR (400 MHz, DMSO-$d_6$) δ ppm: 12.18 (s, 1H), 11.70 (s, 1H), 8.70-8.44 (m, 2H), 8.10-7.98 (m, 1H), 7.87-7.77 (m, 1H), 7.64-7.47 (m, 3H), 7.39-6.97 (m, 8H), 6.90 (s, 1H), 6.46-6.31 (m, 3H), 5.56-5.28 (m, 2H), 4.15-3.98 (m, 1H), 3.91-3.66 (m, 3H), 3.29-3.20 (m, 4H), 3.07-2.81 (m, 3H), 2.11-1.82 (m, 3H), 1.67-1.55 (m, 2H), 1.10-0.88 (m, 2H), 0.80-0.65 (m, 2H). MS (ESI, m/e) [M+1]$^+$ 830.7.

With the slower isomer in SFC (retention time: 1.4 min) as starting material, 3-((1H-pyrrolo[2,3-b]pyridin-5-yl)oxy)-4'-((2S,4R) or (2R,4S)-2-(2-cyclopropylphenyl)-4-fluoropyrrolidin-1-yl)-N-((3-nitro-4-(((tetrahydro-2H-pyran-4-yl)methyl)amino)phenyl)sulfonyl)-[1,1'-biphenyl]-4-carboxamide as example A145b was synthesized following the similar procedures with example A1. MS (ESI, m/e) [M+1]$^+$ 830.7.

Example A145c and Example A145d: 3-((1H-pyrrolo[2,3-b]pyridin-5-yl)oxy)-4'-((2R,4R) or (2S,4S)-2-(2-cyclopropylphenyl)-4-fluoropyrrolidin-1-yl)-N-((3-nitro-4-(((tetrahydro-2H-pyran-4-yl)methyl)amino)phenyl)sulfonyl)-[1,1'-biphenyl]-4-carboxamide; and 3-((1H-pyrrolo[2,3-b]pyridin-5-yl)oxy)-4'-((2S,4S) or (2R,4R)-2-(2-cyclopropylphenyl)-4-fluoropyrrolidin-1-yl)-N-((3-nitro-4-(((tetrahydro-2H-pyran-4-yl)methyl)amino)phenyl)sulfonyl)-[1,1'-biphenyl]-4-carboxamide

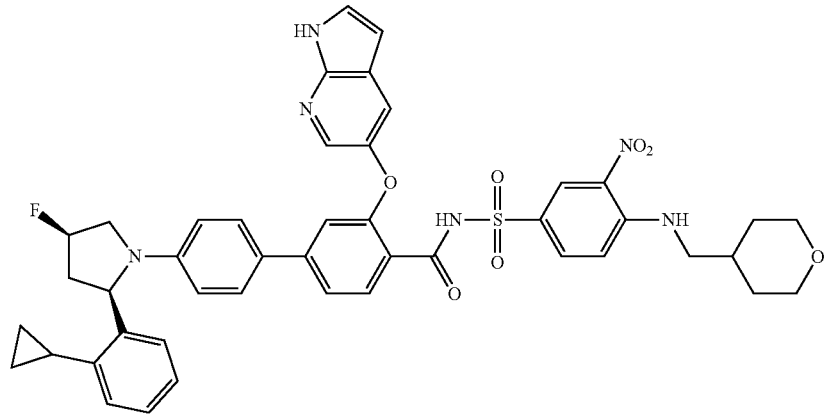

or

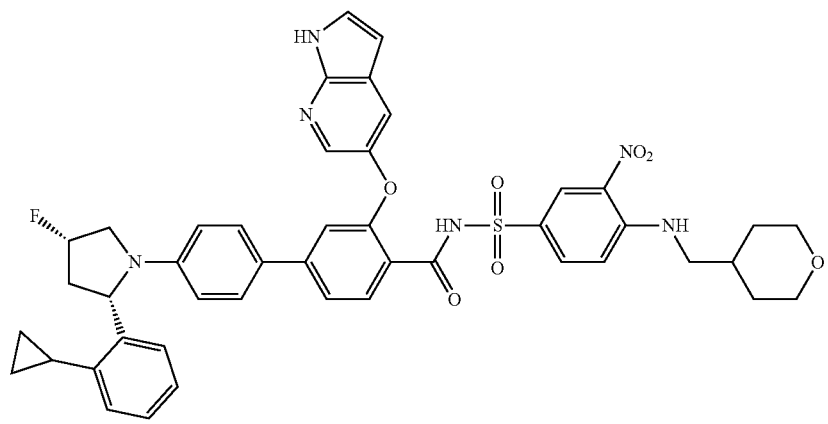

1-(4-bromophenyl)-2-(2-cyclopropylphenyl)-4-cis-fluoropyrrolidine was separated by SFC (Instrument: Thar SFC350 preparative SFC; Column: Chiralcel OD, 250×50 mm i.d. 10 u; Mobile phase: A for $CO_2$ and B for MeOH; Gradient: B %=35%; Flow rate: 200 g/min; Wavelength: 220 nm; Column temperature: 40'C; System back pressure: 100 bar) to obtain two isomers.

With the faster isomer in SFC (retention time: 1.6 min) as the starting material, 3-((1H-pyrrolo[2,3-b]pyridin-5-yl)oxy)-4'-((2R,4R) or (2S,4S)-2-(2-cyclopropylphenyl)-4-fluoropyrrolidin-1-yl)-N-((3-nitro-4-(((tetrahydro-2H-pyran-4-yl)methyl)amino)phenyl)sulfonyl)-[1,1'-biphenyl]-4-carboxamide as example A145c was synthesized following the similar procedures with example A1. $^1$H NMR (DMSO-$d_6$) δ ppm: 12.18 (s, 1H), 11.70 (s, 1H), 8.61 (s, 1H), 8.57 (s, 1H), 8.05 (s, 1H), 7.83 (d, J=9.4 Hz, 1H), 7.59 (s, 1H), 7.56-7.48 (m, 2H), 7.34 (t, J=8.6 Hz, 3H), 7.13-7.09 (m, 2H), 7.05-7.00 (m, 3H), 6.91 (s, 1H), 6.41-6.38 (m, 3H) 5.55 (s, 0.5H), 5.41 (s, 0.5H), 5.27 (d, J=9.7 Hz, 1H), 4.01-3.97 (m, 1H), 3.86-3.81 (m, 2H), 3.78-3.65 (m, 1H), 3.31-3.22 (m, 5H), 2.26-2.15 (m, 1H), 2.01-1.98 (m, 1H), 1.87 (s, 1H), 1.62-1.58 (m, 2H), 1.24 (s, 2H), 1.03-0.92 (m, 2H), 0.81-0.74 (m, 1H), 0.72-0.68 (m, 1H). MS (ESI) m/e [M+1]$^+$ 830.8.

With the slower isomer in SFC (retention time: 1.8 min) as the starting material, 3-((1H-pyrrolo[2,3-b]pyridin-5-yl)oxy)-4'-((2S,4S) or (2R,4R)-2-(2-cyclopropylphenyl)-4-fluoropyrrolidin-1-yl)-N-((3-nitro-4-(((tetrahydro-2H-pyran-4-yl)methyl)amino)phenyl)sulfonyl)-[1,1'-biphenyl]-4-carboxamide as example A145d was synthesized following the similar procedures with example A1. MS (ESI) m/e [M+1]$^+$ 830.8.

Example A146: 3-((1H-pyrrolo[2,3-b]pyridin-5-yl)oxy)-4'-(2-(2-cyclopropylphenyl)-4-fluoro-2,5-dihydro-1H-pyrrol-1-yl)-N-((3-nitro-4-(((tetrahydro-2H-pyran-4-yl)methyl)amino)phenyl)sulfonyl)-[1,1'-biphenyl]-4-carboxamide

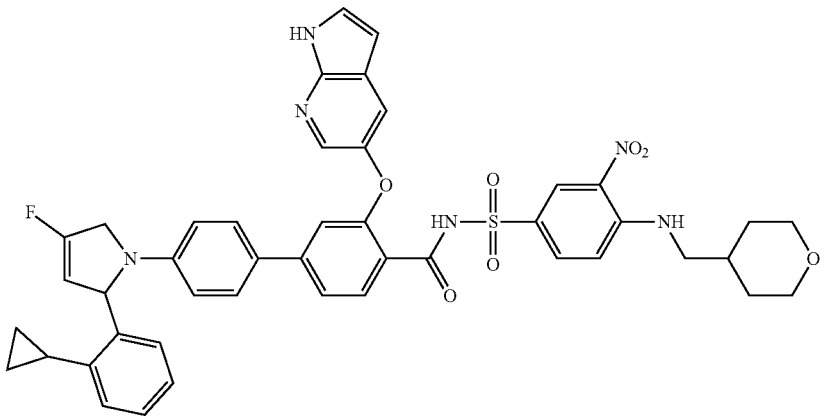 [SMILES: O=C(NS(=O)(=O)c1ccc(NCC2CCOCC2)c([N+](=O)[O-])c1)c1ccc(-c2ccc(N3CC(F)=CC3c3ccccc3C3CC3)cc2)cc1Oc1cnc2[nH]ccc2c1]

The desired compound was synthesized starting from 2-(2-cyclopropylphenyl)-4-fluoro-2,5-dihydro-1H-pyrrole and 1-bromo-4-iodobenzene following the procedures similar to those in Example A1. $^1$H NMR (DMSO-d$_6$) δ ppm: 12.19 (s, 1H), 11.69 (s, 1H), 8.61-8.56 (m, 2H), 8.04 (s, 1H), 7.82 (d, J=8.8 Hz, 1H), 7.52-7.46 (m, 3H), 7.36-7.32 (m, 2H), 7.14-7.05 (m, 4H), 6.91 (s, 1H), 6.39 (d, J=8.1 Hz, 3H), 5.95 (s, 1H), 5.65 (s, 1H), 4.58 (d, J=13.3 Hz, 1H), 4.34 (d, J=13.3 Hz, 1H), 3.84 (d, J=8.5 Hz, 2H), 3.29-3.22 (m, 4H), 2.98 (s, 1H), 2.13 (s, 1H), 2.03-1.94 (m, 1H), 1.87 (s, 1H), 1.60 (d, J=12.1 Hz, 2H), 1.04-0.91 (m, 2H), 0.82-0.68 (m, 2H). MS (ESI, m/e) [M+1]$^+$ 828.7.

Example A147a and Example A147b: (R or S)-3-((1H-pyrrolo[2,3-b]pyridin-5-yl)oxy)-4'-(2-(2-cyclopropylphenyl)-4,4-difluoropyrrolidin-1-yl)-N-((3-nitro-4-(((tetrahydro-2H-pyran-4-yl)methyl)amino)phenyl)sulfonyl)-[1,1'-biphenyl]-4-carboxamide; and (S or R). 3-((1H-pyrrolo[2,3b]pyridin-5-yl)oxy)-4'-(2-(2-cyclopropylphenyl)-4,4-difluoropyrrolidin-1-yl)-N-((3-nitro-4-(((tetrahydro-2H-pyran-4-yl)methyl)amino)phenyl)sulfonyl)-[1,1'-biphenyl]-4-carboxamide

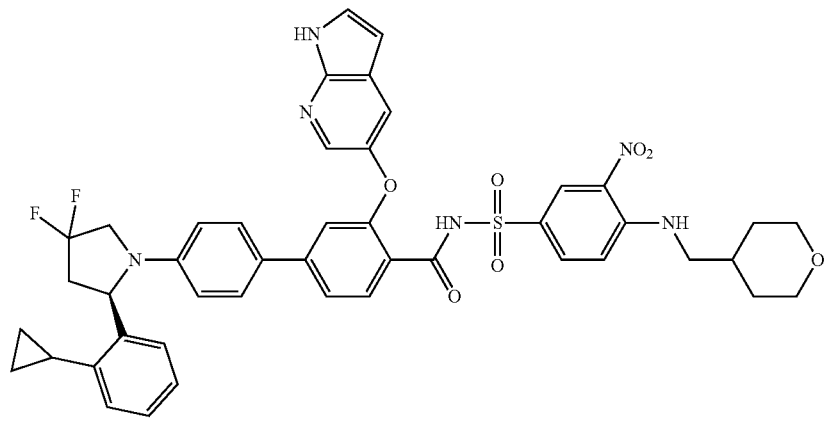

or

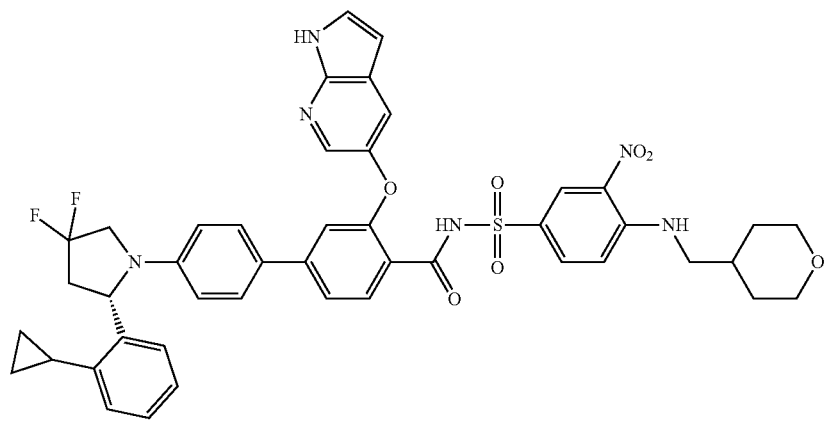

Step 1: 1-(tert-butylsulfonyl)-5-(2-cyclopropylphenyl)pyrrolidin-3-one

To a mixture of 1-(tert-butylsulfonyl)-5-(2-cyclopropylphenyl)pyrrolidin-3-ol (6.5 g, 20.1 mmol) in DCM (70 mL) was added NaHCO$_3$ (1.69 g, 20.1 umol) and DMP (17.1 g, 40.19 mmol) at 0° C., the mixture was stirred at 25° C. for 12 hours. TLC showed the reaction was completed. The mixture was poured into saturated aq. NaHCO$_3$ and was then extracted with EA (100 mL×3). The combined organic phase was washed with brine (200 mL), dried with Na$_2$SO$_4$ and concentrated in vacuum. The residue was purified by column chromatography-on silica gel (eluent: PE/EA=20:1 to 1:1) to give 1-(tert-butylsulfonyl)-5-(2-cyclopropylphenyl)pyrrolidin-3-one (5 g, 77.5% yield) as a white solid.

Step 2: 1-(tert-butylsulfonyl)-2-(2-cyclopropylphenyl)-4,4-difluoropyrrolidine To a mixture of 1-(tert-butylsulfonyl)-5-(2-cyclopropylphenyl)pyrrolidin-3-one (5 g, 15.56 mmol) in DCM (100 mL) was added DAST (7.52 g mg, 46.6 mmol) at 0° C., the mixture was stirred at 25° C. for 2 hours. TLC showed the reaction was completed. The mixture was added to saturated aq, Na$_2$CO$_3$ and was extracted with DCM (100 mL×3), the combined organic phase washed with brine (100 mL) dried with Na$_2$SO$_4$, concentrated in vacuum. The residue was purified by column chromatography on silica gel (eluent: PE/EA=100/1 to 5/1) to give 1-(tert-butylsulfonyl)-2-(2-cyclopropylphenyl)-4,4-difluoropyrrolidine (4 g) as yellow solid.

Step 3: 2-(2-cyclopropylphenyl)-4,4-difluoropyrrolidine

To a mixture of 1-(tert-butylsulfonyl)-2-(2-cyclopropylphenyl)-4,4-difluoropyrrolidin (3.5 g, 10.15 mmol) in TFA (30 mL), the mixture was stirred at 60° C. for 4 hours. TLC showed the reaction was completed. Saturated aq. Na$_2$CO$_3$ was added to adjust pH at 11, the aqueous phase was extracted with EA (50 mL×3). The combined organic phase was washed with brine (50 mL), dried with Na2SO4 and concentrated in vacuum to give 2-(2-cyclopropylphenyl)-4,4-difluoropyrrolidine (1.8 g, crude) as yellow oil.

Step 4: 1-(4-bromophenyl)-2-(2-cyclopropylphenyl)-4,4-difluoropyrrolidine

To a mixture of 2-(2-cyclopropylphenyl)-4,4-difluoropyrrolidine (2 g, 8.96 mmol) and 1-bromo-4-iodobenzene (7.6 g, 26.87 mmol) in toluene (20 mL) was added t-BuOK (3.02 g, 26.87 mmol), BINAP (1.12 g, 1.79 mmol) and Pd$_2$(dba)$_3$ (820 mg, 895 umol). The mixture was stirred at 100° C. for 4 hours. TLC showed the reaction was completed. The mixture was concentrated in vacuum. The residue was purified by column chromatography on silica gel (eluent: PE/EA=100/1 to 20/1). The crude product was separated and purified by prep-SFC (Instrument: Thar SFC80; Column: Chiralcel OJ, 250×25 mm i.d., 10 u; Mobile phase: A for CO$_2$ and B for EtOH; Gradient: B=30%; Flow rate: 65 g/min; Back pressure: 100 bar; Column temperature: 40° C.) to give (R or S)-1-(4-bromophenyl)-2-(2-cyclopropylphenyl)-4,4-difluoropyrrolidine (360 mg) as faster isomer (retention time: 2.9 min) and (S or R)-1-(4-bromophenyl)-2-(2-cyclopropylphenyl)-4,4-difluoropyrrolidine (330 mg) as slower isomer (retention time: 3.1 min).

With the faster isomer in SFC (retention time: 2.9 min) (R or S)-1-(4-bromophenyl)-2-(2-cyclopropylphenyl)-4,4-difluoropyrrolidine as the starting material, (R or S)-3-((1H-pyrrolo[2,3-b]pyridin-5-yl)oxy)-4'-(2-(2-cyclopropylphenyl)-4,4-difluoropyrrolidin-1-yl)-N-((3-nitro-4-(((tetrahydro-2H-pyran-4-yl)methyl)amino)phenyl)sulfonyl)-[1,1'-biphenyl]-4-carboxamide as example A147a was synthesized. $^1$H NMR (DMSO-d$_6$) δ ppm: 12.21 (s, 1H), 11.70 (s, 1H), 8.61 (s, 1H), 8.56 (s, 1H), 8.04 (d, J=2.4 Hz, 1H), 7.83 (d, J=9.4 Hz, 1H), 7.59 (d, J=2.4 Hz, 3H), 7.54 (d, J=8.1 Hz, 1H), 7.51 (s, 1H), 7.34 (t, J=8.1 Hz, 3H), 7.14-7.12 (m, 2H), 7.05-7.01 (m, 3H), 6.92 (s, 1H), 6.45-6.34 (m, 31 If 5.47-5.45 (m, 1H), 4.26-4.13 (m, 1H), 3.98-3.80 (m, 3H), 3.30-3.21 (m, 5H), 2.33 (s, 1H), 2.04-2.00 (m, 1H), 1.87 (s, 1H), 1.61-1.59 (m, 2H), 1.28-1.25 (m, 2H), 1.05-0.92 (m, 2H), 0.82-0.68 (m, 2H). MS (ESI) m/e [M+1]$^+$ 848.7, With the slower isomer in SFC (retention time: 3.1 min) (S or R)-1-(4-bromophenyl)-2-(2-cyclopropylphenyl)-4,4-difluoropyrrolidine as starting material, (S or R)-3-((1H-pyrrolo[2,3-b]pyridin-5-yl)oxy)-4'-(2-(2-cyclopropylphenyl)-4,4-difluoropyrrolidin-1-yl)-N-((3-nitro-4-(((tetrahydro-2H-pyran-4-yl)methyl)amino)phenyl)sulfonyl)-[1,1'-biphenyl]-4-carboxamide as example A147b was synthesized. MS (ESI) m/e [M+1]$^+$ 848.7.

Example A148: 3-((1H-pyrrolo[2,3-b]pyridin-5-yl)oxy)-4'-(4-cyclopropyl-2-(2-cyclopropylphenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide

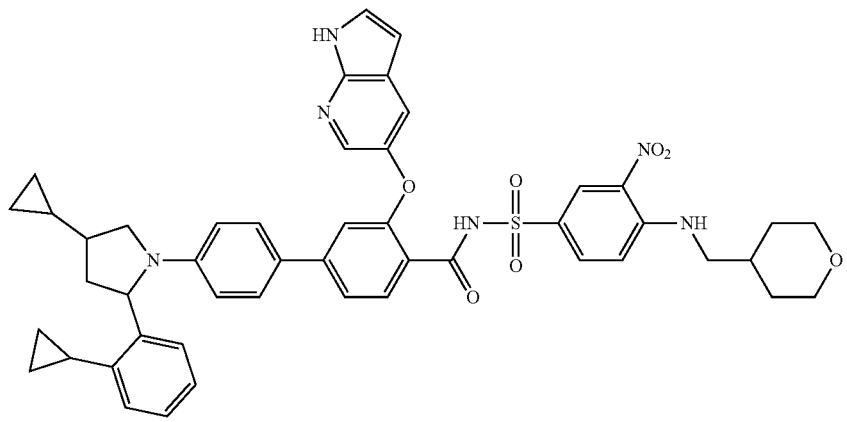 [SMILES: O=C(NS(=O)(=O)c1ccc(NCC2CCOCC2)c([N+](=O)[O-])c1)c1ccc(-c2ccc(N3CC(C4CC4)CC3c3ccccc3C3CC3)cc2)cc1Oc1cnc2[nH]ccc2c1]

The desired compound was synthesized starting from 4-cyclopropyl-2-(2-cyclopropylphenyl)pyrrolidine and 1-bromo-4-iodobenzene following the procedures similar to those in Example A1. $^1$H NMR (DMSO-$d_6$) δ ppm: 12.15 (s, 1H), 11.69 (s, 1H), 8.59-8.57 (m, 2H), 8.04 (s, 1H), 7.82 (d, J=9.1 Hz, 1H), 7.58 (s, 1H), 7.55-7.48 (m, 2H), 7.36-7.22 (m, 3H), 7.12 (d, J=9.1 Hz, 1H), 7.09-6.95 (m, 4H), 6.89 (s, 1H), 6.41-6.30 (m, 3H), 5.17-5.13 (m, 1H), 3.84 (d, J=8.5 Hz, 2H), 3.70-3.68 (m, 1H), 3.53-3.51 (m, 1H), 3.30-3.22 (m, 4H), 2.79-2.70 (m, 1H), 2.09-2.07 (m, 2H), 1.89-1.87 (m, 1H), 1.72-1.70 (m, 1H), 1.60-1.58 (m, 3H), 1.28-1.26 (m, 2H), 0.96 (s, 2H), 0.76 (s, 2H), 0.45-0.33 (m, 2H), 0.17-0.13 (m, 2H). MS (ESI) m/e [M+1]$^+$ 852.8.

Example A149: 3-((1H-pyrrolo[2,3-b]pyridin-5-yl)oxy)-4'-(2-(2-cyclopropylphenyl)-4-phenylpyrrolidin-1-yl)-N-((3-nitro-4-(((tetrahydro-2H-pyran-4-yl)methyl)amino)phenyl)sulfonyl)-[1,1'-biphenyl]-4-carboxamide

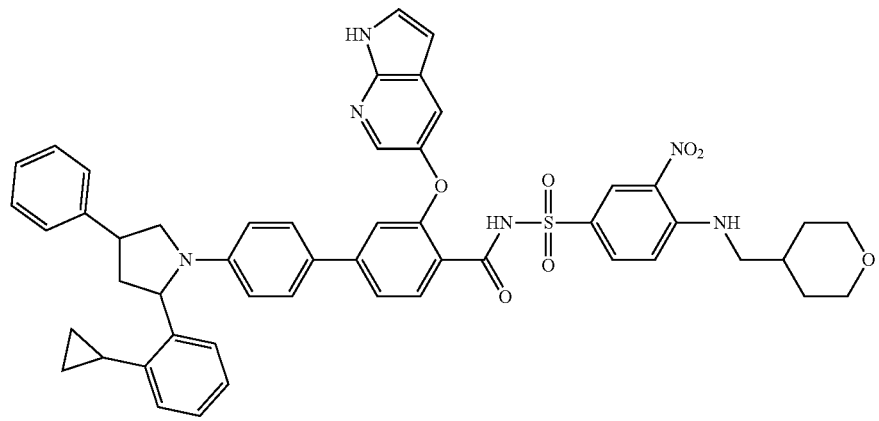 [SMILES: O=C(NS(=O)(=O)c1ccc(NCC2CCOCC2)c([N+](=O)[O-])c1)c1ccc(-c2ccc(N3CC(c4ccccc4)CC3c3ccccc3C3CC3)cc2)cc1Oc1cnc2[nH]ccc2c1]

The desired compound was synthesized starting from 2-(2-cyclopropylphenyl)-4-phenylpyrrolidine and 1-bromo-4-iodobenzene following the procedures similar to those in Example A1. MS (ESI) m/e [M+1]$^+$ 888.8.

Example A150: 3-((1H-pyrrolo[2,3-b]pyridin-5-yl)oxy)-4'-(2-(2-cyclopropylphenyl)-4-methylenepyrrolidin-1-yl)-N-((3-nitro-4-(((tetrahydro-2H-pyran-4-yl)methyl)amino)phenyl)sulfonyl)-[1,1'-biphenyl]-4-carboxamide

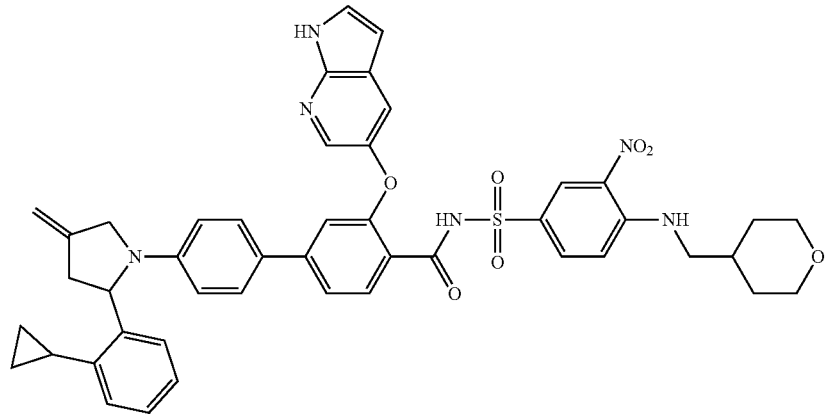

The desired compound was synthesized starting from 2-(2-cyclopropylphenyl)-4-methylenepyrrolidine and 1-bromo-4-iodobenzene following the procedures similar to those in Example A1. $^1$H NMR (400 MHz. DMSO-d$_6$) δ ppm: 12.16 (s, 1H), 11.65 (br, 1H), 8.54-8.52 (m, 2H), 8.03 (s, 1H), 7.83-7.75 (m, 1H), 7.55 (d, J=8.8 Hz, 1H), 7.52-7.45 (m, 2H), 7.33 (d, J=8.0 Hz, 3H), 7.10-6.90 (m, 6H), 6.72 (s, 1H), 6.35-6.28 (m, 3H), 5.45 (d, J=8.8 Hz, 1H), 5.12 (s, 1H), 4.97 (s, 1H), 4.22-4.15 (m, 2H), 3.85 (d, J=8.4 Hz, 2H), 3.33-3.20 (m, 5H), 2.09-1.76 (m, 4H), 1.62 (d, J=13.2 Hz, 2H), 1.05-0.95 (m, 2H), 0.76-0.68 (m, 2H). MS (ESI, m/e) [M+1]$^+$ 824.8.

Example A151: 3-((1H-pyrrolo[2,3-b]pyridin-5-yl)oxy)-4'-(2-(2-cyclopropylphenyl)-4-(dimethylamino)pyrrolidin-1-yl)-N-((3-nitro-4-(((tetrahydro-2H-pyran-4-yl)methyl)amino)phenyl)sulfonyl)-[1,1'-biphenyl]-4-carboxamide

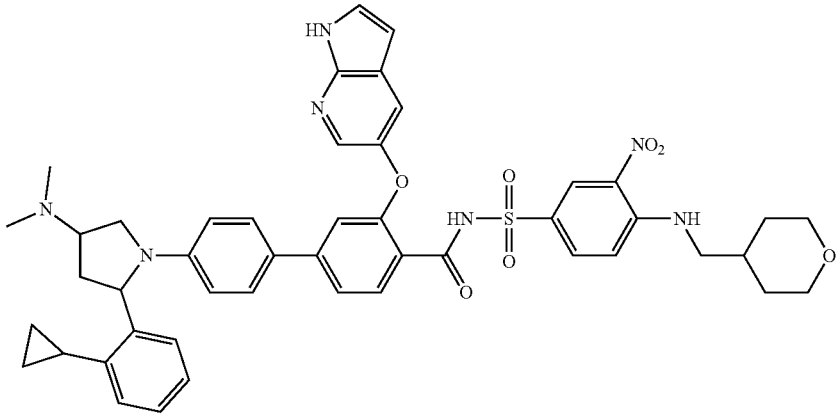 [SMILES: CN(C)C1CC(c2ccccc2C2CC2)N(c2ccc(-c3ccc(C(=O)NS(=O)(=O)c4ccc(NCC5CCOCC5)c([N+](=O)[O-])c4)c(Oc4cnc5[nH]ccc5c4)c3)cc2)C1]

The desired compound was synthesized starting from 5-(2-cyclopropylphenyl)-N,N-dimethylpyrrolidin-3-amine and 1-bromo-4-iodobenzene following the procedures similar to those in Example A1. $^1$H NMR (400 MHz, CDCl$_3$) δ ppm: 11.55 (s, 1H), 9.80 (s, 1H), 8.45-8.28 (m, 2H), 7.95 (s, 1H), 7.74-7.61 (m, 1H), 7.60-7.52 (m, 1H), 7.42 (s, 1H), 7.39-7.31 (m, 1H), 7.31-7.12 (m, 5H), 7.06-6.94 (m, 2H), 6.94-6.77 (m, 2H), 6.44-6.23 (m, 3H), 5.18-4.98 (m, 1H), 3.93-3.64 (m, 4H), 3.31-3.12 (m, 5H), 3.10-2.75 (m, 3H), 2.70-2.53 (m, 6H), 2.45-2.36 (m, 2H), 2.19-1.93 (m, 3H), 1.90-1.72 (m, 3H), 1.66-1.53 (m, 2H), 1.26-1.21 (m, 2H). MS (ESI, m/e) [M+1]+855.8.

Example A152: 3-((1H-pyrrolo[2,3-b]pyridin-5-yl)oxy)-4'-(2-(2-cyclopropylphenyl)piperidin-1-yl)-N-((3-nitro-4-(((tetrahydro-2H-pyran-4-yl)methyl)amino)phenyl)sulfonyl)-[1,1'-biphenyl]-4-carboxamide

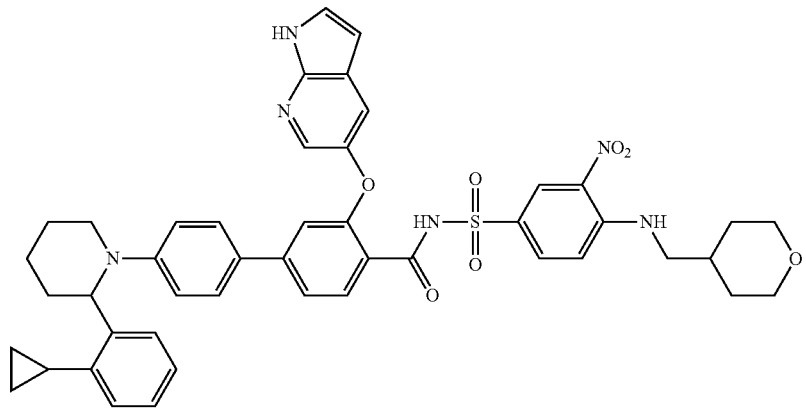 [SMILES: O=C(NS(=O)(=O)c1ccc(NCC2CCOCC2)c([N+](=O)[O-])c1)c1ccc(-c2ccc(N3CCCCC3c3ccccc3C3CC3)cc2)cc1Oc1cnc2[nH]ccc2c1]

The desired compound was synthesized from 1-(4-bromophenyl)-2-(2-cyclopropylphenyl)piperidine following the procedures similar to those in Example A1. MS (ESI, m/e) [M+1]⁺ 827.8.

Example A153: 3-((1H-pyrrolo[2,3-b]pyridin-5-yl)oxy)-4'-(3-(2-cyclopropylphenyl)-5-oxomorpholino)-N-((3-nitro-4-(((tetrahydro-2H-pyran-4-yl)methyl)amino)phenyl)sulfonyl)-[1,1'-biphenyl]-4-carboxamide

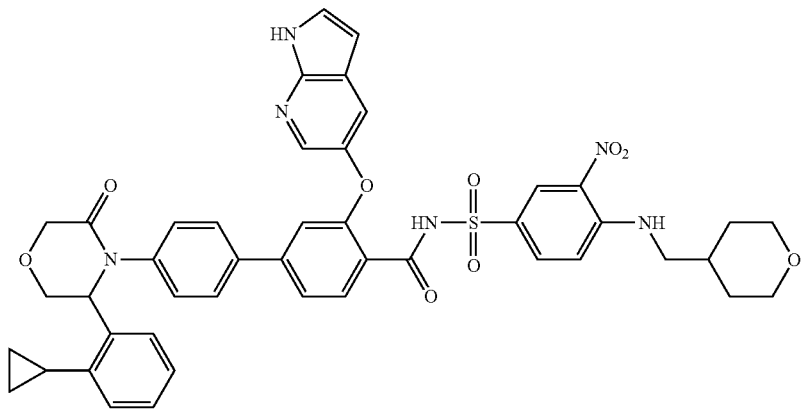 [SMILES: O=C(NS(=O)(=O)c1ccc(NCC2CCOCC2)c([N+](=O)[O-])c1)c1ccc(-c2ccc(N3C(=O)COCC3c3ccccc3C3CC3)cc2)cc1Oc1cnc2[nH]ccc2c1]

The desired compound was synthesized from 4-(4-bromophenyl)-5-(2-cyclopropylphenyl)morpholin-3-one following the procedures similar to those in Example A1. ¹H NMR (400 MHz, DMSO-d₆) δ ppm: 12.41 (s, 1H), 11.72 (s, 1H), 8.60-8.50 (m, 2H), 8.03 (d, J=2.1 Hz, 1H), 7.81 (d, J=8.5 Hz, 1H), 7.58 (d, J=8.5 Hz, 2H), 7.52-7.45 (m, 3H), 7.45-7.34 (m, 4H), 7.20-7.05 (m, 3H), 7.04 (s, 1H), 6.95-6.90 (m, 1H), 6.37 (s, 1H), 5.84 (s, 1H), 4.48 (d, J=16.7 Hz, 1H), 4.37-4.22 (m, 2H), 3.92 (d, J=9.4 Hz, 1H), 3.84 (d, J=8.8 Hz, 2H), 3.30-3.20 (m, 3H), 2.69 (s, 4H), 1.95-1.85 (m, 1H), 1.59 (d, J=12.8 Hz, 2H), 0.90-0.85 (m, 2H), 0.62-0.58 (m, 1H), 0.40-0.32 (m, 1H). MS (ESI, m/e) [M+1]⁺ 842.8.

Example A154: 3-((1H-pyrrolo[2,3-b]pyridin-5-yl)oxy)-4'-(3-(2-cyclopropylphenyl)morpholino)-N-((3-nitro-4-(((tetrahydro-2H-pyran-4-yl)methyl)amino)phenyl)sulfonyl)-[1,1'-biphenyl]-4-carboxamide

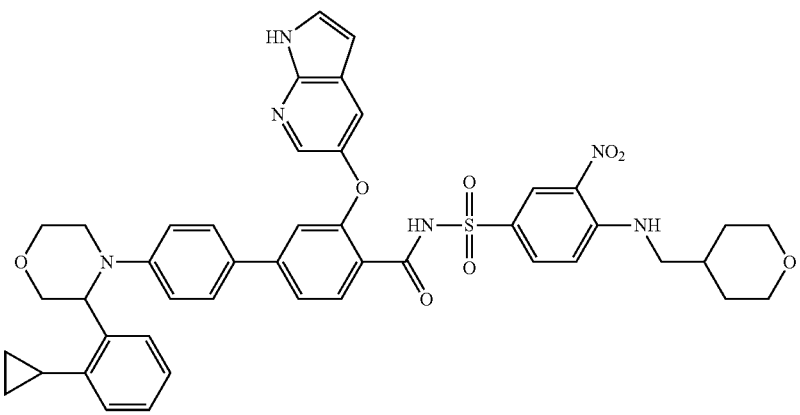 [SMILES: O=C(NS(=O)(=O)c1ccc(NCC2CCOCC2)c([N+](=O)[O-])c1)c1ccc(-c2ccc(N3CCOCC3c3ccccc3C3CC3)cc2)cc1Oc1cnc2[nH]ccc2c1]

Step 1: tert-butyl 3-((1H-pyrrolo[2,3-b]pyridin-5-yl) oxy)-4'-(3-(2-cyclopropyl phenyl)-5-oxomorpholino)-[1,1'-biphenyl]-4-carboxylate A mixture of 4-(4-bromophenyl)-5-(2-cyclopropylphenyl)morpholin-3-one (300 mg, 0.806 mmol), tert-butyl 2-((1H-pyrrolo[2,3-b]pyridin-5-yl)oxy)-4-(4,4,5,5-tetramethyl-1,3,2-dioxaborolan-2-yl)benzoate (422 mg, 0.968 mmol), Pd(dppf)Cl$_2$ (58 mg, 0.08 mmol), Cs$_2$CO$_3$ (523 mg, 1.612 mmol) in dioxane (10 mL) was heated to 100° C. for 16 hours under N$_2$. The mixture was cooled to room temperature and then filtrated. The filtrate was concentrated and purified with column chromatograph on silica gel (eluent: EA/PE=1/1) to afford 260 mg tert-butyl-3-((1H-pyrrolo[2,3-b]pyridin-5-yl)oxy)-4'-(3-(2-cyclopropyl phenyl)-5-oxomorpholino)-[1,1'-biphenyl]-4-carboxylate as a yellow oil. MS (ESI) m/e [M+1]$^+$ 610.9.

Step 2: tert-butyl 3-((1H-pyrrolo[2,3-b]pyridin-5-yl) oxy)-4'-(3-(2-cyclopropylphenyl)morpholino)-[1,1'-biphenyl]-4-carboxylate A solution of tert-butyl 3-((1H-pyrrolo[2,3-b]pyridin-5-yl)oxy)-4'-(3-(2-cyclopropyl phenyl)-5-oxomorpholino)-[1,1'-biphenyl]-4-carboxylate (100 mg, 0.167 mmol) in THF (5 mL) was added BH$_3$—SMe$_2$ (2 N, 1 mL) at room temperature. After stirred at room temperature for 16 hours, the reaction mixture was quenched with aq. HCl acid (1N, 5 mL) and then was extracted with EA (5 mL×3). The combined organic layers were dried over anhydrous Na$_2$SO$_4$, concentrated and purified with column chromatograph on silica gel (eluent: EA/PE=1/1) to afford 60 mg of tert-butyl-3-((1H-pyrrolo[2,3-b]pyridin-5-yl)oxy)-4'-(3-(2-cyclopropylphenyl)-morpholino)-[1,1'-biphenyl]-4-carboxylate (yield: 61.2%). MS (ESI, m/e) [M+1]$^+$ 587.9.

The desired compound was then synthesized from tert-butyl 3-((1H-pyrrolo[2,3-b]pyridin-5-yl)oxy)-4'-(3-(2-cyclopropylphenyl)-morpholino)-[1,1'-biphenyl]4-carboxylate following the procedures similar to those in Example A1. $^1$H NMR (400 MHz, DMSO-d$_6$) δ ppm: 12.28 (s, 1H), 11.72 (s, 1H), 8.64-8.53 (m, 2H), 8.04 (d, J=2.5 Hz, 1H), 7.82 (dd, J=9.1, 1.8 Hz, 1H), 7.60-7.47 (m, 3H), 7.40-7.30 (m, 3H), 7.18 (d, J=7.2 Hz, 1H), 7.12 (d, J=9.3 Hz, 1H), 7.05-7.00 (m, 1H), 6.98-6.90 (m, 3H), 6.87 (d, J=8.7 Hz, 2H), 6.41-6.34 (m, 1H), 4.90-4.80 (m, 1H), 4.01-3.78 (m, 4H), 3.65-3.60 (m, 1H), 3.55-3.50 (m, 1H), 3.30-3.20 (m, 4H), 3.20-3.06 (m, 1H), 2.25-2.10 (m, 1H), 1.95-1.80 (m, 1H), 1.59 (d, J=11.7 Hz, 2H), 1.33-1.18 (m, 2H), 1.05-0.89 (m, 2H), 0.79-0.63 (m, 2H). MS (ESI, m/e) [M+1]$^+$ 828.8.

Example A155: 3-((1H-pyrrolo[2,3-b]pyridin-5-yl) oxy)-4'-(2-(2-cyclopropylphenyl)-4-methylpiperazin-1-yl)-N-((3-nitro-4-(((tetrahydro-2H-pyran-4-yl)methyl)amino)phenyl)sulfonyl)-[1,1'-biphenyl]-4-carboxamide

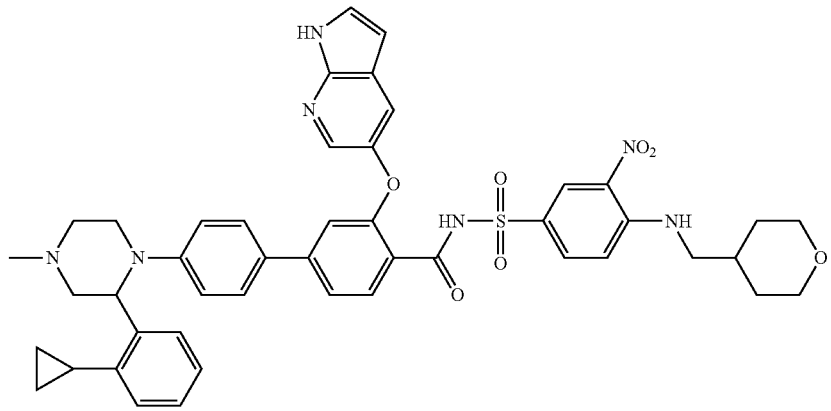 [SMILES: CN1CCN(c2ccc(-c3ccc(C(=O)NS(=O)(=O)c4ccc(NCC5CCOCC5)c([N+](=O)[O-])c4)c(Oc4cnc5[nH]ccc5c4)c3)cc2)C(c2ccccc2C2CC2)C1]

The desired compound was synthesized from 1-(4-bromophenyl)-2-(2-cyclopropylphenyl)-4-methylpiperazine following the procedures similar to those in Example A1. Of NMR (400 MHz, DMSO-$d_6$) δ ppm: 12.32 (s, 1H), 11.70 (s, 1H), 11.20 (s, 1H), 8.58 (s, 1H), 8.54 (s, 1H), 8.02 (s, 1H), 7.80 (d, J=8.4 Hz, 1H), 7.54 (d, J=7.6 Hz, 2H), 7.50 (s, 1H). 7.35 (d, J=8.4 Hz, 3H), 7.26 (d, J=7.6 Hz, 1H), 7.11-7.04 (m, 2H), 7.03-6.88 (m, 5H), 6.36 (s, 1H), 5.15 (s, 1H), 3.84 (d, J=8.3 Hz, 2H), 3.76-3.66 (m, 1H), 3.57-3.49 (m, 1H), 3.29-3.20 (m, 5H), 3.08-2.93 (m, 2H), 2.79 (s, 3H), 2.23-2.16 (m, 1H), 1.91-1.83 (m, 1H), 1.59 (d, J=12.3 Hz, 2H), 1.09-0.96 (m, 3H), 0.87-0.81 (m, 2H), 0.68-0.62 (m, 1H). MS (ESI, m/e) [M+1]$^+$ 841.9.

Example A156: 3-((1H-pyrrolo[2,3-b]pyridin-5-yl)oxy)-4'-(2-(2-cyclopropylphenyl)pyrazolidin-1-yl)-N-((3-nitro-4-(((tetrahydro-2H-pyran-4-yl)methyl)amino)phenyl)sulfonyl)-[1,1'-biphenyl]-4-carboxamide

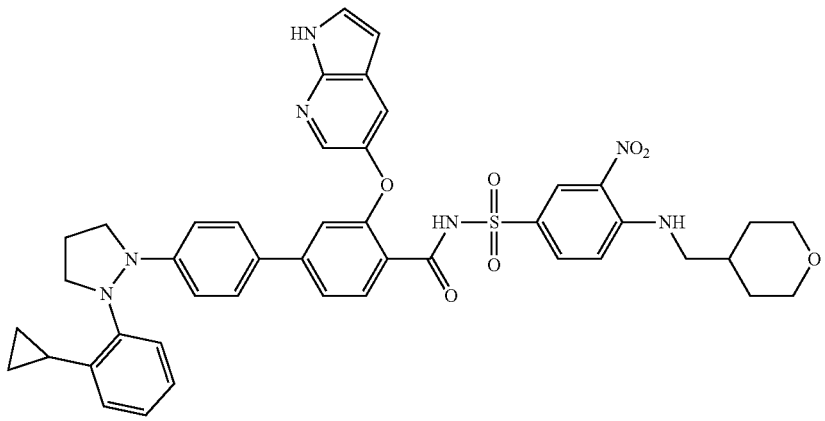 [SMILES: O=C(NS(=O)(=O)c1ccc(NCC2CCOCC2)c([N+](=O)[O-])c1)c1ccc(-c2ccc(N3CCCN3c3ccccc3C3CC3)cc2)cc1Oc1cnc2[nH]ccc2c1]

The desired compound was synthesized from 1-(4-bromophenyl)-2-(2-cyclopropylphenyl)pyrazolidine following the procedures similar to those in Example A1. $^1$H NMR (400 MHz, DMSO-$d_6$) δ ppm: 12.20 (s, 0.5H), 11.59 (s, 1H), 9.70 (s, 0.5H), 8.55-8.31 (m, 2H), 8.00 (s, 1H), 7.79-7.63 (m, 1H), 7.79-7.63 (m, 1H), 7.48-7.52 (m, 6H), 7.00-6.86 (m, 2H), 6.83-6.71 (m, 4H), 6.54-6.45 (m, 1H), 6.33 (s, 1H), 3.90-3.78 (m, 4H), 3.12-3.02 (m, 3H), 2.05-2.01 (m, 4H), 1.90-1.82 (m, 3H), 1.66-1.56 (m, 3H), 1.50-1.41 (m, 2H), 0.87-0.84 (m, 2H), 0.54-0.46 (m, 2H). MS (ESI, m/e) [M+1]$^+$ 813.8.

Example A157: (R)-4'-(2-(2-cyclopropylphenyl)pyrrolidin-1-yl)-N-((3-nitro-4-(((tetrahydro-2H-pyran-4-yl)methyl)amino)phenyl)sulfonyl)-3-(3-(pyrimidin-2-ylamino)phenoxy)-[1,1'-biphenyl]-4-carboxamide

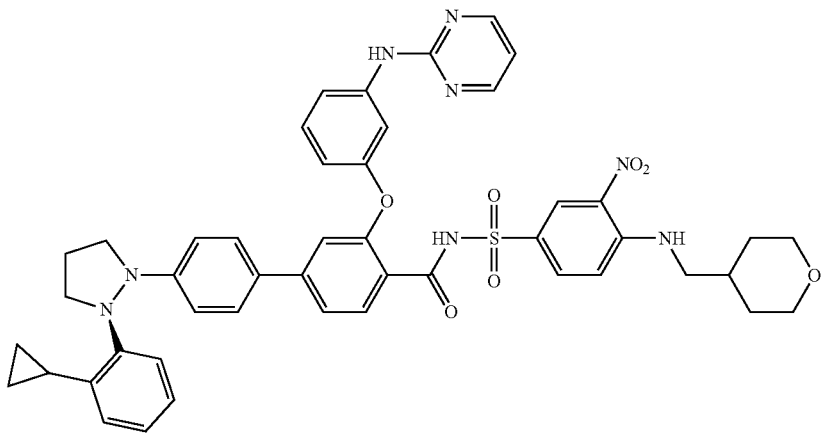

The desired compound was synthesized following the procedures similar to those in Example A1 by replacing 2-phenylpyrrolidine with (R)-2-(2-cyclopropylphenyl)pyrrolidine and replacing tert-butyl 2-((1H-pyrrolo[2,3-b]pyridin-5-yl)oxy)-4-(4,4,5,5-tetramethyl-1,3,2-dioxaborolan-2-yl)benzoate with methyl 2-(3-(pyrimidin-2-ylamino)phenoxy)-4-(4,4,5,5-tetramethyl-1,3,2-dioxaborolan-2-yl)benzoate. MS (ESI, m/e) [M+1]+ 865.8.

Example A158: (R)-5-((4'-(2-(2-cyclopropylphenyl)pyrrolidin-1-yl)-4-(((3-nitro-4-(((tetrahydro-2H-pyran-4-yl)methyl)amino)phenyl)sulfonyl)carbamoyl)-[1,1'-biphenyl]-3-yl)oxy)-N-methylpicolinamide

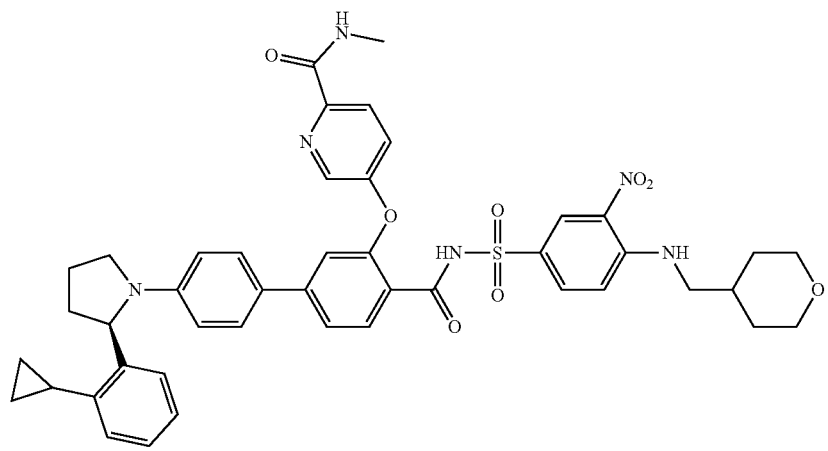 [SMILES: CNC(=O)c1ccc(Oc2cc(-c3ccc(N4CCC[C@@H]4c4ccccc4C4CC4)cc3)ccc2C(=O)NS(=O)(=O)c2ccc(NCC3CCOCC3)c([N+](=O)[O-])c2)cn1]

The desired compound was synthesized following the procedures similar to those in Example A1 by replacing 2-phenylpyrrolidine with (R)-2-(2-cyclopropylphenyl)pyrrolidine and replacing tert-butyl 2-((1H-pyrrolo[2,3-b]pyridin-5-yl)oxy)-4-(4,4,5,5-tetramethyl-1,3,2-dioxaborolan-2-yl)benzoate with methyl 2-((6-(methylcarbamoyl)pyridin-3-yl)oxy)-4-(4,4,5,5-tetramethyl-1,3,2-dioxaborolan-2-yl)benzoate. MS (ESI, m/e) [M+1]+ 830.8.

Example B1: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-((2-phenylpyrrolidin-1-yl)methyl)-[1,1'-biphenyl]-4-carboxamide

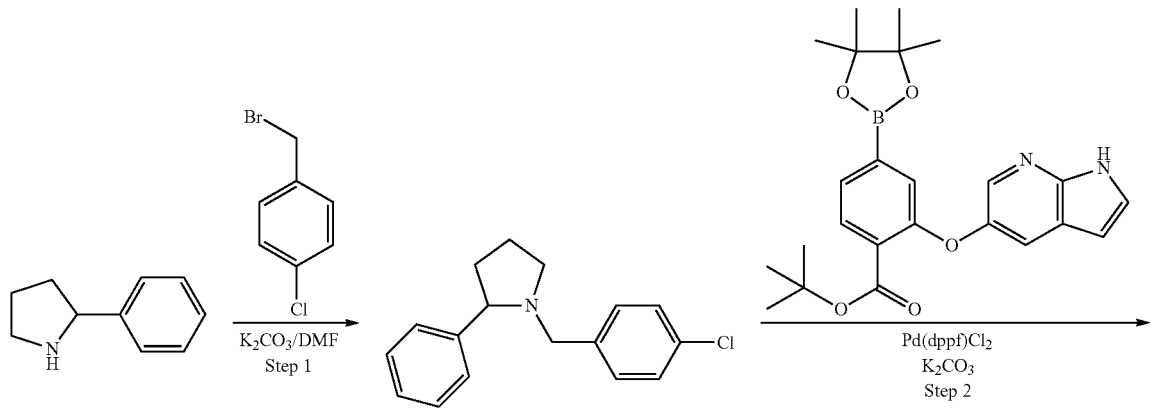

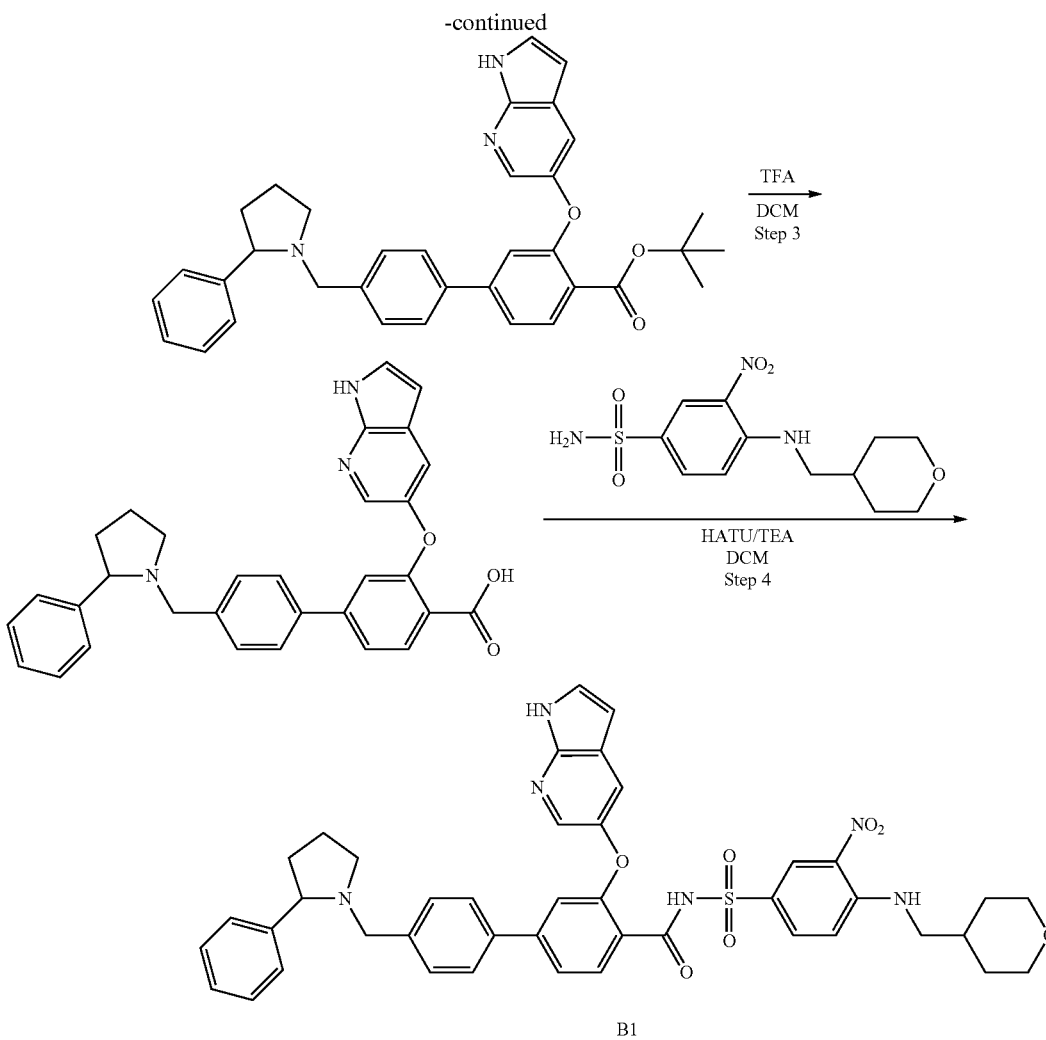

Step 1: 1-(4-chlorobenzyl)-2-phenylpyrrolidine

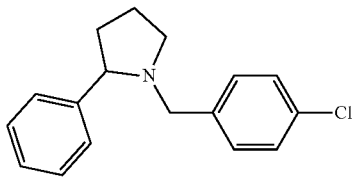 [SMILES: Clc1ccc(CN2CCCC2c2ccccc2)cc1]

The mixture of 2-phenylpyrrolidine (450 mg, 3 mmol), 1-(bromomethyl)-4-chlorobenzene (678 mg, 3.3 mmol) and K$_2$CO$_3$ (828 mg, 6 mmol) in DMF (10 mL) was heated to 50° C. and stirred for 2 hours. Then the reaction mixture was concentrated in vacuo and the residue was diluted with DCM, washed with brine (100 mL), dried over Na$_2$SO$_4$ and evaporated in vacuo, then the crude product was purified by chromatography column on silica (eluent: PE/EA=2/1 to 1/1) to afford a colorless oil (670 mg). $^1$H NMR (400 MHz, CDCl$_3$) δ ppm: 7.46 (d, J=8.0 Hz, 2H), 7.34 (t, J=8.0 Hz, 2H), 7.25-7.20 (m, 5H), 3.80 (d, J=12.0 Hz, 1H), 3.35 (t, J=8.0 Hz, 1H), 3.08-2.99 (m, 2H), 2.21-2.14 (m, 2H), 1.91-1.70 (m, 3H). MS (ESI, m/e) [M+1]$^+$ 272.1.

Step 2: tert-butyl 3-((1H-pyrrolo[2,3-b]pyridin-5-yl)oxy)-4'-((2-phenylpyrrolidin-1-yl)methyl)-[1,1'-biphenyl]-4-carboxylate

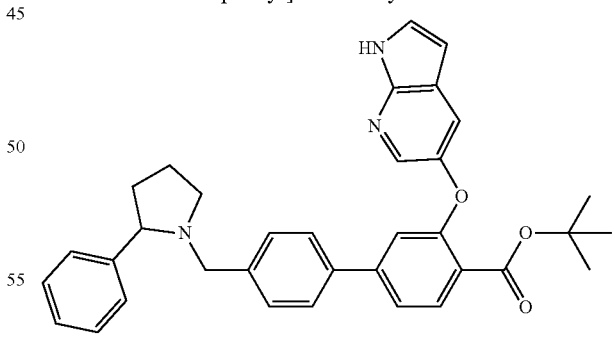

The mixture of 1-(4-chlorobenzyl)-2-phenylpyrrolidine (670 mg, 2.5 mmol), tert-butyl 2-((1H-pyrrolo[2,3-b]pyridin-5-yl)oxy)-4-(4,4,5,5-tetramethyl-1,3,2-dioxaborolan-2-yl)benzoate (1.2 g, 2.75 mmol), 1,1'-Bis(diphenylphosphino)ferrocene-palladium(II)dichloride dichloromethane complex (183 mg, 0.25 mmol), K$_2$CO$_3$ (863 mg, 6.25 mmol) in a solution of 1,4-dioxane (20 mL) and water (10 mL) was heated to 90° C. and stirred overnight. After cooled to room temperature, the reaction mixture was concentrated in vacuo and purified by chromatography column on silica (eluent: EA/PE=1/1) to give the product (211 mg) as a red oil. MS (ESI, m/e) [M+1]+ 546.2.

Step 3: 3-((1H-pyrrolo[2,3-b]pyridin-5-yl)oxy)-4'-((2-phenylpyrrolidin-1-yl)methyl)-[1,1'-biphenyl]-4-carboxylic acid

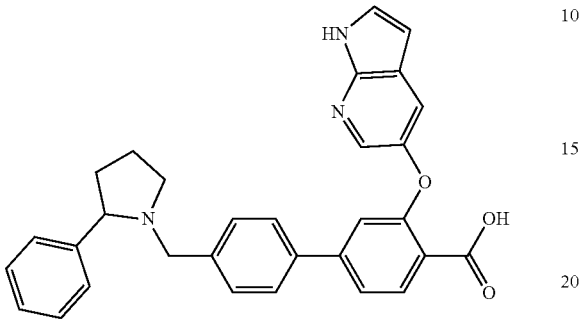 [SMILES: CC(C)(C)OC(=O)c1ccc(-c2ccc(CN3CCCC3c3ccccc3)cc2)cc1Oc1cnc2[nH]ccc2c1]

To a solution of tert-butyl 3-((1H-pyrrolo[2,3-b]pyridin-5-yl)oxy)-4'-((2-phenylpyrrolidin-1-yl)methyl)-[1,1'-biphenyl]-4-carboxylate (200 mg, 0.37 mmol ) in DCM (2 mL) was added trifluoroacetic acid (2 mL) and stirred at room temperature overnight. The mixture was concentrated in vacuo and purified by chromatography column on silica (eluent: DCM/MeOH=10/1) to give the product (170 mg) as a grey solid. MS (ESI, m/e) [M+1]+490.1.

Step 4: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-((2-phenylpyrrolidin-1-yl)methyl)-[1,1'-biphenyl]-4-carboxamide

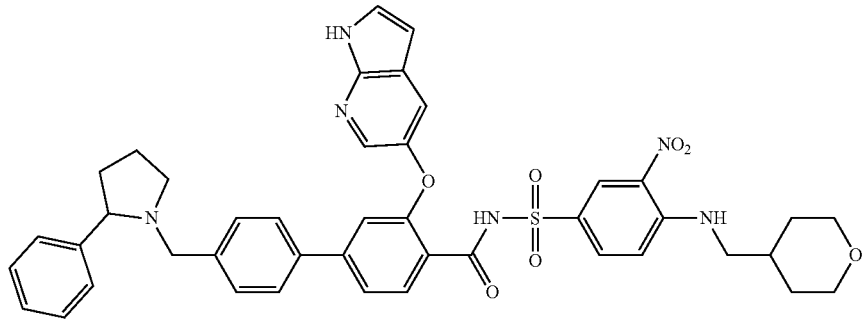 [SMILES: O=C(NS(=O)(=O)c1ccc(NCC2CCOCC2)c([N+](=O)[O-])c1)c1ccc(-c2ccc(CN3CCCC3c3ccccc3)cc2)cc1Oc1cnc2[nH]ccc2c1]

The mixture of 3-((1H-pyrrolo[2,3-b]pyridin-5-yl)oxy)-4'-((2-phenylpyrrolidin-1-yl)methyl)-[1,1'-biphenyl]-4-carboxylic acid (170 mg, 0.35 mmol), triethylamine (106 mg, 1.05 mmol), 2-(7-azabenzotriazol-1-yl)-N,N,N',N'-tetramethyluronium hexafluorophosphate (201 mg, 0.53 mmol) in DCM (10 mL) was stirred for 2 hours at room temperature. To the resulted reaction mixture were added 3-nitro-4-(((tetrahydro-2H-pyran-4-yl)methyl)amino)benzenesulfonamide (167 mg, 0.53 mmol) and DMAP (5 mg, 0.04 mmol) and then stirred overnight. The reaction mixture was extracted with DCM (30 mL) and water (30 mL). The organic layer was concentrated in vacuo and purified by chromatography column on silica (eluent: DCM/MeOH=20/1 to 10/1) to afford a crude product, which was then purified with Pre-HPLC to give the product (14.28 mg). $^1$H NMR (400 MHz, DMSO-$d_6$) δ ppm: 12.41 (br, 1H), 11.67 (br, 1H), 8.51 (br, 2H), 8.04 (m, 1H), 7.79 (d, J=8.0 Hz, 1H), 7.62 (d, J=8.0 Hz, 1H), 7.42-7.27 (m, 12H), 6.99 (m, 2H), 6.37 (m, 1H), 3.85 (d, J=8.0 Hz, 2H), 3.67 (m, 1H), 3.28-3.23 (m, 6H), 3.10-2.96 (m, 2H), 2.15 (m, 2H), 2.01 (m, 1H), 1.87 (m, 2H), 1.61 (d, J=8.0 Hz, 2H), 1.45 (m, 2H). MS (ESI, m/e) [M+1]+ 787.2.

Example B2: 3-((1H-pyrrolo[2,3-b]pyridin-5-yl)
oxy)-4'-((2-(2-chlorophenyl)pyrrolidin-1-yl)methyl)-
N-((3-nitro-4-(((tetrahydro-2H-pyran-4-yl)methyl)
amino)phenyl)sulfonyl)-[1,1'-biphenyl]-4-
carboxamide

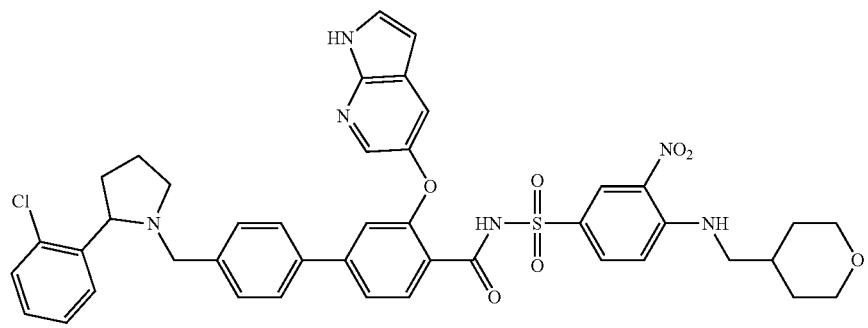 [SMILES: O=C(NS(=O)(=O)c1ccc(NCC2CCOCC2)c([N+](=O)[O-])c1)c1ccc(-c2ccc(CN3CCCC3c3ccccc3Cl)cc2)cc1Oc1cnc2[nH]ccc2c1]

The desired compound was synthesized starting from 2-(2-chlorophenyl)pyrrolidine and 1-(bromomethyl)-4-chlorobenzene following the procedures similar to those in Example B1. $^1$H NMR (400 MHz, DMSO-$d_6$) δ ppm: 12.30 (br, 1H), 11.73 (br, 1H), 8.60-8.58 (m, 2H), 8.09 (d, J=4.0 Hz, 1H), 7.86 (d, J=8.0 Hz, 1H), 7.77 (d, J=12.0 Hz, 1H), 7.64-7.59 (m, 2H), 7.53-7.43 (m, 4H), 7.39-7.31 (m, 4H), 7.23 (t, J=8.0 Hz, 1H), 7.14 (d, J=12.0 Hz, 1H), 6.99 (s, 1H), 6.41 (m, 1H), 3.86 (m, 3H), 3.69 (m, 1H), 3.28-3.23 (m, 4H), 3.01 (m, 1H), 2.32 (m, 2H), 1.87-1.76 (m, 3H), 1.61-1.58 (m, 2H), 1.46 (m, 1H), 1.30-1.21 (m, 3H). MS (ESI, m/e) [M+1]$^+$ 821.1.

Example B3: 3-((1H-pyrrolo[2,3-b]pyridin-5-yl)
oxy)-4'-((2-(2-cyclopropylphenyl)pyrrolidin-1-yl)
methyl)-N-((3-nitro-4-(((tetrahydro-2H-pyran-4-yl)
methyl)amino)phenyl)sulfonyl)-[1,1'-biphenyl]-4-
carboxamide

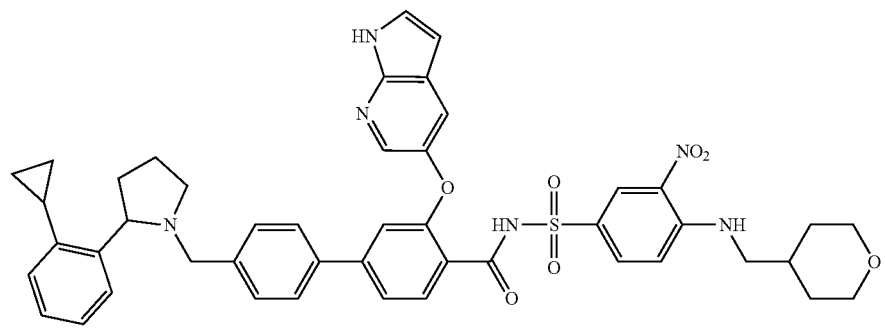 [SMILES: O=C(NS(=O)(=O)c1ccc(NCC2CCOCC2)c([N+](=O)[O-])c1)c1ccc(-c2ccc(CN3CCCC3c3ccccc3C3CC3)cc2)cc1Oc1cnc2[nH]ccc2c1]

The desired compound was synthesized starting from 2-(2-cyclopropylphenyl)pyrrolidine and 1-(bromomethyl)-4-chlorobenzene following the procedures similar to those in Example B1. $^1$H NMR (400 MHz, DMSO-$d_6$) δ ppm: 12.36 (s, 1H), 11.70 (s, 1H), 8.55 (s, 2H), 8.06 (s, 1H), 7.81 (d, J=8.4 Hz, 1H), 7.69-7.56 (m, 3H), 7.56-7.38 (m, 4H), 7.32 (d, J=7.6 Hz, 2H), 7.14 (m, 3H), 7.03-6.90 (m, 2H), 6.39 (s, 1H), 3.90-3.87 (m, 3H), 3.29-3.21 (m, 5H), 3.05-3.01 (m, 1H), 2.15-2.01 (m, 31H), 1.87-1.77 (m, 4H), 1.60 (d, J=12.0 Hz, 3H), 1.33-1.17 (m, 3H), 0.89 (t, J=12.0 Hz, 3H). MS (ESI, m/e) [M+1]$^+$ 827.2

Example B4: 2-((1H-pyrrolo[2,3-b]pyridin-5-yl)oxy)-N-((3-nitro-4-(((tetrahydro-2H-pyran-4-yl)methyl)amino)phenyl)sulfonyl)-4-(1-((1-phenylpyrrolidin-2-yl)methyl)-1,2,3,6-tetrahydropyridin-4-yl)benzamide

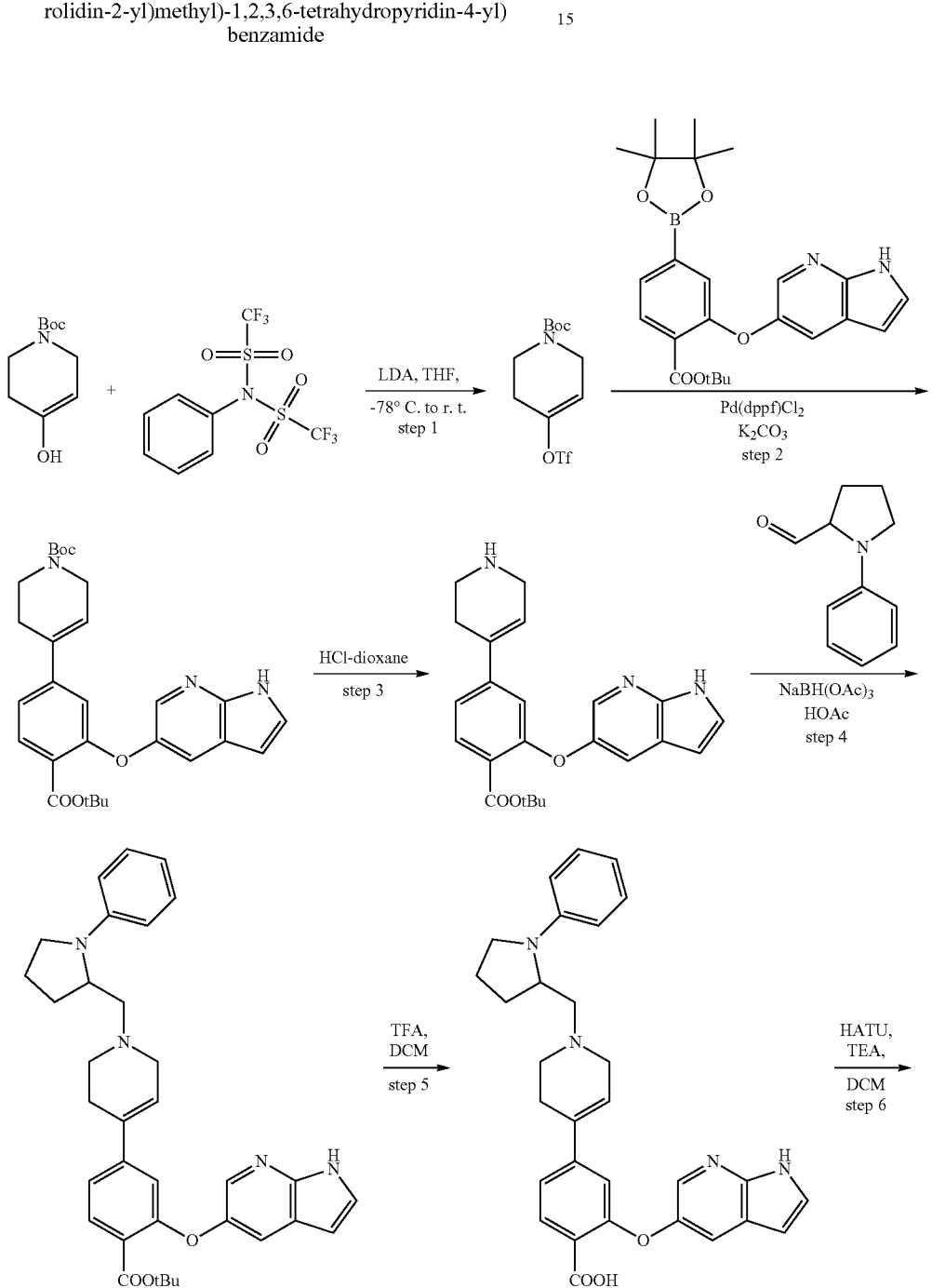

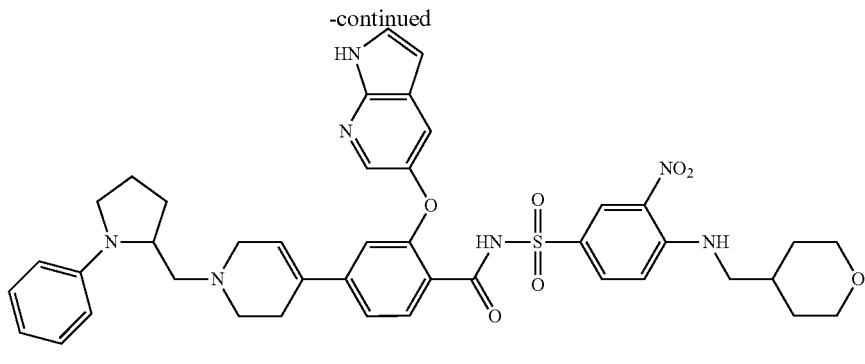

B4

Step 1: tert-butyl 4-(((trifluoromethyl)sulfonyl)oxy)-3,6-dihydropyridine-1(2H)-carboxylate

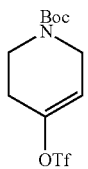

LDA (15 ml, 2M in hexane) was added dropwise to a solution of 4-oxo-piperidine-1-carboxylic acid tert-butyl ester (5 g, 25 mmol) in THF (40 mL). The mixture was stirred for 1 hour at −78° C., and then 1,1,1-trifluoro-N-phenyl-N-((trifluoromethyl)sulfonyl)methanesulfonamide (10.1 g, 27.5 mmol) was added. The mixture was allowed to room temperature and stir overnight. The reaction mixture was extracted with ethyl acetate and the extracts were washed with water. The organic extracts were dried over $Na_2SO_4$, filtered, evaporated, and purified by chromatography on an alumina column to give 4-trifluoromethanesulfonyloxy-3,6-dihydro-2H-pyridine-1-carboxylic acid tert-butyl ester (5 g).

Step 2: tert-butyl 4-(3-((1H-pyrrolo[2,3-b]pyridin-5-yl)oxy)-4-(tert-butoxycarbonyl)phenyl)-3,6-dihydropyridine-1(2H)-carboxylate

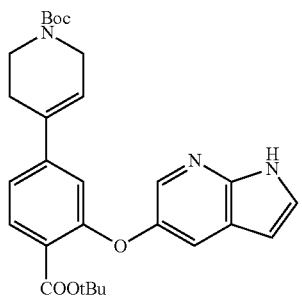

Under nitrogen atmosphere, a mixture of tert-butyl 4-(((trifluoromethyl)sulfonyl)oxy)-3,6-dihydropyridine-1(2H)-carboxylate (331 mg, 1 mmol), tert-butyl 2-((1H-pyrrolo[2,3-b]pyridin-5-yl)oxy)-4-(4,4,5,5-tetramethyl-1,3,2-dioxaborolan-2-yl)benzoate (523 mg, 1.2 mmol), Pd(dppf)Cl$_2$ (73 mg, 0.1 mmol), and $K_2CO_3$ (276 mg, 0.2 mmol) in 1,4-dioxane/$H_2O$ (25 ml/5 ml) was heated to 90° C. with stirring overnight. Then the reaction was cooled to room temperature, the mixture was washed with water, brine and dried over anhydrous $Na_2SO_4$. The organic layers were concentrated and purified by column chromatography with 10%~50% EA/PE as eluent to give tert-butyl 4-(3-((1H-pyrrolo[2,3-b]pyridin-5-yl)oxy)-4-(tert-butoxycarbonyl)phenyl)-3,6-dihydropyridine-1(2H)-carboxylate. MS (ESI, m/e) [M+1]$^+$ 402.2.

Step 3: tert-butyl 2-((1H-pyrrolo[2,3-b]pyridin-5-yl)oxy)-4-(1,2,3,6-tetrahydropyridin-4-yl)benzoate

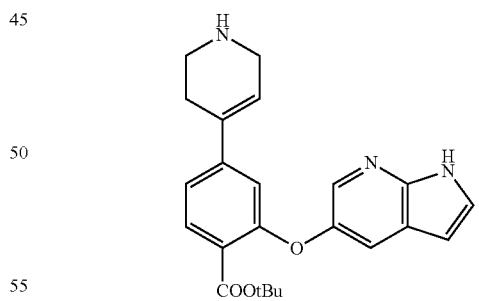

To a solution of tert-butyl 4-(3-((1H-pyrrolo[2,3-b]pyridin-5-yl)oxy)-4-(tert-butoxycarbonyl)phenyl)-3,6-dihydro-pyridine-1(2H)-carboxylate (246 mg, 0.5 mmol) in dioxane (15 mL) was added HCl-dioxane (10 mL). The reaction was stirred for 0.5 hour at r.t, the mixture was basified by sat. NaHCO$_3$ solution in $H_2O$ (10 mL), then extracted with EA. The organic layer was then concentrated to give tert-butyl 2-((1H-pyrrolo[2,3-b]pyridin-5-yl)oxy)-4-(1,2,3,6-tetrahydropyridin-4-yl)benzoate (190 mg) as a colorless oil. MS (ESI, m/e) [M+1]$^+$ 392.1.

Step 4: tert-butyl 2-((1H-pyrrolo[2,3-b]pyridin-5-yl)oxy)-4-(1-((1-phenylpyrrolidin-2-yl)methyl)-1,2,3,6-tetrahydropyridin-4-yl)benzoate

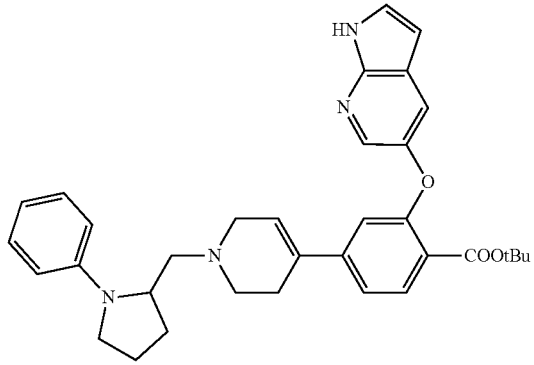

A mixture of 1-phenylpyrrolidine-2-carbaldehyde and tert-butyl 2-((1H-pyrrolo[2,3-b]pyridin-5-yl)oxy)-4-(1,2,3,6-tetrahydropyridin-4-yl)benzoate in DCM (25 mL) was stirred for 0.5 hour, then NaBH(OAc)$_3$ was added. The reaction was continually stirred for 3 hours, then the solvent was removed and the residue was purified by chromatography to give tert-butyl 2-((1H-pyrrolo[2,3-b]pyridin-5-yl)oxy)-4-(1-((1-phenylpyrrolidin-2-yl)methyl)-1,2,3,6-tetrahydropyridin-4-yl)benzoate (80 mg) as a colorless oil MS (ESI, m/e) [M+1]$^+$ 551.2.

Then following the similar procedures in Example B1, proceeded with hydrolysis in step 5 and condensation of the resulted 2-((1H-pyrrolo[2,3-b]pyridin-5-yl)oxy)-4-(1-((1-phenylpyrrolidin-2-yl)methyl)-1,2,3,6-tetrahydropyridin-4-yl)benzoic acid and 3-nitro-4-(((tetrahydro-2H-pyran-4-yl)methyl)amino)benzenesulfonamide in step 6, to afford the product. $^1$H NMR (400 MHz, DMSO-d$_6$) δ ppm: 12.22 (s, 1H), 11.66 (s, 1H), 8.49 (s, 2H), 8.00 (s, 1H), 7.75 (s, 1H), 7.62-7.37 (m, 3H), 7.23 (d, J=8.0 Hz, 1H), 7.14 (t, J=7.5 Hz, 2H), 7.01 (s, 1H), 6.83 (s, 1H), 6.57 (d, J=6.8 Hz, 3H), 6.37 (s, 1H), 6.12 (s, 1H), 3.84 (d, J=8.7 Hz, 3H), 3.30-3.23 (m, 7H), 3.08-3.01 (m, 2H), 2.44-2.37 (m, 1H), 2.08-1.76 (m, 6H), 1.60 (d, J=12.2 Hz, 2H), 1.28-1.21 (m, 5H). MS (ESI, m/e) [M+1]$^+$ 792.2.

Example B5: 3-((1H-pyrrolo[2,3-b]pyridin-5-yl)oxy)-4'-((2-(4-chlorophenyl)pyrrolidin-1-yl)methyl)-N-((3-nitro-4-(((tetrahydro-2H-pyran-4-yl)methyl)amino)phenyl)sulfonyl)-[1,1'-biphenyl]-4-carboxamide

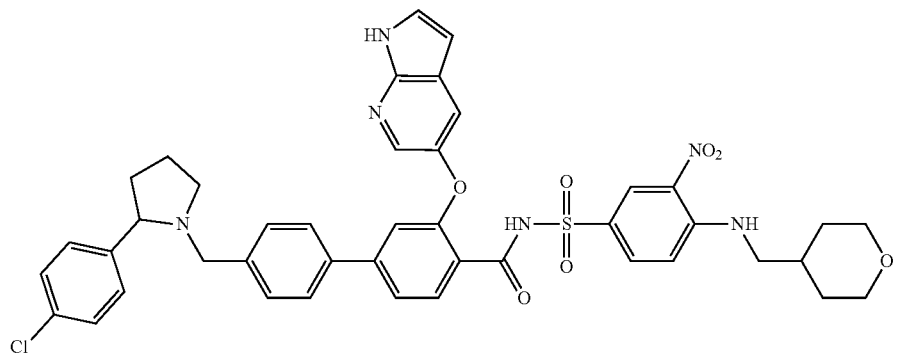 [SMILES: O=C(NS(=O)(=O)c1ccc(NCC2CCOCC2)c([N+](=O)[O-])c1)c1ccc(-c2ccc(CN3CCCC3c3ccc(Cl)cc3)cc2)cc1Oc1cnc2[nH]ccc2c1]

The desired compound was synthesized starting from 2-(4-chlorophenyl)pyrrolidine and 1-(bromomethyl)-4-chlorobenzene following the procedures similar to those in Example B1. $^1$H NMR (400 MHz, DMSO-$d_6$) δ ppm: 12.34 (s, 1H), 11.70 (s, 1H), 8.54 (s, 2H), 8.06 (s, 1H), 7.81 (d, J=7.3 Hz, 1H), 7.59-7.63 (m, 2H), 7.37-7.50 (m, 8H), 7.27-7.34 (m, 2H), 7.07 (s, 1H), 6.99 (s, 1H), 6.39 (s, 1H), 3.85 (d, J=7.9 Hz, 2H), 3.64 (s, 1H), 3.29-3.23 (m, 4H), 2.97 (s, 2H), 2.18 (s, 2H), 1.95-2.04 (m, 1H), 1.77-1.87 (m, 4H), 1.60 (d, J=11.7 Hz, 2H), 1.26 (s, 2H). MS (ESI, m/e) [M+1]$^+$ 821.1.

Example B6: 3-((1H-pyrrolo[2,3-b]pyridin-5-yl)oxy)-4'-((4'-chloro-5,5-dimethyl-3,4,5,6-tetrahydro-[1,1'-biphenyl]-2-yl)methyl)-N-((3-nitro-4-(((tetrahydro-2H-pyran-4-yl)methyl)amino)phenyl)sulfonyl)-[1,1'-biphenyl]-4-carboxamide

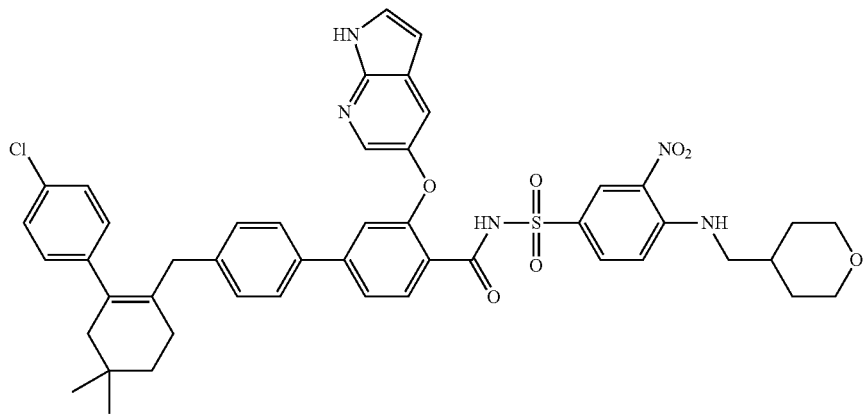 [SMILES: CC1(C)CCC(Cc2ccc(-c3ccc(C(=O)NS(=O)(=O)c4ccc(NCC5CCOCC5)c([N+](=O)[O-])c4)c(Oc4cnc5[nH]ccc5c4)c3)cc2)=C(c2ccc(Cl)cc2)C1]

Step 1:
2-chloro-4,4-dimethylcyclohex-1-ene-1-carbaldehyde

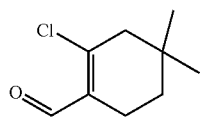

To a mixture of DMF (70 mL) and DCM (600 mL) was added POCl$_3$ (80 mL) dropwise at −10° C. Then the mixture was stirred at r.t. for 0.5 hour. Then 3,3-dimethylcyclohexan-1-one (110 mL) was added. The mixture was stirred at reflux for overnight. The mixture was basified with sat. NaHCO$_3$ solution in water and separated. The organic layer was dried over Na$_2$SO$_4$, concentrated to give the product 130 g as a yellow oil.

Step 2: 4'-chloro-5,5-dimethyl-3,4,5,6-tetrahydro-[1,1'-biphenyl]-2-carbaldehyde

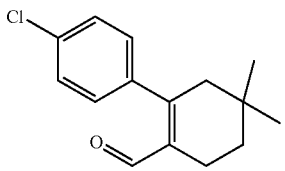 [SMILES: CC1(C)CCC(C=O)=C(c2ccc(Cl)cc2)C1]

To a solution of 2-chloro-4,4-dimethylcyclohex-1-ene-1-carbaldehyde (17.1 g, 100 mmol) and (4-chlorophenyl)boronic acid (17.2 g, 110 mmol) in toluene (150 mL) and H$_2$O (15 mL) were added Pd (PPh$_3$)$_4$ (3.45 g, 3 mmol), K$_2$CO$_3$ (28 g, 200 mmol). The mixture was stirred at 100° C. for 2 hours under nitrogen protection. The mixture was filtered. Then the filtrate was washed with brine, dried over Na$_2$SO$_4$, concentrated and purified by chromatography column on silica (eluent: EA/PE=1/20) to give the product (18 g) as a yellow oil.

Step 3: N'-((4'-chloro-5,5-dimethyl-3,4,5,6-tetrahydro-[1,1'-biphenyl]-2-yl)methylene)-4-methylbenzenesulfonohydrazide

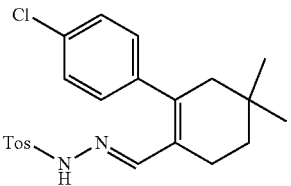

To a solution of 4'-chloro-5,5-dimethyl-3,4,5,6-tetrahydro-[1,1'-biphenyl]-2-carbaldehyde (3 g, 12.06 mmol) in 1,4-dioxane (100 mL) was added 4-methylbenzenesulfonohydrazide (2.695 g, 14.47 mmol). The mixture was stirred at 90° C. for 2 hours. The mixture was concentrated. The residue was dissolved with DCM (200 mL), then washed with brine (200 mL×2), dried over Na$_2$SO$_4$, concentrated and purified by chromatography column on silica (eluent: EA/PE=1/10) to give the product (4.6 g, 91.5%) as a yellow solid. MS (ESI, m/e) [M+1]$^+$ 417.1.

Step 4: 6-(4-bromobenzyl)-4'-chloro-3,3-dimethyl-2,3,4,5-tetrahydro-1,1'-biphenyl

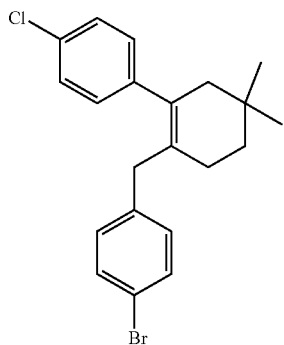 [SMILES: CC1(C)CCC(Cc2ccc(Br)cc2)=C(c2ccc(Cl)cc2)C1]

To a solution of N'-((4'-chloro-5,5-dimethyl-3,4,5,6-tetrahydro-[1,1'-biphenyl]-2-yl)methylene)-4-methylbenzenesulfonohydrazide (2 g, 4.8 mmol) in 1,4-dioxane (50 mL) were added (4-bromophenyl)boronic acid (1.445 g, 7.2 mmol) and $K_2CO_3$ (1.325 g, 9.6 mmol). The mixture was stirred at reflux for overnight under nitrogen protection. The mixture was diluted with DCM (200 ml), washed with brine, dried over $Na_2SO_4$, concentrated and purified by chromatography column on silica (eluent: EA/PE=1/100) to give the product (1.65 g, 88.2%) as a clear oil. $^1$H NMR (400 MHz, DMSO-$d_6$) δ ppm: 7.45 (d, J=8.3 Hz, 2H), 7.39 (d, J=8.2 Hz, 2H), 7.18 (d, J=8.3 Hz, 2H), 7.02 (d, J=8.2 Hz, 2H), 3.18 (s, 2H), 2.04 (s, 2H), 1.90 (t, J=5.8 Hz, 2H), 1.36 (t, J=5.8 Hz, 2H), 0.93 (s, 6H).

Step 5: tert-butyl 3-((1H-pyrrolo[2,3-b]pyridin-5-yl)oxy)-4'-((4'-chloro-5,5-dimethyl-3,4,5,6-tetrahydro-[1,1'-biphenyl]-2-yl)methyl)-[1,1'-biphenyl]-4-carboxylate

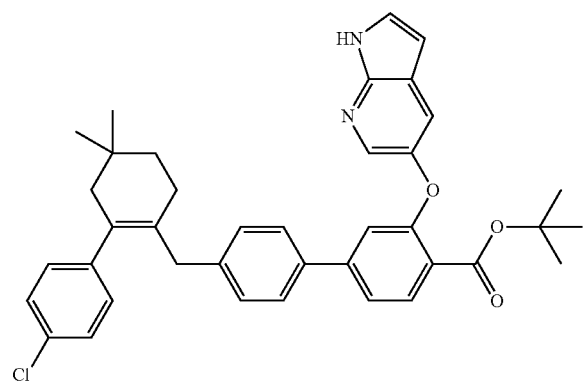 [SMILES: CC1(C)CCC(Cc2ccc(-c3ccc(C(=O)OC(C)(C)C)c(Oc4cnc5[nH]ccc5c4)c3)cc2)=C(c2ccc(Cl)cc2)C1]

To a solution of 6-(4-bromobenzyl)-4'-chloro-3,3-dimethyl-2,3,4,5-tetrahydro-1,1'-biphenyl (200 mg, 0.513 mmol) and tert-butyl 2-((1H-pyrrolo[2,3-b]pyridin-5-yl)oxy)-4-(3,3,4,4-tetramethylborolan-1-yl)benzoate (291 mg, 0.67 mmol) in toluene (30 mL) and $H_2O$ (2 mL) were added Pd(PPh$_3$)$_4$ (118.5 mg, 0.103 mmol) and $K_2CO_3$ (106.2 mg, 0.77 mmol). The mixture was stirred at reflux for overnight under nitrogen protection. The mixture was washed with brine, dried over $Na_2SO_4$, concentrated and purified by chromatography column on silica (eluent: EA/PE=1/2) to give the product (60 mg) as a yellow solid. MS (ESI, m/e) [M+1]$^+$ 619.2.

Step 6: 3-((1H-pyrrolo[2,3-b]pyridin-5-yl)oxy)-4'-((4'-chloro-5,5-dimethyl-3,4,5,6-tetrahydro-[1,1'-biphenyl]-2-yl)methyl)-[1,1'-biphenyl]-4-carboxylic acid

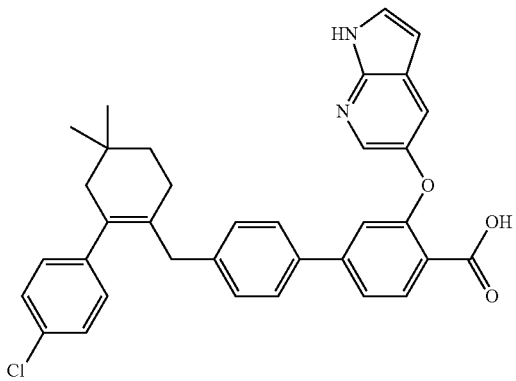 [SMILES: CC1(C)CCC(Cc2ccc(-c3ccc(C(=O)O)c(Oc4cnc5[nH]ccc5c4)c3)cc2)=C(c2ccc(Cl)cc2)C1]

To a solution of tert-butyl 3-((1H-pyrrolo[2,3-b]pyridin-5-yl)oxy)-4'-((4'-chloro-5,5-dimethyl-3,4,5,6-tetrahydro-[1,1'-biphenyl]-2-yl)methyl)-[1,1'-biphenyl]-4-carboxylate (60 mg, 0.097 mmol) in DCM (30 mL) was added TFA (5 mL). The mixture was stirred at room temperature for overnight. The mixture was concentrated and purified by chromatography column on silica (eluent: MeOH/DCM=1/30) to give the product (31 mg) as a brown solid. MS (ESI, m/e) [M+1]$^+$ 563.1.

Step 7: 3-((1H-pyrrolo[2,3-b]pyridin-5-yl)oxy)-4'-((4'-chloro-5,5-dimethyl-3,4,5,6-tetrahydro-[1,1'-biphenyl]-2-yl)methyl)-N-((3-nitro-4-(((tetrahydro-2H-pyran-4-yl)methyl)amino)phenyl)sulfonyl)-[1,1'-biphenyl]-4-carboxamide

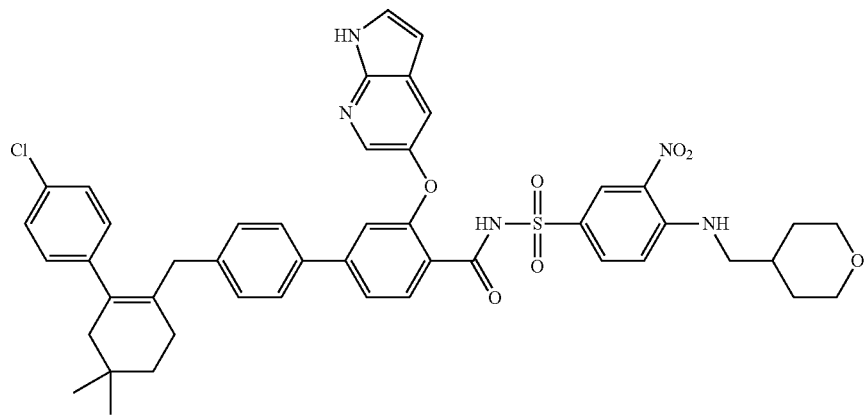 [SMILES: CC1(C)CCC(Cc2ccc(-c3ccc(C(=O)NS(=O)(=O)c4ccc(NCC5CCOCC5)c([N+](=O)[O-])c4)c(Oc4cnc5[nH]ccc5c4)c3)cc2)=C(c2ccc(Cl)cc2)C1]

To a solution of 3-((1H-pyrrolo[2,3-b]pyridin-5-yl)oxy)-4'-((4'-chloro-5,5-dimethyl-3,4,5,6-tetrahydro-[1,1'-biphenyl]-2-yl)methyl)-[1,1'-biphenyl]-4-carboxylic acid (30 mg, 0.0533 mmol) in DCM (50 mL) was added HATU (30.4 mg, 0.08 mmol) and triethylamine (27 mg, 0.267 mmol). The mixture was stirred at room temperature for 1 hour. Then to the mixture were added 3-nitro-4-(((tetrahydro-2H-pyran-4-yl)methyl)amino)benzenesulfonamide (33.6 mg, 0.107 mmol). The mixture was stirred at room temperature for overnight. The mixture was washed with brine, dried over $Na_2SO_4$, concentrated and purified by chromatography column on silica (eluent: EA/PE=1/1 then MeOH/DCM=1/10) to give the crude product. The crude product was further purified by prep-TLC (MeOH/DCM=1/20) to give the product (1.79 mg, 3.9%). $^1$H NMR (400 MHz, DMSO-$d_6$) δ ppm: 12.35 (s, 1H), 11.73 (s, 1H), 8.68-8.50 (m, 2H), 8.10-8.02 (m, 1H), 7.84 (d, J=8.0 Hz, 1H), 7.67-7.56 (m, 2H), 7.56-7.48 (m, 1H), 7.43 (d, J=8.0 Hz, 3H), 7.37 (d, J=8.2 Hz, 2H), 7.17 (d, J=8.2 Hz, 2H), 7.10 (d, J=8.0 Hz, 2H), 6.99 (s, 1H), 6.40 (s, 1H), 5.41-5.21 (m, 1H), 3.85 (d, J=8.5 Hz, 2H), 3.28-3.15 (m, 6H), 2.07-1.94 (m, 4H), 1.94-1.79 (m, 3H), 1.67-1.54 (m, 2H), 1.38-1.31 (m, 2H), 0.91 (s, 6H). MS (ESI, m/e) [M+1]$^+$ 860.1.

Example B8: 2-((1H-pyrrolo[2,3-b]pyridin-5-yl)oxy)-N-((3-nitro-4-(((tetrahydro-2H-pyran-4-yl)methyl)amino)phenyl)sulfonyl)-4-(1-(phenylprolyl)-1,2,3,6-tetrahydropyridin-4-yl)benzamide

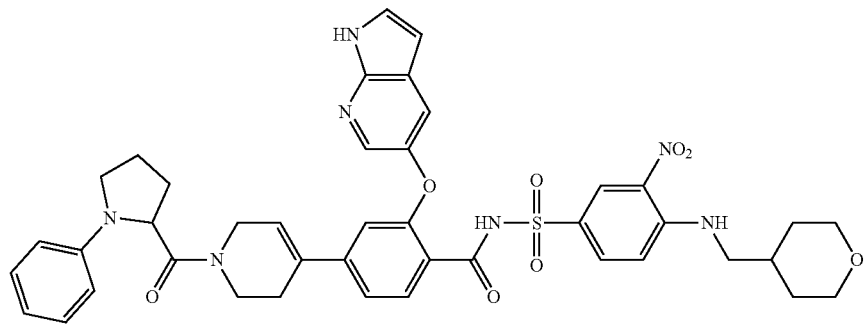 [SMILES: O=C(NS(=O)(=O)c1ccc(NCC2CCOCC2)c([N+](=O)[O-])c1)c1ccc(C2=CCN(C(=O)C3CCCN3c3ccccc3)CC2)cc1Oc1cnc2[nH]ccc2c1]

The desired compound was synthesized starting from phenylproline and tert-butyl 2-((1H-pyrrolo[2,3-b]pyridin-5-yl)oxy)-4-(1,2,3,6-tetrahydropyridin-4-yl)benzoate following the procedures similar to those in Example B4. $^1$H NMR (400 MHz, DMSO-$d_6$) δ ppm: 12.32 (s, 1H), 11.72 (s, 1H), 8.69-8.53 (m, 1H), 8.04 (s, 1H), 7.83 (d, J=8.0 Hz, 1H), 7.64-7.46 (m, 3H), 7.28 (d, J=8.0 Hz, 1H), 7.13 (d, J=8.0 Hz, 1H), 7.10-7.05 (m, 2H), 6.87 (d, J=12.0 Hz, 1H), 6.51 (l, J=8.0 Hz, 1H), 6.40 (s, 1H), 6.35-6.25 (m, 1H), 6.18 (s, 1H), 4.79-4.59 (m, 1H), 4.47-4.15 (m, 1H), 4.11-3.91 (m, 1H), 3.90-3.74 (m, 3H), 3.72-3.47 (m, 4H), 3.29-3.18 (m, 5H), 2.41-2.15 (m, 3H), 2.04-1.72 (m, 5H), 1.61 (d, J=8.0 Hz, 2H), 1.35-1.15 (m, 3H). MS (ESI, m/e) [M+1]$^+$ 806.1.

Example B12: 2-((1H-pyrrolo[2,3-b]pyridin-5-yl)oxy)-4-(3-((2-(2-cyclopropylphenyl)pyrrolidin-1-yl)methyl)azetidin-1-yl)-N-((3-nitro-4-(((tetrahydro-2H-pyran-4-yl)methyl)amino)phenyl)sulfonyl)benzamide

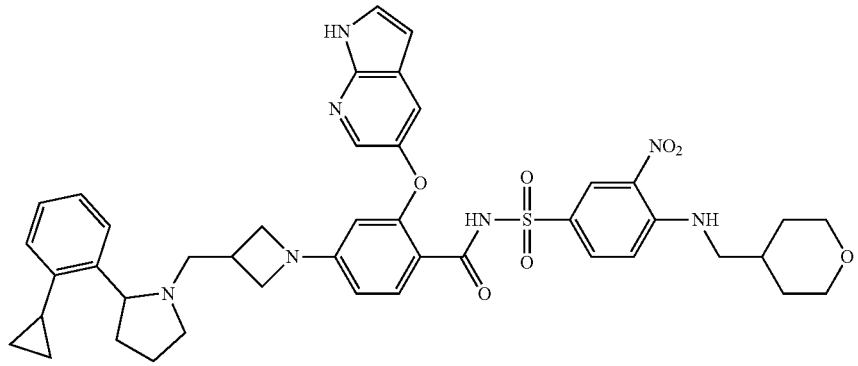 [SMILES: O=C(NS(=O)(=O)c1ccc(NCC2CCOCC2)c([N+](=O)[O-])c1)c1ccc(N2CC(CN3CCCC3c3ccccc3C3CC3)C2)cc1Oc1cnc2[nH]ccc2c1]

Step 1: methyl 2-((1H-pyrrolo[2,3-b]pyridin-5-yl)oxy)-4-fluorobenzoate

To a solution of methyl 2,4-difluorobenzoate (3.44 g, 20.00 mmol) in DMF (50 mL) was added 1H-pyrrolo[2,3-b]pyridin-5-ol (2.70 g, 20.00 mmol) and $K_2CO_3$ (5.6 g, 40.00 mmol), the mixture was stirred at 80° C. for 20 h, Cooled to room temperature, partitioned between EA (40 ml) and $H_2O$ (40 mL), the aqueous layer was extracted with EA (20 mL). The combined organic layers were washed with $H_2O$ (30 mL×3), concentrated and purified by CombiFlash (0-60%, EA/PE) to give the crude product, which was crystallized from EA/PE=1/1 (50 mL) to give the isomer. The mother liquid was left standing over night, the precipitate was collected by filtration to give methyl 2-((1H-pyrrolo[2,3-b]pyridin-5-yl)oxy)-4-fluorobenzoate (600 mg) as a white solid, $[M+1]^+$ 286.9.

Step 2: methyl 2-((1H-pyrrolo[2,3-b]pyridin-5-yl)oxy)-4-(3-((2-(2-cyclopropylphenyl)pyrrolidin-1-yl)methyl)azetidin-1-yl)benzoate To a solution of methyl 2-((T H-pyrrolo[2,3-b]pyridin-5-yl)oxy)-4-fluorobenzoate (200 mg, 0.70 mmol) in DMF (10 mL) was added 1-(azetidin-3-ylmethyl)-2-(2-cyclopropylphenyl)pyrrolidine (180 mg, 0.70 mmol) and TFA (355 mg, 3.50 mmol), the solution was stirred at 100° C. for 6 h, Cooled to ambient temperature, partitioned between DCM (30 mL) and $H_2O$ (50 mL). The organic layer was separated, washed with $H_2O$ (20 mL), dried over $Na_2SO_4$, concentrated and purified by CombiFlash (0-10%, MeOH/DCM) to give methyl 2-((1H-pyrrolo[2,3-b]pyridin-5-yl)oxy)-4-(3-((2-(2-cyclopropylphenyl)pyrrolidin-1-yl)methyl)azetidin-1-yl)benzoate (100 mg) as colorless oil, $[M+1]^+$ 522.9.

Step 3: 2-((1H-pyrrolo[2,3-b]pyridin-5-yl)oxy)-4-(3-((2-(2-cyclopropylphenyl)pyrrolidin-1-yl)methyl)azetidin-1-yl)benzoic acid To a solution of methyl 2-((1H-pyrrolo[2,3-b]pyridin-5-yl)oxy)-4-(3-((2-(2-cyclopropylphenyl)pyrrolidin-1-yl)methyl)azetidin-1-yl)benzoate (100 mg, 0.19 mmol) in $CH_3OH$ (20 mL) was added 6N NaOH (5 mL), the mixture was heated at ambient temperature for 16 h. The mixture was acidified with con. HCl. The mixture was partitioned between DCM (40 mL) and $H_2O$ (30 mL), The organic layer was washed with Brine (10 mL), dried over $Na_2SO_4$ and concentrated to give the crude 2-((1H-pyrrolo[2,3-b]pyridin-5-yl)oxy)-4-(3-((2-(2-cyclopropylphenyl)pyrrolidin-1-yl)methyl)azetidin-1-yl)benzoic acid as white solid (40 mg). $[M+1]^+$ 508.9.

Step 4: 2-((1H-pyrrolo[2,3-b]pyridin-5-yl)oxy)-4-(3-((2-(2-cyclopropylphenyl)pyrrolidin-1-yl)methyl)azetidin-1-yl)-N-((3-nitro-4-(((tetrahydro-2H-pyran-4-yl)methyl)amino)phenyl)sulfonyl)benzamide To a solution of 2-((1H-pyrrolo[2,3-b]pyridin-5-yl)oxy)-4-(3-((2-(2-cyclopropylphenyl)pyrrolidin-1-yl)methyl)azetidin-1-yl)benzoic acid (40 mg, 0.08 mmol) in DCM (10 mL) was added HATH (36 mg, 0.09 mmol) and TFA (86 mg, 0.85 mmol), the solution was stirred for about 0.5 h, 3-nitro-4-(((tetrahydro-2H-pyran-4-yl)methyl)amino)benzenesulfonamide (27 mg, 0.170 mmol) and DMAP (12 mg, 0.09 mmol) was then added, the solution was stirred at r. t for 16 h. The reaction solution was concentrated and purified by column chromatograph on silica gel (100-200 mesh, eluent: MeOH/DCM=1/10) to give the crude product, which was purified by Pre-TLC (MeOH/DCM=1/18) to obtain the desired compound. $^1$H NMR (CDCl3) δ ppm: 10.12 (s, 1H), 9.14 (s, 1H), 8.89 (s, 1H), 8.57-8.46 (m, 1H), 8.24-8.09 (m, 2H), 7.90 (d, J=8.8 Hz, 1H), 7.69 (s, 1H), 7.55-7.37 (m, 2H), 7.16-7.03 (m, 2H), 6.97-6.82 (m, 2H), 6.55 (s, 1H), 6.01 (d, J=8.4 Hz, 1H), 5.37 (s, 1H), 4.10-3.98 (m, 2H), 3.84-3.71 (m, 2H), 3.49-3.14 (m, 7H), 2.80-2.51 (m, 2H), 2.39-2.11 (m, 3H), 2.04-1.67 (m, 7H), 1.50-1.35 (m, 3H), 0.93-0.81 (m, 2H), 0.73-0.46 (m, 2H). MS (ESI, m/e) $[M+1]^+$ 805.8.

Example B13: 3-((1H-pyrrolo[2,3-b]pyridin-5-yl)oxy)-3'-((2-(2-cyclopropylphenyl)pyrrolidin-1-yl)methyl)-N-((3-nitro-4-(((tetrahydro-2H-pyran-4-yl)methyl)amino)phenyl)sulfonyl)-[1,1'-biphenyl]-4-carboxamide

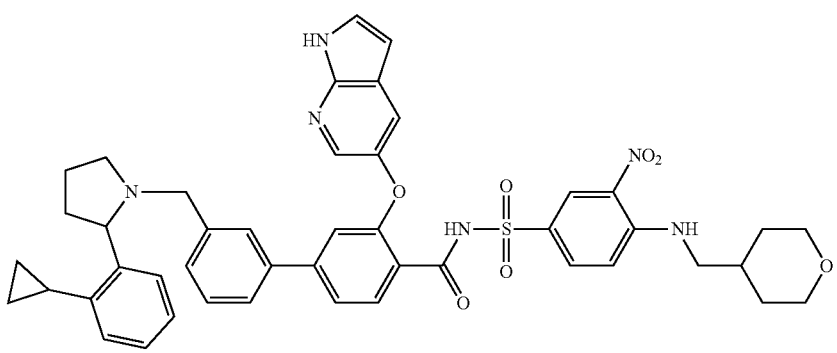 [SMILES: O=C(NS(=O)(=O)c1ccc(NCC2CCOCC2)c([N+](=O)[O-])c1)c1ccc(-c2cccc(CN3CCCC3c3ccccc3C3CC3)c2)cc1Oc1cnc2[nH]ccc2c1]

The desired compound was synthesized following the procedures similar to those in Example B3. MS (ESI, m/e) [M+1]$^+$ 827.5.

Example B14: (R)-3-((1H-pyrrolo[2,3-b]pyridin-5-yl)oxy)-4'-(2-(2-(2-cyclopropylphenyl)pyrrolidin-1-yl)ethyl)-N-((3-nitro-4-(((tetrahydro-2H-pyran-4-yl)methyl)amino)phenyl)sulfonyl)-[1,1'-biphenyl]-4-carboxamide

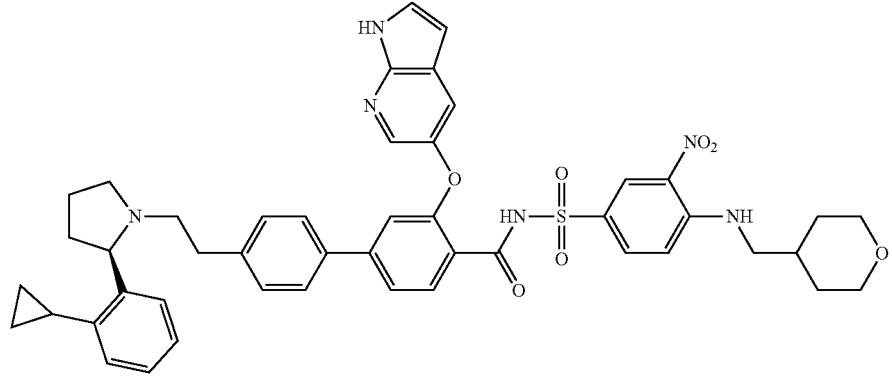 [SMILES: O=C(NS(=O)(=O)c1ccc(NCC2CCOCC2)c([N+](=O)[O-])c1)c1ccc(-c2ccc(CCN3CCC[C@@H]3c3ccccc3C3CC3)cc2)cc1Oc1cnc2[nH]ccc2c1]

The desired compound was synthesized following the procedures similar to those in Example B3. MS (ESI, m/e) [M+1]$^+$ 841.5.

Example B15: (S)-3-((1H-pyrrolo[2,3-b]pyridin-5-yl)oxy)-4'-(2-(2-(2-cyclopropylphenyl)pyrrolidin-1-yl)ethyl)-N-((3-nitro-4-(((tetrahydro-2H-pyran-4-yl)methyl)amino)phenyl)sulfonyl)-[1,1'-biphenyl]-4-carboxamide

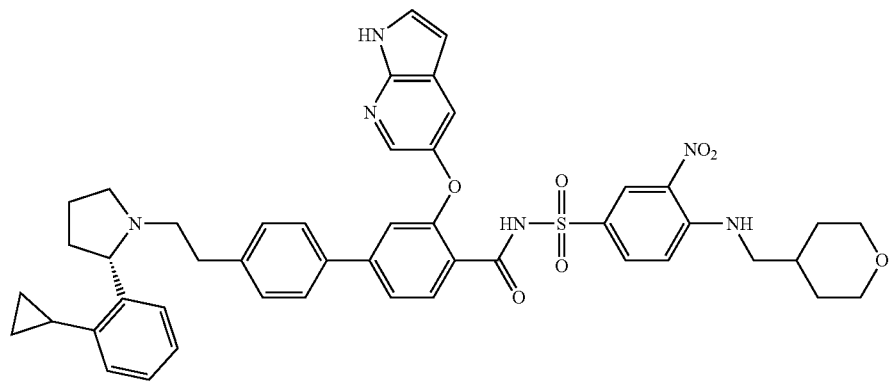 [SMILES: O=C(NS(=O)(=O)c1ccc(NCC2CCOCC2)c([N+](=O)[O-])c1)c1ccc(-c2ccc(CCN3CCC[C@H]3c3ccccc3C3CC3)cc2)cc1Oc1cnc2[nH]ccc2c1]

The desired compound was synthesized following the procedures similar to those in Example B3. $^1$H NMR (400 MHz, DMSO-d$_6$) δ ppm: 12.36 (s, 1H), 11.72 (s, 1H), 8.70-8.50 (m, 2H), 8.06 (s, 1H), 7.83 (d, J=9.0 Hz, 1H), 7.80-7.70 (m, 1H), 7.65-7.56 (m, 2H), 7.52 (s, 1H), 7.50-7.40 (m, 3H), 7.35-7.25 (m, 2H), 7.20-7.05 (m, 4H), 6.97 (s, 1H), 6.39 (s, 1H), 5.15-4.95 (m, 1H), 3.90-3.70 (m, 2H), 3.29-3.21 (m, 3H), 3.10-2.80 (m, 4H), 2.29-1.79 (m, 5H), 1.60 (d, J=9.0 Hz, 2H), 1.30-1.20 (m, 3H), 1.00-0.78 (m, 5H), 0.65-0.55 (m, 2H). MS (ESI, m/e) [M+1]$^+$ 841.5.

Example B16: 3-((1H-pyrrolo[2,3-b]pyridin-5-yl)oxy)-4'-(((S)-2-(2-cyclopropylphenyl)pyrrolidin-1-yl)methyl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

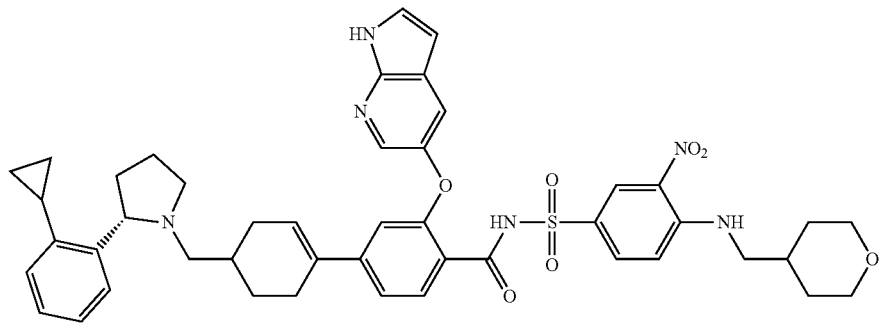 [SMILES: O=C(NS(=O)(=O)c1ccc(NCC2CCOCC2)c([N+](=O)[O-])c1)c1ccc(C2=CCC(CN3CCC[C@H]3c3ccccc3C3CC3)CC2)cc1Oc1cnc2[nH]ccc2c1]

Step 1: 1,4-dioxaspiro[4.5]decane-8-carbaldehyde

To a solution of ethyl 1,4-dioxaspiro[4.5]decane-8-carboxylate (3.21 g, 15.00 mmol) in toluene (40 mL) was added DIBAL-H (10 mL, 15.00 mmol) dropwise at about −65° C., the mixture was stirred at −65° C. under N$_2$ for 0.5 h, Quenched by CH$_3$OH (20 mL), warmed to ambient temperature, Sat. NH$_4$Cl (20 mL) was added. The organic layer was separated, dried over Na$_2$SO$_4$ and concentrated to give the crude product as yellow oil. (2.5 g).

Step 2: (S)-1-((1,4-dioxaspiro[4.5]decan-8-yl)methyl)-2-(2-cyclopropylphenyl)pyrrolidine To a solution of 1,4-dioxaspiro[4.5]decane-8-carbaldehyde (2.5 g, 15.00 mmol) in DCM (50 mL) was added (S)-2-(2-cyclopropylphenyl)pyrrolidine (2.8 g, 15.00 mmol) and NaBH(OAc)$_3$ (6.4 g, 30.00 mmol), the mixture was stirred at ambient temperature for 2 h. The reaction solution was washed with Sat. NaCl (20 mL), concentrated and purified by column chromatograph on silica gel (100-200 mesh, eluent: EA/DCM=1/2) to give the product as brown oil. (2.0 g). [M+1]$^+$ 341.8.

Step 3: (S)-4-((2-(2-cyclopropylphenyl)pyrrolidin-1-yl)methyl)cyclohexan-1-one

To a solution of (S)-1-((1,4-dioxaspiro[4.5]decan-8-yl)methyl)-2-(2-cyclopropylphenyl)pyrrolidine (2.0 g, 5.85 mmol) in DCM (10 mL) and CH$_3$OH (5 mL) was added con. HCl (5 mL), the mixture was stirred at ambient temperature for 2 d. The reaction mixture was partitioned between DCM (40 mL) and 2N NaOH (20 mL). The organic layer was separated, concentrated and purified by column chromatograph on silica gel (100-200 mesh, eluent: EA/DCM=1/2) to give the product as yellow oil. (1.25 g). [M+1]$^+$ 297.8. Step 4: 4-(((S)-2-(2-cyclopropylphenyl)pyrrolidin-1-yl)methyl)cyclohex-1-en-1-yl trifluoromethanesulfonate To a solution of (S)-4-((2-(2-cyclopropylphenyl)pyrrolidin-1-yl)methyl)cyclohexan-1-one (1.2 g, 4.04 mmol) and 1,1,1-trifluoro-N-phenyl-N-((trifluoromethyl)sulfonyl)methanesulfonamide (1.73 g, 4.85 mmol) in THF (40 mL) was added NaHMDS (2.2 ml, 4.44 mmol) dropwise at about −65° C., the solution was stirred at −65° C. under N$_2$ for 1 h, warmed to r. t for about 16 h. The reaction solution was partitioned between EA (20 mL) and Sat. NaCl (20 mL). The organic layer was separated, concentrated and purified by column chromatograph on silica gel (100-200 mesh, eluent: EA:PE=1:10) to give the product as yellow oil. (250 mg), [M+1]$^+$ 429.8. Step 5: tert-butyl 3-((1H-pyrrolo[2,3-b]pyridin-5-yl)oxy)-4'-(((S)-2-(2-cyclopropylphenyl)pyrrolidin-1-yl)methyl)-2',3',4',5'-tetrahydro-[1,1'-biphenyl]-4-carboxylate To a solution of 4-(((S)-2-(2-cyclopropylphenyl)pyrrolidin-1-yl)methyl)cyclohex-1-en-1-yl trifluoromethanesulfonate (230 mg, 0.537 mmol) in 1,4-dioxane (10 mL) was added tert-butyl 2-((1H-pyrrolo[2,3-b]pyridin-5-yl)oxy)-4-(4,4,5,5-tetramethyl-1,3,2-dioxaborolan-2-yl)benzoate (251 mg, 0.645 mmol), Cs$_2$CO$_3$ (700 mg, 2,148 mmol), H$_2$O (2 mL) and Pd(dppf)Cl$_2$ (40 mg, 0.054 mmol), the mixture was stirred at 100° C. under N$_2$ for 6 h. Cooled to r. t, partitioned between EA (20 mL) and Sat. NaCl (10 mL). The organic layer was separated, concentrated and purified by pre-TLC (MeOH/DCM=1/15) to give the product as brown oil, (200 mg). [M+1]$^+$ 589.9.

Step 6: 3-((1H-pyrrolo[2,3-b]pyridin-5-yl)oxy)-4'-(((S)-2-(2-cyclopropylphenyl)pyrrolidin-1-yl)methyl)-2',3',4',5'-tetrahydro-[1,1'-biphenyl]-4-carboxylic acid To a solution of 5-tert-butyl 3-((1H-pyrrolo[2,3-b]pyridin-5-yl)oxy)-4'-(((S)-2-(2-cyclopropylphenyl)pyrrolidin-1-yl)methyl)-2',3',4',5'-tetrahydro-[1,1'-biphenyl]-4-carboxylate (200 mg, 0.340 mmol) in DCM (10 mL) was added TFA (5 ml), the solution was stirred at r. t for 2 h. the reaction solution was concentrated. The residue was partitioned between DCM (50 mL) and H$_2$O (20 mL), the organic layer was washed with Sat. NaCl (20 mL), dried over Na2SO4 and concentrated to give the crude product as yellow solid. (150 mg).

Step 7: 3-((1H-pyrrolo[2,3-b]pyridin-5-yl)oxy)-4'-(((S)-2-(2-cyclopropylphenyl)pyrrolidin-1-yl)methyl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide To a solution of 3-((1H-pyrrolo[2,3-b]pyridin-5-yl)oxy)-4'-(((S)-2-(2-cyclopropylphenyl)pyrrolidin-1-yl)methyl)-2',3',4',5'-tetrahydro-[1,1'-biphenyl]-4-carboxylic acid (150 mg, 0.281 mmol) in DCM (20 mL) was added HATU (128 mg, 0.338 mmol), DMAP (34 mg, 0.281 mmol), TFA (141 mg, 1.405 mmol) and 3-nitro-4-(((tetrahydro-2H-pyran-4-yl)methyl)amino)benzenesulfonamide (106 mg, 0.338 mmol), the solution was stirred at r, t for 16 h. The reaction solution was concentrated and purified by column chromatograph on silica gel (100-200 mesh, eluent: MeOH/DCM=1/20) to give the crude product, which was purified by pre-TLC (MeOH/DCM=1/15) to give the product as yellow solid. (60 mg, 25.7%). $^1$H NMR (DMSO-d$_6$) δ ppm: 12.22 (s, 1H), 11.70 (s, 1H), 8.90-8.42 (m, 2H), 8.01 (s, 1H), 7.85-7.40 (m, 5H), 7.32-6.80 (m, 5H), 6.74-6.61 (m, 1H), 6.39 (s, 1H), 6.10-5.89 (m, 1H), 5.16-4.92 (m, 1H), 3.94-3.66 (m, 3H), 3.53-3.44 (m, 1H), 3.30-3.17 (m, 5H), 2.27-1.96 (m, 7H), 1.91-1.54 (m, 7H), 1.44-1.13 (m, 4H), 1.06-1.01 (m, 1H), 0.94-0.81 (m, 2H), 0.71-0.42 (m, 2H). [M+1]$^+$ 830.8.

Example B17: 2-((1H-pyrrolo[2,3-b]pyridin-5-yl)oxy)-4-(4-((2-(2-cyclopropylphenyl)pyrrolidin-1-yl)methyl)piperidin-1-yl)-N-((3-nitro-4-(((tetrahydro-2H-pyran-4-yl)methyl)amino)phenyl)sulfonyl)benzamide

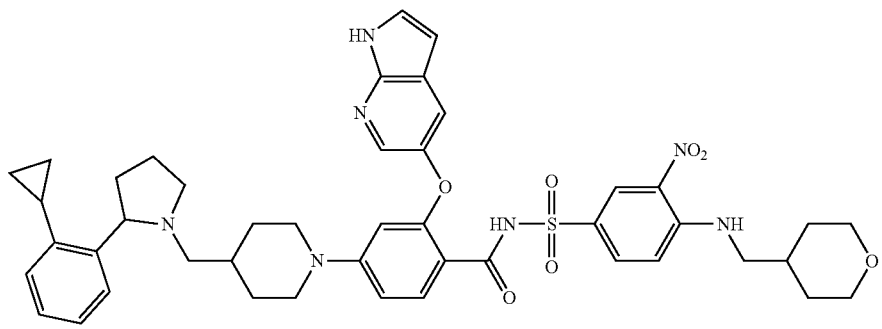 [SMILES: O=C(NS(=O)(=O)c1ccc(NCC2CCOCC2)c([N+](=O)[O-])c1)c1ccc(N2CCC(CN3CCCC3c3ccccc3C3CC3)CC2)cc1Oc1cnc2[nH]ccc2c1]

The desired compound was synthesized following the procedures similar to those in Example B12. $^1$H NMR (400 MHz, DMSO-d$_6$) δ ppm: 11.67 (s, 1H), 11.36 (s, 1H), 8.69-8.44 (m, 2H), 8.10-7.96 (m, 1H), 7.77 (d, J=8.8 Hz, 1H), 7.58-7.36 (m, 4H), 7.17-6.84 (m, 4H), 6.70-6.60 (m, 1H), 6.37 (s, 1H), 6.14 (s, 1H), 3.86-3.69 (m, 3H), 3.60-3.48 (m, 2H), 3.30-3.19 (m, 5H), 2.71-2.59 (m, 2H), 2.24-2.09 (m, 2H), 2.02-1.74 (m, 6H), 1.62-1.56 (m, 2H), 1.50-1.38 (m, 2H), 1.28-1.19 (m, 4H), 0.92-0.80 (m, 4H), 0.68-0.58 (m, 1H), 0.54-0.43 (m, 1H). MS (ESI, m/e) [M+1]$^+$ 833.8.

Example B18: (S)-2-((1H-pyrrolo[2,3-b]pyridin-5-yl)oxy)-4-(4-((2-(2-cyclopropylphenyl)pyrrolidin-1-yl)methyl)piperidin-1-yl)-N-((3-nitro-4-(((tetrahydro-2H-pyran-4-yl)methyl)amino)phenyl)sulfonyl)benzamide

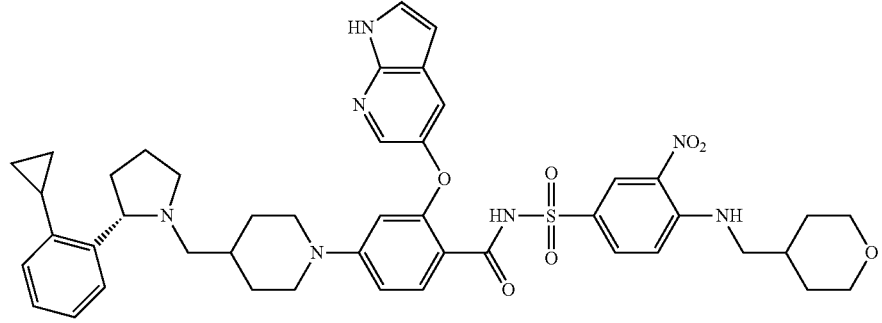 [SMILES: O=C(NS(=O)(=O)c1ccc(NCC2CCOCC2)c([N+](=O)[O-])c1)c1ccc(N2CCC(CN3CCC[C@H]3c3ccccc3C3CC3)CC2)cc1Oc1cnc2[nH]ccc2c1]

The desired compound was synthesized following the procedures similar to those in Example B12. $^1$H NMR (400 MHz, DMSO-d$_6$) δ ppm: 11.70 (s, 1H), 11.39 (s, 1H), 8.74-8.42 (m, 2H), 8.05 (s, 1H), 7.80 (d, J=8.8 Hz, 1H), 7.65-7.35 (m, 4H), 7.25-6.84 (m, 4H), 6.73-6.61 (m, 1H), 6.39 (s, 1H), 6.15 (s, 1H), 3.90-3.68 (m, 3H), 3.65-3.51 (m, 2H), 3.31-3.20 (m, 5H), 2.76-2.59 (m, 2H), 2.28-1.74 (m, 9H), 1.69-1.56 (m, 3H), 1.53-1.34 (m, 2H), 1.32-1.19 (m, 2H), 0.97-0.79 (m, 4H), 0.68-0.46 (m, 2H). MS (ESI, m/e) [M+1]$^+$ 833.9.

Example B19a and Example B19b: (R or S) 2-((1H-pyrrolo[2,3-b]pyridin-5-yl)oxy)-4-(3-(((S)-2-(2-cyclopropylphenyl)pyrrolidin-1-yl)methyl)piperidin-1-yl)-N-((3-nitro-4-(((tetrahydro-2H-pyran-4-yl)methyl)amino)phenyl)sulfonyl)benzamide/(S or R) 2-((1H-pyrrolo[2,3-b]pyridin-5-yl)oxy)-4-(3-(((S)-2-(2-cyclopropylphenyl)pyrrolidin-1-yl)methyl)piperidin-1-yl)-N-((3-nitro-4-(((tetrahydro-2H-pyran-4-yl)methyl)amino)phenyl)sulfonyl)benzamide

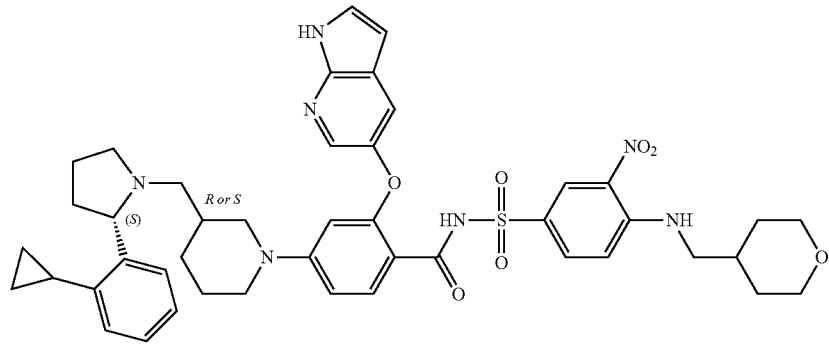

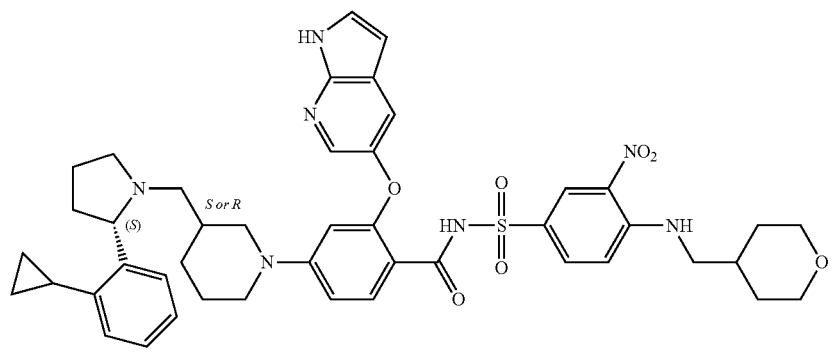

The desired compound was synthesized following the procedures similar to those in Example B12, The faster in column chromatograph on silica gel is Example B19a: MS (ESI, m/e) [M+1]$^+$ 834.8; The slower is Example B19b: MS (ESI, m/e) [M+1]$^+$ 834.8.

Example B20a and Example B20b: (R or S) 2-((1H-pyrrolo[2,3-b]pyridin-5-yl)oxy)-4-(3-(((R)-2-(2-cyclopropylphenyl)pyrrolidin-1-yl)methyl)piperidin-1-yl)-N-((3-nitro-4-((((tetrahydro-2H-pyran-4-yl)methyl)amino)phenyl)sulfonyl)benzamide/(S or R) 2-((1H-pyrrolo[2,3-b]pyridin-5-yl)oxy)-4-(3-(((R)-2-(2-cyclopropylphenyl)pyrrolidin-1-yl)methyl)piperidin-1-yl)-N-((3-nitro-4-((((tetrahydro-2H-pyran-4-yl)methyl)amino)phenyl)sulfonyl)benzamide

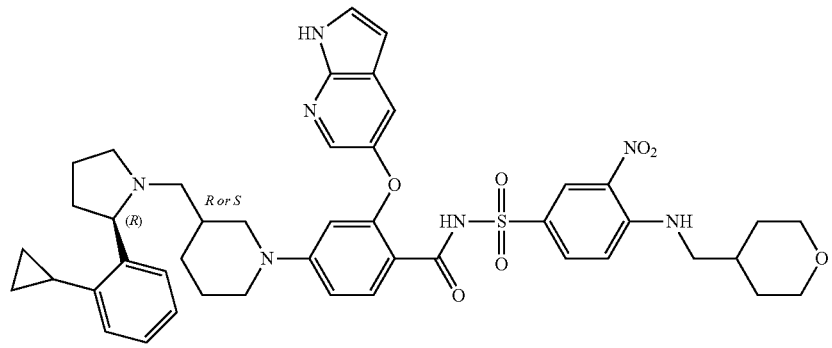

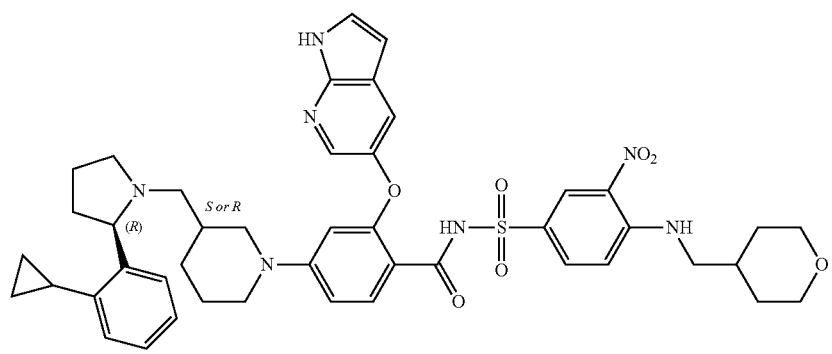

The desired compound was synthesized following the procedures similar to those in Example B12. The faster in column chromatograph on silica gel is Example B20a: MS (ESI, m/e) [M+1]$^+$ 834.8; The slower is Example B20b: MS (ESI, m/e) [M+1]$^+$ 834.8.

Example B21: (S)-3-((1H-pyrrolo[2,3-b]pyridin-5-yl)oxy)-4'-((2-(3-cyclopropylphenyl)pyrrolidin-1-yl)methyl)-N-((3-nitro-4-(((tetrahydro-2H-pyran-4-yl)methyl)amino)phenyl)sulfonyl)-[1,1'-biphenyl]-4-carboxamide

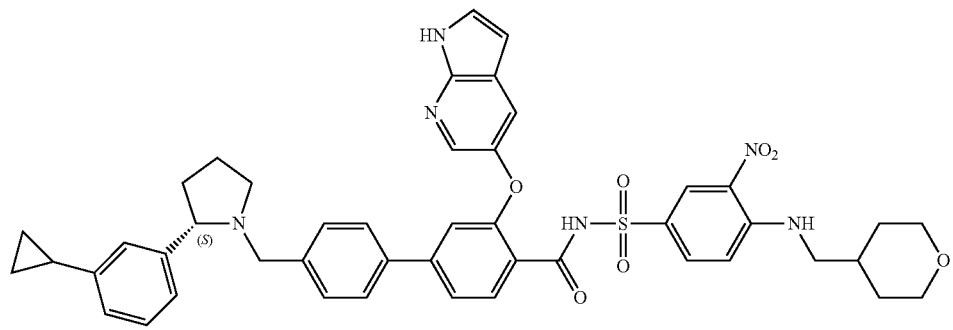

The desired compound was synthesized starting from (S)-2-(3 cyclopropylphenyl)pyrrolidine and 1-(bromomethyl)-4-chlorobenzene following the procedures similar to those in Example B1. $^1$H NMR (DMSO-d$_6$) δ ppm: 12.37 (br, 1H), 11.71 (s, 1H), 8.55 (s, 2H), 8.06 (s, 1H), 7.83 (d, J=8.8 Hz, 1H), 7.65-7.56 (m, 2H), 7.52-7.39 (m, 4H), 7.31-7.26 (m, 2H), 7.20-7.15 (m, 2H), 7.12-7.03 (m, 2H), 6.98 (s, 1H), 6.95-6.89 (m, 1H), 6.39 (s, 1H), 3.85 (d, J=8.4 Hz, 2H), 3.79-3.55 (m, 1H), 3.31-2.90 (m, 8H), 2.29-1.70 (m, 6H), 1.62 (d, J=12.4 Hz, 2H), 1.31-1.26 (m, 2H), 0.93-0.81 (m, 2H), 0.66-0.55 (m, 2H). MS (ESI, m/e) [M+1]$^+$ 826.9.

Example B22: (R)-3-((1H-pyrrolo[2,3-b]pyridin-5-yl)oxy)-4'-((2-(3-cyclopropylphenyl)pyrrolidin-1-yl)methyl)-N-((3-nitro-4-(((tetrahydro-2H-pyran-4-yl)methy 1)amino)phenyl)sulfonyl)-[1,1'-biphenyl]-4-carboxamide

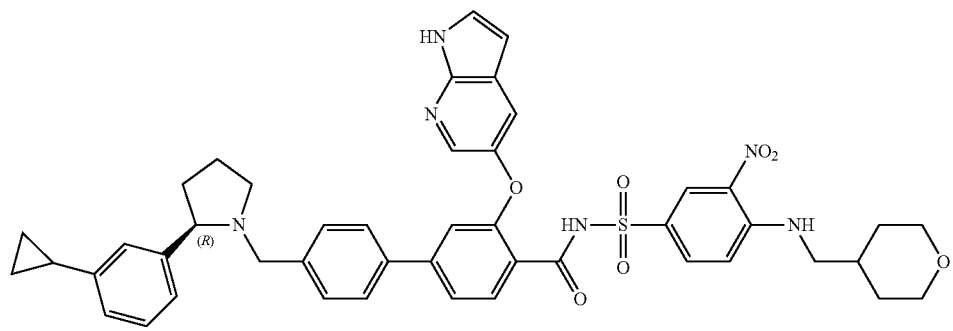

The desired compound was synthesized starting from (R)-2-(3-cyclopropylphenyl)pyrrolidine and 1-bromo-4-(bromomethyl)benzene following the procedures similar to those in Example B1. $^1$H NMR (400 MHz, DMSO-d$_6$) δ ppm: 12.36 (br, 1H), 11.70 (s, 1H), 8.54 (s, 2H), 8.06 (s, 1H), 7.82 (d, J=8.8 Hz, 1H), 7.65-7.56 (m, 2H), 7.52-7.39 (m, 4H), 7.31-7.26 (m, 2H), 7.20-7.15 (m, 2H), 7.12-7.03 (m, 2H), 6.98 (s, 1H), 6.95-6.89 (m, 1H), 6.39 (s, 1H), 3.85 (d, J=8.4 Hz, 2H), 3.79-3.55 (m, 1H), 3.31-2.90 (m, 8H), 2.29-1.70 (m, 6H), 1.62 (d, J=12.4 Hz, 2H), 1.31-1.26 (m, 2H), 0.93-0.81 (m, 2H), 0.66-0.55 (m, 2H). MS (ESI, m/e) [M+1]$^+$ 826.9.

Example B23: 3-((1H-pyrrolo[2,3-b]pyridin-5-yl)oxy)-4'-(2-(2-(2-cyclopropylphenyl)pyrrolidin-1-yl)propan-2-yl)-N-((3-nitro-4-(((tetrahydro-2H-pyran-4-yl)methyl)amino)phenyl)sulfonyl)-[1,1'-biphenyl]-4-carboxamide

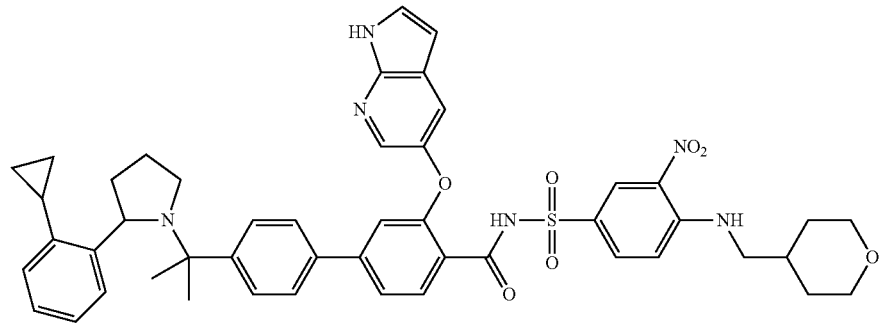 [SMILES: CC(C)(c1ccc(-c2ccc(C(=O)NS(=O)(=O)c3ccc(NCC4CCOCC4)c([N+](=O)[O-])c3)c(Oc3cnc4[nH]ccc4c3)c2)cc1)N1CCCC1c1ccccc1C1CC1]

The desired compound was synthesized starting from 1-(2-(4-bromophenyl)propan-2-yl)-2-(2-cyclopropylphenyl)pyrrolidine and tert-butyl 2-((1H-pyrrolo[2,3-b]pyridin-5-yl)oxy)-4-(4,4,5,5-tetramethyl-1,3,2-dioxaborolan-2-yl)benzoate following the procedures similar to those in Example A1. $^1$H NMR (400 MHz, DMSO-d$_6$) δ ppm: 12.36 (s, 1H), 11.78 (s, 1H), 8.92 (s, 1H), 8.62 (d, J=8.4 Hz, 2H), 8.12 (d, J=14.0 Hz, 1H), 7.88 (s, 1H), 7.78 (d, J=15.6 Hz, 1H), 7.72-7.49 (m, 3H), 7.46-7.30 (m, 3H), 7.18-7.07 (m, 3H), 7.05-6.97 (m, 1H), 6.89-6.78 (m, 1H), 6.62 (s, 0.5H), 6.45 (d, J=14.8 Hz, 1H), 6.18 (s, 0.5H), 4.89-4.71 (m, 1H), 3.93-3.65 (m, 3H), 3.32-3.21 (m, 4H), 2.85-2.70 (m, 1H), 2.45-2.30 (m, 1H), 2.23-2.07 (m, 1H), 1.93-1.84 (m, 1H), 1.81-1.69 (m, 3H), 1.60 (d, J=12.0 Hz, 3H), 1.41-1.39 (m, 1H), 1.25 (d, J=12.0 Hz, 3H), 1.05-0.98 (m, 2H), 0.92-0.73 (m, 2H), 0.71-0.60 (m, 1H), 0.42-0.33 (m, 1H), 0.26-0.08 (m, 1H). MS (ESI, m/e) [M+1]$^+$ 854.8

Example B24: 2-((1H-pyrrolo[2,3-b]pyridin-5-yl)oxy)-4-(5-((2-(2-cyclopropylphenyl)pyrrolidin-1-yl)methyl)furan-2-yl)-N-((3-nitro-4-((((tetrahydro-2H-pyran-4-yl)methyl)amino)phenyl)sulfonyl)benzamide

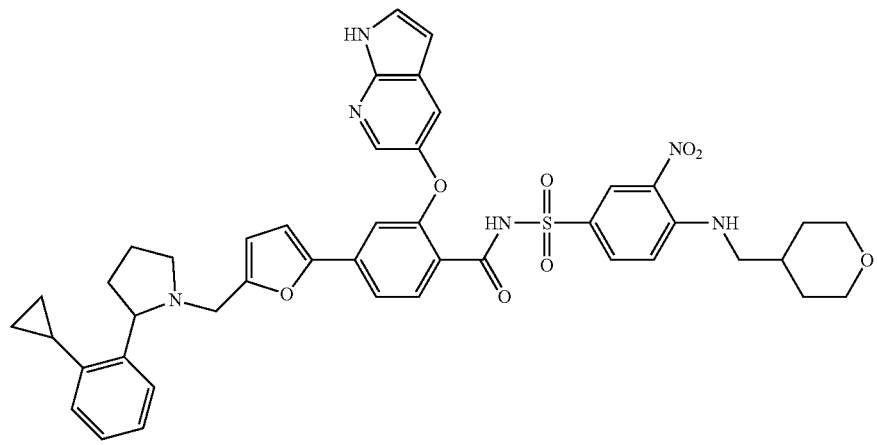 [SMILES: O=C(NS(=O)(=O)c1ccc(NCC2CCOCC2)c([N+](=O)[O-])c1)c1ccc(-c2ccc(CN3CCCC3c3ccccc3C3CC3)o2)cc1Oc1cnc2[nH]ccc2c1]

The desired compound was synthesized following the procedures similar to those in Example B1 by replacing 1-(bromomethyl)-4-chlorobenzene with 1-((5-bromofuran-2-yl)methyl)-2-(2-cyclopropylphenyl)pyrrolidine and replacing 2-phenylpyrrolidine with 2-(2-cyclopropylphenyl) pyrrolidine. MS (ESI, m/e) [M+1]⁺ 816.8

Example B25: 3-((1H-pyrrolo[2,3-b]pyridin-5-yl)oxy)-4'-(3-(2-(2-cyclopropylphenyl)pyrrolidin-1-yl)azetidin-1-yl)-N-((3-nitro-4-(((tetrahydro-2H-pyran-4-yl)methyl)amino)phenyl)sulfonyl)-[1,1'-biphenyl]-4-carboxamide

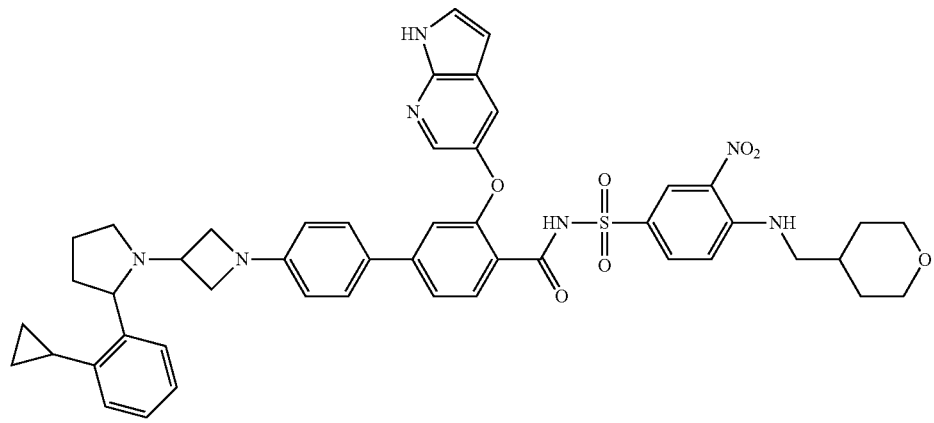 [SMILES: O=C(NS(=O)(=O)c1ccc(NCC2CCOCC2)c([N+](=O)[O-])c1)c1ccc(-c2ccc(N3CC(N4CCCC4c4ccccc4C4CC4)C3)cc2)cc1Oc1cnc2[nH]ccc2c1]

Step 1: tert-butyl 3-(2-(2-cyclopropylphenyl)pyrrolidin-1-yl)azetidine-1-carboxylate A mixture of 2-(2-cyclopropylphenyl)pyrrolidine (300 mg, 1.60 mmol) tert-butyl 3-oxoazetidine-1-carboxylate (820 mg, 4.8 mmol) and NaBH(OAc)₃ (509 mg, 2.4 mmol) in DCM (15 mL) and HOAc (1 drop) was stirred at rt overnight. I was diluted with DCM (30 mL) and washed with brine (30 mL). The organic layer was concentrated. The residue was purified by pre-TLC (eluent: MeOH/DCM=1/30) to give the crude product (234 mg), which was directly used in next step.

Step 2: 1-(azetidin-3-yl)-2-(2-cyclopropylphenyl) pyrrolidine

A solution of tert-butyl 3-(2-(2-cyclopropylphenyl)pyrrolidin-1-yl)azetidine-1-carboxylate (284 mg, 0.83 mmol) in DCM (5 mL) and TFA (2 mL) was stirred at room temperature overnight. The solvents were removed. The residue was dissolved with DCM (50 mL) and washed with aq. NaHCO₃ (30 mL×2), dried over anhydrous Na₂SO₄, filtered and concentrated to give the desired product as a yellow oil (125 mg, 61%). MS (ESI, m/e) [M+1]⁺243.0.

Step 3: 1-(1-(4-bromophenyl)azetidin-3-yl)-2-(2-cyclopropylphenyl)pyrrolidine

A mixture of 1-(azetidin-3-yl)-2-(2-cyclopropylphenyl)pyrrolidine (125 mg, 0.51 mmol), 1-bromo-4-iodobenzene (146 mg, 0.51 mmol), Pd₂(dba)₃ (47 mg, 0.051 mmol), BINAP (63 mg) and t-BuOK (124 mg, 1.02 mmol) in toluene (10 mL) was stirred at 80° C. overnight. It was cooled to room temperature and toluene was removed. The residue was purified by Pre-TLC (eluent: EA/PE=1/5) to give the desired product as a yellow oil (104 mg). MS (ESI, m/e) [M+1]⁺ 396.8

Then 3-((1H-pyrrolo[2,3-b]pyridin-5-yl)oxy)-4'-(3-(2-(2-cyclopropylphenyl)pyrrolidin-1-yl)azetidin-1-yl)-N-((3-nitro-4-(((tetrahydro-2H-pyran-4-yl)methyl)amino)phenyl)sulfonyl)-[1,1'-biphenyl]-4-carboxamide was synthesized following the procedures similar to those in Example A1. ¹H NMR (400 MHz, DMSO-d₆) δ ppm: 12.21 (s, 1H), 11.71 (s, 1H), 8.61-8.56 (m, 2H), 8.05 (s, 1H), 7.82 (d, J=8.0 Hz, 1H), 7.63-7.45 (m, 4H), 7.40-7.26 (m, 3H), 7.12 (s, 3H), 6.95-6.91 (m, 2H), 6.39 (s, 1H), 6.32 (d, J=8.2 Hz, 2H), 4.06 (s, 1H), 3.86-3.83 (m, 2H), 3.71 (s, 1H), 3.62 (s, 2H), 3.30-3.23 (m, 6H), 2.99 (s, 2H), 2.27 (s, 1H), 2.02-1.97 (m, 3H), 1.87 (s, 2H), 1.60 (d, J=11.9 Hz, 2H), 1.45 (s, 1H), 1.26-1.22 (m, 2H), 0.87-0.84 (m, 3H), 0.67 (s, 1H). MS (ESI, m/e) [M+1]⁺ 867.8.

Example B26: 2-((1H-pyrrolo[2,3-b]pyridin-5-yl)oxy)-4-(3-(2-(2-cyclopropylphenyl)pyrrolidin-1-yl)-[1,3'-biazetidin]-1'-yl)-N-((3-nitro-4-(((tetrahydro-2H-pyran-4-yl)methyl)amino)phenyl)sulfonyl)benzamide

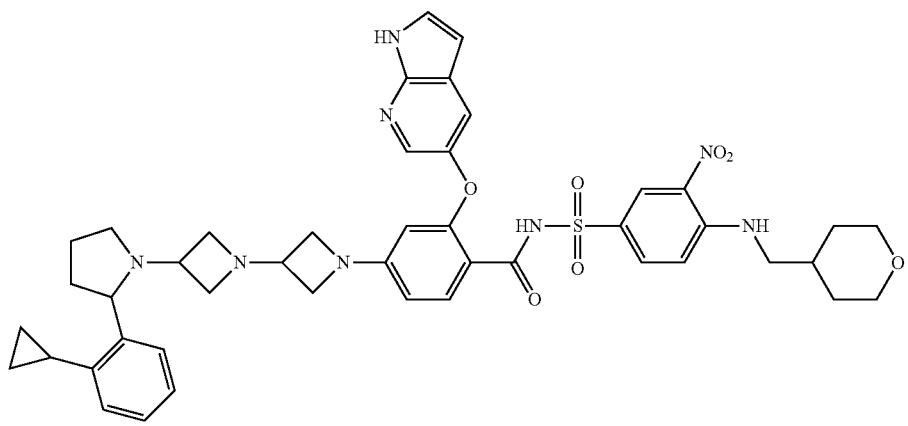 [SMILES: O=C(NS(=O)(=O)c1ccc(NCC2CCOCC2)c([N+](=O)[O-])c1)c1ccc(N2CC(N3CC(N4CCCC4c4ccccc4C4CC4)C3)C2)cc1Oc1cnc2[nH]ccc2c1]

Step 1: tert-butyl 3-(2-(2-cyclopropylphenyl)pyrrolidin-1-yl)azetidine-1-carboxylate To a solution of 2-(2-cyclopropylphenyl)pyrrolidine (375 mg, 2.00 mmol) in DCM (20 mL) was added tert-butyl 3-oxoazetidine-1-carboxylate (342 mg, 2.00 mmol) and NaBH(OAc)$_3$ (848 mg, 4.00 mmol), the mixture was stirred at r.t for 16 hours. The reaction solution was washed with H$_2$O (20 mL), concentrated and purified by column chromatograph on silica gel (eluent: MeOH/DCM=0/20 to 1/20) to give the product as a light yellow oil. (540 mg, 78.9%). MS (ESI, m/e) [M+1]$^+$ 343.0.

Step 2: 1-(azetidin-3-yl)-2-(2-cyclopropylphenyl)pyrrolidine hydrochloride

To a solution of tert-butyl 3-(2-(2-cyclopropylphenyl)pyrrolidin-1-yl)azetidine-1-carboxylate (540 mg, 1.58 mmol) in DCM (5 mL) was added HCl in 1,4-dioxane solution (5 mL, 4 M) was then stirred at r.t for 20 hours. The reaction solution was concentrated to give the crude product as a white solid, (440 mg). MS (ESI, m/e) [M+1]$^+$ 243.0.

Step 3: tert-butyl 3-(2-(2-cyclopropylphenyl)pyrrolidin-1-yl)-[1,3'-biazetidine]-1'-carboxylate To a solution of 1-(azetidin-3-yl)-2-(2-cyclopropylphenyl)pyrrolidine hydrochloride (450 mg, 1.505 mmol) in DCM (20 mL) was added tert-butyl 3-oxoazetidine-1-carboxylate (386 mg, 2.258 mmol) TFA (235 mg, 2.258 mmol) and NaBH(OAc)$_3$ (641 mg, 3.010 mmol) and the mixture was stirred at r.t for 16 hours. The reaction solution was washed with H$_2$O (10 mL), concentrated and purified by column chromatograph on silica gel (eluent: MeOH/DCM=0/20 to 1/20) to give the product as a light yellow oil, (500 mg, 83.2%). MS (ESI, m/e) [M+1]$^+$398.0.

Step 4: 3-(2-(2-cyclopropylphenyl)pyrrolidin-1-yl)-1,3'-biazetidine hydrochloride To a solution of tert-butyl 3-(2-(2-cyclopropylphenyl)pyrrolidin-1-yl)-[1,3'-biazetidine]-1'-carboxylate (500 mg, 1,259 mmol) in DCM (10 mL) was added HCl in 1,4-dioxane solution (10 mL, 4 M) and the solution was stirred at r.t for 4 hours. The reaction solution was concentrated to give the crude product as a brown solid. (500 mg), MS (ESI, m/e) [M+1]$^+$ 298.0.

Then 2-((1H-pyrrolo[2,3-b]pyridin-5-yl)oxy)-4-(3-(2-(2-cyclopropylphenyl)pyrrolidin-1-yl)-[1,3'-biazetidin]-1'-yl)-N-((3-nitro-4-(((tetrahydro-2H-pyran-4-yl)methyl)amino)phenyl)sulfonyl)benzamide was synthesized following the procedures similar to those in Example B12. $^1$H NMR (DMSO-d$_6$) δ ppm: 11.70 (s, 1H), 11.14 (s, 1H), 8.63-8.46 (m, 2H), 8.02 (d, J=2.01 Hz, 1H), 7.80 (d, J=9.2 Hz, 1H), 7.59-7.33 (m, 4H), 7.14-6.97 (m, 3H), 6.86 (s, 1H), 6.37 (s, 1H), 6.08 (d, J=8.8 Hz, 1H), 5.53 (s, 1H), 4.03-3.63 (m, 5H), 3.58-3.37 (m, 4H), 3.27-2.65 (m, 9H), 2.25-2.09 (m, 1H), 2.06-1.94 (m, 1H), 1.90-1.68 (m, 3H), 1.63-1.42 (m, 3H), 1.29-1.14 (m, 3H), 0.90-0.76 (m, 2H), 0.63-0.55 (m, 1H), 0.50-0.40 (m, 1H). MS (ESI, m/e) [M+1]$^+$ 846.9.

Example B27: (S)-2-((1H-pyrrolo[2,3-b]pyridin-5-yl)oxy)-4-(4-(3-(2-(2-cyclopropylphenyl)pyrrolidin-1-yl)cyclobutyl)piperidin-1-yl)-N-((3-nitro-4-(((tetrahydro-2H-pyran-4-yl)methyl)amino)phenyl)sulfonyl)benzamide

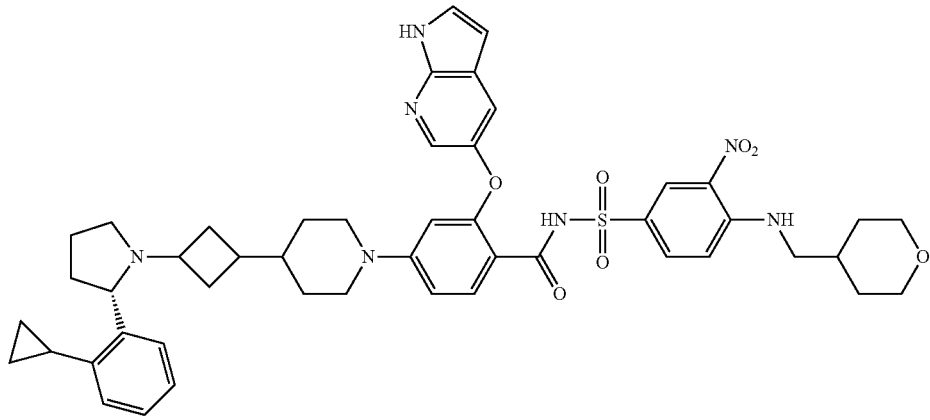 [SMILES: O=C(NS(=O)(=O)c1ccc(NCC2CCOCC2)c([N+](=O)[O-])c1)c1ccc(N2CCC(C3CC(N4CCC[C@H]4c4ccccc4C4CC4)C3)CC2)cc1Oc1cnc2[nH]ccc2c1]

Step 1: methyl (S)-2-((1H-pyrrolo[2,3-b]pyridin-5-yl)oxy)-4-(4-(3-(2-(2-cyclopropylphenyl)pyrrolidin-1-yl)cyclobutyl)piperidinl-yl)benzoate To a solution of (S)-4-(3-(2-(2-cyclopropylphenyl)pyrrolidin-1-yl)cyclobutyl)piperidine (100 mg, 0.3 mmol), methyl 2-((1H-pyrrolo[2,3-b]pyridin-5-yl)oxy)-4-fluorobenzoate (88 mg, 0.3 mmol) in DMF (10 mL) was added Na$_2$CO$_3$ (318 mg, 3 mmol). The mixture was stirred at 100° C. for 18 hours. After the solvent was removed in vacuum, the residue was diluted with DCM (50 mL)/H$_2$O (50 mL) and then stirred for 30 minutes. The organic phase was separated and washed with saturated aq. NaCl (10 mL), H$_2$O (10 mL) and dried over anhydrous Na$_2$SO$_4$, concentrated to give a crude product. The crude was purified by pre-TLC (eluent: PE/EA=3/1) to obtain 120 mg methyl (S)-2-((1H-pyrrolo[2,3-b]pyridin-5-yl)oxy)-4-(4-(3-(2-(2-cyclopropylphenyl)pyrrolidin-1-yl)cyclobutyl)piperidin-1-yl)benzoate. MS (ESI, m/e) [M+1]$^+$ 591.0.

Step 2: (S)-2-((1H-pyrrolo[2,3-b]pyridin-5-yl)oxy)-4-(4-(3-(2-(2-cyclopropylphenyl)pyrrolidin-1-yl)cyclobutyl)piperidin-1-yl)benzoic acid To a mixture of methyl (S)-2-((1H-pyrrolo[2,3-b]pyridin-5-yl)oxy)-4-(4-(3-(2-(2-cyclopropylphenyl)pyrrolidin-1-yl)cyclobutyl)piperidin-1-yl)benzoate (120 mg, 0.2 mmol) in MeOH (5 mL), THF (5 mL), H$_2$O (5 mL) was added NaOH (80 mg, 2 mmol). The mixture was stirred at 50° C. for 14 hours. The mixture was adjusted to PH ~3 with 2N HCl acid and then extracted with DCM (30 ml. 2). The combined the organic phase was washed with saturated aq. NaCl (10 ml). H$_2$O (10 mL) and concentrated to obtain 100 mg (S)-2-((1H-pyrrolo[2,3-b]pyridin-5-yl)oxy)-4-(4-(3-(2-(2-cyclopropylphenyl)pyrrolidin-1-yl)cyclobutyl)piperidin-1-yl) benzoic acid, which used in next step without further purification. MS (ESI, m/e) [M+1]$^+$577.0.

The desired compound was then synthesized following the procedures similar to those in Example B12. $^1$H NMR (400 MHz, DMSO-d$_6$) δ ppm: 11.70 (s, 1H), 11.41 (s, 1H), 9.52 (s, 1H), 8.62 (s, 2H), 8.57 (s, 1H), 8.04 (s, 1H), 7.81 (d, J=9.0 Hz, 1H), 7.61-7.46 (m, 3H) 7.30 (s, 2H), 7.16-7.03 (m, 2H), 6.67 (d, J=9.0 Hz, 1H), 6.39 (s, 1H), 6.15 (s, 1H), 5.02-5.00 (m, 1H), 3.87-3.84 (m, 2H), 3.72-3.52 (m, 4H), 3.35-3.18 (m, 5H), 2.68-2.55 (m, 5H), 2.21-1.98 (m, 6H), 1.93-1.77 (m, 2H), 1.63-1.60 (m, 0.3H), 1.45 (s, 1H), 1.31-1.22 (m, 9H), 0.98-0.95 (m, 2H), 0.85-0.83 (m, 2H), 0.67-0.65 (m, 2H). MS (ESI) m/e [M+1]$^+$ 873.9.

Example B28: (R)-2-((1H-pyrrolo[2,3-b]pyridin-5-yl)oxy)-4-(4-(2-(2-cyclopropylphenyl)pyrrolidin-1-yl)benzyl)-N-((3-nitro-4-(((tetrahydro-2H-pyran-4-yl)methyl)amino)phenyl)sulfonyl)benzamide

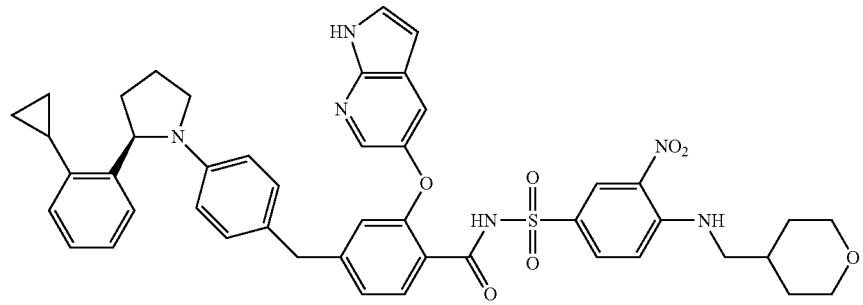 [SMILES: O=C(NS(=O)(=O)c1ccc(NCC2CCOCC2)c([N+](=O)[O-])c1)c1ccc(Cc2ccc(N3CCC[C@@H]3c3ccccc3C3CC3)cc2)cc1Oc1cnc2[nH]ccc2c1]

Step 1: (R)-4-(2-(2-cyclopropylphenyl)pyrrolidin-1-yl)benzaldehyde

To a mixture solution of (R)-1-(4-bromophenyl)-2-(2-cyclopropylphenyl)pyrrolidine (500 mg, 1.50 mmol) in THF (TO mL) was added n-BuLi (1.6 N, 1.2 mL, 1.80 mmol) at −70° C.~−75° C. under N₂. After the mixture was stirred for 30 mins, DMF (219 mg, 3.0 mmol) was added at −70° C.~−75° C. under N₂. Then the mixture was allowed to warm to room temperature and stirred for 2 hours. The reaction was quenched with diluted HCl acid (IN, 5 mL) and extracted with EA (5 mL×3). The combined organic layers were dried over anhydrous Na₂SO₄, concentrated and then purified with column chromatograph on silica gel (eluent: EA/PE=1/1) to afford 200 mg of (R)-4-(2-(2-cyclopropylphenyl)pyrrolidin-1-yl)benzaldehyde, MS (ESI, m/e) [M+1]⁺ 291.9.

Step 2: methyl (R)-2-((1H-pyrrolo[2,3-b]pyridin-5-yl)oxy)-4-(4-(2-(2-cyclopropyl phenyl)pyrrolidin-1-yl)benzyl)benzoate A mixture of (R)-4-(2-(2-cyclopropylphenyl)pyrrolidin-1-yl)benzaldehyde (200 mg, 1.05 mmol), 4-methylbenzenesulfonohydrazide (195 mg, 1.05 mmol) in dioxane (10 mL) was heated to 100° C. and stirred for 2 hours. Then (3-((1H-pyrrolo[2,3-b]pyridin-5-yl)oxy)-4-(methoxycarbonyl)phenyl)boronic acid (326 mg, 1.05 mmol) and K₂CO₃ (290 mg, 2.10 mmol) were added to the mixture and stirred for another 5 hours. After cooled to room temperature, the reaction mixture was quenched with H₂O (20 mL) and extracted with EA (10 mL×3). The combined organic layers were dried over anhydrous Na₂SO₄, concentrated and then purified with column chromatograph on silica gel (eluent: EA/PE=1/1) to afford 280 mg (yield: 49.2%) of methyl (R)-2-((1H-pyrrolo[2,3-b]pyridin-5-yl)oxy)-4-(4-(2-(2-cyclopropylphenyl)pyrrolidin-1-yl)benzyl)benzoate as a yellow solid. MS (ESI, m/e) [M+1]⁺543.9.

The desired compound was then synthesized from methyl (R)-2-((1H-pyrrolo[2,3-b]pyridin-5-yl)oxy)-4-(4-(2-(2-cyclopropyl phenyl)pyrrolidin-1-yl)benzyl)benzoate following the procedures similar to those in Example B1. MS (ESI, m/e) [M+1]⁺ 827.1.

Example B29: 2-((1H-pyrrolo[2,3-b]pyridin-5-yl)oxy)-4-((4-(2-(2-cyclopropylphenyl)pyrrolidin-1-yl)cyclohexyl)methyl)-N-((3-nitro-4-(((tetrahydro-2H-pyran-4-yl)methyl)amino)phenyl)sulfonyl)benzamide

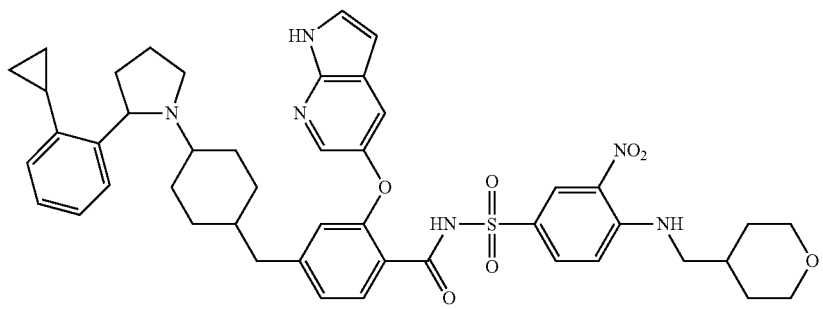 [SMILES: O=C(NS(=O)(=O)c1ccc(NCC2CCOCC2)c([N+](=O)[O-])c1)c1ccc(CC2CCC(N3CCCC3c3ccccc3C3CC3)CC2)cc1Oc1cnc2[nH]ccc2c1]

The desired compound was synthesized with 4-(2-(2-cyclopropylphenyl)pyrrolidin-1-yl)cyclohexane-1-carbaldehyde following the procedures similar to those in Example B28. $^1$H NMR (400 MHz, DMSO-$d_6$) δ ppm: 12.14 (s, 1H), 11.70 (s, 1H), 9.50 (s, 1H), 8.59-8.56 (m, 2H), 7.99 (s, 1H), 7.85-7.71 (m, 2H), 7.48-7.44 (m, 3H), 7.30-7.28 (m, 2H), 7.09 (s, 2H), 6.90-6.86 (m, 1H), 6.53 (d, J=11.8 Hz, 1H), 6.39 (d, J=11.8 Hz, 1H), 5.12-5.09 (m, 1H), 3.85-3.83 (m, 2H), 3.61 (s, 1H), 3.24-3.17 (m, 2H), 2.94 (s, 1H), 2.33-2.30 (m, 2H), 2.06-2.02 (m, 4H), 1.87-1.84 (m, 4H), 1.56-1.53 (m, 5H), 1.29 (s, 5H), 0.96-0.90 (m, 2H), 0.83-0.80 (m, 3H), 0.55-0.52 (m, 1H). MS (ESI) m/e [M+1]$^+$ 832.9

Example B30: 2-((1H-pyrrolo[2,3-b]pyridin-5-yl)oxy)-4-(4-((2-(2-cyclopropylphenyl)pyrrolidin-1-yl)methyl)benzyl)-N-((3-nitro-4-(((tetrahydro-2H-pyran-4-yl)methyl)amino)phenyl)sulfonyl)benzamide

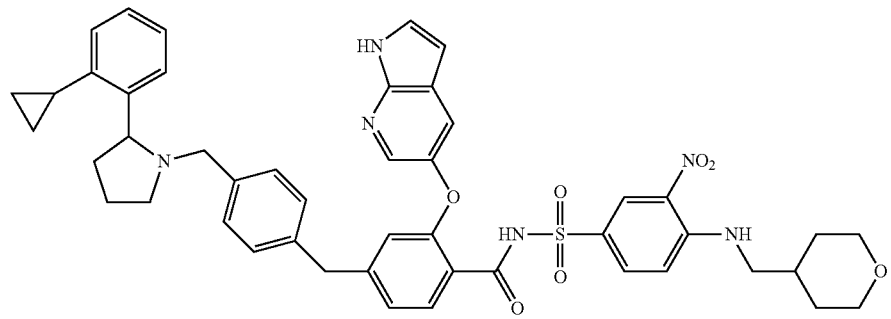 [SMILES: O=C(NS(=O)(=O)c1ccc(NCC2CCOCC2)c([N+](=O)[O-])c1)c1ccc(Cc2ccc(CN3CCCC3c3ccccc3C3CC3)cc2)cc1Oc1cnc2[nH]ccc2c1]

The desired compound was synthesized with 4-((2-(2-cyclopropylphenyl)pyrrolidin-1-yl)methyl)benzaldehyde following the procedures similar to those in Example B28. MS (ESI) m/e [M+1]$^+$ 832.9

Example B31: (S)-2-((1H-pyrrolo[2,3-b]pyridin-5-yl)oxy)-4-((4-(2-(2-cyclopropylphenyl)pyrrolidin-1-yl)phenyl)amino)-N-((3-nitro-4-(((tetrahydro-2H-pyran-4-yl)methyl)amino)phenyl)sulfonyl)benzamide

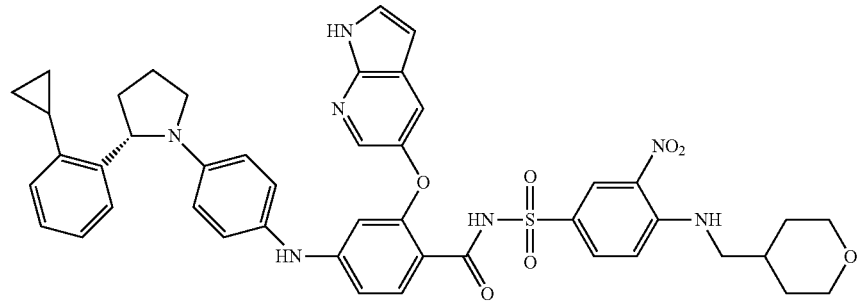 [SMILES: O=C(NS(=O)(=O)c1ccc(NCC2CCOCC2)c([N+](=O)[O-])c1)c1ccc(Nc2ccc(N3CCC[C@H]3c3ccccc3C3CC3)cc2)cc1Oc1cnc2[nH]ccc2c1]

To a solution of (S)-2-((1H-pyrrolo[2,3-b]pyridin-5-yl)oxy)-4-((4-(2-(2-cyclopropylphenyl)pyrrolidin-1-yl)phenyl)amino)benzoic acid (200 mg, 0.38 mmol) in 30 mL dichloromethane was added 2-(7-Azabenzotriazol-1-yl)-N,N,N',N'-tetramethyluronium hexafluorophosphate (160 mg, 0.42 mmol) and 0.3 mL N,N-diisopropyl ethyl amine. It was stirred at room temperature for 1 hour, then 3-nitro-4-(((tetrahydro-2H-pyran-4-yl)methyl)amino)benzenesulfonamide (132 mg, 0.42 mmol) and 4-dimethyl aminopyridine (40 mg, 0.35 mmol) was added. And the mixture was stirred at room temperature for 16 h. Then organic layer was combined, dried over sodium sulfate and it was concentrated in vacuum. The residue was purified by prep-HPLC to give 20 mg the desired compound. $^1$H NMR (400 MHZ, DMSO-$d_6$) δ ppm: 11.77 (s, 1H), 11.18 (s, 1H), 8.69-8.54 (m, 2H), 8.29-8.18 (m, 1H), 8.10 (s, 1H), 7.94-7.86 (m, 1H), 7.77-

7.69 (m, 1H), 7.54 (s, 1H), 7.46-7.40 (m, 1H), 7.25-7.17 (m, 1H), 7.14-7.07 (m, 1H), 7.05-6.98 (m, 2H), 6.93-6.87 (m, 1H), 6.82-6.77 (m, 2H), 6.47-6.37 (m, 2H), 6.28-6.21 (m, 2H), 5.99 (s, 1H), 5.10-5.05 (m, 1H), 3.90-3.80 (m, 2H), 3.71-3.60 (m, 1H), 3.32-3.20 (m, 5H), 2.46-2.35 (m, 1H), 2.10-2.00 (m, 1H), 2.00-1.85 (m, 3H), 1.84-1.77 (m, 1H), 1.66-1.57 (m, 2H), 1.30-1.25 (m, 1H), 1.05-0.93 (m, 3H), 0.76-0.64 (m, 2H). MS (ESI, m/e) [M+1]$^+$ 827.8.

Example B32: 2-((1H-pyrrolo[2,3-b]pyridin-5-yl)oxy)-4-(1-(2-cyclopropylphenyl)-1,8-diazaspiro[4.5]decan-8-yl)-N-((3-nitro-4-(((tetrahydro-2H-pyran-4-yl)methyl)amino)phenyl)sulfonyl)benzamide

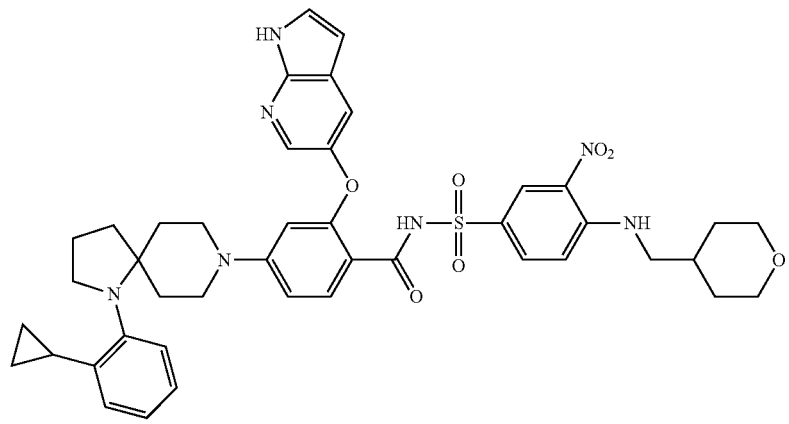 [SMILES: O=C(NS(=O)(=O)c1ccc(NCC2CCOCC2)c([N+](=O)[O-])c1)c1ccc(N2CCC3(CCCN3c3ccccc3C3CC3)CC2)cc1Oc1cnc2[nH]ccc2c1]

The desired compound was synthesized following the procedures similar to those in Example B12 by replacing 1-(azetidin-3-ylmethyl)-2-(2-cyclopropylphenyl)pyrrolidine with 1-(2-cyclopropylphenyl)-1,8-diazaspiro[4.5]decane. $^1$H NMR (400 MHz, DMSO-d$_6$) δ ppm: 11.70 (s, 1H), 11.40 (s, 1H), 8.63-8.58 (m, 2H), 8.02 (s, 1H), 7.79 (d, J=8.9 Hz, 1H), 7.55-7.38 (m, 3H), 7.20-7.07 (m, 2H), 7.06-6.94 (m, 2H), 6.66-6.63 (m, 2H), 6.38 (s, 1H), 6.13 (s, 1H), 3.86-3.84 (m, 2H), 3.60-3.57 (m, 2H), 3.31-3.17 (m, 6H), 2.74-2.72 (m, 2H), 1.88 (s, 5H), 1.59-1.55 (m, 4H), 1.30-1.28 (m, 5H), 0.85-0.83 (m, 2H), 0.54-0.52 (m, 2H). MS (ESI) m/e [M+1]$^+$ 805.8.

Example B33: 3-((1H-pyrrolo[2,3-b]pyridin-5-yl)oxy)-4'-(1-(2-cyclopropylphenyl)-1,8-diazaspiro[4.5]decan-8-yl)-N-((4-((((1r,4r)-4-hydroxy-4-methylcyclohexyl)methyl)amino)-3-nitrophenyl)sulfonyl)-[1,1'-biphenyl]-4-carboxamide

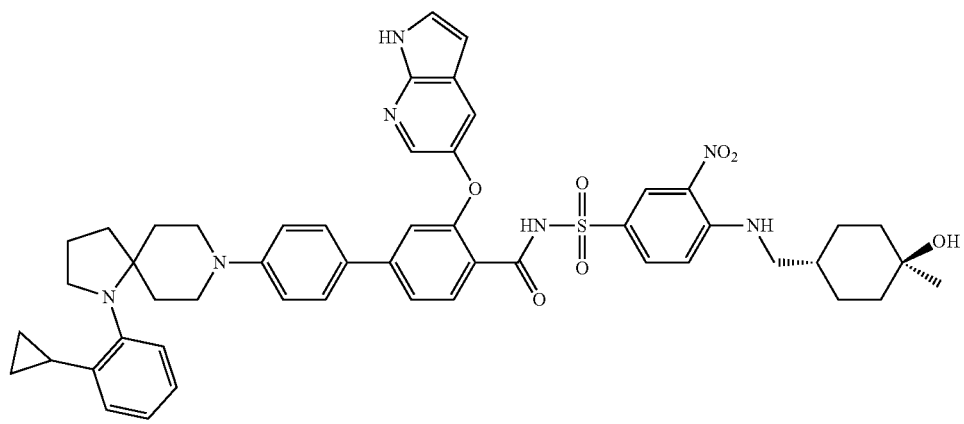 [SMILES: C[C@]1(O)CC[C@H](CNc2ccc(S(=O)(=O)NC(=O)c3ccc(-c4ccc(N5CCC6(CCCN6c6ccccc6C6CC6)CC5)cc4)cc3Oc3cnc4[nH]ccc4c3)cc2[N+](=O)[O-])CC1]

The desired compound was synthesized with 3-((1H-pyrrolo[2,3-b]pyridin-5-yl)oxy)-4'-(1-(2-cyclopropylphenyl)-1,8-diazaspiro[4.5]decan-8-yl)-[1,1'-biphenyl]-4-carboxylic acid and 4-(((((1r,4r)-4-hydroxy-4-methylcyclohexyl)methyl)amino)-3-nitrobenzenesulfonamide following the procedures similar to those in Example B32. MS (ESI) m/e [M+1]$^+$ 909.8.

Example B34: 2-((1H-pyrrolo[2,3-b]pyridin-5-yl)oxy)-4-(1-(2-bromophenyl)-1,8-diazaspiro[4.5]decan-8-yl)-N-((3-nitro-4-(((tetrahydro-2H-pyran-4-yl)methyl)amino)phenyl)sulfonyl)benzamide

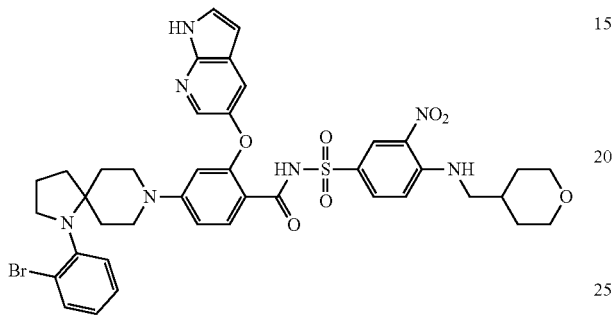

The desired compound was synthesized following the procedures similar to those in Example B12 by replacing 1-(azetidin-3-ylmethyl)-2-(2-cyclopropylphenyl)pyrrolidine with 1-(2-bromophenyl)-1,8-diazaspiro[4.5]decane. MS (ESI) m/e [M+1]$^+$ 843.7.

Example B35: 2-((1H-pyrrolo[2,3-b]pyridin-5-yl)oxy)-4-(6-((S)-2-(2-cyclopropylphenyl)pyrrolidin-1-yl)-5,6,7,8-tetrahydronaphthalen-2-yl)-N-((4-(((((1r,4r)-4-hydroxy-4-methylcyclohexyl)methyl)amino)-3-nitrophenyl)sulfonyl)benzamide

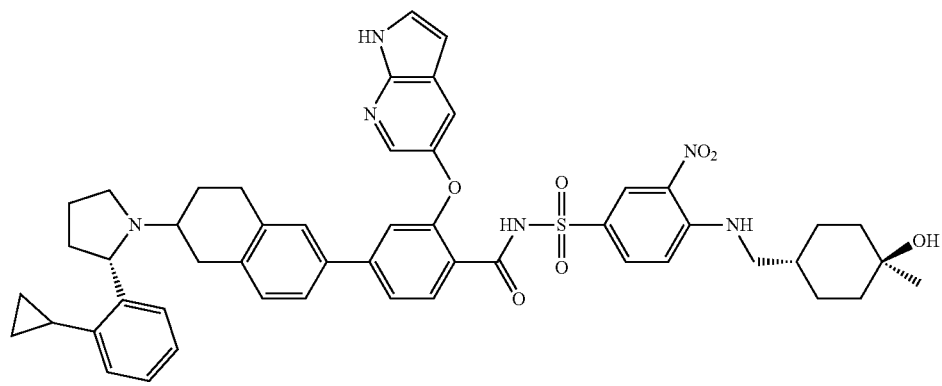 [SMILES: C[C@]1(O)CC[C@H](CNc2ccc(S(=O)(=O)NC(=O)c3ccc(-c4ccc5c(c4)CCC(N4CCC[C@H]4c4ccccc4C4CC4)C5)cc3Oc3cnc4[nH]ccc4c3)cc2[N+](=O)[O-])CC1]

The desired compound was synthesized following the procedures similar to those in Example A1 by replacing 1-(4-bromophenyl)-2-phenylpyrrolidine with (2S)-1-(6-bromo-1,2,3,4-tetrahydronaphthalen-2-yl)-2-(2-cyclopropylphenyl)pyrrolidine. $^1$H NMR (DMSO-d$_6$) δ ppm: 12.32 (s, 1H), 11.62 (s, 1H), 9.56-9.36 (m, 1H), 8.48-8.45 (m, 2H), 8.01 (s, 1H), 7.73 (s, 1H), 7.60-7.58 (m, 1H), 7.46 (s, 2H), 7.35 (d, J=7.8 Hz, 1H), 7.20 (s, 2H), 7.09-7.07 (m, 1H), 6.99-6.96 (m, 3H), 6.34 (s, 1H), 4.40 (s, 1H), 4.23 (s, 1H), 3.62 (d, J=4.4 Hz, 1H), 3.26-3.20 (m, 3H), 2.86 (s, 1H), 2.67 (s, 3H), 2.06-1.93 (m, 2H), 1.77 (s, 1H), 1.69-1.67 (m, 3H), 1.56-1.50 (m, 3H), 1.30-1.20 (m, 9H), 1.15-1.08 (m, 5H), 0.98-0.84 (m, 2H), 0.70 (s, 1H), 0.52 (s, 1H). MS (ESI) m/e [M+1]$^+$ 894.8

Example B36: 2-((1H-pyrrolo[2,3-b]pyridin-5-yl)oxy)-4-(2-(2-(2-cyclopropylphenyl)pyrrolidin-1-yl)-1H-benzo[d]imidazol-5-yl)-N-((3-nitro-4-(((tetrahydro-2H-pyran-4-yl)methyl)amino)phenyl)sulfonyl)benzamide

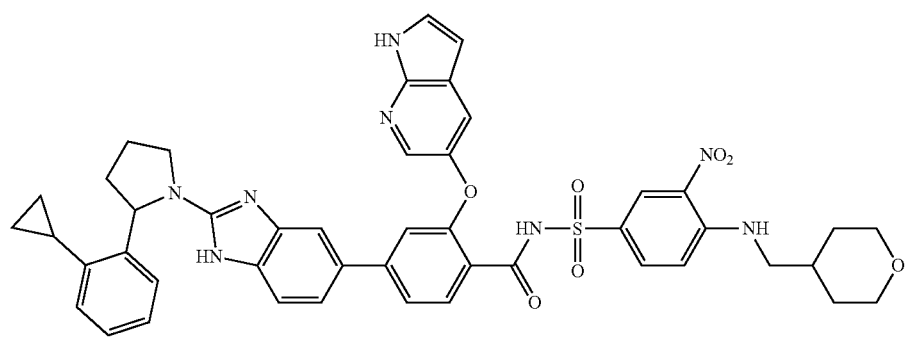 [SMILES: O=C(NS(=O)(=O)c1ccc(NCC2CCOCC2)c([N+](=O)[O-])c1)c1ccc(-c2ccc3[nH]c(N4CCCC4c4ccccc4C4CC4)nc3c2)cc1Oc1cnc2[nH]ccc2c1]

The desired compound was synthesized following the procedures similar to those in Example A1 by replacing 1-(4-bromophenyl)-2-phenylpyrrolidine with 5-bromo-2-(2-(2-cyclopropylphenyl)pyrrolidin-1-yl)-1H-benzo[d]imidazole. MS (ESI) m/e [M+1]$^+$ 852.8

Example B37: 3-((1H-pyrrolo[2,3-b]pyridin-5-yl)oxy)-4'-(1-(2-(2-cyclopropylphenyl)pyrrolidin-1-yl)ethyl)-N-((3-nitro-4-(((tetrahydro-2H-pyran-4-yl)methyl)amino)phenyl)sulfonyl)-[1,1'-biphenyl]-4-carboxamide

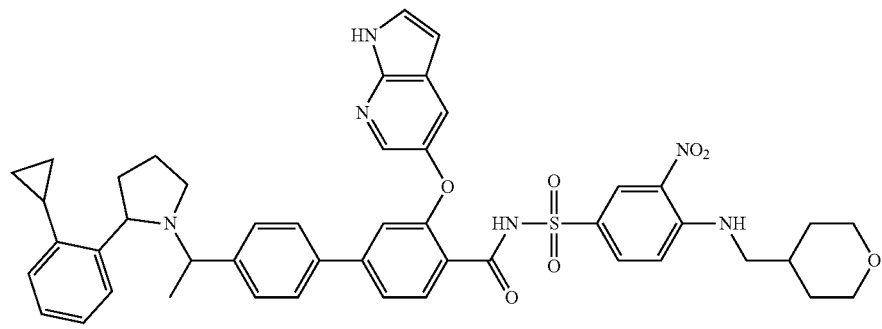 [SMILES: CC(c1ccc(-c2ccc(C(=O)NS(=O)(=O)c3ccc(NCC4CCOCC4)c([N+](=O)[O-])c3)c(Oc3cnc4[nH]ccc4c3)c2)cc1)N1CCCC1c1ccccc1C1CC1]

The desired compound was synthesized starting from 1-(1-(4-bromophenyl)ethyl)-2-(2-cyclopropylphenyl)pyrrolidine and tert-butyl 2-((1H-pyrrolo[2,3-b]pyridin-5-yl)oxy)-4-(4,4,5,5-tetramethyl-1,3,2-dioxaborolan-2-yl)benzoate following the procedures similar to those in Example A1. MS (ESI) m/e [M+1]+ 840.8.

Example B38: (S)-2-((1H-pyrrolo[2,3-b]pyridin-5-yl)oxy)-4-(1-(3-(2-(2-cyclopropylphenyl)pyrrolidin-1-yl)cyclobutyl)-1H-pyrazol-4-yl)-N-((3-nitro-4-(((tetrahydro-2H-pyran-4-yl)methyl)amino)phenyl)sulfonyl)benzamide

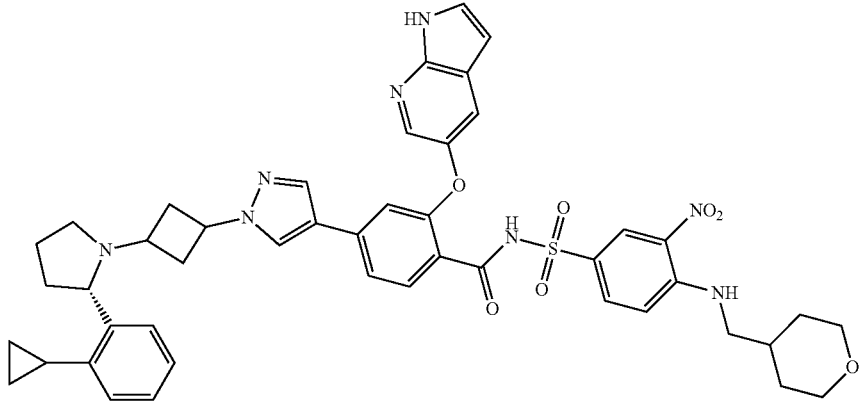 [SMILES: O=C(NS(=O)(=O)c1ccc(NCC2CCOCC2)c([N+](=O)[O-])c1)c1ccc(-c2cnn(C3CC(N4CCC[C@H]4c4ccccc4C4CC4)C3)c2)cc1Oc1cnc2[nH]ccc2c1]

Step 1: tert-butyl (S)-2-((1H-pyrrolo[2,3-b]pyridin-5-yl)oxy)-4-(1-(3-(2-(2-cyclopropylphenyl)pyrrolidin-1-yl)cyclobutyl)-1H-pyrazol-4-yl)benzoate The mixture of (S)-1-(3-(2-(2-cyclopropylphenyl)pyrrolidin-1-yl)cyclobutyl)-4-(4,4,5,5-tetramethyl-1,3,2-dioxaborolan-2-yl)-1H-pyrazole (520 mg, 1.2 mmol), tert-butyl 2-((1H-pyrrolo[2,3-b]pyridin-5-yl)oxy)-4-bromobenzoate (389 mg, 1.0 mmol), Pd(dppf)$_2$Cl$_2$ (146 mg, 0.2 mmol), Cs$_2$CO$_3$ (975 mg, 3 mmol) in a 1,4-dioxane (40 mL) and water (5 mL) was heated to 100° C. and stirred for overnight. The reaction was concentrated in vacuo and purified by chromatography column on silica gel (eluent: EA/PE=1/10 to 1/2) to give the target product (412 mg). MS (ESI, m/e) [M+1]+ 615.9.

The desired compound was synthesized starting from tert-butyl (S)-2-((1H-pyrrolo[2,3-b]pyridin-5-yl)oxy)-4-(1-(3-(2-(2-cyclopropylphenyl)pyrrolidin-1-yl)cyclobutyl)-1H-pyrazol-4-yl)benzoate following the procedures similar to those in Example A1. $^1$H NMR (400 MHz, DMSO-d$_6$) δ ppm: 12.20 (br, 1H), 11.63 (s, 1H), 8.60-8.45 (m, 2H), 8.14 (s, 1H), 8.00 (d, J=2.4 Hz, 1H), 8.85 (s, 1H), 7.74 (d, J=9.2 Hz, 1H), 7.65-7.58 (m, 1H), 7.56 (d, J=8.0 Hz, 1H), 7.47 (t, J=2.8 Hz, 1H), 7.43-7.41 (m, 1H), 7.37 (d, J=8.0 Hz, 1H), 7.22-7.10 (m, 2H), 7.04 (s, 1H), 7.00-6.95 (m, 2H), 6.35-6.32 (m, 1H), 4.43-4.40 (m, 1H), 3.86 (dd, J=11.6 Hz, J=3.2 Hz, 2H), 3.30-3.25 (m, 5H), 2.67-2.59 (m, 1H), 2.44-2.25 (m, 2H), 2.20-1.80 (m, 7H), 1.62 (d, J=11.2 Hz, 2H), 1.30-1.20 (m, 4H), 0.92-0.80 (m, 3H), 0.66-0.52 (m, 2H). MS (ESI, m/e) [M+1]+ 856.8.

Example B39: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(3-phenyl-6,7-dihydrothieno[3,2-c]pyridin-5(4H)-yl)-[1,1'-biphenyl]-4-carboxamide

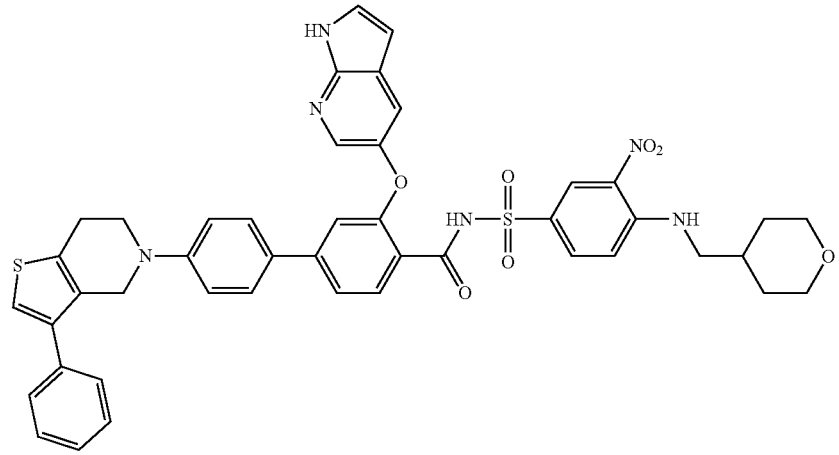 [SMILES: O=C(NS(=O)(=O)c1ccc(NCC2CCOCC2)c([N+](=O)[O-])c1)c1ccc(-c2ccc(N3CCc4scc(-c5ccccc5)c4C3)cc2)cc1Oc1cnc2[nH]ccc2c1]

The desired compound was synthesized following the procedures similar to those in Example A1 by replacing 1-(4-bromophenyl)-2-phenylpyrrolidine with 5-(4-bromophenyl)-3-phenyl-4,5,6,7-tetrahydrothieno[3,2-c]pyridine. MS (ESI) m/e [M+1]$^+$ 841.2

Example B40: 2-((1H-pyrrolo[2,3-b]pyridin-5-yl)oxy)-4-(2-(2-cyclopropylphenyl)-2,9-diazaspiro[5.5]undecan-9-yl)-N-((3-nitro-4-(((tetrahydro-2H-pyran-4-yl)methyl)amino)phenyl)sulfonyl)benzamide

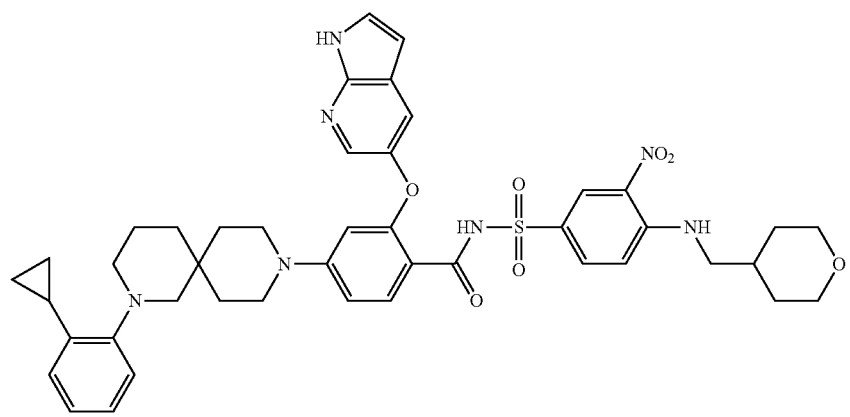 [SMILES: O=C(NS(=O)(=O)c1ccc(NCC2CCOCC2)c([N+](=O)[O-])c1)c1ccc(N2CCC3(CCCN(c4ccccc4C4CC4)C3)CC2)cc1Oc1cnc2[nH]ccc2c1]

The desired compound was synthesized following the procedures similar to those in Example B12 by replacing 1-(azetidin-3-ylmethyl)-2-(2-cyclopropylphenyl)pyrrolidine with 2-(2-cyclopropylphenyl)-2,9-diazaspiro[5.5]undecane. MS (ESI) m/e [M+1]$^+$ 819.8.

Example C1: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-phenylpyrrolidin-1-yl)-2',3',4',5'-tetrahydro-[1,1'-biphenyl]-4-carboxamide

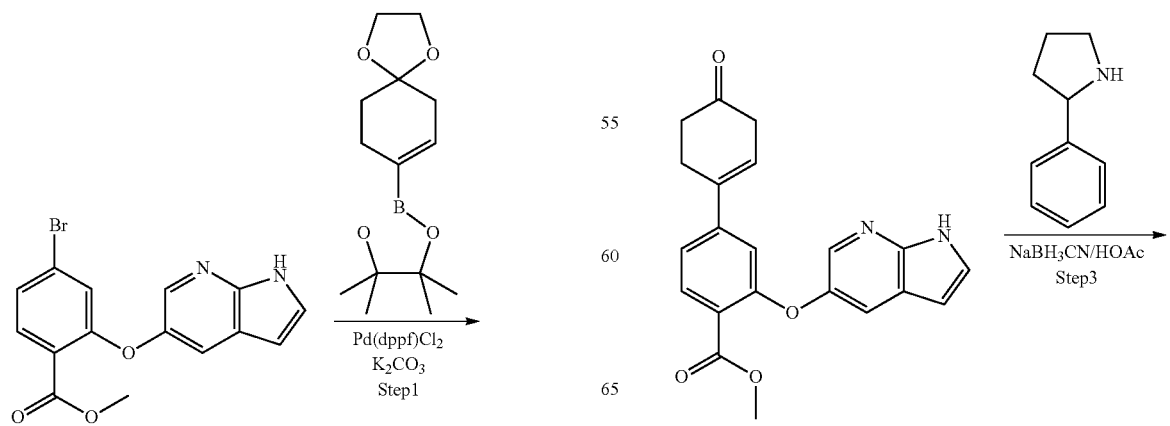

401

-continued

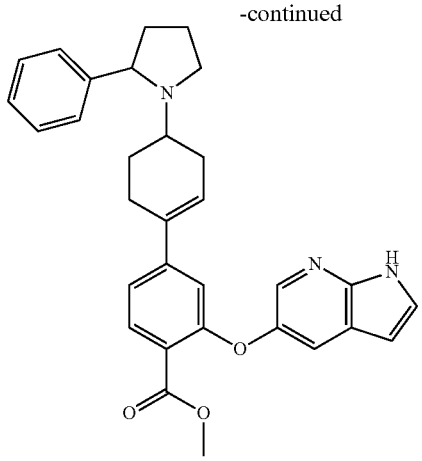

3N NaOH
CH₃OH/H₂O
Step4

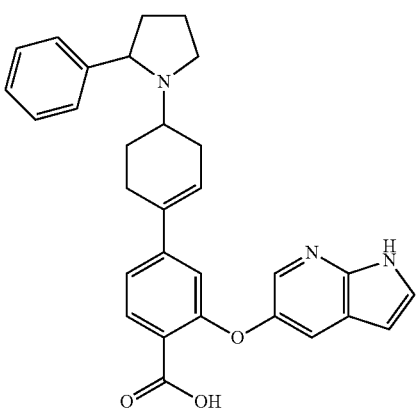

EDCl/DMAP
DIPEA
Step5

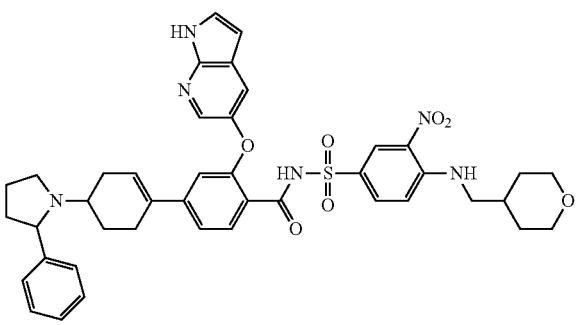

C1

402

Step 1: methyl 2-((1H-pyrrolo[2,3-b]pyridin-5-yl)oxy)-4-(1,4-dioxaspiro[4.5]dec-7-en-8-yl)benzoate

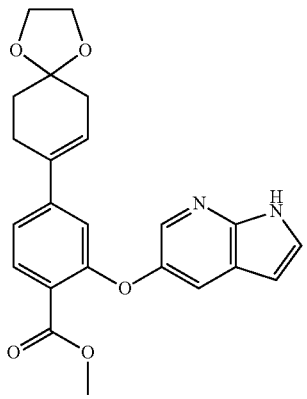 [SMILES: COC(=O)c1ccc(C2=CCC3(CC2)OCCO3)cc1Oc1cnc2[nH]ccc2c1]

To a solution of methyl 2-((1H-pyrrolo[2,3-b]pyridin-5-yl)oxy)-4-bromobenzoate (3.3 g, 9.57 mmol) in 1,4-dioxane (50 mL) were added 4,4,5,5-tetramethyl-2-(1,4-dioxaspiro[4.5]dec-7-en-8-yl)-1,3,2-dioxaborolane (2.8 g, 10.53 mmol), 1N K₂CO₃ (20 mL, H₂O) and Pd(dppf)Cl₂ (700 mg, 0.96 mmol), the reaction was heated at 95° C. under N₂ for about 2.5 h. The reaction mixture was cooled to ambient temperature, concentrated and purified by chromatography on silica gel (eluent: DCM:MeOH=40:1) to afford the desired compound as a yellow solid (3.4 g, 87.8%). MS (ESI, m/e) [M+1]⁺ 407.1.

Step 2: methyl 3-((1H-pyrrolo[2,3-b]pyridin-5-yl)oxy)-4'-oxo-2',3',4',5'-tetrahydro-[1,1'-biphenyl]-4-carboxylate

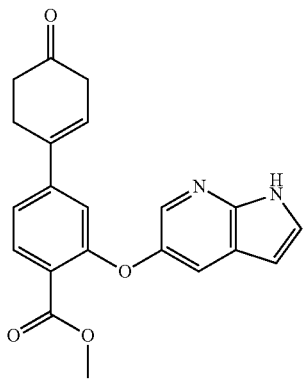 [SMILES: COC(=O)c1ccc(C2=CCC(=O)CC2)cc1Oc1cnc2[nH]ccc2c1]

To a solution of methyl 2-((1H-pyrrolo[2,3-b]pyridin-5-yl)oxy)-4-(1,4-dioxaspiro[4.5]dec-7-en-8-yl)benzoate (2.0 g, 4.93 mmol) in ISA (20 mL) was added 6M HCl acid (10 mL), the mixture was stirred at ambient temperature for about 1 h. The pH of the reaction mixture was adjusted to about 9 with sat. Na₂CO₃, the organic layer was separated, dried over Na₂SO₄ and concentrated to give the crude product as a brown oil (2.0 g). MS (ESI, m/e) [M+1]⁺ 363.0

Step 3: methyl 3-((1H-pyrrolo[2,3-b]pyridin-5-yl)oxy)-4'-(2-phenylpyrrolidin-1-yl)-2',3',4',5'-tetrahydro-[1,1'-biphenyl]-4-carboxylate

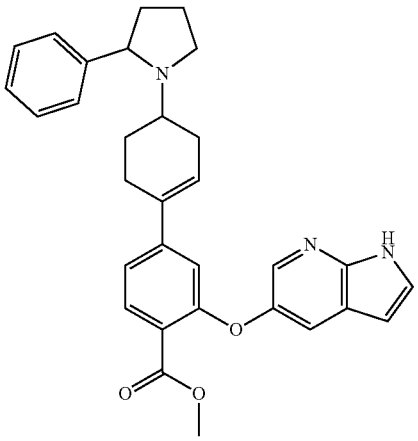 [SMILES: COC(=O)c1ccc(C2=CCC(N3CCCC3c3ccccc3)CC2)cc1Oc1cnc2[nH]ccc2c1]

To a solution of methyl 3-((1H-pyrrolo[2,3-b]pyridin-5-yl)oxy)-4'-oxo-2',3',4',5'-tetrahydro-[1,1'-biphenyl]-4-carboxylate (2.0 g, 5.52 mmol) in DCM (10 mL) and EtOH (20 mL) were added 2-phenylpyrrolidine (1.22 g, 8.29 mmol) and HOAc (0.5 mL), the solution was stirred at ambient temperature for 1.5 h, NaBH$_3$CN (1.7 g, 27.62 mmol) was then added, the reaction was stirred at ambient temperature for 1 h. The reaction mixture was portioned between DCM (50 mL) and H$_2$O (20 mL). The organic layer was washed with H$_2$O (20 mL), concentrated and purified by chromatography on silica gel (eluent: DCM: MeOH=15:1) to afford the desired compound as a yellow solid (1.4 g, 51.4%). MS (ESI, m/e) [M+1]$^+$ 494.1

Step 4: 3-((1H-pyrrolo[2,3-b]pyridin-5-yl)oxy)-4'-(2-phenylpyrrolidin-1-yl)-2',3',4',5'-tetrahydro-[1,1'-biphenyl]-4-carboxylic acid

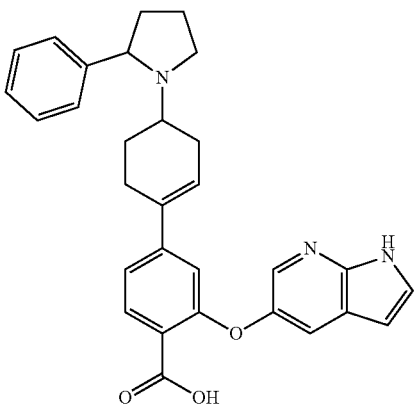 [SMILES: O=C(O)c1ccc(C2=CCC(N3CCCC3c3ccccc3)CC2)cc1Oc1cnc2[nH]ccc2c1]

To a mixture of methyl 3-((1H-pyrrolo[2,3-b]pyridin-5-yl)oxy)-4'-(2-phenylpyrrolidin-1-yl)-2',3',4',5'-tetrahydro-[1,1'-biphenyl]-4-carboxylate (200 mg, 0.45 mmol) in MeOH (10 mL) was added 3N NaOH (5 mL), the reaction was stirred at ambient temperature for about 20 h. The pH of the reaction mixture was adjusted to about 4 with 1M HCl acid, the resulting solution was concentrated. The residue was slurried with DCM/MeOH (20 mL/2 mL), filtered, the filtrate was concentrated to afford the crude product as yellow solid (200 mg). MS (ESI, m/e) [M+1]$^+$ 480.1.

Step 5: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-phenylpyrrolidin-1-yl)-2',3',4',5'-tetrahydro-[1,1'-biphenyl]-4-carboxamide

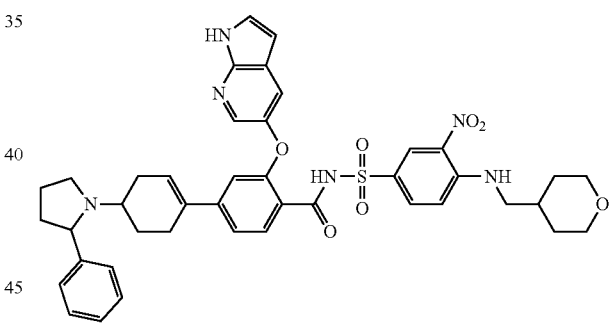

A mixture of 3-((1H-pyrrolo[2,3-b]pyridin-5-yl)oxy)-4'-(2-phenylpyrrolidin-1-yl)-2',3',4',5'-tetrahydro-[1,1'-biphenyl]-4-carboxylic acid (200 mg, 0.416 mmol), 3-nitro-4-(((tetrahydro-2H-pyran-4-yl)methyl)amino)benzenesulfonamide (131 mg, 0.416 mmol), EDCl (120 mg, 0.624 mmol), DMAP (76 mg, 0.624 mmol) and DIPEA (161 mg, 1.247 mmol) in DCM (10 mL) was stirred at ambient temperature for 20 h. The reaction solution was concentrated and purified by pre-HPLC to give the product (30 mg). $^1$H NMR (DMSO-d$_6$) δ ppm: 11.63 (s, 1H), 8.46 (s, 2H), 7.96 (I, J=4.0 Hz, 1H), 7.73 (d, J=8.0 Hz, 1H), 7.55-6.97 (m, 11H), 6.72 (s, 1H), 6.34 (s, 1H), 5.98-5.86 (m, 1H), 3.84 (dd, J=12.0, 4.0 Hz, 2H), 3.28-3.22 (m, 5H), 2.33-1.83 (m, 10H), 1.61-1.58 (d, J=12.0 Hz, 4H), 1.29-1.18 (m, 3H). MS (ESI) m/e [M+1]$^+$ 777.2.

Example C2: 3-((1H-pyrrolo[2,3-b]pyridin-5-yl)oxy)-4'-(2-(2-bromophenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

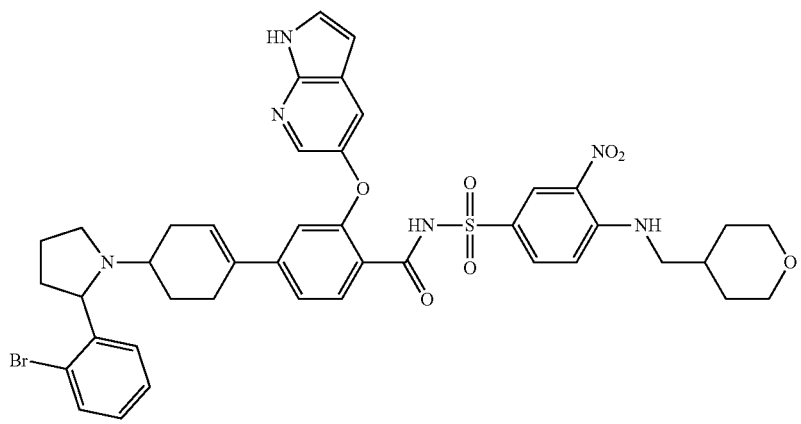

The desired compound was synthesized starting from 2-(2-bromophenyl)pyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. $^1$H NMR (400 MHz, DMSO-$d_6$) δ ppm: 12.20 (br, 1H), 11.86 (br, 1H), 8.56-8.53 (m, 2H), 8.00 (m, 1H), 7.78 (m, 1H), 7.65-7.58 (m, 1H), 7.50-7.45 (m, 4H), 7.31 (m, 1H), 7.14-7.08 (m, 3H), 6.72 (d, J=4.0, 1H), 6.38 (m, 1H), 6.01-5.77 (m, 1H), 4.10 (m, 1H), 3.85 (m, 2H), 3.28-3.22 (m, 5H), 2.67 (m, 1H), 2.31-2.00 (m, 5H), 1.86 (m, 2H), 1.72 (m, 2H), 1.61 (d, J=12.0, 2H), 1.28-1.21 (m, 5H). MS (ESI, m/e) [M+1]$^+$ 855.1, 857.1.

Example C3: 3-((1H-pyrrolo[2,3-b]pyridin-5-yl)oxy)-4'-(2-(2-cyclopropylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

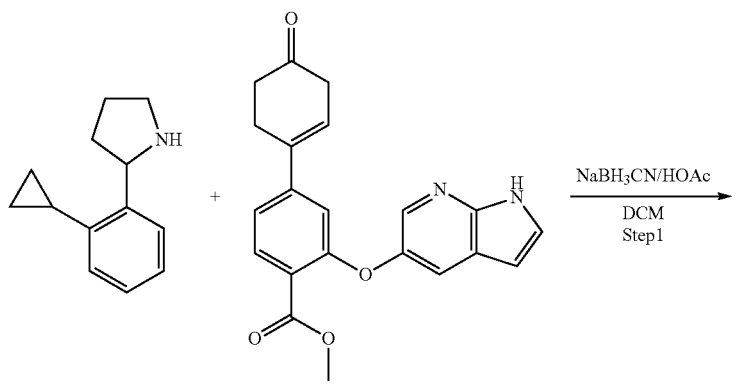

-continued
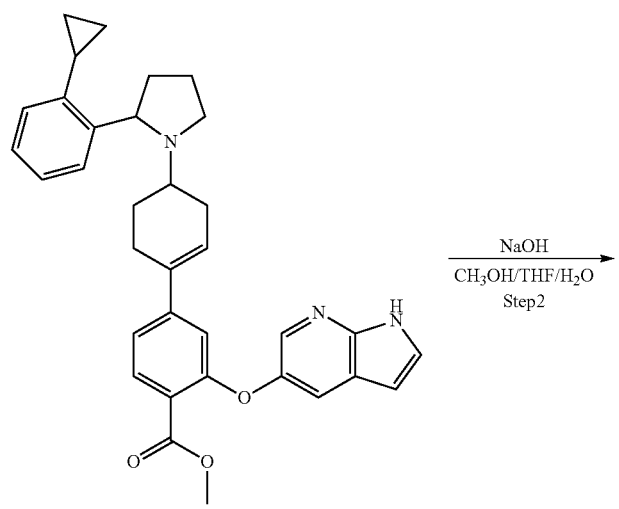
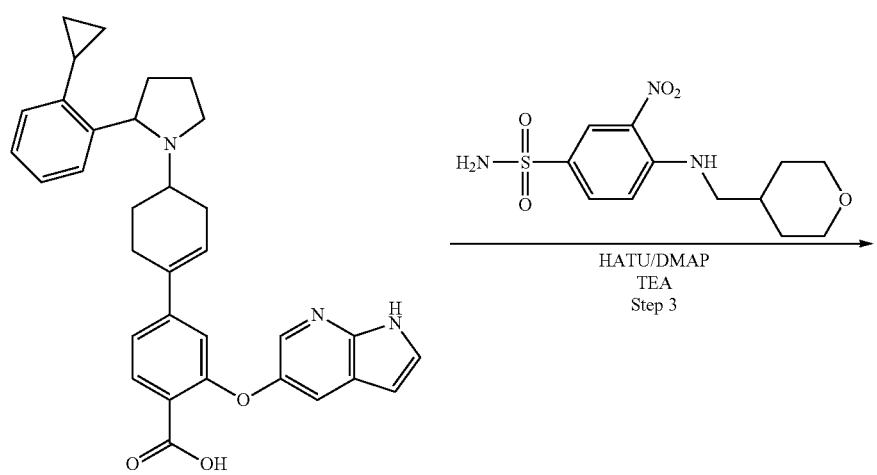
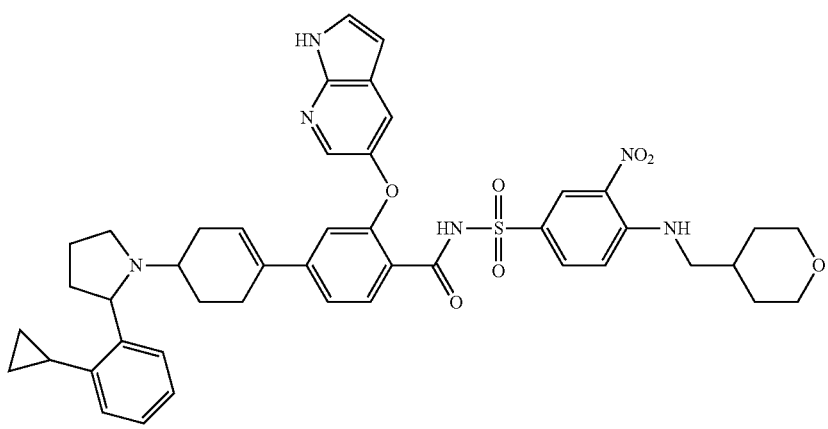
C3

409

Step 1: methyl 3-((1H-pyrrolo[2,3-b]pyridin-5-yl)oxy)-4'-(2-(2-cyclopropylphenyl)pyrrolidin-1-yl)-2',3',4',5'-tetrahydro-[1,1'-biphenyl]-4-carboxylate

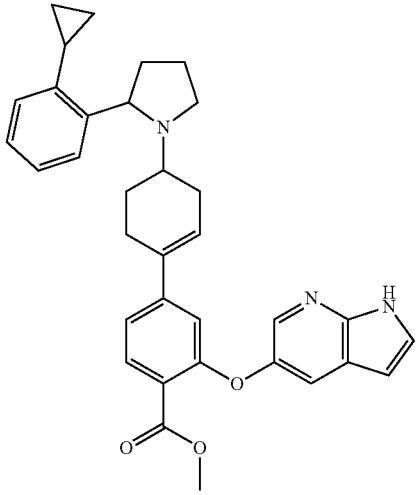 [SMILES: COC(=O)c1ccc(C2=CCC(N3CCCC3c3ccccc3C3CC3)CC2)cc1Oc1cnc2[nH]ccc2c1]

To a mixture of methyl 3-((1H-pyrrolo[2,3-b]pyridin-5-yl)oxy)-4'-oxo-2',3',4',5'-tetrahydro-[1,1'-biphenyl]-4-carboxylate (764 mg, 2.1 mmol), 2-(2-cyclopropylphenyl)pyrrolidine (473 mg, 2.53 mmol) in MeOH was added AcOH (0.2 mL) and the resultant mixture was stirred for 1 h. To the reaction was added NaBH$_3$CN (889 mg, 4 mmol) and stirred for another 1 hour. Then the reaction mixture was concentrated in vacuum and diluted with EA (200 mL), washed with NaHCO$_3$ (200 mL), brine (100 mL), dried over Na$_2$SO$_4$, concentrated in vacuum and purified by chromatography column on silica (eluent: EA/PE=5/1 to 1/2) to give the product (412 mg, 36.76%) as alight yellow solid. $^1$H NMR (400 MHz, CDCl$_3$) δ ppm: 11.70 (br, 1H), 8.01 (s, 1H), 7.75 (d, J=0.8 Hz, 1H), 7.56-7.51 (m, 3H), 7.23 (d, J=0.8 Hz, 1H), 7.09-7.02 (m, 1H), 6.98-6.96 (m, 1H), 6.91-6.85 (m, 1H), 4.32-4.25 (m, 1H), 3.74 (s, 3H), 3.18-2.97 (m, 2H), 2.38-1.99 (m, 7H), 1.73 (m, 2H), 1.54-1.41 (m, 2H), 0.89-0.85 (m, 2H), 0.65-0.52 (m, 2H). MS (ESI, m/e) [M+1]$^+$ 534.2.

410

Step 2: 3-((1H-pyrrolo[2,3-b]pyridin-5-yl)oxy)-4'-(2-(2-cyclopropylphenyl)pyrrolidin-1-yl)-2',3',4',5'-tetrahydro-[1,1'-biphenyl]-4-carboxylic acid

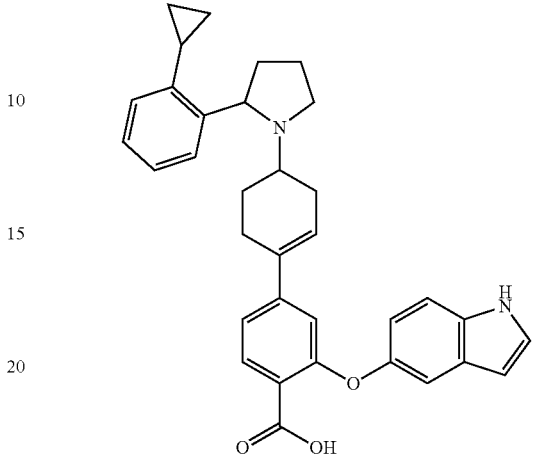

To the solution of methyl 3-((1H-pyrrolo[2,3-b]pyridin-5-yl)oxy)-4'-(2-(2-cyclopropylphenyl)pyrrolidin-1-yl)-2',3',4',5'-tetrahydro-[1,1'-biphenyl]-4-carboxylate (700 mg, 1.31 mmol) in a mixture solvent of MeOH (10 mL), THF (10 mL), H$_2$O (2 mL) was added NaOH (524 mg, 13.1 mmol) and the resultant mixture was stirred overnight. The reaction was quenched with HCl acid (6 M) to pH ~4, extracted with DCM (400 mL), washed with brine (100 ml), dried over Na$_2$SO$_4$ and evaporated in vacuum Then the reaction mixture was concentrated in vacuum to afford a crude product (836 mg, crude). $^1$H NMR (400 MHz, CDCl$_3$) δ ppm: 12.91 (br, 1H), 11.60 (br, 1H), 8.01 (s, 1H), 786-7.76 (m, 1H), 7.78 (d, J=0.8 Hz, 1H), 7.50-7.47 (m, 2H), 7.30-7.27 (m, 3H), 7.10-7.02 (m, 1H), 6.89-6.88 (m, 1H), 6.39 (s, 1H), 6.05-5.96 (m, 1H), 5.25-5.09 (m, 1H), 3.75-3.68 (m, 3H), 2.37-2.06 (m, 7H), 1.76-1.60 (m, 2H), 1.23 (m, 2H), 0.96 (m, 2H), 0.72-0.61 (m, 2H). MS (ESI, m/e) [M+1]$^+$ 520.2

Step 3: 3-((TH-pyrrolo[2,3-b]pyridin-5-yl)oxy)-4'-(2-(2-cyclopropylphenyl)pyrrolidin-1-yl)-N-((3-nitro-4-((((tetrahydro-2H-pyran-4-yl)methyl)amino)phenyl)sulfonyl)-2',3',4',5'-tetrahydro-[1,1'-biphenyl]-4-carboxamide

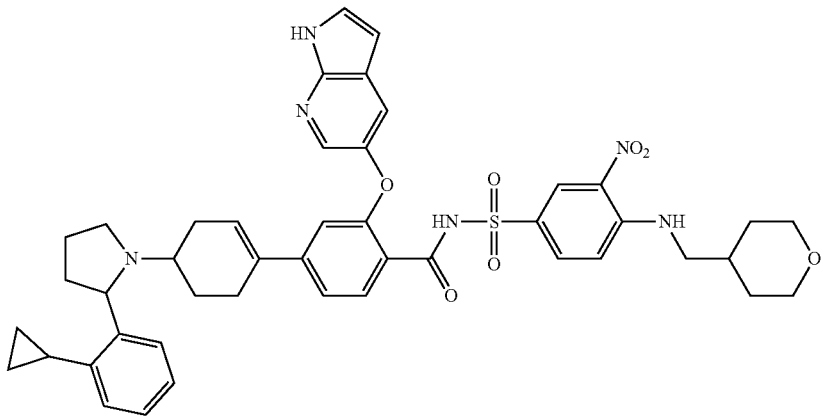 [SMILES: O=C(NS(=O)(=O)c1ccc(NCC2CCOCC2)c([N+](=O)[O-])c1)c1ccc(C2=CCC(N3CCCC3c3ccccc3C3CC3)CC2)cc1Oc1cnc2[nH]ccc2c1]

The mixture of 3-((1H-pyrrolo[2,3-b]pyridin-5-yl)oxy)-4'-(2-(2-cyclopropylphenyl)pyrrolidin-1-yl)-2',3',4',5'-tetrahydro-[1,1'-biphenyl]-4-carboxylic acid (700 mg, 1.34 mmol), triethylamine (106 mg, 4.05 mmol), 2-(7-azabenzotriazol-1-yl)-N,N,N',N'-tetramethyluronium hexafluorophosphate (616 mg, 1.62 mmol) in DCM (10 mL) was stirred for 2 hours at room temperature. To the reaction mixture was added 3-nitro-4-(((tetrahydro-2H-pyran-4-yl)methyl)amino)benzenesulfonamide (512 mg, 1.62 mmol) and DMAP (17 mg, 0.14 mmol) and stirred overnight. The reaction mixture was washed with brine, dried over $Na_2SO_4$ and concentrated in vacuo, then purified by chromatography column on silica (eluent: DCM/MeOH=50/1 to 15/1) to afford a crude product (490 mg). The crude product was purified with Pre-HPLC to give the product (1.65 mg, 1.26%). $^1$H NMR (400 MHz, DMSO-$d_6$) δ ppm: 12.25 (br, 1H), 11.68 (br, 1H), 8.51 (m, 2H), 7.99 (s, 1H), 7.79 (d, J=12.0 Hz, 1H), 7.61-7.47 (m, 4H), 7.28-7.07 (m, 5H), 6.73 (s, 1H), 6.37 (s, 1H), 5.99-5.85 (m, 1H), 5.32-5.28 (m, 1H), 3.85 (d, J=8.0 Hz, 2H), 3.75-3.51 (m, 2H), 3.22 (m, 5H), 2.42-1.97 (m, 8H), 1.86 (s, 2H), 1.73 (s, 1H), 1.61-1.57 (m, 2H), 1.45-1.37 (m, 1H), 1.23 (m, 2H), 1.07-0.93 (m, 2H), 0.71-0.59 (m, 2H). MS (ESI, m/e) [M+1]$^+$ 817.2.

Example C3a and Example C3b: (R or S)-3-((1H-pyrrolo[2,3-b]pyridin-5-yl)oxy)-4'-((S)-2-(2-cyclopropylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide; and (S or R)-3-((1H-pyrrolo[2,3-b]pyridin-5-yl)oxy)-4'-((S)-2-(2-cyclopropylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

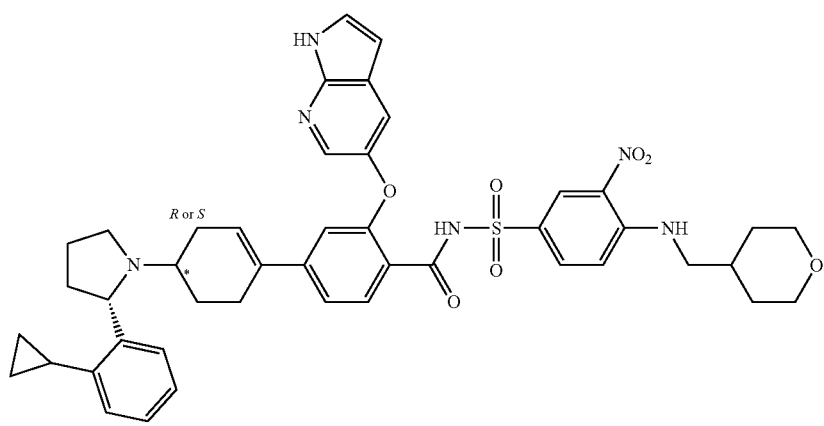

C3a (faster isomer)

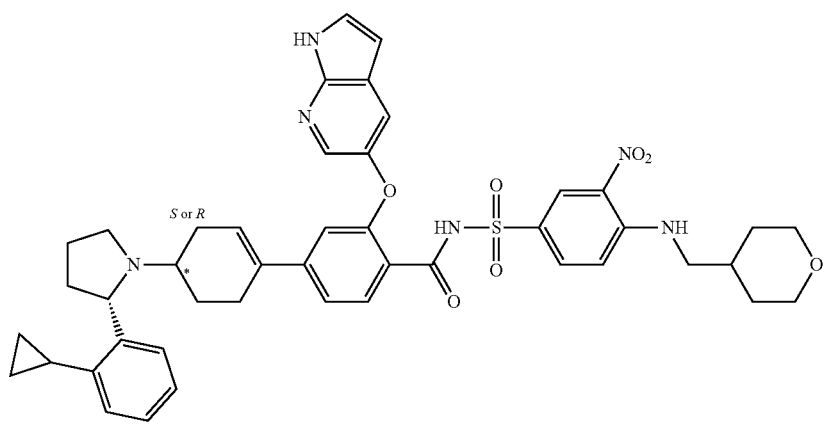

C3b (slower isomer)

Step 1: tert-butyl (S)-2-(2-bromophenyl)pyrrolidine-1-carboxylate

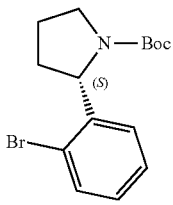

To a solution of (S)-2-(2-bromophenyl)pyrrolidine (5.0 g, 22.12 mmol) in DCM (50 mL) was added Boc$_2$O (5.3 g, 24.34 mmol) slowly, the resulted solution was stirred at room temperature for 20 min. Then the reaction mixture was concentrated to give the product (7.8 g, crude) as a brown solid. MS (ESI, m/e) [M+1]$^+$ 270.0, 271.9.

Step 2: tert-butyl (S)-2-(2-cyclopropylphenyl)pyrrolidine-1-carboxylate

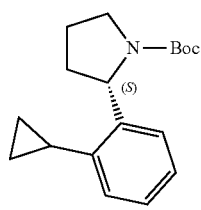

To a solution of tert-butyl (S)-2-(2-bromophenyl)pyrrolidine-1-carboxylate (7.8 g, 22.12 mmol) in 1,4-dioxane (150 ml) was added cyclopropylboronic acid (5.78 g, 66.36 mmol), Pd(dppf)Cl$_2$ (810 mg, 1.11 mmol), K$_2$CO$_3$ (9.16 g, 66.36 mmol) and water (2.5 ml), the mixture was stirred at 90° C. under N$_2$ atmosphere for 4 h. After cooled to r.t, the reaction mixture was filtered. The filtrate was concentrated and purified by prep-MPLC (eluent: 0-5%, EA/PE) to give the product (5.0 g, 78.4%) as a colorless oil. MS (ESI, m/e) [M+1]$^+$ 232.1

Step 3: (S)-2-(2-cyclopropylphenyl)pyrrolidine

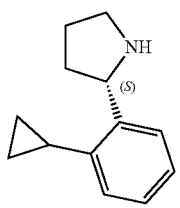

To a solution of tert-butyl (S)-2-(2-cyclopropylphenyl)pyrrolidine-1-carboxylate (5.0 g, 17.54 mmol) in MeOH (50 mL) was added HCl (1,4-dioxane solution, 4M, 50 mL) and stirred at room temperature for 1 hour. The reaction solution was concentrated in vacuum. The residue was partitioned between EA (20 mL) and H$_2$O (100 mL). Then aqueous layer was extracted with EA (20 mL). The aqueous layer was separated, basified with Sat. NaHCO$_3$, then extracted with DCM (50 mL×3). The combined organic layers were dried over Na$_2$SO$_4$ and concentrated to give the product (2.5 g, 77.0%) as a brown oil without further purification for next synthesis. MS (ESI, m/e) [M+1]$^+$ 188.2.

Step 4: methyl 3-((1H-pyrrolo[2,3-b]pyridin-5-yl)oxy)-4'-((S)-2-(2-cyclopropylphenyl)pyrrolidin-1-yl)-2',3',4',5'-tetrahydro-[1,1'-biphenyl]-4-carboxylate

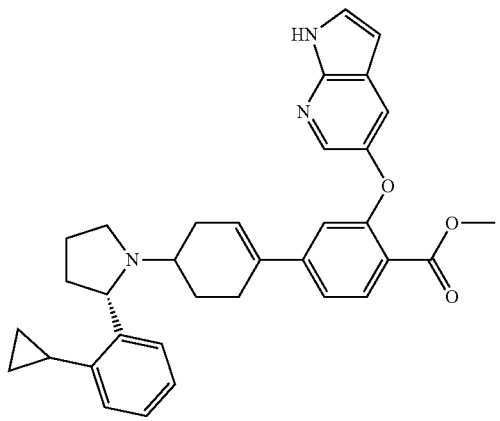 [SMILES: COC(=O)c1ccc(C2=CCC(N3CCC[C@H]3c3ccccc3C3CC3)CC2)cc1Oc1cnc2[nH]ccc2c1]

To a solution of (S)-2-(2-cyclopropylphenyl)pyrrolidine (555 mg, 3.00 mmol) in DCM (30 mL) was added methyl 3-((1H-pyrrolo[2,3-b]pyridin-5-yl)oxy)-4'-oxo-2',3',4',5'-tetrahydro-[1,1'-biphenyl]-4-carboxylate (1.09 g, 3.00 mmol), AcOH (2 drops) and NaBH(OAc)$_3$ (1.27 g, 6.00 mmol), the solution was stirred at room temperature for overnight. The reaction solution was washed with H$_2$O (20 mL), concentrated and purified by prep-MPLC (eluent: MeOH/DCM=0/10 to 1/10) to give the product (1.3 g, 81.3%) as a yellow solid. MS (ESI, m/e) [M+1]$^+$ 534.

Step 5: 3-((1H-pyrrolo[2,3-b]pyridin-5-yl)oxy)-4'-((S)-2-(2-cyclopropylphenyl)pyrrolidin-1-yl)-2',3',4',5'-tetrahydro-[1,1'-biphenyl]-4-carboxylic acid

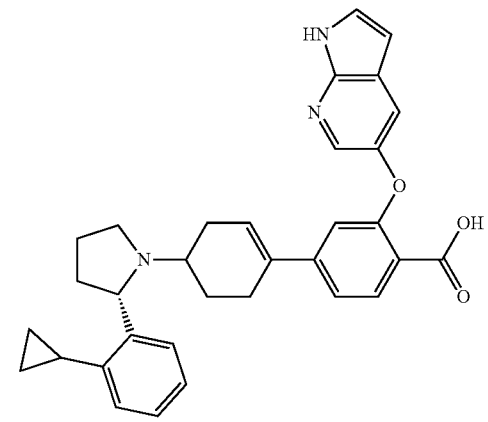 [SMILES: O=C(O)c1ccc(C2=CCC(N3CCC[C@H]3c3ccccc3C3CC3)CC2)cc1Oc1cnc2[nH]ccc2c1]

To the solution of methy 3-((1H-pyrrolo[2,3-b]pyridin-5-yl)oxy)-4'-((S)-2-(2-cyclopropylphenyl)pyrrolidin-1-yl)-2',3',4',5'-tetrahydro-[1,1'-biphenyl]-4-carboxylate (700 mg, 1.31 mmol) in MeOH (15 mL) was added THF (15 mL) and NaOH (6M, 10 mL) and stirred at room temperature for 3 hours. The PH value of the reaction mixture was adjusted to 3 with Con. HCl acid. The resulting mixture was concentrated in vacuum. The residue was washed with DCM/MeOH=10/1 (v/v, 50 mL), filtered. The filtrate was concentrated to give the product as a yellow solid (650 mg, crude). MS (ESI, m/e) [M+1]$^+$ 520.2

Step 6: 3-((1H-pyrrolo[2,3-b]pyridin-5-yl)oxy)-4'-((S)-2-(2-cyclopropylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

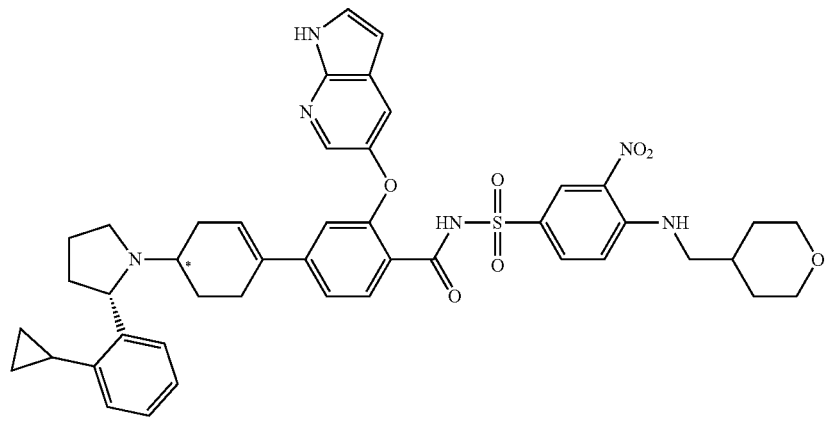 [SMILES: O=C(NS(=O)(=O)c1ccc(NCC2CCOCC2)c([N+](=O)[O-])c1)c1ccc(C2=CCC(N3CCC[C@H]3c3ccccc3C3CC3)CC2)cc1Oc1cnc2[nH]ccc2c1]

The a mixture of 3-((1H-pyrrolo[2,3-b]pyridin-5-yl)oxy)-4'-((S)-2-(2-cyclopropylphenyl)pyrrolidin-1-yl)-2',3',4',5'-tetrahydro-[1,1'-biphenyl]-4-carboxylic acid (650 mg, 1.25 mmol) in DCM (20 mL) was added EDCl (480 mg, 2.50 mmol), triethylamine (630 mg, 6.26 mmol), 3-nitro-4-(((tetrahydro-2H-pyran-4-yl)methyl)amino)benzenesulfonamide (395 mg, 1.25 mmol) and DMAP (306 mg, 2.50 mmol), the solution was stirred at r.t for 40 h. The reaction solution was washed with $H_2O$ (30 mL×3), concentrated and purified by chromatography column on silica (eluent: MeOH/DCM=0/25 to 1/25) to afford the product (700 mg, 68.5%), MS (ESI, m/e) [M+1]$^+$ 817.2. $^1$H NMR (40G MHz, DMSO-$d_6$) δ ppm: 11.64 (s, 1H), 8.48 (s, 2H), 7.96 (s, 1H), 7.80-7.40 (m, 5H), 7.30-6.84 (m, 5H), 6.73 (s, 1H), 6.35 (s, 1H), 6.04-5.79 (m, 1H), 3.88-3.81 (m, 2H), 3.32-3.16 (m, 6H), 2.38-1.21 (m, 18H), 0.97-0.84 (m, 2H), 0.72-0.50 (m, 2H). MS (ESI) m/e [M+1]$^+$ 763.2. MS (ESI) m/e [M+1]$^+$ 805.2

Two enantiomers C3a (faster isomer) and C3b (slower isomer) were separated by chiral preparative HPLC. The chiral separation conditions are shown below. The faster enantiomer was eluted at retention time of 1.8 min to give C3a. The slower enantiomer was eluted at retention time of 2.6 min to give C3b.

| Column | CHIRAL ART Cellulose-SB |
|---|---|
| Column size | 2 cm × 25 cm, 5 um |
| Injection | 1.2 mL |
| Mobile phase | $CO_2$:[MeOH:DCM = 2:1(0.1% MSA + NH4HCO3)] = 60:40 |
| Flow rate | 45 mL/min |
| Wave length | UV 220 nm |
| Temperature | 25° C. |
| Sample solution | 18 mg/mL in MeOH:DCM = 3:1 |
| Prep-SFC | Prep-SFC-100-1 |

Example C3c and Example C3d: (R or S)-3-((1H-pyrrolo[2,3-b]pyridin-5-yl)oxy)-4'-((R)-2-(2-cyclopropylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide; and (S or R)-3-((1H-pyrrolo[2,3-b]pyridin-5-yl)oxy)-4'-((R)-2-(2-cyclopropylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

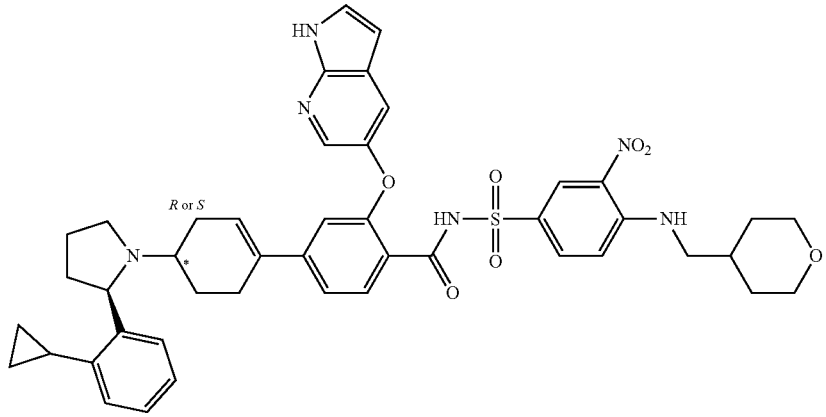

C3c (faster isomer)

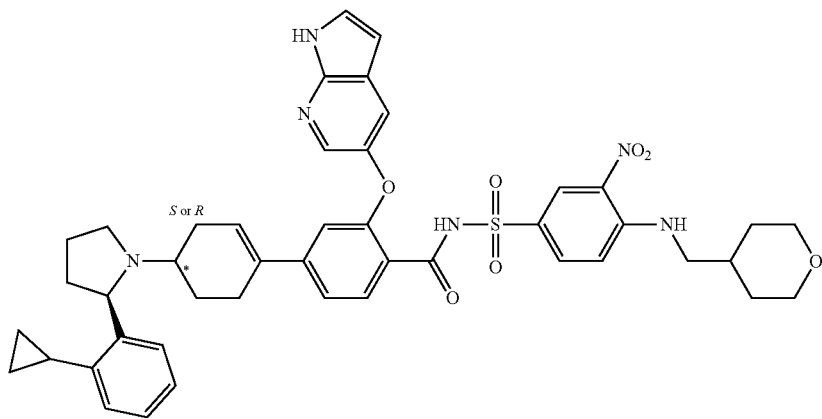

C3d (slower isomer)

Using (R)-2-(2-cyclopropylphenyl)pyrrolidine instead of (S)-2-(2-cyclopropylphenyl)pyrrolidine in the reductive amination step and then following the similar procedures in Example C3a and Example C3 h, the mixture of Example C3c and Example C3d were afforded, then proceeded by chiral-HPLC separation, Two enantiomers C3c (faster isomer) and C3d (slower isomer) were separated. The chiral separation conditions are shown below. The faster enantiomer was eluted at retention time of 8.4 min to give C3c. The slower enantiomer was eluted at retention time of 9.6 min to give C3d,

| Column | CHIRALPAK IA |
|---|---|
| Column size | 2 cm × 25 cm, 5 um |
| Injection | 1.0 mL |
| Mobile phase | MTBE:MeOH(0.2% MSA) = 60:40 |
| Flow rate | 20 mL/min |
| Wave length | UV 220 nm |
| Temperature | 25° C. |
| Sample solution | 13.7 mg/ml in MeOH:DCM = 3:1 |
| Prep-HPLC equipment | Prep-Gilson-HPLC |

Example C4: 3-((1H-pyrrolo[2,3-b]pyridin-5-yl)oxy)-4'-(2-(3-cyclopropylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

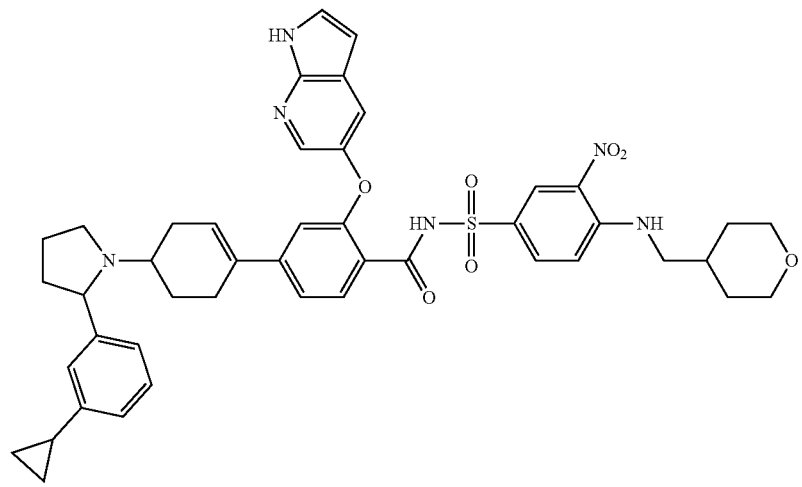 [SMILES: O=C(NS(=O)(=O)c1ccc(NCC2CCOCC2)c([N+](=O)[O-])c1)c1ccc(C2=CCC(N3CCCC3c3cccc(C4CC4)c3)CC2)cc1Oc1cnc2[nH]ccc2c1]

The desired compound was synthesized starting from 2-(3-cyclopropylphenyl)pyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C3. $^1$H NMR (400 MHz, DMSO-$d_6$) δ ppm: 12.61 (br, 1H), 11.61 (br, 1H), 8.44 (m, 2H), 7.95 (s, 1H), 7.72 (d, J=8.0 Hz, 1H), 7.48-7.40 (m, 3H), 7.20-6.93 (m, 6H), 6.73 (s, 1H), 6.34 (s, 1H), 5.98-5.88 (m, 1H), 3.85-3.82 (m, 2H), 3.28-3.00 (m, 6H), 2.33-1.86 (m, 11H), 1.61 (d, J=12.0 Hz, 2H), 1.45-1.25 (m, 4H), 0.92-0.84 (m, 2H), 0.65-0.59 (m, 2H). MS (ESI, m/e) [M+1]$^+$ 817.2.

Example C5: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(pyridin-3-yl)pyrrolidin-1-yl)-2',3',4',5'-tetrahydro-[1,1'-biphenyl]-4-carboxamide

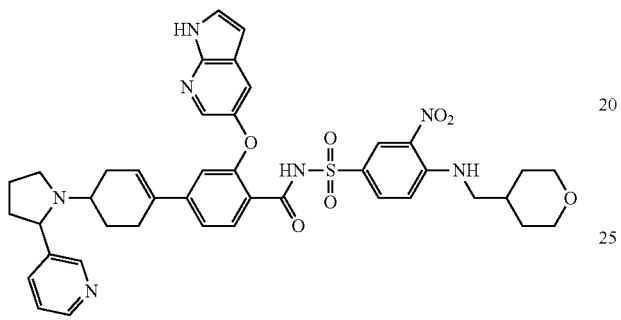

The desired compound was synthesized starting from 3-(pyrrolidin-2-yl)pyridine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. $^1$H NMR (400 MHz, DMSO-$d_6$) δ ppm: 12.27 (s, 1H), 11.73 (s, 1H), 9.90-9.69 (m, 1H), 8.78 (s, 1H), 8.67-8.59 (m, 1H), 8.56 (s, 1H), 8.11-8.04 (m, 1H), 8.02 (s, 1H), 7.82 (d, J=9.0 Hz, 1H), 7.61-7.42 (m, 4H), 7.22-7.06 (m, 2H), 6.71 (s, 1H), 6.40 (s, 1H), 6.05-5.86 (m, 1H), 3.90-3.76 (m, 5H), 3.35-3.14 (m, 4H), 2.55-2.41 (m, 4H), 2.22-1.99 (m, 4H), 1.93-1.78 (m, 1H), 1.64-1.51 (m, 3H), 1.33-1.13 (m, 4H), MS (ESI) m/e [M+1]$^+$ 778.1.

Example C6: 3-((1H-pyrrolo[2,3-b]pyridin-5-yl)oxy)-4'-(2-benzylpyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

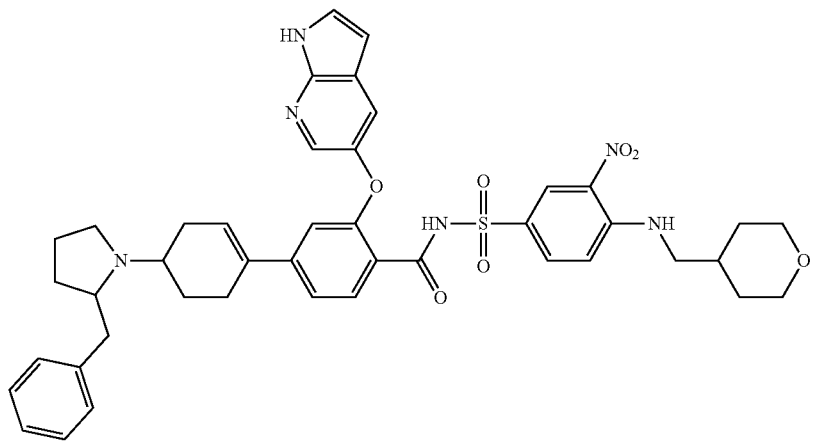 [SMILES: O=C(NS(=O)(=O)c1ccc(NCC2CCOCC2)c([N+](=O)[O-])c1)c1ccc(C2=CCC(N3CCCC3Cc3ccccc3)CC2)cc1Oc1cnc2[nH]ccc2c1]

The desired compound was synthesized starting from 2-benzylpyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. $^1$H NMR (400 MHz, DMSO-$d_6$) δ ppm: 11.59 (s, 1H), 9.41 (Brs, 1H), 8.42 (s, 1H), 8.37 (s, 1H), 7.96 (d, J=2.0 Hz, 1H), 7.72-7.64 (m, 1H), 7.52 (d, J=8.0 Hz, 1H), 7.45 (s, 1H), 7.39 (s, 1H), 7.35-7.25 (m, 4H), 7.25-7.18 (m, 1H), 7.17-7.09 (m, 1H), 6.92-6.83 (m, 1H), 6.78 (d, J=8.0 Hz, 1H), 6.34 (s, 1H), 6.03 (s, 1H), 3.92-3.76 (m, 3H), 3.45-3.335 (s, 1H), 3.30-3.19 (m, 6H), 2.46-2.32 (m, 4H), 2.26-2.10 (m, 1H), 1.95-1.73 (m, 5H), 1.68-1.53 (m, 3H), 1.30-1.19 (m, 3H). MS (ESI) m/e [M+1]$^+$ 791.2.

Example C7: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(pyridin-2-yl)pyrrolidin-1-yl)-2',3',4',5'-tetrahydro-[1,1'-biphenyl]-4-carboxamide

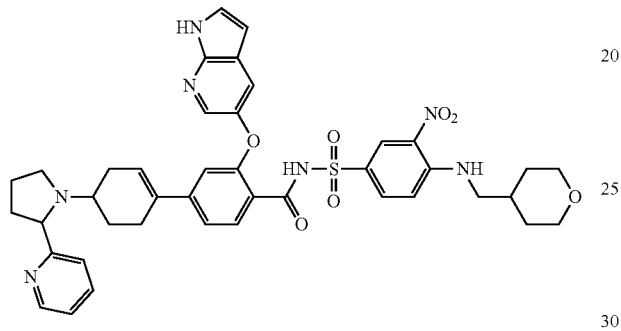

The desired compound was synthesized starting from 2-(pyrrolidin-2-yl)pyridine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. $^1$H NMR (400 MHz, DMSO-$d_6$) δ ppm: 12.43 (br, 1H), 11.62 (s, 1H), 8.55 (s, 1H), 8.44 (s, 2H), 7.95 (s, 2H), 7.72 (s, 1H), 7.62-7.23 (m, 5H), 7.11 (d, J=7.6 Hz, 1H), 6.93 (s, 1H), 6.73 (s, 1H), 6.34 (s, 1H), 5.97-5.85 (m, 1H), 3.84 (d, J=9.4 Hz, 2H), 3.29-3.16 (m, 5H), 2.45-2.25 (m, 5H), 2.12-1.75 (m, 6H), 1.59 (d, J=12.6 Hz, 3H), 1.31-1.16 (m, 4H), MS (ESI, m/e) [M+1]$^+$ 778.2

Example C8: 3-((1H-pyrrolo[2,3-b]pyridin-5-yl)oxy)-4'-(2-(2-(furan-3-yl)phenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

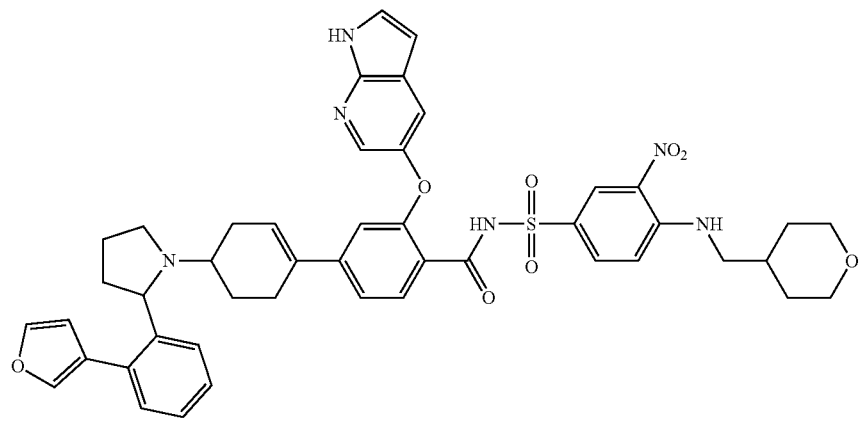 [SMILES: O=C(NS(=O)(=O)c1ccc(NCC2CCOCC2)c([N+](=O)[O-])c1)c1ccc(C2=CCC(N3CCCC3c3ccccc3-c3ccoc3)CC2)cc1Oc1cnc2[nH]ccc2c1]

The desired compound was synthesized starting from 2-(2-(furan-3-yl)phenyl)pyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. $^1$H NMR (400 MHZ, DMSO-$d_6$) δ ppm: 12.22 (br, 1H), 11.63 (s, 1H), 8.46 (s, 2H), 7.95 (s, 1H), 7.82-7.62 (m, 4H), 7.52-7.35 (m, 4H), 7.27-7.03 (m, 3H), 6.99-6.86 (m, 1H), 6.76-6.49 (m, 2H), 6.34 (s, 1H), 5.92-5.74 (m, 1H), 3.84 (d, J=10.9 Hz, 3H), 3.29-3.20 (m, 5H), 3.16-2.93 (un 2H), 2.20-1.64 (m, 9H), 1.60 (d, J=12.7 Hz, 3H), 1.24 (s, 3H). MS (ESI, m/e) [M+1]$^+$ 843.1

Example C9: 3-((1H-pyrrolo[2,3-b]pyridin-5-yl)oxy)-4'-(2-(2-chlorophenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

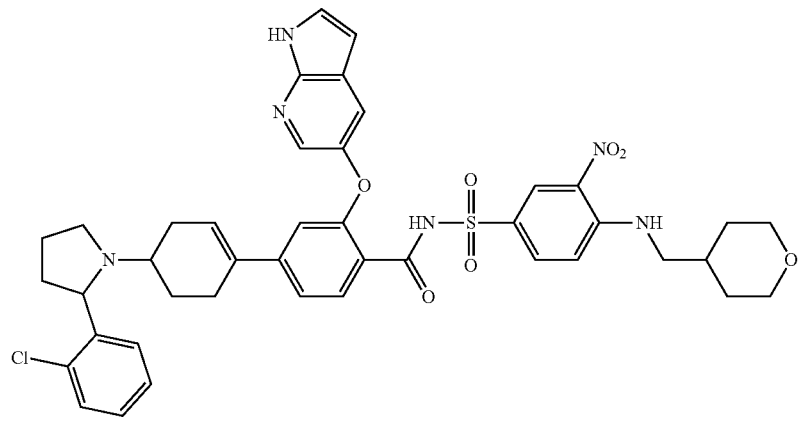 [SMILES: O=C(NS(=O)(=O)c1ccc(NCC2CCOCC2)c([N+](=O)[O-])c1)c1ccc(C2=CCC(N3CCCC3c3ccccc3Cl)CC2)cc1Oc1cnc2[nH]ccc2c1]

The desired compound was synthesized starting from 2-(2-chlorophenyl)pyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. $^1$H NMR (400 MHz, DMSO-$d_6$) δ ppm: 12.23 (br, 1H), 11.69 (br, 1H), 8.57-8.53 (m, 2H), 7.99 (s, 1H), 7.80 (d, J=8.0 Hz, 1H), 7.70-7.61 (m, 1H), 7.51 (s, 2H), 7.48 (d, J=8.0 Hz, 1H), 7.36-7.21 (m, 2H), 7.14 (d, J=8.0 Hz, 1H), 7.09-7.01 (m, 2H), 6.72 (s, 1H), 6.38 (s, 1H), 6.01-5.79 (m, 1H), 4.15-4.09 (m, 1H), 3.85 (d, J=8.0 Hz, 2H), 3.26-3.22 (m, 4H), 3.17-2.90 (m, 2H), 2.67-2.55 (m, 1H), 2.32-2.08 (m, 6H), 1.86-1.67 (m, 5H), 1.61 (d, J=12.0 Hz, 2H), 1.47-1.23 (m, 2H). MS (ESI, m/e) [M+1]$^+$ 811.1.

Example C10: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(2-(trifluoromethyl)phenyl)pyrrolidin-1-yl)-2',3',4',5'-tetrahydro-[1,1'-biphenyl]-4-carboxamide

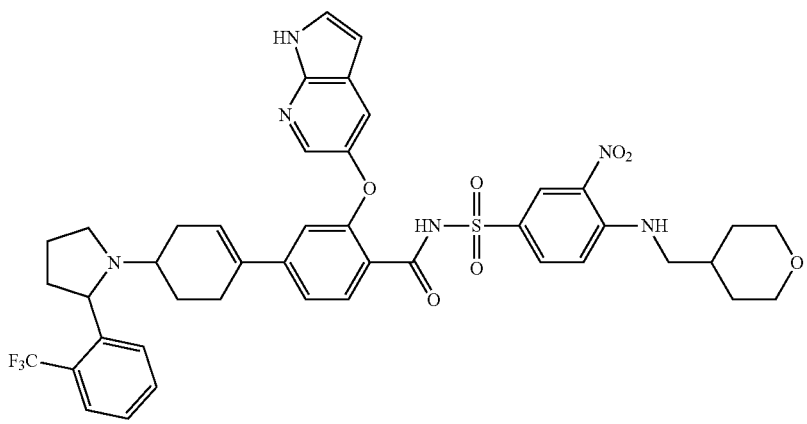 [SMILES: O=C(NS(=O)(=O)c1ccc(NCC2CCOCC2)c([N+](=O)[O-])c1)c1ccc(C2=CCC(N3CCCC3c3ccccc3C(F)(F)F)CC2)cc1Oc1cnc2[nH]ccc2c1]

The desired compound was synthesized with 2-(2-(trifluoromethyl)phenyl)pyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. ¹H NMR (400 MHz, DMSO-d₆) δ ppm: 12.21 (s, 1H), 11.60 (s, 1H), 8.43 (s, 2H), 8.01-7.82 (m, 2H), 7.78-7.58 (m, 3H), 7.50-7.26 (m, 4H), 7.07 (s, 1H), 6.92 (s, 1H), 6.71 (d, J=8.0 Hz, 1H), 6.33 (s, 1H), 5.99-5.72 (m, 1H), 4.24-4.06 (m, 2H), 3.84 (d, J=9.0 Hz, 2H), 3.28-3.14 (m, 5H), 2.62-2.56 (m, 1H), 2.40-2.10 (m, 4H), 1.94-1.82 (m, 2H), 1.7-1.68 (m, 2H), 1.62-1.56 (m, 2H), 1.45-1.35 (m, 2H), 1.30-1.18 (m, 2H), 0.95-0.83 (m, 1H). MS (ESI, m/e) [M+1]⁺ 845.1.

Example C11: 3-((1H-pyrrolo[2,3-b]pyridin-5-yl)oxy)-4'-(2-(naphthalen-1-yl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

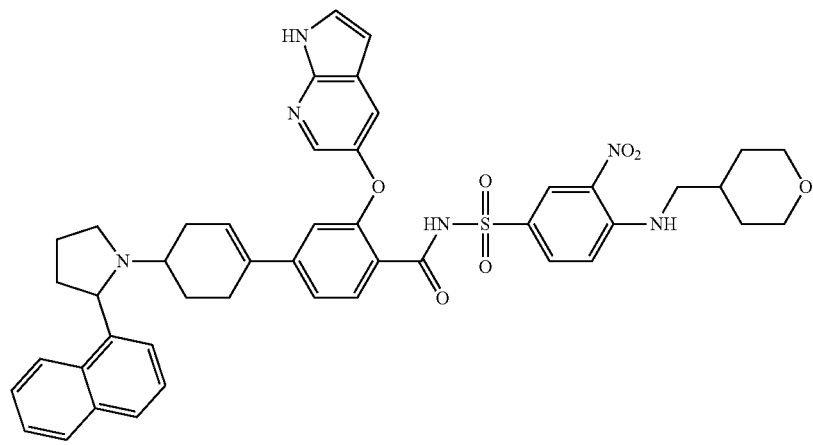 [SMILES: O=C(NS(=O)(=O)c1ccc(NCC2CCOCC2)c([N+](=O)[O-])c1)c1ccc(C2=CCC(N3CCCC3c3cccc4ccccc34)CC2)cc1Oc1cnc2[nH]ccc2c1]

The desired compound was synthesized with 2-(naphthalen-1-yl)pyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. ¹H NMR (400 MHz, DMSO-d₆) δ ppm: 9.61 (s, 1H), 8.90 (s, 1H), 8.53 (s, 1H), 8.25-7.35 (m, 11H), 7.10-6.85 (m, 2H), 6.65-6.40 (m, 2H), 6.02-5.60 (m, 1H), 4.50 (s, 1H), 4.12-3.92 (m, 2H), 3.52-3.14 (m, 5H), 2.82-2.52 (m, 2H), 2.40-1.91 (m, 7H), 1.87-1.54 (m, 6H), 1.49-1.34 (m, 2H). MS (ESI) m/e [M+1]⁺ 827.1

Example C12: 3-((1H-pyrrolo[2,3-b]pyridin-5-yl)oxy)-4'-(4,4-dimethyl-2-phenylpyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

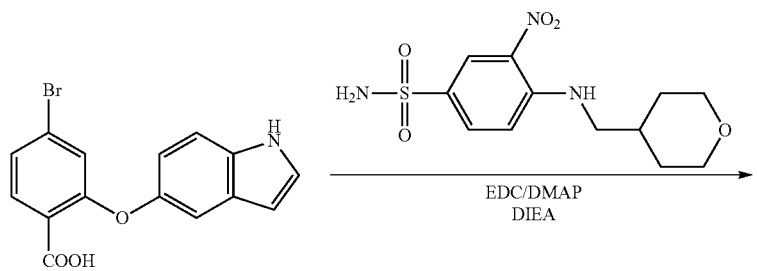

-continued
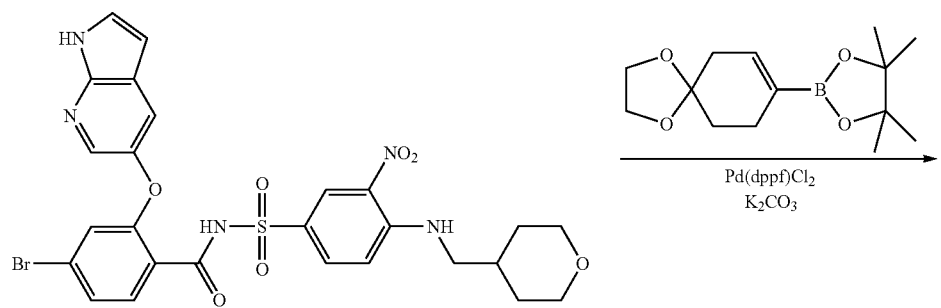
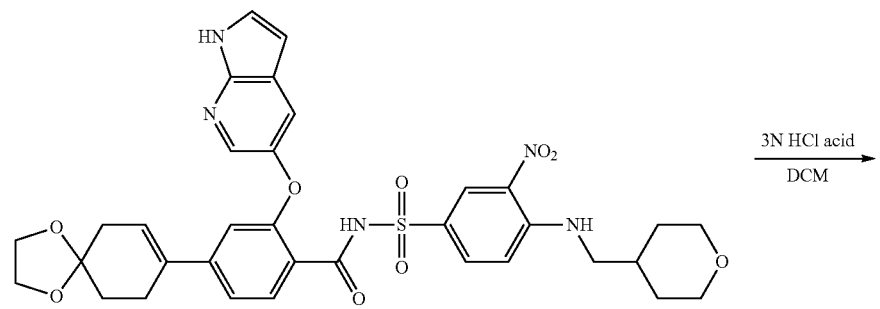
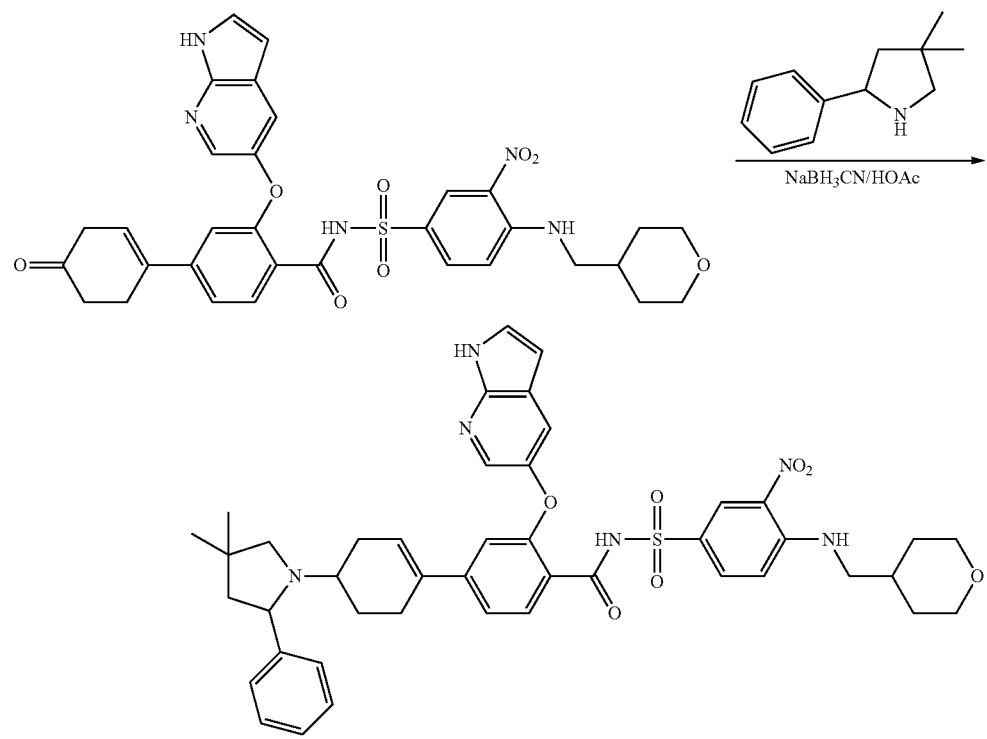
C12

Step 1: 2-((1H-pyrrolo[2,3-b]pyridin-5-yl)oxy)-4-bromo-N-((3-nitro-4-(((tetrahydro-2H-pyran-4-yl)methyl)amino)phenyl)sulfonyl)benzamide

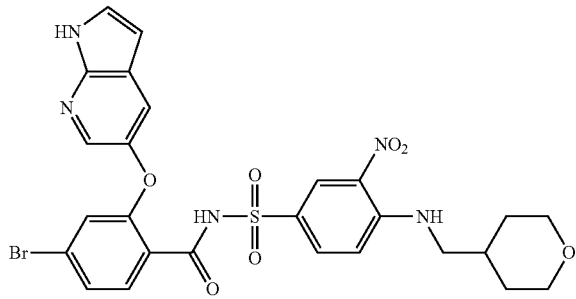 [SMILES: O=C(NS(=O)(=O)c1ccc(NCC2CCOCC2)c([N+](=O)[O-])c1)c1ccc(Br)cc1Oc1cnc2[nH]ccc2c1]

To a mixture of 2-((1H-pyrrolo[2,3-b]pyridin-5-yl)oxy)-4-bromobenzoic acid (6.6 g, 19.88 mol) in DCM (200 mL) were added 3-nitro-4-(((tetrahydro-2H-pyran-4-yl)methyl)amino)benzenesulfonamide (6.3 g, 19.88 mmol), EDCl (8.0 g, 41.75 mmol), DMAP (3.6 g, 29.82 mmol) and TFA (5.0 g, 49.70 mmol), the mixture was stirred at room temperature for about 2 days, 1 M HCl acid (100 mL) was added. The precipitate was filtered and dried under vacuum to give the product (9 g, 61.3%) as a yellow solid without further purification for next step, MS (ESI, m/e) [M+1]+ 630.0, 632.0.

Step 2: 2-((1H-pyrrolo[2,3-b]pyridin-5-yl)oxy)-N-((3-nitro-4-(((tetrahydro-2H-pyran-4-yl)methyl)amino)phenyl)sulfonyl)-4-(1,4-dioxaspiro[4.5]dec-7-en-8-yl)benzamide

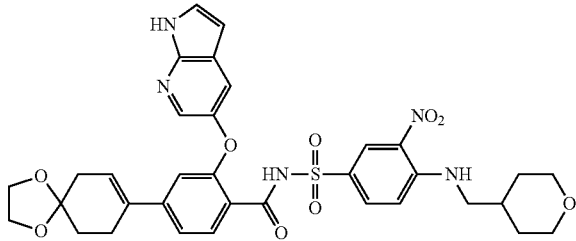 [SMILES: O=C(NS(=O)(=O)c1ccc(NCC2CCOCC2)c([N+](=O)[O-])c1)c1ccc(C2=CCC3(CC2)OCCO3)cc1Oc1cnc2[nH]ccc2c1]

A mixture of 2-((1H-pyrrolo[2,3-b]pyridin-5-yl)oxy)-4-bromo-N-((3-nitro-4-(((tetrahydro-2H-pyran-4-yl)methyl)amino)phenyl)sulfonyl)benzamide (100 mg, 0.16 mmol), 4,4,5,5-tetramethyl-2-(1,4-dioxaspiro[4.5]dec-7-en-8-yl)-1,3,2-dioxaborolane (64 mg, 0.24 mmol), Pd(dppf)Cl$_2$ (12 mg, 0.016 mmol) and K$_2$CO$_3$ (44 mg, 0.32 mmol) in dioxane (5 mL) and H$_2$O (0.5 mL) was stirred at 95° C. under N$_2$ overnight. It was cooled to r.t. and filtered off the inorganic salt. The filtrate was concentrated. The residue was purified by pre-TLC (MeOH/DCM=1/10) to give the desired product as a yellow solid (76 mg, 68%). $^1$H NMR (400 MHz, DMSO-d$_6$) δ 12.24 (s, 1H), 11.70 (s, 1H), 8.56-8.59 (m, 2H), 8.03 (s, 1H), 7.82 (d, J=8.3 Hz, 1H), 7.48-7.58 (m, 3H), 7.20 (d, J=7.9 Hz, 1H), 7.12 (d, J=7.9 Hz, 1H), 6.76 (s, 1H), 6.40 (s, 1H), 5.95 (s, 1H), 3.85 (s, 6H), 3.23-3.27 (m, 2H), 2.98 (s, 2H), 2.37 (s, 2H), 2.28 (s, 2H), 2.03-1.96 (m, 2H), 1.87 (s, 1H), 1.71 (t, J=6.2 Hz, 2H), 1.60 (d, J=12.4 Hz, 2H). MS (ESI, m/e) [M+1]+ 690.1.

Step 3: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-oxo-2',3',4',5'-tetrahydro-[1,1'-biphenyl]-4-carboxamide

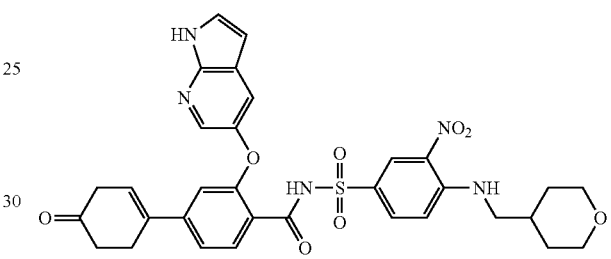

A solution of 2-((1H-pyrrolo[2,3-b]pyridin-5-yl)oxy)-N-((3-nitro-4-(((tetrahydro-2H-pyran-4-yl)methyl)amino)phenyl)sulfonyl)-4-(1,4-dioxaspiro[4.5]dec-7-en-8-yl)benzamide (76 mg, 0.11 mmol ) in DCM (5 mL) and 3 M HCl (1 mL) was stirred at room temperature overnight. It was diluted with DCM (20 mL) and neutralized with aq, NaHCO$_3$. The organic layer was dried over anhydrous Na$_2$SO$_4$, filtered and concentrated to give the desired product as a yellow solid (42 mg, 59%) without further purification for next step. MS (ESI, m/e) [M+1]+ 646.1.

Step 4: 3-((1H-pyrrolo[2,3-b]pyridin-5-yl)oxy)-4'-(4,4-dimethyl-2-phenylpyrrolidin-i-yl)-N-((3-nitro-4-(((tetrahydro-2H-pyran-4-yl)methyl)amino)phenyl)sulfonyl)-2',3',4',5'-tetrahydro-[1,1-biphenyl]-4-carboxamide

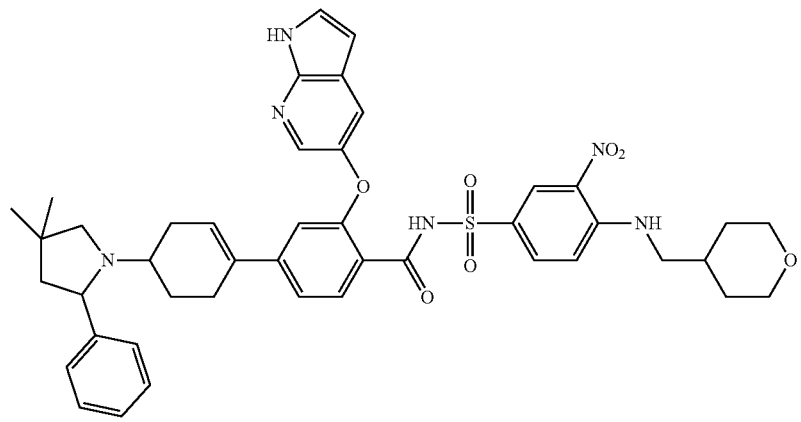 [SMILES: CC1(C)CC(c2ccccc2)N(C2CC=C(c3ccc(C(=O)NS(=O)(=O)c4ccc(NCC5CCOCC5)c([N+](=O)[O-])c4)c(Oc4cnc5[nH]ccc5c4)c3)CC2)C1]

A solution of 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-oxo-2',3',4',5'-tetrahydro-[1,1'-biphenyl]-4-carboxamide (32 mg, 0.05 mmol) and 4,4-dimethyl-2-phenylpyrrolidine (13 mg, 0,075 mmol) in THF was stirred at r.t. for 30 min, NaBH(OAc)$_3$ was added and stirred overnight. THF was removed and the residue was purified by pre-HPLC to give the desired product (5 mg, 12%). $^1$H NMR (400 MHz, DMSO-d$_6$) δ ppm: 12.28 (s, 1H), 11.72 (s, 1H), 9.79 (d, J=52.7 Hz, 1H), 8.61 (s, 1H), 8.54 (s, 1H), 8.00 (s, 1H), 7.81 (d, J=8.7 Hz, 1H), 7.61-7.63 (m, 2H), 7.54 (s, 2H), 7.36-7.44 (m, 3H), 7.22-7.10 (m, 2H), 6.72 (d, J=6.1 Hz, 1H), 6.66 (s, 1H), 6.39 (s, 1H), 5.98-5.88 (m, 1H), 4.94-4.78 (m, 1H), 3.84 (d, J=8.9 Hz, 2H), 3.22-3.27 (m, 5H), 2.99 (s, 5H), 2.28 (s, 1H), 1.97-2.07 (m, 4H), 1.86 (s, 1H), 1.59 (d, J=12.5 Hz, 2H), 1.45 (s, 1H), 1.24 (s, 6H). MS (ESI, m/e) [M+1]$^+$ 805.2.

Example C13: 3-((1H-pyrrolo[2,3-b]pyridin-5-yl)oxy)-4'-(2-(2,6-dichlorophenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

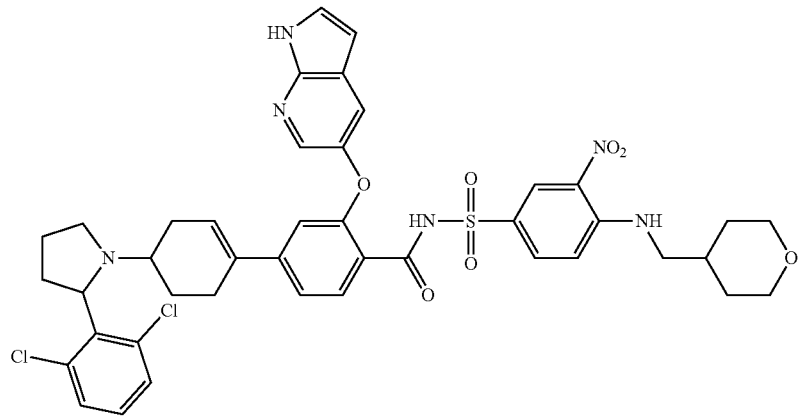 [SMILES: O=C(NS(=O)(=O)c1ccc(NCC2CCOCC2)c([N+](=O)[O-])c1)c1ccc(C2=CCC(N3CCCC3c3c(Cl)cccc3Cl)CC2)cc1Oc1cnc2[nH]ccc2c1]

The desired compound was synthesized with 2-(2,6-dichlorophenyl)pyrrolidine and 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-oxo-2',3',4',5'-tetrahydro-[1,1'-biphenyl]-4-carboxamide following the procedures similar to those in Example C12. $^1$H NMR (400 MHz, DMSO-d$_6$) δ ppm: 12.23 (br, 1H), 11.71 (br, 1H), 8.58-8.54 (m, 2H), 7.99 (s, 1H), 7.81 (d, J=8.0 Hz, 1H), 7.52-7.48 (m, 2H), 7.44 (d, J=8.0 Hz, 1H), 7.34-7.30 (m, 1H), 7.20-7.11 (m, 4H), 6.71 (d, J=16.0 Hz, 1H), 6.39 (s, 1H), 6.01-5.67 (m, 1H), 4.52-4.49 (m, 1H), 3.85 (d, J=8.0 Hz, 2H), 3.27-3.22 (m, 4H), 3.17-3.09 (m, 2H), 2.67-2.63 (m, 1H), 2.33-1.76 (m, 11H), 1.61 (d, J=12.0 Hz, 2H), 1.47-1.23 (m, 2H). MS (ESI, m/e) [M+1]$^+$ 845.1.

Example C14: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(2-propylphenyl)pyrrolidin-1-yl)-2',3',4',5'-tetrahydro-[1,1'-biphenyl]-4-carboxamide

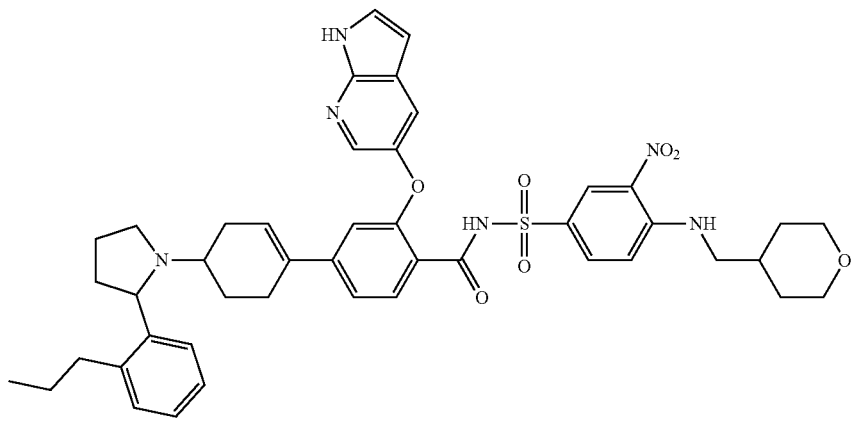 [SMILES: CCCc1ccccc1C1CCCN1C1CC=C(c2ccc(C(=O)NS(=O)(=O)c3ccc(NCC4CCOCC4)c([N+](=O)[O-])c3)c(Oc3cnc4[nH]ccc4c3)c2)CC1]

The desired compound was synthesized with 2-(2-propylphenyl)pyrrolidine and 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-oxo-2',3',4',5'-tetrahydro-[1,1'-biphenyl]-4-carboxamide following the procedures similar to those in Example C12. $^1$H NMR (400 MHz, DMSO-d$_6$) δ ppm: 12.24 (br, 0.5H), 11.65 (s, 1H), 9.34 (br, 0.5H), 8.49 (s, 2H), 7.96 (s, 1H), 7.79-7.67 (m, 1H), 7.55-7.40 (m, 4H), 7.33-7.21 (m, 3H), 7.15-6.96 (m, 3H), 7.72-6.67 (m, 1H), 6.35 (s, 1H), 5.98-5.82 (m, 1H), 4.74 (s, 1H), 3.84 (d, J=8.6 Hz, 2H), 3.28-3.22 (m, 4H), 3.05-2.84 (m, 2H), 2.20-2.07 (m, 2H), 2.02-1.97 (m, 2H), 1.91-1.78 (m, 2H), 1.76-1.64 (m, 2H), 1.62-1.28 (m, 7H), 0.99-0.81 (m, 6H). MS (ESI, m/e) [M+1]$^+$ 819.2.

Example C15: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(2-(thiophen-2-yl)phenyl)pyrrolidin-1-yl)-2',3',4',5'-tetrahydro-[1,1'-biphenyl]-4-carboxamide

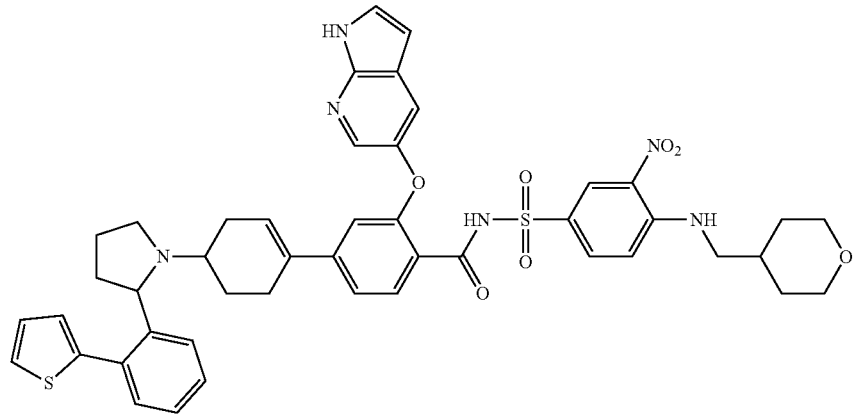 [SMILES: O=C(NS(=O)(=O)c1ccc(NCC2CCOCC2)c([N+](=O)[O-])c1)c1ccc(C2=CCC(N3CCCC3c3ccccc3-c3cccs3)CC2)cc1Oc1cnc2[nH]ccc2c1]

The desired compound was synthesized starting from 2-(2-(thiophen-2-yl)phenyl)pyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. $^1$H NMR (400 MHz, DMSO-d$_6$) δ ppm: 12.26 (s, 1H), 11.68 (s, 1H), 8.49-8.30 (m, 2H), 7.97 (s, 1H), 7.75 (d, J=7.9 Hz, 3H), 7.54-7.22 (m, 6H), 7.22-6.88 (m, 4H), 6.70 (d, J=3.7 Hz, 1H), 6.36 (s, 1H), 5.95-5.70 (m, 1H), 3.90-3.84 (m, 2H), 3.50-3.30 (m, 1H), 3.30-3.10 (m, 4H), 3.00-2.90 (m, 2H), 2.25-2.17 (m, 6H), 1.92-1.80 (m, 3H), 1.65-1.59 (m, 3H). 1.50-1.40 (m, 1H), 1.35-1.20 (m, 3H). MS (ESI, m/e) [M+1]$^+$ 859.1.

Example C16: 3-((1H-pyrrolo[2,3-b]pyridin-5-yl)oxy)-4'-(2-(2-benzylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1-biphenyl]-4-carboxamide

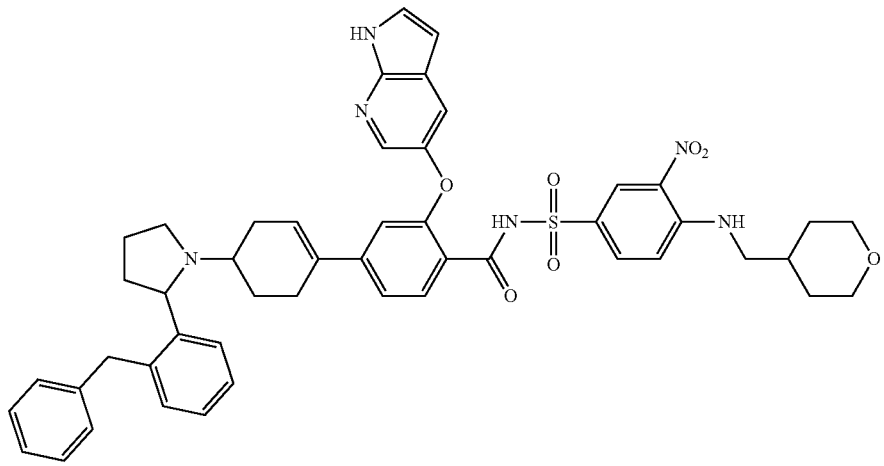 [SMILES: O=C(NS(=O)(=O)c1ccc(NCC2CCOCC2)c([N+](=O)[O-])c1)c1ccc(C2=CCC(N3CCCC3c3ccccc3Cc3ccccc3)CC2)cc1Oc1cnc2[nH]ccc2c1]

The desired compound was synthesized with 2-(2-benzylphenyl)pyrrolidine and 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-oxo-2',3',4',5'-tetrahydro-[1,1'-biphenyl]-4-carboxamide following the procedures similar to those in Example C12. $^{1}$H NMR (400 MHz, DMSO-$d_6$) δ ppm: 12.22 (s, 1H), 11.71 (s, 1H), 8.52 (s, 2H), 8.01 (s, 1H), 7.79 (s, 1H), 7.36-7.56 (m, 5H), 6.88-7.08 (m, 9H), 6.59 (s, 1H), 6.40 (s, 1H), 5.75 (s, 1H), 3.93-4.04 (m, 2H), 3.83-3.85 (m, 3H), 3.22-3.27 (m, 5H), 3.02 (s, 2H), 2.46-2.36 (m, 1H), 2.28-2.07 (m, 2H), 2.04-1.96 (m, 2H), 1.86 (s, 2H), 1.59 (d, J=12.3 Hz, 5H), 1.23-1.28 (m, 2H). MS (ESI, m/e) [M+1]$^{+}$ 867.2

Example C17: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(pyridin-4-yl)pyrrolidin-1-yl)-2',3',4',5'-tetrahydro-[1,1'-biphenyl]-4-carboxamide

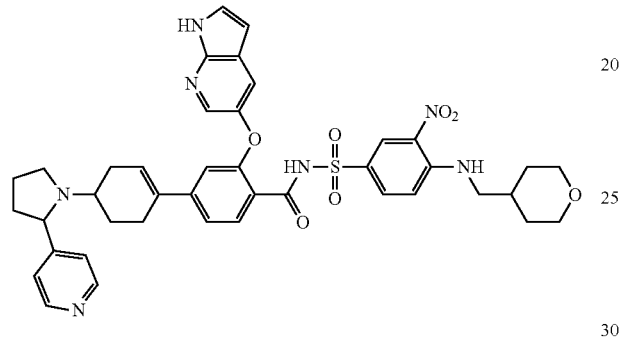

The desired compound was synthesized with 4-(pyrrolidin-2-yl)pyridine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. $^{1}$H NMR (400 MHz, DMSO-$d_6$) δ ppm: 12.14 (s, 1H), 11.67 (s, 1H), 8.53-8.46 (m, 4H), 7.97 (d, J=2.2 Hz, 1H), 7.76 (d, J=8.8 Hz, 1H), 7.58-7.29 (m, 5H), 7.12 (d, J=8.0 Hz, 1H), 7.03 (d, J=8.8 Hz, 1H), 6.71 (s, 1H), 6.36 (s, 1H), 5.99 (s, 1H), 3.84 (d, J=8.4 Hz, 2H), 3.25-3.22 (m, 5H), 2.33-2.08 (m, 4H), 1.91-1.76 (m, 4H), 1.61-1.53 (m, 3H), 1.50-1.43 (m, 1H), 1.31-1.18 (m, 6H). MS (ESI, m/e) [M+1]$^{+}$ 778.2.

Example C18: 3-((1H-pyrrolo[2,3-b]pyridin-5-yl)oxy)-4'-(2-(2-isopropylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

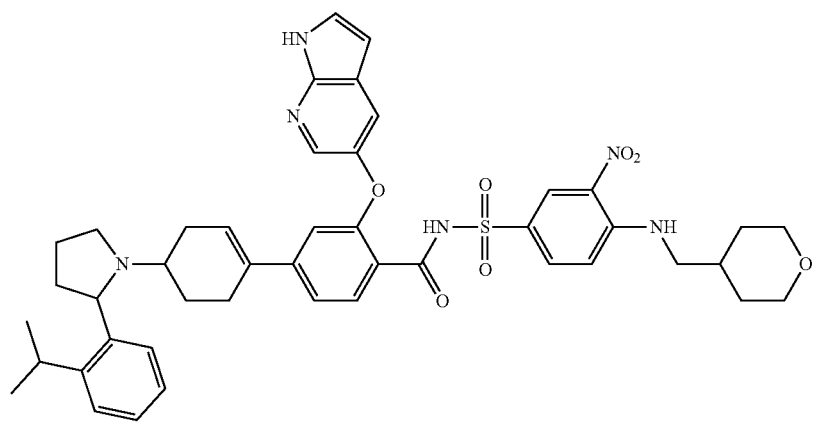 [SMILES: CC(C)c1ccccc1C1CCCN1C1CC=C(c2ccc(C(=O)NS(=O)(=O)c3ccc(NCC4CCOCC4)c([N+](=O)[O-])c3)c(Oc3cnc4[nH]ccc4c3)c2)CC1]

The desired compound was synthesized with 2-(2-isopropylphenyl)pyrrolidine and 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-oxo-2',3',4',5'-tetrahydro-[1,1'-biphenyl]-4-carboxamide following the procedure similar to those in Example C12. $^{1}$H NMR (400 MHz, DMSO-d$_6$) δ ppm: 12.27 (s, 1H), 11.71 (s, 1H), 9.480 (s, 0.5H), 9.283 (s, 0.5H), 8.60 (s, 1H), 8.54 (s, 1H), 7.99 (s, 1H), 7.80 (d, J=9.0 Hz, 1H), 7.61 (d, J=7.5 Hz, 1H), 7.52 (s, 2H), 7.48 (d, J=8.0 Hz, 1H), 7.22-7.42 (m, 3H), 7.16 (d, J=8.0 Hz, 1H), 7.11 (d, J=9.0 Hz, 1H), 6.73 (s, 1H), 6.38 (s, 1H), 5.98-5.84 (m, 1H), 5.11-4.94 (m, 1H), 3.84 (d, J=8.6 Hz, 2H), 3.63-3.70 (m, 1H), 3.20-3.32 (m, 7H), 3.00-2.93 (m, 2H), 2.42-2.38 (m, 1H), 2.28-2.20 (m, 1H), 2.12-2.16 (m, 2H), 1.96-2.20 (m, 1H), 1.83-1.91 (m, 2H), 1.59 (d, J=12.0 Hz, 2H), 1.19-1.22 (m, 7H), 1.13 (d, J=6.6 Hz, 3H), MS (ESI, m/e) [M+1]$^{+}$ 819.2.

Example C19: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(2-(prop-1-en-2-yl)phenyl)pyrrolidin-1-yl)-2',3',4',5'-tetrahydro-[1,1'-biphenyl]-4-carboxamide

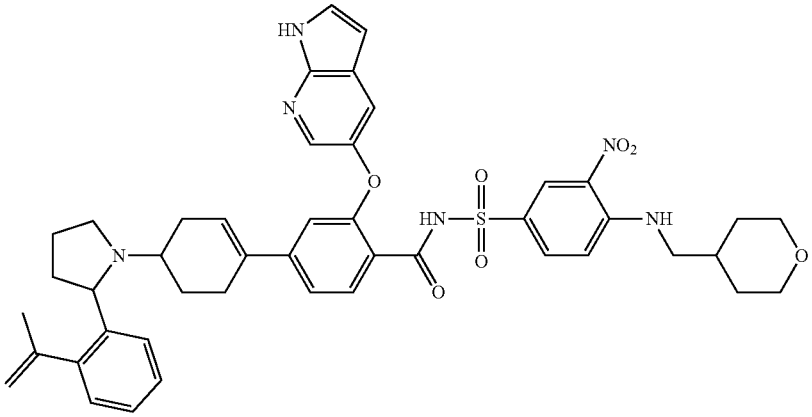 [SMILES: C=C(C)c1ccccc1C1CCCN1C1CC=C(c2ccc(C(=O)NS(=O)(=O)c3ccc(NCC4CCOCC4)c([N+](=O)[O-])c3)c(Oc3cnc4[nH]ccc4c3)c2)CC1]

The desired compound was synthesized with 2-(2-(prop-1-en-2-yl)phenyl)pyrrolidine and 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-oxo-2',3',4',5'-tetrahydro-[1,1'-biphenyl]-4-carboxamide following the procedure similar to those in Example C12. $^{1}$H NMR (400 MHz, DMSO-d$_6$) δ 12.25 (s, 1H), 11.64 (s, 1H), 8.48 (s, 1H), 7.98-7.94 (m, 1H), 7.80-7.70 (m, 1H), 7.47-7.45 (m, 4H), 7.12-7.00 (m, 4H), 6.73 (s, 1H), 6.35 (s, 1H), 5.98-5.82 (m, 0.5H), 5.22 (s, 0.5H), 4.90-4.60 (m, 2H), 4.10-3.84 (m, 2H), 3.28-3.22 (m, 4H), 3.20-3.15 (m, 2H), 2.30-2.10 (m, 4H), 1.99-1.90 (m, 6H), 1.88-1.80 (m, 2H), 1.75-1.70 (m, 2H), 1.65-1.55 (m, 2H), 1.50-1.40 (m, 1H), 1.30-1.20 (m, 4H). MS (ESI, m/e) [M+1]$^{+}$ 817.2.

Example C21: 3-((1H-pyrrolo[2,3-b]pyridin-5-yl)oxy)-4'-(2-(2-isobutylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

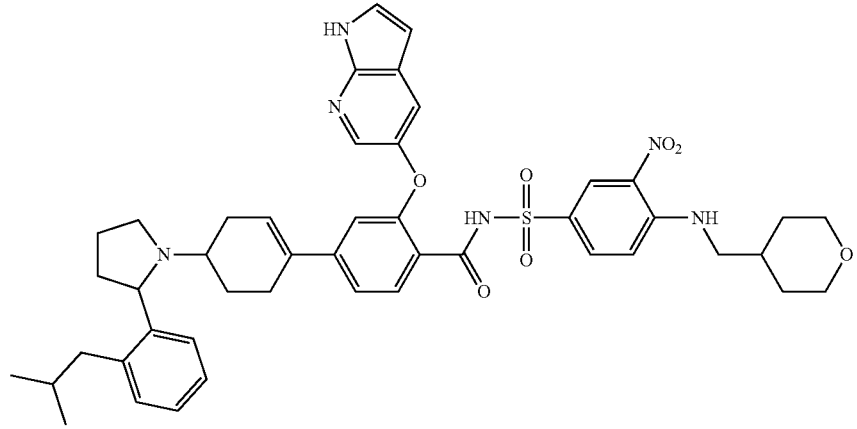

The desired compound was synthesized with 2-(2-isobutylphenyl)pyrrolidine and 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-oxo-2',3',4',5'-tetrahydro-[1,1'-biphenyl]-4-carboxamide following the procedure similar to those in Example C12. MS (ESI, m/e) [M+1]⁺ 832.8.

Example C22: 3-((1H-pyrrolo[2,3-b]pyridin-5-yl)oxy)-4'-(2-(2-(cyclopropylmethyl)phenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

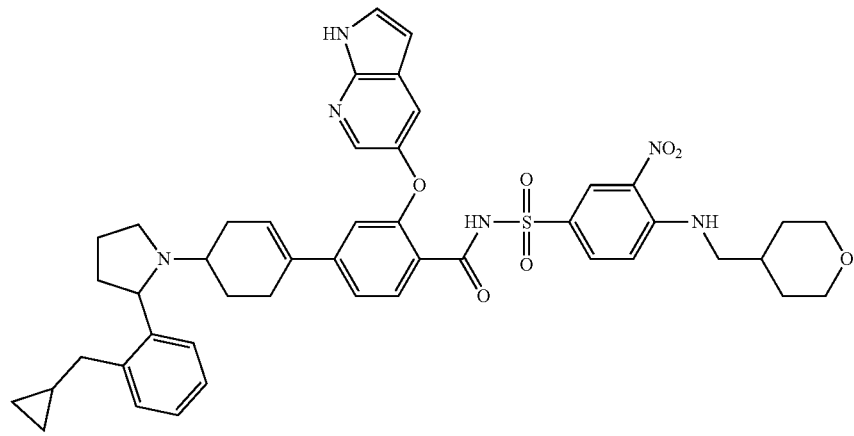 [SMILES: O=C(NS(=O)(=O)c1ccc(NCC2CCOCC2)c([N+](=O)[O-])c1)c1ccc(C2=CCC(N3CCCC3c3ccccc3CC3CC3)CC2)cc1Oc1cnc2[nH]ccc2c1]

The desired compound was synthesized with 2-(2-(cyclopropylmethyl)phenyl)pyrrolidine and 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-oxo-2',3',4',5'-tetrahydro-[1,1'-biphenyl]-4-carboxamide following the procedure similar to those in Example C12, MS (ESI, m/e) [M+1]⁺ 830.8.

Example C26a and C26b: cis- or trans-3-((1H-pyrrolo[2,3-b]pyridin-5-yl)oxy)-4'-(2-(2-(2-cyanocyclopropyl)phenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide/trans- or cis-3-((1H-pyrrolo[2,3-b]pyridin-5-yl)oxy)-4'-(2-(2-(2-cyanocyclopropyl)phenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

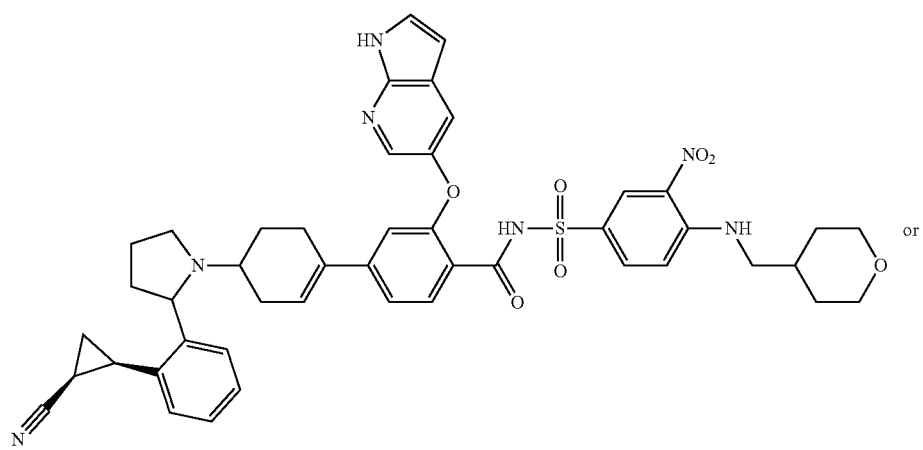

or

-continued

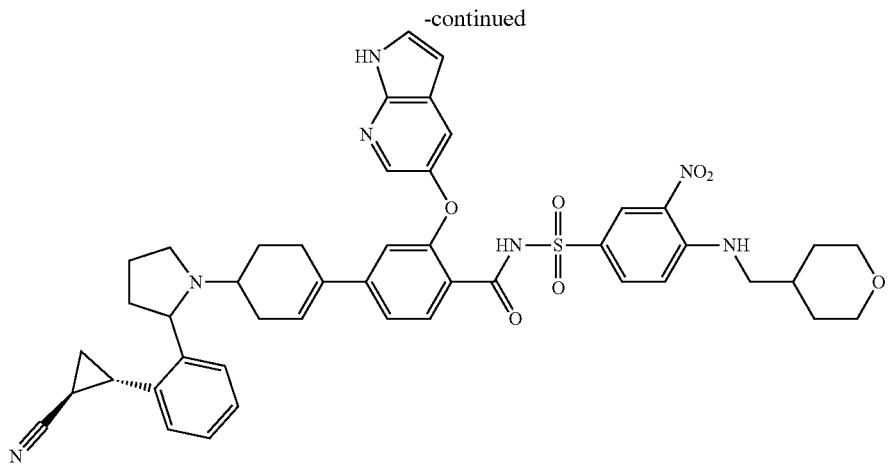

C24a was synthesized with cis- or trans-2-(2-(pyrrolidin-2-yl)phenyl)cyclopropane-1-carbonitrile (faster peak in HPLC) and 3-((1H-pyrrolo[2,3-b]pyridin-5-yl)oxy)-N-((3-nitro-4-(((tetrahydro-2H-pyran-4-yl) methyl)amino)phenyl)sulfonyl)-4'-oxo-2',3',4',5'-tetrahydro-[1,1'-biphenyl]-4-carboxamide following the procedure similar to those in Example C12. $^1$H NMR (400 MHz, DMSO-d$_6$) δ ppm: 12.22 (s, 1H), 11.67 (s, 1H), 8.51 (s, 2H), 7.98 (s, 1H), 7.75 (s, 1H), 7.64-7.58 (m, 1H), 7.55-7.38 (m, 4H), 7.20-7.12 (m, 4H), 6.70-6.66 (m, 2H), 6.36 (s, 1H), 5.99-5.82 (m, 1H), 4.19 (s, 1H), 3.84 (d, J=8.8 Hz, 2H), 3.28-3.22 (m, 5H), 2.98 (s, 3H), 2.75-2.67 (m, 1H), 2.26-2.18 (s, 5H), 2.01-1.97 (m, 5H), 1.73 (s, 2H), 1.59 (d, J=12.5 Hz, 2H), 1.45 (s, 2H), 0.91-0.84 (m, 2H). MS (ESI, m/e) [M+1]$^+$ 841.8. With trans- or cis-2-(2-(pyrrolidin-2-yl)phenyl)cyclopropane-1-carbonitrile (slower peak in HPLC) was C24b synthesized. MS (ESI, m/e) [M+1]$^+$ 841.8.

Example C26a and C26 h: 3-((1H-pyrrolo[2,3-b]pyridin-5-yl)oxy)-4'-(2-(2-((S or R)-2,2-difluorocyclopropyl)phenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide/3-((1H-pyrrolo[2,3-b]pyridin-5-yl)oxy)-4'-(2-(2-((R or S)-2,2-difluorocyclopropyl)phenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

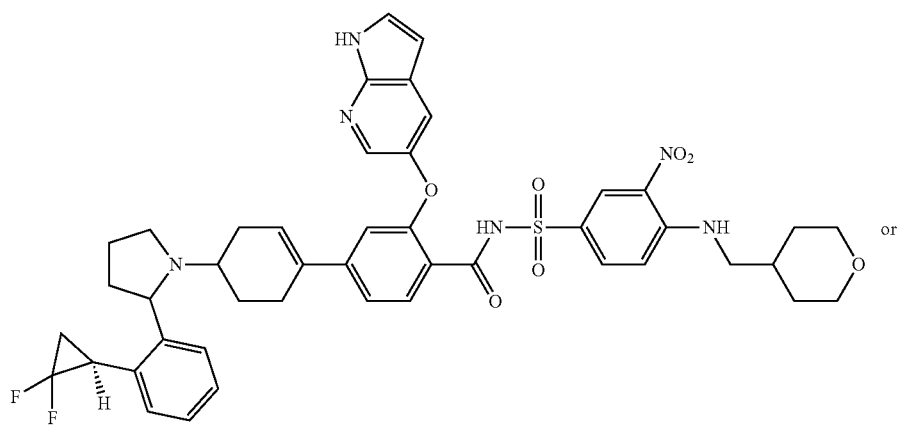

or

-continued

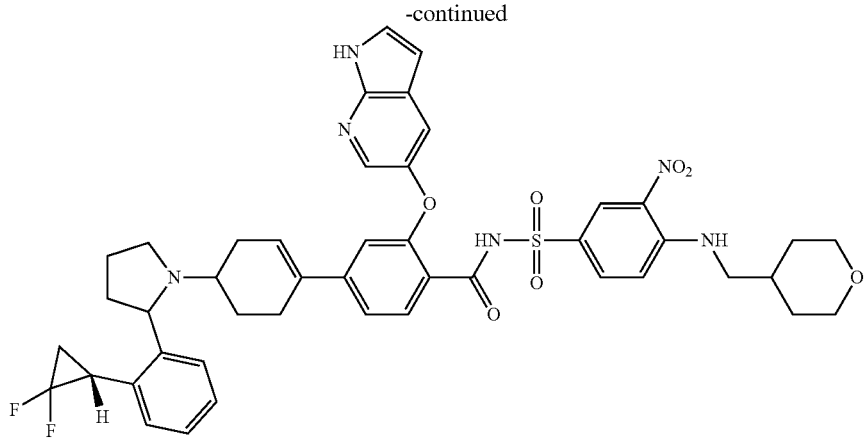

The desired compound 26a was synthesized with 2-(2-((S or R)-2,2-difluorocyclopropyl)phenyl)pyrrolidine (faster peak in HPLC) and 3-((1H-pyrrolo[2,3-b]pyridin-5-yl)oxy)-N-((3-nitro-4-(((tetrahydro-2H-pyran-4-yl) meth yl)amino) phenyl)sulfonyl)-4'-oxo-2',3',4',5'-tetrahydro-[1,1'-biphenyl]-4-carboxamide following the procedure similar to those in Example C12. $^1$H NMR (DMSO-d$_6$) δ ppm: 12.23 (s, 1H), 11.68 (s, 1H), 8.65-8.42 (m, 2H), 7.98 (s, 1H), 7.77 (s, 1H), 7.63-7.39 (m, 4H), 7.27-7.00 (m, 5H), 6.76-6.54 (m, 1H), 6.37 (s, 1H), 6.07-5.70 (m, 1H), 4.01 (s, 1H), 3.91-3.76 (m, 2H), 3.27-3.19 (m, 4H), 3.17-3.04 (m, 2H), 3.01-2.89 (m, 1H), 2.29-2.09 (m, 3H), 2.06-1.83 (m, 5H), 1.78-1.69 (m, 2H), 1.64-1.54 (m, 2H), 1.47-1.34 (m, 2H), 1.31-1.24 (m, 3H). MS (ESI) m/e [M+1]$^+$ 852.7. With 2-(2-((R or S)-2,2-difluorocyclopropyl)phenyl)pyrrolidine (slower peak in HPLC), 26b was synthesized. MS (ESI, m/e) [M+1]$^+$ 852.7.

Example C28: 3-((1H-pyrrolo[2,3-b]pyridin-5-yl)oxy)-4'-(2-(2-cyclobutylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

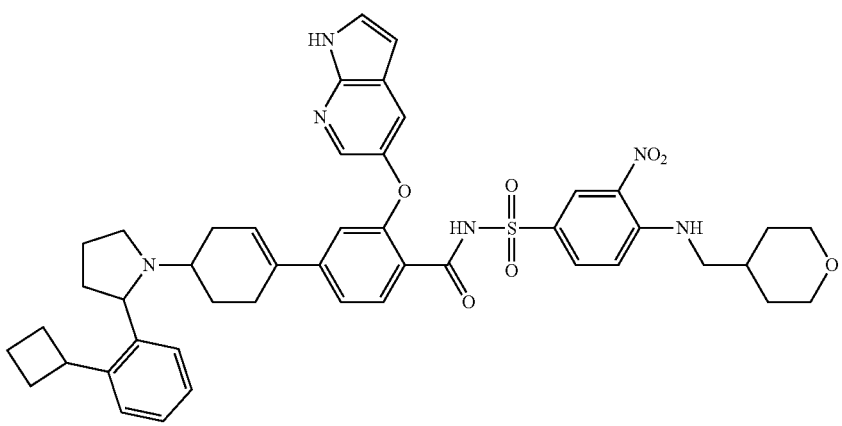 [SMILES: O=C(NS(=O)(=O)c1ccc(NCC2CCOCC2)c([N+](=O)[O-])c1)c1ccc(C2=CCC(N3CCCC3c3ccccc3C3CCC3)CC2)cc1Oc1cnc2[nH]ccc2c1]

The desired compound was synthesized with 2-(2-cyclobutylphenyl)pyrrolidine and 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-oxo-2',3',4',5'-tetrahydro-[1,1'-biphenyl]-4-carboxamide following the procedure similar to those in Example C12. $^1$H NMR (400 MHz, DMSO-d$_6$) δ 12.22 (s, 1H), 11.64 (s, 1H), 8.60-8.40 (m, 2H), 7.96 (s, 1H), 7.85-7.65 (m, 1H), 7.60-7.40 (m, 4H), 7.35-7.15 (m, 2H), 7.11 (d, J=8.0 Hz, 1H), 7.05-6.90 (m, 2H), 6.72 (s, 1H), 6.35 (s, 1H), 5.98 (s, 0.5H), 5.79 (s, 0.5H), 3.88-3.80 (m, 3H), 3.75-3.60 (m, 1H), 3.30-3.20 (m, 5H), 3.15-2.85 (m, 2H), 2.41-1.91 (m, 10H), 1.90-1.64 (m, 5H), 1.59 (d, J=12.4 Hz, 2H), 1.55-1.40 (m, 1H), 1.35-1.15 (m, 3H). MS (ESI, m/e) [M+1]$^+$ 830.9.

Example C31: 3-((1H-pyrrolo[2,3-b]pyridin-5-yl)oxy)-4'-(2-(2-(dimethylamino)phenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

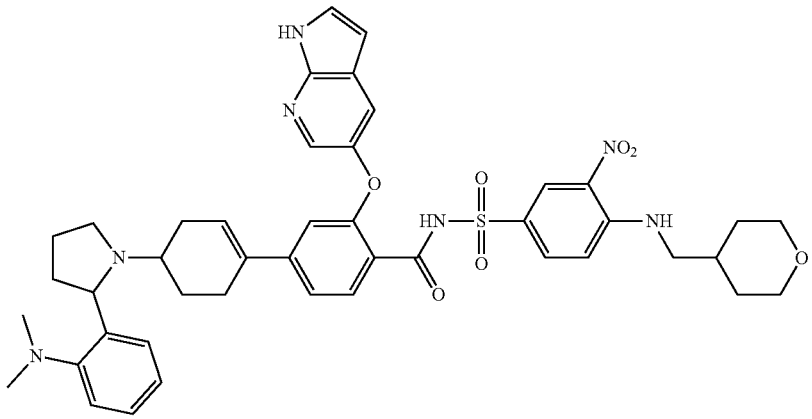

The desired compound was synthesized with N,N-dimethyl-2-(pyrrolidin-2-yl)aniline and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. $^1$H NMR (400 MHz, DMSO-d$_6$) δ 11.60 (s, 1H), 8.42 (s, 2H), 7.93 (s, 1H), 7.73-7.63 (m, 1H), 7.62-7.51 (m, 1H), 7.51-7.41 (m, 2H), 7.39-7.29 (m, 1H), 7.12-7.01 (m, 1H), 6.96-6.81 (m, 1H), 6.79-6.66 (m, 1H), 6.38-6.27 (m, 1H), 6.02-5.77 (m, 1H), 3.92-3.77 (m, 2H), 3.27-3.13 (m, 6H), 2.67-3.55 (m, 7H), 2.32-2.22 (m, 3H), 2.13-1.95 (m, 4H), 1.91-1.79 (m, 2H), 1.67-1.52 (m, 4H), 1.33-1.24 (m, 6H). MS (ESI) m/e [M+1]$^+$ 802.8.

Example C36: 3-((1H-pyrrolo[2,3-b]pyridin-5-yl)oxy)-4'-(2-(2-(difluoromethoxy)phenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

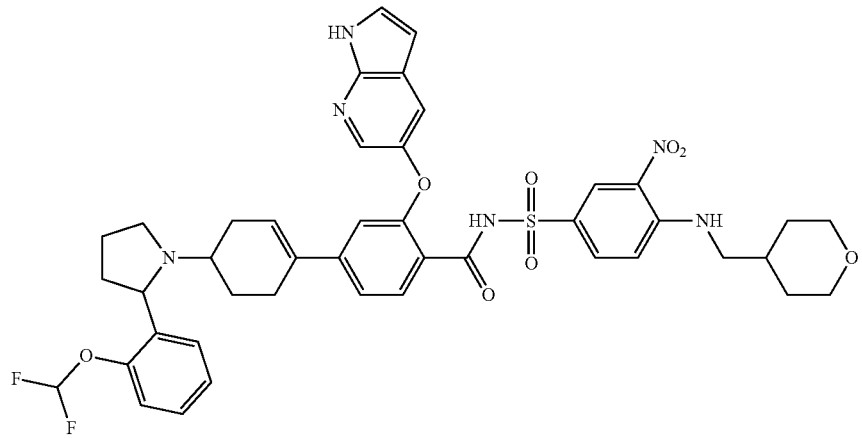 [SMILES: O=C(NS(=O)(=O)c1ccc(NCC2CCOCC2)c([N+](=O)[O-])c1)c1ccc(C2=CCC(N3CCCC3c3ccccc3OC(F)F)CC2)cc1Oc1cnc2[nH]ccc2c1]

The desired compound was synthesized with 2-(2-(difluoromethoxy)phenyl) pyrrolidine and 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-oxo-2',3',4',5'-tetrahydro-[1,1'-biphenyl]-4-carboxamide following the procedure similar to those in Example C12. $^1$H NMR (400 MHz, DMSO-$d_6$) δ 12.24 (s, 1H), 11.68 (s, 1H), 8.60-8.45 (m, 2H), 8.05-7.95 (m, 1H), 7.85-7.70 (m, 2H), 7.60-7.37 (m, 3H), 7.30-6.90 (m, 5H), 6.72 (s, 1H), 6.37 (s, 1H), 6.01 (s, 0.5H), 5.81 (s, 0.5H), 4.20-4.00 (m, 1H), 3.98-3.71 (m, 2H), 3.35-3.20 (m, 5H), 2.65-2.55 (m, 2H), 2.40-2.00 (m, 6H), 1.95-1.80 (m, 2H), 1.75-1.65 (m, 2H), 1.65-1.55 (m, 2H), 1.45-1.35 (m, 1H), 1.35-1.20 (m, 3H ). MS (ESI, m/e) [M+1]$^+$ 842.8.

Example C37: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(2-(trifluoromethoxy)phenyl)pyrrolidin-1-yl)-2',3',4',5'-tetrahydro-[1,1'-biphenyl]-4-carboxamide

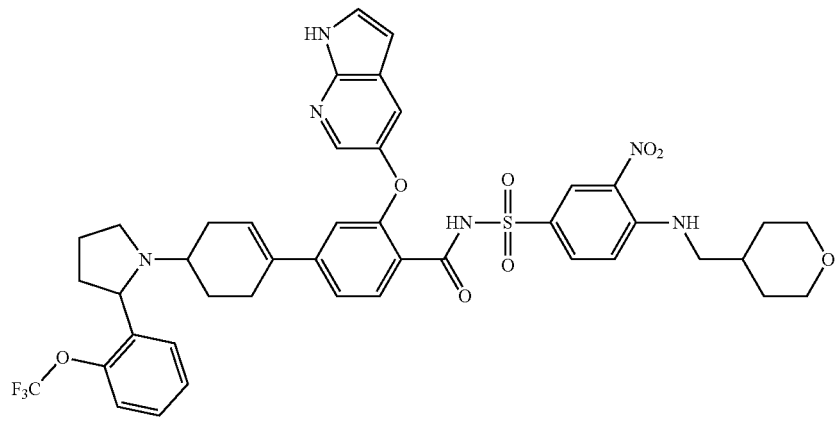

The desired compound was synthesized with 2-(2-(trifluoromethoxy)phenyl)pyrrolidine and 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-oxo-2',3',4',5'-tetrahydro[1,1'-biphenyl]-4-carboxamide following the procedure similar to those in Example C12. $^1$H NMR (400 MHz, DMSO-$d_6$) δ ppm: 12.35 (s, 1H), 11.63 (s, 1H), 8.46 (s, 2H), 7.96 (s, 1H), 7.75-7.63 (m, 2H), 7.50-7.47 (m, 2H), 7.36-7.15 (m, 4H), 7.10 (d, J=7.2 Hz, 1H), 6.96 (s, 1H), 6.72 (d, J=12 Hz, 1H), 6.35 (s, 1H), 6.00-5.78 (m, 1H), 4.07 (s, 1H), 3.84 (d, J=8.4 Hz, 2H), 3.29-3.22 (m, 4H), 3.17-3.08 (m, 1H), 2.62-2.53 (m, 2H), 2.36-2.28 (m, 1H), 2.25-2.10 (m, 3H), 1.93-1.80 (m, 2H), 1.78-1.65 (m, 3H), 1.62-1.58 (m, 2H), 1.50-1.37 (m, 2H), 1.33-1.27 (m, 2H). MS (ESI, m/e) [M+1]$^+$ 861.1.

Example C39: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(2-propoxyphenyl)pyrrolidin-1-yl)-2',3',4',5'-tetrahydro-[1,1'-biphenyl]M-carboxamide

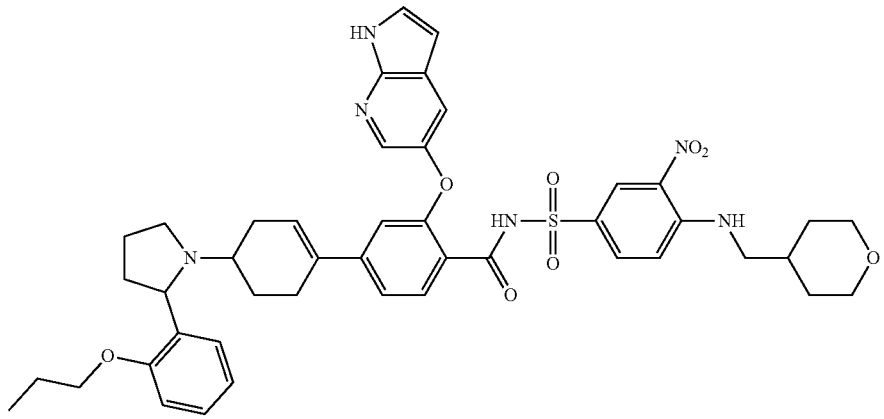 [SMILES: CCCOc1ccccc1C1CCCN1C1CC=C(c2ccc(C(=O)NS(=O)(=O)c3ccc(NCC4CCOCC4)c([N+](=O)[O-])c3)c(Oc3cnc4[nH]ccc4c3)c2)CC1]

The desired compound was synthesized starting from 2-(2-propoxyphenyl)pyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. $^1$H NMR (400 MHz, DMSO-$d_6$) δ ppm: 11.59 (s, 1H), 8.50-8.35 (m, 2H), 7.95-7.90 (m, 1H), 7.75-7.65 (m, 1H), 7.57-7.41 (m, 3H), 7.37-7.30 (m, 1H), 7.12-7.05 (m, 1H), 6.95-6.85 (m, 3H), 6.75-6.70 (m, 1H), 6.38-6.30 (m, 1H), 5.98-5.80 (m, 1H), 5.78-5.75 (m, 1H), 5.76 (s, 1H), 4.10 (q, J=5.2 Hz, 2H), 4.00-3.90 (m, 2H), 3.88-3.75 (m, 2H), 3.30-3.25 (m, 5H), 3.20-3.15 (m, 3H), 2.40-2.25 (m, 3H), 2.20-1.90 (m, 3H), 1.88-1.80 (m, 2H), 1.76-1.66 (m, 2H), 1.65-1.55 (m, 2H), 1.36-1.13 (m, 3H), 0.95 (t, J=7.3 Hz, 3H), MS (ESI, m/e) [M+1]$^+$ 835.2.

Example C40: 3-((1H-pyrrolo[2,3-b]pyridin-5-yl)oxy)-4'-(2-(2-(2-methoxyethoxy)phenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

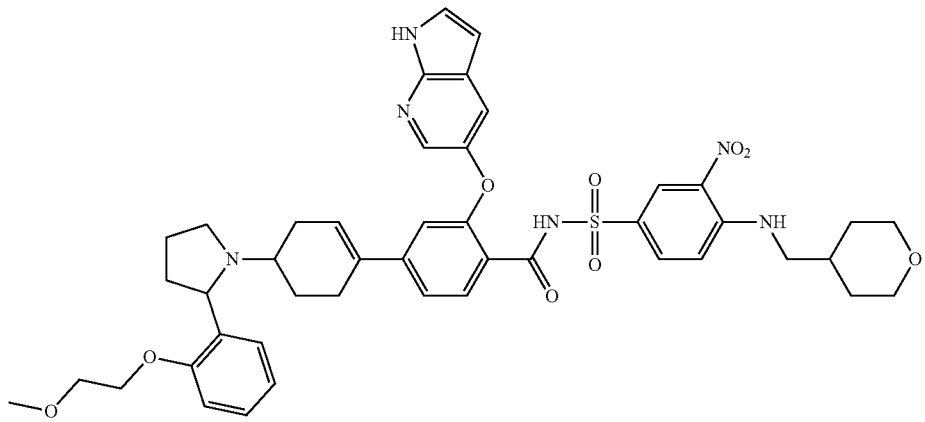 [SMILES: COCCOc1ccccc1C1CCCN1C1CC=C(c2ccc(C(=O)NS(=O)(=O)c3ccc(NCC4CCOCC4)c([N+](=O)[O-])c3)c(Oc3cnc4[nH]ccc4c3)c2)CC1]

The desired compound was synthesized with 2-(2-(2-methoxyethoxy)phenyl)pyrrolidine and 3-((1H-pyrrolo[2,3-h]pyridin-5-yl)oxy)-N-((3-nitro-4-(((tetrahydro-2H-pyran-4-yl)methyl)amino)phenyl)sulfonyl)-4'-oxo-2',3',4',5'-tetrahydro-[1,1'-biphenyl]-4-carboxamide following the procedure similar to those in Example C12. $^1$H NMR (400 MHz, DMSO-$d_6$) δ ppm: 11.59 (s, 1H), 8.50-8.33 (m, 2H), 7.94 (s, 1H), 7.68 (d, J=8.6 Hz, 1H), 7.60-7.44 (m, 3H), 7.40-7.38 (m, 1H), 7.15-7.05 (m, 2H), 7.00-6.85 (m, 3H), 6.70 (s, 1H), 6.33 (s, 1H), 5.97-5.85 (m, 1H), 4.30-4.10 (m, 2H), 3.90-3.80 (m, 2H), 3.75-3.65 (m, 2H), 3.27-3.15 (m, 9H), 2.40-2.10 (m, 7H), 1.90-1.80 (m, 2H), 1.70-1.50 (m, 4H), 1.45-1.35 (m, 1H), 1.32-1.14 (m, 3H). MS (ESI, m/e) [M+1]$^+$ 851.2.

Example C41: 3-((1H-pyrrolo[2,3-b]pyridin-5-yl)oxy)-4'-(2-(2-isopropoxyphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

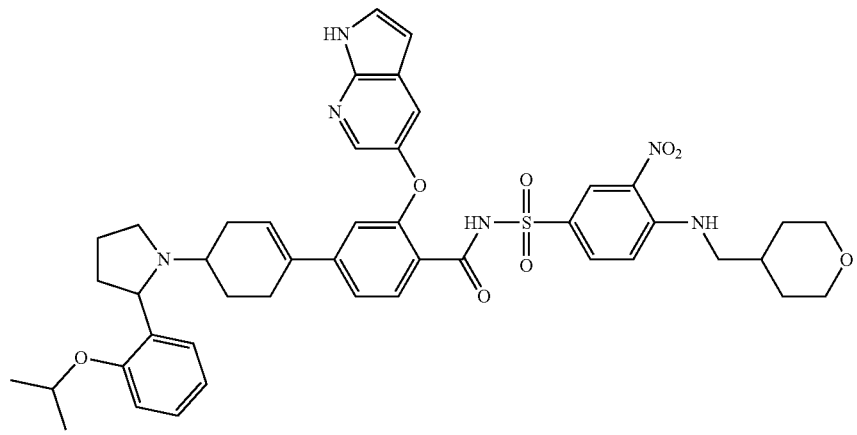 [SMILES: CC(C)Oc1ccccc1C1CCCN1C1CC=C(c2ccc(C(=O)NS(=O)(=O)c3ccc(NCC4CCOCC4)c([N+](=O)[O-])c3)c(Oc3cnc4[nH]ccc4c3)c2)CC1]

The desired compound was synthesized with 2-(2-isopropoxyphenyl)pyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. $^1$H NMR (400 MHz, DMSO-d$_6$) δ 12.28 (s, 1H), 11.74 (s, 1H), 8.66-8.52 (m, 2H), 8.02 (s, 1H), 7.82 (d, J=9.1 Hz, 1H), 7.71-7.46 (m, 4H), 7.40-7.30 (m, 1H), 7.25-7.06 (m, 3H), 7.05-6.95 (m, 1H), 6.71 (s, 1H), 6.40 (s, 1H), 6.01 (s, 0.5H), 5.93 (s, 0.5H), 5.05-4.90 (m, 1H), 4.76-4.57 (m, 1H), 3.85 (d, J=10.6 Hz, 2H), 3.31-3.15 (m, 5H), 2.40-2.20 (m, 4H), 2.18-2.05 (m, 4H), 2.00-1.85 (m, 2H), 1.70-1.55 (m, 3H), 1.35-1.15 (m, 10H). MS (ESI) m/e [M+1]$^+$ 834.8.

Example C42: 3-((1H-pyrrolo[2,3-b]pyridin-5-yl)oxy)-4'-(2-(2-cyclopropoxyphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

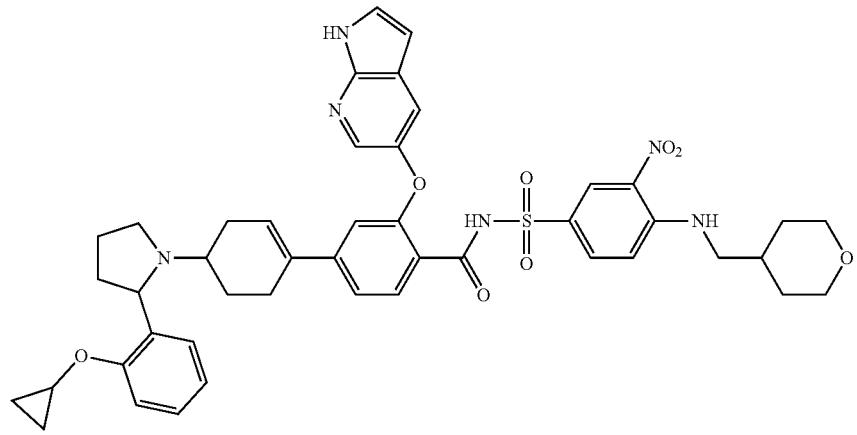 [SMILES: O=C(NS(=O)(=O)c1ccc(NCC2CCOCC2)c([N+](=O)[O-])c1)c1ccc(C2=CCC(N3CCCC3c3ccccc3OC3CC3)CC2)cc1Oc1cnc2[nH]ccc2c1]

The desired compound was synthesized with 2-(2-cyclopropoxyphenyl)pyrrolidine and 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-oxo-2',3',4',5'-tetrahydro-[1,1'-biphenyl]-4-carboxamide following the procedure similar to those in Example C12. $^1$H-NMR (400 MHz, d6-DMSO) δ ppm: 12.28 (s, 1H), 11.71 (s, 1H), 8.60-8.52 (m, 2H), 8.00 (s, 1H), 7.92-7.77 (m, 2H), 7.50-7.48 (m, 3H), 7.43-7.32 (m, 2H), 7.16 (d, J=7.4 Hz, 1H), 7.06 (d, J=7.4 Hz, 1H), 7.05-7.02 (m, 1H), 6.74 (s, 1H), 6.39 (s, 1H), 5.95-5.90 (m, 1H), 4.88-4.75 (m, 1H), 3.88-3.73 (m, 3H), 3.52 (s, 1H), 3.29-3.20 (m, 5H), 2.43-2.23 (m, 5H), 2.15-1.95 (m, 5H), 1.89-1.75 (m, 1H), 1.59 (d, J=11.9 Hz, 3H), 1.24-1.15 (m, 3H), 0.79-0.65 (m, 3H). MS (ESI, m/e) [M+1]$^+$ 832.8.

Example C45: 3-((1H-pyrrolo[2,3-b]pyridin-5-yl)oxy)-4'-(2-(2-chloro-6-cyclopropylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

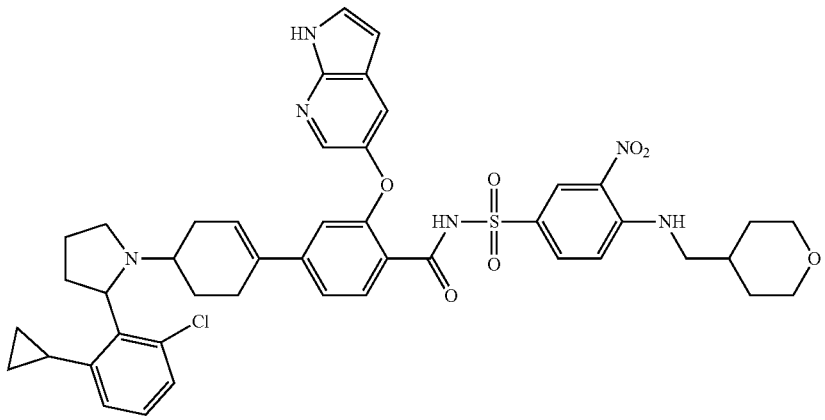 [SMILES: O=C(NS(=O)(=O)c1ccc(NCC2CCOCC2)c([N+](=O)[O-])c1)c1ccc(C2=CCC(N3CCCC3c3c(Cl)cccc3C3CC3)CC2)cc1Oc1cnc2[nH]ccc2c1]

The desired compound was synthesized with 2-(2-chloro-6-cyclopropylphenyl) pyrrolidine and 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-oxo-2',3',4',5'-tetrahydro-[1,1'-biphenyl]-4-carboxamide following the procedure similar to those in Example C12. $^1$H NMR (400 MHz, DMSO-d$_6$) δ 12.24 (s, 1H), 11.70 (s, 1H), 8.59-8.53 (m, 2H), 7.99 (s, 1H), 7.80 (d, J=8.8 Hz, 1H), 7.60-7.39 (m, 3H), 7.23-6.95 (m, 4H), 6.72-6.61 (m, 2H), 6.38 (s, 1H), 6.03-5.79 (m, 1H), 4.52-4.47 (m, 1H), 3.84 (d, J=8.8 Hz, 2H), 3.28-3.22 (m, 4H), 3.12-3.03 (m, 2H), 2.20-2.10 (m, 2H), 2.01-1.97 (m, 3H), 1.90-1.73 (m, 4H), 1.65-1.50 (m, 2H), 1.50-1.40 (m, 1H), 1.30-1.20 (m, 6H), 0.98-0.79 (m, 3H), MS (ESI, m/e) [M+1]$^+$ 850.8.

Example C46: 3-((1H-pyrrolo[2,3-b]pyridin-5-yl)oxy)-4'-(2-(2,6-dimethylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

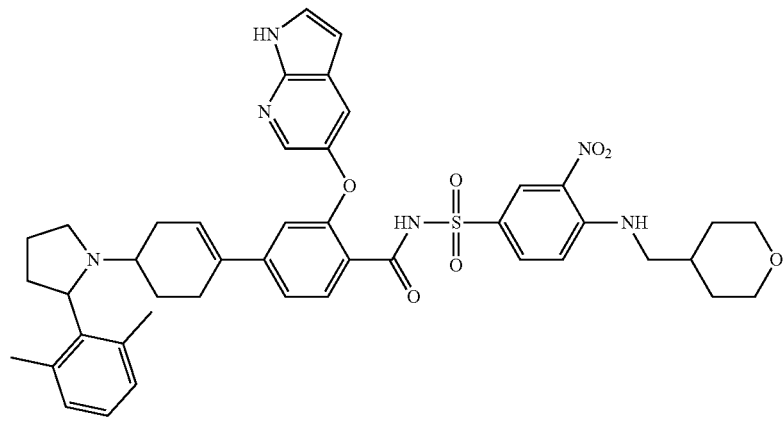

The desired compound was synthesized with 2-(2,6-dimethylphenyl)pyrrolidine and 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-oxo-2',3',4',5'-tetrahydro-[1,1'-biphenyl]-4-carboxamide following the procedure similar to those in Example C12. $^1$H NMR (400 MHz, DMSO-d$_6$) δ ppm: 12.27 (s, 1H), 11.69 (s, 1H), 8.65-8.48 (m, 2H), 7.98 (s, 1H), 7.78 (d, J=8.4 Hz, 1H), 7.51 (s, 2H), 7.44 (d, J=8.4 Hz, 1H), 7.20-7.05 (m, 2H), 7.03-6.79 (m, 3H), 6.72 (d, J=8.0 Hz, 1H), 6.38 (s, 1H), 6.00-5.72 (m, 1H), 4.15-3.75 (m, 4H), 3.30-3.17 (m, 4H), 3.15-2.98 Cm. 1H), 2.45-2.25 (m, 8H), 2.18-2.05 (m, 3H), 1.99-1.53 (m, 8H), 1.51-1.35 (m, 1H), 1.28-1.18 (m, 4H). MS (ESI, m/e) [M+1]$^+$ 805.2.

Example C47: 3-((1H-pyrrolo[2,3-b]pyridin-5-yl)oxy)-4'-(2-(2-chloro-3-fluorophenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

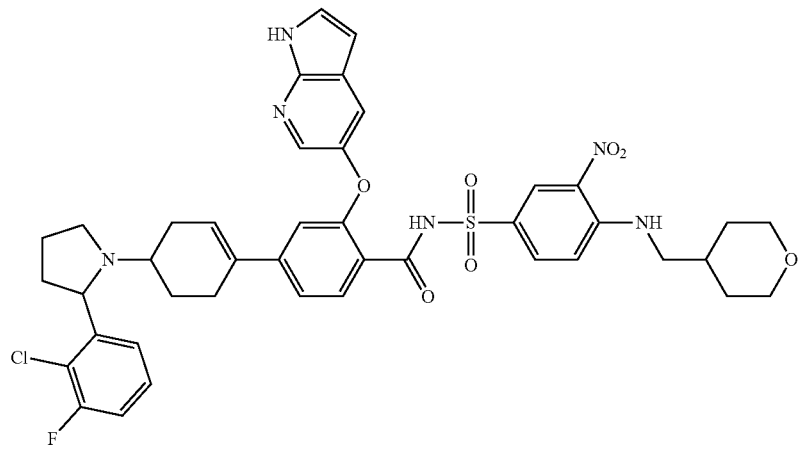 [SMILES: O=C(NS(=O)(=O)c1ccc(NCC2CCOCC2)c([N+](=O)[O-])c1)c1ccc(C2=CCC(N3CCCC3c3cccc(F)c3Cl)CC2)cc1Oc1cnc2[nH]ccc2c1]

The desired compound was synthesized with 2-(2-chloro-3-fluorophenyl)pyrrolidine and 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-oxo-2',3',4',5'-tetrahydro-[1,1'-biphenyl]-4-carboxamide following the procedure similar to those in Example C12. $^1$H NMR (400 MHz, DMSO-d$_6$) δ 11.68 (s, 1H), 8.60-8.45 (m, 2H), 8.05-7.95 (m, 1H), 7.80-7.70 (m, 1H), 7.62-7.44 (m, 4H), 7.35-7.20 (m, 1H), 7.18-7.10 (m, 2H), 7.09-6.92 (m, 2H), 6.70 (d, J=8.1 Hz, 1H), 6.37 (s, 1H), 6.01 (s, 0.5H), 5.80 (s, 0.5H), 4.2-4.05 (m, 1H), 3.84 (d, J=8.2 Hz, 2H), 3.30-3.20 (m, 4H), 3.18-2.90 (m, 2H), 2.40-2.05 (m, 4H), 2.00-1.80 (m, 2H), 1.78-1.65 (m, 2H), 1.59 (d, J=12.6 Hz, 3H), 1.50-1.40 (m, 1H), 1.36-1.13 (m, 4H). MS (ESI) m/e [M+1]$^+$ 828.7.

Example C48: 3-((1H-pyrrolo[2,3-b]pyridin-5-yl)oxy)-4'-(2-(2,3-dichlorophenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

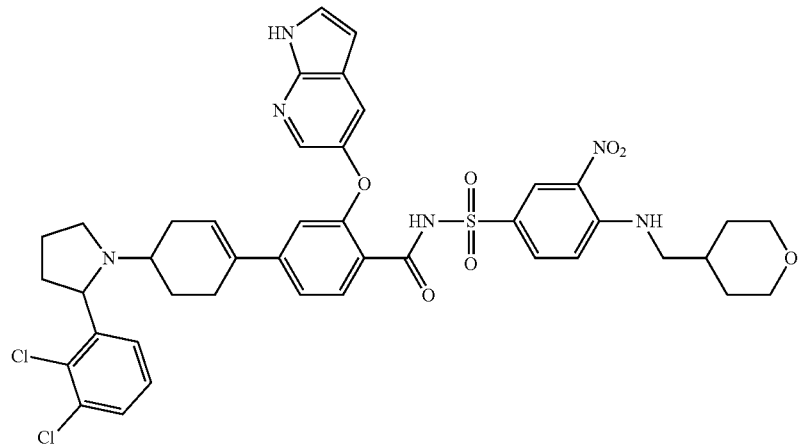 [SMILES: O=C(NS(=O)(=O)c1ccc(NCC2CCOCC2)c([N+](=O)[O-])c1)c1ccc(C2=CCC(N3CCCC3c3cccc(Cl)c3Cl)CC2)cc1Oc1cnc2[nH]ccc2c1]

The desired compound was synthesized starting from 2-(2,3-dichlorophenyl)pyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. $^1$H NMR (400 MHz, DMSO-d$_6$) δ ppm: 12.21 (s, 1H), 11.71 (s, 1H), 8.7-8.5 (m, 2H), 8.05-7.95 (m, 1H), 7.85-7.75 (m, 1H), 7.70-7.65 (m, 1H), 7.60-7.40 (m, 4H), 7.38-7.22 (m, 1H), 7.20-7.00 (m, 2H), 6.70 td, J=9.7 Hz, 1H), 6.40 (s, 1H), 6.01-5.84 (m, 1H), 4.25-4.00 (m, 2H), 3.84 (d, J=10.5 Hz, 2H), 3.30-3.19 (m, 4H), 2.42-1.99 (m, 5H), 1.95-1.86 (m, 3H), 1.79-1.52 (m, 5H), 1.50-1.35 (m, 1H), 1.30-1.15 (m, 3H). MS (ESI, m/e) [M+1]$^+$845.1.

Example C51: 3-((1H-pyrrolo[2,3-b]pyridin-5-yl)oxy)-4'-(2-(3-chloro-2-cyclopropylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

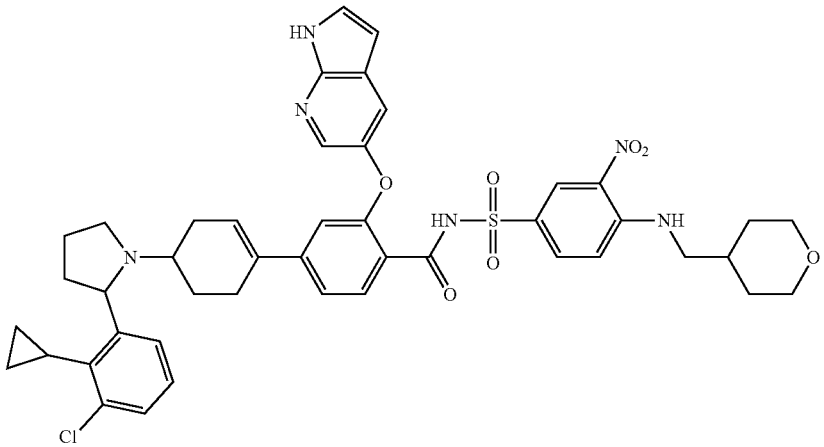 [SMILES: O=C(NS(=O)(=O)c1ccc(NCC2CCOCC2)c([N+](=O)[O-])c1)c1ccc(C2=CCC(N3CCCC3c3cccc(Cl)c3C3CC3)CC2)cc1Oc1cnc2[nH]ccc2c1]

The desired compound was synthesized with 2-(3-chloro-2-cyclopropylphenyl) pyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. $^1$H NMR (400 MHz, DMSO-d$_6$) δ 12.25 (s, 1H), 11.70 (s, 1H), 8.65-8.45 (m, 2H), 7.99 (s, 1H), 7.79 (d, J=8.7 Hz, 1H), 7.60-7.40 (m, 4H), 7.38-7.25 (m, 1H), 7.20-7.00 (m, 3H), 6.72 (s, 1H), 6.38 (s, 1H), 5.98 (s, 0.5H), 5.90-5.75 (m, 0.5H), 4.60-4.45 (m, 1H), 3.84<dd, J=11.1, 2 Hz, 2H), 3.76-3.56 (m, 2H), 3.30-3.20 (m, 5H), 2.65-2.55 (m, 1H), 2.44-1.98 (m, 6H), 1.95-1.65 (m, 4H), 1.59 (d, J=12.4 Hz, 2H), 1.31-1.15 (m, 3H), 1.12-1.05 (m, 2H), 0.70-0.60 (m, 1H), 0.55-0.45 (m, 1H). MS (ESI, m/e) [M+1]$^+$ 850.8.

Example C52: 3-((1H-pyrrolo[2,3-b]pyridin-5-yl)oxy)-4'-(2-(2-cyclopropyl-3-fluorophenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

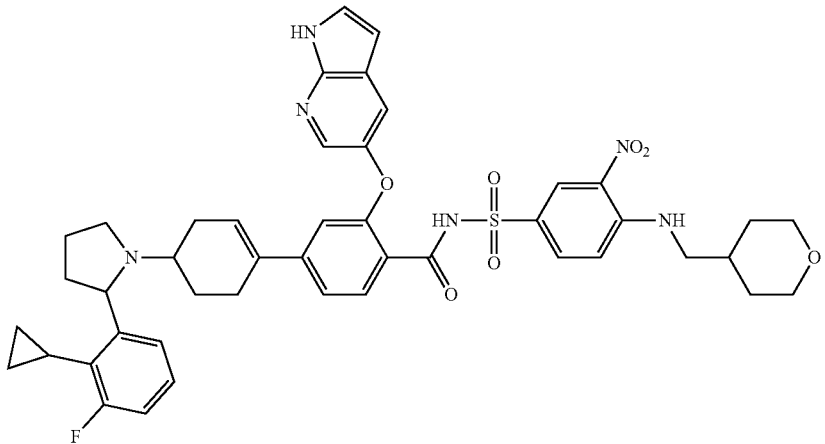 [SMILES: O=C(NS(=O)(=O)c1ccc(NCC2CCOCC2)c([N+](=O)[O-])c1)c1ccc(C2=CCC(N3CCCC3c3cccc(F)c3C3CC3)CC2)cc1Oc1cnc2[nH]ccc2c1]

The desired compound was synthesized with 2-(2-cyclopropyl-3-fluorophenyl) pyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. $^1$H NMR (DMSO-d$_6$) δ 12.22 (s, 1H), 11.59 (s, 1H), 8.52-8.32 (m, 2H), 7.94 (s, 1H), 7.69 (s, 1H), 7.53-7.28 (m, 4H), 7.18-7.02 (m, 2H), 6.92-6.67 (m, 3H), 6.33 (s, 1H), 6.00-5.71 (m, 1H), 4.36 (s, 1H), 3.93-3.73 (m, 2H), 3.30-2.85 (m, 7H) 2.30-2.13 (m, 3H), 2.05-1.79 (m, 4H), 1.77-1.53 (m, 5H), 1.49-1.37 (m, 2H), 1.02-0.91 (m, 2H), 0.89-0.81 (m, 2H), 0.77-0.67 (m, 1H), 0.62-0.48 (m, 1H). MS (ESI) m/e [M+1]$^+$ 834.8.

Example C53: 3-((1H-pyrrolo[2,3-b]pyridin-5-yl)oxy)-4'-(2-(2-cyclopropyl-4-fluorophenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

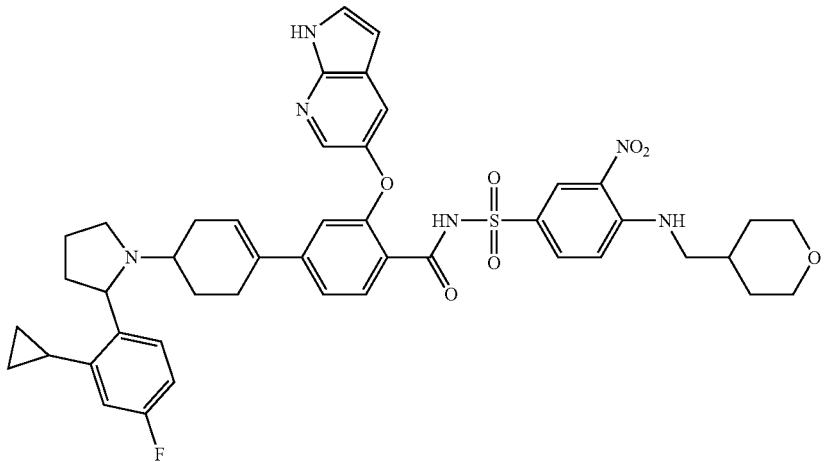

The desired compound was synthesized with 2-(2-cyclopropyl-4-fluorophenyl) pyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. $^1$H NMR (400 MHz, DMSO-d$_6$) δ 12.22 (s, 1H), 11.65 (s, 1H), 8.60-8.40 (m, 2H), 7.97 (d, J=2.2 Hz, 1H), 7.75 (d, J=8.3 Hz, 1H), 7.65-7.55 (m, 1H), 7.50-7.40 (m, 3H), 7.12 (d, J=8.3 Hz, 1H), 7.05-6.95 (m, 1H), 6.96-6.80 (m, 1H), 6.80-6.65 (m, 2H), 6.38-6.32 (m, 1H), 6.00 (s, 0.5H), 5.87 (s, 0.5H), 4.40-4.05 (m, 1H), 3.84 (dd, J=11.4, 3.0 Hz, 2H), 3.30-3.15 (m, 5H), 2.40-3.15 (m, 5H), 2.05-1.95 (m, 3H), 1.90-1.80 (m, 2H), 1.78-1.65 (m, 2H), 1.59 (d, J=11.3 Hz, 2H), 1.53-1.33 (m, 2H), 1.30-1.15 (m, 2H), 0.95-0.85 (m, 2H), 0.75-0.65 (m, 1H), 0.63-0.52 (m, 1H). MS (ESI, m/e) [M+1]+834.8

Example C54: 3-((1H-pyrrolo[2,3-b]pyridin-5-yl)oxy)-4'-(2-(2-cyclopropyl-5-fluorophenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

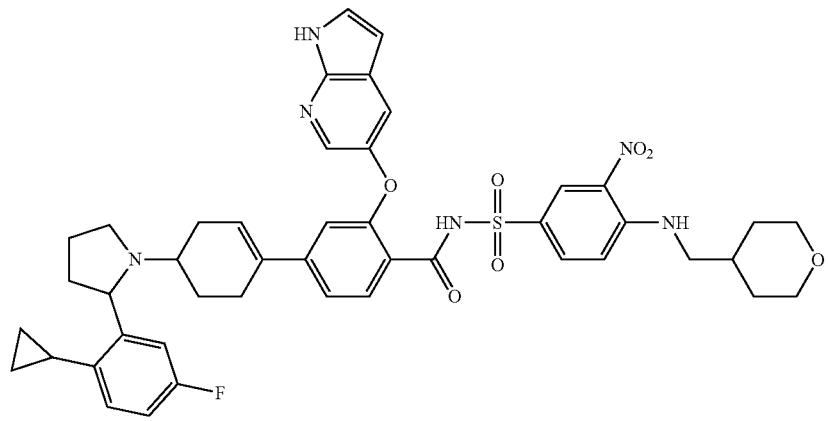 [SMILES: O=C(NS(=O)(=O)c1ccc(NCC2CCOCC2)c([N+](=O)[O-])c1)c1ccc(C2=CCC(N3CCCC3c3cc(F)ccc3C3CC3)CC2)cc1Oc1cnc2[nH]ccc2c1]

The desired compound was synthesized with 2-(2-cyclopropyl-5-fluorophenyl) pyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. $^1$H NMR (400 MHz, DMSO-d$_6$) δ 12.23 (s, 1H), 11.67 (s, 1H), 8.60-8.45 (m, 2H), 7.98 (s, 1H), 7.77 (d, J=8.4 Hz, 1H), 7.59-7.41 (m, 3H), 7.39-7.21 (m, 1H), 7.18-6.77 (m, 4H), 6.73 (s, 1H), 6.37 (s, 1H), 6.01 (s, 0.5H), 5.85 (s, 0.5H), 4.40-4.20 (m, 1H), 3.84 (d, J=8.3 Hz, 2H), 3.30-3.15 (m, 5H), 2.40-2.15 (m, 3H), 2.06-1.82 (m, 4H), 1.80-1.65 (m, 2H), 1.59 (d, J=12.1 Hz, 3H), 1.50-1.35 (m, 1H), 1.33-1.14 (m, 5H), 0.95-0.79 (m, 2H), 0.70-0.60 (m, 1H), 0.55-0.45 (m, 1H). MS (ESI, m/e) [M+1]$^+$ 834.8.

Example C55: 3-((1H-pyrrolo[2,3-b]pyridin-5-yl)oxy)-4'-(2-(2-cyclopropyl-6-fluorophenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

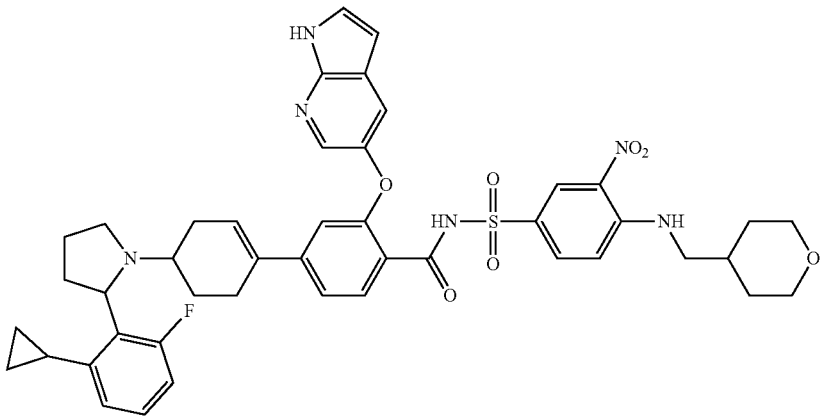 [SMILES: O=C(NS(=O)(=O)c1ccc(NCC2CCOCC2)c([N+](=O)[O-])c1)c1ccc(C2=CCC(N3CCCC3c3c(F)cccc3C3CC3)CC2)cc1Oc1cnc2[nH]ccc2c1]

The desired compound was synthesized with 2-(2-cyclopropyl-6-fluorophenyl) pyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. $^1$H NMR (400 MHz, DMSO-d$_6$) δ ppm: 12.25 (s, 1H), 11.68 (s, 1H), 8.60-8.45 (m, 2H), 7.98 (s, 1H), 7.85-7.70 (m, 1H), 7.55-7.30 (m, 3H), 7.20-6.50 (m, 6H), 6.37 (s, 1H), 6.10-5.79 (m, 1H), 4.50-4.20 (m, 1H), 3.84 (dd, J=11.1, 2.7 Hz, 2H), 3.74-3.42 (m, 2H), 3.30-3.20 (m, 5H), 2.40-1.65 (m, 10H), 1.59 (d, J=12.3 Hz, 2H), 1.35-1.10 (m, 3H), 1.05-0.65 (m, 4H), 0.60-0.45 (m, 1H). MS (ESI) m/e [M+1]$^+$ 834.8.

Example C57: 3-((1H-pyrrolo[2,3-b]pyridin-5-yl)oxy)-4'-(2-(3-cyclopropylthiophen-2-yl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

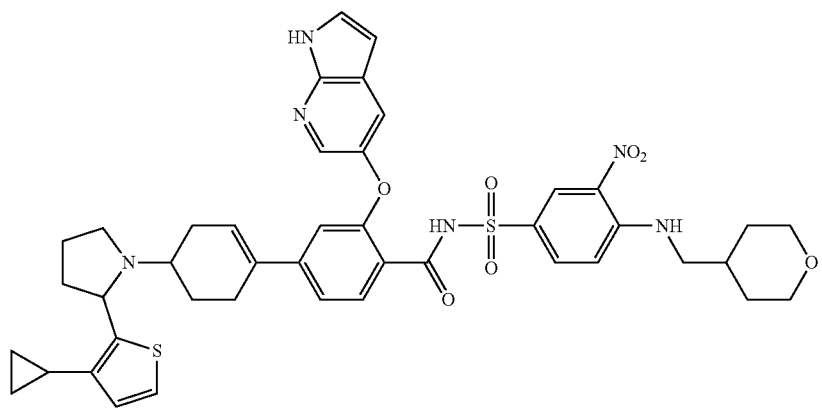 [SMILES: O=C(NS(=O)(=O)c1ccc(NCC2CCOCC2)c([N+](=O)[O-])c1)c1ccc(C2=CCC(N3CCCC3c3sccc3C3CC3)CC2)cc1Oc1cnc2[nH]ccc2c1]

The desired compound was synthesized with 2-(3-cyclopropylthiophen-2-yl)pyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. ¹H NMR (400 MHz, DMSO-d₆) δ ppm: 12.23 (s, 0.5H), 11.67 (s, 1H), 9.55 (s, 0.5H), 8.51 (s, 2H), 7.99 (s, 1H), 7.77 (s, 1H), 7.50-7.46 (m, 3H), 7.21-6.96 (m, 3H), 6.75 (s, 1H), 6.50 (s, 1H), 6.37 (s, 1H), 6.03 (s, 0.5H), 5.94 (s, 0.5H), 4.41-4.28 (m, 1H), 3.91-3.72 (m, 2H), 3.49-3.41 (m, 1H), 3.29-3.18 (m, 6H), 3.08-2.91 (m, 2H), 2.31-2.19 (m, 4H), 1.89-1.71 (m, 3H), 1.69-1.59 (m, 3H), 1.32-1.15 (m, 3H), 0.95-0.78 (m, 3H), 0.54 (s, 2H). MS (ESI, m/e) [M+1]⁺ 822.7.

Example C60: 3-((1H-pyrrolo[2,3-b]pyridin-5-yl)oxy)-4'-(2-cyclohexylpyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

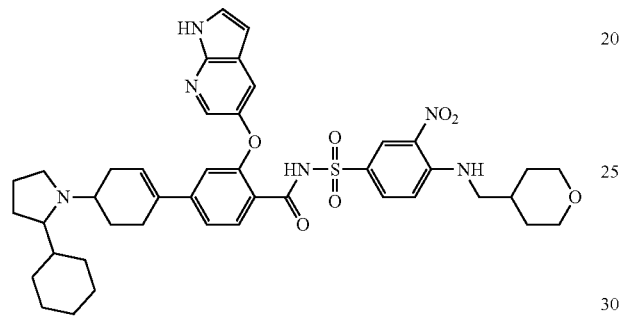

The desired compound was synthesized starting from 2-cyclohexylpyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. ¹H NMR (400 MHz, DMSO-d₆) δ ppm: 11.60 (s, 1H), 8.96 (s, 1H), 8.42 (s, 1H), 8.37 (s, 1H), 7.96 (s, 1H), 7.69 (d, J=8.8 Hz, 1H), 7.47 (d, J=7.2 Hz, 1H), 7.45 (s, 1H), 7.39 (s, 1H), 7.13 (d, J=7.2 Hz, 1H), 6.88 (d, J=8.8 Hz, 1H), 6.76 (s, 1H), 6.34 (s, 1H), 6.00 (s, 1H), 3.84 (d, J=8.4 Hz, 2H), 3.48-3.39 (m, 2H), 3.30-3.16 (m, 6H), 2.44-2.28 (m, 2H), 2.22-2.09 (m, 1H), 2.02-1.93 (m, 1H), 1.88-1.78 (m, 3H), 1.76-1.66 (m, 3H), 1.66-1.53 (m, 4H), 1.31-1.13 (m, 6H), 1.13-0.91 (m, 3H). MS (ESI, m/e) [M+1]⁺ 783.2.

Example C62: 3-((1H-pyrrolo[2,3-b]pyridin-5-yl)oxy)-4'-(2-(benzo[b]thiophen-7-yl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

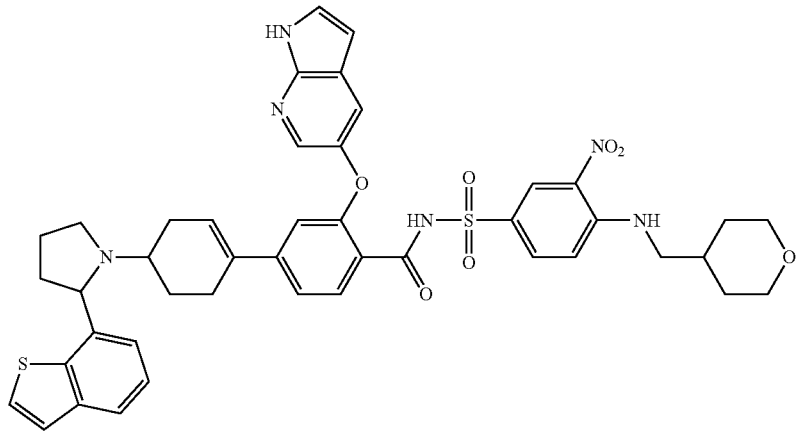 [SMILES: O=C(NS(=O)(=O)c1ccc(NCC2CCOCC2)c([N+](=O)[O-])c1)c1ccc(C2=CCC(N3CCCC3c3cccc4ccsc34)CC2)cc1Oc1cnc2[nH]ccc2c1]

The desired compound was synthesized with 2-(benzo[b]thiophen-7-yl)pyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. $^1$H NMR (400 MHz, DMSO-d$_6$) δ 12.20 (s, 1H), 11.69 (s, 1H), 8.64-8.33 (m, 2H), 7.97 (s, 1H), 7.77 (s, 1H), 7.72-7.58 (m, 2H), 7.59-7.45 (m, 2H), 7.45-7.40 (m, 2H), 7.30-7.14 (m, 2H), 7.18-7.03 (m, 2H), 6.68 (d, J=10.1 Hz, 1H), 6.36 (s, 1H), 6.03-5.78 (m, 1H), 4.20-4.07 (m, 1H), 3.88-3.80 (m, 2H), 3.30-3.17 (m, 4H), 3.09-2.88 (m, 4H), 2.28-2.09 (m, 3H), 2.05-1.94 (m, 3H), 1.90-1.73 (m, 3H), 1.69-1.54 (m, 3H), 1.49-1.39 (m, 2H). MS (ESI) m/e [M+1]$^+$ 832.7.

Example C63: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(phenylethynyl)pyrrolidin-1-yl)-2',3',4',5'-tetrahydro-[1,1'-biphenyl]-4-carboxamide

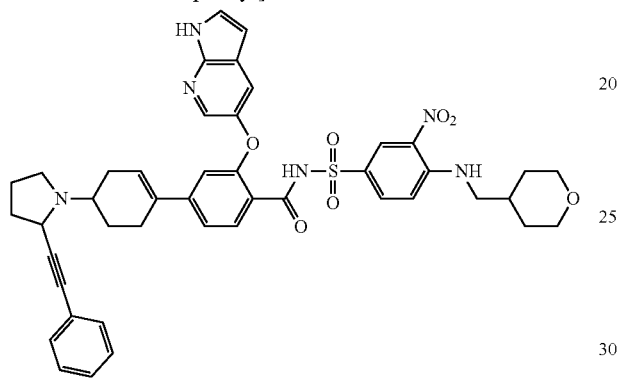

The desired compound was synthesized with 2-(phenylethynyl)pyrrolidine and 3-((1H-pyrrolo[2,3-b]pyridin-5-yl)oxy)-N-((3-nitro-4-(((tetrahydro-2H-pyran-4-yl) methyl) amino) phenyl)sulfonyl)-4'-oxo-2',3',4',5'-tetrahydro-[1,1'-biphenyl]-4-carboxamide following the procedure similar to those in Example C12. $^1$H NMR (400 MHz, DMSO-d$_6$) δ 12.06 (s, 1H), 11.69 (s, 1H), 8.56-8.53 (m, 2H), 8.01 (d, J=2.2 Hz, 1H), 7.78 (d, J=8.8 Hz, 1H), 7.56-7.32 (m, 8H), 7.22 (d, J=8.1 Hz, 1H), 7.07 (d, J=8.8 Hz, 1H), 6.80 (d, J=3.8 Hz, 1H), 6.38 (s, 1H), 6.07 (s, 1H), 3.90-3.80 (m, 2H), 3.35-3.23 (m, 5H), 3.05-2.95 (m, 1H), 2.41-2.23 (m, 2H), 2.24-1.95 (m, 5H), 1.90-1.75 (m, 2H), 1.65-1.55 (m, 2H), 1.35-1.25 (m, 6H), MS (ESI, m/e) [M+1]$^+$ 800.8.

Example C66: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(2-(piperidin-4-yl)phenyl)pyrrolidin-1-yl)-2',3',4',5'-tetrahydro-[1,1'-biphenyl]-4-carboxamide

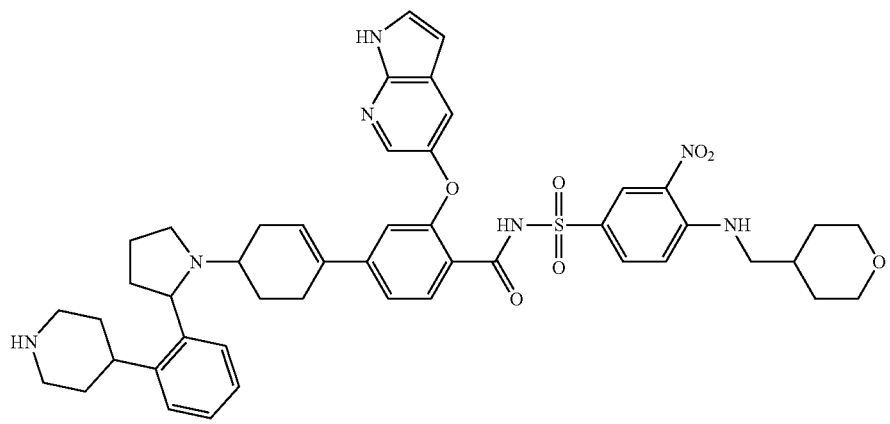 [SMILES: O=C(NS(=O)(=O)c1ccc(NCC2CCOCC2)c([N+](=O)[O-])c1)c1ccc(C2=CCC(N3CCCC3c3ccccc3C3CCNCC3)CC2)cc1Oc1cnc2[nH]ccc2c1]

3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(2-(N-Boc-piperidin-4-yl)phenyl)pyrrolidin-1-yl)-2',3',4',5'-tetrahydro-[1,1-biphenyl]-4-carboxamide was synthesized with tert-butyl 4-(2-(pyrrolidin-2-yl)phenyl)piperidine-1-carboxylate and 3-((1H-pyrrolo[2,3-b]pyridin-5-yl)oxy)-N-((3-nitro-4-(((tetrahydro-2H-pyran-4-yl) methyl)amino)phenyl)sulfonyl)-4'-oxo-2',3',4',5'-tetrahydro-[1,1'-biphenyl]-4-carboxamide following the procedure similar to those in Example C12. Then after deprotection with TFA, the desired compound was obtained. $^1$H NMR (400 MHz, DMSO-d$_6$) δ ppm: 11.54 (s, 1H), 8.38-8.36 (m, 1H), 8.35-8.30 (m, 1H), 7.92-7.88 (m, 1H), 7.68-7.60 (m, 1H), 7.59-7.49 (m, 1H), 7.49-7.38 (m, 2H), 7.35-7.25 (m, 1H), 7.21-6.96 (m, 4H), 6.85-6.75 (m, 1H), 6.72-6.68 (m, 1H), 6.29 (s, 1H), 5.98 (s, 0.5H), 5.80 (s, 0.5H), 4.10-4.00 (m, 1H), 3.85-3.72 (m, 2H), 3.29-3.17 (m, 5H), 3.15-2.90 (m, 6H), 2.80-2.65 (m, 2H), 2.30-2.10 (m, 4H), 2.05-1.80 (m, 2H), 1.79-1.46 (m, 9H), 1.40-1.30 (m, 2H), 1.25-1.10 (m, 2H). MS (ESI, m/e) [M+1]$^+$ 859.8.

Example C67: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(2-phenoxyphenyl)pyrrolidin-1-yl)-2',3',4',5'-tetrahydro-[1,1'-biphenyl]-4-carboxamide

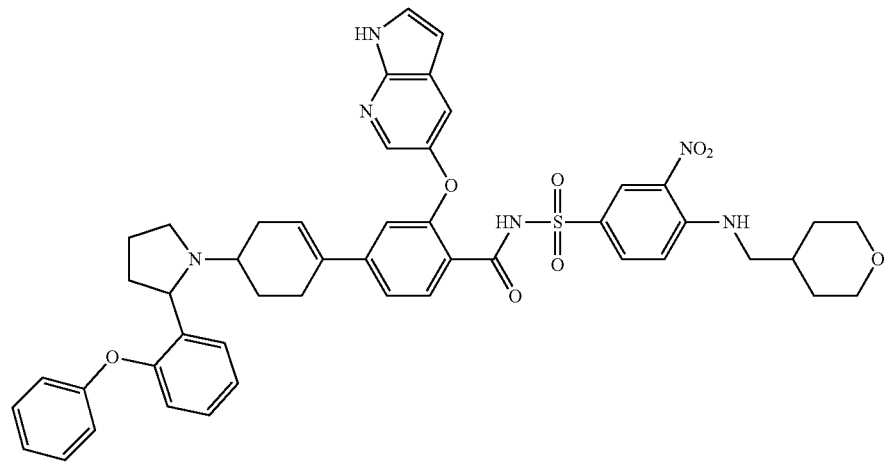 [SMILES: O=C(NS(=O)(=O)c1ccc(NCC2CCOCC2)c([N+](=O)[O-])c1)c1ccc(C2=CCC(N3CCCC3c3ccccc3Oc3ccccc3)CC2)cc1Oc1cnc2[nH]ccc2c1]

The desired compound was synthesized with 2-(2-phenoxyphenyl)pyrrolidine and 3-((1H-pyrrolo[2,3-b]pyridin-5-yl)oxy)-N-((3-nitro-4-(((tetrahydro-2H-pyran-4-yl) methyl)amino)phenyl)sulfonyl)-4'-oxo-2',3',4',5'-tetrahydro-[1,1'-biphenyl]-4-carboxamide following the procedure similar to those in Example C12. $^1$H NMR (400 MHz, DMSO-d$_6$) δ 12.20 (s, 1H), 11.71 (s, 1H), 8.60-8.40 (m, 2H), 8.30-8.10 (m, 1H), 7.98 (s, 1H), 7.78 (d, J=7.6 Hz, 1H), 7.60-7.45 (m, 2H), 7.47-7.35 (m, 2H), 7.35-7.18 (m, 4H), 7.10-6.85 (m, 6H), 6.57 (s, 1H), 6.39 (s, 1H), 4.95-4.75 (m, 1H), 3.84 (d, J=8.6 Hz, 2H), 3.30-3.20 (m, 5H), 2.40-2.25 (m, 2H), 2.20-2.00 (m, 3H), 1.95-1.77 (m, 2H), 1.76-1.52 (m, 4H), 1.50-1.30 (m, 2H), 1.28-1.05 (m, 4H). MS (ESI, m/e) [M+1]$^+$ 868.8.

Example C69: 3-((1H-pyrrolo[2,3-b]pyridin-5-yl)oxy)-4'-(2-(2-cyclopropyl-5-methoxyphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

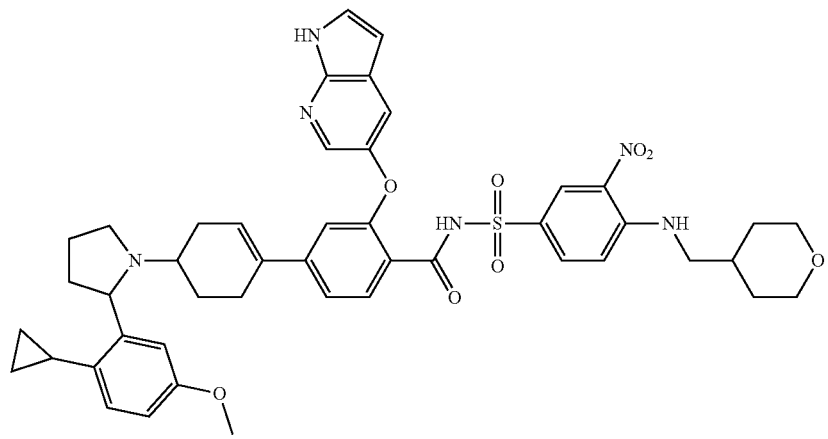 [SMILES: COc1ccc(C2CC2)c(C2CCCN2C2CC=C(c3ccc(C(=O)NS(=O)(=O)c4ccc(NCC5CCOCC5)c([N+](=O)[O-])c4)c(Oc4cnc5[nH]ccc5c4)c3)CC2)c1]

The desired compound was synthesized with 2-(2-cyclopropyl-5-methoxyphenyl)pyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. $^1$H NMR (400 MHz, DMSO-d$_6$) δ ppm: 12.25 (s, 1H), 11.62 (s, 1H), 8.57-8.35 (m, 1H), 7.95 (s, 1H), 7.79-7.67 (m, 1H), 7.53-7.34 (m, 3H), 7.18-7.05 (m, 2H), 7.03-6.81 (m, 2H), 6.75 (s, 1H), 6.66-6.53 (m, 1H), 6.34 (s, 1H), 6.05-5.76 (m, 1H), 4.36-4.20 (m, 1H), 3.87-3.80 (m, 2H), 3.77-3.57 (m, 4H), 3.31-3.18 (m, 6H), 2.25-2.15 (m, 2H), 1.95-1.81 (m, 3H), 1.76-1.65 (m, 2H), 1.65-1.54 (m, 3H), 1.30-1.22 (m, 5H), 0.89-0.74 (m, 4H), 0.67-0.41 (m, 2H). MS (ESI, m/e) [M+1]$^+$ 857.8.

Example C81: 3-((1H-pyrrolo[2,3-b]pyridin-5-yl)oxy)-4'-(2-(2-cyclopropylphenyl)-2,5-dihydro-1H-pyrrol-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

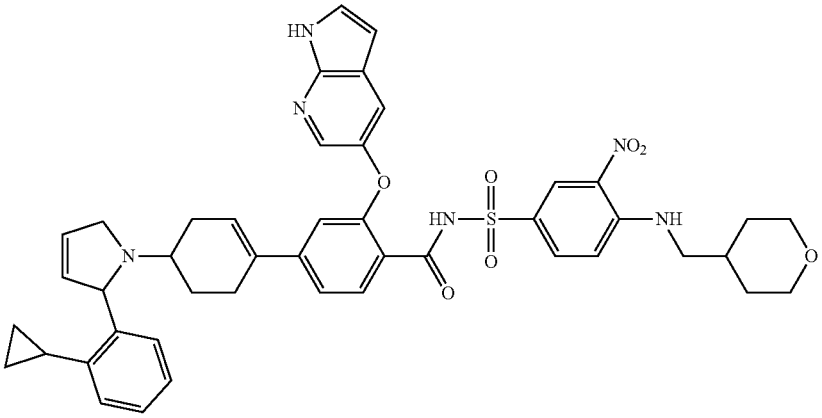 [SMILES: O=C(NS(=O)(=O)c1ccc(NCC2CCOCC2)c([N+](=O)[O-])c1)c1ccc(C2=CCC(N3CC=CC3c3ccccc3C3CC3)CC2)cc1Oc1cnc2[nH]ccc2c1]

The desired compound was synthesized with 2-(2-cyclopropylphenyl)-2,5-dihydro-1H-pyrrole and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. $^1$H NMR (400 MHz, DMSO-d$_6$) δ ppm: 12.22 (s, 1H), 11.69 (s, 1H), 8.57-8.48 (m, 2H), 7.99 (s, 1H), 7.79 (s, 1H), 7.59-7.40 (m, 3H), 7.13-7.05 (m, 4H), 6.99-6.90 (m, 1H), 6.73-6.65 (m, 1H), 6.38 (s, 1H), 6.02 (s, 1H), 5.85-5.63 (m, 2H), 5.29 (s, 1H), 3.84 (d, J=8.3 Hz, 2H), 3.61-3.51 (m, 1H), 3.31-3.11 (m, 5H), 2.99-2.91 (m, 2H), 2.21-2.08 (m, 3H), 1.96-1.76 (m, 2H), 1.59 (d, J=12.1 Hz, 3H), 1.29-1.17 (m, 3H), 0.88 (s, 3H), 0.75-0.60 (m, 2H). MS (ESI, m/e) [M+1]$^+$ 814.8.

Example C86: 3-((1H-pyrrolo[2,3-b]pyridin-5-yl)oxy)-4'-(1-(2-cyclopropylphenyl)isoindolin-2-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

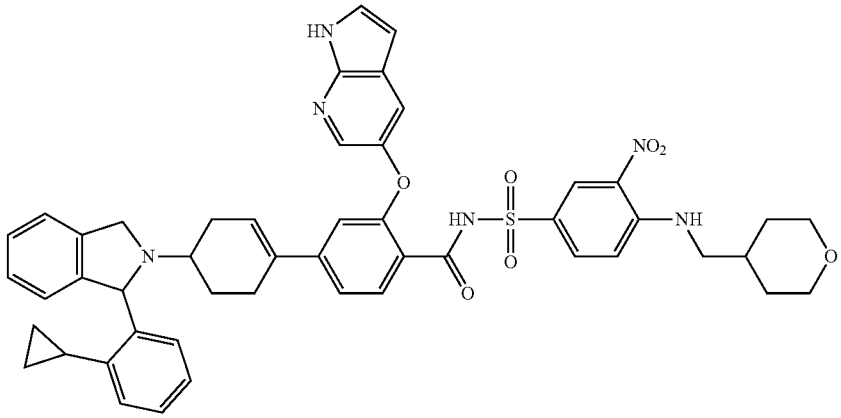 [SMILES: O=C(NS(=O)(=O)c1ccc(NCC2CCOCC2)c([N+](=O)[O-])c1)c1ccc(C2=CCC(N3Cc4ccccc4C3c3ccccc3C3CC3)CC2)cc1Oc1cnc2[nH]ccc2c1]

The desired compound was synthesized with 1-(2-cyclopropylphenyl)isoindoline and 3-((1H-pyrrolo[2,3-b]pyridin-5-yl)oxy)-N-((3-nitro-4-(((tetrahydro-2H-pyran-4-yl) methyl)amino)phenyl)sulfonyl)-4'-oxo-2',3',4',5'-tetrahydro-[1,1'-biphenyl]-4-carboxamide following the procedure similar to those in Example C12, MS (ESI, m/e) [M+1]$^+$ 865.3.

Example C87: 3-((1H-pyrrolo[2,3-b]pyridin-5-yl)oxy)-4'-(4-hydroxy-2-phenylpyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

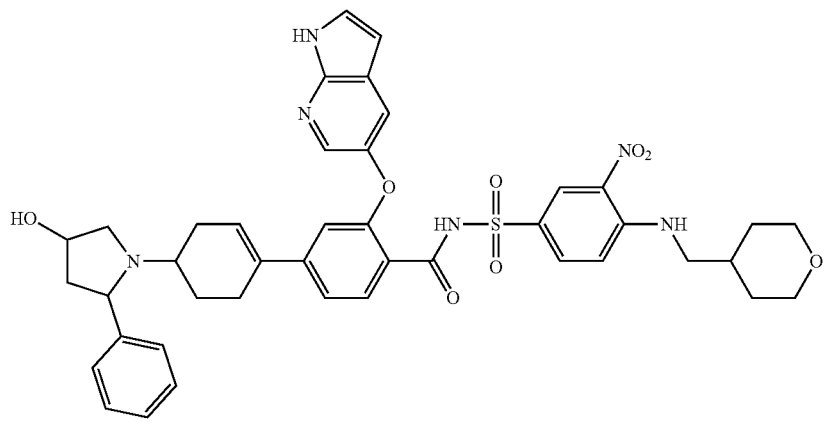 [SMILES: O=C(NS(=O)(=O)c1ccc(NCC2CCOCC2)c([N+](=O)[O-])c1)c1ccc(C2=CCC(N3CC(O)CC3c3ccccc3)CC2)cc1Oc1cnc2[nH]ccc2c1]

The desired compound was synthesized with 5-phenylpyrrolidin-3-ol and 3-((1H-pyrrolo[2,3-b]pyridin-5-yl)oxy)-N-((3-nitro-4-(((tetrahydro-2H-pyran-4-yl) methyl) amino) phenyl)sulfonyl)-4'-oxo-2',3',4',5'-tetrahydro-[1,1'-biphenyl]-4-carboxamide following the procedure similar to those in Example C12. $^1$H NMR (400 MHz, DMSO-$d_6$) δ ppm: 12.22 (s, 1H), 11.64 (s, 1H), 8.47-8.42 (m, 2H), 7.96 (s, 1H), 7.73-7.72 (m, 1H), 7.65-7.62 (m, 1H), 7.47-7.20 (m, 7H), 7.11-7.10 (m, 1H), 6.98-6.94 (m, 1H), 6.71 (s, 1H), 6.35 (s, 1H), 5.76 (s, 0.5H), 5.31 (s, 0.5H), 4.75-4.73 (m, 1H), 4.23-4.21 (m, 1H), 3.85 (d, J=8.0 Hz, 2H), 3.22-3.09 (m, 4H), 3.00-2.95 (m, 2H), 2.33-1.85 (m, 8H), 1.61 (d, J=12.0 Hz, 2H), 1.47-1.23 (m, 4H) MS (ESI, m/e) [M+1]$^+$ 792.8.

Example C88a and Example C88b: 3-((1H-pyrrolo[2,3-b]pyridin-5-yl)oxy)-4'-((4S or 4R)-2-(2-cyclopropylphenyl)-4-methoxypyrrolidin-1-yl)-N-((3-nitro-4-(((tetrahydro-2H-pyran-4-yl)methyl) amino) phenyl)sulfonyl)-2',3',4',5'-tetrahydro-[1,1'-biphenyl]-4-carboxamide/3-((1H-pyrrolo[2,3-b]pyridin-5-yl)oxy)-4'-((4R or 4S)-2-(2-cyclopropylphenyl)-4-methoxypyrrolidin-1-yl)-N-((3-nitro-4-(((tetrahydro-2H-pyran-4-yl)methyl) amino)phenyl)sulfonyl)-2',3',4',5'-tetrahydro-[1,1'-biphenyl]-4-carboxamide

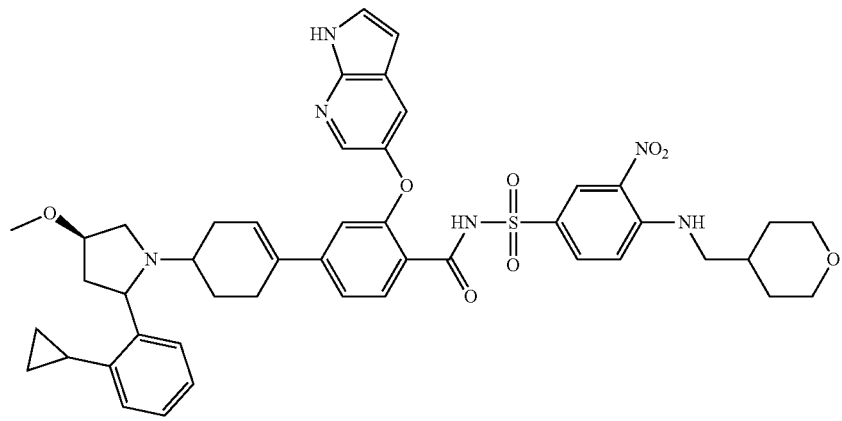

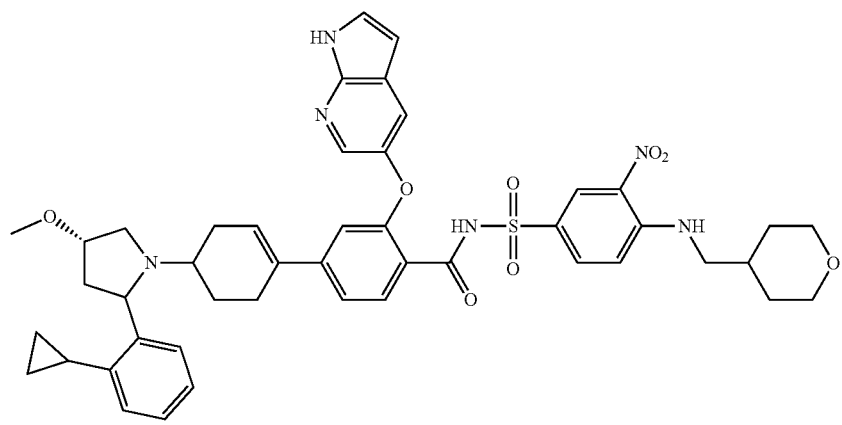

The desired compounds were synthesized with 2-(2-cyclopropylphenyl)-4-methoxypyrrolidine and 3-((1H-pyrrolo[2,3-b]pyridin-5-yl)oxy)-N-((3-nitro-4-(((tetrahydro-2H-pyran-4-yl) methyl)amino)phenyl)sulfonyl)-4'-oxo-2',3',4',5'-tetrahydro-[1,1'-biphenyl]-4-carboxamide following the procedure similar to those in Example C12. After purification with prep-HPLC, faster peak C88a was obtained. $^1$H NMR (400 MHz, DMSO-$d_6$) δ ppm: 12.24 (br, 1H), 11.67 (s, 1H), 8.59-8.48 (m, 2H), 7.97 (s, 1H), 7.81-7.73 (m, 1H), 7.59-7.41 (m, 4H), 7.23-6.86 (m, 5H), 6.72 (s, 1H), 6.36 (s, 1H), 5.99 (s, 0.5H), 5.84 (s, 0.5H), 4.34-4.19 (m, 1H), 3.85 (d, J=8.8 Hz, 2H), 3.25-3.11 (m, 10H), 2.68-2.60 (m, 1H), 2.29-2.11 (m, 3H), 2.09-1.95 (m, 4H), 1.92-1.69 (m, 3H), 1.61 (d, J=12.4 Hz, 2H), 1.55-1.33 (m, 2H), 0.95-0.84 (m, 2H), 0.68-0.45 (m, 2H). MS (ESI, m/e) [M+1]$^+$ 846.8; slower peak C88b. $^1$H NMR (400 MHz, DMSO-$d_6$) δ ppm: 12.22 (br, 1H), 11.65 (s, 1H), 8.59-8.41 (m, 2H), 7.96 (s, 1H), 7.80-7.69 (m, 1H), 7.57-7.40 (m, 4H), 7.20-6.92 (m, 5H), 6.72 (s, 1H), 6.35 (s, 1H), 6.00 (s, 0.5H), 5.84 (s, 0.5H), 4.55-4.41 (m, 1H), 3.95-3.87 (m, 1H), 3.84 (d, J=8.8 Hz, 2H), 3.47-3.35 (m, 1H), 3.25-3.16 (m, 8H), 2.67-2.51 (m, 2H), 2.29-2.11 (m, 4H), 2.09-1.95 (m, 3H), 1.92-1.69 (m, 2H), 1.61 (d, J=12.4 Hz, 2H), 1.55-1.33 (m, 2H), 0.95-0.84 (m, 2H), 0.68-0.45 (m, 2H), MS (ESI, m/e) [M+1]$^+$ 846.8.

Example C89: 3-((1H-pyrrolo[2,3-b]pyridin-5-yl)oxy)-4'-(2-(2-Cyclopropylphenyl)-4-fluoropyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

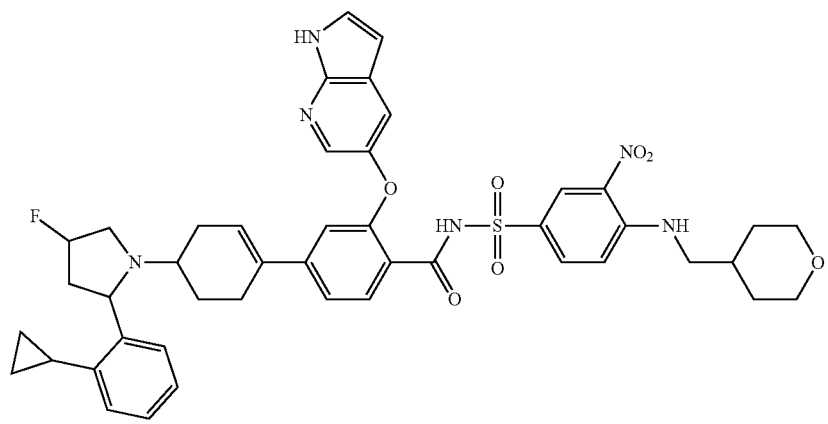 [SMILES: O=C(NS(=O)(=O)c1ccc(NCC2CCOCC2)c([N+](=O)[O-])c1)c1ccc(C2=CCC(N3CC(F)CC3c3ccccc3C3CC3)CC2)cc1Oc1cnc2[nH]ccc2c1]

The desired compound was synthesized with 2-(2-cyclopropylphenyl)-4-fluoropyrrolidine and methyl 3-((1H-pyrrolo[2,3-b]pyridin-5-yl)oxy)-4'-oxo-2',3',4',5'-tetrahydro-[1,1-biphenyl]-4-carboxylate following the next procedures similar to those in Example C1, $^1$H NMR (400 MHz, DMSO-$d_6$) δ 12.23 (s, 1H), 11.70 (s, 1H), 8.65-8.50 (m, 2H), 8.05-7.95 (m, 1H), 7.80 (d, J=8.7 Hz, 1H), 7.67-7.38 (m, 4H), 7.19-7.02 (m, 3H), 7.02-6.95 (m, 1H), 6.95-6.85 (m, 1H), 6.71 (d, J=4.4 Hz, 1H), 6.38 (s, 1H), 6.01 (s, 0.5H), 5.81 (s, 0.5H), 5.26 (s, 0.5H), 5.12 (s, 0.5H), 4.39-4.22 (m, 1H), 3.84 (dd, J=11.1, 2.7 Hz, 2H), 3.30-3.15 (m, 5H), 2.80-2.60 (m, 2H), 2.37-1.79 (m, 8H), 1.70-1.50 (m, 4H), 1.50-1.35 (m, 1H), 1.30-1.15 (m, 3H), 0.95-0.80 (m, 2H), 0.70-0.60 (m, 1H), 0.55-0.45 (m, 1H). MS (ESI) m/e [M+1]$^+$ 834.8.

Example C90: 3-((1H-pyrrolo[2,3-b]pyridin-5-yl)oxy)-4'-(2-(2-cyclopropylphenyl)-4,4-difluoropyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

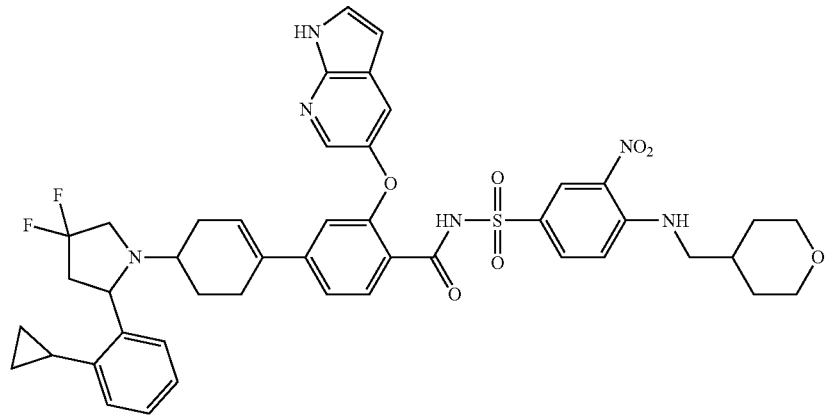 [SMILES: O=C(NS(=O)(=O)c1ccc(NCC2CCOCC2)c([N+](=O)[O-])c1)c1ccc(C2=CCC(N3CC(F)(F)CC3c3ccccc3C3CC3)CC2)cc1Oc1cnc2[nH]ccc2c1]

The desired compound was synthesized with 2-(2-cyclopropylphenyl)-4,4-difluoropyrrolidine and methyl 3-((1H-pyrrolo[2,3-b]pyridin-5-yl)oxy)-4'-oxo-2',3',4',5'-tetrahydro-[1,1-biphenyl]-4-carboxylate following the next procedures similar to those in Example C1. ¹H NMR (400 MHz, CDCl₃) δ 10.28 (s, 1H), 9.42 (s, 1H), 8.94-8.88 (m, 1H), 8.56-8.50 (m, 1H), 8.20-8.15 (m, 2H), 8.02 (d, J=8.4 Hz, 1H), 7.68 (s, 1H), 7.65-7.53 (m, 1H), 7.47 (s, 1H), 7.20-7.10 (m, 2H), 7.08-7.04 (m, 1H), 6.98 (d, J=12 Hz, 1H), 6.92 (d, J=8.4 Hz, 1H), 6.61 (s, 1H), 6.55 (s, 1H), 5.92 (s, 0.5H), 5.83 (s, 0.5H), 4.75-4.55 (m, 1H), 4.02 (d, J=11.4 Hz, 2H), 3.55-3.35 (m, 3H), 3.30-3.20 (m, 2H), 2.80-2.55 (m, 2H), 2.22-1.80 (m, 8H), 1.75-1.55 (m, 4H), 1.50-1.35 (m, 2H), 1.00-0.80 (m, 2H), 0.70-0.62 (m, 1H), 0.60-0.50 (m, 1H). MS (ESI) m/e [M+1]⁺ 852.8.

Example C99: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-phenylazetidin-1-yl)-2',3',4',5'-tetrahydro-[1,1'-biphenyl]-4-carboxamide

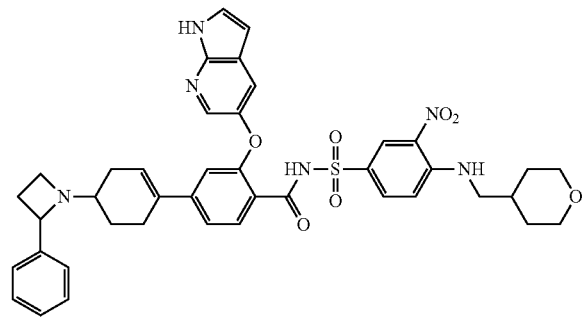 [SMILES: O=C(NS(=O)(=O)c1ccc(NCC2CCOCC2)c([N+](=O)[O-])c1)c1ccc(C2=CCC(N3CCC3c3ccccc3)CC2)cc1Oc1cnc2[nH]ccc2c1]

The desired compound was synthesized with 2-phenylazetidine and 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-oxo-2',3',4',5'-tetrahydro-[1,1'-biphenyl]-4-carboxamide following the procedure similar to those in Example C12. ¹H NMR (400 MHz, DMSO-d₆) δ ppm: 9.82 (s, 1H), 8.92 (s, 1H), 8.61-8.45 (m, 1H), 8.19-8.13 (m, 1H), 8.10-7.94 (m, 2H), 7.77-7.30 (m, 7H), 7.15-6.82 (m, 3H), 6.62-6.47 (m, 2H), 5.86-5.54 (m, 1H), 4.08-3.96 (m, 2H), 3.49 (s, 1H), 3.45-3.38 (m, 2H), 3.29-3.23 (m, 2H), 2.54-2.42 (m, 1H), 2.33-2.22 (m, 1H), 2.14-1.82 (m, 5H), 1.78-1.60 (m, 4H), 1.51-1.36 (m, 3H), 1.33-1.16 (m, 2H). MS (ESI) m/e [M+1]⁺ 763.2.

Example C118: 3-((1H-pyrrolo[2,3-b]pyridin-5-yl)oxy)-4'-(2-(2-cyclopropylbenzyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

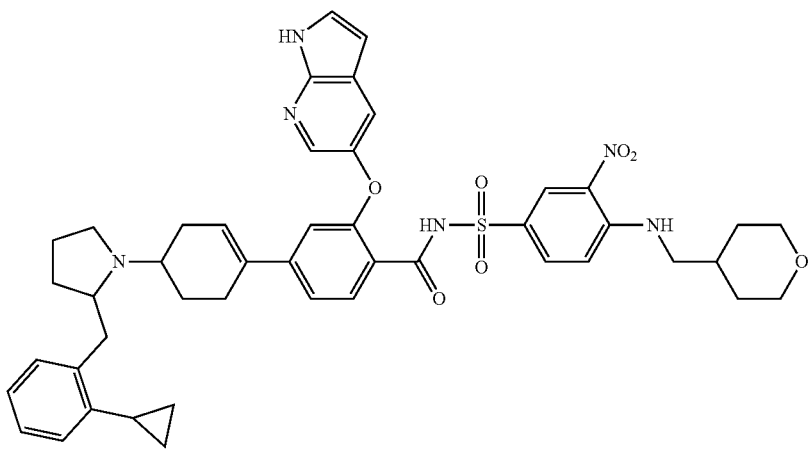

The desired compound was synthesized with 2-(2-cyclopropylbenzyl)pyrrolidine and 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-oxo-2',3',4',5'-tetrahydro-[1,1'-biphenyl]-4-carboxamide following the procedure similar to those in Example C12. $^1$H NMR (400 MHz, DMSO-d$_6$) δ ppm: 12.28 (s, 1H), 11.73 (s, 1H), 8.59-8.55 (m, 2H), 8.03 (s, 1H), 7.82 (d, J=8.3 Hz, 1H), 7.58-7.52 (m, 3H), 7.22-7.13 (m, 5H), 6.96 (d, J=6.2 Hz, 1H), 6.76 (t, J=11.4 Hz, 1H), 6.41 (s, 1H), 6.04 (s, 1H), 3.85 (d, J=8.7 Hz, 2H), 3.64 (s, 1H), 3.30-3.21 (m, 5H), 3.06-2.95 (m, 3H), 2.43 (s, 2H), 2.24 (s, 1H), 2.00 (dd, J=14.2, 6.8 Hz, 3H), 1.92-1.82 (m, 3H), 1.70 (s, 1H), 1.60 (d, J=12.3 Hz, 2H), 1.45 (s, 1H), 0.92-0.84 (m, 4H), 0.63 (s, 2H), MS (ESI, m/e) [M+1]$^+$ 830.8.

Example C125: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(o-tolyl)pyrrolidin-1-yl)-2',3',4',5'-tetrahydro-[1,1'-biphenyl]-4-carboxamide

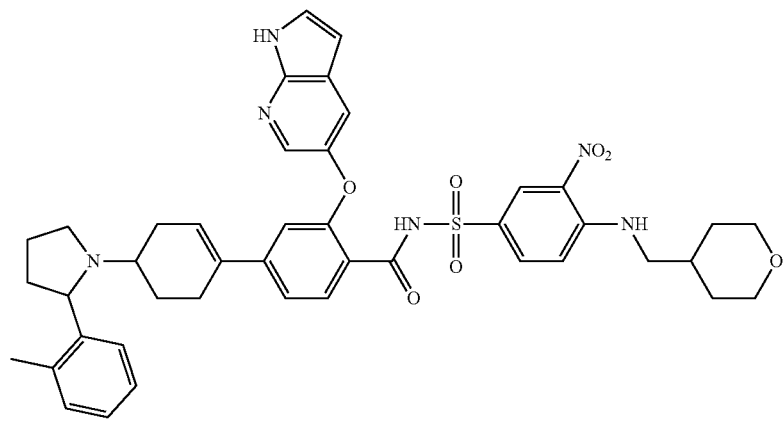 [SMILES: Cc1ccccc1C1CCCN1C1CC=C(c2ccc(C(=O)NS(=O)(=O)c3ccc(NCC4CCOCC4)c([N+](=O)[O-])c3)c(Oc3cnc4[nH]ccc4c3)c2)CC1]

The desired compound was synthesized with 2-(o-tolyl)pyrrolidine and 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-oxo-2',3',4',5'-tetrahydro-[1,1'-biphenyl]-4-carboxamide following the procedure similar to those in Example C12. $^1$H NMR (400 MHz, DMSO-d$_6$) δ ppm: 12.28 (s, 1H), 11.72 (s, 1H), 8.65-8.51 (m, 2H), 8.00 (d, J=2.2 Hz, 1H), 7.81 (dd, J=8.0, 2.2 Hz, 1H), 7.64-7.60 (m, 1H), 7.56-7.51 (m, 2H), 7.48 (d, J=8.0 Hz, 1H), 7.28-7.25 (m, 3H), 7.20-7.07 (m, 2H), 6.73 (d, J=8.0 Hz, 1H), 6.43-6.34 (m, 1H), 5.97-5.86 (m, 1H), 4.88-4.73 (m, 1H), 3.84 (d, J=8.4 Hz, 2H), 3.30-3.21 (m, 6H), 2.54 (s, 2H), 2.35 (s, 3H), 2.30 (s, 2H), 2.33-2.23 (m, 2H), 2.15-2.05 (m, 1H), 1.92-1.78 (m, 2H), 1.63-1.55 (m, 2H), 1.30-1.21 (m, 5H). MS (ESI, m/e) [M+1]$^+$ 791.2.

Example C126: 3-((1H-pyrrolo[2,3-b]pyridin-5-yl)oxy)-4'-(2-(2-ethylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

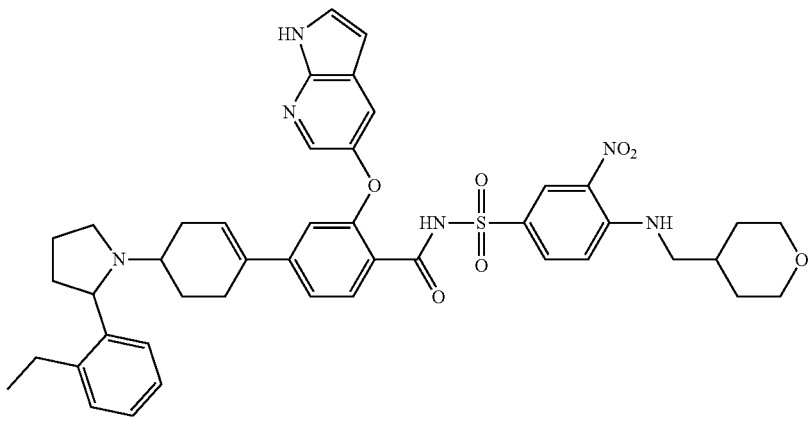 [SMILES: CCc1ccccc1C1CCCN1C1CC=C(c2ccc(C(=O)NS(=O)(=O)c3ccc(NCC4CCOCC4)c([N+](=O)[O-])c3)c(Oc3cnc4[nH]ccc4c3)c2)CC1]

The desired compound was synthesized starting from 2-(2-ethylphenyl)pyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. $^1$H NMR (400 MHz, DMSO-d$_6$) δ ppm: 12.25 (br, 1H), 11.67 (s, 1H), 8.51 (s, 2H), 7.98 (s, 1H), 7.87-7.60 (m, 2H), 7.55-7.42 (m, 3H), 7.31-6.94 (m, 5H), 6.74 (s, 1H), 6.36 (s, 1H), 5.97-5.81 (m, 1H), 3.36 (s, 1H), 6.03-5.77 (m, 1H), 3.94-3.78 (m, 2H), 3.30-3.15 (m, 6H), 2.72-2.60 (m, 2H), 2.45-1.78 (m, 8H), 1.70-1.47 (m, 4H), 1.32-1.04 (m, 6H). MS (ESI) m/e [M+1]$^+$ 763.2. MS (ESI) m/e [M+1]$^+$ 805.2

Example C127: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(2-vinylphenyl)pyrrolidin-1-yl)-2',3',4',5'-tetrahydro-[1,1'-biphenyl]-4-carboxamide

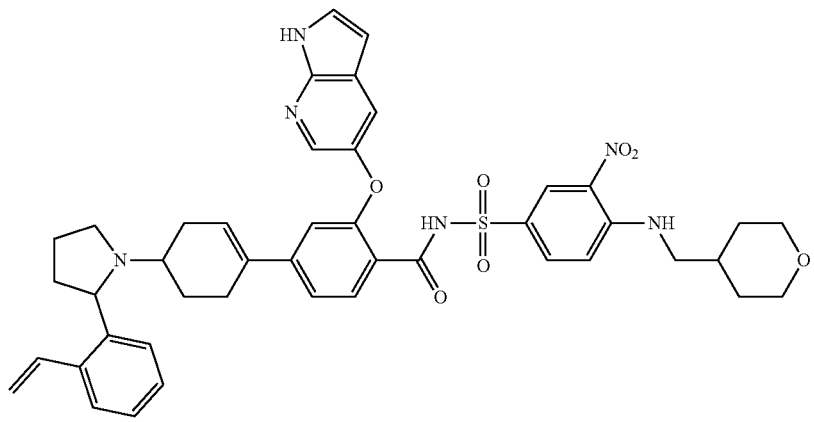 [SMILES: C=Cc1ccccc1C1CCCN1C1CC=C(c2ccc(C(=O)NS(=O)(=O)c3ccc(NCC4CCOCC4)c([N+](=O)[O-])c3)c(Oc3cnc4[nH]ccc4c3)c2)CC1]

The desired compound was synthesized with 2-(2-vinylphenyl)pyrrolidine and 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-oxo-2',3',4',5'-tetrahydro-[1,1'-biphenyl]-4-carboxamide following the procedure similar to those in Example C12. $^1$H NMR (400 MHz, DMSO-d$_6$) δ ppm: 12.21 (s, 1H), 11.66 (s, 1H), 8.49 (s, 2H), 7.97 (s, 1H), 7.76 (s, 1H), 7.61-7.34 (m, 5H), 7.27-6.86 (m, 5H), 6.71 (s, 1H), 6.36 (s, 1H), 5.97-5.81 (m, 1H), 5.64 (br, 1H), 5.29 (s, 1H), 3.84 (d, J=8.4 Hz, 2H), 3.28-3.22 (m, 3H), 3.08-2.82 (m, 1H), 2.29-2.07 (m, 6H), 1.88-1.79 (m, 2H), 1.70 (s, 1H), 1.60-1.45 (m, 3H), 1.39 (s, 1H), 1.30-1.01 (m, 4H). MS (ESI, m/e) [M+1]$^+$ 803.2.

Example C128: 3-((1H-pyrrolo[2,3-b]pyridin-5-yl)oxy)-4'-(2-(2-chloro-4-fluorophenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

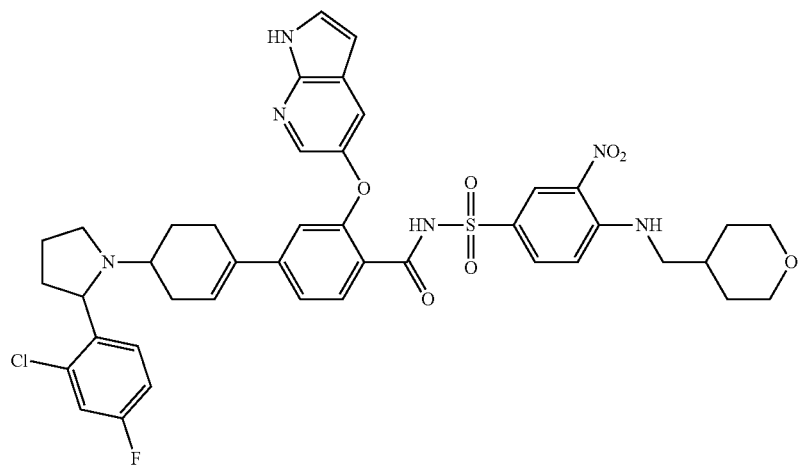 [SMILES: O=C(NS(=O)(=O)c1ccc(NCC2CCOCC2)c([N+](=O)[O-])c1)c1ccc(C2=CCC(N3CCCC3c3ccc(F)cc3Cl)CC2)cc1Oc1cnc2[nH]ccc2c1]

The desired compound was synthesized with 2-(2-chloro-4-fluorophenyl)pyrrolidine and 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-oxo-2',3',4',5'-tetrahydro-[1,1'-biphenyl]-4-carboxamide following the procedure similar to those in Example C12. $^1$H NMR (400 MHz, DMSO-d$_6$) δ ppm: 12.21 (s, 1H), 11.68 (s, 1H), 8.52 (s, 2H), 7.99 (s, 1H), 7.79 (s, 1H), 7.68-7.61 (m, 1H), 7.59-7.41 (m, 3H), 7.31 (s, 1H), 7.23-6.99 (m, 3H), 6.72 (s, 1H), 6.37 (s, 1H), 6.00-5.85 (m, 1H), 4.11 (s, 1H), 3.84 (d, J=11.3 Hz, 2H), 3.30-3.22 (m, 5H), 2.99-2.90 (m, 3H), 2.19 (s, 3H), 1.88-1.82 (m, 2H), 1.70 (s, 2H), 1.59 (d, J=12.6 Hz, 3H), 1.25-1.18 (m, 4H). MS (ESI, m/e) [M+1]$^+$ 829.1

Example C129: 3-((1H-pyrrolo[2,3-b]pyridin-5-yl)oxy)-4'-(2-(2-bromo-6-chlorophenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

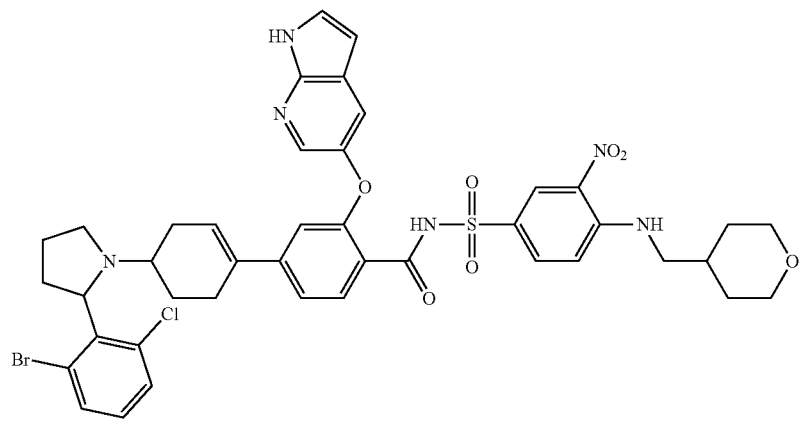

The desired compound was synthesized with 2-(2-bromo-6-chlorophenyl)pyrrolidine and 3-((1H-pyrrolo[2,3-b]pyridin-5-yl)oxy)-N-((3-nitro-4-((((tetrahydro-2H-pyran-4-yl)methyl)amino)phenyl)sulfonyl)-4'-oxo-2',3',4',5'-tetrahydro-[1,1'-biphenyl]-4-carboxamide following the procedure similar to those in Example C12. $^1$H NMR (400 MHz, DMSO-$d_6$) δ ppm: 12.24 (s, 1H), 11.71 (s, 1H), 8.54 (s, 2H), 8.00 (s, 1H), 7.80 (s, 1H), 7.68-7.23 (m, 5H), 7.25-6.98 (m, 3H), 6.75-6.63 (m, 1H), 6.38 (s, 1H), 6.01-5.67 (m, 1H), 4.51 (s, 1H), 3.84 (d, J=7.8 Hz, 2H), 3.28-3.05 (m, 5H), 2.68-2.55 (s, 2H), 2.38-2.27 (m, 1H), 2.23-2.02 (m, 3H), 2.01-1.73 (m, 5H), 1.65-1.58 (m, 2H), 1.59-1.33 (m, 1H), 1.31-1.12 (m, 3H). MS (ESI, m/e) [M+1]$^+$ 889.0, 891.0.

Example C131: 3-((1H-pyrrolo[2,3-b]pyridin-5-yl)oxy)-4'-(2-cyclopentylpyrrolidin-1-yl)-N-((3-nitro-4-((((tetrahydro-2H-pyran-4-yl)methyl)amino)phenyl)sulfonyl)-2',3',4',5'-tetrahydro-[1,1'-biphenyl]-4-carboxamide

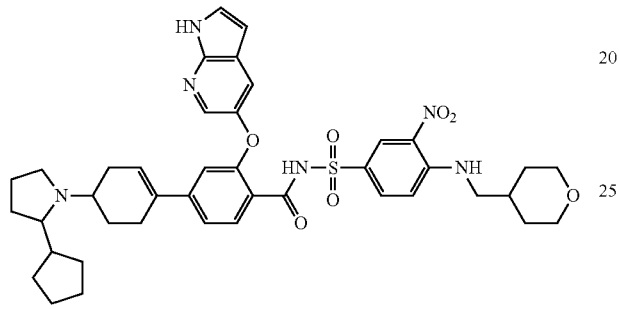

The desired compound was synthesized with 2-cyclopentylpyrrolidine and 3-((1H-pyrrolo[2,3-b]pyridin-5-yl)oxy)-N-((3-nitro-4-((((tetrahydro-2H-pyran-4-yl)methyl)amino)phenyl)sulfonyl)-4'-oxo-2',3',4',5'-tetrahydro-[1,1'-biphenyl]-4-carboxamide following the procedure similar to those in Example C12. $^1$H NMR (400 MHz, DMSO-$d_6$) δ ppm: 11.59 (s, 1H), 9.06 (s, 1H), 8.43-8.29 (m, 2H), 7.95 (s, 1H), 7.69 (d, J=8.9 Hz, 1H), 7.51 (d, J=8.0 Hz, 1H), 7.45 (s, 1H), 7.38 (s, 1H), 7.13 (d, J=8.0 Hz, 1H), 6.87 (d, J=8.9 Hz, 1H), 6.77 (s, 1H), 6.33 (s, 1H), 6.00 (s, 1H), 3.84 (d, J=8.8 Hz, 2H), 3.65-3.55 (m, 1H), 3.30-3.15 (m, 6H), 2.48-2.40 (m, 1H), 2.41-2.32 (m, 1H), 2.08-1.95 (m, 3H), 1.95-1.78 (m, 4H), 1.78-1.70 (m, 3H), 1.69-1.65 (m, 4H), 1.55-1.40 (m, 3H), 1.30-1.15 (m, 6H). MS (ESI, m/e) [M+1]$^+$ 768.8.

Example C132: 3-((1H-pyrrolo[2,3-b]pyridin-5-yl)oxy)-4'-(2-(2-butylphenyl)pyrrolidin-1-yl)-N-((3-nitro-4-((((tetrahydro-2H-pyran-4-yl)methyl)amino)phenyl)sulfonyl)-2',3',4',5'-tetrahydro-[1,1'-biphenyl]-4-carboxamide

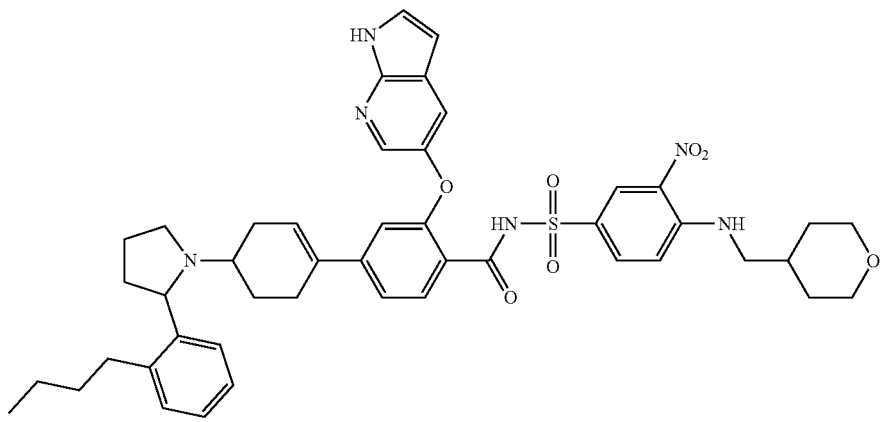

The desired compound was synthesized with 2-(2-butylphenyl)pyrrolidine and methyl 3-((1H-pyrrolo[2,3-b]pyridin-5-yl)oxy)-4'-oxo-2',3',4',5'-tetrahydro-[1,1-biphenyl]-4-carboxylate following the next procedures similar to those in Example C1. $^1$H NMR (400 MHz, DMSO-d$_6$) δ 12.24 (s, 1H), 11.65 (s, 1H), 8.48 (s, 2H), 7.96 (s, 1H), 7.74 (s, 1H), 7.62-7.39 (m, 4H), 7.27 (s, 1H), 7.17-6.94 (m, 3H), 6.72 (s, 1H), 6.35 (s, 1H), 6.06-5.77 (m, 1H), 3.90-3.78 (m, 2H), 3.27-2.94 (m, 6H), 2.72-2.58 (m, 3H), 2.29-2.09 (m, 3H), 2.02-1.94 (m, 2H), 1.93-1.80 (m, 2H), 1.77-1.66 (m, 2H), 1.64-1.52 (m, 2H), 1.52-1.39 (m, 2H), 1.35-1.18 (m, 8H), 0.92-0.75 (m, 4H). MS (ESI) m/e [M+1]$^+$ 832.9.

Example C133: 3-((1H-pyrrolo[2,3-b]pyridin-5-yl)oxy)-4'-(2-(5-bromo-2-isopropoxyphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

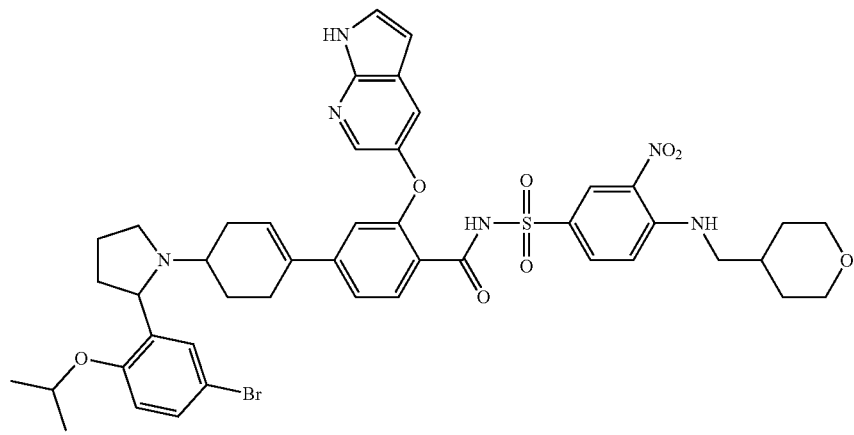 [SMILES: CC(C)Oc1ccc(Br)cc1C1CCCN1C1CC=C(c2ccc(C(=O)NS(=O)(=O)c3ccc(NCC4CCOCC4)c([N+](=O)[O-])c3)c(Oc3cnc4[nH]ccc4c3)c2)CC1]

The desired compound was synthesized with 2-(5-bromo-2-isopropoxyphenyl) pyrrolidine and 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-oxo-2',3',4',5'-tetrahydro-[1,1'-biphenyl]-4-carboxamide following the procedure similar to those in Example C12. $^1$H NMR (400 MHz, DMSO-d$_6$) δ 8.95-8.80 (m, 1H), 8.55-8.45 (m, 1H), 8.20-8.10 (m, 2H), 8.05-7.95 (m, 1H), 7.75-7.60 (m, 2H), 7.50-7.40 (m, 1H), 7.23-7.05 (m, 2H), 6.95-6.80 (m, 1H), 6.71-6.59 (m, 2H), 6.55-6.45 (m, 1H), 5.97 (s, 0.5H), 5.83 (s, 0.5H), 4.55-4.41 (m, 1H), 4.16-3.94 (m, 3H), 3.42 (m, 2H), 3.30-3.15 (m, 3H), 2.67-2.46 (m, 3H), 2.32-2.13 (m, 4H), 2.10-1.94 (m, 3H), 1.55-1.40 (m, 4H), 1.31-1.24 (m, 9H). MS (ESI, m/e) [M+1]$^+$ 912.7 and 914.7.

Example C134: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(m-tolyl)pyrrolidin-1-yl)-2',3',4',5'-tetrahydro-[1,1'-biphenyl]-4-carboxamide

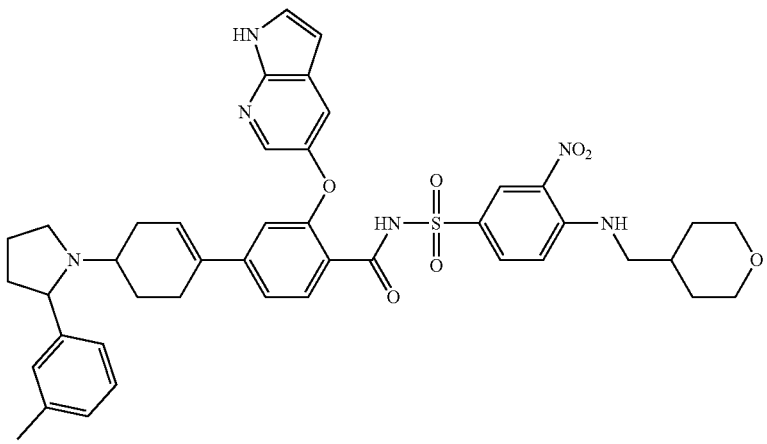 [SMILES: Cc1cccc(C2CCCN2C2CC=C(c3ccc(C(=O)NS(=O)(=O)c4ccc(NCC5CCOCC5)c([N+](=O)[O-])c4)c(Oc4cnc5[nH]ccc5c4)c3)CC2)c1]

The desired compound was synthesized with 2-(m-tolyl)pyrrolidine and 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-oxo-2',3',4',5'-tetrahydro-[1,1'-biphenyl]-4-carboxamide following the procedure similar to those in Example C12. $^1$H NMR (400 MHz, DMSO-d$_6$) δ 12.25 (s, 1H), 11.66 (s, 1H), 8.65-8.40 (m, 2H), 8.05-7.95 (m, 1H), 7.80-7.65 (m, 1H), 7.57-7.25 (m, 5H), 7.25-6.90 (m, 5H), 6.73 (s, 1H), 6.35 (s, 1H), 5.98 (s, 0.5H), 5.90 (s, 0.5H), 4.67-4.45 (m, 1H), 3.84 (d, J=8.6 Hz, 2H), 3.65-3.65 (m, 1H), 3.30-3.22 (m, 4H), 3.20-1.85 (m, 3H), 2.35-2.20 (m, 5H), 2.11-1.94 (m, 4H), 1.90-1.80 (m, 1H), 1.65-1.55 (m, 2H), 1.50-1.40 (m, 1H), 1.30-1.15 (m, 3H). MS (ESI, m/e) [M+1]$^+$ 790.8.

Example C135: 3-((1H-pyrrolo[2,3-b]pyridin-5-yl)oxy)-4'-(2-(3-isopropylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

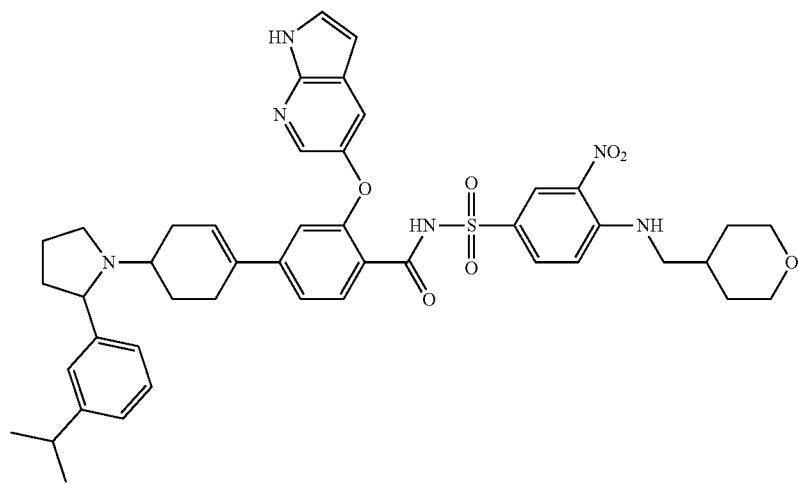 [SMILES: CC(C)c1cccc(C2CCCN2C2CC=C(c3ccc(C(=O)NS(=O)(=O)c4ccc(NCC5CCOCC5)c([N+](=O)[O-])c4)c(Oc4cnc5[nH]ccc5c4)c3)CC2)c1]

The desired compound was synthesized with 2-(3-isopropylphenyl)pyrrolidine and 3-((1H-pyrrolo[2,3-b]pyridin-5-yl)oxy)-N-((3-nitro-4-(((tetrahydro-2H-pyran-4-yl) methyl)amino)phenyl)sulfonyl)-4'-oxo-2',3',4',5'-tetrahydro-[1,1'-biphenyl]-4-carboxamide following the procedure similar to those in Example C12. $^1$H NMR (400 MHz, DMSO-d$_6$) δ 11.92 (s, 1H), 11.57 (s, 1H), 8.45-8.30 (m, 2H), 7.92 (s, 1H), 7.70-7.60 (m, 1H), 7.50-7.40 (m, 2H), 7.38-7.25 (m, 2H), 7.24-6.97 (m, 4H), 6.90-6.80 (m, 1H), 6.72 (s, 1H), 6.31 (s, 1H), 5.98 (s, 0.5H), 5.86 (s, 0.5H), 3.83 (d, J=8.0 Hz, 3H), 3.30-3.20 (m, 5H), 2.40-2.00 (m, 6H), 1.95-1.82 (s, 2H), 1.80-1.70 (m, 2H), 1.60 (d, J=12.5 Hz, 3H), 1.50-1.40 (m, 2H), 1.31-1.08 (m, 9H), MS (ESI) m/e [M+1]$^+$ 818.8.

Example C136: 3-((1H-pyrrolo[2,3-b]pyridin-5-yl)oxy)-4'-(2-(3-methoxyphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

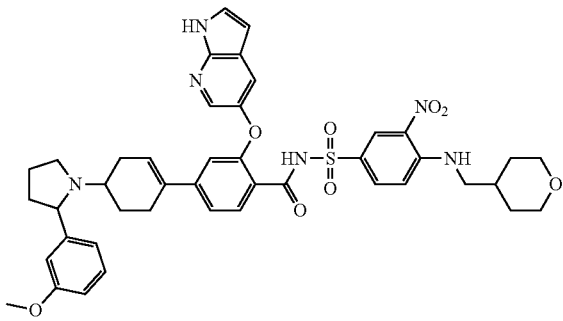 [SMILES: COc1cccc(C2CCCN2C2CC=C(c3ccc(C(=O)NS(=O)(=O)c4ccc(NCC5CCOCC5)c([N+](=O)[O-])c4)c(Oc4cnc5[nH]ccc5c4)c3)CC2)c1]

The desired compound was synthesized with 2-(3-methoxyphenyl)pyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. $^1$H NMR (400 MHz, DMSO-d$_6$) δ 12.27 (s, 1H), 11.68 (s, 1H), 8.61-8.46 (m, 2H), 7.98 (s, 1H), 7.84-7.70 (m, 1H), 7.58-7.43 (m, 3H), 7.39-7.30 (m, 1H), 7.26-6.93 (m, 5H), 6.73 (s, 1H), 6.37 (m, 1H), 4.67-4.54 (m, 1H), 3.90-3.80 (m, 241). 3.76 (s, 3H), 3.31-3.19 (m, 4H), 3.10-2.87 (m, 3H), 2.43-2.36 (m, 2H), 2.13-1.99 (m, 4H), 1.92-1.81 (m, 2H), 1.67-1.54 (m, 4H), 1.32-1.20 (m, 4H). MS (ESI, m/e) [M+1]$^+$ 806.8.

Example C137: 3-((1H-pyrrolo[2,3-b]pyridin-5-yl)oxy)-4'-(2-(3-cyanophenyl)pyrrolidin-1-yl)-N-((3-nitro-4-(((tetrahydro-2H-pyran-4-yl)methyl)amino)phenyl)sulfonyl)-2',3',4',5'-tetrahydro[1,1'-biphenyl]-4-carboxamide

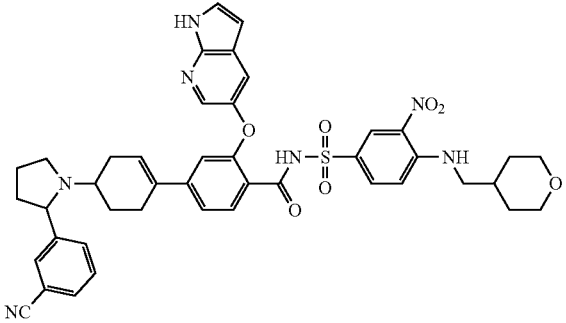 [SMILES: N#Cc1cccc(C2CCCN2C2CC=C(c3ccc(C(=O)NS(=O)(=O)c4ccc(NCC5CCOCC5)c([N+](=O)[O-])c4)c(Oc4cnc5[nH]ccc5c4)c3)CC2)c1]

The desired compound was synthesized with 3-(pyrrolidin-2-yl)benzonitrile and 3-((1H-pyrrolo[2,3-b]pyridin-5-yl)oxy)-N-((3-nitro-4-(((tetrahydro-2H-pyran-4-yl) methyl)amino)phenyl)sulfonyl)-4'-oxo-2',3',4',5'-tetrahydro-[1,1'-biphenyl]-4-carboxamide following the procedure similar to those in Example C12. MS (ESI, m/e) [M+1]$^+$ 801.8.

Example C138: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(3-vinylphenyl)pyrrolidin-1-yl)-2',3',4',5'-tetrahydro-[1,1'-biphenyl]-4-carboxamide

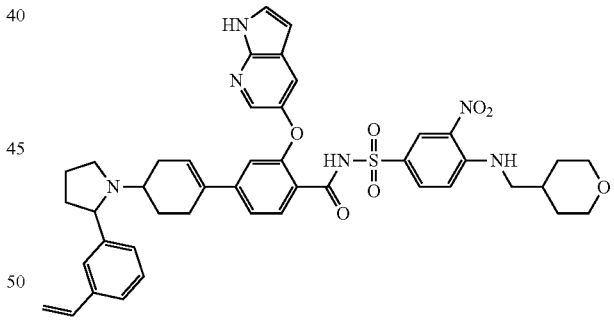

The desired compound was synthesized with 2-(3-vinylphenyl)pyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. $^1$H NMR (400 MHz, DMSO-d$_6$) δ 12.23 (s, 1H), 11.63 (s, 1H), 8.46 (s, 2H), 7.95 (s, 1H), 7.76-7.61 (m, 2H), 7.56-7.32 (m, 6H), 7.16-7.04 (m, 1H), 7.02-6.88 (m, 1H), 6.69-6.63 (m, 2H), 6.34 (s, 1H), 6.00-5.78 (m, 2H), 5.35-5.20 (m, 2H), 3.90-3.78 (m, 2H), 3.30-3.18 (m, 5H), 2.32-2.15 (m, 4H), 2.05-1.93 (m, 3H), 1.91-1.78 (m, 2H), 1.66-1.54 (m, 4H), 1.52-1.38 (m, 1H), 1.35-1.24 (m, 3H). MS (ESI) m/e [M+1]$^+$ 802.8.

Example C139: 3-((1H-pyrrolo[2,3-b]pyridin-5-yl)oxy)-4'-(2-(benzo[d][1,3]dioxol-4-yl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

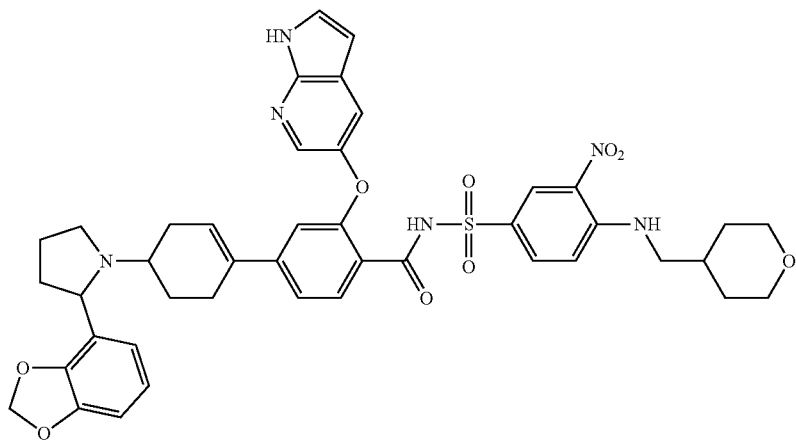 [SMILES: O=C(NS(=O)(=O)c1ccc(NCC2CCOCC2)c([N+](=O)[O-])c1)c1ccc(C2=CCC(N3CCCC3c3cccc4c3OCO4)CC2)cc1Oc1cnc2[nH]ccc2c1]

The desired compound was synthesized with 2-(benzo[d][1,3]dioxol-4-yl)pyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. $^1$H NMR (400 MHz, DMSO-$d_6$) δ 12.27 (s, 1H), 11.69 (s, 1H), 8.65-8.45 (m, 2H), 7.99 (s, 1H), 7.78 (d, J=8.8 Hz, 1H), 7.55-7.42 (m, 3H), 7.30-7.20 (m, 1H), 7.17 (d, J=8.8 Hz, 1H), 7.06 (d, J=8.8 Hz, 1H), 7.00-6.90 (m, 1H), 6.80-6.70 (m, 1H), 6.38 (s, 1H), 6.04 (s, 1H), 6.01 (s, 0.5H), 5.93 (s, 0.5H), 4.80-4.50 (m, 1H), 3.87-3.80 (m, 2H), 3.70-3.40 (m, 2H), 3.30-3.15 (m, 5H), 2.40-2.00 (m, 10H), 1.90-1.75 (m, 2H), 1.59 (d, J=12.1 Hz, 2H), 1.31-1.10 (m, 3H). MS (ESI, m/e) [M+1]$^+$ 820.8.

Example C140: 3-((1H-pyrrolo[2,3-b]pyridin-5-yl)oxy)-4'-(2-(2,2-difluorobenzo[d][1,3]dioxol-4-yl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

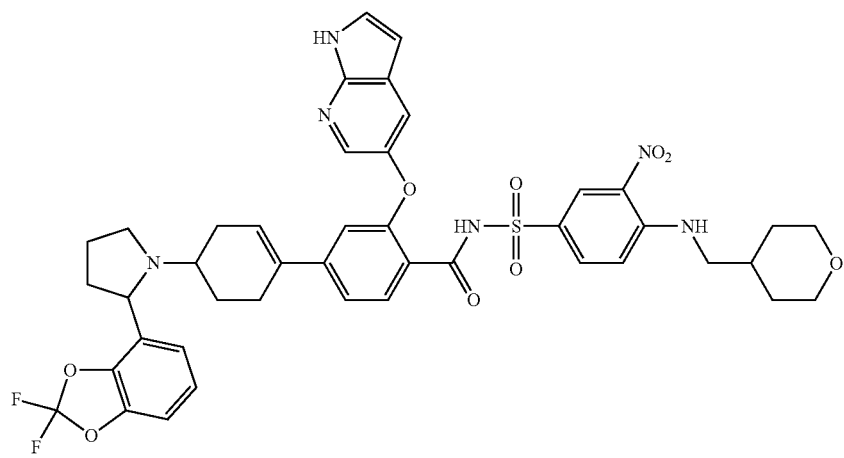 [SMILES: O=C(NS(=O)(=O)c1ccc(NCC2CCOCC2)c([N+](=O)[O-])c1)c1ccc(C2=CCC(N3CCCC3c3cccc4c3OC(F)(F)O4)CC2)cc1Oc1cnc2[nH]ccc2c1]

The desired compound was synthesized with 2-(2,2-difluorobenzo[d][1,3]dioxol-4-yl) pyrrolidine and 3-((1H-pyrrolo[2,3-b]pyridin-5-yl)oxy)-N-((3-nitro-4-(((tetrahydro-2H-pyran-4-yl) methyl)amino)phenyl)sulfonyl)-4'-oxo-2',3',4',5'-tetrahydro-[1,1'-biphenyl]-4-carboxamide following the procedure similar to those in Example C12. $^1$H NMR (400 MHz, DMSO-$d_6$) δ 12.11 (s, 1H), 11.66 (s, 1H), 8.58-8.42 (m, 2H), 8.05-7.95 (m, 1H), 7.80-7.70 (m, 1H), 7.55-7.41 (m, 3H), 7.30-7.16 (m, 2H), 7.15-7.06 (m, 2H), 7.05-6.95 (m, 1H), 6.75-6.65 (m, 1H), 6.36 (s, 1H), 6.01 (s, 0.5H), 5.83 (s, 0.5H), 4.05-3.95 (m, 1H), 3.90-3.75 (m, 2H), 3.27-3.18 (m, 4H), 3.15-2.94 (m, 1H), 2.25-2.05 (m, 4H), 2.02-1.95 (m, 2H), 1.90-1.80 (m, 2H), 1.75-1.65 (m, 2H), 1.60-1.55 (m, 2H), 1.50-1.40 (m, 1H), 1.35-1.15 (m, 3H). MS (ESI, m/e) [M+1]$^+$ 818.9.

Example C141: 3-((1H-pyrrolo[2,3-b]pyridin-5-yl)oxy)-4'-(2-(2-cyclopropylphenyl)-3-methylpyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

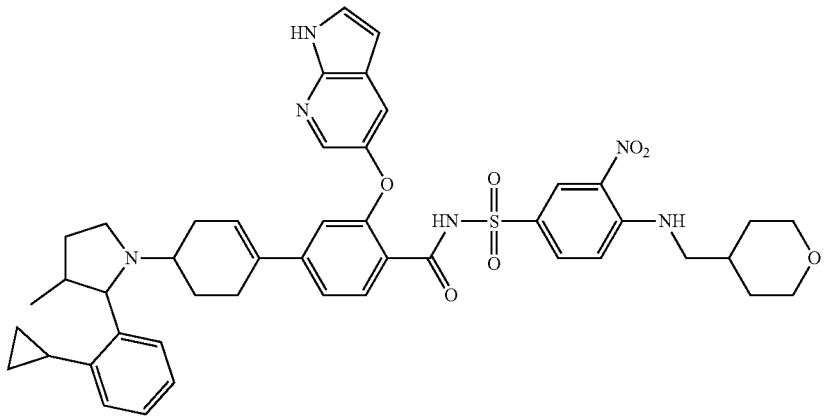 [SMILES: CC1CCN(C2CC=C(c3ccc(C(=O)NS(=O)(=O)c4ccc(NCC5CCOCC5)c([N+](=O)[O-])c4)c(Oc4cnc5[nH]ccc5c4)c3)CC2)C1c1ccccc1C1CC1]

The desired compound was synthesized with 2-(2-cyclopropylphenyl)-3-methyl pyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. $^1$H NMR (400 MHz, DMSO-$d_6$) δ 12.22 (s, 1H), 11.66 (s, 1H), 8.65-8.35 (m, 2H), 7.97 (s, 1H), 7.76 (d, J=8.5 Hz, 1H), 7.65-7.35 (m, 4H), 7.37-6.85 (m, 5H), 6.73 (s, 1H), 6.36 (s, 1H), 5.98 (s, 0.5H), 5.85 (s, 0.5H), 4.60-4.20 (m, 1H), 3.84 (d, J=8.4 Hz, 2H), 3.30-3.10 (m, 5H), 2.40-2.05 (m, 5H), 2.04-1.75 (m, 4H), 1.70-1.35 (m, 5H), 1.33-1.12 (m, 3H), 0.95-0.80 (m, 2H), 0.78-0.66 (m, 1H), 0.60-0.25 (m, 4H), MS (ESI) m/e [M+1]$^+$ 830.8.

Example C142: 3-((1H-pyrrolo[2,3-b]pyridin-5-yl)oxy)-4'-(2-(2-cyclopropylphenyl)-3,3-dimethylpyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

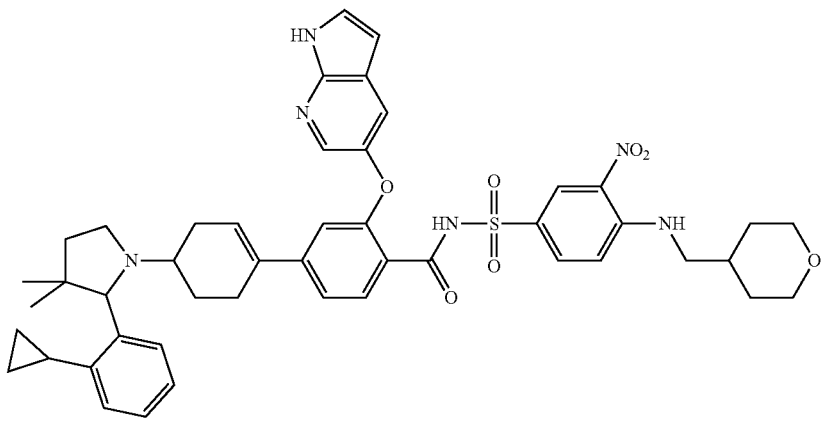 [SMILES: CC1(C)CCN(C2CC=C(c3ccc(C(=O)NS(=O)(=O)c4ccc(NCC5CCOCC5)c([N+](=O)[O-])c4)c(Oc4cnc5[nH]ccc5c4)c3)CC2)C1c1ccccc1C1CC1]

The desired compound was synthesized with 2-(2-cyclopropylphenyl)-3,3-dimethyl pyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. $^1$H NMR (400 MHz, DMSO-d$_6$) δ 12.24 (s, 1H), 11.67 (s, 1H), 8.65-8.40 (m, 2H), 7.98 (s, 1H), 7.85-7.80 (m, 1H), 7.69-7.20 (m, 5H), 7.15-6.80 (m, 4H), 6.72 (s, 1H), 6.36 (s, 1H), 6.04-5.71 (m, 1H), 4.30-4.10 (m, 1H), 3.84 (d, J=9.3 Hz, 2H), 3.75-3.50 (m, 1H), 3.30-3.20 (m, 4H), 3.10-2.90 (m, 1H), 2.80-2.60 (m, 1H), 2.41-1.79 (m, 8H), 1.35-1.20 (m, 5H), 1.15-1.05 (m, 3H), 1.10-0.65 (m, 5H), 0.60-0.35 (m, 3H). MS (ESI) m/e [M+1]$^+$ 844.8.

Example C143: 3-((1H-pyrrolo[2,3-b]pyridin-5-yl)oxy)-4'-(2-(4-chloro-2-cyclopropylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

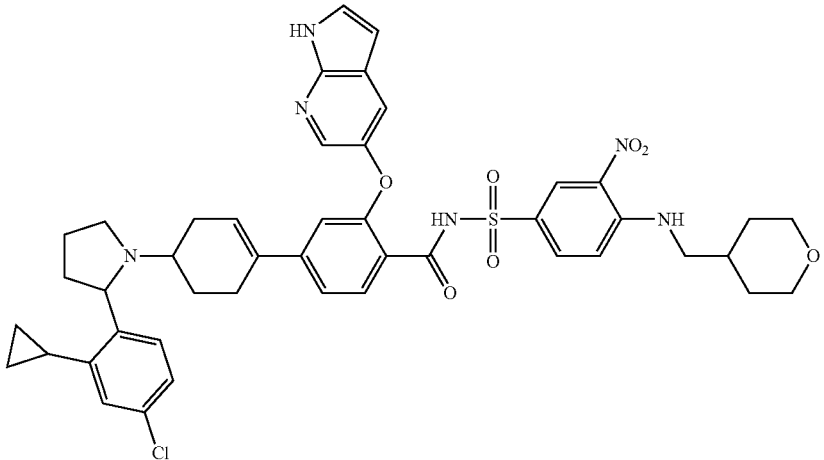

The desired compound was synthesized with 2-(4-chloro-2-cyclopropylphenyl)pyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. $^1$H NMR (400 MHz, DMSO-d$_6$) δ 12.24 (s, 1H), 11.68 (s, 1H), 8.64-8.47 (m, 2H), 7.98 (s, 1H), 7.77 (s, 1H), 7.50 (s, 4H), 7.25-7.01 (m, 4H), 6.73 (s, 1H), 6.37 (s, 1H), 6.05-5.95 (m, 0.5H), 5.90-5.85 (m, 0.5H), 4.45-4.25 (m, 1H), 3.89-3.79 (m, 2H), 3.25-3.10 (m, 5H), 3.04-2.16 (m, 5H), 2.06-1.70 (m, 5H), 1.64-1.57 (m, 2H), 1.49-1.38 (m, 2H), 1.34-1.26 (m, 3H), 0.99-0.85 (m, 4H), 0.79-0.54 (m, 1H). MS (ESI) m/e [M+1]$^+$ 850.8.

Example C144: 3-((1H-pyrrolo[2,3-b]pyridin-5-yl)oxy)-4'-(2-(5-chloro-2-cyclopropylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

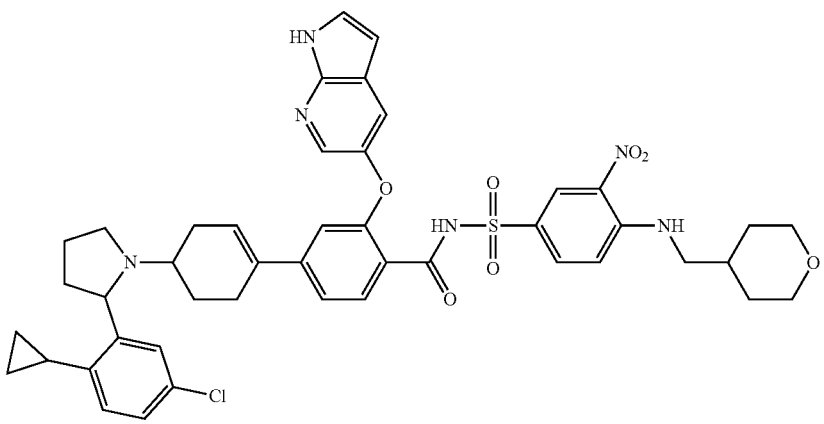

The desired compound was synthesized with 2-(5-chloro-2-cyclopropylphenyl) pyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. $^1$H NMR (400 MHz, DMSO-$d_6$) δ 10.31 (s, 1H), 9.63 (s, 1H), 8.95-8.85 (m, 1H), 8.54 (t, J=4.9 Hz, 1H), 8.25-8.10 (m, 2H), 8.03 (d, J=8.4 Hz, 1H), 7.72-7.68 (m, 1H), 7.60 (d, J=23.7 Hz, 1H), 7.47 (s, 1H), 7.15-7.06 (m, 1H), 7.05-6.95 (m, 1H), 6.92 (d, J=8.4 Hz, 1H), 6.90-6.80 (m, 1H), 6.70-6.60 (m, 1H), 6.58-6.50 (m, 1H), 5.97 (s, 0.5H), 5.80 (s, 0.5H), 4.35-4.20 (m, 1H), 4.08-3.94 (m, 2H), 3.42 (t, J=11.8 Hz, 2H), 3.25 (t, J=5.9 Hz, 2H), 3.20-3.15 (m, 1H), 2.70-2.45 (m, 2H), 2.40-2.10 (m, 4H), 2.01-1.91 (m, 2H), 1.90-1.80 (m, 2H), 1.77-1.35 (m, 8H), 1.10-0.80 (m, 2H), 0.70-0.60 (m, 1H), 0.55-0.45 (m, 1H). MS (ESI) m/e [M+1]$^+$ 850.7.

Example C145: 3-((1H-pyrrolo[2,3-b]pyridin-5-yl)oxy)-4'-(2-(2-(1,1-difluoroethyl)phenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

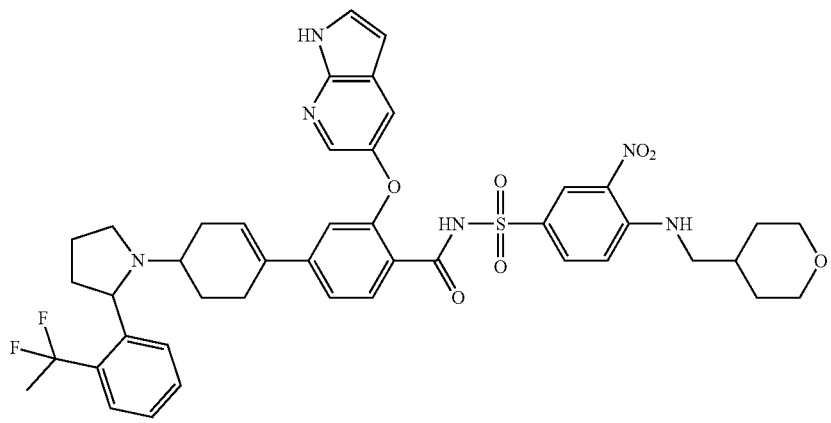 [SMILES: CC(F)(F)c1ccccc1C1CCCN1C1CC=C(c2ccc(C(=O)NS(=O)(=O)c3ccc(NCC4CCOCC4)c([N+](=O)[O-])c3)c(Oc3cnc4[nH]ccc4c3)c2)CC1]

The desired compound was synthesized with 2-(2-(1,1-difluoroethyl)phenyl)pyrrolidine and methyl 3-((1H-pyrrolo[2,3-b]pyridin-5-yl)oxy)-4'-oxo-2',3',4',5'-tetra hydro-[1,1'-biphenyl]-4-carboxylate following the next procedures similar to those in Example C1. MS (ESI) m/e [M+1]$^+$ 840.8.

Example C146: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(2-(2,2,2-trifluoroethyl)phenyl)pyrrolidin-1-yl)-2',3',4',5'-tetrahydro-[1,1'-biphenyl]-4-carboxamide

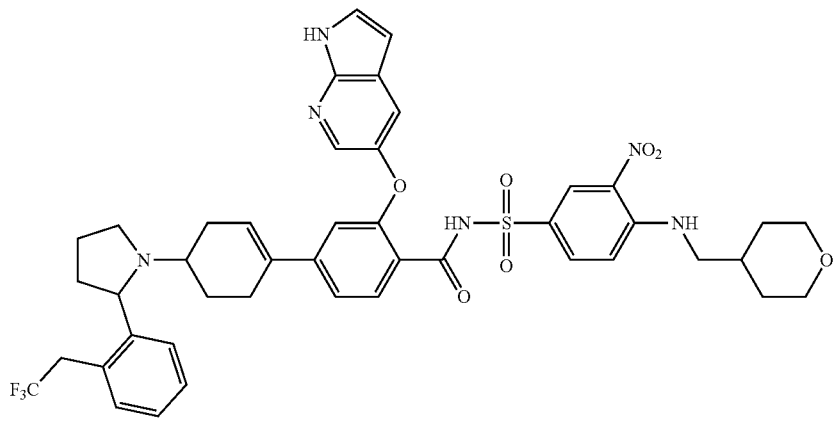

The desired compound was synthesized with 2-(2-(2,2,2-trifluoroethyl)phenyl)pyrrolidine and 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-oxo-2',3',4',5'-tetrahydro-[1,1'-biphenyl]-4-carboxamide following the procedure similar to those in Example C12. MS (ESI) m/e [M+1]$^+$ 858.8.

Example C152: 3-((1H-pyrrolo[2,3-b]pyridin-5-yl)oxy)-4'-(2-(2-cyclopentylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

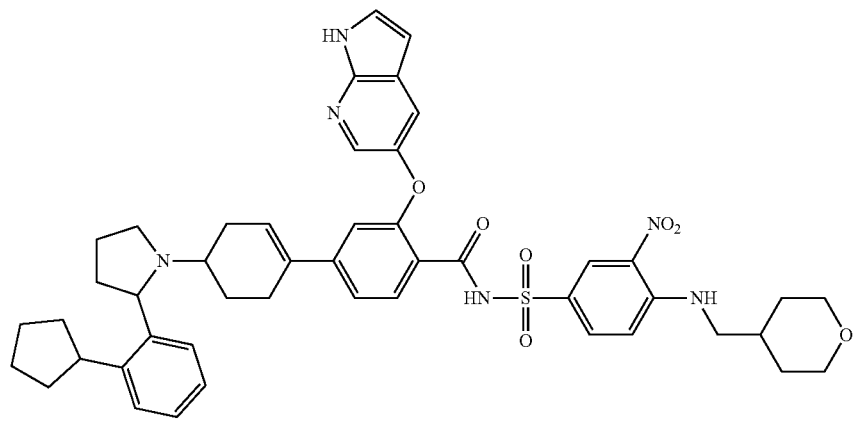 [SMILES: O=C(NS(=O)(=O)c1ccc(NCC2CCOCC2)c([N+](=O)[O-])c1)c1ccc(C2=CCC(N3CCCC3c3ccccc3C3CCCC3)CC2)cc1Oc1cnc2[nH]ccc2c1]

The desired compound was synthesized with 2-(2-cyclopentylphenyl)pyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. MS (ESI, m/e) [M+1]$^+$ 844.8.

Example C161: 3-((1H-pyrrolo[2,3-b]pyridin-5-yl)oxy)-4'-(2-(2,2-dimethylbenzo[d][1,3]dioxol-4-yl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

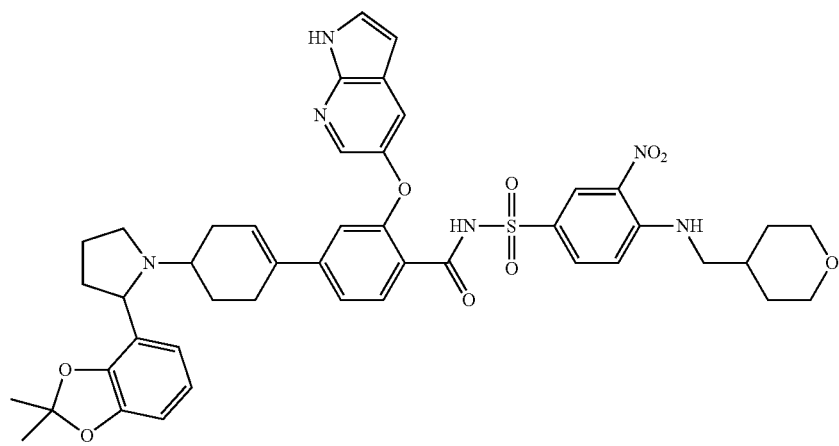 [SMILES: CC1(C)Oc2cccc(C3CCCN3C3CC=C(c4ccc(C(=O)NS(=O)(=O)c5ccc(NCC6CCOCC6)c([N+](=O)[O-])c5)c(Oc5cnc6[nH]ccc6c5)c4)CC3)c2O1]

The desired compound was synthesized with 2-(2,2-dimethylbenzo[d][1,3]dioxol-4-yl)pyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. $^1$H NMR (400 MHz, DMSO-$d_6$) δ 9.39 (s, 1H), 8.91 (s, 1H), 8.59-8.49 (m, 1H), 8.23-8.10 (m, 2H), 8.03 (d, J=8.3 Hz, 1H), 7.68 (s, 1H), 7.46 (s, 1H), 7.08-7.03 (m, 2H), 6.92 (d, J=9.3 Hz, 1H), 6.82-6.70 (m, 1H), 6.67-6.51 (m, 3H), 5.96-5.75 (m, 1H), 4.07-4.00 (m, 2H), 3.49-3.33 (m, 2H), 3.31-3.21 (m, 2H), 2.93-2.81 (m, 2H), 2.43-2.24 (m, 4H), 2.17-1.88 (m, 8H), 1.82-1.68 (m, 3H), 1.68-1.61 (m, 3H), 1.61-1.48 (m, 3H), 1.47-1.39 (m, 3H). MS (ESI) m/e [M+1]$^+$ 848.8.

Example C162: 3-((1H-pyrrolo[2,3-b]pyridin-5-yl)oxy)-4'-(2-(3-ethynylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

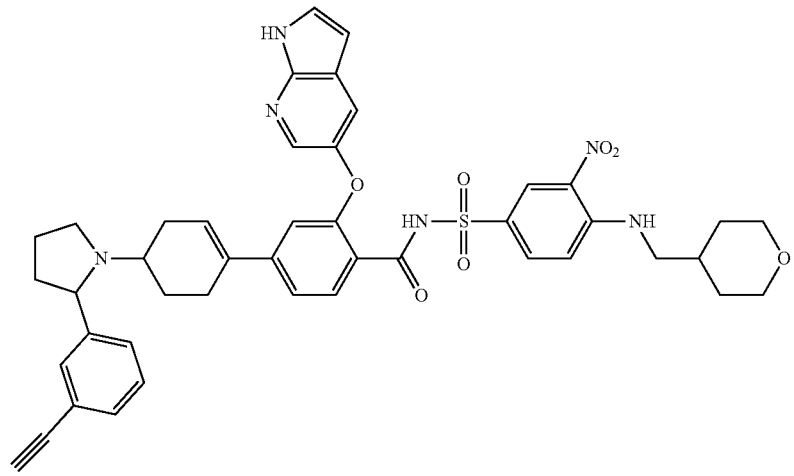 [SMILES: C#Cc1cccc(C2CCCN2C2CC=C(c3ccc(C(=O)NS(=O)(=O)c4ccc(NCC5CCOCC5)c([N+](=O)[O-])c4)c(Oc4cnc5[nH]ccc5c4)c3)CC2)c1]

The desired compound was synthesized with 2-(3-ethynylphenyl)pyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. $^1$H NMR (400 MHz, DMSO-$d_6$) δ 12.25 (s, 1H), 11.68 (s, 1H), 8.60-8.40 (m, 2H), 7.98 (s, 1H), 7.80-7.60 (m, 2H), 7.55-7.35 (m, 5H), 7.30-7.20 (m, 1H), 7.18-6.96 (m, 2H), 6.72 (s, 1H), 6.37 (s, 1H), 6.05-5.85 (m, 1H), 4.80-4.50 (m, 1H), 4.35-4.15 (m, 1H), 3.89-3.73 (m, 2H), 3.30-3.18 (m, 5H), 2.40-2.25 (m, 3H), 2.20-1.95 (m, 5H), 1.90-1.80 (m, 2H), 1.75-1.65 (m, 1H), 1.59 (d, J=11.7 Hz, 2H), 1.50-1.35 (m, 1H), 1.31-1.16 (m, 3H). MS (ESI) m/e [M+1]$^+$ 800.8.

Example C163: 3-((1H-pyrrolo[2,3-b]pyridin-5-yl)oxy)-4'-(3-cyano-2-(2-cyclopropylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

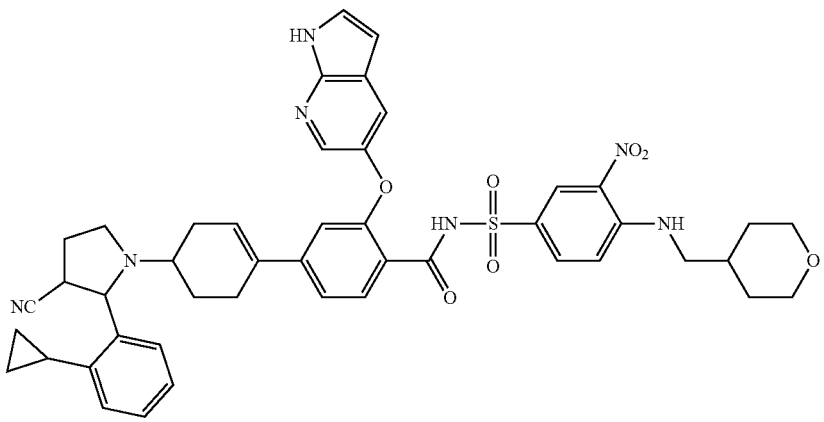 [SMILES: N#CC1CCN(C2CC=C(c3ccc(C(=O)NS(=O)(=O)c4ccc(NCC5CCOCC5)c([N+](=O)[O-])c4)c(Oc4cnc5[nH]ccc5c4)c3)CC2)C1c1ccccc1C1CC1]

The desired compound was synthesized with 2-(2-cyclopropylphenyl)pyrrolidine-3-carbonitrile and methyl 3-((1H-pyrrolo[2,3-b]pyridin-5-yl)oxy)-4'-oxo-2',3',4',5'-tetrahydro-[1,1-biphenyl]-4-carboxylate following the next procedures similar to those in Example C1. $^1$H NMR (400 MHz, DMSO-d$_6$) δ 12.22 (s, 1H), 11.69 (s, 1H), 8.65-8.45 (m, 2H), 8.05-7.95 (m, 1H), 7.79 (d, J=8.9, 1H), 7.55-7.40 (m, 4H), 7.20-6.94 (m, 5H), 6.74-6.68 (m, 1H), 6.02 (s, 0.5H), 5.81 (s, 0.5H), 4.64-4.47 (m, 1H), 3.91-3.78 (m, 2H), 3.29-3.15 (m, 5H), 3.05-2.95 (m, 2H), 2.8-2.74 (m, 1H), 2.26-1.81 (m, 10H), 1.64-1.52 (m, 3H), 1.30-1.15 (m, 3H), 0.99-0.88 (m, 2H), 0.79-0.68 (m, 1H), 0.63-0.50 (m, 1H). MS (ESI) m/e [M+1]$^+$ 841.8.

Example C164: 3-((1H-pyrrolo[2,3-b]pyridin-5-yl)oxy)-4'-(2-(2-cyclopropylphenyl)-3-ethynylpyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

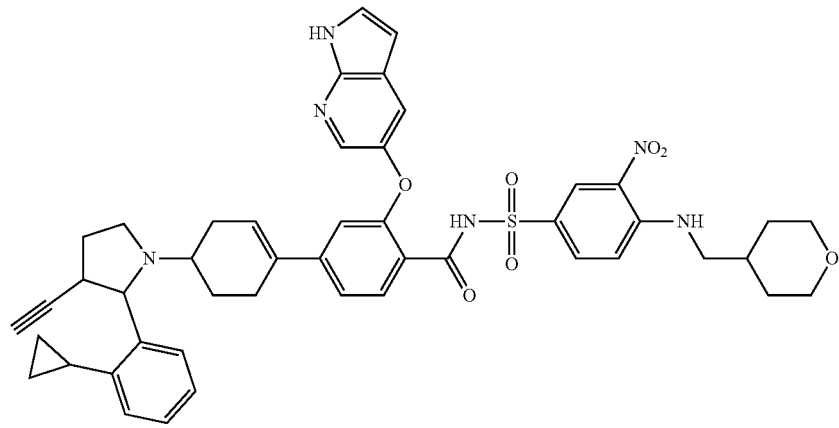 [SMILES: C#CC1CCN(C2CC=C(c3ccc(C(=O)NS(=O)(=O)c4ccc(NCC5CCOCC5)c([N+](=O)[O-])c4)c(Oc4cnc5[nH]ccc5c4)c3)CC2)C1c1ccccc1C1CC1]

The desired compound was synthesized with 2-(2-cyclopropylphenyl)-3-ethynylpyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example CL NMR (400 MHz, DMSO-d$_6$) δ 12.21 (s, 1H), 11.68 (s, 1H), 8.67-8.40 (m, 2H), 7.98 (s, 1H), 7.84-7.72 (m, 1H), 7.56-7.36 (m, 4H), 7.17-7.08 (m, 4H), 6.94 (s, 1H), 6.71 (s, 1H), 6.37 (s, 1H), 6.06-5.75 (m, 1H), 4.35-4.05 (m, 1H), 3.91-3.76 (m, 2H), 3.30-3.20 (m, 4H), 3.15-3.05 (m, 2H), 2.40-1.95 (m, 8H), 1.90-1.65 (m, 4H), 1.64-1.55 (m, 2H), 1.50-1.35 (m, 2H), 1.30-1.10 (m, 2H), 1.05-0.95 (m, 1H), 0.85-0.80 (m, 1H). MS (ESI) m/e [M+1]$^+$ 840.8.

Example C165: 3-((1H-pyrrolo[2,3-b]pyridin-5-yl)oxy)-4'-(2-(2-methoxyphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

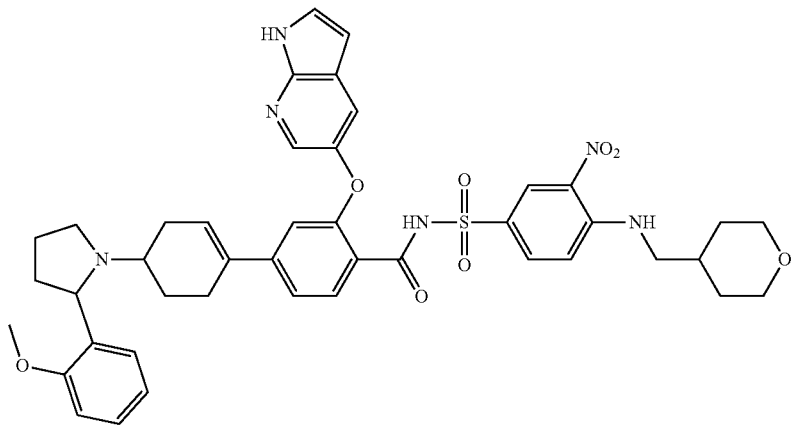 [SMILES: COc1ccccc1C1CCCN1C1CC=C(c2ccc(C(=O)NS(=O)(=O)c3ccc(NCC4CCOCC4)c([N+](=O)[O-])c3)c(Oc3cnc4[nH]ccc4c3)c2)CC1]

The desired compound was synthesized with 2-(2-methoxyphenyl)pyrrolidine and 3-((1H-pyrrolo[2,3-b]pyridin-5-yl)oxy)-N-((3-nitro-4-(((tetrahydro-2H-pyran-4-yl) methyl)amino)phenyl)sulfonyl)-4'-oxo-2',3',4',5'-tetrahydro-[1,1'-biphenyl]-4-carboxamide following the procedure similar to those in Example C12. $^1$H NMR (400 MHz, DMSO-$d_6$) δ 11.54 (s, 1H), 8.38-8.33 (m, 2H), 7.91 (s, 1H), 7.69-7.60 (m, 1H), 7.58-7.38 (m, 3H), 7.30 (d, J=6.1 Hz, 1H), 7.24-7.02 (m, 2H), 6.95-6.78 (m, 3H), 6.73 (s, 1H), 6.30 (s, 1H), 5.98-5.79 (m, 1H), 4.12 (s, 1H), 3.83 (d, J=8.4 Hz, 2H), 3.76 (s, 3H), 3.30-3.21 (m, 4H), 3.15-2.95 (m, 2H), 2.25-2.15 (m, 1H), 2.06 (d, J=18.4, 6.0 Hz, 2H), 2.03-1.97 (m, 3H), 1.95-1.82 (m, 1H), 1.72-1.56 (m, 5H), 1.48-1.45 (m, 1H), 1.30-1.20 (m, 3H). MS (ESI, m/e) [M+1]+806.8.

Example C166: 3-((1H-pyrrolo[2,3-b]pyridin-5-yl)oxy)-4'-(2-(benzo[b]thiophen-3-yl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

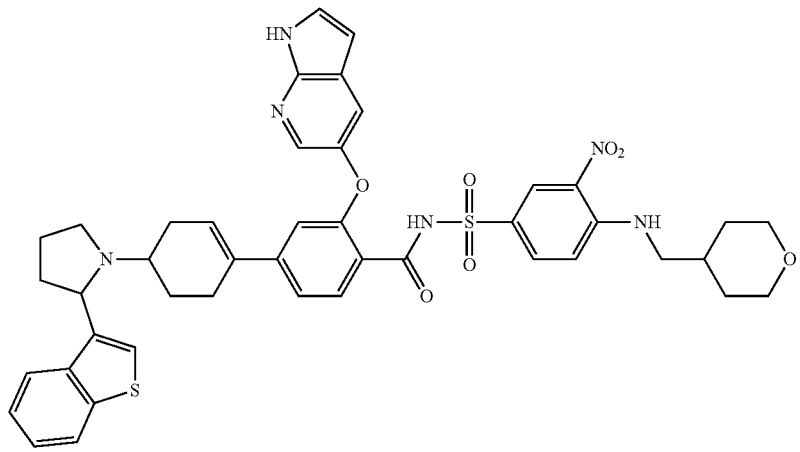 [SMILES: O=C(NS(=O)(=O)c1ccc(NCC2CCOCC2)c([N+](=O)[O-])c1)c1ccc(C2=CCC(N3CCCC3c3csc4ccccc34)CC2)cc1Oc1cnc2[nH]ccc2c1]

The desired compound was synthesized with 2-(benzo[b]thiophen-3-yl)pyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. $^1$H NMR (400 MHz, DMSO-$d_6$) δ 12.23 (s, 1H), 11.66 (s, 1H), 8.60-8.40 (m, 2H), 8.10-7.85 (m, 3H), 7.80-7.65 (m, 1H), 7.60-7.25 (m, 6H), 7.18-6.88 (m, 2H), 6.70 (s, 1H), 6.36 (s, 1H), 5.98 (s, 0.5H), 5.86 (s, 0.5H), 4.22 (s, 1H), 3.83 (d, J=8.4 Hz, 2H), 3.30-3.10 (m, 5H), 2.40-2.20 (m, 7H), 2.10-1.85 (m, 3H), 1.65-1.40 (m, 4H), 1.30-1.15 (m, 3H).

Example C167: 3-((1H-pyrrolo[2,3-b]pyridin-5-yl)oxy)-4'-(3-(2-chlorophenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

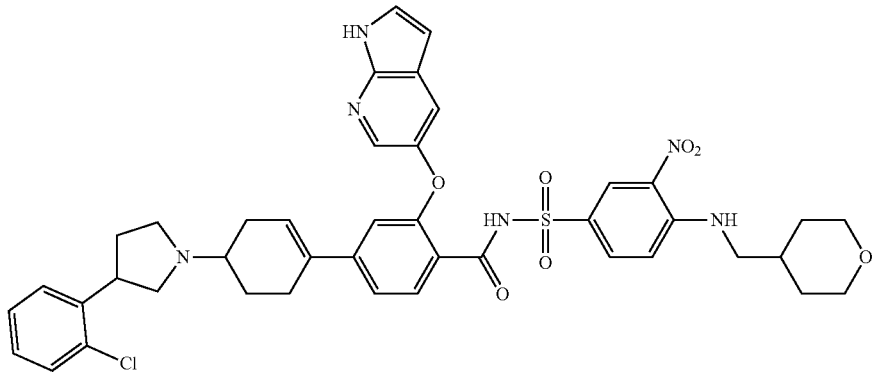 [SMILES: O=C(NS(=O)(=O)c1ccc(NCC2CCOCC2)c([N+](=O)[O-])c1)c1ccc(C2=CCC(N3CCC(c4ccccc4Cl)C3)CC2)cc1Oc1cnc2[nH]ccc2c1]

The desired compound was synthesized with 3-(2-chlorophenyl)pyrrolidine and 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-oxo-2',3',4',5'-tetrahydro-[1,1'-biphenyl]-4-carboxamide following the procedure similar to those in Example C12. $^1$H NMR (400 MHz, DMSO-d$_6$) δ ppm: 12.32 (s, 1H), 11.70 (s, 1H), 8.65-8.45 (m, 2H), 8.02 (d, J=2.1 Hz, 1H), 7.80 (d, J=9.0 Hz, 1H), 7.65-7.45 (m, 5H), 7.38 (t, J=7.5 Hz, 1H), 7.32 (t, J=7.5 Hz, 1H), 7.24 (d, J=8.4 Hz, 1H), 7.07 (d, J=9.0 Hz, 1H), 6.80 (s, 1H), 6.39 (s, 1H), 6.04 (s, 1H), 3.90-3.65 (m, 4H), 3.30-3.20 (m, 5H), 2.70-2.55 (m, 1H), 2.45-2.30 (m, 4H), 2.25-2.15 (m, 1H), 2.10-1.91 (m, 2H), 1.90-1.70 (m, 3H), 1.60 (d, J=11.9 Hz, 2H), 1.34-1.15 (m, 3H). MS (ESI) m/e [M+1]$^+$ 810.8.

Example C168: 3-((1H-pyrrolo[2,3-b]pyridin-5-yl)oxy)-4'-(2-(5-cyclopropyl-2-fluorophenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

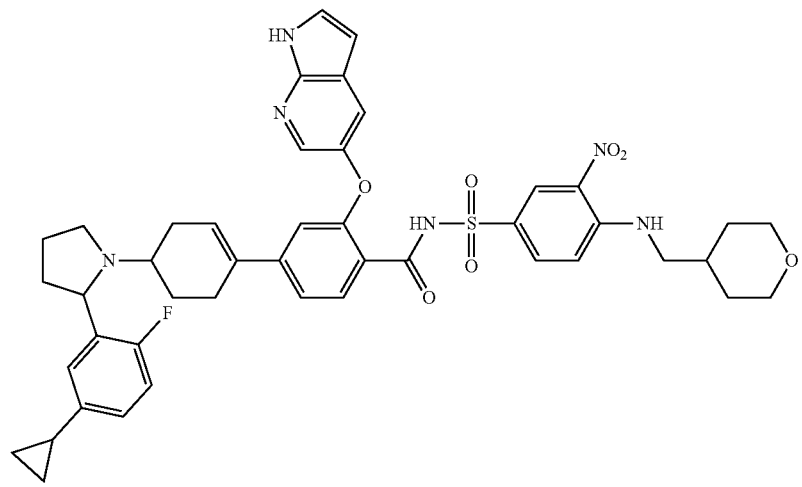

The desired compound was synthesized with 2-(5-cyclopropyl-2-fluorophenyl)pyrrolidine and methyl 3-((1H-pyrrolo[2,3-b]pyridin-5-yl)oxy)-4'-oxo-2',3',45'-tetrahydro[1,1'-biphenyl]-4-carboxylate following the next procedures similar to those in Example C1. $^1$H NMR (DMSO-$d_6$) δ ppm: 12.23 (s, 0.5H), 11.66 (s, 1H), 8.50 (s, 2H), 7.97 (s, 1H), 7.82-7.73 (m, 1H), 7.55-7.39 (m, 3H), 7.34-6.83 (m, 5H), 6.75 (s, 1H), 6.36 (s, 1H), 6.07-5.84 (m, 1H), 4.10-4.00 (m, 1H), 3.94-3.75 (m, 2H), 3.30-3.15 (m, 5H), 2.34-2.00 (m, 6H), 1.86 (s, 3H), 1.75-1.65 (m, 1H), 1.65-1.53 (m, 3H), 1.51-1.40 (m, 1H), 1.35-1.15 (m, 5H), 0.99-0.76 (m, 2H), 0.72-0.44 (m, 2H). MS (ESI) m/e [M+1]$^+$ 834.8.

Example C169: 3-((1H-pyrrolo[2,3-b]pyridin-5-yl)oxy)-4'-(2-(2-chloro-5-cyclopropylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

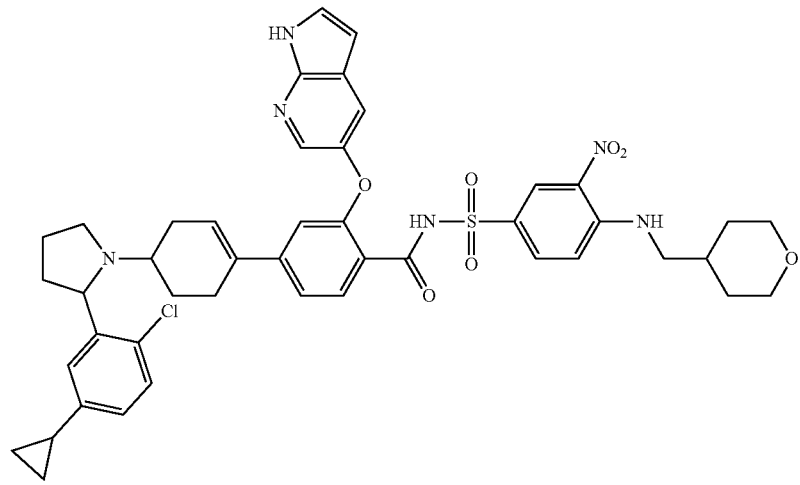 [SMILES: O=C(NS(=O)(=O)c1ccc(NCC2CCOCC2)c([N+](=O)[O-])c1)c1ccc(C2=CCC(N3CCCC3c3cc(C4CC4)ccc3F)CC2)cc1Oc1cnc2[nH]ccc2c1]

The desired compound was synthesized with 2-(5-cyclopropyl-2-chlorophenyl)pyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. MS (ESI) m/e [M+1]$^+$ 850.7.

Example C170: 3-((1H-pyrrolo[2,3-b]pyridin-5-yl)oxy)-4'-(2-(2-cyclopropyl-5-methylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

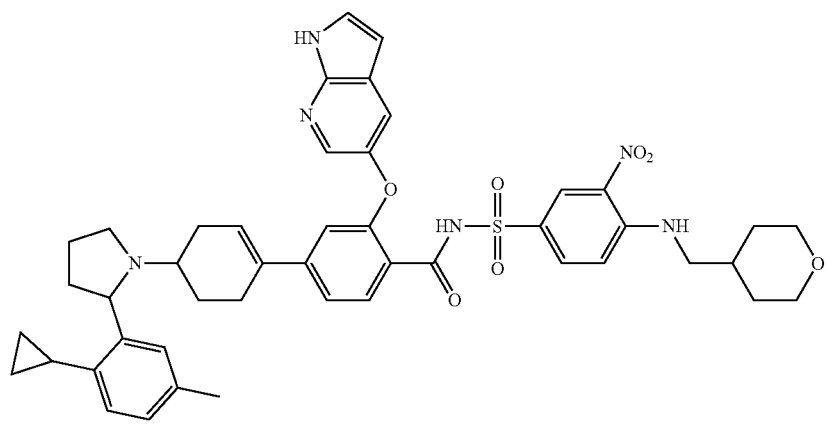

The desired compound was synthesized with 2-(5-cyclopropyl-2-chlorophenyl)pyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. $^1$H NMR (DMSO-d$_6$) δ ppm: 12.24 (s, 0.3H), 11.61 (s, 1H), 8.45 (s, 2H), 7.95 (s, 1H), 7.76-7.63 (m, 1H), 7.52-7.32 (m, 4H), 7.11 (d, J=7.9, 1H), 7.06-6.72 (m, 4H), 6.33 (s, 1H), 6.04-5.80 (m, 1H), 4.26 (s, 1H), 3.91-3.78 (m, 2H), 3.25-3.17 (m, 5H), 2.38-2.07 (m, 8H), 2.05-1.81 (m, 4H), 1.72 (s, 1H), 1.65-1.52 (m, 3H), 1.30-1.17 (m, 3H), 0.98-0.79 (m, 2H), 0.70-0.40 (m, 2H). MS (ESI) m/e [M+1]$^+$ 830.8.

Example C171: 3-((1H-pyrrolo[2,3-b]pyridin-5-yl)oxy)-4'-(2-(2-cyclopropyl-5-((2-(dimethylamino)ethyl)(methyl)amino)phenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

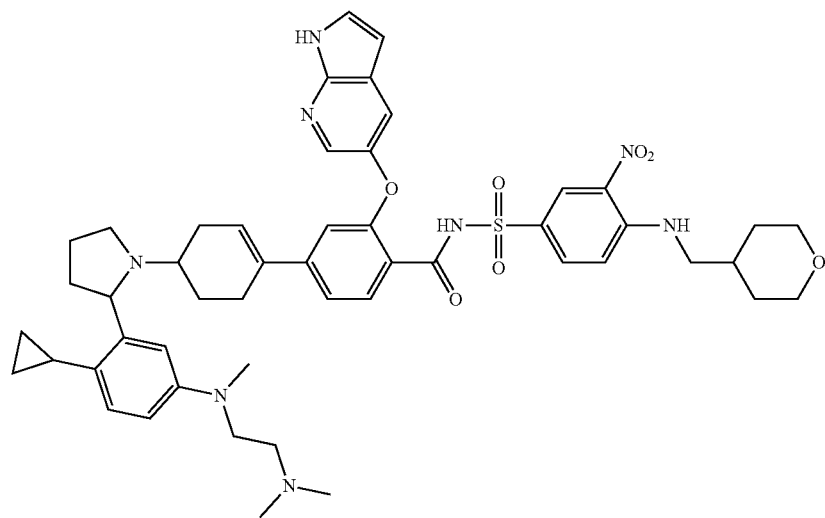 [SMILES: CN(C)CCN(C)c1ccc(C2CC2)c(C2CCCN2C2CC=C(c3ccc(C(=O)NS(=O)(=O)c4ccc(NCC5CCOCC5)c([N+](=O)[O-])c4)c(Oc4cnc5[nH]ccc5c4)c3)CC2)c1]

The desired compound was synthesized with N1-(4-cyclopropyl-3-(pyrrolidin-2-yl)phenyl)-N1,N2,N2-trimethylethane-1,2-diamine and 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-oxo-2',3',4',5'-tetrahydro-[1,1'-biphenyl]-4-carboxamide following the procedure similar to those in Example 02, 41 NMR (400 MHz, DMSO-d$_6$) δ ppm: 11.53 (s, 1H), 8.38 (s, 1H), 8.35-8.31 (m, 1H), 7.91 (s, 1H), 7.64 (d, J=8.8 Hz, 1H), 7.48 (d, J=8.0 Hz, 1H), 7.42 (s, 1H), 7.29 (s, 1H), 7.06-7.00 (m, 2H), 6.82-6.71 (m, 3H), 6.35-6.29 (m, 2H), 5.99 (s, 0.5H), 5.85 (s, 0.5H), 4.26-4.20 (m, 1H), 3.84 (d, J=8.8 Hz, 2H), 3.27-2.98 (m, 8H), 2.85-2.65 (m, 5H), 2.34-2.15 (m, 5H), 2.13-1.92 (m, 8H), 1.83-1.66 (m, 4H), 1.61 (d, J=12.8 Hz, 2H), 1.45-1.35 (m, 4H), 0.85-0.74 (m, 2H), 0.58-0.34 (m, 2H). MS (ESI, m/e) [M+1]$^+$ 916.8.

Example C172: 3-((1H-pyrrolo[2,3-b]pyridin-5-yl)oxy)-4'-(2-(2-cyclopropyl-5-((2-(dimethylamino)ethyl)amino)phenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

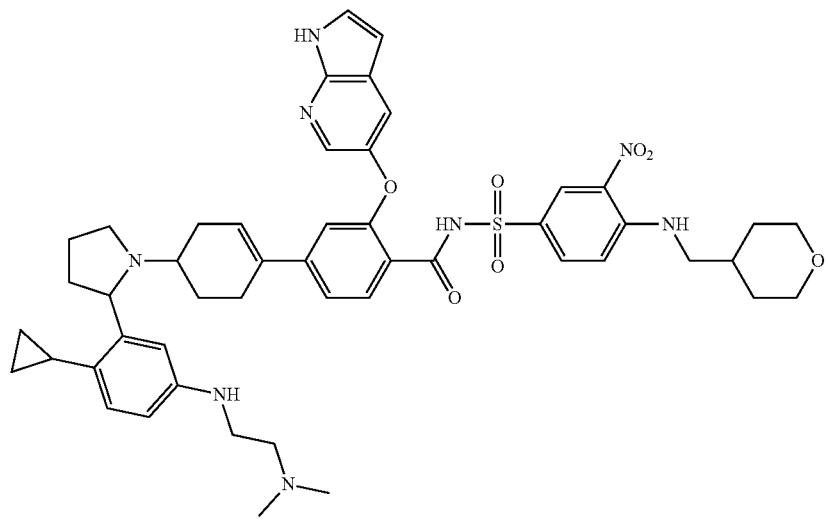 [SMILES: CN(C)CCNc1ccc(C2CC2)c(C2CCCN2C2CC=C(c3ccc(C(=O)NS(=O)(=O)c4ccc(NCC5CCOCC5)c([N+](=O)[O-])c4)c(Oc4cnc5[nH]ccc5c4)c3)CC2)c1]

The desired compound was synthesized with N1-(4-cyclopropyl-3-(pyrrolidin-2-yl)phenyl)-N2,N2-dimethylethane-1,2-diamine and 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-oxo-2',3',4',5'-tetrahydro-[1,1'-biphenyl]-4-carboxamide following the procedure similar to those in Example C12. $^1$H NMR (DMSO-d$_6$) δ ppm: 12.30 (s, 1H), 11.73 (s, 1H), 10.06-9.35 (m, 2H), 8.67-8.48 (m, 2H), 8.05-7.95 (m, 1H), 7.87-7.76 (m, 1H), 7.60-7.39 (m, 3H), 7.22-7.06 (m, 2H), 6.96-6.71 (m, 3H), 6.57 (d, J=8.41 Hz, 1H), 6.45-6.32 (m, 1H), 5.97 (d, J=26.41 Hz, 1H), 5.18-4.98 (m, 1H), 3.87-3.80 (m, 2H), 3.75-3.63 (m, 1H), 3.49-3.17 (m, 10H), 2.89-2.72 (m, 6H), 2.47-2.27 (m, 4H), 2.17-1.81 (m, 6H), 1.73-1.55 (m, 3H), 1.28-1.18 (m, 2H), 0.90-0.79 (m, 2H), 0.61-0.38 (m, 2H). MS (ESI, m/e) [M+1]$^+$ 902.8.

Example C173: 3-((1H-pyrrolo[2,3-b]pyridin-5-yl)oxy)-4'-(2-(2-(but-1-on-1-yl)phenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

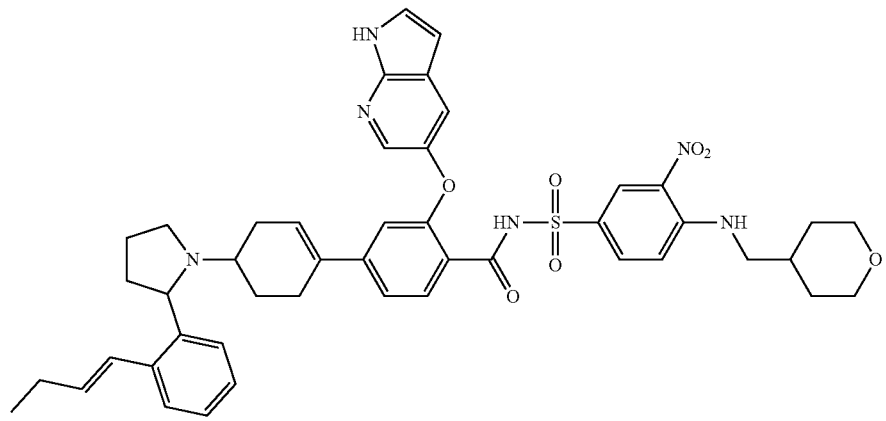 [SMILES: CC/C=C/c1ccccc1C1CCCN1C1CC=C(c2ccc(C(=O)NS(=O)(=O)c3ccc(NCC4CCOCC4)c([N+](=O)[O-])c3)c(Oc3cnc4[nH]ccc4c3)c2)CC1]

The desired compound was synthesized with 2-(2-(but-1-en-1-yl)phenyl)pyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. MS (ESI, m/e) [M+1]$^+$ 830.8.

Example C174: 3-((1H-pyrrolo[2,3-b]pyridin-5-yl)oxy)-4'-(2-(2-(cyclopropyl(methyl)amino)phenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

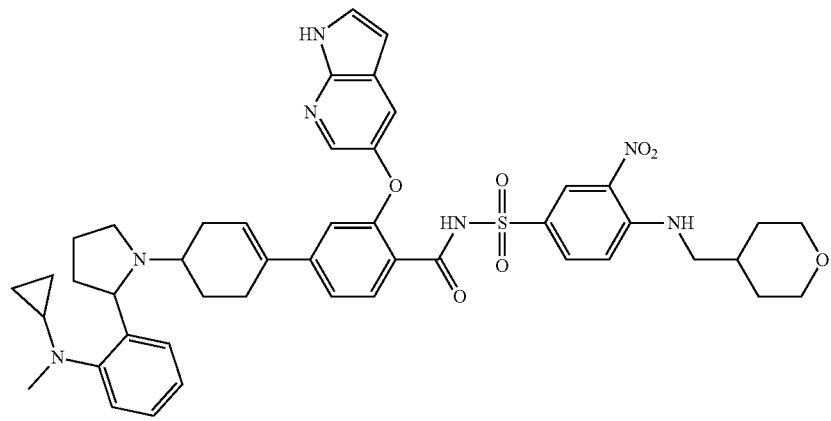 [SMILES: CN(c1ccccc1C1CCCN1C1CC=C(c2ccc(C(=O)NS(=O)(=O)c3ccc(NCC4CCOCC4)c([N+](=O)[O-])c3)c(Oc3cnc4[nH]ccc4c3)c2)CC1)C1CC1]

The desired compound was synthesized with N-cyclopropyl-N-methyl-2-(pyrrolidin-2-yl)aniline and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. $^1$H NMR (400 MHz, DMSO-d$_6$) δ ppm: 12.48-12.08 (m, 0.5H), 11.68 (s, 1H), 9.84-9.42 (m, 0.5H), 7.99 (s, 1H), 8.81-8.26 (m, 2H), 7.87-6.85 (m, 10H), 6.74-6.53 (m, 1H), 6.38 (s, 1H), 5.93-5.75 (m, 1H), 5.41-5.23 (m, 1H), 5.00-4.61 (m, 1H), 3.90-3.75 (m, 2H), 3.28-2.86 (m, 9H), 2.71-2.60 (m, 3H), 2.38-1.78 (m, 11H), 1.65-1.38 (m, 4H), 0.61-0.26 (m, 2H). MS (ESI, m/e) [M+1]$^+$ 845.8.

Example C175: 3-((1H-pyrrolo[2,3-b]pyridin-5-yl)oxy)-4'-(2-(2-(1-methyl-1,2,3,6-tetrahydropyridin-4-yl)phenyl)pyrrolidin-1-yl)-N-((3-nitro-4-((((tetrahydro-2H-pyran-4-yl)methyl)amino)phenyl)sulfonyl)-2',3',4',5'-tetrahydro-[1,1'-biphenyl]-4-carboxamide

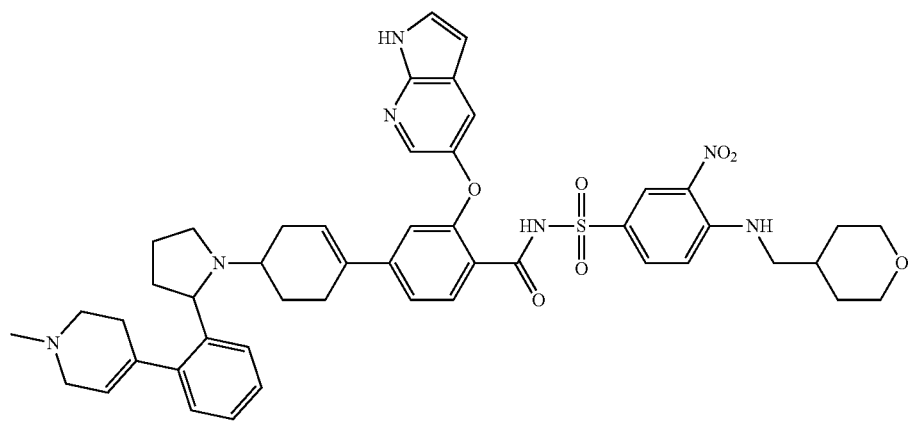 [SMILES: CN1CC=C(c2ccccc2C2CCCN2C2CC=C(c3ccc(C(=O)NS(=O)(=O)c4ccc(NCC5CCOCC5)c([N+](=O)[O-])c4)c(Oc4cnc5[nH]ccc5c4)c3)CC2)CC1]

The desired compound was synthesized with 1-methyl-4-(2-(pyrrolidin-2-yl)phenyl)-1,2,3,6-tetrahydropyridine and methyl 3-((1H-pyrrolo[2,3-b]pyridin-5-yl)oxy)-4'-oxo-2',3',4',5'-tetrahydro-[1,1-biphenyl]-4-carboxylate following the next procedures similar to those in Example C1. $^1$H NMR (400 MHz, DMSO-d$_6$) δ ppm: 11.56 (s, 1H), 8.52-8.18 (m, 2H), 7.98-7.81 (m, 1H), 7.74-6.78 (m, 11H), 6.72 (s, 1H), 6.30 (s, 1H), 6.02-5.73 (m, 1H), 5.55-5.26 (m, 1H), 3.88-3.77 (m, 2H), 3.62-3.39 (m, 7H), 3.28-3.02 (m, 7H), 3.02-2.65 (m, 3H), 2.30-1.30 (m, 12H), 1.07-0.98 (m, 2H). MS (ESI, m/e) [M+1]$^+$ 871.8.

Example C176: 3-((1H-pyrrolo[2,3-b]pyridin-5-yl)oxy)-4'-(2-(2-(1-acetyl-1,2,3,6-tetrahydropyridin-4-yl)phenyl)pyrrolidin-1-yl)-N-((3-nitro-4-((((tetrahydro-2H-pyran-4-yl)methyl)amino)phenyl)sulfonyl)-2',3',4',5'-tetrahydro-[1,1'-biphenyl]-4-carboxamide

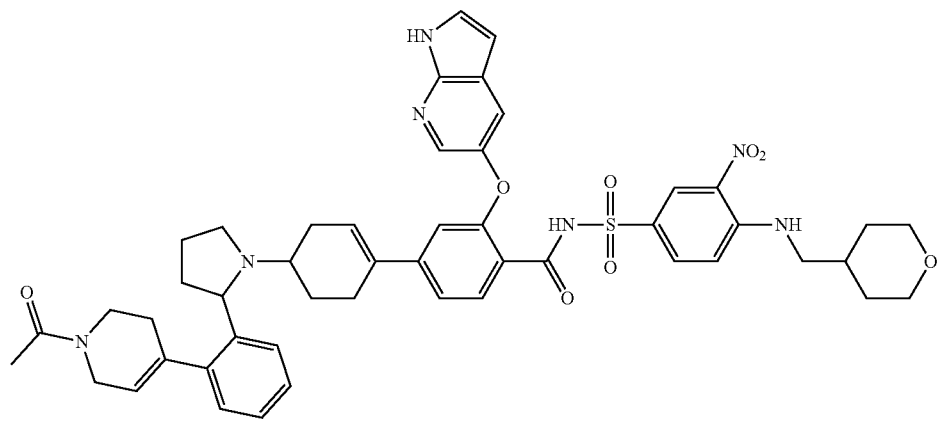 [SMILES: CC(=O)N1CC=C(c2ccccc2C2CCCN2C2CC=C(c3ccc(C(=O)NS(=O)(=O)c4ccc(NCC5CCOCC5)c([N+](=O)[O-])c4)c(Oc4cnc5[nH]ccc5c4)c3)CC2)CC1]

The desired compound was synthesized with 1-(4-(2-(pyrrolidin-2-yl)phenyl)-3,6-dihydropyridin-1 (2H)-yl)ethan-1-one and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. $^1$H NMR (400 MHz, DMSO-d$_6$) δ ppm: 12.43-12.02 (m, 0.3H), 11.63 (s, 1H), 9.98-9.26 (m, 0.7H), 8.71-8.22 (m, 2H), 8.22-6.53 (m, 13H), 6.34 (s, 1H), 6.07-5.73 (m, 1H), 5.60-5.41 (m, 1H), 4.12-3.97 (m, 2H), 3.87-3.78 (m, 2H), 3.70-3.42 (m, 7H), 3.28-3.18 (m, 3H), 3.16-2.92 (m, 1H), 2.25-1.24 (m, 16H), 1.08-0.98 (m, 2H). MS (ESI, m/e) [M+1]$^+$ 899.8.

Example C177: 3-((1H-pyrrolo[2,3-b]pyridin-5-yl)oxy)-4'-(2-(4-cyclopropylthiophen-2-yl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

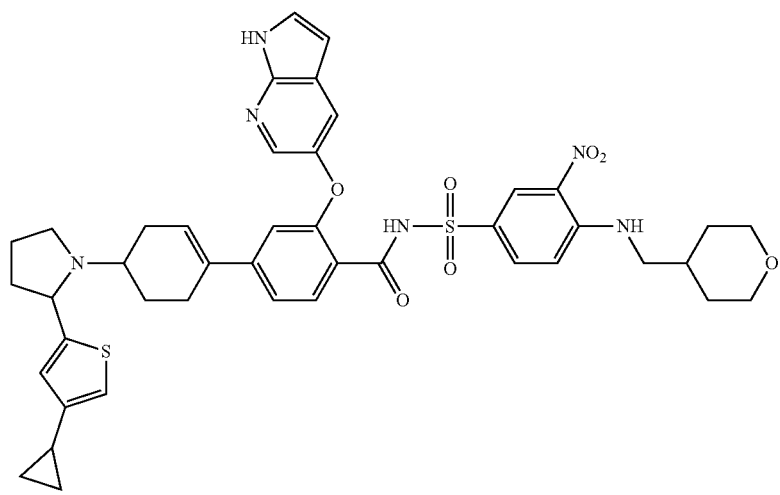 [SMILES: O=C(NS(=O)(=O)c1ccc(NCC2CCOCC2)c([N+](=O)[O-])c1)c1ccc(C2=CCC(N3CCCC3c3cc(C4CC4)cs3)CC2)cc1Oc1cnc2[nH]ccc2c1]

The desired compound was synthesized with 2-(4-cyclopropylthiophen-2-yl)pyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. $^1$H NMR (400 MHz, DMSO-$d_6$) δ ppm: 12.19 (s, 0.5H), 11.67 (s, 1H), 9.65 (s, 0.5H), 8.50 (s, 2H), 7.99 (s, 1H), 7.76 (d, J=7.5 Hz, 1H), 7.49 (s, 3H), 7.20-6.88 (m, 3H), 6.75 (s, 2H), 6.37 (s, 1H), 6.01-5.88 (m, 1H), 3.84 (d, J=8.5 Hz, 2H), 3.30-3.15 (m, 5H), 3.10-2.91 (m, 2H), 2.33-2.10 (m, 6H), 1.95-1.75 (m, 4H), 1.70-1.55 (m, 4H), 1.35-1.21 (m, 3H), 0.91-0.75 (m, 2H), 0.75-0.55 (m, 2H). MS (ESI, m/e) [M+1]$^+$ 822.7.

Example C178: 3-((1H-pyrrolo[2,3-b]pyridin-5-yl)oxy)-4'-(2-(1-cyclopropyl-1H-pyrazol-3-yl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

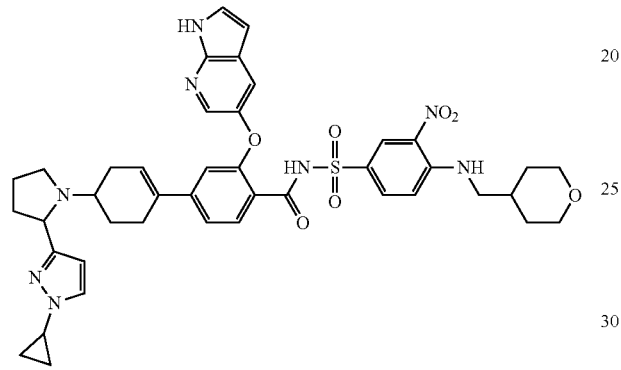

The desired compound was synthesized with 1-cyclopropyl-3-(pyrrolidin-2-yl)-1H-pyrazole and 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-oxo-2',3',4',5'-tetrahydro-[1,1'-biphenyl]-4-carboxamide following the procedure similar to those in Example C12, MS (ESI, m/e) [M+1]+806.8.

Example C179: 3-((1H-pyrrolo[2,3-b]pyridin-5-yl)oxy)-4'-(4-chloro-2-(2-cyclopropylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

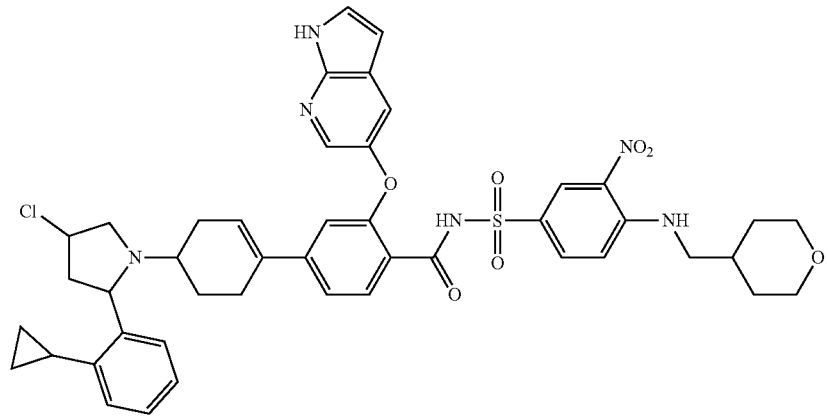

The desired compound was synthesized with 4-chloro-2-(2-cyclopropylphenyl)pyrrolidine and 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-oxo-2',3',4',5'-tetrahydro-[1,1'-biphenyl]-4-carboxamide following the procedure similar to those in Example C12. $^1$H NMR (DMSO-$d_6$) δ ppm: 12.28 (s, 1H), 11.76 (s, 1H), 8.71-8.57 (m, 2H), 8.10-8.01 (m, 1H), 7.91-7.83 (m, 1H), 7.80-7.49 (m, 5H), 7.25-6.92 (m, 6H), 6.81-6.74 (m, 1H), 6.48-6.41 (m, 1H), 6.11-6.02 (m, 0.5H), 5.90-5.83 (m, 0.5H), 4.71-4.62 (m, 1H), 4.49-4.36 (m, 1H), 3.93-3.86 (m, 2H), 3.35-3.29 (m, 4H), 3.18-3.09 (m, 1H), 3.03-2.94 (m, 1H), 2.69-2.59 (m, 1H), 2.29-2.21 (m, 2H), 2.14-1.73 (m, 6H), 1.68-1.61 (m, 2H), 1.34-1.26 (m, 4H), 0.95-0.87 (m, 2H), 0.73-0.54 (m, 2H). MS (ESI, m/e) [M+1]$^+$ 850.7.

Example C180: 3-((1H-pyrrolo[2,3-b]pyridin-5-yl)oxy)-4'-(2-(2-cyclopropylphenyl)-4-methylenepyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

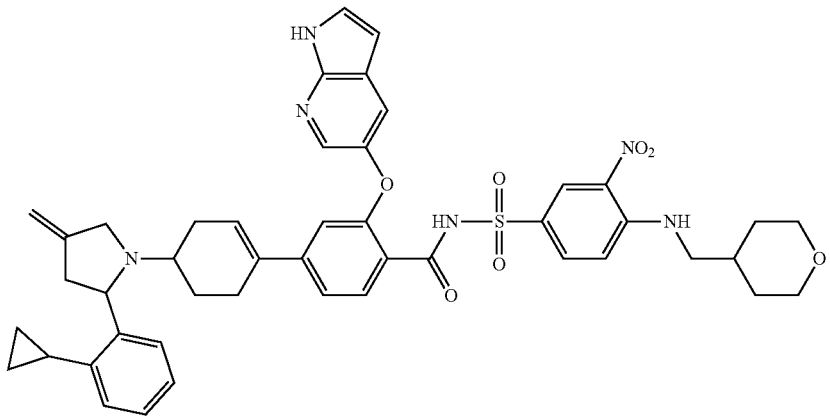 [SMILES: C=C1CC(c2ccccc2C2CC2)N(C2CC=C(c3ccc(C(=O)NS(=O)(=O)c4ccc(NCC5CCOCC5)c([N+](=O)[O-])c4)c(Oc4cnc5[nH]ccc5c4)c3)CC2)C1]

The desired compound was synthesized with 2-(2-cyclopropylphenyl)-4-methylenepyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. $^1$H NMR (400 MHz, DMSO-$d_6$) δ ppm: 12.21 (s, 0.5H), 11.65 (s, 1H), 9.71-9.48 (m, 0.5H), 8.49 (s, 2H), 7.97 (s, 1H), 7.75 (s, 1H), 7.56-7.34 (m, 4H), 7.12-6.94 (m, 5H), 6.72 (s, 1H), 6.35 (s, 1H), 5.99 (s, 0.5H), 5.86 (s, 0.5H), 4.92 (s, 1H), 4.84 (s, 1H), 4.48-4.39 (m, 1H), 3.83 (s, 2H), 3.69 (d, J=13.8 Hz, 1H), 3.30-3.15 (m, 5H), 2.99-2.78 (m, 2H), 2.18-2.11 (m, 6H), 1.96-1.65 (m, 3H), 1.63-1.55 (m, 2H), 1.26-1.21 (m, 3H), 0.96-0.81 (m, 3H). MS (ESI, m/e) [M+1]$^+$ 828.8.

Example C181: 3-((1H-pyrrolo[2,3-b]pyridin-5-yl)oxy)-4'-(1-(2-cyclopropylphenyl)hexahydrocyclopenta[c]pyrrol-2(1H)-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

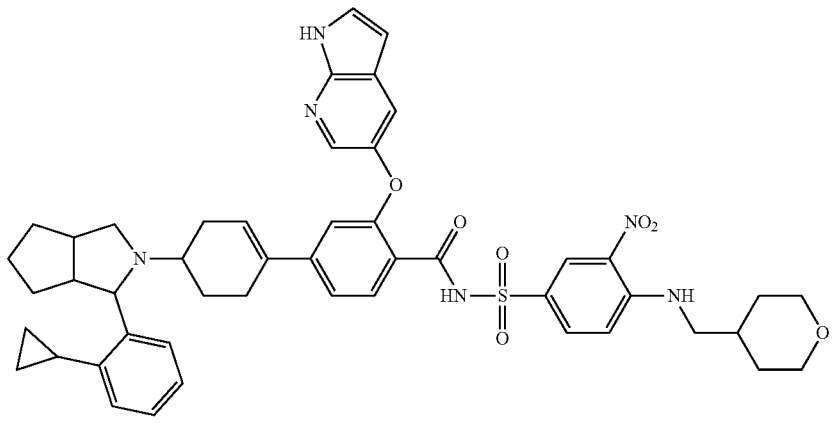 [SMILES: O=C(NS(=O)(=O)c1ccc(NCC2CCOCC2)c([N+](=O)[O-])c1)c1ccc(C2=CCC(N3CC4CCCC4C3c3ccccc3C3CC3)CC2)cc1Oc1cnc2[nH]ccc2c1]

The desired compound was synthesized with 1-(2-cyclopropylphenyl)octahydrocyclopenta[c]pyrrole and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. MS (ESI, m/e) [M+1]$^+$ 856.8.

Example C182: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(1-phenylisoindolin-2-yl)-2',3',4',5'-tetrahydro-[1,1'-biphenyl]-4-carboxamide

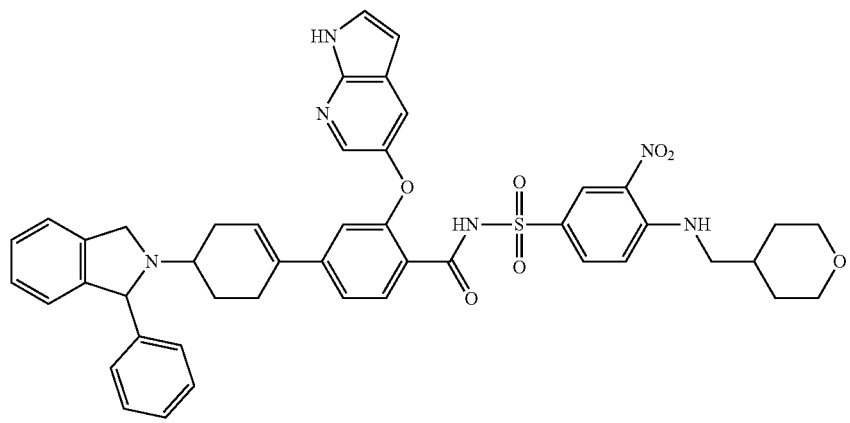 [SMILES: O=C(NS(=O)(=O)c1ccc(NCC2CCOCC2)c([N+](=O)[O-])c1)c1ccc(C2=CCC(N3Cc4ccccc4C3c3ccccc3)CC2)cc1Oc1cnc2[nH]ccc2c1]

The desired compound was synthesized with 1-phenylisoindoline and 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-oxo-2',3',4',5'-tetrahydro-[1,1'-biphenyl]-4-carboxamide following the procedure similar to those in Example C12. MS (ESI, m/e) [M+1]$^+$ 824.8.

Example C183: 3-((1H-pyrrolo[2,3-b]pyridin-5-yl)oxy)-4'-(2-((2-cyclopropylphenyl)(methoxy)methyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

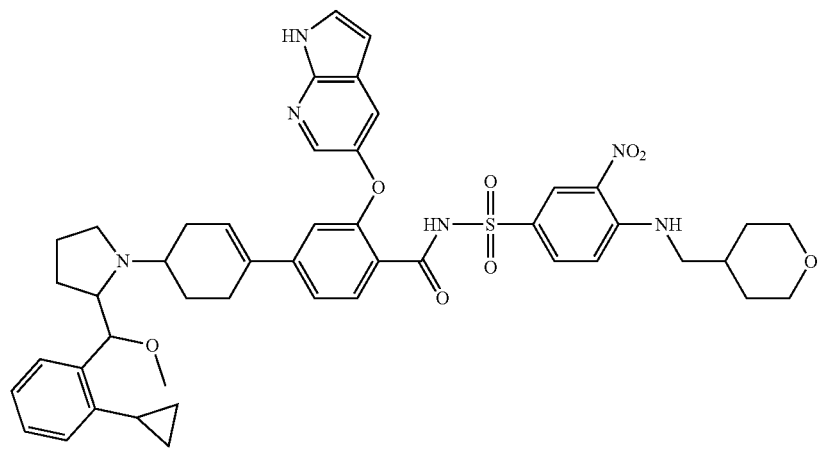 [SMILES: COC(c1ccccc1C1CC1)C1CCCN1C1CC=C(c2ccc(C(=O)NS(=O)(=O)c3ccc(NCC4CCOCC4)c([N+](=O)[O-])c3)c(Oc3cnc4[nH]ccc4c3)c2)CC1]

The desired compound was synthesized with 2-((2-cyclopropylphenyl)(methoxy)methyl)pyrrolidine and 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-oxo-2',3',4',5'-tetrahydro-[1,1'-biphenyl]-4-carboxamide following the procedure similar to those in Example C12. $^1$H NMR (400 MHz, DMSO-d$_6$) δ ppm: 12.28 (s, 1H), 11.72 (s, 1H), 8.56 (s, 2H), 8.03 (s, 1H), 7.81 (s, 1H), 7.54-7.52 (m, 2H), 7.43 (s, 1H), 7.26-7.21 (m, 4H), 7.06 (s, 1H), 6.79 (s, 1H), 6.66 (s, 1H), 6.39 (s, 1H), 6.06 (s, 1H), 5.04 (s, 1H), 4.07 (s, 1H), 3.84 (d, J=9.1 Hz, 3H), 3.67 (s, 1H), 3.51 (s, 3H), 3.25-3.23 (m, 4H), 3.06-2.97 (m, 7H), 2.03-1.97 (m, 3H), 1.88 (s, 2H), 1.60 (d, J=12.8 Hz, 2H), 1.47-1.43 (m, 2H), 0.97 (s, 2H), 0.86-0.84 (m, 4H). MS (ESI, m/e) [M+1]$^+$ 860.8.

Example C184: 3-((1H-pyrrolo[2,3-b]pyridin-5-yl)oxy)-4'-(2-(2-isopropylbenzyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

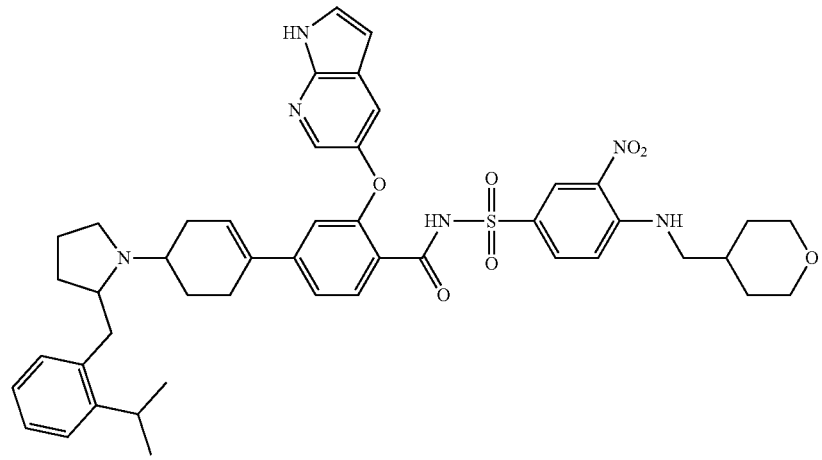 [SMILES: CC(C)c1ccccc1CC1CCCN1C1CC=C(c2ccc(C(=O)NS(=O)(=O)c3ccc(NCC4CCOCC4)c([N+](=O)[O-])c3)c(Oc3cnc4[nH]ccc4c3)c2)CC1]

The desired compound was synthesized with 2-(2-isopropylbenzyl)pyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. $^1$H NMR (400 MHz, DMSO-d$_6$) δ ppm: 11.63 (s, 1H), 9.70-9.28 (m, 1H), 8.50-8.40 (m, 2H), 7.98 (s, 1H), 7.72 (d, J=8.4, 1H), 7.56-7.45 (m 3H), 7.30-7.10 (m, 6H), 6.92 (s, 1H), 6.82-6.73 (m, 1H), 6.36 (s, 1H), 6.04 (s, 1H), 3.90-3.80 (m, 3H), 3.30-3.20 (m, 7H), 3.08 (s, 1H), 2.85 (s, 1H), 2.41-2.32 (m, 1H), 2.14 (s, 1H), 1.90-1.80 (m, 6H), 1.65-1.56 (m, 3H), 1.32-1.10 (m, 10H). MS (ESI) m/e [M+1]$^+$ 832.8.

Example C185: 3-((1H-pyrrolo[2,3-b]pyridin-5-yl)oxy)-4'-(3-(2-cyclopropylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

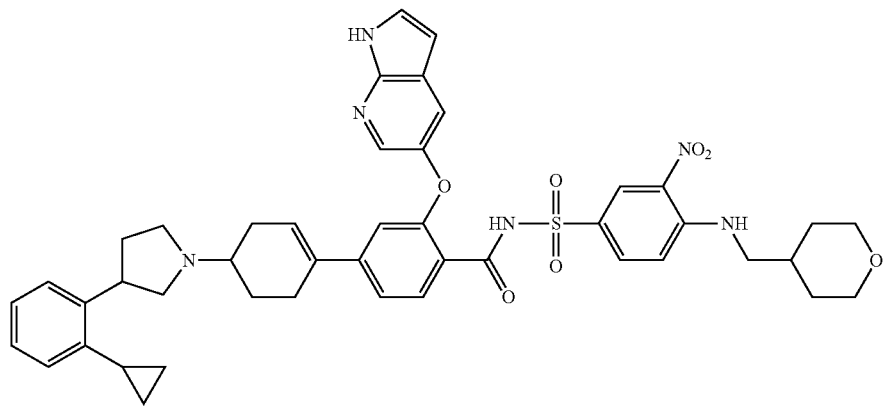 [SMILES: O=C(NS(=O)(=O)c1ccc(NCC2CCOCC2)c([N+](=O)[O-])c1)c1ccc(C2=CCC(N3CCC(c4ccccc4C4CC4)C3)CC2)cc1Oc1cnc2[nH]ccc2c1]

The desired compound was synthesized with 3-(2-cyclopropylphenyl)pyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. MS (ESI) m/e [M+1]$^+$ 816.8.

Example C186: 3-((1H-pyrrolo[2,3-b]pyridin-5-yl)oxy)-4'-(3-(2-isopropylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

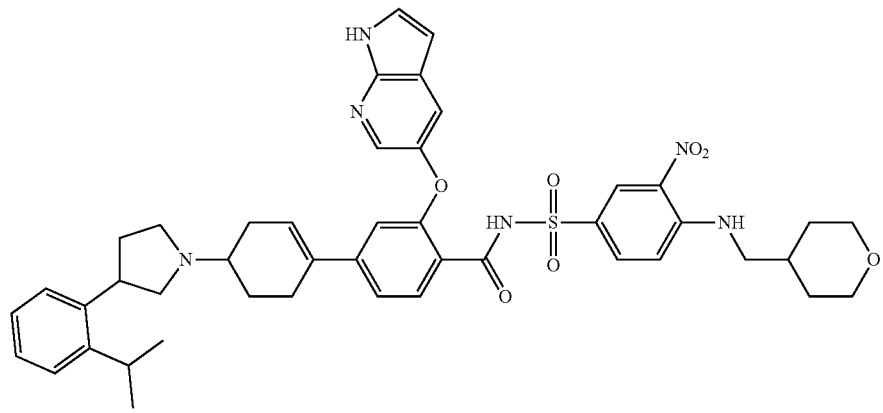 [SMILES: CC(C)c1ccccc1C1CCN(C2CC=C(c3ccc(C(=O)NS(=O)(=O)c4ccc(NCC5CCOCC5)c([N+](=O)[O-])c4)c(Oc4cnc5[nH]ccc5c4)c3)CC2)C1]

The desired compound was synthesized with 3-(2-isopropylphenyl)pyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. MS (ESI) m/e [M+1]⁺ 818.8.

Example C189: 3-((1H-pyrrolo[2,3-b]pyridin-5-yl)oxy)-4'-(2-(3-fluoro-2-methylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

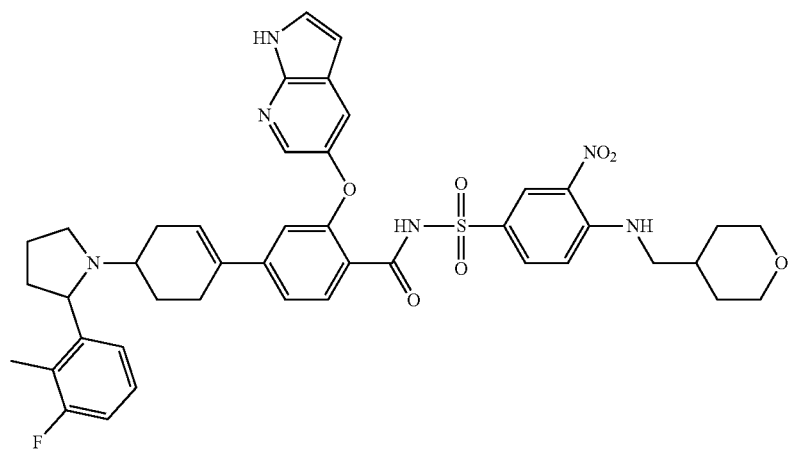 [SMILES: Cc1c(F)cccc1C1CCCN1C1CC=C(c2ccc(C(=O)NS(=O)(=O)c3ccc(NCC4CCOCC4)c([N+](=O)[O-])c3)c(Oc3cnc4[nH]ccc4c3)c2)CC1]

The desired compound was synthesized with 2-(3-fluoro-2-methylphenyl)pyrrolidine and 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-oxo-2',3',4',5'-tetrahydro-[1,1'-biphenyl]-4-carboxamide following the procedure similar to those in Example C12. $^1$H NMR (400 MHz, DMSO-d$_6$) δ ppm: 12.22 (s, 1H), 11.68 (s, 1H), 8.70-8.40 (m, 2H), 8.02-7.95 (m, 1H), 7.85-7.75 (m, 1H), 7.60-7.31 (m, 4H), 7.20-6.90 (m, 3H), 6.85-6.75 (m, H ), 6.71 (s, 1H), 6.37 (s, 1H), 5.99 (s, 0.5H), 5.80 (s, 0.5H), 4.05-3.90 (m, 1H), 3.85-3.80 (m, 3H), 3.35-3.20 (m, 5H), 2.55-2.40 (m, 2H), 2.25-2.10 (m, 6H), 2.00-1.80 (m, 2H), 1.75-1.65 (m, 3H), 1.60-1.55 (m, 3H), 1.31-1.17 (m, 3H ). MS (ESI, m/e) [M+1]$^+$ 809.2.

Example C190: 3-((1H-pyrrolo[2,3-b]pyridin-5-yl)oxy)-4'-(2-(2-(2-methylprop-1-en-1-yl)phenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

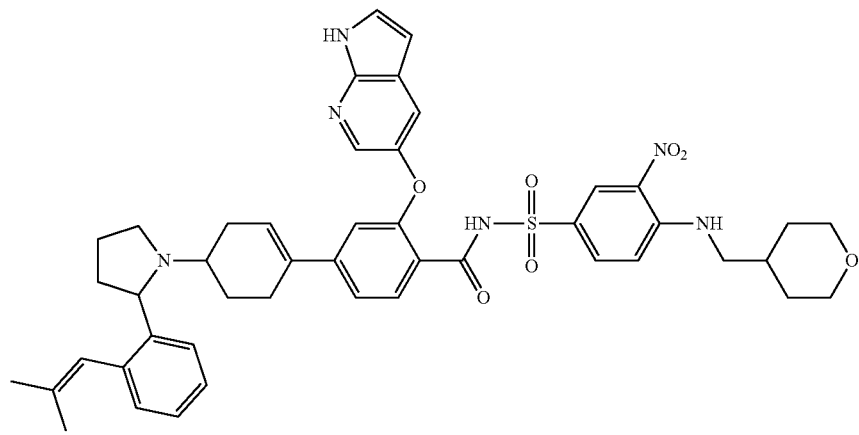 [SMILES: CC(C)=Cc1ccccc1C1CCCN1C1CC=C(c2ccc(C(=O)NS(=O)(=O)c3ccc(NCC4CCOCC4)c([N+](=O)[O-])c3)c(Oc3cnc4[nH]ccc4c3)c2)CC1]

The desired compound was synthesized with 2-(2-(2-methylprop-1-en-1-yl)phenyl)pyrrolidine and 3-((1H-pyrrolo[2,3-b]pyridin-5-yl)oxy)-N-((3-nitro-4-((((tetrahydro-2H-pyran-4-yl)methyl) amino)phenyl)sulfonyl)-4'-oxo-2',3',4',5'-tetrahydro-[1,1'-biphenyl]-4-carboxamide following the procedure similar to those in Example C12. $^1$H NMR (400 MHz, DMSO-d$_6$) δ ppm: 11.62 (s, 1H), 8.46 (s, 2H), 7.95 (s, 1H), 7.78-7.66 (m, 2H), 7.53-7.36 (m, 4H), 7.15-6.92 (m, 4H), 6.69 (d, J=8.0 Hz, 1H), 6.40-6.28 (m, 21 If 5.94 (s, 0.5H), 5.82 (s, 0.5H), 3.92-3.77 (m, 3H), 3.28-3.22 (m, 5H), 3.18-2.95 (m, 2H), 2.23-1.95 (m, 5H), 1.82 (s, 6H), 1.64-1.45 (m, 7H), 1.31-1.16 (m, 3H). MS (ESI, m/e) [M+1]+ 831.2.

Example C191: 3-((1H-pyrrolo[2,3-b]pyridin-5-yl)oxy)-4'-(2-(benzo[b]thiophen-2-yl)pyrrolidin-1-yl)-N-((3-nitro-4-((((tetrahydro-2H-pyran-4-yl)methyl) amino)phenyl)sulfonyl)-2',3',4',5'-tetrahydro-[1,1'-biphenyl]-4-carboxamide

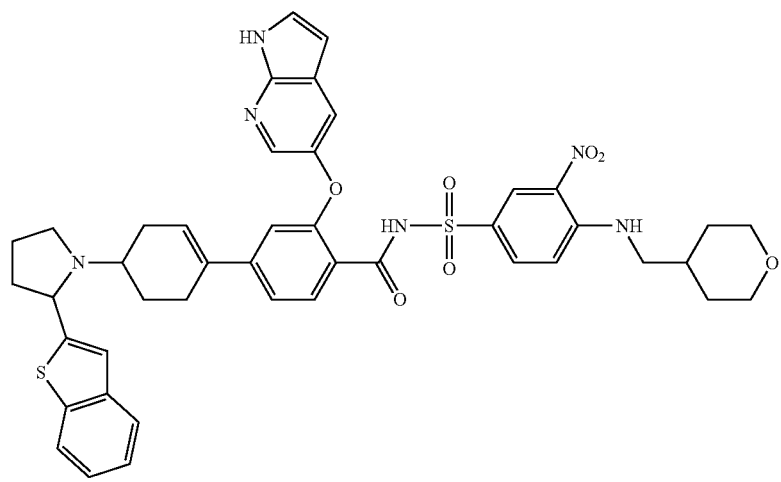 [SMILES: O=C(NS(=O)(=O)c1ccc(NCC2CCOCC2)c([N+](=O)[O-])c1)c1ccc(C2=CCC(N3CCCC3c3cc4ccccc4s3)CC2)cc1Oc1cnc2[nH]ccc2c1]

The desired compound was synthesized with 2-(benzo[b]thiophen-2-yl)pyrrolidine and 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-oxo-2',3',4',5'-tetrahydro-[1,1'-biphenyl]-4-carboxamide following the procedure similar to those in Example C12. $^1$H NMR (400 MHz, DMSO-d$_6$) δ ppm: 12.19 (s, 1H), 11.67 (s, 1H), 8.58-8.52 (m, 2H), 7.98 (s, 1H), 7.94-7.60 (m, 3H), 7.54-7.40 (m, 3H), 7.28 (s, 3H), 7.18-7.00 (m, 2H), 6.72 (s, 1H), 6.36 (s, 1H), 6.01-5.95 (m, 1H), 4.23 (s, 1H), 3.84 (d, J=8.5 Hz, 2H), 3.28-3.22 (m, 4H), 3.05 (s, 1H), 2.70 (s, 1H), 2.33-2.14 (m, 5H), 2.04-1.95 (m, 1H), 1.86 (s, 2H), 1.79-1.71 (m, 1H), 1.59 td, J=13.0 Hz, 2H), 1.47 (s, 1H), 1.27-1.23 (s, 4H). MS (ESI, m/e) [M+1]$^+$ 833.1.

Example C192: 3-((1H-pyrrolo[2,3-b]pyridin-5-yl)oxy)-4'-(2-(4-cyclopropylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

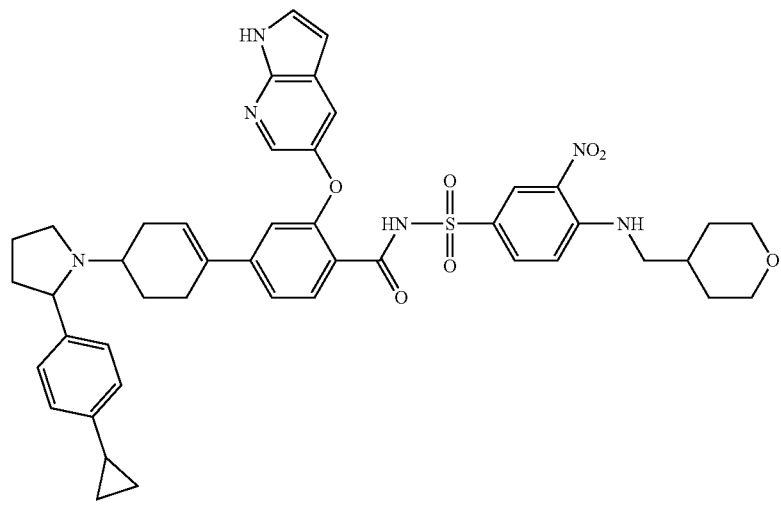 [SMILES: O=C(NS(=O)(=O)c1ccc(NCC2CCOCC2)c([N+](=O)[O-])c1)c1ccc(C2=CCC(N3CCCC3c3ccc(C4CC4)cc3)CC2)cc1Oc1cnc2[nH]ccc2c1]

The desired compound was synthesized with 2-(4-cyclopropylphenyl)pyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. $^1$H NMR (400 MHz, DMSO-$d_6$) δ ppm: 11.60 (s, 1H), 8.43 (m, 2H), 7.94 (s, 1H), 7.68 (m, 1H), 7.48-7.46 (m, 2H), 7.37-7.12 (m, 3H), 7.10-7.04 (m, 3H), 6.92 (m, 1H), 6.74 (s, 1H), 6.33 (s, 1H), 5.97 (s, 0.5H), 5.89 (s, 0.5H), 3.85 (d, J=8.0 Hz, 2H), 3.27-3.23 (m, 6H), 2.27-2.01 (m, 5H), 1.87-1.64 (m, 6H), 1.61 (d, J=12.8 Hz, 2H), 1.45-1.43 (m, 2H), 1.20-1.16 (m, 3H), 0.93-0.86 (m, 2H), 0.68-0.64 (m, 2H). MS (ESI, m/e) [M+1]$^+$ 817.2.

Example C193: 3-((1H-pyrrolo[2,3-b]pyridin-5-yl)oxy)-4'-(1-butylhexahydrocyclopenta[c]pyrrol-2(1H)-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

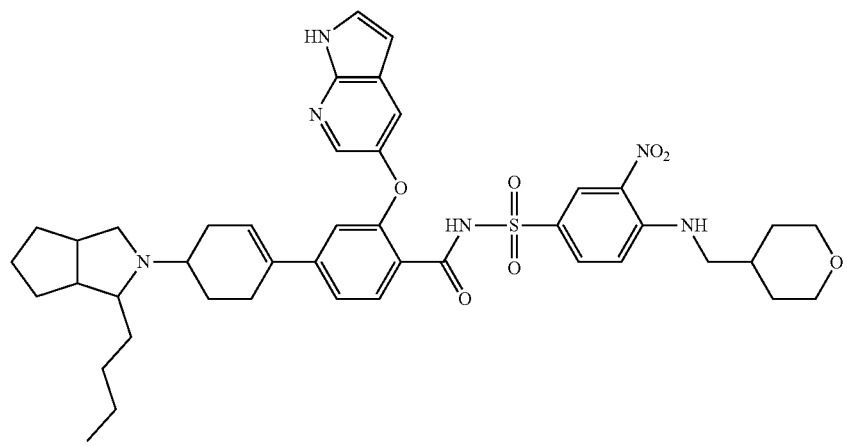 [SMILES: CCCCC1C2CCCC2CN1C1CC=C(c2ccc(C(=O)NS(=O)(=O)c3ccc(NCC4CCOCC4)c([N+](=O)[O-])c3)c(Oc3cnc4[nH]ccc4c3)c2)CC1]

The desired compound was synthesized with 1-butyloctahydrocyclopenta[c]pyrrole and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. $^1$H NMR (400 MHz, DMSO-$d_6$) δ ppm: 12.27 (s, 1H), 11.71 (s, 1H), 10.25-9.75 (m, 1H), 8.66-8.49 (m, 2H), 8.02 (s, 1H), 7.81 (d, J=8.6 Hz, 1H), 7.61-7.46 (m, 1H), 7.21 (d, J=8.6 Hz, 1H), 7.14-7.08 (m, 1H), 6.79-6.70 (m, 1H), 6.40 (s, 1H), 6.09-5.93 (m, 1H), 3.91-3.78 (m, 2H), 3.65-3.51 (m, 2H), 3.30-3.17 (m, 5H), 3.15-3.08 (m, 1H), 2.98-2.95 (m, 1H), 2.77-2.64 (m, 2H), 2.49-2.32 (m, 4H), 1.95-1.87 (m, 2H), 1.70-1.45 (m, 11H), 1.39-1.17 (m, 5H), 0.92-0.80 (m, 3H). MS (ESI) m/e [M+1]$^+$ 796.8.

Example C194: 3-((1H-pyrrolo[2,3-b]pyridin-5-yl)oxy)-4'-(2-(3-chloro-2-methylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide

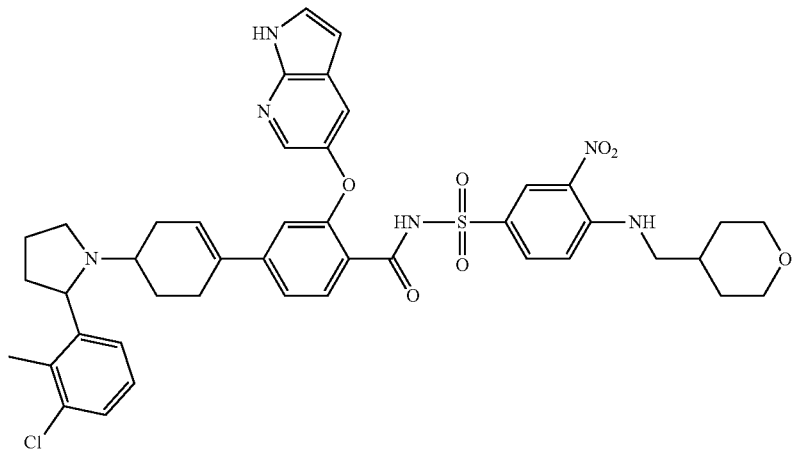 [SMILES: Cc1c(Cl)cccc1C1CCCN1C1CC=C(c2ccc(C(=O)NS(=O)(=O)c3ccc(NCC4CCOCC4)c([N+](=O)[O-])c3)c(Oc3cnc4[nH]ccc4c3)c2)CC1]

The desired compound was synthesized with 2-(3-chloro-2-methylphenyl)pyrrolidine and methyl 3-((1H-pyrrolo[2,3-b]pyridin-5-yl)oxy)-4'-oxo-2',3',4',5'-tetrahydro-[1,1'-biphenyl]-4-carboxylate following the next procedures similar to those in Example C1. $^1$H NMR (400 MHz, DMSO-d$_6$) δ ppm: 12.23 (s, 1H), 11.68 (s, 1H), 8.65-8.45 (m, 2H), 7.99 (d, J=4.7 Hz, 1H), 7.85-7.70 (m, 1H), 7.60-7.30 (m, 4H), 7.25-6.85 (m, 4H), 6.75-6.65 (m, 1H), 6.37 (s, 1H), 6.00 (s, 0.5H), 5.76 (s, 0.5H), 4.25-4.05 (m, 1H), 3.84 (d, J=8.3 Hz, 2H), 3.30-3.10 (m, 5H), 2.40-2.01 (m, 8H), 1.90-1.80 (m, 2H), 1.78-1.50 (m, 5H), 1.46-1.11 (m, 5H). MS (ESI) m/e [M+1]$^+$ 824.8.

Example C195: 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(2-(1,2,3,6-tetrahydropyridin-4-yl)phenyl)pyrrolidin-1-yl)-2',3',4',5'-tetrahydro-[1,1'-biphenyl]-4-carboxamide

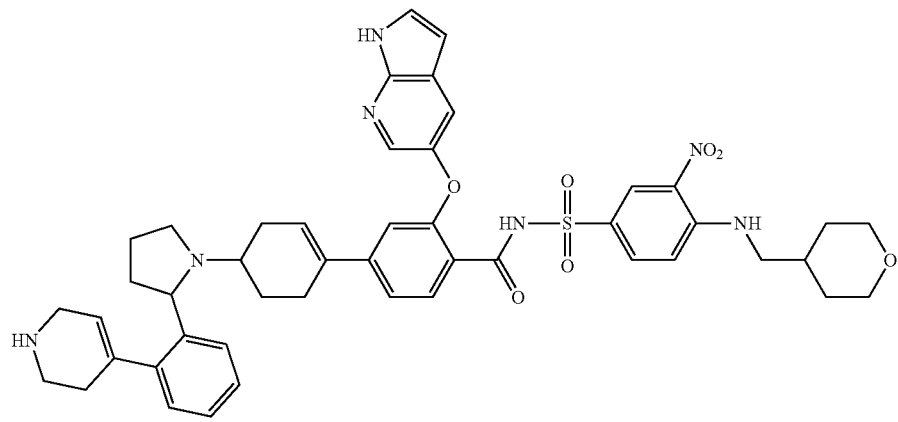 [SMILES: O=C(NS(=O)(=O)c1ccc(NCC2CCOCC2)c([N+](=O)[O-])c1)c1ccc(C2=CCC(N3CCCC3c3ccccc3C3=CCNCC3)CC2)cc1Oc1cnc2[nH]ccc2c1]

The desired compound was synthesized with tert-butyl 4-(2-(pyrrolidin-2-yl)phenyl)-3,6-dihydropyridine-1(2H)-carboxylate and 3-((1H-pyrrolo[2,3-b]pyridin-5-yl)oxy)-N-((3-nitro-4-(((tetrahydro-2H-pyran-4-yl)methyl)amino)phenyl)sulfonyl)-4'-oxo-2',3',4',5'-tetrahydro-[1,1'-biphenyl]-4-carboxamide following the procedure similar to those in Example C66. NMR (400 MHz, DMSO-d$_6$) δ ppm: 11.54 (s, 1H), 8.42-8.28 (m, 2H), 7.90 (s, 1H), 7.67-7.58 (m, 1H), 7.57-7.37 (m, 4H), 7.31-7.24 (m, 1H), 7.15-7.00 (m, 3H), 6.98-6.89 (m, 2H), 6.85-6.73 (m, 1H), 6.77-6.66 (m, 1H), 6.29 (s, 1H), 5.84-5.74 (m, 1H), 5.52-5.38 (m, 1H), 3.92-3.78 (m, 4H), 3.32-3.19 (m, 6H), 3.16-3.05 (m, 3H), 2.91-2.79 (m, 2H), 2.04-1.91 (m, 3H), 1.88-1.75 (m, 3H), 1.63-1.54 (m, 3H), 1.51-1.38 (m, 3H 1.20-1.08 (m, 2H), 0.80-0.70 (m, 2H). MS (ESI, m/e) [M+1]$^+$ 806.8.

Example D1a and Example D1b: (cis- or trans-)2-((1H-pyrrolo[2,3-b]pyridin-5-yl)oxy)-4-(4-(2-(2-chlorophenyl)pyrrolidin-1-yl)cyclohexyl)-N-((3-nitro-4-(((tetrahydro-2H-pyran-4-yl)methyl)amino)phenyl)sulfonyl)benzamide; (trans- or cis-)-2-((1H-pyrrolo[2,3-b]pyridin-5-yl)oxy)-4-(4-(2-(2-chlorophenyl)pyrrolidin-1-yl)cyclohexyl)-N-((3-nitro-4-(((tetrahydro-2H-pyran-4-yl)methyl)amino)phenyl)sulfonyl)benzamide D1a

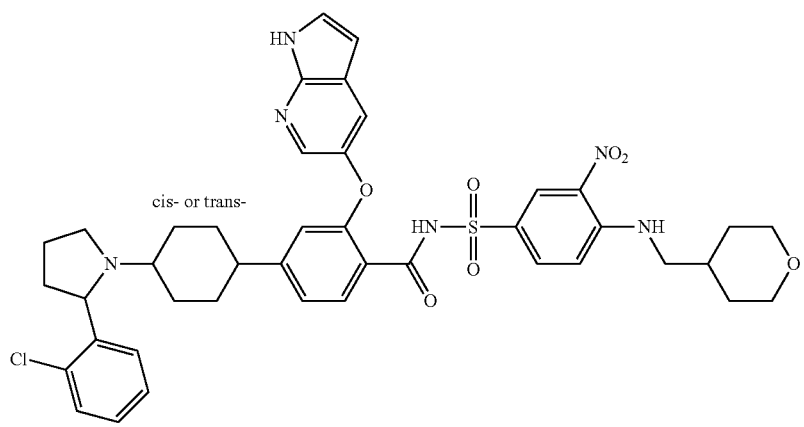

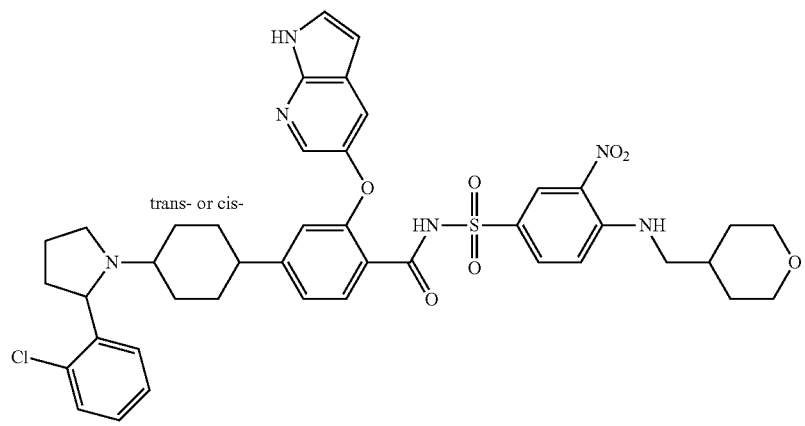
D1b
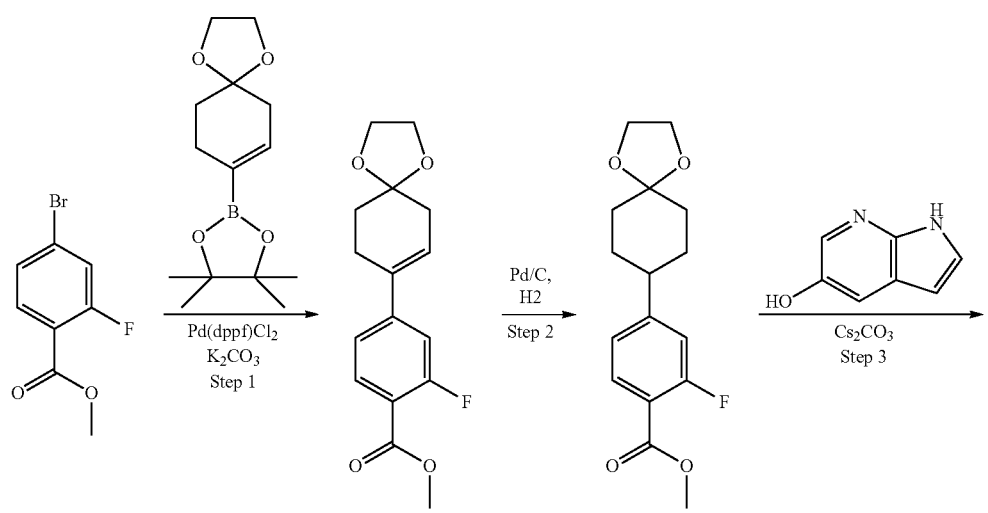
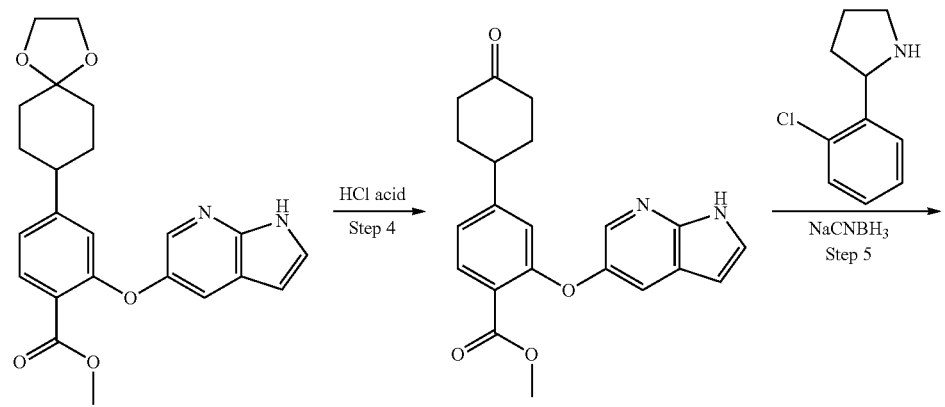

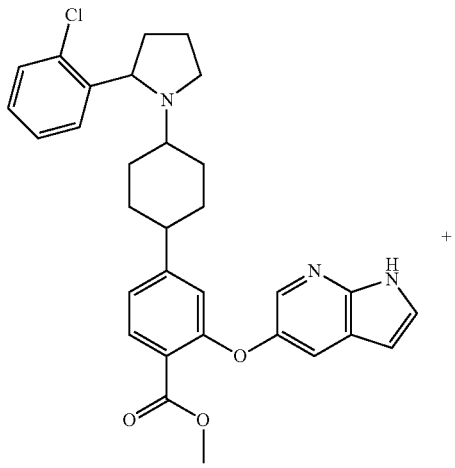

P1 (cis- or trans-, faster isomer)

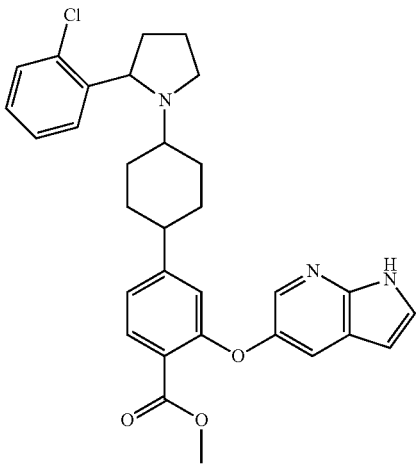

P2 (trans- or cis-, slower isomer)

Step 1: methyl 2-fluoro-4-(1,4-dioxaspiro[4.5]dec-7-en-8-yl)benzoate

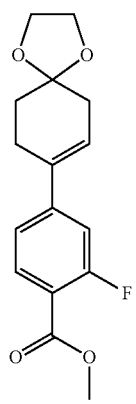

The mixture of methyl 4-bromo-2-fluorobenzoate (2.33 g, 10 mmol), 4,4,5,5-tetramethyl-2-(1,4-dioxaspiro[4.5]dec-7-en-8-yl)-1,3,2-dioxaborolane (2.93 g, 11 mmol), 1,1'-bis(diphenylphosphino)ferrocene-palladium(II)dichloride dichloromethane complex (731 mg, 1 mmol), $K_2CO_3$ (3.45 g, 25 mmol) in a solution of 1,4-dioxane (100 mL) and water (5 mL) was heated to 90° C. and stirred overnight. After cooled to room temperature, the reaction mixture was concentrated in vacuum and purified by chromatography column on silica (eluent: EA/PE=1/5) to give the product (2.7 g, 92.46%) as a white solid. $^1$H NMR (400 MHz, CDCl3) δ ppm: 7.87 (t, J=8.0 Hz, 1H), 7.24 (d, J=8.0 Hz, 1H), 7.16 (d, J=8.0 Hz, 1H), 6.16-6.11 (m, 1H), 4.03 (s, 4H), 3.92 (s, 3H), 2.64-2.62 (m, 2H), 2.50-2.48 (m, 2H), 1.93-1.82 (m, 2H).

Step 2: methyl 2-fluoro-4-(1,4-dioxaspiro[4.5]decan-8-yl)benzoate

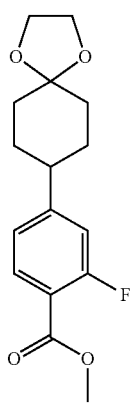 [SMILES: COC(=O)c1ccc(C2=CCC3(CC2)OCCO3)cc1F]

The mixture of methyl 2-fluoro-4-(1,4-dioxaspiro[4.5]dec-7-en-8-yl)benzoate (2.7 g, 9.24 mmol) and Pd/C (0.5 g) in MeOH (100 mL) was stirred overnight under $H_2$ atmosphere (1 atm) at room temperature. The mixture was filtrated, then the filtrate was concentrated in vacuum to afford the tittle product (2.6 g, 95.61%) as a white solid. $^1$H NMR (400 MHz, CDCl3) δ ppm: 7.85 (t, J=8.0, 1H), 7.09 (d, J=8.0 Hz, 1H), 7.03 (d, J=12.0 Hz, 1H), 4.03 (s, 4H), 3.93 (s, 3H), 2.60-2.57 (m, 1H), 1.88-1.86 (m, 4H), 1.79-1.65 (m, 4H).

Step 3: methyl 2-((1H-pyrrolo[2,3-b]pyridin-5-yl)oxy)-4-(1,4-dioxaspiro[4.5]decan-8-yl)benzoate

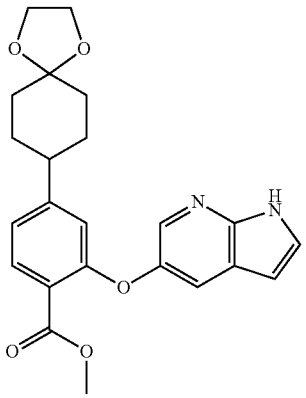 [SMILES: COC(=O)c1ccc(C2CCC3(CC2)OCCO3)cc1Oc1cnc2[nH]ccc2c1]

The mixture of methyl 2-fluoro-4-(1,4-dioxaspiro[4.5]decan-8-yl)benzoate (2.6 g, 8.83 mmol) and 1H-pyrrolo[2,3-b]pyridin-5-ol (1.42 g, 10.60 mmol) and Cs$_2$CO$_3$ in DMF (100 mL) was heated to 100° C. and stirred overnight. After cooled to room temperature, the reaction mixture was concentrated in vacuum and purified by chromatography column on silica (eluent: EA/PE=1/5) to give the product (1.16 g, 32.20%) as a yellow solid. MS (ESI, m/e) [M+1]$^+$ 409.1

Step 4: methyl 2-((1H-pyrrolo[2,3-b]pyridin-5-yl)oxy)-4-(4-oxocyclohexyl)benzoate

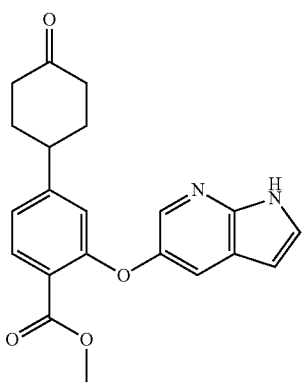 [SMILES: COC(=O)c1ccc(C2CCC(=O)CC2)cc1Oc1cnc2[nH]ccc2c1]

The mixture of methyl 2-((1H-pyrrolo[2,3-b]pyridin-5-yl)oxy)-4-(1,4-dioxaspiro[4.5]decan-8-yl)benzoate (1.16 g, 2.85 mmol) and HCl acid (6M, 4 mL) in EA (50 mL) was stirred for 30 mins at room temperature. The reaction was quenched with NaOH (1 M) solution and adjusted to pH8, washed with brine, dried over Na$_2$SO$_4$ and concentrated in vacuum to afford the tittle product (1.03 g) as a yellow solid. $^1$H NMR (400 MHz, CDCl$_3$) δ ppm: 10.37 (br, 1H), 8.20 (s, 1H), 7.91 (d, J=8.0 Hz, 1H), 7.61 (s, 1H), 7.41 (s, 1H), 7.03 (d, J=8.0 Hz, 1H), 6.75 (s, 1H), 6.48 (s, 1H), 3.88 (s, 3H), 2.96-2.90 (m, 1H), 2.45-2.61 (m, 4H), 2.15-2.05 (m, 2H), 1.86-1.80 (m, 2H). MS (ESI, m/e) [M+1]$^+$ 365.1

Step 5: (cis- or trans-) methyl 2-((1H-pyrrolo[2,3-b]pyridin-5-yl)oxy)-4-(4-(2-(2-chlorophenyl)pyrrolidin-1-yl)cyclohexyl)benzoate; (trans- or cis-)methyl 2-((1H-pyrrolo[2,3-b]pyridin-5-yl)oxy)-4-(4-(2-(2-chlorophenyl)pyrrolidin-1-yl)cyclohexyl)benzoate

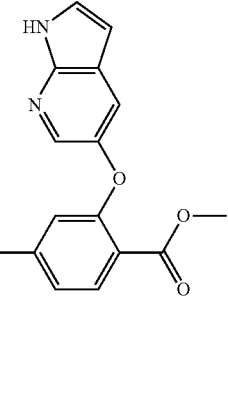

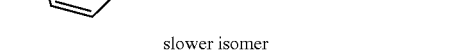
cis- or trans-

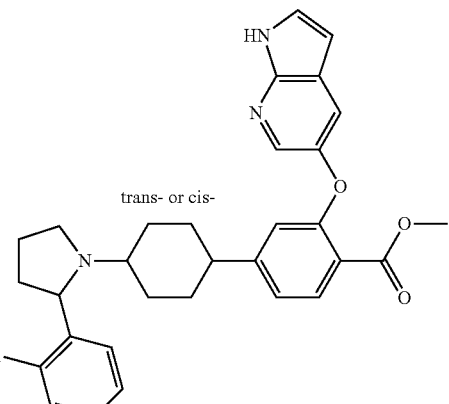
faster isomer

trans- or cis-slower isomer

The mixture of methyl 2-((1H-pyrrolo[2,3-b]pyridin-5-yl)oxy)-4-(4-oxocyclohexyl)benzoate (437 mg, 1.20 mmol), 2-(2-chlorophenyl)pyrrolidine (262 mg, 1.44 mmol), AcOH (0.2 mL) in MeOH was stirred for 1 hour at room temperature. To the reaction was added NaCNBH$_3$ (276 mg, 4.40 mmol) and stirred for another 1 hour. Then the reaction mixture was concentrated in vacuum and purified by chromatography column on silica: with the eluent of EA/PE=1/5 to give the faster isomer P1 (130 mg, 20.43%) as a white solid. $^1$H NMR (400 MHz, CDCl$_3$) δ ppm: 9.29 (br, 1H), 8.19-8.15 (m, 1H), 7.86 (d, J=8.0, 1H), 7.68-7.65 (m, 1H), 7.53-7.49 (m, 1H), 7.36-7.27 (m, 1H), 7.21-7.18 (m, 1H), 6.98-6.93 (m, 3H), 6.71 (s, 1H), 6.47-6.42 (m, 1H), 4.22 (d, J=8.0, 1H), 3.84 (s, 3H), 3.24-3.18 (m, 1H), 2.60-2.53 (m, 2H), 2.43-2.38 (m, 2H), 2.19-2.15 (m, 1H), 1.83-1.71 (m, 5H), 1.49-1.43 (m, 4H), 1.36-1.24 (m, 2H). MS (ESI, m/e) [M+1]$^+$ 530.1; then with the eluent of EA/PE=1/1 to give the slower isomer P2 (70 mg, 11,00%) as a white solid. $^1$H NMR (400 MHz, CDCl$_3$) δ ppm: 8.86 (br, 1H), 8.15-8.11 (m, 1H), 7.84 (d, J=8.0, 1H), 7.70 (d, J=8.0, 1H), 7.52-7.47 (m, 1H), 7.34-7.25 (m, 2H), 7.21 (t, J=8.0, 1H), 7.11 (t, J=8.0, 1H), 6.95 (d, J=8.0, 1H), 6.66 (s, 1H), 6.46-6.42 (m, 1H), 4.22-4.17 (m, 1H), 3.84 (s, 3H), 3.24-3.15-3.10 (m, 1H), 2.60-2.53 (m, 2H), 2.37-2.29 (m, 2H), 2.21-2.08 (m, 1H), 1.81-1.72 (m, 5H), 1.56-1.50 (m, 2H), 1.32-1.21 (m, 4H). MS (ESI, m/e) [M+1]$^+$ 530.1.

Step 6: (cis- or trans-) 2-((1H-pyrrolo[2,3-b]pyridin-5-yl)oxy)-4-(4-(2-(2-chlorophenyl)pyrrolidin-1-yl)cyclohexyl)benzoic-acid

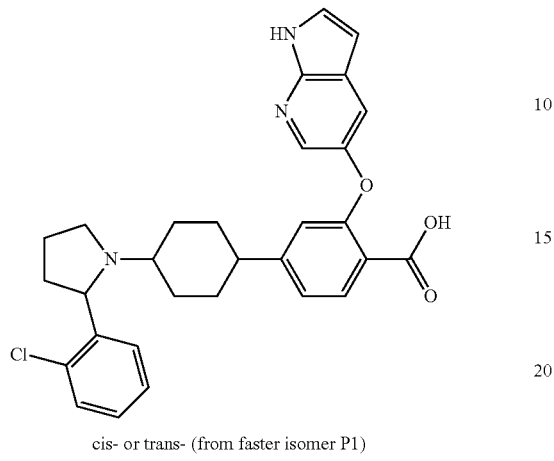

cis- or trans- (from faster isomer P1)

The mixture of (cis- or trans-) methyl 2-((1H-pyrrolo[2,3-b]pyridin-5-yl)oxy)-4-(4-(2-(2-chlorophenyl)pyrrolidin-1-yl)cyclohexyl)benzoate (PI) (130 mg, 0.25 mmol) in a solution of MeOH (10 mL)/THF (2 mL)/H$_2$O (1 mL) was added NaOH (100 mg, 2.5 mmol) and stirred overnight. Then the reaction was quenched with HCl acid (6N) and adjusted to pH ~4, extracted with DCM (20 mL), washed with brine (10 mL), dried over Na$_2$SO$_4$ and concentrated in vacuum to afford a crude product (142 mg, crude). MS (ESI, m/e) [M+1]$^+$ 516.1.

Step 7: (cis- or trans-) 2-((1H-pyrrolo[2,3-b]pyridin-5-yl)oxy)-4-(4-(2-(2-chlorophenyl)pyrrolidin-1-yl)cyclohexyl)-N-((3-nitro-4-((((tetrahydro-2H-pyran-4-yl)methyl)amino)phenyl)sulfonyl)benzamide (D1a)

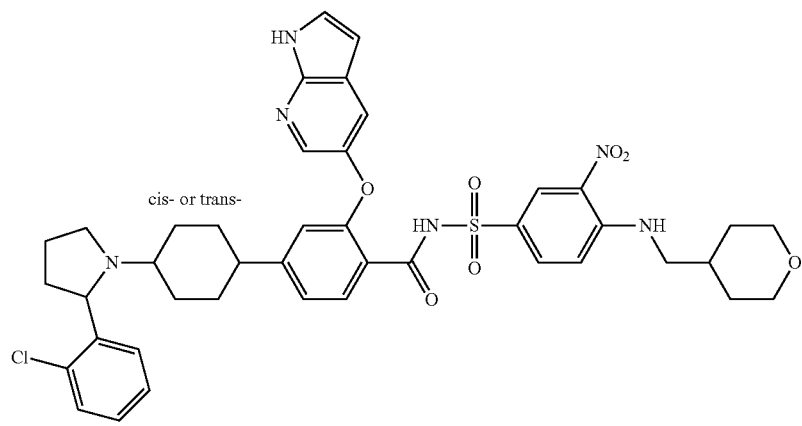

D1a

The mixture of (cis- or trans-)-2-((1H-pyrrolo[2,3-b]pyridin-5-yl)oxy)-4-(4-(2-(2-chlorophenyl)pyrrolidin-1-yl)cyclohexyl)benzoic acid (142 mg, 0.28 mmol; product of step 6), triethylamine (85 mg, 0.84 mmol), 2-(7-azabenzotriazol-1-yl)-N,N,N',N'-tetramethyluronium hexafluorophosphate (125 mg, 0.33 mmol) in DCM (20 mL) was stirred for 2 hours. To the resulting reaction were added 3-nitro-4-(((tetrahydro-2H-pyran-4-yl)methyl)amino)benzenesulfonamide (104 mg, 0.33 mmol) and DMAP (3 mg, 0.03 mmol) and stirred overnight. The reaction mixture was concentrated in vacuum and purified by chromatography column on silica (eluent: PE/EA=1/1 to DCM/MeOH=10/1) to afford a crude product, which was purified with Pre-TLC (DCM/MeOH, 25/1) to give the product Example D1a (17.5 mg, 7.71%). $^1$H NMR (400 MHz, DMSO-$d_6$) δ ppm: 12.16 (br, 1H), 11.78 (br, 1H), 8.61 (m, 2H), 8.05 (s, 1H), 7.85 (d, J=8.0 Hz, 1H), 7.63 (s, 1H), 7.55 (m, 1H), 7.51 (d, J=8.0 Hz, 1H), 7.45 td, J=8.0 Hz, 1H), 7.27 (d, J=8.0 Hz, 1H), 7.16 (d, J=8.0 Hz, 1H), 7.00 (t, J=8.0 Hz, 1H), 6.94 (d, J=8.0 Hz, 1H), 6.86 (t, J=8.0 Hz, 1H), 6.51 (s, 1H), 6.44 (s, 1H), 4.10 (d, J=8.0 Hz, 1H), 3.85 (d, J=8.0 Hz, 2H), 3.30-3.23 (m, 5H), 3.16-3.10-3.04 (m, 2H), 2.67-2.55 (m, 1H), 2.42-2.33 (m, 3H), 2.13-1.99 (m, 2H), 1.87-1.82 (m, 2H), 1.67-1.58 (m, 4H), 1.41-1.26 (m, 6H), MS (ESI, m/e) [M+1]$^+$ 813.2.

Example D1b: (trans- or cis-) 2-((1H-pyrrolo[2,3-b]pyridin-5-yl)oxy)-4-(4-(2-(2-chlorophenyl)pyrrolidin-1-yl)cyclohexyl)-N-((3-nitro-4-(((tetrahydro-2H-pyran-4-yl)methyl)amino)phenyl)sulfonyl)benzamide

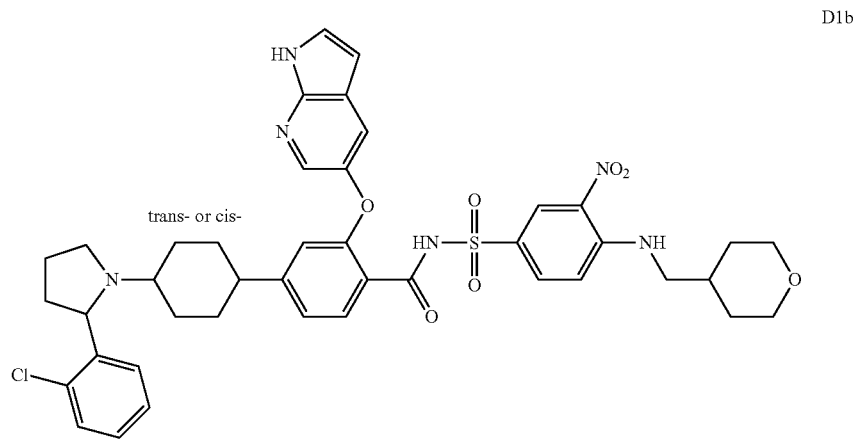 [SMILES: O=C(NS(=O)(=O)c1ccc(NCC2CCOCC2)c([N+](=O)[O-])c1)c1ccc(C2CCC(N3CCCC3c3ccccc3Cl)CC2)cc1Oc1cnc2[nH]ccc2c1]

Using the slower isomer P2 in the hydrolysis reaction of step 6 and then proceeded with a condensation reaction following similar procedure of Example D1a gave Example D1b (11 mg, 8.46%). $^{1}$H NMR (400 MHz, DMSO-d$_{6}$) δ ppm: 12.14 (br, 1H), 11.68 (br, 1H), 8.51-8.42 (m, 2H), 7.97 (s, 1H), 7.79 (d, J=8.0 Hz, 1H), 7.68-7.65 (m, 1H), 7.50-7.47 (m, 2H), 7.42 (d, J=8.0 Hz, 1H), 7.34-7.30 (m, 2H), 7.20-7.16 (m, 1H), 7.07-7.01 (m, 1H), 6.98 (d, J=8.0 Hz, 1H), 6.60 (s, 1H), 6.38 (s, 1H), 4.14 (m, 1H), 3.85 (d, J=12.0 Hz, 2H), 3.26-3.22 (m, 5H), 3.13-2.98 (m, 2H), 2.67-2.59 (m, 1H), 2.33-2.18 (m, 4H), 2.03-1.97 (m, 1H), 1.86-1.80 (m, 2H), 1.68-1.57 (m, 8H), 1.45-1.26 (m, 2H). MS (ESI, m/e) [M+1]$^{+}$ 813.2.

Example D2a and Example D2b: (cis- or trans-) 2-((1H-pyrrolo[2,3-b]pyridin-5-yl)oxy)-4-(4-(2-(2-cyclopropylphenyl)pyrrolidin-1-yl)cyclohexyl)-N-((3-nitro-4-(((tetrahydro-2H-pyran-4-yl)methyl)amino)phenyl)sulfonyl)benzamide; and (trans- or cis-) 2-((1H-pyrrolo[2,3-b]pyridin-5-yl)oxy)-4-(4-(2-(2-cyclopropylphenyl)pyrrolidin-1-yl)cyclohexyl)-N-((3-nitro-4-(((tetrahydro-2H-pyran-4-yl)methyl)amino)phenyl)sulfonyl)benzamide

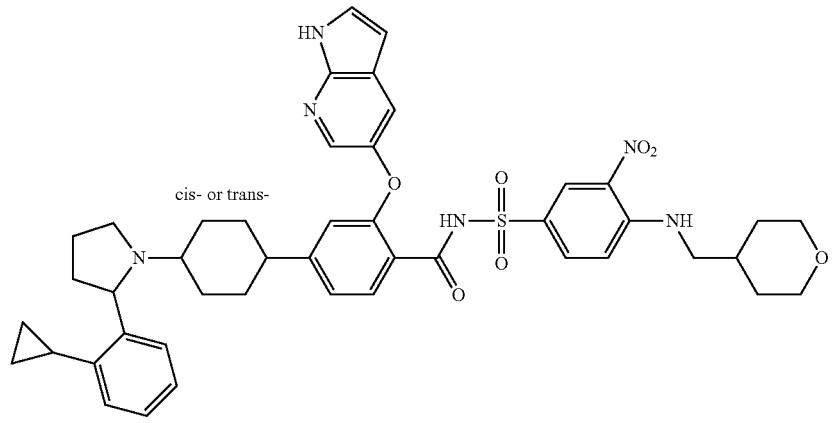

D2a


D2b

Using 2-(2-cyclopropylphenyl)pyrrolidine in the reductive amination step, and then following the next similar procedures of Example D1a and D1b, compounds D2a and D2b were obtained correspondingly.

Example D2a: 12.16 (br, 1H), 11.73-11.67 (m, 1H), 8.55 (m, 2H), 8.03-7.97 (m, 1H), 7.81-7.58 (m, 2H), 7.49-7.43 (m, 3H), 7.24-6.92 (m, 3H), 6.87-6.81 (m, 1H), 6.67 (m, 1H), 6.53 (s, 1H), 6.42-6.36 (m, 1H), 5.13 (m, 0.5H), 4.23 (m, 0.5H), 3.85 (d, J=8.0 Hz, 2H), 3.70 (m, 1H), 3.40 (m, 1H), 3.28-3.16 (m, 5H), 2.67 (m, 1H), 2.42-1.87 (m, 8H), 1.67 (m, 2H), 1.61 (d, J=12.0 Hz, 2H), 1.45-1.23 (m, 6H), 0.91-0.85 (m, 2H), 0.69-0.45 (m, 2H). MS (ESI, m/e) [M+1]$^+$ 819.2.

Example D2b: 12.26 (br, 1H), 11.88 (br, 1H), 8.48 (m, 2H), 7.95 (s, 1H), 7.74 (m, 1H), 7.51-7.43 (m, 3H), 7.30 (m, 2H), 7.09-6.94 (m, 4H), 6.59 (s, 1H), 6.36 (s, 1H), 5.14 (m, 0.5H), 4.27 (m, 0.5H), 3.84 (d, J=8.0 Hz, 1H), 3.62 (m, 1H), 3.25-3.13 (m, 4H), 3.10-2.98 (m, 2H), 2.41 (m, 2H), 2.10-1.99 (m, 6H), 1.86 (m, 2H), 1.67-1.61 (m, 4H), 1.60 (d, J=8.0 Hz, 2H), 1.41-1.26 (m, 4H), 0.93 (m, 2H), 0.72-0.59 (m, 2H). MS (ESI, m/e) [M+1]$^+$ 819.2.

Example D2a-S and D2b-S: (cis- or trans-) (S)-2-((1H-pyrrolo[2,3-b]pyridin-5-yl)oxy)-4-(4-(2-(2-cyclopropylphenyl)pyrrolidin-1-yl)cyclohexyl)-N-((3-nitro-4-((((tetrahydro-2H-pyran-4-yl)methyl)amino)phenyl)sulfonyl)benzamide; and (trans- or cis-) (S)-2-((1H-pyrrolo[2,3-b]pyridin-5-yl)oxy)-4-(4-(2-(2-cyclopropylphenyl)pyrrolidin-1-yl)cyclohexyl)-N-((3-nitro-4-((((tetrahydro-2H-pyran-4-yl)methyl)amino)phenyl)sulfonyl)benzamide

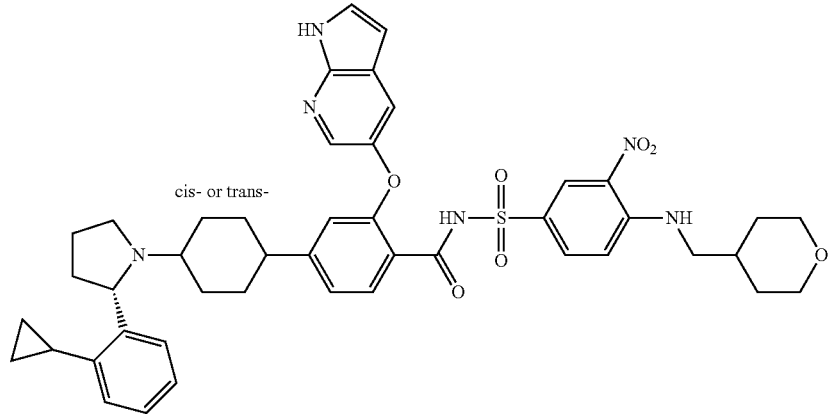

D2a-S

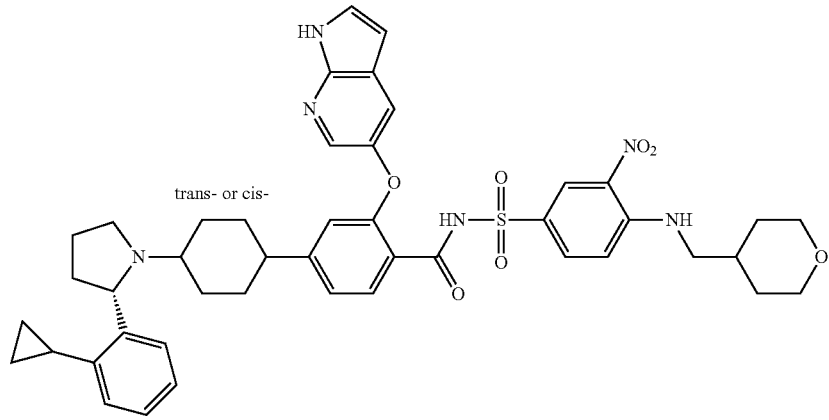

D2b-S

Step 1: (cis- or trans-) methyl (S)-2-((1H-pyrrolo[2,3-b]pyridin-5-yl)oxy)-4-(4-(2-(2-cyclopropylphenyl)pyrrolidin-1-yl)cyclohexyl)benzoate; (trans- or cis-) methyl (S)-2-((1H-pyrrolo[2,3-b]pyridin-5-yl)oxy)-4-(4-(2-(2-cyclopropylphenyl)pyrrolidin-1-yl)cyclohexyl)benzoate

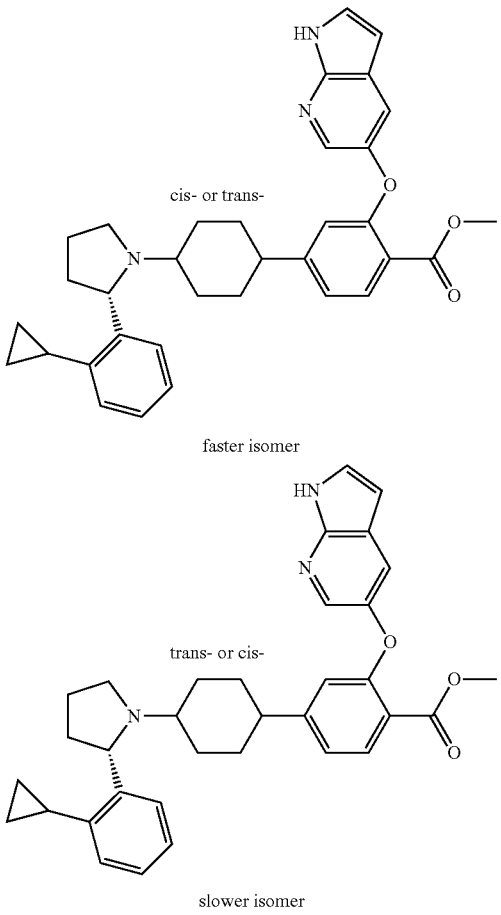

To a solution of methyl 2-((1H-pyrrolo[2,3-b]pyridin-5-yl)oxy)-4-(4-oxocyclohexyl)benzoate (364 mg, 1.00 mmol), (S)-2-(2-cyclopropylphenyl)pyrrolidine (185 mg, 1.00 mmol), AcOH (1 drop) in DCM (20 mL) was added NaBH(OAc)$_3$ (424 mg, 2.00 mmol), the solution was stirred at r.t for 16 h. The reaction solution was washed with H$_2$O (20 mL), dried over Na$_2$SO$_4$, concentrated and purified by prep-MPLC to afford two products as cis-/trans-isomer of cyclohexyl, the faster isomer PI (eluent: 40% (v), EA/PE) as a white solid (250 mg, 41.4%), MS (ESI, m/e) [M+1]$^+$ 536.2; the slower isomer P2 (eluent: 80% (v), EA/PE) as a white solid (230 mg, 46.7%), MS (ESI, m/e) [M+1]$^+$ 536.2.

Step 2: (cis- or trans-) (S)-2-((1H-pyrrolo[2,3-b]pyridin-5-yl)oxy)-4-(4-(2-(2-cyclopropylphenyl)pyrrolidin-1-yl)cyclohexyl)benzoic acid

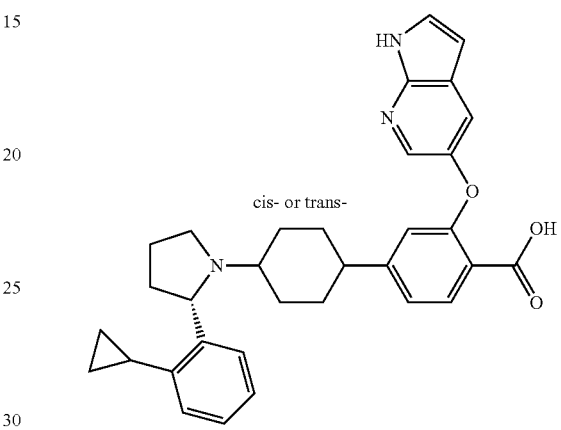

The solution of methyl (cis- or trans-) (S)-2-((1H-pyrrolo[2,3-b]pyridin-5-yl)oxy)-4-(4-(2-(2-cyclopropylphenyl)pyrrolidin-1-yl)cyclohexyl)benzoate (PI) (250 mg, 0.0.467 mmol) in THF (20 mL) was added NaOH (6M, 6 mL), the mixture was stirred for 3 h at room temperature. Then the pH value of the reaction solution was adjusted to 3 with Con. HCl acid and concentrated in vacuum. The residue was washed with DCM/MeOH=10/1 (50 mL), filtered, the filtrate was concentrated to afford the product (200 mg, crude) as a yellow solid. MS (ESI, m/e) [M+1]$^+$ 522.2.

Step 3: (cis- or trans-) (S)-2-((1H-pyrrolo[2,3-b]pyridin-5-yl)oxy)-4-(4-(2-(2-cyclopropylphenyl)pyrrolidin-1-yl)cyclohexyl)-N-((3-nitro-4-(((tetrahydro-2H-pyran-4-yl)methyl)amino)phenyl)sulfonyl)benzamide D2a-S

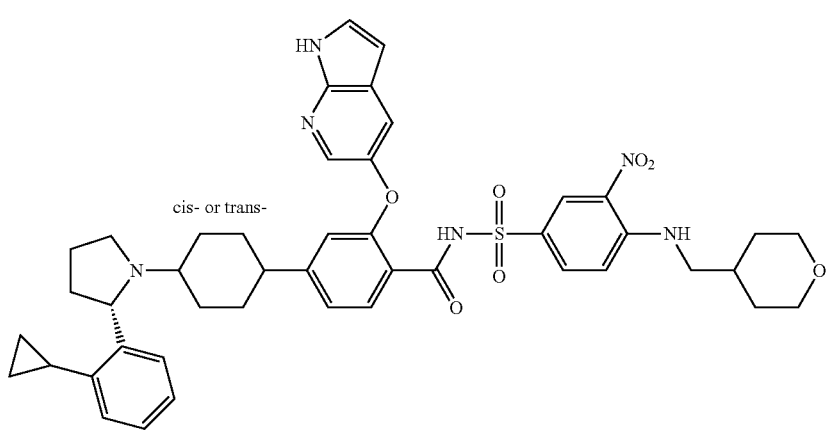

To a mixture of (cis- or trans-) (S)-2-((1H-pyrrolo[2,3-b]pyridin-5-yl)oxy)-4-(4-(2-(2-cyclopropylphenyl)pyrrolidin-1-yl)cyclohexyl)benzoic acid (200 mg, 0.384 mmol) in DCM (20 mL) was added 3-nitro-4-((((tetrahydro-2H-pyran-4-yl)methyl)amino)benzenesulfonamide (145 mg, 0.460 mmol), HATU (175 mg, 0.0.460 mmol), DMAP (47 mg, 0.84 mmol) and triethylamine (194 mg, 1,919 mmol), the solution was stirred at room temperature for 18 hours. Then the reaction mixture was washed with $H_2O$ (10 mL) and separated. The organic layer was then concentrated and purified by chromatography column on silica (eluent: DCM/MeOH, 20/0 to 20/1) to afford the crude product, which was further purified by pre-TLC (eluent: MeOH/DCM=1/20) to give compound D2a-S (200 mg, 63.7%) as a yellow solid. $^1$H NMR (400 MHz, DMSO-$d_6$) δ ppm: 11.70 (s, 1H), 8.53 (s, 2H), 8.10-7.42 (m, 6H), 7.20-6.22 (m, 8H), 3.87-3.81 (m, 2H), 3.30-3.12 (m, 6H), 2.00-1.13 (m, 20H), 0.94-0.77 (m, 3H), 0.67-0.64 (m, 2H). MS (ESI, m/e) $[M+1]^+$ 819.2.

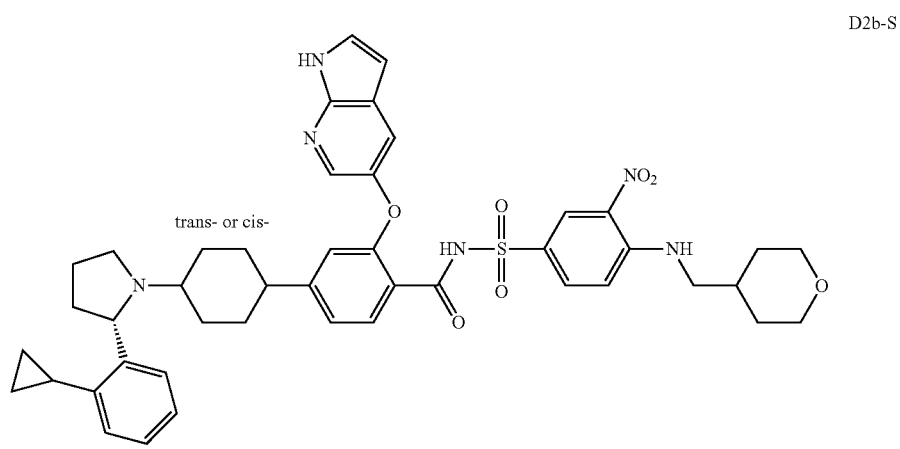 [SMILES: O=C(NS(=O)(=O)c1ccc(NCC2CCOCC2)c([N+](=O)[O-])c1)c1ccc(C2CCC(N3CCC[C@H]3c3ccccc3C3CC3)CC2)cc1Oc1cnc2[nH]ccc2c1]

D2b-S

To a mixture of (trans- or cis-) (S)-2-((1H-pyrrolo[2,3-b]pyridin-5-yl)oxy)-4-(4-(2-(2-cyclopropylphenyl)pyrrolidin-1-yl)cyclohexyl)benzoic acid (200 mg, 0.384 mmol, prepared from intermediate P2 using the same procedure in example D2a-S) in DCM (20 mL) was added 3-nitro-4-(((tetrahydro-2H-pyran-4-yl)methyl)amino)benzenesulfonamide (121 mg, 0.384 mmol), EDO (148 mg, 0.768 mmol), DMAP (94 mg, 0.768 mmol) and triethylamine (195 mg, 1.92 mmol), the resulted mixture was stirred at room temperature for 40 hours. Then the reaction mixture was washed with $H_2O$ (10 mL×3), the organic phase was concentrated and purified by chromatography column on silica (eluent: DCM/MeOH, 20/0 to 20/1) to afford compound D2b-S (80 mg, 25.5%). $^1$H NMR (400 MHz, $CDCl_3$-$d_6$) δ ppm: 9.53 (s, 1H), 8.90 (s, 1H), 8.53 (s, 1H), 8.24-8.07 (m, 2H), 8.00 (d, J=8.4 Hz, 1H), 7.83-7.38 (m, 3H), 7.21-7.05 (m, 2H), 7.01-6.95 (m, 3H), 6.59-6.39 (m, 2H), 4.51-4.18 (m, 1H), 4.10-3.95 (m, 2H), 3.46-3.36 (t, J=12.0 Hz, 2H), 3.29-3.22 (t, J=6.0 Hz, 2H), 2.63 (m, 1H), 2.32-2.19 (m, 2H), 2.00-1.85 (m, 4H), 1.78-1.63 (m, 6H), 1.48-1.39 (m, 2H), 1.36-1.11 (m, 6H), 0.96-0.77 (m, 3H), 0.73-0.50 (m, 2H). MS (ESI, m/e) [M+1]$^+$ 819.2.

Example D2a-R and D2b-R: (cis- or trans-) (R)-2-((1H-pyrrolo[2,3-b]pyridin-5-yl)oxy)-4-(4-(2-(2-cyclopropylphenyl)pyrrolidin-1-yl)cyclohexyl)-N-((3-nitro-4-((((tetrahydro-2H-pyran-4-yl)methyl)amino)phenyl)sulfonyl)benzamide (trans- or cis-)(R)-2-((1H-pyrrolo[2,3-b]pyridin-5-yl)oxy)-4-(4-(2-(2-cyclopropylphenyl)pyrrolidin-1-yl)cyclohexyl)-N-((3-nitro-4-((((tetrahydro-2H-pyran-4-yl)methyl)amino)phenyl)sulfonyl)benzamide

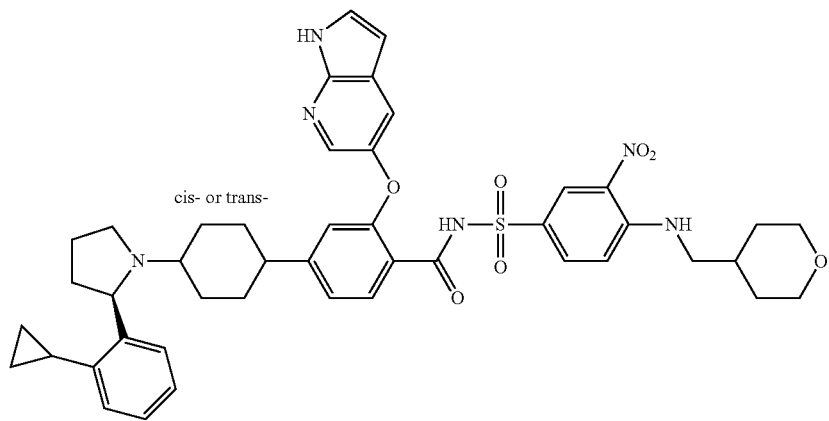

D2a-R

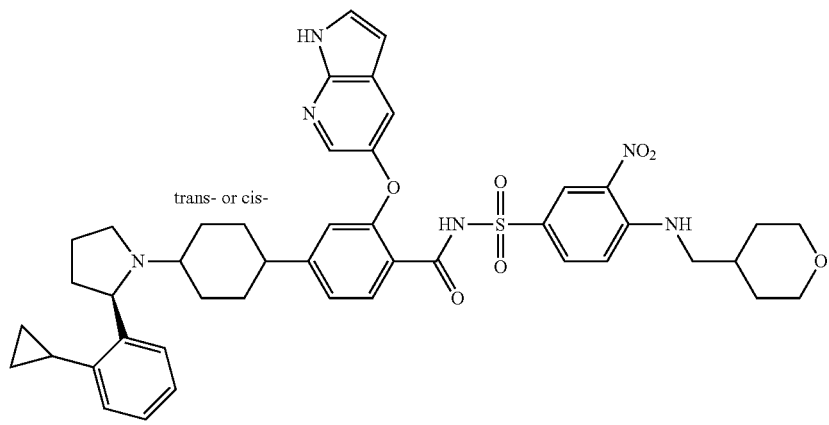

D2b-R

Using (R)-2-(2-cyclopropylphenyl)pyrrolidine instead of (S)-2-(2-cyclopropylphenyl)pyrrolidine in the reductive animation step, and then following the next similar procedures of Example D2a-S, compounds D2a-R and D2b-R were obtained correspondingly.

Example D2a-R: $^1$H NMR (400 MHz, DMSO-$d_6$) δ ppm: 11.59 (br, 1H), 8.42 (s, 1H), 8.35 (l, J=4.0 Hz, 1H), 7.95 (s, 1H), 7.72 (d, J=12.0 Hz, 1H), 7.49-7.46 (m, 3H), 7.36 (s, 1H), 6.87-6.82 (m, 4H), 6.73 (t, J=8.0 Hz, 1H), 6.56 (s, 1H), 6.34-6.31 (m, 1H), 4.26 (d, J=8.0 Hz, 1H), 3.85 (d, J=8.0 Hz, 2H), 3.29-3.17 (m, 6H), 2.54-2.48 (m, 1H), 2.38-2.34 (m, 2H), 2.19-2.14 (m, 1H), 1.96-1.68 (m, 6H), 1.62 (d, J=12.0 Hz, 2H), 1.42-1.21 (m, 8H), 0.89-0.82 (m, 2H), 0.65-0.62 (m, 1H), 0.49-0.45 (m, 1H). MS (ESI, m/e) [M+1]$^+$ 819.2.

Example D2b-R: $^1$H NMR (400 MHz, DMSO-$d_6$) δ ppm: 11.53 (br, 1H), 8.37 (s, 1H), 8.32 (t, J=4.0 Hz, 1H), 7.89 (d, J=2.0 Hz, 1H), 7.65 (d, J=8.0 Hz, 1H), 7.56 (d, J=8.0 Hz, 1H), 7.42-7.40 (m, 2H), 7.30 (d, J=2.0 Hz, 1H), 7.11 (t, J=4.0 Hz, 1H), 7.05 (t, J=8.0 Hz, 1H), 6.92 (d, J=8.0 Hz, 1H), 6.88 (d, J=8.0 Hz, 1H), 6.83 (d, J=8.0 Hz, 1H), 6.58 (s, 1H), 6.30-6.27 (m, 1H), 4.30 (t, J=8.0 Hz, 1H), 3.85 (d, J=8.0 Hz, 2H), 3.30-3.11 (m, 6H), 2.59-2.53 (m, 1H), 2.33-2.31 (m, 2H), 2.20-2.17 (m, 1H), 1.99-1.93 (m, 1H), 1.86-1.80 (m, 2H), 1.72-1.58 (m, 7H), 1.42-1.21 (m, 6H), 0.90-0.84 (m, 2H), 0.65-0.63 (m, 1H), 0.53-0.50 (m, 1H). MS (ESI, m/e) [M+1]$^+$ 819.2.

Example D3a and Example D3b: (cis- or trans-)2-((1H-pyrrolo[2,3-b]pyridin-5-yl)oxy)-4(4-(2-(3-cyclopropylphenyl)pyrrolidin-1-yl)cyclohexyl)-N-((3-nitro-4-(((tetrahydro-2H-pyran-4-yl)methyl)amino)phenyl)sulfonyl)benzamide; (trans- or cis-)2-((1H-pyrrolo[2,3-b]pyridin-5-yl)oxy)-4-(4-(2-(3-cyclopropylphenyl)pyrrolidin-1-yl)cyclohexyl)-N-((3-nitro-4-(((tetrahydro-2H-pyran-4-yl)methyl)amino)phenyl)sulfonyl)benzamide

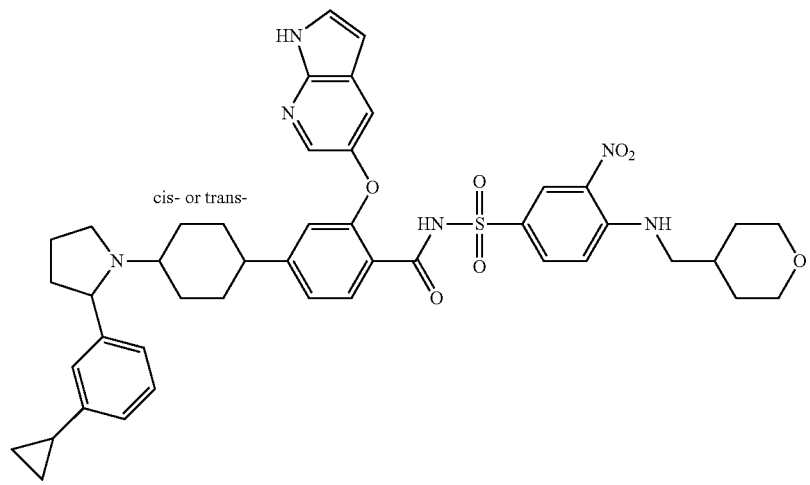

D3a

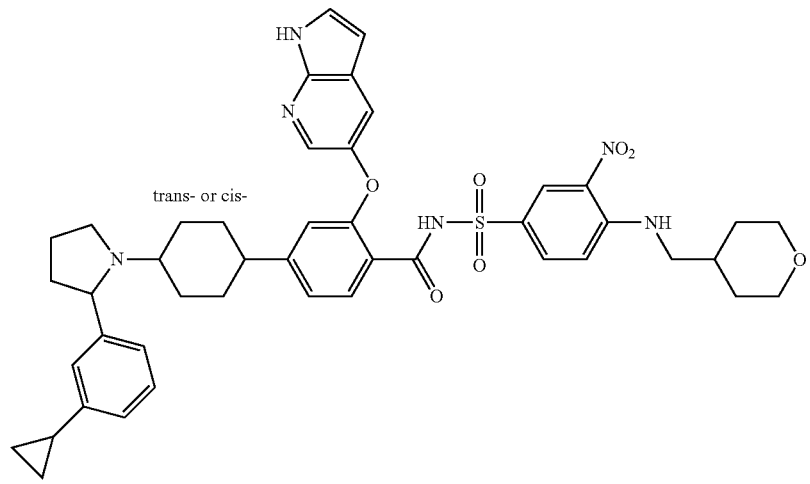

D3b

Using 2-(3-cyclopropylphenyl)pyrrolidine in the reductive animation step, and then following the next similar procedures of Example D1a and D1b, compounds D3a and D3b were obtained correspondingly.

Example D3a: $^1$H NMR/400 MHz, DMSO-$d_6$) δ ppm: 12.20 (br, 1H), 11.66 (br, 1H), 9.62 (br, 0.5H), 8.50-8.45 (m, 2H), 7.98 (s, 1H), 7.76-7.73 (m, 1H), 7.49-7.46 (m, 2H), 7.35-6.51 (m, 7H), 6.36 (s, 1H), 5.76 (s, 1H), 4.49-4.39 (m, 1H), 3.85 (d, J=8.0 Hz, 2H), 3.62-3.45 (m, 1H), 3.29-3.01 (m, 6H), 2.65-2.39 (m, 1H), 2.35-2.15 (m, 1H), 2.01-1.85 (m, 6H), 1.83-1.60 (m, 6H), 1.45-1.27 (m, 5H), 0.97-0.94 (m, 2H), 0.73-0.67 (m, 2H). MS (ESI, m/e) [M+1]$^+$819.2.

Example D3b: $^1$H NMR (400 MHz, DMSO-$d_6$) δ ppm: 12.18 (br, 1H), 11.68 (br, 1H), 9.73 (br, 0.5H), 8.51 (m, 2H), 7.97 (s, 1H), 7.79 (d, J=8.0 Hz, 1H), 7.50-7.47 (m, 2H), 7.44 (d, J=8.0 Hz, 1H), 7.34-7.29 (m, 3H), 7.10-7.01 (m, 2H), 6.97 (d, J=8.0 Hz, 1H), 6.59 (s, 1H), 6.38 (m, 1H), 4.53-4.48 (m, 1H), 3.85 (d, J=8.0 Hz, 2H), 3.55-3.46 (m, 1H), 3.29-3.01 (m, 6H), 2.36-2.25 (m, 2H), 2.01-1.85 (m, 8H), 1.83-1.66 (m, 2H), 1.60 (d, J=12.0 Hz, 2H), 1.45-1.27 (m, 5H), 0.97-0.94 (m, 2H), 0.73-0.67 (m, 2H). MS (ESI, m/e) [M+1]$^+$ 819.2.

Example D4a and Example D4b: (cis- or trans-)2-((1H-pyrrolo[2,3-b]pyridin-5-yl)oxy)-4-(4-(2-(4-cyclopropylphenyl)pyrrolidin-1-yl)cyclohexyl)-N-((3-nitro-4-(((tetrahydro-2H-pyran-4-yl)methyl)amino)phenyl)sulfonyl)benzamide; (trans- or cis-)2-((1H-pyrrolo[2,3-b]pyridin-5-yl)oxy)-4-(4-(2-(4-cyclopropylphenyl)pyrrolidin-1-yl)cyclohexyl)-N-((3-nitro-4-(((tetrahydro-2H-pyran-4-yl)methyl)amino)phenyl)sulfonyl)benzamide

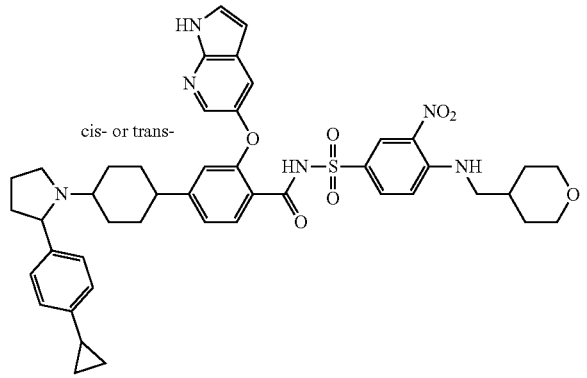

D4a

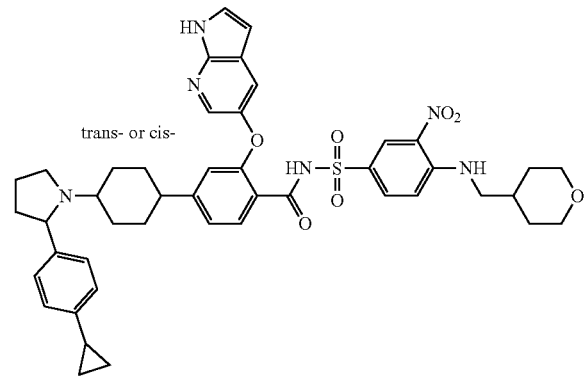

D4b

Using 2-(4-cyclopropylphenyl)pyrrolidine in the reductive animation step, and then following the next similar procedures of Example D1a and D1b, compounds D4a and D4b were obtained correspondingly. Example D4a: MS (ESI, m/e) [M+1]$^+$ 819.2. Example D4b: $^1$H NMR (400 MHz, DMSO-$d_6$) δ ppm: 12.18 (br, 0.5H), 11.72 (m, 1H), 9.71 (br, 0.5H), 8.49 (m, 2H), 7.96 (s, 1H), 7.77 (d, J=9.2 Hz, 2H), 7.59-7.42 (m, 4H), 7.12-6.94 (m, 4H), 6.59 (s, 1H), 6.37 (s, 1H), 4.54 (s, 1H), 3.85 (d, J=8.0 Hz, 2H), 3.51 (s, 1H), 3.27-3.23 (m, 4H), 2.33-2.01 (m, 2H), 1.85-1.66 (m, 9H), 1.61 (d, J=12.8 Hz, 2H), 1.45-1.21 (m, 8H), 0.96-0.84 (m, 2H), 0.70-0.66 (m, 2H). MS (ESI, m/e) [M+1]$^+$ 819.2.

Example D5: trans- or cis-2-((1H-pyrrolo[2,3-b]pyridin-5-yl)oxy)-4-(4-(2-(2-isopropylphenyl)pyrrolidin-1-yl)cyclohexyl)-N-((3-nitro-4-(((tetrahydro-2H-pyran-4-yl)methyl)amino)phenyl)sulfonyl)benzamide

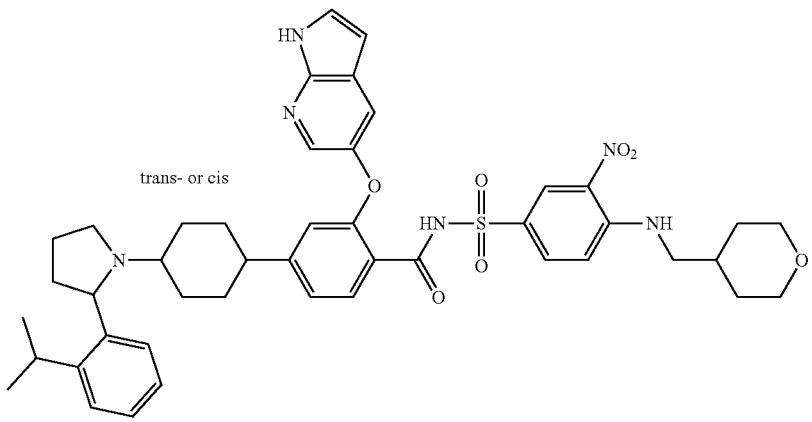 [SMILES: CC(C)c1ccccc1C1CCCN1C1CCC(c2ccc(C(=O)NS(=O)(=O)c3ccc(NCC4CCOCC4)c([N+](=O)[O-])c3)c(Oc3cnc4[nH]ccc4c3)c2)CC1]

Using 2-(2-isopropylphenyl)pyrrolidine in the reductive animation step, and then following the next similar procedures of Example D1b, compound D5 was obtained. $^1$H NMR (400 MHz, DMSO-d$_6$) δ ppm: 12.15 (s, 1H), 11.63 (s, 1H), 8.47 (s, 2H), 7.94 (s, 1H), 7.73 (s, 1H), 7.56 (s, 1H), 7.52-6.88 (m, 8H), 6.59 (s, 1H), 6.35 (s, 1H), 3.83 (d, J=8.6 Hz, 2H), 3.24-3.16 (m, 5H), 3.09 (s, 1H), 2.33 (s, 2H), 2.15-2.13 (m, 1H), 1.85 (s, 3H), 1.75-1.57 (m, 6H), 1.27-1.13 (m, 13H). MS (ESI, m/e) [M+1]$^+$ 821.2.

Example D6: trans- or cis-2-(1H-pyrrolo[2,3-b]pyridin-5-yl)oxy)-N-((3-nitro-4-((((tetrahydro-2H-pyran-4-yl)methyl)amino)phenyl)sulfonyl)-4-(4(2-(2-(prop-1-en-2-yl)phenyl)pyrrolidin-1-yl)cyclohexyl)benzamide

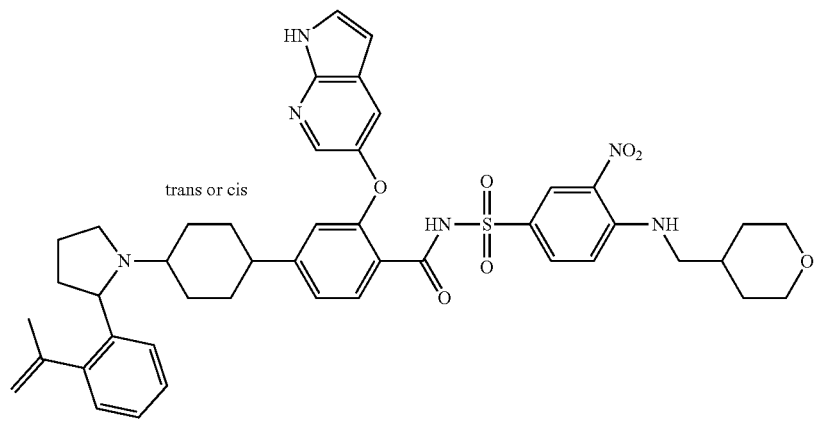 [SMILES: C=C(C)c1ccccc1C1CCCN1C1CCC(c2ccc(C(=O)NS(=O)(=O)c3ccc(NCC4CCOCC4)c([N+](=O)[O-])c3)c(Oc3cnc4[nH]ccc4c3)c2)CC1]

Using 2-(2-(prop-1-en-2-yl)phenyl)pyrrolidine in the reductive amination step, and then following the next similar procedures of Example D1b, compound D 6 was obtained. $^1$H NMR (400 MHz, DMSO-$d_6$) δ ppm: 12.17 (s, 1H), 11.62 (s, 1H), 8.60-8.40 (m, 2H), 7.93 (s, 1H), 7.80-7.60 (m, 2H), 7.55-7.30 (m, 4H), 7.30-6.80 (m, 4H), 6.59 (s, 1H), 6.34 (s, 1H), 5.35-5.15 (m, 1H), 4.90-4.50 (m, 1H), 3.84 (d, J=11.0 Hz, 2H), 3.30-3.20 (m, 4H), 3.05-2.85 (m, 2H), 2.40-2.20 (m, 2H), 2.15-1.90 (m, 5H), 1.85-1.50 (m, 8H), 1.45-1.05 (m, 8H). MS (ESI, m/e) [M+1]$^+$ 818.9.

Example D131a and Example D13-1b: (cis- or trans-) 2-((1H-pyrrolo[2,3-b]pyridin-5-yl)oxy)-4-(4-(2-(3-chlorophenyl)pyrrolidin-1-yl)cyclohexyl)-N-((3-nitro-4-(((tetrahydro-2H-pyran-4-yl)methyl) amino)phenyl)sulfonyl)benzamide; and (trans- or cis-) 2-((1H-pyrrolo[2,3-b]pyridin-5-yl)oxy)-4-(4-(2-(3-chlorophenyl)pyrrolidin-1-yl)cyclohexyl)-N-((3-nitro-4-(((tetrahydro-2H-pyran-4-yl)methyl) amino)phenyl)sulfonyl)benzamide Example D14-1a and Example D14-1b (cis- or trans-) 2-((1H-pyrrolo[2,3-b]pyridin-5-yl)oxy)-4-(4-(2-(4-chlorophenyl)pyrrolidin-1-yl)cyclohexyl)-N-((3-nitro-4-(((tetrahydro-2H-pyran-4-yl)methyl) amino)phenyl)sulfonyl)benzamide (trans- or cis-) 2-((1H-pyrrolo[2,3-b]pyridin-5-yl) oxy)-4-(4-(2-(4-chlorophenyl)pyrrolidin-1-yl)cyclo-hexyl)-N-((3-nitro-4-(((tetrahydro-2H-pyran-4-yl) methyl)amino)phenyl)sulfonyl)benzamide

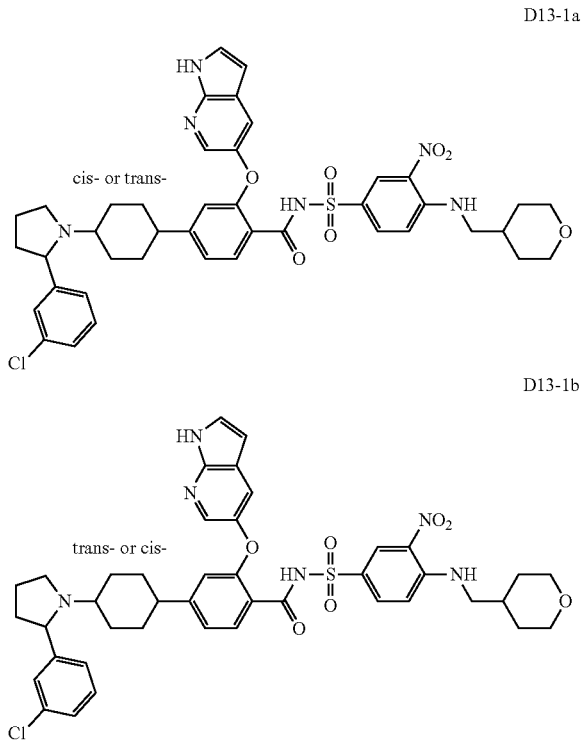

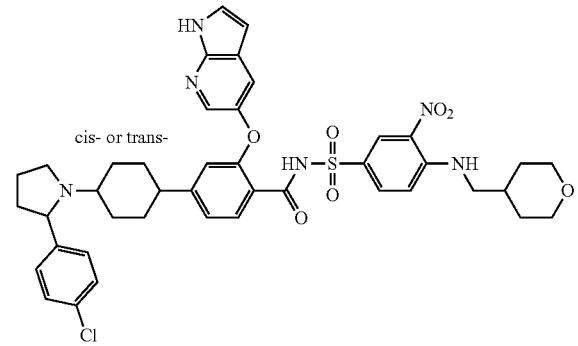

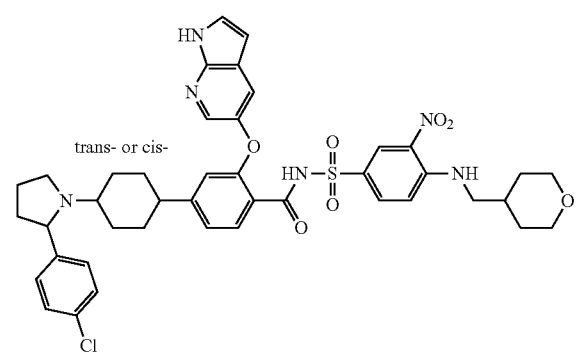

Using 2-(3-chlorophenyl)pyrrolidine in the reductive amination step, and then following the next similar procedures of Example D1a and D1b, compounds D13-1a and D13-1b were obtained correspondingly.

Example D13-1a: $^1$H NMR (400 MHz, DMSO-$d_6$) δ ppm: 12.16 (s, 1H), 11.72 (s, 1H), 8.70-8.35 (m, 2H), 8.01 (s, 1H), 7.83-7.70 (m, 1H), 7.64-7.30 (m, 5H), 7.22-7.00 (m, 4H), 6.99-6.84 (m, 1H), 6.53 (s, 1H), 6.44-6.31 (m, 1H), 3.93-3.79 (m, 2H), 3.78-3.63 (m, 1H), 3.16-2.97 (m, 2H), 2.42-2.28 (m, 2H), 2.19-1.94 (m, 2H), 1.94-1.68 (m, 4H), 1.68-1.52 (m, 4H), 1.51-1.33 (m, 3H), 1.33-1.23 (s, 5H), MS (ESI) m/e [M+1]$^+$ 813.1.

Example D13-1b: $^1$H NMR (400 MHz, CDCl$_3$) δ ppm: 10.27 (s, 0.5H), 8.99 (s, 1H), 8.90 (s, 1H), 8.53 (s, 1H), 8.21-8.11 (m, 2H), 8.02 (d, J=8.1 Hz, 1H), 7.69 (s, 1H), 7.45 (s, 1H), 7.21-7.08 (m, 5H), 6.99-6.87 (m, 2H), 6.56 (s, 1H), 6.48 (s, 1H), 4.11-3.96 (m, 2H), 3.48-3.35 (m, 2H), 3.30-3.19 (m, 2H), 2.31-2.20 (m, 3H), 2.08-1.94 (m, 3H), 1.82-1.72 (m, 4H), 1.48-1.39 (m, 3H), 1.38-1.26 (m, 7H). MS (ESI) m/e [M+1]$^+$ 813.1.

Using 2-(4-chlorophenyl)pyrrolidine in the reductive amination step, and then following the next similar procedures of Example D1a and D1b, compounds D14-1a and D14-1b were obtained correspondingly.

Example D14-1a: $^1$H NMR (400 MHz, DMSO-$d_6$) δ ppm: 12.14 (s, 1H), 11.74 (s, 1H), 8.70-8.49 (m, 2H), 8.11-7.49 (m, 1H), 7.90-7.78 (m, 1H), 7.69-7.57 (m, 1H), 7.56-7.37 (m, 3H), 7.28-7.01 (m, 4H), 6.96-6.84 (m, 1H), 6.74-6.58 (m, 1H), 6.52 (s, 1H), 6.47-6.37 (s, 1H), 3.89-3.79 (m, 2H), 3.72-3.62 (m, 1H), 3.28-3.17 (m, 3H), 3.11-2.86 (m, 4H), 2.46-2.29 (m, 1H), 2.15-1.92 (m, 3H), 1.92-1.79 (m, 2H), 1.73-1.52 (m, 5H), 1.49-1.28 (m, 7H). MS (ESI) m/e [M+1]$^+$ 813.1.

Example D14-1b: $^1$H NMR (400 MHz, DMSO-$d_6$) δ ppm: 12.16 (br, 1H), 11.65 (s, 1H), 8.48 (s, 2H), 7.95 (s, 1H), 7.82-7.23 (m, 8H), 7.09-6.86 (m, 2H), 6.58 (s, 1H), 6.36 (s, 1H), 3.90-3.78 (m, 2H), 3.27-3.17 (m, 4H), 3.09-2.87 (m, 3H), 2.41-2.28 (m, 2H), 2.09-1.92 (m, 3H), 1.91-1.63 (m, 4H), 1.63-1.53 (m, 3H), 1.45-1.36 (m, 2H), 1.34-1.23 (m, 4H). MS (ESI) m/e [M+1]+ 813.1.

Example D63a and Example D63b (cis- or trans-) 2-((1H-pyrrolo[2,3-b]pyridin-5-yl)oxy)-N-((3-nitro-4-(((tetrahydro-2H-pyran-4-yl)methyl)amino)phenyl)sulfonyl)-4-(4-(2-phenylpyrrolidin-1 yl)cyclohexyl)benzamide (trans- or cis-) 2-((1H-pyrrolo[2,3-b]pyridin-5-yl)oxy)-N-((3-nitro-4-(((tetrahydro-2H-pyran-4-yl)methyl)amino)phenyl)sulfonyl)-4-(4-(2-phenylpyrrolidin-1-yl)cyclohexyl)benzamide D63a

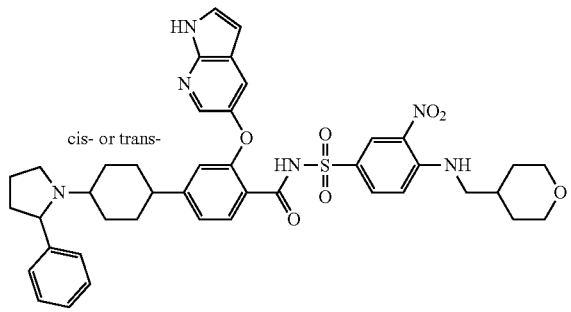

D63b

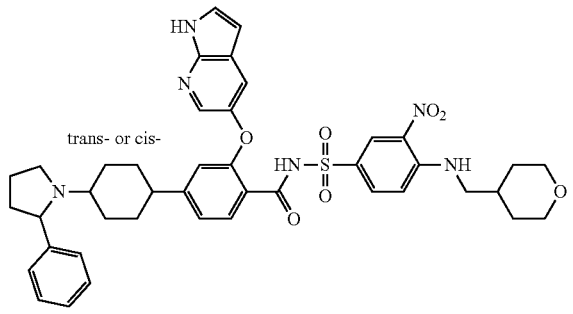

Using 2-phenylpyrrolidine in the reductive amination step, and then following the next similar procedures of Example D1a and D1b, compounds D 63a and D 63b were obtained correspondingly. Example D63a: ¹H NMR (400 MHz, DMSO-d₆) δ ppm: 12.17 (s, 1H), 11.80-11.55 (m, 1H), 8.65-8.35 (m, 2H), 8.05-1.90 (m, 1H), 7.85-7.65 (m, 1H), 7.60-7.30 (m, 5H), 7.25-6.80 (m, 5H), 6.74-6.26 (m, 2H), 4.65-4.50 (m, 1H), 3.84 (dd, J=11.1, 2.8 Hz, 2H), 3.30-3.20 (m, 5H), 2.45-2.25 (m, 3H), 2.18-1.93 (m, 3H), 1.80-1.50 (m, 9H), 1.48-1.10 (m, 5H). MS (ESI) m/e [M+1]+ 778.8. Example D63b: 4s NMR (400 MHz, DMSO-d₆) δ ppm: 12.17 (s, 1H), 11.64 (s, 1H), 8.60-8.30 (m, 2H), 7.95 (s, 1H), 7.80-7.70 (m, 1H), 7.65-7.10 (m, 8H), 6.98-6.85 (m, 2H), 6.58 (s, 1H), 6.36 (s, 1H), 4.70-4.50 (m, 1H), 3.83 (d, J=8.7 Hz, 2H), 3.30-3.20 (m, 5H), 2.45-2.20 (m, 3H), 2.15-1.92 (m, 5H), 1.90-1.80 (m, 2H), 1.78-1.65 (m, 3H), 1.59 (d, J=12.3 Hz, 2H), 1.48-1.35 (m, 3H), 1.33-1.13 (m, 2H). MS (ESI) m/e [M+1]+ 778.8.

Example D96: trans- or cis-2-((1H-pyrrolo[2,3-b]pyridin-5-yl)oxy)-N-((3-nitro-4-(((tetrahydro-2H-pyran-4-yl)methyl)amino)phenyl)sulfonyl)-4-(4-(2-(o-tolyl)pyrrolidin-1-yl)cyclohexyl)benzamide

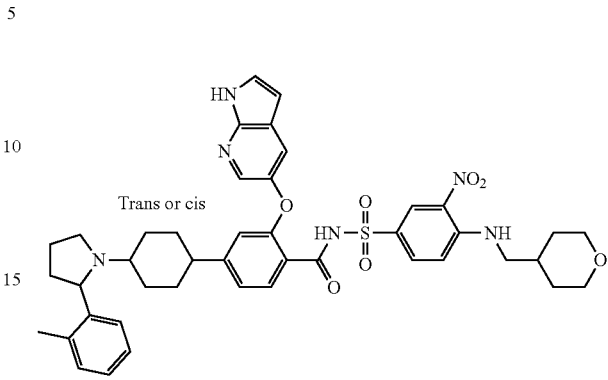

Using 2-(o-tolyl)pyrrolidine in the reductive amination step, and then following the next similar procedures of Example D1b, compound D 96 was obtained. ¹H NMR (400 MHz, DMSO-d₆) δ ppm: 12.21 (s, 1H), 11.66 (s, 1H), 8.60-8.35 (m, 2H), 8.20-8.05 (m, 1H), 7.95 (s, 1H), 7.85-7.65 (m, 1H), 7.62-7.35 (m, 3H), 7.30-6.80 (m, 5H), 6.60 (s, 1H), 6.35 (s, 1H), 4.80-4.60 (m, 1H), 3.83 (d, J=9.0 Hz, 2H), 3.75-3.55 (m, 1H), 3.30-3.20 (m, 5H), 2.50-2.22 (m, 5H), 2.20-1.95 (m, 2H), 1.90-1.75 (m, 3H), 1.70-1.45 (m, 6H), 1.40-1.12 (m, 6H). MS (ESI) m/e [M+1]+ 792.9.

Example D97a and Example B97b: (cis- or trans-) 2-((1H-pyrrolo[2,3-b]pyridin-5-yl)oxy)-4-(4-(2-(2-ethylphenyl)pyrrolidin-1-yl)cyclohexyl)-N-((3-nitro-4-(((tetrahydro-2H-pyran-4-yl)methyl)amino)phenyl)sulfonyl)benzamide (trans- or cis-) 2-((1H-pyrrolo[2,3-b]pyridin-5-yl)oxy)-4-(4-(2-(2-ethylphenyl)pyrrolidin-1-yl)cyclohexyl)-N-((3-nitro-4-(((tetrahydro-2H-pyran-4-yl)methyl)amino)phenyl)sulfonyl)benzamide

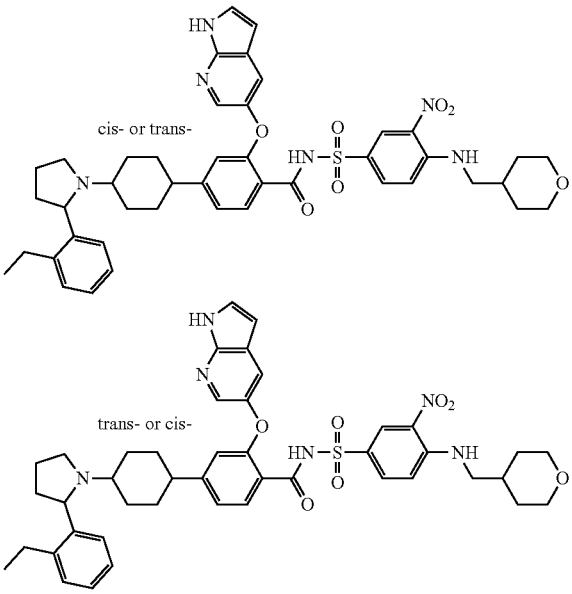

Using 2-(2-ethylphenyl)pyrrolidine in the reductive animation step, and then following the next similar procedures of Example D1a and D1b, compounds D 97-a and D 97-b were obtained correspondingly. Example D97-a: MS (ESI) m/e [M+1]+ 806.9. Example D97-h: NMR (400 MHz, DMSO-$d_6$) δ ppm: 11.58 (s, 1H), 8.50-8.27 (m, 2H), 7.91 (d, J=2.0 Hz, 1H), 7.74-7.51 (m, 2H), 7.47-7.31 (m, 3H), 7.27-7.02 (m, 3H), 6.89 (d, J=7.6 Hz, 2H), 6.58 (s, 1H), 6.32 (s, 1H), 4.05-3.90 (m, 1H) 3.87-3.79 (m, 2H), 3.29-3.06 (m, 5H), 2.68-2.60 (m, 2H), 2.37-2.24 (m, 2H), 1.89-1.55 (m, 10H), 1.40-1.20 (m, 8H), 1.13 (t, J=7.5 Hz, 3H). MS (ESI) m/e [M+1]+ 806.9.

Example D99: trans- or cis-2-((1H-pyrrolo[2,3-b]pyridin-5-yl)oxy)-4-(4-(3-(3-chlorophenyl)pyrrolidin-1-yl)cyclohexyl)-N-((3-nitro-4-(((tetrahydro-2H-pyran-4-yl)methyl)amino)phenyl)sulfonyl)benzamide

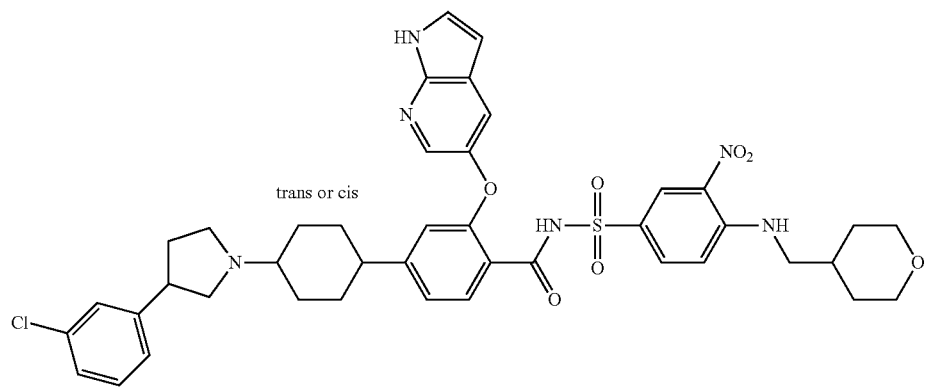 [SMILES: O=C(NS(=O)(=O)c1ccc(NCC2CCOCC2)c([N+](=O)[O-])c1)c1ccc(C2CCC(N3CCC(c4cccc(Cl)c4)C3)CC2)cc1Oc1cnc2[nH]ccc2c1]

Using 3-(3-chlorophenyl)pyrrolidine in the reductive animation step, and then following the next similar procedures of Example D1b, compound D 99 was obtained. $^1$H NMR (400 MHz, DMSO-$d_6$) δ ppm: 12.25 (s, 1H), 11.68 (s, 1H), 8.60-8.47 (m, 2H), 8.00 (s, 1H), 7.85-7.65 (m, 1H), 7.60-7.43 (m, 4H), 7.41-7.29 (m, 3H), 7.28-7.21 (m, 1H), 7.14-7.01 (m, 1H), 6.83-6.74 (m, 1H), 6.38 (m, 1H), 4.01-3.94 (m, 1H), 3.90-3.79 (m, 2H), 3.75-3.50 (m, 2H), 3.31-3.19 (m, 5H), 3.15-3.08 (m, 1H), 2.16-2.04 (m, 2H), 2.03-1.92 (m, 3H), 1.91-1.73 (m, 5H), 1.67-1.49 (m, 5H), 1.32-1.25 (m, 2H), MS (ESI, m/e) [M+1]+ 812.7.

Example D100: trans- or cis-2-((1H-pyrrolo[2,3-b]pyridin-5-yl)oxy)-N-((3-nitro-4-(((tetrahydro-2H-pyran-4-yl)methyl)amino)phenyl)sulfonyl)-4-(4-(2-(2-phenoxyphenyl)pyrrolidin-1-yl)cyclohexyl)benzamide

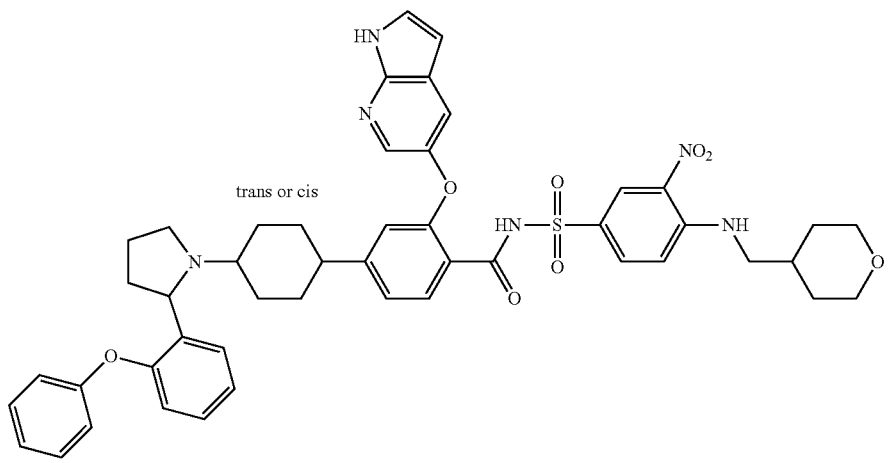 [SMILES: O=C(NS(=O)(=O)c1ccc(NCC2CCOCC2)c([N+](=O)[O-])c1)c1ccc(C2CCC(N3CCCC3c3ccccc3Oc3ccccc3)CC2)cc1Oc1cnc2[nH]ccc2c1]

Using 2-(2-phenoxyphenyl)pyrrolidine in the reductive amination step, and then following the next similar procedures of Example D1b, compound D 100 was obtained. $^1$H NMR (400 MHz, DMSO-d$_6$) δ ppm: 12.20 (s, 1H), 11.71 (s, 1H), 8.65-8.45 (m, 2H), 8.30-8.15 (m, 1H), 7.98 (s, 1H), 7.78 (d, J=7.6 Hz, 1H), 7.57-7.36 (m, 4H), 7.34-7.16 (m, 3H), 7.16-6.78 (m, 6H), 6.57 (s, 1H), 6.39 (s, 1H), 5.00-4.85 (m, 1H), 3.84 (d, J=8.6 Hz, 2H), 3.60-3.45 (m, 1H), 3.30-3.20 (m, 4H), 3.15-3.05 (m, 1H), 2.40-2.25 (m, 2H), 2.20-1.95 (m, 3H), 1.90-1.76 (m, 3H), 1.74-1.51 (m, 5H), 1.50-1.03 (m, 6H). MS (ESI, m/e) [M+1]$^+$ 871.8.

Example D101: trans- or cis-2-((1H-pyrrolo[2,3-b]pyridin-5-yl)oxy)-4-(4-(2-(2-cyclopropylstyryl)pyrrolidin-1-yl)cyclohexyl)-N-((3-nitro-4-(((tetrahydro-2H-pyran-4-yl)methyl)amino)phenyl)sulfonyl)benzamide

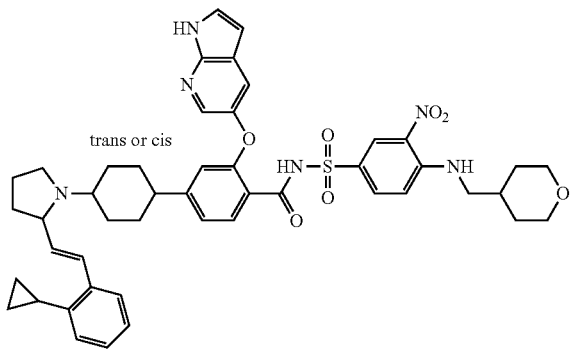 [SMILES: O=C(NS(=O)(=O)c1ccc(NCC2CCOCC2)c([N+](=O)[O-])c1)c1ccc(C2CCC(N3CCCC3/C=C/c3ccccc3C3CC3)CC2)cc1Oc1cnc2[nH]ccc2c1]

Using 2-(2-cyclopropylstyryl)pyrrolidine in the reductive amination step, and then following the next similar procedures of Example D1b, compound D101 was obtained. $^1$H NMR (400 MHz, DMSO-d$_6$) δ ppm: 11.57 (s, 1H), 9.49 (s, 1H), 8.60-8.30 (m, 2H), 7.92 (d, J=1.9 Hz, 1H), 7.69 (d, J=8.9 Hz, 1H), 7.60-7.30 (m, 5H), 7.25-7.05 (m, 2H), 7.01 (d, J=8.9 Hz, 1H), 6.95-6.85 (m, 2H), 6.60 (s, 1H), 6.32 (s, 1H), 6.13 (s, 1H), 4.50-4.20 (m, 1H), 3.83 (d, J=8.8 Hz, 2H), 3.30-3.20 (m, 6H), 3.10-2.80 (m, 1H), 2.29-1.71 (m, 10H), 1.68-1.14 (m, 8H), 1.10-0.75 (m, 3H), 0.68-0.45 (m, 2H). MS (ESI, m/e) [M+1]$^+$ 844.8.

Example D102: 2-((1H-pyrrolo[2,3-b]pyridin-5-yl)oxy)-N-((3-nitro-4-(((tetrahydro-2H-pyran-4-yl)methyl)amino)phenyl)sulfonyl)-4-(4-(2-styrylpyrrolidin-1-yl)cyclohexyl)benzamide

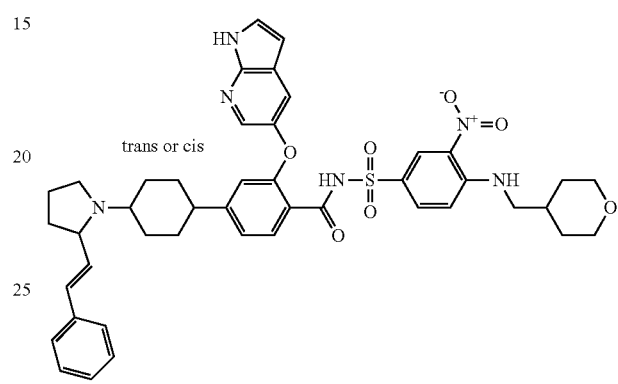

Using 2-styrylpyrrolidine in the reductive amination step, and then following the next similar procedures of Example D1b, compound D102 was obtained. MS (ESI, m/e) [M+1]$^+$ 806.2

Example D103: 2-((1H-pyrrolo[2,3-b]pyridin-5-yl)oxy)-4-(4-(2-(2-methoxyphenyl)pyrrolidin-1-yl)cyclohexyl)-N-((3-nitro-4-(((tetrahydro-2H-pyran-4-yl)methyl)amino)phenyl)sulfonyl)benzamide

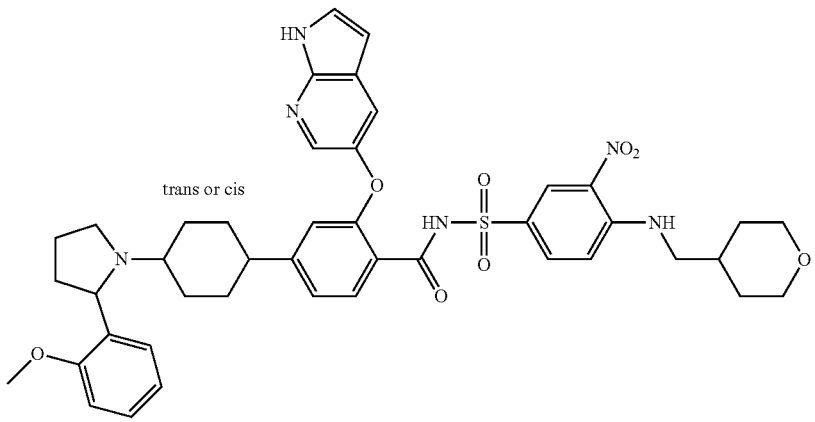 [SMILES: COc1ccccc1C1CCCN1C1CCC(c2ccc(C(=O)NS(=O)(=O)c3ccc(NCC4CCOCC4)c([N+](=O)[O-])c3)c(Oc3cnc4[nH]ccc4c3)c2)CC1]

Using 2-(2-methoxyphenyl)pyrrolidine in the reductive animation step, and then following the next similar procedures of Example D1b, compound D103 was obtained. ¹H NMR (400 MHz, DMSO-d$_6$) δ ppm: 12.08 (s, 1H), 11.71 (s, 1H), 8.02 (s, 1H), 7.87 (s, 1H), 7.72 (s, 1H), 7.52-7.45 (m, 3H), 7.28-7.074 (m, 4H), 6.95-6.89 (m, 1H), 6.70 (s, 2H), 6.40 (s, 1H), 5.98-5.79 (m, 1H), 4.33-4.19 (m, 1H), 3.82 (d, J=8.8 Hz, 2H), 3.22 (t, J=11.3 Hz, 2H), 3.08 (s, 2H), 2.98 (s, 2H), 2.18 (s, 3H), 2.02-1.97 (m, 4H), 1.80-1.71 (m, 4H), 1.56 (d, J=12.6 Hz, 2H), 1.4-7-1.33 (m, 2H), 1.23-1.15 (m, 5H). MS (ESI, m/e) [M+1]⁺ 809.2.

Example D104: 2-((1H-pyrrolo[2,3-b]pyridin-5-yl)oxy)-4-(4-(dibenzylamino)cyclohexyl)-N-((3-nitro-4-(((tetrahydro-2H-pyran-4-yl)methyl)amino)phenyl)sulfonyl)benzamide

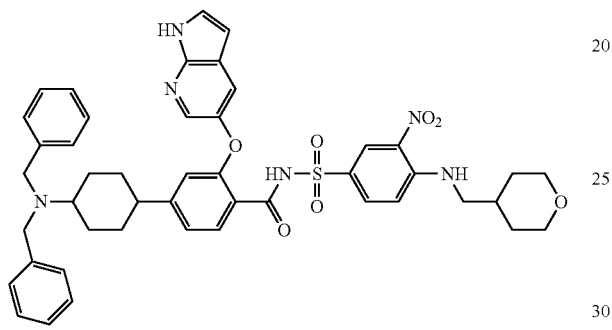

¹H NMR (DMSO-d$_6$) δ ppm: 12.16 (s, 1H), 11.70 (s, 1H), 8.64-8.48 (m, 2H), 8.07-7.93 (m, 1H), 7.87-7.74 (m, 1H), 7.63-7.40 (m, 2H), 7.44-7.38 (m, 1H), 7.37-7.07 (m, 11H), 7.03-6.94 (m, 1H), 6.71-6.53 (m, 1H), 6.43-6.30 (m, 1H), 3.90-3.80 (m, 2H), 3.66-3.42 (m, 4H), 3.25-3.17 (m, 5H), 2.44-2.30 (m, 1H), 1.99-1.73 (m, 4H), 1.65-1.55 (m, 3H), 1.55-1.40 (m, 3H), 1.33-1.24 (s, 2H). MS (ESI) m/e [M+1]⁺ 829.2.

Example D105: 2-((1H-pyrrolo[2,3-b]pyridin-5-yl)oxy)-4-(4-(benzhydrylamino)cyclohexyl)-N-((3-nitro-4-(((tetrahydro-2H-pyran-4-yl)methyl)amino)phenyl)sulfonyl)benzamide

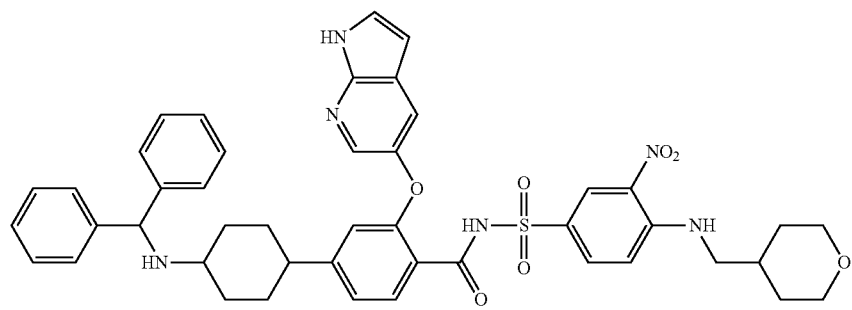 [SMILES: O=C(NS(=O)(=O)c1ccc(NCC2CCOCC2)c([N+](=O)[O-])c1)c1ccc(C2CCC(NC(c3ccccc3)c3ccccc3)CC2)cc1Oc1cnc2[nH]ccc2c1]

$^1$H NMR (DMSO-d$_6$) δ ppm: 12.17 (s, 1H), 11.59 (s, 1H), 9.20 (s, 1H), 8.62-8.27 (m, 2H), 7.95 (s, 1H), 7.81-7.57 (m, 3H), 7.52-7.01 (m, 12H), 6.78-6.63 (m, 1H), 6.34 (s, 1H), 5.75 (s, 0.5H), 4.83 (s, 0.5H), 3.92-3.7 (m, 2H), 3.25-3.17 (m, 4H), 3.15-2.90 (m, 2H), 2.07-1.94 (m, 2H), 1.94-1.67 (m, 5H), 1.64-1.53 (m, 3H), 1.41-1.35 (m, 1H), 1.30-1.24 (m, 3H). MS (ESI) m/e [M+1]$^+$ 814.8.

Example D106: (R)-2-((1H-pyrrolo[2,3-b]pyridin-5-yl)oxy)-4-(4-(methyl(1-phenylethyl)amino)cyclohexyl)-N-((3-nitro-4-(((tetrahydro-2H-pyran-4-yl)methyl)amino)phenyl)sulfonyl)benzamide

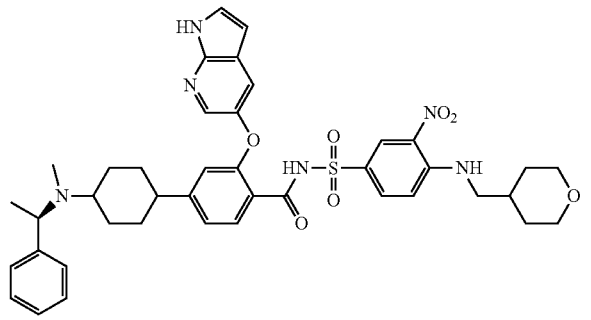 [SMILES: C[C@H](c1ccccc1)N(C)C1CCC(c2ccc(C(=O)NS(=O)(=O)c3ccc(NCC4CCOCC4)c([N+](=O)[O-])c3)c(Oc3cnc4[nH]ccc4c3)c2)CC1]

Using (R)—N-methyl-1-phenylethan-1-amine in the reductive amination step, and then following the next similar procedures of Example D1b, compound D106 was obtained. NMR (400 MHz, DMSO-d$_6$) δ ppm: 12.23 (s, 1H), 11.66 (s, 1H), 9.17-9.04 (m, 1H), 8.62-8.47 (m, 2H), 7.99 (s, 1H), 7.83-7.71 (m, 1H), 7.63-7.43 (m, 7H), 7.23-7.08 (m, 1H), 7.03-6.93 (m, 1H), 6.83-6.70 (m, 1H), 6.36 (m, 1H), 4.70 (m, 1H), 3.88-3.80 (m, 2H), 3.30-3.17 (m, 6H), 2.64-2.52 (m, 1H), 2.05-1.92 (m, 2H), 1.92-1.69 (m, 5H), 1.66-1.50 (m, 5H), 1.49-1.37 (m, 2H), 1.32-1.24 (m, 3H). MS (ESI, m/e) [M+1]$^+$ 766.8.

Example D107a and Example D107b: 2-((1H-pyrrolo[2,3-b]pyridin-5-yl)oxy)-4-(cis-4-(3-(2-(2-cyclopropylphenyl)pyrrolidin-1-yl)azetidin-1-yl)cyclohexyl)-N-((3-nitro-4-(((tetrahydro-2H-pyran-4-yl)methyl)amino)phenyl)sulfonyl)benzamide or 2-((1H-pyrrolo[2,3-b]pyridin-5-yl)oxy)-4-(trans-4-(3-(2-(2-cyclopropylphenyl)pyrrolidin-1-yl)azetidin-1-yl)cyclohexyl)-N-((3-nitro-4-(((tetrahydro-2H-pyran-4-yl)methyl)amino)phenyl)sulfonyl)benzamide

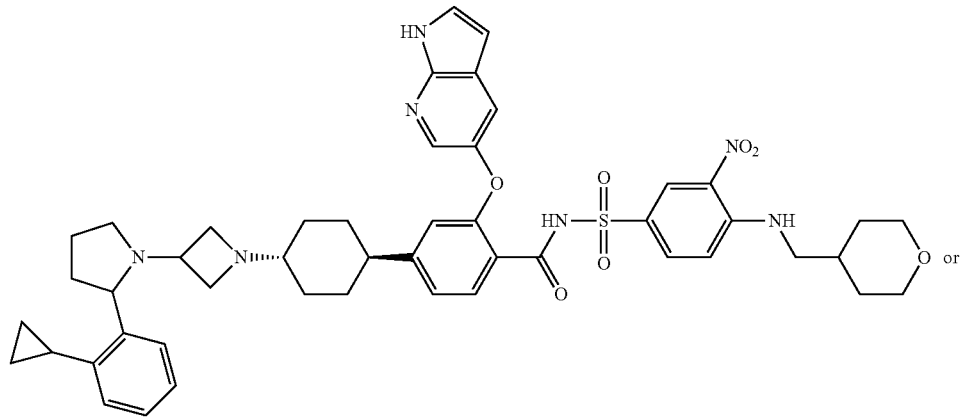

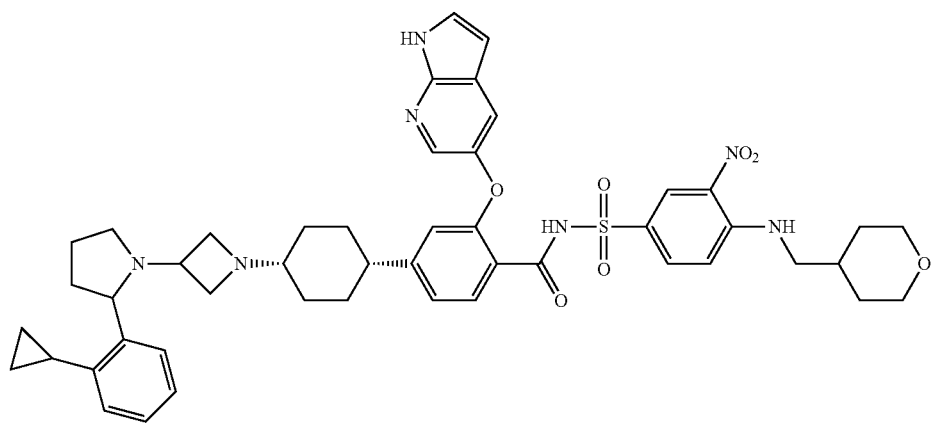

Step 1: 2-((1H-pyrrolo[2,3-b]pyridin-5-yl)oxy)-4-(4-oxocyclohexyl)benzoic acid To the solution of methyl 2-((1H-pyrrolo[2,3-b]pyridin-5-yl)oxy)-4-(4-oxocyclohexyl)benzoate (8.0 g, 22.0 mmol) in THF (100 mL) and H$_2$O (50 mL) was added NaOH (800 mg). The reaction mixture was stirred at ambient temperature for 20 hours. After removal of THF, the mixture was adjusted to pH ~4 with 1M HCl acid and then extracted with EA (50 mL×2). The combined organic phase was washed with brine, dried over anhydrous Na$_2$SO$_4$, concentrated in vacuum. The residue was slurried in DCM/MeOH (20 mL/2 mL), filtered, and the filtrate was concentrated to afford 2-(OH -pyrrolo[2,3-b]pyridin-5-yl)oxy)-4-(4-oxocyclohexyl)benzoic acid (2.2 g), MS (ESI, m/e) [M+1]$^+$ 351.1.

Step 2: 2-((1H-pyrrolo[2,3-b]pyridin-5-yl)oxy)-N-((3-nitro-4-(((tetrahydro-2H-pyran-4-yl)methyl)amino)phenyl)sulfonyl)-4-(4-oxocyclohexyl)benzamide A mixture of 2-((1H-pyrrolo[2,3-b]pyridin-5-yl)oxy)-4-(4-oxocyclohexyl)benzoic acid (2.0 g, 5.71 mmol), 3-nitro-4-(((tetrahydro-2H-pyran-4-yl)methyl)amino)benzene sulfonamide (1.8 g, 5.71 mmol), EDCl (1.64 g, 8.57 mmol), DMAP (1.05 g, 8.57 mmol) and TFA (1.15 g, 16.42 mmol) in DCM (20 mL) was stirred at ambient temperature for 20 hours. The reaction mixture was concentrated in vacuum, then purified by chromatography column on silica (eluent: DCM/MeOH=100/1 to 50/1) to afford 2-((1H-pyrrolo[2,3-b]pyridin-5-yl)oxy)-N-((3-nitro-4-(((tetrahydro-2H-pyran-4-yl)methyl)amino)phenyl)sulfonyl)-4-(4-oxocyclohexyl)benzamide (1.5 g). MS (ESI) m/e [M+1]$^+$ 648.1.

Step 3:

To a solution of 2-((1H-pyrrolo[2,3-b]pyridin-5-yl)oxy)-N-((3-nitro-4-(((tetrahydro-2H-pyran-4-yl)methyl)amino)phenyl)sulfonyl)-4(4-oxocyclohexyl)benzamide (400 mg, 0.7 mmol) and 1-(azetidin-3-yl)-2-(2-cyclopropylphenyl)pyrrolidine (200 mg, 0.9 mmol) in DCM (40 mL) was added NaBH(OAc)$_3$ (600 mg, 3 mmol). The mixture was stirred at room temperature for 14 hours. Then aq, NH$_4$Cl (30 mL) was added to the reaction mixture. The organic phase was washed with saturated aq. NaCl (10 mL), dried over anhydrous Na$_2$SO$_4$, concentrated. The crude product was then purified by pre-TLC to give 20 mg of 2-((1H-pyrrolo[2,3-b]pyridin-5-yl)oxy)-4-(cis-4-(3-(2-(2-cyclopropylphenyl)pyrrolidin-1-yl)azetidin-1-yl)cyclohexyl)-N-((3-nitro-4-(((tetrahydro-2H-pyran-4-yl)methyl)amino)phenyl)sulfonyl)benzamide (the faster isomer) as example D107a. MS (ESI, m/e) [M+1]$^+$ 874.0; and 10 mg of 2-((1H-pyrrolo[2,3-b]pyridin-5-yl)oxy)-4-(cis-4-(3-(2-(2-cyclopropylphenyl)pyrrolidin-1-yl)azetidin-1-yl)cyclohexyl)-N-((3-nitro-4-(((tetrahydro-2H-pyran-4-yl)methyl)amino)phenyl)sulfonyl)benzamide (the slower isomer) as example D107b. $^1$H NMR (DMSO-d$_6$) δ ppm: 12.19 (s, 1H), 11.74 (s, 1H), 8.60-8.56 (m, 2H), 8.02 (s, 1H), 7.83 (d, J=8.7 Hz, 1H), 7.61 (s, 1H), 7.54 (s, 1H), 7.48-7.40 (m, 2H), 7.19-7.12 (m, 3H), 6.99-6.85 (m, 2H), 6.57 (s, 1H), 6.42 (s, 1H), 4.01 (s, 3H), 3.88-3.82 (m, 2H), 3.69-3.64 (m, 2H), 3.49 (s, 1H), 3.30-3.25 (m, 4H), 3.16 (s, 1H), 2.99 (s, 2H), 2.41 (s, 1H), 2.24 (s, 1H), 2.03 (s, 1H), 1.85-1.65 (m, 8H), 1.65-1.56 (m, 3H), 1.25-1.23 (m, 2H), 1.20-1.08 (m, 3H), 0.90-0.85 (m, 2H), 0.65 (s, 1H), 0.57 (s, 1H). MS (ESI) m/e [M+1]$^+$ 873.9.

Example E1: 2-((1H-pyrrolo[2,3-b]pyridin-5-yl)oxy)-N-((3-nitro-4-(((tetrahydro-2H-pyran-4-yl)methyl)amino)phenyl)sulfonyl)-4-(6-(2-phenylpyrrolidin-1-yl)pyridin-3-yl)benzamide

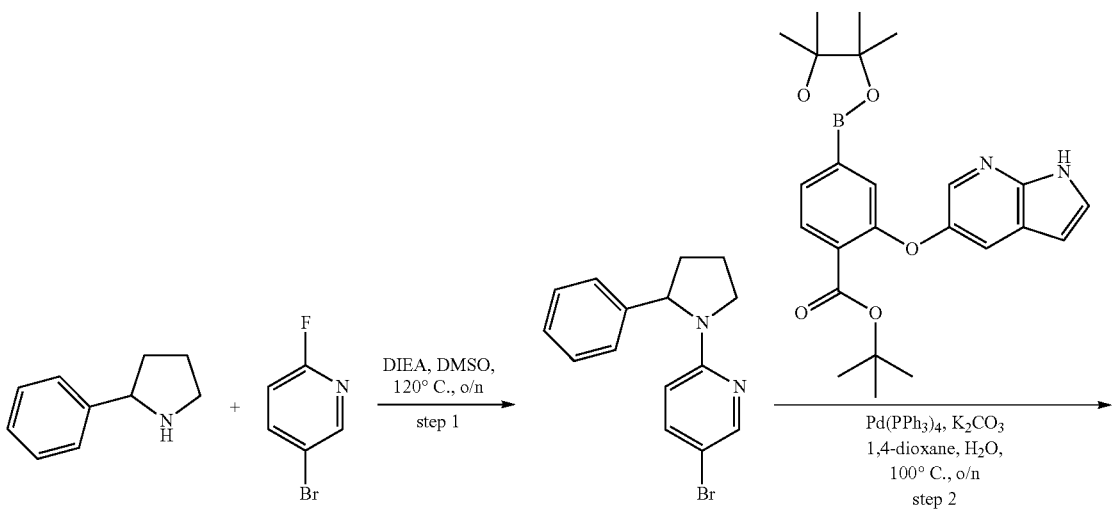

-continued
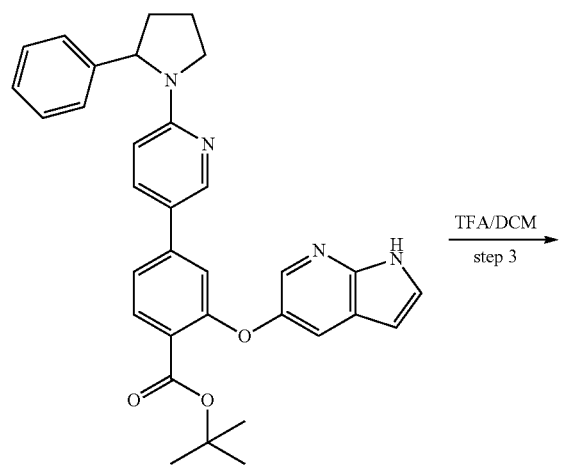
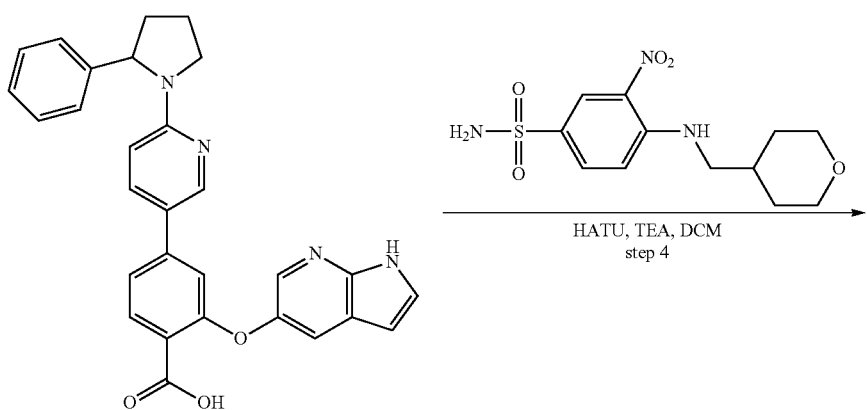
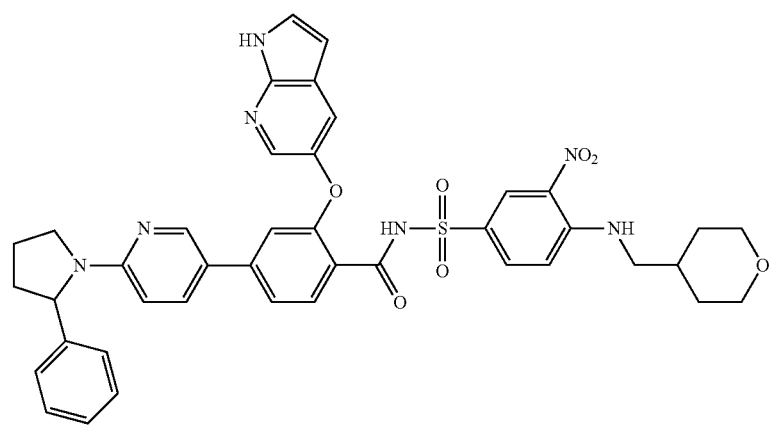
E1

Step 1: 5-bromo-2-(2-phenylpyrrolidin-1-yl)pyridine

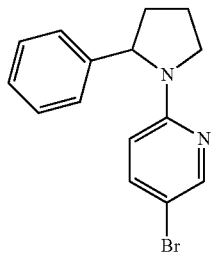 [SMILES: Brc1ccc(N2CCCC2c2ccccc2)nc1]

A mixture of 2-phenylpyrrolidine (441 mg, 3 mmol), 5-bromo-2-fluoropyridine (633 mg, 3.6 mmol) and N, N-Diisopropylethylamine (2 g, 15 mmol) in DMSO (50 mL) was heated to 120° C. with stirring overnight. Then the reaction was cooled to room temperature, the mixture was washed with water, brine and dried over anhydrous $Na_2SO_4$. The organic layers were concentrated and purified by column chromatography with 5%~20% EA/PE to give 5-bromo-2-(2-phenylpyrrolidin-1-yl)pyridine (400 mg, 44.4%) as a colorless oil. $^1$H NMR (400 MHz, DMSO-$d_6$) δ ppm: 8.07 (d, J=2.4 Hz, 1H), 7.54 (dd, J=9.0, 2.4 Hz, 1H), 7.29 (t, J=7.6 Hz, 2H), 7.21 (d, J=7.6 Hz, 1H), 7.17 (t, J=6.2 Hz, 2H), 6.24 (d, J=7.3 Hz, 1H), 5.00 (d, J=7.3 Hz, 1H), 3.83-3.64 (m, 1H), 3.53 (dd, J=17.5, 8.6 Hz, 1H), 2.38 (dd, J=13.1, 5.4 Hz, 1H), 2.01-1.77 (m, 3H). MS (ESI, m/e) [M+1]$^+$ 303.0, 305.0

Step 2: tert-butyl 2-((1H-pyrrolo[2,3-b]pyridin-5-yl)oxy)-4-(6-(2-phenylpyrrolidin-1-yl)pyridin-3-yl)benzoate

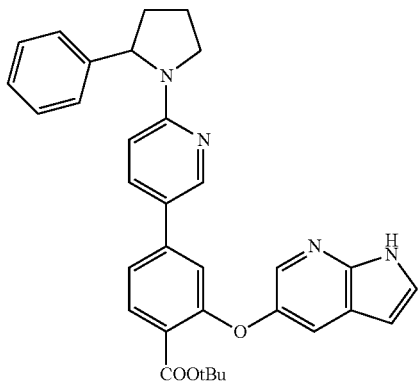

Under nitrogen atmosphere, a mixture of 5-bromo-2-(2-phenylpyrrolidin-1-yl)pyridine (260 mg, 0.86 mmol), tert-butyl 2-((1H-pyrrolo[2,3-b]pyridin-5-yl)oxy)-4-(4,4,5,5-tetramethyl-1,3,2-dioxaborolan-2-yl)benzoate (375 mg, 0.86 mmol), Pd(PPh$_3$)$_4$ (96 mg, 0.086 mmol), and Cs$_2$CO$_3$ (555 mg, 1.72 mmol) in 1,4-dioxane/H$_2$O (50 mL/10 mL) was heated to 90° C. with stirring overnight. Then the reaction was cooled to room temperature, the mixture was washed with water, brine and dried over anhydrous Na$_2$SO$_4$. The organic layers were concentrated and purified by column chromatography with 5%~20% EA/PE to give tert-butyl 2-((1H-pyrrolo[2,3-b]pyridin-5-yl)oxy)-4-(6-(2-phenylpyrrolidin-1-yl)pyridin-3-yl)benzoate product (300 mg, 65.6%). MS(ESI, m/e) [M+1]$^+$ 533.1.

Step 3: 2-((1H-pyrrolo[2,3-b]pyridin-5-yl)oxy)-4-(6-(2-phenylpyrrolidin-1-yl)pyridin-3-yl)benzoic acid

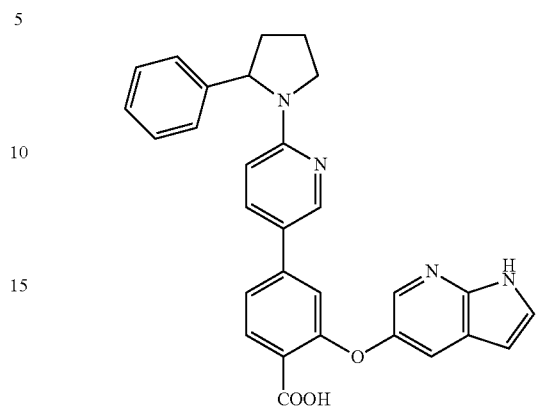

To a solution of tert-butyl 2-((1H-pyrrolo[2,3-b]pyridin-5-yl)oxy)-4-(6-(2-phenylpyrrolidin-1-yl)pyridin-3-yl)benzoate (266 mg, 0.5 mmol) in dichloromethane (25 mL) was added trifluoroacetic acid (5 mL). The reaction was stirred overnight at r.t., then the excess solvent was removed under reduced pressure. The residue was purified by column chromatography on silica gel to give 2-((1H-pyrrolo[2,3-b]pyridin-5-yl)oxy)-4-(6-(2-phenylpyrrolidin-1-yl)pyridin-3-yl)benzoic acid (200 mg, 84%) as a white foam. MS (ESI, m/e) [M+1]$^+$ 477.1.

Step 4: 2-((1H-pyrrolo[2,3-b]pyridin-5-yl)oxy)-N-((3-nitro-4-((((tetrahydro-2H-pyran-4-yl)methyl)amino)phenyl)sulfonyl)-4-(6-(2-phenylpyrrolidin-1-yl)pyridin-3-yl)benzamide

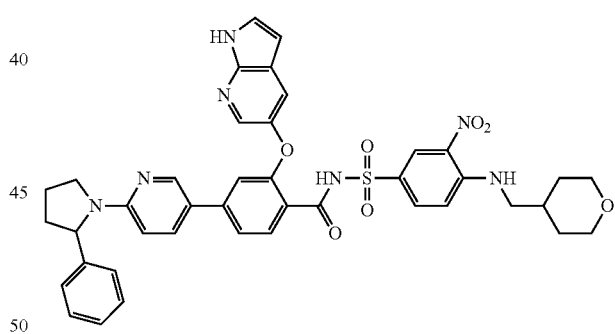

To a solution of 2-((1H-pyrrolo[2,3-b]pyridin-5-yl)oxy)-4-(6-(2-phenylpyrrolidin-1-yl)pyridin-3-yl)benzoic acid (150 mg, 0.32 mmol) in dichloromethane (25 mL) were added o-(7-azabenzotriazol-1-yl)-N,N,N',N'-tetramethyluronium hexafluorophosphate (182 mg, 0.48 mmol), triethylamine (1 mL) and 4-Dimethylaminopyridine (40 mg, 0.32 mmol). The mixture was stirred for 0.5 h at r.t. Then 3-nitro-4-(((tetrahydro-2H-pyran-4-yl)methyl)amino)benzenesulfonamide (199 mg, 0.64 mmol) was added. The reaction was continually stirred overnight at r.t. Afterwards, the mixture was washed with water (15 mL) and the organic layers were dried over anhydrous Na$_2$SO$_4$ and concentrated. The residue was further purified by prep-HPLC to give the product (40 mg, 16.2% ). $^1$H NMR (400 MHz, DMSO-d$_6$) δ ppm: 12.25 (s, 1H), 11.69 (s, 1H), 8.61 (s, 1H), 8.56 (d, J=2.0 Hz, 1H), 8.25 (s, 1H), 8.03 (d, J=2.0 Hz, 1H), 7.82 (d, J=7.3 Hz, 1H), 7.68-7.46 (m, 4H), 7.38 (d, J=8.2 Hz, 1H), 7.27 (t, J=7.3 Hz, 2H), 7.22-7.07 (m, 4H), 6.97 (s, 1H), 6.38 (s, 1H), 6.30 (d, J=8.2 Hz, 1H), 5.05 (d, J=7.1 Hz, 1H), 3.83 (t, J=10.0 Hz, 3H), 3.57 (d, J=9.3 Hz, 1H), 3.31-3.18 (m, 4H), 2.42-2.27 (m, 1H), 1.88-1.78 (m, 4H), 1.60 (d, J=12.2 Hz, 2H), 1.31-1.14 (m, 2H). MS (ESI, m/e) [M+1]⁺ 774.1
Example E2 2-((1H-pyrrolo[2,3-b]pyridin-5-yl)oxy)-N-((3-nitro-4-(((tetrahydro-2H-pyran-4-yl)methyl)amino)phenyl)sulfonyl)-4-(4-(2-phenylpyrrolidin-1-yl)piperidin-1-yl)benzamide
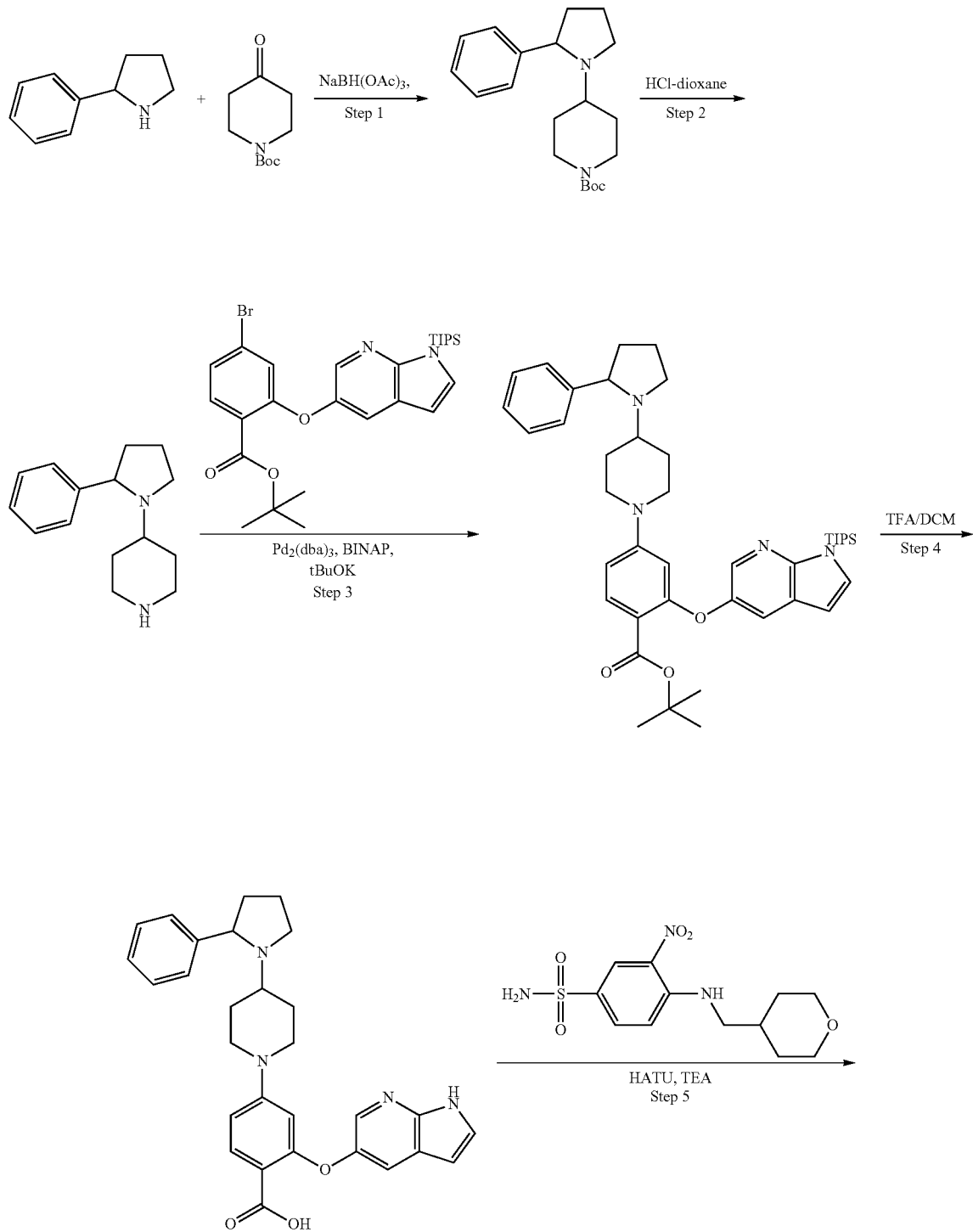

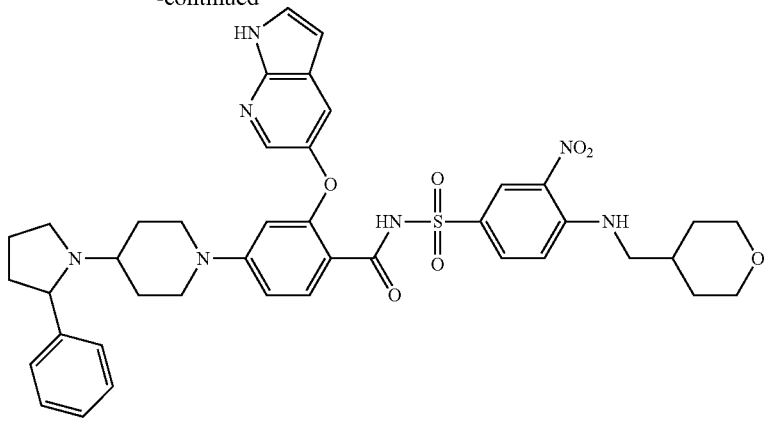

E2

Step 1: tert-butyl 4-(2-phenylpyrrolidin-1-yl)piperidine-1-carboxylate

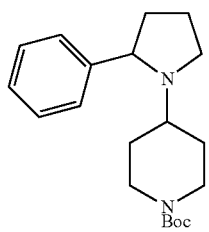 [SMILES: CC(C)(C)OC(=O)N1CCC(N2CCCC2c2ccccc2)CC1]

To a solution of 2-phenylpyrrolidine (1.46 g, 10 mmol) in dichloromethane (100 mL) was added tert-butyl 4-oxopiperidine-1-carboxylate (1.99 g, 10 mmol) at 0° C. The mixture was stirred for 1 h and sodium triacetoxyborohydride (3.8 g, 15 mmol) was added in portions. Then the mixture was warmed to room temperature and stirred overnight. The mixture was washed with water, brine and dried over anhydrous $Na_2SO_4$. Solvent was removed in vacuum to give tert-butyl 4-(2-phenylpyrrolidin-1-yl)piperidine-1-carboxylate (3.30 g, 100%) as a white solid, which was used directly without further purification, MS (ESI, m/e) [M+1]$^+$ 331.2.

Step 2: 4-(2-phenylpyrrolidin-1-yl)piperidine

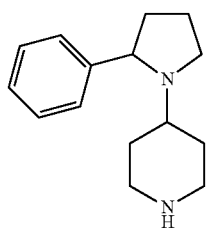 [SMILES: c1ccc(C2CCCN2C2CCNCC2)cc1]

A mixture of tert-butyl 4-(2-phenylpyrrolidin-1-yl)piperidine-1-carboxylate (3.3 g, 10 mmol) and HCl in 1,4-dioxane (4 N, 25 mL) was stirred for 3 h at room temperature. Solvent was removed under reduced pressure and the residue was basified by sat. aq. NaHCO$_3$ (50 mL) until pH >7. Then the mixture was extracted with dichloromethane (25 mL×3), the combined organic layers were concentrated to give 4-(2-phenylpyrrolidin-1-yl)piperidine (1 g, 43.4%) as a colorless oil. $^1$H NMR (400 MHz, CDCl$_3$) δ ppm: 7.37-7.24 (m, 4H), 7.20 (t, J=7.0 Hz, 1H), 5.90 (s, 1H), 3.72 (dd, J=8.2, 6.4 Hz, 1H), 3.26 (d, J=12.4 Hz, 1H), 3.19-3.02 (m, 2H), 2.71-2.48 (m, 4H), 2.15 (dq, J=12.4, 8.1 Hz, 1H), 2.00-1.82 (m, 2H), 1.82-1.56 (m, 5H). MS (ESI, m/e) [M+1]$^+$ 231.1.

Step 3: tert-butyl 2-(1-(triisopropylsilyl)-1H-pyrrolo[2,3-b]pyridin-5-yloxy)-4-(4-(2-phenylpyrrolidin-1-yl)piperidin-1-yl)benzoate

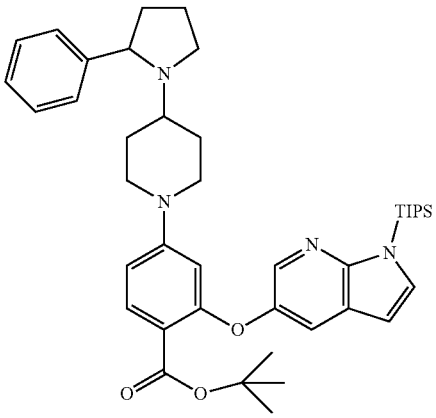

To a degassed mixture of 4-(2-phenylpyrrolidin-1-yl)piperidine (230 mg, 1 mmol), tert-butyl 2-(1-(triisopropylsilyl)-1H-pyrrolo[2,3-b]pyridin-5-yloxy)-4-bromobenzoate (643 mg, 1.1 mmol), BINAP (125 mg, 0.2 mmol) and t-BuOK (224 mg, 2 mmol) in toluene (50 mL) was added Pd$_2$(dba)$_3$ (92 mg, 0.1 mmol). Nitrogen was bubbled through the mixture for 5 min and then heated to 90° C. with stirring overnight. Then the reaction was cooled to room temperature, the mixture was washed with water, brine and dried over anhydrous Na$_2$SO$_4$. The organic layers were concentrated and purified by column chromatography with 5%~20% EA/PE to give tert-butyl 2-(1-(triisopropylsilyl)-1H-pyrrolo[2,3-b]pyridin-5-yloxy)-4-(4-(2-phenylpyrrolidin-1-yl)piperidin-1-yl)benzoate (400 mg, 57.6%). $^1$H NMR (400 MHz, DMSO-d$_6$) δ ppm: 7.94 (s, 1H), 7.65 (d, J=8.9

Hz, 1H), 7.48-7.39 (m, 1H), 7.33 (d, J=13 Hz, 2H). 7.26 (t, J=7.3 Hz, 2H), 7.18 (s, 2H), 6.78 (d, J=8.8 Hz, 1H), 6.50 (s, 2H), 3.88-3.64 (m, 3H), 3.31 (d, J=9.5 Hz, 1H), 3.07 (s, 1H), 2.64 (d, J=11.3 Hz, 2H), 2.17-2.03 (m, 1H), 1.90-1.63 (m, 6H), 1.61-1.26 (m, 4H), 1.17 (s, 9H), 1.06 (s, 9H), 1.03 (s, 9H). MS (ESI, m/e) [M+1]$^+$ 695.3.

Step 4: 2-((1H-pyrrolo[2,3-b]pyridin-5-yl)oxy)-4-(4-(2-phenylpyrrolidin-1-yl)piperidin-1-yl)benzoic acid

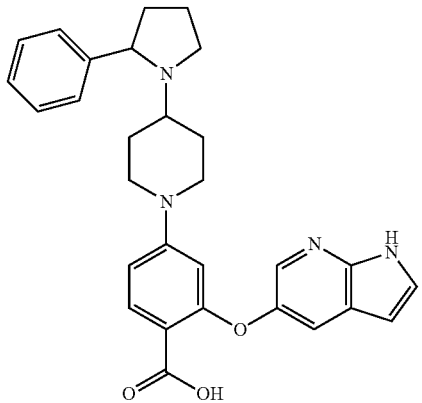 [SMILES: O=C(O)c1ccc(N2CCC(N3CCCC3c3ccccc3)CC2)cc1Oc1cnc2[nH]ccc2c1]

To a solution of tert-butyl 2-(1-(triisopropylsilyl)-1H-pyrrolo[2,3-b]pyridin-5-yloxy)-4-(4-(2-phenylpyrrolidin-1-yl)piperidin-1-yl)benzoate (347 mg, 0.5 mmol) in dichloromethane (25 mL) was added trifluoroacetic acid (5 mL). The reaction was stirred overnight at r.t. then the excess solvent was removed under reduced pressure. The residue was purified by column chromatography on silica gel to give 2-((1H-pyrrolo[2,3-b]pyridin-5-yl)oxy)-4-(4-(2-phenylpyrrolidin-1-yl)piperidin-1-yl)benzoic acid (200 mg, 83%). MS (ESI, m/e) [M+1]$^+$483.1.

Step 5: 2-((1H-pyrrolo[2,3-b]pyridin-5-yl)oxy)-N-((3-nitro-4-(((tetrahydro-2H-pyran-4-yl)methyl)amino)phenyl)sulfonyl)-4-(4-(2-phenylpyrrolidin-1-yl)piperidin-1-yl)benzamide

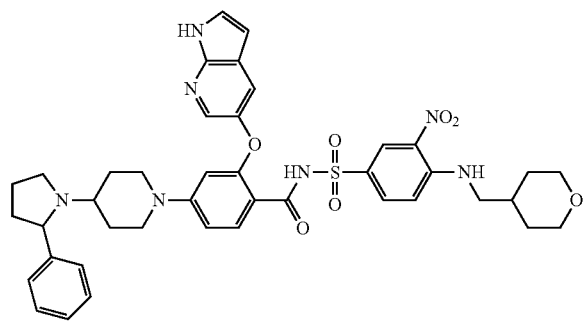 [SMILES: O=C(NS(=O)(=O)c1ccc(NCC2CCOCC2)c([N+](=O)[O-])c1)c1ccc(N2CCC(N3CCCC3c3ccccc3)CC2)cc1Oc1cnc2[nH]ccc2c1]

To a solution of 2-((1H-pyrrolo[2,3-b]pyridin-5-yl)oxy)-4-(4-(2-phenylpyrrolidin-1-yl)piperidin-1-yl)benzoic acid (145 mg, 0.3 mmol) in dichloromethane (25 mL) were added o-(7-azabenzotriazol-1-yl)-N,N,N',N'-tetramethyluronium hexafluorophosphate (171 mg, 0.45 mmol), triethylamine (1 mL) and 4-dimethylaminopyridine (36 mg, 0.3 mmol). The mixture was stirred for 0.5 h at r.t. Then 3-nitro-4-(((tetrahydro-2H-pyran-4-yl)methyl)amino)benzenesulfonamide (189 mg, 0.6 mmol) was added. The reaction was continually stirred overnight at r.t. Afterwards, the mixture was washed with water (10 mL) and the organic layers were dried over anhydrous Na$_2$SO$_4$ and concentrated. The residue was further purified by prep-HPLC to give the desired product (50 mg, 21.5%). $^1$H NMR (400 MHz, DMSO-d$_6$) δ ppm: 11.68 (m, 2H), 8.58 (d, J=5.6 Hz, 1H), 8.54 (d, J=2.4 Hz, 1H), 8.02 (d, J=2.4 Hz, 1H), 7.77 (d, J=9.2 Hz, 1H), 7.60-7.40 (m, 5H), 7.33-7.25 (m, 3H), 7.07 (d, J=9.2 Hz, 1H), 6.68 (d, J=7.8 Hz, 1H), 6.37 (d, J=1.5 Hz, 1H), 6.20 (s, 1H), 3.93-3.77 (m, 2H), 3.64 (s, 2H), 3.31-3.20 (m, 6H), 2.59 (s, 3H), 2.28-2.22 (m, 1H), 1.88 (m, 5H), 1.61 (d, J=12.1 Hz, 3H), 1.38 (s, 2H), 1.32-1.16 (m, 3H). MS (ESI, m/e) [M+1]$^+$ 780.2.

Example E3: 2-((1H-pyrrolo[2,3-b]pyridin-5-yl)oxy)-4-(4-(2-(2-chlorophenyl)pyrrolidin-1-yl)piperidin-1-yl)-N-((3-nitro-4-(((tetrahydro-2H-pyran-4-yl)methyl)amino)phenyl)sulfonyl)benzamide

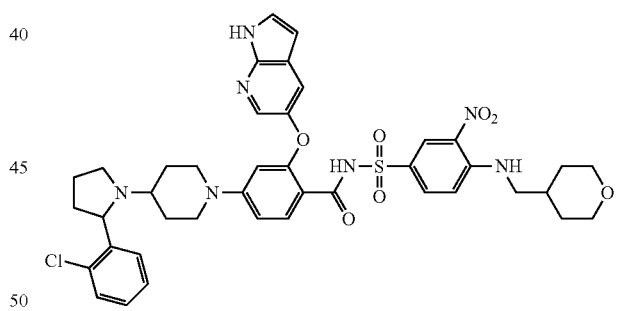

The desired compound was synthesized starting from 2-(2-chlorophenyl)pyrrolidine and tert-butyl 4-oxopiperidine-1-carboxylate following the next procedures similar to those in Example E2. $^1$H NMR (400 MHz, DMSO-d$_6$) δ ppm: 11.69 (s, 1H), 11.44 (s, 1H), 8.62 (s, 1H), 8.56 (s, 1H), 8.03 (d, J=2.4 Hz, 1H), 7.79 (d, J=9.6 Hz, 1H), 7.63 (s, 1H), 7.51-7.48 (m, 3H), 7.33 (s, 1H), 7.27 (s, 1H), 7.18 (s, 1H), 7.11 (d, J=8.6 Hz, 1H), 6.67 (d, J=7.8 Hz, 1H), 6.38 (s, 1H), 6.18 (s, 1H), 4.15-4.11 (m, 1H), 3.84-3.75 (m, 2H), 3.65-3.60 (m, 1H), 3.55-3.50 (m, 1H), 3.30-3.25 (m, 2H), 3.25-3.20 (m, 2H), 3.14-3.10 (m, 2H), 2.74-2.57 (m, 3H), 2.20 (br, 1H), 1.89-1.87 (m, 1H), 1.69-1.65 (m, 3H), 1.47-1.41 (m, 3H), 1.29-1.12 (m, 5H). (ESI, m/e) [M+1]$^+$ 814.1.

Example E4: 2-((1H-pyrrolo[2,3-b]pyridin-5-yl)oxy)-4-(4-(2-(3-chlorophenyl)pyrrolidin-1-yl)piperidin-1-yl)-N-((3-nitro-4-(((tetrahydro-2H-pyran-4-yl)methyl)amino)phenyl)sulfonyl)benzamide

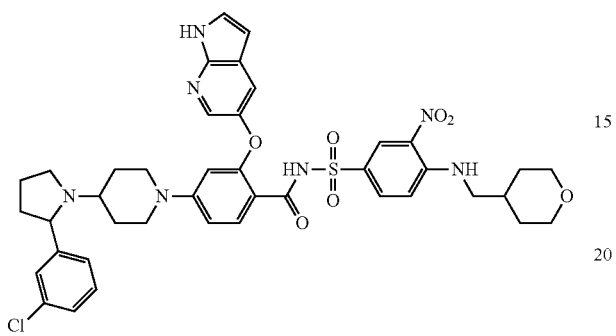

The desired compound was synthesized starting from 2-(3-chlorophenyl)pyrrolidine and tert-butyl 4-oxopiperidine-1-carboxylate following the next procedures similar to those in Example E2. $^1$H NMR (400 MHz, DMSO-d$_6$) δ ppm: 11.66 (s, 1H), 11.41 (s, 1H), 8.57 (s, 1H), 8.53 (s, 1H), 8.01 (s, 1H), 7.76 (d, J=8.5 Hz, 1H), 7.49 (d, J=8.4 Hz, 3H), 7.37 (s, 1H), 7.29-7.23 (m, 3H), 7.07 (s, 1H), 6.66 (d, J=8.3 Hz, 1H), 6.37 (s, 1H), 6.18 (s, 1H), 3.85 (d, J=8.4 Hz, 3H), 3.61-3.54 (m, 2H), 3.27-3.07 (m, 4H), 3.07 (s, 1H), 2.67-2.55 (m, 3H), 2.12 (br, 1H), 1.88 (br, 1H), 1.81-1.41 (m, 7H), 1.41-1.13 (m, 5H). MS (ESI, m/e) [M+1]$^+$ 814.1.

Example E12: 2-((1H-pyrrolo[2,3-b]pyridin-5-yl)oxy)-4-(4-(2-(2-cyclopropylphenyl)pyrrolidin-1-yl)piperidin-1-yl)-N-((3-nitro-4-(((tetrahydro-2H-pyran-4-yl)methyl)amino)phenyl)sulfonyl)benzamide

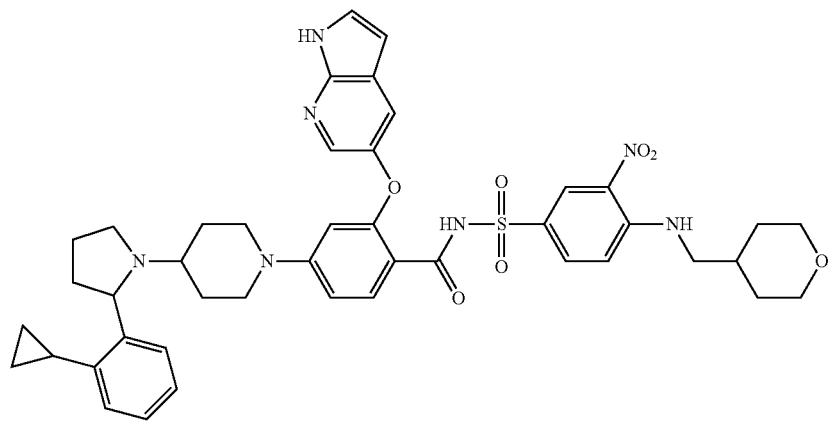 [SMILES: O=C(NS(=O)(=O)c1ccc(NCC2CCOCC2)c([N+](=O)[O-])c1)c1ccc(N2CCC(N3CCCC3c3ccccc3C3CC3)CC2)cc1Oc1cnc2[nH]ccc2c1]

The desired compound was synthesized starting from 2-(2-cyclopropylphenyl)pyrolidine and tert-butyl 4-oxopiperidine-1-carboxylate following the next procedures similar to those in Example E2. $^1$H NMR (400 MHz, DMSO-$d_6$) δ 11.67 (s, 1H), 11.43 (s, 1H), 8.65-8.45 (m, 2H), 8.02 (s, 1H), 7.5-7.70 (m, 1H), 7.60-7.40 (m, 4H), 7.20-6.98 (m, 3H), 6.95-7.85 (m, 1H), 6.66 (d, J=8.3 Hz, 1H), 6.37 (s, 1H), 6.18 (s, 1H), 4.40-4.20 (m, 1H), 3.85 (d, J=8.4 Hz, 2H), 3.76-3.50 (m, 2H), 3.31-3.19 (m, 4H), 2.70-2.60 (m, 2H), 2.30-2.15 (m, 1H), 2.05-1.80 (m, 3H), 1.81-1.57 (m, 5H), 1.50-1.35 (m, 3H), 1.32-1.11 (m, 4H), 0.95-0.80 (m, 3H), 0.70-0.60 (m, 1H), 0.55-0.45 (m, 1H). MS (ESI, m/e) [M+1]$^+$ 819.9.

Example E13: 2-((1H-pyrrolo[2,3-b]pyridin-5-yl)oxy)-4-(5-(2-(2-cyclopropylphenyl)pyrrolidin-1-yl)pyridin-2-yl)-N-((3-nitro-4-(((tetrahydro-2H-pyran-4-yl)methyl)amino)phenyl)sulfonyl)benzamide

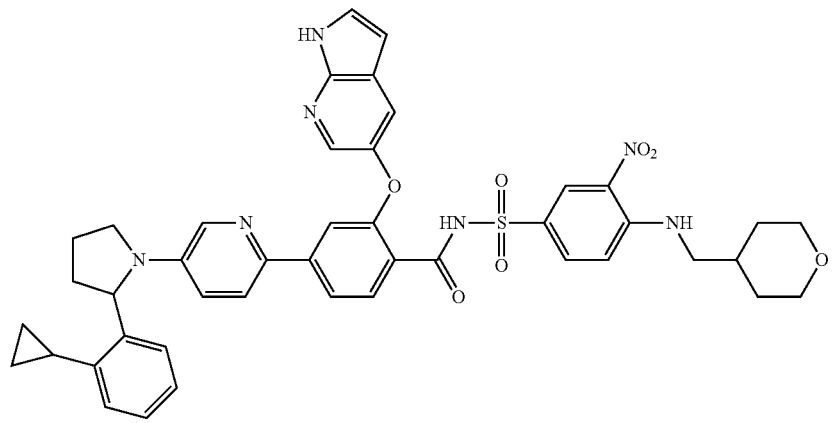 [SMILES: O=C(NS(=O)(=O)c1ccc(NCC2CCOCC2)c([N+](=O)[O-])c1)c1ccc(-c2ccc(N3CCCC3c3ccccc3C3CC3)cn2)cc1Oc1cnc2[nH]ccc2c1]

The desired compound was synthesized from 2-bromo-5-(2-(2-cyclopropylphenyl)pyrrolidin-1-yl)pyridine following the procedures similar to those in Example A1. $^1$H NMR (400 MHz, DMSO-$d_6$) δ ppm: 12.20 (s, 1H), 11.75 (s, 1H), 8.63-8.58 (m, 2H), 8.06 (s, 1H), 7.86 (d, J=9.2 Hz, 1H), 7.73 (s, 1H), 7.65-7.59 (m, 3H), 7.55-7.52 (m, 2H), 7.35 (s, 1H), 7.17-6.98 (m, 4H), 6.83 (d, J=7.2 Hz, 1H), 6.65 (d, J=8.8 Hz, 1H), 6.41 (s, 1H), 5.26 (d, J=8.0 Hz, 1H), 3.85 (d, J=11.2 Hz, 2H), 3.81-3.70 (m, 1H), 3.47-3.39 (m, 1H), 3.32-3.22 (m, 4H), 2.45-2.41 (m, 1H), 2.11-1.82 (m, 5H), 1.61 (d, J=8.4 Hz, 2H), 1.30-1.15 (m, 2H), 1.04-0.91 (m, 2H), 0.78-0.66 (m, 2H). MS (ESI, m/e) [M+1]$^+$ 813.8.

Example F1: 2-((1H-pyrrolo[2,3-b]pyridin-5-yl)oxy)-N-((3-nitro-4-(((tetrahydro-2H-pyran-4-yl)methyl)amino)phenyl)sulfonyl)-4-(5-(2-phenylpyrrolidin-1-yl)pyrazolo[1,5-a]pyrimidin-2-yl)benzamide

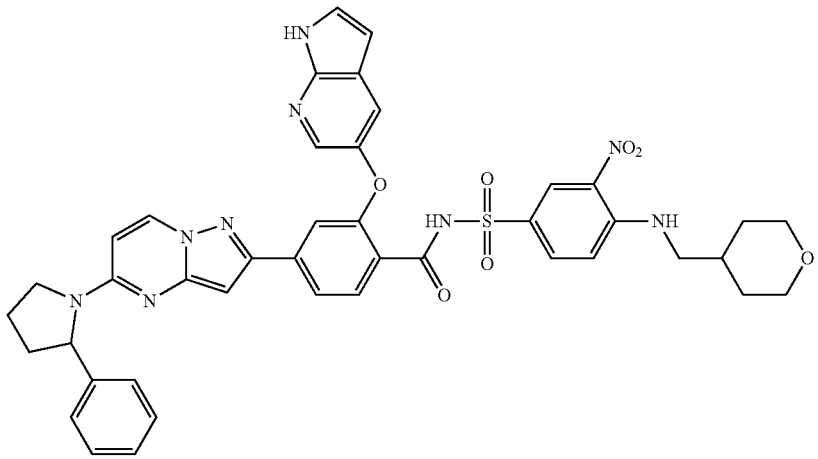 [SMILES: O=C(NS(=O)(=O)c1ccc(NCC2CCOCC2)c([N+](=O)[O-])c1)c1ccc(-c2cc3nc(N4CCCC4c4ccccc4)ccn3n2)cc1Oc1cnc2[nH]ccc2c1]

607

Step 1: 2-bromopyrazolo[1,5-a]pyrimidin-5-ol

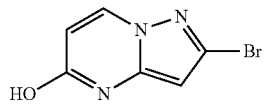

To a solution of 3-bromo-1H-pyrazol-5-amine (3.2 g, 20.0 mmol) in DMF (60 mL) were added Cs$_2$CO$_3$ (13.0 g, 40.0 mmol) and ethyl-3-ethoxyacrylate (8.6 g, 60.0 mmol), the reaction mixture was stirred at 125° C. for about 2 h. The reaction mixture was cooled to ambient temperature, poured into H$_2$O (200 mL), acidified by 1N HCl acid solution, extracted with EA (100 mL×3). The combined organic layers were washed with H$_2$O (100 mL), concentrated and purified by chromatography on silica gel (eluent: DCM/MeOH=10/1) to afford the desired compound as a yellow solid (2.0 g). MS (ESI, m/e) [M+1]$^+$ 213.9, 214.9.

Step 2: 2-bromo-5-chloropyrazolo[1,5-a]pyrimidine

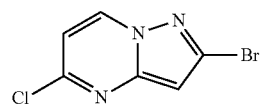 [SMILES: Clc1ccn2nc(Br)cc2n1]

To a mixture of 2-bromopyrazolo[1,5-a]pyrimidin-5-ol (2.0 g, 9.40 mmol) in CH$_3$CN (20 mL) was added phosphoryl trichloride (7 mL), the mixture was heated at 95° C. for about 16 h. Cooled to ambient temperature, poured into H$_2$O (100 mL) slowly. The precipitate was collected by filtration and dried under vacuum to give the product as yellow solid (1.8 g). MS (ESI, m/e) [M+1]$^+$ 231.9, 233.9.

Step 3: 2-bromo-5-(2-phenylpyrrolidin-1-yl)pyrazolo[1,5-a]pyrimidine

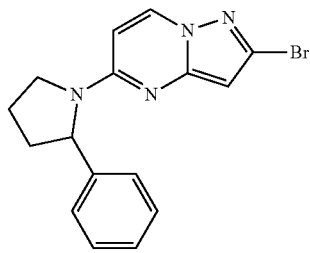 [SMILES: Brc1cc2nc(N3CCCC3c3ccccc3)ccn2n1]

To a solution of 2-bromo-5-chloropyrazolo[1,5-a]pyrimidine (1.8 g, 7.80 mmol) in DMF (20 mL) were added 2-phenylpyrrolidine (1.26 g, 8.57 mmol) and DIPEA (3.0 g, 23.41 mmol), the reaction was stirred at 120° C. for about 1 h. The reaction mixture was cooled to ambient temperature, poured into H$_2$O (100 mL), extracted with EA (50 mL×2). The combined organic layers were concentrated and purified by chromatography on silica gel (eluent: DCM/EA=10/1) to afford the desired compound as a yellow solid (1.7 g). MS (ESI, m/e) [M+1]$^+$ 343.0, 345.0.

Step 4: tert-butyl 2-((1H-pyrrolo[2,3-b]pyridin-5-yl)oxy)-4-(5-(2-phenylpyrrolidin-1-yl)pyrazolo[1,5-a]pyrimidin-2-yl)benzoate

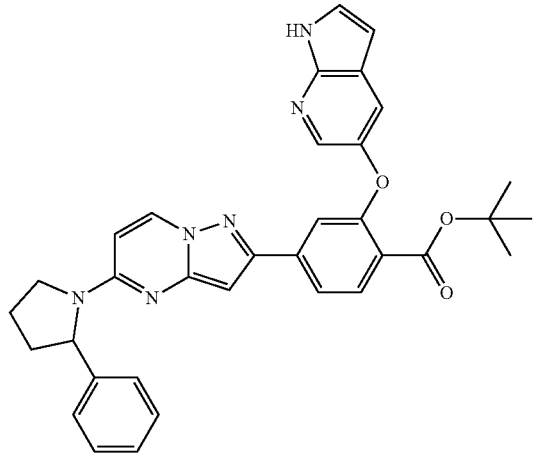 [SMILES: CC(C)(C)OC(=O)c1ccc(-c2cc3nc(N4CCCC4c4ccccc4)ccn3n2)cc1Oc1cnc2[nH]ccc2c1]

To a solution of 2-bromo-5-(2-phenylpyrrolidin-1-yl)pyrazolo[1,5-a]pyrimidine (850 mg, 2.50 mmol) in 1,4-dioxane (30 mL) were added tert-butyl 2-((1H-pyrrolo[2,3-b]pyridin-5-yl)oxy)-4-(4,4,5,5-tetramethyl-1,3,2-dioxaborolan-2-yl)benzoate (1.3 g, 3.00 mmol), K$_2$CO$_3$ aqueous solution (1M, 5 mL) and Pd(dppf)Cl$_2$ (180 mg, 0.25 mmol), the reaction was heated at 95° C. under N$_2$ for about 16 h. The mixture was cooled to ambient temperature and concentrated. The residue was portioned between DCM (30 mL) and H$_2$O (10 mL), the organic layer was concentrated and purified by column chromatograph on silica gel (eluent: DCM/MeOH=50/1) to afford the product as a yellow solid (1.3 g). MS (ESI, m/e) [M+1]$^+$573.2.

Step 5: 2-((1H-pyrrolo[2,3-b]pyridin-5-yl)oxy)-4-(5-(2-phenylpyrrolidin-1-yl)pyrazolo[1,5-a]pyrimidin-2-yl)benzoic acid

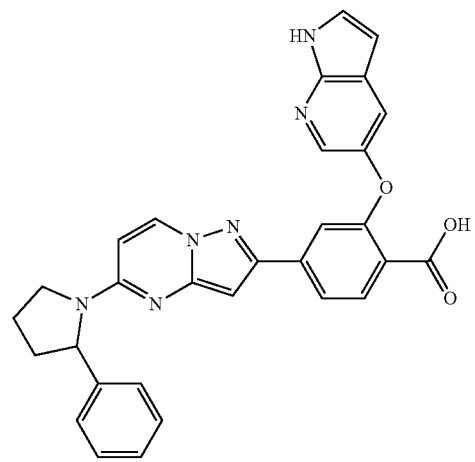 [SMILES: O=C(O)c1ccc(-c2cc3nc(N4CCCC4c4ccccc4)ccn3n2)cc1Oc1cnc2[nH]ccc2c1]

To a solution of tert-butyl 2-((1H-pyrrolo[2,3-b]pyridin-5-yl)oxy)-4-(5-(2-phenylpyrrolidin-1-yl)pyrazolo[1,5-a]pyrimidin-2-yl)benzoate (700 mg, 1.22 mmol) in DCM (10 mL) was added TFA (2.5 mL), the solution was stirred at ambient temperature for about 4 h. The solution was diluted with DCM (30 mL), washed with H₂O (20 mL×2), dried over anhydrous Na₂SO₄, filtered and concentrated to give the crude product as a yellow solid (500 mg).

Step 5: 2-((1H-pyrrolo[2,3-b]pyridin-5-yl)oxy)-N-((3-nitro-4-(((tetrahydro-2H-pyran-4-yl)methyl)amino)phenyl)sulfonyl)-4-(5-(2-phenylpyrrolidin-1-yl)pyrazolo[1,5-a]pyrimidin-2-yl)benzamide

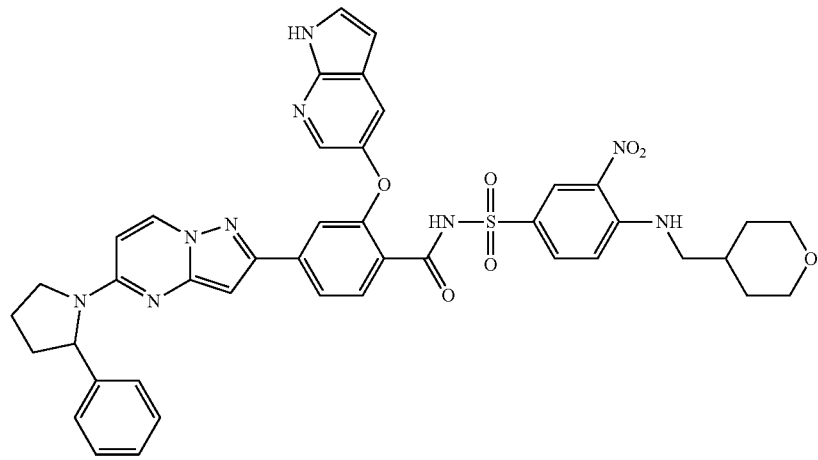 [SMILES: O=C(NS(=O)(=O)c1ccc(NCC2CCOCC2)c([N+](=O)[O-])c1)c1ccc(-c2cc3nc(N4CCCC4c4ccccc4)ccn3n2)cc1Oc1cnc2[nH]ccc2c1]

A mixture of 2-((1H-pyrrolo[2,3-b]pyridin-5-yl)oxy)-4-(5-(2-phenylpyrrolidin-1-yl)pyrazolo[1,5-a]pyrimidin-2-yl (benzoic acid (250 mg, 0.484 mmol), 3-nitro-4-(((tetrahydro-2H-pyran-4-yl)methyl)amino)benzenesulfonamide (150 mg, 0.484 mmol), EDCl (196 mg, 0.969 mmol), DMAP (88 mg, 0.727 mmol) and TFA (150 mg, 1.452 mol) in DCM (10 ml) was stirred at ambient temperature for 4 d. The reaction solution was washed with H₂O (10 mL), concentrated, purified by column chromatograph on silica gel (100-200 mesh, eluted with DCM: MeOH=20:1) to give a crude product, the crude product was purified by pre-HPLC to give the product (80 mg). ¹H NMR (DMSO-d₆) δ ppm: 12.35 (s, 1H), 11.79 (s, 1H), 8.69-8.31 (m, 3H), 8.09 (d, J=2.4 Hz, 1H), 7.87 (dd, J=9.2, 2.4 Hz, 1H), 7.77-7.50 (m, 4H), 7.31-7.15 (m, 7H), 6.50-6.43 (m, 2H), 5.15 (s, 1H), 3.89-3.82 (m, 3H), 3.64 (s, 1H), 3.30-3.21 (m, 5H), 2.39-2.33 (m, 1H), 1.93-1.82 (m, 4H), 1.59 (d, J=12.0 Hz, 2H), 1.29-1.18 (m, 2H). MS (ESI, m/e) [M+1]⁺ 814.1.

Example F2: 2-((1H-pyrrolo[2,3-b]pyridin-5-yl)oxy)-N-((3-nitro-4-(((tetrahydro-2H-pyran-4-yl)methyl)amino)phenyl)sulfonyl)-4-(5-(2-phenylpyrrolidin-1-yl)benzo[b]thiophen-2-yl)benzamide

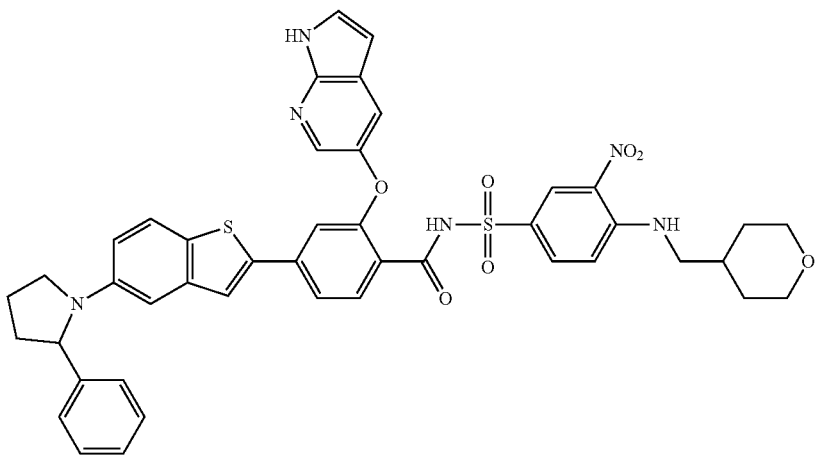 [SMILES: O=C(NS(=O)(=O)c1ccc(NCC2CCOCC2)c([N+](=O)[O-])c1)c1ccc(-c2cc3cc(N4CCCC4c4ccccc4)ccc3s2)cc1Oc1cnc2[nH]ccc2c1]

$^1$H NMR (400 MHz, DMSO-$d_6$) δ 12.38 (s, 1H), 11.73 (s, 1H), 8.70-8.45 (m, 2H), 8.07 (s, 1H), 7.82 (d, J=9.5 Hz, 1H), 7.70-7.50 (m, 5H), 7.50-7.45 (m, 1H), 7.30-7.25 (m, 2H), 7.20-7.15 (m, 3H), 7.10-7.00 (m, 2H), 6.74 (s, 1H), 6.55-6.50 (m, 1H), 6.41 (s, 1H), 4.85-4.75 (m, 1H), 3.90-3.82 (m, 2H), 3.80-3.65 (m, 1H), 3.30-3.10 (m, 3H), 3.05-2.95 (m, 1H), 2.44-2.32 (m, 1H), 2.04-1.74 (m, 4H), 1.70-1.60 (m, 2H), 1.35-1.16 (m, 3H). MS (ESI, m/e) [M+1]$^+$829.1.

Example F9: (trans- or cis-)-2-((1H-pyrrolo[2,3-b]pyridin-5-yl)oxy)-4-((4-(2-(2-cyclopropylphenyl)pyrrolidin-1-yl)cyclohexyl)oxy)-N-((3-nitro-4-(((tetrahydro-2H-pyran-4-yl)methyl)amino)phenyl)sulfonyl)benzamide

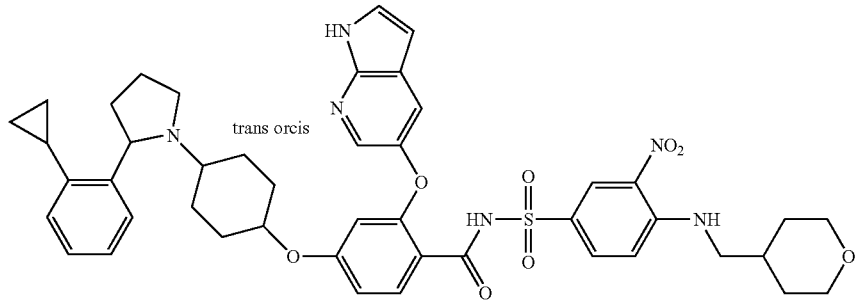 [SMILES: O=C(NS(=O)(=O)c1ccc(NCC2CCOCC2)c([N+](=O)[O-])c1)c1ccc(OC2CCC(N3CCCC3c3ccccc3C3CC3)CC2)cc1Oc1cnc2[nH]ccc2c1]

Step 1: methyl 4-bromo-2-((1-(phenylsulfonyl)-1H-pyrrolo[2,3-b]pyridine-5-yl)oxy)benzoate To a solution of methyl 2-((1H-pyrrolo[2,3-b]pyridin-5-yl)oxy)-4-bromobenzoate (6.96 g, 20.04 mmol) in tetrahydrofuran (80 mL) was added sodium hydride (960 mg, 24.0 mmol) at 0° C. and the resulted mixture was stirred at room temperature for 0.5 h. Then benzenesulfonyl chloride (4.30 g, 24.3 mmol) was added dropwise. Then stirred at room temperature for 6 h, the mixture was quenched with aq. ammonium chloride. Then after extracted with EA, the organic layer was combined, dried over sodium sulfate and concentrated in vacuum. The residue was purified by chromatography column on silica (PE/EA=10/1 to 3/1) to give the product (3.80 g) as a white solid. MS (ESI, m/e) [M+1]$^+$ 486.9.

Step 2: methyl 2-((1-(phenylsulfonyl)-1H-pyrrolo[2,3-b]pyridin-5-yl)oxy)-4-(4,4,5,5-tetramethyl-1,3,2-dioxaborolan-2-yl)benzoate To a solution of methyl 4-bromo-2-((1-(phenylsulfonyl)-1H-pyrrolo[2,3-b]pyridine-5-yl)oxy)benzoate (1.00 g, 2.05 mmol), 4,4,4',4',5,5,5',5'-octamethyl-2,2'-bi(1,3,2-dioxaborolane) (608 mg, 2.39 mmol) in dioxane (25 mL) was added [1,1'-bis(diphenylphosphino)ferrocene]dichloropalladium(II) (147 mg, 0.20 mmol) and potassium acetate (600 mg, 6.12 mmol) under N$_2$ atmosphere. After addition, the reaction mixture was heated to 90° C. and stirred for 16 h. After cooled to room temperature, the mixture was filtered, and the filtrate was evaporated. The resulted residue was purified by chromatography column on silica (PE/EA=2/1 to 1/1) to give the product (920 mg) as a yellow gel. MS (ESI, m/e) [M+1]$^+$ 535.0.

Step 3: methyl 4-hydroxy-2-((1-(phenylsulfonyl)-1H-pyrrolo[2,3-b]pyridin-5-yl)oxy)benzoate To a solution of methyl 2-((1-(phenylsulfonyl)-1H-pyrrolo[2,3-b]pyridine-5-yl)oxy)-4-(4,4,5,5-tetramethyl-1,3,2-dioxaborolan-2-yl)benzoate (900 mg, 1.68 mmol) in acetic acid (10 mL)/water (10 mL) was added hydrogen peroxide (30%) (3.0 mL), After addition, the reaction mixture was stirred at room temperature for 16 h. Then aq. sodium bicarbonate was added and adjusted PH to ~8. After extracted with EA, the organic layer was combined, dried over sodium sulfate and concentrated in vacuum. The resultant residue was purified by chromatography column on silica (PE/EA=5/1 to 1/1 then DCM/MeOH=40/1) to give the product (700 mg) as a white solid. MS (ESI, m/e) [M+1]$^+$ 424.8.

Step 4: methyl 4-((4-oxocyclohexyl)oxy)-2-((1-(phenylsulfonyl)-1H-pyrrolo[2,3-b]pyridin-5-yl)oxy)benzoate To a solution of methyl 4-hydroxy-2-((1-(phenylsulfonyl)-1H-pyrrolo[2,3-b]pyridin-5-yl)oxy)benzoate (460 mg, 1.08 mmol), 4-hydroxycyclohexan-1-one (130 mg, 1.1 mmol) and triphenylphosphine (390 mg, 1.49 mmol) in tetrahydrofuran (15 mL) was added diisopropyl azodicarboxylate (440 mg 2.17 mmol) at 0° C. under N$_2$. After stirred at room temperature for 3 h, the reaction mixture was diluted with water and extracted with EA. The organic layer was combined, dried over sodium sulfate and concentrated in vacuum. The resulted residue was purified by chromatography column on silica (PE/EA=2/1) to give 550 mg crude product directly for next step, MS (ESI, m/e) [M+1]$^+$ 520.8

Step 5: methyl 4-((4-(2-(2-cyclopropylphenyl)pyrrolidin-1-yl)cyclohexyl)oxy)-2-((1-(phenylsulfonyl)-1H-pyrrolo[2,3-b]pyridin-5-yl)oxy)benzoate To a solution of methyl 4-((4-oxocyclohexyl)oxy)-2-((1-(phenylsulfonyl)-1H-pyrrolo[2,3-b]pyridin-5-yl)oxy)benzoate (550 mg, 1.06 mmol) and 2-(2-cyclopropylphenyl)pyrrolidine (195 mg, 1.06 mmol) in DCM (20 mL) was added acetic acid (0.08 mL) for 30 min. Then it was added sodium triacetoxyborohydride (460 mg, 2.10 mmol) and it was stirred at room temperature for 2 h. The mixture was diluted with water and it was extracted with dichloromethane. The organic layer was combined, dried over sodium sulfate and it was concentrated in vacuum. The residue was purified by chromatography column on silica (PE/EA=5/1 to 1/1 then DCM/MeOH=40/1) to give the faster P1 (200 mg, cis or trans) and slower P2 (240 mg, trans or cis). MS (ESI, m/e) [M+1]$^+$ 691.8.

Step 6: (trans- or cis-) 2-((1H-pyrrolo[2,3-b]pyridin-5-yl)oxy)-4-((4-(2-(2-cyclopropyl phenyl)pyrrolidin-1-yl)cyclohexyl)oxy)benzoic acid To a solution of (trans- or cis-)methyl 4-((4-(2-(2-cyclopropylphenyl)pyrrolidin-1-yl)cyclohexyl)oxy)-2-((i-(phenylsulfonyl)-1H-pyrrolo[2,3-b]pyridin-5-yl)oxy)benzoate (240 mg, 0.35 mmol) in MeOH/THF (6 mL 16 mL) was added 3N NaOH solution (5 mL) and stirred at room temperature for 16 h. Then the reaction mixture was adjusted PH to 3-4 with 2N HCl solution. After extracted with DCM, the organic layer was combined, dried over sodium sulfate and concentrated in vacuum to give crude 100 mg white solid without purification for the next step. MS (ESI, m/e) [M+1]$^+$ 537.9.

The desired compound was synthesized with 3-nitro-4-(((tetrahydro-2H-pyran-4-yl)methyl)amino)benzenesulfonamide and (trans- or cis-) 2-((1H-pyrrolo[2,3-b]pyridin-5-yl)oxy)-4-((4-(2-(2-cyclopropyl phenyl)pyrrolidin-1-yl) cyclohexyl)oxy)benzoic acid following the procedures similar to those in Example A1. $^1$H NMR (400 MHz, DMSO-d$_6$) δ ppm: 11.89 (s, 1H), 11.85-11.73 (m, 1H), 9.52-9.37 (m, 1H), 8.67-8.50 (m, 2H), 8.07 (s, 1H), 7.89-7.79 (m, 1H), 7.72-7.63 (m, 1H), 7.62-7.50 (m, 2H), 7.32-7.12 (m, 3H), 7.08-6.96 (m, 1H), 6.86 (s, 1H), 6.53-6.40 (m, 1H), 6.17-6.00 (m, 1H), 5.12-5.02 (m, 1H), 4.54-4.45 (m, 1H), 3.90-3.78 (m, 2H), 3.71-3.59 (m, 1H), 3.30-3.18 (m, 4H), 3.11-2.89 (m, 2H), 2.13-2.03 (m, 1H), 2.00-1.92 (m, 2H), 1.90-1.77 (m, 4H), 1.74-1.55 (m, 4H), 1.55-1.45 (m, 2H), 1.44-1.34 (m, 2H), 1.33-1.16 (m, 4H), 0.88-0.75 (m, 2H), 0.65-0.57 (m, 1H), 0.48-0.40 (m, 1H). MS (ESI, m/e) [M+1]$^+$834.8.

Example F11: (trans- or cis-) 2-((1H-pyrrolo[2,3-b]pyridin-5-yl)oxy)-4-((4-(2-(2-cyclopropylphenyl)pyrrolidin-lyl)cyclohexyl)(methyl)amino)-N-((3-nitro-4-((((tetrahydro-2H-pyran-4-yl)methyl)amino)phenyl)sulfonyl)benzamide

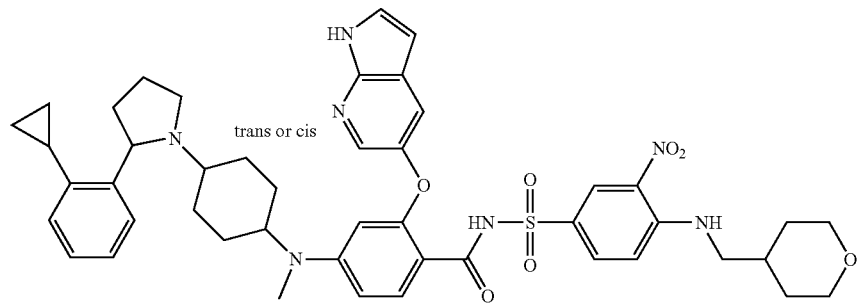 [SMILES: CN(c1ccc(C(=O)NS(=O)(=O)c2ccc(NCC3CCOCC3)c([N+](=O)[O-])c2)c(Oc2cnc3[nH]ccc3c2)c1)C1CCC(N2CCCC2c2ccccc2C2CC2)CC1]

The desired compound was synthesized with 3-nitro-4-(((tetrahydro-2H-pyran-4-yl)methyl)amino)benzenesulfonamide and (trans- or cis-) 2-((1H-pyrrolo[2,3-b]pyridin-5-yl)oxy)-4-((4-(2-(2-cyclopropylphenyl)pyrrolidin-1-yl)cyclohexyl)(methyl)amino)benzoic acid following the procedures similar to those in Example A1. $^1$H NMR (400 MHz, DMSO-$d_6$) δ ppm: 11.68 (s, 1H), 11.31-11.16 (m, 1H), 8.69-8.50 (m, 2H), 8.10-7.98 (m, 1H), 7.83-7.70 (m, 1H), 7.61-7.45 (m, 4H), 7.20-7.01 (m, 3H), 6.97-6.87 (m, 1H), 6.63-6.50 (m, 1H), 6.43-6.34 (m, 1H), 5.95 (s, 1H), 4.30-4.21 (m, 1H), 3.91-3.80 (m, 2H), 3.50-3.41 (m, 1H), 3.30-3.21 (m, 5H), 3.11-2.94 (m, 2H), 2.53 (s, 3H), 2.08-1.98 (m, 1H), 1.93-1.85 (m, 1H), 1.66-1.56 (m, 3H), 1.33-1.27 (m, 2H), 1.20-1.15 (m, 3H), 0.95-0.85 (m, 4H), 0.81-0.72 (m, 4H), 0.70-0.60 (m, 2H), 0.58-0.44 (m, 2H). MS (ESI, m/e) [M+1]$^+$ 848.2.

Example F21: 2-((1H-pyrrolo[2,3-b]pyridin-5-yl)oxy)-4-(2-((S)-2-(2-cyclopropylphenyl)pyrrolidin-1-yl)-7-azaspiro[3.5]nonan-7-yl)-N-((4-((((1r,4r)-4-hydroxy-4-methylcyclohexyl)methyl)amino)-3-nitrophenyl)sulfonyl)benzamide

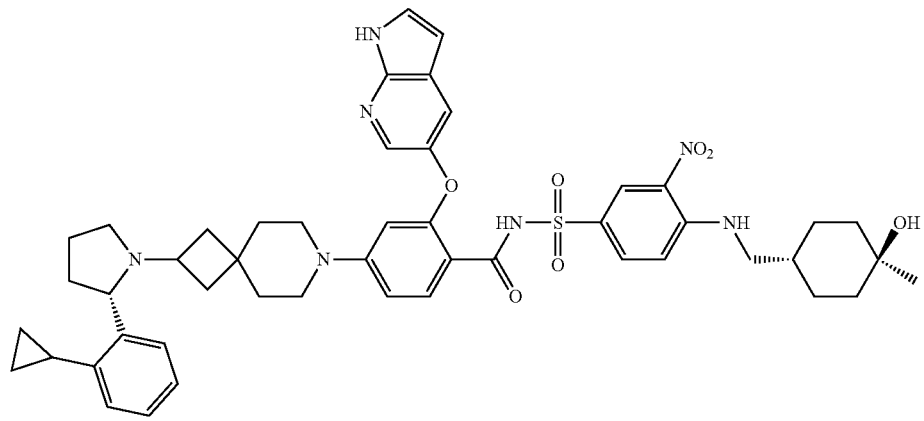 [SMILES: C[C@]1(O)CC[C@H](CNc2ccc(S(=O)(=O)NC(=O)c3ccc(N4CCC5(CC4)CC(N4CCC[C@H]4c4ccccc4C4CC4)C5)cc3Oc3cnc4[nH]ccc4c3)cc2[N+](=O)[O-])CC1]

Step 1: tert-butyl (S)-2-(2-bromophenyl)pyrrolidine-1-carboxylate

To a solution of (S)-2-(2-bromophenyl)pyrrolidine (70 g, 311 mmol) in DCM (200 mL) were added Boc$_2$O (72.6 g, 333 mmol) and DMAP (cat) at 0° C. After addition, the mixture was stirred at room temperature for 1 hour. Then the mixture solution was washed with saturated aq, NaHCO$_3$ (100 mL×3), brine. The organic phase was dried with anhydrous NaSO$_4$, filtered, and concentrated to obtain pale brown solid (95 g, crude), which was not further purified for next step. MS (ESI, m/e) [M+1]$^+$ 326.1/328.2.

Step 2: tert-butyl (S)-2-(2-cyclopropylphenyl)pyrrolidine-1-carboxylate

Under a N$_2$ atmosphere, a mixture of tert-butyl (S)-2-(2-bromophenyl)pyrrolidine-1-carboxylate (88 g, 270 mmol), cyclopropyl boronic acid (68.9 g, 810 mmol), Pd(dppf)$_2$Cl$_2$ (19.7 g, 27 mmol) and K$_2$CO$_3$ (150 g, 1.08 mol) in 1,4-dioxane (270 mL) and H$_2$O (30 mL) was stirred at 90° C. for 16 hours. After the reaction mixture was cooled to room temperature, the mixture was filtered, and the filtrate was concentrated in vacuum. The residue was purified by chromatography column on silica (eluent: DCM/CH$_3$OH=20/1) to obtain tert-butyl (S)-2-(2-cyclopropylphenyl)pyrrolidine-1-carboxylate as pale yellow oil 70 g (yield: 90%). MS (ESI, m/e) [M+1]$^+$ 288.1.

Step 3: (S)-2-(2-cyclopropylphenyl)pyrrolidine

To a solution of tert-butyl (S)-2-(2-cyclopropylphenyl)pyrrolidine-1-carboxylate (70 g, 244 mmol) in DCM (200 mL) was added HCl solution (200 mL, 4M in dioxane). After addition, the mixture was stirred for overnight at room temperature. After removal of solvent, the residue was diluted with water (200 mL) and EA (100 mL) under stirring, the separated water phase was adjusted to PH ~11 and exacted with DCM (100 mL×2). The combined organic phase was dried with anhydrous NaSO$_4$, filtered, and concentrated to obtain (S)-2-(2-cyclopropylphenyl)pyrrolidine (42 g, crude) as brown oil. MS (ESI, m/e) [M+1]$^+$ 188.2.

Step 4: tert-butyl (S)-2-(2-(2-cyclopropylphenyl)pyrrolidin-1-yl)-7-azaspiro[3.5]nonane-7-carboxylate To the mixture of (S)-2-(2-cyclopropylphenyl)pyrrolidine (3.74 g, 20 mmol) and tert-butyl 2-oxo-7-azaspiro[3.5]nonane-7-carboxylate (4.78 g, 20 mmol) in DCM (100 mL) was added NaBH(AcO)$_3$ (8.48 g, 40 mmol) at room temperature and stirred for 2 hours. The reaction mixture was quenched with aq. NaHCO$_3$ solution (200 mL), and then extracted with DCM (200 mL×2). The organic layer was combined, washed with brine and dried over Na$_2$SO$_4$. After evaporation in vacuum, the crude product (8.21 g) was obtained as a colorless oil without further purification for next step. MS (ESI, m/e) [M+1]$^+$ 411.0.

Step 5: (S)-2-(2-(2-cyclopropylphenyl)pyrrolidin-1-yl)-7-azaspiro[3,5]nonane To a solution of tert-butyl (S)-2-(2-(2-cyclopropylphenyl)pyrrolidin-1-yl)-7-azaspiro[3.5]nonane-7-carboxylate (8.2 g, 20 mmol) in DCM (200 mL) was added TFA (40 mL) at 20° C. and stirred at room temperature overnight. The mixture was concentrated in vacuum and diluted with DCM (200 mL) and aq. NaOH solution (IN, 200 mL) was added under stirring. Then the organic layer was collected and dried over Na$_2$SO$_4$. After evaporation in vacuum, the crude product (6.2 g) was obtained as a brown oil without further purification for next step. $^1$H NMR (400 MHz, CDCl3) δ ppm: 7.61 (dd, J=8.0 Hz, J=4.0 Hz, 1H), 7.22-7.11 (m, 2H), 7.00-6.96 (m, 1H), 3.94 (t, J=8.0 Hz, 1H), 3.23-3.03 (m, 2H), 2.71-2.60 fin. 4H), 2.42-2.20 (m, 2H), 2.07-1.55 (m, 10H), 1.41-1.37 (m, 3H), 0.95-0.87 (m, 2H), 0.64-0.53 (m, 2H). MS (ESI, m/e) [M+1]$^+$ 311.0.

Step 6: methyl 2-((1H-pyrrolo[2,3-b]pyridin-5-yl)oxy)-4-fluorobenzoate (F21-3)

The mixture of methyl 2,4-difluorobenzoate (17.2 g, 0.1 mol), 1H-pyrrolo[2,3-b]pyridin-5-ol (28.1 g, 0.21 mol), K$_3$PO$_4$ (36 g, 0.17 mol) in 2-methoxyethyl ether (560 mL) was heated to 120° C. and stirred for overnight. The reaction mixture was cooled to room temperature and then poured into water (3 L) to form precipitation. After filtration, the resulted solid was further purified by recrystallization (eluent: PE/EA=3/1, 500 mL) to give the product (13.2 g) as an off-white solid. MS (ESI, m/e) [M+1]$^+$ 287.1.

Step 7: methyl (S)-2-((1H-pyrrolo[2,3-b]pyridin-5-yl)oxy)-4-(2-(2-(2-cyclopropylphenyl)pyrrolidin-1-yl)-7-azaspiro[3.5]nonan-7-yl)benzoate (F21-2)

The mixture of (S)-2-(2-(2-cyclopropylphenyl)pyrrolidin-1-yl)-7-azaspiro[3.5]nonane (6.2 g, 20 mmol), methyl 2-((1H-pyrrolo[2,3-b]pyridin-5-yl)oxy)-4-fluorobenzoate (6.89 g, 24 mmol), Na$_2$CO$_3$ (21.2 g, 200 mmol) in DMF (100 mL) was heated to 105° C. and stirred overnight. After cooling down to room temperature, the reaction mixture was diluted with EA (300 mL), washed with brine (300 mL×2), dried over Na$_2$SO$_4$ and concentrated in vacuum. The resulted residue was purified by chromatography column on silica (eluent: EA/PE, 1/5 to 1/1) to give the product (6.3 g) as an off-white solid. MS (ESI, m/e) [M+1]$^+$ 576.9.

Step 8: (S)-2-((1H-pyrrolo[2,3-b]pyridin-5-yl)oxy)-4-(2-(2-(2-cyclopropylphenyl)pyrrolidin-1-yl)-7-azaspiro[3.5]nonan-7-yl)benzoic acid (F21-1)

To the solution of methyl (S)-2-((1H-pyrrolo[2,3-b]pyridin-5-yl)oxy)-4-(2-(2-(2-cyclopropylphenyl)pyrrolidin-1-yl)-7-azaspiro[3.5]nonan-7-yl)benzoate (6.3 g, 11.21 mmol) in MeOH (180 mL) and THF (180 mL) was added aq. NaOH solution (3N, 373 mL). After addition, the reaction mixture was heated to 50° C. and stirred for 2 hours. Then the mixture was adjusted to pH5 with HCl acid (6N), and extracted with DCM (500 mL×2). The organic layer was combined, dried over Na$_2$SO$_4$ and then evaporated in vacuum to afford a crude product (6.0 g) as off-white solid. $^1$H NMR (400 MHz, DMSO-d$_6$) δ ppm: 11.99 (s, 1H), 11.25-11.04 (m, 1H), 8.10-7.94 (m, 2H), 7.76 (d, J=8.0 Hz, 1H), 7.47 (s, 1H), 7.38 (s, 1H), 7.28 (s, 2H), 7.12-7.02 (s, 1H), 6.75 (d, J=8.0 Hz, 1H), 6.36 (s, 2H), 5.02-4.94 (m, 1H), 3.91-3.67 (m, 4H), 3.17-2.96 (m, 4H), 2.33-2.04 (m, 5H), 1.81-1.72 (m, 2H), 1.56-1.37 (m, 4H), 0.91-0.89 (m, 2H), 0.69-0.62 (m, 2H). MS (ESI, m/e) [M+1]$^+$ 562.9.

Step 9: 2-((1H-pyrrolo[2,3-b]pyridin-5-yl)oxy)-4-(2-((S)-2-(2-cyclopropylphenyl)pyrrolidin-1-yl)-7-azaspiro[3.5]nonan-7-yl)-N-((4-((((1r,4r)-4-hydroxy-4-methylcyclohexyl)methyl)amino)-3-nitrophenyl)sulfonyl)benzamide The mixture of (S)-2-((1H-pyrrolo[2,3-b]pyridin-5-yl)oxy)-4-(2-(2-(2-cyclopropylphenyl)pyrrolidin-1-yl)-7-azaspiro[3.5]nonan-7-yl)benzoic acid (3 g, 5.33 mmol), triethylamine (3.2 g, 32 mmol), HATU (2.43 g, 6.40 mmol) in DCM (100 mL) was stirred for 4 hours at room temperature. Then to the resulting reaction mixture was added 4-((((1r,4r)-4-hydroxy-4-methylcyclohexyl)methyl)amino)-3-nitrobenzenesulfonamide (2.20 g, 6.40 mmol) and DMAP (122 mg, 2 mmol). After stirring overnight, the reaction mixture was washed with brine, dried over Na$_2$SO$_4$, filtered and concentrated in vacuum. The resulted residue was purified by chromatography column on silica (eluent: PE/EA=1/1 (2 L), then DCM/MeOH=100/1 to 40/1), and then the desired compound was obtained (2.0 g, yield: 42.2%) as yellow solid. $^1$H NMR (400 MHz, DMSO-d$_6$) δ ppm: 11.65 (s, 1H), 11.34 (br, 1H), 8.55-8.47 (m, 2H), 8.00 (s, 1H), 7.75 (d, J=8.0 Hz, 1H), 7.59-7.44 (m, 4H), 7.24-7.09 (m, 2H), 7.00-6.90 (m. 2H), 6.67 (d, J=8.0 Hz, 1H), 6.36 (s, 1H), 6.18 (s, 1H), 4.24 (s, 1H), 3.32-3.25 (m, 3H), 3.05-2.63 (m, 5H), 2.33-2.28 (m, 1H), 2.04-2.01 (m, 2H) 1.73-1.52 (m, 12H), 1.46-1.29 (m, 8H), 1.16-1.13 (m, 5H), 0.91-0.89 (m, 2H), 0.64-0.56 (m, 2H). MS (ESI, m/e) [M+1]$^+$ 888.8

Example F22: (S)-2-((1H-pyrrolo[2,3-b]pyridin-5-yl)oxy)-4-(2-(2-(2-cyclopropylphenyl)pyrrolidin-1-yl)-7-azaspiro[3.5]nonan-7-yl)-N-((4-(((4-fluorotetrahydro-2H-pyran-4-yl)methyl)amino)-3-nitrophenyl)sulfonyl)benzamide

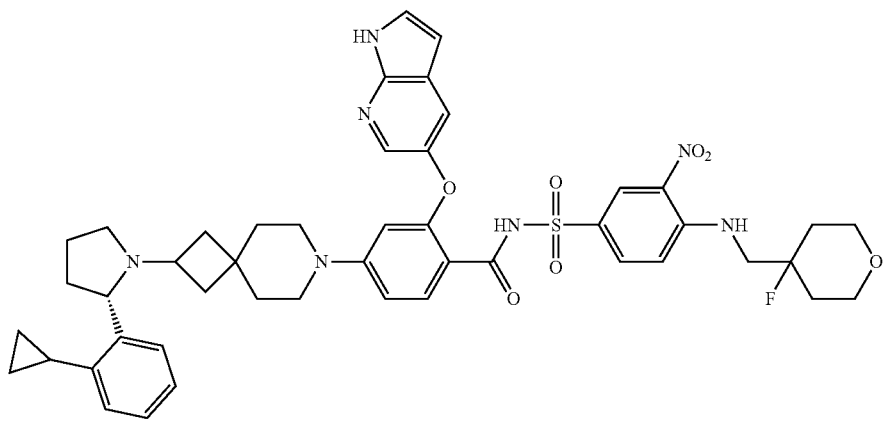 [SMILES: O=C(NS(=O)(=O)c1ccc(NCC2(F)CCOCC2)c([N+](=O)[O-])c1)c1ccc(N2CCC3(CC2)CC(N2CCC[C@H]2c2ccccc2C2CC2)C3)cc1Oc1cnc2[nH]ccc2c1]

The desired compound was synthesized with 4-(((4-fluorotetrahydro-2H-pyran-4-yl)methyl)amino)-3-nitrobenzenesulfonamide and (S)-2-((1H-pyrrolo[2,3-b]pyridin-5-yl)oxy)-4-(2-(2-(2-cyclopropylphenyl)pyrrolidin-1-yl)-7-azaspiro[3.5]nonan-7-yl)benzoic acid following the procedures similar to those in Example F21. $^1$H NMR (DMSO-d$_6$) δ ppm: 11.65 (s, 1H), 11.23 (br, 1H), 8.63-8.47 (m, 2H), 8.00 (s, 1H), 7.80-7.74 (m, 1H), 7.61-7.38 (m, 5H), 7.30-6.96 (m, 5H), 6.69-6.63 (m, 1H), 6.36 (s, 1H), 6.17 (s, 1H), 3.81-3.72 (m, 4H), 3.57-3.49 (m, 4H), 3.05-2.92 (m, 4H), 2.42-2.32 (m, 2H), 2.09-1.99 (m, 2H), 1.86-1.72 (m, 6H), 1.58-1.47 (m, 3H), 1.46-1.24 (m, 6H), 1.00-0.54 (m, 4H). MS (ESI, m/e) [M+1]$^+$ 877.8.

Example F23: (S)-2-((1H-pyrrolo[2,3-b]pyridin-5-yl)oxy)-4-(2-(2-(2-cyclopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide

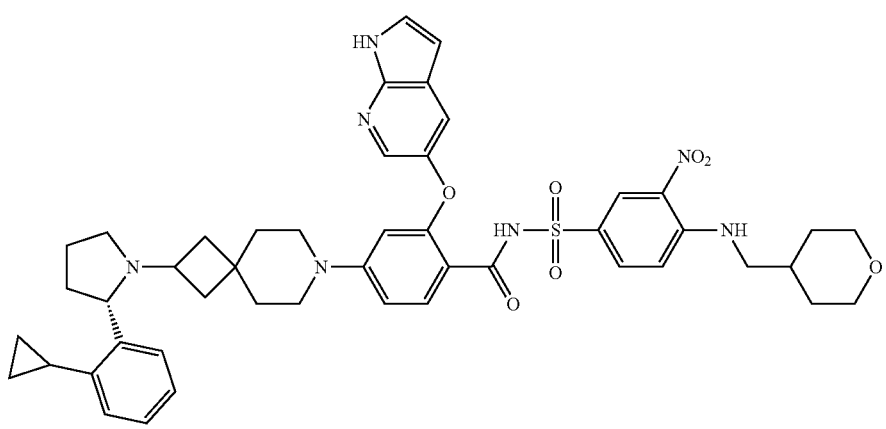

The mixture of (S)-2-((1H-pyrrolo[2,3-b]pyridin-5-yl)oxy)-4-(2-(2-(2-cyclopropylphenyl)pyrrolidin-1-yl)-7-azaspiro[3.5]nonan-7-yl)benzoic acid (2.0 g, 3.56 mmol), triethylamine (1.08 g, 10.68 mmol), 2-(7-Azabenzotriazol-1-yl)-N,N,N',N'-tetramethyluronium hexafluorophosphate (1.62 g, 4.27 mmol) in DCM (100 mL) was stirred for 4 hours at room temperature. Then to the resulting reaction mixture was added 3-nitro-4-(((tetrahydro-2H-pyran-4-yl)methyl)amino)benzenesulfonamide (1.35 g, 4.27 mmol) and DMAP (50 mg, 0.40 mmol). After stirred overnight, the reaction mixture was quenched and washed with $NH_4Cl$, dried over $Na_2SO_4$ and concentrated in vacuum. The resulted residue was purified by chromatography column on silica (eluent: PE/EA=1/1, then DCM/MeOH=60/1 to 40/1), and then the desired compound was obtained (1.3 g, yield: 42.5%). $^1$H NMR (400 MHz, DMSO-$d_6$) δ ppm: 11.63 (s, 1H), 11.30 (br, 1H), 8.58-8.47 (m, 2H), 7.99 (s, 1H), 7.74 (d, J=8.8 Hz, 1H), 7.55-7.42 (m, 4H), 7.19-7.08 (m, 2H), 7.04-6.90 (m, 2H), 6.66 (d, J=8.8 Hz, 1H), 6.35 (s, 1H), 6.18 (m, 1H), 4.34-4.08 (m, 1H), 3.85 (d, J=8.8 Hz, 2H), 3.31-3.18 (m, 6H), 3.05-2.93 (m, 4H), 2.67-2.51 (m, 1H), 2.35-2.25 (m, 1H), 2.07-2.01 (m, 1H), 1.95-1.68 (m, 6H), 1.62 (d, J=12.8 Hz, 2H), 1.55-1.21 (m, 9H), 0.92-0.85 (m, 2H), 0.65-0.53 (m, 2H). MS (ESI, m/e) [M+1]$^+$ 859.8.

Example F24: (S)-2-((1H-pyrrolo[2,3-b]pyridin-5-yl)oxy)-4-(2-(2-(2-ethylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide

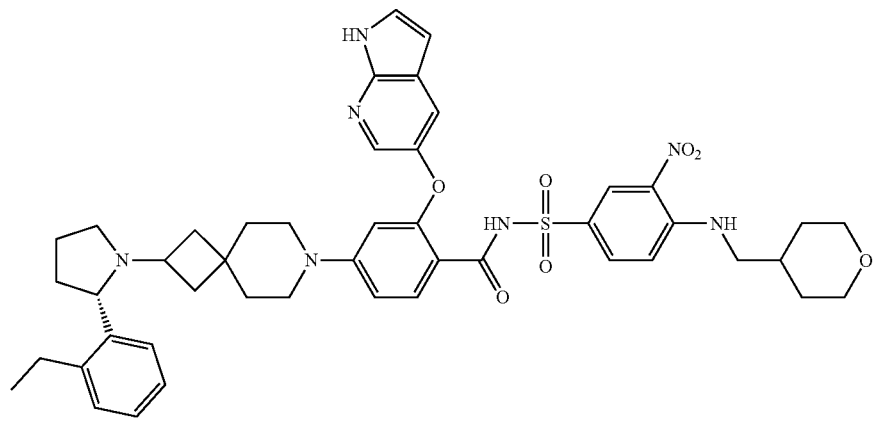 [SMILES: CCc1ccccc1[C@@H]1CCCN1C1CC2(CCN(c3ccc(C(=O)NS(=O)(=O)c4ccc(NCC5CCOCC5)c([N+](=O)[O-])c4)c(Oc4cnc5[nH]ccc5c4)c3)CC2)C1]

The desired compound was synthesized following the procedures similar to those in Example F21 by replacing (S)-2-(2-cyclopropylphenyl)pyrrolidine with (S)-2-(2-ethylphenyl)pyrrolidine, and replacing 4-((((1r,4r)-4-hydroxy-4-methylcyclohexyl)methyl)amino)-3-nitrobenzenesulfonamide with 3-nitro-4-(((tetrahydro-2H-pyran-4-yl)methyl)amino)benzenesulfonamide. $^1$H NMR (DMSO-$d_6$) δ ppm: 11.69 (s, 1H), 11.45 (s, 1H), 10.06 (s, 1H), 8.62-8.56 (m, 2H), 8.03 (d, J=2.3 Hz, 1H), 7.80-7.76 (m, 2H), 7.51-7.47 (m, 3H), 7.31 (s, 1H), 7.24 (s, 1H), 7.11 (d, J=9.2 Hz, 1H), 6.68 (d, J=9.2 Hz, 1H), 6.38 (s, 1H), 6.17 (s, 1H), 4.64 (s, 1H), 3.87-3.84 (m, 3H), 3.66 (s, 1H), 3.29-3.21 (m, 3H), 3.04 (s, 2H), 2.94 (s, 2H), 2.77-2.75 (m, 1H), 2.67-2.57 (m, 2H), 2.08 (s, 4H), 2.03-1.97 (m, 2H), 1.88 (s, 1H), 1.62-1.60 (m, 2H), 1.43 (s, 3H), 1.35-1.29 (m, 4H), 1.12 (t, J=7.5 Hz, 3H), 0.85 (t, J=6.6 Hz, 1H). MS (ESI, m/e) [M+1]$^+$ 847.9.

Example F25: (S)-2-((1H-pyrrolo[2,3-b]pyridin-5-yl)oxy)-4-(2-(2-(2-ethylphenyl)pyrrolidin-1-yl)-7-azaspiro[3.5]nonan-7-yl)-N-((4-(((4-fluorotetrahydro-2H-pyran-4-yl)methyl)amino)-3-nitrophenyl)sulfonyl)benzamide

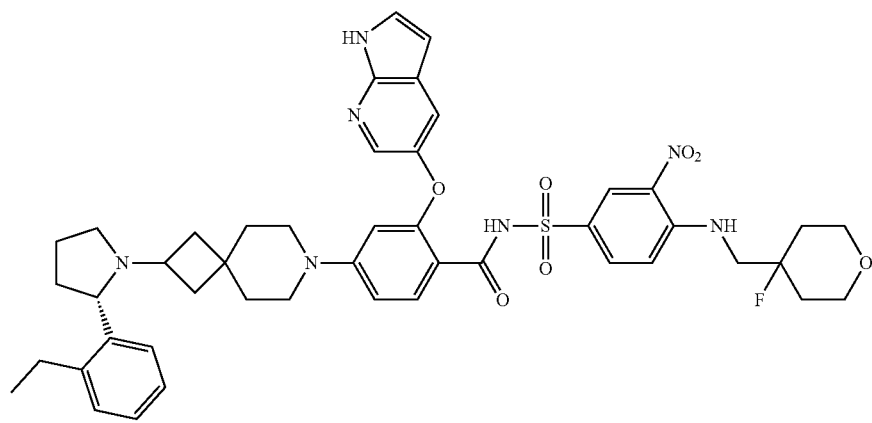 [SMILES: CCc1ccccc1[C@@H]1CCCN1C1CC2(CCN(c3ccc(C(=O)NS(=O)(=O)c4ccc(NCC5(F)CCOCC5)c([N+](=O)[O-])c4)c(Oc4cnc5[nH]ccc5c4)c3)CC2)C1]

The desired compound was synthesized following the procedures similar to those in Example F21 by replacing (S)-2-(2-cyclopropylphenyl)pyrrolidine with (S)-2-(2-ethylphenyl)pyrrolidine, and replacing 4-((((1r,4r)-4-hydroxy-4-methylcyclohexyl)methyl)amino)-3-nitrobenzenesulfonamide with 4-(((4-fluorotetrahydro-2H-pyran-4-yl)methyl)amino)-3-nitrobenzenesulfonamide. $^1$H NMR (DMSO-$d_6$) δ ppm: 11.70 (s, 1H), 11.46 (s, 1H), 10.53 (s, 1H), 8.64 (t, J=6.1 Hz, 1H), 8.56 (d, J=1.8 Hz, 1H), 8.03 (d, J=2.3 Hz, 1H), 7.89 (s, 1H), 7.81 (d, J=7.9 Hz, 1H), 7.52-7.46 (m, 3H), 7.35-7.24 (m, 3H), 6.68 (d, J=9.0 Hz, 1H), 6.38 (s, 1H), 6.17 (s, 1H), 4.61 (d, J=7.5 Hz, 1H), 3.86 (d, J=8.1 Hz, 1H), 3.75-3.62 (m, 6H), 3.52-3.43 (m, 2H), 3.17-2.94 (m, 3H), 2.78-2.75 (m, 1H), 2.65-2.58 (m, 1H), 2.43-2.42 (m, 1H), 2.19-1.95 (m, 7H), 1.84-1.74 (m, 4H), 1.45-1.34 (m, 5H), 1.12 (t, J=7.5 Hz, 3H). MS (ESI, m/e) [M+1]$^+$ 866.8.

Example F26: 2-((1H-pyrrolo[2,3-b]pyridin-5-yl)oxy)-4-(2-((S)-2-(2-ethylphenyl)pyrrolidin-1-yl)-7-azaspiro[3.5]nonan-7-yl)-N-((4-((((1r,4r)-4-hydroxy-4-methylcyclohexyl)methyl)amino)-3-nitrophenyl)sulfonyl)benzamide

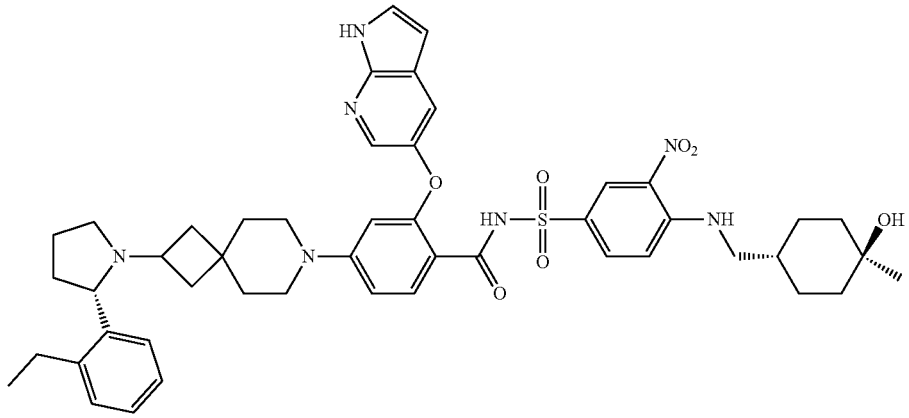 [SMILES: CCc1ccccc1[C@@H]1CCCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1]

The desired compound was synthesized following the procedures similar to those in Example F21 by replacing (S)-2-(2-cyclopropylphenyl)pyrrolidine with (S)-2-(2-ethylphenyl)pyrrolidine. $^1$H NMR (DMSO-$d_6$) δ ppm: 11.70 (s, 1H), 11.44 (s, 1H), 10.67 (s, 1H), 8.58-8.55 (m, 2H), 8.03 (d, J=2.2 Hz, 1H), 7.78 (d, J=9.2 Hz, 1H), 7.51-7.46 (m, 3H), 7.30-7.22 (m, 3H), 7.08 (d, J=9.2 Hz, 1H), 6.68 (d, J=8.4 Hz, 1H), 6.38 (s, 1H), 6.17 (s, 1H), 4.60 (d, J=8.0 Hz, 1H), 4.25 (s, 1H), 3.86 (d, J=8.3 Hz, 1H), 3.66 (s, 1H), 3.30-3.26 (m, 2H), 3.08-2.94 (m, 3H), 2.78-2.58 (m, 2H), 2.44-2.42 (m, 1H), 2.20-1.96 (m, 7H), 1.69-1.66 (m, 3H), 1.52-1.45 (m, 2H), 1.33-1.24 (m, 8H), 1.14-1.12 (m, 6H). MS (ESI, m/e) [M+1]$^+$ 876.9.

Example F27: (R)-2-((1H-pyrrolo[2,3-b]pyridin-5-yl)oxy)-4-(2-(2-(2-cyclopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide

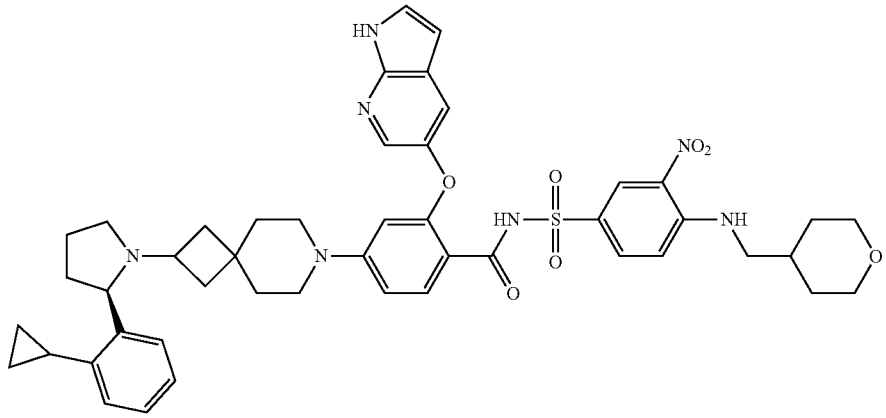 [SMILES: O=C(NS(=O)(=O)c1ccc(NCC2CCOCC2)c([N+](=O)[O-])c1)c1ccc(N2CCC3(CC2)CC(N2CCC[C@@H]2c2ccccc2C2CC2)C3)cc1Oc1cnc2[nH]ccc2c1]

The desired compound was synthesized following the procedures similar to those in Example F21 by replacing (S)-2-(2-cyclopropylphenyl)pyrrolidine with (R)-2-(2-cyclopropylphenyl)pyrrolidine, and replacing 4-((((1r,4r)-4-hydroxy-4-methylcyclohexyl)methyl)amino)-3-nitrobenzenesulfonamide with 3-nitro-4-(((tetrahydro-2H-pyran-4-yl)methyl)amino)benzenesulfonamide. $^1$H NMR (DMSO-d$_6$) δ ppm: 11.69 (s, 1H), 11.44 (s, 1H), 10.37 (s, 1H), 8.61 (s, 1H), 8.56 (s, 1H), 8.03 (d, J=1.8 Hz, 1H), 7.85-7.76 (m, 2H), 7.55-7.45 (m, 3H), 7.28 (s, 2H), 7.14-6.99 (m, 2H), 6.69 (d, J=8.7 Hz, 1H), 6.38 (s, 1H), 6.17 (s, 1H), 4.97 (s, 1H), 3.85 (d, J=8.5 Hz, 3H), 3.67-3.61 (m, 1H), 3.30-3.21 (m, 4H), 3.08-3.01 (m, 2H), 2.98-2.91 (m, 2H), 2.12-2.05 (m, 4H), 1.92-1.87 (m, 1H), 1.66-1.58 (m, 3H), 1.53-1.45 (m, 1H), 1.44-1.36 (m, 4H), 1.30-1.22 (m, 4H), 0.98-0.93 (m, 2H), 0.86-0.80 (m, 3H), 0.69-0.60 (s, 2H). MS (ESI, m/e) [M+1]$^+$ 859.8.

Example F28: (R)-2-((1H-pyrrolo[2,3-b]pyridin-5-yl)oxy)-4-(2-(2-(2-cyclopropylphenyl)pyrrolidin-1-yl)-7-azaspiro[3.5]nonan-7-yl)-N-((4-(((4-fluorotetrahydro-2H-pyran-4-yl)methyl)amino)-3-nitrophenyl)sulfonyl)benzamide

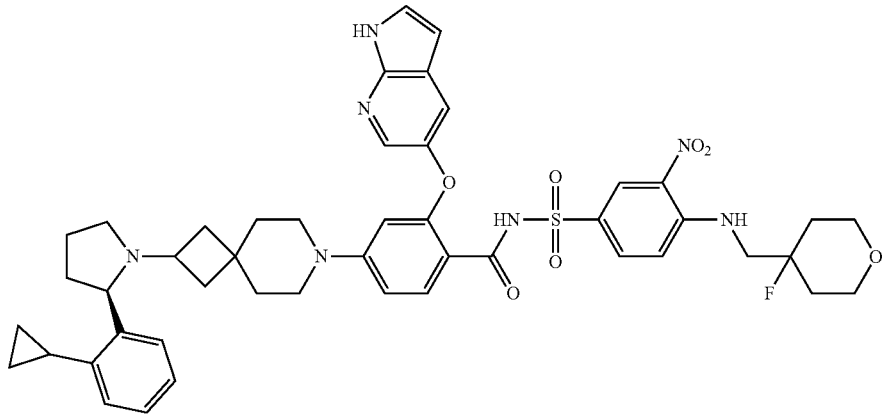 [SMILES: O=C(NS(=O)(=O)c1ccc(NCC2(F)CCOCC2)c([N+](=O)[O-])c1)c1ccc(N2CCC3(CC2)CC(N2CCC[C@@H]2c2ccccc2C2CC2)C3)cc1Oc1cnc2[nH]ccc2c1]

The desired compound was synthesized following the procedures similar to those in Example F21 by replacing (S)-2-(2-cyclopropylphenyl)pyrrolidine with (R)-2-(2-cyclopropylphenyl)pyrrolidine, and replacing 4-((((1r,4r)-4-hydroxy-4-methylcyclohexyl)methyl)amino)-3-nitrobenzenesulfonamide with 4-(((4-fluorotetrahydro-2H-pyran-4-yl)methyl)amino)-3-nitrobenzenesulfonamide. $^1$H NMR (DMSO-d$_6$) δ ppm: 11.69 (s, 1H), 11.04 (s, 1H), 8.62 (s, 1H), 8.55 (s, 1H), 8.02 (s, 1H), 7.80 (d, J=8.8 Hz, 1H), 7.54-7.49 (m, 2H), 7.24-7.21 (m, 2H), 7.05 (s, 1H), 6.68 (d, J=8.0 Hz, 1H), 6.37 (s, 1H), 6.17 (s, 1H), 4.95 (s, 1H), 3.80-3.70 (m, 5H), 3.57-3.47 (m, 2H), 3.15-2.95 (m, 6H), 2.17-2.95 (m, 5H), 1.86-1.72 (m, 4H), 1.50-1.31 (m, 6H), 0.98-0.91 (m, 2H), 0.87-0.79 (m, 2H), 0.70-0.59 (s, 2H). MS (ESI, m/e) [M+1]$^+$ 877.8.

Example F29: 2-((1H-pyrrolo[2,3-b]pyridin-5-yl)oxy)-4-(2-((R)-2-(2-cyclopropylphenyl)pyrrolidin-1-yl)-7-azaspiro[3.5]nonan-7-yl)-N-((4-((((1r,4r)-4-hydroxy-4-methylcyclohexyl)methyl)amino)-3-nitrophenyl)sulfonyl)benzamide

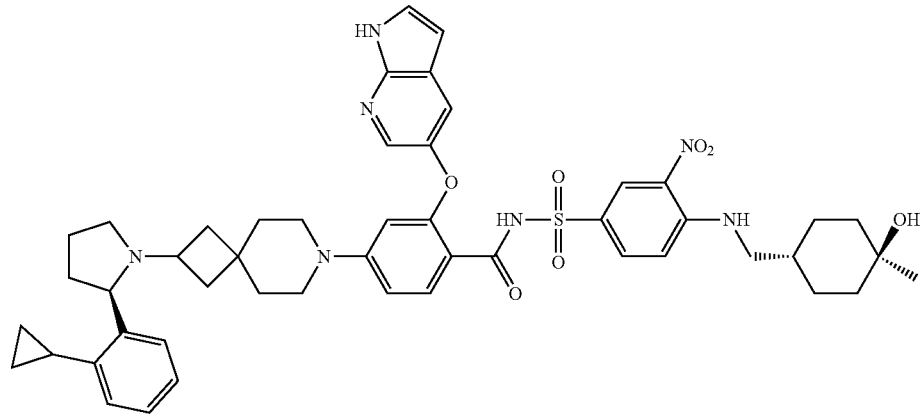 [SMILES: C[C@]1(O)CC[C@H](CNc2ccc(S(=O)(=O)NC(=O)c3ccc(N4CCC5(CC4)CC(N4CCC[C@@H]4c4ccccc4C4CC4)C5)cc3Oc3cnc4[nH]ccc4c3)cc2[N+](=O)[O-])CC1]

The desired compound was synthesized following the procedures similar to those in Example F21 by replacing (S)-2-(2-cyclopropylphenyl)pyrrolidine with (R)-2-(2-cyclopropylphenyl)pyrrolidine. ¹H NMR (DMSO-d₆) δ ppm: 11.69 (s, 1H), 10.88 (s, 1H), 9.76 (s, 1H), 8.55 (s, 2H), 8.21 (d, J=5.6 Hz, 1H), 8.07-7.95 (m, 2H), 7.78 (d, J=8.4 Hz, 1H), 7.53-7.48 (m, 2H), 7.27 (s, 1H), 7.13-7.05 (m, 2H), 6.98 (s, 1H), 6.68 (d, J=8.4 Hz, 1H), 6.38 (s, 1H), 6.17 (s, 1H), 5.01-4.93 (m, 1H), 4.32-4.28 (m, 1H), 3.89-3.81 (m, 1H), 3.72-3.65 (m, 1H), 2.97-2.88 (m, 4H), 2.25-2.08 (m, 5H), 1.78-1.60 (m, 4H), 1.58-1.54 (m, 2H), 1.47-1.38 (m, 5H), 1.36-1.29 (m, 3H), 1.27-1.23 (m, 2H), 1.16-1.12 (m, 2H), 1.10 (s, 3H), 1.01-0.89 (m, 2H), 0.86-0.82 (m, 1H), 0.70-0.58 (m, 2H). MS (ESI, m/e) [M+1]⁺ 888.9.

Example F30: (S)-2-((1H-pyrrolo[2,3-b]pyridin-5-yl)oxy)-4-(7-(2-(2-cyclopropylphenyl)pyrrolidin-1-yl)-2-azaspiro[3.5]nonan-2-yl)-N-((3-nitro-4-(((tetrahydro-2H-pyran-4-yl)methyl)amino)phenyl)sulfonyl)benzamide

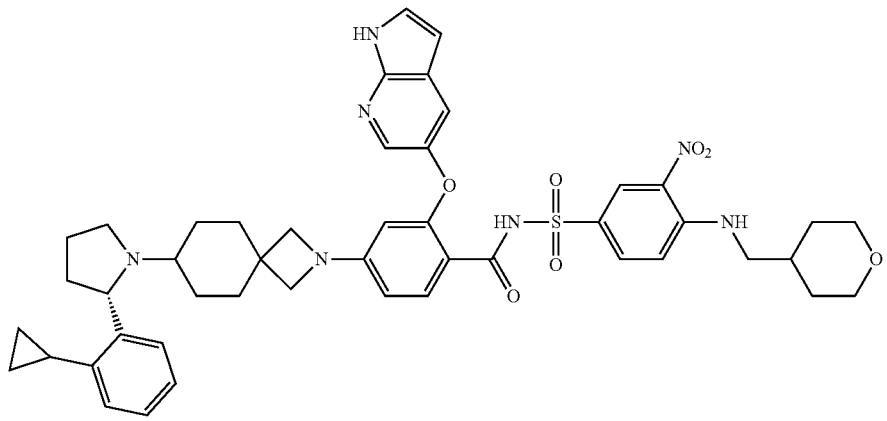 [SMILES: O=C(NS(=O)(=O)c1ccc(NCC2CCOCC2)c([N+](=O)[O-])c1)c1ccc(N2CC3(CCC(N4CCC[C@H]4c4ccccc4C4CC4)CC3)C2)cc1Oc1cnc2[nH]ccc2c1]

The desired compound was synthesized following the procedures similar to those in Example F21 by replacing tert-butyl 2-oxo-7-azaspiro[3.5]nonane-7-carboxylate with tert-butyl 7-oxo-2-azaspiro[3.5]nonane-2-carboxylate, and replacing 4-((((1r,4r)-4-hydroxy-4-methylcyclohexyl)methyl)amino)-3-nitrobenzenesulfonamide with 3-nitro-4-(((tetrahydro-2H-pyran-4-yl)methyl)amino)benzenesulfonamide. ¹H NMR (DMSO-d₆) δ ppm: 11.76 (s, 1H), 11.28 (s, 1H), 8.69-8.55 (m, 2H), 8.08 (s, 1H), 7.96 (s, 1H), 7.89-7.59 (m, 3H), 7.56-7.44 (m, 2H), 7.34-7.23 (m, 1H), 7.23-7.13 (m, 1H), 7.09-6.85 (m, 2H), 6.44 (s, 1H), 6.14-6.06 (m, 1H), 5.55-5.43 (m, 1H), 5.21-4.18 (m, 1H), 3.90-3.81 (m, 2H), 3.47-3.36 (m, 3H), 3.31-3.17 (m, 5H), 3.07-2.94 (m, 2H), 2.12-1.94 (m, 3H), 1.92-1.75 (m, 5H), 1.73-1.66 (m, 2H), 1.65-1.55 (m, 3H), 1.36-1.27 (m, 3H), 0.94-0.79 (m, 3H), 0.78-0.61 (m, 2H), 0.56-0.45 (m, 1H). MS (ESI, m/e) [M+1]⁺ 859.8.

Example F31: (R)-2-((1H-pyrrolo[2,3-b]pyridin-5-yl)oxy)-4-(7-(2-(2-cyclopropylphenyl)pyrrolidin-1-yl)-2-azaspiro[3.5]nonan-2-yl)-N-((3-nitro-4-(((tetrahydro-2H-pyran-4-yl)methyl)amino)phenyl)sulfonyl)benzamide

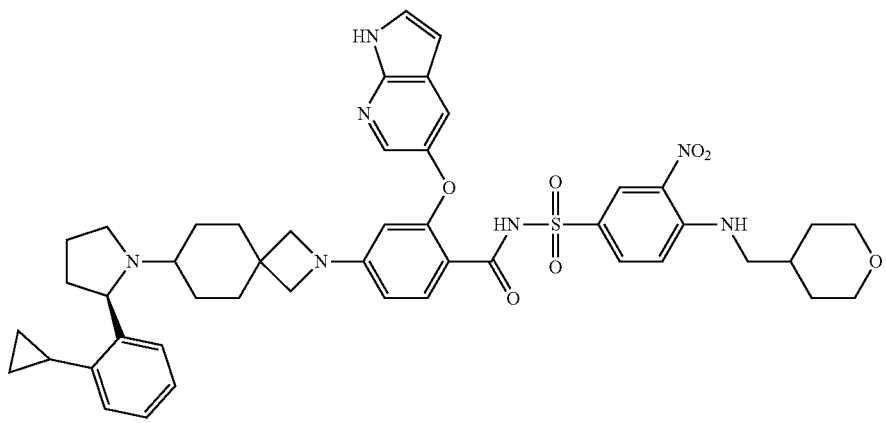 [SMILES: O=C(NS(=O)(=O)c1ccc(NCC2CCOCC2)c([N+](=O)[O-])c1)c1ccc(N2CC3(CCC(N4CCC[C@@H]4c4ccccc4C4CC4)CC3)C2)cc1Oc1cnc2[nH]ccc2c1]

The desired compound was synthesized following the procedures similar to those in Example F30 by replacing (S)-2-(2-cyclopropylphenyl)pyrrolidine with (R)-2-(2-cyclopropylphenyl)pyrrolidine. ¹H NMR (DMSO-d₆) δ ppm: 11.78 (s, 1H), 11.42-11.09 (m, 0.5H), 9.97-9.53 (m, 0.5H), 8.78-8.42 (m, 2H), 8.14-8.06 (m, 1H), 7.97-7.75 (m, 2H), 7.75-7.62 (m, 1H), 7.62-7.43 (m, 2H), 7.42-7.10 (m, 3H), 7.10-6.84 (m, 1H), 6.45 (s, 1H), 6.20-6.00 (m, 1H), 5.47 (s, 1H), 5.22-4.96 (m, 1H), 3.94-3.75 (m, 2H), 3.70-3.54 (m, 1H), 3.54-3.37 (m, 6H), 3.31-3.13 (m, 4H), 3.08-2.91 (m, 1H), 2.21-1.49 (m, 10H), 1.40-1.15 (m, 6H), 1.00-0.81 (m, 2H), 0.80-0.43 (m, 2H). MS (ESI, m/e) [M+1]⁺ 859.8.

Example F32: (S)-2-((1H-pyrrolo[2,3-b]pyridin-5-yl)oxy)-4-(9-(2-(2-cyclopropylphenyl)pyrrolidin-1-yl)-3-azaspiro[5.5]undecan-3-yl)-N-((3-nitro-4-(((tetrahydro-2H-pyran-4-yl)methyl)amino)phenyl)sulfonyl)benzamide

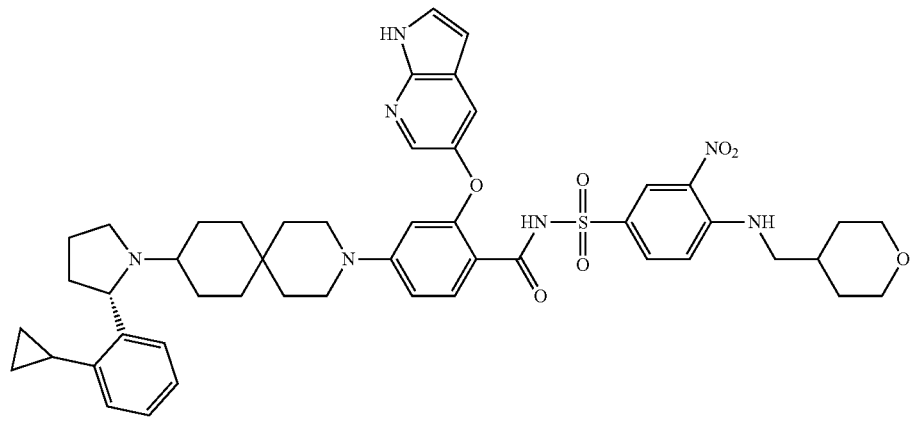 [SMILES: O=C(NS(=O)(=O)c1ccc(NCC2CCOCC2)c([N+](=O)[O-])c1)c1ccc(N2CCC3(CCC(N4CCC[C@H]4c4ccccc4C4CC4)CC3)CC2)cc1Oc1cnc2[nH]ccc2c1]

The desired compound was synthesized following the procedures similar to those in Example F21 by replacing tert-butyl 2-oxo-7-azaspiro[3.5]nonane-7-carboxylate with tert-butyl 9-oxo-3-azaspiro[5.5]undecane-3-carboxylate, and replacing 4-((((1r,4r)-4-hydroxy-4-methylcyclohexyl)methyl)amino)-3-nitrobenzenesulfonamide with 3-nitro-4-(((tetrahydro-2H-pyran-4-yl)methyl)amino)benzenesulfonamide. ¹H NMR (DMSO-d₆) δ ppm: 11.73 (s, 1H), 11.41 (s, 1H), 10.37 (s, 1H), 8.65-8.60 (m, 1H), 8.58 (d, J=2.2 Hz, 1H), 8.10-8.00 (m, 1H), 7.81 (d, J=9.5 Hz, 1H), 7.57 (d, J=2.2 Hz, 1H), 7.54-7.43 (m, 2H), 7.32-7.22 (m, 2H), 7.14 (d, J=9.3 Hz, 1H), 7.10-7.00 (m, 1H), 6.68 (d, J=9.0 Hz, 1H), 6.45-6.32 (m, 1H), 6.13 (s, 1H), 5.15-5.05 (m, 1H), 3.88-3.80 (m, 2H), 3.70-3.60 (m, 1H), 3.31-3.21 (m, 5H), 3.10-3.00 (m, 2H), 2.22-2.00 (m, 4H), 1.90-1.81 (m, 2H), 1.80-1.51 (m, 7H), 1.45-1.35 (m, 4H), 1.05-0.90 (m, 6H), 0.88-0.72 (m, 4H). MS (ESI, m/e) [M+1]⁺ 887.8.

Example F33: (R)-2-((1H-pyrrolo[2,3-b]pyridin-5-yl)oxy)-4-(9-(2-(2-cyclopropylphenyl)pyrrolidin-1-yl)-3-azaspiro[5.5]undecan-3-yl)-N-((3-nitro-4-(((tetrahydro-2H-pyran-4-yl)methyl)amino)phenyl)sulfonyl)benzamide

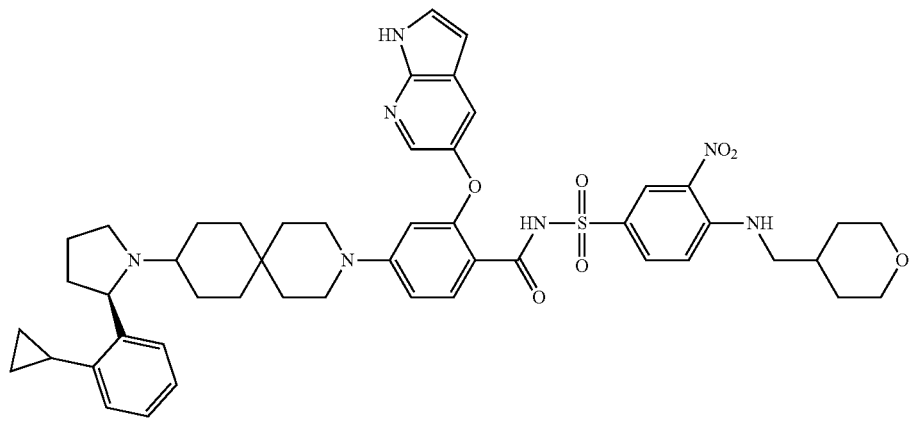 [SMILES: O=C(NS(=O)(=O)c1ccc(NCC2CCOCC2)c([N+](=O)[O-])c1)c1ccc(N2CCC3(CCC(N4CCC[C@@H]4c4ccccc4C4CC4)CC3)CC2)cc1Oc1cnc2[nH]ccc2c1]

The desired compound was synthesized following the procedures similar to those in Example F32 by replacing (S)-2-(2-cyclopropylphenyl)pyrrolidine with (R)-2-(2-cyclopropylphenyl)pyrrolidine. $^1$H NMR (DMSO-d$_6$) δ ppm: 11.72 (s, 1H), 11.40 (s, 1H), 8.70-8.53 (m, 2H), 8.06 Id, J=2.3 Hz, 1H), 7.82 Id, J=9.1 Hz, 1H), 7.52 (dd, J=19.0, 15.6 Hz, 3H), 7.29 (s, 2H), 7.14 (d, J=9.1 Hz, 1H), 7.10-7.05 (m, 2H), 6.40 (s, 1H), 6.13 (s, 1H), 5.15-5.10 (m, 1H), 3.85 (d, J=8.3 Hz, 2H), 3.70-3.60 (m, 1H), 3.30-3.20 (m, 4H), 3.10-3.2.95 (m, 5H), 2.15-2.05 (m, 3H), 1.95-1.85 (m, 2H), 1.80-1.50 (m, 7H), 1.45-1.35 (m, 3H), 1.34-1.12 (m, 6H), 1.00-0.90 (m, 4H), 0.80-0.70 (m, 1H), 0.60-0.50 (m, 1H). MS (ESI, m/e) [M+1]$^+$ 887.8.

Example F34: (S)-2-((1H-pyrrolo[2,3-b]pyridin-5-yl)oxy)-4-(6-(2-(2-cyclopropylphenyl)pyrrolidin-1-yl)-2-azaspiro[3.3]heptan-2-yl)-N-((3-nitro-4-(((tetrahydro-2H-pyran-4-yl)methyl)amino)phenyl)sulfonyl)benzamide

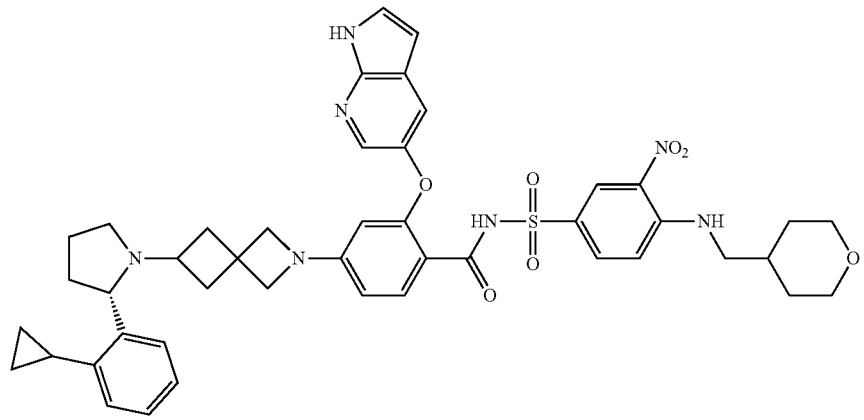 [SMILES: O=C(NS(=O)(=O)c1ccc(NCC2CCOCC2)c([N+](=O)[O-])c1)c1ccc(N2CC3(CC(N4CCC[C@H]4c4ccccc4C4CC4)C3)C2)cc1Oc1cnc2[nH]ccc2c1]

The desired compound was synthesized following the procedures similar to those in Example F21 by replacing tert-butyl 2-oxo-7-azaspiro[3.5]nonane-7-carboxylate with tert-butyl 6-oxo-2-azaspiro[3.3]heptane-2-carboxylate, and replacing 4-((((1r,4r)-4-hydroxy-4-methylcyclohexyl)methyl)amino)-3-nitrobenzenesulfonamide with 3-nitro-4-(((tetrahydro-2H-pyran-4-yl)methyl)amino)benzenesulfonamide. $^1$H NMR (400 MHz, DMSO-d$_6$) δ ppm: 11.74 (s, 1H), 11.35 (br, 1H), 8.64 (t, J=6.0 Hz, 2H), 8.59 (s, 1H), 8.06 (d, J=2.0 Hz, 1H), 7.85 (d, J=8.0 Hz, 1H), 7.69-7.60 (m, 2H), 7.55-7.52 (m, 1H), 7.48 (d, J=8.8 Hz, 1H), 7.33-7.23 (m, 2H), 7.18 (d, J=9.6 Hz, 1H), 7.06 (s, 1H), 6.42 (s, 1H), 6.09 (d, J=8.8 Hz, 1H), 5.49 (s, 1H), 5.02-4.82 (m, 1H), 3.85 (d, J=8.4 Hz, 2H), 3.79-3.56 (m, 6H), 3.31-3.23 (m, 6H), 2.50-2.38 (m, 1H), 2.18-1.72 (m, 7H), 1.62 (d, J=12.8 Hz, 2H), 1.34-1.22 (m, 2H), 1.02-0.88 (m, 2H), 0.70-0.58 (m, 2H). MS (ESI, m/e) [M+1]$^+$ 832.7.

Example F35: (R)-2-((1H-pyrrolo[2,3-b]pyridin-5-yl)oxy)-4-(6-(2-(2-cyclopropylphenyl)pyrrolidin-1-yl)-2-azaspiro[3.3]heptan-2-yl)-N-((3-nitro-4-(((tetrahydro-2H-pyran-4-yl)methyl)amino)phenyl)sulfonyl)benzamide

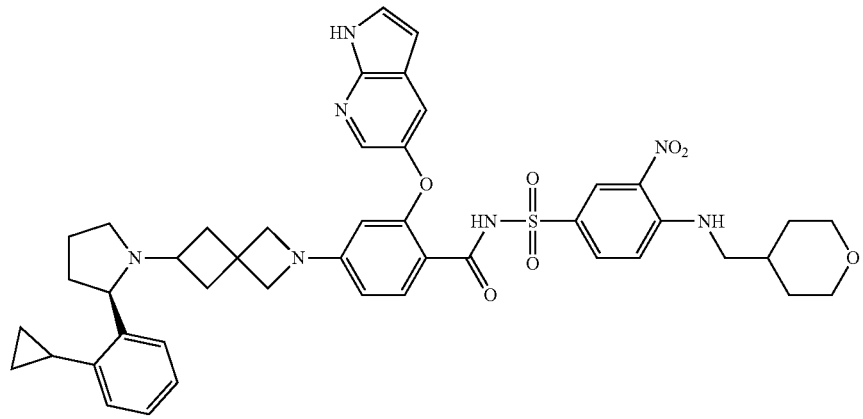 [SMILES: O=C(NS(=O)(=O)c1ccc(NCC2CCOCC2)c([N+](=O)[O-])c1)c1ccc(N2CC3(CC(N4CCC[C@@H]4c4ccccc4C4CC4)C3)C2)cc1Oc1cnc2[nH]ccc2c1]

The desired compound was synthesized following the procedures similar to those in Example F34 by replacing (S)-2-(2-cyclopropylphenyl)pyrrolidine with (R)-2-(2-cyclopropylphenyl)pyrrolidine. ¹H NMR (400 MHz, DMSO-d₆) δ ppm: 11.66 (s, 1H), 11.23 (br, 1H), 8.60-8.45 (m, 2H), 8.00 (s, 1H), 7.78 (d, J=7.6 Hz, 1H), 7.59-7.43 (m, 4H), 7.15-7.00 (m, 3H), 6.92 (d, J=6.8 Hz, 1H), 6.38 (s, 1H), 6.06 (d, J=8.4 Hz, 1H), 5.54 (s, 1H), 4.05-3.82 (m, 3H), 3.70-3.50 (m, 4H), 3.35-3.21 (m, 4H), 3.15-2.90 (m, 2H), 2.41-1.95 (m, 5H), 1.93-1.70 (m, 5H), 1.63 (d, J=12.4 Hz, 2H), 1.56-1.27 (m, 3H), 0.92-1.81 (m, 2H), 0.67-0.46 (m, 2H), MS (ESI, m/e) [M+1]⁺ 832.8.

Example F36: 2-((1H-pyrrolo[2,3-b]pyridin-5-yl)oxy)-4-(2-(2-(3-chloro-2-(dimethylamino)phenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide

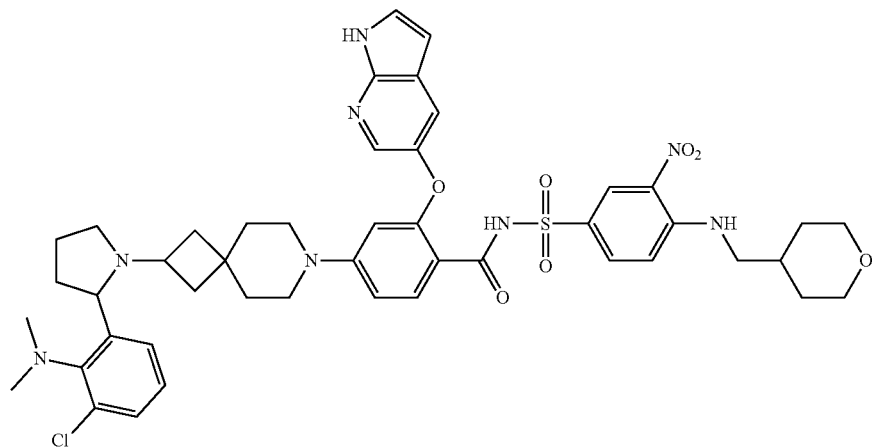 [SMILES: CN(C)c1c(Cl)cccc1C1CCCN1C1CC2(CCN(c3ccc(C(=O)NS(=O)(=O)c4ccc(NCC5CCOCC5)c([N+](=O)[O-])c4)c(Oc4cnc5[nH]ccc5c4)c3)CC2)C1]

The desired compound was synthesized following the procedures similar to those in Example F21 by replacing (S)-2-(2-cyclopropylphenyl)pyrrolidine with 2-chloro-N,N-dimethyl-6-(pyrrolidin-2-yl)aniline, and replacing 4-((((1r,4r)-4-hydroxy-4-methylcyclohexyl)methyl)amino)-3-nitrobenzenesulfonamide with 3-nitro-4-(((tetrahydro-2H-pyran-4-yl)methyl)amino)benzenesulfonamide. ¹H NMR (DMSO-d₆) δ ppm: 11.70 (s, 1H), 11.45 (s, 1H), 11.16 (s, 1H), 8.70-8.60 (m, 1H), 8.58 (s, 1H), 8.15-7.93 (m, 2H), 7.76 (d, J=9.3 Hz, 1H), 7.58-7.37 (m, 3H), 7.35-7.25 (m, 1H), 7.11 (d, J=9.3 Hz, 1H), 6.75-6.65 (m, 1H), 6.40-6.35 (m, 1H), 6.18 (s, 1H), 4.98 (s, 1H), 3.85 (d, J=8.8 Hz, 2H), 3.81-3.58 (m, 3H), 3.30-3.20 (m, 5H), 3.10-2.76 (m, 4H), 2.75-2.56 (m, 6H), 2.45-2.40 (m, 1H), 2.21-2.00 (m, 4H), 1.90-1.75 (m, 2H), 1.65-1.50 (m, 3H), 1.45-1.40 (m, 3H), 1.25-1.10 (m, 3H). MS (ESI, m/e) [M+1]⁺ 896.8.

Example F37: N-((4-((((S)-1,4-dioxan-2-yl)methyl)amino)-3-nitrophenyl)sulfonyl)-2-((1H-pyrrolo[2,3b]pyridin-5-yl)oxy)-4-(2-((S)-2-(2-cyclopropylphenyl)pyrrolidin-1-yl)-7-azaspiro[3.5]nonan-7-yl) benzamide

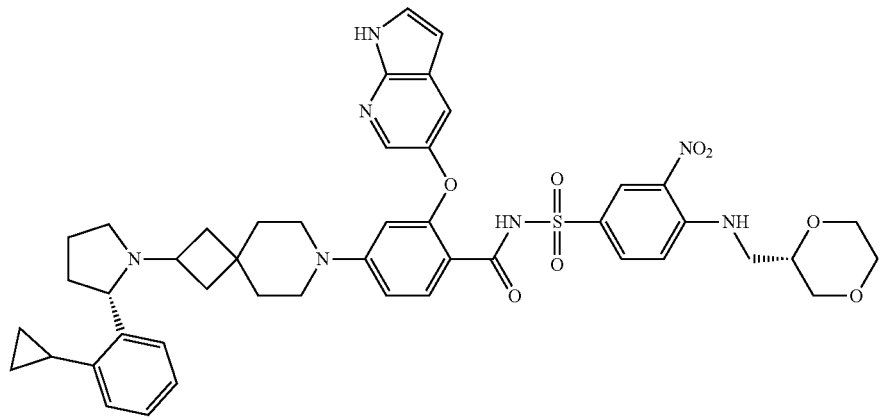 [SMILES: O=C(NS(=O)(=O)c1ccc(NC[C@H]2COCCO2)c([N+](=O)[O-])c1)c1ccc(N2CCC3(CC2)CC(N2CCC[C@H]2c2ccccc2C2CC2)C3)cc1Oc1cnc2[nH]ccc2c1]

The desired compound was synthesized with (S)-4-(((1,4-dioxan-2-yl)methyl)amino)-3-nitrobenzenesulfonamide and (S)-2-((1H-pyrrolo[2,3-b]pyridin-5-yl)oxy)-4-(2-(2-(2-cyclopropylphenyl)pyrrolidin-1-yl)-7-azaspiro[3.5]nonan-7-yl)benzoic acid following the procedures similar to those in Example F21. $^1$H NMR (DMSO-d$_6$) δ ppm: 11.81 (s, 1H), 11.28 (br, 1H), 8.68-8.34 (m, 2H), 8.01 (s, 1H), 7.78 (d, J=8.41 Hz, 1H), 7.66-7.40 (m, 4H), 7.33-6.87 (m, 4H), 6.67 (d, J=8.8 Hz, 1H), 6.37 (s, 1H), 6.18 (s, 1H), 3.86-3.57 (m, 6H), 3.53-3.37 (m, 3H), 3.28-2.77 (m, 7H), 2.23-1.70 (m, 6H), 1.67-1.17 (m, 8H), 0.99-0.84 (m, 2H), 0.69-0.51 (m, 2H). MS (ESI, m/e) [M+1]$^+$ 862.8. MS (ESI, m/e) [M+1]$^+$ 862.8.

Example F38: N-((4-((((R)-1,4-dioxan-2-yl)methyl)amino)-3-nitrophenyl)sulfonyl)-2-((1H-pyrrolo[2,3-b]pyridin-5-yl)oxy)-4-(2-((S)-2-(2-cyclopropylphenyl)pyrrolidin-1-yl)-7-azaspiro[3.5]nonan-7-yl)benzamide

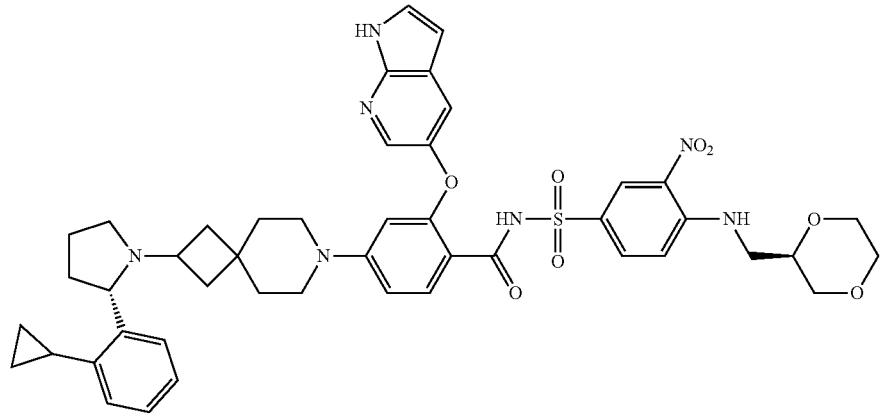 [SMILES: O=C(NS(=O)(=O)c1ccc(NC[C@@H]2COCCO2)c([N+](=O)[O-])c1)c1ccc(N2CCC3(CC2)CC(N2CCC[C@H]2c2ccccc2C2CC2)C3)cc1Oc1cnc2[nH]ccc2c1]

The desired compound was synthesized with (R)-4-(((1,4-dioxan-2-yl)methyl)amino)-3-nitrobenzenesulfonamide and (S)-2-((1H-pyrrolo[2,3-b]pyridin-5-yl)oxy)-4-(2-(2-(2-cyclopropylphenyl)pyrrolidin-1-yl)-7-azaspiro[3.5]nonan-7-yl)benzoic acid following the procedures similar to those in Example F21. $^1$H NMR (DMSO-d$_6$) δ ppm: 11.68 (s, 1H), 10.11 (s, 1H), 8.58-8.55 (m, 2H), 8.22 (d, J=7.3 Hz, 1H), 8.03 (d, J=2.2 Hz, 1H), 7.86-7.63 (m, 2H), 7.52-7.46 (m, 2H), 7.28 (s, 2H), 7.10-7.06 (m, 2H), 6.98 (d, J=7.3 Hz, 1H), 6.68 (d, J=9.2 Hz, 1H), 6.37 (s, 1H), 6.18 (s, 1H), 4.98 (s, 1H), 3.81-3.77 (m, 3H), 3.69-3.57 (m, 3H), 3.54-3.44 (m, 2H), 3.44-3.36 (m, 1H), 3.18 (s, 4H), 3.05 (s, 1H), 2.95 (s, 2H), 2.15-1.96 (m, 6H), 1.53 (s, 1H), 1.44-1.37 (m, 4H), 1.25 (s, 2H), 1.04-0.93 (m, 2H), 0.85 (t, J=6.6 Hz, 1H), 0.64 (s, 2H). MS (ESI, m/e) [M+1]$^+$ 862.8.

Example F39a and Example F39b: (S or R) 2-((1H-pyrrolo[2,3-b]pyridin-5-yl)oxy)-4-(2-((S)-2-(2-cyclopropylphenyl)pyrrolidin-1-yl)-8-azaspiro[4.5]decan-8-yl)-N-((3-nitro-4-(((tetrahydro-2H-pyran-4-yl)methyl)amino)phenyl)sulfonyl)benzamide/(R or S) 2-((1H-pyrrolo[2,3-b]pyridin-5-yl)oxy)-4-(2-((S)-2-(2-cyclopropylphenyl)pyrrolidin-1-yl)-8-azaspiro[4.5]decan-8-yl)-N-((3-nitro-4-(((tetrahydro-2H-pyran-4-yl)methyl)amino)phenyl)sulfonyl)benzamide

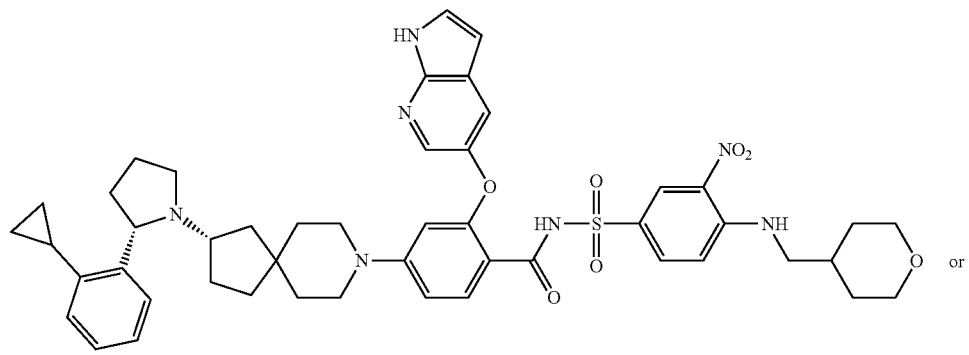

or

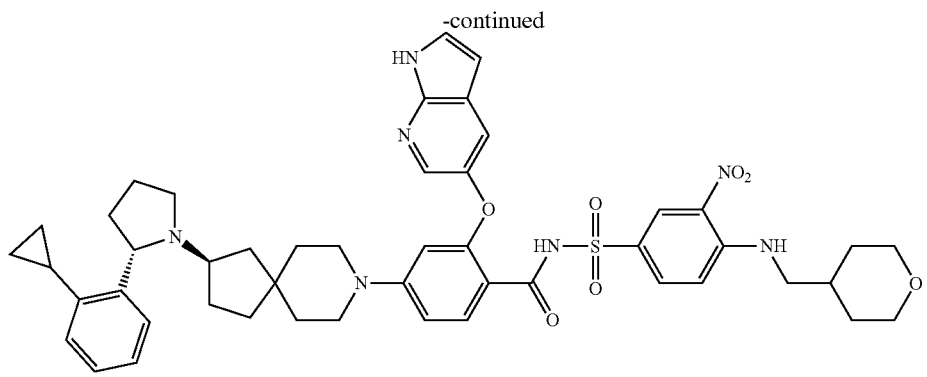

The desired compounds were synthesized following the procedures similar to those in Example F21 by replacing tert-butyl 2-oxo-7-azaspiro[3.5]nonane-7-carboxylate with tert-butyl 2-oxo-8-azaspiro[4.5]decane-8-carboxylate, and replacing 4-((((1r,4r)-4-hydroxy-4-methylcyclohexyl)methyl)amino)-3-nitrobenzenesulfonamide with 3-nitro-4-(((tetrahydro-2H-pyran-4-yl)methyl)amino)benzenesulfonamide, After separation and purification with prep-HPLC, F39a was obtained as faster peak in HPLC. $^1$H NMR (DMSO-d$_6$) δ ppm: 11.72 (s, 1H), 11.45 (s, 1H), 9.33 (s, 1H), 8.70-8.52 (m, 2H), 8.05 (d, J=2.1 Hz, 1H), 7.81 (d, J=9.2 Hz, 1H), 7.56-7.48 (m, 4H), 7.36-7.24 (m, 2H), 7.14 (d, J=9.2 Hz, 1H), 7.10-6.97 (m, 1H), 6.68 (d, J=8.6 Hz, 1H), 6.40 (s, 1H), 6.13 (s, 1H), 5.12-5.06 (m, 1H), 3.85 (d, J=8.4 Hz, 2H), 3.72 (d, J=6.8 Hz, 2H), 3.33-3.25 (m, 4H), 3.11-3.04 (m, 2H), 2.99-2.91 (m, 2H), 2.85-2.77 (m, 1H), 2.21-2.10 (m, 2H), 2.07-1.95 (m, 4H), 1.94-1.84 (m, 2H), 1.63-1.60 (m, 2H), 1.46-1.39 (m, 3H), 1.33-1.25 (m, 6H), 0.96-0.94 (m, 2H), 0.86-0.84 (m, 2H), 0.76-0.68 (m, 1H), 0.62-0.54 (m, 1H). MS (ESI, m/e) [M+1]$^+$ 874.8; F39b was obtained as slower peak in HPLC, $^1$H NMR (DMSO-d$_6$) δ ppm: 11.72 (s, 1H), 11.44 (s, 1H), 9.41 (s, 1H), 8.71-8.55 (m, 2H), 8.06 (d, J=2.2 Hz, 1H), 7.81 (d, J=8.0 Hz, 1H), 7.65-7.45 (m, 4H), 7.37-7.25 (m, 2H), 7.18-7.03 (m, 3H), 6.73 (d, J=8.3 Hz, 1H), 6.40 (s, 1H), 6.18 (s, 1H), 5.10-5.04 (m, 1H), 3.85 (d, J=8.5 Hz, 2H), 3.74-3.72 (m, 2H), 3.30-3.24 (m, 5H), 3.10 (s, 3H), 2.98 (s, 1H), 2.19-2.04 (m, 4H), 1.99-1.88 (m, 5H), 1.63-. 160 (m, 3H), 1.50-1.45 (m, 2H), 1.38-1.27 (m, 5H), 0.95-0.91 (m, 2H), 0.89-0.84 (m, 2H), 0.66 (s, 2H). MS (ESI, m/e) [M+1]$^+$ 874.8.

Example F40: N-((4-((((S)-1,4-dioxan-2-yl)methyl)amino)-3-nitrophenyl)sulfonyl)-2-((1H-pyrrolo[2,3-b]pyridin-5-yl)oxy)-4-(2-((S)-2-(2-ethylphenyl)pyrrolidin-1-yl)-7-azaspiro[3.5]nonan-7-yl)benzamide

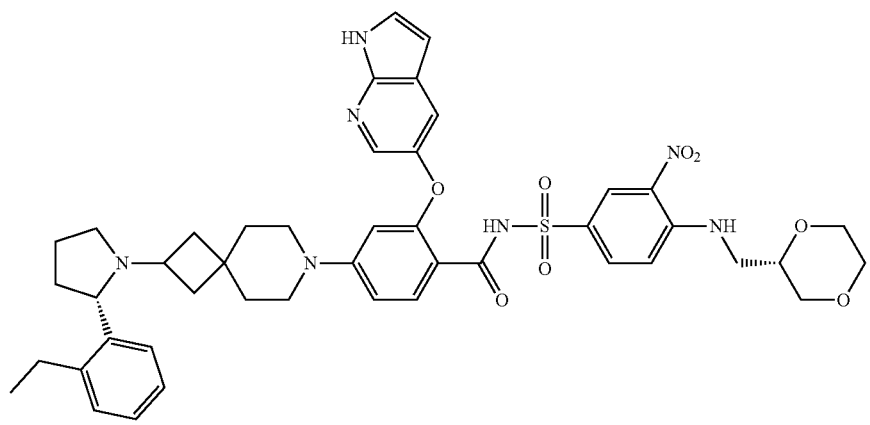 [SMILES: CCc1ccccc1[C@@H]1CCCN1C1CC2(CCN(c3ccc(C(=O)NS(=O)(=O)c4ccc(NC[C@H]5COCCO5)c([N+](=O)[O-])c4)c(Oc4cnc5[nH]ccc5c4)c3)CC2)C1]

Step 1: 7-azaspiro[3.5]nonan-2-one hydrochloride

A solution of tert-butyl 2-oxo-7-azaspiro[3.5]nonane-7-carboxylate (47.8 g, 200 mmol) in HCl/dioxane solution (150 mL, 4 mol/L) and DCM (300 mL) was stirred at room temperature overnight. After removal of solvent by vacuum, 7-azaspiro[3.5]nonan-2-one hydrochloride was obtained as a pale yellow solid.

Step 2: methyl 2-((1H-pyrrolo[2,3-b]pyridin-5-yl)oxy)-4-(2-oxo-7-azaspiro[3.5]nonan-7-yl)benzoate 2-((1H-pyrrolo[2,3-b]pyridin-5-yl)oxy)-4-fluorobenzoate (2.08 g, 7.3 mmol) and 7-azaspiro[3.5]nonan-2-one hydrochloride (3.83 g, 21.9 mmol) in DMSO (40 mL) was stirred at 110° C. for 2 days. After cooled to room temperature, the reaction mixture was poured into water (200 mL) under stirring. Then the precipitated solid was filtered and the filtered cake was further purified by column chromatography on silica gel (eluent: MeOH/DCM=1/50 to 1/30) to obtain methyl 2-((1H-pyrrolo[2,3-b]pyridin-5-yl)oxy)-4-(2-oxo-7-azaspiro[3.5]nonan-7-yl)benzoate as a yellow oil (470 mg). MS (ESI, m/e) [M+1]$^+$ 405.9.

Step 3: methyl (S)-2-((1H-pyrrolo[2,3-b]pyridin-5-yl)oxy)-4-(2-(2-(2-ethylphenyl)pyrrolidin-1-yl)-7-azaspiro[3.5]nonan-7-yl)benzoate To the mixture of 2-((1H-pyrrolo[2,3-b]pyridin-5-yl)oxy)-4-(2-oxo-7-azaspiro[3.5]nonan-7-yl)benzoate (470 mg, 1.16 mmol), (S)-2-(2-ethylphenyl)pyrrolidine (204 mg, 1.16 mmol) in DCM (20 mL) was added NaBH(OAc)$_3$ (369 mg, 1.74 mmol) and HOAc (1 drop) and stirred at room temperature overnight. After removal of solvent, the residue was purified by column chromatography on silica gel (eluent: MeOH/DCM=1/50 to 1/10) to obtain S)-2-((1H-pyrrolo[2,3-b]pyridin-5-yl)oxy)-4-(2-(2-(2-ethylphenyl)pyrrolidin-1-yl)-7-azaspiro[3.5]nonan-7-yl)benzoate as a yellow solid (440 mg). MS (ESI, m/e) [M+1]$^+$ 565.0.

Step 4: (S)-2-((1H-pyrrolo[2,3-b]pyridin-5-yl)oxy)-4-(2-(2-(2-ethylphenyl)pyrrolidin-1-yl)-7-azaspiro[3.5]nonan-7-yl)benzoic acid To the solution of methyl (S)-2-((1H-pyrrolo[2,3-b]pyridin-5-yl)oxy)-4-(2-(2-(2-ethylphenyl)pyrrolidin-1-yl)-7-azaspiro[3.5]nonan-7-yl)benzoate (530 mg, 0.94 mmol) in THF (4 mL) and MeOH (4 mL) was added aq, NaOH solution (4 mL, 6 mol/L) and stirred at 60° C. for 2 h. After removal of THF and MeOH, the mixture was acidified with 6 N HCl acid to pH 3 and then was extracted with DCM/i-PrOH=3/1 (60 mL). The organic layer was washed with brine (40 mL), dried over anhydrous Na$_2$SO$_4$, filtered and concentrated to give (S)-2-((1H pyrrolo[2,3-b]pyridin-5-yl)oxy)-4-(2-(2-(2-ethylphenyl)pyrrolidin-1-yl)-7-azaspiro[3.5]nonan-7-yl)benzoic acid as a yellow solid (450 mg). MS (ESI, m/e) [M+1]$^+$ 550.9.

Step 5: N-((4-((((S)-1,4-dioxan-2-yl)methyl)amino)-3-nitrophenyl)sulfonyl)-2-((1H-pyrrolo[2,3-b]pyridin-5-yl)oxy)-4-(2-((S)-2-(2-ethylphenyl)pyrrolidin-1-yl)-7-azaspiro[3.5]nonan-7-yl) benzam ide To a mixture of (S)-2-((1H-pyrrolo[2,3-b]pyridin-5-yl)oxy)-4-(2-(2-(2-ethylphenyl)pyrrolidin-1-yl)-7-azaspiro[3.5]nonan-7-yl)benzoic acid (200 mg, 0.364 mmol) in DCM (20 mL) were added EDCI (105 mg, 0.546 mmol), DMAP (66 mg, 0.546 mmol), (S)-4-(((1,4-dioxan-2-yl)methyl)amino)-3-nitrobenzenesulfonamide (138 mg, 0,436 mmol) and TFA (184 mg, 1.820 mmol), the mixture was stirred at ambient temperature for about 20 hours. The reaction mixture was concentrated and purified by column chromatograph on silica gel (100-200 mesh, eluent: EA/DCM=1/1 to MeOH/DCM=1/15) to give the crude product, which was purified by pre-TLC (eluent: MeOH/DCM=1/15) to give the desired compound as yellow solid. (70 mg, yield: 22.6%). $^1$H NMR (DMSO-d$_6$) δ ppm: 11.73 (s, 1H), 11.32 (br, 1H), 8.63-8.49 (m, 2H), 8.02 (d, J=2.0 Hz, 1H), 7.92-7.68 (m, 2H), 7.57-7.42 (m, 3H), 7.36-7.16 (m, 3H), 7.14-7.02 (m, 1H), 6.68 (d, J==8.8 Hz, 1H), 6.37 (s, 1H), 6.18 (s, 1H), 3.92-3.36 (m, 11H), 3.20-2.84 (m, 6H), 2.80-2.56 (m, 2H), 2.42-1.86 (m, 6H), 1.50-1.28 (m, 6H), 1.12 (t, J=7.6 Hz, 3H), 0.99-0.84 (m, 2H), 0.69-0.51 (m, 2H). MS (ESI, m/e) [M+1]$^+$ 849.8.

Example F41: N-((4-((((R) 1,4-dioxan-2-yl)methyl)amino)-3-nitrophenyl)sulfonyl)-2-((1H-pyrrolo[2,3-b]pyridin-5-yl)oxy)-4-(2-((S)-2-(2-ethylphenyl)pyrrolidin-1-yl)-7-azaspiro[3.5]nonan-7-yl) benzamide

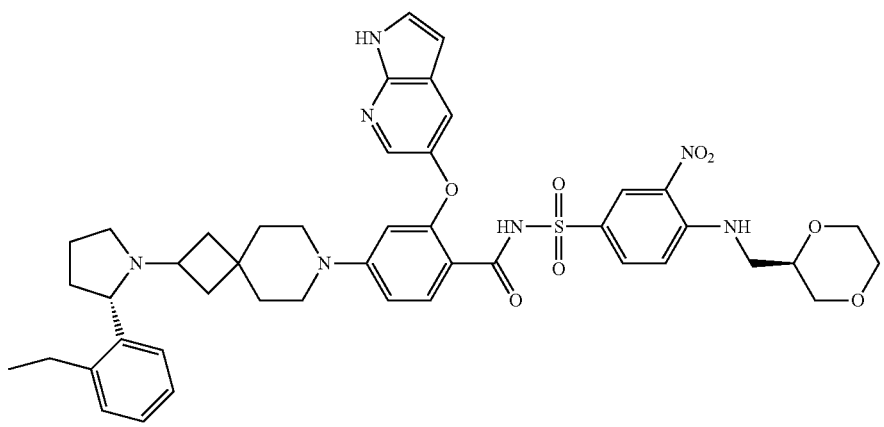 [SMILES: CCc1ccccc1[C@@H]1CCCN1C1CC2(CCN(c3ccc(C(=O)NS(=O)(=O)c4ccc(NC[C@@H]5COCCO5)c([N+](=O)[O-])c4)c(Oc4cnc5[nH]ccc5c4)c3)CC2)C1]

The desired compound was synthesized following the procedures similar to those in Example F40 by replacing (S)-4-(((1,4-dioxan-2-yl)methyl)amino)-3-nitrobenzenesulfonamide with (R)-4-(((1,4-dioxan-2-yl)methyl)amino)-3-nitrobenzenesulfonamide. ¹H NMR (DMSO-d₆) δ ppm: 11.73-11.32 (m, 2H), 8.63-8.49 (m, 2H), 8.02 (d, J=2.0 Hz, 1H), 7.92-7.68 (m, 2H), 7.57-7.42 (m, 3H), 7.36-7.16 (m, 3H), 7.14-7.02 (m, 1H), 6.68 (d, J=8.8 Hz, 1H), 6.37 (s, 1H), 6.18 (s, 1H), 3.92-3.36 (m, 11H), 3.20-2.84 (m, 6H), 2.80-2.56 (m, 2H), 2.42-1.86 (m, 6H), 1.50-1.28 (m, 6H), 1.12 (t, J=7.6H, 3H), 0.99-0.84 (m, 2H), 0.69-0.51 (m, 2H). MS (ESI, m/e) [M+1]⁺ 849.8 MS (ESI, m/e) [M+1]⁺ 849.8.

Example F42: (S)-2-((1H-pyrrolo[2,3-b]pyridin-5-yl)oxy)-4-(8-(2-(2-cyclopropylphenyl)pyrrolidin-1-yl)-2-azaspiro[4.5]decan-2-yl)-N-((3-nitro-4-(((tetrahydro-2H-pyran-4-yl)methyl)amino)phenyl)sulfonyl)benzamide

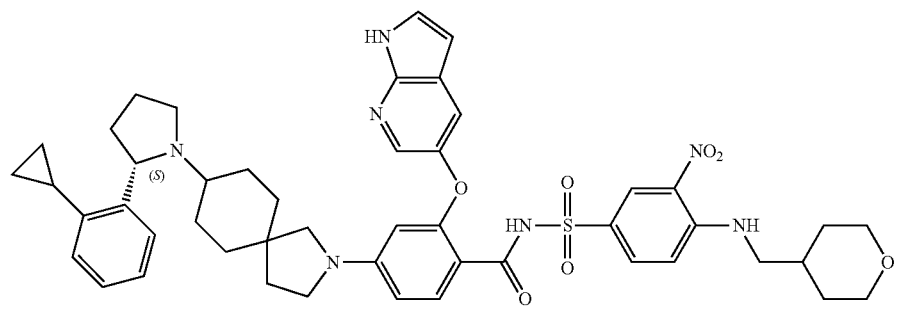

The desired compounds were synthesized following the procedures similar to those in Example F21 by replacing tert-butyl 2-oxo-7-azaspiro[3.5]nonane-7-carboxylate with tert-butyl 8-oxo-2-azaspiro[4.5]decane-2-carboxylate, and replacing 4-((((1r,4r)-4-hydroxy-4-methylcyclohexyl)methyl)amino)-3-nitrobenzenesulfonamide with 3-nitro-4-(((tetrahydro-2H-pyran-4-yl)methyl)amino)benzenesulfonamide. ¹H NMR (400 MHz, DMSO-d₆) δ ppm: 11.68 (s, 1H), 11.24 (s, 1H), 8.67-8.44 (m, 2H), 8.05 (s, 1H), 7.84-7.65 (m, 1H), 7.61-7.42 (m, 4H), 7.17-6.99 (m, 3H), 6.94-6.85 (m, 1H), 6.41-6.26 (m, 2H), 5.82 (s, 1H), 4.33-4.22 (m, 1H), 3.89-3.81 (m, 2H), 3.30-3.21 (m, 4H), 3.17-2.91 (m, 6H), 2.05-1.95 (m, 2H), 1.92-1.82 (m, 2H), 1.74-1.65 (m, 3H), 1.66-1.59 (m, 5H), 1.19-1.14 (m, 4H), 0.89-0.83 (m, 4H), 0.78-0.72 (m, 3H), 0.52-0.46 (m, 1H). MS (ESI, m/e) [M+1]⁺ 873.9.

Example F43: 2-((1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)benzamide

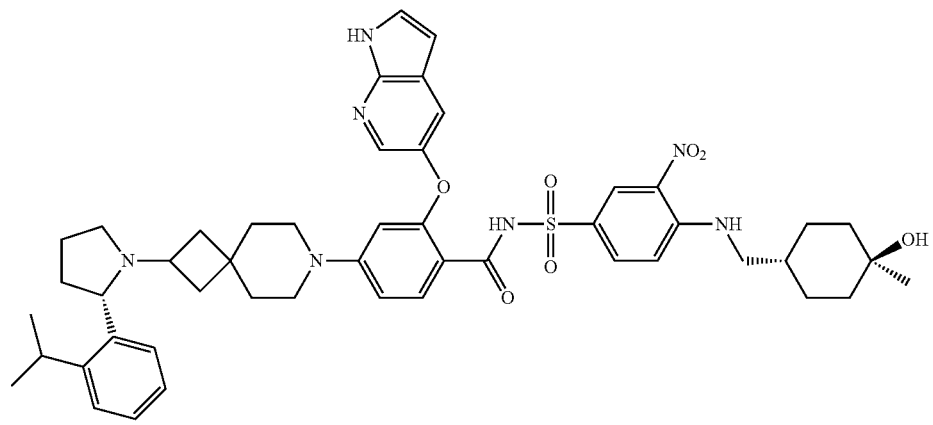 [SMILES: CC(C)c1ccccc1[C@@H]1CCCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1]

Step 1: 2,2-dimethoxy-7-azaspiro[3.5]nonane hydrochloride

To the solution of tert-butyl 2-oxo-7-azaspiro[3.5]nonane-7-carboxylate (500 g, 2.09 mol) in MeOH (750 mL) and EA (750 mL) was added conc. HCl acid (350 mL, 4.18 mol) at room temperature and stirred for 4 hours. After concentrated in vacuum, MeOH (750 mL) was added into the residue and then the resulting mixture was concentrated in vacuum (repeated this work-up twice). The brown residue was suspended in EA (1250 mL) and stirred for 1 hour. The solid precipitation was filtered and dried in vacuum to afford the tittle product as an off-white powder (350 g, yield: 76.0%). $^1$H NMR (400 MHz, DMSO-d$_6$) δ ppm: 3.03 (s, 6H), 2.96-2.89 (m, 4H), 1.93 (s, 4H), 1.74-1.67 (m, 4H). MS (ESI, m/e) [M+1]$^+$ 186.0.

Step 2: methyl 2-((1H-pyrrolo[2,3-b]pyridin-5-yl)oxy)-4-(2,2-dimethoxy-7-azaspiro[3.5]nonan-7-yl)benzoate The mixture of methyl 2-((1H-pyrrolo[2,3-b]pyridin-5-yl)oxy)-4-fluorobenzoate (100 g), 2,2-dimethoxy-7-azaspiro[3.5]nonane hydrochloride (116 g, 1.5 eq.) and DBU (160 g, 3.0 eq.) in NMP (500 mL) was stirred for 16 hours at 85° C. After the reaction was completed, the mixture was cooled to 50±5° C. and citric acid in water (2%, 5 L) was added drop-wise into the system under stirring. After filtered, the cake was collected and dissolved with DCM (1.5 L). The solution of crude product was washed with citric acid in water (2%, 1.5 L), saturated aq. NaHCO$_3$ (1.5 L) and 15% aq. NaCl (1.5 L), and then dried over anhydrous Na$_2$SO$_4$. Silica gel (100 g) was added into the solution of crude product under stirring and then filtered. The filtrate was concentrated to 300 mL. MTBE (500 mL) was poured into the system. After stirred for 2 hours, the cake was collected after filtration and was dried in vacuum to give an off-white solid (192 g, yield: 72.1%). $^1$H NMR (400 MHz, DMSO-d$_6$) δ ppm: 11.63 (s, 1H), 8.00 (d, J=2.4 Hz, 1H), 7.76 (d, J=9.2 Hz, 1H), 7.47 (t, J=3.2 Hz, 1H), 7.42 (d, J=2.4 Hz, 1H), 6.79 (dd, J=2.4 Hz, J=9.2 Hz, 1H), 6.39-6.36 (m, 2H), 3.64 (s, 3H), 3.17-3.12 (m, 4H), 3.01 (s, 6H), 1.86 (s, 4H), 1.54-1.50 (m, 4H). MS (ESI, m/e) [M+1]$^+$ 451.9.

Step 3: methyl 2-((1H-pyrrolo[2,3-b]pyridin-5-yl)oxy)-4-(2-oxo-7-azaspiro[3,5]nonan-7-yl)benzoate To the solution of methyl 2-((1H-pyrrolo[2,3-b]pyridin-5-yl)oxy)-4-(2,2-dimethoxy-7-azaspiro[3.5]nonan-7-yl)benzoate (176 g, 0.39 mol) in DCM (2 L) was added diluted HCl acid (1M, 1.5 L) and stirred for overnight. After the reaction was completed, the mixture was cooled to 10° C. and was adjusted to pH=8-9 with aqueous NaOH solution (4 M) under stirring. The organic phase was separated and washed with 15% aq, NaCl (1 L), then washed with H$_2$O (1 L). After the organic phase was concentrated to 500 mL, MTBE (1 L) was poured into the solution and then the system was concentrated to 500 mL (repeated this work-up 3 times). The resulting system was stirred for 0.5 hour. After filtration, the cake was collected and then dried in vacuum to obtain the tittle product as a white solid (152 g, yield: 96.23%). $^1$H NMR (400 MHz, DMSO-d$_6$) δ ppm: 11.64 (s, 1H), 8.02 (d, J=2.4 Hz, 1H), 7.78 (d, J=9.2 Hz, 1H), 7.47 (t, J=3.2 Hz, 1H), 7.44 (d, J=2.4 Hz, 1H), 6.83 (dd, J=2.4 Hz, J=9.2 Hz, 1H), 6.43 (d, J=2.4 Hz, 1H), 6.38-6.36 (m, 1H), 3.65 (s, 3H), 3.24-3.21 (m, 4H), 2.80 (s, 4H), 1.70-1.67 (m, 4H). MS (ESI, m/e) [M+1]$^+$ 405.9.

Step 4: (S)-tert-butyl 2-(2-(prop-1-en-2-yl)phenyl)pyrrolidine-1-carboxylate To a mixture of (S)-tert-butyl 2-(2-bromophenyl)pyrrolidine-1-carboxylate (50 g, 153.3 mmol) and 4,4,5,5-tetramethyl-2-(prop-1 en-2-yl)-1,3,2-dioxaborolane (38.6 g, 229.9 mmol) in dioxane (500 mL) and H$_2$O (50 mL) was added Cs$_2$CO$_3$ (100 g, 305 mmol) and Pd(dppf)Cl$_2$ (6.6 g, 7.5 mmol). The mixture was stirred at 100° C. for 8 hours. TLC showed the reaction was completed. The mixture was concentrated in vacuum. The residue was purified by column chromatography on silica gel (eluent: PE/EA (v/v)=100/1 to 10/1) to obtain (S)-tert-butyl 2-(2-(prop-1-en-2-yl)phenyl)pyrrolidine-1-carboxylate (65 g, crude). The crude product was used directly in next step.

Step 5: (S)-tert-butyl 2-(2-isopropylphenyl)pyrrolidine-1-carboxylate

To a solution of (S)-tert-butyl 2-(2 (prop-1-en-2-yl)phenyl)pyrrolidine-1-carboxylate (30 g, 104.39 mmol) in MeOH (500 mL) was added Pd/C (10 g, 10%) and the mixture was stirred at 20° C. under H$_2$ (15 Psi) for 12 hours. TLC showed the reaction was completed. The mixture was filtered and the filtrate was concentrated in vacuum to give (S)-tert-butyl 2-(2-isopropylphenyl (pyrrolidine-1-carboxylate (60 g, crude), which was used in next step without further purification. $^1$H NMR (400 MHz, CDCl$_3$) δ ppm: 7.39-6.90 (m, 4H), 5.36-5.04 (m, 1H), 3.77-3.52 (m, 2H), 3.20-3.17 (m, 1H), 2.47-2.24 (m, 1H), 1.96-1.65 (m, 3H), 1.54-1.38 (m, 2H), 1.31-1.22 (un 8H), 1.17 (s, 7H).

Step 6: (S)-2-(2-isopropylphenyl)pyrrolidine hydrochloride

To a solution of tert-butyl 2-(2-isopropylphenyl)pyrrolidine-1-carboxylate (55 g, 190 mmol) in DCM (50 mL) was added HCl in 1,4-dioxane (4 M, 142 mL, 570 mmol) dropwise at room temperature. The mixture was stirred at room temperature for overnight. The mixture was concentrated in vacuum. The resulting residue was slurried with EA (100 mL) and then filtered, dried in vacuum to give (S)-2-(2-isopropylphenyl)pyrrolidine hydrochloride 26 g (yield: 60.4%). $^1$H NMR (400 MHz, DMSO-d$_6$) δ ppm: 9.93 (s, 1H), 8.81 (s, 1H), 7.63-7.57 (m, 1H), 7.41-7.34 (m, 2H), 7.32-7.24 (m, 1H), 4.91-4.75 (m, 1H), 3.47-3.35 (m, 1H), 3.31-3.25 (m, 1H), 2.40-2.21 (m, 1H), 2.19-1.86 (m, 3H), 1.25 (d, J=6.7 Hz, 3H), 1.17 (d, J=6.7 Hz, 3H). MS (ESI, m/e) [M+1]$^+$ 190.0.

Step 7: methyl (S)-2-((1H-pyrrolo[2,3-b]pyridin-5-yl)oxy)-4-(2-(2-(2-isopropylphenyl)pyrrolidin-1-yl)-7-azaspiro[3.5]nonan-7-yl)benzoate A mixture of (S)-2-(2-isopropylphenyl)pyrrolidine hydrochloride (120 g, 0.535 mole) and methyl 2-((1H-pyrrolo[2,3-b]pyridin-5-yl)oxy)-4-(2-oxo-7-azaspiro[3.5]nonan-7-yl)benzoate (218 g, 0.509 mole) in DCM (2.2 L) was charged into a reactor. The temperature was controlled blow 30° C. and NaBH(OAc)$_3$ (216 g, 1.018 mole) was added into the reactor in 5-6 portions. Then the reaction mixture was stirred at room temperature and monitored by TLC. After the starting material ketone was consumed completely, the mixture was adjusted to pH=4-5 with diluted HCl acid (0.5 M).

The separated organic phase was washed with H$_2$O (600 mL×2) and then washed with aq. NaHCO$_3$ (600 mL×2), saturated aq. NaCl (600 mL), The organic phase was collected, then dried over anhydrous Na$_2$SO$_4$ and concentrated. 256 g off-white solid was obtained as crude product, which was used in next step directly. MS (ESI, m/e) [M+1]$^+$ 579.0.

Step 8: (S)-2-((1H-pyrrolo[2,3-b]pyridin-5-yl)oxy)-4-(2-(2-(2-isopropylphenyl)pyrrolidin-1-yl)-7-azaspiro[3.5]nonan-7-yl)benzoic acid To a solution of methyl (S)-2-((1H-pyrrolo[2,3-b]pyridin-5-yl)oxy)-4-(2-(2-(2-isopropylphenyl)pyrrolidin-1-yl)-7-azaspiro[3.5]nonan-7-yl)benzoate (105 g, 181.7 mmol) in THF (525 mL) and MeOH (525 mL) was added aq. NaOH (3.5 M). It was stirred at room temperature overnight. After THF and MeOH were removed in vacuum, 3.5 L of water was added into the residue. The resulting mixture was adjusted to pH=5-6 with 3 N HCl acid at room temperature with stirring. The precipitate was filtered and dried in vacuum to give the product as a white solid (102.4 g, yield: 99%). $^1$H NMR (400 MHz, DMSO-d$_6$) δ ppm: 12.13 (s, 1H), 11.58 (s, 1H), 7.95 (s, 1H), 7.67 (d, J=8.0 Hz, 1H), 7.56-7.40 (m, 2H), 7.35 (s, 1H), 7.27-7.04 (m, 3H), 6.68 (d, J=8.0 Hz, 1H), 6.32 (s, 2H), 3.62 (s, 1H), 3.32-3.26 (m, 1H), 3.10-3.04 (m, 4H), 2.35-2.30 (m, 1H), 2.9-2.15 (m, 1H), 1.74-1.64 (m, 4H), 1.52-1.37 (m, 6H), 1.28-1.06 (m, 6H). MS (ESI, m/e) [M+1]$^+$ 564.9.

Step 9: 2-((1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)benzamide A mixture of (S)-2-((1H-pyrrolo[2,3-b]pyridin-5-yl)oxy)-4-(2-(2-(2-isopropylphenyl)pyrrolidin-1-yl)-7-azaspiro[3.5]nonan-7-yl)benzoic acid (44 g, 78 mmol), 4-((((1r,4r)-4-hydroxy-4-methylcyclohexyl)methyl)amino)-3-nitrobenzenesulfonamide (26.8 g, 78 mmol), TFA (15.7 g, 156 mmol), EDCl (19.4 g, 101 mmol) and DMAP (19 g, 156 mmol) in anhydrous DCM (880 mL) was stirred overnight at room temperature. The reaction was monitored by HPLC. After starting material of (S)-2-((1H-pyrrolo[2,3-b]pyridin-5-yl)oxy)-4-(2-(2-(2-isopropylphenyl)pyrrolidin-1-yl)-7-azaspiro[3.5]nonan-7-yl)benzoic acid was consumed completely, the reaction mixture was heated to ~35° C. and N$^1$,N$^1$-dimethylethane-1,2-diamine (17.2 g, 195 mmol) was added in one portion. The reaction was stirred for another 12 hours. The mixture was washed twice with 10 wt % aq. AcOH solution (300 mL×2) and then washed with saturated aq. NaHCO$_3$ (300 mL×2). The organic layer was collected and concentrated to about 90 mL. 22 g of silica gel was added and stirred for 2 hours. After filtration, 180 mL EA was added into the filtrate at reflux and further stirred for 5 hours. After the mixture was cooled to room temperature, the precipitate was filtered and then the wet cake was washed twice with EA (180 mL). After drying in vacuum at 80-90° C., the desired compound was obtained (48 g, yield: 69.5%). $^1$H NMR (DMSO-d$_6$) δ ppm: 11.65 (s, 1H), 11.11 (br, 1H), 8.58-8.39 (m, 2H), 8.00 (d, J=2.8 Hz, 1H), 7.74 (d, J=8.8 Hz, 1H), 7.57-7.37 (m, 4H), 7.30-7.10 (m, 3H), 7.00 (d, J=9.2 Hz, 1H), 6.65 (d, J=1.2 Hz, 1H), 6.35 (s, 1H), 6.17 (s, 1H), 4.24 (s, 1H), 3.39-3.20 (m, 5H), 3.04-2.88 (m, 4H), 2.23 (s, 1H), 1.94-1.47 (m, 11H), 1.44-1.26 (m, 7H), 1.19 (d, J=8.0 Hz, 3H), 1.14 (d, J=8.0 Hz, 3H), 1.10 (s, 4H). MS (ESI, m/e) [M+1]$^+$ 889.9.

Example F44: N-((4-((((S)-1,4-dioxan-2-yl)methyl)amino)-3-nitrophenyl)sulfonyl)-2-((1H-pyrrolo[2,3-b]pyridin-5-yl)oxy)-4-(2-((S)-2-(2-isopropylphenyl)pyrrolidin-1-yl)-7-azaspiro[3.5]nonan-7-yl)benzamide

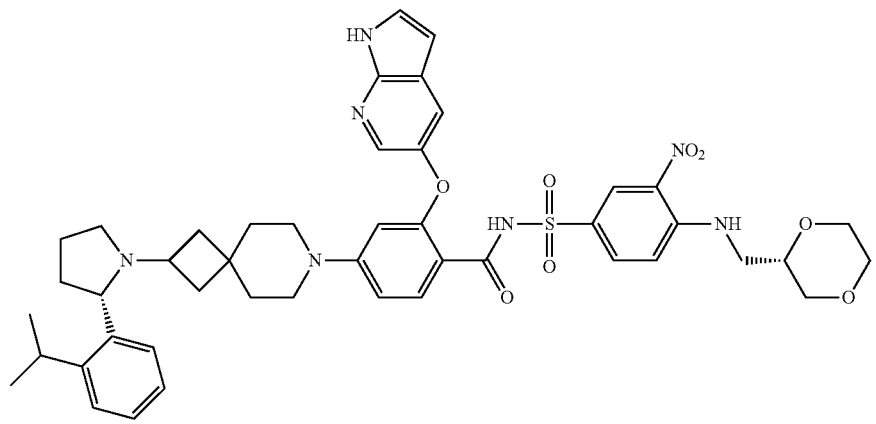 [SMILES: CC(C)c1ccccc1[C@@H]1CCCN1C1CC2(CCN(c3ccc(C(=O)NS(=O)(=O)c4ccc(NC[C@H]5COCCO5)c([N+](=O)[O-])c4)c(Oc4cnc5[nH]ccc5c4)c3)CC2)C1]

A mixture of (S)-2-((1H-pyrrolo[2,3-b]pyridin-5-yl)oxy)-4-(2-(2-(2-isopropylphenyl)pyrrolidin-1-yl)-7-azaspiro[3.5]nonan-7-yl)benzoic acid (78 g, 138 mmol), (S)-4-(((1,4-dioxan-2-yl)methyl)amino)-3-nitrobenzenesulfonamide (64 g, 138 mmol), TFA (78 mL, 565 mmol), EDCI (32 g, 170 mmol) and DMAP (34.5 g, 283 mmol) in anhydrous DCM (2 L) was stirred overnight at room temperature. The reaction was monitored by HPLC. After the starting material (S)-2-((1H-pyrrolo[2,3-b]pyridin-5-yl)oxy)-4-(2-(2-(2-isopropylphenyl)pyrrolidin-1-yl)-7-azaspiro[3.5]nonan-7-yl) benzoic acid was consumed completely, the mixture was washed with 10% HOAc (600 mL×2) and then with saturated aq. NaHCO$_3$ (600 mL×2). The organic layers were collected and dried over anhydrous Na$_2$SO$_4$ and then purified by column chromatography on silica gel (eluent: DCM/EA (v/v)=1/1, then 2% MeOH in DCM to 5% MeOH in DCM) to give a crude product (95 g), which was further purified to obtain the desired compound (40 g, yield: 41%). $^1$H NMR (400 MHz, DMSO-d$_6$): II. 68 ppm: (s, 1H), 11.47 (s, 1H), 8.59-8.55 (m, 2H), 8.03 (s, 1H), 7.80 (d, J=8.4 Hz, 2H), 7.63-7.41 (m, 3H), 7.35-7.28 (m, 3H), 7.10 (d, J=9.2 Hz, 1H), 6.68 (d, J=9.2 Hz, 1H), 6.37 (s, 1H), 6.18 (s, 1H), 4.76 (s, 1H), 3.89-3.79 (m, 4H), 3.68-3.59 (m, 3H), 3.52-3.41 (m, 2H), 3.43-3.38 (m, 1H), 3.31-3.21 (m, 2H), 3.17-2.88 (m, 5H), 2.18-2.11 (m, 5H), 1.40-1.31 (m, 7H), 1.24 (d, J=8.0 Hz, 3H), 1.11 (d, J=8.0 Hz, 3H). MS (ESI, m/e) [M+1]$^+$ 863.9.

Example F45: (S)-2-((1H-pyrrolo[2,3-b]pyridin-5-yl)oxy)-4-(2-(2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide

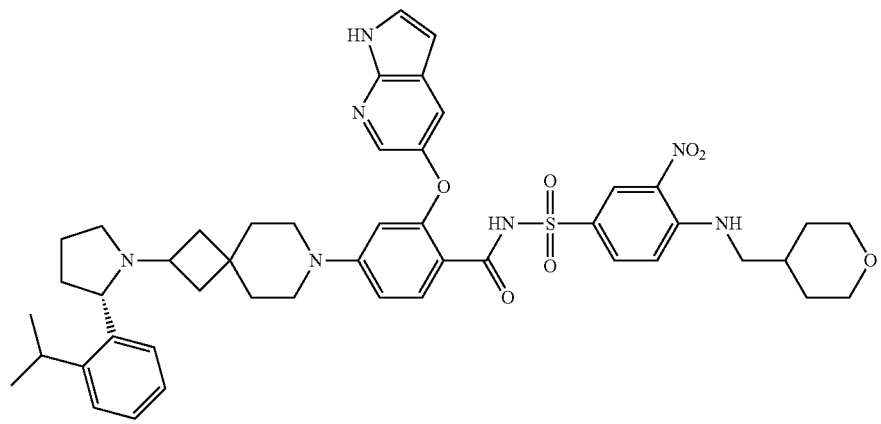

The desired compound was synthesized following the procedures similar to those in Example F43 by replacing 4-((((1r,4r)-4-hydroxy-4-methylcyclohexyl)methyl)amino)-3-nitrobenzenesulfonamide with 3-nitro-4-(((tetrahydro-2H-pyran-4-yl)methyl)amino)benzenesulfonamide. $^1$H NMR (400 MHz, DMSO-$d_6$) δ ppm: 11.69 (s, 1H), 11.44 (br, 1H), 8.61 (s, 1H), 8.55 (s, 1H), 8.03 (s, 1H), 7.79 (d, J=8.8 Hz, 1H), 7.67 (s, 1H), 7.55-7.46 (m, 3H), 7.41-7.25 (m, 3H), 7.17-7.05 (m, 1H), 6.68 (d, J=8.8 Hz, 1H), 6.38 (s, 1H), 6.17 (s, 1H), 4.85-4.70 (m, 1H), 3.85 (d, J=8.4 Hz, 3H), 3.72-3.60 (m, 1H), 3.27-3.21 (m, 4H), 3.12-2.89 (m, 8H), 2.18-1.99 (m, 4H), 1.95-1.83 (m, 1H), 1.61 (d, J=12.5 Hz, 2H), 1.48-1.39 (m, 3H), 1.38-1.17 (m, 9H), 1.15-0.97 (s, 3H). MS (ESI, m/e) [M+1]$^+$ 861.9.

Example F46: (SV2-((1H-pyrrolo[2,3-b]pyridin-5-yl)oxy)-N-((4-(((4-fluorotetrahydro-2H-pyran-4-yl)methyl)amino)-3-nitrophenyl)sulfonyl)-4-(2-(2-(2-isopropylphenyl)pyrrolidin-1-yl)-7-azaspiro[3.5]nonan-7-yl)benzamide

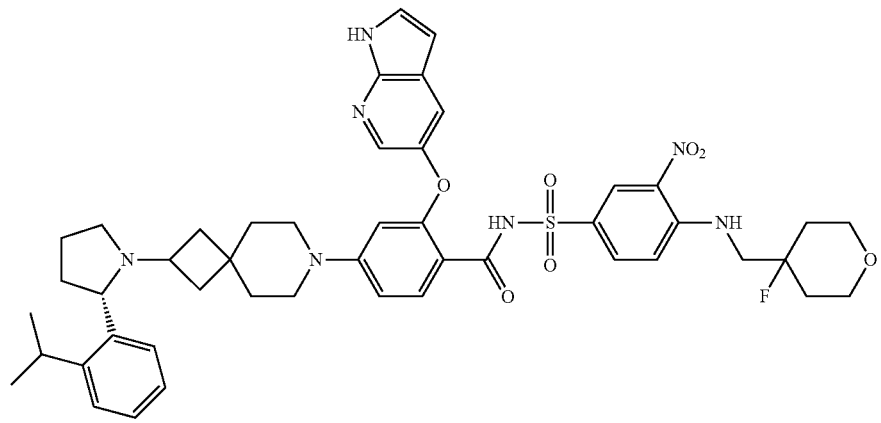 [SMILES: CC(C)c1ccccc1[C@@H]1CCCN1C1CC2(CCN(c3ccc(C(=O)NS(=O)(=O)c4ccc(NCC5(F)CCOCC5)c([N+](=O)[O-])c4)c(Oc4cnc5[nH]ccc5c4)c3)CC2)C1]

The desired compound was synthesized following the procedures similar to those in Example F43 by replacing 4-((((1r,4r)-4-hydroxy-4-methylcyclohexyl)methyl)amino)-3-nitrobenzenesulfonamide with 4-(((4-fluorotetrahydro-2H-pyran-4-yl)methyl)amino)-3-nitrobenzenesulfonamide. $^1$H NMR (400 MHz, DMSO-$d_6$) δ ppm: 11.70 (s, 1H), 11.47 (br, 1H), 8.65 (t, J=6.0 Hz, 1H), 8.57 (d, J=1.6 Hz, 1H), 8.04 (d, J=1.6 Hz, 1H), 7.82 (d, J=8.8 Hz, 1H), 7.60 (d, J=7.6 Hz, 1H), 7.52 (d, J=7.6 Hz, 2H), 7.48 (d, J=8.8 Hz, 1H), 7.37 (d, J=4.0 Hz, 2H), 7.31 (dd, J=7.6, 4.0 Hz, 1H), 7.26 (d, J=8.8 Hz, 1H), 6.68 (d, J=8.8 Hz, 1H), 6.38 (s, 1H), 6.17 (s, 1H), 4.86-4.73 (m, 1H), 3.89 (dd, J=16.0, 8.0 Hz, 1H), 3.79-3.64 (m, 4H), 3.60-3.47 (m, 2H), 3.33-3.22 (m, 2H), 3.22-3.11 (m, 1H), 3.06 (s, 2H), 2.95 (s, 2H), 2.49-2.40 (m, 2H), 2.22-1.92 (m, 5H), 1.88-1.65 (m, 4H), 1.55-1.30 (m, 5H), 1.25 (d, J=6.4 Hz, 3H), 1.10 (d, J=6.4 Hz, 3H). MS (ESI, m/e) [M+1]$^+$ 879.9.

Example F47: N-((4-(((((R)-1,4-dioxan-2-yl)methyl)amino)-3-nitrophenyl)sulfonyl)-2-((1H-pyrrolo[2,3-b]pyridin-5-yl)oxy)-4-(2-((S)-2-(2-isopropylphenyl)pyrrolidin-1-yl)-7-azaspiro[3.5]nonan-7-yl)benzamide

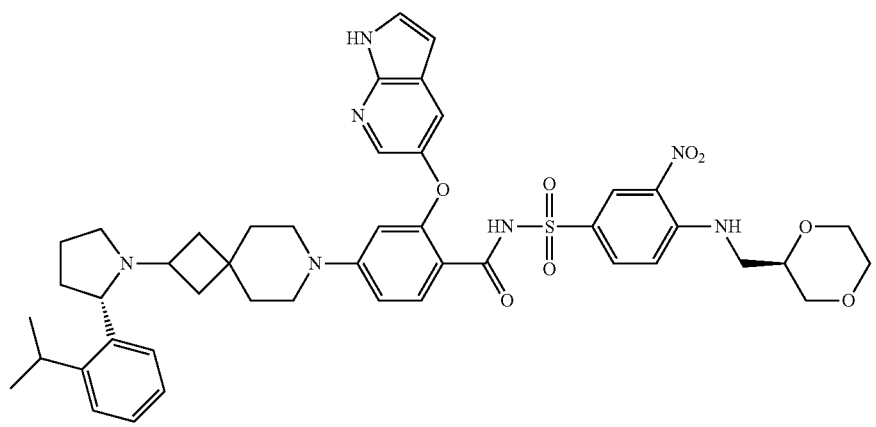 [SMILES: CC(C)c1ccccc1[C@@H]1CCCN1C1CC2(CCN(c3ccc(C(=O)NS(=O)(=O)c4ccc(NC[C@@H]5COCCO5)c([N+](=O)[O-])c4)c(Oc4cnc5[nH]ccc5c4)c3)CC2)C1]

The desired compound was synthesized following the procedures similar to those in Example F43 by replacing 4-((((1r,4r)-4-hydroxy-4-methylcyclohexyl)methyl)amino)-3-nitrobenzenesulfonamide with (R)-4-(((1,4-dioxan-2-yl)methyl)amino)-3-nitrobenzenesulfonamide. $^1$H NMR (400 MHz, DMSO-d$_6$) δ ppm: 11.68 (s, 1H), 11.47 (br, 1H), 8.59-8.55 (m, 2H), 8.03 (d, J=1.8 Hz, 1H), 7.80 (d, J=8.1 Hz, 2H), 7.63-7.41 (m, 3H), 7.35-7.28 (m, 3H), 7.10 (d, J=9.2 Hz, 1H), 6.68 (d, J=8.8 Hz, 1H), 6.37 (s, 1H), 6.18 (s, 1H), 4.76 (s, 1H), 3.89-3.79 (m, 4H), 3.68-3.59 (m, 3H), 3.52-3.41 (m, 2H), 3.43-3.38 (m, 1H), 3.31-3.21 (m, 2H), 3.17-2.88 (m, 5H), 2.18-2.11 (m, 5H), 1.40-1.31 (m, 7H), 1.24 (d, J=6.0 Hz, 3H), 1.11 (d, J=6.0 Hz, 3H). MS (ESI, m/e) [M+1]$^+$ 863.9.

Example F48: 2-((1H-pyrrolo[2,3-b]pyridin-5-yl)oxy)-N-((4-(((((1s,4s)-4-hydroxy-4-methylcyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)benzamide

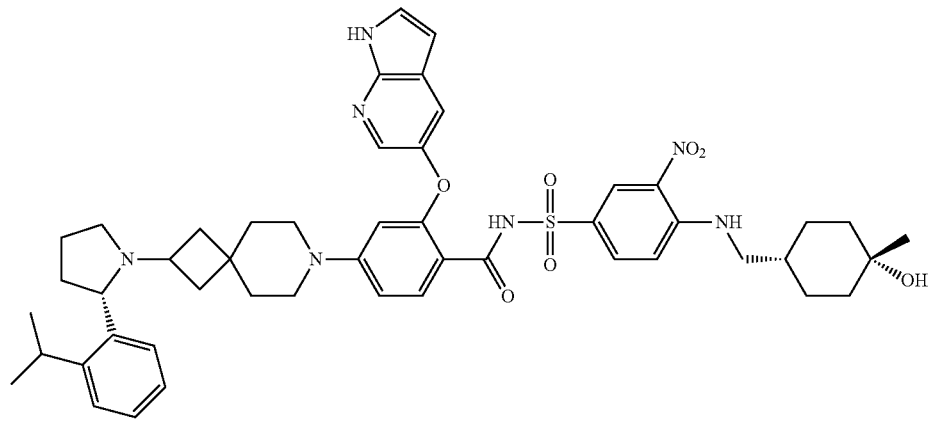 [SMILES: CC(C)c1ccccc1[C@@H]1CCCN1C1CC2(CCN(c3ccc(C(=O)NS(=O)(=O)c4ccc(NC[C@H]5CC[C@@](C)(O)CC5)c([N+](=O)[O-])c4)c(Oc4cnc5[nH]ccc5c4)c3)CC2)C1]

The desired compound was synthesized following the procedures similar to those in Example F43 by replacing 4-((((1r,4r)-4-hydroxy-4-methylcyclohexyl)methyl)amino)-3-nitrobenzenesulfonamide with 4-((((1s,4s)-4-hydroxy-4-methylcyclohexyl)methyl)amino)-3-nitrobenzenesulfonamide. $^1$H NMR (400 MHz, DMSO-d$_6$) δ ppm: 11.65 (s, 1H), 11.24 (br, 1H), 8.53-8.51 (m, 2H), 8.00 (s, 1H), 7.73 (d, J=7.8 Hz, 1H), 7.51-7.48 (m, 4H), 7.23-7.16 (m, 3H), 6.99 (s, 1H), 6.65 (d, J=8.3 Hz, 1H), 6.36 (s, 1H), 6.17 (s, 1H), 3.95 (s, 1H), 3.27-3.24 (m, 4H), 3.01 (s, 2H), 2.93 (s, 2H), 2.24 (s, 1H), 1.83-1.74 (m, 4H), 1.58-1.46 (m, 7H), 1.43-1.33 (m, 6H), 1.27-1.10 (m, 10H), 1.08 (s, 3H). MS (ESI, m/e) [M+1]$^+$ 889.9.

Example F49: 2-((1H-pyrrolo[2,3-b]pyridin-5-yl)oxy)-N-((4-(((((1r,4r)-4-hydroxy-4-methylcyclohexyl)methyl)amino)-3-nitrophenyl)sulfonyl)-4-(2-((R)-2-(2-isopropylphenyl)pyrrolidin-1-yl)-7-azaspiro[3.5]nonan-7-yl)benzamide

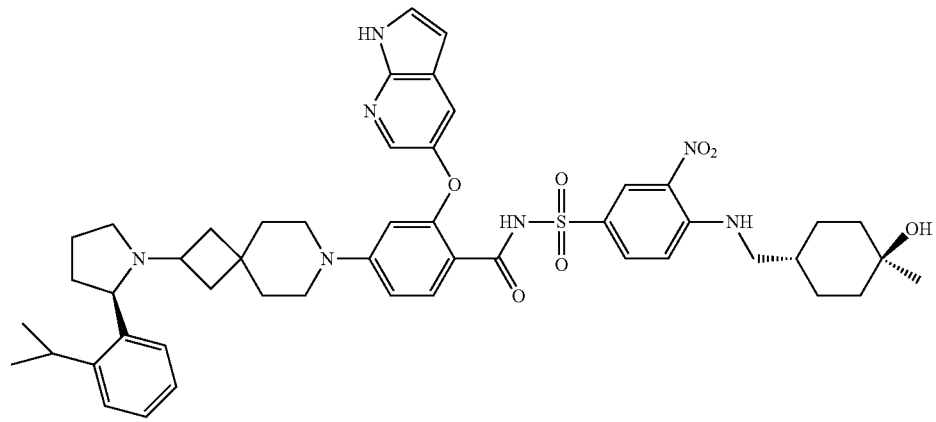 [SMILES: CC(C)c1ccccc1[C@H]1CCCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1]

The desired compound was synthesized following the procedures similar to those in Example F43 by replacing (S)-2-(2-isopropylphenyl)pyrrolidine with (R)-2-(2-isopropylphenyl)pyrrolidine. ¹H NMR (400 MHz, DMSO-d₆) δ ppm: 11.70 (s, 1H), 11.44 (br, 1H), 8.57 (s, 1H), 8.55 (s, 1H), 8.03 (s, 1H), 7.98 (s, 1H), 7.78 (d, J=8.4 Hz, 1H), 7.55-7.42 (m, 3H), 7.33 (s, 2H), 7.26 (s, 1H), 7.07 (d, J=8.4 Hz, 1H), 6.68 (d, J=8.8 Hz, 1H), 6.38 (s, 1H), 6.18 (s, 1H), 4.74 (s, 1H), 4.25 (s, 1H), 3.96-3.51 (m, 2H), 3.28 (s, 3H), 3.14-2.85 (m, 5H), 2.38 (s, 1H), 2.30-1.88 (m, 5H), 1.74-1.60 (m, 3H), 1.54 (d, J=12.6 Hz, 2H), 1.48-1.28 (m, 8H), 1.24 (d, J=5.4 Hz, 3H), 1.16-1.05 (m, 8H). MS (ESI, m/e) [M+1]⁺ 889.9.

Example F50: 2-((1H-pyrrolo[2,3-b]pyridin-5-yl)oxy)-N-((4-((((1s,4s)-4-hydroxy-4-methylcyclohexyl)methyl)amino)-3-nitrophenyl)sulfonyl)-4-(2-((R)-2-(2-isopropylphenyl)pyrrolidin-1-yl)-7-azaspiro[3.5]nonan-7-yl)benzamide

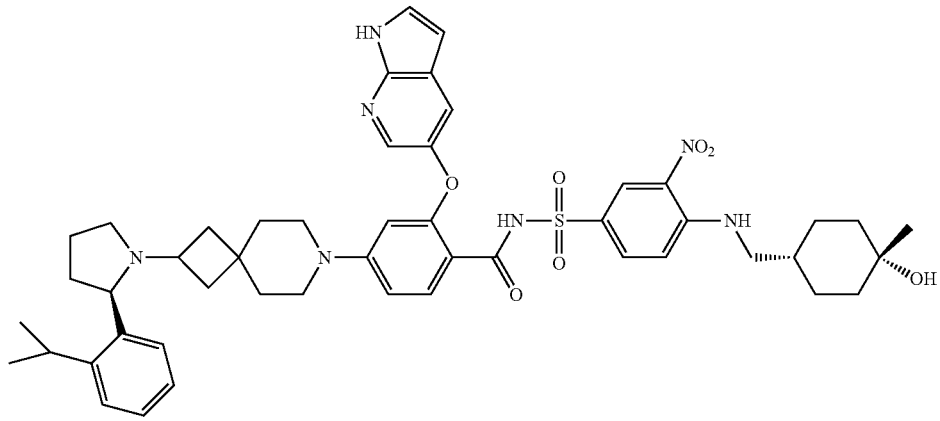 [SMILES: CC(C)c1ccccc1[C@H]1CCCN1C1CC2(CCN(c3ccc(C(=O)NS(=O)(=O)c4ccc(NC[C@H]5CC[C@@](C)(O)CC5)c([N+](=O)[O-])c4)c(Oc4cnc5[nH]ccc5c4)c3)CC2)C1]

The desired compound was synthesized following the procedures similar to those in Example F43 by replacing (S)-2-(2-isopropylphenyl)pyrrolidine with (R)-2-(2-isopropylphenyl)pyrrolidine and replacing 4-((((1r,4r)-4-hydroxy-4-methylcyclohexyl)methyl)amino)-3-nitrobenzenesulfonamide with 4-((((1s,4s)-4-hydroxy-4-methylcyclohexyl)methyl)amino)-3-nitrobenzenesulfonamide. ¹H NMR (400 MHz, DMSO-d₆) δ ppm: 11.71 (s, 1H), 11.44 (br, 1H), 10.87 (s, 1H), 8.61 (s, 1H), 8.56 (s, 1H), 8.04 (s, 1H), 7.98 (s, 1H), 7.78 (d, J=9.0 Hz, 1H), 7.55-7.42 (m, 3H), 7.33 (s, 2H), 7.27 (s, 1H), 7.07 (d, J=9.0 Hz, 1H), 6.68 (d, J=8.8 Hz, 1H), 6.38 (s, 1H), 6.18 (s, 1H), 4.73 (s, 1H), 3.97 (s, 1H), 3.82 (s, 1H), 3.67 (s, 1H), 3.26 (s, 3H), 3.14-2.85 (m, 5H), 2.39 (s, 1H), 2.30-1.88 (m, 5H), 1.60-1.30 (m, 12H), 1.24 (d, J=6.0 Hz, 5H), 1.15-1.03 (m, 6H). MS (ESI, m/e) [M+1]⁺ 889.9.

Example F51: 2-((1H-pyrrolo[2,3-b]pyridin-5-yl)oxy)-4-(2-(2-(2-cyclobutylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide

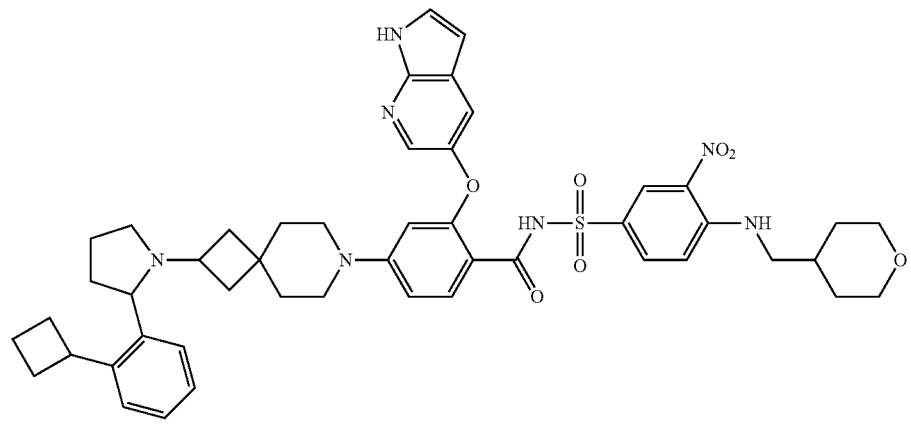 [SMILES: O=C(NS(=O)(=O)c1ccc(NCC2CCOCC2)c([N+](=O)[O-])c1)c1ccc(N2CCC3(CC2)CC(N2CCCC2c2ccccc2C2CCC2)C3)cc1Oc1cnc2[nH]ccc2c1]

The desired compound was synthesized following the procedures similar to those in Example F40 by replacing (S)-2-(2-ethylphenyl)pyrrolidine with 2-(2-cyclobutylphenyl)pyrrolidine and replacing (S)-4-(((1,4-dioxan-2-yl)methyl)amino)-3-nitrobenzenesulfonamide with 3-nitro-4-(((tetrahydro-2H-pyran-4-yl)methyl)amino)benzenesulfonimidamide. $^1$H NMR (DMSO-d$_6$) δ ppm: 11.69 (s, 1H), 11.43 (br, 1H), 8.61-8.53 (m, 2H), 8.02 (s, 1H), 7.78-7.70 (m, 2H), 7.49-7.45 (m, 3H), 7.29 (s, 3H), 7.10-7.06 (m, 1H), 6.70-6.62 (m, 1H), 6.37 (s, 1H), 6.17 (s, 1H), 4.46 (s, 1H), 3.81-3.75 (m, 5H), 3.31-3.21 (m, 4H), 2.99-2.95 (m, 4H), 2.30-1.87 (m, 13H), 1.65-1.58 (m, 2H), 1.47-1.18 (m, 1 OH). MS (ESI) m/e [M+1]$^+$ 873.8.

Example F52: (S)-2-((1H-pyrrolo[2,3-b]pyridin-5-yl)oxy)-4-(2-(2-(2-isobutylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide

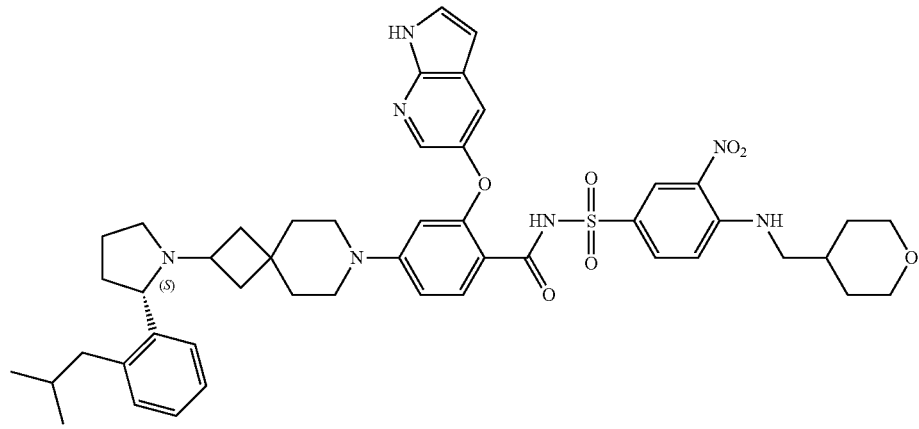

The desired compound was synthesized following the procedures similar to those in Example F40 by replacing (S)-2-(2-ethylphenyl)pyrrolidine with (S)-2-(2-isobutylphenyl)pyrrolidine and replacing (S)-4-(((1,4-dioxan-2-yl)methyl)amino)-3-nitrobenzenesulfonamide with 3-nitro-4-(((tetrahydro-2H-pyran-4-yl)methyl)amino)benzenesulfonimidamide. $^1$H NMR (DMSO-d$_6$) δ ppm: 11.52 (s, 1H), 9.64 (s, 1H), 8.67-8.26 (m, 2H), 8.02-7.86 (m, 1H), 7.71-7.34 (m, 4H), 7.29-6.92 (m, 4H), 6.88-6.56 (m, 2H), 6.37-6.10 (m, 1H), 5.39-5.23 (m, 1H), 3.89-3.77 (m, 2H), 3.60-3.46 (m, 1H), 3.28-3.21 (m, 4H), 3.15-2.81 (m, 8H), 2.21-1.55 (m, 13H), 1.51-1.40 (m, 4H), 0.893-0.79 (m, 7H). MS (ESI, m/e) [M+1]$^+$ 875.9.

Example F53: 2-((1H-pyrrolo[2,3-b]pyridin-5-yl)oxy)-4-(2-(2-(3-cyclopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide

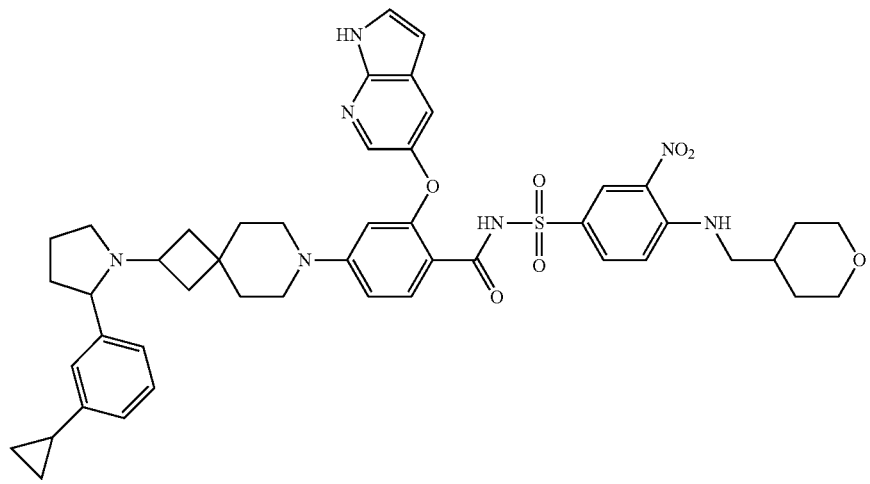 [SMILES: O=C(NS(=O)(=O)c1ccc(NCC2CCOCC2)c([N+](=O)[O-])c1)c1ccc(N2CCC3(CC2)CC(N2CCCC2c2cccc(C4CC4)c2)C3)cc1Oc1cnc2[nH]ccc2c1]

The desired compound was synthesized following the procedures similar to those in Example F40 by replacing (S)-2-(2-ethylphenyl)pyrrolidine with 2-(3-cyclopropylphenyl)pyrrolidine and replacing (S)-4-(((1,4-dioxan-2-yl)methyl)amino)-3-nitrobenzenesulfonamide with 3-nitro-4-(((tetrahydro-2H-pyran-4-yl)methyl)amino)benzenesulfonimidamide. $^1$H NMR (DMSO-d$_6$) δ ppm: 11.68 (s, 1H), 11.45 (br, 1H), 8.54 (s, 2H), 8.03 (s, 1H), 7.77 (s, 1H), 7.50 (s, 3H), 7.27 (s, 3H), 7.10 (s, 2H), 6.73-6.65 (m, 1H), 6.38 (s, 1H), 6.18 (s, 1H), 4.28 (s, 1H), 3.90-3.80 (m, 3H), 3.62 (s, 1H), 3.30-3.23 (m, 3H), 3.10-2.91 (m, 6H), 2.10-1.92 (m, 1H), 1.65-1.59 (m, 3H), 1.45-1.25 (m, 8H), 0.99-0.92 (m, 2H), 0.68 (s, 2H). MS (ESI) m/e [M+1]$^+$ 860.0.

Example F54: (S)-2-((1H-pyrrolo[2,3-b]pyridin-5-yl)oxy)-N-((3-nitro-4-(((tetrahydro-2H-pyran-4-yl)methyl)amino)phenyl)sulfonyl)-4-(2-(2-(o-tolyl)pyrrolidin-1-yl)-7-azaspiro[3.5]nonan-7-yl)benzamide

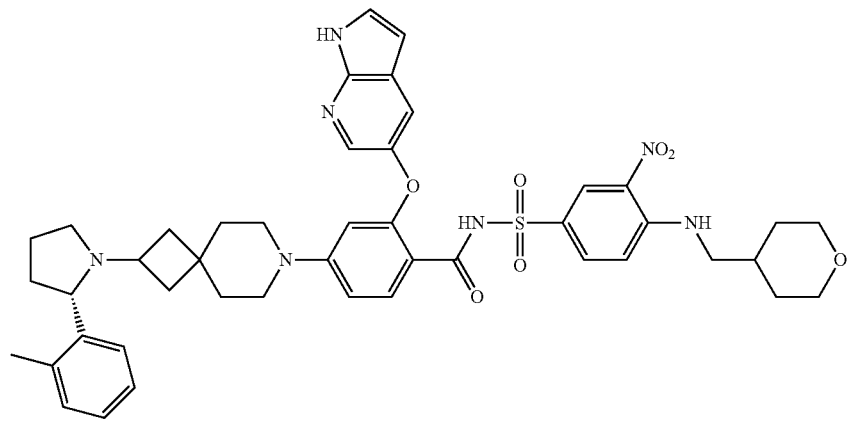 [SMILES: Cc1ccccc1[C@@H]1CCCN1C1CC2(CCN(c3ccc(C(=O)NS(=O)(=O)c4ccc(NCC5CCOCC5)c([N+](=O)[O-])c4)c(Oc4cnc5[nH]ccc5c4)c3)CC2)C1]

The desired compound was synthesized following the procedures similar to those in Example F40 by replacing (S)-2-(2-ethylphenyl)pyrrolidine with (S)-2-(o-tolyl)pyrrolidine and replacing (S)-4-(((1,4-dioxan-2-yl)methyl)amino)-3-nitrobenzenesulfonamide with 3-nitro-4-(((tetrahydro-2H-pyran-4-yl)methyl)amino)benzenesulfonimidamide. $^1$H NMR (DMSO-d$_6$) δ ppm: 11.68 (s, 1H), 11.44 (s, 1H), 8.62 (t, J=6.0 Hz, 1H), 8.56 (d, J=2.4 Hz, 1H), 8.03 (d, J=2.4 Hz, 1H), 7.87 (s, 1H), 7.79 (dd, J=9.0, 2.0 Hz, 1H), 7.57-7.45 (m, 3H), 7.30-7.16 (m, 3H), 7.11 (d, J=9.0 Hz, 1H), 6.69 (d, J=9.0 Hz, 1H), 6.38 (dd, J=3.2, 1.8 Hz, 1H), 6.18 (s, 1H), 4.55 (s, 1H), 3.85 (dd, J=11.2, 3.0 Hz, 2H), 3.33-0.3.22 (m, 4H), 3.14-2.85 (m, 5H), 2.36 (s, 4H), 2.21-1.96 (m, 5H), 1.92-1.83 (m, 1H), 1.61 (d, J=12.8 Hz, 2H), 1.49-1.35 (m, 5H), 1.31-1.17 (m, 2H). MS (ESI, m/e) [M+1]$^+$ 833.9.

Example F55: (S)-2-((1H-pyrrolo[2,3-b]pyridin-5-yl)oxy)-4-(2-(2-(2-chlorophenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide

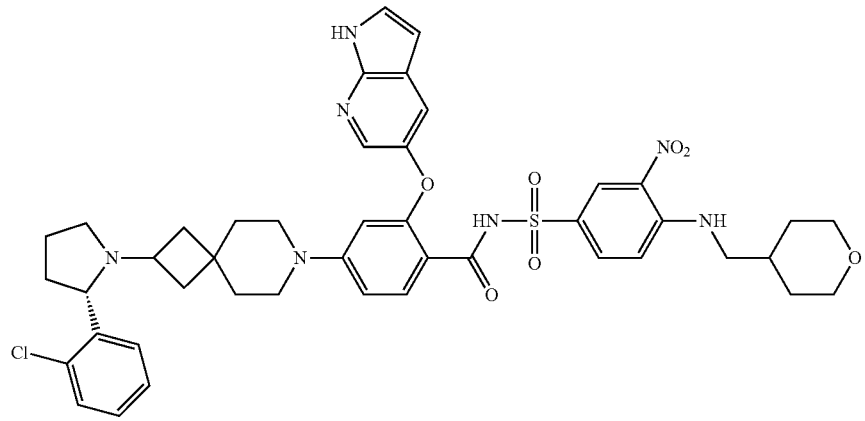 [SMILES: O=C(NS(=O)(=O)c1ccc(NCC2CCOCC2)c([N+](=O)[O-])c1)c1ccc(N2CCC3(CC2)CC(N2CCC[C@H]2c2ccccc2Cl)C3)cc1Oc1cnc2[nH]ccc2c1]

The desired compound was synthesized following the procedures similar to those in Example F40 by replacing (S)-2-(2-ethylphenyl)pyrrolidine with (S)-2-(2-chlorophenyl)pyrrolidine and replacing (S)-4-(((1,4-dioxan-2-yl)methyl)amino)-3-nitrobenzenesulfonamide with 3-nitro-4-(((tetrahydro-2H-pyran-4-yl)methyl)amino)benzenesulfonimidamide. $^1$H NMR (DMSO-d$_6$) δ ppm: 11.70 (s, 1H), 11.46 (br, 1H), 8.65-8.61 (m, 1H), 8.56 (d, J=2.2 Hz, 1H), 8.04 (d, J=2.5 Hz, 2H), 7.80 (d, J=9.1 Hz, 1H), 7.56-7.31 (m, 5H), 7.11 (d, J=9.4 Hz, 1H), 6.69 (d, J=9.0 Hz, 1H), 6.39 (d, J=1.7 Hz, 1H), 6.18 (s, 1H), 5.31 (s, 1H), 4.80 (s, 1H), 3.85 (d, J=8.1 Hz, 2H), 3.69-3.61 (m, 1H), 3.41-3.34 (m, 1H), 3.30-3.21 (m, 1H), 3.14-3.00 (m, 4H), 2.96 (s, 3H), 2.40-2.19 (m, 3H), 1.65-1.60 (m, 3H), 1.54-1.40 (m, 6H), 1.32-1.20 (m, 5H). MS (ESI, m/e) [M+1]$^+$ 853.8.

Example F56: (S)-2-((1H-pyrrolo[2,3-b]pyridin-5-yl)oxy)-4-(2-(2-(2-bromophenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide

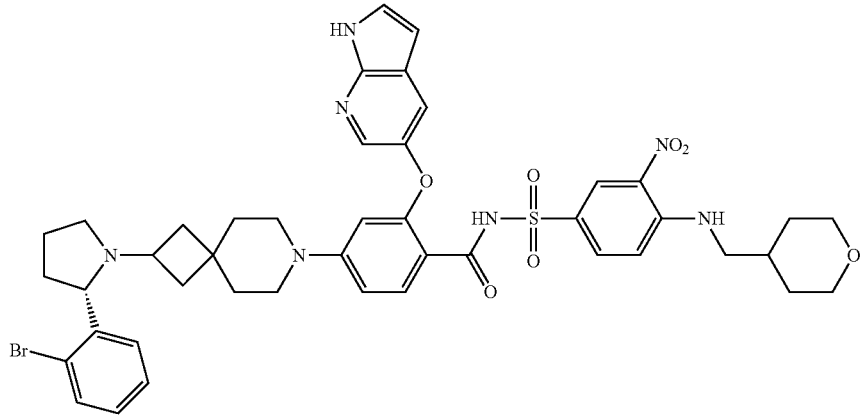

The desired compound was synthesized following the procedures similar to those in Example F40 by replacing (S)-2-(2-ethylphenyl)pyrrolidine with (S)-2-(2-bromophenyl)pyrrolidine and replacing (S)-4-(((1,4-dioxan-2-yl)methyl)amino)-3-nitrobenzenesulfonamide with 3-nitro-4-(((tetrahydro-2H-pyran-4-yl)methyl)amino)benzenesulfonimidamide. $^1$H NMR (DMSO-d$_6$) δ ppm: 11.72 (s, 1H), 11.68 (br, 1H), 8.61 (t, J=5.6 Hz, 1H), 8.56 (d, J=2.0 Hz, 1H), 8.04 (d, J=2.0 Hz, 1H), 7.87-7.74 (m, 1H), 7.59 (s, 1H), 7.53-7.46 (m, 3H), 7.42 (s, 1H), 7.25 (s, 1H), 7.11 (d, J=9.0 Hz, 1H), 6.68 (d, J=7.4 Hz, 1H), 6.44-6.30 (m, 1H), 6.18 (s, 1H), 3.85 (dd, J=11.2, 2.8 Hz, 2H), 3.62-3.12 (m, 8H), 3.12-2.83 (m, 5H), 2.43-2.27 (m, 1H), 2.12-1.76 (m, 5H), 1.61 (d, J=12.0 Hz, 2H), 1.58-1.31 (m, 6H), 1.30-1.19 (m, 2H). MS (ESI, m/e) [M+1]$^+$ 897.7.

Example F57: (R)-2-((1H-pyrrolo[2,3-b]pyridin-5-yl)oxy)-4-(2-(2-(2-chlorophenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide

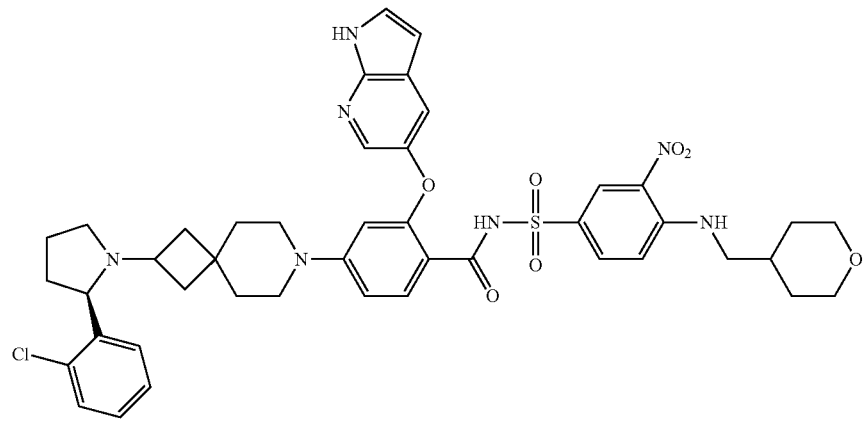 [SMILES: O=C(NS(=O)(=O)c1ccc(NCC2CCOCC2)c([N+](=O)[O-])c1)c1ccc(N2CCC3(CC2)CC(N2CCC[C@@H]2c2ccccc2Cl)C3)cc1Oc1cnc2[nH]ccc2c1]

The desired compound was synthesized following the procedures similar to those in Example F40 by replacing (S)-2-(2-ethylphenyl)pyrrolidine with (R)-2-(2-chlorophenyl)pyrrolidine and replacing (S)-4-(((1,4-dioxan-2-yl)methyl)amino)-3-nitrobenzenesulfonamide with 3-nitro-4-(((tetrahydro-2H-pyran-4-yl)methyl)amino)benzenesulfonimidamide. $^{1}$H NMR (DMSO-d$_{6}$) δ ppm: 11.70 (s, 1H), 11.44 (br, 1H), 8.63 (t, J=5.6 Hz, 1H), 8.56 (d, J=1.8 Hz, 1H), 8.04-7.99 (m, 2H), 7.79 (d, J=9.1 Hz, 1H), 7.52-7.43 (m, 5H), 7.12 (d, J=9.3 Hz, 1H), 6.69 (d, J=8.7 Hz, 1H), 6.39 (s, 1H), 6.17 (s, 1H), 4.81 (s, 1H), 3.85 (d, J=8.4 Hz, 2H), 3.63 (s, 1H), 3.29-3.23 (m, 4H), 3.05 (s, 2H), 2.97 (s, 2H), 2.10 (s, 2H), 2.02-1.97 (m, 1H), 1.89 (s, 2H), 1.63-1.60 (m, 3H), 1.43-1.38 (m, 5H), 1.31-1.19 (m, 4H). MS (ESI, m/e) [M+1]$^{+}$ 853.7.

Example F58: (S)-2-((1H-pyrrolo[2,3-b]pyridin-5-yl)oxy)-4-(2-(2-(3-chlorophenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide

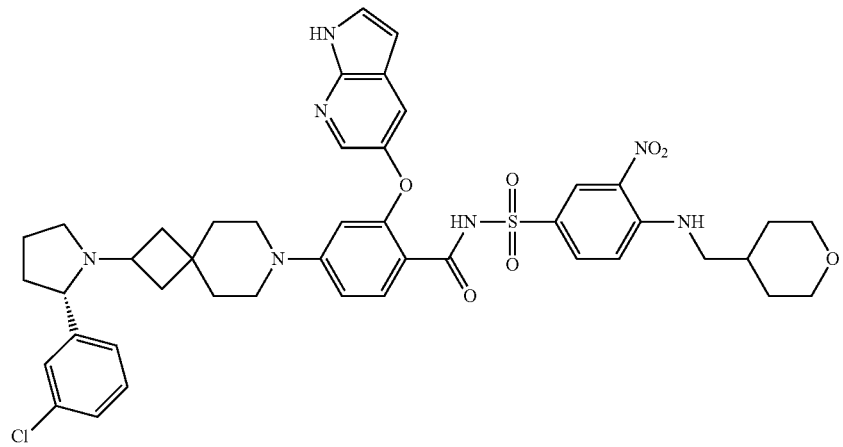 [SMILES: O=C(NS(=O)(=O)c1ccc(NCC2CCOCC2)c([N+](=O)[O-])c1)c1ccc(N2CCC3(CC2)CC(N2CCC[C@H]2c2cccc(Cl)c2)C3)cc1Oc1cnc2[nH]ccc2c1]

The desired compound was synthesized following the procedures similar to those in Example F40 by replacing (S)-2-(2-ethylphenyl)pyrrolidine with (S)-2-(3-chlorophenyl)pyrrolidine and replacing (S)-4-(((1,4-dioxan-2-yl)methyl)amino)-3-nitrobenzenesulfonamide with 3-nitro-4-(((tetrahydro-2H-pyran-4-yl)methyl)amino)benzenesulfonimidamide. $^{1}$H NMR (DMSO-d$_{6}$) δ ppm: 11.70 (s, 1H), 11.45 (br, 1H), 8.69-8.49 (m, 2H), 8.11-7.96 (m, 1H), 7.90-7.22 (m, 8H), 7.20-7.03 (m, 1H), 6.76-6.59 (m, 1H), 6.38 (s, 1H), 6.27-6.06 (m, 1H), 4.54-4.11 (m, 1H), 4.00-3.50 (m, 3H), 3.31-3.22 (m, 4H), 3.11-2.82 (m, 5H), 2.30-1.73 (m, 6H), 1.69-1.53 (m, 3H), 1.53-1.18 (m, 8H). MS (ESI, m/e) [M+1]$^{+}$ 853.8.

Example F59: (R)-2-((1H-pyrrolo[2,3-b]pyridin-5-yl)oxy)-4-(2-(2-(3-chlorophenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide

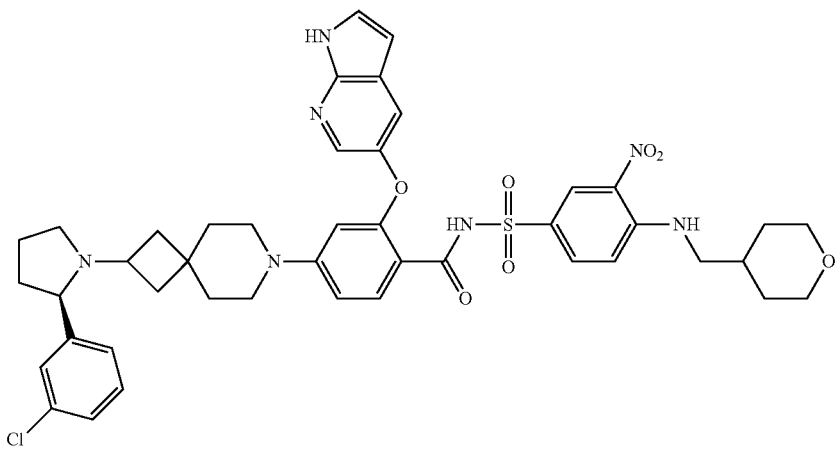 [SMILES: O=C(NS(=O)(=O)c1ccc(NCC2CCOCC2)c([N+](=O)[O-])c1)c1ccc(N2CCC3(CC2)CC(N2CCC[C@@H]2c2cccc(Cl)c2)C3)cc1Oc1cnc2[nH]ccc2c1]

The desired compound was synthesized following the procedures similar to those in Example F40 by replacing (S)-2-(2-ethylphenyl)pyrrolidine with (R)-2-(3-chlorophenyl)pyrrolidine and replacing (S)-4-(((1,4-dioxan-2-yl)methyl)amino)-3-nitrobenzenesulfonamide with 3-nitro-4-(((tetrahydro-2H-pyran-4-yl)methyl)amino)benzenesulfonimidamide. $^1$H NMR (DMSO-$d_6$) δ ppm: 11.69 (s, 1H), 11.44 (br, 1H), 8.62 (s, 1H), 8.55 (s, 1H), 8.03 (d, J=1.9 Hz, 1H), 7.79 (d, J=9.1 Hz, 1H), 7.51-7.34 (M, 6H), 7.11 (d, J=8.7 Hz, 1H), 6.69 (d, J=8.6 Hz, 1H), 6.38 (s, 1H), 6.17 (s, 1H), 4.38 (s, 1H), 3.85 (d, J=8.5 Hz, 2H), 3.63 (s, 1H), 3.29-3.23 (M, 4H), 3.05 (s, 2H), 2.96 (s, 2H), 2.11 (s, 1H), 2.02-1.97 (m, 1H), 1.91-1.89 (m, 2H), 1.63-1.60 (m, 3H), 1.43 (s, 2H), 1.36 (s, 2H), 1.31-1.23 (m, 6H), MS (ESI, m/e) [M+1]$^+$ 854.1.

Example F60: (S)-2-((1H-pyrrolo[2,3-b]pyridin-5-yl)oxy)-4-(2-(2-(4-chlorophenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide

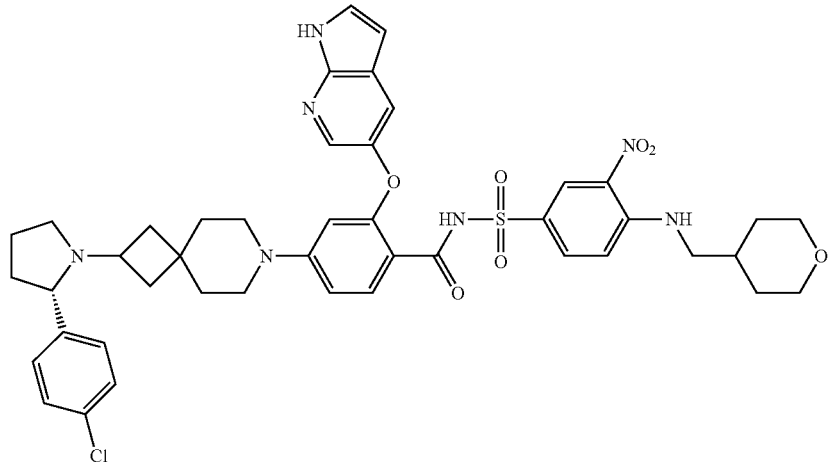 [SMILES: O=C(NS(=O)(=O)c1ccc(NCC2CCOCC2)c([N+](=O)[O-])c1)c1ccc(N2CCC3(CC2)CC(N2CCC[C@H]2c2ccc(Cl)cc2)C3)cc1Oc1cnc2[nH]ccc2c1]

The desired compound was synthesized following the procedures similar to those in Example F40 by replacing (S)-2-(2-ethylphenyl)pyrrolidine with (S)-2-(4-chlorophenyl)pyrrolidine and replacing (S)-4-(((1,4-dioxan-2-yl)methyl)amino)-3-nitrobenzenesulfonamide with 3-nitro-4-(((tetrahydro-2H-pyran-4-yl)methyl)amino)benzenesulfonimidamide. $^1$H NMR (DMSO-$d_6$) δ ppm: 11.68 (s, 1H), 8.61 (t, 0.7-5.9 Hz, 1H), 8.56 (d, J=2.2 Hz, 1H), 8.03 (d, J=2.6 Hz, 1H), 7.79 (dd, J=9.2, 2.1 Hz, 1H), 7.63 (d, J=7.6 Hz, 2H), 7.54-7.43 (m, 5H), 7.10 (d, J=9.4 Hz, 1H), 6.70 (dd, J=9.0, 1.8 Hz, 1H), 6.39 (dd, J=3.2, 1.8 Hz, 1H), 6.18 (d, J=1.7 Hz, 1H), 4.25 (s, 1H), 3.89-3.83 (m, 3H), 3.34-3.19 (m, 6H), 3.13-2.90 (m, 6 III 2.34 (s, 1H), 2.10-2.06 (m, 5H), 1.94-1.82 (m, 1H), 1.65-1.58 (m, 3H), 1.51-1.33 (m, 5H), 1.26-1.19 (m, 2H). MS (ESI, m/e) [M+1]$^+$ 853.8.

Example F61: (S)-2-((1H-pyrrolo[2,3-b]pyridin-5-yl)oxy)-4-(2-(2-(2-ethoxyphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide

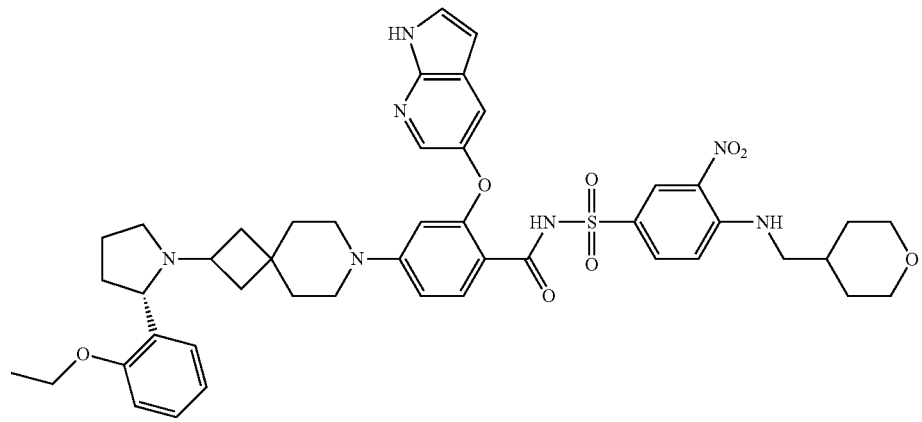 [SMILES: CCOc1ccccc1[C@@H]1CCCN1C1CC2(CCN(c3ccc(C(=O)NS(=O)(=O)c4ccc(NCC5CCOCC5)c([N+](=O)[O-])c4)c(Oc4cnc5[nH]ccc5c4)c3)CC2)C1]

The desired compound was synthesized following the procedures similar to those in Example F40 by replacing (S)-2-(2-ethylphenyl)pyrrolidine with (S)-2-(2-ethoxyphenyl)pyrrolidine and replacing (S)-4-(((1,4-dioxan-2-yl)methyl)amino)-3-nitrobenzenesulfonamide with 3-nitro-4-(((tetrahydro-2H-pyran-4-yl)methyl)amino)benzenesulfonimidamide. $^1$H NMR (DMSO-$d_6$) δ ppm: 11.68 (s, 1H), 11.45 (s, 1H), 9.97 (s, 1H), 8.58-8.52 (m, 2H), 8.02 (s, 1H), 7.78-7.76 (m, 1H), 7.65-7.23 (m, 5H), 7.05-7.01 (m, 3H), 6.72-6.58 (m, 1H), 6.37 (s, 1H), 6.20 (s, 1H), 4.68 (s, 1H), 4.10 (s, 2H), 3.87-3.83 (m, 3H), 3.30-3.23 (m, 3H), 3.05-3.01 (m, 5H), 2.05-1.98 (m, 9H), 1.67-1.17 (m, 14H). MS (ESI) m/e [M+1]$^+$ 863.8.

Example F62: (S)-2-((1H-pyrrolo[2,3-b]pyridin-5-yl)oxy)-4-(2-(2-(2-(dimethylamino)phenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide

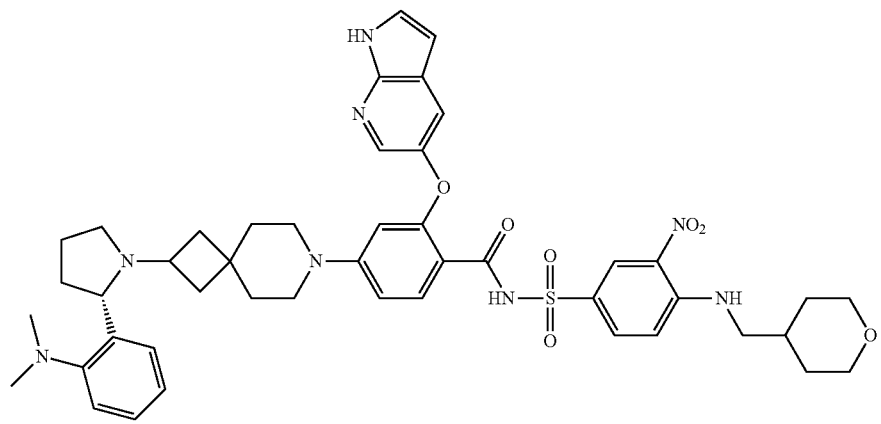 [SMILES: CN(C)c1ccccc1[C@@H]1CCCN1C1CC2(CCN(c3ccc(C(=O)NS(=O)(=O)c4ccc(NCC5CCOCC5)c([N+](=O)[O-])c4)c(Oc4cnc5[nH]ccc5c4)c3)CC2)C1]

The desired compound was synthesized following the procedures similar to those in Example F40 by replacing (S)-2-(2-ethylphenyl)pyrrolidine with (S)—N,N-dimethyl-2-(pyrrolidin-2-yl)aniline and replacing (S)-4-(((1,4-dioxan-2-yl)methyl)amino)-3-nitrobenzenesulfonamide with 3-nitro-4-(((tetrahydro-2H-pyran-4-yl)methyl)amino)benzenesulfonimidamide. $^1$H NMR (DMSO-$d_6$) δ ppm: 11.70 (s, 1H), 11.45 (s, 1H), 10.17 (s, 1H), 8.67-8.59 (m, 1H), 8.59-8.52 (m 1H), 8.08-7.99 (m, 1H), 7.83-7.76 (m, 1H), 7.71 (s, 1H), 7.57-7.45 (m, 3H), 7.44-7.33 (m, 1H), 7.31-7.24 (m, 1H), 7.24-7.16 (m, 1H), 7.16-7.06 (m, 1H), 6.73-6.64 (m, 1H), 6.42-6.31 (m, 1H), 6.21-6.11 (m, 1H), 4.99-4.83 (m, 1H), 3.91-3.80 (m, 2H), 3.80-3.67 (m, 1H), 3.67-3.51 (m, 1H), 3.32-3.22 (m, 4H), 3.20-2.90 (m, 6H), 2.60 (s, 6H), 2.23-1.79 (m, 6H), 1.70-1.57 (m, 2H), 1.57-1.49 (m, 1H), 1.44-1.20 (m, 7H). MS (ESI, m/e) [M+1]$^+$ 862.9.

Example F63: 2-((1H-pyrrolo[2,3-b]pyridin-5-yl)oxy)-4-(2-((S)-2-(2-(dimethylamino)phenyl)pyrrolidin-1-yl)-7-azaspiro[3.5]nonan-7-yl)-N-((4-((((1r,4r)-4-hydroxy-4-methylcyclohexyl)methyl)amino)-3-nitrophenyl)sulfonyl)benzamide

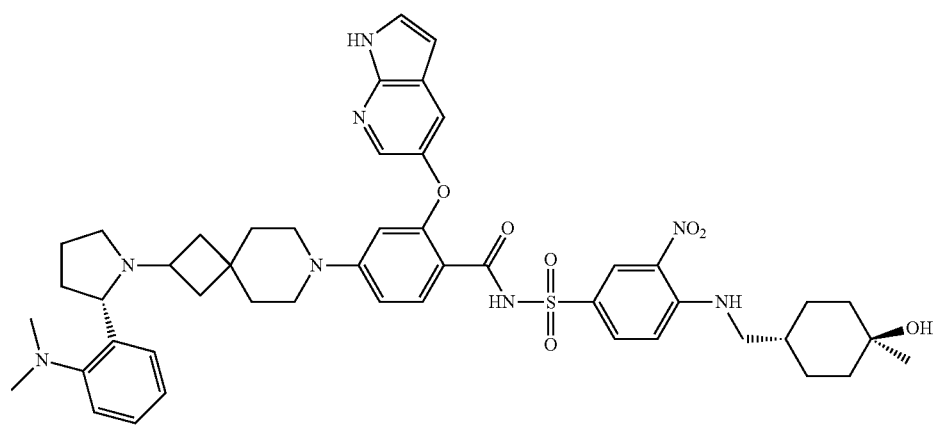 [SMILES: CN(C)c1ccccc1[C@@H]1CCCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1]

The desired compound was synthesized following the procedures similar to those in Example F21 by replacing (S)-2-(2-cyclopropylphenyl)pyrrolidine with (S)—N,N-dimethyl-2-(pyrrolidin-2-yl)aniline. $^1$H NMR (DMSO-d$_6$) δ ppm: 11.60 (s, 1H), 11.37 (s, 1H), 8.66-8.52 (m, 2H), 8.05 (s, 1H), 7.83 (d, J=8.9 Hz, 1H), 7.56-7.52 (m, 3H), 7.36-7.30 (m, 4H), 7.17-7.15 (m, 2H), 7.03-7.00 (m, 1H), 6.94-6.80 (m, 2H), 6.39-6.35 (m, 3H), 5.06 (s, 1H), 4.56 (s, 1H), 3.96-3.81 (m, 3H), 3.71-3.70 (m, 1H), 3.29-3.10 (m, 6H), 2.67 (s, 6H), 2.07-2.04 (m, 3H), 1.99 (s, 2H), 1.86 (s, 3H), 1.66-1.60 (m, 5H), 1.45-1.43 (m, 1H). MS (ESI) m/e [M+1]$^+$ 890.9.

Example F64: 2-((1H-pyrrolo[2,3-b]pyridin-5-yl) oxy)-4-(2-((S)-2-(2-(bis(methyl-d3)amino)phenyl) pyrrolidin-1-yl)-7-azaspiro[3.5]nonan-7-yl)-N-((4-((((1r,4r)-4-hydroxy-4-methylcyclohexyl)methyl) amino)-3-nitrophenyl)sulfonyl)benzamide

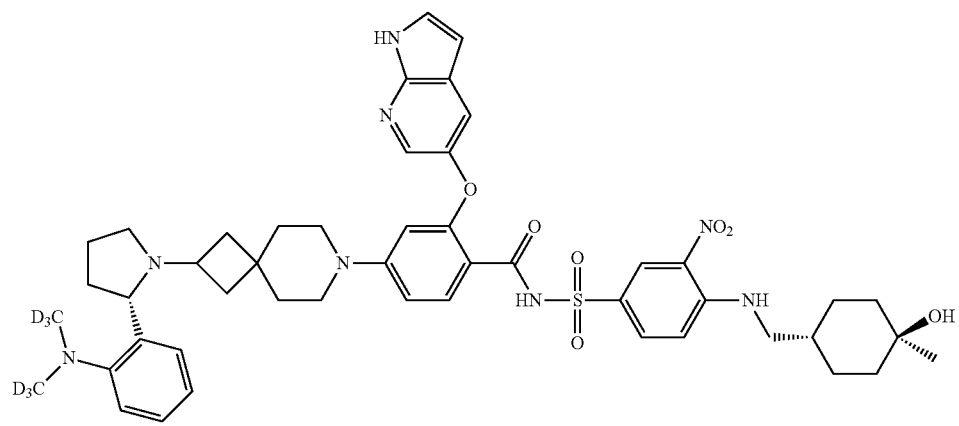 [SMILES: [2H]C([2H])([2H])N(c1ccccc1[C@@H]1CCCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1)C([2H])([2H])[2H]]

The desired compound was synthesized following the procedures similar to those in Example F21 by replacing (S)-2-(2-cyclopropylphenyl)pyrrolidine with (S)—N,N-bis(methyl-d3)-2-(pyrrolidin-2-yl)aniline. $^1$H NMR (DMSO-$d_6$) δ ppm: 11.69 (s, 1H), 11.43 (s, 1H), 10.14 (s, 1H), 8.56 (s, 2H), 8.04 (s, 1H), 7.81-7.75 (m, 1H), 7.69 (s, 1H), 7.51-7.43 (m, 3H), 7.38 (s, 1H), 7.29-7.16 (m, 2H), 7.11-7.06 (m, 1H), 6.70-6.72 (m, 1H), 6.38 (s, 1H), 6.18 (s, 1H), 4.90 (s, 1H), 4.24 (s, 1H), 3.68-3.64 (m, 2H), 3.30-3.01 (m, 7H), 2.11-2.06 (m, 5H), 1.72-1.65 (m, 2H), 1.61-1.60 (m, 3H), 1.38-1.30 (m, 7H), 1.13-1.05 (m, 5H). MS (ESI) m/e [M+1]$^+$ 896.9.

Example F65: 2-((1H-pyrrolo[2,3-b]pyridin-5-yl)oxy)-N-((3-nitro-4-(((tetrahydro-2H-pyran-4-yl)methyl)amino)phenyl)sulfonyl)-4-(2-(2-(2-(pyrrolidin-1-yl)phenyl)pyrrolidin-1-yl)-7-azaspiro[3.5]nonan-7-yl)benzamide

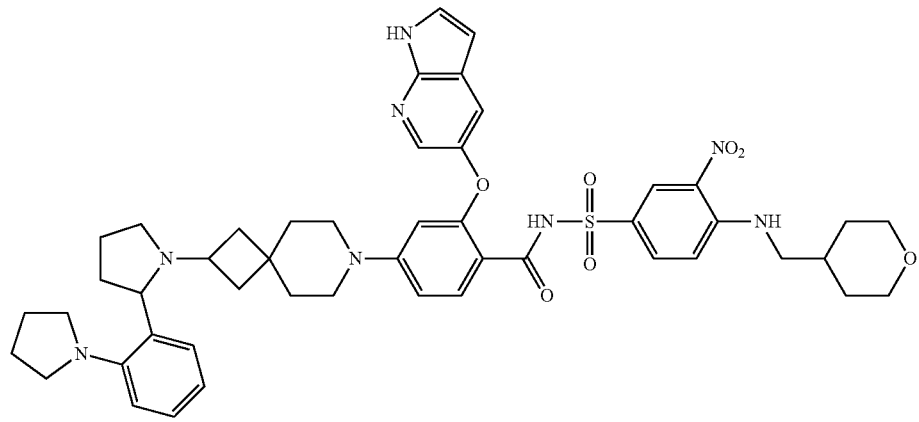 [SMILES: O=C(NS(=O)(=O)c1ccc(NCC2CCOCC2)c([N+](=O)[O-])c1)c1ccc(N2CCC3(CC2)CC(N2CCCC2c2ccccc2N2CCCC2)C3)cc1Oc1cnc2[nH]ccc2c1]

The desired compound was synthesized following the procedures similar to those in Example F40 by replacing (S)-2-(2-ethylphenyl)pyrrolidine with 1-(2-(pyrrolidin-2-yl)phenyl)pyrrolidine and replacing (S)-4-(((1,4-dioxan-2-yl)methyl)amino)-3-nitrobenzenesulfonamide with 3-nitro-4-(((tetrahydro-2H-pyran-4-yl)methyl)amino)benzenesulfonimidamide. $^1$H NMR (DMSO-$d_6$) δ ppm: 11.70 (s, 1H), 11.46 (s, 1H), 8.57-8.55 (m, 2H), 8.03 (s, 1H), 7.79 (d, J=8.8 Hz, 1H), 7.67 (s, 1H), 7.50-7.48 (m, 3H), 7.32 (s, 1H), 7.10 (s, 3H), 6.70-6.68 (m, 1H), 6.38 (s, 1H), 6.18 (s, 1H), 4.79 (s, 1H), 3.86-3.84 (m, 2H), 3.71 (s, 1H), 3.53 (s, 1H), 3.30-3.26 (m, 6H), 2.98-2.92 (m, 5H), 2.81 (s, 2H), 2.13 (s, 3H), 2.05-1.77 (m, 8H), 1.63-1.59 (m, 2H), 1.56-1.48 (m, 1H), 1.35-1.26 (m, 7H). MS (ESI) m/e [M+1]$^+$ 888.8.

Example F66: (S)-2-((1H-pyrrolo[2,3-b]pyridin-5-yl)oxy)-4-(2-(2-(2-(1-methyl-1,2,3,6-tetrahydropyridin-4-yl)phenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide

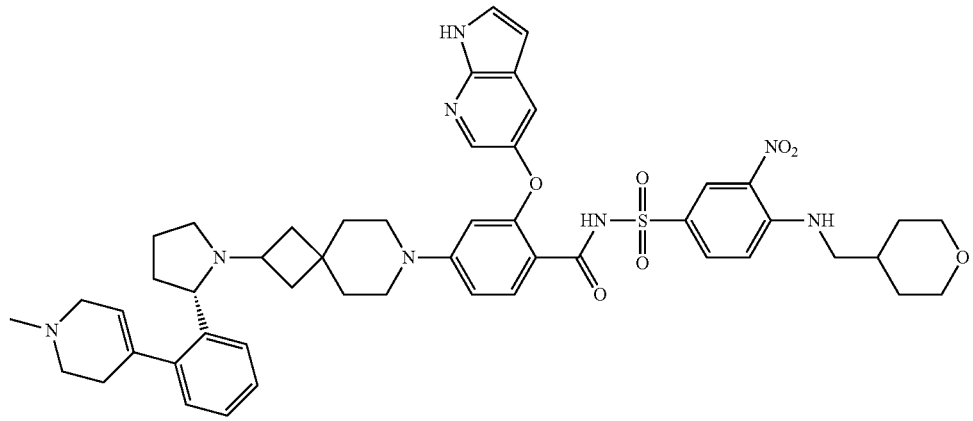

The desired compound was synthesized following the procedures similar to those in Example F23 by replacing (S)-2-(2-cyclopropylphenyl)pyrrolidine with (S)-1-methyl-4-(2-(pyrrolidin-2-yl)phenyl)-1,2,3,6-tetrahydropyridine. MS (ESI, m/e) [M+1]⁺ 914.8.

Example F67: (S)-2-((1H-pyrrolo[2,3-b]pyridin-5-yl)oxy)-4-(2-(2-(2-(1-methylpiperidin-4-yl)phenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide

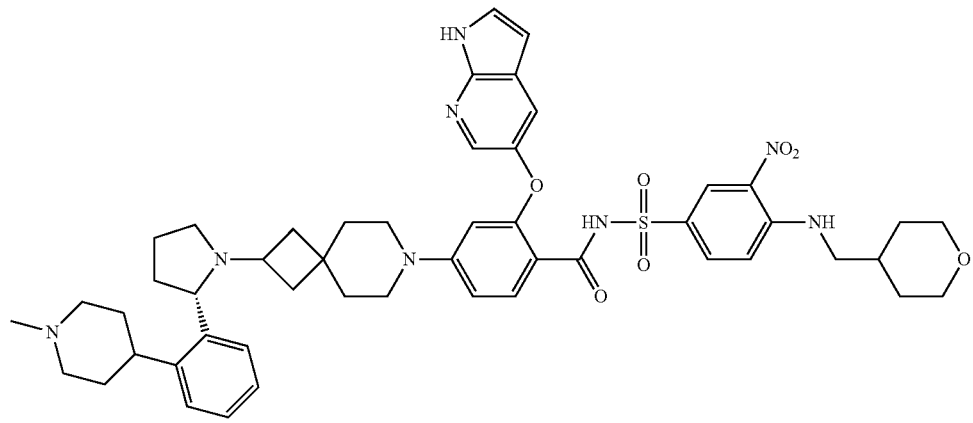 [SMILES: CN1CC=C(c2ccccc2[C@@H]2CCCN2C2CC3(CCN(c4ccc(C(=O)NS(=O)(=O)c5ccc(NCC6CCOCC6)c([N+](=O)[O-])c5)c(Oc5cnc6[nH]ccc6c5)c4)CC3)C2)CC1]

The desired compound was synthesized following the procedures similar to those in Example F23 by replacing (S)-2-(2-cyclopropylphenyl)pyrrolidine with (S)-1-methyl-4-(2-(pyrrolidin-2-yl)phenyl)piperidine. MS (ESI, m/e) [M+1]⁺ 916.8.

Example F68: (S)-2-((1H-pyrrolo[2,3-b]pyridin-5-yl)oxy)-4-(2-(2-(2-methoxyphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide

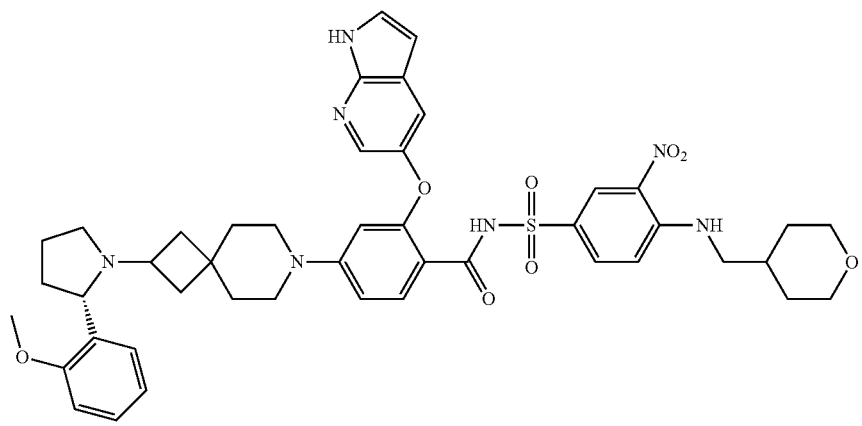 [SMILES: COc1ccccc1[C@@H]1CCCN1C1CC2(CCN(c3ccc(C(=O)NS(=O)(=O)c4ccc(NCC5CCOCC5)c([N+](=O)[O-])c4)c(Oc4cnc5[nH]ccc5c4)c3)CC2)C1]

The desired compound was synthesized following the procedures similar to those in Example F40 by replacing (S)-2-(2-ethylphenyl)pyrrolidine with (S)-2-(2-methoxyphenyl)pyrrolidine and replacing (S)-4-(((1,4-dioxan-2-yl)methyl)amino)-3-nitrobenzenesulfonamide with 3-nitro-4-(((tetrahydro-2H-pyran-4-yl)methyl)amino)benzenesulfonamide. $^1$H NMR (400 MHz, DMSO-d$_6$) δ ppm: 11.70 (s, 1H), 11.46 (s, 1H), 9.38 (s, 1H), 8.72-8.47 (m, 2H), 8.04 (s, 1H), 7.85-7.71 (m, 1H), 7.57-7.38 (m, 4H), 7.19-6.92 (m, 3H), 6.77-6.62 (m, 1H), 6.38 (s, 1H), 6.19 (s, 1H), 4.73-4.56 (m, 1H), 3.93-3.76 (m, 5H), 3.59-3.40 (m, 2H), 3.29-2.89 (m, 9H), 2.37-1.72 (m, 8H), 1.68-1.55 (m, 2H), 1.53-1.33 (m, 4H), 1.32-1.24 (m, 3H). MS (ESI, m/e) [M+1]$^+$ 849.9.

Example F69: (S)-2-((1H-pyrrolo[2,3-b]pyridin-5-yl)oxy)-4-(2-(2-(2-isopropoxyphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide

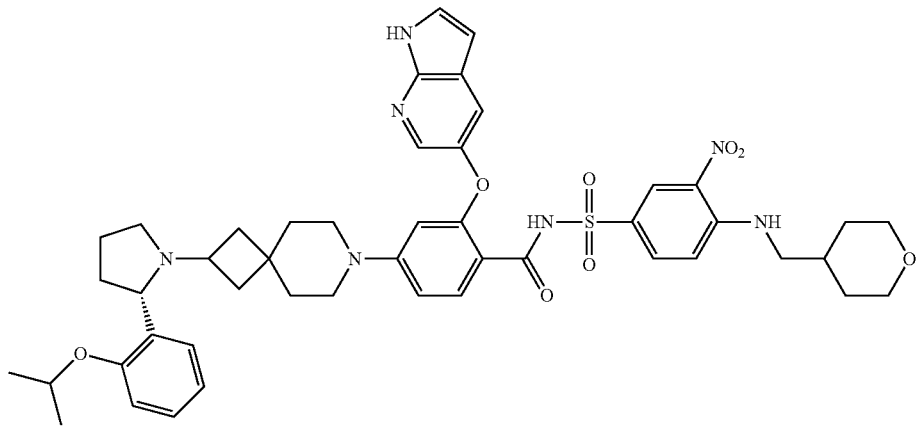 [SMILES: CC(C)Oc1ccccc1[C@@H]1CCCN1C1CC2(CCN(c3ccc(C(=O)NS(=O)(=O)c4ccc(NCC5CCOCC5)c([N+](=O)[O-])c4)c(Oc4cnc5[nH]ccc5c4)c3)CC2)C1]

The desired compound was synthesized following the procedures similar to those in Example F43 by replacing (S)-2-(2-isopropylphenyl)pyrrolidine with (S)-2-(2-isopropoxyphenyl)pyrrolidine and replacing 4-((((1r,4r)-4-hydroxy-4-methylcyclohexyl)methyl)amino)-3-nitrobenzenesulfonamide with 3-nitro-4-(((tetrahydro-2H-pyran-4-yl)methyl)amino)benzenesulfonamide. $^1$H NMR (400 MHz, DMSO-d$_6$) δ ppm: 11.70 (s, 1H), 11.46 (s, 1H), 8.75-8.41 (m, 2H), 8.04 (s, 1H), 7.89-7.72 (m, 1H), 7.72-7.55 (m, 1H), 7.55-7.41 (m, 3H), 7.41-7.28 (m, 1H), 7.20-6.89 (m, 3H), 6.79-6.61 (m, 1H), 6.38 (s, 1H), 6.20 (s, 1H), 4.82-4.58 (m, 2H), 3.99-3.71 (m, 3H), 3.62-3.47 (m, 1H), 3.30-3.22 (m, 3H), 3.20-2.85 (m, 5H), 2.40-1.68 (m, 9H), 1.65-1.38 (m, 7H), 1.37-1.26 (m, 7H). MS (ESI, m/e) [M+1]$^+$ 877.9.

Example F70: 2-((1H-pyrrolo[2,3-b]pyridin-5-yl)oxy)-4-(2-(2-(2-(methoxymethyl)phenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide

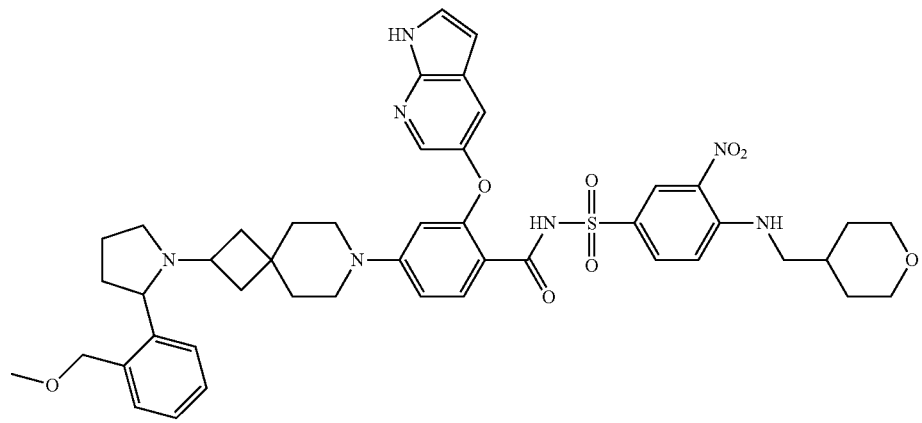 [SMILES: COCc1ccccc1C1CCCN1C1CC2(CCN(c3ccc(C(=O)NS(=O)(=O)c4ccc(NCC5CCOCC5)c([N+](=O)[O-])c4)c(Oc4cnc5[nH]ccc5c4)c3)CC2)C1]

The desired compound was synthesized following the procedures similar to those in Example F40 by replacing (S)-2-(2-ethylphenyl)pyrrolidine with 2-(2-(methoxymethyl)phenyl)pyrrolidine and replacing (S)-4-((((1,4-dioxan-2-yl)methyl)amino)-3-nitrobenzenesulfonamide with 3-nitro-4-(((tetrahydro-2H-pyran-4-yl)methyl)amino)benzenesulfonamide. $^1$H NMR (400 MHz, DMSO-d$_6$) δ ppm: 11.69 (s, 1H), 11.44 (br, 1H), 8.62-8.55 (m, 2H), 8.02 (s, 1H), 8.87-7.77 (m, 2H), 7.51-7.42 (m, 3H), 7.37 (s, 1H), 7.21 (s, 1H), 7.11 (s, 1H), 6.67 (d, J=7.3 Hz, 1H), 6.37 (s, 1H), 6.17 (s, 1H), 4.55-4.50 (m, 1H), 4.45 (s, 1H), 3.85 (d, J=8.1 Hz, 2H), 3.67 (s, 1H), 3.31-3.22 (m, 10H), 3.02 (s, 2H), 2.94 (s, 2H), 2.10 (s, 1H), 2.02-1.97 (m, 2H), 1.88 (s, 1H), 1.61 (d, J=12.2 Hz, 2H), 1.45 (s, 4H), 1.25-1.23 (m, 7H). MS (ESI, m/e) [M+1]$^+$ 863.8.

Example F71: 2-((1H-pyrrolo[2,3-b]pyridin-5-yl)oxy)-4-(2-(2-(2-(hydroxymethyl)phenyl)pyrrolidin-1-yl)-7-azaspiro[3.5]nonan-7-yl)-N-((3-nitro-4-((((tetrahydro-2H-pyran-4-yl)methyl)amino)phenyl)sulfonyl)benzamide

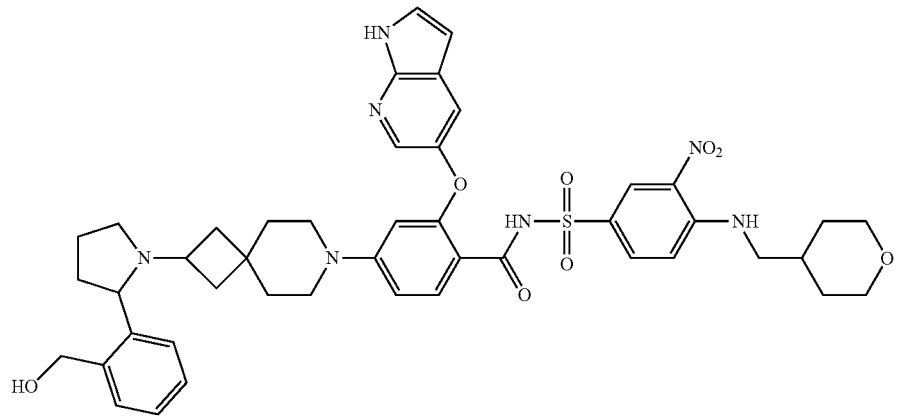 [SMILES: O=C(NS(=O)(=O)c1ccc(NCC2CCOCC2)c([N+](=O)[O-])c1)c1ccc(N2CCC3(CC2)CC(N2CCCC2c2ccccc2CO)C3)cc1Oc1cnc2[nH]ccc2c1]

The desired compound was synthesized following the procedures similar to those in Example F40 by replacing (S)-2-(2-ethylphenyl)pyrrolidine with (2-(pyrrolidin-2-yl)phenyl)methanol and replacing (S)-4-(((1,4-dioxan-2-yl)methyl)amino)-3-nitrobenzenesulfonamide with 3-nitro-4-((((tetrahydro-2H-pyran-4-yl)methyl)amino)benzenesulfonamide. $^1$H NMR (400 MHz, DMSO-$d_6$) δ ppm: 11.65 (s, 1H), 8.55-8.51 (m, 2H), 8.20 (d, J=6.5 Hz, 2H), 8.00 (s, 1H), 7.73 (d, J=8.9 Hz, 1H), 7.50-7.44 (m, 2H), 7.32-7.27 (m, 2H), 7.03 (d, J=8.8 Hz, 1H), 6.94 (d, J=6.4 Hz, 2H), 6.66 (d, J=7.9 Hz, 1H), 6.36 (s, 1H), 6.18 (s, 1H), 4.64-4.50 (m, 2H), 3.84 (d, J=9.3 Hz, 2H), 3.31-3.23 (m, 8H), 3.01 (s, 2H), 2.92 (s, 2H), 2.02-1.98 (m, 2H), 1.88 (s, 2H), 1.61 (d, J=12.1 Hz, 2H), 1.45 (s, 1H), 1.39-1.36 (m, 4H), 1.23 (s, 6H). MS (ESI, m/e) [M+1]$^+$ 849.8.

Example F72a and Example F72b: (R or S)-2-((1H-pyrrolo[2,3-b]pyridin-5-yl)oxy)-4-(2-(2-(3-chloro-2-cyclopropylphenyl)pyrrolidin-1-yl)-7-azaspiro[3.5]nonan-7-yl)-N-((3-nitro-4-((((tetrahydro-2H-pyran-4-yl)methyl)amino)phenyl)sulfonyl)benzamide; (S or R)-2-((1H-pyrrolo[2,3-b]pyridin-5-yl)oxy)-4-(2-(2-(3-chloro-2-cyclopropylphenyl)pyrrolidin-1-yl)-7-azaspiro[3.5]nonan-7-yl)-N-((3-nitro-4-((((tetrahydro-2H-pyran-4-yl)methyl)amino)phenyl)sulfonyl)benzamide

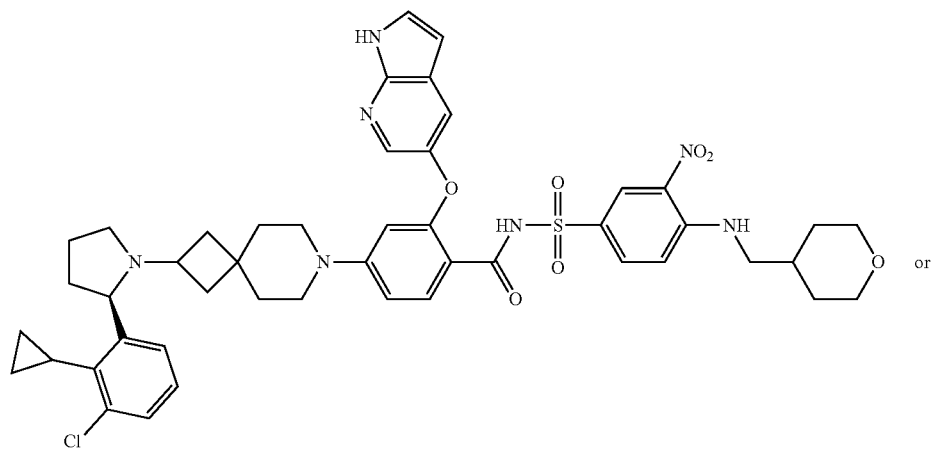 or

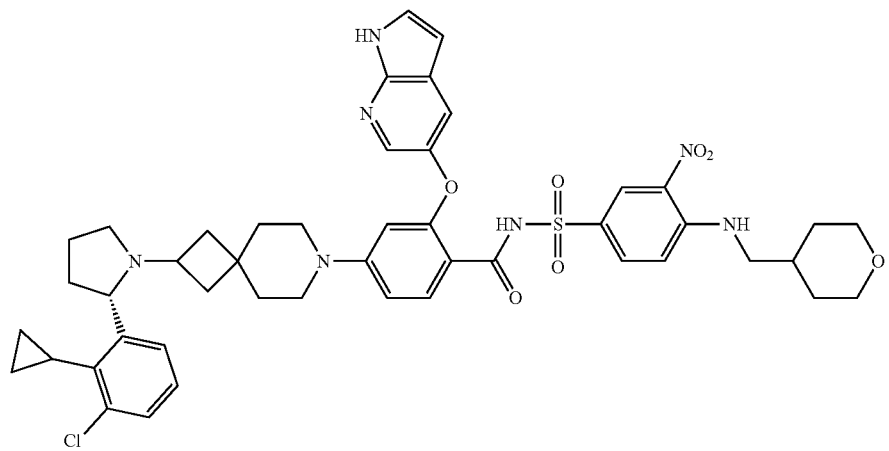

The desired compound 72a was synthesized following the procedures similar to those in Example F40 by replacing (S)-2-(2-ethylphenyl)pyrrolidine with (R or S)-2-(3-chloro-2-cyclopropylphenyl)pyrrolidine (faster peak in SFC) and replacing (S)-4-(((1,4-dioxan-2-yl)methyl)amino)-3-nitrobenzenesulfonamide with 3-nitro-4-(((tetrahydro-2H-pyran-4-yl)methyl)amino)benzenesulfonamide. $^1$H NMR (400 MHz, DMSO-$d_6$) δ ppm: 11.66 (s, 1H), 11.38 (br, 1H), 8.56-8.52 (m, 2H), 8.01 (s, 1H), 7.74-7.72 (m, 1H), 7.58-7.49 (m, 4H), 7.35-7.04 (m, 3H), 6.65 (m, 1H), 6.36 (s, 1H), 6.17 (s, 1H), 4.12-4.09 (m, 1H), 3.85-3.71 (m, 2H), 3.33-3.21 (m, 4H), 3.21-2.90 (m, 5H), 2.67-2.61 (m, 1H), 2.33-1.08 (m, 19H), 0.85-0.81 (m, 2H), 0.52-0.44 (m, 2H). MS (ESI, m/e) [M+1]$^+$ 893.8; Compound 72b was synthesized following the procedures similar to those in Example F40 by replacing (S)-2-(2-ethylphenyl)pyrrolidine with (S or R)-2-(3-chloro-2-cyclopropylphenyl)pyrrolidine (slower peak in SFC) and replacing (S)-4-(((1,4-dioxan-2-yl)methyl)amino)-3-nitrobenzenesulfonamide with 3-nitro-4-(((tetrahydro-2H-pyran-4-yl)methyl)amino)benzenesulfonamide. MS (ESI, m/e) [M+1]$^+$ 893.8.

Example F73: 2-((1H-pyrrolo[2,3-b]pyridin-5-yl)oxy)-4-(2-(2-(5-chloro-2-cyclopropylphenyl)pyrrolidin-1-yl)-7-azaspiro[3.5]nonan-7-yl)-N -((3-nitro-4-(((tetrahydro-2H -pyran-4-yl)methyl)amino)phenyl)sulfonyl)benzamide

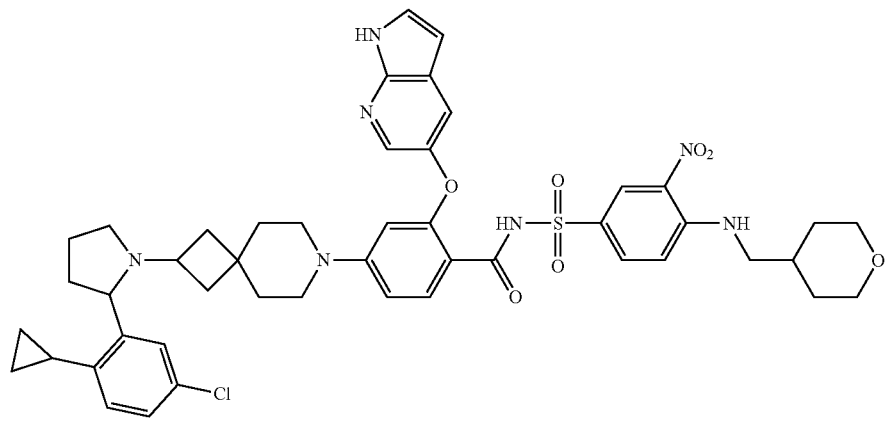 [SMILES: O=C(NS(=O)(=O)c1ccc(NCC2CCOCC2)c([N+](=O)[O-])c1)c1ccc(N2CCC3(CC2)CC(N2CCCC2c2cc(Cl)ccc2C2CC2)C3)cc1Oc1cnc2[nH]ccc2c1]

The desired compound was synthesized following the procedures similar to those in Example F40 by replacing (S)-2-(2-ethylphenyl)pyrrolidine with 2-(5-chloro-2-cyclopropylphenyl)pyrrolidine and replacing (S)-4-(((1,4-dioxan-2-yl)methyl)amino)-3-nitrobenzenesulfonamide with 3-nitro-4-(((tetrahydro-2H-pyran-4-yl)methyl)amino)benzenesulfonamide. $^1$H NMR (400 MHz, DMSO-d$_6$) δ ppm: 11.63 (s, 1H), 8.56-8.52 (m, 2H), 8.01 (s, 1H), 7.71-7.69 (m, 1H), 7.58-7.49 (m, 4H), 7.35-7.04 (m, 3H), 6.65-6.63 (m, 1H), 6.36 (s, 1H), 6.19 (s, 1H), 4.11-3.86 (m, 1H), 3.85<d, J=8.4 Hz, 2H), 3.33-2.90 (m, 12H), 2.67-2.61 (m, 1H), 2.33-2.21 (m, 1H), 2.02-1.08 (m, 15H), 0.85-0.81 (m, 2H), 0.64-0.53 (m, 2H), MS (ESI, m/e) [M+1]$^+$ 893.8.

Example F74a and Example F74b: (R or S)-2-((1H-pyrrolo[2,3-b]pyridin-5-yl)oxy)-4-(2-(2-(3-chloro-2-ethylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide; (S or R)-2-((1H-pyrrolo[2,3-b]pyridin-5-yl)oxy)-4-(2-(2-(3-chloro-2-ethylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide

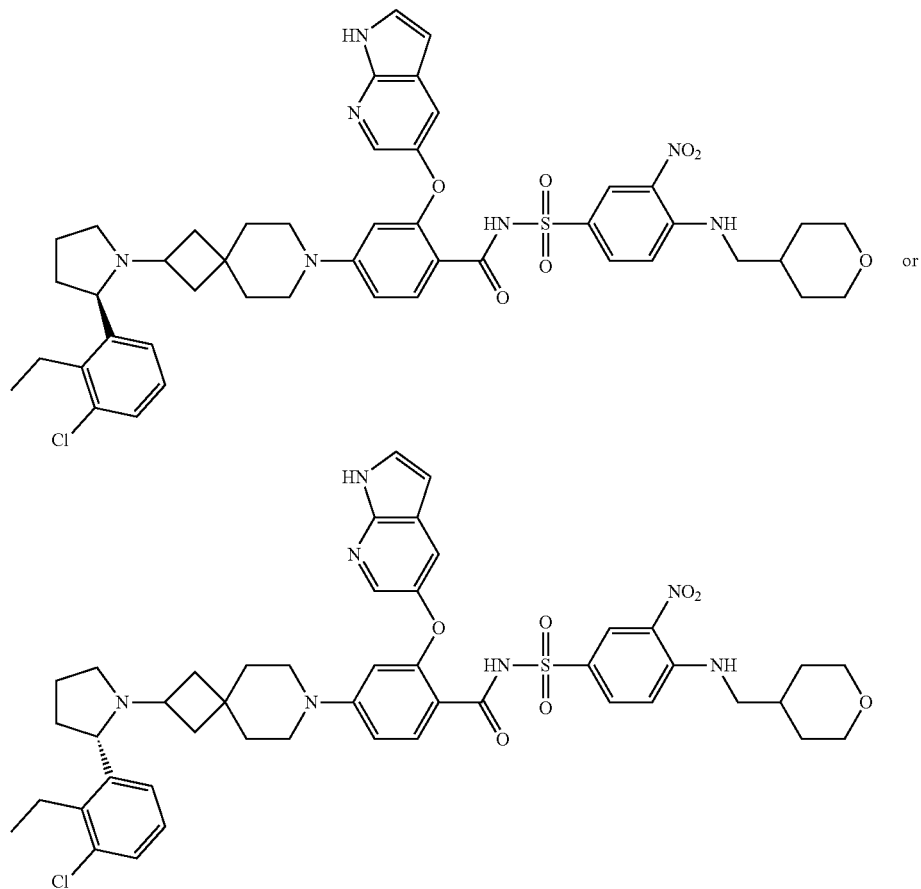

The desired compound 72a was synthesized following the procedures similar to those in Example F40 by replacing (S)-2-(2-ethylphenyl)pyrrolidine with (R or S) 2-(3-chloro-2-ethylphenyl)pyrrolidine (faster peak in SFC) and replacing (S)-4-(((1,4-dioxan-2-yl)methyl)amino)-3-nitrobenzenesulfonamide with 3-nitro-4-(((tetrahydro-2H-pyran-4-yl)methyl)amino)benzenesulfonamide. $^1$H NMR (400 MHz, DMSO-d$_6$) δ ppm: 11.70 (s, 1H), 11.45 (s, 1H), 10.08 (s, 1H), 8.70-8.55 (m, 2H), 8.04 (s, 1H), 7.85-7.70 (m, 2H), 7.66-7.24 (m, 4H), 7.40-7.20 (m, 1H), 6.69 (d, J=8.7 Hz, 1H), 6.35 (d, J=25.1 Hz, 1H), 6.17 (s, 1H), 5.76 (s, 1H), 4.75-4.60 (m, 1H), 3.90-3.75 (m, 2H), 3.76-3.56 (m, 1H), 3.31-3.21 (m, 2H), 3.19-2.90 (m, 4H), 2.15-1.85 (m, 5H), 1.61 (d, J=12.1 Hz, 2H), 1.56-1.19 (m, 10H), 1.15-1.10 (m, 2H), 0.90-0.79 (m, 3H), MS (ESI, m/e) [M+1]$^+$ 881.8; Compound 74b was synthesized following the procedures similar to those in Example F40 by replacing (S)-2-(2-ethylphenyl)pyrrolidine with (S or R)-2-(3-chloro-2-ethylphenyl)pyrrolidine (slower peak in SFC) and replacing (S)-4-(((1,4-dioxan-2-yl)methyl)amino)-3-nitrobenzenesulfonamide with 3-nitro-4-(((tetrahydro-2H-pyran-4-yl)methyl)amino)benzenesulfonamide. MS (ESI, m/e) [M+1]$^+$ 881.8.

Example F75: 2-((1H-pyrrolo[2,3-b]pyridin-5-yl)oxy)-4-(2-(2-(2,4-dicyclopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide

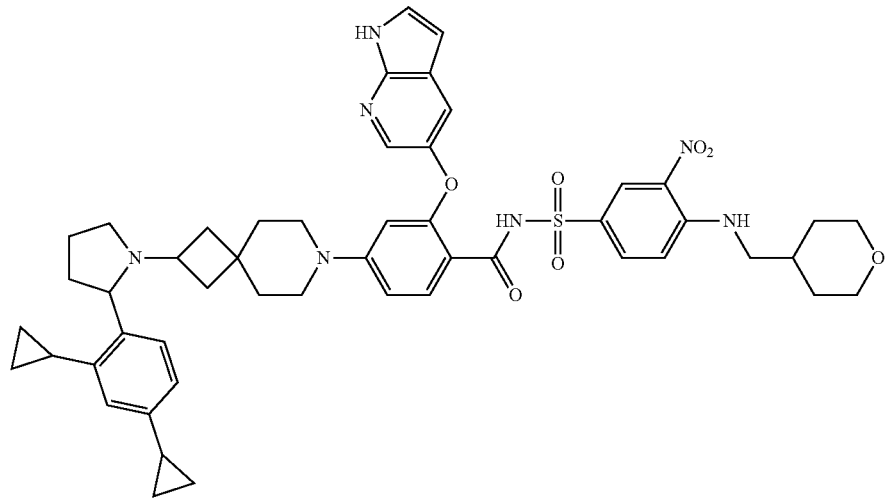 [SMILES: O=C(NS(=O)(=O)c1ccc(NCC2CCOCC2)c([N+](=O)[O-])c1)c1ccc(N2CCC3(CC2)CC(N2CCCC2c2ccc(C4CC4)cc2C2CC2)C3)cc1Oc1cnc2[nH]ccc2c1]

The desired compound was synthesized following the procedures similar to those in Example F40 by replacing (S)-2-(2-ethylphenyl)pyrrolidine with 2-(2,4-dicyclopropylphenyl)pyrrolidine and replacing (S)-4-(((1,4-dioxan-2-yl)methyl)amino)-3-nitrobenzenesulfonamide with 3-nitro-4-(((tetrahydro-2H-pyran-4-yl)methyl)amino)benzenesulfonamide. $^1$H NMR (400 MHz, DMSO-d$_6$) δ ppm: 11.69 (s, 1H), 11.45 (br, 1H), 8.62-8.56 (m, 2H), 8.03 (s, 1H), 7.78 (s, 1H), 7.56-7.47 (m, 3H), 7.20-7.12 (m, 1H), 6.94 (d, J=8.1 Hz, 1H), 6.76 (s, HI). 6.69 (d, J=9.2 Hz, 1H), 6.38 (s, 1H), 6.18 (s, 1H), 4.90 (s, 1H), 3.85 (d, J=8.2 Hz, 2H), 3.64 (s, 1H), 3.31-3.23 (m, 4H), 3.08-2.97 (m, 8H), 2.11 (s, 2H), 2.03-1.97 (m, 4H), 1.89 (s, 2H), 1.63-1.59 (m, 3H), 1.45 (s, 2H), 1.38 (s, 2H), I. 24-1.19 (m, 10H). MS (ESI, m/e) [M+1]$^+$ 899.8.

Example F76: 2-((1H-pyrrolo[2,3-b]pyridin-5-yl)oxy)-4-(2-(2-(2,5-dicyclopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide

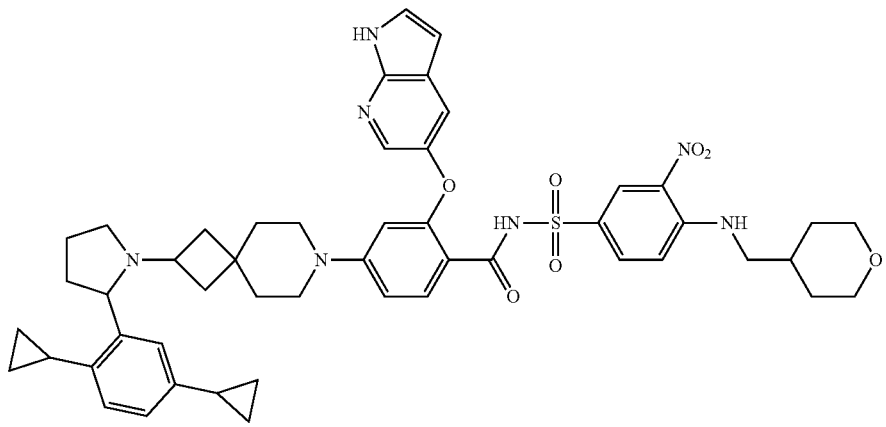 [SMILES: O=C(NS(=O)(=O)c1ccc(NCC2CCOCC2)c([N+](=O)[O-])c1)c1ccc(N2CCC3(CC2)CC(N2CCCC2c2cc(C4CC4)ccc2C2CC2)C3)cc1Oc1cnc2[nH]ccc2c1]

The desired compound was synthesized following the procedures similar to those in Example F40 by replacing (S)-2-(2-ethylphenyl)pyrrolidine with 2-(2,5-dicyclopropylphenyl)pyrrolidine and replacing (S)-4-(((1,4-dioxan-2-yl)methyl)amino)-3-nitrobenzenesulfonamide with 3-nitro-4-(((tetrahydro-2H-pyran-4-yl)methyl)amino)benzenesulfonamide. $^1$H NMR (400 MHz, DMSO-d$_6$) δ ppm: 11.66 (s, 1H), II. 44 (br, 1H), 8.67-8.44 (m, 2H), 8.06-7.94 (m, 1H), 7.82-7.67 (m, 1H), 7.58-7.22 (m, 4H), 7.05-6.95 (m, 4H), 6.39-6.33 (m, 1H), 6.24-6.12 (m, 1H), 3.88-3.81 (m, 2H), 3.31-3.21 (m, 5H), 3.10-2.90 (m, 5H), 2.13-1.73 (m, 8H), 1.70-1.17 (m, 13H), 0.94-0.83 (m, 4H), 0.68-0.48 (m, 4H). MS (ESI, m/e) [M+1]$^+$ 899.9.

Example F77: 2-((1H-pyrrolo[2,3-b]pyridin-5-yl)oxy)-4-(2-(2-(3-(2-chlorophenyl)thiophen-2-yl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide

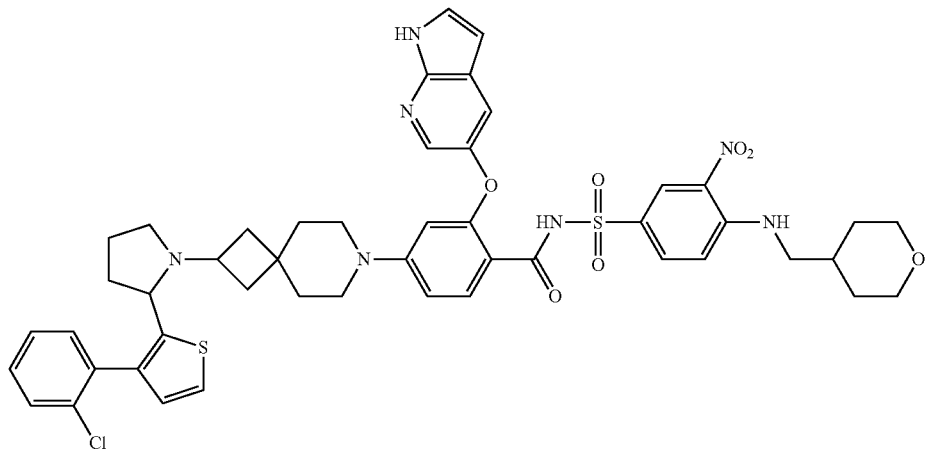 [SMILES: O=C(NS(=O)(=O)c1ccc(NCC2CCOCC2)c([N+](=O)[O-])c1)c1ccc(N2CCC3(CC2)CC(N2CCCC2c2sccc2-c2ccccc2Cl)C3)cc1Oc1cnc2[nH]ccc2c1]

The desired compound was synthesized following the procedures similar to those in Example F40 by replacing (S)-2-(2-ethylphenyl)pyrrolidine with 2-(3-(2-chlorophenyl)thiophen-2-yl)pyrrolidine and replacing (S)-4-(((1,4-dioxan-2-yl)methyl)amino)-3-nitrobenzenesulfonamide with 3-nitro-4-(((tetrahydro-2H-pyran-4-yl)methyl)amino)benzenesulfonamide. $^1$H NMR (400 MHz, DMSO-d$_6$) δ ppm: 11.71 (s, 1H), 11.44 (s, 1H), 8.63 (s, 1H), 8.57 (s, 1H), 8.05 (s, 1H), 7.81 (d, J=9.0 Hz, 1H), 7.56-7.46 (m, 4H), 7.39 (s, 2H), 7.27 (s, 1H), 7.12 (d, J=9.0 Hz, 1H), 6.88 (s, 1H), 6.70 (d, J=8.6 Hz, 1H), 6.40 (s, 1H), 6.17 (s, 1H), 3.85 (d, J=8.4 Hz, 2H), 3.33-3.25 (m, 4H), 3.10-2.95 (m, 7H), 2.05-1.96 (m, 1H), 1.89 (s, 2H), 1.66-1.58 (m, 5H), 1.51 (s, 3H), 1.42-1.25 (m, 7H). MS (ESI) m/e [M+1]$^+$ 935.7.

Example F78: 2-((1H-pyrrolo[2,3-b]pyridin-5-yl)oxy)-4-(2-(2-(2-cyclopropylphenyl)-4-methylpyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide

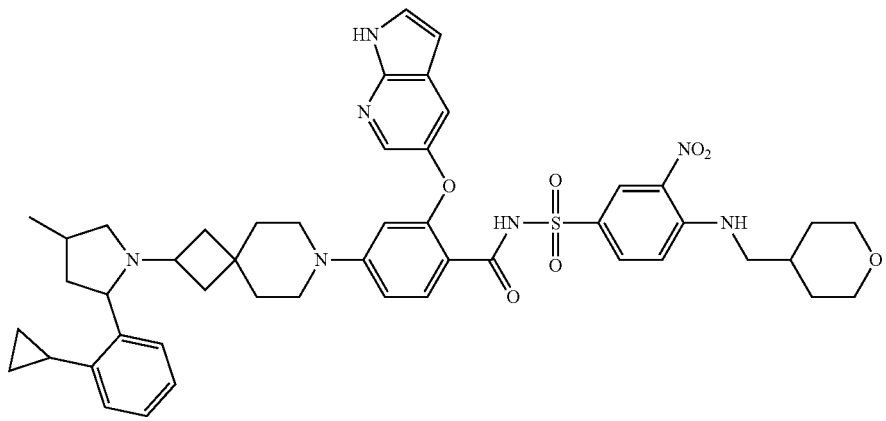 [SMILES: CC1CC(c2ccccc2C2CC2)N(C2CC3(CCN(c4ccc(C(=O)NS(=O)(=O)c5ccc(NCC6CCOCC6)c([N+](=O)[O-])c5)c(Oc5cnc6[nH]ccc6c5)c4)CC3)C2)C1]

The desired compound was synthesized following the procedures similar to those in Example F40 by replacing (S)-2-(2-ethylphenyl)pyrrolidine with 2-(2-cyclopropytphenyl)-4-methylpyrrolidine and replacing (S)-4-(((1,4-dioxan-2-yl)methyl)amino)-3-nitrobenzenesulfonamide with 3-nitro-4-(((tetrahydro-2H-pyran-4-yl)methyl)amino)benzenesulfonamide. $^1$H NMR (400 MHz, DMSO-d$_6$) δ ppm: 11.70 (s, 1H), 11.49 (br, 1H), 8.63 (t, J=5.9 Hz, 1H), 8.56 (d, J=2.2 Hz, 1H), 8.04 (d, J=2.5 Hz, 1H), 7.91-7.75 (m, 2H), 7.57-7.42 (m, 3H), 7.35-7.25 (m, 2H), 7.12 (d, J=9.3 Hz, 1H), 7.15-7.18 (m, 1H), 6.69 (d, J=9.0 Hz, 1H), 6.43-6.31 (m, 1H), 6.17 (s, 1H), 5.02 (s, 1H), 3.88-3.71 (m, 3H), 3.29-3.21 (m, 5H), 3.12-2.95 (m, 4H), 2.58-2.54 (m, 2H), 2.11-2.05 (m, 3H), 1.95-1.77 (m, 2H), 1.65-1.60 (m, 4H), 1.55-1.10 (m, 11H), 1.04-0.88 (m, 3H). MS (ESI, m/e) [M+1]$^+$ 873.9.

Example F79: 2-((1H-pyrrolo[2,3-b]pyridin-5-yl)oxy)-4-(2-(4-cyclopropyl-2-(2-cyclopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide

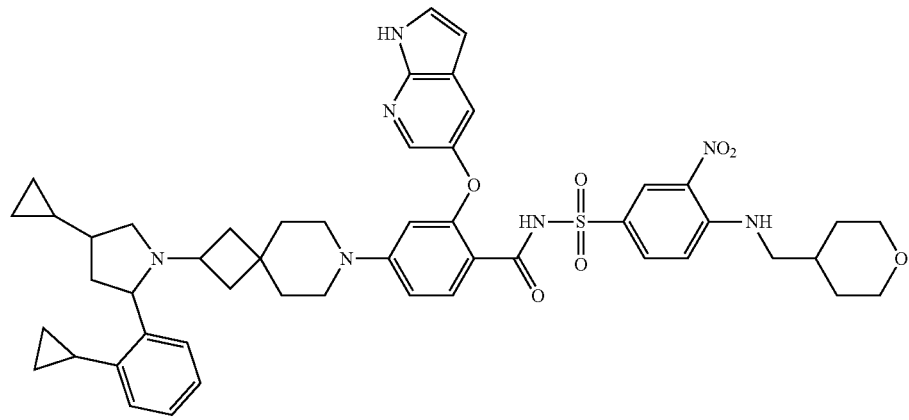 [SMILES: O=C(NS(=O)(=O)c1ccc(NCC2CCOCC2)c([N+](=O)[O-])c1)c1ccc(N2CCC3(CC2)CC(N2CC(C4CC4)CC2c2ccccc2C2CC2)C3)cc1Oc1cnc2[nH]ccc2c1]

The desired compound was synthesized following the procedures similar to those in Example F40 by replacing (S)-2-(2-ethylphenyl)pyrrolidine with 4-cyclopropyl-2-(2-cyclopropylphenyl)pyrrolidine and replacing (S)-4-(((1,4-dioxan-2-yl)methyl)amino)-3-nitrobenzenesulfonamide with 3-nitro-4-(((tetrahydro-2H-pyran-4-yl)methyl)amino)benzenesulfonamide. $^1$H NMR (400 MHz, DMSO-d$_6$) δ ppm: 11.70 (s, 1H), 11.46 (s, 1H), 8.619-8.52 (m, 2H), 8.039-7.99 (m, 1H), 7.948-7.88 (m, 1H), 7.87-7.73 (m, 1H), 7.62-7.40 (m, 3H), 7.38-7.20 (m, 2H), 7.20-7.91 (m, 2H), 6.74-6.63 (m, 1H), 6.42 (s, 1H), 6.19 (s, 1H), 4.51-4.42 (m, 1H), 3.95-3.77 (m, 3H), 3.54-3.42 (m, 1H), 3.30-3.22 (m, 4H), 3.08-2.86 (m, 5H), 2.22-1.81 (m, 6H), 1.67-1.14 (m, 11H), 1.09-0.79 (m, 3H), 0.73-0.56 (m, 2H), 0.52-0.36 (m, 2H), 0.31-0.12 (m, 2H). MS (ESI, m/e) [M+1]$^+$ 899.9.

Example F80: 2-((1H-pyrrolo[2,3-b]pyridin-5-yl)oxy)-4-(2-(2-(2-cyclopropylphenyl)-4-phenyl-2,5-dihydro-1H-pyrrol-1-yl)-7-azaspiro[3.5]nonan-7-yl)-N-((3-nitro-4-(((tetrahydro-2H-pyran-4-yl)methyl)amino)phenyl)sulfonyl)benzamide

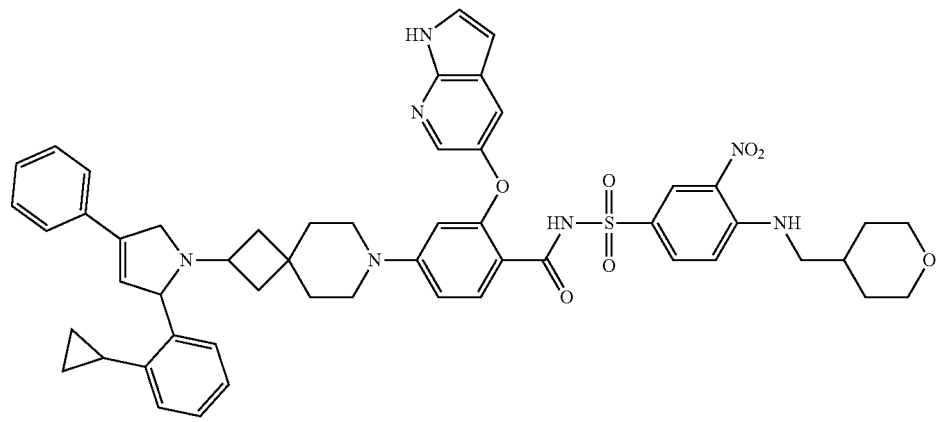 [SMILES: O=C(NS(=O)(=O)c1ccc(NCC2CCOCC2)c([N+](=O)[O-])c1)c1ccc(N2CCC3(CC2)CC(N2CC(c4ccccc4)=CC2c2ccccc2C2CC2)C3)cc1Oc1cnc2[nH]ccc2c1]

The desired compound was synthesized following the procedures similar to those in Example F40 by replacing (S)-2-(2-ethylphenyl)pyrrolidine with 2-(2-cyclopropylphenyl)-4-phenyl-2,5-dihydro-1H-pyrrole and replacing (S)-4-(((1,4-dioxan-2-yl)methyl)amino)-3-nitrobenzenesulfonamide with 3-nitro-4-(((tetrahydro-2H-pyran-4-yl)methyl)amino)benzenesulfonamide. ¹H NMR (400 MHz, DMSO-d₆) δ ppm: 11.70 (s, 1H), 11.42 (s, 1H), 8.62 (s, 1H), 8.56 (s, 1H), 8.05 (s, 1H), 7.80 (d, J=8.6 Hz, 1H), 7.53-7.48 (m, 6H), 7.33-7.29 (m, 3H), 7.12 (s, 3H), 6.99 (s, 1H), 6.70<d, J=8.6 Hz, 1H), 6.39 (s. 1H), 6.25 (s, 1H), 6.18 (s, 1H), 5.31-5.29 (m, 1H), 4.23 (s, 1H), 3.86-3.84 (m, 3H), 3.26-3.24 (m, 3H), 3.09 (s, 2H), 3.00 (s, 2H), 2.11 (s, 1H), 1.91-1.85 (m, 4H), 1.63-1.59 (m, 2H), 1.45 (s, 4H), 1.24 (s, 4H), 0.89 (s, 3H), 0.73 (s, 1H), 0.58 (s, 1H). MS (ESI) m/e [M+1]⁺ 933.8.

Example F81: 2-((1H-pyrrolo[2,3-b]pyridin-5-yl)oxy)-4-(2-(6-(2-cyclopropylphenyl)-5-azaspiro[2.4]heptan-5-yl)-7-azaspiro[3.5]nonan-7-yl)-N-((3-nitro-4-(((tetrahydro-2H-pyran-4-yl)methyl)amino)phenyl)sulfonyl)benzamide

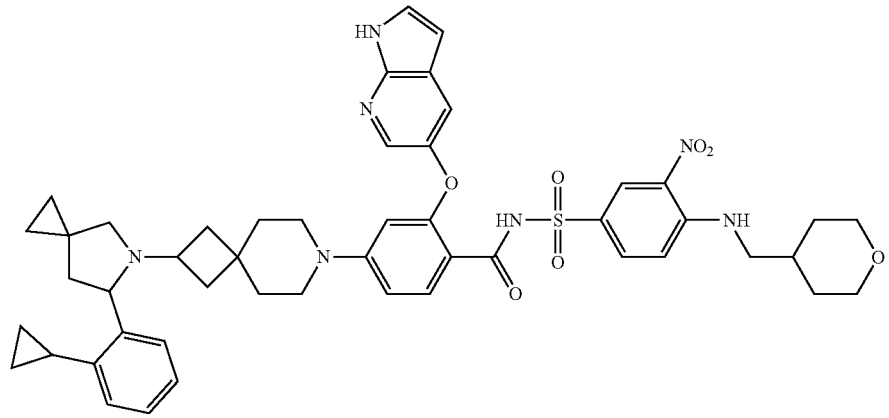 [SMILES: O=C(NS(=O)(=O)c1ccc(NCC2CCOCC2)c([N+](=O)[O-])c1)c1ccc(N2CCC3(CC2)CC(N2CC4(CC4)CC2c2ccccc2C2CC2)C3)cc1Oc1cnc2[nH]ccc2c1]

The desired compound was synthesized following the procedures similar to those in Example F40 by replacing (S)-2-(2-ethylphenyl)pyrrolidine with 6-(2-cyclopropylphenyl)-5-azaspiro[2.4]heptane and replacing (S)-4-(((1,4-dioxan-2-yl)methyl)amino)-3-nitrobenzenesulfonamide with 3-nitro-4-(((tetrahydro-2H-pyran-4-yl)methyl)amino)benzenesulfonamide. ¹H NMR (400 MHz, DMSO-d₆) δ ppm: 11.69 (s, 1H), 11.46 (s, 1H), 8.65-8.50 (m, 2H), 8.02 (s, 1H), 7.95-7.85 (m, 1H), 7.80-7.75 (m, 1H), 7.58-7.38 (m, 3H), 7.30-7.20 (m, 2H), 7.17-6.98 (m, 2H), 6.70-6.60 (m, 1H), 6.36 (s, 1H), 6.15 (s, 1H), 4.15-4.05 (m, 1H), 4.02-3.95 (m, 2H), 3.90-3.75 (m, 2H), 3.30-3.19 (m, 3H), 3.18-3.10 (m, 2H), 3.08-2.90 (m, 2H), 2.50-2.40 (m, 2H), 1.90-1.80 (m, 2H), 1.65-1.55 (m, 2H), 1.50-1.30 (m, 5H), 1.29-1.06 (m, 5H), 1.00-0.90 (m, 2H), 0.80-0.50 (m, 8H). MS (ESI, m/e) [M+1]⁺ 885.8.

Example F82: 2-((1H-pyrrolo[2,3-b]pyridin-5-yl)oxy)-4-(2-(2-(2-cyclopropylphenyl)-4,4-dimethylpyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide

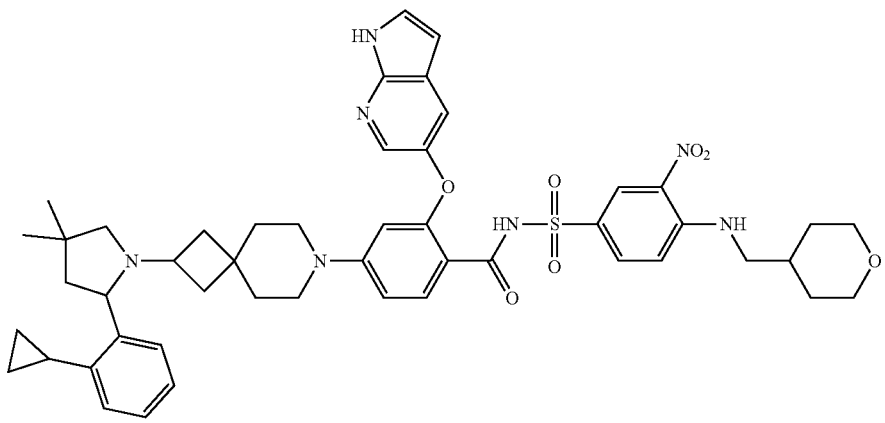 [SMILES: CC1(C)CC(c2ccccc2C2CC2)N(C2CC3(CCN(c4ccc(C(=O)NS(=O)(=O)c5ccc(NCC6CCOCC6)c([N+](=O)[O-])c5)c(Oc5cnc6[nH]ccc6c5)c4)CC3)C2)C1]

The desired compound was synthesized following the procedures similar to those in Example F40 by replacing (S)-2-(2-ethylphenyl)pyrrolidine with 2-(2-cyclopropylphenyl)-4,4-dimethylpyrrolidine and replacing (S)-4-(((1,4-dioxan-2-yl)methyl)amino)-3-nitrobenzenesulfonamide with 3-nitro-4-(((tetrahydro-2H-pyran-4-yl)methyl)amino)benzenesulfonamide. $^1$H NMR (400 MHz, DMSO-$d_6$) δ ppm: 11.68 (s, 1H), 11.43 (s, 1H), 8.61 (s, 1H), 8.56 (s, 1H), 8.03 (s, 1H), 7.79 (d, J=8.7 Hz, 2H), 7.60-7.43 (m, 3H), 7.29 (s, 1H), 7.11 (d, J=9.3 Hz, 2H 6.68 (d, J=8.6 Hz, 1H), 6.38 (s, 1H), 6.16 (s, 1H), 5.13 (s, 1H), 3.89-3.85 (m, 3H), 3.28-0.3.21 (m, 1H), 2.98-2.93 (m, 5H), 2.26-1.86 (m, 6H), 1.63-1.59 (m, 2H), 1.30-1.26 (m, 16H), 1.14-0.86 (m, 4H), 0.66-0.63 (m, 2H). MS (ESI) m/e [M+1]$^+$ 887.9.

Example F83: 2-((1H-pyrrolo[2,3-b]pyridin-5-yl)oxy)-4-(2-(2-(2-cyclopropylphenyl)-4,4-difluoropyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide

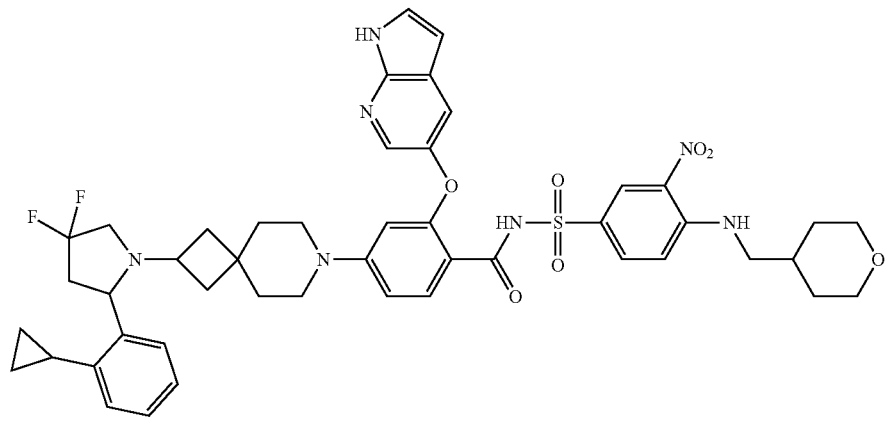 [SMILES: O=C(NS(=O)(=O)c1ccc(NCC2CCOCC2)c([N+](=O)[O-])c1)c1ccc(N2CCC3(CC2)CC(N2CC(F)(F)CC2c2ccccc2C2CC2)C3)cc1Oc1cnc2[nH]ccc2c1]

The desired compound was synthesized following the procedures similar to those in Example F40 by replacing (S)-2-(2-ethylphenyl)pyrrolidine with 2-(2-cyclopropylphenyl)-4,4-difluoropyrrolidine and replacing (S)-4-(((1,4-dioxan-2-yl)methyl)amino)-3-nitrobenzenesulfonamide with 3-nitro-4-(((tetrahydro-2H-pyran-4-yl)methyl)amino)benzenesulfonamide. $^1$H NMR (400 MHz, DMSO-$d_6$) δ ppm: 11.71 (s, 1H), 11.42 (s, 1H), 8.63 (t, J=2.0 Hz, 1H), 8.57 (d, J=2.0 Hz, 1H), 8.41 (d, J=2.4 Hz, 1H), 7.82 (d, J=8.8 Hz, 1H), 7.55-7.46 (m, 4H), 7.19-7.11 (m, 3H), 6.97 (d, J=7.6 Hz, 1H), 6.69 (d, J=7.6 Hz, 1H), 6.40-6.39 (m, 1H), 6.15 (s, 1H), 4.24 (t, J=8.4 Hz, 1H), 3.85 (d, J=10.8 Hz, 2H), 3.49-3.44 (m, 1H), 3.32-3.23 (m, 4H), 3.12-2.69 (m, 6H), 2.08-1.89 (m, 3H), 1.66-1.21 (m, 13H), 0.90-0.85 (m, 2H), 0.64-0.50 (m, 2H). MS (ESI, m/e) [M+1]$^+$ 895.9.

Example F84: 2-((1H-pyrrolo[2,3-b]pyridin-5-yl)oxy)-4-(2-(2-(2-cyclopropylphenyl)-4-(trifluoromethyl)pyrrolidin-1-yl)-7-azaspiro[3.5]nonan-7-yl)-N-((4-((((1r,4r)-4-hydroxy-4-methylcyclohexyl)methyl)amino)-3-nitrophenyl)sulfonyl)benzamide

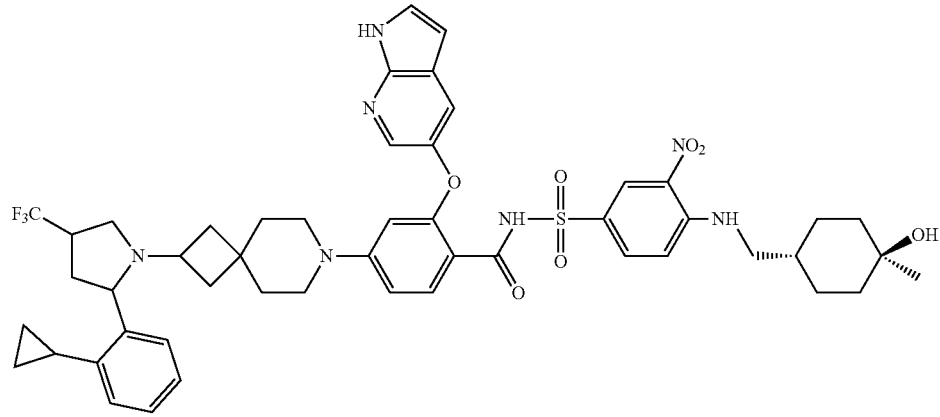 [SMILES: C[C@]1(O)CC[C@H](CNc2ccc(S(=O)(=O)NC(=O)c3ccc(N4CCC5(CC4)CC(N4CC(C(F)(F)F)CC4c4ccccc4C4CC4)C5)cc3Oc3cnc4[nH]ccc4c3)cc2[N+](=O)[O-])CC1]

The desired compound was synthesized following the procedures similar to those in Example F40 by replacing (S)-2-(2-ethylphenyl)pyrrolidine with 2-(2-cyclopropylphenyl)-4-(trifluoromethyl)pyrrolidine. $^1$H NMR (400 MHz, DMSO-$d_6$) δ ppm: 11.70 (s, 1H), 11.41 (s, 1H), 8.65-8.44 (m, 2H), 8.04 (d, J=2.0 Hz, 1H), 7.79 (d, J=8.8 Hz, 1H), 7.56-7.40 (m, 4H), 7.24-7.04 (m, 3H), 6.93 (d, J=7.3 Hz, 1H), 6.67 (d, J=8.8 Hz, 1H), 6.39 (s, 1H), 6.15 (s, 1H), 4.24 (s, 1H), 3.96 (t, J=7.9 Hz, 1H), 3.28 (t, J=6.0 Hz, 3H), 3.21-3.08 (m, 2H), 3.05-2.89 (m, 5H), 2.72-2.61 (m, 1H), 2.14-2.02 (m, 1H), 1.75-1.43 (m, 9H), 1.41-1.24 (m, 7H), 1.19-1.03 (m, 5H), 0.92-0.80 (m, 3H), 0.70-0.45 (m, 2H). MS (ESI, m/e) [M+1]$^+$ 955.9.

Example F85: 2-((1H-pyrrolo[2,3-b]pyridin-5-yl)oxy)-4-(2-(2-(2-cyclopropylphenyl)-4-(dimethylamino)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide

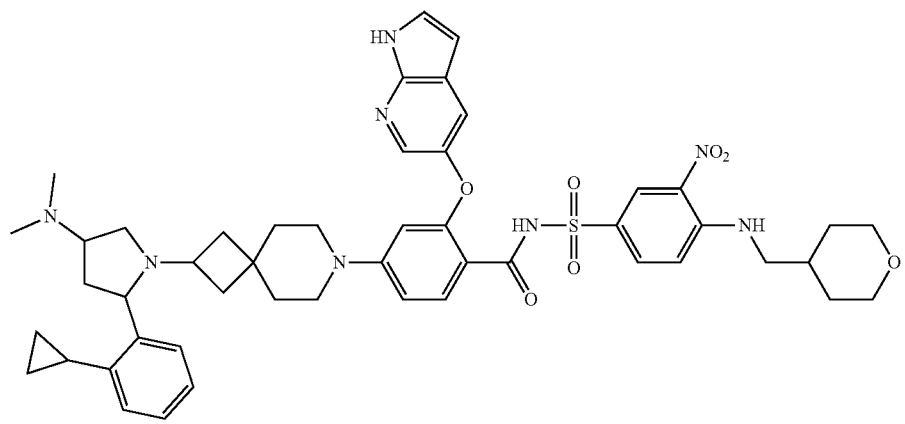 [SMILES: CN(C)C1CC(c2ccccc2C2CC2)N(C2CC3(CCN(c4ccc(C(=O)NS(=O)(=O)c5ccc(NCC6CCOCC6)c([N+](=O)[O-])c5)c(Oc5cnc6[nH]ccc6c5)c4)CC3)C2)C1]

The desired compound was synthesized following the procedures similar to those in Example F40 by replacing (S)-2-(2-ethylphenyl)pyrrolidine with 5-(2-cyclopropylphenyl)-N,N-dimethylpyrrolidin-3-amine and replacing (S)-4-(((1,4-dioxan-2-yl)methyl)amino)-3-nitrobenzenesulfonamide with 3-nitro-4-(((tetrahydro-2H-pyran-4-yl)methyl)amino)benzenesulfonamide. $^1$H NMR (400 MHz, DMSO-$d_6$) δ ppm: 11.56 (s, 1H), 8.41-8.33 (m, 2H), 7.94 (s, 1H), 7.57 (d, J=8.8 Hz, 1H), 7.54-7.48 (m, 2H), 7.46 (s, 1H), 7.27 (s, 1H), 7.17-7.12 (m, 2H), 7.03-6.84 (m, 2H), 6.62 (d, J=8.0 Hz, 1H), 6.31 (s, 1H), 6.21 (s, 1H), 4.03-4.02 (m, 1H), 3.83 (d, J=8.4 Hz, 2H), 3.53-3.34 (m, 2H), 3.33-3.29 (m, 4H), 3.05-2.72 (m, 6H), 2.60 (s, 6H), 2.45-2.42 (m, 1H), 2.01-1.51 (m, 15H), 1.01-0.85 (m, 2H), 0.64-0.51 (m, 2H). MS (ESI, m/e) [M+1]$^+$ 902.9.

Example F86: 2-((1H-pyrrolo[2,3-b]pyridin-5-yl)oxy)-4-(2-(2-(2-cyclopropylphenyl)-4-(2-(dimethylamino)ethoxy)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide

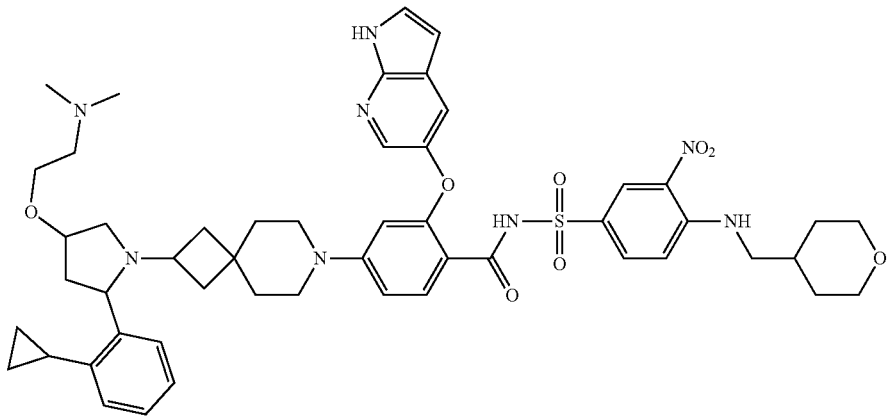 [SMILES: CN(C)CCOC1CC(c2ccccc2C2CC2)N(C2CC3(CCN(c4ccc(C(=O)NS(=O)(=O)c5ccc(NCC6CCOCC6)c([N+](=O)[O-])c5)c(Oc5cnc6[nH]ccc6c5)c4)CC3)C2)C1]

The desired compound was synthesized following the procedures similar to those in Example F40 by replacing (S)-2-(2-ethylphenyl)pyrrolidine with 2-((5-(2-cyclopropylphenyl)pyrrolidin-3-yl)oxy)-N,N-dimethylethan-1-amine and replacing (S)-4-(((1,4-dioxan-2-yl)methyl)amino)-3-nitrobenzenesulfonamide with 3-nitro-4-(((tetrahydro-2H-pyran-4-yl)methyl)amino)benzenesulfonamide. $^1$H NMR (400 MHz, DMSO-d$_6$) δ ppm: 11.60 (s, 1H), 11.46 (s, 1H), 8.89 (s, 1H), 8.56-8.46 (m, 1H), 8.24-8.10 (m, 2H), 7.96-7.85 (m, 1H), 7.71 (s, 1H), 7.50-7.41 (m, 1H), 7.13-6.82 (m, 3H), 6.61-6.43 (m, 2H), 5.92 (s, 1H), 5.43-5.21 (m, 3H), 4.53-4.24 (m, 1H), 4.11-3.72 (m, 4H), 3.50-3.32 (m, 3H), 3.32-3.19 (m, 3H), 3.05-2.72 (m, 7H), 2.26-2.15 (m, 2H), 2.08-1.93 (m, 5H), 1.83-1.42 (m, 14H), 0.92-0.80 (m, 5H). MS (ESI, m/e) [M+1]$^+$ 947.0.

Example F87: 2-((1H-pyrrolo[2,3-b]pyridin-5-yl)oxy)-4-(2-(3-(2-cyclopropylphenyl)-2-azabicyclo[3.1.0]hexan-2-yl)-7-azaspiro[3.5]nonan-7-yl)-N-((3-nitro-4-(((tetrahydro-2H-pyran-4-yl)methyl)amino)phenyl)sulfonyl)benzamide

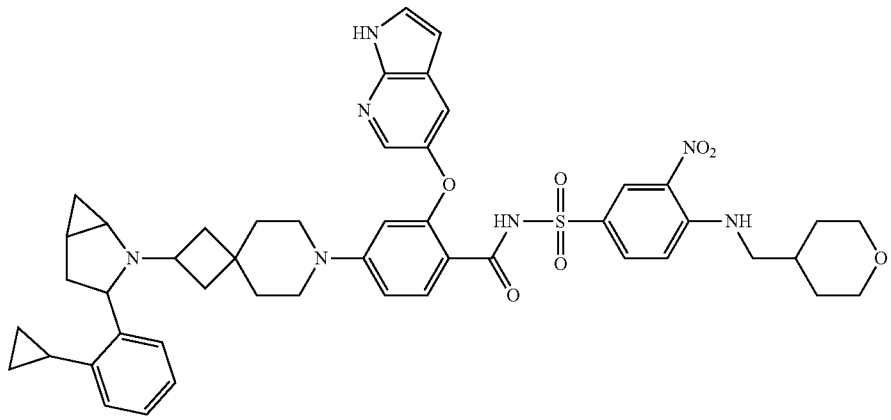 [SMILES: O=C(NS(=O)(=O)c1ccc(NCC2CCOCC2)c([N+](=O)[O-])c1)c1ccc(N2CCC3(CC2)CC(N2C(c4ccccc4C4CC4)CC4CC42)C3)cc1Oc1cnc2[nH]ccc2c1]

The desired compound was synthesized following the procedures similar to those in Example F23 by replacing (S)-2-(2-cyclopropylphenyl)pyrrolidine with 3-(2-cyclopropylphenyl)-2-azabicyclo[3.1.0]hexane. $^1$H NMR (400 MHz, DMSO-d$_6$) δ ppm: 11.70 (s, 1H), 11.44 (s, 1H), 8.72-8.48 (m, 2H), 8.12-7.95 (m, 1H), 7.83-7.70 (m, 1H), 7.62-7.42 (m, 3H), 7.37-7.16 (m, 2H), 7.15-7.08 (m, 1H), 7.06-6.86 (m, 1H), 6.72-6.65 (m, 1H), 6.42-6.35 (m, 1H), 6.22-6.12 (m, 1H), 5.78-5.73 (m, 1H), 3.90-3.78 (m, 2H), 3.44-3.21 (m, 6H), 3.06 (s, 2H), 2.99-2.87 (m, 2H), 2.35-1.99 (m, 3H), 1.99-1.77 (m, 3H), 1.70-1.09 (m, 12H), 1.00-0.76 (m, 4H), 0.73-0.43 (m, 3H). MS (ESI, m/e) [M+1]$^+$ 871.9.

Example F88: 2-((1H-pyrrolo[2,3-b]pyridin-5-yl)oxy)-4-(2-(1-(2-cyclopropylphenyl)hexahydrocyclopenta[c]pyrrol-2(1H)-yl)-7-azaspiro[3.5]nonan-7-yl)-N-((3-nitro-4-(((tetrahydro-2H-pyran-4-yl)methyl)amino)phenyl)sulfonyl)benzamide

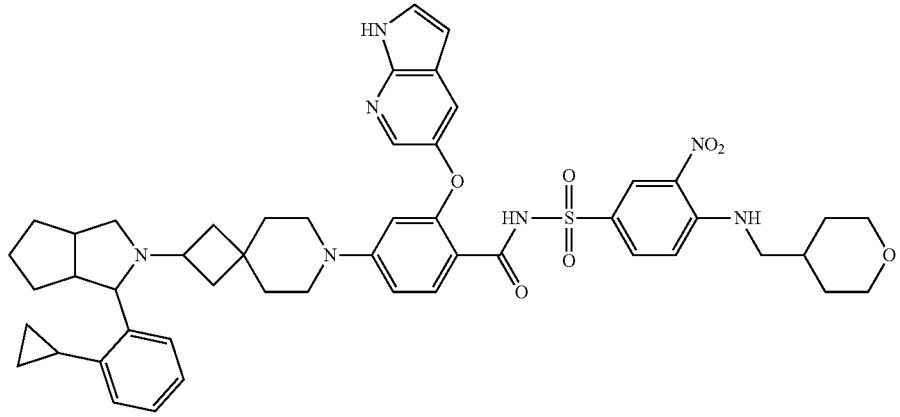 [SMILES: O=C(NS(=O)(=O)c1ccc(NCC2CCOCC2)c([N+](=O)[O-])c1)c1ccc(N2CCC3(CC2)CC(N2CC4CCCC4C2c2ccccc2C2CC2)C3)cc1Oc1cnc2[nH]ccc2c1]

The desired compound was synthesized following the procedures similar to those in Example F23 by replacing (S)-2-(2-cyclopropylphenyl)pyrrolidine with 1-(2-cyclopropylphenyl)octahydrocyclopenta[c]pyrrole. ¹H NMR (400 MHz, DMSO-d₆) δ ppm: 11.66 (s, 1H), 11.40 (br, 1H), 8.68-8.41 (m, 2H), 8.01 (s, 1H), 7.84-7.64 (m, 1H), 7.65-7.21 (m, 5H), 7.21-6.85 (m, 4H), 6.72-6.60 (m, 1H), 6.37 (s, 1H), 6.17 (s, 1H), 4.00-3.89 (m, 1H), 3.89-3.79 (m, 2H), 3.31-3.21 (m, 4H), 3.19-3.09 (m, 1H), 3.06-2.90 (m, 4H), 2.90-2.73 (m, 2H), 2.71-2.56 (m, 1H), 1.96-1.75 (m, 4H), 1.73-1.57 (m, 4H), 1.56-1.24 (m, 10H), 1.01-0.79 (m, 4H), 0.69-0.41 (m, 2H). MS (ESI, m/e) [M+1]⁺ 899.9.

Example F89: 2-((1H-pyrrolo[2,3-b]pyridin-5-yl)oxy)-4-(2-(2-(2-cyclopropylphenyl)-3,3-dimethylpyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide

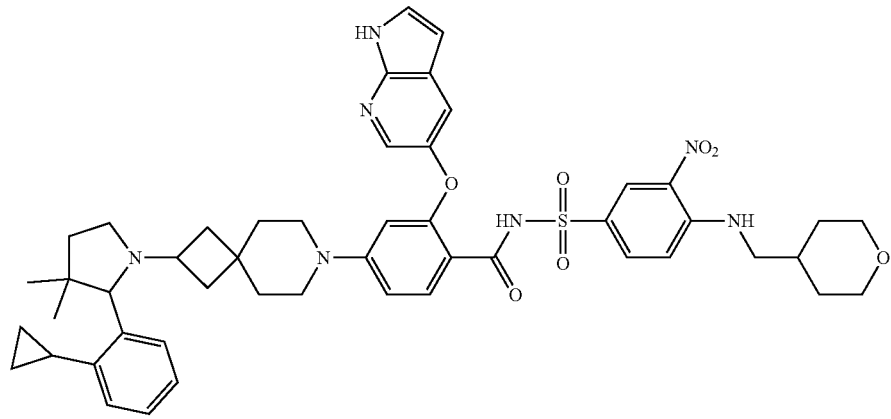 [SMILES: CC1(C)CCN(C2CC3(CCN(c4ccc(C(=O)NS(=O)(=O)c5ccc(NCC6CCOCC6)c([N+](=O)[O-])c5)c(Oc5cnc6[nH]ccc6c5)c4)CC3)C2)C1c1ccccc1C1CC1]

The desired compound was synthesized following the procedures similar to those in Example F23 by replacing (S)-2-(2-cyclopropylphenyl)pyrrolidine with 2-(2-cyclopropylphenyl)-3,3-dimethylpyrrolidine. ¹H NMR (400 MHz, DMSO-d₆) δ ppm: 11.57 (s, 1H), 11.40 (s, 1H), 8.74-8.16 (m, 2H), 7.95 (s, 1H), 7.78-7.31 (m, 5H), 7.28-6.75 (m, 5H), 6.70-6.56 (m, 1H), 6.41-6.04 (m, 2H), 3.98-3.89 (m, 1H), 3.89-3.77 (m, 2H), 3.31-3.18 (m, 5H), 3.11-2.85 (m, 6H), 2.69-2.57 (m, 1H), 2.02-1.95 (m, 1H), 1.95-1.81 (m, 2H), 1.73-1.52 (m, 6H), 1.47-1.35 (m, 5H), 1.08 (s, 3H), 0.92-0.81 (m, 2H), 0.75-0.66 (m, 1H), 0.63-0.39 (m, 4H). MS (ESI, m/e) [M+1]⁺ 887.9.

Example F90: 2-((1H-pyrrolo[2,3-b]pyridin-5-yl)oxy)-4-(2-(2-(2-cyclopropylphenyl)-4-methylpiperazin-1-yl)-7-azaspiro[3.5]nonan-7-yl)-N-((3-nitro-4-(((tetrahydro-2H-pyran-4-yl)methyl)amino)phenyl)sulfonyl)benzamide

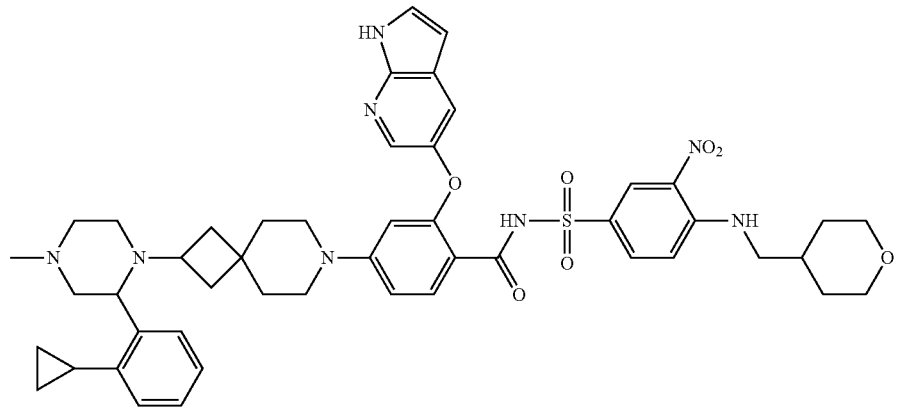 [SMILES: CN1CCN(C2CC3(CCN(c4ccc(C(=O)NS(=O)(=O)c5ccc(NCC6CCOCC6)c([N+](=O)[O-])c5)c(Oc5cnc6[nH]ccc6c5)c4)CC3)C2)C(c2ccccc2C2CC2)C1]

Step 1: methyl 2-bromo-2-(2-bromophenyl)acetate

To a solution of methyl 2-(2-bromophenyl)acetate (25 g, 109.14 mmol) in CCl$_4$ (250 mL) was added NBS (21.37 g, 120.65 mmol) and BPO (1.32 g, 5.46 mmol). The mixture was stirred at 85° C. for 5 hours. TLC showed reactant was consumed completely. The mixture was poured into H$_2$O (200 mL) and extracted with DCM (200 mL×3), washed with brine, dried over Na$_2$SO$_4$, filtered and concentrated. The residue was purified by prep-MPLC. Methyl 2-bromo-2-(2-bromophenyl)acetate (20 g) was obtained as a colorless oil. $^1$H NMR (400 MHz, CDCl$_3$) δ ppm: 7.79 (dd, J=1.0, 8.0 Hz, 1H), 7.58 (dd, J=1.0, 8.0 Hz, 1H), 7.40-7.34 (m, 1H), 7.21 (dt, J=1.5, 7.7 Hz, 1H), 5.98-5.83 (m, 1H), 3.82 (s, 3H).

Step 2: 3-(2-bromophenyl)piperazin-2-one

To a solution of methyl 2-bromo-2-(2-bromophenyl)acetate (20 g, 64.94 mmol) in MeOH (200 mL) was added DIEA (12.67 g, 98.04 mmol) and ethane-1,2-diamine (7.86 g, 130.72 mmol). The mixture was stirred at 25° C. for 12 hours, TLC showed reactant was consumed completely. The mixture was diluted with H$_2$O (200 mL) and extracted with EA (200 mL×3), washed with brine, dried over Na$_2$SO$_4$, filtered and concentrated to give crude 3-(2-bromophenyl)piperazin-2-one (14 g) as a white solid, which used in next step without further purification.

Step 3: tert-butyl 2-(2-(2-bromophenyl)-3-oxopiperazin-1-yl)-7-azaspiro[3.5]nonane-7-carboxylate To a solution of 3-(2-bromophenyl)piperazin-2-one (7 g, 27.44 mmol) and tert-butyl 2-oxo-7-azaspiro[3.5]nonane-7-carboxylate (7.22 g, 30.18 mmol) in DCE (150 mL) was added AcOH (3.3 g, 54.88 mmol) and NaBH(OAc)$_3$ (11.63 g, 54.88 mmol). The mixture was stirred at 25° C. for 12 hours. TLC showed reactant was consumed completely. The reaction mixture was extracted with aq. Na$_2$CO$_3$ (150 mL) and EA (150 mL×3), dried over Na$_2$SO$_4$, filtered and concentrated. The residue was purified by prep-MPLC. Tert-butyl 2-(2-(2-bromophenyl)-3-oxopiperazin-1-yl)-7-azaspiro[3.5]nonane-7-carboxylate (8 g) was obtained as a white solid.

Step 4: tert-butyl 2-(2-(2-cyclopropylphenyl)-3-oxopiperazin-1-yl)-7-azaspiro[3.5]nonane-7-carboxylate To a solution of tert-butyl 2-(2-(2-bromophenyl)-3-oxopiperazin-1-yl)-7-azaspiro[3.5]nonane-7-carboxylate (8 g, 16.72 mmol) and cyclopropylboronic acid (2.15 g, 25.08 mmol) in dioxane (100 mL) and H$_2$O (10 mL) was added Cs$_2$CO$_3$ (16.34 g, 50.16 mmol) and Pd(dppf)Cl$_2$ (1.22 g, 1.67 mmol) under N$_2$ atmosphere. The mixture was stirred at 85° C. for 2 hours. LC/MS showed reactant was consumed completely and one main peak with desired MS signal. The reaction mixture was filtered and concentrated. The residue was diluted with H$_2$O (50 mL)/EA (50 mL) and extracted with EA (50 mL×2), dried over Na$_2$SO$_4$, filtered and concentrated. The residue was purified by prep-MPLC. Tert-butyl 2-(2-(2-cyclopropylphenyl)-3-oxopiperazin-1-yl)-7-azaspiro[3.5]nonane-7-carboxylate (5 g, 68.02% yield) was obtained as a yellow solid. MS (ESI, m/e) [M+1]$^+$ 440.2.

Step 5: tert-butyl 2-(2-(2-cyclopropylphenyl)-4-methyl-3-oxopiperazin-1-yl)-7-azaspiro[3.5]nonane-7-carboxylate To a solution of tert-butyl 2-(2-(2-cyclopropylphenyl)-3-oxopiperazin-1-yl)-7-azaspiro[3.5]nonane-7-carboxylate (5 g, 11.37 mmol) in THF (50 mL) was added NaH (0.5 g, 12.51 mmol, 60%) at 0° C. The mixture was stirred at 0° C. for 10 minutes. Then MeI (3.23 g, 22.75 mmol) was added at 0° C. The mixture was stirred at 25° C. for 5 hours. LC/MS showed reactant was consumed completely and one main peak with desired MS signal. The reaction mixture was diluted with H$_2$O (50 mL) and extracted with EA (50 mL×3), dried over Na$_2$SO$_4$, filtered and concentrated. The residue was purified by prep-MPLC. Tert-butyl 2-(2(2-cyclopropylphenyl)-4-methyl-3-oxopiperazin-1-yl)-7-azaspiro[3.5]nonane-7-carboxylate (4.7 g, 91.09% yield) was obtained as a white solid. MS (ESI, m/e) [M+1]$^+$ 454.2.

Step 6: tert-butyl 2-(2-(2-cyclopropylphenyl)-4-methylpiperazin-1-yl)-7-azaspiro[3.5]nonane-7-carboxylate A mixture of tert-butyl 2-(2-(2-cyclopropylphenyl)-4-methyl-3-oxopiperazin-1-yl)-7-azaspiro[3.5]nonane-7-carboxylate (4.7 g, 10.36 mmol, 1 eq) in BH$_3$.THF (50 mL) was stirred at 70° C. for 12 hours. LC/MS showed reactant was consumed completely and one main peak with desired MS signal. The reaction mixture was quenched by MeOH (50 mL) at 0° C. and stirred at 25° C. for 30 minutes. Then the mixture was concentrated to afford tert-butyl 2-(2-(2-cyclopropylphenyl)-4-methylpiperazin-1-yl)-7-azaspiro[3.5]nonane-7-carboxylate (4.5 g). MS (ESI, m/e) [M+1]$^+$ 440.3.

Step 7: 2-(2-(2-cyclopropylphenyl)-4-methylpiperazin-1-yl)-7-azaspiro[3,5]nonane A mixture of tert-butyl 2-(2-(2-cyclopropylphenyl)-4-methylpiperazin-1-yl)-7-azaspiro[3.5]nonane-7-carboxylate (4.5 g, 10.24 mmol) in DCM (25 mL) and TFA (25 mL) was stirred at 25° C. for 1 hr. LC/MS showed reactant was consumed completely and one main peak with desired MS signal. The reaction mixture was concentrated under reduced pressure to remove solvent. The residue was purified by prep-HPLC (TFA condition). The desired collection was concentrated and was dilute with H$_2$O (20 mL) and added aq. Na$_2$CO$_3$ to adjust pH to 9. The mixture was extracted with EA (20 mL×3), dried over Na$_2$SO$_4$, filtered and concentrated under reduced pressure to remove solvent. 2-(2-(2-cyclopropylphenyl)-4-methylpiperazin-1-yl)-7-azaspiro[3.5] (1.2 g) was obtained as a white solid. $^1$H NMR (400 MHz, CDCl$_3$) δ ppm: 7.48 (s, 1H), 7.22-7.12 (m, 2H), 7.01 (s, 1H), 6.39 (s, 1H), 3.96 (d, J=7.3 Hz, 1H), 3.04-2.96 (m, 1H), 2.95-2.87 (m, 2H), 2.85-2.65 (m, 5H), 2.30 (s, 3H), 2.27 (s, 2H), 2.12 (s, 1H), 1.99 (s, 1H), 1.90-1.81 (m, 1H), 1.75-1.66 (m, 1H), 1.60-1.43 (m, 4H), 1.38-1.28 (m, 1H), 1.11 (d, J=4.4, 7.2, 11.5 Hz, 1H), 0.99-0.91 (m, 2H), 0.70 (s, 1H), 0.63-0.52 (m, 1H). MS (ESI, m/e) [M+1]$^+$ 340.3.

Then the desired compound was synthesized following the procedures similar to those in Example F23 by replacing (S)-2-(2-(2-cyclopropylphenyl)pyrrolidin-1-yl)-7-azaspiro[3.5]nonane with 2-(2-(2-cyclopropylphenyl)-4-methylpiperazin-1-yl)-7-azaspiro[3.5]nonane. $^1$H NMR (400 MHz, DMSO-d$_6$) δ ppm: 11.71 (s, 1H), 11.45 (s, 1H), 8.58 (s, 1H), 8.54 (s, 1H), 8.02 (s, 1H), 7.80 (d, J=8.4 Hz, 1H), 7.54 (d, J=7.6 Hz, 2H), 7.50 (s, 1H), 7.35 (d, J=8.4 Hz, 3H), 7.26 (d, J=7.6 Hz, 1H), 7.11-7.04 (m, 2H), 7.03-6.88 (m, 5H), 6.36 (s, 1H), 5.15 (s, 1H), 3.84 (d, J=8.3 Hz, 2H), 3.76-3.66 (m, 1H), 3.57-3.49 (m, 1H), 3.29-3.20 (m, 5H), 3.08-2.93 (m, 2H), 2.79 (s, 3H), 2.23-2.16 (m, 1H), 1.91-1.83 (m, 1H), 1.59 (d, J=12.3 Hz, 2H), 1.09-0.96 (m, 3H), 0.87-0.81 (m, 2H), 0.68-0.62 (m, 1H). MS (ESI, m/e) [M+1]$^+$ 841.9.

Example F91a and Example F91b: 2-((1H-pyrrolo[2,3-b]pyridin-5-yl)oxy)-4-(2-((S or R)-2-(2-cyclopropylphenyl)-4-methylpiperazin-1-yl)-7-azaspiro[3.5]nonan-7-yl)-N-((4-((((1r,4r)-4-hydroxy-4-methylcyclohexyl)methyl)amino)-3-nitrophenyl)sulfonyl)benzamide; 2-((1H-pyrrolo[2,3-b]pyridin-5-yl)oxy)-4-(2-((R or S)-2-(2-cyclopropylphenyl)-4-methylpiperazin-1-yl)-7-azaspiro[3.5]nonan-7-yl)-N-((4-((((1r,4r)-4-hydroxy-4-methylcyclohexyl)methyl)amino)-3-nitrophenyl)sulfonyl)benzamide

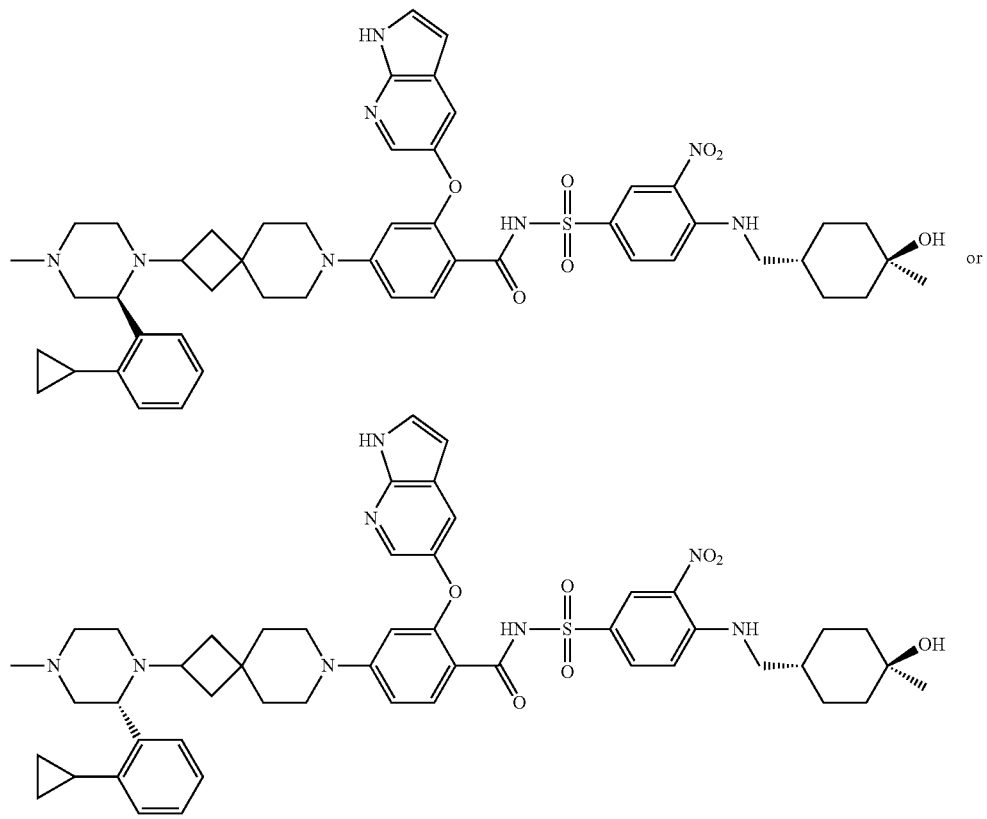

2-(2-(2-cyclopropylphenyl)-4-methylpiperazin-1-yl)-7-azaspiro[3.5]nonane was separated and purified by SFC to obtain 2 pure isomers (Instalment: Thar SFC350 preparative SFC; Column: Phenomenex-C2, 250×50 mm i.d. 10 u; Mobile phase: A for $CO_2$ and B for MeOH (0.1% $NH_3.H_2O$); Gradient: B %=50%; Flow rate: 200 g/min; Wavelength: 220 nm; Column temperature: 40° C.; System back pressure: 100 bar): (S or R)-2-(2(2-cyclopropylphenyl)-4-methylpiperazin-1-yl)-7-azaspiro[3.5]nonane as faster peak in SFC (retention time: 2.7 min) (1.05 g) was obtained as a yellow oil. $^1$H NMR (400 MHz, CDCl3) δ ppm: 7.49 (s, 1H), 7.14 (d, J=3.1 Hz, 2H), 7.01 (s, 1H), 3.96 (d, J=5.1 Hz, 1H), 3.02 (d, J=6.6 Hz, 1H), 2.96-2.85 (m, 2H), 2.73-2.52 (m, 7H), 2.29 (s, 3H), 2.12 (s, 1H), 2.00 (s, 1H), 1.82 (s, 1H), 1.65 (t, J=9.9 Hz, 1H), 1.48-1.22 (m, 6H), 1.10 (d, J=4.3 Hz, 1H), 0.95 (d, J=8.1 Hz, 2H), 0.69 (s, 1H), 0.64-0.54 (m, 1H). MS (ESI, m/e) [M+1]$^+$ 340.3. (R or S)-2-(2-(2-cyclopropylphenyl)-4-methylpiperazin-1-yl)-7-azaspiro[3.5]nonane (slower peak in SFC, retention time: 3.4 min) (1.13 g) was obtained as a white solid.

With the isomer of faster peak in SFC as starting material, Example F91a was synthesized following the procedures similar to those in Example F21. To a solution of (S or R)-2-((1H-pyrrolo[2,3-b]pyridin-5-yl)oxy)-4-(2-(2-(2-cyclopropylphenyl)-4-methylpiperazin 1-yl)-7-azaspiro[3.5]nonan-7-yl)benzoic acid (117.2 mg, 0.198 mmol) in DCM (20 ml) was added HATH (113 mg, 0.297 mmol) and triethylamine (100 mg, 0.99 mmol). The mixture was stirred at room temperature for 1 hour. Then to the mixture was added 4-((((1r,4r)-4-hydroxy-4-methylcyclohexyl)methyl)amino)-3-nitrobenzenesulfonamide (136 mg, 0.396 mmol) and DMAP (24 mg, 0,198 mmol). The mixture was stirred at room temperature for overnight. The mixture was washed with saturated aq. $NaHCO_3$, brine, dried over $Na_2SO_4$, concentrated and purified by prep-HPLC to give the desired compound (19 mg). $^1$H NMR (400 MHz, DMSO-d$_6$) δ ppm: 11.67 (s, 1H), 10.71 (s 1H), 8.58-8.41 (m, 2H), 8.03 (d, J=2.5 Hz, 1H), 7.77-7.68 (m, 1H), 7.57 (d, J=8.8 Hz, 1H), 7.54-7.38 (m, 3H), 7.30-7.11 (m, 2H), 7.11-6.90 (m, 2H), 6.75-6.60 (m, 1H), 6.42-6.35 (m, 1H), 6.30-6.15 (m, 1H), 4.30 (s, 1H), 4.10-3.85 (m, 1H), 3.35-3.25 (m, 2H), 3.16-2.82 (m, 8H), 2.47 (s, 3H), 2.31-1.99 (m, 2H), 1.82-1.53 (m, 7H), 1.46-1.31 (m, 7H), 1.23-1.12 (m, 5H), 1.10-0.86 (m, 1H), 0.82-0.52 (m, 2H). MS (ESI, m/e) [M+1]$^+$ 916.9.

With the isomer of slower peak in SFC as starting material, Example F91b was synthesized following the procedures similar to those in Example F21. $^1$H NMR (400 MHz, DMSO-$d_6$) δ ppm: 11.58 (s, 1H), 10.61 (s, 1H), 8.43 (s, 2H), 7.95 (s, 1H), 7.67-7.63 (m, 1H), 7.47-7.42 (m, 4H), 7.13 (s, 2H), 6.96-6.93 (m, 2H), 6.62-6.60 (m, 1H), 6.32 (s, 1H), 6.17 (s, 1H), 4.24 (s, 1H), 3.24 (s, 2H), 2.93-2.90 (m, 9H), 2.33 (s, 2H), 2.19 (s, 2H), 2.03-1.95 (m, 2H), 1.75-1.50 (m, 8H), 1.33-1.25 (m, 8H), 1.09 (s, 5H), 0.89-0.87 (m, 4H), 0.68 (s, 1H), 0.53 (s, 1H). MS (ESI) m/e [M+1]$^+$ 916.9.

Example F92: 2-((1H-pyrrolo[2,3-b]pyridin-5-yl)oxy)-4-(2-(2-(2-cyclopropylphenyl)-4-isopropylpiperazin-1-yl)-7-azaspiro[3.5]nonan-7-yl)-N-((3-nitro-4-(((tetrahydro-2H-pyran-4-yl)methyl)amino)phenyl)sulfonyl)benzamide

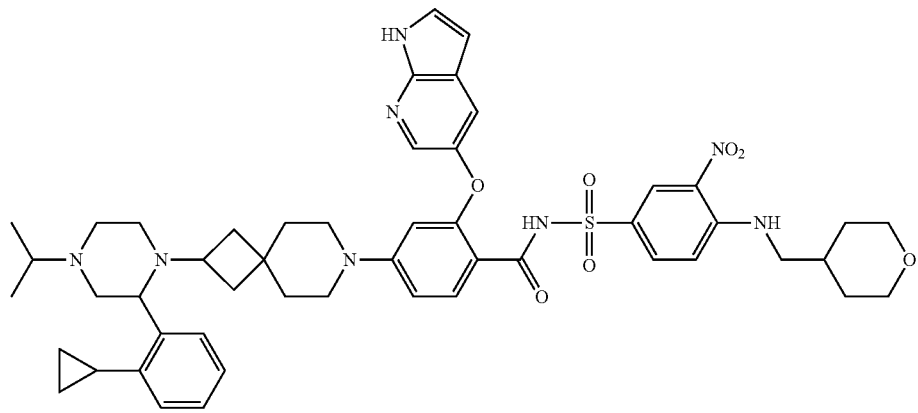

The desired compound was synthesized following the procedures similar to those in Example F90 by replacing (S)-2-(2-(2-cyclopropylphenyl)pyrrolidin-1-yl)-7-azaspiro[3.5]nonane with 2-(2-(2-cyclopropylphenyl)-4-isopropylpiperazin-1-yl)-7-azaspiro[3.5]nonane. $^1$H NMR (400 MHz, DMSO-$d_6$) δ ppm: 11.70 (s, 1H), 11.43 (s, 1H), 8.69-8.50 (m, 2H), 8.06-7.97 (m, 1H), 7.84-7.74 (m, 1H), 7.61-7.38 (m, 4H), 7.35-6.94 (m, 4H), 6.75-6.58 (m, 1H), 6.38 (s, 1H), 6.13 (s, 1H), 4.25 (s, 1H), 3.91-3.80 (m, 2H), 3.34-3.09 (m, 8H), 3.10-2.80 (m, 6H), 2.23-1.71 (m, 4H), 1.67-1.45 (m, 3H), 1.44-1.25 (m, 10H), 1.10-0.66 (m, 5H). MS (ESI, m/e) [M+1]$^+$ 916.9.

Example F93: 2-((1H-pyrrolo[2,3-b]pyridin-5-yl)oxy)-4-(2-(2'-cyclopropyl-[1,1'-biphenyl]-2-yl)-7-azaspiro[3.5]nonan-7-yl)-N-((3-nitro-4-(((tetrahydro-2H-pyran-4-yl)methyl)amino)phenyl)sulfonyl)benzamide

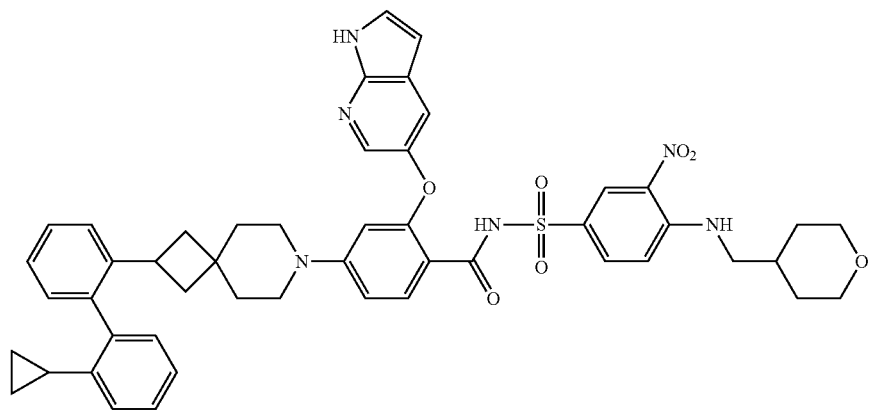 [SMILES: O=C(NS(=O)(=O)c1ccc(NCC2CCOCC2)c([N+](=O)[O-])c1)c1ccc(N2CCC3(CC2)CC(c2ccccc2-c2ccccc2C2CC2)C3)cc1Oc1cnc2[nH]ccc2c1]

The desired compound was synthesized following the procedures similar to those in Example F23 by replacing (S)-2-(2-cyclopropylphenyl)pyrrolidin-1-yl)-7-azaspiro[3.5]nonane with 2-(2'-cyclopropyl-[1,1-biphenyl]-2-yl)-7-azaspiro[3,5]nonane. $^1$H NMR (400 MHz, DMSO-d$_6$) δ ppm: 11.68 (s, 1H), 11.42 (s, 1H), 9.90 (s, 1H), 8.63 (s, 2H), 8.55 (s, 1H), 7.99 (s, 1H), 7.75-7.71 (m, 2H), 7.50 (s, 3H), 7.30-7.25 (m, 3H), 7.09 (s, 1H), 6.67 (d, J=8.7 Hz, 1H), 6.37 (s, 1H), 6.17 (s, 1H), 5.66 (s, 1H), 4.77 (s, 1H), 3.87 (s, 1H), 3.66 (s, 1H), 3.30-3.28 (m, 2H), 3.00-2.98 (m, 7H), 2.05-2.02 (m, 4H), 1.69-1.67 (m, 7H), 1.48-1.32 (m, 21H), 1.24-1.21 (m, 5H), 1.13 (s, 4H). MS (ESI) m/e [M+1]$^+$ 866.8.

Example F94: 2-((1H-pyrrolo[2,3-b]pyridin-5-yl)oxy)-N-((3-nitro-4-(((tetrahydro-2H-pyran-4-yl)methyl)amino)phenyl)sulfonyl)-4-(2-(2-(o-tolyl)azepan-1-yl)-7-azaspiro[3.5]nonan-7-yl)benzamide

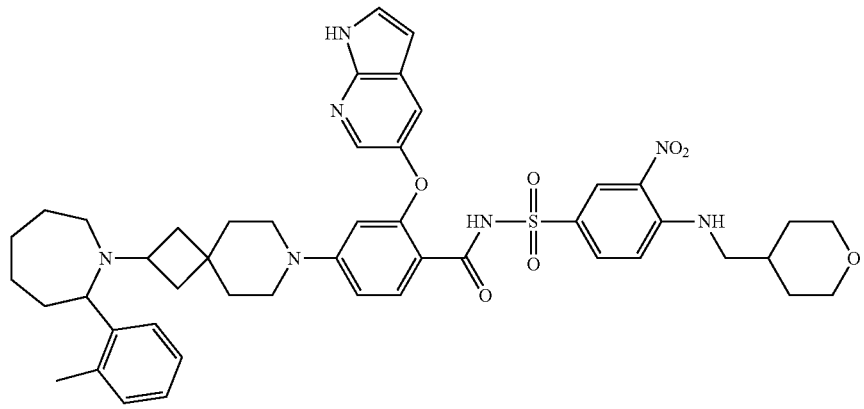 [SMILES: Cc1ccccc1C1CCCCCN1C1CC2(CCN(c3ccc(C(=O)NS(=O)(=O)c4ccc(NCC5CCOCC5)c([N+](=O)[O-])c4)c(Oc4cnc5[nH]ccc5c4)c3)CC2)C1]

The desired compound was synthesized following the procedures similar to those in Example F23 by replacing (S)-2-(2-cyclopropylphenyl)pyrrolidine with 2-(o-tolyl)azepane. $^1$H NMR (400 MHz, DMSO-d$_6$) δ ppm: 11.71 (s, 1H), 11.47 (s, 1H), 9.82 (s, 1H), 8.70-8.60 (m, 1H), 8.56 (s, 1H), 8.04 (s, 1H), 7.79 (d, J=9.0 Hz, 1H), 7.75-6.95 (m, 1H), 7.60-7.40 (m, 3H), 7.35-7.15 (m, 3H), 7.12 (d, J=9.0 Hz, 1H), 6.69 (d, J=8.4 Hz, 1H), 6.39 (s, 1H), 6.18 (s, 1H), 4.45-4.35 (m, 1H), 4.10-3.90 (m, 1H), 3.85 (d, J=10.4 Hz, 2H), 3.60-3.50 (m, 2H), 3.35-3.20 (m, 5H), 3.15-2.85 (m, 4H), 2.35 (s, 3H), 2.25-2.00 (m, 4H), 1.98-1.67 (m, 5H), 1.65-1.55 (m, 2H), 1.51-1.16 (m, 8H). MS (ESI, m/e) [M+1]$^+$ 861.9.

Example F95: 2-((1H-pyrrolo[2,3-b]pyridin-5-yl)oxy)-4-(2-(2-(2-cyclopropylphenyl)azepan-1-yl)-7-azaspiro[3.5]nonan-7-yl)-N-((3-nitro-4-(((tetrahydro-2H-pyran-4-yl)methyl)amino)phenyl)sulfonyl)benzamide

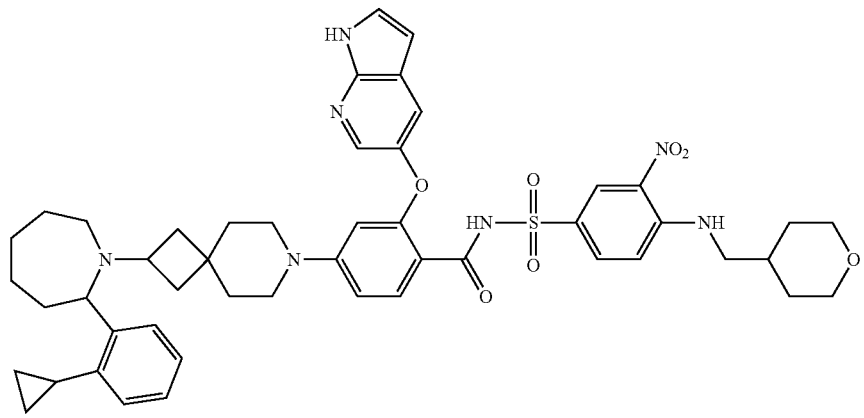 [SMILES: O=C(NS(=O)(=O)c1ccc(NCC2CCOCC2)c([N+](=O)[O-])c1)c1ccc(N2CCC3(CC2)CC(N2CCCCCC2c2ccccc2C2CC2)C3)cc1Oc1cnc2[nH]ccc2c1]

The desired compound was synthesized following the procedures similar to those in Example F23 by replacing (S)-2-(2-cyclopropylphenyl)pyrrolidine with 2-(2-cyclopropylphenyl)azepane. $^1$H NMR (400 MHz, DMSO-d$_6$) δ ppm: 11.68 (s, 1H), 11.44 (s, 1H), 8.67-8.46 (m, 2H), 8.03 (s, 1H), 7.86-7.71 (m, 1H), 7.65-7.36 (m, 4H), 7.34-7.20 (m, 2H), 7.20-6.88 (m, 3H), 6.74-6.55 (m, 1H), 6.38 (s, 1H), 6.22-6.11 (m, 1H), 4.92-4.73 (m, 1H), 4.15-3.97 (m, 1H), 3.92-3.77 (m, 2H), 3.66-3.45 (m, 1H), 3.30-3.19 (m, 3H), 3.19-2.78 (m, 6H), 2.21-1.66 (m, 10H), 1.63-1.26 (m, 11H), 1.06-0.90 (m, 2H), 0.76-0.45 (m, 2H). MS (ESI, m/e) [M+1]$^+$ 887.9.

Example F96: 2-((1H-pyrrolo[2,3-h]pyridin-5-yl)oxy)-4-(2-(2-(2-cyclopropylphenyl)pyrazolidin-1-yl)-7-azaspiro[3.5]nonan-7-yl)-N-((3-nitro-4-(((tetrahydro-2H-pyran-4-yl)methyl)amino)phenyl)sulfonyl)benzamide

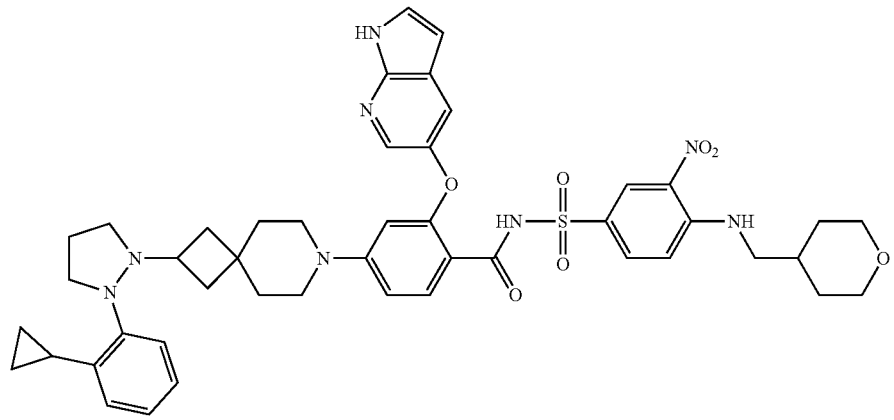 [SMILES: O=C(NS(=O)(=O)c1ccc(NCC2CCOCC2)c([N+](=O)[O-])c1)c1ccc(N2CCC3(CC2)CC(N2CCCN2c2ccccc2C2CC2)C3)cc1Oc1cnc2[nH]ccc2c1]

The desired compound was synthesized following the procedures similar to those in Example F23 by replacing (S)-2-(2-(2-cyclopropylphenyl)pyrrolidin-1-yl)-7-azaspiro[3.5]nonane with 2-(2-(2-cyclopropylphenyl)pyrazolidin-1-yl)-7-azaspiro[3.5]nonane. $^1$H NMR (400 MHz, DMSO-d$_6$) δ ppm: 11.69 (s, 1H), 11.40 (s, 1H), 8.67-8.52 (m, 2H), 8.05 (d, J=2.3 Hz, 1H), 7.80 (d, J=9.2 Hz, 1H), 7.59-7.44 (m, 3H), 7.35 (d, J=8.0 Hz, 1H), 7.12 (d, J=9.4 Hz, 1H), 6.96 (s, 1H), 6.75-6.70 (m, 3H), 6.39 (s, 1H), 6.18 (s, 1H), 3.86-3.84 (m, 2H), 3.26-3.24 (m, 2H), 3.09 (s, 2H), 3.02 (s, 2H), 2.91 (s, 2H), 2.08 (s, 1H), 1.94-1.79 (m, 5H), 1.59-1.57 (m, 4H), 1.46-1.12 (m, 4H), 1.32-1.19 (m, 7H), 0.93-0.90 (m, 2H), 0.62 (s, 2H). MS (ESI) m/e [M+1]$^+$ 860.9.

Example F97: 2-((1H-pyrrolo[2,3-b]pyridin-5-yl)oxy)-4-(2-((S)-2-(2-cyclopropylphenyl)pyrrolidin-1-yl)-7-azaspiro[3.5]nonan-7-yl)-N-((4-(((((1s,4s) or (1r,4r))-4-(((dimethyl(oxo)-16-sulfaneylidene)amino)cyclohexyl)methyl)amino)-3-nitrophenyl)sulfonyl)benzamide

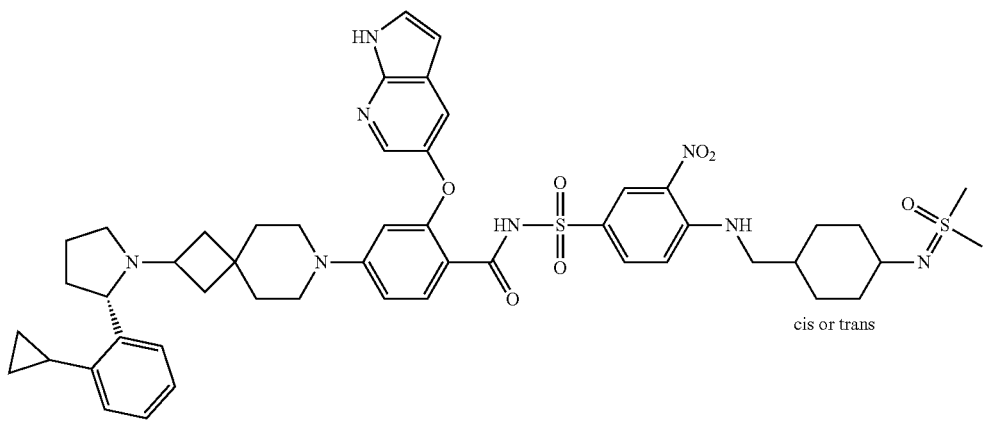 [SMILES: CS(C)(=O)=NC1CCC(CNc2ccc(S(=O)(=O)NC(=O)c3ccc(N4CCC5(CC4)CC(N4CCC[C@H]4c4ccccc4C4CC4)C5)cc3Oc3cnc4[nH]ccc4c3)cc2[N+](=O)[O-])CC1]

cis or trans

The desired compound was synthesized following the procedures similar to those in Example F21 by replacing 4-((((1r,4r)-4-hydroxy-4-methylcyclohexyl)methyl)amino)-3-nitrobenzenesulfonamide with 4-(((((1s,4s) or (1r,4r))-4-((dimethyl(oxo)-16-sulfaneylidene)amino)cyclohexyl)methyl)amino)-3-nitrobenzenesulfonamide. $^1$H NMR (400 MHz, DMSO-d$_6$) δ ppm: 11.76 (s, 1H), 10.16 (s, 1H), 8.70-8.64 (m, 1H), 8.62-8.60 (m, 1H), 8.15-8.06 (m, 1H), 7.91-7.74 (m, 2H), 7.62-7.49 (m, 3H), 7.41-7.28 (m, 2H), 7.15-7.10 (m, 2H), 6.75 (d, J=9.2 Hz, 1H), 6.48-6.42 (m, 1H), 6.25-6.20 (m, 1H), 5.05-4.95 (m, 1H), 4.05-3.85 (m, 1H), 3.80-3.70 (m, 1H), 3.40-3.20 (m, 4H), 3.18-3.05 (m, 4H), 2.65-2.55 (m, 6H), 2.30-2.00 (m, 4H), 1.94-1.76 (m, 3H), 1.70-1.41 (m, 8H), 1.40-1.25 (m, 2H), 1.24-1.11 (m, 3H), 1.10-0.96 (m, 2H), 0.95-0.85 (m, 2H), 0.75-0.65 (m, 2H). MS (ESI, m/e) [M+1]$^+$ 948.8.

Example F98: 2-((1H-pyrrolo[2,3-b]pyridin-5-yl)oxy)-4-(2-((S)-2-(2-cyclopropylphenyl)pyrrolidin-1-yl)-7-azaspiro[3.5]nonan-7-yl)-N-(methyl(3-nitro-4-(((tetrahydro-2H-pyran-4-yl)methyl)amino)phenyl)(oxo)-16-sulfaneylidene)benzamide

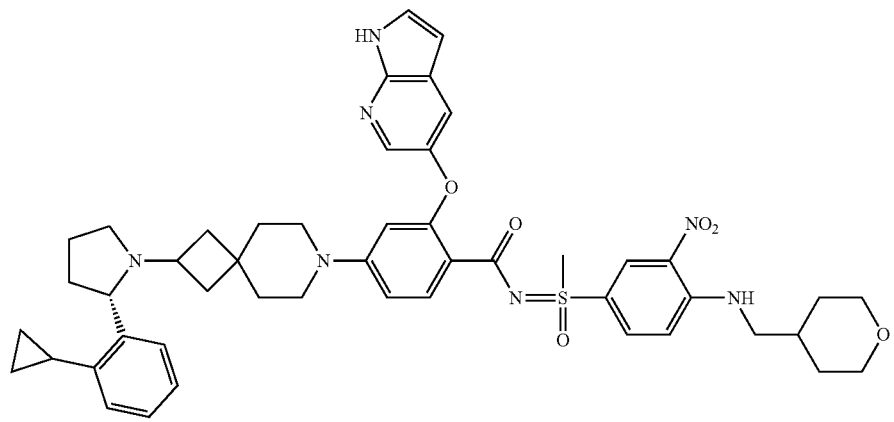 [SMILES: CS(=O)(=NC(=O)c1ccc(N2CCC3(CC2)CC(N2CCC[C@H]2c2ccccc2C2CC2)C3)cc1Oc1cnc2[nH]ccc2c1)c1ccc(NCC2CCOCC2)c([N+](=O)[O-])c1]

To a solution of 3-((1H-pyrrolo[2,3-b]pyridin-5-yl)oxy)-4'-(2-(2-cyclopropylphenyl)pyrrolidin-1-yl)-[1,1'-biphenyl]-4-carboxylic acid (100 mg, 0.194 mmol) in DCM (30 ml) was added EDCl (56 mg, 0,291 mmol) and DMAP (71 mg, 0,582 mmol). The mixture was stirred at room temperature for 0.5 hour. Then to the mixture was added imino(methyl)(3-nitro-4-(((tetrahydro-2H-pyran-4-yl)methyl)amino)phenyl)-16-sulfanone (138 mg, 0.388 mmol). The mixture was stirred at room temperature for 2 days. The mixture was diluted with DCM (100 ml), washed with saturated aq. NaHCO$_3$, brine, dried over Na$_2$SO$_4$, concentrated and purified by chromatography column on silica gel (eluent: DCM: EA=1:1 then MeOH/DCM=1/10) to give the crude product. The crude product was further purified by prep-MPLC (eluent: MeOH/DCM=1/10) to give the product (9 mg). $^1$H NMR (400 MHz, DMSO-d$_6$) δ ppm: 11.63 (s, 1H), 8.71-8.63 (m, 1H), 8.61-8.54 (m, 1H), 8.08-7.96 (m, 1H), 7.91-7.84 (m, 1H), 7.74-7.65 (m, 1H), 7.51-7.34 (s, 5H), 7.16-6.95 (m, 5H), 6.91-6.83 (m, 1H), 6.45-6.31 (m, 3H), 5.28-5.13 (m, 1H), 3.91-3.79 (m, 2H), 3.79-3.67 (m, 1H), 3.46-3.39 (m, 4H), 3.32-3.20 (m, 4H), 3.11-2.85 (m, 1H), 2.49-2.38 (m, 1H), 2.09-1.82 (m, 5H), 1.65-1.53 (m, 2H), 1.32-1.26 (m, 1H), 1.10-0.91 (m, 2H), 0.85-0.66 (m, 2H). MS (ESI, m/e) [M+1]$^+$ 810.8.

Example F99: 2-((1H-pyrrolo[2,3-b]pyridin-5-yl)oxy)-N-((4-(((-3-oxabicyclo[3.1.0]hexan-6-yl)methyl)amino)-3-nitrophenyl)sulfonyl)-4-(2-((S)-2-(2-isopropylphenyl)pyrrolidin-1-yl)-7-azaspiro[3.5]nonan-7-yl)benzamide

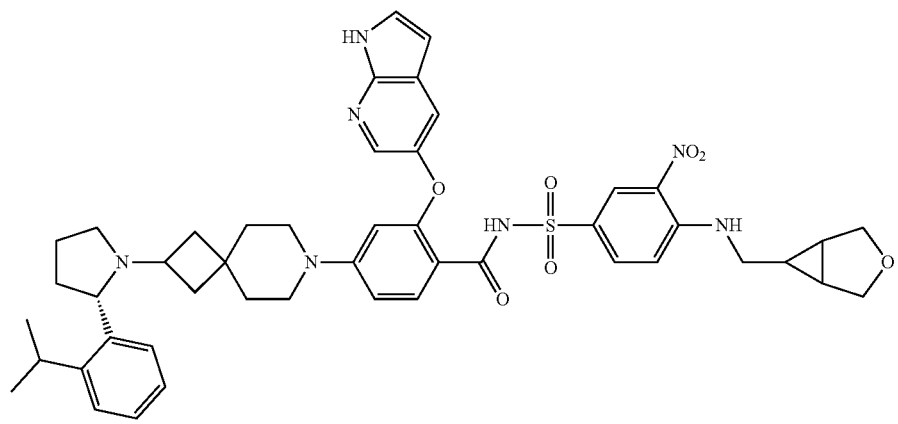 [SMILES: CC(C)c1ccccc1[C@@H]1CCCN1C1CC2(CCN(c3ccc(C(=O)NS(=O)(=O)c4ccc(NCC5C6COCC56)c([N+](=O)[O-])c4)c(Oc4cnc5[nH]ccc5c4)c3)CC2)C1]

The desired compound was synthesized following the procedures similar to those in Example F43 by replacing 4-((((1r,4r)-4-hydroxy-4-methylcyclohexyl)methyl)amino)-3-nitrobenzenesulfonamide with 4-(((3-oxabicyclo[3.1.0]hexan-6-yl)methyl)amino)-3-nitrobenzenesulfonamide. $^1$H NMR (400 MHz, DMSO-d$_6$) δ ppm: 11.70 (s, 1H), 11.45 (s, 1H), 8.60-8.58 (m, 2H), 8.03 (s, 1H), 7.80 (d, J=8.7 Hz, 1H), 7.59 (s, 1H), 7.50-7.48 (m, 3H), 7.35-7.32 (m, 3H), 7.09 (d, J=8.9 Hz, 1H), 6.68 (d, J=8.4 Hz, 1H), 6.38 (s, 1H), 6.17 (s, 1H), 4.78 (s, 1H), 3.89 (s, 1H), 3.72-3.70 (m, 3H), 3.56 (d, J=7.7 Hz, 2H), 3.27 (s, 1H), 3.17 (s, 1H), 3.05-2.95 (m, 4H), 2.46-2.36 (m, 1H), 2.05-2.03 (m, 5H), 1.71 (s, 2H), 1.54-1.17 (m, 11H), 1.15-0.98 (m, 4H). MS (ESI) m/e [M+1]$^+$ 859.9.

Example F100: (S)-2-((1H-pyrrolo[2,3-b]pyridin-5-yl)oxy)-4-(2-(2-(2-cyclopropylphenyl)pyrrolidin-1-yl)-7-azaspiro[3.5]nonan-7-yl)-N-((4-(((4-hydroxy-4-(trifluoromethyl)cyclohexyl)methyl)amino)-3-nitrophenyl)sulfonyl)benzamide

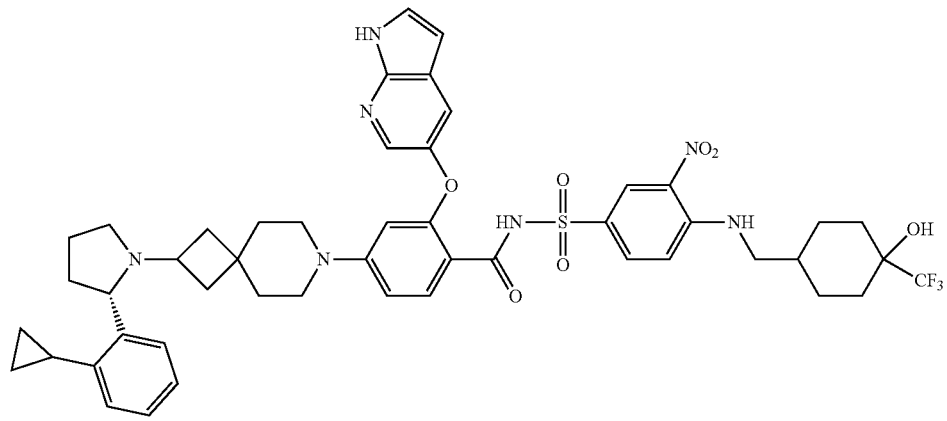 [SMILES: O=C(NS(=O)(=O)c1ccc(NCC2CCC(O)(C(F)(F)F)CC2)c([N+](=O)[O-])c1)c1ccc(N2CCC3(CC2)CC(N2CCC[C@H]2c2ccccc2C2CC2)C3)cc1Oc1cnc2[nH]ccc2c1]

The desired compound was synthesized following the procedures similar to those in Example F43 by replacing (S)-2-(2-isopropylphenyl)pyrrolidine with (S)-2-(2-cyclopropylphenyl)pyrrolidine and replacing 4-(((((1r,4r)-4-hydroxy-4-methylcyclohexyl)methyl)amino)-3-nitrobenzenesulfonamide with 4-(((4-hydroxy-4-(trifluoromethyl)cyclohexyl)methyl)amino)-3-nitrobenzenesulfonamide. $^1$H NMR (400 MHz, DMSO-d$_6$) δ ppm: 11.70 (s, 1H), 11.44 (s, 1H), 8.66 (s, 1H), 8.56 (s, 1H), 8.03 (s, 1H), 7.79 (d, J=9.0 Hz, 2H), 7.50-7.48 (m, 3H), 7.28 (s, 2H), 7.06 (s, 2H), 6.68 (d, J=8.4 Hz, 1H), 6.38 (s, 1H), 6.17 (s, 1H), 5.69-5.67 (m, 1H), 4.97 (s, 1H), 3.87 (s, 1H), 3.67 (s, 1H), 3.40 (s, 1H), 3.29 (s, 1H), 3.05-2.98 (m, 6H), 2.05-2.01 (m, 6H), 1.76-1.72 (m, 5H), 1.55-1.29 (m, 10H), 0.95 (s, 2H), 0.64 (s, 2H). MS (ESI) m/e [M+1]$^+$ 941.8.

Example F101a: 2-((1H-pyrrolo[2,3-b]pyridin-5-yl)oxy)-N-((4-(((((1r,4r)-4-hydroxy-4-(trifluoromethyl)cyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)benzamide; Example F101b: 2-((1H-pyrrolo[2,3-b]pyridin-5-yl)oxy)-N-((4-(((((1s,4s)-4-hydroxy-4-(trifluoromethyl)cyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)benzamide

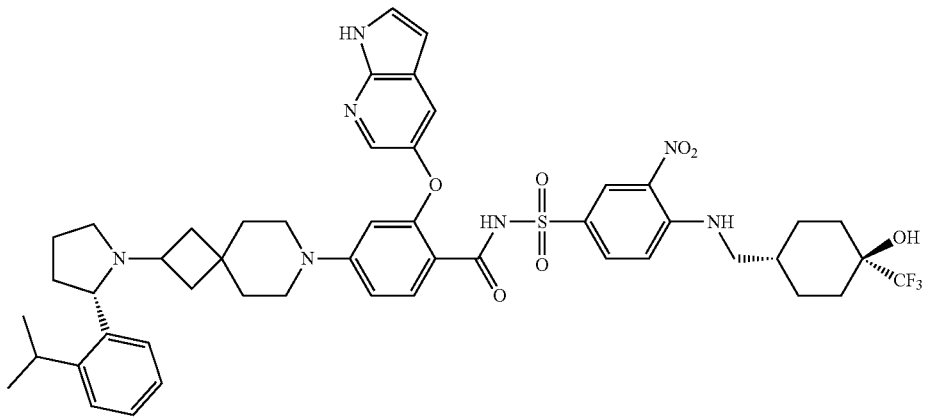
F101a

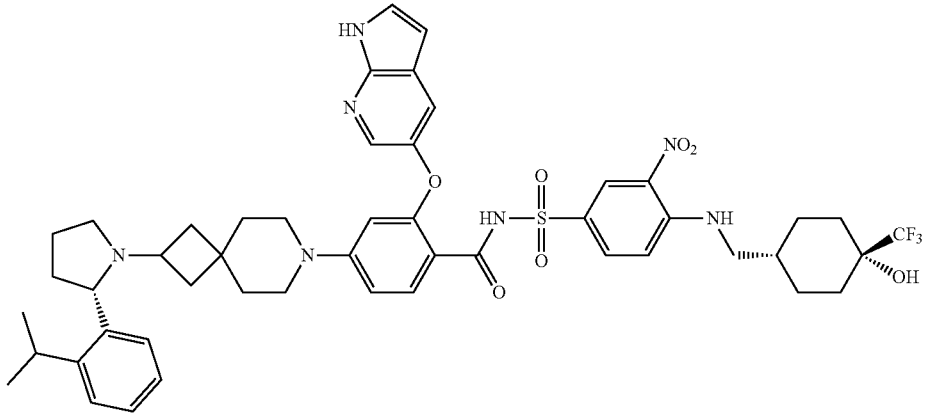
F101b

The desired compound F101a was synthesized following the procedures similar to those in Example F43 by replacing 4-(((((1r,4r)-4-hydroxy-4-methylcyclohexyl)methyl)amino)-3-nitrobenzenesulfonamide with 4-(((((1r,4r)-4-hydroxy-4-(trifluoromethyl)cyclohexyl)methyl)amino)-3-nitrobenzenesulfonamide. $^1$H NMR (400 MHz, DMSO-d$_6$) δ ppm: 11.69 (s, 1H), 11.44 (s, 1H), 8.80-8.45 (m, 2H), 8.03 (s, 1H), 7.90-7.65 (m, 2H), 7.64-6.93 (m, 7H), 6.77-6.59 (m, 1H), 6.38 (s, 1H), 6.17 (s, 1H), 5.69 (s, 1H), 4.99 (br, 1H), 3.93 (br, 1H), 3.73-3.36 (m, 3H), 3.30-3.21 (m, 1H), 3.19-2.86

(m, 5H), 2.46-2.35 (m, 1H), 2.23-1.90 (m, 5H), 1.85-1.70 (m, 4H), 1.58-1.32 (m, 9H), 1.23 (s, 6H), 1.17-1.01 (m, 3H). MS (ESI, m/e) [M+1]⁺ 943.9; F101b was synthesized by replacing 4-((((1r,4r)-4-hydroxy-4-methylcyclohexyl)methyl)amino)-3-nitrobenzenesulfonamide with 4-((((1s,4s)-4-hydroxy-4-(trifluoromethyl)cyclohexyl)methyl)amino)-3-nitrobenzenesulfonamide. ¹H NMR (400 MHz, DMSO-d₆) δ ppm: 11.68 (s, 1H), 11.42 (s, 1H), 9.90 (s, 1H), 8.63 (s, 2H), 8.55 (s, 1H), 7.99 (s, 1H), 7.75-7.71 (m, 2H), 7.50 (s, 3H), 7.30-7.25 (m, 3H), 7.09 (s, 1H), 6.67 (d, J=8.7 Hz, 1H), 6.37 (s, 1H), 6.17 (s, 1H), 5.66 (s, 1H), 4.77 (s, 1H), 3.87 (s, 1H), 3.66 (s, 1H), 3.30-3.28 (m, 2H), 3.00-2.98 (m, 7H), 2.05-2.02 (m, 4H), 1.69-1.67 (m, 7H), 1.48-1.32 (m, 21H), 1.24-1.21 (m, 5H), 1.13 (s, 4H). MS (ESI) m/e [M+1]⁺ 943.8.

Example F102: 2-((1H-pyrrolo[2,3-b]pyridin-5-yl)oxy)-4-(2-((S)-2-(2-isopropylphenyl)pyrrolidin-1-yl)-7-azaspiro[3.5]nonan-7-yl)-N-((4-((((1r,4r)-4-methoxy-4-methylcyclohexyl)methyl)amino)-3-nitrophenyl)sulfonyl)benzamide

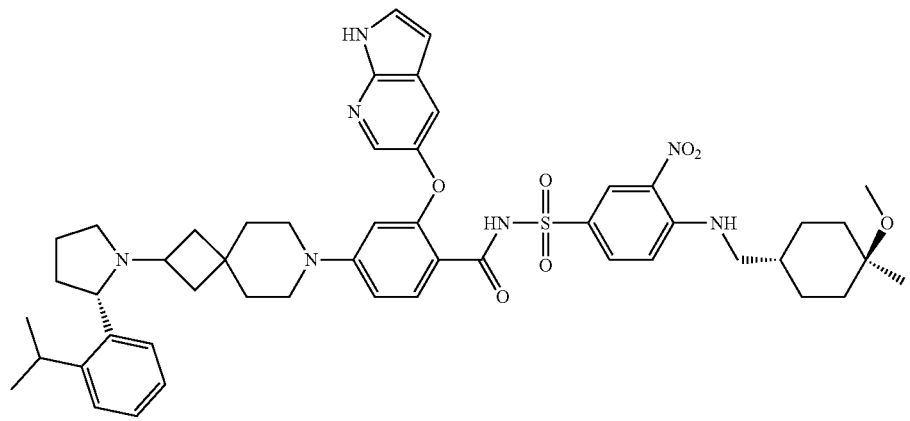 [SMILES: CO[C@]1(C)CC[C@@H](CNc2ccc(S(=O)(=O)NC(=O)c3ccc(N4CCC5(CC4)CC(N4CCC[C@H]4c4ccccc4C(C)C)C5)cc3Oc3cnc4[nH]ccc4c3)cc2[N+](=O)[O-])CC1]

The desired compound was synthesized following the procedures similar to those in Example F43 by replacing 4-((((1r,4r)-4-hydroxy-4-methylcyclohexyl)methyl)amino)-3-nitrobenzenesulfonamide with 4-((((1r,4r)-4-methoxy-4-methylcyclohexyl)methyl)amino)-3-nitrobenzenesulfonamide. ¹H NMR (400 MHz, DMSO-d₆) δ ppm: 11.69 (s, 1H), 11.43 (br, 1H), 8.62-8.53 (m, 2H), 8.02 (s, 2H), 7.79 (d, J=9.6 Hz, 1H), 7.49-7.46 (m, 3H), 7.39-7.15 (m. 3H), 7.08 (d, J=9.6 Hz, 1H), 6.68 (d, J=8.8 Hz, 1H), 6.40-6.32 (m, 1H), 6.17 (s, 1H), 4.74-4.72 (m, 1H), 3.88-3.55 (m, 2H), 3.30-3.25 (m, 2H), 3.09 (s, 3H), 3.03-2.85 (m, 4H), 2.44-2.30 (m, 1H), 2.25-1.94 (m, 4H), 1.75-1.56 (m, 6H), 1.49-1.30 (m, 9H), 1.26-1.10 (m. 12H). MS (ESI, m/e) [M+1]⁺ 903.9.

Example F103: 2-((1H-pyrrolo[2,3-b]pyridin-5-yl)oxy)-4-(2-((S)-2-(2-isopropylphenyl)pyrrolidin-1-yl)-7-azaspiro[3.5]nonan-7-yl)-N-((4-((((S)-4-methylcyclohex-3-en-1-yl)methyl)amino)-3-nitrophenyl)sulfonyl)benzamide

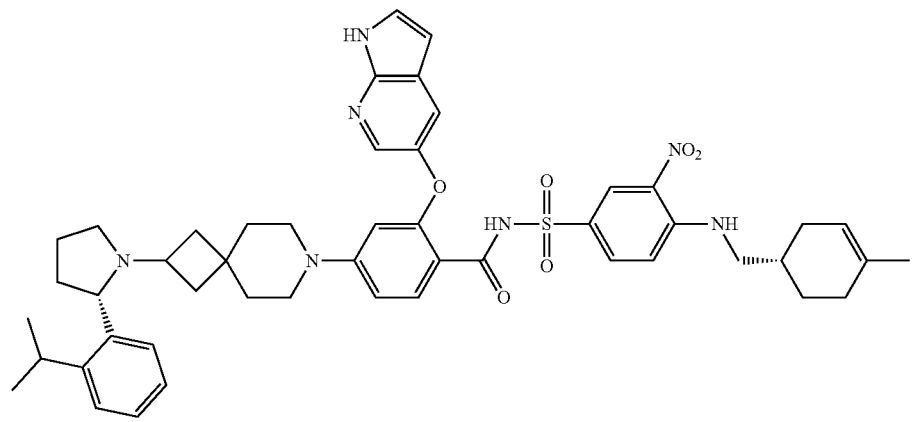 [SMILES: CC1=CC[C@@H](CNc2ccc(S(=O)(=O)NC(=O)c3ccc(N4CCC5(CC4)CC(N4CCC[C@H]4c4ccccc4C(C)C)C5)cc3Oc3cnc4[nH]ccc4c3)cc2[N+](=O)[O-])CC1]

The desired compound was synthesized following the procedures similar to those in Example F43 by replacing 4-((((1r,4r)-4-hydroxy-4-methylcyclohexyl)methyl)amino)-3-nitrobenzenesulfonamide with (S)-4-(((4-methylcyclohex-3-en-1-yl)methyl)amino)-3-nitrobenzenesulfonamide. ¹H NMR (400 MHz, DMSO-d₆) δ ppm: 11.69 (s, 1H), 11.44 (br, 1H), 8.62-8.53 (m, 2H), 8.03 (d, J=2.4 Hz, 1H), 7.99-7.80 (m, 1H), 7.78 (d, J=9.6 Hz, 1H), 7.50-7.46 (m, 3H), 7.39-7.22 (m, 3H), 7.08 (d, J=9.6 Hz, 1H), 6.68 (d, J=8.8 Hz, 1H), 6.40-6.32 (m, 1H), 6.17 (s, 1H), 5.35 (s, 1H), 4.74-4.72 (m, 1H), 3.88-3.55 (m, 2H), 3.30-3.25 (m, 2H), 3.09-2.85 (m, 4H), 2.44-2.30 (m, 1H), 2.20-1.70 (m, 12H), 1.6 (s, 3H), 1.49-1.30 (m, HID. 1.12 (d, J=6.8 Hz, 1H). MS (ESI, m/e) [M+1]⁺ 871.9.

Example F104: 2-((1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(2-((S)-2-(2-(prop-1-en-2-yl)phenyl)pyrrolidin-1-yl)-7-azaspiro[3.5]nonan-7-yl)benzamide

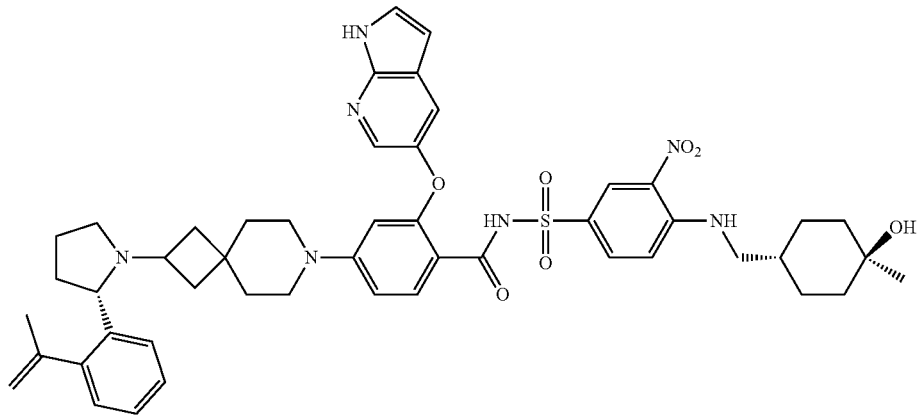 [SMILES: C=C(C)c1ccccc1[C@@H]1CCCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1]

The desired compound was synthesized following the procedures similar to those in Example F43 by replacing (S)-2-(2-isopropylphenyl)pyrrolidine with (S)-2-(2-(prop-1-en-2-yl)phenyl)pyrrolidine. ¹H NMR (400 MHz, DMSO-d₆) δ ppm: 11.70 (s, 1H), 11.44 (s, 1H), 10.37 (br, 1H), 8.60-8.55 (m, 2H), 8.04 (d, J=2.4 Hz, 1H), 7.95-7.9 (m, 1H), 7.80 (dd, J=9.6 Hz, J=2.4 Hz, 1H), 7.52-7.46 (m, 3H), 7.38-7.35 (m, 2H), 7.20 (d, J=6.8 Hz, 1H), 7.10 (d, J=0.2 Hz, 1H), 6.69 (d, J=9.2 Hz, 1H), 6.40-6.32 (m, 1H), 6.17 (s, 1H), 5.31 (s, 1H), 4.80 (s, 1H), 4.44-4.40 (m, 1H), 3.68-3.61 (m, 2H), 3.30-2.95 (m, 7H), 2.17-2.06 (m, 5H), 2.02 (s, 3H), 1.69-1.20 (m, 19H), MS (ESI, m/e) [M+1]⁺ 887.9.

Example F105: 2-((1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(2-((S)-2-(2-propylphenyl)pyrrolidin-1-yl)-7-azaspiro[3.5]nonan-7-yl)benzamide

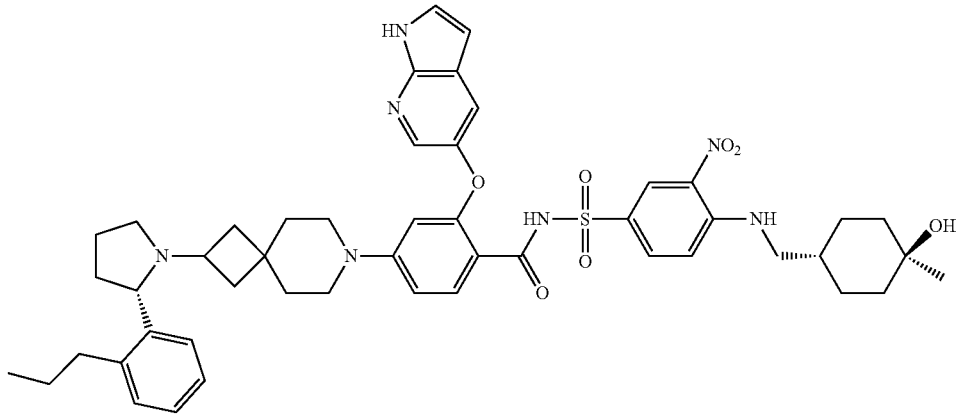 [SMILES: CCCc1ccccc1[C@@H]1CCCN1C1CC2(CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)C1]

The desired compound was synthesized following the procedures similar to those in Example F43 by replacing (S)-2-(2-isopropylphenyl)pyrrolidine with (S)-2-(2-propylphenyl)pyrrolidine. $^1$H NMR (400 MHz, DMSO-$d_6$) δ ppm: 11.69 (s, 1H), 11.44 (s, 1H), 10.37 (br, 1H), 8.61-8.55 (m, 2H), 8.03 (d, J=2.4 Hz, 1H), 7.99-7.85 (m, 1H), 7.79 (d, J=9.6 Hz, 1H), 7.52-7.46 (m, 3H), 7.27-7.20 (m, 2H), 7.08 (d, J=9.6 Hz, 1H), 6.69 (d, J=8.8 Hz, 1H), 6.40-6.32 (m, 1H), 6.17 (s, 1H), 4.61-4.57 (m, 1H), 4.25 (s, 1H), 3.88-3.61 (m, 2H), 3.30-2.90 (m, 7H), 2.80-2.50 (m, 2H), 2.44-2.36 (m, 1H), 2.19-1.90 (m, 4H), 1.69-1.23 (m, 17H), 1.17-1.05 (m, 5H), 0.92 (t, J=3.2 Hz, 3H). MS (ESI, m/e) [M+1]$^+$ 889.9.

Example F106: 2-((1H-pyrrolo[2,3-b]pyridin-5-yl)oxy)-4-(6-((S)-2-(2-cyclopropylphenyl)pyrrolidin-1-yl)-2-azaspiro[3.3]heptan-2-yl)-N-((4-((((1r,4r)-4-hydroxy-4-methylcyclohexyl)methyl)amino)-3-nitrophenyl)sulfonyl)benzamide

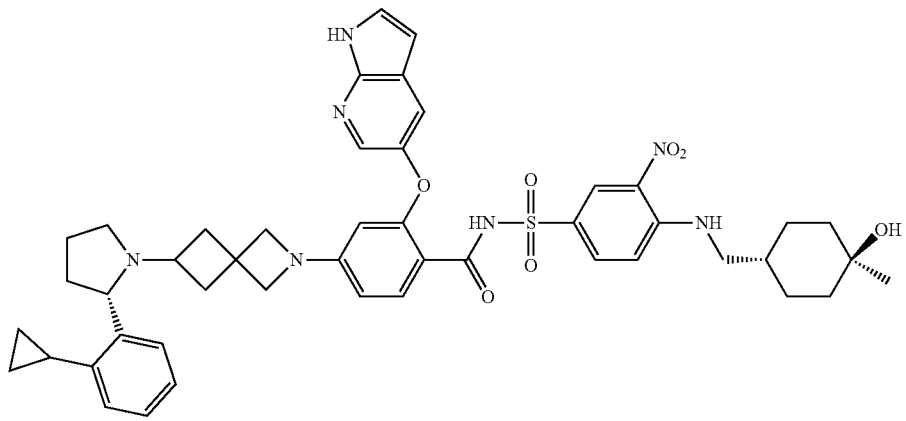 [SMILES: C[C@]1(O)CC[C@H](CNc2ccc(S(=O)(=O)NC(=O)c3ccc(N4CC5(CC(N6CCC[C@H]6c6ccccc6C6CC6)C5)C4)cc3Oc3cnc4[nH]ccc4c3)cc2[N+](=O)[O-])CC1]

Step 1: tert-butyl (S)-6-(2-(2-cyclopropylphenyl)pyrrolidin-1-yl)-2-azaspiro[3.3]heptane-2-carboxylate To the mixture of (S)-2-(2-cyclopropylphenyl)pyrrolidine (18.7 g, 0.1 mol) and tert-butyl 6-oxo-2-azaspiro[3.3]heptane-2-carboxylate (21.12 g, 0.1 mol) in DCM (200 mL) was added NaBH(AcO)$_3$ (42 g, 0.2 mol) at room temperature and stirred for overnight. The mixture was quenched with aq. NaHCO$_3$ (200 mL), extracted with DCM (200 mL). the combined organic layers was washed with brine (200 mL), dried over Na$_2$SO$_4$ and evaporated in vacuum to afford the tittle product (38.2 g) without further purification for next step. MS (ESI, m/e) [M+1]$^+$ 383.0.

Step 2: (S)-6-(2-(2-cyclopropylphenyl)pyrrolidin-1-yl)-2-azaspiro[3.3]heptane

To a solution of tert-butyl tert-butyl (S)-6-(2-(2-cyclopropylphenyl)pyrrolidin-1-yl)-2-azaspiro[3.3]heptane-2-carboxylate (38 g, 0.1 mmol) in DCM (50 mL) was added TFA (100 mL) at 20° C. and stirred at room temperature for overnight. The mixture was concentrated in vacuum and diluted with DCM (200 mL), then was adjusted to pH 8~9 with aq. NaOH (1M). Then the organic layer was washed with brine, dried over Na$_2$SO$_4$ and concentrated in vacuum to afford the crude product (28.2 g) without further purification for next step. MS (ESI, m/e) [M+1]$^+$ 283.0.

Step 3: (S)-2-((1H-pyrrolo[2,3-b]pyridin-5-yl)oxy)-4-(6-(2-(2-cyclopropylphenyl)pyrrolidin-1-yl)-2-azaspiro[3.3]heptan-2-yl)benzoate The mixture of (S)-6-(2-(2-cyclopropylphenyl)pyrrolidin-1-yl)-2-azaspiro[3.3]heptane (28.3 g, 0.1 mmol), methyl 2-((1H-pyrrolo[2,3-b]pyridin-5-yl)oxy)-4-fluorobenzoate (31.57 g, 0.11 mmol), Na$_2$CO$_3$ (106 g, 1 mol) in DMF (500 mL) was heated to 105° C. and stirred for overnight. After cooled to room temperature, the reaction mixture was diluted with EA (1000 mL), washed with brine (1000 mL×2), dried over Na$_2$SO$_4$ and concentrated in vacuum to afford a residue, which was purified by chromatography column on silica gel (eluent: EA/PE=1/5 to 1/1) to give the product (11.2 g) as an off-white solid. MS (ESI, m/e) [M+1]$^+$ 548.9.

Step 4: (S)-2-((1H-pyrrolo[2,3-b]pyridin-5-yl)oxy)-4-(6-(2-(2-cyclopropylphenyl)pyrrolidin-1-yl)-2-azaspiro[3.3]heptan-2-yl)benzoic acid To the mixture of methyl (S)-2-((1H-pyrrolo[2,3-b]pyridin-5-yl)oxy)-4-(6-(2-(2-cyclopropylphenyl)pyrrolidin-1-yl)-2-azaspiro[3.3]heptan-2-yl)benzoate (11.2 g, 20.42 mmol) in a solution of MeOH (200 mL). THF (200 mL) and aq. NaOH (166 mL, 1 mol) and heated to 50° C. for overnight. The reaction was quenched with HCl acid (6 M) and adjusted to pH 4~5, extracted with DCM (500 mL), washed with brine (200 mL). To the organic layer was added triethylamine to adjust pH at 8, then evaporated in vacuum to afford the tittle product (10.5 g) as an off-white solid. MS (ESI, m/e) [M+1]$^+$ 534.9.

Step 5: 2-((1H-pyrrolo[2,3-b]pyridin-5-yl)oxy)-4-(6-((S)-2-(2-cyclopropylphenyl)pyrrolidin-1-yl)-2-azaspiro[3.3]heptan-2-yl)-N-((4-((((1r,4r)-4-hydroxy-4-methylcyclohexyl)methyl)amino)-3-nitrophenyl)sulfonyl)benzamide The mixture of (S)-2-((1H-pyrrolo[2,3-b]pyridin-5-yl)oxy)-4-(6-(2-(2-cyclopropylphenyl)pyrrolidin-1-yl)-2-azaspiro[3.3]heptan-2-yl)benzoic acid (1.07 g, 2 mmol), triethylamine (1.20 g, 12 mmol) and 2-(7-Azabenzotriazol-1-yl)-N,N,N',N'-tetramethyluronium hexafluorophosphate (1.14 g, 3.0 mmol) in DCM (100 mL) was stirred for 2 hours at 50° C., To the mixture was added 4-(((4-hydroxy-4-methylcyclohexyl)methyl)amino)-3-nitrobenzenesulfonamide (1.37 g, 4 mmol) and DMAP (24 mg, 0.2 mmol) and then stirred for overnight at 35° C. The mixture was quenched with aq. NH$_4$Cl (500 mL), extracted with DCM (300 mL), washed with NaHCO$_3$ (300 mL), dried over Na$_2$SO$_4$ and concentrated in vacuum. The crude residue was then purified by chromatography column on silica gel (eluent: PE/EA=1/1, then DCM/EA=1/1 then DCM/MeOH=50/1 to 40/1) to afford the desired compound (1.02 g). $^1$H NMR (400 MHz, DMSO-d$_6$) δ ppm: 11.71 (s, 1H), 11.12 (br, 1H), 8.55-8.53 (m, 2H), 8.04 (s, 1H), 7.85 (d, J=8.0 Hz, 1H), 7.51-7.47 (m, 4H), 7.15-7.05 (m, 3H), 6.92-6.90 (m, 1H), 6.40 (s, 1H), 6.07 (d, J=8.8 Hz, 1H), 5.52 (s, 1H), 4.25 (s, 1H), 4.04-3.89 (m, 1H), 3.85-3.34 (m, 8H), 3.31-3.23 (m, 2H), 2.41-1.58 (m, 18H), 1.41-1.05 (m, 2H), 0.89-0.87 (m, 2H), 0.64-0.53 (m, 2H). MS (ESI, m/e) [M+1]$^+$ 859.9.

Example F107: N-((4-((((S)-1,4-dioxan-2-yl)methyl)amino)-3-nitrophenyl)sulfonyl)-2-((1H-pyrrolo[2,3-b]pyridin-5-yl)oxy)-4-(6-((S)-2-(2-cyclopropylphenyl)pyrrolidin-1-yl)-2-azaspiro[3.3]heptan-2-yl)benzamide

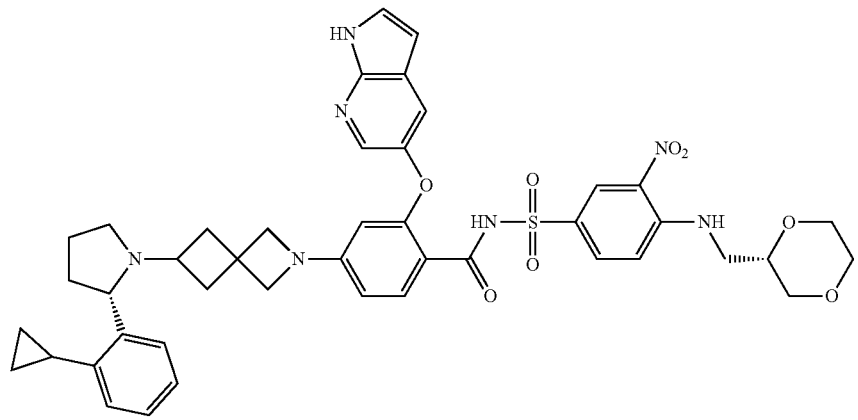 [SMILES: O=C(NS(=O)(=O)c1ccc(NC[C@H]2COCCO2)c([N+](=O)[O-])c1)c1ccc(N2CC3(CC(N4CCC[C@H]4c4ccccc4C4CC4)C3)C2)cc1Oc1cnc2[nH]ccc2c1]

The desired compound was synthesized following the procedures similar to those in Example F106 by replacing 4-((((1r,4r)-4-hydroxy-4-methylcyclohexyl)methyl)amino)-3-nitrobenzenesulfonamide with (S)-4-(((1,4-dioxan-2-yl)methyl)amino)-3-nitrobenzenesulfonamide. ¹H NMR (400 MHz, DMSO-d₆) δ ppm: 11.70 (s, 1H), 11.24 (br, 1H), 8.55-8.52 (m, 2H), 8.03 (s, 1H), 7.85 (d, J=8.0 Hz, 1H), 7.51-7.47 (m, 4H), 7.15-7.05 (m, 3H), 6.92-6.90 (m, 1H), 6.39-6.37 (m, 1H), 6.07 td, J=8.8 Hz, 1H), 5.52 (s, 1H), 4.12-4.04 (m, 1H), 3.85-3.29 (m, 15H), 3.31-3.23 (m, 1H), 2.31-1.58 (m, 9H), 0.89-0.87 (m, 2H), 0.64-0.62 (m, 2H). MS (ESI, m/e) [M+1]⁺ 833.8.

Example F108: N-((4-((((R)-1,4-dioxan-2-yl)methyl)amino)-3-nitrophenyl)sulfonyl)-2-((1H-pyrrolo[2,3-b]pyridin-5-yl)oxy)-4-(6-((S)-2-(2-cyclopropylphenyl)pyrrolidin-1-yl)-2-azaspiro[3.3]heptan-2-yl)benzamide

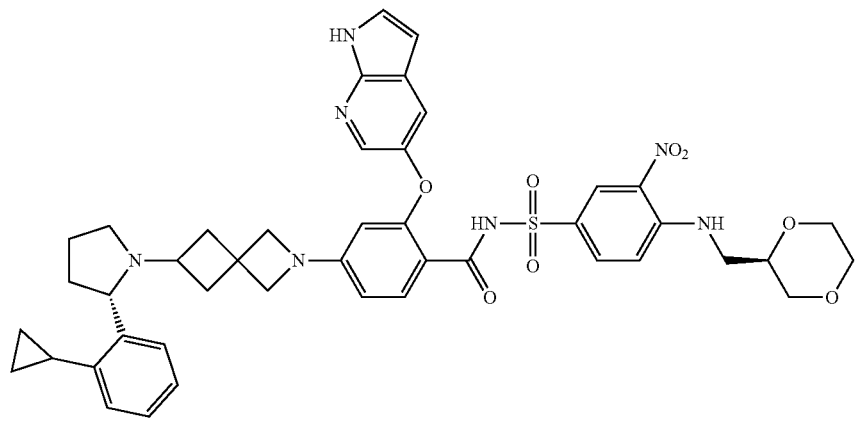 [SMILES: O=C(NS(=O)(=O)c1ccc(NC[C@@H]2COCCO2)c([N+](=O)[O-])c1)c1ccc(N2CC3(CC(N4CCC[C@H]4c4ccccc4C4CC4)C3)C2)cc1Oc1cnc2[nH]ccc2c1]

The desired compound was synthesized following the procedures similar to those in Example F106 by replacing 4-((((1r,4r)-4-hydroxy-4-methylcyclohexyl)methyl)amino)-3-nitrobenzenesulfonamide with (R)-4-(((1,4-dioxan-2-yl)methyl)amino)-3-nitrobenzenesulfonamide. ¹H NMR (400 MHz, DMSO-d₆) δ ppm: 11.73 (s, 1H), 11.33 (br, 1H), 8.59-8.55 (m, 2H), 8.06 (d, J=2.0 Hz, 1H), 7.85 (d, J=8.0 Hz, 1H), 7.69-7.52 (m, 4H), 7.35-7.01 (m, 3H), 6.42 (s, 1H), 6.06 (d, J=8.8 Hz, 1H), 5.50 (s, 1H), 5.02-4.92 (m, 1H), 3.85 (d, J=8.4 Hz, 2H), 3.79-3.31 (m, 12H), 3.31-3.23 (m, 2H), 2.50-2.38 (m, 2H), 2.18-1.72 (m, 7H), 1.02-0.88 (m, 2H), 0.70-0.58 (m, 2H). MS (ESI, m/e) [M+1]⁺ 833.8.

Example F109: 2-((1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(6-((S)-2-(2-isopropylphenyl)pyrrolidin-1-yl)-2-azaspiro[3.3]heptan-2-yl)benzamide

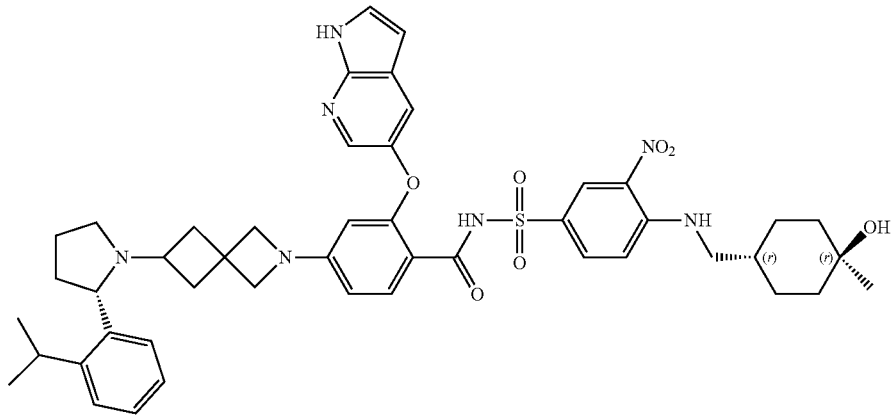

The desired compound was synthesized following the procedures similar to those in Example F106 by replacing (S)-2-(2-cyclopropylphenyl)pyrrolidine with (S)-2-(2-isopropylphenyl)pyrrolidine. ¹H NMR (400 MHz, DMSO-d₆) δ ppm: 11.73 (s, 1H), 11.28 (s, 1H), 8.57 (s, 2H), 8.05 (d, J=2.3 Hz, 1H), 7.82 (d, J=8.8 Hz, 1H), 7.63-7.42 (m, 4H), 7.35-7.04 (m, 5H), 6.41 (s, 1H), 6.06 (d, J=8.9 Hz, 1H), 5.50 (s, 1H), 4.24 (s, 1H), 3.65-3.55 (m, 5H), 3.30-3.19 (m, 4H), 3.07-2.90 (m, 2H), 2.08-1.99 (m, 2H), 1.86-1.59 (m, 6H), 1.66-1.52 (m, 2H), 1.35-1.31 (m, 3H), 1.25-1.11 (m, 12H). MS (ESI, m/e) [M+1]⁺ 862.1.

Example F110: N-((4-((((S) 1,4-dioxan-2-yl)methyl) amino)-3-nitrophenyl)sulfonyl)-2-((1H-pyrrolo[2,3-b]pyridin-5-yl)oxy)-4(6-((S)-2-(2-isopropylphenyl) pyrrolidin-1-yl)-2-azaspiro[3.3]heptan-2-yl) benzamide

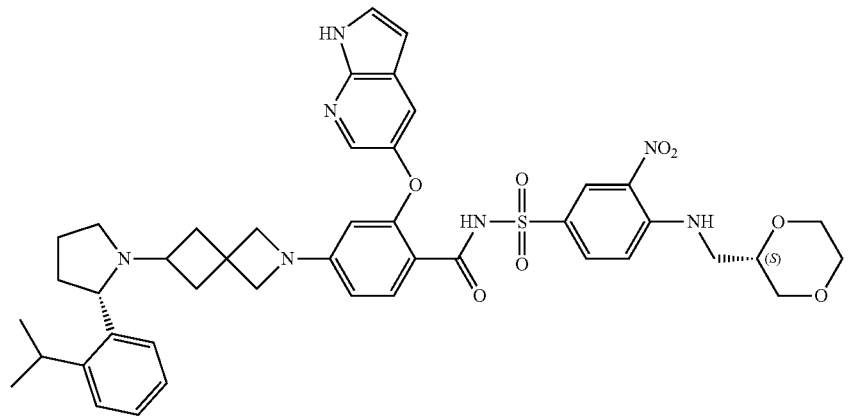

The desired compound was synthesized following the procedures similar to those in Example F106 by replacing (S)-2-(2-cyclopropylphenyl)pyrrolidine with (S)-2-(2-isopropylphenyl)pyrrolidine and replacing 4-((((1r,4r)-4-hydroxy-4-methylcyclohexyl)methyl)amino)-3-nitrobenzenesulfonamide with (S)-4-(((1,4-dioxan-2-yl)methyl)amino)-3-nitrobenzenesulfonamide. ¹H NMR (400 MHz, DMSO-d₆) δ ppm: 11.69 (s, 1H), 11.23 (s, 1H), 8.55 (s, 2H), 8.03 (d, J=1.5 Hz, 1H), 7.82 (d, J=8.9 Hz, 1H), 7.66-7.40 (m, 4H), 7.33-6.98 (m, 4H), 6.39 (s, 1H), 6.06 (d, J=8.6 Hz, 1H), 5.51 (s, 1H), 3.89-3.73 (m, 3H), 3.73-3.56 (m, 7H), 3.56-3.43 (m, 3H), 3.43-3.20 (m, 4H), 2.19-2.11 (m, 3H), 1.90-1.64 (m, 5H), 1.51 (s, 1H), 1.18-1.11 (m, 6H). MS (ESI, m/e) [M+1]⁺ 835.9.

Example F111: 2-((1H-pyrrolo[2,3-b]pyridin-5-yl) oxy)-4-(6-((S)-2-(2-ethylphenyl)pyrrolidin-1-yl)-2-azaspiro[3.3]heptan-2-yl)-N-((4-((((1r,4r)-4-hydroxy-4-methylcyclohexyl)methyl)amino)-3-nitrophenyl)sulfonyl)benzamide

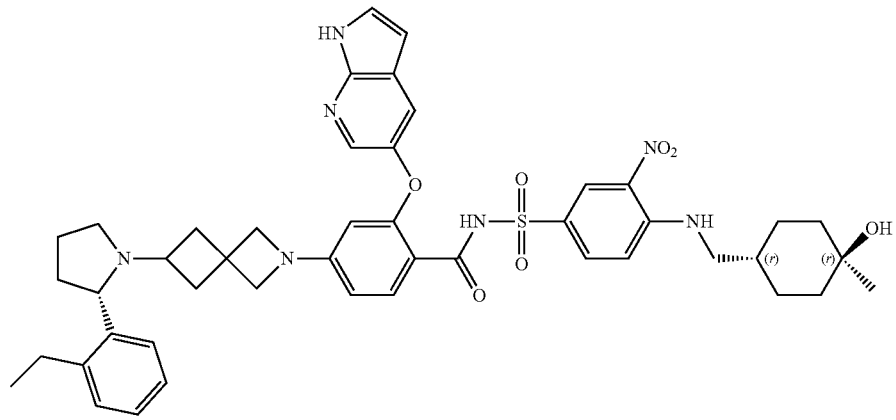

The desired compound was synthesized following the procedures similar to those in Example F106 by replacing (S)-2-(2-cyclopropylphenyl)pyrrolidine with (S)-2-(2-ethylphenyl)pyrrolidine. ¹H NMR (400 MHz, DMSO-d₆) δ ppm: 11.74 (s, 1H), 11.32 (s, 1H), 8.58 (s, 2H), 8.05 (s, 1H), 7.83 (d, J=8.6 Hz, 1H), 7.67-7.61 (m, 2H), 7.53 (s, 1H), 7.46 (d, J=8.6 Hz, 1H), 7.31 (s, 1H), 7.24 (s, 1H), 7.12 (d, J=9.2 Hz, 2H), 6.41 (s, 1H), 6.06 (d, J=8.6 Hz, 1H), 5.49 (s, 1H), 4.62 (s, 1H), 4.24 (s, 1H), 3.63-3.53 (m, 4H), 3.29 (s, 3H), 2.61 (s, 1H), 2.44-2.40 (m, 1H), 2.07 (s, 2H), 1.97-1.99 (m, 1H), 1.79 (s, 1H), 1.66 (s, 4H), 1.54-1.52 (m, 2H), 1.45 (s, 1H), 1.32-1.29 (m, 3H), 1.23 (s, 6H), 1.09 (s, 3H). MS (ESI, m/e) [M+1]⁺ 847.9.

Example F112: N-((4-(((((S)-1,4-dioxan-2-yl)methyl) amino)-3-nitrophenyl)sulfonyl)-2-((1H-pyrrolo[2,3-b]pyridin-5-yl)oxy)-4-(6-((S)-2-(2-ethylphenyl)pyrrolidin-1-yl)-2-azaspiro[3.3]heptan-2-yl) benzamide

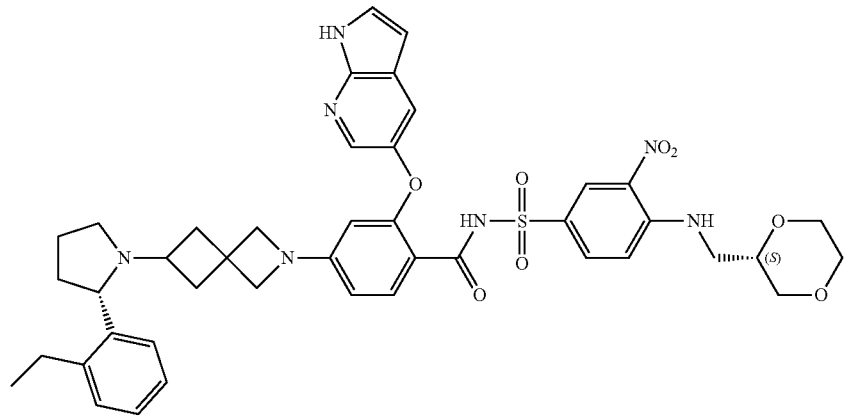

The desired compound was synthesized following the procedures similar to those in Example F106 by replacing (S)-2-(2-cyclopropylphenyl)pyrrolidine with (S)-2-(2-ethylphenyl)pyrrolidine and replacing 4-((((1r,4r)-4-hydroxy-4-methylcyclohexyl)methyl)amino)-3-nitrobenzenesulfonamide with (S)-4-(((1,4-dioxan-2-yl)methyl)amino)-3-nitrobenzenesulfonamide. ¹H NMR (400 MHz, DMSO-d₆) δ ppm: 11.73 (s, 1H), 11.34 (s, 1H), 10.19 (s, 1H), 8.59-8.58 (m, 2H), 8.05 (d, J=2.0 Hz, 1H), 7.85 (d, J=8.8 Hz, 1H), 7.77 (s, 1H), 7.60 (s, 1H), 7.53 (s, 1H), 7.46 (d, J=8.6 Hz, 1H), 7.29-7.14 (m, 4H), 6.41 (s, 1H), 6.07 (d, J=8.3 Hz, 1H), 5.49 (s, 1H), 4.61 (s, 1H), 3.80-3.77 (m, 3H), 3.67-3.60 (m, 4H), 3.56-3.53 (m, 1H), 3.52-3.47 (m, 2H), 3.43-3.38 (m, 1H), 3.35 (s, 1H), 3.29 (s, 1H), 3.08 (s, 1H), 2.74 (s, 1H), 2.64-2.57 (m, 1H), 2.41 (s, 1H), 2.08 (s, 1H), 1.99-1.97 (m, 1H), 1.77 (s, 1H), 1.71 (d, J=9.1 Hz, 1H), 1.23 (s, 3H), 1.13-1.10 (m, 3H), MS (ESI, m/e) [M+1]⁺ 821.9.

Example F113: 2-((1H-pyrrolo[2,3-b]pyridin-5-yl) oxy)-4-(6-((2-(2-cyclopropylphenyl)pyrrolidin-1-yl) methyl)-2-azaspiro[3.3]heptan-2-yl)-N-((3-nitro-4-(((tetrahydro-2H-pyran-4-yl)methyl)amino)phenyl) sulfonyl)benzamide

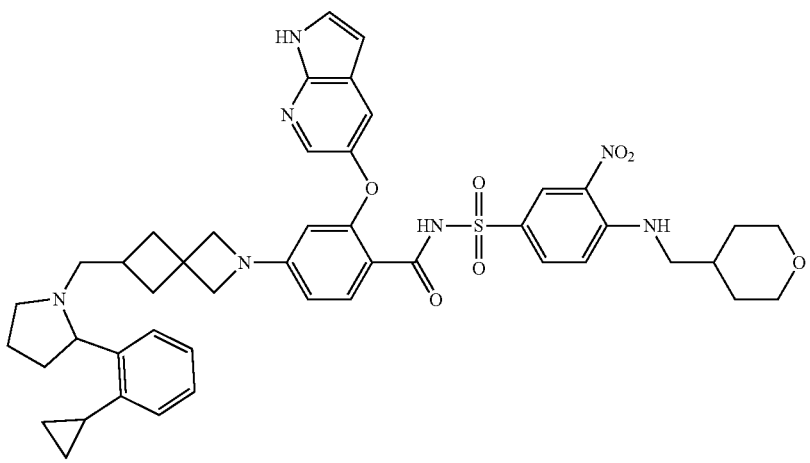 [SMILES: O=C(NS(=O)(=O)c1ccc(NCC2CCOCC2)c([N+](=O)[O-])c1)c1ccc(N2CC3(CC(CN4CCCC4c4ccccc4C4CC4)C3)C2)cc1Oc1cnc2[nH]ccc2c1]

The desired compound was synthesized following the procedures similar to those in Example F21 by replacing (S)-2-(2-(2-cyclopropylphenyl)pyrrolidin-1-yl)-7-azaspiro[3.5]nonane with 6-((2-(2-cyclopropylphenyl)pyrrolidin-1-yl)methyl)-2-azaspiro[3.3]heptane and replacing 4-((((1r,4r)-4-hydroxy-4-methylcyclohexyl)methyl)amino)-3-nitrobenzenesulfonamide with 3-nitro-4-(((tetrahydro-2H-pyran-4-yl)methyl)amino)benzenesulfonamide. ¹H NMR (DMSO-d₆) δ ppm: 11.78 (s, 1H), 11.41 (br, 1H), 8.64-8.60 (m, 2H), 8.09 (s, 1H), 7.86 (d, J=9.2 Hz, 1H), 7.66 (s, 2H), 7.56 (s, 1H), 7.48 (d, J=8.5 Hz, 1H), 7.18 (d, J=9.2 Hz, 3H), 6.99-6.96 (m, 1H), 6.45 (s, 1H), 6.07 (d, J=8.5 Hz, 1H), 5.46 (s, 1H), 3.87-3.83 (m, 2H), 3.71 (s, 3H), 3.51 (s, 1H), 3.36 (s, 1H), 3.30-3.24 (m, 3H), 3.19 (s, 1H), 3.08 (s, 1H), 2.78 (s, 1H), 2.33 (s, 2H), 2.17 (s, 3H), 2.06-2.04 (m, 2H), 1.90 (s, 2H), 1.71 (s, 1H), 1.64-1.60 (m, 2H), 1.36-1.17 (m, 4H), 0.92 (s, 2H), 0.63 (s, 2H). MS (ESI) m/e [M+1]⁺ 845.9.

Example F114: 2-((1H-pyrrolo[2,3-b]pyridin-5-yl)oxy)-4-(6-((1-(2-cyclopropylphenyl)pyrrolidin-2-yl)methyl)-2,6-diazaspiro[3.3]heptan-2-yl)-N-((3-nitro-4-(((tetrahydro-2H-pyran-4-yl)methyl)amino)phenyl)sulfonyl)benzamide

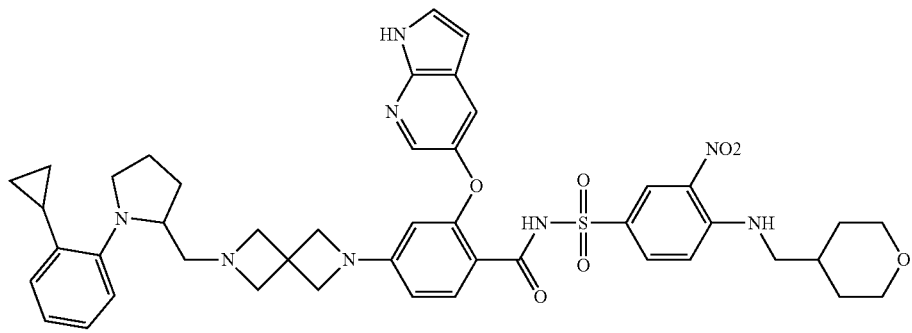 [SMILES: O=C(NS(=O)(=O)c1ccc(NCC2CCOCC2)c([N+](=O)[O-])c1)c1ccc(N2CC3(CN(CC4CCCN4c4ccccc4C4CC4)C3)C2)cc1Oc1cnc2[nH]ccc2c1]

The desired compound was synthesized following the procedures similar to those in Example F21 by replacing (S)-2-(2-(2-cyclopropylphenyl)pyrrolidin-1-yl)-7-azaspiro[3.5]nonane with 2-((1-(2-cyclopropylphenyl)pyrrolidin-2-yl)methyl)-2,6-diazaspiro[3.3]heptane and replacing 4-((((1r,4r)-4-hydroxy-4-methylcyclohexyl)methyl)amino)-3-nitrobenzenesulfonamide with 3-nitro-4-(((tetrahydro-2H-pyran-4-yl)methyl)amino)benzenesulfonamide. ¹H NMR (DMSO-d₆) δ ppm: 11.68 (s, 1H), 9.64 (s, 1H), 8.52 (s, 2H), 8.02 (s, 1H), 7.75 (s, 1H), 7.54-7.51 (m, 3H), 7.12-6.97 (m, 3H), 6.89 (s, 1H), 6.80 (s, 1H), 6.38 (s, 1H), 6.16 (d, J=8.2 Hz, 1H), 5.60 (s, 1H), 3.83 (s, 10H), 3.60-3.58 (m, 1H), 3.30-3.22 (m, 4H), 2.78-2.75 (m, 3H), 2.09 (s, 2H), 1.64-1.61 (m, 6H), 1.26-1.24 (m, 4H), 1.01 (s, 1H), 0.80-0.78 (m, 2H). MS (ESI) m/e [M+1]⁺ 846.9.

Example F115: (S)-2-((1H-pyrrolo[2,3-b]pyridin-5-yl)oxy)-4-(2-((2-(2-cyclopropylphenyl)pyrrolidin-1-yl)methyl)-7-azaspiro[3.5]nonan-7-yl)-N-((3-nitro-4-(((tetrahydro-2H-pyran-4-yl)methyl)amino)phenyl)sulfonyl)benzamide

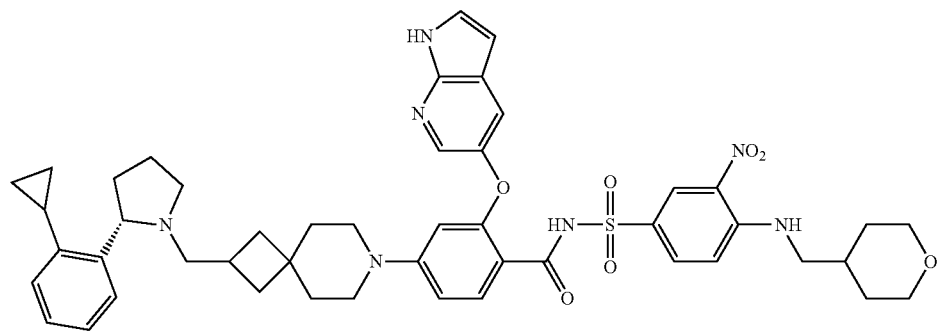 [SMILES: O=C(NS(=O)(=O)c1ccc(NCC2CCOCC2)c([N+](=O)[O-])c1)c1ccc(N2CCC3(CC2)CC(CN2CCC[C@H]2c2ccccc2C2CC2)C3)cc1Oc1cnc2[nH]ccc2c1]

The desired compound was synthesized following the procedures similar to those in Example F21 by replacing (S)-2-(2-(2-cyclopropylphenyl)pyrrolidin-1-yl)-7-azaspiro[3,5]nonane with (S)-2-((2-(2-cyclopropylphenyl)pyrrolidin-1-yl)methyl)-7-azaspiro[3.5]nonane and replacing 4-((((1r,4r)-4-hydroxy-4-methylcyclohexyl)methyl)amino)-3-nitrobenzenesulfonamide with 3-nitro-4-(((tetrahydro-2H-pyran-4-yl)methyl)amino)benzenesulfonamide. $^1$H NMR (DMSO-d$_6$) δ ppm: 11.70 (s, 1H), 11.44 (s, 1H), 8.56-8.52 (m, 2H), 8.05 (s, 1H), 7.79-7.73 (m, 2H), 7.51-7.49 (m, 3H), 7.31-7.04 (m, 2H), 7.12-7.10 (m, 1H), 6.72 Cd, J=8.8 Hz, 1H), 6.39 (s, 1H), 6.18 (s, 1H), 4.11-3.86 (m, 1H), 3.85 (d, J=8.4 Hz, 2H), 3.66-3.62 (m, 1H), 3.33-2.90 (m, 9H), 2.20-1.80 (m, 10H), 1.62 (d, J=12.4 Hz, 2H), 1.48-1.25 (m, 10H), 0.85-0.81 (m, 2H), 0.68-0.63 (m, 2H). MS (ESI, m/e) [M+1]$^+$ 873.9.

Example F116: (S)-2-((1H-pyrrolo[2,3-b]pyridin-5-yl)oxy)-4-(2-(2-(2-cyclopropylphenyl)pyrrolidin-1-yl)-7-azaspiro[3.5]nonan-7-yl)-N-((3-nitro-4-((2-(tetrahydro-2H-pyran-4-yl)ethyl)amino)phenyl)sulfonyl)benzamide

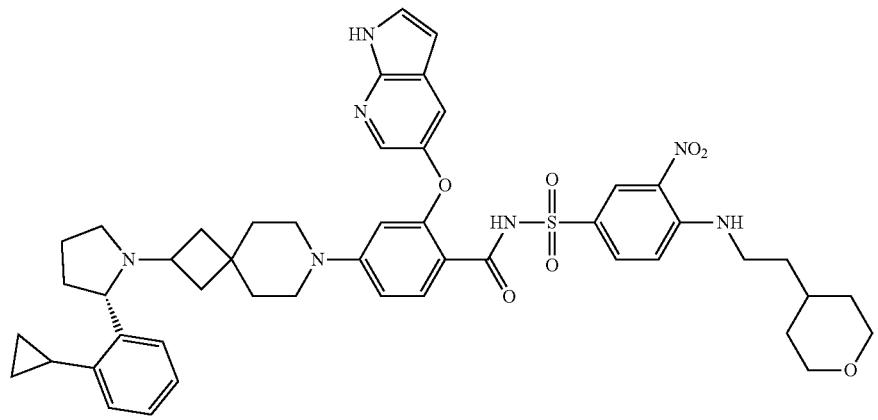 [SMILES: O=C(NS(=O)(=O)c1ccc(NCCC2CCOCC2)c([N+](=O)[O-])c1)c1ccc(N2CCC3(CC2)CC(N2CCC[C@H]2c2ccccc2C2CC2)C3)cc1Oc1cnc2[nH]ccc2c1]

The desired compound was synthesized following the procedures similar to those in Example F40 by replacing (S)-2-(2-ethylphenyl)pyrrolidine with (S)-2-(2-cyclopropylphenyl)pyrrolidine and replacing (S)-4-(((1,4-dioxan-2-yl)methyl)amino)-3-nitrobenzenesulfonamide with 3-nitro-4-((2-(tetrahydro-2H-pyran-4-yl)ethyl)amino)benzenesulfonamide. $^1$H NMR (DMSO-d$_6$) δ ppm: 11.70 (s, 1H), 11.47 (s, 1H), 8.60-8.50 (m, 2H), 8.10-8.00 (m, 1H), 7.98-7.85 (m, 1H), 7.84-7.75 (m, 1H), 7.57-7.42 (m, 3H), 7.30-7.20 (m, 2H), 7.10-7.00 (m, 2H), 6.75-6.65 (m, 1H), 6.38 (s, 1H), 6.18 (s, 1H), 5.76 (s, 1H), 4.95 (s, 1H), 3.83 (d, J=7.9 Hz, 2H), 3.75-3.60 (m, 1H), 3.50-3.40 (m, 2H), 3.25-3.15 (m, 2H), 3.10-2.80 (m, 2H), 2.45 (s, 1H), 2.20-1.85 (m, 4H), 1.70-1.51 (m, 5H), 1.51-1.30 (m, 6H), 1.25-1.10 (m, 4H), 1.03-0.89 (m, 3H), 0.89-0.77 (m, 2H), 0.70-0.55 (m, 2H). MS (ESI, m/e) [M+1]$^+$ 873.9.

Example F117: (S)-2-((1H-pyrrolo[2,3-b]pyridin-5-yl)oxy)-4-(2-(2-(2-cyclopropylphenyl)pyrrolidin-1-yl)-7-azaspiro[3.5]nonan-7-yl)-N-((4-((2-morpholinoethyl)amino)-3-nitrophenyl)sulfonyl)benzamide

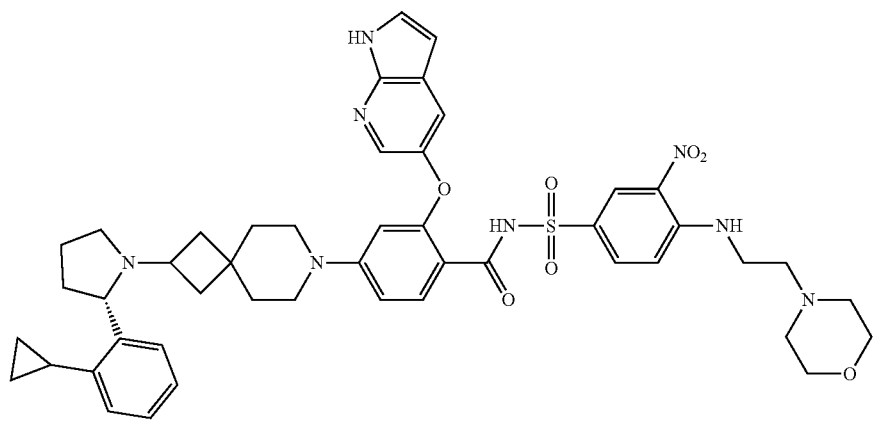

The desired compound was synthesized following the procedures similar to those in Example F40 by replacing (S)-2-(2-ethylphenyl)pyrrolidine with (S)-2-(2-cyclopropylphenyl)pyrrolidine and replacing (S)-4-(((1,4-dioxan-2-yl)methyl)amino)-3-nitrobenzenesulfonamide with 4-((2-morpholinoethyl)amino)-3-nitrobenzenesulfonamide. $^1$H NMR (DMSO-d$_6$) δ ppm: 11.73 (s, 1H), 11.62 (s, 1H), 8.85-8.75 (m, 1H), 8.60-8.50 (m, 1H), 8.25-8.05 (m, 1H), 8.01 (d, J=2.4 Hz, 1H), 7.78 (d, J=8.0 Hz, 1H), 7.53-7.40 (m, 3H), 7.30-7.20 (m, 2H), 7.10-7.00 (m, 2H), 6.67 (d, J=7.7 Hz, 1H), 6.36 (s, 1H), 6.19 (s, 1H), 5.05-4.75 (m, 1H), 4.25-4.10 (m, 1H), 3.85-3.75 (m, 1H), 3.70-3.60 (m, 4H), 3.55-3.45 (m, 2H), 3.20-3.15 (m, 2H), 3.14-2.88 (m, 4H), 2.80-2.70 (m, 2H), 2.65-2.50 (m, 4H), 2.45-2.20 (m, 2H), 2.15-1.90 (m, 4H), 1.61-1.29 (m, 4H), 1.25-1.15 (m, 1H), 1.02-0.87 (m, 2H), 0.65-0.55 (m, 2H). MS (ESI, m/e) [M+1]$^+$ 874.9.

Example F118: (S)-2-((1H-pyrrolo[2,3-b]pyridin-5-yl)oxy)-4-(2-(2-(2-cyclopropylphenyl)pyrrolidin-1-yl)-7-azaspiro[3.5]nonan-7-yl)-N-((3-nitro-4-((2-(3-oxomorpholino)ethyl)amino)phenyl)sulfonyl)benzamide

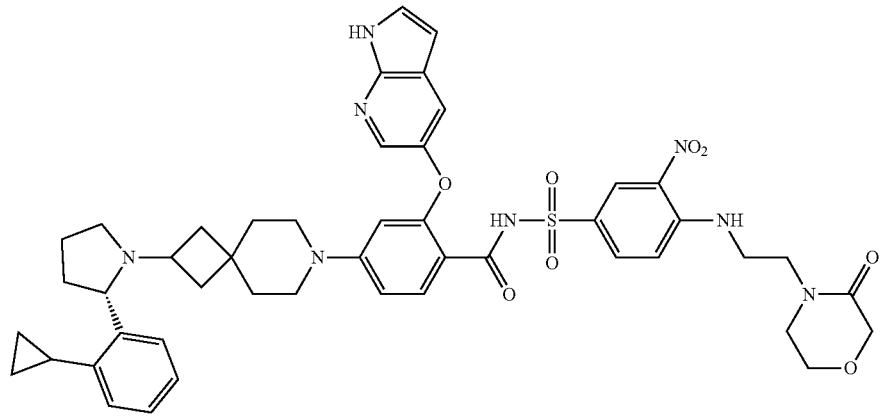 [SMILES: O=C(NS(=O)(=O)c1ccc(NCCN2CCOCC2=O)c([N+](=O)[O-])c1)c1ccc(N2CCC3(CC2)CC(N2CCC[C@H]2c2ccccc2C2CC2)C3)cc1Oc1cnc2[nH]ccc2c1]

The desired compound was synthesized following the procedures similar to those in Example F43 by replacing (S)-2-(2-isopropylphenyl)pyrrolidine with (S)-2-(2-cyclopropylphenyl)pyrrolidine and replacing 4-(((((1r,4r)-4-hydroxy-4-methylcyclohexyl)methyl)amino)-3-nitrobenzenesulfonamide with 3-nitro-4-((2-(3-oxomorpholino)ethyl)amino)benzenesulfonamide. $^1$H NMR (DMSO-d$_6$) δ ppm: 11.64 (s, 1H), 11.40 (s, 1H), 8.61 (s, 1H), 8.51 (s, 1H), 8.00 (s, 1H), 7.77 (s, 1H), 7.48 (s, 4H), 7.10-6.99 (m, 4H), 6.66 (d, J=8.4 Hz, 1H), 6.36 (s, 1H), 6.17 (s, 1H), 3.99 (s, 2H), 3.77 (s, 2H), 3.58 (s, 4H), 3.41 (s, 2H), 3.02 (s, 2H), 2.94 (s, 2H), 2.11-1.94 (m, 3H), 1.78 (s, 3H), 1.55 (s, 1H), 1.42-1.37 (m, 6H), 1.24 (s, 2H), 0.91 (s, 3H), 0.63-0.59 (m, 2H). MS (ESI) m/e [M+1]$^+$ 888.8.

Example F119: 2-((1H-pyrrolo[2,3-b]pyridin-5-yl)oxy)-N-((4-(((3-oxabicyclo[3.1.0]hexan-6-yl)methyl)amino)-3-nitrophenyl)sulfonyl)-4-(2-((S)-2-(2-cyclopropylphenyl)pyrrolidin-1-yl)-7-azaspiro[3.5]nonan-7-yl)benzamide

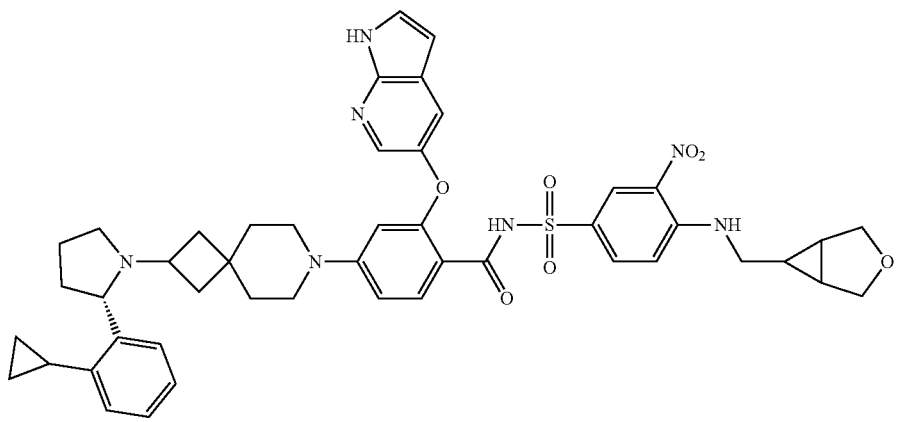 [SMILES: O=C(NS(=O)(=O)c1ccc(NCC2C3COCC23)c([N+](=O)[O-])c1)c1ccc(N2CCC3(CC2)CC(N2CCC[C@H]2c2ccccc2C2CC2)C3)cc1Oc1cnc2[nH]ccc2c1]

The desired compound was synthesized following the procedures similar to those in Example F43 by replacing (S)-2-(2-isopropylphenyl)pyrrolidine with (S)-2-(2-cyclopropylphenyl)pyrrolidine and replacing 4-((((1r,4r)-4-hydroxy-4-methylcyclohexyl)methyl)amino)-3-nitrobenzenesulfonamide with 4-(((3-oxabicyclo[3.1.0]hexan-6-yl)methyl)amino)-3-nitrobenzenesulfonamide. $^1$H NMR (DMSO-d$_6$) δ ppm: 11.68 (s, 1H), 11.43 (s, FH), 10.39 (s, 1H), 8.61 (s, 1H), 8.55 (s, 1H), 8.03 (s, 1H), 7.79 (d, J=8.5 Hz, 2H), 7.49-7.46 (m, 3H), 7.26 (s, 2H), 7.06 (s, 2H), 6.68 (d, J=8.5 Hz, 1H), 6.37 (s, 1H), 6.18 (s, 1H), 4.96 (s, 1H), 3.88-3.84 (m, 1H), 3.73-3.70 (m, 3H), 3.57-3.53 (m, 2H), 3.03-2.98 (m, 5H), 2.05-2.00 (m, 6H), 1.71 (s, 2H), 1.39-1.35 (m, 8H), 0.97-0.93 (m, 3H), 0.64 (s, 2H). MS (ESI) m/e [M+1]$^+$ 857.9.

Example F120: 2-((1H-pyrrolo[2,3-b]pyridin-5-yl)oxy)-4-(2-((S)-2-(2-cyclopropylphenyl)pyrrolidin-1-yl)-7-azaspiro[3.5]nonan-7-yl)-N-((4-(((2,6-dimethyltetrahydro-2H-pyran-4-yl)methyl)amino)-3-nitrophenyl)sulfonyl)benzamide The desired compound was synthesized following the procedures similar to those in Example F43 by replacing (S)-2-(2-isopropylphenyl)pyrrolidine with (S)-2-(2-cyclopropylphenyl)pyrrolidine and replacing 4-((((1r,4r)-4-hydroxy-4-methylcyclohexyl)methyl)amino)-3-nitrobenzenesulfonamide with 4-(((2,6-dimethyltetrahydro-2H-pyran-4-yl)methyl)amino)-3-nitrobenzenesulfonamide. $^1$H NMR (DMSO-d$_6$) δ ppm: 11.69 (s, 1H), 11.44 (s, 1H), 8.62 (s, 1H), 8.55 (s, 1H), 8.03 (s, 1H), 7.79 (s, 2H), 7.50-7.48 (m, 3H), 7.27 (s, 2H), 7.07 (s, 2H), 6.68 (d, J=8.3 Hz, 1H), 6.38 (s, 1H), 6.17 (s, 1H), 4.97 (s, 1H), 3.71-3.68 (m, 3H), 3.27 (s, 2H), 2.99-2.98 (m, 5H), 2.04-2.01 (m, 7H), 1.67-1.65 (m, 2H), 1.57-1.21 (m, 9H), 1.08-1.04 (m, 6H), 0.95 (s, 2H), 0.84-0.82 (m, 2H), 0.64 (s, 2H). MS (ESI) m/e [M+1]$^+$ 887.9.

Example F121: (S)-2-((1H-pyrrolo[2,3-b]pyridin-5-yl)oxy)-4-(2-(2-(2-cyclopropylphenyl)pyrrolidin-1-yl)-7-azaspiro[3.5]nonan-7-yl)-N-((3-nitro-4-(((2,2,6,6-tetramethyltetrahydro-2H-pyran-4-yl)methyl)amino)phenyl)sulfonyl)benzamide The desired compound was synthesized following the procedures similar to those in Example F43 by replacing (S)-2-(2-isopropylphenyl)pyrrolidine with (S)-2-(2-cyclopropylphenyl)pyrrolidine and replacing 4-((((1r,4r)-4-hydroxy-4-methylcyclohexyl)methyl)amino)-3-nitrobenzenesulfonamide with 3-nitro-4-(((2,2,6,6-tetramethyltetrahydro-2H-pyran-4-yl)methyl)amino)benzenesulfonamide. $^1$H NMR (DMSO-d$_6$) δ ppm: 11.69 (s, 1H), 11.45 (s, 1H), 8.58-8.56 (m, 2H), 8.03 (s, 1H), 7.81-7.78 (m, 2H), 7.49-7.46 (m, 3H), 7.27 (s, 2H), 7.16-6.98 (m, 2H), 6.68 (d, J=8.3 Hz, 1H), 6.38 (s, 1H), 6.17 (s, 1H), 4.96 (s, 1H), 3.77-3.75 (m, 2H), 3.28 (s, 2H), 3.00-2.98 (m, 5H), 2.33-1.94 (m, 7H), 1.62-1.60 (m, 2H), 1.42-1.40 (m, 6H), 1.19-1.15 (m, 14H), 1.04-0.91 (m, 4H), 0.64 (s, 2H), MS (ESI) m/e [M+1]$^+$ 915.9.

Example F122: 2-((1H-pyrrolo[2,3-b]pyridin-5-yl)oxy)-4-(2-((S)-2-(2-cyclopropylphenyl)pyrrolidin-1-yl)-6-azaspiro[3.4]octan-6-yl)-N-((4-((((1r,4r)-4-hydroxy-4-methylcyclohexyl)methyl)amino)-3-nitrophenyl)sulfonyl)benzamide

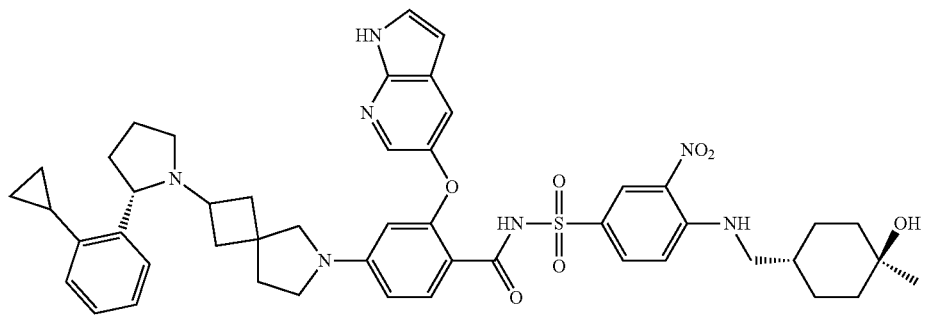 [SMILES: C[C@]1(O)CC[C@H](CNc2ccc(S(=O)(=O)NC(=O)c3ccc(N4CCC5(CC(N6CCC[C@H]6c6ccccc6C6CC6)C5)C4)cc3Oc3cnc4[nH]ccc4c3)cc2[N+](=O)[O-])CC1]

The desired compound was synthesized following the procedures similar to those in Example F21 by replacing (S)-2-(2-(2-cyclopropylphenyl)pyrrolidin-1-yl)-7-azaspiro[3.5]nonane with (S)-2-(2-(2-cyclopropylphenyl)pyrrolidin-1-yl)-6-azaspiro[3.4]octane. $^1$H NMR (DMSO-d$_6$) δ ppm: 11.68 (s, 1H), 11.18 (s, 1H), 8.54 (s, 2H), 8.04 (s, 1H), 7.78 (s, 1H), 7.49 (s, 4H), 7.07 (s, 3H), 6.90 (s, 1H), 6.38 (s, 1H), 6.24 (s, 1H), 5.73 (s, 1H), 5.32 (s, 1H), 4.23 (s, 1H), 3.27-3.23 (m, 1H), 3.11-2.97 (m, 6H), 2.20 (s, 1H), 2.02-2.00 (m, 3H), 1.78-1.54 (m, 7H), 1.32-1.30 (m, 3H), 1.11-1.09 (m, 5H), 0.86-0.84 (m, 3H), 0.63 (s, 1H), 0.49 (s, 1H). MS (ESI) m/e [M+1]$^+$ 873.9.

Example F123: 2-((1H-pyrrolo[2,3-b]pyridin-5-yl)oxy)-4-(6-((S)-2-(2-cyclopropylphenyl)pyrrolidin-1-yl)-2-azaspiro[3.4]octan-2-yl)-N-((4-((((1r,4r)-4-hydroxy-4-methylcyclohexyl)methyl)amino)-3-nitrophenyl)sulfonyl)benzamide

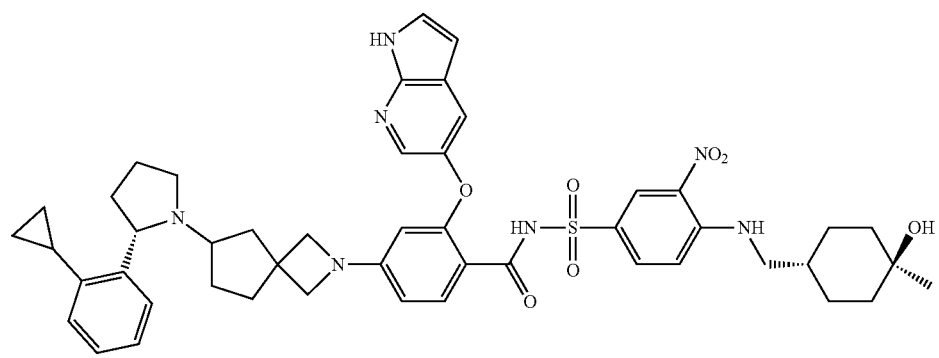 [SMILES: C[C@]1(O)CC[C@H](CNc2ccc(S(=O)(=O)NC(=O)c3ccc(N4CC5(CCC(N6CCC[C@H]6c6ccccc6C6CC6)C5)C4)cc3Oc3cnc4[nH]ccc4c3)cc2[N+](=O)[O-])CC1]

The desired compound was synthesized following the procedures similar to those in Example F21 by replacing (S)-2-(2-(2-cyclopropylphenyl)pyrrolidin-1-yl)-7-azaspiro[3.5]nonane with 6-((S)-2-(2-cyclopropylphenyl)pyrrolidin-1-yl)-2-azaspiro[3.4]octane. $^1$H NMR (DMSO-d$_6$) δ ppm: 11.76 (s, 1H), 11.32 (s, 1H), 9.46 (s, 1H), 8.61 (s, 2H), 8.09 (s, 1H), 7.87 (d, J=8.8 Hz, 1H), 7.68 (s, 1H), 7.56-7.48 (m, 3H), 7.30 (s, 2H), 7.21-7.05 (m, 2H), 6.44 (s, 1H), 6.15-6.07 (m, 1H), 5.48-5.43 (m, 1H), 5.03 (s, 1H), 3.63 (s, 2H), 3.58-3.54 (m, 1H), 3.47 (s, 2H), 3.31 (s, 3H), 2.54 (s, 1H), 1.92-1.88 (m, 6H), 1.67 (s, 3H), 1.56-1.53 (m, 2H), 1.38-1.22 (m, 8H), 1.15-1.10 (m, 4H), 0.96-0.92 (m, 3H), 0.64 (s, 2H). MS (ESI) m/e [M+1]$^+$ 873.9.

Example F124a and Example F124b: 2-((1H-pyrrolo[2,3-b]pyridin-5-yl)oxy)-4-((7R or 7S)-7-((S)-2-(2-cyclopropylphenyl)pyrrolidin-1-yl)-2-azaspiro[4.4]nonan-2-yl)-N-((4-((((1r,4r)-4-hydroxy-4-methylcyclohexyl)methyl)amino)-3-nitrophenyl)sulfonyl)benzamide; 2-((1H-pyrrolo[2,3-b]pyridin-5-yl)oxy)-4-((7S or 7R)-7-((S)-2-(2-cyclopropylphenyl)pyrrolidin-1-yl)-2-azaspiro[4.4]nonan-2-yl)-N-((4-((((1r,4r)-4-hydroxy-4-methylcyclohexyl)methyl)amino)-3-nitrophenyl)sulfonyl)benzamide

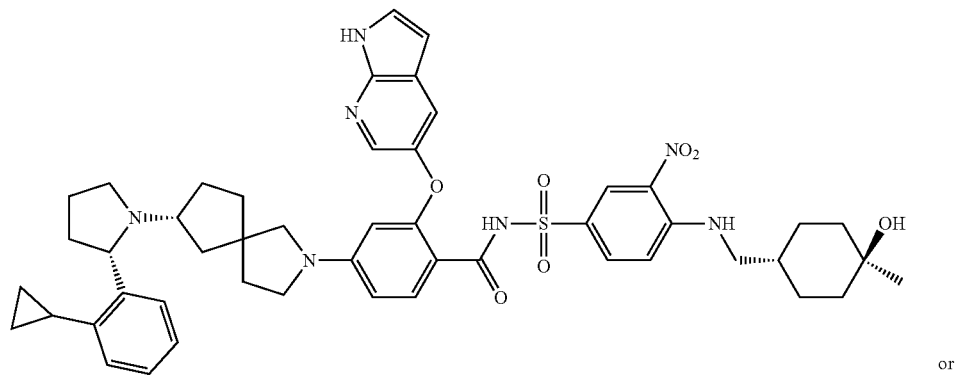

or

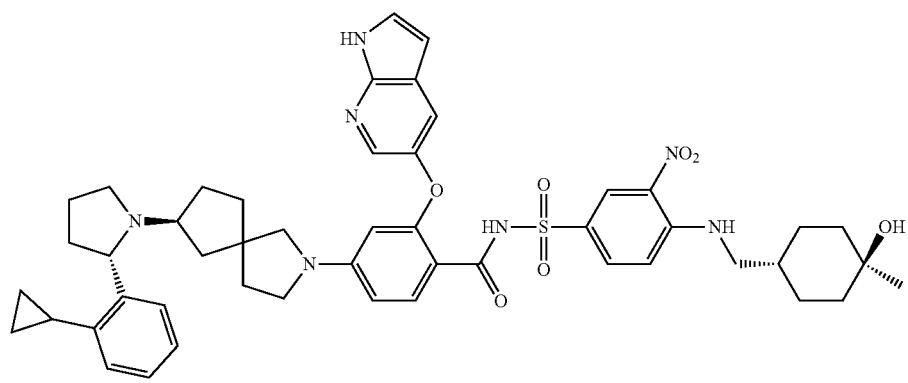

The desired compounds were synthesized following the procedures similar to those in Example F21 by replacing (S)-2-(2-(2-cyclopropylphenyl)pyrrolidin-1-yl)-7-azaspiro[3.5]nonane with 7-((S)-2-(2-cyclopropylphenyl)pyrrolidin-1-yl)-2-azaspiro[4.4]nonane. F124a was obtained as faster peak by separation and purification of crude product with prep-HPLC. $^1$H NMR (DMSO-d$_6$) δ ppm: 11.63 (s, 1H), 11.20 (s, OH), 8.46 (s, 2H), 8.00 (s, 1H), 7.64-7.37 (m, 4H), 7.28-6.94 (m, 4H), 6.89-6.84 (m, 1H), 6.66 (s, 1H), 6.34 (s, 1H), 6.22 (s, 1H), 5.73 (s, 1H), 5.32 (s, 1H), 4.24 (s, 1H), 4.08 (s, 1H), 3.25 (s, 2H), 3.16 (s, 1H), 3.04 (s, 1H), 2.95-2.90 (m, 2H), 2.86-2.81 (m, 1H), 2.22 (s, 1H), 2.02-1.95 (m, 3H), 1.73-1.65 (m, 5H), 1.56-1.52 (m, 2H), 1.45 (s, 2H), 1.34-1.28 (m, 3H), 1.24 (s, 5H), 1.13-1.05 (m, 4H), 0.85 (s, 3H), 0.63 (s, 1H), 0.44 (s, 1H). MS (ESI) m/e [M+1]$^+$ 887.8; F124b was obtained as slower peak by separation and purification of crude product with prep-HPLC. MS (ESI) m/e [M+1]$^+$ 887.8

Example F125: 2-((1H-pyrrolo[2,3-b]pyridin-5-yl)oxy)-4-(2-((S)-2-(2-cyclopropylphenyl)pyrrolidin-1-yl)spiro[3.5]non-6-en-7-yl)-N-((4-((((1r,4r)-4-hydroxy-4-methylcyclohexyl)methyl)amino)-3-nitrophenyl)sulfonyl)benzamide

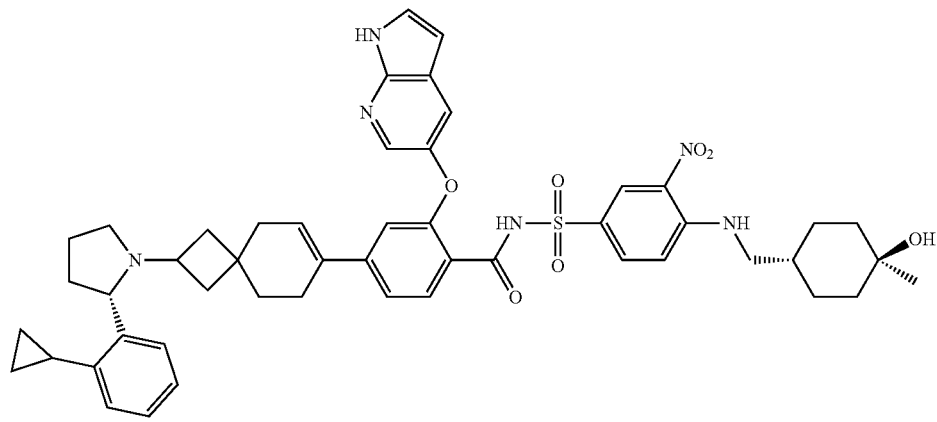 [SMILES: C[C@]1(O)CC[C@H](CNc2ccc(S(=O)(=O)NC(=O)c3ccc(C4=CCC5(CC4)CC(N4CCC[C@H]4c4ccccc4C4CC4)C5)cc3Oc3cnc4[nH]ccc4c3)cc2[N+](=O)[O-])CC1]

Step 1: methyl tert-butyl (S)-2-((1H-pyrrolo[2,3-b]pyridin-5-yl)oxy)-4-(2-(2-(2-cyclopropylphenyl)pyrrolidin-1-yl)spiro[3,5]non-6-en-7-yl)benzoate To a mixture of (S)-2-(2-cyclopropylphenyl)-1-(7-(4,4,5,5-tetramethyl-1,3,2-dioxaborolan-2-yl)spiro[3,5]non-6-en-2-yl)pyrrolidine (200 mg, 0,461 mmol) and tert-butyl 2-((1H-pyrrolo[2,3-b]pyridin-5-yl)oxy)-4-bromobenzoate (160 mg, 0.461 mmol) in 1,4-dioxane (20 ml) and H$_2$O (2 ml) was added Pd(dppf)Cl$_2$ (67.4 mg, 0.0922 mmol) and Cs$_2$CO$_3$ (450 mg, 1.383 mmol). The mixture was stirred at 100° C. for overnight under nitrogen protection. The mixture was cooled to room temperature and diluted with DCM (100 ml), then washed with brine, dried over Na$_2$SO$_4$, concentrated and purified by chromatography column on silica gel (eluent: PE:EA=2/1 to 1/1) to give the product 60 mg. MS (ESI, m/e) [M+1]$^+$ 616.0.

Step 2: (S)-2-((1H-pyrrolo[2,3-b]pyridin-5-yl)oxy)-4-(2-(2-(2-cyclopropylphenyl)pyrrolidin-1-yl)spiro[3.5]non-6-en-7-yl)benzoic acid To a solution of tert-butyl (S)-2-((1H-pyrrolo[2,3-b]pyridin-5-yl)oxy)-4-(2-(2-(2-cyclopropylphenyl)pyrrolidin-1-yl)spiro[3.5]non-6-en-7-yl)benzoate (60 mg, 0.0974 mmol) in DCM (10 ml) was added TFA (5 ml). The mixture was stirred at room temperature for overnight. The mixture was concentrated in vacuum to give the crude product, which was used directly for next step. MS (ESI, m/e) [M+1]$^+$ 559.9.

Step 3: 2-((1H-pyrrolo[2,3-b]pyridin-5-yl)oxy)-4-(2-((S)-2-(2-cyclopropylphenyl)pyrrolidin-1-yl)spiro[3.5]non-6-en-7-yl)-N-((4-((((1r,4r)-4-hydroxy-4-methylcyclohexyl)methyl)amino)-3-nitrophenyl)sulfonyl)benzamide To a solution of (S)-2-((1H-pyrrolo[2,3-b]pyridin-5-yl)oxy)-4-(2-(2-(2-cyclopropylphenyl)pyrrolidin-1-yl)spiro[3.5]non-6-en-7-yl)benzoic acid (54.5 mg, 0.0974 mmol) in DCM (20 ml) was added HATH (55.6 mg, 0,146 mmol) and triethylamine (49 mg, 0.487 mmol). The mixture was stirred at room temperature for 1 hour. Then to the mixture was added 4-((((1r,4r)-4-hydroxy-4-methylcyclohexyl)methyl)amino)-3-nitrobenzenesulfonamide (66.9 mg, 0,195 mmol) and DMAP (11.9 mg, 0.0974 mmol). The mixture was stirred at room temperature for overnight. The mixture was washed with saturated aq. NaHCO$_3$, brine, dried over Na$_2$SO$_4$, concentrated and purified by prep-TLC (eluent: DCM/MeOH=20/1) to give the desired compound (18.5 mg). $^1$H NMR (400 MHz, DMSO-d$_6$) δ ppm: 12.19 (s, 1 IB. 11.60 (s, 1H), 8.64-8.20 (m, 2H), 7.95 (s, 1H), 7.79-7.17 (m, 7H), 7.17-6.78 (m, 4H), 6.73 (s, 1H), 6.34 (s, 1H), 6.03-5.83 (m, 1H), 4.23 (s, 1H), 4.03-3.77 (m, 1H), 3.77-3.49 (m, 1H), 3.28-3.06 (m, 3H), 2.28-1.85 (m, 9H), 1.75-1.42 (m, 10H), 1.39-1.29 (m, 3H), 1.16-1.04 (m, 5H), 1.01-0.85 (m, 2H), 0.71-0.54 (m, 2H). MS (ESI, m/e) [M+1]$^+$ 884.9.

Example F126: (S)-2-((6-amino-5-chloropyridin-3-yl)oxy)-4-(2-(2-(2-cyclopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide

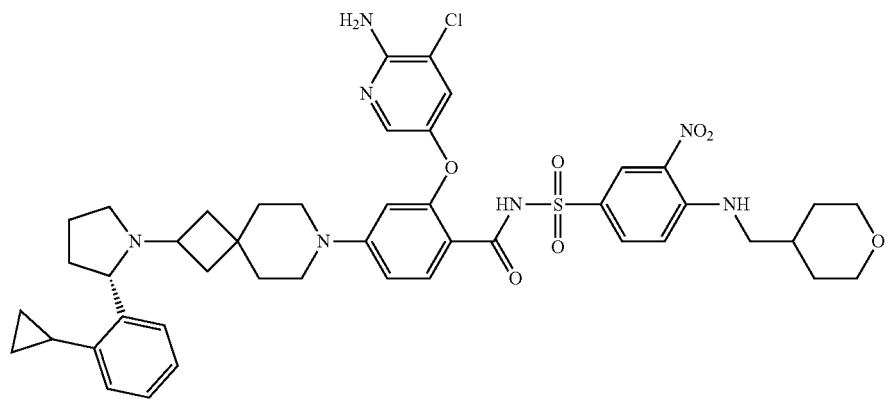 [SMILES: Nc1ncc(Oc2cc(N3CCC4(CC3)CC(N3CCC[C@H]3c3ccccc3C3CC3)C4)ccc2C(=O)NS(=O)(=O)c2ccc(NCC3CCOCC3)c([N+](=O)[O-])c2)cc1Cl]

The desired compound was synthesized following the procedures similar to those in Example F21 by replacing (methyl 2-((1H-pyrrolo[2,3-b]pyridin-5-yl)oxy)-4-fluorobenzoate with methyl 2-((6-amino-5-chloropyridin-3-yl)oxy)-4-fluorobenzoate and replacing 4-((((1r,4r)-4-hydroxy-4-methylcyclohexyl)methyl)amino)-3-nitrobenzenesulfonamide with 4-(((2,2-dimethyltetrahydro-2H-pyran-4-yl)methyl)amino)-3-nitrobenzenesulfonamide, $^1$H NMR (DMSO-d$_6$) δ ppm: 11.36 (s, 1H), 9.50 (s, 1H), 8.82-8.32 (m, 2H), 7.96-7.63 (m, 2H), 7.63-7.40 (m, 2H), 7.40-6.80 (m, 5H), 6.77-6.54 (m, 1H), 6.33-5.86 (m, 3H), 4.13-3.74 (m, 3H), 3.30-3.21 (m, 3H), 3.21-2.85 (m, 6H), 2.21-1.68 (m, 7H), 1.68-1.53 (m, 3H), 1.53-1.33 (m, 5H), 1.33-1.17 (m, 4H), 0.95-0.80 (m, 2H), 0.69-0.51 (m, 2H). MS (ESI, m/e) [M+1]$^+$ 869.8.

Example F127: 2-((1H-pyrrolo[2,3-b]pyridin-5-yl)oxy)-4-(2-((S)-2-(2-cyclopropylphenyl)pyrrolidin-1-yl)-7-azaspiro[3.5]nonan-7-yl)-N-((4-(((2,2-dimethyltetrahydro-2H-pyran-4-yl)methyl)amino)-3-nitrophenyl)sulfonyl)benzamide

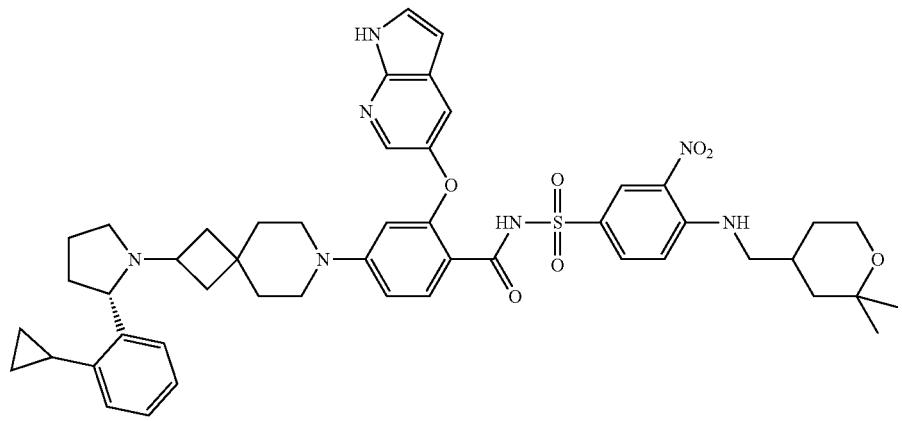 [SMILES: CC1(C)CC(CNc2ccc(S(=O)(=O)NC(=O)c3ccc(N4CCC5(CC4)CC(N4CCC[C@H]4c4ccccc4C4CC4)C5)cc3Oc3cnc4[nH]ccc4c3)cc2[N+](=O)[O-])CCO1]

The desired compound was synthesized following the procedures similar to those in Example F43 by replacing (S)-2-(2-isopropylphenyl)pyrrolidine with (S)-2-(2-cyclopropylphenyl)pyrrolidine and replacing 4-((((1r,4r)-4-hydroxy-4-methylcyclohexyl)methyl)amino)-3-nitrobenzenesulfonamide with 4-(((2,2-dimethyltetrahydro-2H-pyran-4-yl)methyl)amino)-3-nitrobenzenesulfonamide. $^1$H NMR (DMSO-d$_6$) δ ppm: 11.62 (s, 1H), 8.48 (s, 2H), 7.98 (d, J=2.5 Hz, 1H), 7.71 (d, J=9.0 Hz, 1H), 7.55-7.53 (m, 2H), 7.46 (t, J=2.5 Hz, 1H), 7.41 (s, 1H), 7.13 (s, 2H), 7.03-6.86 (m, 3H), 6.65 (d, J=9.0 Hz, 1H), 6.34 (s, 1H), 6.19 (s, 1H), 3.64-3.51 (m, 3H), 3.23-3.21 (m, 3H), 3.13 (s, 1H), 3.01 (s, 2H), 2.93 (s, 2H), 2.26 (s, 1H), 2.09-2.01 (m, 3H), 1.84 (s, 4H), 1.59-1.56 (m, 3H), 1.39-1.38 (m, 6H), 1.14-1.12 (m, 7H), 0.93-0.86 (m, 2H), 0.67-0.60 (m, 1H), 0.55 (s, 1H). MS (ESI) m/e [M+1]$^+$ 887.9.

Example F128: (S)-2-((1H-pyrrolo[2,3-b]pyridin-5-yl)oxy)-4-(2-(2-(2-cyclopropylphenyl)pyrrolidin-1-yl)-7-azaspiro[3.5]nonan-7-yl)-N-((4-(3-methyl-3-((tetrahydro-2H-pyran-4-yl)methyl)ureido)-3-nitrophenyl)sulfonyl)benzamide The desired compound was synthesized following the procedures similar to those in Example F43 by replacing (S)-2-(2-isopropylphenyl)pyrrolidine with (S)-2-(2-cyclopropylphenyl)pyrrolidine and replacing 4-((((1r,4r)-4-hydroxy-4-methylcyclohexyl)methyl)amino)-3-nitrobenzenesulfonamide with 4-(3-methyl-3-((tetrahydro-2H-pyran-4-yl)methyl)ureido)-3-nitrobenzenesulfonamide. $^1$H NMR (DMSO-d$_6$) δ ppm: 11.54 (s, 1H), 9.53 (s, 1H), 8.33 (d, J=1.9 Hz, 1H), 8.18 (d, J=7.2 Hz, 1H), 7.96-7.93 (m, 2H), 7.88-7.86 (m, 1H), 7.55-7.53 (m, 2H), 7.42-7.40 (m, 1H), 7.33-7.31 (m, 1H), 7.16-7.14 (m, 2H), 6.95-6.94 (m, 1H), 6.88 (d, J=7.2 Hz, 1H), 6.62-6.60 (m, 1H), 6.32-6.29 (m, 1H), 6.19 (d, J=2.0 Hz, 1H), 3.85-3.84 (m, 2H), 3.26-3.24 (m, 5H), 3.12 (s, 4H), 3.02 (s, 3H), 2.97 (s, 2H), 2.89 (s, 2H), 2.28 (s, 1H), 2.05 (s, 1H), 1.85 (s, 3H), 1.55-1.53 (m, 3H), 1.42-1.40 (m, 5H), 1.22-1.20 (m, 4H), 0.89-0.88 (m, 2H), 0.66-0.60 (m, 1H), 0.55 (s, 1H). MS (ESI) m/e [M+1]$^+$ 916.9.

Example F129: 2-((1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(2-((S)-2-phenylpyrrolidin-1-yl)-7-azaspiro[3.5]nonan-7-yl)benzamide

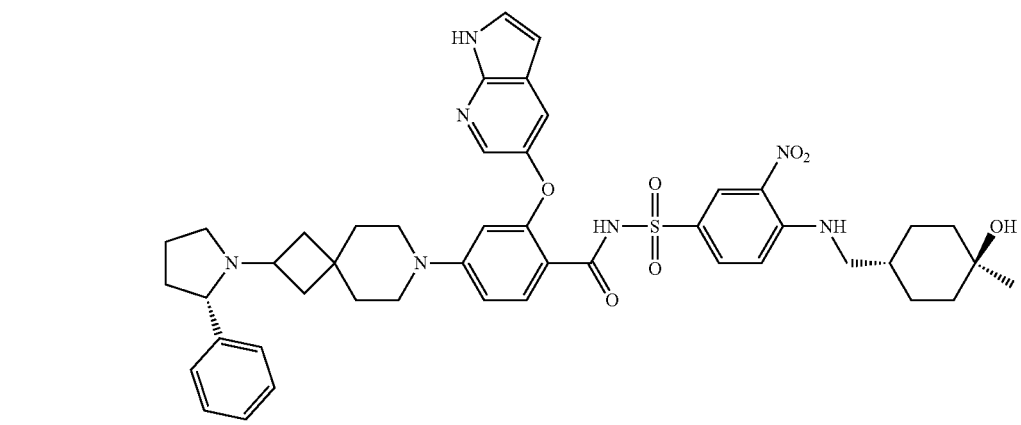 [SMILES: C[C@]1(O)CC[C@H](CNc2ccc(S(=O)(=O)NC(=O)c3ccc(N4CCC5(CC4)CC(N4CCC[C@H]4c4ccccc4)C5)cc3Oc3cnc4[nH]ccc4c3)cc2[N+](=O)[O-])CC1]

The desired compound was synthesized following the procedures similar to those in Example F43 by replacing (S)-2-(2-isopropylphenyl)pyrrolidine with (S)-2-phenylpyrrolidine. $^1$H NMR (400 MHz, DMSO-d$_6$) δ ppm: 11.69 (s, 1H), 10.58 (br, 1H), 8.61-8.55 (m, 2H), 8.04 (d, J=2.8 Hz, 1H), 7.79 (d, J=8.8 Hz, 1H), 7.65-7.55 (m, 2H), 7.52-7.47 (m, 3H), 7.45-7.38 (m, 3H), 7.08 (d, J=9.2 Hz, 1H), 6.69 (d, J=9.2 Hz, 1H), 6.40-6.32 (m, 1H), 6.17 (s, 1H), 4.47-4.30 (m, 1H), 4.25 (s, 1H), 3.84-3.66 (m, 2H), 3.25-2.95 (m, 6H), 2.44-2.36 (m, 1H), 2.20-1.89 (m, 5H), 1.75-1.10 (m, 19H). MS (ESI, m/e) [M+1]$^+$ 847.8.

Example F130: 2-((1H-pyrrolo[2,3-b]pyridin-5-yl)oxy)-4-(2-(2-(2-cyclopropylphenyl)-4-ethylpiperazin-1-yl)-7-azaspiro[3,5]nonan-7-yl)-N-((3-nitro-4-((((tetrahydro-2H-pyran-4-yl)methyl)amino)phenyl)sulfonyl)benzamide

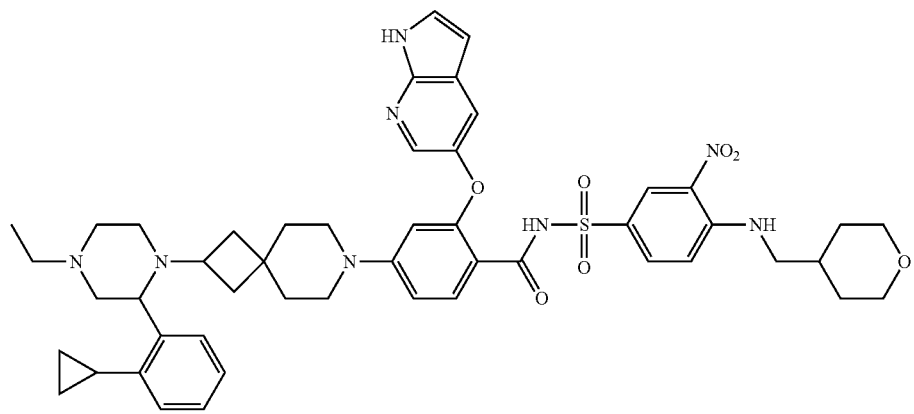 [SMILES: CCN1CCN(C2CC3(CCN(c4ccc(C(=O)NS(=O)(=O)c5ccc(NCC6CCOCC6)c([N+](=O)[O-])c5)c(Oc5cnc6[nH]ccc6c5)c4)CC3)C2)C(c2ccccc2C2CC2)C1]

The desired compound was synthesized following the procedures similar to those in Example F23 by replacing (S)-2-(2-(2-cyclopropylphenyl)pyrrolidin-1-yl)-7-azaspiro[3.5]nonane with 2-(2-(2-cyclopropylphenyl)-4-ethylpiperazin-1-yl)-7-azaspiro[3.5]nonane. $^1$H NMR (400 MHz, DMSO-d$_6$) δ ppm: 11.60 (s, 1H), 10.51 (s, 1H), 8.35-8.60 (m, 2H), 7.96 (s, 1H), 7.69 (d, J=8.2 Hz, 1H), 7.62-7.28 (m, 4H), 7.28-7.06 (m, 2H), 7.06-6.85 (m, 2H), 6.75-6.56 (m, 1H), 6.33 (s, 1H), 6.17 (s, 1H), 4.09-3.91 (m, 1H), 3.89-3.78 (m, 2H), 3.32-3.21 (m, 5H), 3.08-2.82 (m, 7H), 2.27-2.14 (m, 1H), 2.06-1.68 (m, 3H), 1.65-1.52 (m, 3H), 1.47-1.15 (m, 10H), 1.12-0.82 (m, 6H), 0.77-0.46 (m, 2H). MS (ESI, m/e) [M+1]$^+$ 902.9.

Example F131a and Example F131b: 2-((1H-pyrrolo[2,3-b]pyridin-5-yl)oxy)-4-(2-((S)-2-(2-cyclopropylphenyl)pyrrolidin-1-yl)-7-azaspiro[3.5]nonan-7-yl)-N-((4-((((cis or trans)-4-hydroxytetrahydrofuran-2-yl)methyl)amino)-3-nitrophenyl)sulfonyl)benzamide; 2-((1H-pyrrolo[2,3-b]pyridin-5-yl)oxy)-4-(2-((S)-2-(2-cyclopropylphenyl)pyrrolidin-1-yl)-7-azaspiro[3.5]nonan-7-yl)-N-((4-((((trans or cis)-4-hydroxytetrahydrofuran-2-yl)methyl)amino)-3-nitrophenyl)sulfonyl)benzamide

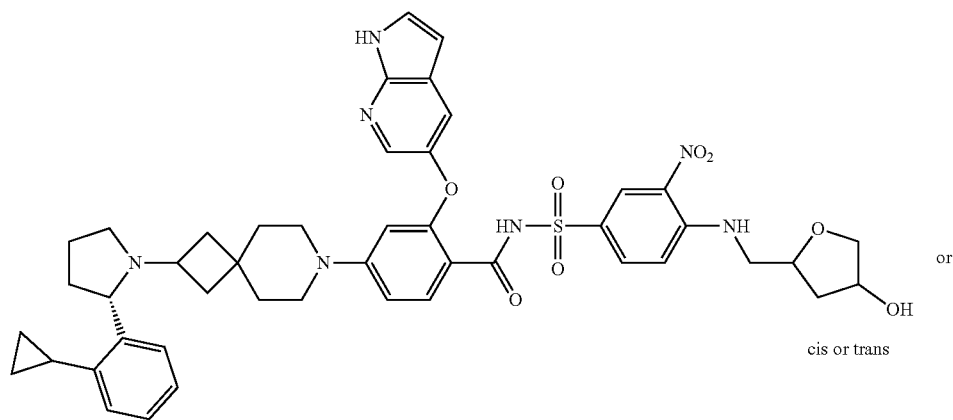

cis or trans

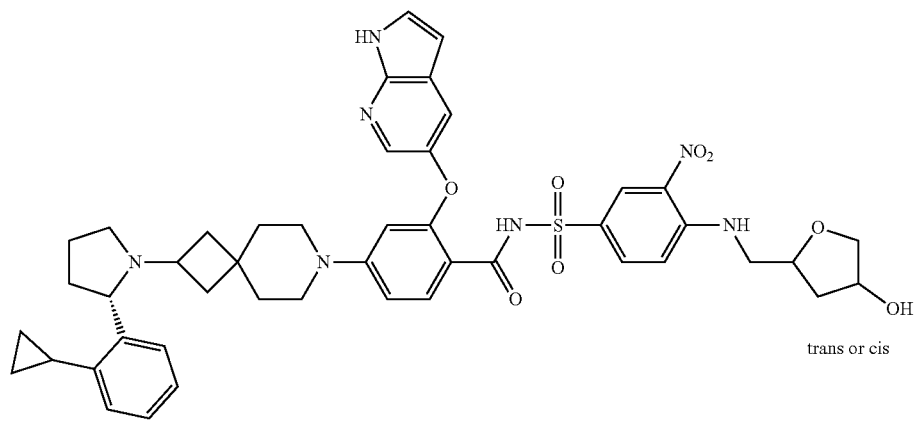

trans or cis

The desired compound was synthesized following the procedures similar to those in Example F43 by replacing (S)-2-(2-isopropylphenyl)pyrrolidine with (S)-2-(2-cyclopropylphenyl)pyrrolidine and replacing 4-((((1r,4r)-4-hydroxy-4-methylcyclohexyl)methyl)amino)-3-nitrobenzenesulfonamide with 4-(((4-hydroxytetrahydrofuran-2-yl)methyl)amino)-3-nitrobenzenesulfonamide. After separation and purification with prep-HPLC, the faster isomers was obtained as Example F131a. $^1$H NMR (DMSO-d$_6$) δ ppm: 11.68 (s, 1H), 11.50 (s, 1H), 8.75-8.40 (m, 2H), 8.10-7.97 (m, 1H), 7.86-7.36 (m, 5H), 7.33-6.91 (m, 4H), 6.74-6.68 (m, 1H), 6.41 (s, 1H), 6.25 (s, 1H), 5.06-4.96 (m, 1H), 4.46-4.26 (m, 2H), 3.97-3.87 (m, 1H), 3.70-3.55 (m, 2H), 3.12-2.96 (m, 5H), 2.40-2.32 (m, 2H), 2.13-1.55 (m, 16H), 1.01-0.96 (m, 2H), 0.73-0.63 (m, 2H). MS (ESI, m/e) [M+1]$^+$ 861.9; the slower isomers was obtained as Example F131b. $^1$H NMR (DMSO-d$_6$) δ ppm: 11.67 (s, 1H), 11.43 (s, 1H), 8.80-8.40 (m, 2H), 8.04 (s, 1H), 7.90-7.70 (m, 1H), 7.65-7.38 (m, 4H), 7.33-6.92 (m, 5H), 6.80-6.65 (m, 1H), 6.40 (s, 1H), 6.25 (s, 1H), 5.15-5.05 (m, 1H), 4.45-4.35 (m, 1H), 4.25-4.12 (m, 1H), 3.78-3.68 (m, 2H), 3.66-3.53 (m, 3H), 3.15-2.93 (m, 5H), 2.40-2.25 (m, 2H), 2.15-1.99 (m, 3H), 1.70-1.57 (m, 3H), 1.52-1.39 (m, 6H), 1.03-0.94 (m, 2H), 0.75-0.55 (m, 2H). MS (ESI, m/e) [M+1]$^+$ 861.9.

Example F132a and Example F132b: 2-((1H-pyrrolo[2,3-b]pyridin-5-yl)oxy)-4-(2-((S or R)-2-(2-isopropylphenyl)-4-methylpiperazin-1-yl)-7-azaspiro[3.5]nonan-7-yl)-N-((4-((((1r,4r)-4-hydroxy-4-methylcyclohexyl)methyl)amino)-3-nitrophenyl)sulfonyl)benzamide; 2-((1H-pyrrolo[2,3-b]pyridin-5-yl)oxy)-4-(2-((R or S)-2-(2-isopropylphenyl)-4-methylpiperazin-1-yl)-7-azaspiro[3.5]nonan-7-yl)-N-((4-((((1r,4r)-4-hydroxy-4-methylcyclohexyl)methyl)amino)-3-nitrophenyl)sulfonyl)benzamide

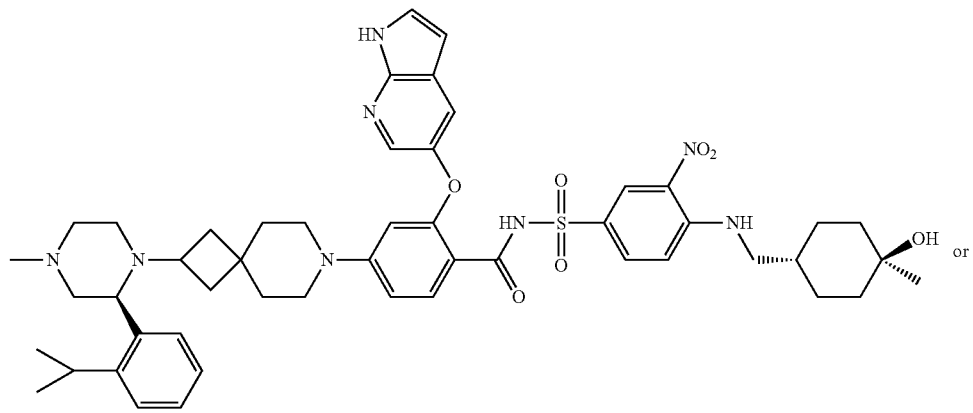

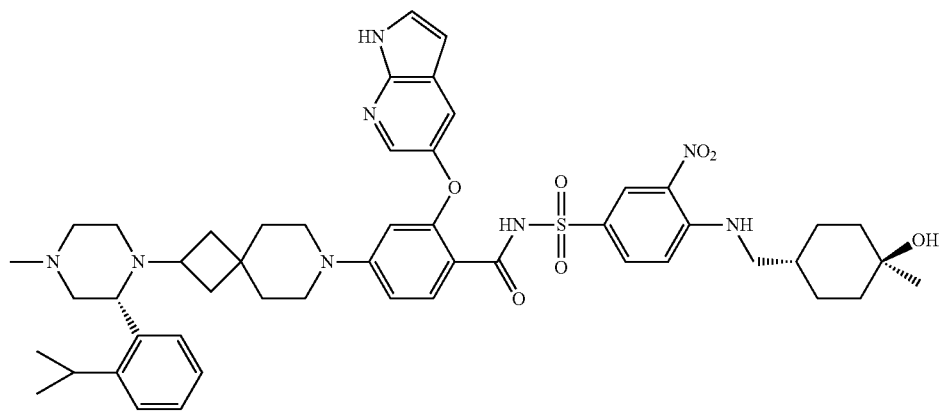

2-(2-(2-isopropylphenyl)-4-methylpiperazin-1-yl)-7-azaspiro[3.5]nonane was separated and purified by SFC to obtain 2 pure isomers (Instrument: Waters SFC80Q preparative SFC; Column: Lux Cellulose-2, 250×30 mm i.d., 10 um; Mobile phase: A for $CO_2$ and B for MeOH (0.1% $NH_3.H_2O$); Gradient: B %=60%; Flow rate: 80 g/min; Column temperature: 40° C.; System back pressure: 100 bar): (S or R)-2-(2-(2-isopropylphenyl)-4-methylpiperazin-1-yl)-7-azaspiro[3.5]nonane as faster peak in SFC (0.4 g, retention time: 2.2 min). $^1$H NMR (400 MHz, CDCl$_3$) δ ppm: 7.53-7.44 (m, 1H), 7.26-7.21 (m, 2H), 7.16-7.09 (m, 1H), 3.71-3.59 (m, 1H), 3.45-3.31 (m, 1H), 2.98 (d, J=8.4 Hz, 1H), 2.93-2.74 (m, 6H), 2.64 (d, J=10.8 Hz, 1H), 2.29 (s, 3H), 2.28 (s, 1H), 2.26 (s, 1H), 2.19-2.10 (m, 1H), 1.87-1.77 (m, 1H), 1.76-1.68 (m, 1H), 1.63-1.47 (m, 4H), 1.40-1.30 (m, 1H), 1.23 (d, J=6.8 Hz, 3H), 1.20 (d, J=6.8 Hz, 3H), 1.17-1.09 (m, 1H). MS (ESI, m/e) [M+1]$^+$ 342.4. (R or S)-2-(2-(2-isopropylphenyl)-4-methylpiperazin-1-yl)-7-azaspiro[3,5]nonane (slower peak in SFC, retention time: 3.9 min) (340 mg) was obtained as a white solid.

With the isomer of faster peak in SFC as starting material, Example FI 32a was synthesized following the procedures similar to those in Example F91. $^1$H NMR (400 MHz, DMSO-d$_6$) δ ppm: 11.59 (s, 1H), 8.49-8.40 (m, 2H), 7.95 (s, 1H), 7.68-7.65 (m, 1H), 7.52 (d, J=8.4 Hz, 1H), 7.46-7.10 (m, 7H), 6.95-6.87 (m, 1H), 6.63 (d, J=8.4 Hz, 1H), 6.32 (s, 1H), 6.17 (s, 1H), 4.24 (s, 1H), 3.67-3.55 (m, 1H), 3.26-3.24 (m, 3H), 3.01-2.82 (m, 9H), 2.25-2.19 (m, 1H), 2.05-1.97 (m, 2H), 1.71-1.50 (m, 8H), 1.33-1.01 (m, 20H). MS (ESI, m/e) [M+1]$^+$ 919.0.

With the isomer of slower peak in SFC as starting material, Example F1321b was synthesized following the procedures similar to those in Example F91. $^1$H NMR (400 MHz, DMSO-d$_6$) δ ppm: 11.66 (s, 1H), 10.55 (s, 1H), 8.51 (d, J=2.5 Hz, 2H), 8.00 (d, J=2.5 Hz, 1H), 7.74 (d, J=9.2 Hz, 1H), 7.52-7.40 (m, 4H), 7.29-7.21 (m, 2H), 7.19-7.14 (m, 1H), 7.02 (d, J=9.2 Hz, 1H), 6.64 (d, J=8.6 Hz, 1H), 6.36 (s, 1H), 6.15 (s, 1H), 4.25 (s, 1H), 3.72 (s, 1H), 3.30-3.16 (m, 4H), 3.09-2.72 (m, 10H), 2.65-2.60 (m, 3H), 2.35-2.30 (m, 2H), 1.69-1.52 (m, 8H), 1.38-1.14 (m, 16H). MS (ESI, m/e) [M+1]$^+$ 919.0.

Example F133: 2-((1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(2-oxo-7-azaspiro[3.5]nonan-7-yl)benzamide

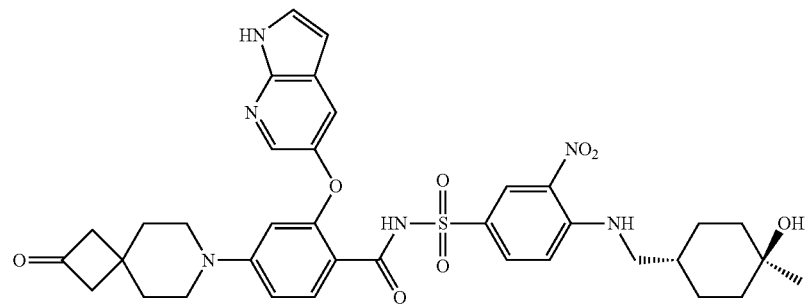 [SMILES: C[C@]1(O)CC[C@H](CNc2ccc(S(=O)(=O)NC(=O)c3ccc(N4CCC5(CC4)CC(=O)C5)cc3Oc3cnc4[nH]ccc4c3)cc2[N+](=O)[O-])CC1]

Step 1: 2-((1H-pyrrolo[2,3-b]pyridin-5-yl)oxy)-4-(2,2-dimethoxy-7-azaspiro[3.5]nonan-7-yl)-N-((4-((((1r,4r)-4-hydroxy-4-methylcyclohexyl)methyl)amino)-3-nitrophenyl) sulfonyl)benzamide The mixture of 2-((1H-pyrrolo[2,3-b]pyridin-5-yl)oxy)-4-(2,2-dimethoxy-7-azaspiro[3.5]nonan-7-yl)benzoic acid (437 mg, 1.0 mmol), triethylamine (303 mg, 3.0 mmol), EDO (229 mg, 1.2 mmol), DMAP (366 mg, 3.0 mmol) and 4-((((1r,4r)-4-hydroxy-4-methylcyclohexyl)methyl)amino)-3-nitrobenzenesulfonamide (343 mg, 1.0 mmol) in DCM (50 mL) was heated to reflux and stirred for overnight. The mixture was cooled to r.t. and then washed with brine, dried over $Na_2SO_4$ and concentrated in vacuo, then purified by chromatography column on silica (eluent: PE/EA=1/1 to DCM/EA=1/1) to give the target product (424 mg, 55.58%). MS (ESI, m/e) $[M+1]^+$ 762.8.

Step 2: 2-((1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(2-oxo-7-azaspiro[3.5]nonan-7-yl)benzamide To the mixture of 2-((1H-pyrrolo[2,3-b]pyridin-5-yl)oxy)-4-(2,2-dimethoxy-7-azaspiro[3.5]nonan-7-yl)-N-((4-((((1r,4r)-4-hydroxy-4-methylcyclohexyl)methyl)amino)-3-nitrophenyl)sulfonyl)benzamide (100 mg, 0.13 mmol) in DCM (5 mL) was added HCl solution (4M in 1,4-dioxane, 1 mL) and stirred for 30 mins. The reaction was quenched with aq. $NaHCO_3$ (30 mL), extracted with DCM (30 mL), concentrated in vacuum and purified by pre-TLC (eluent: DCM/MeOH=20/1) to afford the desired compound (42 mg, 45.12%) as a yellow solid. $^1$H NMR (400 MHz, DMSO-$d_6$) δ ppm: 11.71 (s, 1H), 11.46 (s, 1H), 8.62-8.53 (m, 2H), 8.08 (d, J=2.4 Hz, 1H), 7.82 (d, J=7.6 Hz, 1H), 7.57-7.5 Urn. 3H), 7.11 (d, J=8.8 Hz, 1H), 6.79 (d, J=8.8 Hz, 1H), 6.41-6.38 (m, 1H), 6.24 (s, 1H), 4.25 (s, 1H), 3.30-3.25 (m, 2H), 3.21-3.12 (m, 4H), 2.78 (s, 4H), 1.75-1.52 (m, 10H), 1.41-1.10 (m, 6H). MS (ESI, m/e) $[M+1]^+$ 716.8.

Example G1: 3-((1H-pyrrolo[2,3-b]pyridin-5-yl)oxy)-4'-(2-(2-chlorophenyl)pyrrolidin-1-yl)-N-((4-((4-fluorotetrahydro-2H-pyran-4-yl)methoxy)-3-nitrophenyl)sulfonyl)-[1,1'-biphenyl]-4-carboxamide

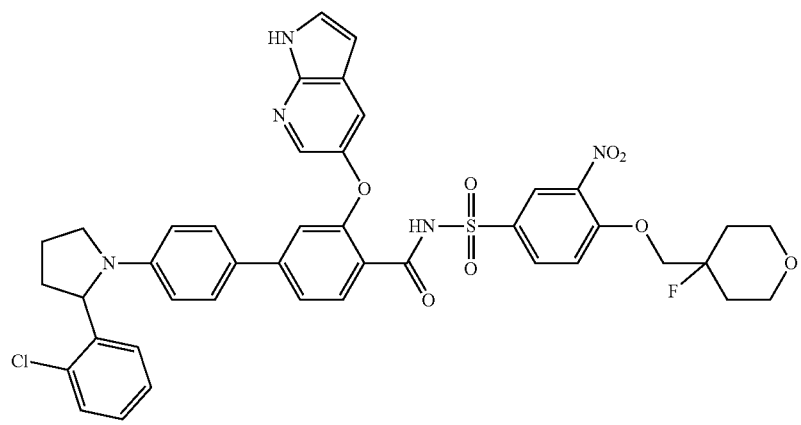 [SMILES: O=C(NS(=O)(=O)c1ccc(OCC2(F)CCOCC2)c([N+](=O)[O-])c1)c1ccc(-c2ccc(N3CCCC3c3ccccc3Cl)cc2)cc1Oc1cnc2[nH]ccc2c1]

The mixture of 3-((1H-pyrrolo[2,3-b]pyridin-5-yl)oxy)-4'-(2-(2-chlorophenyl)pyrrolidin-1-yl)-[1,1'-biphenyl]-4-carboxylic acid (51 mg, 0.1 mmol), triethylamine (30 mg, 0.3 mmol), 2(7-azabenzotriazol-1-yl)-N,N,N',N'-tetramethyluronium hexafluorophosphate (59 mg, 0.15 mmol) in DCM (10 mL) was stirred for 2 h. To the resulting reaction were added 4-((4-fluorotetrahydro-2H-pyran-4-yl)methoxy)-3-nitrobenzenesulfonamide (50 mg, 0.15 mmol) and DMAP (1 mg, 0.01 mmol) and stirred for overnight. The mixture was purified by chromatography column on silica (eluent: PE/EA=1/1 to DCM/MeOH=20/1) to afford a crude, which was purified with Pre-HPLC to give the product (25 mg). $^1$H NMR (400 MHz, DMSO-$d_6$) δ ppm: 12.20 (br, 1H), 11.64 (br, 1H), 8.30 (hr. 1H), 8.01 (m, 2H), 7.57 (d, J=4.0 Hz, 1H), 7.56-7.46 (m, 3H), 7.54 (m, 2H), 7.33-7.18 (m, 3H), 7.02 (d, J=4.0 Hz, 1H), 6.90 (s, 1H), 6.36 (m, 3H), 4.98 (d, J=8.0 Hz, 1H), 4.36 (d, J=24.0 Hz, 2H), 3.79-3.72 (m, 3H), 3.61-3.56 (m, 2H), 3.39-3.32 (m, 1H), 2.41 (m, 1H), 1.99-1.81 (m, 5H). MS (ESI, m/e) [M+1]$^+$ 826.0.

Example G1C: 3-((1H-pyrrolo[2,3-b]pyridin-5-yl)oxy)-4'-(2-(2-cyclopropylphenyl)pyrrolidin-1-yl)-N-((4-((4-fluorotetrahydro-2H-pyran-4-yl)methoxy)-3-nitrophenyl)sulfonyl)-2',3',4',5'-tetrahydro-[1,1'-biphenyl]-4-carboxamide

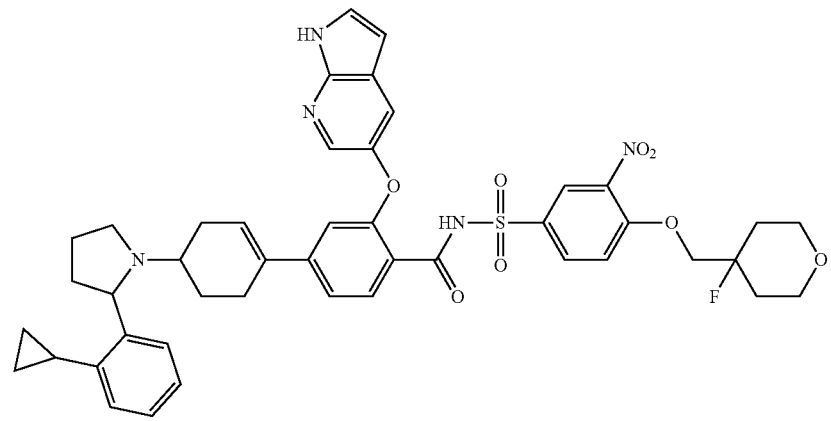 [SMILES: O=C(NS(=O)(=O)c1ccc(OCC2(F)CCOCC2)c([N+](=O)[O-])c1)c1ccc(C2=CCC(N3CCCC3c3ccccc3C3CC3)CC2)cc1Oc1cnc2[nH]ccc2c1]

The desired compound was synthesized with 4-((4-fluorotetrahydro-2H-pyran-4-yl)methoxy)-3-nitrobenzenesulfonamide and 3-((1H-pyrrolo[2,3-b]pyridin-5-yl)oxy)-4'-(2-(2-cyclopropylphenyl)pyrrolidin-1-yl)-2',3',4',5'-tetrahydro-[1,1'-biphenyl]-4-carboxylic acid following the procedure similar to those in Example C3. MS (ESI, m/e) [M+1]$^+$ 836.2.

Example G2: 3-((1H-pyrrolo[2,3-b]pyridin-5-yl)oxy)-4'-(2-(2-chlorophenyl)pyrrolidin-1-yl)-N-((4-(((1-methylpiperidin-4-yl)methyl)amino)-3-nitrophenyl)sulfonyl)-[1,1'-biphenyl]-4-carboxamide

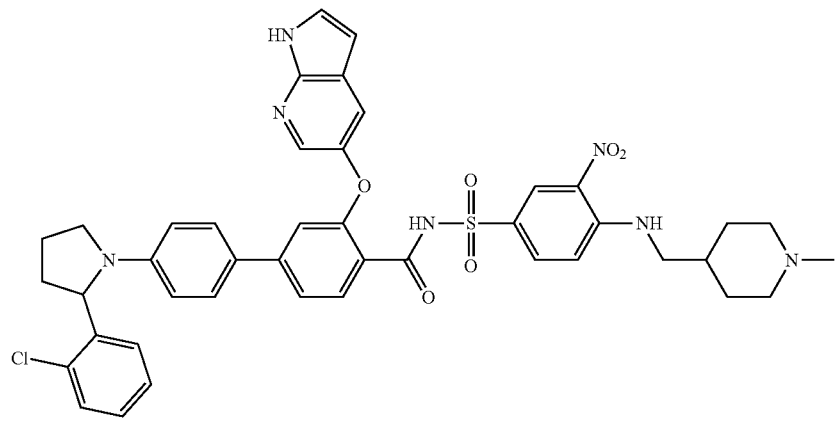 [SMILES: CN1CCC(CNc2ccc(S(=O)(=O)NC(=O)c3ccc(-c4ccc(N5CCCC5c5ccccc5Cl)cc4)cc3Oc3cnc4[nH]ccc4c3)cc2[N+](=O)[O-])CC1]

The desired compound G2 was synthesized with 4-(((1-methylpiperidin-4-yl)methyl)amino)-3-nitrobenzenesulfonamide and 3-((1H-pyrrolo[2,3-b]pyridin-5-yl)oxy)-4'-(2-(2-chlorophenyl)pyrrolidin-1-yl)-[1,1'-biphenyl]-4-carboxylic acid following the procedures similar to those in Example G1. $^1$H NMR (400 MHz, DMSO-d$_6$) δ ppm: 11.55 (s, 1H), 9.32 (br, 1H), 8.49-8.33 (m, 2H), 7.99-7.95 (m, 1H), 7.73-7.65 (m, 1H), 7.57 (d, J=8.0 Hz, 1H), 7.47 (d, J=8.0 Hz, 1H), 7.45-7.41 (m, 1H), 7.41-7.36 (m, 1H), 7.32 (d, J=8.4 Hz, 2H), 7.29-7.16 (m, 3H), 7.06-6.99 (m, 1H), 6.96-6.84 (m, 2H), 6.40-6.28 (m, 3H), 4.97 (d, J=8.5 Hz, 1H), 3.80-3.70 (m, 1H), 3.40-3.34 (m, 2H), 3.31-3.27 (m, 4H), 2.87-2.74 (m, 1H), 2.74-2.61 (m, 3H), 2.05-1.96 (m, 1H), 1.96-1.74 (m, 6H), 1.44-1.32 (m, 2H). MS (ESI, m/e) [M+1]$^+$ 820.1.

Example G2C: 3-((1H-pyrrolo[2,3-b]pyridin-5-yl)oxy)-4'-(2-(2-cyclopropylphenyl)pyrrolidin-1-yl)-N-((4-(((1-methylpiperidin-4-yl)methyl)amino)-3-nitrophenyl)sulfonyl)-2',3',4',5'-tetrahydro-[1,1'-biphenyl]-4-carboxamide

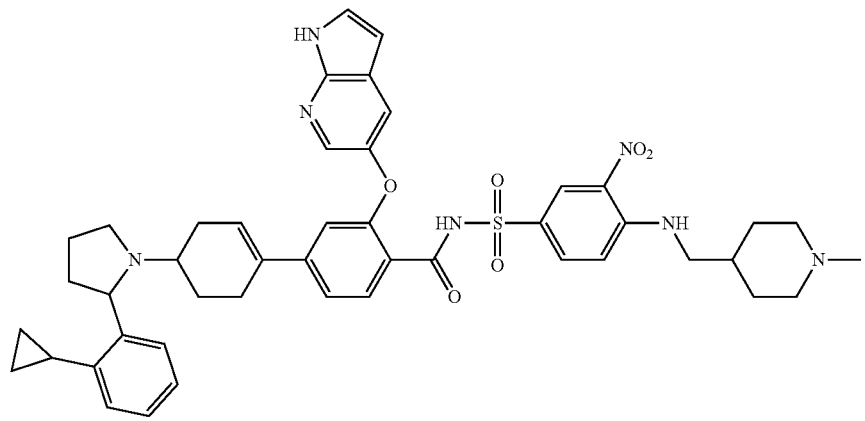 [SMILES: CN1CCC(CNc2ccc(S(=O)(=O)NC(=O)c3ccc(C4=CCC(N5CCCC5c5ccccc5C5CC5)CC4)cc3Oc3cnc4[nH]ccc4c3)cc2[N+](=O)[O-])CC1]

The desired compound was synthesized with 4-(((1-methylpiperidin-4-yl)methyl)amino)-3-nitrobenzenesulfonamide and 3-((1H-pyrrolo[2,3-b]pyridin-5-yl)oxy)-4'-(2-(2-cyclopropylphenyl)pyrrolidin-1-yl)-2',3',4',5'-tetrahydro-[1,1'-biphenyl]-4-carboxylic acid following the procedure similar to those in Example C3. $^1$H NMR (400 MHz, DMSO-$d_6$) δ ppm: 11.55 (s, 1H), 8.8.42-8.27 (m, 2H), 7.91 (s, 1H), 7.66-7.57 (m, 1H), 7.58-7.44 (m, 2H), 7.41-7.38 (m, 1H), 7.11-7.02 (m, 2H), 7.00-6.95 (m, 1H), 6.93-6.85 (m, 1H), 6.83-6.77 (m, 1H), 6.75-6.70 (m, 1H), 6.30 (s, 1H), 6.01-5.77 (m, 1H), 4.38-4.20 (m, 1H), 3.27-3.07 (m, 4H), 2.90-2.73 (m, 2H), 2.62-2.50 (m, 2H), 2.26-2.15 (m, 4H), 2.07-1.90 (m, 3H), 1.76-1.63 (m, 4H), 1.20-1.13 (m, 4H), 0.97-0.84 (m, 3H), 0.82-0.44 (m, 4H). MS (ESI, m/e) [M+1]$^+$ 829.9.

Example G3: 3-((1H-pyrrolo[2,3-b]pyridin-5-yl)oxy)-4'-(2-(2-chlorophenyl)pyrrolidin-1-yl)-N-((3-nitro-4-((1-(tetrahydro-2H-pyran-4-yl)azetidin-3-yl)amino)phenyl)sulfonyl)-[1,1'-biphenyl]-4-carboxamide

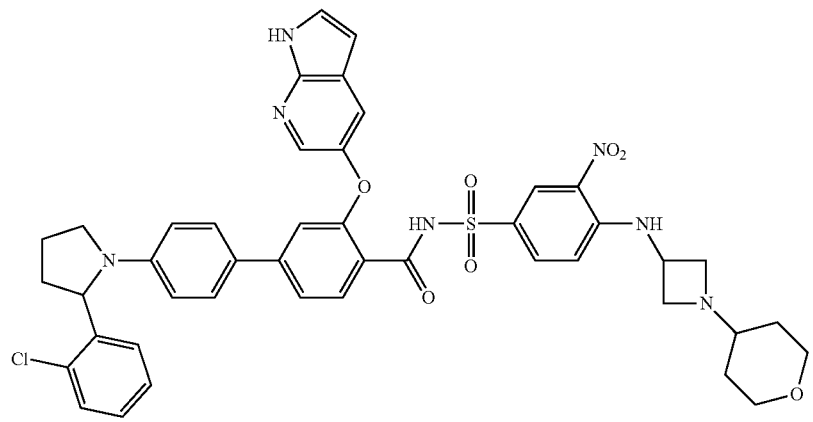 [SMILES: O=C(NS(=O)(=O)c1ccc(NC2CN(C3CCOCC3)C2)c([N+](=O)[O-])c1)c1ccc(-c2ccc(N3CCCC3c3ccccc3Cl)cc2)cc1Oc1cnc2[nH]ccc2c1]

The desired compound G3 was synthesized with 3-nitro-4-((1-(tetrahydro-2H-pyran-4-yl)azetidin-3-yl)amino)benzenesulfonamide and 3-((1H-pyrrolo[2,3-b]pyridin-5-yl)oxy)-4'-(2-(2-chlorophenyl)pyrrolidin-1-yl)-[1,1'-biphenyl]-4-carboxylic acid following the procedures similar to those in Example G1. $^1$H NMR (400 MHz, DMSO-$d_6$) δ ppm: 11.57 (s, 1H), 8.48-8.43 (m, 1H), 8.39-8.30 (m, 1H), 7.98-7.94 (m, 1H), 7.81-7.72 (m, 1H), 7.50-7.42 (m, 2H), 7.42-7.37 (m, 1H), 7.33 (d, J=8.4 Hz, 2H), 7.29-7.15 (m, 3H), 7.04-6.98 (m, 1H), 6.94-6.89 (m, 1H), 6.82-6.68 (m, 1H), 6.35 (d, J=8.4 Hz, 2H), 6.33-6.29 (m, 1H), 5.00-4.94 (m, 1H), 4.53-4.24 (m, 1H), 3.94-3.83 (m, 2H), 3.79-3.71 (m, 1H), 3.42-3.36 (m, 1H), 3.31-3.17 (m, 5H), 2.46-2.36 (m, 2H), 2.04-1.67 (m, 6H), 1.33-1.25 (m, 2H). MS (ESI, m/e) [M+1]$^+$ 848.1.

Example G4: 3-((1H-pyrrolo[2,3-b]pyridin-5-yl)oxy)-4'-(2-(2-chlorophenyl)pyrrolidin-1-yl)-N-((3-nitro-4-((1-(oxetan-3-yl)piperidin-4-yl)amino)phenyl)sulfonyl)-[1,1'-biphenyl]-4-carboxamide

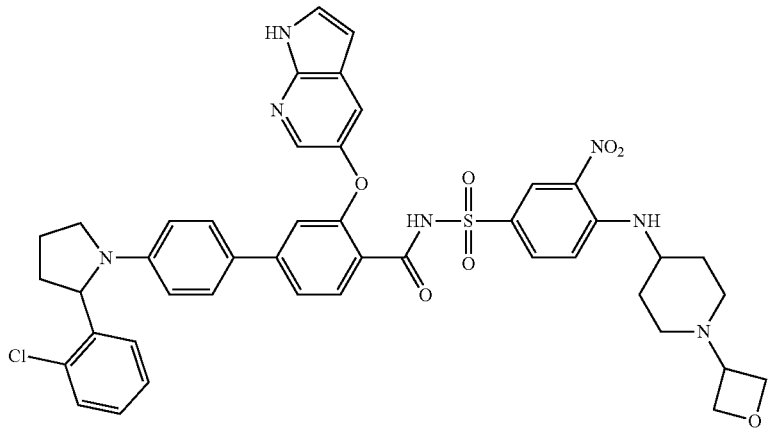 [SMILES: O=C(NS(=O)(=O)c1ccc(NC2CCN(C3COC3)CC2)c([N+](=O)[O-])c1)c1ccc(-c2ccc(N3CCCC3c3ccccc3Cl)cc2)cc1Oc1cnc2[nH]ccc2c1]

The desired compound G4 was synthesized with 3-nitro-4-((1-(oxetan-3-yl)piperidin-4-yl)amino)benzenesulfonamide and 3-((1H-pyrrolo[2,3b]pyridin-5-yl)oxy)-4'-(2-(2 chlorophenyl)pyrrolidin-1-yl)-[1,1'-biphenyl]-4-carboxylic acid following the procedures similar to those in Example G1. $^1$H NMR (400 MHz, DMSO-d$_6$) δ ppm: 12.23 (s, 1H), 11.69 (s, 1H), 10.90-10.05 (m, 1H), 8.63-8.48 (m, 1H), 8.27-8.12 (m, 1H), 8.04 (d, J=1.8 Hz, 1H), 7.90 (d, J=8.1 Hz, 1H), 7.59 (d, J=1.8 Hz, 1H), 7.55-7.43 (m, 3H), 7.38-7.26 (m, 3H), 7.26-7.14 (m, 3H), 7.00 (d, J=7.4 Hz, 1H), 6.90 (s, 1H), 6.44-6.28 (m, 3H), 4.97 (d, J=8.0 Hz, 1H), 4.85-4.66 (m, 3H), 4.45-4.26 (m, 1H), 3.93-3.88 (m, 1H), 3.55-3.32 (m, 3H), 3.04-2.82 (m, 2H), 2.44-2.35 (m, 1H), 2.28-2.09 (m, 2H), 2.09-1.94 (m, 2H), 1.94-1.68 (m, 2H), 1.23-1.02 (m, 2H). MS (ESI, m/e) [M+1]$^+$ 848.1.

Example G5: 3-((1H-pyrrolo[2,3-b]pyridin-5-yl)oxy)-4'-(2-(2-chlorophenyl)pyrrolidin-1-yl)-N-((4-(((3-hydroxyoxetan-3-yl)methyl)amino)-3-nitrophenyl)sulfonyl)-[1,1'-biphenyl]-4-carboxamide

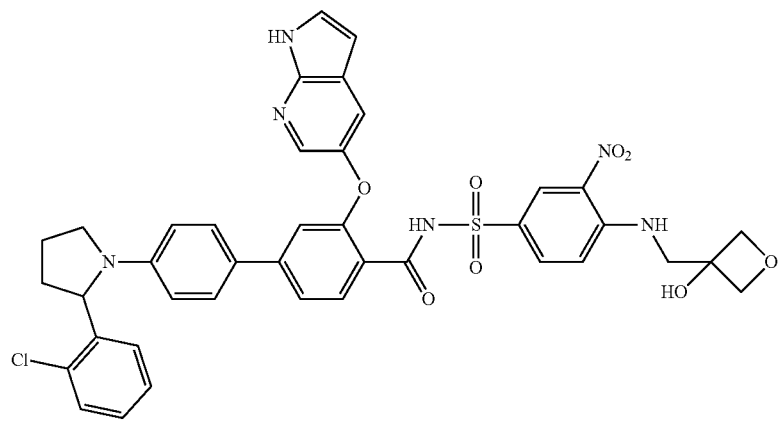 [SMILES: O=C(NS(=O)(=O)c1ccc(NCC2(O)COC2)c([N+](=O)[O-])c1)c1ccc(-c2ccc(N3CCCC3c3ccccc3Cl)cc2)cc1Oc1cnc2[nH]ccc2c1]

Synthesis of TBS-G5: 3-((1H-pyrrolo[2,3-h]pyridin-5-yl)oxy)-N-((4-(((3-((tert-butyldimethylsilyl)oxy)oxetan-3-yl)methyl)amino)-3-nitrophenyl)sulfonyl)-4'-(2-(2-chlorophenyl)pyrrolidin-1 yl)-[1,1'-biphenyl]-4-carboxamide

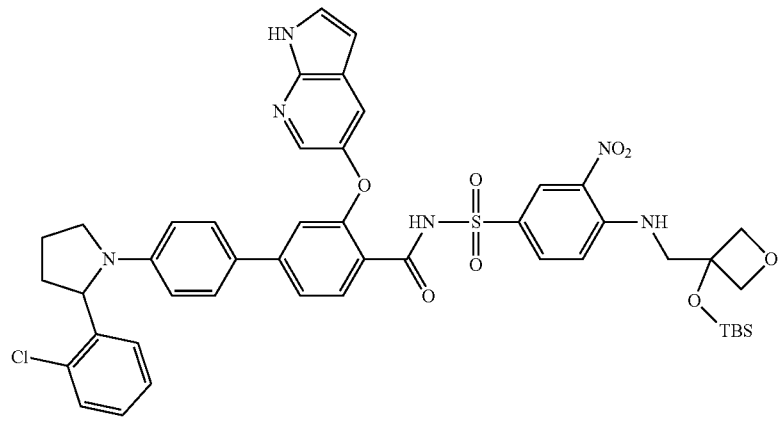

To a solution of 3-((1H-pyrrolo[2,3b]pyridin-5-yl)oxy)-4'-(2-(2-chlorophenyl)pyrrolidin-1-yl)-[1,1'-biphenyl]-4-carboxylic acid (54 mg, 0.106 mmol) in DCM (50 mL) was added HATU (60 mg, 0.159 mmol) and triethylamine (53.5 mg, 0.53 mmol). The mixture was stirred at room temperature for 1 hour. Then to the mixture were added 4-(((3-(((tert-butyldimethylsilyl)oxy)oxetan-3-yl)methyl)amino)-3-nitrobenzenesulfonamide (88.5 mg, 0.212 mmol). The mixture was stirred at room temperature overnight. The mixture was washed with brine, dried over $Na_2SO_4$, concentrated. The residue was purified by chromatography column on silica (eluent: EA/PE=1/1 to MeOH/DCM=1/10) to give the crude product. The crude product was further purified by prep-TLC (MeOH/DCM=1/20) to afford product (36 mg, 37.3%) as a yellow solid. MS (ESI, m/e) $[M+1]^+$ 909.1.

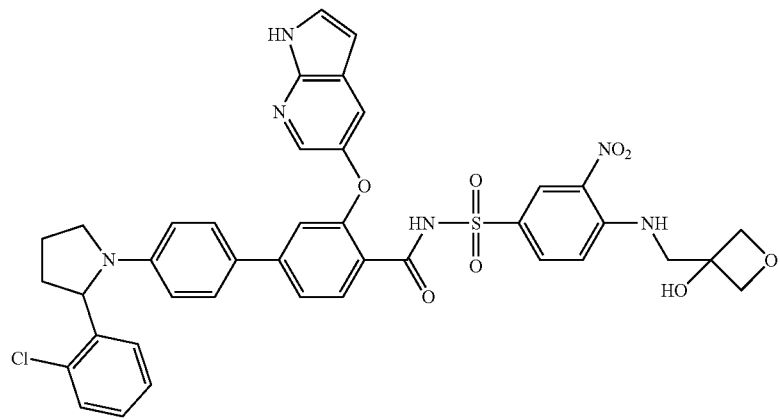 [SMILES: O=C(NS(=O)(=O)c1ccc(NCC2(O)COC2)c([N+](=O)[O-])c1)c1ccc(-c2ccc(N3CCCC3c3ccccc3Cl)cc2)cc1Oc1cnc2[nH]ccc2c1]

To a solution of 3-((1H-pyrrolo[2,3-b]pyridin-5-yl)oxy)-N-((4-(((3-(((tert-butyldimethylsilyl)oxy)oxetan-3-yl)methyl)amino)-3-nitrophenyl)sulfonyl)-4'-(2-(2-chlorophenyl)pyrrolidin-1-yl)-[1,1'-biphenyl]-4-carboxamide (TBS-G5) in DCM (50 ml) was added TBAF (100.6 mg, 0.385 mmol). The mixture was stirred at r.t. for 2 h. The mixture was washed with brine (50 ml×2), dried over $Na_2SO_4$, concentrated. The residue was purified by prep-HPLC to give the desired product in Example G5. $^1$H NMR (400 MHz, DMSO-$d_6$) δ ppm: 12.17 (s, 1H), 11.69 (s, 1H), 8.57 (s, 2H), 8.06 (s, 1H), 7.85 (d, J=8.7 Hz, 1H), 7.60 (s, 1H), 7.57-7.42 (m, 3H), 7.39-7.28 (m, 3H), 7.28-7.14 (m, 3H), 7.01 (d, J=7.1 Hz, 1H), 6.91 (s, 1H), 4.98 (d, J=7.7 Hz, 1H), 4.48 (d, J=6.2 Hz, 2H), 4.44 (d, J=6.2 Hz, 2H), 3.81-3.65 (m, 3H), 3.48-3.39 (m, 1H), 2.45-2.33 (m, 2H), 2.05-1.94 (m, 2H), 1.94-1.76 (m, 2H), 1.26-1.24 (m, 2H) MS (ESI, m/e) $[M+1]^+$ 795.1.

Example G6: 3-((1H-pyrrolo[2,3-b]pyridin-5-yl)oxy)-4'-(2-(2-chlorophenyl)pyrrolidin-1-yl)-N-((4-((4-hydroxycyclohexyl)methoxy)-3-nitrophenyl)sulfonyl)-[1,1'-biphenyl]-4-carboxamide

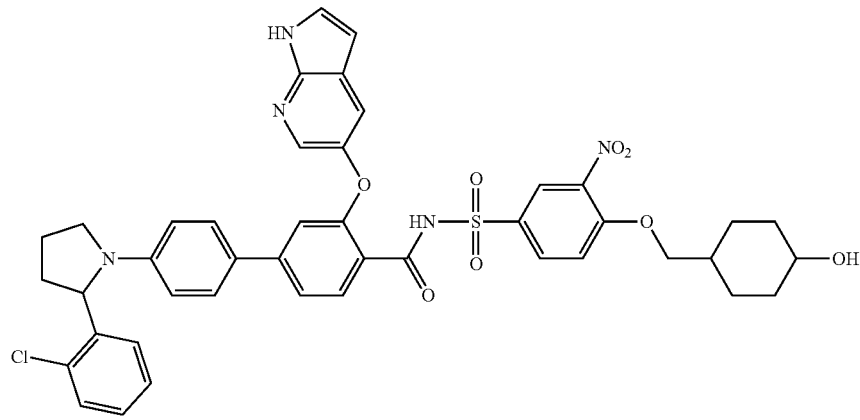 [SMILES: O=C(NS(=O)(=O)c1ccc(OCC2CCC(O)CC2)c([N+](=O)[O-])c1)c1ccc(-c2ccc(N3CCCC3c3ccccc3Cl)cc2)cc1Oc1cnc2[nH]ccc2c1]

The desired compound was synthesized from 4-((4-(((tert-butyldimethylsilyl)oxy)cyclohexyl)methoxy)-3-nitrobenzenesulfonamide and 3-((1H-pyrrolo[2,3-b]pyridin-5-yl)oxy)-4'-(2-(2-chlorophenyl)pyrrolidin-1-yl)-[1,1'-biphenyl]-4-carboxylic acid following the procedures similar to those in Example G5 to get TBS-G6, then proceeded with a deprotection step to afford the product. $^1$H NMR (400 MHz, DMSO-$d_6$) δ ppm: 12.36 (s, 1H), 11.73 (s, 1H), 8.38 (d, J=2.2 Hz, 1H), 8.13-8.01 (m, 2H), 7.62 (d, J=2.2 Hz, 1H), 7.57-7.49 (m, 2H), 7.49-7.39 (m, 2H), 7.37-7.28 (m, 3H), 7.28-7.15 (m, 2H), 7.04-6.97 (m, 1H), 6.89 (s, 1H), 6.44-6.38 (m, 1H), 6.35 (d, J=8.7 Hz, 2H), 4.97 (d, J=7.8 Hz, 1H), 4.01-3.93 (m, 4H), 3.78-3.69 (m, 2H), 3.42-3.28 (m, 2H), 2.06-1.95 (m, 2H), 1.91-1.82 (m, 3H), 1.82-1.72 (m, 2H), 1.18-0.97 (m, 4H). MS (ESI, m/e) [M+1]$^+$ 822.1.

Example G7: 3-((1H-pyrrolo[2,3-b]pyridin-5-yl)oxy)-4'-(2-(2-chlorophenyl)pyrrolidin-1-yl)-N-((3-nitro-4-(7-oxa-2-azaspiro[3.5]nonan-2-yl)phenyl)sulfonyl)-[1,1'-biphenyl]-4-carboxamide

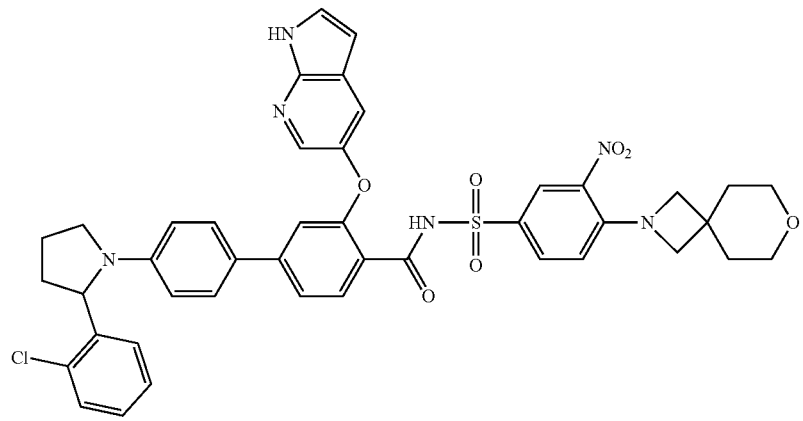 [SMILES: O=C(NS(=O)(=O)c1ccc(N2CC3(CCOCC3)C2)c([N+](=O)[O-])c1)c1ccc(-c2ccc(N3CCCC3c3ccccc3Cl)cc2)cc1Oc1cnc2[nH]ccc2c1]

The desired compound was synthesized with 3-nitro-4-(7-oxa-2-azaspiro[3.5]nonan-2-yl)benzenesulfonamide and 3-((1H-pyrrolo[2,3-b]pyridin-5-yl)oxy)-4'-(2-(2-chlorophenyl)pyrrolidin-1-yl)-[1,1'-biphenyl]-4-carboxylic acid following the procedures similar to those in Example G1, and afforded the product. $^1$H NMR (400 MHz, DMSO-$d_6$) δ ppm: 12.15 (s, 1H), 11.74 (s, 1H), 8.28-8.25 (m, 1H), 8.09-8.05 (m, 1H), 7.81-7.77 (m, 1H), 7.66-7.62 (m, 1H), 7.56-7.50 (m, 2H), 7.49-7.44 (m, 1H), 7.36-7.16 (m, 5H), 7.00 (d, J=7.3 Hz, 1H), 6.88 (s, 1H), 6.74 (d, J=8.4 Hz, 2H), 6.43-6.40 (m, 1H), 6.35 (d, J=8.4 Hz, 2H), 4.97 (d, J=7.9 Hz, 1H), 3.81-3.70 (m, 5H), 3.55-3.40 (m, 4H), 2.04-1.95 (m, 2H), 1.90-1.79 (m, 2H), 1.74-1.65 (m, 4H). MS (ESI, m/e) [M+1]$^+$ 819.1.

Example G8: N-((4-((((S)-1,4-dioxan-2-yl)methyl)amino)-3-nitrophenyl)sulfonyl)-3-((1H-pyrrolo[2,3-b]pyridin-5-yl)oxy)-4'-(2-(2-cyclopropylphenyl)pyrrolidin-1-yl)-2',3',4',5'-tetrahydro-[1,1'-biphenyl]-4-carboxamide

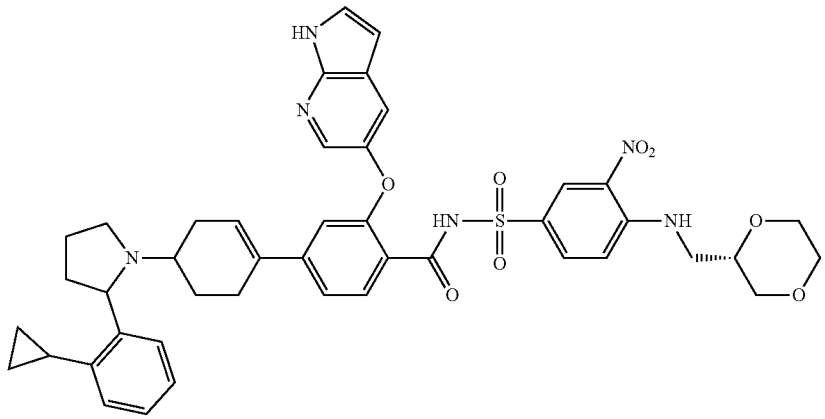 [SMILES: O=C(NS(=O)(=O)c1ccc(NC[C@H]2COCCO2)c([N+](=O)[O-])c1)c1ccc(C2=CCC(N3CCCC3c3ccccc3C3CC3)CC2)cc1Oc1cnc2[nH]ccc2c1]

To a solution of 3-(((1H-pyrrolo[2,3-b]pyridin-5-yl)oxy)-4'-(2(2-cyclopropylphenyl)pyrrolidin-1-yl)-2',3',4',5'-tetrahydro-[1,1'-biphenyl]-4-carboxylic acid (60 mg, 0.115 mmol) in DCM (50 ml) were added HATH (52.6 mg, 0.138 mmol) and triethylamine (34.8 mg, 0.345 mmol). The mixture was stirred at room temperature for 1 hour. Then to the mixture was added (S)-4-(((1,4-dioxan-2-yl)methyl)amino)-3-nitrobenzenesulfonamide (43.8 mg, 0.138 mmol). The mixture was stirred at room temperature overnight. The mixture was washed with brine, dried over $Na_2SO_4$, concentrated. The residue was purified by prep-HPLC to give the product (2 mg, 1.9%). $^1$H NMR (400 MHz, DMSO-$d_6$) δ ppm: 12.28 (s, 1H), 11.71 (s, 1H), 9.43 (br, 1H), 8.63-8.47 (m, 2H), 8.00 (s, 1H), 7.82 (d, J=9.1 Hz, 1H), 7.65-7.58 (m, 1H), 7.56-7.45 (m, 3H), 7.35-7.21 (m, 2H), 7.21-7.02 (m, 3H), 6.74 (d, J=6.2 Hz, 1H), 6.39 (s, 1H), 6.00-5.93 (m, 1H), 529-5.07 (m, 1H), 3.80-3.62 (m, 8H), 3.40-3.28 (m, 4H), 2.26-1.96 (m, 6H), 1.91-1.70 (m, 2H), 1.64-1.41 (m, 2H), 1.00-0.90 (m, 2H), 0.77-0.69 (m, 1H), 0.64-0.56 (m, 1H). MS (ESI, m/e) [M+1]$^+$ 819.1.

Example G8-S: N-((4-((((S)-1,4-dioxan-2-yl)methyl)amino)-3-nitrophenyl)sulfonyl)-3-((1H-pyrrolo[2,3-b]pyridin-5-yl)oxy)-4'-((S)-2-(2-cyclopropylphenyl)pyrrolidin-1-yl)-2',3',4',5'-tetrahydro-[1,1'-biphenyl]-4-carboxamide

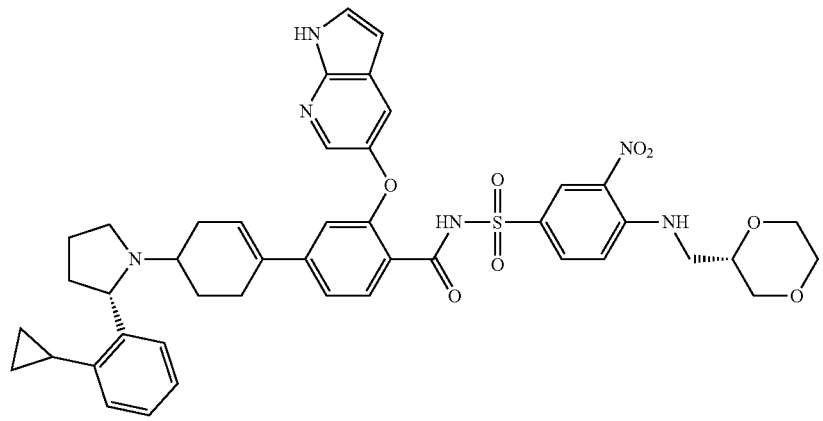 [SMILES: O=C(NS(=O)(=O)c1ccc(NC[C@H]2COCCO2)c([N+](=O)[O-])c1)c1ccc(C2=CCC(N3CCC[C@H]3c3ccccc3C3CC3)CC2)cc1Oc1cnc2[nH]ccc2c1]

The desired compound was synthesized with (S)-4-(((1,4-dioxan-2-yl)methyl)amino)-3-nitrobenzenesulfonamide and 3-((1H-pyrrolo[2,3-b]pyridin-5-yl)oxy)-4'-((S)-2-(2-cyclopropylphenyl)pyrrolidin-1-yl)-2',3',4',5'-tetrahydro-[1,1'-biphenyl]-4-carboxylic acid following the procedures similar to those in Example G8. $^1$H NMR (400 MHz, DMSO-$d_6$) δ ppm: 12.35 (br, 1H), δ 11.64 (s, 1H), 8.61-8.35 (m, 2H), 7.97 (s, 1H), 7.84-7.68 (m, 1H), 7.66-7.36 (m, 4H), 7.33-6.80 (m, 5H), 6.74 (s, 1H), 6.35 (s, 1H), 6.03-5.77 (m, 1H), 5.43-4.93 (m, 0.5H), 4.56-4.05 (m, 0.5H), 3.83-3.71 (m, 3H) 3.69-3.56 (m, 2H), 3.51-3.40 (m, 2H), 3.32-3.26 (m, 2H), 3.21-2.89 (m, 1H), 2.45-1.27 (m, 13H), 0.98-0.82 (m, 2H), 0.76-0.46 (m, 2H). MS (ESI, m/e) [M+1]$^+$ 818.8.

Two enantiomers G8-a (faster isomer) and G8-b (slower isomer) were separated by chiral preparative HPLC. The chiral separation conditions are shown below. The faster enantiomer was eluted at retention time of 3.3 min to give G8a. The slower enantiomer was eluted at retention time or 4.7 min to give G8-b.

| Column | CHIRAL ART Cellulose-SB |
|---|---|
| Column size | 2 cm × 25 cm, 5 um |
| Injection | 0.8 mL |
| Mobile phase | MTBE:MeOH (0.2% MSA) = 70:30 |
| Flow rate | 20 mL/min |
| Wave length | UV 220 nm |
| Temperature | 25° C. |
| Sample solution | 12 mg/mL in MeOH:DCM = 3:1 |
| Prep-HPLC equipment | Prep-Gilson-HPLC |

Example G8-a: $^1$H NMR (400 MHz, DMSO-$d_6$) δ ppm: 12.40 (br, 1H), 11.63 (s, 1H), 8.65-8.24 (m, 2H), 7.96 (s, 1H), 7.83-7.34 (m, 5H), 7.34-7.17 (m, 1H), 7.17-6.81 (m, 4H), 6.73 (s, 1H), 6.34 (s, 1H), 5.82 (s, 1H), 5.37-5.09 (m, 0.5H), 4.50-4.16 (m, 0.5H), 3.86-3.69 (m, 3H), 3.69-3.54 (m, 2H), 3.54-3.40 (m, 2H), 3.31-3.10 (m, 2H), 3.08-2.82 (m, 1H), 2.50-1.81 (m, 10H), 1.81-1.35 (m, 3H), 1.02-0.79 (m, 2H), 0.76-0.42 (m, 2H). MS (ESI, m/e) [M+1]$^+$ 818.8.
Example G8-b: $^1$H NMR (400 MHz, DMSO-$d_6$) δ ppm: 12.56-11.98 (m, 0.3H), 11.61 (s, 1H), 10.19-9.41 (m, 0.4H), 8.67-8.20 (m, 2H), 8.13-7.51 (m, 2H), 7.95 (s, 1H), 7.51-7.33 (m, 3H), 7.35-6.80 (m, 5H), 6.74 (s, 1H), 6.33 (s, 1H), 5.99 (s, 1H), 5.30-4.82 (m, 0.5H), 4.42-4.06 (m, 0.5H), 3.87-3.71 (m, 3H), 3.71-3.54 (m, 2H), 3.54-3.39 (m, 2H), 3.31-2.90 (m, 3H), 2.72-2.50 (m, 2H), 2.41-1.60 (m, 9H), 1.56-1.23 (m, 2H), 1.04-0.77 (m, 2H), 0.77-0.42 (m, 2H). MS (ESI, m/e) [M+1]$^+$ 818.8.

Example G9: N-((4-((((R)-1,4-dioxan-2-yl)methyl)amino)-3-nitrophenyl)sulfonyl)-3-((1H-pyrrolo[2,3-b]pyridin-5-yl)oxy)-4'-(2-(2-cyclopropylphenyl)pyrrolidin-1-yl)-2',3',4',5'-tetrahydro-[1,1'-biphenyl]-4-carboxamide

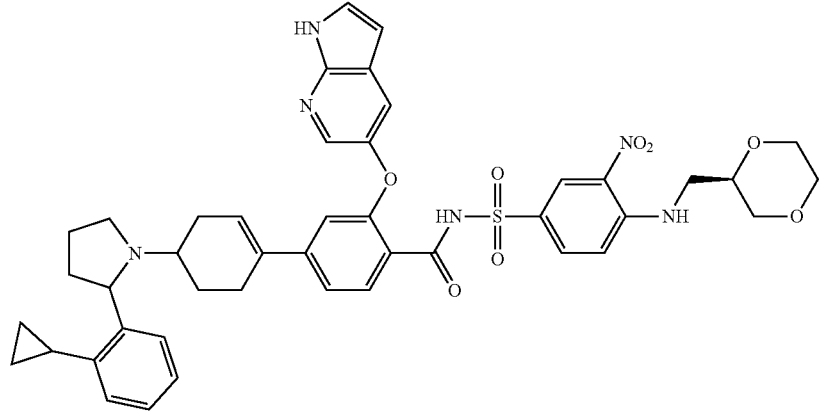 [SMILES: O=C(NS(=O)(=O)c1ccc(NC[C@@H]2COCCO2)c([N+](=O)[O-])c1)c1ccc(C2=CCC(N3CCCC3c3ccccc3C3CC3)CC2)cc1Oc1cnc2[nH]ccc2c1]

The desired compound was synthesized with (R)-4-(((1,4-dioxan-2-yl)methyl)amino)-3-nitrobenzenesulfonamide and 3-((1H-pyrrolo[2,3-b]pyridin-5-yl)oxy)-4'-(2-(2-cyclopropylphenyl)pyrrolidin-1-yl)-2',3',4',5'-tetrahydro-[1,1'-biphenyl]-4-carboxylic acid following the procedures similar to those in Example G8. $^1$H NMR (400 MHz, DMSO-d$_6$) δ ppm: 12.24 (br, 0.3H), 11.62 (s, 1H), 9.86-9.16 (m, 1H), 8.45 (s, 2H), 7.95 (s, 1H), 7.84-7.34 (m, 4H), 7.34-7.184 (m, 1H), 7.15-6.81 (m, 4H), 6.79-6.64 (m, 1H), 6.74 (s, 1H), 6.34 (s, 1H), 6.34 (s, 1H), 5.99-5.81 (m, 1H), 4.42-4.12 (m, 1H), 3.85-3.70 (m, 3H), 3.70-3.53 (m, 2H), 3.53-3.34 (m, 6H), 3.21-2.81 (m, 2H), 2.35-1.84 (m, 6H), 1.84-1.25 (m, 4H), 1.03-0.77 (m, 2H), 0.77-0.40 (m, 2H). MS (ESI, m/e) [M+1]$^+$ 819.2.

Example G9-a and Example G9-b: (R or S)—N-((4-((((R)-1,4-dioxan-2-yl)methyl)amino)-3-nitrophenyl)sulfonyl)-3-((1H-pyrrolo[2,3-b]pyridin-5-yl)oxy)-4'-((S)-2-(2-cyclopropylphenyl)pyrrolidin-1-yl)-2',3',4',5'-tetrahydro-[1,1'-biphenyl]-4-carboxamide/(S or R)—N-((4-((((R)-1,4-dioxan-2-yl)methyl)amino)-3-nitrophenyl)sulfonyl)-3-((1H-pyrrolo[2,3-b]pyridin-5-yl)oxy)-4'-((S)-2-(2-cyclopropylphenyl)pyrrolidin-1-yl)-2',3',4',5'-tetrahydro-[1,1'-biphenyl]-4-carboxamide

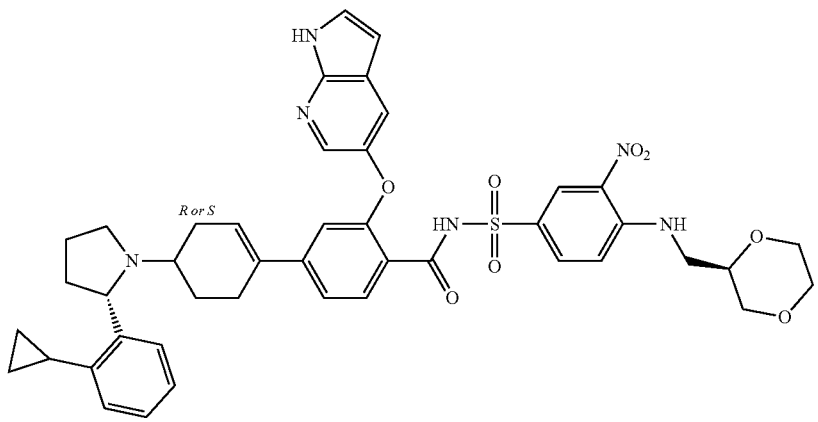

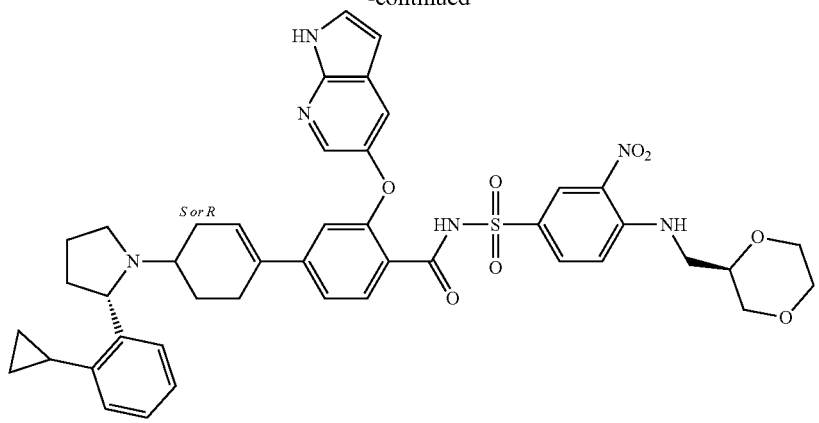

N-((4-((((R)-1,4-dioxan-2-yl)methyl)amino)-3-nitrophenyl)sulfonyl)-3-((1H-pyrrolo[2,3-b]pyridin-5-yl)oxy)-4'-((S)-2-(2-cyclopropylphenyl)pyrrolidin-1-yl)-2',3',4',5'-tetrahydro-[1,1'-biphenyl]-4-carboxamide was synthesized with (R)-4-(((1,4-dioxan-2-yl)methyl)amino)-3-nitrobenzenesulfonamide and 3-((1H-pyrrolo[2,3-b]pyridin-5-yl)oxy)-4'-((S)-2-(2-cyclopropylphenyl)pyrrolidin-1-yl)-2',3',4',5'-tetrahydro-[1,1'-biphenyl]-4-carboxylic acid following the procedures similar to those in Example G8. Then two enantiomers G9-a (faster isomer) and G9-b (slower isomer) were separated by chiral preparative HPLC. The chiral separation conditions are shown below. The faster enantiomer was eluted at retention time of 1.8 min to give G9-a. The slower enantiomer was eluted at retention time of 2.1 min to give G9-b.

| Column | CHIRAL ART Cellulose-SB |
|---|---|
| Column size | 2 cm × 25 cm, 5 um |
| Injection | 0.5 mL |
| Mobile phase | MTBE:[MeOH:DCM = 1:1 (0.1% MSA)] = 50:50 |
| Flow rate | 20 mL/min |
| Wave length | UV 220 nm |
| Temperature | 25° C. |
| Sample solution | 32 mg ml in EtOH:DCM = 3:1 |
| Prep-HPLC equipment | Prep-Gilson-HPLC |

Example G9-a: $^1$H NMR (400 MHz, DMSO-$d_6$) δ ppm: 12.24 (s, 1H), 11.64 (s, 1H), 8.53-8.41 (m, 2H), 7.97 (s, 1H), 7.83-7.66 (m, 1H), 7.60-7.37 (m, 3H), 7.32-7.18 (m, 1H), 7.16-7.02 (m, 3H), 7.01-6.83 (m, 1H), 6.73 (s, 1H), 6.35 (s, 1H), 5.82 (s, 1H), 5.37-5.15 (m, 1H), 4.36-4.22 (m, 1H), 3.82-3.74 (m, 3H), 3.67-3.56 (m, 3H), 3.50-3.37 (m, 3H), 3.24-3.06 (m, 1H), 3.04-2.88 (m, 1H), 2.29-2.12 (m, 3H), 2.10-1.83 (m, 3H), 1.80-1.62 (m, 1H), 1.32-1.18 (m, 2H), 1.02-0.79 (m, 4H), 0.79-0.64 (m, 2H), 0.61-0.47 (m, 1H). MS (ESI, m/e) [M+1]$^+$ 818.8. Example G9-b: $^1$H NMR (400 MHz, DMSO-$d_6$) δ ppm: 12.25 (s, 1H), 11.61 (s, 1H), 8.51-8.37 (m, 2H), 7.95 (s, 1H), 7.83-7.66 (m, 1H), 7.60-7.37 (m, 3H), 7.32-7.18 (m, 1H), 7.16-7.02 (m, 3H), 7.01-6.83 (m, 1H), 6.74 (s, 1H), 6.33 (s, 1H), 5.99 (s, 1H), 5.38-5.03 (m, 1H), 4.36-4.22 (m, 1H), 3.82-3.74 (m, 3H), 3.67-3.56 (m, 3H), 3.50-3.37 (m, 3H), 3.24-3.06 (m, 1H), 3.04-2.91 (m, 1H), 2.29-2.14 (m, 3H), 2.10-1.96 (m, 2H), 1.82-1.64 (m, 2H), 1.23-1.04 (m, 3H), 1.00-0.82 (m, 3H), 0.79-0.64 (m, 2H), 0.61-0.47 (m, 1H), MS (ESI, m/e) [M+1]$^+$ 818.8.

Example G10a and Example G10b: (cis- or leans-) 3-((1H-pyrrolo[2,3-b]pyridin-5-yl)oxy)-4'-(2-(2-cyclopropylphenyl)pyrrolidin-1-yl)-N-((4-((4-hydroxy-4-methylcyclohexyl)methoxy)-3-nitrophenyl)sulfonyl)-2',3',4',5'-tetrahydro-[1,1'-biphenyl]-4-carboxamide; and (trans- or cis-) 3-((1H-pyrrolo[2,3-b]pyridin-5-yl)oxy)-4'-(2-(2-cyclopropylphenyl)pyrrolidin-1-yl)-N-((4-((4-hydroxy-4-methylcyclohexyl)methoxy)-3-nitrophenyl)sulfonyl)-2',3',4',5'-tetrahydro-[1,1'-biphenyl]-4-carboxamide G10a

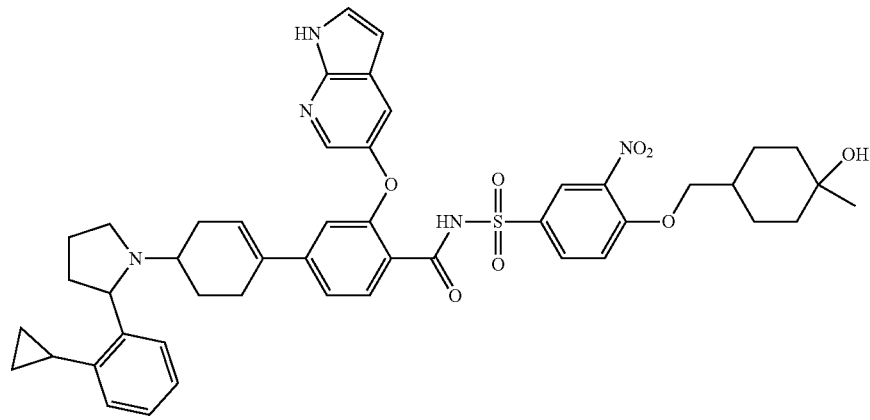 [SMILES: CC1(O)CCC(COc2ccc(S(=O)(=O)NC(=O)c3ccc(C4=CCC(N5CCC[C@H]5c5ccccc5C5CC5)CC4)cc3Oc3cnc4[nH]ccc4c3)cc2[N+](=O)[O-])CC1]

cis- or trans-

G10b

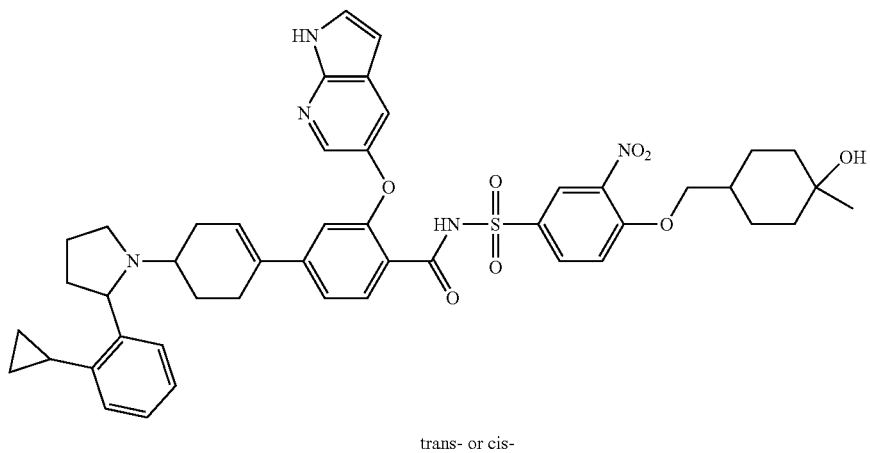

trans- or cis-

Step 1: 4-(hydroxymethyl)-1-methylcyclohexan-1-ol

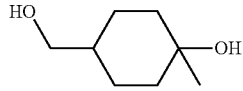

To a solution of 4-(hydroxymethyl)cyclohexan-i-one (1 g, 7.93 mmol) in THF (100 ml) was added CH₃MgBr (1 M in THF solution) (39.6 ml, 39.6 mmol ) at 0° C. for 5 mins. The mixture was stirred at r.t. for 3 hours. Then the reaction mixture was poured into saturated aq. NH₄Cl (200 ml), extracted with ethyl acetate (200 mL×2). The combined organic phase was sequentially washed with brine, dried over Na₂SO₄ and concentrated. The resulted residue was purified by chromatography column on silica (eluent: MeOH/DCM=1/40) to give the product (650 mg, 56.8%) as a yellow oil. MS (ESI, m/e) [M+1]⁺ 127.1.

Step 2: (cis- or trans-) 4-((4-hydroxy-4-methylcyclohexyl)methoxy)-3-nitrobenzenesulfonamide; (trans- or cis-) 4-((4-hydroxy-4-methylcyclohexyl)methoxy)-3-nitrobenzene sulfonamide

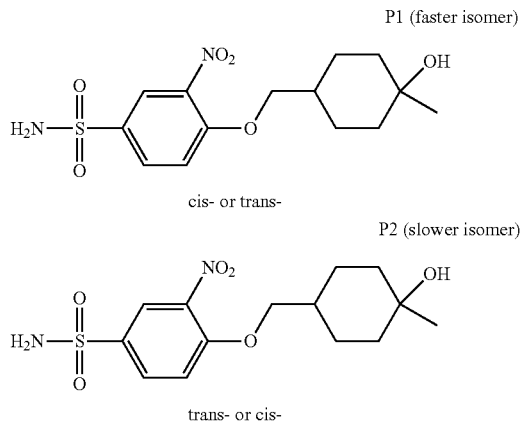

To a solution 4-(hydroxymethyl)-1-methylcyclohexan-1-ol (575 mg, 3.99 mmol) in THF (50 mL) was added NaH (957.6 mg, 23.94 mmol). The mixture was stirred at room temperature for 0.5 hour. Then to the mixture was added 4-fluoro-3-nitrobenzenesulfonamide (616.5 mg, 2.8 mmol). The reaction mixture was stirred at room temperature for 5 days and then was poured into saturated aq. NH₄Cl (200 ml). After extracted with EA (200 mL×3), the combined organic phase was washed with brine, dried over Na₂SO₄, concentrated. The resulted residue was purified by prep-HPLC to give isomer (faster peak) PI (100 mg) as a yellow solid. ¹H NMR (400 MHz, DMSO-d₆) δ ppm: 8.28 (d, J=2.2 Hz, 1H), 8.03 (dd, J=9.0, 2.2 Hz, 1H), 7.56 (d, J=9.0 Hz, 1H), 7.50 (s, 2H), 4.36-4.15 (m, 1H), 4.12 (d, J=5.8 Hz, 3H), 1.82-1.64 (m, 3H), 1.60-1.50 (m, 2H), 1.43-1.30 (m, 2H), 1.30-1.15 (m, 2H), 1.10 (s, 3H); and other isomer (slower peak) P2 (250 mg) as a yellow solid. ¹H NMR (400 MHz, DMSO-d₆) δ ppm: 8.27 (d, J=2.2 Hz, 1H), 8.03 (dd, J=9.0, 2.2 Hz, 1H), 7.57 Cd, J=9.0 Hz, 1H), 7.50 (s, 2H), 4.07 (d, J=6.6 Hz, 2H), 3.92 (s, 1H), 1.76-1.63 (m, 1H), 1.62-1.50 (m, 4H), 1.49-11.35 (m, 2H), 1.34-1.21 (m, 2H), 1.10 (s, 3H).

Step 3: the reaction of 3-((1H-pyrrolo[2,3-b]pyridin-5-yl)oxy)-4'-(2-(2-cyclopropylphenyl)pyrrolidin-1-yl)-2',3',4',5'-tetrahydro-[1,1'-biphenyl]-4-carboxylic acid with P1 following the procedures similar to those in Example G8 the desired compound (310a was afforded, and with P2 following the procedures similar to those in Example G8 the desired compound G10b was afforded.

Compound of Example G10a ¹H NMR (400 MHz, DMSO-d₆) δ ppm: 12.43 (s, 1H), 11.61 (s, 1H), 8.29-8.06 (m, 1H), 7.94 (s, 1H), 7.89-7.73 (m, 1H), 7.72-7.58 (m, 1H), 7.52-7.41 (m, 2H), 7.40-7.23 (m, 2H), 7.17-7.02 (m, 2H), 7.00-6.84 (m, 1H), 6.79-6.61 (m, 1H), 6.34 (s, 1H), 5.98-5.85 (m, 1H), 5.382-5.195 (m, 1H), 4.26 (s, 1H), 3.99 (s, 2H), 3.77-3.57 (m, 1H), 3.54-3.34 (m, 2H), 3.06-2.88 (m, 1H), 2.32-1.81 (m, 7H), 1.79-1.63 (m, 4H), 1.60-1.48 (m, 2H), 1.42-1.29 (m, 3H), 1.24-1.13 (m, 4H), 1.10 (s, 3H), 1.00-0.85 (m, 2H), 0.77-0.55 (m, 2H).

Compound of Example G10b NMR (400 MHz, DMSO-d₆) δ ppm: 12.43 (br, 1H), 11.62 (s, 1H), 8.18 (s, 1H), 7.94 (s, 1H), 7.90-7.76 (m, 1H), 7.71-7.33 (m, 4H), 7.33-6.83 (m, 5H), 6.75 (s, 1H), 6.34 (s, 1H), 5.98 (s, 1H), 5.84 (s, 1H), 5.51-4.98 (m, 1H), 4.46-4.15 (m, 0.3H), 4.09-3.83 (m, 3H), 3.80-3.58 (m, 0.7H), 3.57-3.33 (m, 4H), 2.39-1.79 (m, 7H), 1.77-1.45 (m, 6H), 1.45-1.34 (m, 3H), 1.33-1.17 (m, 3H), 1.09 (s, 3H), 1.02-0.79 (m, 2H), 0.78-0.43 (m, 2H), MS (ESI, m/e) [M+1]$^+$ 846.2.

Example G10b-S: (trans- or cis-)-3-((1H-pyrrolo[2,3-b]pyridin-5-yl)oxy)-4'-((S)-2-(2-cyclopropylphenyl)pyrrolidin-1-yl)-N-((4-((4-hydroxy-4-methylcyclohexyl)methoxy)-3-nitrophenyl)sulfonyl)-2',3',4',5'-tetrahydro-[1,1'-biphenyl]-4-carboxamide

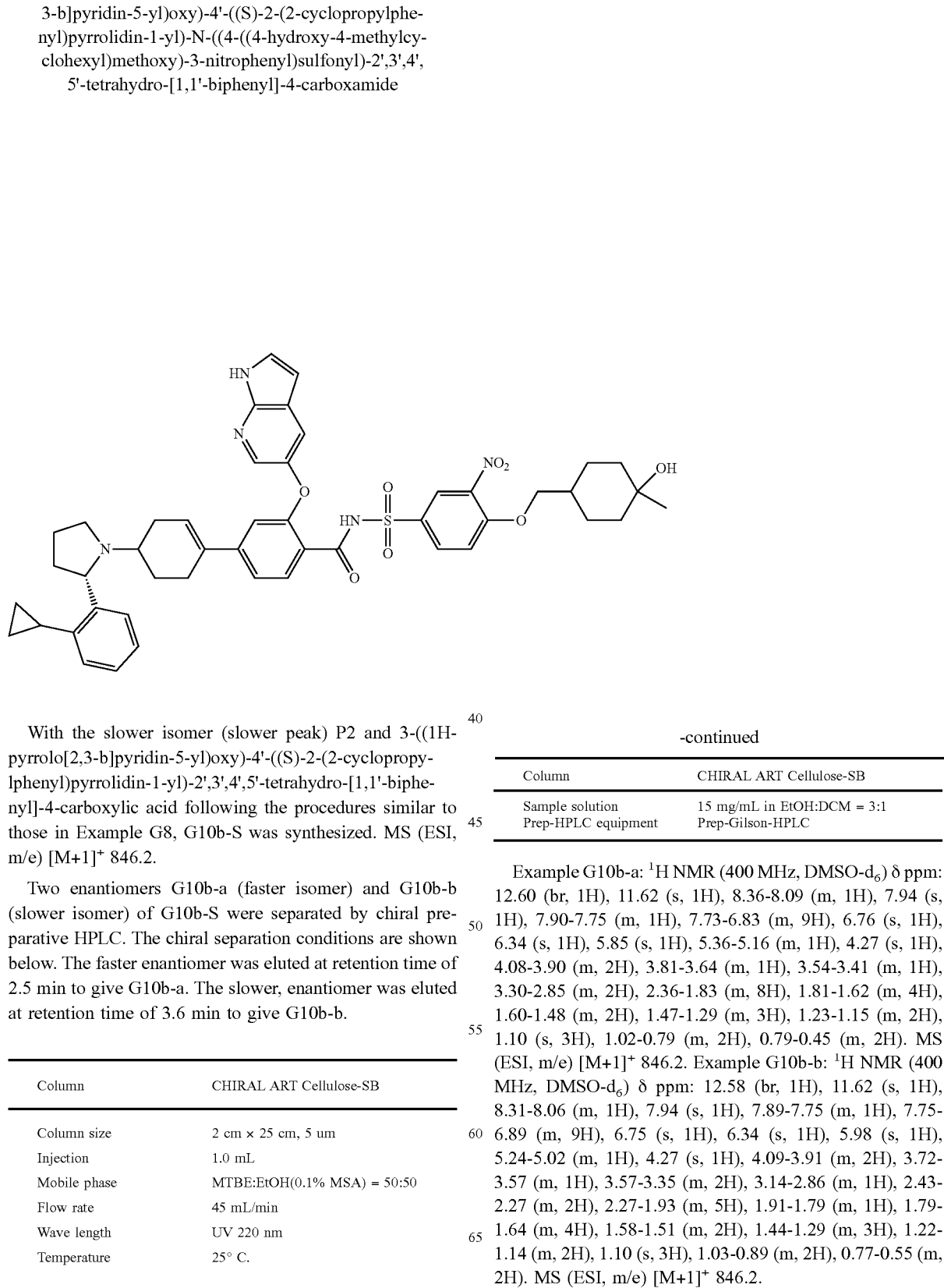

With the slower isomer (slower peak) P2 and 3-((1H-pyrrolo[2,3-b]pyridin-5-yl)oxy)-4'-((S)-2-(2-cyclopropylphenyl)pyrrolidin-1-yl)-2',3',4',5'-tetrahydro-[1,1'-biphenyl]-4-carboxylic acid following the procedures similar to those in Example G8, G10b-S was synthesized. MS (ESI, m/e) [M+1]$^+$ 846.2.

Two enantiomers G10b-a (faster isomer) and G10b-b (slower isomer) of G10b-S were separated by chiral preparative HPLC. The chiral separation conditions are shown below. The faster enantiomer was eluted at retention time of 2.5 min to give G10b-a. The slower, enantiomer was eluted at retention time of 3.6 min to give G10b-b.

| Column | CHIRAL ART Cellulose-SB |
| --- | --- |
| Column size | 2 cm × 25 cm, 5 um |
| Injection | 1.0 mL |
| Mobile phase | MTBE:EtOH(0.1% MSA) = 50:50 |
| Flow rate | 45 mL/min |
| Wave length | UV 220 nm |
| Temperature | 25° C. |

-continued

| Column | CHIRAL ART Cellulose-SB |
| --- | --- |
| Sample solution | 15 mg/mL in EtOH:DCM = 3:1 |
| Prep-HPLC equipment | Prep-Gilson-HPLC |

Example G10b-a: $^1$H NMR (400 MHz, DMSO-d$_6$) δ ppm: 12.60 (br, 1H), 11.62 (s, 1H), 8.36-8.09 (m, 1H), 7.94 (s, 1H), 7.90-7.75 (m, 1H), 7.73-6.83 (m, 9H), 6.76 (s, 1H), 6.34 (s, 1H), 5.85 (s, 1H), 5.36-5.16 (m, 1H), 4.27 (s, 1H), 4.08-3.90 (m, 2H), 3.81-3.64 (m, 1H), 3.54-3.41 (m, 1H), 3.30-2.85 (m, 2H), 2.36-1.83 (m, 8H), 1.81-1.62 (m, 4H), 1.60-1.48 (m, 2H), 1.47-1.29 (m, 3H), 1.23-1.15 (m, 2H), 1.10 (s, 3H), 1.02-0.79 (m, 2H), 0.79-0.45 (m, 2H). MS (ESI, m/e) [M+1]$^+$ 846.2. Example G10b-b: $^1$H NMR (400 MHz, DMSO-d$_6$) δ ppm: 12.58 (br, 1H), 11.62 (s, 1H), 8.31-8.06 (m, 1H), 7.94 (s, 1H), 7.89-7.75 (m, 1H), 7.75-6.89 (m, 9H), 6.75 (s, 1H), 6.34 (s, 1H), 5.98 (s, 1H), 5.24-5.02 (m, 1H), 4.27 (s, 1H), 4.09-3.91 (m, 2H), 3.72-3.57 (m, 1H), 3.57-3.35 (m, 2H), 3.14-2.86 (m, 1H), 2.43-2.27 (m, 2H), 2.27-1.93 (m, 5H), 1.91-1.79 (m, 1H), 1.79-1.64 (m, 4H), 1.58-1.51 (m, 2H), 1.44-1.29 (m, 3H), 1.22-1.14 (m, 2H), 1.10 (s, 3H), 1.03-0.89 (m, 2H), 0.77-0.55 (m, 2H). MS (ESI, m/e) [M+1]$^+$ 846.2.

Example G11: 3-((1H-pyrrolo[2,3-b]pyridin-5-yl)oxy)-4'-(2-(2-cyclopropylphenyl)pyrrolidin-1-yl)-N-((3-nitro-4-(((4-(oxetan-3-yl)morpholin-2-yl)methyl)amino)phenyl)sulfonyl)-2',3',4',5'-tetrahydro-[1,1'-biphenyl]-4-carboxamide

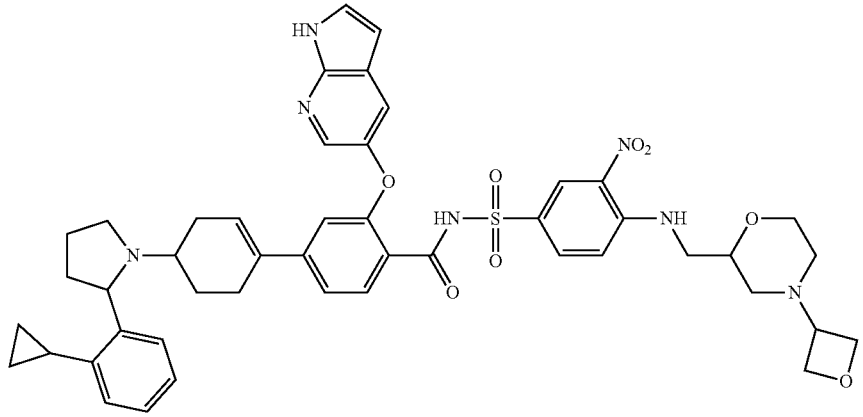 [SMILES: O=C(NS(=O)(=O)c1ccc(NCC2CN(C3COC3)CCO2)c([N+](=O)[O-])c1)c1ccc(C2=CCC(N3CCCC3c3ccccc3C3CC3)CC2)cc1Oc1cnc2[nH]ccc2c1]

To a solution of 3-((1H-pyrrolo[2,3-b]pyridin-5-yl)oxy)-4'-(2-(2-cyclopropylphenyl)pyrrolidin-1-yl)-2',3',4',5'-tetrahydro-[1,1'-biphenyl]-4-carboxylic acid (52 mg, 0.10 mmol) and 3-nitro-4-(((4-(oxetan-3-yl)morpholin-2-yl)methyl)amino)benzenesulfonamide (56 mg, 0.15 mmol) in 15 mL of DCM were added 1-ethyl-3-(3-dimethylaminopropyl)carbodiimide hydrochloride (58 mg, 0.3 mmol), 4-dimethylaminopyridine (37 mg, 0.3 mmol) and triethylamine (0.1 mL). The mixture was stirred at room temperature for 72 h, then it was diluted with water and extracted with DCM:i-PrOH=5:1. The organic layer was combined, dried over sodium sulfate and it was concentrated in vacuum. The residue was purified by chromatography column on silica (eluent: PE/EA=1/2 then DCM/MeOH=10/1 plus 1% $NH_3$—$H_2O$) to give the crude as a yellow gel, which was purified with Pre-HPLC to give the product (1.14 mg, 1.30%). $^1$H NMR (400 MHz, DMSO-$d_6$) δ ppm: 11.64 (s, 1H), 9.95-9.65 (m, 1H), 8.59-8.40 (m, 2H), 8.01-7.91 (m, 1H), 7.81-7.70 (m, 2H), 7.52-7.36 (m, 3H), 7.34-7.23 (m, 1H), 7.15-7.08 (m, 2H), 7.06-7.04 (d, J=8.1 Hz, 2H), 6.98-6.93 (m, 1H), 6.74 (s, 1H), 6.35 (s, 1H), 5.99-5.84 (m, 1H), 5.23-5.13 (m, 1H), 4.55-4.54 (m, 2H), 3.49-4.40 (m, 2H), 3.91-3.83 (m, 2H), 3.80-3.69 (m, 2H), 3.60-3.40 (m, 7H), 2.73-2.67 (m, 2H), 2.63-2.50 (m, 3H), 2.35-2.31 (m, 1H), 2.08-1.90 (m, 4H), 1.82-1.77 (m, 3H), 1.02-0.80 (m, 2H), 0.76-0.50 (m, 1H). MS (ESI, m/e) [M+1]$^+$ 874.2.

Example G12: 3-((1H-pyrrolo[2,3-b]pyridin-5-yl)oxy)-N-((4-((2-oxaspiro[3.5]nonan-7-yl)methoxy)-3-nitrophenyl)sulfonyl)-4'-(2-(2-cyclopropylphenyl)pyrrolidin-1-yl)-2',3',4',5'-tetrahydro-[1,1'-biphenyl]-4-carboxamide

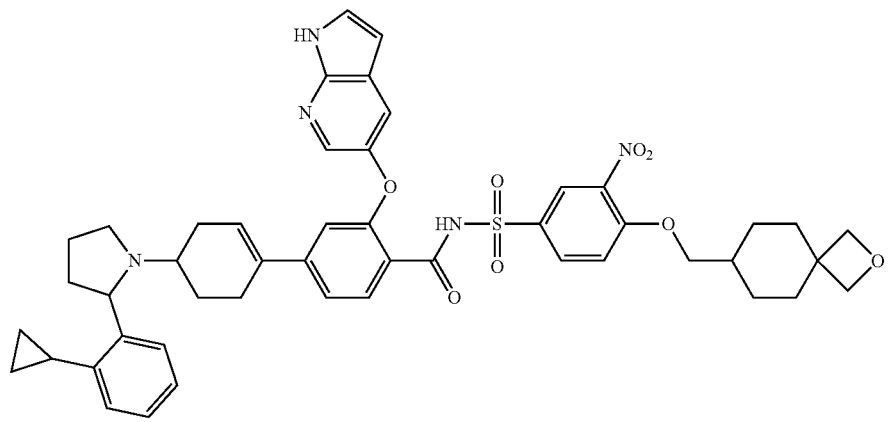 [SMILES: O=C(NS(=O)(=O)c1ccc(OCC2CCC3(CC2)COC3)c([N+](=O)[O-])c1)c1ccc(C2=CCC(N3CCCC3c3ccccc3C3CC3)CC2)cc1Oc1cnc2[nH]ccc2c1]

To a solution of 3-((1H-pyrrolo[2,3-b]pyridin-5-yl)oxy)-4'-(2-(2-cyclopropylphenyl)pyrrolidin-1-yl)-2',3',4',5'-tetrahydro-[1,1'-biphenyl]-4-carboxylic acid (52 mg, 0.10 mmol) and 4-((2-oxaspiro[3.5]nonan-7-yl)methoxy)-3-nitrobenzenesulfonamide (C-8) (53 mg, 0.15 mmol) in 15 mL of DCM were added 1-ethyl-3-(3-dimethylaminopropyl)carbodiimide hydrochloride (58 mg, 0.3 mmol), 4-dimethylaminopyridine (37 mg, 0.3 mmol) and triethylamine (0.1 mL). The mixture was stirred at room temperature for 72 h, then it was diluted with water and extracted with DCM:i-PrOH=10:1. The organic layer was combined, dried over sodium sulfate and was concentrated in vacuum. The residue was purified by chromatography column on silica (eluent: PE/EA=1/2 then DCM/MeOH=10/1) to give the crude as a yellow gel, which was purified with Pre-HPLC to give the product (4.0 mg, 4.67%). $^1$H NMR (400 MHz, DMSO-$d_6$) δ ppm: 11.62 (s, 1H), 9.75-9.52 (m, 1H), 8.19 (s, 1H), 7.94-7.87 (m, 2H), 7.74-7.65 (m, 1H), 7.53-7.44 (m, 2H), 7.43-7.39 (m, 1H), 7.39-7.28 (m, 2H), 7.15-7.04 (m, 3H), 6.74 (s, 1H), 6.34 (s, 1H), 5.97-5.85 (m, 1H), 5.24-5.12 (m, 1H), 4.29 (s, 2H), 4.20 (s, 2H), 3.92-3.91 (d, J=4.9 Hz, 2H), 3.74-3.63 (m, 1H), 3.50-3.33 (m, 2H), 2.36-2.27 (m, 2H), 2.20-1.98 (m, 6H), 1.93-1.84 (m, 2H), 1.75-1.64 (m, 4H), 1.46-1.35 (m, 3H), 1.10-0.85 (m, 5H), 0.77-0.54 (m, 2H). MS (ESI, m/e) [M+1]$^+$858.2.

Example G13: 3-((1H-pyrrolo[2,3-b]pyridin-5-yl)oxy)-N-((4-(((1r,4r)-4-(bis(cyclopropylmethyl)amino)cyclohexyl)amino)-3-nitrophenyl)sulfonyl)-4'-(2-(2-cyclopropylphenyl)pyrrolidin-1-yl)-2',3',4',5'-tetrahydro-[1,1'-biphenyl]-4-carboxamide

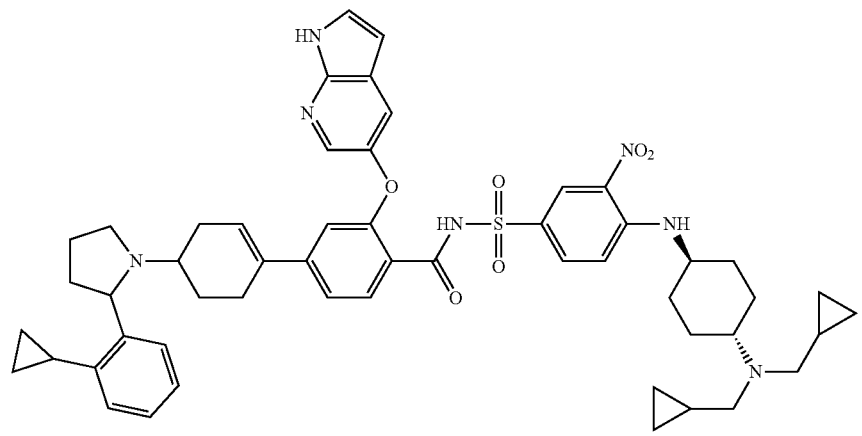 [SMILES: O=C(NS(=O)(=O)c1ccc(N[C@H]2CC[C@H](N(CC3CC3)CC3CC3)CC2)c([N+](=O)[O-])c1)c1ccc(C2=CCC(N3CCCC3c3ccccc3C3CC3)CC2)cc1Oc1cnc2[nH]ccc2c1]

The desired compound was synthesized with 4-(((1r,4r)-4-(bis(cyclopropylmethyl)amino)cyclohexyl)amino)-3-nitrobenzenesulfonamide and 3-((1H-pyrrolo[2,3-b]pyridin-5-yl)oxy)-4'-(2-(2-cyclopropylphenyl)pyrrolidin-1-yl)-2',3',4',5'-tetrahydro-[1,1'-biphenyl]-4-carboxylic acid following the procedures similar to those in Example G8. $^1$H NMR (400 MHz, DMSO-$d_6$) δ ppm: 11.54 (s, 1H), 9.15 (s, 1H), 8.39 (s, 1H), 7.99 (d, J=7.3 Hz, 1H), 7.95-7.88 (m, 1H), 7.76-7.62 (m, 1H), 7.61-7.38 (m, 3H), 7.38-7.26 (m, 1H), 7.14-6.91 (m, 3H), 6.91-6.79 (m, 2H), 6.77-6.66 (m, 1H), 6.35-6.25 (m, 1H), 6.04-5.91 (m, 0.5H), 5.84-5.72 (m, 0.5H), 4.39-4.15 (m, 1H), 3.68-3.41 (m, 2H), 3.23-2.81 (m, 5H), 2.62-2.52 (m, 3H), 2.41-2.30 (m, 1H), 2.30-1.86 (m, 10H), 1.81-1.61 (m, 4H), 1.55-1.31 (m, 4H), 1.23-1.08 (m, 2H), 0.97-0.78 (m, 2H), 0.76-0.59 (m, 4H), 0.58-0.29 (m, 5H). MS (ESI, m/e) [M+1]$^+$ 924.3.

Example G16: 3-((1H-pyrrolo[2,3-b]pyridin-5-yl)oxy)-N-((4-(((4-cyclopropylmorpholin-2-yl)methyl)amino)-3-nitrophenyl)sulfonyl)-4'-(2-(2-cyclopropylphenyl)pyrrolidin-1-yl)-2',3',4',5'-tetrahydro-[1,1'-biphenyl]-4-carboxamide

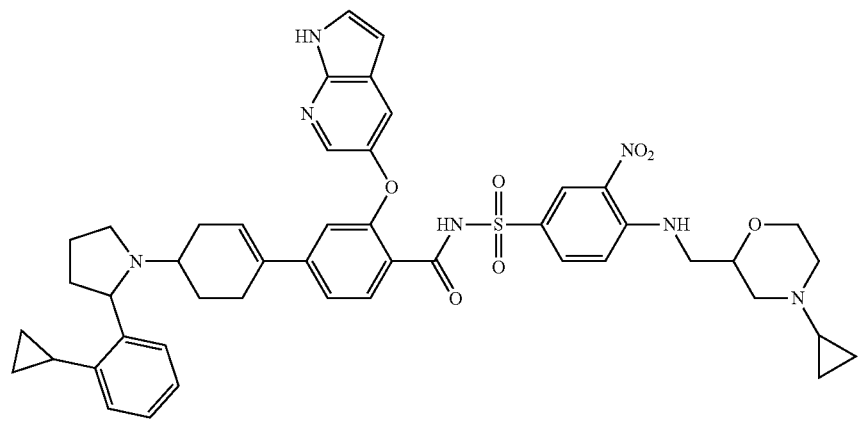 [SMILES: O=C(NS(=O)(=O)c1ccc(NCC2CN(C3CC3)CCO2)c([N+](=O)[O-])c1)c1ccc(C2=CCC(N3CCCC3c3ccccc3C3CC3)CC2)cc1Oc1cnc2[nH]ccc2c1]

The desired compound was synthesized with 4-(((4-cyclopropylmorpholin-2-yl)methyl)amino)-3-nitrobenzenesulfonamide and 3-((1H-pyrrolo[2,3-b]pyridin-5-yl)oxy)-4'-(2-(2-cyclopropylphenyl)pyrrolidin-1-yl)-2',3',4',5'-tetrahydro-[1,1'-biphenyl]-4-carboxylic acid following the procedures similar to those in Example G8. $^1$H NMR (400 MHz, DMSO-d$_6$) δ ppm: 12.20-12.16 (m, 1H), 11.63 (s, 1H), 8.56-8.40 (m, 2H), 8.01-7.91 (m, 1H), 7.76-7.68 (m, 1H), 7.54-7.33 (m, 3H), 7.33-7.23 (m, 1H), 7.16-7.00 (m, 2H), 7.00-6.86 (m, 2H), 6.80-6.64 (m, 1H), 6.36-6.28 (s, 1H), 6.02-5.77 (m, 1H), 4.31-4.22 (m, 1H), 3.96-3.88 (m, 1H), 3.85-3.75 (m, 2H), 3.66-3.55 (m, 2H), 3.52-3.33 (m, 3H), 3.05-2.98 (m, 2H), 2.96-2.86 (m, 2H), 2.78-2.66 (m, 2H), 2.37-2.27 (m, 2H), 2.23-2.09 (m, 3H), 2.05-1.93 (m, 2H), 1.76-1.63 (m, 4H), 0.98-0.78 (m, 4H), 0.48-0.29 (m, 3H). MS (ESI, m/e) [M+1]$^+$ 858.2.

Example G18: 3-((1H-pyrrolo[2,3-b]pyridin-5-yl)oxy)-4'-(2-(2-cyclopropylphenyl)pyrrolidin-1-yl)-N-((4-(((4-(dimethylglycyl)morpholin-2-yl)methyl)amino)-3-nitrophenyl)sulfonyl)-2',3',4',5'-tetrahydro-[1,1'-biphenyl]-4-carboxamide

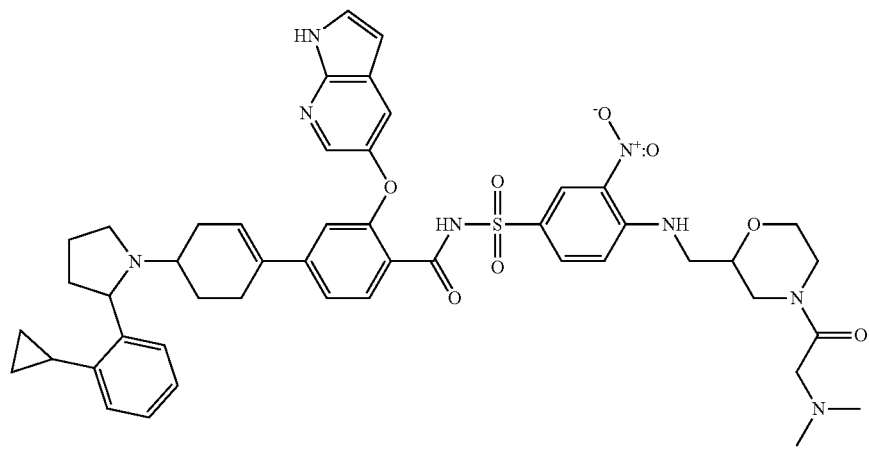

The desired compound was synthesized with 4-(((4-(dimethylglycyl)morpholin-2-yl)methyl)amino)-3-nitrobenzenesulfonamide and 3-((1H-pyrrolo[2,3-b]pyridin-5-yl)oxy)-4'-(2-(2-cyclopropylphenyl)pyrrolidin-1-yl)-2',3',4',5'-tetrahydro-[1,1'-biphenyl]-4-carboxylic acid following the procedures similar to those in Example G8. $^1$H NMR (400 MHz, DMSO-d$_6$) δ ppm: 11.56 (s, 1H), 8.46-8.35 (m, 2H), 7.93 (s, 1H), 7.81-7.62 (m, 1H), 7.59-7.41 (m, 3H), 7.38-7.33 (m, 1H), 7.15-7.04 (m, 2H), 7.02-6.86 (m, 3H), 6.75-6.70 (m, 1H), 6.33-6.28 (m, 1H), 6.02-5.77 (m, 1H), 4.39-4.24 (m, 2H), 4.16-4.10 (m, 1H), 3.98-3.88 (m, 2H), 3.82-3.74 (m, 1H), 3.64-3.55 (m, 2H), 3.52-3.47 (m, 2H), 3.23-3.10 (m, 1H), 3.06-2.98 (m, 1H), 2.90-2.75 (m, 1H), 2.66-2.52 (m, 8H), 2.29-2.11 (m, 3H), 2.07-1.94 (m, 2H), 1.81-1.65 (m, 3H), 1.51-1.30 (m, 2H), 0.96-0.78 (m, 3H), 0.69-0.60 (m, 1H), 0.59-0.48 (m, 1H). MS (ESI, m/e) [M+1]$^+$ 903.2.

Example G20: 3-((1H-pyrrolo[2,3-b]pyridin-5-yl)oxy)-4'-(2-(2-cyclopropylphenyl)pyrrolidin-1-yl)-N-((3-nitro-4-((tetrahydro-2H-pyran-4-yl)methoxy)phenyl)sulfonyl)-2',3',4',5'-tetrahydro-[1,1'-biphenyl]-4-carboxamide

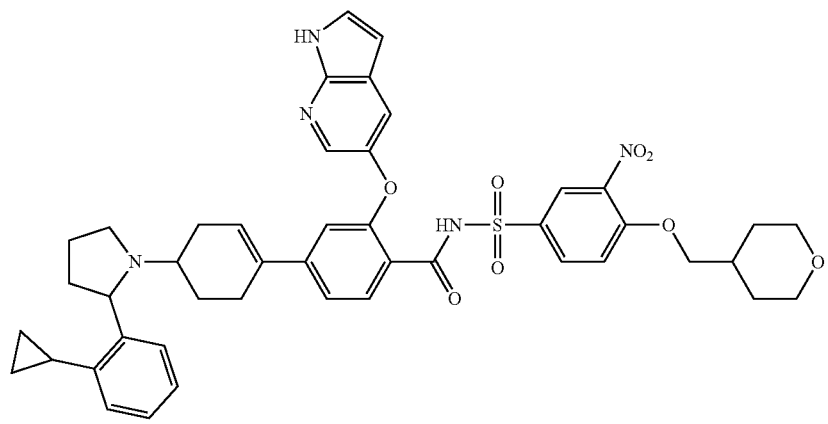 [SMILES: O=C(NS(=O)(=O)c1ccc(OCC2CCOCC2)c([N+](=O)[O-])c1)c1ccc(C2=CCC(N3CCCC3c3ccccc3C3CC3)CC2)cc1Oc1cnc2[nH]ccc2c1]

The desired compound was synthesized with 3-nitro-4-((tetrahydro-2H-pyran-4-yl)methoxy)benzenesulfonamide and 3-((1H-pyrrolo[2,3-b]pyridin-5-yl)oxy)-4'-(2-(2-cyclopropylphenyl)pyrrolidin-1-yl)-2',3',4',5'-tetrahydro[1,1'-biphenyl]-4-carboxylic acid following the procedures similar to those in Example G8. $^1$H NMR (400 MHz, DMSO-d$_6$) δ ppm: 11.57 (s, 1H), 9.876-9.349 (m, 0.7H), 8.14 (s, 1H), 7.92 (s, 1H), 7.87-7.71 (m, 1H), 7.54-7.39 (m, 2H), 7.39-7.17 (m, 2H), 7.17-6.76 (m, 4H), 6.76-6.60 (m, 1H), 6.32 (s, 1H), 6.05-5.69 (m, 1H), 5.41-5.03 (m, 1H), 4.36-4.18 (m, 1H), 3.98 (d, J=5.9 Hz, 2H), 3.92-3.80 (m, 2H), 3.20-2.81 (m, 2H), 2.29-1.81 (m, 6H), 1.80-1.52 (m, 4H), 1.52-1.23 (m, 7H), 1.01-0.85 (m, 2H), 0.78-0.42 (m, 2H). MS (ESI, m/e) [M+1]$^+$ 818.2.

Example G24b: (trans- or cis-)-3-((1H-pyrrolo[2,3-b]pyridin-5-yl)oxy)-4'-(2-(2 cyclopropylphenyl) pyrrolidin-1-yl)-N-((4-(((4-hydroxy-4-methylcyclohexyl)methyl)amino)-3-nitrophenyl)sulfonyl)-2',3', 4',5'-tetrahydro-[1,1'-biphenyl]-4-carboxamide

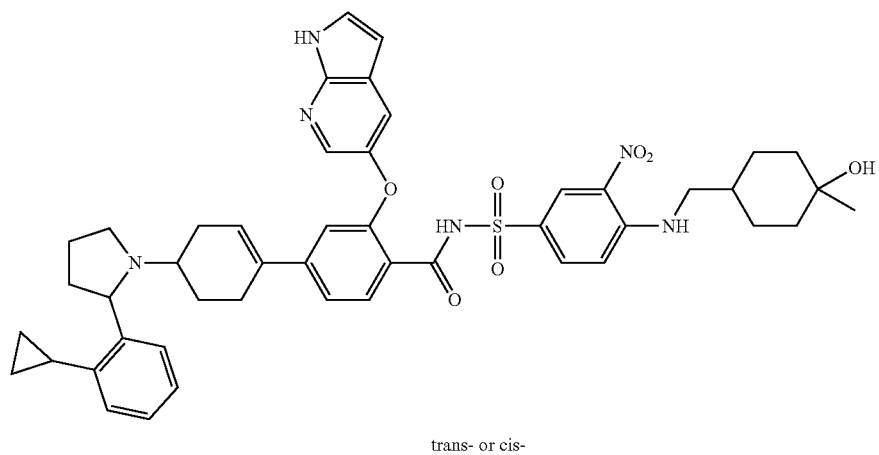 [SMILES: CC1(O)CCC(CNc2ccc(S(=O)(=O)NC(=O)c3ccc(C4=CCC(N5CCCC5c5ccccc5C5CC5)CC4)cc3Oc3cnc4[nH]ccc4c3)cc2[N+](=O)[O-])CC1]

trans- or cis-

Step 1: tert-butyl ((4-hydroxy-4-methylcyclohexyl)methyl)carbamate

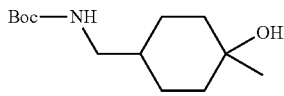

To a solution of tert-butyl ((4-oxocyclohexyl)methyl) carbamate (500 mg, 2.2 mmol) in THE (500 mL) was added CH$_3$MgBr (1 M solution in THE) (8.8 ml, 8.8 mmol) at −78° C. for 15 mins. After addition, the reaction mixture was stirred at −78° C. for 2 hours and then at 0° C. for 3 hours. The mixture was poured into saturated aq. NH$_4$Cl (200 mL), extracted with EA (200 mL×3). The combined organic phase was concentrated to give the crude product, which was used directly for next step.

Step 2: 4-(aminomethyl)-1-methylcyclohexan-1-ol 2,2,2-trifluoroacetate

To a solution of tert-butyl ((4-hydroxy-4-methylcyclohexyl)methyl)carbamate (535 mg, 2.2 mmol) in DCM (50 mL) was added TFA (10 mL). After addition, the reaction mixture was stirred at room temperature overnight. The mixture was then concentrated in vacuum to remove solvent, and the crude product was obtained, which was used directly for next step without no further purification.

Step 3: (cis- or trans-)-4-(((4-hydroxy-4-methylcyclohexyl)methyl)amino)-3-nitrobenzenesulfonamide; (trans- or cis-)-4-(((4-hydroxy-4-methylcyclohexyl)methyl)amino)-3-nitrobenzenesulfonamide

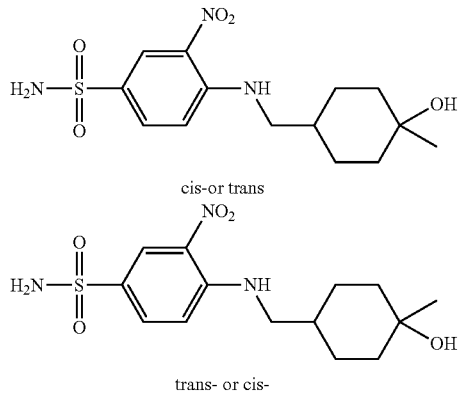

cis- or transtrans- or cis-

To a solution 4-(aminomethyl)-1-methylcyclohexan-1-ol 2,2,2-trifluoroacetate (566 mg, 2.2 mmol) in THF (50 mL) was added 4-fluoro-3-nitrobenzenesulfonamide (484 mg, 2.2 mmol), and triethylamine (1.1 g, 11 mmol). The mixture was stirred at room temperature overnight. After removal of solvent, the resulted residue was purified by chromatography column on silica (eluent: MeOH/DCM=1/40) to give the crude product. The crude product was further purified by prep-HPLC to give the product PI (fast peak, 80 mg) as a yellow solid. MS (ESI, m/e) [M+1]$^+$ 344.0; and product P2 (slower, 150 mg) as a yellow solid. $^1$H NMR (400 MHz, DMSO-$d_6$) δ ppm: 8.57 (t, J=5.6 Hz, 1H), 8.46 (d, J=2.2 Hz, 1H), 7.82 (dd, J=9.2, 2.2 Hz, 1H), 7.32 (s, 2H), 7.26 (d, J=9.2 Hz, 1H), 3.95 (s, 1H), 3.32-3.28 (m, 2H), 1.65-1.31 (m, 7H), 1.28-1.20 (m, 2H), 1.08 (s, 3H). MS (ESI, m/e) [M+1]$^+$ 326.0

Then with P2 ((trans- or cis-)-4-(((4-hydroxy-4-methylcyclohexyl)methyl)amino)-3-nitrobenzenesulfonamide) and 3-((1H-pyrrolo[2,3-h]pyridin-5-yl)oxy)-4'-(2-(2-cyclopropylphenyl)pyrrolidin-1-yl)-2',3',4',5'-tetrahydro-[1,1'-biphenyl]-4-carboxylic acid following the procedures similar to those in Example G8, the desired compound was afforded. $^1$H NMR (400 MHz, DMSO-$d_6$) δ ppm: 12.21 (br, 1H), 11.64 (s, 1H), 8.68-8.19 (m, 2H), 7.96 (s, 1H), 7.83-7.20 (m, 6H), 7.18-6.79 (m, 4H), 6.73 (s, 1H), 6.35 (s, 1H), 6.05-5.74 (m, 1H), 5.46-4.86 (m, 1H), 4.38-4.13 (m, 1H), 3.95 (s, 1H), 3.83-3.56 (m, 1H), 3.26-3.10 (m, 3H), 3.05-2.89 (m, 1H), 2.26-1.87 (m, 5H), 1.71-1.62 (m, 1H), 1.62-1.30 (m, 9H), 1.30-1.15 (m, 3H), I. 07 (s, 3H), 1.00-0.77 (m, 2H), 0.75-0.42 (m, 2H). MS (ESI, m/e) [M+1]$^+$ 845.2.

Two enantiomers G24b-a (faster isomer) and G24b-b (slower isomer) of (trans- or cis-) 3-((1H-pyrrolo[2,3-b]pyridin-5-yl)oxy)-4'-(2-(S)-(2-cyclopropylphenyl)pyrrolidin-1-yl)-N-((4-(((4-hydroxy-4-methylcyclohexyl)methyl)amino)-3-nitrophenyl)sulfonyl)-2',3',4',5'-tetrahydro-[1,1'-biphenyl]-4-carboxamide were separated by chiral preparative HPLC, The chiral separation conditions are shown below. The faster enantiomer was eluted at retention time of 2.6 min to give G24b-a. The slower enantiomer was eluted at retention time of 3.8 min to give G24b-b.

| Column | CHIRAL ART Cellulose-SB |
|---|---|
| Column size | 2 cm × 25 cm, 5 um |
| Injection | 1.0 mL |
| Mobile phase | MtBE:EtOH (0.2% MSA) = 50:50 |
| Flow rate | 95 mL/min |
| Wave length | UV 220 nm |
| Temperature | 25° C. |
| Sample solution | 28 mg/mL in EtOH:DCM = 3:1 |
| Prep-HPLC equipment | Prep-HPLC-YMC |

Example G24b-a: $^1$H NMR (400 MHz, DMSO-$d_6$) δ ppm: 12.38-12.06 (m, 0.5H). 11.64 (s, 1H), 9.47-9.10 (m, 0.5H), 8.65-8.28 (m, 2H), 7.97 (s, 1H), 7.82-7.67 (m, 1H), 7.67-7.35 (m, 4H), 7.35-6.82 (m, 5H), 6.73 (s, 1H), 6.35 (s, 1H), 5.82 (s, 1H), 5.41-5.04 (m, 0.5H), 4.41-4.27 (m, 0.5H), 4.24 (s, 1H), 3.78-3.32 (m, 2H), 3.27-3.11 (m, 3H), 2.67-2.54 (m, 1H), 2.33-1.86 (m, 7H), 1.81-1.46 (m, 8H), 1.39-1.28 (m, 2H), 1.19-1.02 (m, 5H), 0.99-0.79 (m, 2H), 0.76-0.42 (m, 2H). MS (ESI, m/e) [M+1]$^+$ 844.8. Example G24b-b: $^1$H NMR (400 MHz, DMSO-$d_6$) δ ppm: 12.48-11.94 (m, 0.5H), 11.64 (s, 1H), 9.74-9.13 (m, 0.5H), 8.60-8.27 (m, 2H), 7.96 (s, 1H), 7.85-6.79 (m, 10H), 6.73 (s, 1H), 6.46-6.27 (m, 1H), 6.04-5.91 (m, 1H), 5.37-4.75 (m, 0.5H), 4.54-4.29 (m, 0.5H), 4.24 (s, 1H), 3.69-3.33 (m, 2H), 3.27-3.01 (m, 3H), 2.75-2.50 (m, 2H), 2.45-1.89 (m, 7H), 1.87-1.46 (m, 7H), 1.38-1.26 (m, 2H), 1.19-0.97 (m, 5H), 0.97-0.78 (m, 2H), 0.76-0.44 (m, 2H). MS (ESI, m/e) [M+1]$^+$ 844.8.

Example G27: 3-((1H-pyrrolo[2,3-b]pyridin-5-yl)oxy)-4'-(2-(2-cyclopropylphenyl)pyrrolidin-1-yl)-N-((4-((morpholin-2-ylmethyl)amino)-3-nitrophenyl)sulfonyl)-2',3',4',5'-tetrahydro-[1,1'-biphenyl]-4-carboxamide

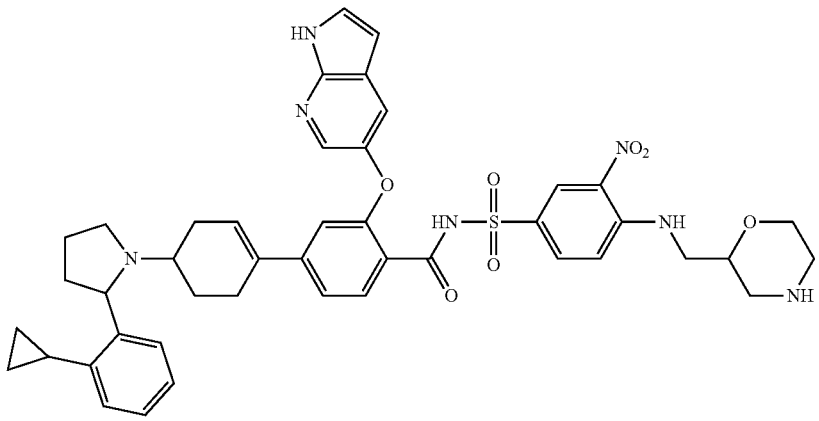 [SMILES: O=C(NS(=O)(=O)c1ccc(NCC2CNCCO2)c([N+](=O)[O-])c1)c1ccc(C2=CCC(N3CCCC3c3ccccc3C3CC3)CC2)cc1Oc1cnc2[nH]ccc2c1]

The desired compound was synthesized with 4-((morpholin-2-ylmethyl)amino)-3-nitrobenzenesulfonamide and 3-((1H-pyrrolo[2,3-b]pyridin-5-yl)oxy)-4'-(2-(2-cyclopropylphenyl)pyrrolidin-1-yl)-2',3',4',5'-tetrahydro-[1,1'-biphenyl]-4-carboxylic acid following the procedures similar to those in Example G8. $^1$H NMR (400 MHz, DMSO-$d_6$) δ ppm: 11.57 (s, 1H), 8.45-8.28 (m, 2H), 7.91 (s, 1H), 7.70-7.61 (m, 1H), 7.57-7.44 (m, 2H), 7.43-7.39 (m, 1H), 7.31-7.26 (m, 1H), 7.11-7.03 (m, 2H), 7.02-6.98 (m, 1H), 6.95-6.83 (m, 2H), 6.77-6.69 (m, 1H), 6.30 (s, 1H), 6.00-5.78 (m, 1H), 4.32-4.20 (m, 1H), 4.00-3.86 (m, 2H), 3.78-3.67 (m, 1H), 3.58-3.48 (m, 1H), 3.24-3.14 (m, 3H), 3.09-3.01 (m, 1H), 2.93-2.86 (m, 1H), 2.81-2.71 (m, 1H), 2.65-2.52 (m, 2H), 2.31-2.11 (m, 2H), 2.05-1.95 (m, 2H), 1.82-1.65 (m, 2H), 1.58-1.41 (m, 3H), 0.85-0.42 (m, 7H). MS (ESI, m/e) [M+1]$^+$ 818.8.

Example G30: 3-((1H-pyrrolo[2,3-b]pyridin-5-yl)oxy)-4'-(2-(2-cyclopropylphenyl)pyrrolidin-1-yl)-N-((4-(((4-fluorotetrahydro-2H-pyran-4-yl)methyl)amino)-3-nitrophenyl)sulfonyl)-2',3',4',5'-tetrahydro-[1,1'-biphenyl]-4-carboxamide

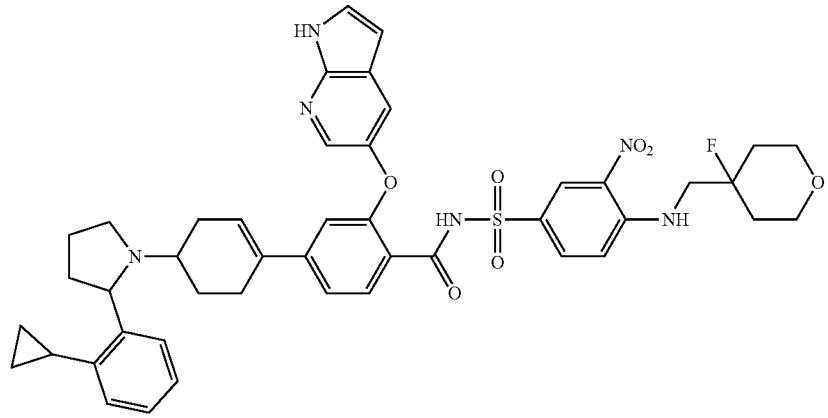 [SMILES: O=C(NS(=O)(=O)c1ccc(NCC2(F)CCOCC2)c([N+](=O)[O-])c1)c1ccc(C2=CCC(N3CCCC3c3ccccc3C3CC3)CC2)cc1Oc1cnc2[nH]ccc2c1]

The desired compound was synthesized with 4-(((4-fluorotetrahydro-2H-pyran-4-yl)methyl)amino)-3-nitrobenzenesulfonamide and 3-((1H-pyrrolo[2,3-b]pyridin-5-yl)oxy)-4'-(2-(2-cyclopropylphenyl)pyrrolidin-1-yl)-2',3',4',5'-tetrahydro-[1,1'-biphenyl]-4-carboxylic acid following the procedures similar to those in Example G8, and was afforded. $^1$H NMR (400 MHz, DMSO-$d_6$) δ ppm: 12.20 (br, 1H), 11.60 (s, 1H), 8.46 (s, 2H), 7.95 (s, 1H), 7.84-7.65 (m, 1H), 7.60-7.36 (m, 3H), 7.35-6.82 (m, 5H), 6.73 (s, 1H), 6.33 (s, 1H), 6.06-5.74 (m, 1H), 5.40-4.85 (m, 1H), 4.42-4.14 (m, 1H), 3.79-3.60 (m, 4H), 3.60-3.47 (m, 2H), 3.46-3.30 (m, 5H), 3.21-2.85 (m, 2H), 2.34-1.91 (m, 5H), 1.90-1.63 (m, 5H), 1.47-1.23 (m, 1H), 1.01-0.79 (m, 1H), 0.76-0.44 (m, 2H). MS (ESI, m/e) [M+1]$^+$ 819.1.

Example G30-S: 3-((1H-pyrrolo[2,3-b]pyridin-5-yl)oxy)-4'-((S)-2-(2-cyclopropylphenyl)pyrrolidin-1-yl)-N-((4-(((4-fluorotetrahydro-2H-pyran-4-yl)methyl)amino)-3-nitrophenyl)sulfonyl)-2',3',4',5'-tetrahydro-[1,1'-biphenyl]-4-carboxamide

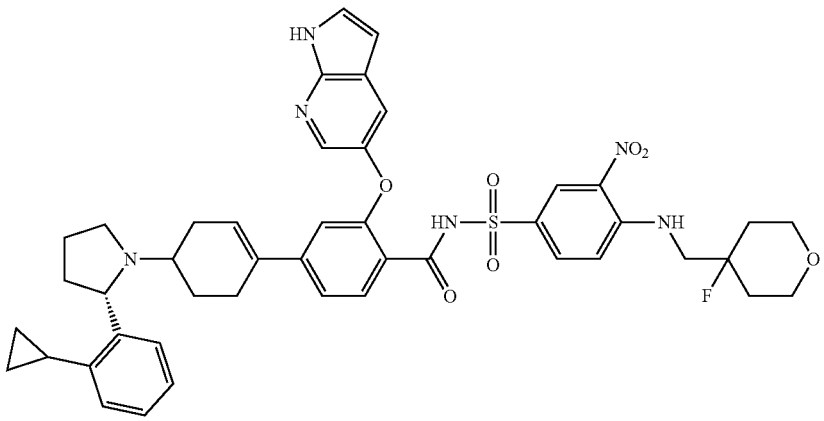 [SMILES: O=C(NS(=O)(=O)c1ccc(NCC2(F)CCOCC2)c([N+](=O)[O-])c1)c1ccc(C2=CCC(N3CCC[C@H]3c3ccccc3C3CC3)CC2)cc1Oc1cnc2[nH]ccc2c1]

The desired compound was synthesized with 4-(((4-fluorotetrahydro-2H-pyran-4-yl)methyl)amino)-3-nitrobenzenesulfonamide and 3-((1H-pyrrolo[2,3-b]pyridin-5-yl)oxy)-4'-((S)-2-(2-cyclopropylphenyl)pyrrolidin-1-yl)-2',3',4',5'-tetrahydro-[1,1'-biphenyl]-4-carboxylic acid following the procedures similar to those in Example G8. MS (ESI, m/e) [M+1]$^+$ 834.8.

Two enantiomers G30-a (faster isomer) and G30-b (slower isomer) of G30-S were separated by chiral preparative HPLC. The chiral separation conditions are shown below. The faster enantiomer was eluted at retention time of 3.6 min to give G30-a. The slower enantiomer was eluted at retention time of 5.5 min to give G30-b.

| Column | CHIRAL ART Cellulose-SB |
| --- | --- |
| Column size | 2 cm × 25 cm, 5 um |
| Injection | 1.5 mL |
| Mobile phase | MTBE:EtOH (0.1% MSA) = 50:50 |
| Flow rate | 20 mL/min |
| Wave length | UV 220 nm |
| Temperature | 25° C. |
| Sample solution | 7 mg/mL in EtOH:DCM = 3:1 |
| Prep-HPLC equipment | Prep-Gilson-HPLC |

Example G30-a: $^1$H NMR (400 MHz, DMSO-d$_6$) δ ppm: 12.57 (br, 1H), 11.61 (s, 1H), 8.65-8.24 (m, 2H), 7.95 (s, 1H), 7.85-7.64 (m, 1H), 7.64-7.31 (m, 4H), 7.31-6.81 (m, 5H), 6.72 (s, 1H), 6.33 (s, 1H), 5.81 (s, 1H), 5.43-5.01 (m, 0.3H), 4.48-4.16 (m, 1H), 4.01-3.59 (m, 4H), 3.59-3.45 (m, 2H), 3.32-2.95 (m, 2H), 2.48-1.88 (m, 8H), 1.88-1.23 (m, 8H), 1.00-0.79 (m, 2H), 0.75-0.41 (m, 2H). [M+1]$^+$ 834.8.

Example G30b: $^1$H NMR (400 MHz, DMSO-d$_6$) δ ppm: 12.51-12.04 (m, 0.4H), 11.62 (s, 1H), 10.39-9.96 (m, 0.4H), 8.62-8.25 (m, 2H), 7.91-7.83 (m, 2H), 7.95 (s, 1H), 7.60-6.85 (m, 8H), 6.73 (s, 1H), 6.33 (s, 1H), 5.98 (s, 1H), 5.28-4.89 (m, 0.5H), 4.47-3.98 (m, 0.7H), 3.81-3.61 (m, 4H), 3.59-3.45 (m, 2H), 3.32-2.79 (m, 2H), 2.49-1.95 (m, 2H), 1.94-1.23 (m, 8H), 1.04-0.79 (m, 2H), 0.78-0.42 (m, 2H). (MS (ESI, m/e) [M+1]$^+$834.8

Example G30-R: 3-((1H-pyrrolo[2,3-b]pyridin-5-yl)oxy)-4'-((R)-2-(2-cyclopropylphenyl)pyrrolidin-1-yl)-N-((4-(((4-fluorotetrahydro-2H-pyran-4-yl)methyl)amino)-3-nitrophenyl)sulfonyl)-2',3',4',5'-tetrahydro-[1,1'-biphenyl]-4-carboxamide

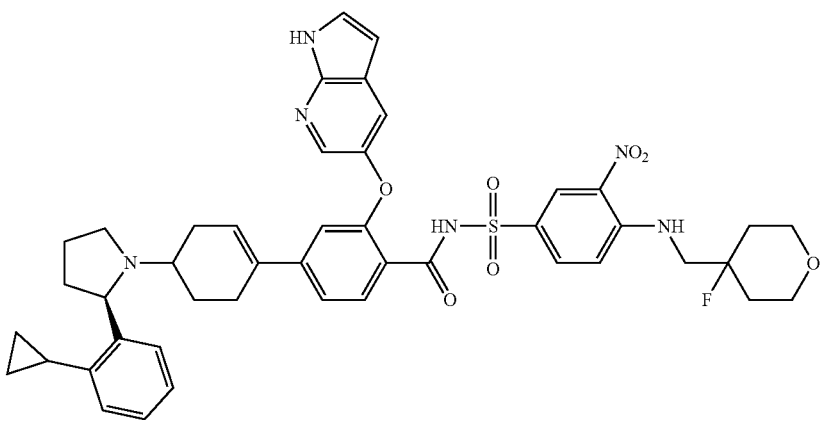 [SMILES: O=C(NS(=O)(=O)c1ccc(NCC2(F)CCOCC2)c([N+](=O)[O-])c1)c1ccc(C2=CCC(N3CCC[C@@H]3c3ccccc3C3CC3)CC2)cc1Oc1cnc2[nH]ccc2c1]

The desired compound was synthesized with 4-(((4-fluorotetrahydro-2H-pyran-4-yl)methyl)amino)-3-nitrobenzenesulfonamide and 3-((1H-pyrrolo[2,3-b]pyridin-5-yl)oxy)-4'-((R)-2-(2-cyclopropylphenyl)pyrrolidin-1-yl)-2',3',4',5'-tetrahydro-[1,1'-biphenyl]-4-carboxylic acid following the procedures similar to those in Example (38, MS (ESI, m/e) [M+1]$^+$ 834.8

Example G31: 3-((1H-pyrrolo[2,3-b]pyridin-5-yl)oxy)-4'-(2-(2-cyclopropylphenyl)pyrrolidin-1-yl)-N-((4-(((4-methylmorpholin-2-yl)methyl)amino)-3-nitrophenyl)sulfonyl)-2',3',4',5'-tetrahydro-[1,1'-biphenyl]-4-carboxamide

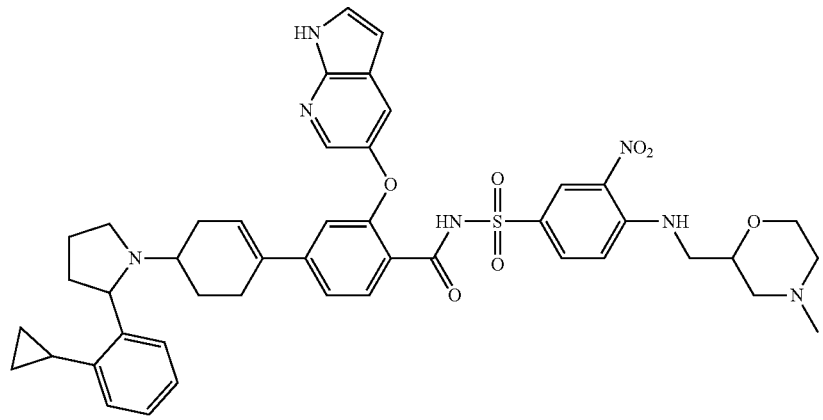 [SMILES: CN1CCOC(CNc2ccc(S(=O)(=O)NC(=O)c3ccc(C4=CCC(N5CCCC5c5ccccc5C5CC5)CC4)cc3Oc3cnc4[nH]ccc4c3)cc2[N+](=O)[O-])C1]

The desired compound was synthesized with 4-(((4-methylmorpholin-2-yl)methyl)amino)-3-nitrobenzenesulfonamide and 3-((1H-pyrrolo[2,3-b]pyridin-5-yl)oxy)-4'-(2-(2-cyclopropylphenyl)pyrrolidin-1-yl)-2',3',4',5'-tetrahydro-[1,1'-biphenyl]-4-carboxylic acid following the procedures similar to those in Example G8. $^1$H NMR (400 MHz, DMSO-d$_6$) δ ppm: 11.62 (s, 1H), 8.47 (s, 2H), 7.95 (s, 1H), 7.74 (s, 1H), 7.60-7.34 (m, 4H), 7.29-7.21 (m, 1H), 7.11-7.10 (m, 2H), 6.98-6.89 (m, 2H), 6.73-6.69 (m, 1H), 6.34 (s, 1H), 5.99-5.80 (m, 1H), 4.29 (s, 1H), 3.91 (s, 1H), 3.80 (s, 1H), 3.63-3.57 (m, 1H), 3.51-3.44 (m, 2H), 3.12-2.99 (m, 7H), 2.45-2.40 (m, 1H), 2.20-2.12 (m, 4H), 2.02-1.97 (m, 4H), 1.71 (s, 2H), 1.47-1.44 (m, 2H), 1.28 (s, 2H), 0.96-0.84 (m, 4H). MS (ESI, m/e) [M+1]$^+$ 832.8.

Example G32: 3-((1H-pyrrolo[2,3-b]pyridin-5-yl)oxy)-N-((4-(((4-acetylmorpholin-2-yl)methyl)amino)-3-nitrophenyl)sulfonyl)-4'-(2-(2-cyclopropylphenyl)pyrrolidin-1-yl)-2',3',4',5'-tetrahydro-[1,1'-biphenyl]-4-carboxamide

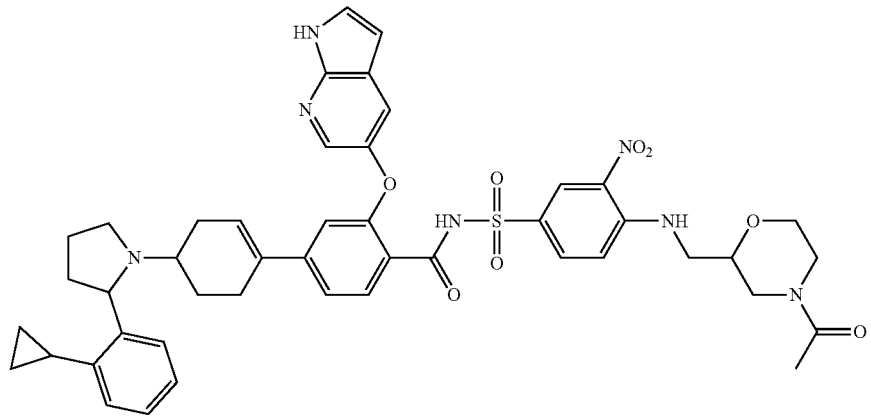 [SMILES: CC(=O)N1CCOC(CNc2ccc(S(=O)(=O)NC(=O)c3ccc(C4=CCC(N5CCCC5c5ccccc5C5CC5)CC4)cc3Oc3cnc4[nH]ccc4c3)cc2[N+](=O)[O-])C1]

The desired compound was synthesized with 4-(((4-acetylmorpholin-2-yl)methyl)amino)-3-nitrobenzenesulfonamide and 3-((1H-pyrrolo[2,3-b]pyridin-5-yl)oxy)-4'-(2-(2-cyclopropylphenyl)pyrrolidin-1-yl)-2',3',4',5'-tetrahydro-[1,1'-biphenyl]-4-carboxylic acid following the procedures similar to those in Example G8. $^1$H NMR (400 MHz, DMSO-$d_6$) δ ppm: 11.52 (s, 1H), 8.40-8.33 (m, 2H), 7.90 (s, 1H), 7.72-7.49 (m, 2H), 7.48 (d, J=12 Hz, 1H), 7.42 (s, 1H), 7.33-7.27 (m, 1H), 7.15-6.81 (m, 5H), 6.72 (s, 1H), 6.29 (s, 1H), 5.99 (s, 0.5H), 5.79 (s, 0.5H), 4.36-4.25 (m, 2H), 4.14-3.82 (m, 2H), 3.67-3.34 (m, 6H), 3.22-2.98 (m, 1H), 2.72-2.56 (m, 2H), 2.40-2.11 (m, 4H), 2.05-1.90 (m, (nil 1.78-1.65 (m, 2H), 1.60-1.35 (m, 2H), 0.95-0.81 (m, 2H), 0.71-0.47 (m, 2H). MS (ESI, m/e) [M+1]$^+$ 859.8.

Example G35-S: 3-((1H-pyrrolo[2,3-b]pyridin-5-yl)oxy)-4'-((S)-2-(2-cyclopropylphenyl)pyrrolidin-1-yl)-N-((4-((4-fluoro-1 (oxetan-3-yl)piperidin-4-yl)methoxy)-3-nitrophenyl)sulfonyl)-2',3',4',5'-tetrahydro-[1,1'-biphenyl]-4-carboxamide

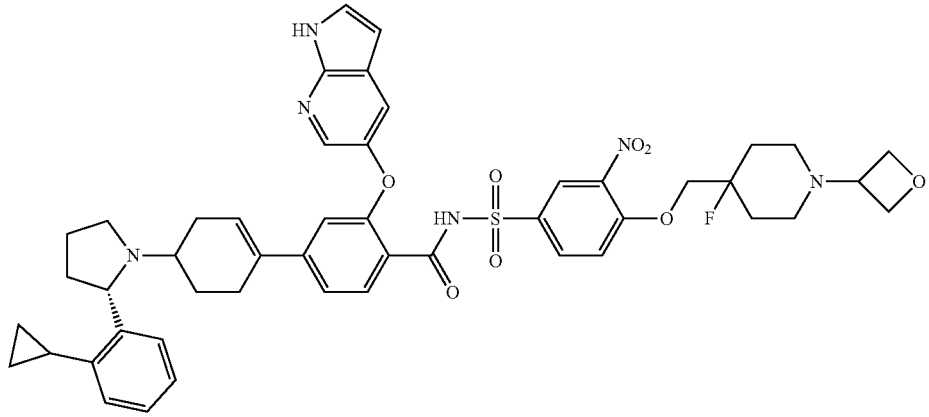 [SMILES: O=C(NS(=O)(=O)c1ccc(OCC2(F)CCN(C3COC3)CC2)c([N+](=O)[O-])c1)c1ccc(C2=CCC(N3CCC[C@H]3c3ccccc3C3CC3)CC2)cc1Oc1cnc2[nH]ccc2c1]

The desired compound was synthesized with 4-((4-fluoro-1-(oxetan-3-yl)piperidin-4-yl)methoxy)-3-nitrobenzenesulfonamide and 3-((1H-pyrrolo[2,3-b]pyridin-5-yl)oxy)-4'-((S)-2-(2-cyclopropylphenyl)pyrrolidin-1-yl)-2',3',4',5'-tetrahydro-[1,1'-biphenyl]-4-carboxylic acid following the procedures similar to those in Example G8. $^1$H NMR (400 MHz, DMSO-$d_6$) δ ppm: 11.59 (s, 1H), 10.23-9.66 (m, 1H), (8.18 (s, 1H), 7.98-7.90 (m, 1H), 7.90-7.69 (m, 2H), 7.62-7.42 (m, 2H), 7.42-7.13 (m, 3H), 7.13-6.82 (m, 3H), 6.82-6.68 (m, 1H), 6.33 (s, 1H), 6.07-5.70 (m, 1H), 5.36-5.01 (m, 1H), 4.55 (t, J=6.5 Hz, 2H), 4.45 (t, J=5.7 Hz, 2H), 4.26 (d, J=20.3 Hz, 2H), 3.94-3.57 (m, 1H), 3.57-3.37 (m, 3H), 3.21-2.87 (m, 1H), 2.72-2.54 (m, 3H), 2.47-1.67 (m, 14H), 1.04-1.34 (m, 1H), 1.02-0.79 (m, 2H), 0.79-0.44 (m, 2H). MS (ESI, m/e) [M+1]$^+$ 890.8.

Two enantiomers G35a (faster isomer) and G35-b (slower isomer) were separated by chiral preparative HPLC. The chiral separation conditions are shown below. The faster enantiomer was eluted at retention time of 4.6 min to give G35-a. The slower enantiomer was eluted at retention time of 6.0 min to give G354v

| Column | CHIRAL ART Cellulose-SB |
|---|---|
| Column size | 2 cm × 25 cm, 5 um |
| Injection | 0.5 mL |
| Mobile phase | MtBE:MeOH (0.2% MSA) = 70:30 |

| -continued | |
|---|---|
| Column | CHIRAL ART Cellulose-SB |
| Flow rate | 20 ml/min |
| Wave length | UV 220 nm |
| Temperature | 25° C. |
| Sample solution | 16 mg/ml in MeOH:DCM = 3:1 |
| Prep-HPLC equipment | Prep-Gilson-HPLC |

Example G35a: $^1$H NMR (400 MHz, DMSO-$d_6$) δ ppm: 11.60 (s, 1H), 9.44-9.06 (m, 1H), 8.38-8.08 (m, 1H), 8.08-7.76 (m, 2H), 7.76-6.83 (m, 9H), 6.83-6.66 (m, 1H), 6.34 (s, 1H), 5.94-5.65 (m, 1H), 5.37-5.11 (m, 1H), 4.63-4.51 (m, 2H), 4.51-4.39 (m, 2H), 4.39-4.14 (m, 2H), 3.82-3.63 (m, 1H), 3.63-3.41 (m, 2H), 3.18-2.77 (m, 2H), 2.77-2.55 (m, 3H), 2.42-1.62 (m, 14H), 1.62-1.38 (m, 1H), 0.96-0.84 (m, 2H), 0.80-0.55 (m, 2H). MS (ESI, m/e) [M+1]$^+$ 890.8.
Example G35b: $^1$H NMR (400 MHz, DMSO-$d_6$) δ ppm: 11.60 (s, 1H), 9.58-9.27 (m, 1H), 8.29-8.10 (m, 1H), 8.05-7.75 (m, 2H), 7.67-7.53 (m, 1H), 7.53-7.42 (m, 2H), 7.42-7.16 (m, 3H), 7.16-6.86 (m, 3H), 6.74 (s, 1H), 6.33 (s, 1H), 6.03-5.91 (m, 1H), 5.25-4.99 (m, 1H), 4.60-4.50 (m, 2H), 4.50-4.38 (m, 2H), 4.36-4.18 (m, 2H), 3.74-3.32 (m, 4H), 3.24-2.86 (m, 1H), 2.79-2.53 (m, 3H), 2.46-1.58 (m, 14H), 1.53-1.35 (m, 1H), 1.03-0.88 (m, 2H), 0.77-0.49 (m, 2H). MS (ESI, m/e) [M+1]$^+$ 890.8.

Example G36: 3-((1H-pyrrolo[2,3-b]pyridin-5-yl)oxy)-4'-(2-(2-cyclopropylphenyl)pyrrolidin-1-yl)-N-((4-((4-fluoro-1-(tetrahydro-2H-pyran-4-yl)piperidin-4-yl)methoxy)-3-nitrophenyl)sulfonyl)-2',3',4',5'-tetrahydro-[1,1'-biphenyl]-4-carboxamide

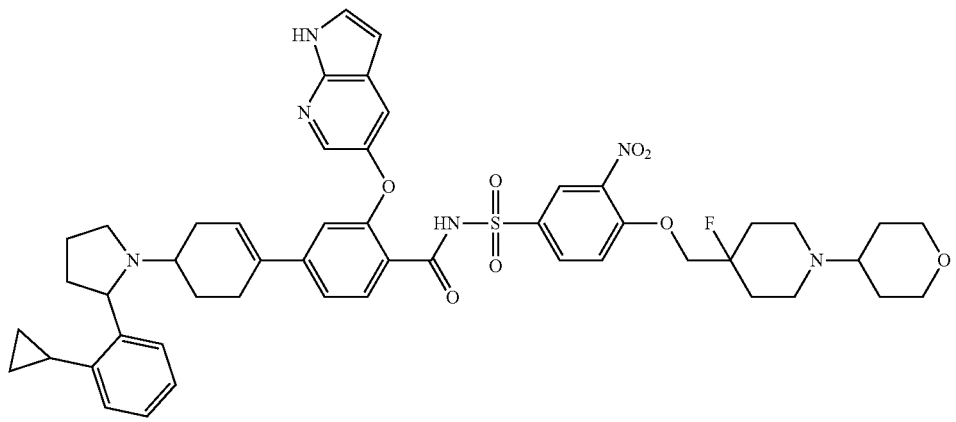 [SMILES: O=C(NS(=O)(=O)c1ccc(OCC2(F)CCN(C3CCOCC3)CC2)c([N+](=O)[O-])c1)c1ccc(C2=CCC(N3CCCC3c3ccccc3C3CC3)CC2)cc1Oc1cnc2[nH]ccc2c1]

The desired compound was synthesized with 4-((4-fluoro-1-(tetrahydro-2H-pyran-4-yl)piperidin-4-yl)methoxy)-3-nitrobenzenesulfonamide and 3-((1H-pyrrolo[2,3-b]pyridin-5-yl)oxy)-4'-(2-(2-cyclopropylphenyl)pyrrolidin-1-yl)-2',3',4',5'-tetrahydro-[1,1'-biphenyl]-4-carboxylic acid following the procedures similar to those in Example G8. $^1$H NMR (400 MHz, DMSO-$d_6$) δ ppm: 11.56 (s, 1H), 9.33 (s, 1H), 8.19 (s, 1H), 8.01-7.79 (m, 2H), 7.59-7.39 (m, 3H), 7.39-7.15 (m, 3H), 7.10-7.01 (m, 3H), 6.93-6.83 (m, 1H), 6.72 (s, 1H), 6.32 (s, 1H), 5.98 (s, 0.5H), 5.79 (s, 0.5H), 4.41-4.25 (m, 3H), 3.98-3.95 (m, 2H), 3.31-3.21 (m, 5H), 3.10-2.85 (m, 3H), 2.28-1.81 (m, 15H), 1.74-1.39 (m, 8H), 0.99-0.79 (m, 4H). MS (ESI, m/e) [M+1]$^+$ 918.8.

Example G37: 3-((1H-pyrrolo[2,3-b]pyridin-5-yl)oxy)-4'-(2-(2-cyclopropylphenyl)pyrrolidin-1-yl)-N-((3-nitro-4-((((R)-1-(oxetan-3-yl)pyrrolidin-3-yl)methyl)amino)phenyl)sulfonyl)-2',3',4',5'-tetrahydro-[1,1'-biphenyl]-4-carboxamide

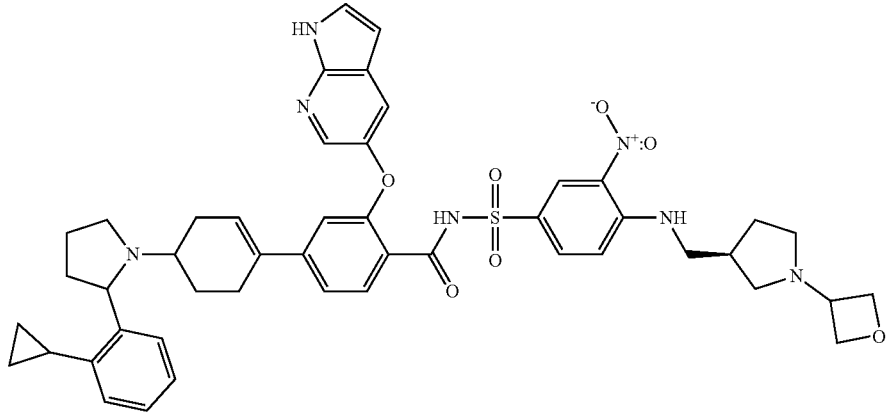

The desired compound was synthesized with (R)-3-nitro-4-(((1-(oxetan-3-yl)pyrrolidin-3-yl)methyl)amino)benzenesulfonamide and 3-((1H-pyrrolo[2,3-b]pyridin-5-yl)oxy)-4'-(2-(2-cyclopropylphenyl)pyrrolidin-1-yl)-2',3',4',5'-tetrahydro-[1,1'-biphenyl]-4-carboxylic acid following the procedures similar to those in Example G8. $^1$H NMR (400 M Hz, DMSO-d$_6$) δ ppm: 11.62 (s, 1H), 8.67-8.58 (m, 1H), 8.46 (s, 1H), 7.95 (s, 1H), 7.80-7.52 (m, 2H), 7.51-7.44 (m, 2H), 7.43-7.35 (m, 1H), 7.29-7.01 (m, 3H), 6.99-6.86 (m, 2H), 6.73 (s, 1H), 6.34 (s, 1H), 6.01-5.76 (m, 1H), 465-4.44 (m, 4H), 4.38-4.23 (m, 1H), 3.79-3.63 (m, 1H), 3.24-2.85 (m, 2H), 2.83-2.69 (m, 1H), 2.66-2.54 (m, 6H), 2.29-2.10 (m, 3H), 2.10-1.89 (m, 4H), 1.80-1.67 (m, 3H), 1.61-1.50 (m, 2H), 1.28-1.07 (m, 4H), 0.99-0.81 (m, 3H), 0.80-0.45 (m, 3H). MS (ESI, m/e) [M+1]$^+$ 857.8.

Example G39: 3-((1H-pyrrolo[2,3-b]pyridin-5-yl)oxy)-4'-(2-(2-cyclopropylphenyl)pyrrolidin-1-yl)-N-((3-nitro-4-((((S)-1-(oxetan-3-yl)pyrrolidin-3-yl)methyl)amino)phenyl)sulfonyl)-2',3',4',5'-tetrahydro-[1,1'-biphenyl]-4-carboxamide

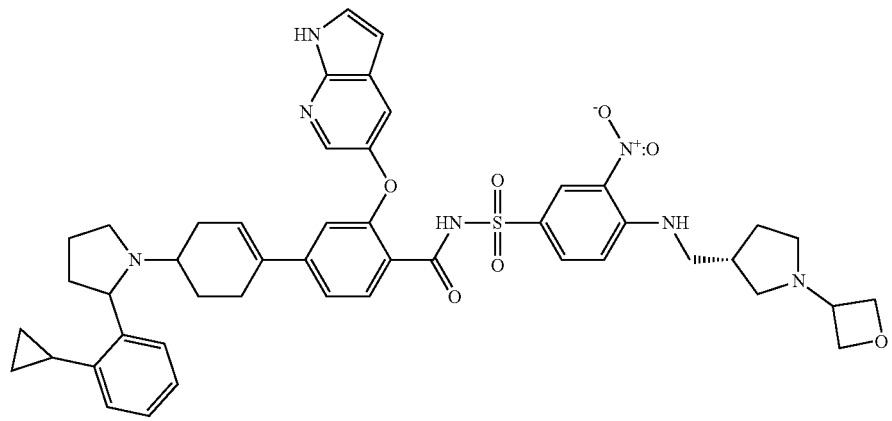

The desired compound was synthesized with (S)-3-nitro-4-(((1-(oxetan-3-yl)pyrrolidin-3-yl)methyl)amino)benzenesulfonamide and 3-((1H-pyrrolo[2,3-b]pyridin-5-yl)oxy)-4'-(2-(2-cyclopropylphenyl)pyrrolidin-1-yl)-2',3',4',5'-tetrahydro-[1,1'-biphenyl]-4-carboxylic acid following the procedures similar to those in Example G8. $^1$H NMR (400 MHz, DMSO-d$_6$) δ ppm: 12.00 (s, 1H), 11.66 (s, 1H), 10.42-9.76 (m, 1H), 8.68 (s, 1H), 8.50 (s, 1H), 7.97 (s, 1H), 7.77 (s, 1H), 7.55-7.37 (m, 4H), 7.37-7.20 (m, 2H), 7.17-6.91 (m, 4H), 6.74 (s, 1H), 6.36 (s, 1H), 6.03-5.82 (m, 1H), 5.26-5.06 (m, 1H), 4.62 (s, 5H), 3.50-3.34 (m, 5H), 3.04-2.86 (m, 2H), 2.71-2.60 (m, 3H), 2.33 (s, 2H), 2.04-1.97 (m, 3H), 1.80-1.53 (m, 3H), 1.52-1.38 (m, 1H), 0.98-0.83 (m, 4H), 0.76-0.63 (m, 1H), 0.62-0.51 (m, 1H). MS (ESI) m/e [M+1]$^+$857.8.

Example G43a and Example G43b: (cis- or trans-) 3-((1H-pyrrolo[2,3-b]pyridin-5-yl)oxy)-4'-((S)-2-(2-cyclopropylphenyl)pyrrolidin-1-yl)-N-((4-(((4-ethyl-4-hydroxycyclohexyl)methyl)amino)-3-nitrophenyl)sulfonyl)-2',3',4',5'-tetrahydro-[1,1'-biphenyl]-4-carboxamide/(trans- or cis-) 3-((1H-pyrrolo[2,3-b]pyridin-5-yl)oxy)-4'-((S)-2-(2-cyclopropylphenyl)pyrrolidin-1-yl)-N-((4-(((4-ethyl-4-hydroxycyclohexyl)methyl)amino)-3-nitrophenyl)sulfonyl)-2',3',4',5'-tetrahydro-[1,1'-biphenyl]-4-carboxamide

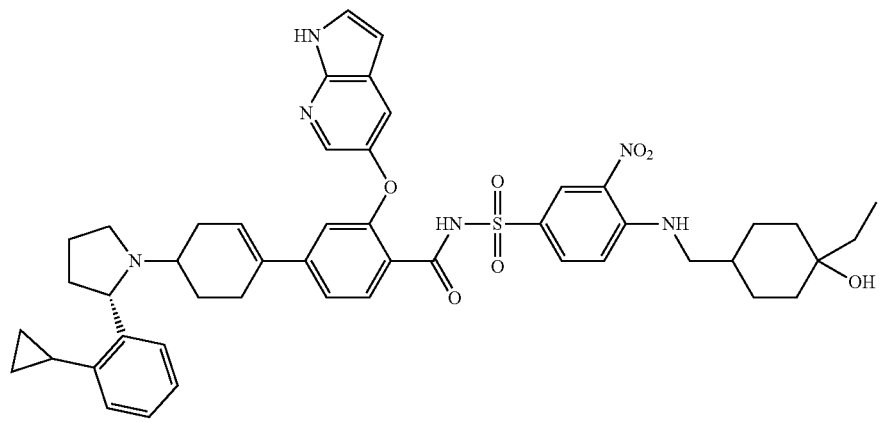

cis or trans

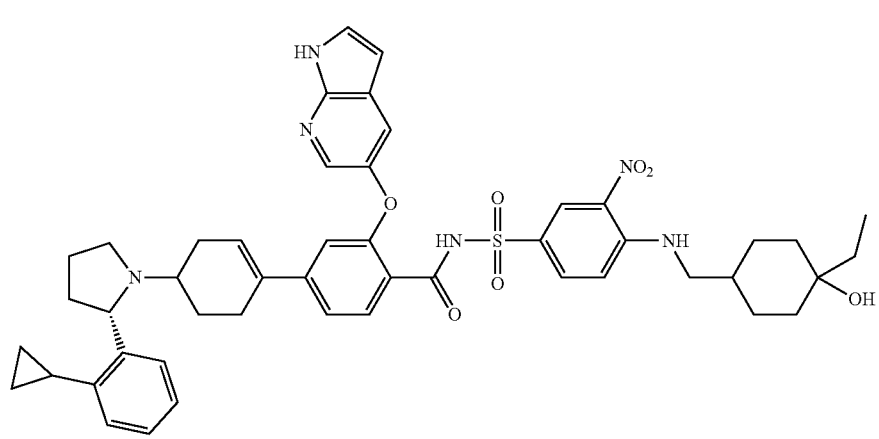

trans or cis

The desired compound G43a was synthesized with (cis- or trans-)4-(((4-ethyl-4-hydroxycyclohexyl)methyl)amino)-3-nitrobenzenesulfonamide (faster peak in HPLC) and 3-((1H-pyrrolo[2,3-b]pyridin-5-yl)oxy)-4'-((S)-2-(2-cyclopropylphenyl)pyrrolidin-1-yl)-2',3',4',5'-tetrahydro-[1,1'-biphenyl]-4-carboxylic acid following the procedures similar to those in Example G8. $^1$H NMR (400 MHz, DMSO-$d_6$) δ ppm: 12.43 (br, 0.4H), 11.65 (s, 1H), 8.65-8.26 (m, 2H), 7.97 (s, 1H), 7.83-7.66 (m, 1H), 7.66-6.80 (m, 9H), 6.08-5.70 (m, 1H), 6.73 (s, 1H), 6.35 (s, 1H), 5.47-4.93 (m, 0.5H), 4.61-4.08 (m, 0.5H), 3.77 (s, 1H), 3.26-3.14 (m, 2H), 2.40-1.65 (m, 9H), 1.60-1.07 (m, 15H), 1.00-0.76 (m, 6H), 0.73-0.39 (m, 2H). MS (ESI, m/e) [M+1]$^+$ 840.8; The desired compound G43b was synthesized with (trans- or cis-) 4-(((4-ethyl-4-hydroxycyclohexyl)methyl)amino)-3-nitrobenzenesulfonamide (slower peak in HPLC) and 3-((1H-pyrrolo[2,3-b]pyridin-5-yl)oxy)-4'-((S)-2-(2-cyclopropylphenyl)pyrrolidin-1-yl)-2',3',4',5'-tetrahydro-[1,1'-biphenyl]-4-carboxylic acid following the procedures similar to those in Example G8. $^1$H NMR (400 MHz, DMSO-$d_6$) δ ppm: 12.34 (br, 1H), 11.64 (s, 1H), 8.72-8.23 (m, 2H), 7.97 (s, 1H), 7.87-6.79 (m, 10H), 6.73 (s, 1H), 6.35 (s, 1H), 6.10-5.67 (m, 1H), 5.44-4.92 (m, 0.4H), 4.46-4.12 (m, 0.6H), 3.98 (s, 1H), 3.27-3.18 (m, 2H), 2.38-1.83 (m, 7H), 1.82-1.50 (m, 7H), 1.50-1.33 (m, 3H), 1.33-1.15 (m, 4H), 1.15-0.99 (m, 3H), 0.98-0.76 (m, 6H), 0.76-0.41 (m, 2H). MS (ESI, m/e) [M+1]$^+$ 840.8.

Example G63: 3-((1H-pyrrolo[2,3-b]pyridin-5-yl)oxy)-N-((4-((1-cyclopropyl-4-fluoropiperidin-4-yl)methoxy)-3-nitrophenyl)sulfonyl)-4'-(2-(2-cyclopropylphenyl)pyrrolidin-1-yl)-2',3',4',5'-tetrahydro-[1,1'-biphenyl]-4-carboxamide

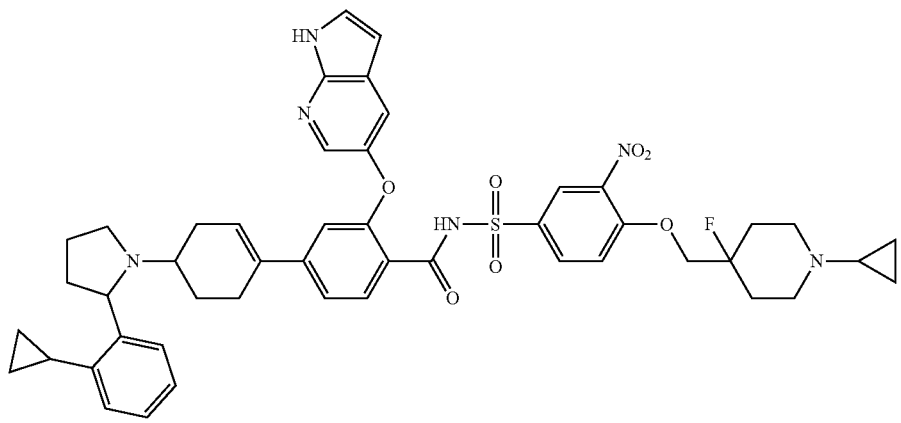 [SMILES: O=C(NS(=O)(=O)c1ccc(OCC2(F)CCN(C3CC3)CC2)c([N+](=O)[O-])c1)c1ccc(C2=CCC(N3CCCC3c3ccccc3C3CC3)CC2)cc1Oc1cnc2[nH]ccc2c1]

The desired compound was synthesized with 4-((1-cyclopropyl-4-fluoropiperidin-4-yl)methoxy)-3-nitrobenzenesulfonamide and 3-((1H-pyrrolo[2,3-b]pyridin-5-yl)oxy)-4'-(2-(2-cyclopropylphenyl)pyrrolidin-1-yl)-2',3',4',5'-tetrahydro-[1,1'-biphenyl]-4-carboxylic acid following the procedures similar to those in Example G8. $^1$H NMR (400 MHz, DMSO-$d_6$) δ ppm: 12.53 (s, 1H), 11.71 (s, 1H), 9.95 (s, 1H), 9.31 (s, 2H), 8.37-7.68 (m, 3H), 7.54-7.46 (m, 2H), 7.32-7.20 (m, 2H), 7.15-7.07 (m, 2H), 6.75 (d, J=4.5 Hz, 1H), 6.38 (s, 1H), 5.97-5.88 (m, 1H), 5.31-5.22 (m, 1H), 4.38 (d, J=19.7 Hz, 2H), 3.73-3.55 (m, 3H), 2.97 (s, 4H), 2.41 (s, 1H), 2.24-1.95 (m, 8H), 1.90 (s, 1H), 1.66-1.55 (m, 1H), 1.49-1.45 (m, 2H), 1.06 (s, 2H), 0.94 (d, J=8.3 Hz, 2H), 0.87-0.83 (m, 2H). MS (ESI, m/e) [M+1]$^+$ 874.8.

Example G64: 3-((1H-pyrrolo[2,3-b]pyridin-5-yl)oxy)-4'-(2-(2-cyclopropylphenyl)pyrrolidin-1-yl)-N-((4-(((R)-1-(1,3-difluoropropan-2-yl)pyrrolidin-3-yl)amino)-3-nitrophenyl)sulfonyl)-2',3',4',5'-tetrahydro-[1,1'-biphenyl]-4-carboxamide

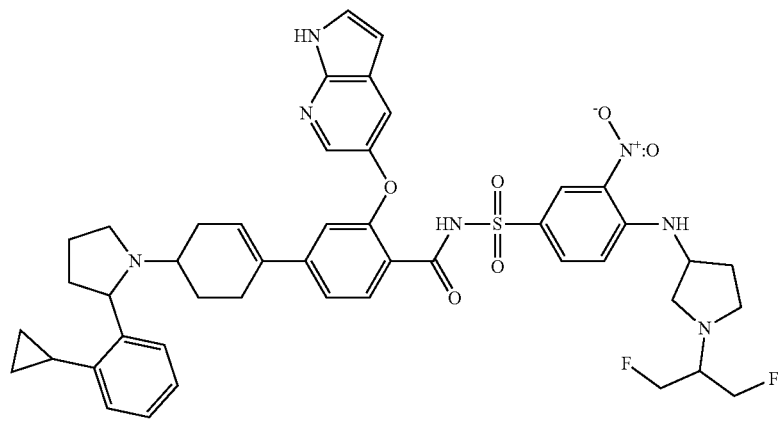

The desired compound was synthesized with (R)-4-((1-(1,3-difluoropropan-2-yl)pyrrolidin-3-yl)amino)-3-nitrobenzenesulfonamide and 3-((1H-pyrrolo[2,3-b]pyridin-5-yl)oxy)-4'-(2-(2-cyclopropylphenyl)pyrrolidin-1-yl)-2',3',4',5'-tetrahydro-[1,1'-biphenyl]-4-carboxylic acid following the procedures similar to those in Example G8. $^1$H NMR (400 MHz, DMSO-$d_6$) δ ppm: 12.21 (s, 0.5H), 11.62 (s, 1H), 9.41 (s, 0.5H ). 8.46 (s, 1H), 8.26 (s, 1H), 7.95 (s, 1H), 7.75 (s, 1H), 7.68-7.50 (m, 1H), 7.49-7.39 (m, 3H), 7.24-7.15 (m, 3H), 7.10-6.88 (m, 2H), 6.74 (s, 1H), 6.34 (s, 1H), 5.99 (s, 0.5H), 5.82 (s, 0.5H), 4.67 (d, J=4.6 Hz, 2H), 4.56 (d, J=4.5 Hz, 2H), 4.17 (s, 1H), 3.09-2.86 (m, 5H), 2.77 (d, J=6.9 Hz, 2H), 2.68 (d, J=6.8 Hz, 2H), 2.35-2.16 (m, 4H), 2.12-2.05 (m, 3H), 1.77-1.59 (m, 4H), 1.32-1.14 (m, 3H), 0.97-0.80 (m, 4H). MS (ESI, m/e; [M+1]$^+$ 865.8.

Example G70: 3-((1H-pyrrolo[2,3-b]pyridin-5-yl)oxy)-N-((3-chloro-4-(((tetrahydro-2H-pyran-4-yl)methyl)amino)phenyl)sulfonyl)-4'-(2-(2-cyclopropylphenyl)pyrrolidin-1-yl)-2',3',4',5'-tetrahydro-[1,1'-biphenyl]-4-carboxamide

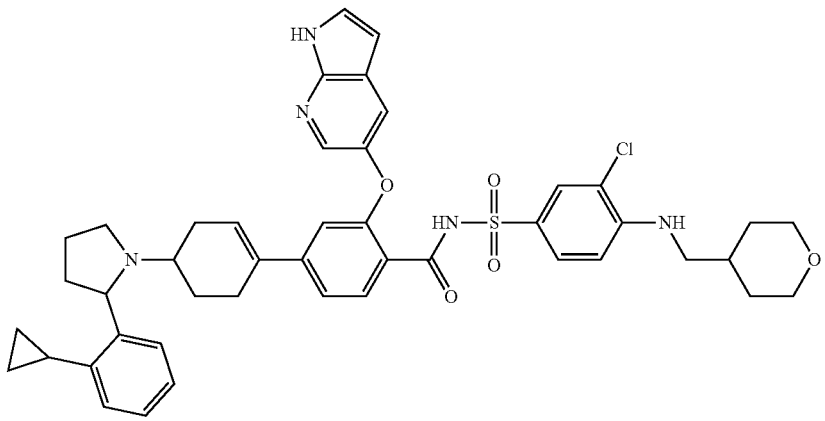 [SMILES: O=C(NS(=O)(=O)c1ccc(NCC2CCOCC2)c(Cl)c1)c1ccc(C2=CCC(N3CCCC3c3ccccc3C3CC3)CC2)cc1Oc1cnc2[nH]ccc2c1]

The desired compound was synthesized with 3-chloro-4-((((tetrahydro-2H-pyran-4-yl)methyl)amino)benzenesulfonamide and 3-((1H-pyrrolo[2,3-b]pyridin-5-yl)oxy)-4'-(2-(2-cyclopropylphenyl)pyrrolidin-1-yl)-2',3',4',5'-tetrahydro-[1,1'-biphenyl]-4-carboxylic acid following the procedures similar to those in Example G8. ¹H NMR (400 MHz, DMSO-d₆) δ ppm: 12.00 (s, 1H), 11.75 (s, 1H), 8.06 (s, 1H), 7.76-7.42 (m, 6H), 7.28-6.87 (m, 4H), 6.81-6.65 (m, 2H), 6.43 (s, 2H), 5.97 (s, 1H), 4.28 (s, 1H), 3.82 (d, J=9.0 Hz, 2H), 3.75-3.61 (m, 1H), 3.29-3.20 (m, 2H), 3.07 (s, 2H), 3.00 (s, 1H), 2.16 (s, 3H), 2.05-1.95 (m, 3H), 1.81 (s, 1H), 1.71 (s, 1H), 1.57 (d, J=12.3 Hz, 3H), 1.47-1.44 (m, 1H), 1.24 (s, 4H), 1.21-1.13 (m, 2H), 0.99-0.81 (m, 4H). MS (ESI, m/e) [M+1]⁺ 805.8.

Example G72: 3-((1H-pyrrolo[2,3-b]pyridin-5-yl)oxy)-N-((3-cyano-4-(((tetrahydro-2H-pyran-4-yl)methyl)amino)phenyl)sulfonyl)-4'-(2-(2-cyclopropylphenyl)pyrrolidin-1-yl)-2',3',4',5'-tetrahydro-[1,1'-biphenyl]-4-carboxamide

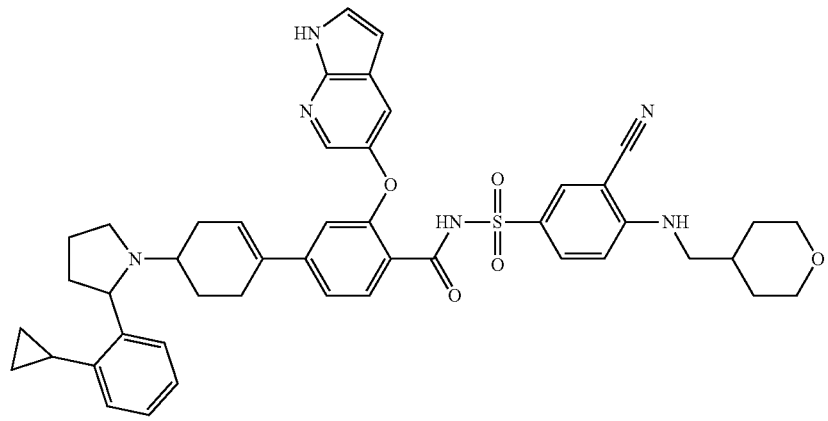 [SMILES: N#Cc1cc(S(=O)(=O)NC(=O)c2ccc(C3=CCC(N4CCCC4c4ccccc4C4CC4)CC3)cc2Oc2cnc3[nH]ccc3c2)ccc1NCC1CCOCC1]

The desired compound was synthesized with 3-cyano-4-((((tetrahydro-2H-pyran-4-yl)methyl)amino)benzenesulfonamide and 3-((1H-pyrrolo[2,3-b]pyridin-5-yl)oxy)-4'-(2-(2-cyclopropylphenyl)pyrrolidin-1-yl)-2',3',4',5'-tetrahydro-[1,1'-biphenyl]-4-carboxylic acid following the procedures similar to those in Example G8. ¹H NMR (400 MHz, DMSO-d₆) δ ppm: 12.08 (s, 1H), 11.71 (s, 1H), 8.02 (s, 1H), 7.87 (s, 1H), 7.72 (s, 1H), 7.52-7.45 (m, 3H), 7.28-7.04 (m, 4H), 6.95-6.89 (m, 1H), 6.78-6.66 (m, 2H), 6.40 (s, 1H), 5.98 (s, 1H), 5.79 (s, 1H), 4.33-4.19 (m, 1H), 3.82 (d, J=8.8 Hz, 2H), 3.22-3.19 (m, 2H), 3.08 (s, 2H), 2.98 (s, 2H), 2.18 (s, 3H), 2.02-1.97 (m, 4H), 1.80-1.71 (m, 4H), 1.56 (d, J=12.6 Hz, 3H), 1.45-1.39 (m, 2H), 1.23-1.15 (m, 5H). MS (ESI, m/e) [M+1]⁺ 797.2.

Example G73: 3-((1H-pyrrolo[2,3-b]pyridin-5-yl)oxy)-4'-(2-(2-cyclopropylphenyl)pyrrolidin-1-yl)-N-((4-(((tetrahydro-2H-pyran-4-yl)methyl)amino)-3-((trifluoromethyl)sulfonyl)phenyl)sulfonyl)-2',3',4',5'-tetrahydro-[1,1'-biphenyl]-4-carboxamide

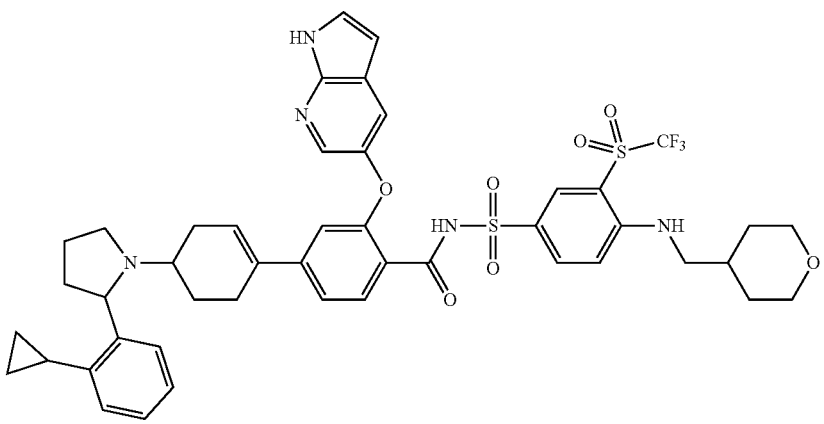 [SMILES: O=C(NS(=O)(=O)c1ccc(NCC2CCOCC2)c(S(=O)(=O)C(F)(F)F)c1)c1ccc(C2=CCC(N3CCCC3c3ccccc3C3CC3)CC2)cc1Oc1cnc2[nH]ccc2c1]

The desired compound was synthesized with 4-(((tetrahydro-2H-pyran-4-yl)methyl)amino)-3-((trifluoromethyl)sulfonyl)benzenesulfonamide and 3-((1H-pyrrolo[2,3-b]pyridin-5-yl)oxy)-4'-(2-(2-cyclopropylphenyl)pyrrolidin-1-yl)-2(3',4',5'-tetrahydro-[1,1'-biphenyl]-4-carboxylic acid following the procedures similar to those in Example G8. $^1$H NMR (400 MHz, DMSO-$d_6$) δ ppm: 12.30 (s, 1H), 11.69 (s, 1H), 8.09 (s, 1H), 7.99 (s, 1H), 7.87 (s, 1H), 7.78 (s, 1H), 7.50-7.45 (m, 3H), 7.29 (s, 2H), 7.14-6.96 (m, 3H), 6.73 (s, 1H), 6.38 (s, 1H), 5.97-5.80 (m, 1H), 5.25-5.11 (m, 1H), 3.83 (d, J=8.5 Hz, 2H), 3.72-3.66 (m, 1H), 3.37 (s, 1H), 3.23-3.19 (m, 4H), 3.01-2.98 (m, 2H), 2.82-2.75 (m, 1H), 2.56 (s, 3H), 2.33 (s, 1H), 2.12 (s, 1H), 2.03-1.97 (m, 2H), 1.8-1.721 (m, 2H), 1.53 (d, J=12.2 Hz, 2H), 1.22-1.17 (m, 8H). MS (ESI, m/e) [M+1]$^+$ 904.1.

Example G75: 3-((1H-pyrrolo[2,3-b]pyridin-5-yl)oxy)-4'-(2-(2-cyclopropylphenyl)pyrrolidin-1-yl)-N-((3-nitro-4-(((1-(oxetan-3-yl)piperidin-4-yl)methyl)amino)phenyl)sulfonyl)-2',3',4',5'-tetrahydro-[1,1'-biphenyl]-4-carboxamide

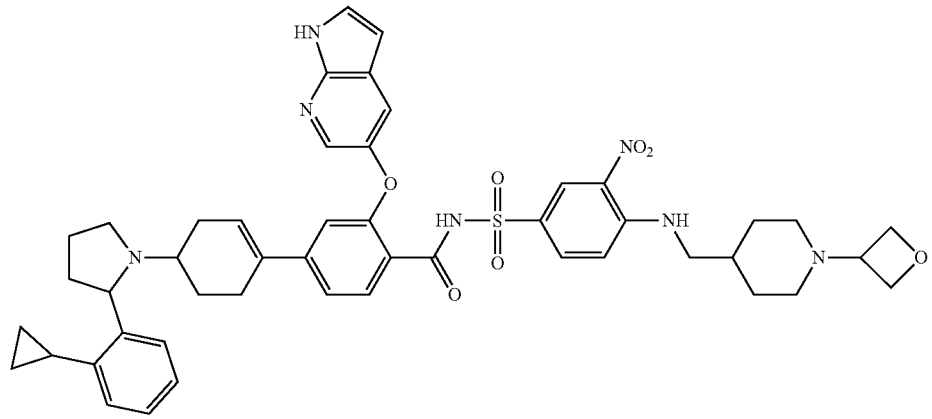 [SMILES: O=C(NS(=O)(=O)c1ccc(NCC2CCN(C3COC3)CC2)c([N+](=O)[O-])c1)c1ccc(C2=CCC(N3CCCC3c3ccccc3C3CC3)CC2)cc1Oc1cnc2[nH]ccc2c1]

The desired compound was synthesized with 3-nitro-4-(((1-(oxetan-3-yl)piperidin-4-yl)methyl)amino)benzenesulfonamide 2,2,2-trifluoroacetate and 3-((1H-pyrrolo[2,3-b]pyridin-5-yl)oxy)-4'-(2-(2-cyclopropylphenyl)pyrrolidin-1-yl)-2',3',4',5'-tetrahydro-[1,1'-biphenyl]-4-carboxylic acid following the procedures similar to those in Example G8. $^1$H NMR (400 MHz, DMSO-$d_6$) δ ppm: 11.61 (s, 1H), 9.81-9.27 (m, 1H), 8.56-8.32 (m, 2H), 7.94 (s, 1H), 7.71 (s, 1H), 7.59-7.17 (m, 4H), 7.16-6.79 (m, 4H), 6.78-6.68 (m, 1H), 6.61-6.50 (m, 3H), 6.34 (s, 1H), 5.99-5.69 (m, 1H), 5.44-5.03 (m, 4H), 4.34-4.16 (m, 1H), 3.31-3.21 (m, 2H), 3.20-2.67 (m, 4H), 2.20-1.85 (m, 7H), 1.85-1.53 (m, 6H), 1.48-1.20 (m, 7H), 0.98-0.82 (m, 2H), 0.70-0.43 (m, 2H), MS (ESI, m/e) [M+1]$^+$ 872.2.

Two enantiomers G75-a (faster isomer) and G75b (slower isomer) of 3-((1H-pyrrolo[2,3-b]pyridin-5-yl)oxy)-4'-((S)-2-(2-cyclopropylphenyl)pyrrolidin-1-yl)-N-((3-nitro-4-(((1-(oxetan-3-yl)piperidin-4-yl)methyl)amino)phenyl)sulfonyl)-2',3',4',5'-tetrahydro-[1,1'-biphenyl]-4-carboxamide were separated by chiral preparative HPLC. The chiral separation conditions are shown below. The faster enantiomer was eluted at retention time of 1.1 min to give G75-a. The slower enantiomer was eluted at retention time of 1.5 min to give G75-b.

| Column | CHIRAL ART Cellulose-SB |
|---|---|
| Column size | 2 cm × 25 cm, 5 um |
| Injection | 1.0 mL |
| Mobile phase | CO$_2$:[EtOH:CAN = 1:1(0.2% MSA)] = 50:50 |
| Flow rate | 40 mL/min |
| Wave length | UV 220 nm |
| Temperature | 35° C. |
| Sample solution | 26.7 mg/mL in MeOH:DCM = 3:1 |
| Prep-SFC equipment | Prep-SFC-80-2 |

Example G75-a: $^1$H NMR (DMSO-$d_6$) δ ppm: 11.63 (s, 1H), 8.46 (s, 2H), 7.95 (s, 1H), 7.78-7.66 (m, 1H), 7.62-7.35 (m, 4H), 7.33-6.60 (m, 7H), 6.34 (s, 1H), 5.81 (s, 1H), 4.68-4.20 (m, 5H), 3.30-3.14 (m, 3H), 2.90-2.69 (m, 2H), 2.61-2.54 (m, 1H), 2.40-1.82 (m, 10H), 1.80-1.18 (m, 10H), 0.98-0.80 (m, 2H), 0.74-0.44 (m, 2H). MS (ESI, m/e) [M+1]$^+$ 871.8. Example G75-b: $^1$H NMR (CDCl3-$d_6$) δ ppm: 9.45 (s, 1H), 8.90 (s, 1H), 8.52 (s, 1H), 8.25-7.90 (m, 3H), 7.78-7.38 (m, 3H), 7.18-6.78 (m, 5H), 6.58 (d, J=36.8 Hz, 2H), 5.95 (s, 1H), 4.75-4.54 (m, 4H), 4.42-4.16 (m, 1H), 3.57-3.40 (m, 1H), 3.33-3.05 (m, 3H), 2.89-2.52 (m, 4H), 2.38-2.09 (m, 6H), 1.97-1.79 (m, 8H), 1.50-1.33 (m, 4H), 0.92-0.84 (m, 2H), 0.72-0.50 (m, 2H). MS (ESI, m/e) [M+1]$^+$ 871.8.

Example G76: (trans- or cis-) N-((4-((((R)-1,4-dioxan-2-yl)methyl)amino)-3-nitrophenyl)sulfonyl)-2-((1H-pyrrolo[2,3-h]pyridin-5-yl)oxy)-4-(4-(2-(2-cyclopropylphenyl)pyrrolidin-1-yl)cyclohexyl)benzamide

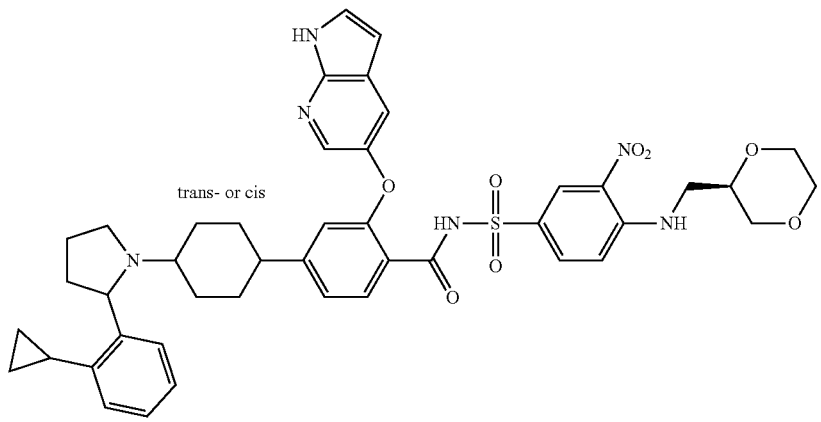 [SMILES: O=C(NS(=O)(=O)c1ccc(NC[C@@H]2COCCO2)c([N+](=O)[O-])c1)c1ccc(C2CCC(N3CCCC3c3ccccc3C3CC3)CC2)cc1Oc1cnc2[nH]ccc2c1]

With (R)-4-(((1,4-dioxan-2-yl)methyl)amino)-3-nitrobenzenesulfonamide and (trans- or cis-) 2-((1H-pyrrolo[2,3-b]pyridin-5-yl)oxy)-4-(4-(2-(2-cyclopropylphenyl)pyrrolidin-1-yl)cyclohexyl)benzoic acid, the desired compound was afforded following the similar procedure of Example D2b. $^1$H NMR (400 MHz, DMSO-$d_6$) δ ppm: 12.17 (br, 1H), 11.60 (s, 1H), 8.66-8.10 (m, 2H), 7.93 (s, 1H), 7.83-7.18 (m, 6H), 7.18-6.71 (m, 4H), 6.59 (s, 1H), 6.33 (s, 1H), 5.24-5.06 (m, 1H), 3.83-3.71 (m, 3H), 3.71-3.58 (m, 2H), 3.53-3.39 (m, 3H), 3.22-2.79 (m, 5H), 2.25-1.56 (m, 9H), 1.50-1.26 (m, 4H), 0.96-0.82 (m, 2H), 0.75-0.48 (m, 2H). MS (ESI, m/e) [M+1]$^+$ 821.2.

Example G76-S: (trans- or cis-) N-((4-((((R)-1,4-dioxan-2-yl)methyl)amino)-3-nitrophenyl)sulfonyl)-2-((1H-pyrrolo[2,3-b]pyridin-5-yl)oxy)-4-(4-((S)-2-(2-cyclopropylphenyl)pyrrolidin-1-yl)cyclohexyl)benzamide

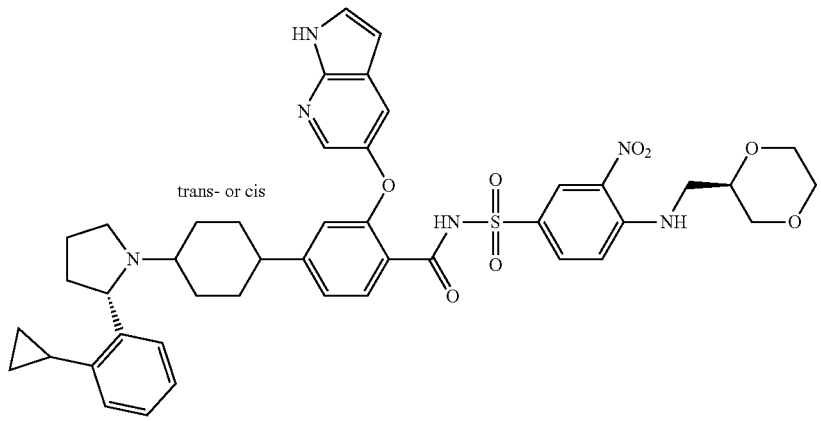 [SMILES: O=C(NS(=O)(=O)c1ccc(NC[C@@H]2COCCO2)c([N+](=O)[O-])c1)c1ccc(C2CCC(N3CCC[C@H]3c3ccccc3C3CC3)CC2)cc1Oc1cnc2[nH]ccc2c1]

The desired compound was synthesized with (R)-4-(((1,4-dioxan-2-yl)methyl)amino)-3-nitrobenzenesulfonamide and (trans- or cis-) (S)-2-((1H-pyrrolo[2,3-b]pyridin-5-yl)oxy)-4-(4-(2-(2-cyclopropylphenyl)pyrrolidin-1-yl)cyclohexyl)benzoic acid following the procedures similar to those in Example D2b. $^1$H NMR (400 MHz, DMSO-$d_6$) δ ppm: 11.61 (s, 1H), 8.50-8.35 (m, 2H), 7.93 (s, 1H), 7.74-7.72 (d, 1H, J=8.8), 7.65-7.55 (m, 1H), 7.50-7.45 (m, 1H), 7.44-7.38 (m, 2H), 7.30-7.10 (m, 2H), 7.08-6.87 (m, 3H), 6.59 (s, 1H), 6.34 (s, 1H), 3.82-3.73 (m, 3H), 3.61-3.55 (m, 2H), 3.53-3.40 (m, 3H), 3.33-3.26 (m, 3H), 3.18-3.14 (m, 1H), 2.43-2.26 (m, 2H), 2.10-1.84 (m, 4H), 1.81-1.53 (m, 4H), 1.47-1.07 (m, 5H), 0.98-0.83 (m, 2H), 0.76-0.64 (m, 1H), 0.61-0.50 (m, 1H). MS (ESI, m/e) [M+1]$^+$ 821.2.

Example G77: (trans- or cis-) N-((4-((((S)-1,4-dioxan-2-yl)methyl)amino)-3-nitrophenyl)sulfonyl)-2-((1H-pyrrolo[2,3-b]pyridin-5-yl)oxy)-4-(4-(2-(2-cyclopropylphenyl)pyrrolidin-1-yl)cyclohexyl)benzamide

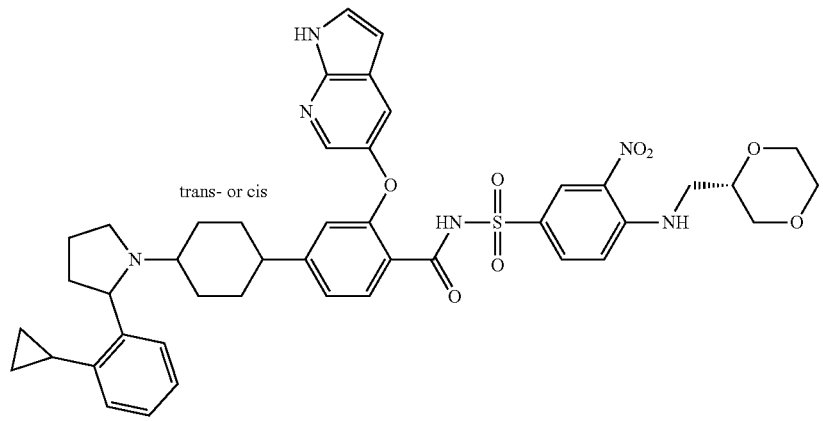 [SMILES: O=C(NS(=O)(=O)c1ccc(NC[C@H]2COCCO2)c([N+](=O)[O-])c1)c1ccc(C2CCC(N3CCCC3c3ccccc3C3CC3)CC2)cc1Oc1cnc2[nH]ccc2c1]

With (S)-4-(((1,4-dioxan-2-yl)methyl)amino)-3-nitrobenzenesulfonamide instead of 3-nitro-4-(((tetrahydro-2H-pyran-4-yl)methyl)amino)benzenesulfonamide, the desired compound was afforded by following the similar procedure of Example D2b. $^1$H NMR (400 MHz, DMSO-$d_6$) δ ppm: 12.18 (br, 1H), 11.60 (s, 1H), 8.59-8.20 (m, 2H), 7.93 (s, 1H), 7.87-7.20 (m, 6H), 7.20-6.79 (m, 4H), 6.60 (s, 1H), 6.33 (s, 1H), 5.32-4.91 (m, 1H), 3.86-3.71 (m, 3H), 3.71-3.54 (m, 2H), 3.54-3.38 (m, 3H), 3.31-2.79 (m, 5H), 2.21-1.54 (m, 9H), 1.53-1.23 (m, 4H), 1.02-0.81 (m, 2H), 0.78-0.40 (m, 2H). MS (ESI, m/e) [M+1]$^+$ 821.2.

Example G77-S: (trans- or cis-) N-((4-((((S)-1,4-dioxan-2-yl)methyl)amino)-3-nitrophenyl)sulfonyl)-2-((1H-pyrrolo[2,3-b]pyridin-5-yl)oxy)-4-(4-((S)-2-(2-cyclopropylphenyl)pyrrolidin-1-yl)cyclohexyl)benzamide

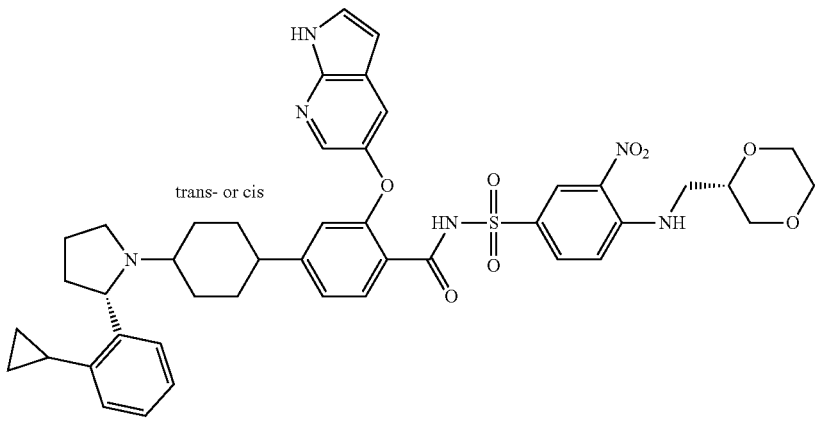 [SMILES: O=C(NS(=O)(=O)c1ccc(NC[C@H]2COCCO2)c([N+](=O)[O-])c1)c1ccc(C2CCC(N3CCC[C@H]3c3ccccc3C3CC3)CC2)cc1Oc1cnc2[nH]ccc2c1]

The desired compound was synthesized with (S)-4-(((1,4-dioxan-2-yl)methyl)amino)-3-nitrobenzenesulfonamide and (trans- or cis-) (S)-2-((1H-pyrrolo[2,3-b]pyridin-5-yl)oxy)-4-(4-(2-(2-cyclopropylphenyl)pyrrolidin-1-yl)cyclohexyl)benzoic acid following the procedures similar to those in Example D2 h. $^1$H NMR (400 MHz, DMSO-$d_6$) δ ppm: 12.19 (br, 1H), 11.61 (s, 1H), 8.61-8.21 (m, 2H), 7.93 (s, 1H), 7.85-7.63 (m, 2H), 7.62-7.38 (m, 3H), 7.34-6.80 (m, 5H), 6.60 (s, 1H), 6.34 (s, 1H), 5.23-5.03 (m, 0.5H), 4.49-4.12 (m, 0.5H), 3.84-3.72 (m, 3H), 3.68-3.55 (m, 2H), 3.52-3.40 (m, 2H), 3.32-3.27 (m, 4H), 3.21-2.99 (m, 1H), 2.41-1.11 (m, 14H), 1.03-0.80 (m, 2H), 0.79-0.44 (m, 2H). MS (ESI, m/e) [M+1]$^+$ 821.2.

Example G80a: (cis- or trans-)3-((1H-pyrrolo[2,3-b]pyridin-5-yl)oxy)-N-((4-((4-((tert-butyldimethylsilyl)oxy)cyclohexyl)methoxy)-3-nitrophenyl)sulfonyl)-4'-((S)-2-(2-cyclopropylphenyl)pyrrolidin-1-yl)-2',3',4',5'-tetrahydro-[1,1'-biphenyl]-4-carboxamide

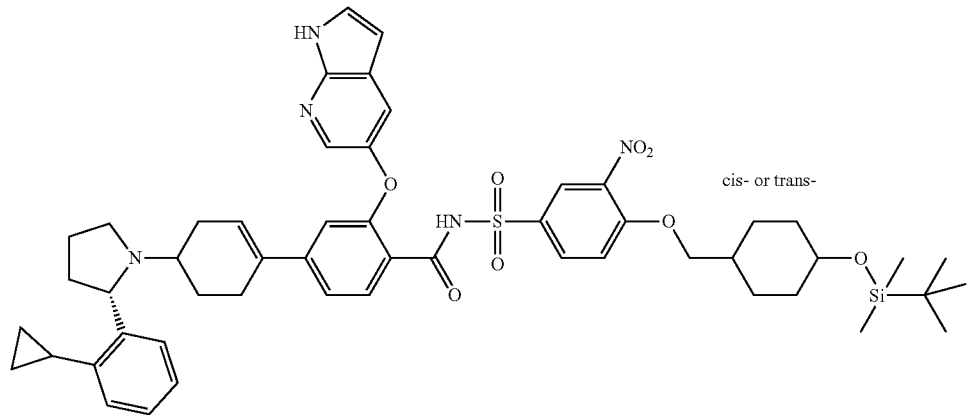 [SMILES: CC(C)(C)[Si](C)(C)OC1CCC(COc2ccc(S(=O)(=O)NC(=O)c3ccc(C4=CCC(N5CCC[C@H]5c5ccccc5C5CC5)CC4)cc3Oc3cnc4[nH]ccc4c3)cc2[N+](=O)[O-])CC1]

The desired compound was synthesized with (cis- or trans-)4-((4-((tert-butyldimethylsilyl)oxy)cyclohexyl)methoxy)-3-nitrobenzenesulfonamide and 3-((1H-pyrrolo[2,3-b]pyridin-5-yl)oxy)-4'-((S)-2-(2-cyclopropylphenyl)pyrrolidin-1-yl)-2',3',4',5'-tetrahydro-[1,1'-biphenyl]-4-carboxylic acid following the procedures similar to those in Example G8. MS (ESI, m/e) [M+1]$^+$ 954.8.

Example C80b: (trans- or cis-) 3-((1H-pyrrolo[2,3-b]pyridin-5-yl)oxy)-N-((4-((4-((tert-butyldimethylsilyl)oxy)cyclohexyl)methoxy)-3-nitrophenyl)sulfonyl)-4'-((S)-2-(2-cyclopropylphenyl)pyrrolidin-1-yl)-2',3',4',5'-tetrahydro-[1,1'-biphenyl]-4-carboxamide

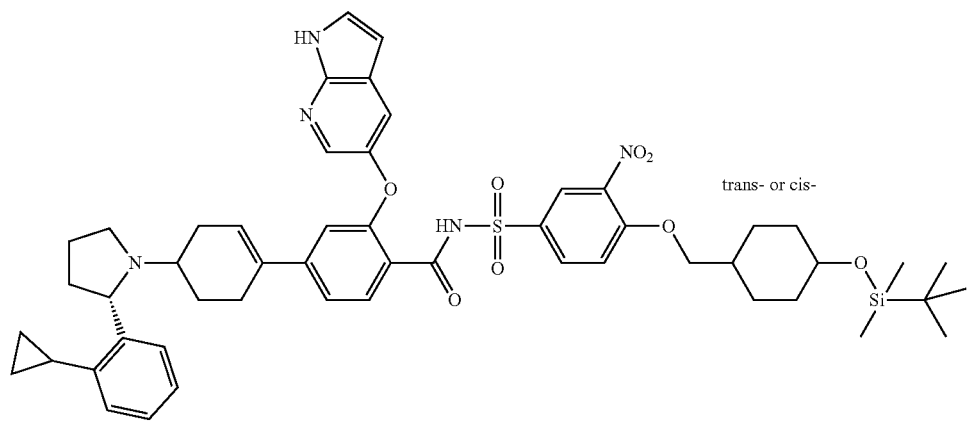 [SMILES: CC(C)(C)[Si](C)(C)OC1CCC(COc2ccc(S(=O)(=O)NC(=O)c3ccc(C4=CCC(N5CCC[C@H]5c5ccccc5C5CC5)CC4)cc3Oc3cnc4[nH]ccc4c3)cc2[N+](=O)[O-])CC1]

The desired compound was synthesized with (trans- or cis-) 4-((4-((tert-butyldimethylsilyl)oxy)cyclohexyl)methoxy)-3-nitrobenzenesulfonamide and 3-((1H-pyrrolo[2,3-b]pyridin-5-yl)oxy)-4'-((S)-2-(2-cyclopropylphenyl)pyrrolidin-1-yl)-2',3',4',5'-tetrahydro-[1,1'-biphenyl]-4-carboxylic acid following the procedures similar to those in Example G8. MS (ESI, m/e) [M+1]+ 954.8.

After deprotection of tert-butyldimethyl-silanyl for G80a, Example G81a: (cis- or trans-) 3-((1H-pyrrolo[2,3-b]pyridin-5-yl)oxy)-4'-((S)-2-(2-cyclopropylphenyl)pyrrolidin-1-yl)-N-((4-((4-hydroxycyclohexyl)methoxy)-3-nitrophenyl)sulfonyl)-2',3',4',5'-tetrahydro-[1,1'-biphenyl]-4-carboxamide was obtained.

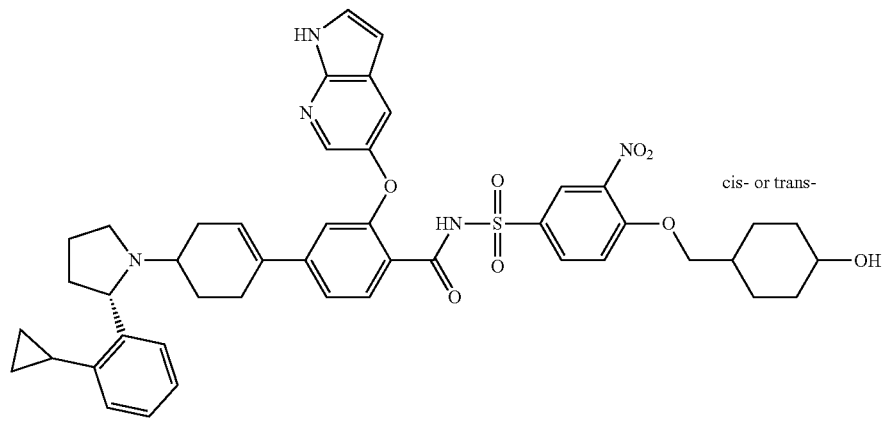 [SMILES: O=C(NS(=O)(=O)c1ccc(OCC2CCC(O)CC2)c([N+](=O)[O-])c1)c1ccc(C2=CCC(N3CCC[C@H]3c3ccccc3C3CC3)CC2)cc1Oc1cnc2[nH]ccc2c1]

cis- or trans-

¹H NMR (400 MHz, DMSO-d₆) δ ppm: 12.91 (br, 1H), 11.61 (s, 1H), 8.16 (s, 1H), 7.94 (s, 1H), 7.90-7.64 (m, 2H), 7.64-6.83 (m, 8H), 6.33 (s, 1H), 6.07-5.74 (m, 1H), 5.38-4.95 (m, 0.7H), 4.40-4.14 (m, 1H), 4.04-3.86 (m, 2H), 3.85-3.38 (m, 3H), 3.25-2.84 (m, 1H), 2.46-1.80 (m, 8H), 1.80-1.24 (m, 11H), 1.02-0.79 (m, 2H), 0.78-0.43 (m, 2H). MS (ESI, m/e) [M+1]+ 831.8.

After deprotection of tert-butyldimethyl-silanyl for G80b, Example G81b: (trans- or cis-) 3-((1H-pyrrolo[2,3-b]pyridin-5-yl)oxy)-4'-((S)-2-(2-cyclopropylphenyl)pyrrolidin-1-yl)-N-((4-((4-hydroxycyclohexyl)methoxy)-3-nitrophenyl)sulfonyl)-2',3',4',5'-tetrahydro-[1,1'-biphenyl]-4-carboxamide was obtained. ¹H NMR (400 MHz, DMSO-d₆) δ ppm: 12.77 (br, 1H), 11.62 (s, 1H), 8.18 (s, 1H), 7.94 (s, 1H), 7.90-7.75 (m, 1H), 7.75-6.83 (m, 9H), 6.74 (s, 1H), 6.34 (s, 1H), 6.08-5.09 (m, 1H), 5.42-4.92 (m, 0.7H), 4.61-4.47 (m, 1H), 4.03-3.82 (m, 2H), 3.82-3.35 (m, 3H), 3.23-2.89 (m, 1H), 2.40-1.44 (m, 14H), 1.22-1.00 (m, 5H), 0.98-0.87 (m, 2H), 0.79-0.47 (m, 2H). MS (ESI, m/e) [M+1]+ 831.8.

Example G84: N-(4-(N-(3-((1H-pyrrolo[2,3-b]pyridin-5-yl)oxy)-4'-(2-(2-cyclopropylphenyl)pyrrolidin-1-yl)-2',3',4',5'-tetrahydro-[1,1'-biphenyl]-4-carbonyl)sulfamoyl)-2-nitrophenyl)morpholine-4-carboxamide

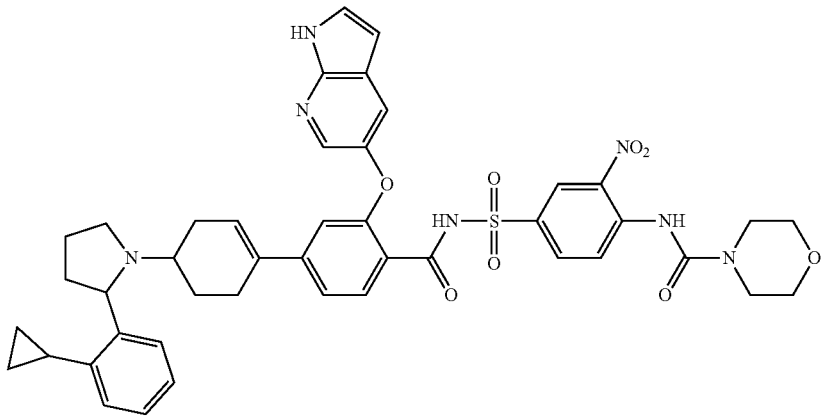 [SMILES: O=C(NS(=O)(=O)c1ccc(NC(=O)N2CCOCC2)c([N+](=O)[O-])c1)c1ccc(C2=CCC(N3CCCC3c3ccccc3C3CC3)CC2)cc1Oc1cnc2[nH]ccc2c1]

The desired compound was synthesized with N-(2-nitro-4-sulfamoylphenyl)morpholine-4-carboxamide and 3-((1H-pyrrolo[2,3-b]pyridin-5-yl)oxy)-4'-(2-(2-cyclopropylphenyl)pyrrolidin-1-yl)-2',3',4',5'-tetrahydro-[1,1'-biphenyl]-4-carboxylic acid following the procedures similar to those in Example G8. $^1$H NMR (400 MHz, DMSO-$d_6$) δ ppm: 12.48 (s, 1H), 11.67 (s, 1H), 9.67 (s, 1H), 8.33 (s, 1H), 8.00-7.99 (m, 2H), 7.99-7.78 (m, 2H), 7.49-7.47 (m, 3H), 7.30-7.25 (m, 2H), 7.12-7.10 (m, 2H), 6.71 (s, 1H), 6.38 (s, 1H), 6.02-5.76 (m, 1H), 5.22-5.10 (m, 1H), 3.61-3.52 (m, 4H), 3.47-3.44 (m, 4H), 3.25-3.22 (m, 3H), 2.45-2.04 (m, 8H), 2.02-1.48 (m, 3H), 0.93-0.84 (m, 2H), 0.62-0.55 (m, 2H). MS (ESI, m/e) [M+1]$^+$ 831.8.

Example G85-S: (S)-3-((1H-pyrrolo[2,3-b]pyridin-5-yl)oxy)-N-((4-(((4-fluorotetrahydro-2H-pyran-4-yl)methyl)amino)-3-nitrophenyl)sulfonyl)-4'-(2-(2-isopropylphenyl)pyrrolidin-1-yl)-[1,1'-biphenyl]-4-carboxamide

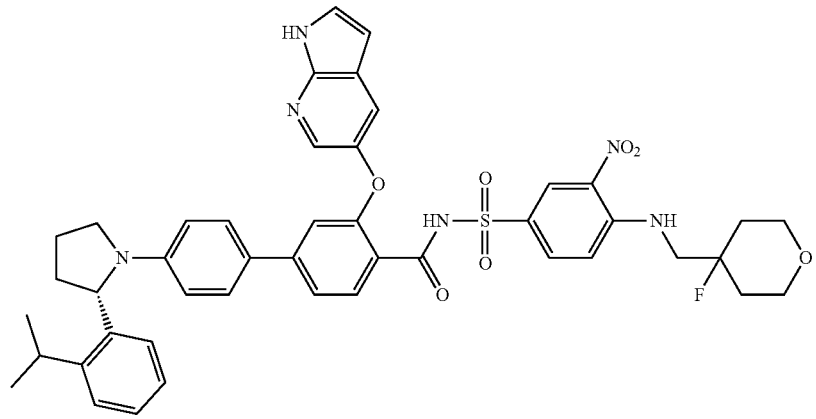

The desired compound was synthesized following the procedures similar to those in Example A1 by replacing 2-phenylpyrrolidine with (S)-2-(2-isopropylphenyl)pyrrolidine, and 3-nitro-4-(((tetrahydro-2H-pyran-4-yl)methyl)amino)benzenesulfonamide with 4-(((4 fluorotetrahydro-2H-pyran-4-yl)methyl)amino)-3-nitrobenzenesulfonamide. $^1$H NMR (400 MHz, DMSO-$d_6$) δ ppm: 12.17 (s, 1H), 11.70 (s, 1H), 8.64 (s, 1H), 8.57 (s, 1H), 8.05 (d, J=2.1 Hz, 1H), 7.84 (d, J=9.0 Hz, 1H), 7.59 (s, 1H), 7.54-7.51 (m, 2H), 7.37-7.23 (m, 5H), 7.17 (t, J=7.4 Hz, 1H), 6.98 (1, J=7.4 Hz, 1H), 6.91 (s, 1H), 6.82 (d, J=7.6 Hz, 1H), 6.37-6.35 (m, 2H), 4.99 (d, J=7.9 Hz, 1H), 3.79-3.67 (m, 5H), 3.54-3.52 (m, 2H), 3.38-3.29 (m, 2H), 2.06-1.92 (m, 2H), 1.86-1.75 (m, 6H), 1.27-1.23 (m, 6H). MS (ESI, m/e) [M+1]$^+$ 832.8.

Example G85-R: (R)-3-((1H-pyrrolo[2,3-b]pyridin-5-yl)oxy)-N-((4-(((4-fluorotetrahydro-2H-pyran-4-yl)methyl)amino)-3-nitrophenyl)sulfonyl)-4'-(2-(2-isopropylphenyl)pyrrolidin-1-yl)-[1,1'-biphenyl]-4-carboxamide

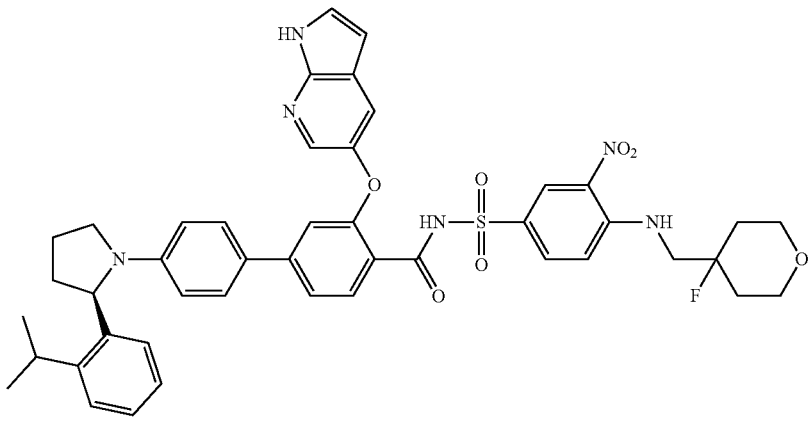 [SMILES: CC(C)c1ccccc1[C@H]1CCCN1c1ccc(-c2ccc(C(=O)NS(=O)(=O)c3ccc(NCC4(F)CCOCC4)c([N+](=O)[O-])c3)c(Oc3cnc4[nH]ccc4c3)c2)cc1]

The desired compound was synthesized following the procedures similar to those in Example A1 by replacing 2-phenylpyrrolidine with (R)-2-(2-isopropylphenyl)pyrrolidine, and 3-nitro-4-(((tetrahydro-2H-pyran-4-yl)methyl)amino)benzenesulfonamide with 4-(((4-fluorotetrahydro-2H-pyran-4-yl)methyl)amino)-3-nitrobenzenesulfonamide. $^1$H NMR (400 MHz, DMSO-$d_6$) δ ppm: 12.17 (s, 1H), 11.69 (s, 1H), 8.62-8.56 (m, 2H), 8.04 (s, 1H), 7.82 (s, 1H), 7.58-7.50 (m, 3H), 7.35-7.29 (m, 4H), 7.19-7.15 (m, 2H), 7.00-6.97 (m, 1H), 6.91 (s, 1H), 6.82 (d, J=7.6 Hz, 1H), 6.66 (s, 1H), 6.37-6.35 (m, 3H), 4.99 (d, J=7.7 Hz, 1H), 3.73-3.66 (m, 5H), 3.54-3.48 (m, 2H), 3.38-3.32 (m, 2H), 2.55 (s, 1H), 2.03-1.97 (m, 4H), 1.84-1.75 (m, 3H), 1.47-1.45 (m, 1H), 1.28-1.25 (m, 6H). MS (ESI, m/e) [M+1]$^+$ 832.8.

Example G86: 3-((1H-pyrrolo[2,3-b]pyridin-5-yl)oxy)-4'-(2-(2-cyclopropylphenyl)pyrrolidin-1-yl)-N-((4-(((4-(methoxymethyl)cyclohexyl)methyl)amino)-3-nitrophenyl)sulfonyl)-2',3',4',5'-tetrahydro-[1,1'-biphenyl]-4-carboxamide

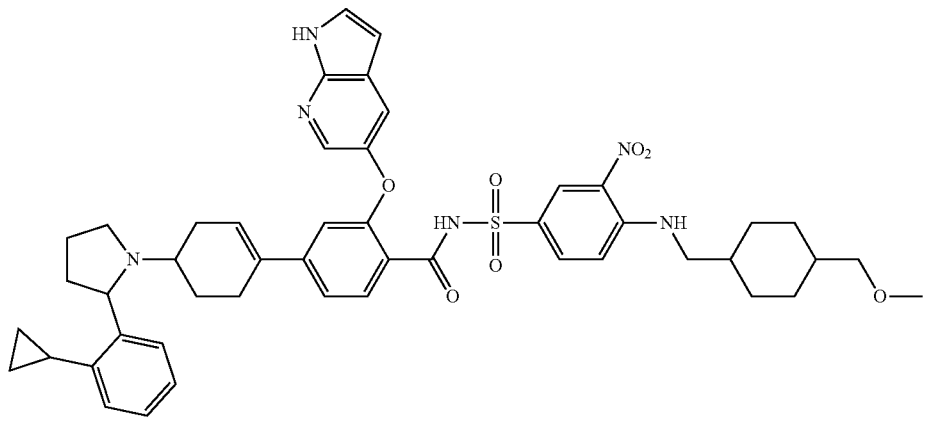 [SMILES: COCC1CCC(CNc2ccc(S(=O)(=O)NC(=O)c3ccc(C4=CCC(N5CCCC5c5ccccc5C5CC5)CC4)cc3Oc3cnc4[nH]ccc4c3)cc2[N+](=O)[O-])CC1]

The desired compound was synthesized with 4-(((4-(methoxymethyl)cyclohexyl)methyl)amino)-3-nitrobenzenesulfonamide and 3-((1H-pyrrolo[2,3-b]pyridin-5-yl)oxy)-4'-(2-(2-cyclopropylphenyl)pyrrolidin-1-yl)-2',3',4',5'-tetrahydro-[1,1'-biphenyl]-4-carboxylic acid following the procedures similar to those in Example (38. $^1$H NMR (400 MHz, DMSO-$d_6$) δ ppm: 12.23 (br, 1H), 11.64 (s, 1H), 8.50-8.40 (m, 2H), 7.97 (s, 1H), 7.85-7.50 (m, 2H), 7.49-7.44 (m, 3H), 7.40-7.19 (m, 1H), 7.13-7.05 (m, 2H), 7.01-6.85 (m, 2H), 6.72 (s, 1H), 6.35 (s, 1H), 5.99 (s, 0.5H), 5.81 (s, 0.5H), 5.30-5.12 (m, 0.5H), 4.30-4.26 (m, 0.5H), 3.33-3.21 (m, 5H), 3.12 (d, J=6.0 Hz, 2H), 3.06-2.90 (m, 2H), 2.29-2.10 (m, 4H), 2.08-1.95 (m, 4H), 1.81-1.67 (m, 6H), 1.58-1.41 (m, 5H), 1.02-0.81 (m, 5H), 0.67-0.50 (m, 2H). MS (ESI, m/e) [M+1]$^+$ 858.9.

Example G87: 3-((1H-pyrrolo[2,3-b]pyridin-5-yl)oxy)-4'-(2-(2-cyclopropylphenyl)pyrrolidin-1-yl)-N-((3-nitro-4-((((S)-1-(tetrahydro-2H-pyran-4-yl)pyrrolidin-3-yl)methyl)amino)phenyl)sulfonyl)-2',3',4',5'-tetrahydro-[1,1'-biphenyl]-4-carboxamide

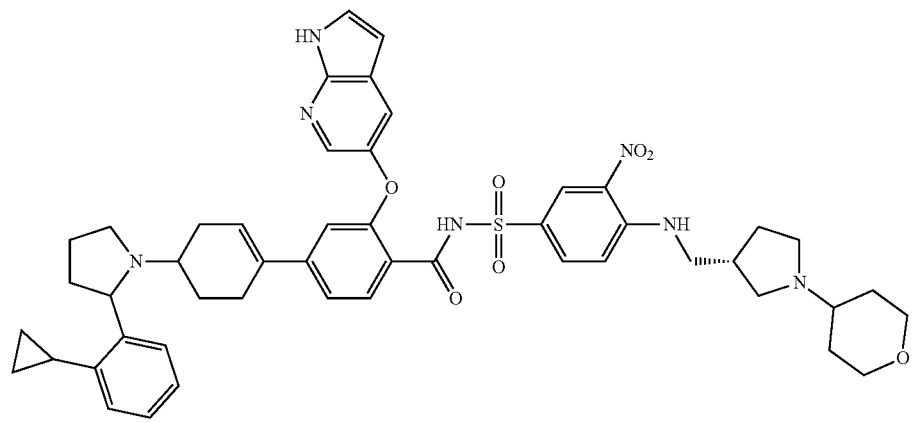 [SMILES: O=C(NS(=O)(=O)c1ccc(NC[C@@H]2CCN(C3CCOCC3)C2)c([N+](=O)[O-])c1)c1ccc(C2=CCC(N3CCCC3c3ccccc3C3CC3)CC2)cc1Oc1cnc2[nH]ccc2c1]

The desired compound was synthesized with (S)-3-nitro-4-((((1-(tetrahydro-2H-pyran-4-yl)pyrrolidin-3-yl)methyl)amino)benzenesulfonamide and 3-((1H-pyrrolo[2,3-b]pyridin-5-yl)oxy)-4'-(2-(2-cyclopropylphenyl)pyrrolidin-1-yl)-2',3',4',5'-tetrahydro-[1,1'-biphenyl]-4-carboxylic acid following the procedures similar to those in Example (38. $^1$H NMR (400 MHz, DMSO-d$_6$) δ ppm: 11.55 (s, 1H), 9.62 (s, 1H), 8.64-8.34 (m, 2H), 7.92 (s, 1H), 7.76-7.53 (m, 2H), 7.52-7.40 (m, 3H), 7.31 (s, 1H), 7.10-6.96 (m, 3H), 6.90-6.85 (m, 2H), 6.75-6.68 (m, 1H), 6.31 (s, 1H), 6.04-5.70 (m, 1H) 3.87 (s, 2H), 3.30-3.10 (m, 5H), 3.05-2.83 (m, 3H), 2.27-2.13 (m, 3H), 2.06-1.91 (m, 4H), 1.72 (s, 3H), 1.55-1.36 (m, 5H), 1.33-1.24 (m, 3H), 0.96-0.80 (m, 4H), 0.65 (s, 1H), 0.51 (s, 1H). MS (ESI) m/e [M+1]$^+$ 885.9.

Example G88-S: N-((4-((((S)-1,4-dioxan-2-yl)methyl)amino)-3-nitrophenyl)sulfonyl)-3-((1H-pyrrolo[2,3-b]pyridin-5-yl)oxy)-4'-((S)-2-(2-isopropylphenyl)pyrrolidin-1-yl)-[1,1'-biphenyl]-4-carboxamide

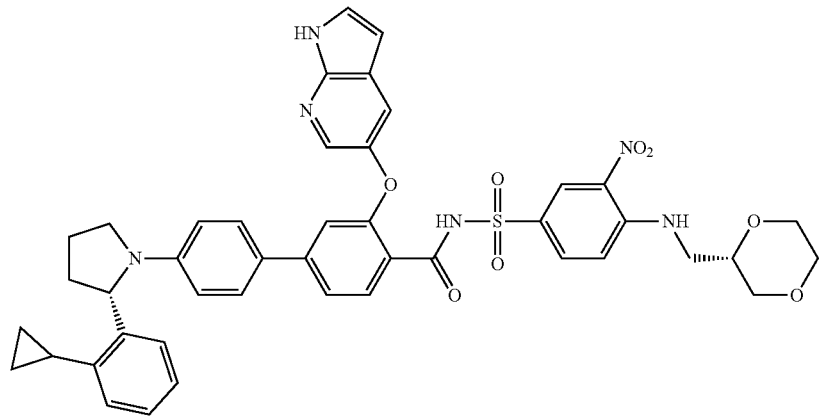 [SMILES: O=C(NS(=O)(=O)c1ccc(NC[C@H]2COCCO2)c([N+](=O)[O-])c1)c1ccc(-c2ccc(N3CCC[C@H]3c3ccccc3C3CC3)cc2)cc1Oc1cnc2[nH]ccc2c1]

The desired compound was synthesized following the procedures similar to those in Example A1 by replacing 2-phenylpyrrolidine with (S)-2-(2-isopropylphenyl)pyrrolidine, and replacing 3-nitro-4-(((tetrahydro-2H-pyran-4-yl)methyl)amino)benzenesulfonamide with (S)-4-(((1,4-dioxan-2-yl)methyl)amino)-3-nitrobenzenesulfonamide. $^1$H NMR (400 MHz, DMSO-d$_6$) δ ppm: 12.17 (s, 1H), 11.68 (s, 1H), 8.56 (s, 1H), 8.04 (s, 1H), 7.82 (s, 1H), 7.57-7.50 (m, 3H), 7.35-7.30 (m, 4H), 7.20-7.15 (m, 3H), 6.99 (t, J=7.5 Hz, 1H), 6.92 (s, 1H), 6.82 (d, J=7.1 Hz, 1H), 6.67 (s, 1H), 6.37-6.35 (m, 2H), 4.99 (d, J=8.4 Hz, 1H), 3.80-3.75 (m, 3H), 3.73-3.56 (m, 4H), 3.51-3.44 (m, 2H), 3.37-3.28 (m, 2H), 2.43 (s, 1H), 1.91-1.84 (m, 1H), 1.72-1.67 (m, 1H), 1.47-1.44 (m, 2H), 1.23 (s, 6H). MS (ESI, m/e) [M+1]$^+$ 816.8.

Example G89-S: N-((4-((((R)-1,4-dioxan-2-yl)methyl)amino)-3-nitrophenyl)sulfonyl)-3-((1H-pyrrolo[2,3-b]pyridin-5-yl)oxy)-4'-((S)-2-(2-isopropylphenyl)pyrrolidin-1-yl)-[1,1'-biphenyl]-4-carboxamide

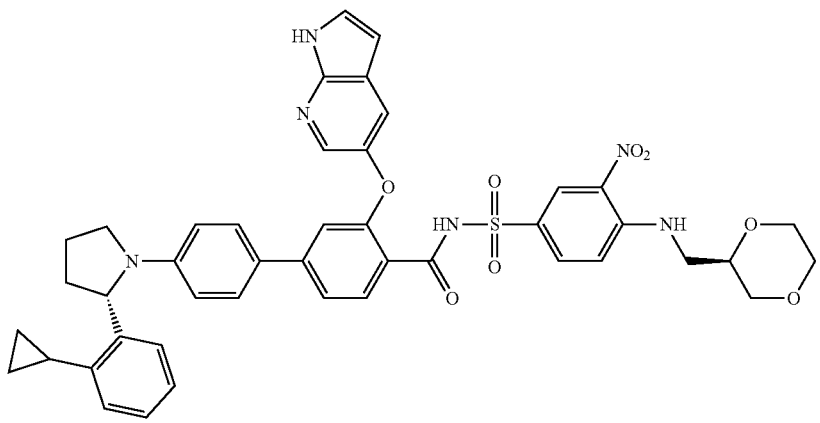 [SMILES: O=C(NS(=O)(=O)c1ccc(NC[C@@H]2COCCO2)c([N+](=O)[O-])c1)c1ccc(-c2ccc(N3CCC[C@H]3c3ccccc3C3CC3)cc2)cc1Oc1cnc2[nH]ccc2c1]

The desired compound was synthesized following the procedures similar to those in Example A1 by replacing 2-phenylpyrrolidine with (S)-2-(2-isopropylphenyl)pyrrolidine, and replacing 3-nitro-4-(((tetrahydro-2H-pyran-4-yl)methyl)amino)benzenesulfonamide with (R)-4-(((1,4-dioxan-2-yl)methyl)amino)-3-nitrobenzenesulfonamide. $^1$H NMR (400 MHz, DMSO-d$_6$) δ ppm: 12.17 (s, 1H), 11.69 (s, 1H), 8.59-8.56 (m, 2H), 8.04 (s, 1H), 7.83 (d, J=8.4 Hz, 1H), 7.57-7.50 (m, 3H), 7.35-7.30 (m, 4H), 7.17-7.10 (m, 3H), 6.98 (t, J=7.5 Hz, 1H), 6.92 (s, 1H), 6.82 (d, J=7.6 Hz, 1H), 6.37-6.35 (m, 2H), 4.99 (d, J=7.8 Hz, 1H), 3.83-3.75 (m, 3H), 3.70-3.58 (m, 4H), 3.53-3.43 (m, 2H), 3.37-3.29 (m, 2H), 2.43-2.40 (m, 1H), 1.90-1.84 (m, 1H), 1.72-167 (m, 1H), 1.46-1.43 (m, 1H), 1.30-1.23 (m, 7H). MS (ESI, m/e) [M+1]$^+$ 816.8.

Example G90-S: 3-((1H-pyrrolo[2,3-b]pyridin-5-yl)oxy)-4'-((S)-2-(2-ethylphenyl)pyrrolidin-1-yl)-N-((4-(((4-fluorotetrahydro-2H-pyran-4-yl)methyl)amino)-3-nitrophenyl)sulfonyl)-2',3',4',5'-tetrahydro-[1,1'-biphenyl]-4-carboxamide

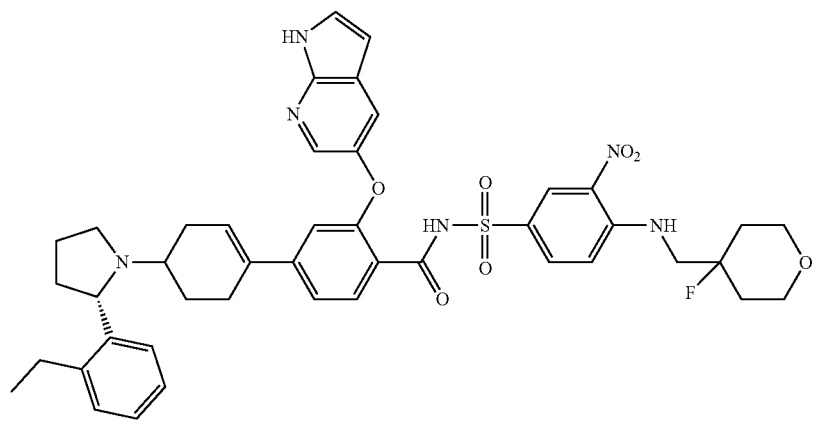

The desired compound was synthesized with 4-(((4-fluorotetrahydro-2H-pyran-4-yl)methyl)amino)-3-nitrobenzenesulfonamide and 3-((1H-pyrrolo[2,3-b]pyridin-5-yl)oxy)-4'-((S)-2-(2-ethylphenyl)pyrrolidin-1-yl)-2',3',4',5'-tetrahydro-[1,1'-biphenyl]-4-carboxylic acid following the procedures similar to those in Example G8. $^1$H NMR (DMSO-d$_6$) δ ppm: 11.64 (s, 1H), 8.59-8.15 (m, 2H), 7.94 (s, 1H), 7.71 (d, J=8.4 Hz, 1H), 7.55-6.90 (m, 8H), 6.75 (s, 1H), 6.32 (s, 1H), 5.98-5.77 (m, 1H), 3.81-3.61 (m, 4H), 3.59-3.37 (m, 7H), 2.83-2.60 (m, 2H), 2.44-1.93 (m, 7H), 1.88-1.35 (m, 6H), 1.24-1.03 (m, 3H). MS (ESI, m/e) [M+1]$^+$ 822.8.

Two enantiomers G90-a (faster isomer) and G90-b (slower isomer) were separated by chiral preparative HPLC. The chiral separation conditions are shown below. The faster enantiomer was eluted at retention time of 3.7 min to give G90-a. The slower enantiomer was eluted at retention time of 5.5 min to give G90-b.

| Column | CHIRAL ART Cellulose-SB |
|---|---|
| Column size | 5 cm × 25 cm, 5 um |
| Injection | 3.0 mL |
| Mobile phase | MTBE:[MeOH (0.2% MSA)] = 70:30 |
| Flow rate | 95 ml/min |
| Wave length | UV 220 nm |
| Temperature | 25° C. |
| Sample solution | 32 mg/mL in MeOH:DCM = 3:1 |
| Prep-HPLC equipment | Prep-HPLC-YMC |

Example G90-a: $^1$H NMR (DMSO-d$_6$) δ ppm: 11.64 (s, 1H), 8.49 (s, 2H), 7.97 (s, 1H), 7.83-6.86 (m, 10H), 6.72 (s, 1H), 6.35 (s, 1H), 5.81 (s, 1H), 3.87-3.40 (m, 7H), 3.20-2.94 (m, 1H), 2.73-2.59 (m, 2H), 2.43-1.21 (m, 16H), 1.13 (t, J=7.6 Hz, 3H). MS (ESI, m/e) [M+1]$^+$ 822.8. Example G90-b: $^1$H NMR (DMSO-d$_6$) δ ppm: 11.63 (s, 1H), 8.48 (s, 2H), 7.96 (d, J=2.0 Hz, 1H), 7.76 (d, J=8.0 Hz, 1H), 7.64-7.39 (m, 4H), 7.34-6.97 (m, 5H), 6.72 (s, 1H), 6.35 (s, 1H), 5.98 (s, 1H), 3.80-3.46 (m, 7H), 2.77-2.55 (m, 3H), 2.45-1.21 (m, 16H), 1.14 (t, J=7.2 Hz, 3H). MS (ESI, m/e) [M+1]⁺ 822.8.

Example G91-R: 3-((1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4'-((R)-2-(2-isopropylphenyl)pyrrolidin-1-yl)-[1,1'-biphenyl]-4-carboxamide

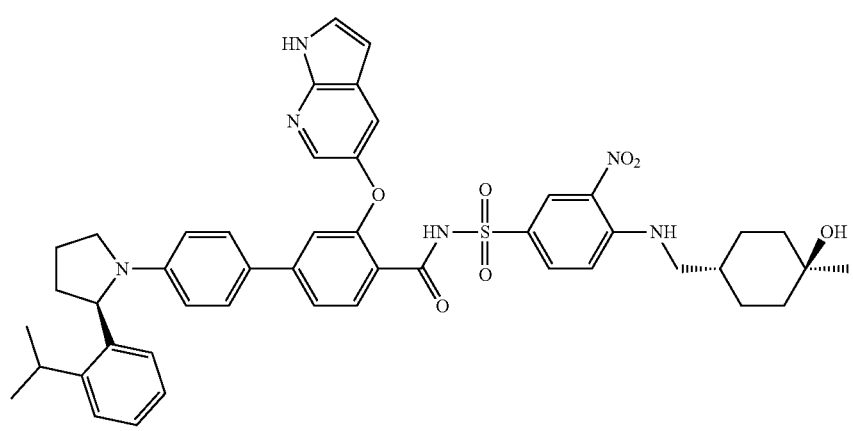 [SMILES: CC(C)c1ccccc1[C@H]1CCCN1c1ccc(-c2ccc(C(=O)NS(=O)(=O)c3ccc(NC[C@H]4CC[C@](C)(O)CC4)c([N+](=O)[O-])c3)c(Oc3cnc4[nH]ccc4c3)c2)cc1]

The desired compound was synthesized following the procedures similar to those in Example A1 by replacing 2-phenylpyrrolidine with (R)-2-(2-isopropylphenyl)pyrrolidine, and replacing 3-nitro-4-(((tetrahydro-2H-pyran-4-yl)methyl)amino)benzenesulfonamide with 4-((((1r,4r)-4-hydroxy-4-methylcyclohexyl)methyl)amino)-3-nitrobenzenesulfonamide. ¹H NMR (400 MHz, DMSO-d₆) δ ppm: 12.15 (s, 1H), 11.69 (s, 1H), 8.55 (s, 2H), 8.04 (s, 1H), 7.80 (s, 1H), 7.68 (s, 1H), 7.61-7.44 (m, 3H), 7.29 (d, J=8.6 Hz, 2H), 7.22 (d, J=7.4 Hz, 1H), 7.17-7.11 (m, 1H), 7.01 (t, J=7.2 Hz, 1H), 6.91-6.82 (m, 2H), 6.36-6.34 (m, 3H), 4.92 (d, J=7.7 Hz, 1H), 4.25 (s, 1H), 3.70 (s, 1H), 2.83-2.76 (m, 1H), 2.73-2.67 (m, 1H), 2.03-1.97 (m, 5H), 1.69-1.66 (m, 3H), 1.55-1.52 (m, 2H), 1.47-1.43 (m, 1H), 1.32-1.25 (m, 6H). MS (ESI, m/e) [M+1]⁺ 842.8.

Example G92-R: 3-((1H-pyrrolo[2,3-b]pyridin-5-yl)oxy)-4'-((R)-2-(2-cyclopropylphenyl)pyrrolidin-1-yl)-N-((4-((((1r,4r)-4-hydroxy-4-methylcyclohexyl)methyl)amino)-3-nitrophenyl)sulfonyl)-[1,1'-biphenyl]-4-carboxamide

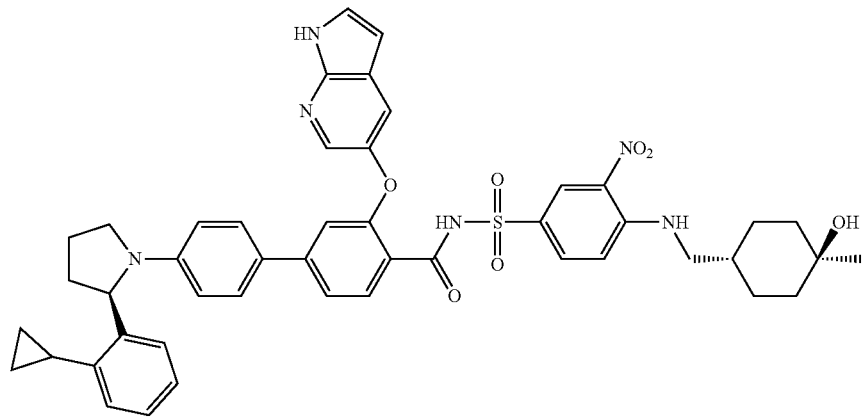 [SMILES: C[C@]1(O)CC[C@H](CNc2ccc(S(=O)(=O)NC(=O)c3ccc(-c4ccc(N5CCC[C@@H]5c5ccccc5C5CC5)cc4)cc3Oc3cnc4[nH]ccc4c3)cc2[N+](=O)[O-])CC1]

The desired compound was synthesized following the procedures similar to those in Example A1 by replacing 2-phenylpyrrolidine with (R)-2-(2-cyclopropylphenyl)pyrrolidine, and replacing 3-nitro-4-(((tetrahydro-2H-pyran-4-yl)methyl)amino)benzenesulfonamide with 4-(((((1r,4r)-4-hydroxy-4-methylcyclohexyl)methyl)amino)-3-nitrobenzenesulfonamide. $^1$H NMR (400 MHz, DMSO-$d_6$) δ ppm: 12.14 (s, 1H), 11.70 (s, 1H), 8.65-8.45 (m, 2H), 8.06 (d, J=2.4 Hz, 1H), 7.83 (dd, J=9.2 Hz, 1.6 Hz, 1H), 7.65-7.45 (m, 31H. 7.40-7.22 (m, 3H), 7.17-6.96 (m, 4H), 6.93-6.78 (m, 2H), 6.47-6.27 (m, 3H), 5.20 (d, J=8.0 Hz, 1H), 4.24 (s, 1H), 3.71 (t, J=7.6 Hz, 1H), 3.45-3.37 (m, 1H), 3.29-3.20 (m, 2H), 2.47-2.36 (m, 1H), 2.10-1.79 (m, 4H), 1.73-1.49 (m, 5H), 1.40-1.27 (m, 2H), 1.18-1.06 (m, 5H), 1.04-0.90 (m, 2H), 0.82-0.64 (m, 2H). MS (ESI, m/e) [M+1]$^+$ 840.8.

Example G92-S: 3-((1H-pyrrolo[2,3-b]pyridin-5-yl)oxy)-4'-((S)-2-(2-cyclopropylphenyl)pyrrolidin-1-yl)-N-((4-((((1r,4r)-4-hydroxy-4-methylcyclohexyl)methyl)amino)-3-nitrophenyl)sulfonyl)-[1,1'-biphenyl]-4-carboxamide

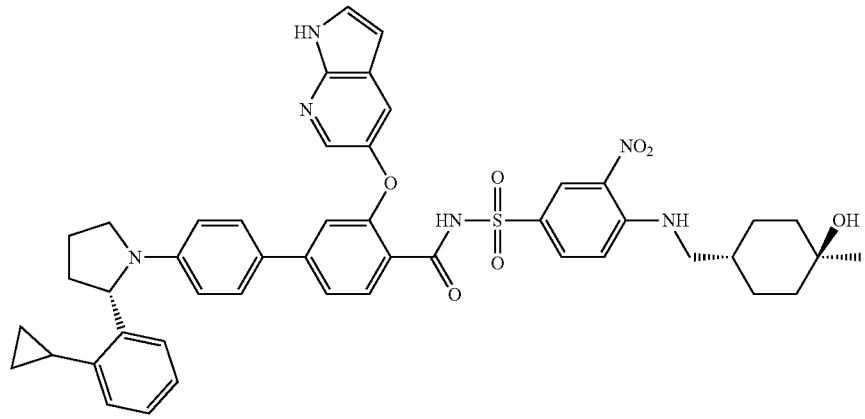 [SMILES: C[C@]1(O)CC[C@H](CNc2ccc(S(=O)(=O)NC(=O)c3ccc(-c4ccc(N5CCC[C@H]5c5ccccc5C5CC5)cc4)cc3Oc3cnc4[nH]ccc4c3)cc2[N+](=O)[O-])CC1]

The desired compound was synthesized following the procedures similar to those in Example A1 by replacing 2-phenylpyrrolidine with (S)-2-(2-cyclopropylphenyl)pyrrolidine, and replacing 3-nitro-4-(((tetrahydro-2H-pyran-4-yl)methyl)amino)benzenesulfonamide with 4-(((((1r,4r)-4-hydroxy-4-methylcyclohexyl)methyl)amino)-3-nitrobenzenesulfonamide. $^1$H NMR (400 MHz, DMSO-$d_6$) δ ppm: 12.15 (s, 1H), 11.69 (s, 1H), 8.65-8.42 (m, 2H), 8.07-8.01 (m, 1H), 7.88-7.73 (m, 1H), 7.64-7.43 (m, 3H), 7.39-7.21 (m, 3H), 7.16-6.95 (m, 4H), 6.95-6.76 (m, 2H), 6.44-6.25 (m, 3H), 5.25-5.13 (m, 1H), 4.24 (s, 1H), 3.76-3.65 (m, 1H), 3.47-3.35 (m, 1H), 3.30-3.20 (m, 2H), 3.18-2.84 (m, 1H), 2.47-2.36 (m, 1H), 2.11-1.77 (m, 4H), 1.74-1.58 (m, 3H), 1.58-1.46 (m, 2H), 1.40-1.27 (m, 2H), 1.16-1.10 (m, 1H), 1.09 (s, 3H), 1.04-0.91 (m, 2H), 0.82-0.65 (m, 2H). MS (ESI, m/e) [M+1]$^+$ 840.8.

Example G93-R: 3-((1H-pyrrolo[2,3-b]pyridin-5-yl)oxy)-4'-((R)-2-(2-cyclopropylphenyl)pyrrolidin-1-yl)-N-((4-(((((1s,4s)-4-hydroxy-4-methylcyclohexyl)methyl)amino)-3-nitrophenyl)sulfonyl)-[1,1'-biphenyl]-4-carboxamide

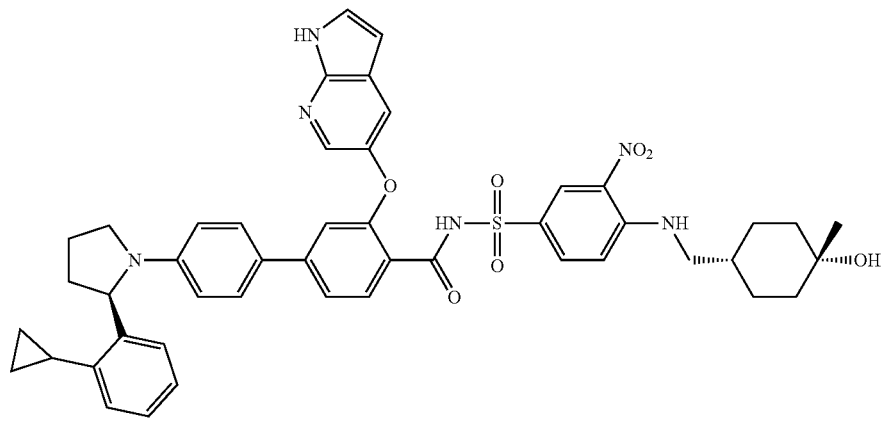 [SMILES: C[C@]1(O)CC[C@@H](CNc2ccc(S(=O)(=O)NC(=O)c3ccc(-c4ccc(N5CCC[C@@H]5c5ccccc5C5CC5)cc4)cc3Oc3cnc4[nH]ccc4c3)cc2[N+](=O)[O-])CC1]

The desired compound was synthesized following the procedures similar to those in Example A1 by replacing 2-phenylpyrrolidine with (R)-2-(2-cyclopropylphenyl)pyrrolidine, and replacing 3-nitro-4-(((tetrahydro-2H-pyran-4-yl)methyl)amino)benzenesulfonamide with 4-(((((1s,4s)-4-hydroxy-4-methylcyclohexyl)methyl)amino)-3-nitrobenzenesulfonamide. $^1$H NMR (400 MHz, DMSO-d$_6$) δ ppm: 12.14 (s, 1H), 11.70 (s, 1H), 8.66-8.48 (m, 2H), 8.10-8.01 (m, 1H), 7.88-7.74 (m, 1H), 7.63-7.45 (m, 3H), 7.39-7.23 (m, 3H), 7.14-6.94 (m, 4H), 6.93-6.77 (m, 2H), 6.45-6.24 (m, 3H), 5.26-5.09 (m, 1H), 3.96 (s, 1H), 3.80-3.63 (m, 1H), 3.42-3.37 (m, 1H), 3.28-3.17 (m, 2H), 2.47-2.37 (m, 1H), 2.12-1.76 (m, 4H), 1.62-1.23 (m, 9H), 1.08 (s, 4H), 1.03-0.90 (m, 2H), 0.81-0.64 (m, 2H). MS (ESI, m/e) [M+1]$^+$ 840.8.

Example G93-S: 3-((1H-pyrrolo[2,3-b]pyridin-5-yl)oxy)-4'-((S)-2-(2-cyclopropylphenyl)pyrrolidin-1-yl)-N-((4-((((1s,4s)-4-hydroxy-4-methylcyclohexyl)methyl)amino)-3-nitrophenyl)sulfonyl)-[1,1'-biphenyl]-4-carboxamide

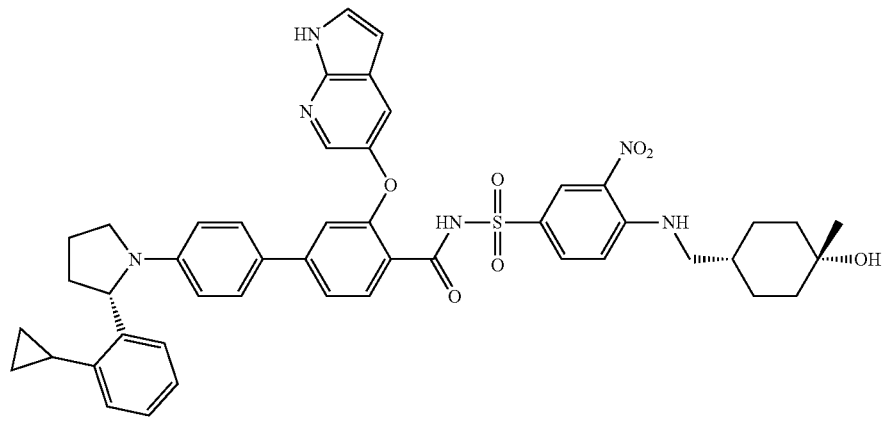 [SMILES: C[C@]1(O)CC[C@@H](CNc2ccc(S(=O)(=O)NC(=O)c3ccc(-c4ccc(N5CCC[C@H]5c5ccccc5C5CC5)cc4)cc3Oc3cnc4[nH]ccc4c3)cc2[N+](=O)[O-])CC1]

The desired compound was synthesized following the procedures similar to those in Example A1 by replacing 2-phenylpyrrolidine with (S)-2-(2-cyclopropylphenyl)pyrrolidine, and replacing 3-nitro-4-(((tetrahydro-2H-pyran-4-yl)methyl)amino)benzenesulfonamide with 4-(((((1s,4s)-4-hydroxy-4-methylcyclohexyl)methyl)amino)-3-nitrobenzenesulfonamide. MS (ESI, m/e) [M+1]$^+$ 840.8.

Example G94-R: (R)-3-((1H-pyrrolo[2,3-b]pyridin-5-yl)oxy)-4'-(2-(2-cyclopropylphenyl)pyrrolidin-1-yl)-N-((4-(((4-fluorotetrahydro-2H-pyran-4-yl)methyl)amino)-3-nitrophenyl)sulfonyl)-[1,1'-biphenyl]-4-carboxamide

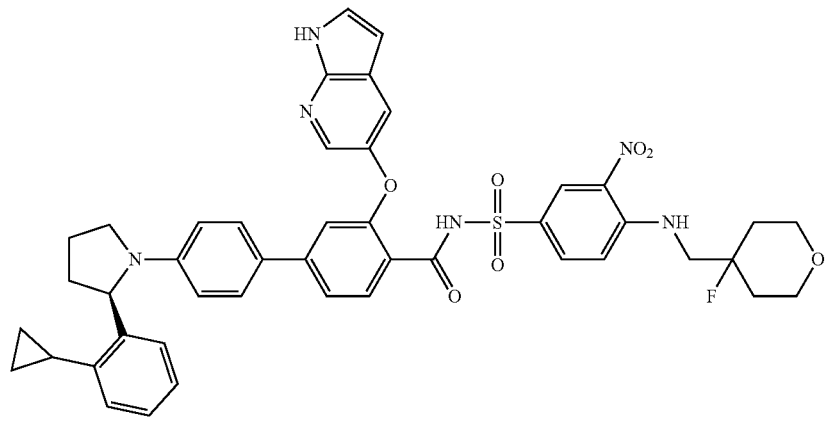 [SMILES: O=C(NS(=O)(=O)c1ccc(NCC2(F)CCOCC2)c([N+](=O)[O-])c1)c1ccc(-c2ccc(N3CCC[C@@H]3c3ccccc3C3CC3)cc2)cc1Oc1cnc2[nH]ccc2c1]

The desired compound was synthesized following the procedures similar to those in Example A1 by replacing 2-phenylpyrrolidine with (R)-2-(2-cyclopropylphenyl)pyrrolidine, and replacing 3-nitro-4-(((tetrahydro-2H-pyran-4-yl)methyl)amino)benzenesulfonamide with 4-(((4-fluorotetrahydro-2H-pyran-4-yl)methyl)amino)-3-nitrobenzenesulfonamide. $^1$H NMR (400 MHz, DMSO-$d_6$) δ ppm: 12.17 (s, 1H), 11.70 (s, 1H), 8.64 (s, 1H), 8.57 (s, 1H), 8.05 (s, 1H), 7.84 (d, J=9.2 Hz, 1H), 7.65-7.44 (m, 3H), 7.37-7.22 (m, 4H), 7.14-7.06 (m, 1H), 7.05-6.96 (m, 2H), 6.92-6.81 (m, 2H), 6.45-6.32 (m, 3H), 5.28-5.10 (m, 1H), 3.82-3.68 (m, 5H), 3.63-3.49 (m, 2H), 2.48-2.40 (m, 1H), 2.08-1.70 (m, 8H), 1.09-0.89 (m, 2H), 0.84-0.74 (m, 2H). MS (ESI) m/e [M+1]$^+$ 830.7.

Example G94-S: (S)-3-((1H-pyrrolo[2,3-b]pyridin-5-yl)oxy)-4'-(2-(2-cyclopropylphenyl)pyrrolidin-1-yl)-N-((4-(((4-fluorotetrahydro-2H-pyran-4-yl)methyl)amino)-3-nitrophenyl)sulfonyl)-[1,1'-biphenyl]-4-carboxamide

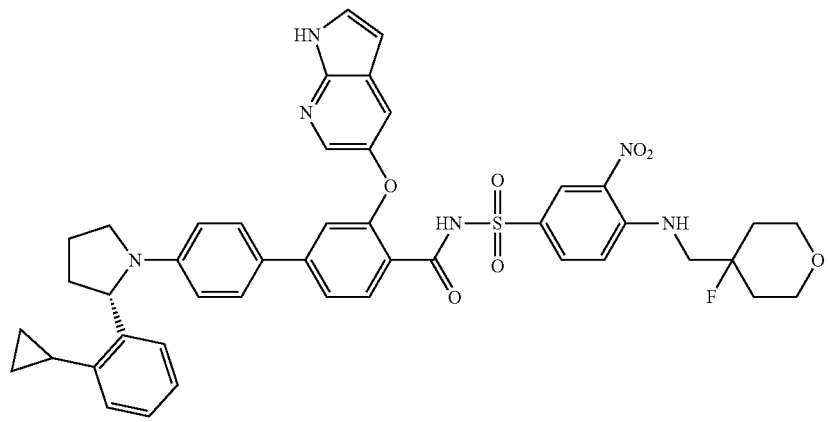 [SMILES: O=C(NS(=O)(=O)c1ccc(NCC2(F)CCOCC2)c([N+](=O)[O-])c1)c1ccc(-c2ccc(N3CCC[C@H]3c3ccccc3C3CC3)cc2)cc1Oc1cnc2[nH]ccc2c1]

The desired compound was synthesized following the procedures similar to those in Example A1 by replacing 2-phenylpyrrolidine with (S)-2-(2-cyclopropylphenyl)pyrrolidine, and replacing 3-nitro-4-(((tetrahydro-2H-pyran-4-yl)methyl)amino)benzenesulfonamide with 4-(((4-fluorotetrahydro-2H-pyran-4-yl)methyl)amino)-3-nitrobenzenesulfonamide. $^1$H NMR (400 MHz, DMSO-$d_6$) δ ppm: 12.15 (s, 1H), 11.69 (s, 1H), 8.69-8.58 (m, 1H), 8.58-8.52 (m, 1H), 8.10-7.99 (m, 1H), 7.89-7.77 (m, 1H), 7.63-7.45 (m, 3H), 7.41-7.21 (m, 4H), 7.16-7.05 (m, 1H), 7.05-6.96 (m, 2H), 6.90 (s, 1H), 6.87-6.80 (m, 1H), 6.44-6.28 (m, 31B. 5.29-5.07 (m, 1H), 3.82-3.65 (m, 5H), 3.59-3.46 (m, 2H), 3.43-3.36 (m, 1H), 2.47-2.34 (m, 1H), 2.14-1.67 (m, 8H), 1.07-0.88 (m, 2H), 0.83-0.63 (m, 2H). MS (ESI) m/e [M+1]$^+$ 830.8.

Example G95-R: N-((4-((((S)-1,4-dioxan-2-yl)methyl)amino)-3-nitrophenyl)sulfonyl)-3-((1H-pyrrolo[2,3-b]pyridin-5-yl)oxy)-4'-((R)-2-(2-cyclopropylphenyl)pyrrolidin-1-yl)-[1,1'-biphenyl]-4-carboxamide

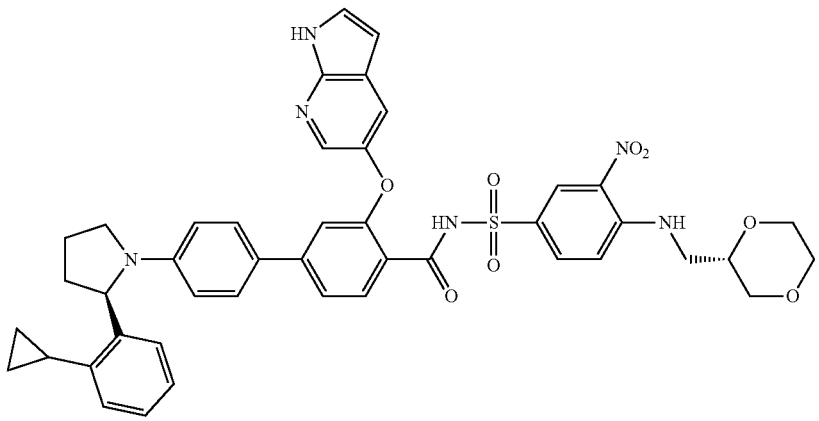 [SMILES: O=C(NS(=O)(=O)c1ccc(NC[C@H]2COCCO2)c([N+](=O)[O-])c1)c1ccc(-c2ccc(N3CCC[C@@H]3c3ccccc3C3CC3)cc2)cc1Oc1cnc2[nH]ccc2c1]

The desired compound was synthesized following the procedures similar to those in Example A1 by replacing 2-phenylpyrrolidine with (R)-2-(2-cyclopropylphenyl)pyrrolidine, and replacing 3-nitro-4-(((tetrahydro-2H-pyran-4-yl)methyl)amino)benzenesulfonamide with (S)-4-(((1,4-dioxan-2-yl)methyl)amino)-3-nitrobenzenesulfonamide. $^1$H NMR (400 MHz, DMSO-$d_6$) δ ppm: 12.16 (s, 1H), 11.68 (s, 1H), 8.64-8.49 (m, 2H), 8.10-7.99 (m, 1H), 7.91-7.71 (m, 1H), 7.65-7.41 (m, 3H), 7.41-7.20 (m, 3H), 7.18-7.06 (m, 2H), 7.06-6.95 (m, 2H), 6.90 (s, 1H), 6.87-6.78 (m, 1H), 6.42-6.27 (m, 3H), 5.32-5.10 (m, 1H), 3.85-3.55 (m, 6H), 3.55-3.43 (m, 2H), 3.43-3.36 (m, 1H), 3.20-2.79 (m, 1H), 2.46-2.33 (m, 1H), 2.19-1.77 (m, 4H), 1.09-0.89 (m, 2H), 0.85-0.61 (m, 2H). MS (ESI, m/e) [M+1]$^+$ 814.7.

Example G95-S: N-((4-((((S)-1,4-dioxan-2-yl)methyl)amino)-3-nitrophenyl)sulfonyl)-3-((1H-pyrrolo[2,3-b]pyridin-5-yl)oxy)-4'-((S)-2-(2-cyclopropylphenyl)pyrrolidin-1-yl)-[1,1'-biphenyl]-4-carboxamide

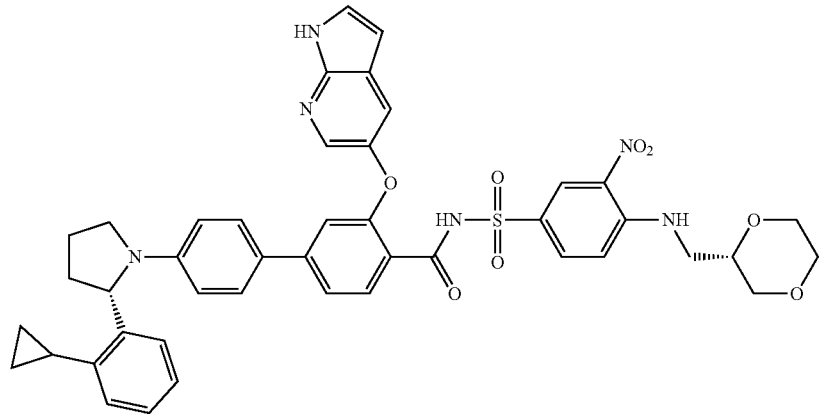 [SMILES: O=C(NS(=O)(=O)c1ccc(NC[C@H]2COCCO2)c([N+](=O)[O-])c1)c1ccc(-c2ccc(N3CCC[C@H]3c3ccccc3C3CC3)cc2)cc1Oc1cnc2[nH]ccc2c1]

The desired compound was synthesized following the procedures similar to those in Example A1 by replacing 2-phenylpyrrolidine with (S)-2-(2-cyclopropylphenyl)pyrrolidine, and replacing 3-nitro-4-(((tetrahydro-2H-pyran-4-yl)methyl)amino)benzenesulfonamide with (S)-4-(((1,4-dioxan-2-yl)methyl)amino)-3-nitrobenzenesulfonamide. MS (ESI, m/e) [M+1]$^+$ 814.7.

Example G96-R: N-((4-((((R)-1,4-dioxan-2-yl)methyl)amino)-3-nitrophenyl)sulfonyl)-3-((1H-pyrrolo[2,3-b]pyridin-5-yl)oxy)-4'-((R)-2-(2-cyclopropylphenyl)pyrrolidin-1-yl)-[1,1'-biphenyl]-4-carboxamide

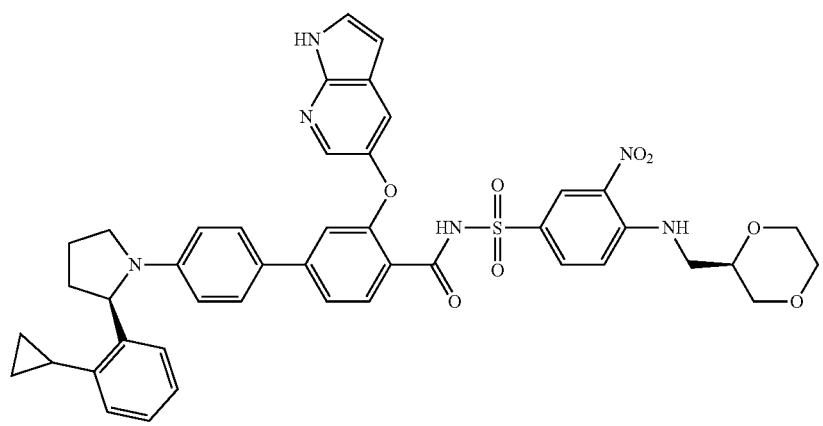 [SMILES: O=C(NS(=O)(=O)c1ccc(NC[C@@H]2COCCO2)c([N+](=O)[O-])c1)c1ccc(-c2ccc(N3CCC[C@@H]3c3ccccc3C3CC3)cc2)cc1Oc1cnc2[nH]ccc2c1]

The desired compound was synthesized following the procedures similar to those in Example A1 by replacing 2-phenylpyrrolidine with (R)-2-(2-cyclopropylphenyl)pyrrolidine, and replacing 3-nitro-4-(((tetrahydro-2H-pyran-4-yl)methyl)amino)benzenesulfonamide with (R)-4-(((1,4-dioxan-2-yl)methyl)amino)-3-nitrobenzenesulfonamide. ¹H NMR (400 MHz, DMSO-d₆) δ ppm: 12.15 (s, 1H), 11.68 (s, 1H), 8.60-8.55 (m, 2H), 8.05 (s, 1H), 7.84 (d, J=9.0 Hz, 1H), 7.58-7.51 (m, 3H), 7.35-7.30 (m, 3H), 7.15-7.06 (m, 2H), 7.04-6.97 (m, 2H), 6.90 (s, 1H), 6.86-6.80 (m, 1H), 6.39-6.33 (m, 3H), 5.22-5.10 (m, 1H), 3.82-3.71 (m, 4H), 3.65-3.58 (m, 2H), 3.53-3.45 (m, 2H), 3.38 (s, 1H), 2.06-1.82 (m, 4H), 1.03-0.94 (m, 2H), 0.80-0.75 (m, 1H), 0.75-0.68 (m, 1H). MS (ESI) m/e [M+1]⁺ 814.7.

Example G96-S: N-((4-((((R)-1,4-dioxan-2-yl)methyl)amino)-3-nitrophenyl)sulfonyl)-3-((1H-pyrrolo[2,3-b]pyridin-5-yl)oxy)-4'-((S)-2-(2-cyclopropylphenyl)pyrrolidin-1-yl)-[1,1'-biphenyl]-4-carboxamide

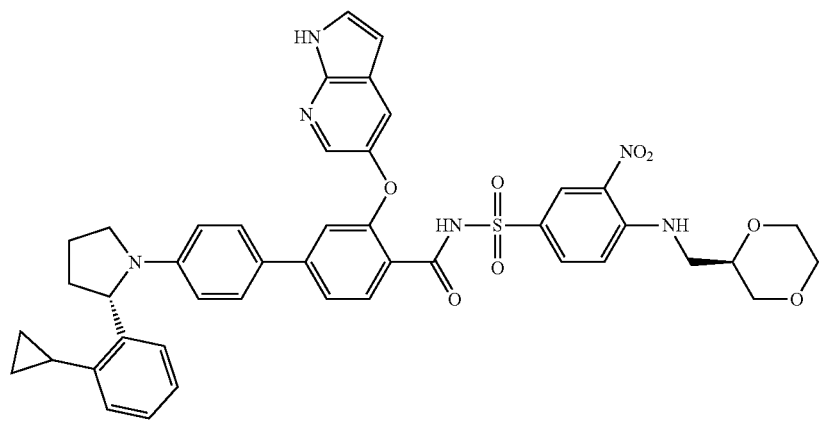 [SMILES: O=C(NS(=O)(=O)c1ccc(NC[C@@H]2COCCO2)c([N+](=O)[O-])c1)c1ccc(-c2ccc(N3CCC[C@H]3c3ccccc3C3CC3)cc2)cc1Oc1cnc2[nH]ccc2c1]

The desired compound was synthesized following the procedures similar to those in Example A1 by replacing 2-phenylpyrrolidine with (S)-2-(2-cyclopropylphenyl)pyrrolidine, and replacing 3-nitro-4-(((tetrahydro-2H-pyran-4-yl)methyl)amino)benzenesulfonamide with (R)-4-(((1,4-dioxan-2-yl)methyl)amino)-3-nitrobenzenesulfonamide. ¹H NMR (400 MHz, DMSO-d₆) δ ppm: 12.32-12.04 (m, 1H), 11.67 (s, 1H), 8.76-8.38 (m, 2H), 8.11-7.96 (m, 1H), 7.91-7.72 (m, 1H), 7.66-7.43 (m, 3H), 7.43-7.21 (m, 3H), 7.21-6.95 (m, 4H), 6.95-6.73 (m, 2H), 6.46-6.23 (m, 3H), 5.26-5.08 (m, 1H), 3.90-3.58 (m, 5H), 3.58-3.34 (m, 6H), 2.44-2.35 (m, 1H), 2.07-1.83 (m, 4H), 1.08-0.90 (m, 2H), 0.83-0.62 (m, 2H). MS (ESI, m/e) [M+1]⁺ 814.8.

Example G97-R: (R)-3-((1H-pyrrolo[2,3-b]pyridin-5-yl)oxy)-4'-(2-(2-cyclopropylphenyl)pyrrolidin-1-yl)-N-((4-((4-fluoro-1-(oxetan-3-yl)piperidin-4-yl)methoxy)-3-nitrophenyl)sulfonyl)[1,1'-biphenyl]-4-carboxamide

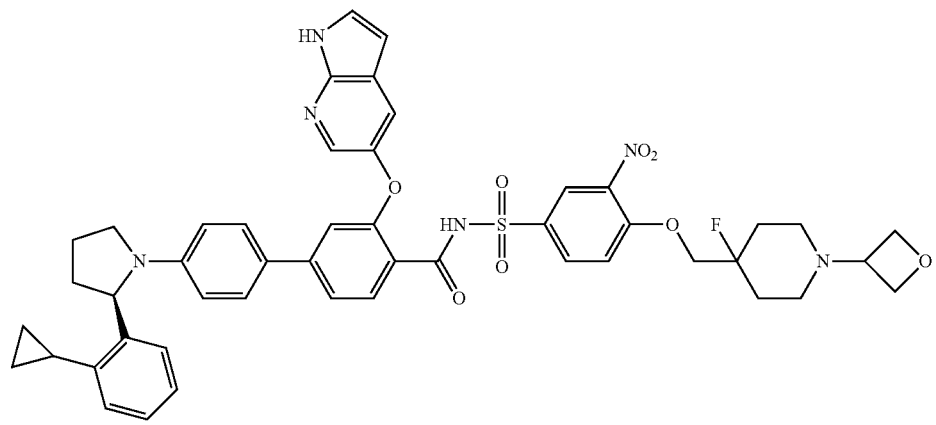 [SMILES: O=C(NS(=O)(=O)c1ccc(OCC2(F)CCN(C3COC3)CC2)c([N+](=O)[O-])c1)c1ccc(-c2ccc(N3CCC[C@@H]3c3ccccc3C3CC3)cc2)cc1Oc1cnc2[nH]ccc2c1]

The desired compound was synthesized following the procedures similar to those in Example A1 by replacing 2-phenylpyrrolidine with (R)-2-(2-cyclopropylphenyl)pyrrolidine, and replacing 3-nitro-4-(((tetrahydro-2H-pyran-4-yl)methyl)amino)benzenesulfonamide with 4-((4-fluoro-1-(oxetan-3-yl)piperidin-4-yl)methoxy)-3-nitrobenzenesulfonamide. $^1$H NMR (400 MHz, DMSO-$d_6$) δ ppm: 12.43-11.83 (m, 1H), 11.68 (s, 1H), 8.36 (s, 1H), 8.15-7.95 (m, 2H), 7.65-7.37 (m, 4H), 7.37-7.18 (m, 3H), 7.15-6.94 (m, 3H), 6.94-6.80 (m, 2H), 6.44-6.26 (m, 3H), 5.27-5.11 (m, 1H), 4.66-4.44 (m, 3H), 4.44-4.26 (m, 2H), 3.77-3.67 (m, 1H), 3.46-3.31 (m, 2H), 3.01-2.60 (m, 2H), 2.50-1.69 (m, 12H), 1.07-0.89 (m, 2H), 0.85-0.61 (m, 2H). MS (ESI, m/e) [M+1]$^+$ 886.7.

Example G97-S: (S)-3-((1H-pyrrolo[2,3-b]pyridin-5-yl)oxy)-4'-(2-(2-cyclopropylphenyl)pyrrolidin-1-yl)-N-((4-((4-fluoro-1-(oxetan-3-yl)piperidin-4-yl)methoxy)-3-nitrophenyl)sulfonyl)-[1,1'-biphenyl]-4-carboxamide

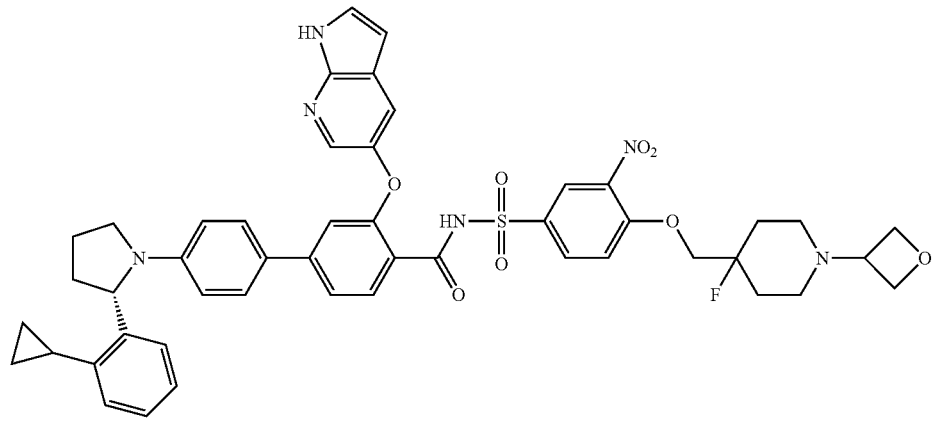 [SMILES: O=C(NS(=O)(=O)c1ccc(OCC2(F)CCN(C3COC3)CC2)c([N+](=O)[O-])c1)c1ccc(-c2ccc(N3CCC[C@H]3c3ccccc3C3CC3)cc2)cc1Oc1cnc2[nH]ccc2c1]

The desired compound was synthesized following the procedures similar to those in Example A1 by replacing 2-phenylpyrrolidine with (S)-2-(2-cyclopropylphenyl)pyrrolidine, and replacing 3-nitro-4-(((tetrahydro-2H-pyran-4-yl)methyl)amino)benzenesulfonamide with 4-((4-fluoro-1-(oxetan-3-yl)piperidin-4-yl)methoxy)-3-nitrobenzenesulfonamide. MS (ESI, m/e) [M+1]$^+$ 886.7.

Example G98: (R)-3-((1H-pyrrolo[2,3-b]pyridin-5-yl)oxy)-4'-(2-(2-cyclopropylphenyl)pyrrolidin-1-yl)-N-((4-(((4-fluoro-1-(oxetan-3-yl)piperidin-4-yl)methyl)amino)-3-nitrophenyl)sulfonyl)-[1,1'-biphenyl]-4-carboxamide

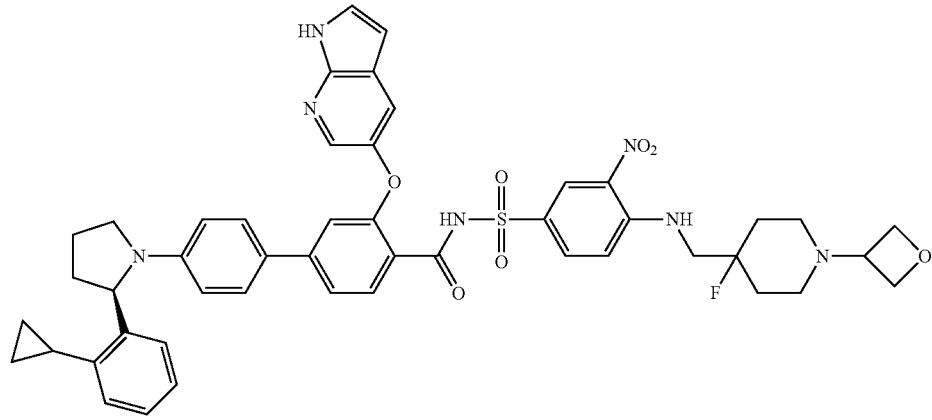 [SMILES: O=C(NS(=O)(=O)c1ccc(NCC2(F)CCN(C3COC3)CC2)c([N+](=O)[O-])c1)c1ccc(-c2ccc(N3CCC[C@@H]3c3ccccc3C3CC3)cc2)cc1Oc1cnc2[nH]ccc2c1]

The desired compound was synthesized following the procedures similar to those in Example A1 by replacing 2-phenylpyrrolidine with (R)-2-(2-cyclopropylphenyl)pyrrolidine, and replacing 3-nitro-4-(((tetrahydro-2H-pyran-4-yl)methyl)amino)benzenesulfonamide with 4-(((4-fluoro-1-(oxetan-3-yl)piperidin-4-yl)methyl)amino)-3-nitrobenzenesulfonamide. $^1$H NMR (400 MHz, DMSO-$d_6$) δ ppm: 12.24-11.87 (m, 1H), 11.68 (s, 1H) 8.70-8.43 (m, 2H), 8.12-7.91 (m, 1H), 7.86-7.75 (m, 1H), 7.62-7.43 (m, 3H), 7.38-7.15 (m, 4H), 7.14-7.04 (m, 1H), 7.04-6.95 (m, 2H), 6.95-6.75 (m, 2H), 6.47-6.28 (m, 2H), 5.30-5.08 (m, 1H), 4.70-4.34 (m, 4H), 3.84-3.61 (m, 3H), 3.61-3.33 (m, 3H), 2.70-2.53 (m, 2H), 2.47-2.35 (m, 1H), 2.16-1.66 (m, 9H), 1.06-0.90 (m, 2H), 0.82-0.63 (m, 2H). MS (ESI, m/e) [M+1]$^+$ 885.7.

Example G99: (R)-3-((1H-pyrrolo[2,3-b]pyridin-5-yl)oxy)-N-((4-((2-oxaspiro[3.5]nonan-7-yl)methoxy)-3-nitrophenyl)sulfonyl)-4'-(2-(2-cyclopropylphenyl)pyrrolidin-1-yl)-[1,1'-biphenyl]-4-carboxamide

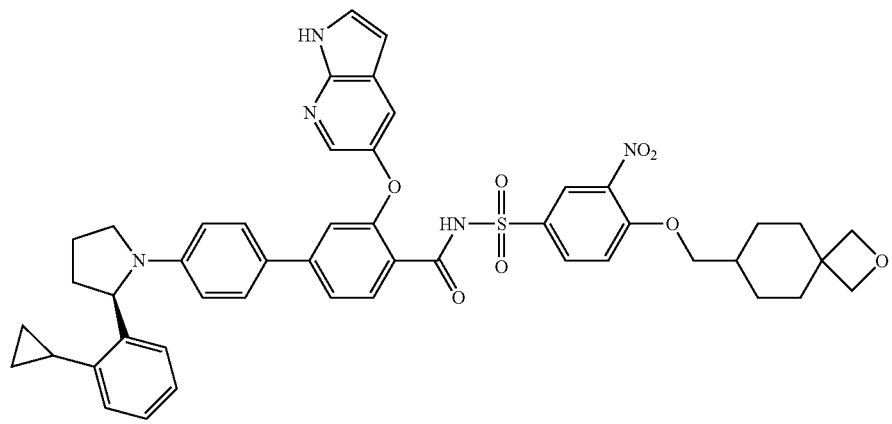 [SMILES: O=C(NS(=O)(=O)c1ccc(OCC2CCC3(CC2)COC3)c([N+](=O)[O-])c1)c1ccc(-c2ccc(N3CCC[C@@H]3c3ccccc3C3CC3)cc2)cc1Oc1cnc2[nH]ccc2c1]

The desired compound was synthesized following the procedures similar to those in Example A1 by replacing 2-phenylpyrrolidine with (R)-2-(2-cyclopropylphenyl)pyrrolidine, and replacing 3-nitro-4-(((tetrahydro-2H-pyran-4-yl)methyl)amino)benzenesulfonamide with 4-((2-oxaspiro[3,5]nonan-7-yl)methoxy)-3-nitrobenzenesulfonamide. $^1$H NMR (400 MHz, DMSO-$d_6$) δ ppm: 12.34 (s, 1H), 11.71 (s, 1H), 8.38 (s, 1H), 8.12-8.00 (m, 2H), 7.62-7.58 (m, 1H), 7.56-7.49 (m, 2H), 7.43-7.38 (m, 1H), 7.35-7.26 (m, 3H), 7.12-7.06 (m, 1H), 7.05-6.97 (m, 2H), 6.89 (m, 1H), 6.86-6.84 (m, 1H), 6.42-6.31 (m, 3H), 5.25-5.15 (m, 1H), 4.29 (s, 2H), 4.21 (s, 2H), 4.00-3.91 (m, 2H), 3.77-3.67 (m, 1H), 3.42-3.38 (m, 1H), 2.45-2.37 (m, 1H), 2.12-2.01 (m, 3H), 2.00-1.78 (m, 3H), 1.74-1.62 (m, 3H), 1.48-1.38 (m, 2H), 1.10-0.90 (m, 4H), 0.82-0.65 (m, 2H). MS (ESI, m/e) [M+1]$^+$ 853.7.

Example G100a and Example G100b: (cis- or trans-)(R)-3-((1H-pyrrolo[2,3-b]pyridin-5-yl)oxy)-4'-(2-(2-cyclopropylphenyl)pyrrolidin-1-yl)-N-((4-(((1-fluoro-4-hydroxy-4-methylcyclohexyl)methyl)amino)-3-nitrophenyl)sulfonyl)-[1,1'-biphenyl]-4-carboxamide /(trans- or cis-)(R)-3-((1H-pyrrolo[2,3-b]pyridin-5-yl)oxy)-4'-(2-(2-cyclopropylphenyl)pyrrolidin-1-yl)-N-((4-(((1-fluoro-4-hydroxy-4-methylcyclohexyl)methyl)amino)-3-nitrophenyl)sulfonyl)-[1,1'-biphenyl]-4-carboxamide

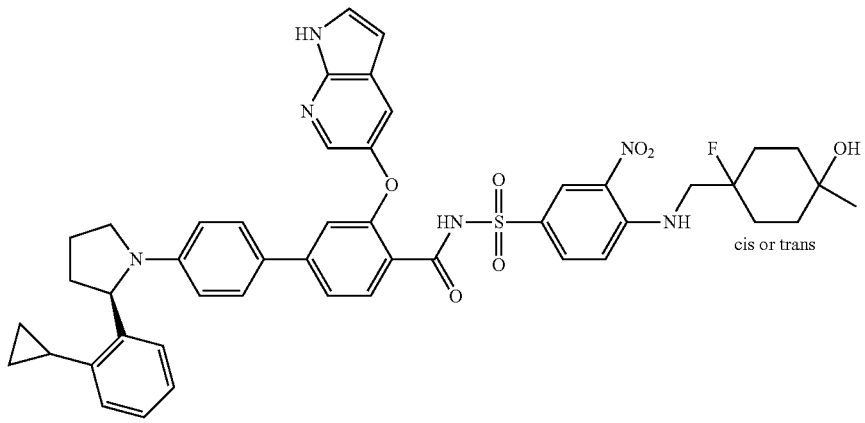

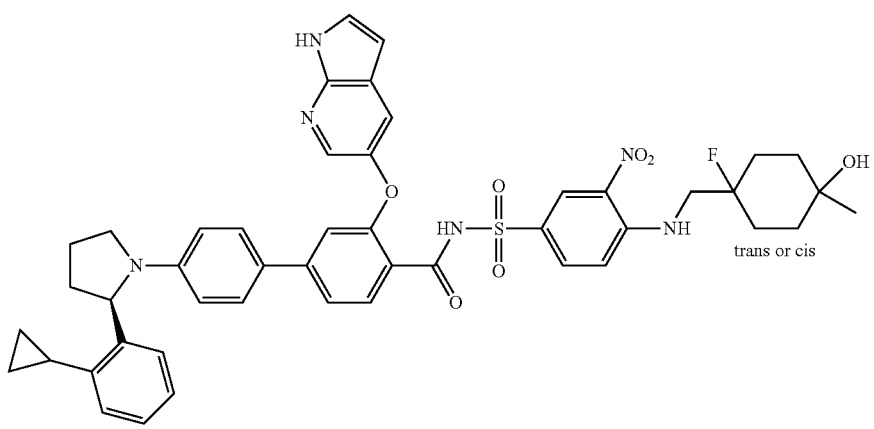

The desired compound G100a was synthesized following the procedures similar to those in Example A1 by replacing 2-phenylpyrrolidine with (R)-2-(2-cyclopropylphenyl)pyrrolidine, and replacing 3-nitro-4-(((tetrahydro-2H-pyran-4-yl)methyl)amino)benzenesulfonamide with (cis- or trans-) 4-(((1-fluoro-4-hydroxy-4-methylcyclohexyl)methyl)amino)-3-nitrobenzenesulfonamide (faster peak in HPLC). $^1$H NMR (400 MHz, DMSO-$d_6$) δ ppm: 12.14 (s, 1H), 11.54 (s, 1H), 8.50-8.36 (m, 2H), 7.97 (s, 1H), 7.71 (s, 1H), 7.55 (d, J=8.1 Hz, 1H), 7.55 (d, J=8.1 Hz, 1H), 7.50-7.39 (m, 2H), 7.30 (d, J=8.8 Hz, 2H), 7.28-7.20 (m, 1H), 7.10 (t, J=6.8 Hz, 1H), 7.06-6.94 (m, 2H), 6.95-6.81 (m, 2H), 6.36 (d, J=8.8 Hz, 2H), 6.31 (s, 1H), 5.20 (d, J=8.2 Hz, 1H), 4.34 (s, 1H), 3.76-3.53 (m, 3H), 3.43-3.35 (m, 1H), 2.47-2.38 (m, 1H), 2.10-1.79 (m, 8H), 1.71-1.51 (m, 5H), 1.51-1.38 (m, 2H), 1.09-0.93 (m, 2H), 0.91-0.74 (m, 1H), 0.72-0.65 (m, 1H). MS (ESI, m/e) [M+1]$^+$ 858.7. The desired compound G100b was synthesized following the procedures similar to those in Example A1 by replacing 2-phenylpyrrolidine with (R)-2-(2-cyclopropylphenyl)pyrrolidine, and 3-nitro-4-(((tetrahydro-2H -pyran-4-yl)methyl)amino)benzenesulfonamide with (trans- or cis-) 4-(((1-fluoro-4-hydroxy-4-methylcyclohexyl)methyl)amino)-3-nitrobenzenesulfonamide (slower peak in HPLC). $^1$H NMR (400 MHz, DMSO-$d_6$) δ ppm: 12.43 (s, 1H), 11.97 (s, 1H), 8.92 (s, 1H), 8.84 (s, 1H), 8.34 (s, 1H), 8.10 (d, J=9.2 Hz, 1H), 7.87 (s, 1H), 7.85-7.78 (m, 2H), 7.63-7.55 (m, 3H), 7.51 (d, J=9.2 Hz, 1H), 7.40-7.35 (m, 1H), 7.32-7.25 (m, 2H), 7.18-7.08 (m, 2H), 6.70-6.59 (m, 3H), 5.50-5.47 (m, 1H), 4.45 (s, 1H), 4.02-3.86 (m, 3H), 2.73-2.68 (m, 1H), 2.37-2.22 (m, 3H), 2.16-2.10 (m, 2H), 2.01-1.95 (m, 2H), 1.74 (s, 4H), 1.51 (s, 3H), 1.41 (s, 3H), 1.30-1.24 (m, 2H), 1.10-1.05 (m, 1H), 1.00-0.93 (m, 1H). MS (ESI, m/e) [M+1]$^+$ 858.7.

Example G101a and Example G101b: (cis- or trans-) (R)-3-((1H-pyrrolo[2,3-b]pyridin-5-yl)oxy)-4'-(2-(2-cyclopropylphenyl)pyrrolidin-1-yl)-N-((4-(((4-methoxy-4-methylcyclohexyl)methyl)amino)-3-nitrophenyl)sulfonyl)-[1,1'-biphenyl]-4-carboxamide /(trans- or cis-) (R)-3-((1H-pyrrolo[2,3-b]pyridin-5-yl)oxy)-4'-(2-(2-cyclopropylphenyl)pyrrolidin-1-yl)-N-((4-(((4-methoxy-4-methylcyclohexyl)methyl)amino)-3-nitrophenyl)sulfonyl)-[1,1'-biphenyl]-4-carboxamide

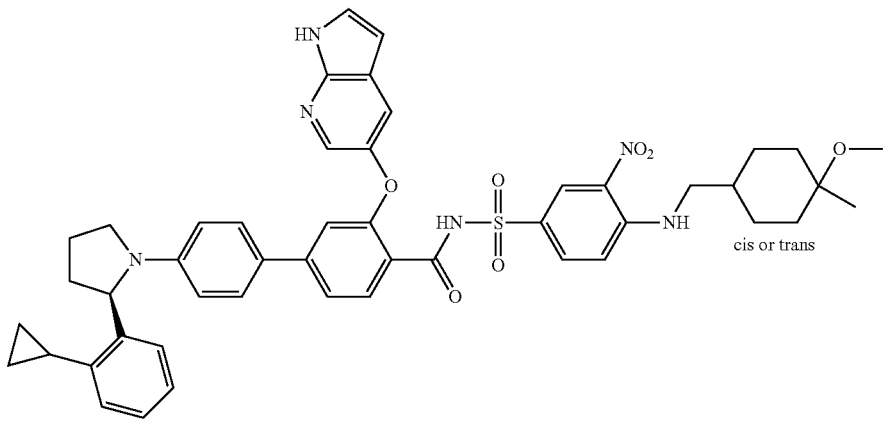

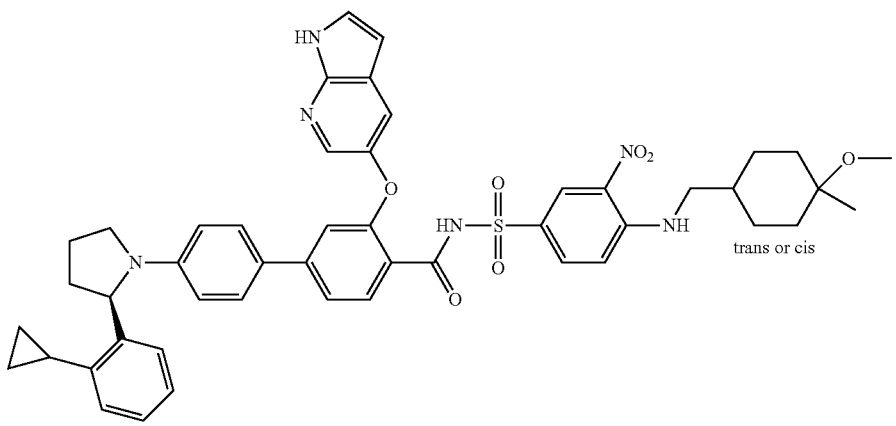

The desired compound G101a was synthesized following the procedures similar to those in Example A1 by replacing 2-phenylpyrrolidine with (R)-2-(2-cyclopropylphenyl)pyrrolidine, and replacing 3-nitro-4-(((tetrahydro-2H-pyran-4-yl)methyl)amino)benzenesulfonamide with (cis- or trans-) 4-(((4-methoxy-4-methylcyclohexyl)methyl)amino)-3-nitrobenzenesulfonamide (faster peak in HPLC). $^1$H NMR (400 MHz, DMSO-$d_6$) δ ppm: 12.14 (s, 1H), 11.69 (s, 1H), 8.65-8.50 (m, 2H), 8.09-8.01 (m, 1H), 7.87-7.77 (m, 1H), 7.14-7.05 (m, 2H), 7.05-6.96 (m, 2H), 6.93-6.80 (m, 2H), 6.44-6.31 (m, 3H), 5.25-5.08 (m, 1H), 3.83-3.62 (m, 1H), 3.31-3.26 (m, 2H), 3.09 (s, 4H), 3.01-2.85 (m, 1H), 2.17-1.76 (m, 4H), 1.76-1.53 (m, 5H), 1.39-1.29 (m, 2H), 1.27-1.21 (m, 1H), 1.19-1.07 (m, 5H), 1.05-0.92 (m, 2H), 0.81-0.63 (m, 2H). MS (ESI, m/e) [M+1]$^+$ 854.8. The desired compound G101b was synthesized following the procedures similar to those in Example A1 by replacing 2-phenylpyrrolidine with (R)-2-(2-cyclopropylphenyl)pyrrolidine, and 3-nitro-4-(((tetrahydro-2H-pyran-4-yl)methyl)amino)benzenesulfonamide with (trans- or cis-) 4-(((4-methoxy-4-methylcyclohexyl)methyl)amino)-3-nitrobenzenesulfonamide (slower peak in HPLC). $^1$H NMR (400 MHz, DMSO-$d_6$) δ ppm: 12.14 (s, 1H), 11.70 (s, 1H), 8.63-8.55 (m, 1H), 8.05 (d, J=2.6 Hz, 1H), 7.82 (dd, J=9.3, 2.0 Hz, 1H), 7.60-7.57 (m, 1H), 7.54-7.48 (m, 2H), 7.35-7.26 (m, 3H), 7.13-7.06 (m, 2H), 7.04-6.97 (m, 2H), 6.89 (s, 1H), 6.86-6.82 (m, 1H), 6.40-6.31 (m, 3H), 5.25-5.15 (m, 1H), 3.73-3.68 (m, 1H), 3.42-3.38 (m, 1H), 3.26-3.21 (m, 2H), 3.05 (s, 3H), 2.46-2.39 (m, 1H), 2.09-1.80 (m, 5H), 1.78-1.74 (m, 2H), 1.57 (s, 0H), 1.49-1.43 (m, 2H), 1.24-1.18 (m, 1H), 1.03 (s, 3H), 1.01-0.92 (m, 2H), 0.79-0.75 (m, 1H), 0.70-0.67 (m, 1H). MS (ESI, m/e) [M+1]$^+$ 854.8.

Example G102: 3-((1H-pyrrolo[2,3-b]pyridin-5-yl)oxy)-4'-((R)-2-(2-cyclopropylphenyl)pyrrolidin-1-yl)-N-((4-(((4-methylcyclohex-3-en-1-yl)methyl)amino)-3-nitrophenyl)sulfonyl)-[1,1'-biphenyl]-4-carboxamide

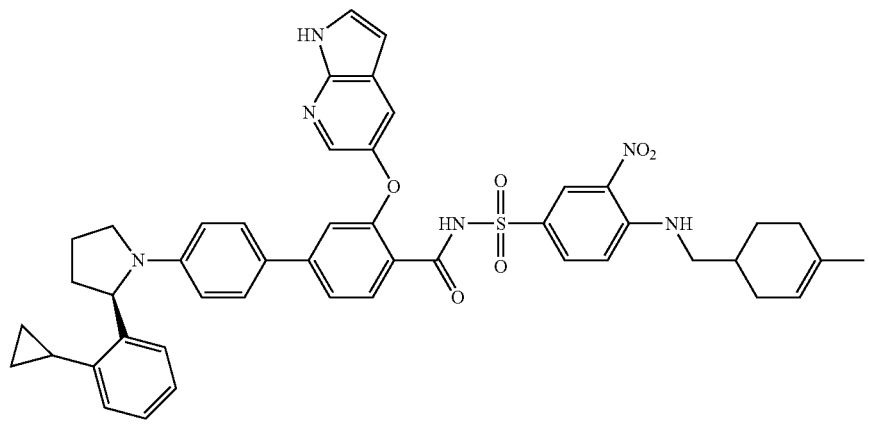 [SMILES: CC1=CCC(CNc2ccc(S(=O)(=O)NC(=O)c3ccc(-c4ccc(N5CCC[C@@H]5c5ccccc5C5CC5)cc4)cc3Oc3cnc4[nH]ccc4c3)cc2[N+](=O)[O-])CC1]

The desired compound was synthesized following the procedures similar to those in Example A1 by replacing 2-phenylpyrrolidine with (R)-2-(2-cyclopropylphenyl)pyrrolidine, and replacing 3-nitro-4-(((tetrahydro-2H-pyran-4-yl)methyl)amino)benzenesulfonamide with 4-(((4-methylcyclohex-3-en-1-yl)methyl)amino)-3-nitrobenzenesulfonamide. $^1$H NMR (400 MHz, DMSO-$d_6$) δ ppm: 12.14 (s, 1H), 11.70 (s, 1H), 8.61-8.56 (m, 2H), 8.05 (s, 1H), 7.82 (d, J=9.0 Hz, 1H), 7.58 (s, 1H), 7.55-7.48 (m, 2H), 7.35-7.28 (m, 3H), 7.14-7.06 (m, 2H), 7.04-6.98 (m, 2H), 6.89 (s, 1H), 6.86-6.82 (m, 1H), 6.38-6.33 (m, 3H), 5.34 (s, 1H), 5.23-5.18 (m, 1H), 3.75-3.70 (m, 1H), 3.42-3.36 (m, 1H), 2.45-2.37 (m, 1H), 2.11-1.71 (m, 11H), 1.61 (s, 3H), 1.31-1.22 (m, 1H), 0.99-0.93 (m, 2H), 0.78 (s, 1H), 0.70 (s, 1H). MS (ESI) m/e [M+1]$^+$ 822.8.

Example G103: 3-((1H-pyrrolo[2,3-h]pyridin-5-yl)oxy)-4'-((R)-2-(2-ethylphenyl)pyrrolidin-1-yl)-N-((4-((((1r,4r)-4-hydroxy-4-methylcyclohexyl)methyl)amino)-3-nitrophenyl)sulfonyl)-[1,1'-biphenyl]-4-carboxamide

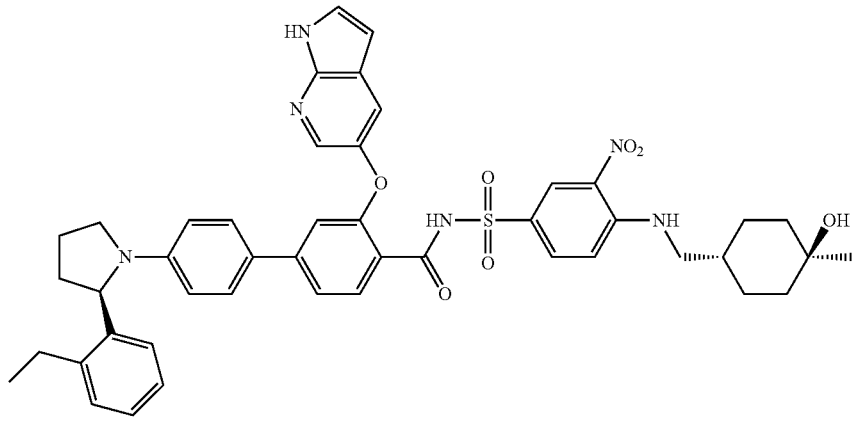 [SMILES: CCc1ccccc1[C@H]1CCCN1c1ccc(-c2ccc(C(=O)NS(=O)(=O)c3ccc(NC[C@H]4CC[C@](C)(O)CC4)c([N+](=O)[O-])c3)c(Oc3cnc4[nH]ccc4c3)c2)cc1]

The desired compound was synthesized following the procedures similar to those in Example A1 by replacing 2-phenylpyrrolidine with (R)-2-(2-ethylphenyl)pyrrolidine, and replacing 3-nitro-4-(((tetrahydro-2H-pyran-4-yl)methyl)amino)benzenesulfonamide with 4-((((1r,4r)-4-hydroxy-4-methylcyclohexyl)methyl)amino)-3-nitrobenzenesulfonamide. $^1$H NMR (400 MHz, DMSO-$d_6$) δ ppm: 12.15 (s, 1H), 11.69 (s, 1H), 8.55 (s, 2H), 8.04 (s, 1H), 7.80 (s, 1H), 7.68 (s, 1H), 7.61-7.44 (m, 3H), 7.30-7.28 (m, 2H), 7.22- (d, J=7.2 Hz, 1H), 7.17-7.11 (m, 1H), 7.01 (t, J=7.2 Hz, 1H), 6.91-6.82 (m, 2H), 6.36-6.34 (m, 3H), 4.92 (d, J=7.7 Hz, 1H), 4.25 (s, 1H), 3.70 (s, 1H), 2.83-2.76 (m, 1H), 2.71-2.67 (m, 1H), 2.03-1.97 (m, 5H), 1.69-1.66 (m, 3H), 1.55-1.52 (m, 2H), 1.47-1.43 (m, 1H), 1.29-1.26 (m, 6H). MS (ESI, m/e) [M+1]$^+$ 828.8.

Example G104: (R)-3-((1H-pyrrolo[2,3-b]pyridin-5-yl)oxy)-4'-(2-(2-ethylphenyl)pyrrolidin-1-yl)-N-((4-((4-fluoro-1-(oxetan-3-yl)piperidin-4-yl)methoxy)-3-nitrophenyl)sulfonyl)-[1,1'-biphenyl]-4-carboxamide

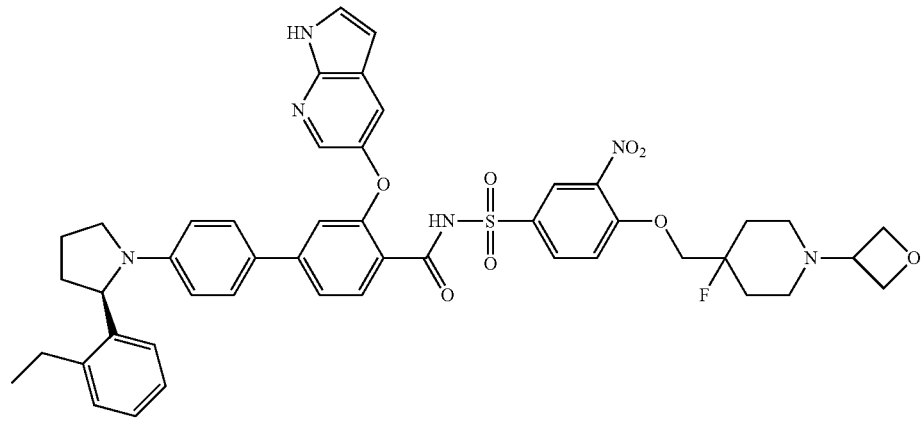 [SMILES: CCc1ccccc1[C@H]1CCCN1c1ccc(-c2ccc(C(=O)NS(=O)(=O)c3ccc(OCC4(F)CCN(C5COC5)CC4)c([N+](=O)[O-])c3)c(Oc3cnc4[nH]ccc4c3)c2)cc1]

The desired compound was synthesized following the procedures similar to those in Example A1 by replacing 2-phenylpyrrolidine with (R)-2-(2-ethylphenyl)pyrrolidine, and replacing 3-nitro-4-(((tetrahydro-2H-pyran-4-yl)methyl)amino)benzenesulfonamide with 4-((4-fluoro-1-(oxetan-3-yl)piperidin-4-yl)methoxy)-3-nitrobenzenesulfonamide. $^1$H NMR (400 MHz, DMSO-$d_6$) δ ppm: 12.27 (s, 1H), 11.69 (s, 1H), 8.37 (s, 1H), 8.05 (s, 2H), 7.60-7.47 (m, 3H), 7.43 (s, 1H), 7.32-7.27 (m, 3H), 7.22 (d, J=7.2 Hz, 1H), 7.14 (t, J=12 Hz, 1H), 7.01 (t, J=12 Hz, 1H), 6.92-6.82 (m, 2H), 6.44-6.30 (m, 3H), 4.92 (d, J=7.8 Hz, 1H), 4.58-4.50 (m, 4H), 4.39-4.34 (m, 2H), 3.71 (t, J=7.8 Hz, 1H), 3.51 (s, 1H), 2.99 (s, 2H), 2.86-2.64 (m, 4H), 2.02-1.97 (m, 6H), 1.73-1.71 (m, 1H), 1.45 (s, 1H), 1.27-1.24 (m, 3H). MS (ESI, m/e) [M+1]+874.7.

Example G105: (S)-3-((1H-pyrrolo[2,3-b]pyridin-5-yl)oxy)-N-((4-((4-fluoro-1-(oxetan-3-yl)piperidin-4-yl)methoxy)-3-nitrophenyl)sulfonyl)-4'-(2-(2-isopropylphenyl)pyrrolidin-1-yl)-[1,1'-biphenyl]-4-carboxamide

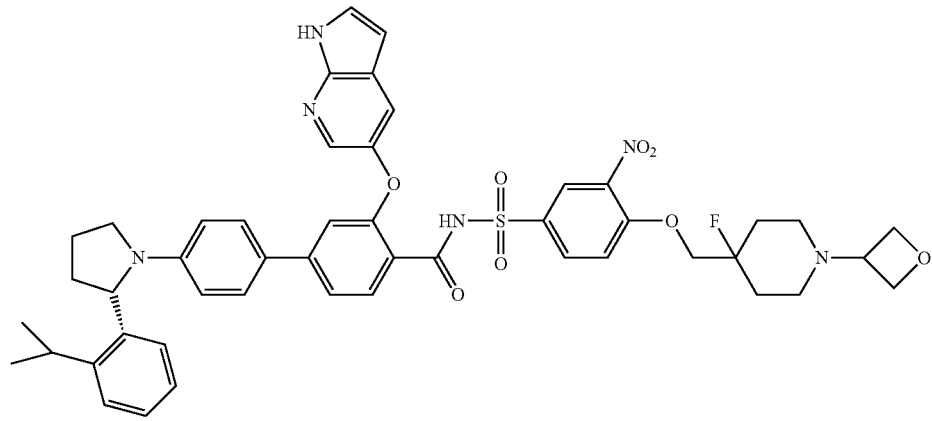

The desired compound was synthesized following the procedures similar to those in Example A1 by replacing 2-phenylpyrrolidine with (S)-2-(2-isopropylphenyl)pyrrolidine, and replacing 3-nitro-4-(((tetrahydro-2H-pyran-4-yl)methyl)amino)benzenesulfonamide with 4-((4-fluoro-1-(oxetan-3-yl)piperidin-4-yl)methoxy)-3-nitrobenzenesulfonamide. $^1$H NMR (400 MHz, DMSO-$d_6$) δ ppm: 11.67 (s, 1H), 8.35 (s, 1H), 8.04 (s, 2H), 7.56-7.54 (m, 2H), 7.49 (s, 1H), 7.41 (s, 1H), 7.35-7.29 (m, 5H), 7.17 (t, J=7.4 Hz, 1H), 6.99 (t, J=7.4 Hz, 1H), 6.91 (s, 1H), 6.83 (d, J=7.7 Hz, 1H), 6.37-6.35 (m, 3H), 4.99 (d, J=8.0 Hz, 1H), 4.58-4.51 (m, 4H), 4.38-4.33 (m, 2H), 3.70 (t, J=8.0 Hz, 1H), 3.38-3.32 (m, 1H), 2.45-2.48 (m, 1H), 2.03-1.97 (m, 5H), 1.92-1.84 (m, 3H), 1.72-1.68 (m, 1H), 1.47-1.44 (m, 1H), 1.28-1.24 (m, 9H). MS (ESI, m/e) [M+1]+ 888.8.

Example G106: 3-((1H-pyrrolo[2,3-b]pyridin-5-yl)oxy)-4'-(2-(3-chloro-2-cyclopropylphenyl)pyrrolidin-1-yl)-N-((4-((((1r,4r)-4-hydroxy-4-methylcyclohexyl)methyl)amino)-3-nitrophenyl)sulfonyl)-2',3',4',5'-tetrahydro-[1,1'-biphenyl]-4-carboxamide

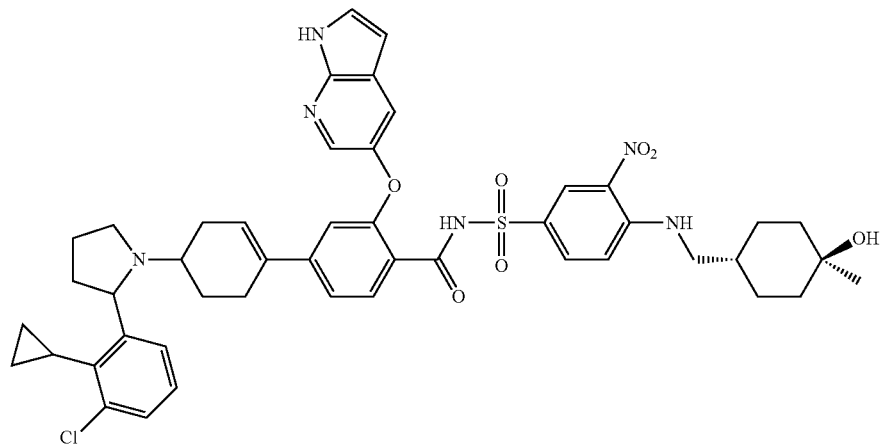 [SMILES: C[C@]1(O)CC[C@H](CNc2ccc(S(=O)(=O)NC(=O)c3ccc(C4=CCC(N5CCCC5c5cccc(Cl)c5C5CC5)CC4)cc3Oc3cnc4[nH]ccc4c3)cc2[N+](=O)[O-])CC1]

The desired compound was synthesized with 4-((((1r,4r)-4-hydroxy-4-methylcyclohexyl)methyl)amino)-3-nitrobenzenesulfonamide and 3-((1H-pyrrolo[2,3-b]pyridin-5-yl)oxy)-4'-(2-(3-chloro-2-cyclopropylphenyl)pyrrolidin-1-yl)-2',3',4',5'-tetrahydro-[1,1'-biphenyl]-4-carboxylic acid following the procedures similar to those in Example G8. $^1$H NMR (400 MHz, DMSO-d$_6$) δ ppm: 12.21 (s, 1H), 11.65 (s, 1H), 8.48 (s, 2H), 7.97 (s, 1H), 7.74 (s, 1H), 7.63-7.37 (m, 5H), 7.26-6.89 (m, 4H), 6.72 (s, 1H), 6.36 (s, 1H), 6.08-5.70 (m, 1H), 4.46 (s, 1H), 4.24 (s, 1H), 3.30-3.10 (m, 3H), 3.10-3.00 (m, 1H), 2.30-2.10 (m, 5H), 2.09-1.90 (m, 2H), 1.76-1.62 (m, 5H), 1.58-1.47 (m, 3H), 1.41-1.30 (m, 3H), 1.14-1.00 (m, 6H), 0.85 (s, 1H), 0.68 (s, 1H), 0.50 (s, 1H). MS (ESI) m/e [M+1]$^+$ 878.8.

Example G107-a and Example G107-b: (R or S)-3-((1H-pyrrolo[2,3-b]pyridin-5-yl)oxy)-4'-((S)-2-(2-ethylphenyl)pyrrolidin-1-yl)-N-((4-((((1r,4r)-4-hydroxy-4-methylcyclohexyl)methyl)amino)-3-nitrophenyl)sulfonyl)-2',3',4',5'-tetrahydro-[1,1'-biphenyl]-4-carboxamide/(S or R)-3-((1H-pyrrolo[2,3-b]pyridin-5-yl)oxy)-4'-((S)-2-(2-ethylphenyl)pyrrolidin-1-yl)-N-((4-((((1r,4r)-4-hydroxy-4-methylcyclohexyl)methyl)amino)-3-nitrophenyl)sulfonyl)-2',3',4',5'-tetrahydro-[1,1'-biphenyl]-4-carboxamide

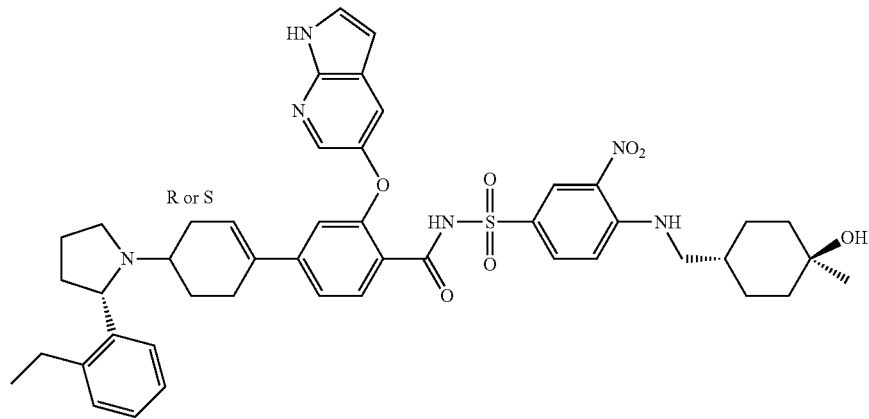

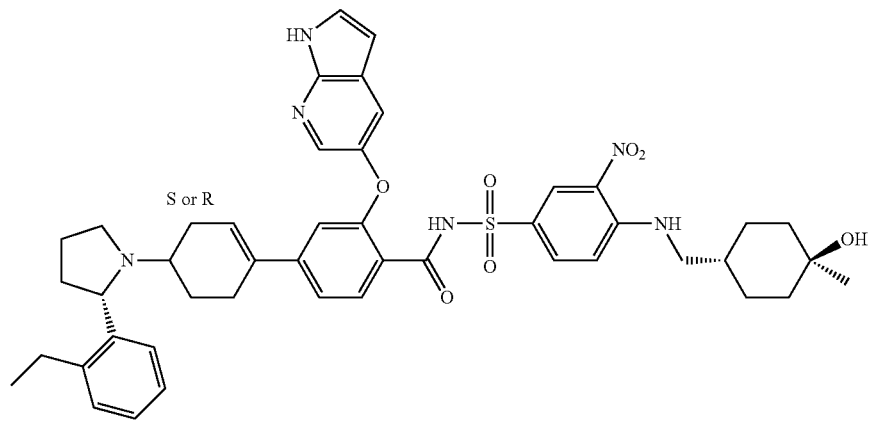

3-((1H-pyrrolo[2,3-b]pyridin-5-yl)oxy)-4'-((S)-2-(2-ethylphenyl)pyrrolidin-1-yl)-N-((4-((((1r,4r)-4-hydroxy-4-methylcyclohexyl)methyl)amino)-3-nitrophenyl)sulfonyl)-2',3',4',5'-tetrahydro-[1,1'-biphenyl]-4-carboxamide was synthesized with 4-((((1r,4r)-4-hydroxy-4-methylcyclohexyl)methyl)amino)-3-nitrobenzenesulfonamide and 3-((1H-pyrrolo[2,3-b]pyridin-5-yl)oxy)-4'-((S)-2-(2-ethylphenyl)pyrrolidin-1-yl)-2',3',4',5'-tetrahydro-[1,1'-biphenyl]-4-carboxylic acid following the procedures similar to those in Example G8. Then two enantiomers G107-a (faster isomer) and G107b (slower isomer) were separated by chiral preparative HPLC. The chiral separation conditions are shown below. The faster enantiomer was eluted at retention time of 2.5 min to give G107-a. The slower enantiomer was eluted at retention time of 3.6 min to give G107-b.

| Column | CHIRAL ART Cellulose-SB |
|---|---|
| Column size | 2 cm × 25 cm, 5 um |
| Injection | 0.5 mL |
| Mobile phase | MTBE:EtOH (0.2% MSA) = 50:50 |
| Flow rate | 20 mL/min |
| Wave length | UV 220 nm |
| Temperature | 25° C. |
| Sample solution | 30 mg/mL in EtOH:DCM = 3:1 |
| Prep-HPLC equipment | Prep-Gilson-HPLC |

Example G107-a: $^1$H NMR (DMSO-$d_6$) δ ppm: 11.65 (s, 1H), 8.56-8.36 (m, 2H), 7.97 (d, J=2.0 Hz, 1H), 7.75 (d, J=8.4 Hz, 1H), 7.61-7.38 (m, 4H), 7.24-6.85 (m, 5H), 6.73 (s, 1H), 6.36 (s, 1H), 5.81 (s, 1H), 4.25 (s, 1H), 3.23 (t, J=6.0 Hz, 3H), 2.68-2.58 (m, 2H), 2.42-1.83 (m, 8H), 1.79-1.44 (m, 8H), 1.36-1.06 (m, 1H). MS (ESI, m/e) [M+1]$^+$ 832.8.

Example G107-b: $^1$H NMR (DMSO-$d_6$) δ ppm: 11.64 (s, 1H), 8.57-8.34 (m, 2H), 7.97 (s, 1H), 7.80-7.66 (m, 1H), 7.61-7.42 (m, 4H), 7.25-6.93 (m, 5H), 6.73 (s, 1H), 6.35 (s, 1H), 5.99 (s, 1H), 4.24 (s, 1H), 3.28-3.16 (m, 3H), 2.70-2.61 (m, 2H), 2.36-2.04 (m, 6H), 1.85-1.48 (m, 9H), 1.33 (t, J=12.0 Hz, 3H), 1.17-1.07 Cm. 9H). MS (ESI, m/e) [M+1]$^+$ 832.9.

Example G108a and Example G108b: (cis- or trans-)3-((1H-pyrrolo[2,3-h]pyridin-5-yl)oxy)-4'-(2-(2-cyclopropylphenyl)pyrrolidin-1-yl)-N-((4-(((1-fluoro-4-hydroxycyclohexyl)methyl)amino)-3-nitrophenyl)sulfonyl)-2',3',4',5'-tetrahydro-[1,1'-biphenyl]-4-carboxamide/(trans- or cis-) 3-((1H-pyrrolo[2,3-b]pyridin-5-yl)oxy)-4'-(2-(2-cyclopropylphenyl)pyrrolidin-1-yl)-N-((4-(((1-fluoro-4-hydroxycyclohexyl)methyl)amino)-3-nitrophenyl)sulfonyl)-2',3',4',5'-tetrahydro-[1,1'-biphenyl]-4-carboxamide

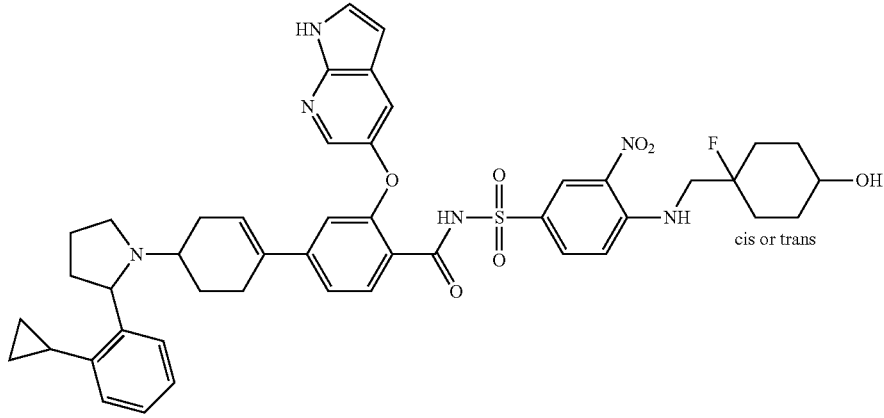

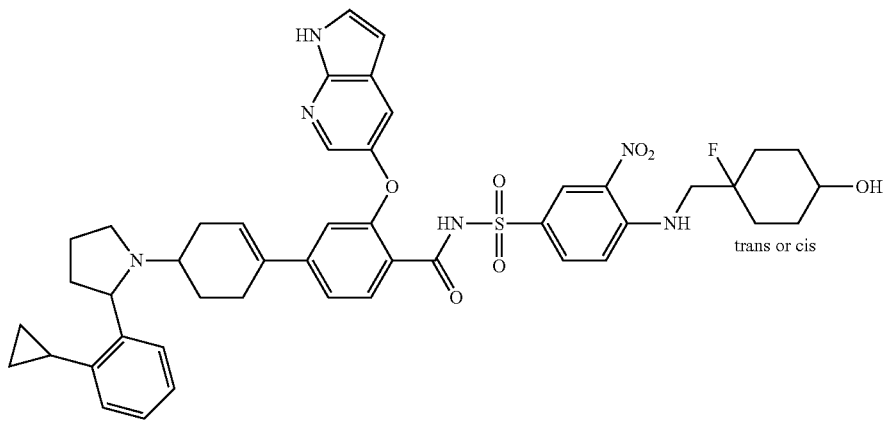

3-((1H-pyrrolo[2,3-b]pyridin-5-yl)oxy)-4'-(2-(2-cyclopropylphenyl)pyrrolidin-1-yl)-N-((4-(((1-fluoro-4-hydroxycyclohexyl)methyl)amino)-3-nitrophenyl)sulfonyl)-2',3',4',5'-tetrahydro-[1,1'-biphenyl]-4-carboxamide was synthesized with 4-(((1-fluoro-4-hydroxycyclohexyl)methyl)amino)-3-nitrobenzenesulfonamide and 3-((1H-pyrrolo[2,3-b]pyridin-5-yl)oxy)-4'-(2-(2-cyclopropylphenyl)pyrrolidin-1-yl)-2',3',4',5'-tetrahydro-[1,1'-biphenyl]-4-carboxylic acid following the procedures similar to those in Example G8. 2 products were obtained after prep-HPLC purification. Example G108a was the faster peak. $^1$H NMR (400 MHz, DMSO-$d_6$) δ ppm: 12.48 (s, 1H), 11.71 (s, 1H), 8.45-8.31 (m, 1H), 8.10-7.95 (m, 2H), 7.69-7.36 (m, 5H), 7.35-7.20 (m, 2H), 7.19-7.04 (m, 2H), 6.80-6.69 (m, 1H), 6.39 (s, 1H), 5.99-5.88 (m, 1H), 5.30-5.10 (m, 1H), 4.67 (s, 1H), 4.29-4.20 (m, 2H), 3.71 (s, 1H), 3.46 (s, 3H), 2.38-2.30 (m, 2H), 2.13 (s, 3H), 2.04-1.93 (m, 4H), 1.78-1.68 (m, 3H), 1.63-1.55 (m, 2H), 1.48-1.35 (m, 3H), 0.98-0.91 (m, 2H), 0.78-0.68 (m, 1H), 0.61 (s, 1H). MS (ESI) m/e [M+1]$^+$ 849.8. Example G108b was the slower peak, MS (ESI) m/e [M+1]$^+$ 849.8.

Example G109: 3-((1H-pyrrolo[2,3-b]pyridin-5-yl)oxy)-4'-((S)-2-(2-cyclopropylphenyl)pyrrolidin-1-yl)-N-((4-(((1-fluoro-4-hydroxycyclohexyl)methyl)amino)-3-nitrophenylsulfonyl)-2',3',4',5'-tetrahydro-[1,1'-biphenyl]-4-carboxamide

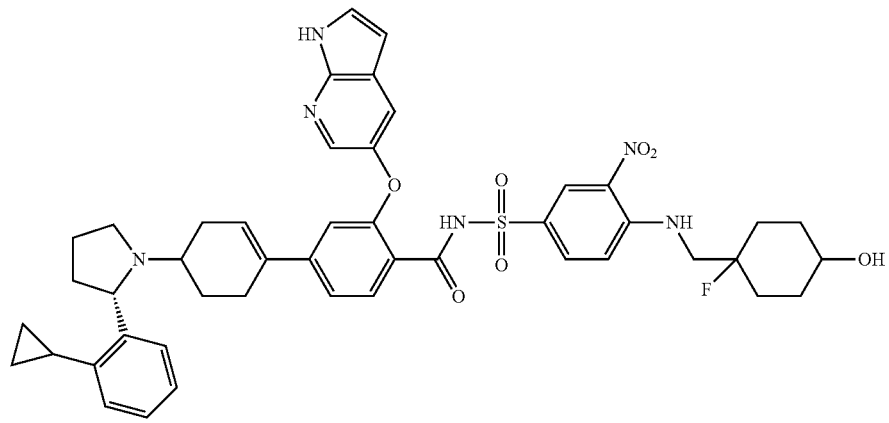 [SMILES: O=C(NS(=O)(=O)c1ccc(NCC2(F)CCC(O)CC2)c([N+](=O)[O-])c1)c1ccc(C2=CCC(N3CCC[C@H]3c3ccccc3C3CC3)CC2)cc1Oc1cnc2[nH]ccc2c1]

The desired compound was synthesized with 4-(((1-fluoro-4-hydroxycyclohexyl)methyl)amino)-3-nitrobenzenesulfonamide and 3-((1H-pyrrolo[2,3-b]pyridin-5-yl)oxy)-4'-((S)-2-(2-cyclopropylphenyl)pyrrolidin-1-yl)-2',3',4',5'-tetrahydro-[1,1'-biphenyl]-4-carboxylic acid following the procedures similar to those in Example G8. $^1$H NMR (400 MHz, DMSO-$d_6$) δ ppm: 12.38-12.19 (m, 0.5H), 11.70 (s, 1H), 10.55-10.05 (m, 0.5H), 8.66-8.43 (m, 2H), 8.11-7.87 (m, 2H), 7.85-7.72 (m, 1H), 7.60-7.39 (m, 3H), 7.37-6.99 (m, 5H), 6.75 (s, 1H), 6.38 (s, 1H), 6.08-5.77 (m, 1H), 5.27-4.97 (m, 1H), 4.77-4.51 (m, 1H), 3.76-3.54 (m, 4H), 3.22-2.89 (m, 3H), 2.36-1.33 (m, 17H), 1.00-0.87 (m, 2H), 0.79-0.49 (m, 2H). MS (ESI, m/e) [M+1]$^+$ 848.8.

Example G110a and Example G110b: (cis- or trans-)3-((1H-pyrrolo[2,3-b]pyridin-5-yl)oxy)-4'-((S)-2-(2-cyclopropylphenyl)pyrrolidin-1-yl)-N-((4-(((4-hydroxycyclohexyl)methyl)amino)-3-nitrophenyl)sulfonyl)-2',3',4',5'-tetrahydro-[1,1'-biphenyl]-4-carboxamide/(trails- or cis-) 3-((1H-pyrrolo[2,3-b]pyridin-5-yl)oxy)-4'-((S)-2-(2-cyclopropylphenyl)pyrrolidin-1-yl)-N-((4-(((4-hydroxycyclohexyl)methyl)amino)-3-nitrophenyl)sulfonyl)-2',3',4',5'-tetrahydro-[1,1'-biphenyl]-4-carboxamide

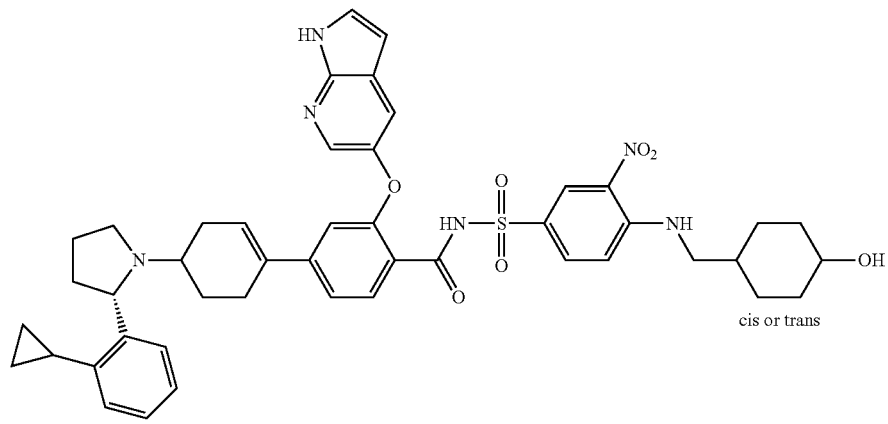

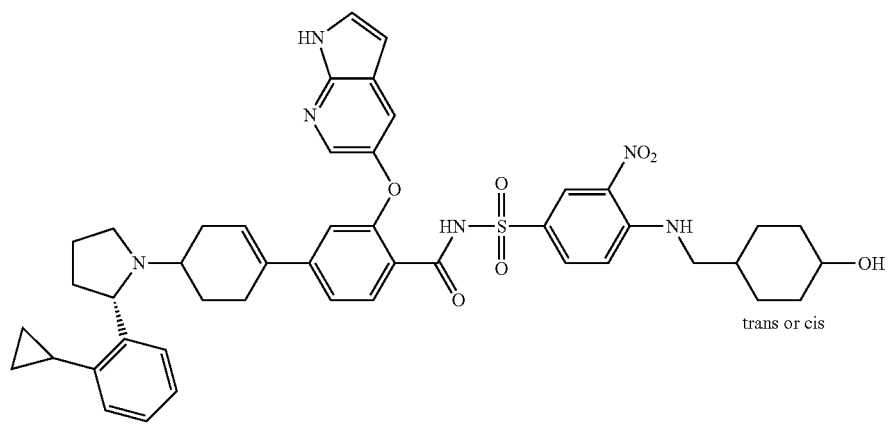

The desired compound G110a was synthesized with (cis- or trans-)4-(((4-hydroxycyclohexyl)methyl)amino)-3-nitrobenzenesulfonamide (faster peak in HPLC) and 3-((1H-pyrrolo[2,3-b]pyridin-5-yl)oxy)-4'-((S)-2-(2-cyclopropylphenyl)pyrrolidin-1-yl)-2',3',4',5'-tetrahydro-[1,1'-biphenyl]-4-carboxylic acid following the procedures similar to those in Example G8. $^1$H NMR (400 MHz, DMSO-d$_6$) δ ppm: 12.44 (br, 1H), ,11.69 (s, 1H), 8.66-8.35 (m, 2H), 7.99 (s, 1H), 7.89-7.70 (m, 2H), 7.61-7.40 (m, 3H), 7.36-6.84 (m, 5H), 6.84-6.66 (m, 1H), 6.74 (s, 1H), 6.45-6.29 (m, 1H), 6.37 (s, 1H), 6.07-5.81 (m, 1H), 5.33-5.01 (m, 1H), 4.56-4.41 (m, 1H), 3.82-3.36 (m, 3H), 3.24-3.11 (m, 2H), 3.08-2.86 (m, 1H), 2.33-1.52 (m, 14H), 1.18-0.81 (m, 7H), 0.77-0.50 (m, 2H). MS (ESI, m/e) [M+1]$^+$ 830.8; The desired compound G110b was synthesized with (trans- or cis-) 4-(((4-hydroxycyclohexyl)methyl)amino)-3-nitrobenzenesulfonamide (slower peak in HPLC) and 3-((1H-pyrrolo[2,3-b]pyridin-5-yl)oxy)-4'-((S)-2-(2-cyclopropylphenyl)pyrrolidin-1-yl)-2',3',4',5'-tetrahydro-[1,1'-biphenyl]-4-carboxylic acid following the procedures similar to those in Example G8. $^1$H NMR (400 MHz, DMSO-d$_6$) δ ppm: 12.36 (br, 1H), 11.68 (s, 1H), 8.64-8.37 (m, 2H), 7.98 (s, 1H), 7.91-7.65 (m, 2H), 7.62-7.38 (m, 3H), 7.37-6.80 (m, 5H), 6.74 (s, 1H), 6.37 (s, 1H), 5.99-5.73 (m, 1H), 5.38-5.01 (m, 1H), 4.37-4.19 (m, 1H), 3.73-3.37 (m, 3H), 3.27-3.17 (m, 2H), 3.08-2.87 (m, 1H), 2.43-1.33 (m, 19H), 0.99-0.82 (m, 2H), 0.77-0.44 (m, 2H). MS (ESI, m/e) [M+1]$^+$ 840.8.

Two enantiomers G110b-a (faster isomer) and G110b-b (slower isomer) of G110b were separated by chiral preparative HPLC. The chiral separation conditions are shown below. The faster enantiomer was eluted at retention time of 2.5 min to give G110b-a. The slower enantiomer was eluted at retention time of 3.8 min to give G110b-b.

| Column | CHIRAL ART Cellulose-SB |
|---|---|
| Column size | 2 cm × 25 cm, 5 um |
| Injection | 0.5 mL |
| Mobile phase | MTBE:EtOH (0.2% MSA) = 50:50 |
| Flow rate | 20 mL/min |
| Wave length | UV 220 nm |
| Temperature | 25° C. |
| Sample solution | 36 mg/mL in EtOH:DCM = 3:1 |
| Prep-HPLC equipment | Prep-Gilson-HPLC |

Example G110b-a: $^1$H NMR (400 MHz, DMSO-d$_6$) δ ppm: 12.60 (br, 1H), 11.61 (s, 1H), 8.40-8.07 (m, 1H), 8.02-7.74 (m, 2H), 7.74-6.83 (m, 9H), 6.83-6.67 (m, 1H), 6.34 (s, 1H), 5.84-5.69 (m, 1H), 5.37-5.12 (m, 1H), 5.41-5.26 (m, 1H), 4.67-4.44 (m, 1H), 4.06-3.82 (m, 2H), 3.82-3.57 (m, 1H), 3.57-3.41 (m, 1H), 3.22-2.91 (m, 1H), 2.41-1.46 (m, 15H), 1.19-0.79 (m, 8H), 0.79-0.45 (m, 2H), MS (ESI, m/e) [M+1]$^+$ 831.8. Example G110b-b: $^1$H NMR (400 MHz, DMSO-d$_6$) δ ppm: 12.66 (br, 1H), 11.61 (s, 1H), 8.32-8.07 (m, 1H), 8.02-7.76 (m, 2H), 7.71-6.84 (m, 9H), 6.74 (s, 1H), 6.34 (s, 1H), 6.06-5.89 (m, 1H), 5.28-4.91 (m, 1H), 4.63-4.45 (m, 1H), 4.06-3.83 (m, 2H), 3.77-3.56 (m, 1H), 3.55-3.41 (m, 1H), 3.22-2.88 (m, 1H), 2.43-1.52 (m, 16H), 1.19-0.83 (m, 7H), 0.78-0.47 (m, 2H). MS (ESI, m/e) [M+1]$^+$ 831.8.

Example G111: 3-((1H-pyrrolo[2,3-b]pyridin-5-yl)oxy)-4'-(2-(2-cyclopropylphenyl)pyrrolidin-1-yl)-N-((3-nitro-4-((((S)-4-(oxetan-3-yl)morpholin-2-yl)methyl)amino)phenyl)sulfonyl)-2',3',4',5'-tetrahydro-[1,1'-biphenyl]-4-carboxamide

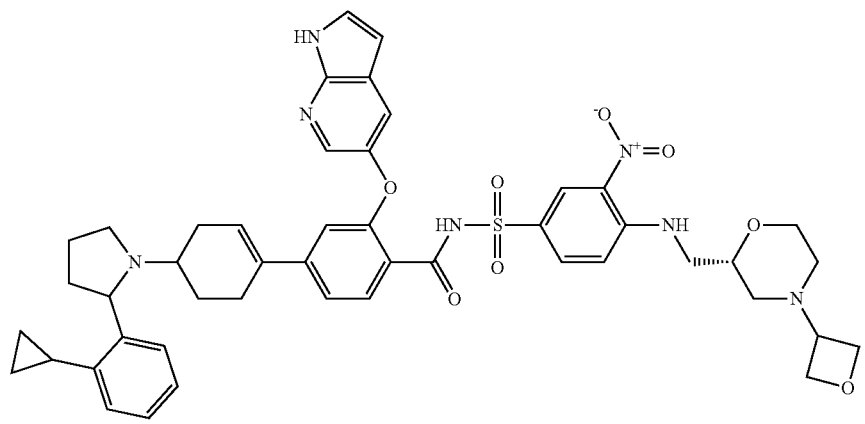

The desired compound was synthesized with (S)-3-nitro-4-(((4-(oxetan-3-yl)morpholin-2-yl)methyl)amino)benzenesulfonamide and 3-((1H-pyrrolo[2,3-b]pyridin-5-yl)oxy)-4'-(2-(2-cyclopropylphenyl)pyrrolidin-1-yl)-2',3',4',5'-tetrahydro-[1,1'-biphenyl]-4-carboxylic acid following the procedures similar to those in Example G8. $^1$H NMR (400 MHz, DMSO-d$_6$) δ ppm: 12.24 (s, 0.5H), 11.66 (s, 1H), 9.58-9.30 (m, 0.5H), 8.50 (s, 2H), 7.97 (s, 1H), 7.76 (s, 1H), 7.61 (s, 1H), 7.55-7.39 (m, 3H), 7.33-6.91 (m, 6H), 6.74 (s, 1H), 6.36 (s, 1H), 6.04-5.80 (m, 1H), 4.60-4.49 (m, 2H), 4.49-4.39 (m, 2H), 3.90-3.67 (m, 3H), 3.59-3.43 (m, 5H), 2.88-2.70 (m, 2H), 2.60-2.50 (m, 2H), 2.07-1.86 (m, 5H), 1.85-1.75 (m, 2H), 1.16-1.07 (m, 2H), 0.99-0.80 (m, 3H), 0.78-0.50 (m, 2H). MS (ESI) m/e [M+1]$^+$ 873.8.

Example G112: 3-((1H-pyrrolo[2,3-b]pyridin-5-yl)oxy)-4'-((S)-2-(2-cyclopropylphenyl)pyrrolidin-1-yl)-N-((3-nitro-4-((((R)-4-(oxetan-3-yl)morpholin-2-yl)methyl)amino)phenyl)sulfonyl)-2',3',4',5'-tetrahydro-[1,1'-biphenyl]-4-carboxamide

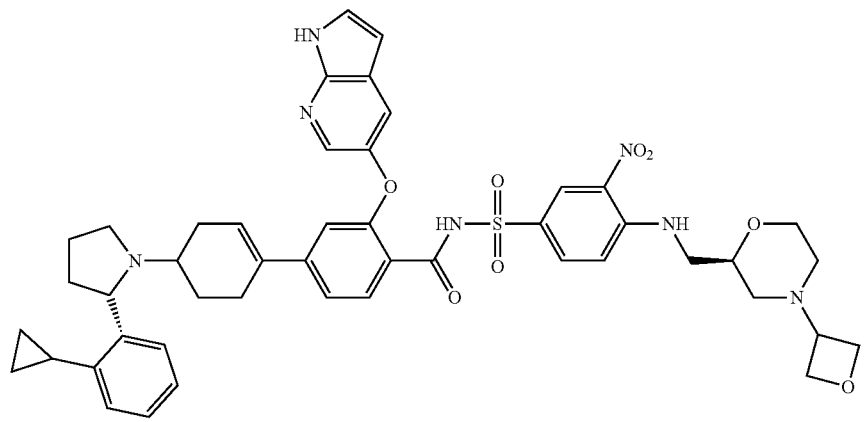

The desired compound was synthesized with (R)-3-nitro-4-(((4-(oxetan-3-yl)morpholin-2-yl)methyl)amino)benzenesulfonamide and 3-((1H-pyrrolo[2,3-b]pyridin-5-yl)oxy)-4'-((S)-2(2-cyclopropylphenyl)pyrrolidin-1-yl)-2',3',4',5'-tetrahydro-[1,1'-biphenyl]-4-carboxylic acid following the procedures similar to those in Example G8. $^1$H NMR (400 MHz, DMSO-d$_6$) δ ppm: 12.27-12.13 (m, 1H), 11.63 (s, 1H), 8.53-8.38 (m, 2H), 7.96 (s, 1H), 7.52-7.40 (m, 3H), 7.35-7.21 (m, 1H), 7.19-7.07 (m, 2H), 7.05-6.83 (m, 3H), 6.74 (s, 1H), 6.35 (s, 1H), 6.04-5.75 (m, 1H), 4.58-4.50 (m, 2H), 4.48-4.40 (m, 2H), 3.90-3.81 (m, 1H), 3.77-3.69 (m, 1H), 3.62-3.38 (m, 5H), 3.21-3.06 (m, 1H), 2.80-2.70 (m, 1H), 2.63-2.53 (m, 2H), 2.35-2.10 (m, 5H), 2.04-1.91 (m, 3H), 1.84-1.70 (m, 3H), 1.39-1.31 (m, 1H), 0.99-0.072 (m, 3H), 0.72-0.45 (m, 2H). MS (ESI, m/e) [M+1]$^+$ 874.8.

Example G113: 3-((1H-pyrrolo[2,3-b]pyridin-5-yl)oxy)-4'-(2-(2-cyclopropylphenyl)pyrrolidin-1-yl)-N-((4-(((4-(methylsulfonyl)morpholin-2-yl)methyl)amino)-3-nitrophenyl)sulfonyl)-2',3',4',5'-tetrahydro-[1,1'-biphenyl]-4-carboxamide

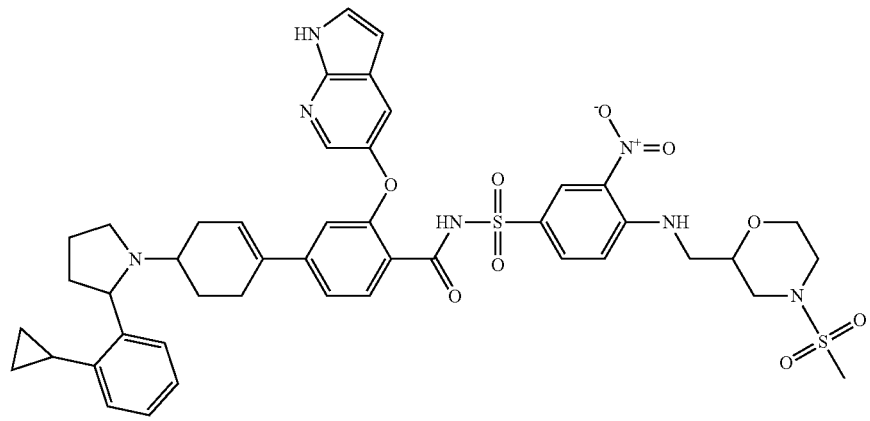

The desired compound was synthesized with 4-(((4-(methylsulfonyl)morpholin-2-yl)methyl)amino)-3-nitrobenzenesulfonamide and 3-((1H-pyrrolo[2,3-b]pyridin-5-yl)oxy)-4'-(2-(2-cyclopropylphenyl)pyrrolidin-1-yl)-2',3',4',5'-tetrahydro-[1,1'-biphenyl]-4-carboxylic acid following the procedures similar to those in Example G8. ¹H NMR (400 MHz, DMSO-d₆) δ ppm: 12.20 (br, 1H), 11.63 (s, 1H), 8.54-8.45 (m, 2H), 7.98 (s, 1H), 7.81-7.74 (m, 1H), 7.62-7.42 (m, 4H), 7.30-6.95 (m, 5H), 6.74 (s, 1H), 6.36 (s, 1H), 5.99 (s, 0.5H), 5.83 (s, 0.51 f ). 3.96 (d, J=12.0 Hz, 1H), 3.76 (s, 1H), 3.63-3.34 (m, 8H), 2.92 (s, 3H), 2.90-2.80 (m, 1H), 2.74-2.66 (m, 1H), 2.49-2.17 (m, 5H), 2.10-1.42 (m, 7H), 0.99-0.81 (m, 2H), 0.78-0.50 (m, 2H). MS (ESI, m/e) [M+1]⁺ 895.7.

Example Gt 14: 3-((1H-pyrrolo[2,3-b]pyridin-5-yl)oxy)-4'-((S)-2-(2-cyclopropylphenyl)pyrrolidin-1-yl)-N-((4-(((4-fluoro-1-(oxetan-3-yl)piperidin-4-yl)methyl)amino)-3-nitrophenyl)sulfonyl)-2',3',4',5'-tetrahydro-[1,1'-biphenyl]-4-carboxamide

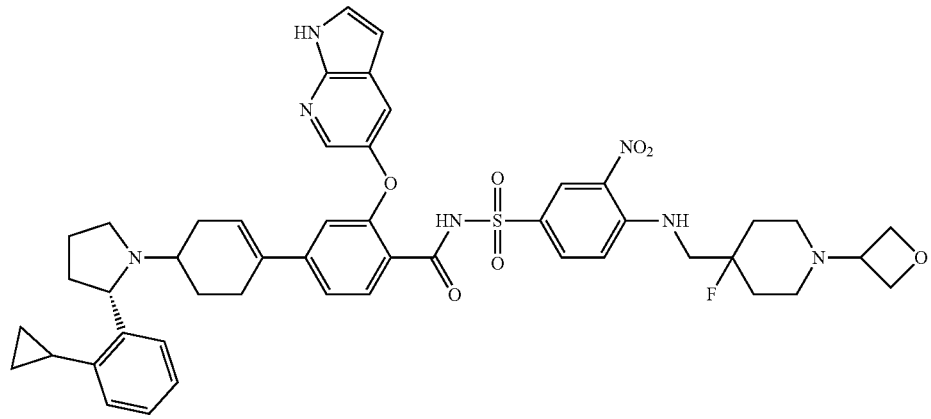 [SMILES: O=C(NS(=O)(=O)c1ccc(NCC2(F)CCN(C3COC3)CC2)c([N+](=O)[O-])c1)c1ccc(C2=CCC(N3CCC[C@H]3c3ccccc3C3CC3)CC2)cc1Oc1cnc2[nH]ccc2c1]

The desired compound was synthesized with 4-(((4-fluoro-1-(oxetan-3-yl)piperidin-4-yl)methyl)amino)-3-nitrobenzenesulfonamide and 3-((1H-pyrrolo[2,3-b]pyridin-5-yl)oxy)-4'-((S)-2-(2-cyclopropylphenyl)pyrrolidin-1-yl)-2',3',4',5'-tetrahydro-[1,1'-biphenyl]-4-carboxylic acid following the procedures similar to those in Example G8. ¹H NMR (400 MHz, DMSO-d₆) δ ppm: 11.63 (s, 1H), 8.58-8.40 (m, 2H) 7.95 (s, 1H), 7.80-7.70 (m, 1H), 7.65-7.36 (m, 4H), 7.34-7.21 (m, 1H), 7.15-7.04 (m, 2H), 6.99-6.85 (m, 2H), 6.72 (s, 1H), 6.34 (s, 1H), 6.01-5.76 (m, 1H), 4.57-4.47 (m, 2H), 4.46-4.37 (m, 2H), 4.33-4.22 (m, 1H), 3.70-3.57 (m, 3H), 3.51-3.41 (m, 3H), 3.06-2.85 (m, 3H), 2.24-2.13 (m, 2H), 2.05-1.93 (m, 3H), 1.86-1.79 (m, 2H), 1.74-1.65 (m, 2H), 1.21-1.10 (m, 2H), 1.09-1.01 (m, 2H), 0.99-0.90 (m, 2H), 0.89-0.82 (m, 2H), 0.73-0.45 (m, 3H), MS (ESI, m/e) [M+1]⁺ 889.8.

Example G115: 3-((1H-pyrrolo[2,3-b]pyridin-5-yl)oxy)-N-((5-chloro-6-((1-(dimethylglycyl)-4-fluoropiperidin-4-yl)methoxy)pyridin-3-yl)sulfonyl)-4'-(2-(2-cyclopropylphenyl)pyrrolidin-1-yl)-2',3',4',5'-tetrahydro-[1,1'-biphenyl]-4-carboxamide

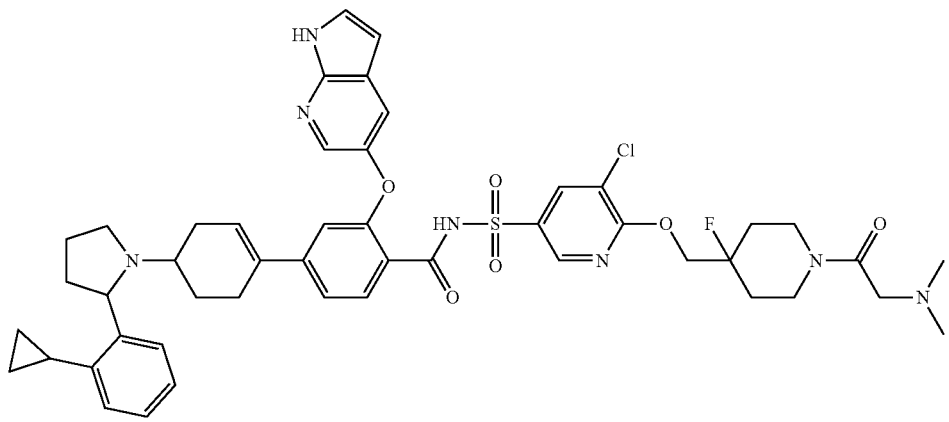 [SMILES: CN(C)CC(=O)N1CCC(F)(COc2ncc(S(=O)(=O)NC(=O)c3ccc(C4=CCC(N5CCCC5c5ccccc5C5CC5)CC4)cc3Oc3cnc4[nH]ccc4c3)cc2Cl)CC1]

The desired compound was synthesized with 4-(((4-(methylsulfonyl)morpholin-2-yl)methyl)amino)-3-nitrobenzenesulfonamide and 3-((1H-pyrrolo[2,3-b]pyridin-5-yl)oxy)-4'-(2-(2-cyclopropylphenyl)pyrrolidin-1-yl)-2',3',4',5'-tetrahydro-[1,1'-biphenyl]-4-carboxylic acid following the procedures similar to those in Example G8. $^1$H NMR (400 MHz, DMSO-$d_6$) δ ppm: 11.54 (s, 1H), 8.30 (s, 1H), 8.04 (s, 1H), 7.99-7.91 (m, 1H), 7.57-7.41 (m, 3H), 7.35-7.32 (m, 1H), 7.16-6.98 (m, 3H), 6.93-6.82 (m, 1H), 6.74-6.72 (m, 1H), 6.34-6.30 (m, 1H), 5.99 (s, 0.5H), 5.79 (s, 0.5H), 4.47 (s, 1H), 4.42 (s, 1H), 4.31-4.18 (m, 2H), 3.95-3.87 (m, 1H), 3.25-3.11 (m, 4H), 2.87-2.81 (m, 1H), 2.67-2.51 (m, 2H), 2.26-2.07 (m, 8H), 2.04-1.91 (m, 6H), 1.78-1.64 (m, 4H), 1.55-1.33 (m, 4H), 0.95-0.84 (m, 2H), 0.68-0.45 (m, 2H), MS (ESI, m/e) [M+1]$^+$ 909.7.

Example G116: 3-((1H-pyrrolo[2,3-b]pyridin-5-yl)oxy)-4'-(2-(3-chloro-2-cyclopropylphenyl)pyrrolidin-1-yl)-N-((4-((4-hydroxycyclohexyl)methoxy)-3-nitrophenyl)sulfonyl)-2',3',4',5'-tetrahydro-[1,1'-biphenyl]-4-carboxamide

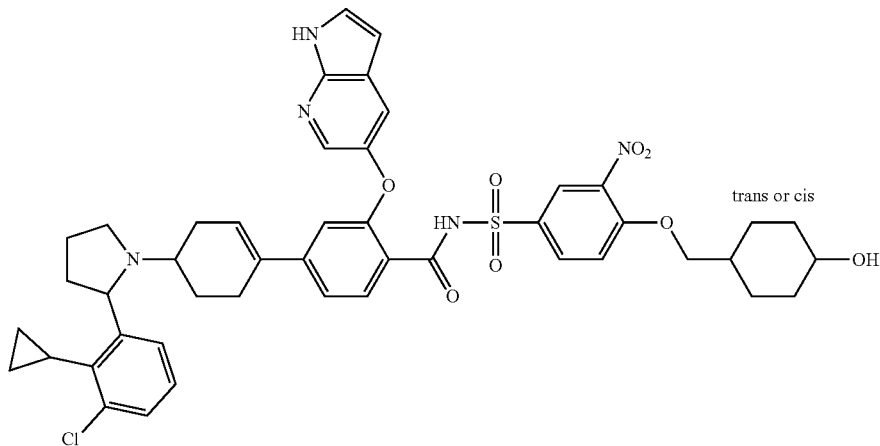 [SMILES: O=C(NS(=O)(=O)c1ccc(OCC2CCC(O)CC2)c([N+](=O)[O-])c1)c1ccc(C2=CCC(N3CCCC3c3cccc(Cl)c3C3CC3)CC2)cc1Oc1cnc2[nH]ccc2c1]

The desired compound was synthesized with (trans- or cis-) 4-((4-hydroxycyclohexyl)methoxy)-3-nitrobenzenesulfonamide and 3-((1H-pyrrolo[2,3-b]pyridin-5-yl)oxy)-4'-(2-(3-chloro-2-cyclopropylphenyl)pyrrolidin-1-yl)-2',3',4',5'-tetrahydro-[1,1'-biphenyl]-4-carboxylic acid following the procedures similar to those in Example G8. $^1$H NMR (400 MHz, DMSO-$d_6$) δ ppm: 12.48 (br, 1H), 11.61 (s, 1H), 8.18 (s, 1H), 7.94 (s, 1H), 7.85 (m, 1H), 7.54-7.37 (m, 5H), 7.25-7.08 (m, 3H), 6.73 (s, 1H), 6.34 (s, 1H), 5.79-5.76 (m, 0.5H), 5.32-5.31 (m, 0.5H), 4.53-4.51 (m, 1H), 3.91 (d, J=6.0 Hz, 2H), 3.82-3.41 (m, 1H), 3.25-3.02 (m, 1H), 2.67-2.65 (m, 2H), 2.45-2.08 (m, 5H), 1.99-1.66 (m, 10H), 1.62-1.53 (m, 2H), 1.36-1.07 (m, 6H), 0.60-0.51 (m, 2H). MS (ESI, m/e) [M+1]$^+$ 865.7.

Example G117: (trans- or cis-) 2-((1H-pyrrolo[2,3-b]pyridin-5-yl)oxy)-4-(4-(2-(2-cyclopropylphenyl)pyrrolidin-1-yl)cyclohexyl)-N-((3-nitro-4-(((4-(oxetan-3-yl)morpholin-2-yl)methyl)amino)phenyl)sulfonyl)benzamide

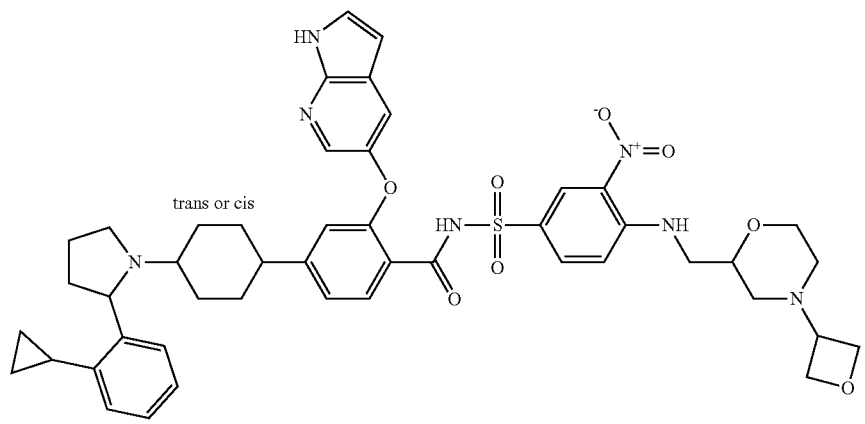

The desired compound was synthesized with 3-nitro-4-(((4-(oxetan-3-yl)morpholin-2-yl)methyl)amino)benzenesulfonamide and (trans- or cis-) 2-((1H-pyrrolo[2,3-b]pyridin-5-yl)oxy)-4-(4-(2-(2-cyclopropylphenyl)pyrrolidin-1-yl)cyclohexyl)benzoic acid following the procedures similar to those in Example D1b. $^1$H NMR (400 MHz, DMSO-$d_6$) δ ppm: 12.48 (br, 0.5H), 11.61 (s, 1H), 9.26 (br, 0.5H), 8.18 (s, 1H), 7.94 (s, 1H), 7.85 (m, 1H), 7.54-7.37 (m, 5H), 7.25-7.08 (m, 3H), 6.73 (s, 1H), 6.34 (s, 1H), 5.79-5.76 (m, 0.5H), 5.32-5.31 (m, 0.5H), 4.53-4.51 (m, 1H), 3.91 (d, J=6.0 Hz, 2H), 3.82-3.41 (m, 1H), 3.25-3.02 (m, 1H), 2.67-2.65 (m, 2H), 2.45-2.08 (m, 5H), 1.99-1.66 (m, 10H), 1.62-1.53 (m, 2H), 1.36-1.07 (m, 6H), 0.60-0.51 (m, 2H). MS (ESI, m/e) [M+1]$^+$ 865.7.

Example G118: 3-((1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4'-((R)-2-(2-(1-methyl-1,2,3,6-tetrahydropyridin-4-yl)phenyl)pyrrolidin-1-yl)-[1,1'-biphenyl]-4-carboxamide

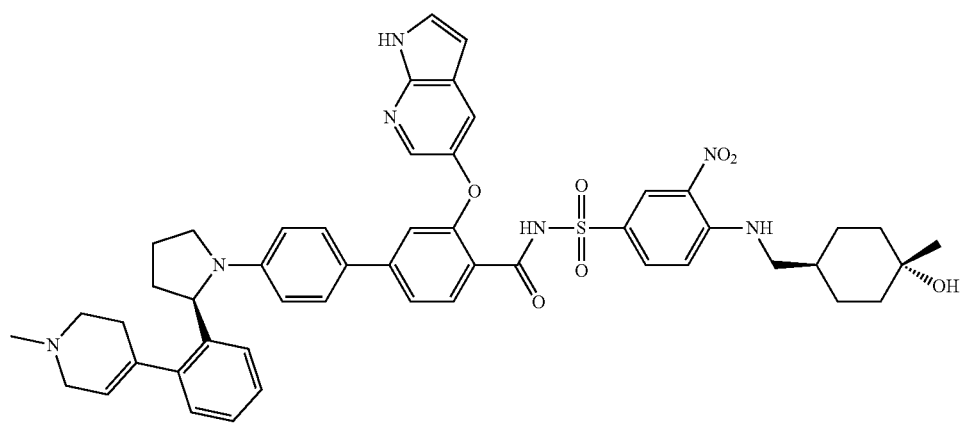

Step 1: (R)-1-(2-(2-bromophenyl)pyrrolidin-1-yl)-2,2,2-trifluoroethan-1-one

To a solution of (R)-2-(2-bromophenyl)pyrrolidine (10 g, 44.22 mmol) in DCM (100 mL) was added triethylamine (6.699 g, 66.33 mmol), then added (CF$_3$CO)$_2$O (10.216 g, 48.65 mmol) at 0° C. After stirred at room temperature for 1 hour, the reaction mixture was concentrated. The resulted residue was dissolved with DCM (500 ml), and then washed with saturated aq. NaHCO$_3$ solution, brine. After dried over Na$_2$SO$_4$, the organic phase was concentrated to obtain the product (14 g) as a brown solid. MS (ESI, m/e) [M+1]$^+$ 321.8.

Step 2: tert-butyl (R)-4-(2-(1-(2,2,2-trifluoroacetyl)pyrrolidin-2-yl)phenyl)-3,6-dihydropyridine-1 (2H)-carboxylate To a solution of (R)-1-(2-(2-bromophenyl)pyrrolidin-1-yl)-2,2,2-trifluoroethan-1-one (5 g, 15.52 mmol) in toluene (100 ml) was added tert-butyl 4-(4,4,5,5-tetramethyl-1,3,2-dioxaborolan-2-yl)-3,6-dihydropyridine-1(2H)-carboxylate (7,189 g, 23.25 mmol), Pd(OAc)$_2$ (348 mg, 1.552 mmol), Tricyclohexyl phosphine (870 mg, 3.1 mmol) and K$_3$PO$_4$ (11.53 g, 54.32 mmol), The mixture was then stirred at 100° C. for 12 hours at N$_2$ atmosphere. After cooled to room temperature, the reaction mixture was washed with brine and dried over Na$_2$SO$_4$. After removal of solvent, the resulted residue was purified by chromatograph column on silica gel (eluent: PE/EA=50/1 to 10/1) to obtain the product (3.66 g) as yellow oil. MS (ESI, m/e) [M−55]$^+$ 368.8.

Step 3: (R)-2,2,2-trifluoro-1-(2-(2-(1,2,3,6-tetrahydropyridin-4-yl)phenyl)pyrrolidin-1-yl)ethan-1-one To a solution of tert-butyl (R)-4-(2-(1-(2,2,2-trifluoroacetyl)pyrrolidin-2-yl)phenyl)-3,6-dihydropyridine-1(2H)-carboxylate (3.66 g, 8.62 mmol) in DCM (100 ml) was added TFA (20 ml). The mixture was stirred at room temperature for 2 hours. After removal of solvent and TFA, the residue was dissolved with DCM (200 ml) and then washed with saturated aq. NaHCO$_3$ solution, brine, dried over Na$_2$SO$_4$. The DCM solution was concentrated to obtain the crude product (2.66 g) as a brown oil, which was used in next step without further purification.

Step 4: (R)-2,2,2-trifluoro-1-(2-(2-(1-methyl-1,2,3,6-tetrahydropyridin-4-yl)phenyl)pyrrolidin-1-yl)ethan-1-one To a solution of (R)-2,2,2-trifluoro-1-(2-(2-(1,2,3,6-tetrahydropyridin-4-yl)phenyl)pyrrolidin-1-yl)ethan-1-one (2.66 g, 8.2 mmol) in MeOH (100 mL) was added HCHO (37%, 3.99 g 49.18 mmol) and NaBH$_3$CN (2.058 g, 32.77 mmol). The mixture was stirred at room temperature for 2 hours. After removal of solvent, the residue was dissolved with EA (200 ml), washed with brine, and then dried over Na$_2$SO$_4$. The EA solution was concentrated to obtain the crude product (2.5 g) as a yellow solid, which was used in next step without further purification. MS (ESI, m/e) [M+1]$^+$ 338.9.

Step 5: (R)-1-methyl-4-(2-(pyrrolidin-2-yl)phenyl)-1,2,3,6-tetrahydropyridine To a solution of (R)-2,2,2-trifluoro-1-(2-(2-(1-methyl-1,2,3,6-tetrahydropyridin-4-yl)phenyl)pyrrolidin-1-yl)ethan-1-one (2.5 g, 7.39 mmol) in MeOH (50 mL) and H$_2$O (50 mL) was added LiOH.H$_2$O (3.1 g, 73.9 mmol). After stirred at 60° C. for 3 hours, the reaction mixture was extracted with DCM (200 mL×3). The combined organic phase was concentrated. The residue was purified by column chromatograph on silica gel (eluent: DCM/MeOH=10/1 (added 1% NH3.H2O)) to obtain the product (1.2 g). MS (ESI, m/e) [M+1]$^+$ 243.0.

Step 6: (R)-4-(2-(1-(4-bromophenyl)pyrrolidin-2-yl)phenyl)-1-methyl-1,2,3,6-tetrahydropyridine To a solution of (R) 1-methyl-4-(2-(pyrrolidin-2-yl)phenyl)-1,2,3,6-tetrahydropyridine (500 mg, 2.07 mmol) in toluene (50 ml) was added 1-bromo-4-iodobenzene (1.165 g, 4.13 mmol), Pd$_2$(dba)$_3$ (189 mg, 0.207 mmol), BINAP (257.5 mg, 0.414 mmol) and t-BuOK (757.6 mg, 6.21 mmol). The mixture was stirred at 90° C. for 12 hours at N$_2$ atmosphere. After cooled to room temperature, the reaction mixture was washed with brine, dried over Na$_2$SO$_4$ and concentrated. The residue was purified by chromatograph column on silica gel (DCM/MeOH=50/1) to obtain the product (508 mg) as a yellow oil. MS (ESI, m/e) [M+1]$^+$ 396.8.

Step 7: tert-butyl (R)-3-((1H-pyrrolo[2,3-b]pyridin-5-yl)oxy)-4'-(2-(2-(1-methyl-1,2,3,6-tetrahydropyridin-4-yl)phenyl)pyrrolidin-1-yl)-[1,1'-biphenyl]-4-carboxylate To a solution of (R)-4-(2-(1-(4-bromophenyl)pyrrolidin-2-yl)phenyl)-1-methyl-1,2,3,6-tetrahydropyridine (508 mg, 1.28 mmol) and tert-butyl 2-((1H-pyrrolo[2,3-b]pyridin-5-yl)oxy)-4-(3,3,4,4-tetramethylborolan-1-yl)benzoate (725.3 mg, 1.66 mmol) in 1,4-dioxane (50 mL) and H$_2$O (5 mL) was added Pd(ddpf)Cl$_2$ (93.6 mg, 0.128 mmol) and Cs$_2$CO$_3$ (1248 mg, 3.84 mmol). The mixture was stirred at 100° C. for 3 hours under N$_2$ protection. After cooled to room temperature, the reaction mixture was diluted with DCM (200 mL), then washed with brine (200 ml. 2) and dried over Na2SO4. After concentration, the residue was purified by chromatography column on silica (eluent: DCM/MeOH=25/1) to obtain the product (367 mg) as a yellow solid. MS (ESI, m/e) [M+1]$^+$ 626.9.

Step 8: (R)-3-((1H-pyrrolo[2,3-b]pyridin-5-yl)oxy)-4'-(2-(2-(1-methyl-1,2,3,6-tetrahydropyridin-4-yl)phenyl)pyrrolidin-1-yl)-[1,1'-biphenyl]-4-carboxylic acid To a solution of tert-butyl (R)-3-((1H-pyrrolo[2,3-b]pyridin-5-yl)oxy)-4'-(2-(2-(1-methyl-1,2,3,6-tetrahydropyridin-4-yl)phenyl)pyrrolidin-1-yl)-[1,1'-biphenyl]-4-carboxylate (367 mg, 0.585 mmol) in DCM (30 mL) was added TFA (15 mL). The mixture was stirred at room temperature for 2 hours. After removal of solvent and TFA, the crude product was obtained as a yellow solid, which was used in next step without further purification, MS (ESI, m/e) [M+1]$^+$ 570.9.

Step 9: 3-((1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4'-((R)-2-(2-(1-methyl-1,2,3,6-tetrahydropyridin-4-yl)phenyl)pyrrolidin-1-yl)-[1,1'-biphenyl]-4-carboxamide To a solution of (R)-3-((1H-pyrrolo[2,3-b]pyridin-5-yl)oxy)-4'-(2-(2-(1-methyl-1,2,3,6-tetrahydropyridin-4-yl)phenyl)pyrrolidin-1-yl)-[1,1'-biphenyl]-4-carboxylic acid (334 mg, 0.585 mmol) in DCM (50 mL) was added HATU (333.5 mg, 0.878 mmol) and triethylamine (295 mg, 2.925 mmol). The mixture was stirred at room temperature for 1 hour and then to the mixture was added 4-((((1r,4r)-4-hydroxy-4-methylcyclohexyl)methyl)amino)-3-nitrobenzenesulfonamide (301.5 mg, 0.878 mmol) and DMAP (35.7 mg, 0.293 mmol). The reaction mixture was stirred at room temperature for overnight. After washed with saturated aq. NaHCO3 solution, brine and dried over Na2SO4, the reaction mixture was concentrated and purified by chromatography column on silica (eluent: MeOH/DCM=1/10) to give the crude product. The erode product was further purified by prep-TLC (eluent: MeOH/DCM=1/10) to obtain the desired product (135 mg) as a yellow solid. $^1$H NMR (400 MHz, DMSO d$_6$) δ 12.32 (br, 1H), 11.70 (s, 1H), 8.71-8.42 (m, 2H), 8.12-7.97 (m, 1H), 7.79-7.71 (m, 1H), 7.62-7.44 (m, 3H), 7.38-6.94 (m, 8H), 6.90 (s, 1H), 6.44-6.25 (m, 3H), 5.86-5.60 (m, 1H), 5.00-4.79 (m, 1H), 4.32-4.17 (m, 1H), 3.9-3.43 (m, 3H), 3.43-34 (m, 2H), 3.28-3.20 (m, 2H), 2.95-2.72 (m, 5H), 2.42-2.31 (m, 2H), 2.06-1.93 (m, 2H), 1.80-1.48 (m, 6H), 1.38-1.26 (m, 2H), 1.17-1.04 (m, 5H). MS (ESI, m/e) [M+1]$^+$ 896.8.

Example G119: (R)-3-((1H-pyrrolo[2,3-b]pyridin-5-yl)oxy)-N-((4-(((4-fluorotetrahydro-2H-pyran-4-yl)methyl)amino)-3-nitrophenyl)sulfonyl)-4'-(2-(2-(1-methyl-1,2,3,6-tetrahydropyridin-4-yl)phenyl)pyrrolidin-1-yl)-[1,1'-biphenyl]-4-carboxamide

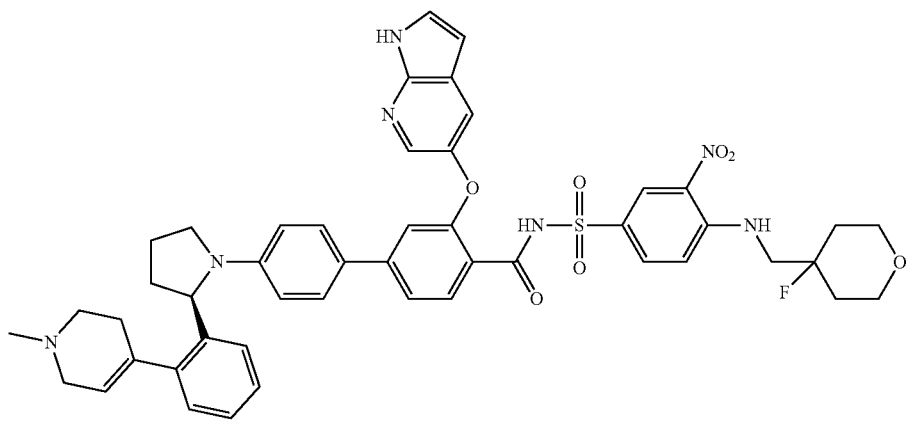 [SMILES: CN1CC=C(c2ccccc2[C@H]2CCCN2c2ccc(-c3ccc(C(=O)NS(=O)(=O)c4ccc(NCC5(F)CCOCC5)c([N+](=O)[O-])c4)c(Oc4cnc5[nH]ccc5c4)c3)cc2)CC1]

The desired compound was synthesized following the procedures similar to those in Example G118 by replacing 4-((((1r,4r)-4-hydroxy-4-methylcyclohexyl)methyl)amino)-3-nitrobenzenesulfonamide with 4-(((4-fluorotetrahydro-2H-pyran-4-yl)methyl)amino)-3-nitrobenzenesulfonamide. $^1$H NMR (400 MHz, DMSO-d$_6$) δ ppm: 12.31 (br, 1H), 11.69 (s, 1H), 8.69-8.46 (m, 2H), 8.01-7.97 (m, 1H), 7.88-7.74 (m, 1H), 7.61-7.42 (m, 3H), 7.39-7.06 (m, 7H), 7.06-6.94 (m, 1H), 6.90 (s, 1H), 6.47-6.27 (m, 3H), 5.71 (s, 1H), 4.96-4.81 (m, 1H), 3.98-3.62 (m, 7H), 3.63-3.34 (m, 5H), 3.06-2.58 (m, 5H), 2.44-2.30 (m, 1H), 2.06-1.92 (m, 2H), 1.88-1.67 (m, 5H). MS (ESI, m/e) [M+1]$^+$ 885.8.

Example G120: N-((4-((((R)-1,4-dioxan-2-yl)methyl)amino)-3-nitrophenyl)sulfonyl)-3-((1H-pyrrolo[2,3-b]pyridin-5-yl)oxy)-4'-((R)-2-(2-(1-methyl-1,2,3,6-tetrahydropyridin-4-yl)phenyl)pyrrolidin-1-yl)-[1,1'-biphenyl]-4-carboxamide

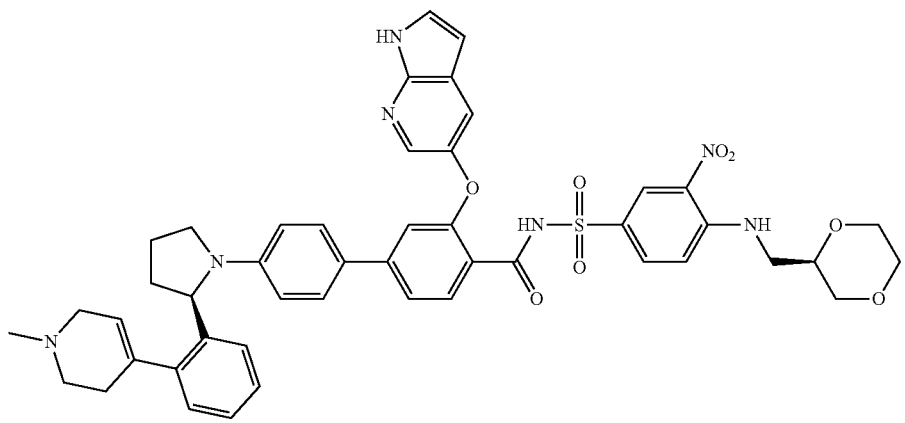 [SMILES: CN1CC=C(c2ccccc2[C@H]2CCCN2c2ccc(-c3ccc(C(=O)NS(=O)(=O)c4ccc(NC[C@@H]5COCCO5)c([N+](=O)[O-])c4)c(Oc4cnc5[nH]ccc5c4)c3)cc2)CC1]

The desired compound was synthesized following the procedures similar to those in Example G118 by replacing 4-((((1r,4r)-4-hydroxy-4-methylcyclohexyl)methyl)amino)-3-nitrobenzenesulfonamide with (R)-4-(((1,4-dioxan-2-yl)methyl)amino)-3-nitrobenzenesulfonamide. $^1$H NMR (DMSO-d$_6$) δ ppm: 12.18 (br, 1H), 11.69 (s, 1H), 8.55 (s, 2H), 8.04 (d, J=1.9 Hz, 1H), 7.82 (d, J=8.9 Hz, 1H), 7.56-7.51 (m, 3H), 7.34-7.28 (m, 3H), 7.26-7.07 (m, 4H), 7.00 (d, J=7.3 Hz, 1H), 6.90 (s, 1H), 6.41-6.32 (m, 3H), 5.70 (s, 1H), 4.88 (d, J=7.0 Hz, 1H), 3.96-3.91 (m, 1H), 3.84-3.70 (m, 6H), 3.65-3.61 (m, 4 IT), 3.53-3.42 (m, 4H), 2.88 (s, 4H), 2.38-2.31 (m, 2H), 1.98 (s, 2H), 1.79-1.71 (m, 1H). MS (ESI, m/e) [M+1]$^+$ 869.8.

Example G121: (R)-3-((1H-pyrrolo[2,3-b]pyridin-5-yl)oxy)-N-((4-(((4-fluoro-1-(oxetan-3-yl)piperidin-4-yl)methyl)amino)-3-nitrophenyl)sulfonyl)-4'-(2-(2-(1-methyl-1,2,3,6-tetrahydropyridin-4-yl)phenyl)pyrrolidin-1-yl)-[1,1'-biphenyl]-4-carboxamide

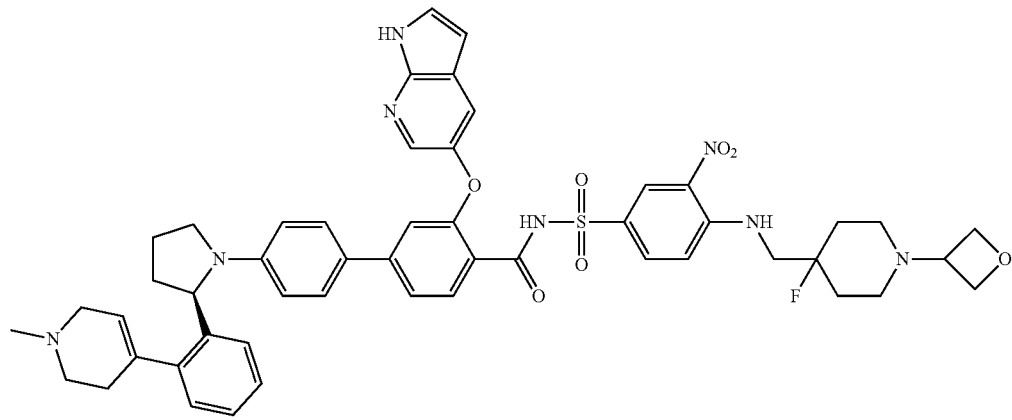 [SMILES: CN1CC=C(c2ccccc2[C@H]2CCCN2c2ccc(-c3ccc(C(=O)NS(=O)(=O)c4ccc(NCC5(F)CCN(C6COC6)CC5)c([N+](=O)[O-])c4)c(Oc4cnc5[nH]ccc5c4)c3)cc2)CC1]

The desired compound was synthesized following the procedures similar to those in Example G118 by replacing 4-((((1r,4r)-4-hydroxy-4-methylcyclohexyl)methyl)amino)-3-nitrobenzenesulfonamide with 4-(((4-fluoro-1-(oxetan-3-yl)piperidin-4-yl)methyl)amino)-3-nitrobenzenesulfonamide. $^1$H NMR (DMSO-d$_6$) δ ppm: 11.56 (s, 1H), 10.11 (s, 1H), 8.52-8.24 (m, 2H), 8.01-7.89 (m, 1H), 7.76-7.63 (m, 1H), 7.62-7.49 (m, 1H), 7.48-7.33 (m, 2H), 7.33-7.09 (m, 6H), 7.09-6.94 (m, 2H), 6.90 (s, 1H), 6.43-6.20 (m, 3H), 5.70 (s, 1H), 4.91-4.76 (m, 1H), 4.59-4.47 (m, 2H), 4.46-4.36 (m, 2H), 3.81-3.51 (m, 5H), 3.48-3.34 (m, 4H), 3.30-2.87 (m, 3H), 2.82-2.68 (m, 3H), 2.68-2.59 (m, 2H), 2.41-2.28 (m, 1H), 2.06-1.91 (m, 4H), 1.88-1.66 (m, 5H). MS (ESI, m/e) [M+1]$^+$ 941.2.

Example G122: 3-((1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4'-((R)-2-(2-(1-methylpiperidin-4-yl)phenyl)pyrrolidin-1-yl)-[1,1'-biphenyl]4-carboxamide

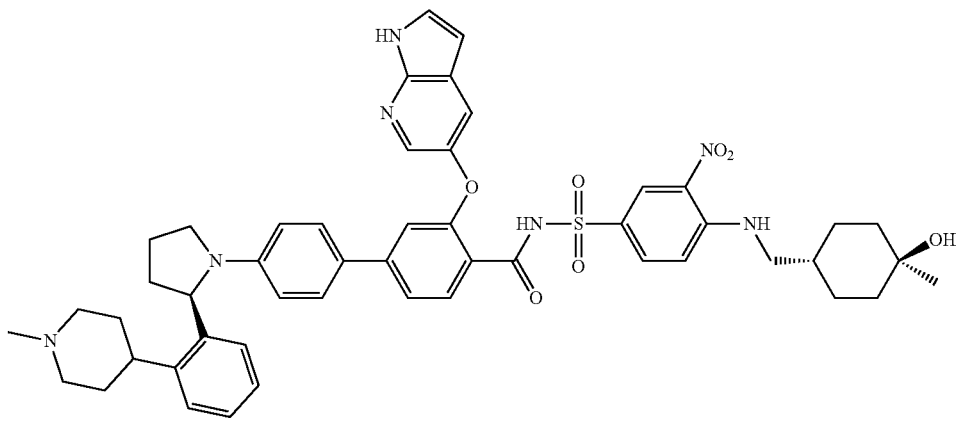 [SMILES: CN1CCC(c2ccccc2[C@H]2CCCN2c2ccc(-c3ccc(C(=O)NS(=O)(=O)c4ccc(NC[C@H]5CC[C@](C)(O)CC5)c([N+](=O)[O-])c4)c(Oc4cnc5[nH]ccc5c4)c3)cc2)CC1]

The desired compound was synthesized following the procedures similar to those in Example A100. To a solution of (R)-3-((1H-pyrrolo[2,3-b]pyridin-5-yl)oxy)-4'-(2-(2-(1-methylpiperidin-4-yl)phenyl)pyrrolidin-1-yl)-[1,1'-biphenyl]-4-carboxylic acid (400 mg, 0.69 mmol) in DCM (25 ml) were added HATU (393 mg, 0.69 mmol) and triethylamine (1 mL). The mixture was stirred at room temperature for 1 hour. Then 4-((((1r,4r)-4-hydroxy-4-methylcyclohexyl)methyl)amino)-3-nitrobenzenesulfonamide (478 mg, 1.40 mmol) and DMAP (171 mg, 1.40 mmol) were added into the reactor and stirred at room temperature overnight. The reaction mixture was washed with saturated aq. NaHCO$_3$, brine, and dried over anhydrous Na$_2$SO$_4$, then concentrated. The residue was purified by prep-HPLC to obtain example G122 (400 mg). $^1$H NMR (DMSO-d$_6$) δ ppm: 11.54 (s, 1H), 9.58 (s, 1H), 8.40 (d, J=2.0 Hz, 1H), 8.30 (t, J=5.6 Hz, 1H), 7.96 (d, J=2.5 Hz, 1H), 7.66 (dd, J=9.2, 1.7 Hz, 1H), 7.56 (d, J=8.6 Hz, 1H), 7.41 (t, J=2.9 Hz, 1H), 7.36 (d, J=2.5 Hz, 1H), 7.26-7.19 (m, 6H), 7.04 (l, J=7.5 Hz, 1H), 6.90 (d, J=6.8 Hz, 2H), 6.82 (d, J=9.2 Hz, 1H), 6.36 (d, J=8.6 Hz, 2H), 6.31-6.27 (m, 1H), 5.00 (d, J=7.5 Hz, 1H), 4.23 (s, 1H), 3.79-3.64 (m, 1H), 3.42-3.35 (m, 3H), 3.25-3.15 (m, 3H), 3.05 (s, 1H), 2.81-2.70 (m, 2H), 2.59 (s, 3H), 2.46-2.36 (m, 1H), 1.97-1.88 (m, 5H), 1.82-1.48 (m, 8H), 1.37-1.31 (m, 2H), 1.17-1.12 (m, 2H). MS (ESI, m/e) [M+1]$^+$ 897.9.

Example G123: 3-((1H-pyrrolo[2,3-b]pyridin-5-yl) oxy)-4'-((R)-2-(2-(1-acetylpiperidin-4-yl)phenyl) pyrrolidin-1-yl)-N-((4-((((1r,4r)-4-hydroxy-4-methylcyclohexyl)methyl)amino)-3-nitrophenyl) sulfonyl)-[1,1'-biphenyl]-4-carboxamide

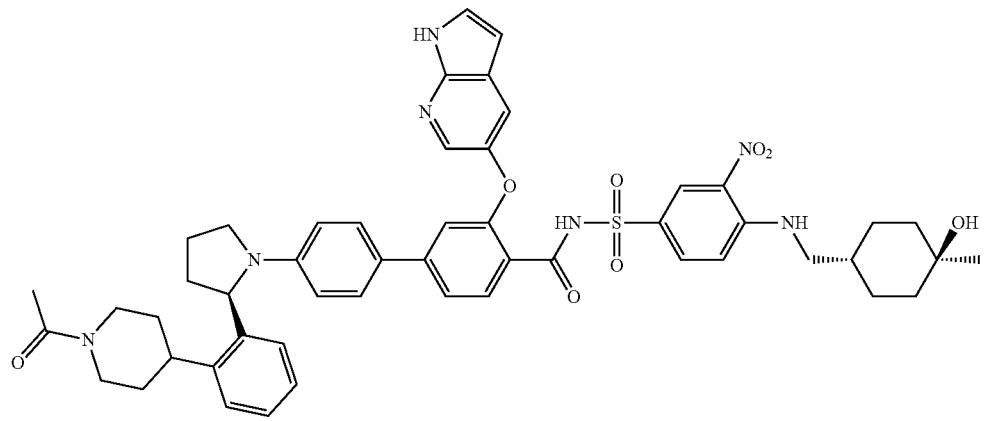 [SMILES: CC(=O)N1CCC(c2ccccc2[C@H]2CCCN2c2ccc(-c3ccc(C(=O)NS(=O)(=O)c4ccc(NC[C@H]5CC[C@](C)(O)CC5)c([N+](=O)[O-])c4)c(Oc4cnc5[nH]ccc5c4)c3)cc2)CC1]

The desired compound was synthesized following the procedures similar to those in Example G122 by replacing (R)-1-methyl-4-(2-(pyrrolidin-2-yl)phenyl)piperidine with (R)-1-(4-(2 (pyrrolidin-2-yl)phenyl)piperidin-1-yl)ethan-1-one. $^1$H NMR (DMSO-d$_6$) δ ppm: 12.14 (s, 1H), 11.70 (s, 1H), 8.57-8.55 (m, 2H), 8.05 (d, J=2.5 Hz, 1H), 7.83 (d, J=9.4 Hz, 1H), 7.59 (s, 1H), 7.54-7.49 (m, 2H), 7.36-7.30 (m, 4H), 7.17-7.08 (m, 2H), 7.03-7.00 (m, 1H), 6.90 (s, 1H), 6.86-6.8 (m, 1H), 6.38-6.36 (m, 3H), 5.06 (s, 1H), 4.55 (s, 1H), 4.24 (s, 1H), 3.93 (s, 1H), 3.71 (s, 1H), 3.39-3.38 (m, 1H), 3.26-3.23 (m, 3H), 3.18-3.16 (m, 2H), 2.70-2.60 (m, 2H), 2.04 (s, 3H), 1.97 (s, 1H), 1.86 (s, 2H), 1.69-1.65 (m, 4H), 1.56-1.53 (m, 2H), 1.33-1.30 (m, 2H), 1.15-1.00 (m, 5H). MS (ESI) m/e [M+1]$^+$ 925.8.

Example G124: 3-((1H-pyrrolo[2,3-b]pyridin-5-yl)oxy)-4'-((R)-2-(2-(1-(dimethylglycyl)piperidin-4-yl)phenyl)pyrrolidin-1-yl)-N-((4-((((1r,4r)-4-hydroxy-4-methylcyclohexyl)methyl)amino)-3-nitrophenyl)sulfonyl)-[1,1'-biphenyl]-4-carboxamide

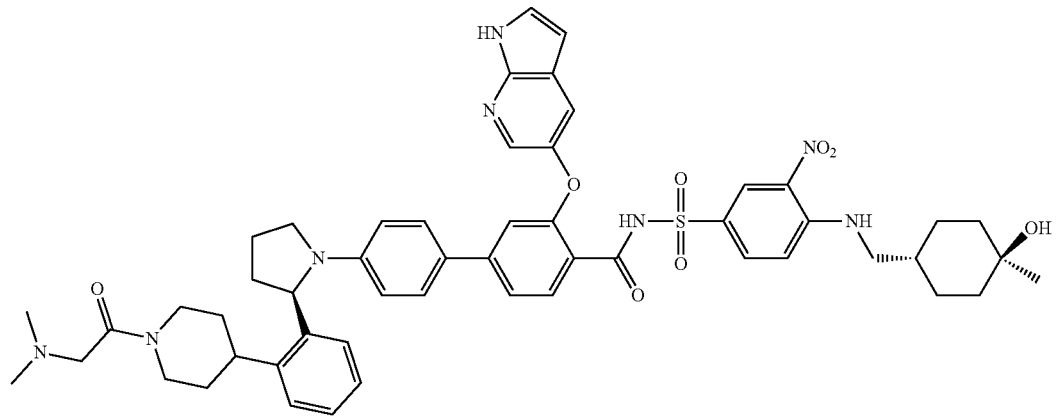

Step 1: (R)-4-(2-(1-(4-bromophenyl)pyrrolidin-2-yl)phenyl)piperidine

A mixture of (R)-tert-butyl 4-(2-(1-(4-bromophenyl)pyrrolidin-2-yl)phenyl)piperidine-1-carboxylate (1 g, 2.1 mmol) in HCl (4 M in EA, 20 mL) was stirred at 20° C. for 2 hours. TLC showed the reaction was complete. The precipitation was filtered off and dried to give (R)-4-(2-(1-(4-bromophenyl)pyrrolidin-2-yl)phenyl)piperidine (600 mg, HCl salt) as an off-white solid. MS (ESI, m/e) [M+1]$^+$ 387.8.

Step 2: (R)-1-(4-(2-(1-(4-bromophenyl)pyrrolidin-2-yl)phenyl)piperidin-1-yl)-2-(dimethylamino) ethenone To a solution of 2-(dimethylamino)acetic acid (175 mg, 1.7 mmol) and TFA (424 mg, 4.2 mmol) in DCM (10 mL) was added HATU (646 mg, 1.7 mmol) at 0° C., and the mixture was stirred at 0° C. for 30 min. Then (R)-4-(2-(1-(4-bromophenyl)pyrrolidin-2-yl)phenyl)piperidine (600 mg, 1.4 mmol) was added and the resulting mixture was stirred at 20° C. for 2 hours, LC/MS showed the reaction was completed. The mixture was washed with water (10 mL), brine (10 mL), dried over Na$_2$SO$_4$, and concentrated in vacuum to give 900 mg of the crude product, which was purified by prep-HPLC to obtain (R)-1-(4-(2-(1-(4-bromophenyl)pyrrolidin-2-yl)phenyl)piperidin-1-yl)-2-(dimethylamino)ethanone (453 mg). $^1$H NMR (400 MHz, CD$_3$OD) δ ppm: 7.28 (d, J=7.6 Hz, 1H), 7.22-7.10 (m, 3H), 7.08-7.03 (m, 1H), 7.01-6.97 (m, 1H), 7.01-6.97 (m, 1H), 6.30 (d, J=8.8 Hz, 2H), 5.03-4.97 (m, 1H), 5.00 (d, J=7.4 Hz, 1H), 4.69 (d, J=13.6 Hz, 1H), 4.17 (d, J=12.6 Hz, 1H), 3.74-3.68 (m, 1H), 3.74-3.68 (m, 1H), 3.46-3.35 (m, 2H), 3.23 (d, J=13.2 Hz, 1H), 2.84-2.73 (m, 1H), 2.59-2.48 (m, 1H), 2.39 (s, 6H), 2.08-1.92 (m, 1H), 2.08-1.92 (m, 3H), 1.85-1.75 (m, 3H), 1.74-1.58 (m, 1H). MS (ESI, m/e) [M+1]$^+$ 470.1.

Step 3: tert-butyl (R)-3-((1H-pyrrolo[2,3-b]pyridin-5-yl)oxy)-4'-(2-(2-(1-(dimethylglycyl)piperidin-4-yl)phenyl)pyrrolidin-1-yl)-[1,1'-biphenyl]-4-carboxylate To a solution of (R)-1-(4-(2-(1-(4-bromophenyl)pyrrolidin-2-yl)phenyl)piperidin-1-yl)-2-(dimethylamino)ethanone (200 mg, 0.425 mmol) in 1,4-dioxane (200 mL) and H$_2$O (2 mL) was added tert-butyl 2-((1H-pyrrolo[2,3-b]pyridin-5-yl)oxy)-4-(4,4,5,5-tetramethyl-1,3,2-dioxaborolan-2-yl)benzoate (203.8 mg, 0.468 mmol) and Pd(dppf)Cl$_2$ (62 mg, 0.085 mmol) and Cs$_2$CO$_3$ (414.4 mg, 1.275 mmol). The mixture was stirred at 100° C. for overnight under nitrogen protection. After cooled to room temperature, the mixture was diluted with DCM (100 mL), washed with brine, dried over Na$_2$SO$_4$, concentrated in vacuum. The residue was purified by chromatography column on silica gel (eluent: DCM/MeOH=20/1 to 10/1) to give the product (130 mg, yield: 43.7%). MS (ESI, m/e) [M+1]$^+$ 699.9.

Step 4: (R)-3-((1H-pyrrolo[2,3-b]pyridin-5-yl)oxy)-4'-(2-(2-(1-(dimethylglycyl)piperidin-4-yl)phenyl)pyrrolidin-1-yl)-[1,1'-biphenyl]-4-carboxylic acid To a solution of tert-butyl 2-((1H-pyrrolo[2,3-b]pyridin-5-yl)oxy)-4-(4,4,5,5-tetramethyl-1,3,2-dioxaborolan-2-yl)benzoate (130 mg, 0.186 mmol) in DCM (10 mL) was added TFA (3 mL). The mixture was stirred at room temperature for 2 hours. The mixture was concentrated in vacuum to give the crude product, which was used directly for next step. MS (ESI, m/e) [M+1]+ 643.8.

Step 5: 3-((1H-pyrrolo[2,3-b]pyridin-5-yl)oxy)-4'-((R)-2-(2-(1-(dimethylglycyl)piperidin-4-yl)phenyl)pyrrolidin-1-yl)-N-((4-((((1r,4r)-4-hydroxy-4-methylcyclohexyl)methyl)amino)-3-nitrophenyl)sulfonyl)-[1,1'-biphenyl]-4-carboxamide To a solution of (R)-3-((1H-pyrrolo[2,3-b]pyridin-5-yl)oxy)-4'-(2-(2-(1-(dimethylglycyl)piperidin-4-yl)phenyl)pyrrolidin-1-yl)-[1,1'-biphenyl]-4-carboxylic acid in DCM (20 ml) was added HATU (106 mg, 0.279 mmol) and TFA (94 mg, 0.930 mmol). The mixture was stirred at room temperature for 1 hour. Then to the mixture was added 4-((((1r,4r)-4-hydroxy-4-methylcyclohexyl)methyl)amino)-3-nitrobenzenesulfonamide (127.7 mg, 0.37 mmol) and DMAP (22.7 mg, 0.186 mmol). The mixture was stirred at room temperature for overnight. The mixture was diluted with DCM (100 mL), and then washed with brine, dried over $Na_2SO_4$, evaporated in vacuum. The resulted residue was purified by prep-HPLC to give the desired compound G124 (18 mg) $^1$H NMR (400 MHz, DMSO-$d_6$) δ ppm 11.56 (s, 1H), 9.65 (s, 1H), 8.46-8.34 (m, 2H), 7.97 (s, 1H), 7.76-7.49 (m, 2H), 7.45-7.12 (m, 7H), 7.08-6.98 (m, 1H), 6.96-6.77 (m, 3H), 6.44-6.19 (m, 3H), 5.18-4.96 (m, 1H), 4.66-4.42 (m, 1H), 4.23 (s, 1H), 4.10-3.78 (m, 3H), 3.79-3.62 (m, 1H), 3.45-3.35 (m, 1H), 3.30-3.03 (m, 5H), 2.89-2.58 (m, 7H), 2.07-1.82 (m, 4H), 1.77-1.59 (m, 6H), 1.57-1.48 (m, 2H), 1.40-1.29 (m, 2H), 1.16-1.044 (m, 5H). MS (ESI, m/e) [M+1]+ 968.9.

Example G125: 3-((1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4'-((R)-2-(2-(1-(methylglycyl)piperidin-4-yl)phenyl)pyrrolidin-1-yl)-[1,1'-biphenyl]-4-carboxamide

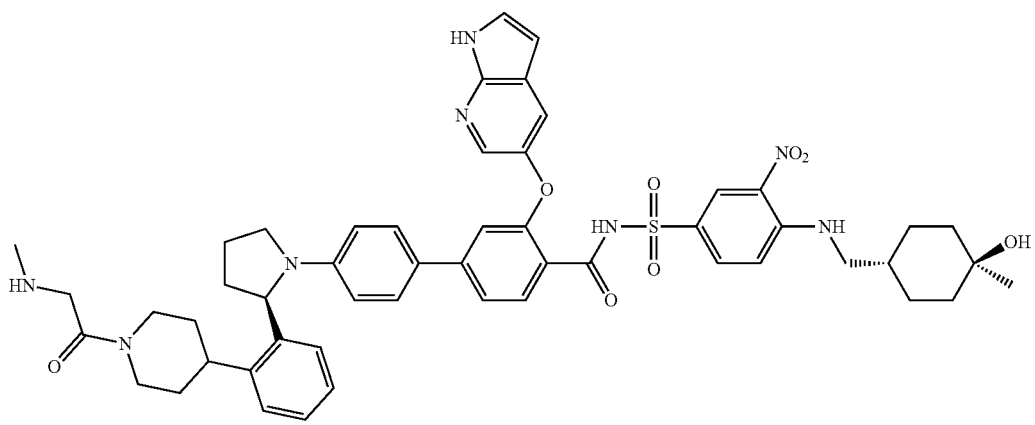 [SMILES: CNCC(=O)N1CCC(c2ccccc2[C@H]2CCCN2c2ccc(-c3ccc(C(=O)NS(=O)(=O)c4ccc(NC[C@H]5CC[C@](C)(O)CC5)c([N+](=O)[O-])c4)c(Oc4cnc5[nH]ccc5c4)c3)cc2)CC1]

The desired compound was synthesized following the procedures similar to those in Example G124 starting from tert-butyl (R)-(2-(4-(2-(1-(4-bromophenyl)pyrrolidin-2-yl)phenyl)piperidin-1-yl)-2-oxoethyl)(methyl)carbamate. $^1$H NMR (400 MHz, DMSO-$d_6$) δ ppm: 11.53 (s, 1H), 8.43-8.23 (m, 2H), 7.95 (s, 1H), 7.68-7.51 (m, 2H), 7.45-7.14 (m, 7H), 7.07-7.00 (m, 1H), 6.96-6.85 (m, 2H), 6.85-6.74 (m, 1H), 6.70-6.51 (m, 1H), 6.43-6.33 (m, 1H), 6.29 (s, 1H), 5.38-5.25 (m, 1H), 5.13-5.01 (m, 1H), 4.60-4.48 (m, 1H), 4.23 (s, 1H), 3.94-3.69 (m, 3H), 3.64-3.53 (m, 1H), 3.43-3.38 (m, 1H), 3.26-3.17 (m, 3H), 3.07-2.76 (m, 5H), 2.04-1.92 (m, 5H), 1.76-1.59 (m, 6H), 1.56-1.43 (m, 4H), 1.13-1.03 (m, 5H). MS (ESI, m/e) [M+1]$^+$ 954.9

Example G126: 3-((1H-pyrrolo[2,3-b]pyridin-5-yl)oxy)-4'-((R)-2-(2-(1-(3-(dimethylamino)propanoyl)piperidin-4-yl)phenyl)pyrrolidin-1-yl)-N-((4-((((1r,4r)-4-hydroxy-4-methylcyclohexyl)methyl)amino)-3-nitrophenyl)sulfonyl)-[1,1'-biphenyl]-4-carboxamide

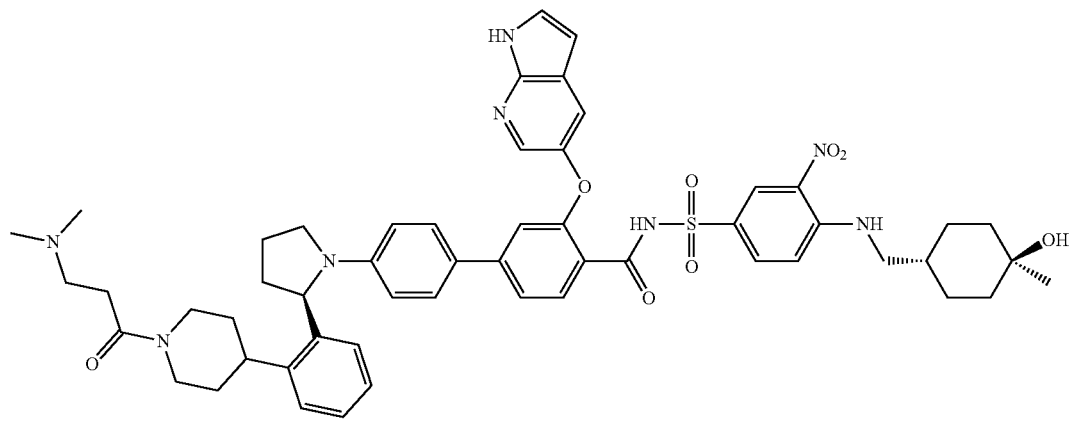

The desired compound was synthesized following the procedures similar to those in Example G124 starting from (R)-1-(4-(2 (1-(4-bromophenyl)pyrrolidin-2-yl)phenyl)piperidin-1-yl)-3-(dimethylamino)propan-1-one. $^1$H NMR (400 MHz, DMSO-$d_6$) δ ppm: 11.56 (s, 1H), 9.17 (s, 1H), 8.52-8.21 (m, 2H), 7.97 (s, 1H), 7.72-7.61 (m, 1H), 7.61-7.48 (m, 1H), 7.47-7.09 (m, 7H), 7.08-6.96 (m, 1H), 6.96-6.74 (m, 3H), 6.45-6.22 (m, 3H), 5.15-4.91 (m, 1H), 4.68-4.49 (m, 1H), 4.23 (s, 1H), 4.02-3.87 (m, 1H), 3.80-3.66 (m, 1H), 3.46-3.36 (m, 1H), 3.29-3.10 (m, 6H), 2.89-2.79 (m, 2H), 2.79-2.72 (m, 6H), 2.71-2.64 (m, 1H), 2.05-1.84 (m, 3H), 1.81-1.40 (m, 10H), 1.40-1.27 (m, 3H), 1.16-1.01 (m, 5H). MS (ESI, m/e) [M+1]$^+$ 982.9.

Example G127: 3-((1H-pyrrolo[2,3-b]pyridin-5-yl)oxy)-4'-((R)-2-(2-(1-(2-amino-2-methylpropanoyl)piperidin-4-yl)phenyl)pyrrolidin-1-yl)-N-((4-((((1r,4r)-4-hydroxy-4-methylcyclohexyl)methyl)amino)-3-nitrophenyl)sulfonyl)-[1,1'-biphenyl]-4-carboxamide

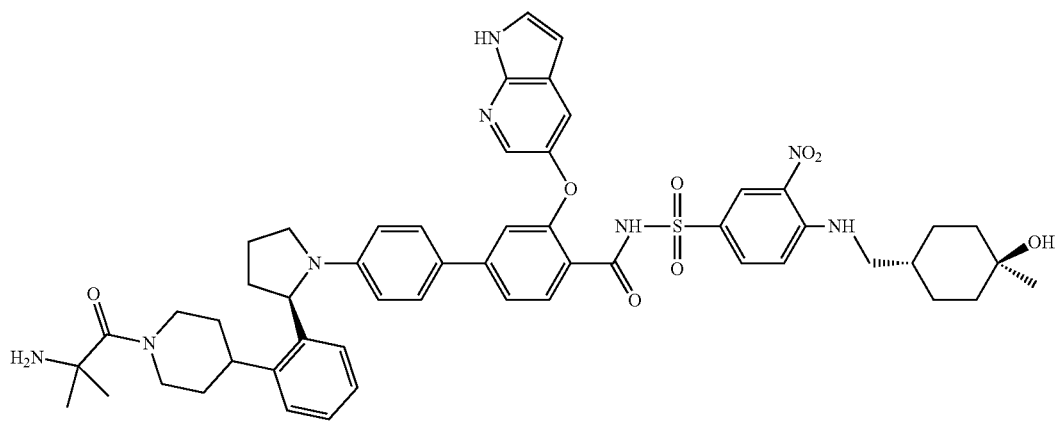 [SMILES: CC(C)(N)C(=O)N1CCC(c2ccccc2[C@H]2CCCN2c2ccc(-c3ccc(C(=O)NS(=O)(=O)c4ccc(NC[C@H]5CC[C@](C)(O)CC5)c([N+](=O)[O-])c4)c(Oc4cnc5[nH]ccc5c4)c3)cc2)CC1]

The desired compound was synthesized following the procedures similar to those in Example G124 starting from tert-butyl (R)-(1-(4-(2-(1-(4-bromophenyl)pyrrolidin-2-yl)phenyl)piperidin-1-yl)-2-methyl-1-oxopropan-2-yl)(tert-butoxycarbonyl)carbamate. $^1$H NMR (400 MHz, DMSO-$d_6$) δ ppm: 11.56 (s, 1H), 8.48-8.26 (m, 2H), 7.97 (s, 1H), 7.80-7.62 (m, 1H), 7.62-7.49 ((m, 1H), 7.48-7.13 (m, 8H), 7.08-6.99 (m, 1H), 6.94-6.83 (m, 2H), 6.42-6.25 (m, 3H), 5.11-5.02 (m, 1H), 4.45-4.32 (m, 1H), 4.23 (s, 1H), 3.77-3.68 (m, 1H), 3.61-3.53 (m, 1H), 3.52-3.49 (m, 1H), 3.43-3.37 (m, 1H), 3.25-3.17 (m, 2H), 2.03-1.89 (m, 10H), 1.70-1.43 (m, 15H), 1.14-1.05 (m, 5H). MS (ESI, m/e) [M+1]$^+$ 968.9.

Example G128: (R)-3-((1H-pyrrolo[2,3-b]pyridin-5-yl)oxy)-N-((4-(((1-acetylpiperidin-4-yl)methyl)amino)-3-nitrophenyl)sulfonyl)-4'-(2-(2-cyclopropylphenyl)pyrrolidin-1-yl)-[1,1'-biphenyl]-4-carboxamide

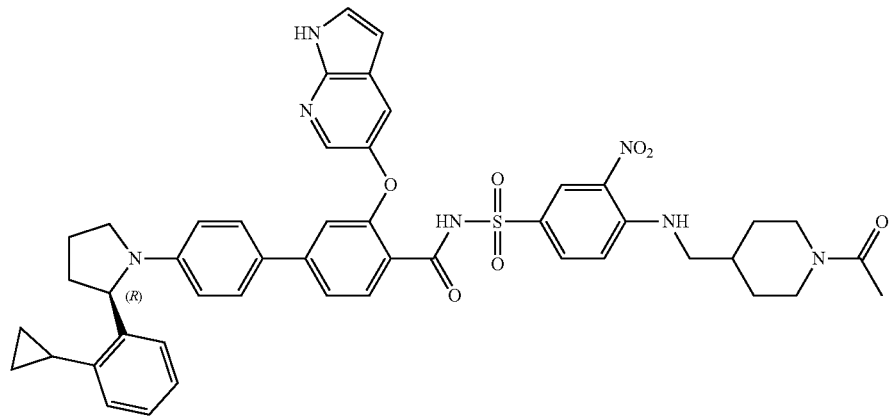

The desired compound was synthesized following the procedures similar to those in Example A1 by replacing 2-phenylpyrrolidine with (R)-2-(2-cyclopropylphenyl)pyrrolidine, and replacing 3-nitro-4-(((tetrahydro-2H-pyran-4-yl)methyl)amino)benzenesulfonamide with 4-(((1-acetylpiperidin-4-yl)methyl)amino)-3-nitrobenzenesulfonamide. $^1$H NMR (400 MHz, DMSO-$d_6$) δ ppm: 12.16 (s, 1H), 11.69 (s, 1H), 8.62 (s, 1H), 8.56 (s, 1H), 8.04 (s, 1H), 7.83 (d, J=8.8 Hz, 1H), 7.58-7.51 (m, 3H), 7.35-7.28 (m, 3H), 7.14-7.04 (m, 4H), 6.90 (s, 1H), 6.85 (d, J=8.8 Hz, 1H), 6.42-6.32 (m, 3H), 5.21 (d, J=8.0 Hz, 1H), 4.38 (d, J=8.8 Hz, 1H), 3.85-3.71 (m, 2H), 3.33-3.31 (m, 2H), 2.92-2.88 (m, 1H), 2.49-2.40 (m, 2H), 2.08-1.65 (m, 11H), 1.12-0.94 (m, 4H), 0.75-0.71 (m, 2H). MS (ESI, m/e) [M+1]$^+$ 853.8.

Example G129: (R)-3-((1H-pyrrolo[2,3-b]pyridin-5-yl)oxy)-4'-(2-(2-cyclopropylphenyl)pyrrolidin-1-yl)-N-((4-(((1-(methylsulfonyl)piperidin-4-yl)methyl)amino)-3-nitrophenyl)sulfonyl)[1,1'-biphenyl]-4-carboxamide

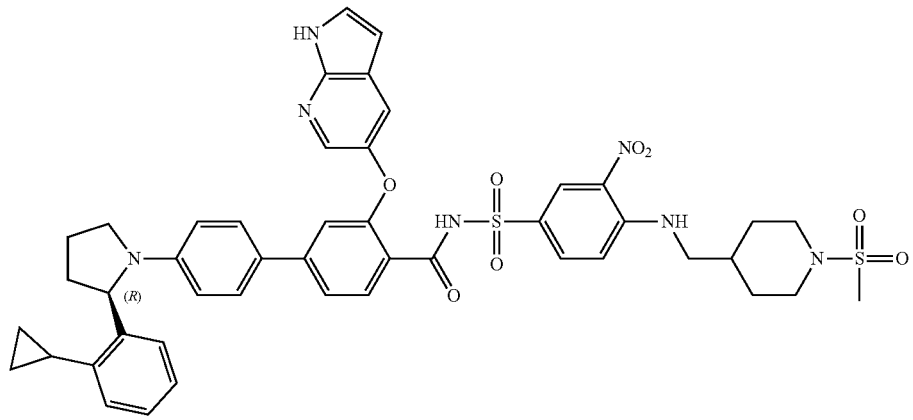

The desired compound was synthesized following the procedures similar to those in Example A1 by replacing 2-phenylpyrrolidine with (R)-2-(2-cyclopropylphenyl)pyrrolidine, and replacing 3-nitro-4-(((tetrahydro-2H-pyran-4-yl)methyl)amino)benzenesulfonamide with 4-(((1-(methylsulfonyl)piperidin-4-yl)methyl)amino)-3-nitrobenzenesulfonamide. ¹H NMR (400 MHz, DMSO-$d_6$) δ ppm: 12.16 (s, 1H), 11.69 (s, 1H), 8.63 (s, 1H), 8.56 (s, 1H), 8.04 (s, 1H), 7.83 (d, J=8.8 Hz, 1H), 7.58-7.51 (m, 3H), 7.34-7.28 (m, 3H), 7.14-7.04 (m, 4H), 6.90 (s, 1H), 6.85 (d, J=8.8 Hz, 1H), 6.42-6.32 (m, 3H), 5.21 (d, J=8.0 Hz, 1H), 3.75-3.45 (m, 4H), 3.03-3.01 (m, 1H), 2.83 (s, 1H), 2.68-2.62 (m, 2H), 2.49-2.40 (m, 1H), 2.08-1.65 (m, 10H), 1.32-1.26 (m, 2H), 1.05-0.91 (m, 2H), 0.79-0.66 (m, 2H). MS (ESI, m/e) [M+1]⁺ 889.8.

Example G130: (R)-3-((1H-pyrrolo[2,3-b]pyridin-5-yl)oxy)-4'-(2-(2-cyclopropylphenyl)pyrrolidin-1-yl)-N-((4-((2-morpholinoethyl)amino)-3-nitrophenyl)sulfonyl)-[1,1'-biphenyl]-4-carboxamide

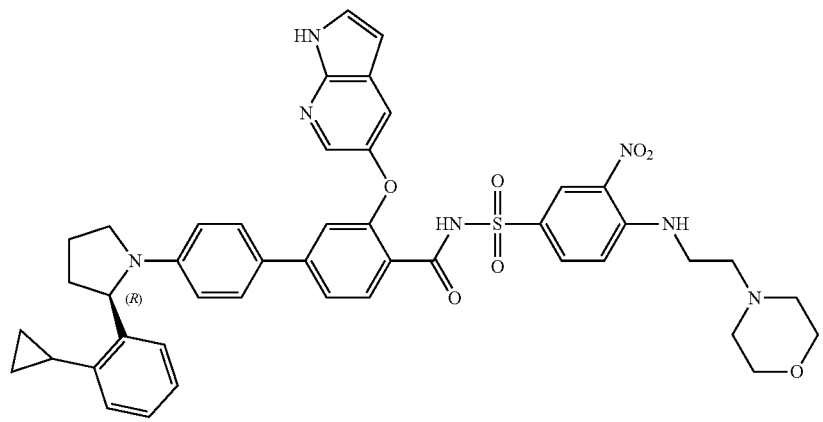

The desired compound was synthesized following the procedures similar to those in Example A1 by replacing 2-phenylpyrrolidine with (R)-2-(2-cyclopropylphenyl)pyrrolidine, and replacing 3-nitro-4-(((tetrahydro-2H-pyran-4-yl)methyl)amino)benzenesulfonamide with 4-((2-morpholinoethyl)amino)-3-nitrobenzenesulfonamide. ¹H NMR (400 MHz, DMSO-$d_6$) δ ppm: 12.01 (br, 1H), 11.70 (s, 1H), 8.80-8.65 (m, 1H), 8.60-8.45 (m, 1H), 8.10-7.95 (m, 1H), 7.82 (d, J=8.0 Hz, 1H), 7.60-7.40 (m, 3H), 7.40-7.20 (m, 3H), 7.15-6.95 (m, 4H), 6.94-6.80 (m, 2H), 6.45-6.25 (m, 3H), 5.25-5.10 (m, 1H), 3.80-3.60 (m, 4H), 3.50-3.30 (m, 4H), 2.80-2.60 (m, 6H), 2.16-1.76 (m, 5H), 1.10-0.90 (m, 2H), 0.80-0.65 (m, 2H). MS (ESI, m/e) [M+1]⁺ 827.8.

Example G131: (R)-3-((1H-pyrrolo[2,3-b]pyridin-5-yl)oxy)-4'-(2-(2-cyclopropylphenyl)pyrrolidin-1-yl)-N-((3-nitro-4-((2-(tetrahydro-2H-pyran-4-yl)-2-azaspiro[3.3]heptan-6-yl)amino)phenyl)sulfonyl)-[1,1'-biphenyl]-4-carboxamide

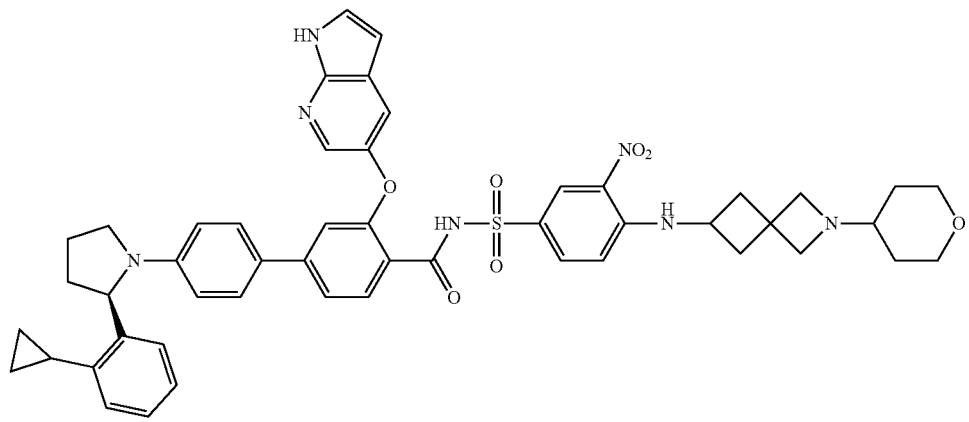 [SMILES: O=C(NS(=O)(=O)c1ccc(NC2CC3(C2)CN(C2CCOCC2)C3)c([N+](=O)[O-])c1)c1ccc(-c2ccc(N3CCC[C@@H]3c3ccccc3C3CC3)cc2)cc1Oc1cnc2[nH]ccc2c1]

The desired compound was synthesized following the procedures similar to those in Example A1 by replacing 2-phenylpyrrolidine with (R)-2-(2-cyclopropylphenyl)pyrrolidine, and replacing 3-nitro-4-(((tetrahydro-2H-pyran-4-yl)methyl)amino)benzenesulfonamide with 3-nitro-4-((2-(tetrahydro-2H-pyran-4-yl)-2-azaspiro[3.3]heptan-6-yl)amino)benzenesulfonamide. $^1$H NMR. (400 MHz, DMSO-$d_6$) δ ppm: 11.54 (s, 1H), 8.38 (s, 1H), 8.08 (s, 1H), 7.94 (s, 1H), 7.66 (s, 1H), 7.55 (d, J=8.0 Hz, 1H), 7.42 (s, 1H), 7.36-7.28 (m, 3H), 7.26-7.24 (m, 1H), 7.11-7.08 (m, 1H), 7.04-6.97 (m, 2H), 6.93-6.84 (m, 2H), 6.63-6.61 (m, 1H), 6.36 (d, 8.6 Hz, 2H), 6.30 (s, 1H), 5.32 (s, 1H), 5.21-5.20 (m, 1H), 4.02-3.69 (m, 5H), 3.28-3.19 (m, 3H), 3.00 (s, 5H), 2.12-1.80 (m, 9H), 1.45 (s, 1H), 1.08-0.93 (m, 3H), 0.84-0.81 (m, 4H), 0.70 (s, 1H). MS (ESI) m/e [M+1]$^+$ 893.9.

Example G132a and Example G132 h: (R)-3-((1H-pyrrolo[2,3-b]pyridin-5-yl)oxy)-4'-(2-(2-cyclopropylphenyl)pyrrolidin-1-yl)-N-((4-(((4-(cis or trans)-((dimethyl(oxo)-16-sulfaneylidene)amino)cyclohexyl)methyl)amino)-3-nitrophenyl)sulfonyl)-[1,1'-biphenyl]-4-carboxamide; (R)-3-((1H-pyrrolo[2,3-b]pyridin-5-yl)oxy)-4'-(2-(2-cyclopropylphenyl)pyrrolidin-1-yl)-N-((4-(((4-(trans or cis)-((dimethyl(oxo)-16-sulfaneylidene)amino)cyclohexyl)methyl)amino)-3-nitrophenyl)sulfonyl)-[1,1'-biphenyl]-4-carboxamide

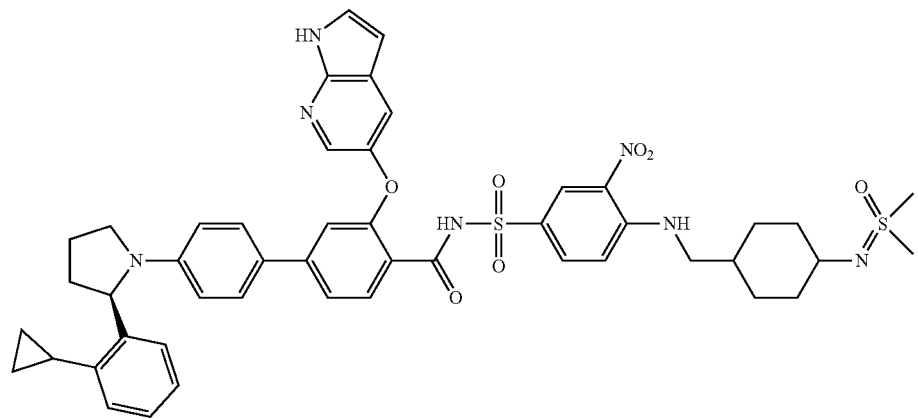

cis- or trans- faster isomer

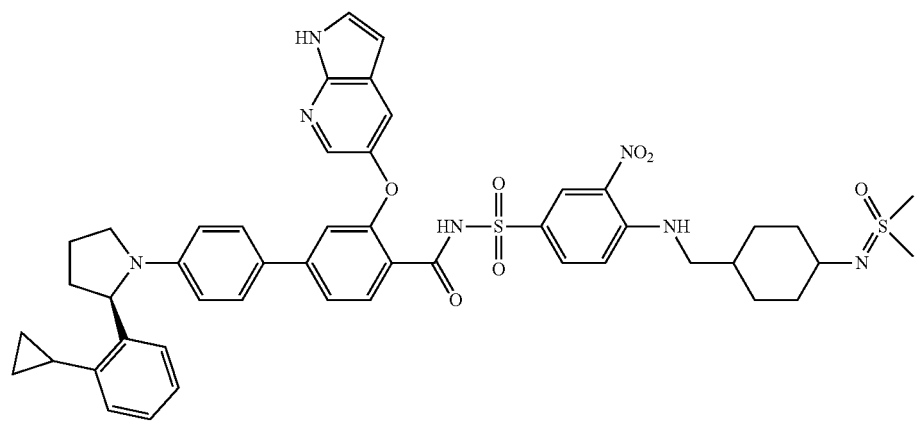

trans- or cis- slower isomer

The desired compounds were synthesized following the procedures similar to those in Example A1 by replacing 2-phenylpyrrolidine with (R)-2-(2-cyclopropylphenyl)pyrrolidine, and replacing 3-nitro-4-((((tetrahydro-2H-pyran-4-yl)methyl)amino)benzenesulfonamide with 3 4-(((4-((dimethyl(oxo)-16-sulfaneylidene)amino)cyclohexyl)methyl)amino)-3-nitrobenzenesulfonamide. G132a was obtained as faster peak by separation and purification of crude product with prep-HPLC/H NMR (400 MHz, DMSO-$d_6$) δ ppm: 12.10 (s, 1H), 11.70 (s, 1H), 8.64-8.47 (m, 2H), 8.04 (d, J=2.2 Hz, 1H), 7.81 (d, J=8.5 Hz, 1H), 7.62-7.45 (m, 3H), 7.38-7.25 (m, 3H), 7.14-6.98 (m, 4H), 6.97-6.80 (m, 2H), 6.47-6.24 (m, 3H), 5.24-5.16 (m, 1H), 3.77-3.65 (m, 1H), 3.52-3.37 (m, 3H), 3.28-3.20 (m, 2H), 3.00 (s, 6H), 2.04-1.83 (m, 4H), 1.74-1.63 (m, 1H), 1.56-1.44 (m, 6H), 1.04-0.92 (m, 2H), 0.88-0.63 (m, 4H). MS (ESI, m/e) $[M+1]^+$ 901.8. G132b was obtained as slower peak by separation and purification of crude product with prep-HPLC. MS (ESI, m/e) $[M+1]^+$ 901.8.

Example G133: (R or S)-3-((1H-pyrrolo[2,3-b]pyridin-5-yl)oxy)-4'-(2-(2-cyclopropylphenyl)-4,4-difluoropyrrolidin-1-yl)-N-((4-(((((1r,4r)-4-hydroxy-4-methylcyclohexyl)methyl)amino)-3-nitrophenyl)sulfonyl)-[1,1'-biphenyl]-4-carboxamide

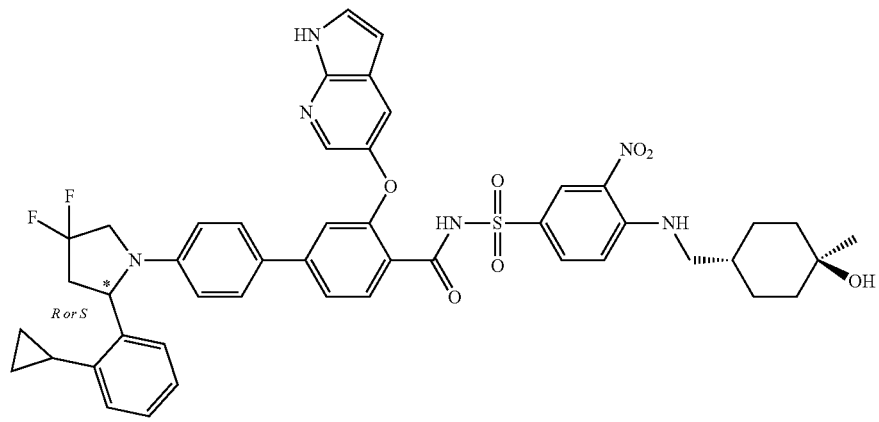

The desired compounds were synthesized following the procedures similar to those in Example A147b by replacing 3-nitro-4-((((tetrahydro-2H-pyran-4-yl)methyl)amino)benzenesulfonamide with 4-((((1r,4r)-4-hydroxy-4-methylcyclohexyl)methyl)amino)-3-nitrobenzenesulfonamide. ¹H NMR (400 MHz, DMSO-d₆) δ ppm: 12.20 (s, 1H), 11.69 (s, 1H), 8.55 (s, 2H), 8.04 (d, J=2.4 Hz, 1H), 7.81 (d, J=9.1 Hz, 1H), 7.58-7.49 (m, 3H), 7.39-7.29 (m, 3H), 7.16-6.99 (m, 5H), 6.92 (s, 1H), 6.47-6.32 (m, 3H), 5.47 (t, J=7.4 Hz, 1H), 4.29-4.14 (m, 2H), 3.98-3.87 (m, 1H), 3.4 (t, J=6.0 Hz, 2H), 2.40-2.30 (m, 1H), 2.03-1.98 (m, 1H), 1.69 (s, 1H), 1.66 (s, 1H), 1.55 (s, 1H), 1.52 (s, 1H), 1.33 (t, J=10.9 Hz, 2H), 1.23 (s, 2H), 1.15-1.12 (m, 1H), 1.09 (s, 3H), 1.00-0.94 (m, 2H), 0.79-0.75 (m, 1H), 0.72-0.70 (m, 1H). MS (ESI, m/e) [M+1]⁺ 876.8.

Example G134: 3-((1H-pyrrolo[2,3-b]pyridin-5-yl)oxy)-4'-(2-(2-cyclopropylphenyl)-4-(trifluoromethyl)pyrrolidin-1-yl)-N-((4-((((1r,4r)-4-hydroxy-4-methylcyclohexyl)methyl)amino)-3-nitrophenyl)sulfonyl)-[1,1'-biphenyl]-4-carboxamide

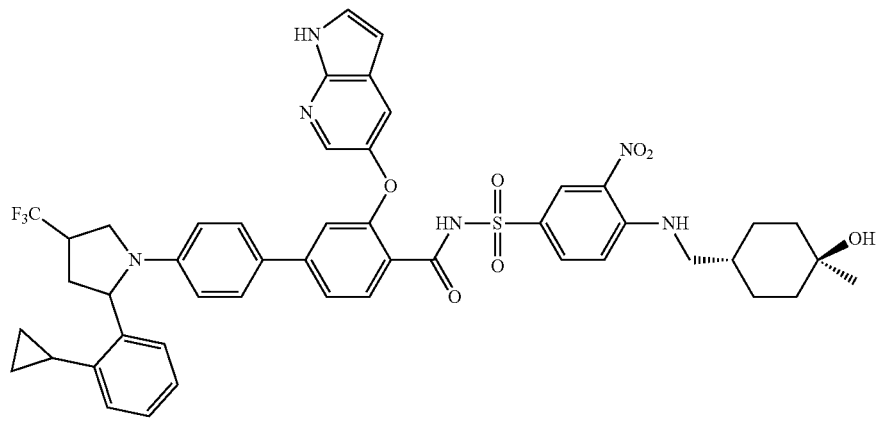 [SMILES: C[C@]1(O)CC[C@H](CNc2ccc(S(=O)(=O)NC(=O)c3ccc(-c4ccc(N5CC(C(F)(F)F)CC5c5ccccc5C5CC5)cc4)cc3Oc3cnc4[nH]ccc4c3)cc2[N+](=O)[O-])CC1]

The desired compounds were synthesized following the procedures similar to those in Example A1 by replacing 2-phenylpyrrolidine with 2-(2-cyclopropylphenyl)-4-(trifluoromethyl)pyrrolidine, and replacing 3-nitro-4-((((tetrahydro-2H-pyran-4-yl)methyl)amino)benzenesulfonamide with 4-((((1r,4r)-4-hydroxy-4-methylcyclohexyl)methyl)amino)-3-nitrobenzenesulfonamide. ¹H NMR (400 MHz, DMSO-d₆) δ ppm: ¹H NMR (400 MHz, DMSO-d₆) δ ppm: 12.18 (s, 1H), 11.70 (s, 1H), 8.65-8.45 (m, 2H), 8.09-7.99 (m, 1H), 7.82 (d, J=9.0 Hz, 1H), 7.67-7.42 (m, 3H), 7.41-7.18 (m, 3H), 7.18-6.81 (m, 6H), 6.52-6.20 (m, 3H), 5.30 (t, J=7.4 Hz, 1H), 4.24 (s, 1H), 3.93-3.73 (m, 2H), 3.60-3.43 (m, 1H), 3.30-3.18 (m, 2H), 3.042-2.90 (m, 1H), 2.16-2.02 (m, 1H), 1.89-1.74 (m, 1H), 1.74-1.42 (m, 5H), 1.40-1.27 (m, 2H), 1.20-1.02 (m, 5H), 1.02-0.89 (m, 2H), 0.80-0.65 (m, 2H). MS (ESI, m/e) [M+1]⁺ 908.7.

Example G134: 4'-((R)-2-(2-cyclopropylphenyl)pyrrolidin-1-yl)-3-((6-fluoro-1H-indol-4-yl)oxy)-N-((4-((((1r,4r)-4-hydroxy-4-methylcyclohexyl)methyl)amino)-3-nitrophenyl)sulfonyl)-[1,1'-biphenyl]-4-carboxamide

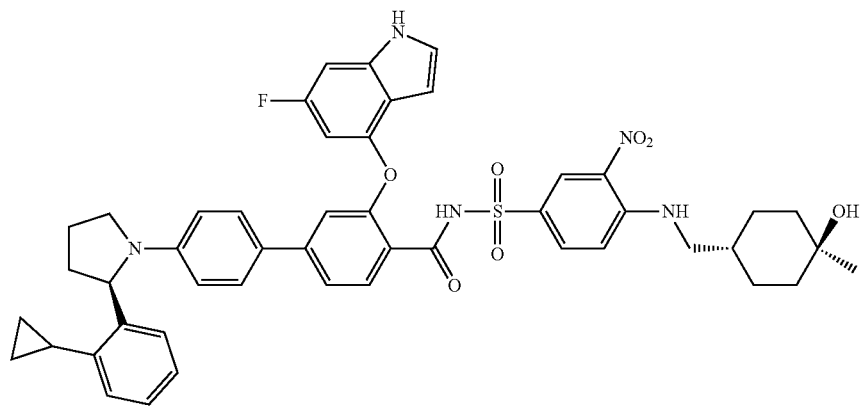 [SMILES: C[C@]1(O)CC[C@H](CNc2ccc(S(=O)(=O)NC(=O)c3ccc(-c4ccc(N5CCC[C@@H]5c5ccccc5C5CC5)cc4)cc3Oc3cc(F)cc4[nH]ccc34)cc2[N+](=O)[O-])CC1]

$^{1}$H NMR (DMSO-d$_6$) δ ppm: 12.21 (s, 1H), 11.26 (s, 1H), 8.56 (s, 1H), 8.44 (s, 1H), 7.68-7.63 (m, 1H), 7.59-7.54 (m, 1H), 7.46-7.43 (m, 1H), 7.38-7.35 (m, 2H), 7.23 (s, 1H), 7.13-7.06 (m, 2H), 7.02-6.95 (m, 3H), 6.88-6.82 (m, 2H), 6.40-6.35 (m, 2H), 6.24-6.13 (m, 2H), 5.26-5.20 (m, 1H), 3.27 (s, 3H), 2.54 (s, 1H), 2.07-1.97 (m, 3H), 1.92-1.80 (m, 1H), 1.72-1.62 (m, 3H), 1.58-1.3 (m, 2H), 1.38-1.30 (m, 3H), 1.10 (s, 4H), 1.03-0.95 (m, 2H), 0.92-0.78 (m, 2H), 0.73-0.65 (m, 1H). MS (ESI) m/e [M+1]$^+$ 857.8.

Example H3: 4'-(2-(2-cyclopropylphenyl)pyrrolidin-1-yl)-N-((3-nitro-4-(((tetrahydro-2H-pyran-4-yl)methyl)amino)phenyl)sulfonyl)-3-(pyrazolo[4,3-b]pyrrolo[3,2-e]pyridin-1(5H)-yl)-2',3',4',5'-tetrahydro-[1,1'-biphenyl]-4-carboxamide

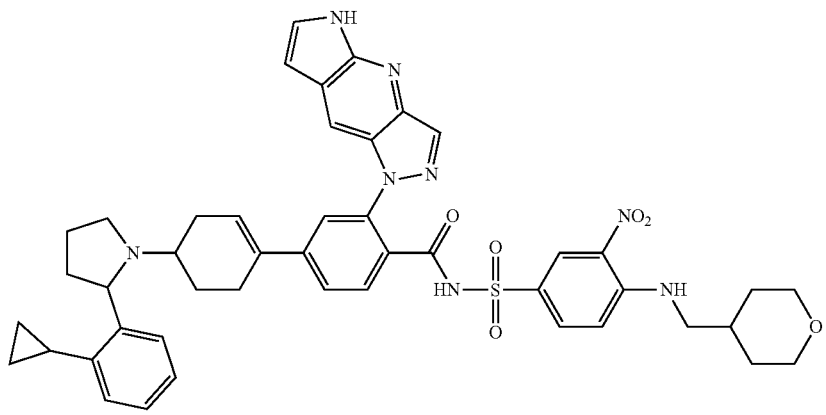 [SMILES: O=C(NS(=O)(=O)c1ccc(NCC2CCOCC2)c([N+](=O)[O-])c1)c1ccc(C2=CCC(N3CCCC3c3ccccc3C3CC3)CC2)cc1-n1ncc2nc3[nH]ccc3cc21]

Step 1: 5-((2-(trimethylsilyl)ethoxy)methyl)-1,5-dihydropyrazolo[4,3-b]pyrrolo[3,2-e]pyridine To the solution of 6-methyl-1-((2-(trimethylsilyl)methyl)-1H-pyrrolo[2,3-b]pyridin-5-amine (1.39 g) and Ac$_2$O (1.94 g) in toluene (15 mL) was added AcOK (1.96 g), and the mixture was stirred at 25° C. for 3 hours under N$_2$ atmosphere. Then isoamyl nitrate (1.46 g) was added and the reaction mixture was stirred at 60° C. for 14 hr. After cooled to room temperature, the mixture was quenched by aq. NaHCO$_3$ (200 mL) and then extracted with DCM (100 mL×3). The combined organic layer was washed with brine (100 mL), dried over anhydrous Na$_2$SO$_4$ and concentrated in vacuum. The resulted residue (2 g) was dissolved in MeOH (25 mL) and K$_2$CO$_3$ (5.5 g) was added. After stirred at 25° C. for 2 hours under N$_2$ atmosphere, the reaction mixture was poured into water (200 mL), and then extracted with DCM (100 ml×3), The combined organic layer was washed with brine (100 mL), dried over anhydrous Na$_2$SO$_4$ and concentrated in vacuum. The crude product was purified by column chromatography on silica gel (eluent: Petroleum ether/Ethyl acetate=100/1 to 5/1) to obtain 5-((2-(trimethylsilyl)ethoxy)methyl)-1,5-dihydropyrazolo[4,3-b]pyrrolo[3,2-e]pyridine (500 mg) as a yellow solid. MS (ESI, m/e) [M+1]$^+$ 288.9.

Step 2: methyl 4-bromo-2-(5-((2-(trimethylsilyl)ethoxy)methyl)pyrazolo[4,3-b]pyrrolo[3,2-e]pyridin-1(5H)-yl)benzoate To the solution of 5-((2-(trimethylsilyl)ethoxy)methyl)-1,5-dihydropyrazolo[4,3-b]pyrrolo[3,2-e]pyridine (600 mg) and methyl 4-bromo-2-fluorobenzoate (700 mg) in DMF (50 mL) was added Cs$_2$CO$_3$ (1.9 g). The mixture was heated to 120° C. and stirred for 6 hours. After cooled to room temperature, the reaction mixture was poured into water and extracted with EA. The organic layers were dried over anhydrous Na$_2$SO$_4$, concentrated and purified by column chromatography on silica gel to obtain methyl 4-bromo-2-(5-((2-(trimethylsilyl)ethoxy)methyl)pyrazolo[4,3-b]pyrrolo[3,2-e]pyridin-1(5H)-yl)benzoate (300 mg). MS (ESI, m/e) [M+1]$^+$ 500.7.

Step 3: methyl 4-(1,4-dioxaspiro[4.5]dec-7-en-8-yl)-2-(5-((2-(trimethylsilyl)ethoxy)methyl)pyrazolo[4,3-b]pyrrolo[3,2-e]pyridin-1(5H)-yl)benzoate Under nitrogen atmosphere, a mixture of methyl 4-bromo-2-(5-((2-(trimethylsilyl)ethoxy)methyl)pyrazolo[4,3-b]pyrrolo[3,2-e]pyridin-1(5H)-yl)benzoate (200 mg), 4,4,5,5-tetramethyl-2-(1,4-dioxaspiro[4.5]dec-7-en-8-yl)-1,3,2-dioxaborolane (160 mg), Pd(dppf)Cl$_2$ (30 mg), and K$_2$CO$_3$ (166 mg) in 1,4-dioxane (50 mL) and H$_2$O (10 mL) was heated to 90° C. and stirred overnight. After cooled to room temperature, the reaction mixture was washed with water, brine and dried over anhydrous Na$_2$SO$_4$. The organic layers were concentrated and purified by column chromatography on silica gel with 10%~50% EA/PE to obtain methyl 4-(1,4-dioxaspiro[4.5]dec-7-en-8-yl)-2-(5-((2-(trimethylsilyl)ethoxy)methyl)pyrazolo[4,3-b]pyrrolo[3,2-e]pyridin-1(5H)-yl)benzoate (300 mg) as a white foam.

Step 4: methyl 4'-oxo-3-(5-((2-(trimethylsilyl)ethoxy)methyl)pyrazolo[4,3-b]pyrrolo[3,2-e]pyridin-1(5H)-yl)-2',3',4',5'-tetrahydro-[1,1'-biphenyl]-4-carboxylate To a solution of methyl 4-(1,4-dioxaspiro[4.5]dec-7-en-8-yl)-2-(5-((2-(trimethylsilyl)ethoxy)methyl)pyrazolo[4,3-b]pyrrolo[3,2e]pyridin-1(5H)-yl)benzoate (300 mg) in THF was added 2 N HCl acid (1 mL) and the mixture was stirred for 3 hours at room temperature. Then the reaction mixture was adjusted to PH ~8 with saturated aq. $NaHCO_3$ solution. After extraction with EA, the organic layers were dried over anhydrous $Na_2SO_4$, concentrated and purified by chromatography on silica gel to give (200 mg) as a white solid.

Step 5: methyl 4'-(2-(2-cyclopropylphenyl)pyrrolidin-1-yl)-3-(5-((2-(trimethylsilyl)ethoxy)methyl)pyrazolo[4,3-b]pyrrolo[3,2-e]pyridin-1(5H)-yl)-2',3',4',5'-tetrahydro-[1,1'-biphenyl]-4-carboxylate To the solution of 2-(2-cyclopropylphenyl)pyrrolidine (50.8 mg, 0.29 mmol), 4'-oxo-3-(5-((2-(trimethylsilyl)ethoxy)methyl)pyrazolo[4,3-b]pyrrolo[3,2-e]pyridin-1(5H)-yl)-2',3',4',5'-tetrahydro-[1,1'-biphenyl]-4-carboxylate (150 mg) in DCM (25 mL) was HOAc (1 drop) and $NaBH(OAc)_3$ added. After stirred overnight at room temperature, the reaction mixture was washed with saturated aq. $NaHCO_3$ solution. The organic layers were dried over anhydrous $Na_2SO_4$, concentrated and purified by chromatography on silica gel to give as a white solid. MS (ESI, m/e) $[M+1]^+$ 687.9.

Step 6: 4'-(2-(2-cyclopropylphenyl)pyrrolidin-1-yl)-3-(5-((2-(trimethylsilyl)ethoxy)methyl)pyrazolo[4,3-b]pyrrolo[3,2e]pyridin-1(5H)-yl)-2',3',4',5'-tetrahydro-[1,1'-biphenyl]-4-carboxylic acid To a solution of methyl 4'-(2-(2-cyclopropylphenyl)pyrrolidin-1-yl)-3-(5-((2-(trimethylsilyl)ethoxy)methyl)pyrazolo[4,3-b]pyrrolo[3,2-e]pyridin-1(5H)-yl)-2',3',4',5'-tetrahydro-[1,1'-biphenyl]-4-carboxylate (150 mg) in MeOH/THF (15 mL/5 mL) was added NaOH (3N, 1 mL). After stirred for 4 hours at room temperature, the reaction mixture was acidified by 1N HCl acid to PH ~5 and was then extracted with DCM. The organic layers were dried over anhydrous $Na_2SO_4$ and concentrated. The crude 4'-(2-(2-cyclopropylphenyl)pyrrolidin-1-yl)-3-(5-((2-(trimethylsilyl)ethoxy)methyl)pyrazolo[4,3-b]pyrrolo[3,2-e]pyridin-1(5H)-yl)-2',3',4',5'-tetrahydro-[1,1'-biphenyl]-4-carboxylic acid was used in next step directly without further purification. MS (ESI, m/e) $[M+1]^+$ 673.9.

Step 7: 4'-(2-(2-cyclopropylphenyl)pyrrolidin-1-yl)-N-((3-nitro-4-(((tetrahydro-2H-pyran-4-yl)methyl)amino)phenyl)sulfonyl)-3-(5-((2-(trimethylsilyl)ethoxy)methyl)pyrazolo[4,3-b]pyrrolo[3,2-e]pyridin-1(5H)-yl)-2',3',4',5'-tetrahydro-[1,1'-biphenyl]-4-carboxamide To a solution of 4'-(2-(2-cyclopropylphenyl)pyrrolidin-1-yl)-3-(5-((2-(trimethylsilyl)ethoxy)methyl)pyrazolo[4,3-b]pyrrolo[3,2-e]pyridin-1(5H)-yl)-2',3',4',5'-tetrahydro-[1,1'-biphenyl]-4-carboxylic acid (100 mg, 0.15 mmol) in dichloromethane (25 mL) was added O-(7-Azabenzotriazol-1-yl)-N,N,N',N'-tetraMethyluroniuMhexafluorophosphate (86 mg, 0.225 mmol) and trimethylamine (0.5 mL). The mixture was stirred for 0.5 hour at room temperature, then 3-nitro-4-(((tetrahydro-2H-pyran-4-yl)methyl)amino)benzenesulfonamide (95 mg, 0.3 mmol) was added. After stirred overnight at room temperature, the mixture was washed with water (10 mL) and the organic layers were dried over anhydrous $Na_2SO_4$ and concentrated in vacuum. The residue was further purified by prep-HPLC to obtain 4'-(2-(2-cyclopropylphenyl)pyrrolidin-1-yl)-N-((3-nitro-4-(((tetrahydro-2H-pyran-4-yl)methyl)amino)phenyl)sulfonyl)-3-(5-((2-(trimethylsilyl)ethoxy)methyl)pyrazolo[4,3-b]pyrrolo[3,2-e]pyridin-1(5H)-yl)-2',3',4',5'-tetrahydro-[1,1'-biphenyl]-4-carboxamide (50 mg), MS (ESI, m/e) $[M+1]^+$ 970.8.

Step 8: 4'-(2-(2-cyclopropylphenyl)pyrrolidin-1-yl)-N-((3-nitro-4-(((tetrahydro-2H-pyran-4-yl)methyl)amino)phenyl)sulfonyl)-3-(pyrazolo[4,3-b]pyrrolo[3,2-e]pyridin-1(5H)-yl)-2',3',4',5'-tetrahydro-[1,1'-biphenyl]-4-carboxamide To a solution of 4'-(2-(2-cyclopropylphenyl)pyrrolidin-1-yl)-N-((3-nitro-4-(((tetrahydro-2H-pyran-4-yl)methyl)amino)phenyl)sulfonyl)-3-(5-((2-(trimethylsilyl)ethoxy)methyl)pyrazolo[4,3-b]pyrrolo[3,2-e]pyridin-1(5H)-yl)-2',3',4',5'-tetrahydro-[1,1'-biphenyl]-4-carboxamide (40 mg) in DCM (10 mL) was added TFA (0.5 mL), the mixture was stirred overnight at room temperature. After removal of solvent, the residue was diluted with 20 mL DCM and was then basified by saturated aq. $NaHCO_3$ solution. The isolated organic layers were concentrated and purified by chromatography on silica gel to obtain the desired compound. $^1H$ NMR (400 MHz, DMSO-$d_6$) δ ppm: 12.43 (s, 0.5H), 11.39 (s, 1H), 10.70 (s, 0.5H), 8.30-8.20 (m, 2H), 8.07 (s, 2H), 7.69-7.39 (m, 5H), 7.35-7.15 (m, 2H), 7.13-7.07 (m, 2H), 6.30-6.15 (m, 2H), 6.13 (s, 1H), 5.33 (d, J=4.7 Hz, 1H), 3.86 (t, J=14.2 Hz, 3H), 3.20-3.15 (m, 3H), 2.15-1.97 (m, 8H), 1.83 (s, 8H), 1.70-1.61 (m, 5H), 1.48-1.35 (m, 2H). MS (ESI, m/e) $[M+1]^+$ 840.8; and Example H3a: 4'-(2-(2-cyclopropylphenyl)pyrrolidin-1-yl)-3-(5-(hydroxymethyl)pyrazolo[4,3-b]pyrrolo[3,2-e]pyridin-1(5H)-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide, MS(ESI, m/e) $[M+1]^+$ 870.8.

Example I7: 3-((1H-pyrrolo[2,3-b]pyridin-5-yl)oxy)-4'-(2-(2-cyclopropylphenyl)pyrrolidin-1-yl)-N-((4-((4-morpholino-1-(phenylthio)butan-2-yl)amino)-3-nitrophenyl)sulfonyl)-2',3',4',5'-tetrahydro-[1,1'-biphenyl]-d-carboxamide

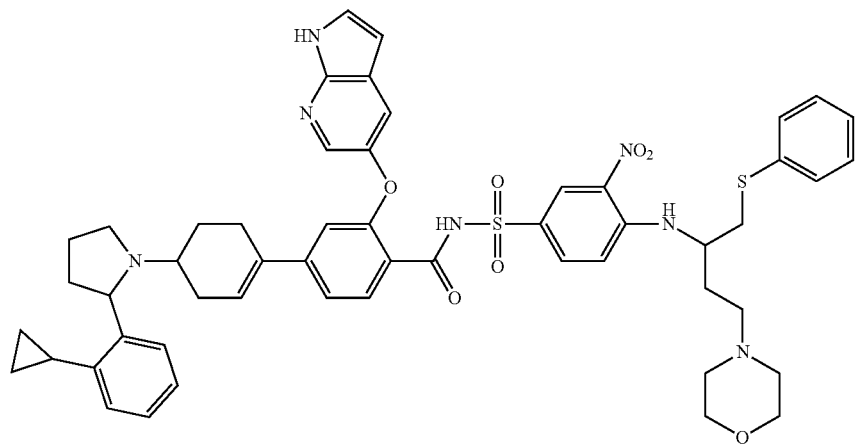 [SMILES: O=C(NS(=O)(=O)c1ccc(NC(CCN2CCOCC2)CSc2ccccc2)c([N+](=O)[O-])c1)c1ccc(C2=CCC(N3CCCC3c3ccccc3C3CC3)CC2)cc1Oc1cnc2[nH]ccc2c1]

The desired compound was synthesized with 4-((4-morpholino-1-(phenylthio)butan-2-yl)amino)-3-nitrobenzenesulfonamide and 3-((1H-pyrrolo[2,3-b]pyridin-5-yl)oxy)-4'-(2-(2-cyclopropylphenyl)pyrrolidin-1-yl)-2',3',4',5'-tetrahydro-[1,1'-biphenyl]-4-carboxylic acid following the procedures similar to those in Example G8. $^1$H NMR (400 MHz, DMSO-d$_6$) δ ppm: 11.66 (s, 1H), 8.42 (s, 1H), 8.33 (s, 1H), 7.98 (s, 1H), 7.81-7.68 (m, 2H), 7.48 (s, 3H), 7.32-6.85 (m, 10H), 6.71 (s, 1H), 6.36 (s, 1H), 5.97-5.82 (m, 1H), 4.10 (s, 1H), 3.55 (s, 4H), 3.18 (s, 1H), 3.00 (s, 1H), 2.33 (s, 3H), 2.20 (s, 3H), 2.11-1.96 (m, 4H), 1.89 (s, 1H), 1.72 (s, 1H), 1.23 (s, 5H), 0.97-0.82 (m, 3H), 0.64 (d, J=44.8 Hz, 2H). MS (ESI, m/e) [M-1]$^+$ 968.7.

Example I8: 4'-(2-(2-cyclopropylphenyl)pyrrolidin-1-yl)-N-((4-((4-morpholino-1-(phenylthio)butan-2-yl)amino)-3-nitrophenyl)sulfonyl)-2',3',4',5'-tetrahydro-[1,1'-biphenyl]-4-carboxamide The desired compound was synthesized with 4-((4-morpholino-1-(phenylthio)butan-2-yl)amino)-3-nitrobenzenesulfonamide and 4'-(2-(2-cyclopropylphenyl)pyrrolidin-1-yl) 2',3',4',5'-tetrahydro-[1,1'-biphenyl]-4-carboxylic acid following the procedures similar to those in Example G8. $^1$H NMR (400 MHz, DMSO-$d_6$) δ ppm: 9.68-9.49 (m, 1H), 8.09 (s, 1H), 7.94 (s, 1H), 7.81-7.73 (m, 3H), 7.38-7.25 (m, 8H), 7.21-7.11 (m, 2H), 6.90 (s, 2H), 6.72 (s, 1H), 6.12-6.03 (m, 1H), 4.02 (s, 1H), 3.76-3.73 (m, 1H), 3.51 (s, 4H), 2.99 (s, 4H), 2.56 (s, 2H), 2.33-2.17 (s, 2H), 2.17-2.10 (m, 5H), 2.03-1.96 (m, 3H), 1.67-1.45 (m, 2H), 1.45 (s, 1H), 1.24 (s, 5H), 1.00 (s, 2H), 0.78 (s, 1H), 0.65 (s, 1H). MS (ESI, m/e) [M+1]$^+$ 922.7.

Example I9: 3-((1H-pyrrolo[2,3-b]pyridin-5-yl)oxy)-4'-(2-(2-cyclopropylphenyl)pyrrolidin-1-yl)-N-((4-((4-morpholino-1-(phenylthio)butan-2-yl)amino)-3-((trifluoromethyl)sulfonyl)phenyl)sulfonyl)-2',3',4',5'-tetrahydro-[1,1'-biphenyl]-4-carboxamide

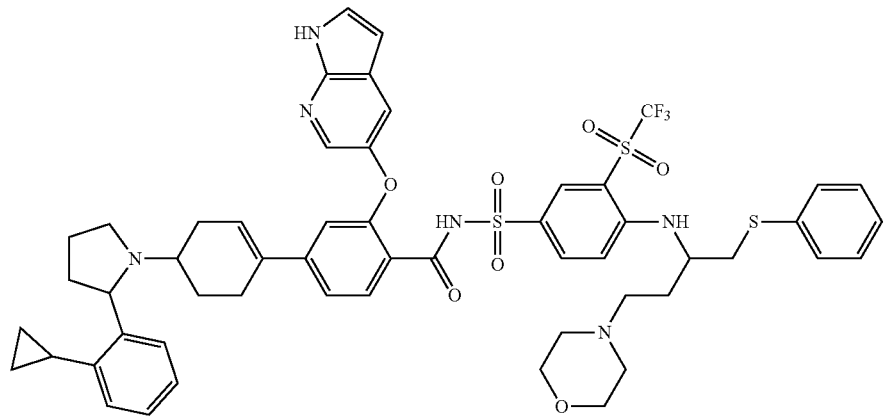 [SMILES: O=C(NS(=O)(=O)c1ccc(NC(CCN2CCOCC2)CSc2ccccc2)c(S(=O)(=O)C(F)(F)F)c1)c1ccc(C2=CCC(N3CCCC3c3ccccc3C3CC3)CC2)cc1Oc1cnc2[nH]ccc2c1]

The desired compound was synthesized with 4-((4-morpholino-1-(phenylthio)butan-2-yl)amino)-3-((trifluoromethyl)sulfonyl)benzenesulfonamide and 3-((1H-pyrrolo[2,3-b]pyridin-5-yl)oxy)-4'-(2(2-cyclopropylphenyl)pyrrolidin-1-yl)-2',3',4',5'-tetrahydro-[1,1'-biphenyl]-4-carboxylic acid following the procedures similar to those in Example G8. MS (ESI, m/e) [M+1]$^+$ 1055.3.

Example I10: 4'-(2-(2-cyclopropylphenyl)pyrrolidin-1-yl)-N-((4-((4-morpholino-1-(phenylthio)butan-2-yl)amino)-3-((trifluoromethyl)sulfonyl)phenyl)sulfonyl)-2',3',4',5'-tetrahydro-[1,1'-biphenyl]-4-carboxamide

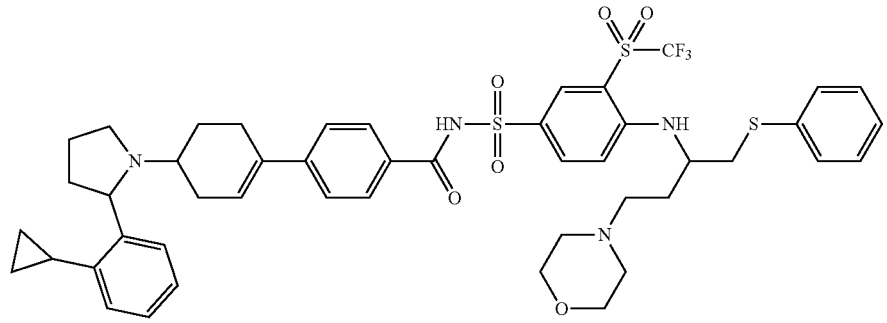 [SMILES: O=C(NS(=O)(=O)c1ccc(NC(CCN2CCOCC2)CSc2ccccc2)c(S(=O)(=O)C(F)(F)F)c1)c1ccc(C2=CCC(N3CCCC3c3ccccc3C3CC3)CC2)cc1]

The desired compound was synthesized with 4-((4-morpholino-1-(phenylthio)butan-2-yl)amino)-3-((trifluoromethyl)sulfonyl)benzenesulfonamide and 4'-(2-(2-cyclopropylphenyl)pyrrolidin-1-yl)-2',3',4',5'-tetrahydro-[1,1'-biphenyl]-4-carboxylic acid following the procedures similar to those in Example G8. MS (ESI, m/e) [M+1]$^+$ 923.3.

Biochemical Assay
Method A: Bcl-2/Bcl-X Fluorescence Polarization Assay

Compounds disclosed herein were tested for blocking of Bcl-2/Bcl-xl protein with its ligand in an assay based on fluorescence polarization methodology. Recombinant human 2.7 nM Bcl-2/1.3 nM Bcl-xl protein was pre-incubated with a serial dilution of compounds disclosed herein (maximum concentration is 1 µM for Bcl-2 assay, and 10 µM or 1 µM for Bcl-xl assay, 3-fold serially diluted, 10 points) at room temperature for 0.5 hour in an assay buffer containing 20 ml potassium phosphate buffer, pH 7.5, 50 mM NaCl, 1 mM EDTA, 0.05% Tween-20, 0.01% BSA. Then the FITC labeled Bak peptide Ac-GQVGRQLAIIGDK (FITC)INR-amide (1 nM for Bcl-2, 0.82 nM for Bcl-xl) was added to plate and further incubated at room temperature for 0.5 h. The FP signals (485 nm-520 nm-520 nm) were read on BMG PHERAstar FS or BMG PHERAstar FSX instalment. The inhibition percentage of Bcl-2/Bcl-xl interaction with its ligand in presence of increasing concentrations of compounds was calculated based on the FP signals. The IC50 for each compound was derived from fitting the data to the four-parameter logistic equation by Graphpad Prism software.

Method B: Bcl-2/Bcl-X TR-FRET Assay

Compounds disclosed herein were tested for blocking of Bcl-2/Bcl-X protein with its ligand in an assay based on Time-Resolved Fluorescence Resonance Energy Transfer (TR-FRET) methodology. Recombinant human 0.05 nM Bcl-2/0.03 nM Bcl-X protein was pre-incubated with a serial dilution of compounds disclosed herein (maximum concentration is 0.1 µM for Bcl-2 assay, and 10 µM for Bcl-xl assay, 3-fold serially diluted, 10 points; or maximum concentration is 0.02 µM for Bcl-2 assay, and 2 µM for Bcl-xl assay, 3-fold serially diluted, 10 points) at room temperature for 0.5 hour in an assay buffer containing 20 mM potassium phosphate buffer, pH 7.5, 50 mM NaCl, 1 mM EDTA, 0.05% Tween-20, 0.01% BSA. Then the FITC labeled Bak peptide Ac-GQVGRQLAIIGDK(FITC)INR-amide (0.5 nM for Bcl-2, 0.3 nM for Bcl-xl) and MAb Anti 6His Tb cryptate Gold were added to plate and further incubated at room temperature for 1 hour. The TR-FRET signals (337 nm-520 nm-490 nm) were read on BMG PHERAstar FSX instrument. The inhibition percentage of Bcl-2/Bcl-X interaction with its ligand in presence of increasing concentrations of compounds was calculated based on the TR-FRET signals. The IC$_{50}$ for each compound was derived from fitting the data to the four-parameter logistic equation by Graphpad Prism software. To improve the assay sensitivity and test more potent compounds in the present application, the bcl-2 concentration was reduced in method B.

Cell Proliferation Assay

The Bcl-2 family proteins are central regulators of apoptosis. Bcl-2 and Bcl-XL are antiapoptotic factors within this family. In our cell proliferation assay, the Bcl-2 dependent acute lymphoblastic leukemia (ALL) cell line, RS4; 11, was used to study the cellular potency of Bcl-2 inhibitors. The cells (ATCC, CRL-1873) were cultured in RPMI-1640 complete medium (RPMI-1640 medium, HEPES (Gibco, 22400-105) supplemented with 10% fetal bovine serum (FBS) (Gibco, 10099-1441), 100 unit/ml penicillin and 100 µg/ml streptomycin (Gibco, 15140122)) and maintained in a humidified chamber at 37° C. containing 5% CO$_2$. Each compound was serially diluted with 1 µM as the maximum concentration. To test the apoptotic effect of the compounds, the cells were seeded at 50,000 in 180 µl per well in 96-well plates and treated with 10-point dilution series of each compound for 48 hours at 37° C. Cell viability was assessed after the treatment using CellTiter-GLO luminescent assay (Promega) according to the manufacturer's recommendations. Briefly, 30 µl of CellTiter-GLO reagent was added into 200 µl of cell culture. Mixture was agitated on an orbital shaker for 5 minutes to ensure cell lysis followed by 7 mins incubation at room temperature to allow development and stabilization of luminescent signals, which corresponded to quantity of ATP and thus the quantity of metabolically active cells. Luminescent signals were measured using PHERAstar FS reader (BMG). Mean IC$_{50}$ values for cell viability were determined with GraphPad Prism software. The Bcl-XL-dependent ALL cell line, Molt-4 (ATCC, CRL-1582) was also used in cell proliferation assay to further evaluate the specificity of these inhibitors. Similarly, the cells were cultured in RPMI-1640 complete medium (RPMI-1640 medium, HEPES (Gibco, 22400-105) supplemented with 10% fetal bovine serum (FBS) (Gibco, 10099-1441), 100 unit/ml penicillin and 100 µg/ml streptomycin (Gibco, 15140122) and 1×GlutaMAX (Gibco, 35050-061)) and maintained in a humidified chamber at 37° C. containing 5% CO$_2$. The anti-proliferative IC$_{50}$s of these compounds were similarly determined as a percentage of viable cells upon treatment compared to the untreated control using CellTiter-GLO luminescent assay.

TABLE 1-A

Biological data tested with Method A

| Example | Biochemical activity (IC$_{50}$, nM) | | Cellular activity (IC$_{50}$, nM) | |
|---|---|---|---|---|
| | BCL-2 | Bcl-xl | RS4; 11 | Molt-4 |
| A1 | 43 | 4570 | 582 | 6230 |
| A2 | 140 | 7152 | 558 | 6191 |
| A3 | 122 | ND | 1191 | 7038 |
| A4 | 16 | 2145 | 74 | >10000 |
| A4a | 3.8 | 987 | 36 | 4134 |
| A4b | 36 | 2697 | 72 | 4145 |
| A5 | 449 | ND | ND | ND |
| A6 | 3689 | ND | ND | ND |
| A7 | 417 | ND | ND | ND |
| A8 | 7.2 | 900 | 48 | 7584 |
| A8a (faster isomer) | 1.9 | 162 | 19 | 1870 |
| A8b (slower isomer) | 33 | 4096 | 147 | >10000 |
| A9 | 1884 | ND | ND | ND |
| A10 | 1075 | ND | ND | ND |
| A11 | 14 | 926 | 50 | >10000 |
| A12 | 6.6 | 645 | 30 | 5156 |
| A13 | 43 | ND | 404 | >10000 |
| A14 | 133 | ND | 1570 | >10000 |
| A15 | 31 | >10000 | 200 | >10000 |
| A16 | 80 | >10000 | 813 | >10000 |
| A17 | 1122 | ND | ND | ND |
| A18 | 14 | 724 | 73 | >10000 |
| A19 | 191 | ND | 1025 | >10000 |
| A20 | 71 | ND | 1505 | >10000 |
| A21 | 41 | 2168 | 6229 | >10000 |
| A22 | 76 | >10000 | 1096 | 8911 |
| A23 | 241 | ND | ND | ND |
| A24 | 13 | 879 | 69 | 4498 |
| A25 | 34 | 2169 | 260 | 9176 |

TABLE 1-A-continued

Biological data tested with Method A

| Example | Biochemical activity (IC$_{50}$, nM) BCL-2 | Biochemical activity (IC$_{50}$, nM) Bcl-xl | Cellular activity (IC$_{50}$, nM) RS4; 11 | Cellular activity (IC$_{50}$, nM) Molt-4 |
|---|---|---|---|---|
| A26 | 54 | 5889 | 454 | 7301 |
| A27 | 10 | 2326 | 203 | >10000 |
| A28 | 281 | ND | 1613 | 6689 |
| A29 | 26 | ND | 1599 | >10000 |
| A30 | 221 | ND | 1144 | 5797 |
| A31 | 20 | 4299 | 85 | >10000 |
| A32 | 26 | 2915 | 123 | 4145 |
| A33 | 87 | ND | 1367 | >10000 |
| A35 | 13 | 1237 | 145 | >10000 |
| A 46 | 130 | ND | ND | ND |
| A47 | 977 | ND | ND | ND |
| A54 | 9.0 | 2693 | 90 | 6249 |
| A55 | 36 | ND | 215 | 8030 |
| A56 | 14 | ND | ND | ND |
| A57 | 27 | 5710 | 156 | 4395 |
| A61 | >1000 | ND | ND | ND |
| A62 | 59 | ND | ND | ND |
| A63 | 29 | >10000 | 328 | >10000 |
| A64 | 31 | ND | ND | ND |
| A65 | 8.5 | 372 | 40 | 3306 |
| A67 | 18 | 1818 | 328 | >10000 |
| A68 | 3.9 | 132 | 20 | >10000 |
| A69 | 40 | ND | 135 | 4900 |
| A70 | 13 | 974 | 123 | 6348 |
| A73 | 2.9 | 138 | 20 | 2107 |
| A74 | 5.3 | 374 | 8.6 | 1847 |
| A75 | 17 | 1692 | 61 | 5336 |
| A76 | 5.2 | 1450 | 47 | 2519 |
| A77 | 23 | 4224 | 55 | 1858 |
| A79 | 56 | ND | ND | ND |
| A80 | 186 | ND | ND | ND |
| A81 | 942 | ND | ND | ND |
| A82 | 15 | 1847 | 217 | 5176 |
| A83 | 43 | ND | ND | ND |
| A84 | 283 | ND | ND | ND |
| A85 | 125 | ND | ND | ND |
| B1 | 49 | >10000 | 560 | >10000 |
| B2 | 83 | ND | 339 | 5519 |
| B3 | 85 | ND | 565 | 5194 |
| B4 | 95 | ND | 2004 | >10000 |
| B5 | 141 | ND | 736 | 5090 |
| B6 | 17 | >10000 | 91 | 7264 |
| B8 | 64 | ND | >10000 | >10000 |
| B12 | 16 | 1923 | 586 | >10000 |
| B17 | 5.3 | 2178 | 48 | 8933 |
| B18 | 2.2 | 310 | 30 | >10000 |
| B21 | 89 | ND | ND | ND |
| C1 | 5.9 | 3696 | 109 | >10000 |
| C2 | 14 | 1501 | 184 | 6757 |
| C3 | 7.3 | 1816 | 56 | 7722 |
| C4 | 7.9 | 5131 | 112 | 5563 |
| C5 | 53 | ND | 4259 | >10000 |
| C6 | 24 | ND | 1295 | >10000 |
| C7 | 30 | ND | 2182 | >10000 |
| C8 | 58 | ND | 694 | >10000 |
| C9 | 26 | 2686 | 185 | >10000 |
| C10 | 31 | 4646 | 147 | 6101 |
| C11 | 89 | ND | 261 | >10000 |
| C12 | 226 | ND | ND | ND |
| C13 | 78 | ND | 335 | >10000 |
| C14 | 18 | >10000 | 93 | 7933 |
| C15 | 62 | ND | ND | ND |
| C16 | 57 | >10000 | 435 | >10000 |
| C17 | 124 | ND | ND | ND |
| C18 | 21 | 4159 | 121 | 9823 |
| C19 | 28 | 5708 | 204 | 7266 |
| C21 | 49 | ND | 132 | 5444 |
| C22 | 60 | ND | ND | ND |
| C24a | 3.0 | 2143 | 105 | >10000 |
| C24b | 20 | 2483 | 852 | >10000 |
| C26a | 32 | 3241 | 353 | 7722 |
| C26b | 62 | ND | ND | ND |
| C28 | 29 | 4324 | 280 | >10000 |
| C31 | 3.3 | 1118 | 41 | 5599 |
| C36 | 41 | 6879 | 233 | 7454 |
| C37 | 51 | ND | ND | ND |
| C39 | 19 | 6310 | 119 | >10000 |
| C40 | 14 | 5539 | 383 | >10000 |
| C41 | 12 | 4975 | 122 | >10000 |
| C42 | 18 | 5457 | 226 | >10000 |
| C45 | 48 | ND | ND | ND |
| C46 | 30 | 8846 | 106 | >10000 |
| C47 | 222 | ND | ND | ND |
| C48 | 117 | ND | ND | ND |
| C51 | 14 | 5761 | 59 | 9477 |
| C52 | 92 | 2317 | ND | ND |
| C53 | 23 | ND | 180 | 4217 |
| C54 | 41 | 5457 | 185 | 5792 |
| C55 | 12 | 1099 | 86 | 5300 |
| C57 | 30 | 5126 | 463 | >10000 |
| C60 | 7.3 | >10000 | 107 | >10000 |
| C62 | 147 | ND | ND | ND |
| C63 | 69 | ND | ND | ND |
| C66 | 14 | 1947 | 3012 | >10000 |
| C67 | 110 | ND | ND | ND |
| C69 | 28 | 4340 | 243 | >10000 |
| C81 | 18 | 2207 | 410 | >10000 |
| C86 | 96 | >10000 | 748 | 9817 |
| C87 | 11 | 2411 | 1055 | >10000 |
| C88a | 20 | 3593 | 155 | 5639 |
| C88b | 26 | 4115 | 198 | 7706 |
| C89 | 15 | 1002 | 328 | 7612 |
| C90 | 63 | 9932 | 291 | 1469 |
| C99 | 15 | 1561 | 645 | >10000 |
| C118 | 11 | >10000 | 339 | 9522 |
| C125 | 13 | 3708 | 104 | >10000 |
| C126 | 3.7 | 1915 | 24 | >10000 |
| C127 | 12 | 2762 | 53 | >10000 |
| C128 | 58 | ND | ND | ND |
| C129 | 92 | ND | ND | ND |
| C131 | 19 | 6594 | 621 | >10000 |
| C132 | 50 | >10000 | 324 | 6885 |
| C133 | 756 | ND | ND | ND |
| C134 | 8.7 | >10000 | 125 | 7126 |
| C135 | 11 | >10000 | 72 | 6550 |
| C136 | 16 | 5406 | 126 | 8660 |
| C137 | 174 | ND | ND | ND |
| C138 | 28 | >10000 | 127 | >10000 |
| C139 | 27 | 7086 | 346 | >10000 |
| C140 | 135 | ND | ND | ND |
| C141 | 14 | 4271 | 94 | 4115 |
| C142 | 34 | 8240 | 153 | 2593 |
| C143 | 59 | ND | 569 | 4992 |
| C144 | 80 | ND | ND | ND |
| C145 | 45 | ND | ND | ND |
| C146 | 79 | ND | ND | ND |
| C152 | 93 | ND | ND | ND |
| C161 | 51 | ND | 400 | >10000 |
| C162 | 90 | ND | 580 | >10000 |
| C163 | 16 | 2300 | 171 | 9054 |
| C164 | 21 | 6594 | 141 | 4139 |
| C165 | 6.7 | 3663 | 96 | >10000 |
| C166 | 72 | ND | ND | ND |
| C167 | 92 | ND | ND | ND |
| C168 | 17 | 4451 | 363 | >10000 |
| C169 | 52 | ND | ND | ND |
| C170 | 6.4 | 3613 | 118 | >10000 |
| C171 | 15 | 1450 | 492 | >10000 |
| C172 | 5.2 | 123 | 131 | >10000 |
| C173 | 121 | ND | ND | ND |
| C174 | 23 | 7700 | 260 | >10000 |
| C175 | 20 | 2826 | 476 | >10000 |
| C176 | 39 | ND | ND | ND |
| C177 | 27 | 8037 | 451 | >10000 |
| C178 | 97 | ND | ND | ND |
| C179 | 36 | 3486 | 151 | 5579 |

TABLE 1-A-continued

Biological data tested with Method A

| Example | Biochemical activity (IC$_{50}$, nM) BCL-2 | Bcl-xl | Cellular activity (IC$_{50}$, nM) RS4; 11 | Molt-4 |
|---|---|---|---|---|
| C180 | 23 | 3998 | 118 | 1989 |
| C181 | 45 | ND | ND | ND |
| C182 | 226 | ND | ND | ND |
| C183 | 4.7 | 1054 | 187 | >10000 |
| C184 | 15 | >10000 | 226 | 7116 |
| C185 | 109 | ND | ND | ND |
| C186 | 98 | ND | ND | ND |
| C187 | 61 | ND | ND | ND |
| C-189 | 29 | ND | 79 | 6506 |
| C190 | 57 | ND | ND | ND |
| C191 | 93 | ND | ND | ND |
| C192 | 21 | 8397 | 57 | 6831 |
| C193 | 19 | >10000 | 159 | 3946 |
| C194 | 61 | ND | ND | ND |
| C195 | 19 | ND | >10000 | >10000 |
| D1a | 3080 | ND | ND | ND |
| D1b | 27 | 3744 | 377 | >10000 |
| D2a | 862 | ND | ND | ND |
| D2b | 6.5 | 1421 | 60 | ND |
| D2a-S | 520 | ND | ND | ND |
| D2b-S | 4.0 | 949 | 19 | 5745 |
| D2a-R | 1016 | ND | ND | ND |
| D2b-R | 12 | 3319 | 108 | >10000 |
| D3a | 865 | ND | ND | ND |
| D3b | 4.0 | 3053 | 47 | >10000 |
| D4a | 2418 | ND | ND | ND |
| D4b | 15 | 7261 | 94 | 6258 |
| D5 | 12 | ND | 43 | 7445 |
| D6 | 19 | 6631 | 178 | 5053 |
| D13-1a | 3846 | ND | ND | ND |
| D13-1b | 22 | ND | ND | ND |
| D14-1a | 2181 | ND | ND | ND |
| D14-1b | 23 | 9747 | 182 | >10000 |
| D63a | 2020 | ND | ND | ND |
| D63b | 12 | >10000 | 259 | >10000 |
| D96 | 5.9 | 3441 | 43 | >10000 |
| D97a | 631 | ND | ND | ND |
| D97b | 4.0 | 1613 | 44 | 8270 |
| D99 | >1000 | ND | ND | ND |
| D100 | 107 | ND | ND | ND |
| D101 | 66 | ND | ND | ND |
| D102 | 36 | >10000 | 1038 | >10000 |
| D103 | 6.7 | 3797 | 144 | >10000 |
| D104 | 1150 | ND | ND | ND |
| D105 | >1000 | ND | ND | ND |
| D106 | >1000 | ND | ND | ND |
| E1 | 54 | ND | 1630 | >10000 |
| E2 | 20 | 6924 | 583 | >10000 |
| E3 | 16 | 1758 | 931 | >10000 |
| E4 | 15 | ND | 798 | >10000 |
| E12 | 7.2 | 763 | 144 | >10000 |
| E13 | 6.8 | 423 | 82 | 3800 |
| F1 | 49 | ND | 1804 | 6553 |
| F2 | 755 | ND | ND | ND |
| F5 | 2.8 | 230 | 4.3 | 6184 |
| F9 | 91 | ND | ND | ND |
| F11 | 37 | 6665 | 329 | >10000 |
| F30 | 34 | >1000 | 290 | >10000 |
| F31 | 107 | ND | ND | ND |
| F32 | 13 | >10000 | 137 | 7038 |
| F33 | 149 | ND | ND | ND |
| F36 | 4.6 | 2000 | 31 | 6086 |
| G1 | 12 | 2490 | 88 | 6773 |
| G1C | 6.9 | 1528 | 37 | 5165 |
| G2 | 16 | 93 | 208 | 8167 |
| G2C | 14 | 187 | 159 | >10000 |
| G3 | 33 | 570 | 455 | >10000 |
| G4 | 24 | 5376 | 241 | >10000 |
| G5 | 19 | 400 | 197 | 4704 |
| G6 | 13 | 7356 | 59 | 6091 |
| G7 | 125 | ND | 3854 | >10000 |
| G8 | 6.4 | 1097 | 64 | >10000 |
| G8-S | 4.8 | 937 | 25 | 2465 |
| G8-a | 5.3 | 884 | 15 | 5645 |
| G8-b | 4.3 | 868 | 10 | 4754 |
| G9 | 6.2 | 936 | 34 | 4469 |
| G9-a | 7.1 | 1491 | 42 | >10000 |
| G9-b | 5.9 | 1727 | 28 | 6450 |
| G9-S | 4.2 | 1099 | 38 | 1091 |
| G10a | 5.5 | 3327 | 12 | 7494 |
| G10b | 17 | 3804 | 72 | 3754 |
| G10b-S | 5.4 | 3294 | 4.6 | 3211 |
| G10b-a | 4.6 | 5372 | 14 | 4112 |
| G10b-b | 3.0 | 5125 | 10 | 4086 |
| G11 | 4.5 | 723 | 40 | >10000 |
| G12 | 18 | 5955 | 51 | >10000 |
| G13 | 5.0 | 407 | 72 | >10000 |
| G16 | 27 | 4982 | 280 | >10000 |
| G18 | 3.4 | 172 | 39 | >10000 |
| G20 | 15 | 4824 | 53 | >10000 |
| G24b | 6.7 | 2184 | 36 | >10000 |
| G24b-S | 2.1 | 1978 | 12 | 4465 |
| G24b-a | 3.6 | 1508 | 10 | 4583 |
| G24b-b | 2.6 | 1052 | 4.9 | 4045 |
| G26 | 7.0 | 551 | 52 | 5038 |
| G27 | 9.5 | 161 | 118 | >10000 |
| G30 | 4.9 | 1019 | 18 | 5329 |
| G30-S | 3.5 | 1250 | 19 | 4831 |
| G30-a | 4.5 | 1362 | 22 | 4607 |
| G30-b | 3.4 | 1362 | 13 | 4157 |
| G30-R | 7.9 | 884 | 121 | >10000 |
| G31 | 6.0 | 302 | 66 | 1230 |
| G32 | 10 | 1183 | 123 | >10000 |
| G35-S | 2.4 | 398 | 14 | 5187 |
| G35-a | 1.9 | 341 | 15 | 7583 |
| G35-b | 2.2 | 287 | 8.2 | 3540 |
| G36 | 5.9 | 137 | 41 | 474 |
| G37 | 4.3 | 643 | 103 | 6627 |
| G39 | 17 | 635 | 116 | 6262 |
| G63 | 20 | 885 | 86 | 8597 |
| G64 | 8.9 | 1657 | 70 | 3738 |
| G70 | 353 | ND | ND | ND |
| G72 | 431 | ND | ND | ND |
| G73 | 252 | ND | ND | ND |
| G75-a | 4.6 | 1024 | 42 | 3246 |
| G75-b | 3.6 | 1088 | 28 | 2090 |
| G75 | 5.2 | 1008 | 46 | >10000 |
| G76 | 5.3 | 1163 | 34 | 6301 |
| G76-S | 4.2 | 1099 | 38 | 8091 |
| G77 | 5.0 | 730 | 24 | >10000 |
| G77-S | 3.1 | 720 | 35 | 7397 |
| G80a | >1000 | ND | ND | ND |
| G80b | 849 | ND | ND | ND |
| G81a | 16 | 8313 | 49 | 5487 |
| G81b | 5.3 | 3571 | 15 | 8809 |
| G84 | 12 | 1118 | 117 | 7311 |
| G85-S | 59 | 3692 | 103 | 4082 |
| G85-R | 2.9 | 150 | 10 | 1837 |
| G86 | 18 | ND | 254 | 9760 |
| G87 | 18 | 65 | 274 | 2011 |
| G88-S | 61 | ND | ND | ND |
| G89-S | 59 | ND | ND | ND |
| G90-S | 2.8 | 1574 | 11 | 6783 |
| G90-a | 3.3 | 1344 | 25 | 3218 |
| G90-b | 2.3 | 1135 | 16 | 4655 |
| G91-R | 2.4 | 249 | 8.5 | 1726 |
| G92-R | 1.8 | 198 | 8.2 | 1266 |
| G92-S | 10 | 1570 | 37 | 4257 |
| G93-R | 3.6 | 346 | 32 | 3249 |
| G93-S | 29 | 4321 | 157 | 2989 |
| G94-R | 2.7 | 157 | 12 | 1423 |
| G94-S | 12 | 1317 | 66 | 2600 |
| G95-R | 3.5 | 110 | 16 | 1439 |
| G95-S | 12 | 1112 | 91 | 6197 |
| G96-R | 4.9 | 227 | 29 | 2065 |
| G96-S | 19 | 924 | 55 | 2744 |

TABLE 1-A-continued

Biological data tested with Method A

| Example | Biochemical activity (IC$_{50}$, nM) BCL-2 | Bcl-xl | Cellular activity (IC$_{50}$, nM) RS4; 11 | Molt-4 |
|---|---|---|---|---|
| G97-R | 2.2 | 37 | 3.9 | 434 |
| G97-S | 8.3 | 733 | 35 | 3030 |
| G98 | 1.5 | 65 | 5.6 | 1351 |
| G100a | 2.8 | 331 | 17 | 3709 |
| G100b | 3.3 | 239 | 34 | 3764 |
| G103 | 13 | 1404 | 58 | 9594 |
| G104 | 6.5 | 167 | 11 | 1314 |
| G105 | 51 | 1249 | 47 | 2669 |
| G106 | 6.0 | 6701 | 15 | 3173 |
| G107-a | 1.6 | 1646 | 18 | 7251 |
| G107-b | 1.2 | 1944 | 11 | >10000 |
| G43a | 8.2 | 5049 | 79 | 2712 |
| G43b | 3.7 | 2719 | 22 | 3042 |
| G108a | 3.2 | 1348 | 31 | >10000 |
| G108b | 5.7 | 1187 | 24 | >10000 |
| G109 | 5.3 | 1828 | 24 | >10000 |
| G110a | 3.3 | 1200 | 13 | 6182 |
| G110b | 6.8 | 2212 | 27 | 5693 |
| G110b-a | 5.9 | 3459 | 17 | 3908 |
| G110b-b | 4.4 | 2936 | 11 | 2930 |
| G111 | 6.2 | 2503 | 253 | >10000 |
| G112 | 2.5 | 660 | 12 | 4278 |
| G113 | 7.4 | 2213 | 124 | >10000 |
| G114 | 3.2 | 640 | 18 | 5969 |
| G115 | 9.0 | 1201 | 91 | >10000 |
| G116 | 12 | 6160 | 20 | >10000 |
| G117 | 4.9 | 698 | 70 | >10000 |
| H3a | 310 | ND | ND | ND |
| H3 | 27 | 4572 | 409 | >10000 |
| I7 | 134 | ND | ND | ND |
| I8 | 882 | ND | ND | ND |
| I9 | >1000 | ND | ND | ND |
| I10 | 559 | ND | ND | ND |

TABLE 1-B

Biological data tested with Method B

| Example | Biochemical activity (IC$_{50}$, nM) BCL-2 | Bcl-xl | Cellular activity (IC$_{50}$, nM) RS4;11 | Molt-4 |
|---|---|---|---|---|
| A37 | 40 | ND | ND | ND |
| A66 | 1.7 | 130 | 289 | >10000 |
| A72 | 33 | 650 | 214 | >10000 |
| A78 | 19 | 4100 | 1411 | >10000 |
| A86 | 42 | ND | ND | ND |
| A87 | 30 | ND | ND | ND |
| A68-S | 4.8 | 1000 | 196 | >10000 |
| A68-R | 0.28 | 34 | 10 | 5241 |
| A88 | 32 | ND | ND | ND |
| A89 | >100 | ND | ND | ND |
| A90 | 3.8 | 280 | 71 | 5605 |
| A91 | >100 | ND | ND | ND |
| A93 | 68 | ND | ND | ND |
| A94 | 21 | ND | ND | ND |
| A95 | >100 | ND | ND | ND |
| A96 | 28 | ND | ND | ND |
| A97 | 0.32 | 16 | 4.8 | 1410 |
| A98 | >100 | ND | ND | ND |
| A99 | 0.56 | 57 | 58 | >10000 |
| A100 | 0.21 | 17 | 4.6 | >10000 |
| A101 | 0.055 | 5.6 | 7.1 | 2410 |
| A102 | 19 | ND | ND | ND |
| A103 | 0.56 | 68 | 11 | >10000 |
| A104 | 1.2 | 126 | 16 | 4613 |
| A105 | 1.3 | 144 | 13 | 3997 |
| A106 | 0.3 | 22 | 175 | >10000 |
| A107 | 3.5 | 254 | 18 | 3177 |
| A108 | 6.6 | ND | 32 | >10000 |
| A109 | 0.68 | 36 | 2.7 | 1317 |
| A110 | 3.0 | 276 | 15 | 1258 |
| A111 | 11 | ND | 31 | 6290 |
| A112 | 0.11 | 12 | 3.4 | 1211 |
| A113 | 0.24 | 19 | 8.6 | 1190 |
| A114 | 0.089 | 9.9 | 2.7 | 589 |
| A115 | 0.8 | 67 | 22 | 3835 |
| A116 | 2.3 | 150 | 65 | 7043 |
| A117a | 0.5 | 61 | 11 | 8962 |
| A117b | 2.5 | 150 | 46 | >10000 |
| A118a | 0.58 | 61 | 3.7 | 979 |
| A118b | 0.15 | 16 | 1.2 | 459 |
| A119 | 0.96 | 143 | 38 | >1000 |
| A120 | 0.47 | 86 | 88 | >10000 |
| A121 | 0.88 | 178 | 6.6 | 1799 |
| A122 | 3.8 | ND | 48 | 6919 |

TABLE 1-B-continued

Biological data tested with Method B

| Example | Biochemical activity (IC$_{50}$, nM) | | Cellular activity (IC$_{50}$, nM) | |
|---|---|---|---|---|
| | BCL-2 | Bcl-xl | RS4;11 | Molt-4 |
| A123 | 0.49 | 89 | 38.5 | 3912 |
| A124 | 4.4 | 242 | 14 | 5844 |
| A125 | 0.23 | 21 | 4.5 | 489 |
| A126 | 0.79 | 32 | 26 | >10000 |
| A127 | 1.4 | 170 | 32 | 4100 |
| A128 | 4.4 | 320 | 115 | >10000 |
| A129 | 5.4 | ND | 45 | 4351 |
| A130 | 1.2 | ND | 31 | >10000 |
| A131 | 0.14 | 24 | 16 | 1350 |
| A132 | 0.63 | 56 | 4.2 | 1993 |
| A133 | 0.38 | 57 | 6.3 | 5958 |
| A134 | 0.35 | 46 | 2.1 | 1392 |
| A135 | 0.25 | 24 | 12 | 751 |
| A136 | 0.28 | 19 | 3.8 | 1412 |
| A137 | 0.74 | 165 | 10 | 3537 |
| A138 | 4.2 | 115 | ND | ND |
| A139 | 6.8 | ND | 2322 | >10000 |
| A140 | 1.8 | 161 | 24 | >10000 |
| A141 | 49 | ND | ND | ND |
| A142 | 12 | 211 | 108 | 2510 |
| A143 | 16 | ND | ND | ND |
| A144 | 36 | >10000 | ND | ND |
| A145a | 8.4 | 1500 | 79 | 5958 |
| A145b | 5.8 | 530 | 36 | 3489 |
| A145c | 0.44 | 32 | 6.8 | 782 |
| A145d | 29 | ND | ND | ND |
| A146 | 13 | 1748 | 22 | 1900 |
| A147a | 20 | 3202 | 24 | 3141 |
| A147b | 1.8 | 230 | 4.9 | 1252 |
| A148 | 62 | ND | ND | ND |
| A149 | >100 | ND | ND | ND |
| A150 | 3.3 | 1354 | 41 | 4108 |
| A151 | 2.7 | ND | 26 | >10000 |
| A152 | 33 | 650 | 214 | >10000 |
| A153 | 5.9 | ND | 424 | >10000 |
| A154 | 22 | ND | ND | ND |
| A155 | 6 | 2064 | 94 | >10000 |
| A156 | 17 | ND | 142 | 4395 |
| A157 | >100 | ND | ND | ND |
| A158 | >100 | ND | ND | ND |
| B13 | >100 | ND | ND | ND |
| B14 | 25 | >10000 | 2552 | >10000 |
| B15 | 8.1 | >10000 | 425 | 9497 |
| B16 | 3.9 | 3900 | 282 | >10000 |
| B19a | >100 | ND | ND | ND |
| B19b | >100 | ND | ND | ND |
| B20a | >100 | ND | ND | ND |
| B20b | >100 | ND | ND | ND |
| B21 | 100 | ND | ND | ND |
| B22 | >100 | ND | ND | ND |
| B23 | >100 | ND | ND | ND |
| B24 | >100 | ND | ND | ND |
| B25 | 24 | ND | 154 | 9873 |
| B26 | 9 | ND | 511 | >10000 |
| B27 | 8.9 | >10000 | 340 | >10000 |
| B28 | 11 | ND | ND | ND |
| B29 | 26 | ND | ND | ND |
| B30 | 47 | ND | ND | ND |
| B31 | 660 | ND | ND | ND |
| B32 | 59 | ND | ND | ND |
| B33 | >100 | ND | ND | ND |
| B34 | 33 | ND | ND | ND |
| B35 | 17 | ND | ND | ND |
| B36 | 87 | ND | ND | ND |
| B37 | >100 | ND | ND | ND |
| B38 | 2.3 | >10000 | 115 | >10000 |
| B39 | >100 | ND | ND | ND |
| B40 | 69 | ND | ND | ND |
| D107a | 29 | ND | ND | ND |
| D107b | 1.7 | ND | 187 | >10000 |
| F5 | 0.045 | 55 | 5.8 | 5890 |
| F23 | 0.039 | 35 | 2.2 | 3736 |
| F22 | 0.032 | 26 | 1.3 | 2825 |

TABLE 1-B-continued

| | Biochemical activity (IC$_{50}$, nM) | | Cellular activity (IC$_{50}$, nM) | |
|---|---|---|---|---|
| Example | BCL-2 | Bcl-xl | RS4;11 | Molt-4 |
| F21 | 0.022 | 24 | 1.1 | 2035 |
| F24 | 0.078 | 58 | 5.9 | 2848 |
| F25 | 0.042 | 36 | 2.0 | 4411 |
| F26 | 0.034 | 43 | 1.9 | >10000 |
| F27 | 1.2 | 3402 | 119 | >10000 |
| F28 | 0.98 | 1523 | 83 | >10000 |
| F29 | 0.63 | 3061 | 86 | >10000 |
| F34 | 0.092 | 74 | 6.7 | 7417 |
| F35 | 1.4 | 1300 | 160 | >10000 |
| F36 | 4.6 | 2000 | 31 | 6086 |
| F37 | 0.041 | 20 | 2.8 | 1442 |
| F38 | 0.07 | 38 | 3.8 | 1745 |
| F39a | 0.21 | 210 | 14 | >10000 |
| F39b | 3.9 | 2300 | 105 | >10000 |
| F40 | 0.045 | 18 | 7.7 | 2702 |
| F41 | 0.059 | 22 | 4.5 | 4302 |
| F42 | 44 | ND | ND | ND |
| F43 | 0.015 | 18 | 0.41 | 2520 |
| F44 | 0.048 | 61 | 1.1 | 1378 |
| F45 | 0.036 | 46 | 1.0 | 5979 |
| F46 | 0.052 | 28 | 0.4 | 2847 |
| F47 | 0.038 | 34 | 0.7 | 1468 |
| F48 | 0.074 | 132 | 1.8 | 3753 |
| F49 | 0.74 | 2907 | 123 | 9342 |
| F50 | 2.1 | 5361 | 349 | 9342 |
| F51 | 1.1 | 1823 | 43 | 7000 |
| F52 | 1.6 | 9125 | 107 | 8988 |
| F53 | 1.0 | 835 | 100 | >10000 |
| F54 | 0.11 | 154 | 0.8 | 1866 |
| F55 | 0.31 | 320 | 44 | >10000 |
| F56 | 0.43 | 323 | 11 | 4016 |
| F57 | 4.4 | 2600 | 342 | >10000 |
| F58 | 4.8 | 1800 | 262 | >10000 |
| F59 | 4.7 | ND | 198 | >10000 |
| F60 | 7.7 | 5500 | 517 | >10000 |
| F61 | 0.081 | 86 | 27 | >10000 |
| F62 | 0.023 | 29 | 1.4 | 991 |
| F63 | 0.021 | 17 | 0.8 | 6819 |
| F64 | 0.02 | 28 | 0.8 | 2442 |
| F65 | 0.32 | 1408 | 45 | >10000 |
| F66 | 57 | ND | ND | ND |
| F67 | 78 | ND | ND | ND |
| F68 | 0.12 | 148 | 13 | >10000 |
| F69 | 0.076 | 133 | 15 | >10000 |
| F70 | 0.24 | 390 | 53 | >10000 |
| F71 | 2.1. | 7700 | 1287 | >10000 |
| F72a | 1.3 | 826 | 25 | 7892 |
| F72b | 2.0 | 1879 | 42 | 4305 |
| F73 | 1.1 | 1507 | 63 | >10000 |
| F74a | 1.9 | 1490 | 30 | 7527 |
| F74b | 1.4 | 372 | 12 | 4138 |
| F75 | 1.5 | >10000 | 36 | 2045 |
| F76 | 12 | 2300 | 2389 | >10000 |
| F77 | 23 | ND | ND | ND |
| F78 | 0.21 | 278 | 1.5 | 3569 |
| F79 | 1.1 | 1860 | 38 | >10000 |
| F80 | 32 | >10000 | ND | ND |
| F81 | 0.56 | 666 | 11 | 1695 |
| F82 | 0.82 | 1067 | 7.6 | 2488 |
| F83 | 6.9 | ND | 60 | 4833 |
| F84 | 3.8 | 7674 | 44 | 2229 |
| F85 | 0.058 | 38 | 3.5 | 3507 |
| F86 | 0.15 | 60 | 32 | >10000 |
| F87 | 1.5 | ND | 36 | >10000 |
| F88 | 1.6 | 2426 | 13 | 6977 |
| F89 | 1.7 | 3077 | 27 | 4013 |
| F90 | 0.094 | 99 | 3.6 | >10000 |
| F91a | 0.071 | 164 | 3.6 | 1880 |
| F91b | 0.063 | 27 | 0.38 | 957 |
| F92 | 0.025 | 22 | 1.2 | 1370 |
| F93 | 15 | >10000 | 900 | >10000 |
| F94 | 0.97 | 1300 | 32 | >10000 |
| F95 | 0.28 | 708 | 7.8 | 4166 |

TABLE 1-B-continued

Biological data tested with Method B

| Example | Biochemical activity (IC$_{50}$, nM) | | Cellular activity (IC$_{50}$, nM) | |
|---|---|---|---|---|
| | BCL-2 | Bcl-xl | RS4;11 | Molt-4 |
| F96 | 27 | ND | ND | ND |
| F97 | 0.047 | 82 | 1.0 | >10000 |
| F98 | 3.3 | 1930 | 14 | >10000 |
| F99 | 0.024 | 52 | 2.6 | 3080 |
| F100 | 0.058 | 133 | 6.4 | 7032 |
| F101a | 0.063 | 364 | 11 | 2960 |
| F101b | 0.098 | 124 | 4.4 | >10000 |
| F102 | 0.087 | 271 | 1.3 | 3410 |
| F103 | 0.57 | 1160 | 8.9 | >10000 |
| F104 | 0.055 | 86 | 0.4 | 1490 |
| F105 | 0.091 | 382 | 11 | 7700 |
| F106 | 0.021 | 67 | 0.7 | 1206 |
| F107 | 0.047 | 20 | 0.9 | 1025 |
| F108 | 0.05 | 31 | 1.1 | 1191 |
| F109 | 0.039 | 167 | 1.2 | 3847 |
| F110 | 0.055 | 106 | 2.7 | 2555 |
| F111 | 0.03 | 61 | 0.4 | 1663 |
| F112 | 0.045 | 42 | 0.7 | 871 |
| F113 | 7.8 | 9004 | 103 | >10000 |
| F114 | 2.6 | 1880 | 152 | 2960 |
| F115 | 6.4 | ND | 123 | >10000 |
| F116 | 0.13 | 167 | 5.4 | 4709 |
| F117 | 0.15 | 45 | 6.5 | 1457 |
| F118 | 0.13 | 60 | 120 | >10000 |
| F119 | 0.044 | 35 | 2.1 | 2804 |
| F120 | 0.025 | 37 | 2.7 | 2520 |
| F121 | 0.092 | 181 | 10 | 4580 |
| F122 | 0.74 | 1960 | 57 | >10000 |
| F123 | 0.27 | 688 | 28.8 | >10000 |
| F124a | 1 | 4459 | 19 | >10000 |
| F124b | 1.3 | 4141 | 27 | >10000 |
| F125 | 0.45 | 4534 | 30 | >10000 |
| F126 | 0.076 | 50 | 7.5 | >10000 |
| F127 | 0.084 | 172 | 2.1 | 1790 |
| F128 | 0.12 | 34 | 7.8 | 1810 |
| F129 | 0.21 | 534 | 29 | >10000 |
| F130 | 0.021 | 23 | 0.5 | 7350 |
| F131a | 0.046 | 17 | 4.9 | >10000 |
| F131b | 0.061 | 28 | 11 | >10000 |
| F132a | 0.17 | 335 | 30 | >10000 |
| F132b | 0.015 | 7.1 | 0.49 | 4260 |
| G85-R | 2.6 | 140 | 10 | 1612 |
| G91-R | 1.5 | 150 | 8.5 | 1726 |
| G92-R | 1.1 | 120 | 8.9 | 1955 |
| G94-R | 1.5 | 67 | 15 | 1935 |
| G95-R | 1.6 | 61 | 16 | 1439 |
| G99 | 3.2 | 540 | 36 | 6905 |
| G101a | 6.1 | ND | ND | ND |
| G101b | 7.3 | 320 | 111 | >10000 |
| G102 | 23 | 1100 | 861 | >10000 |
| G118 | 0.068 | 17 | 2.8 | >10000 |
| G119 | 0.099 | 19 | 3.7 | 7848 |
| G120 | 0.17 | 19 | 9 | >10000 |
| G121 | 0.095 | 12 | 1.6 | >10000 |
| G122 | 0.053 | 19 | 1.6 | >10000 |
| G123 | 1.1 | 176 | 5.4 | 3556 |
| G124 | 0.063 | 22 | 3.8 | >10000 |
| G125 | 0.064 | 14 | 33 | >10000 |
| G126 | 0.084 | 12 | 12 | >10000 |
| G127 | 1.2 | 150 | 60.3 | >10000 |
| G128 | 1.2 | 75 | 21 | 765 |
| G129 | 3.3 | 123 | 35 | 974 |
| G130 | 9.1 | 170 | 82 | 2338 |
| G131 | 14 | ND | ND | ND |
| G132a | 2.6 | 250 | 30 | 5343 |
| G132b | 0.24 | 297 | 20 | 8246 |
| G133 | 1.6 | 170 | 1.5 | 392 |
| G134 | 13 | 3396 | 33 | 1427 |
| G135 | 49 | 2743 | ND | ND |

TABLE 1-B-continued

Biological data tested with Method B

| Example | | Biochemical activity (IC$_{50}$, nM) | | Cellular activity (IC$_{50}$, nM) | |
|---|---|---|---|---|---|
| | | BCL-2 | Bcl-xl | RS4;11 | Molt-4 |
| ABT-199 | 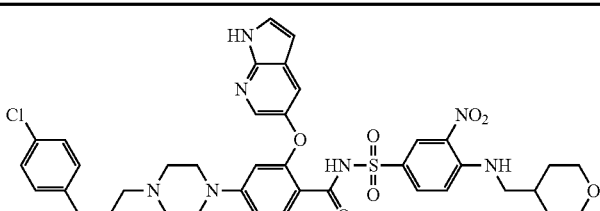 | 0.34 | 190 | 9.5 | 3166 |
| F133 | 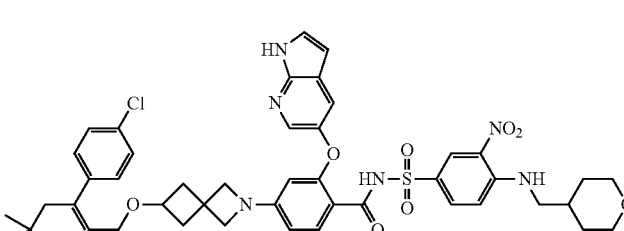 | 49 | >10000 | ND | ND |
| Example 8 in CN106749233A | | 84 | >10000 | ND | ND |

ND: no data.

Bcl-2-G101V Biochemical Assay

Selected compounds disclosed herein were tested for blocking of Bcl-2-G101 protein with its ligand in an assay based on time-resolved fluorescence resonance energy transfer methodology. 0.05 nM of Recombinant human Bcl-2-G101V protein was pre-incubated with a serial dilution of compounds disclosed herein (maximum concentration is 10 µM, 4-fold serially diluted, 10 points; or maximum concentration is 1 uM, 3-fold serially diluted, 10 points) at room temperature for 0.5 hour in an assay buffer containing 20 mM potassium phosphate buffer, pH 7.5, 50 mM NaCl, 1 mM EDTA, 0.05% Tween-20, 0.01% BSA. Then 5 nM of the FITC labeled Bak peptide Ac-GQVGRQLAIIGDK (FITC)INR-amide and Mab Anti-6His Tb cryptate Gold was added to plate and further incubated at room temperature for 1 hour. The TR-FRET signals (ex337 nm, em490 nm/520 nm) were read on BMG PHERAstar FSX instrument. The inhibition percentage of Bcl-2-G101V interaction with its ligand in presence of increasing concentrations of compounds was calculated based on the ratio of fluorescence at 490 nm to that at 520 nm. The IC$_{50}$ for each compound was derived from fitting the data to the four-parameter logistic equation by Graphpad Prism software or Dotmatics. The data was shown in Table 1-C.

TABLE 1-C

Biochemical data of inhibition of mutant Bcl-2-G101V

| Example | Biochemical activity Bcl-2-G101V, IC50 (nM) |
|---|---|
| A114 | 2.7 |
| F21 | 0.93 |
| F26 | 1.2 |
| F43 | 0.42 |
| F44 | 1.6 |
| F48 | 2.1 |
| F63 | 0.52 |
| F85 | 1.3 |
| F90 | 1.4 |
| F91b | 0.25 |
| F92 | 0.86 |
| F99 | 2.5 |
| F106 | 0.72 |
| F126 | 12 |
| F132b | 0.31 |
| G122 | 1.5 |
| G124 | 1.1 |

TABLE 1-C-continued

Biochemical data of inhibition of mutant Bcl-2-G101V

| Example | | Biochemical activity Bcl-2-G101V, IC50 (nM) |
|---|---|---|
| ABT-199 | 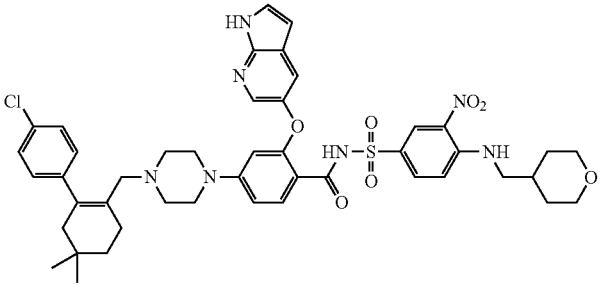 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2ccc(Cl)cc2)C1] | 28 |

To further assess the compound's binding affinity to Bcl-2 Gly101Val mutant, selected compounds in Table 1-C together with ABT-199 were examined in biochemical assay. These compounds were confirmed to be unexpectedly more potent than ABT-199 (28 nM), which indicates these compounds may overcome the BCL2 resistant mutant.

TABLE 2 describes ABT-199, its structurally similar analogs and their activity in both of biochemical assay and cellular assay. As can be seen from the table, these analogs exhibit a dramatic trend of decreasing activity (at least more than 10 fold) for Bcl-2 compared with ABT-199. For example, the most similar analog B6 shows about 14 fold less potent in biochemical assay and more than 20 fold less potent in RS4; 11 cellular proliferation assay. The decrease in activity of ABT-199 analogs from B1 to B5 ranges from 40 fold to greater than 100 fold in biochemical assay, and the drop potency in RS4; 11 cellular proliferation assay are all greater than 80 fold.

TABLE 2

ABT-199 and its structurally similar analogs in the present invention

| Example | | Biochemical activity# (IC$_{50}$, nM) | Cellular activity (IC$_{50}$, nM) |
|---|---|---|---|
| B1 | | 49 | 560 |
| B2 | | 83 | 339 |
| B3 | | 85 | 565 |
| B4 | | 95 | 2004 |
| B5 | | 141 | ND |
| B6 | | 17 | 91 |
| ABT-199 | 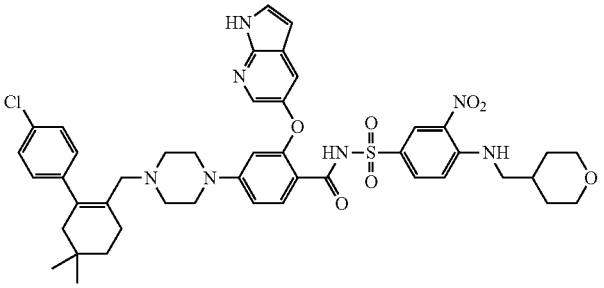 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2ccc(Cl)cc2)C1] | 1.2 | 3.8 |

TABLE 2-continued

ABT-199 and its structurally similar analogs in the present invention

| Example | Biochemical activity# (IC$_{50}$, nM) | Cellular activity (IC$_{50}$, nM) |
|---|---|---|
| ABT-199 analog | ND | ND |

: Data tested with method A.

TABLE 3A describes selected compounds without the carbon atom between two rings A and B and their activity or potency in both of biochemical assay and cellular assay. Compounds in the present patent show unexpected structure-activity relationship (SAR). When ring A is phenyl or spiro ring, compounds (F5, F55, A4, A8) with an or/ho-substituent (e.g., Cl atom or cyclopropyl) on the phenyl group are much more potent (>10 fold) compared to those compounds with the same substituent on other positions of the phenyl group. However, the above SAR with respect to the change of the substitution positions on the phenyl group were not found when the ring A is hexane or hexene group.

TABLE 3A

| Example | Biochemical activity (IC$_{50}$, nM) BCL-2 | Cellular activity (IC$_{50}$, nM) RS4; 11 |
|---|---|---|
| F5$^B$ | 0.045# | 5.8 |
| F53$^B$ | 1.0# | 100 |
| F55$^B$ | 0.31# | 44 |
| F58$^B$ | 4.8# | 262 |
| F60$^B$ | 7.7# | 517 |
| A4$^A$ | 16 | 2145 |
| A3$^A$ | 122 | ND |
| A2$^A$ | 140 | 7152 |
| A8$^A$ | 7.2 | 48 |
| A10$^A$ | 1075 | ND |
| A14$^A$ | 133 | 1570 |
| C3 $^A$ | 7.3 | 56 |
| C4$^A$ | 7.9 | 112 |
| C192$^A$ | 21 | 8397 |
| D1b$^A$ | 27 | 3744 |
| D13-1b$^A$ | 22 | ND |
| D14-1b$^A$ | 23 | 9747 |
| D2b$^A$ | 6.5 | 60 |
| D3b$^A$ | 4.0 | 3053 |
| D4b$^A$ | 15 | 7261 |

Data tested with method B.

Table 3B describes some examples with different ring A and their activity or potency in both of biochemical assay and cellular assay. No —CH$_2$— between Ring A and B. Surprisingly, examples F21, F22, F23, F24, F25, F26, F34, F37, F38, F40, F41, F43-F48, F62-F64, F90, F91b, F92, F99, 1104. F106, F109, F111, F120, F126, F130 and F132b with spiro ring as ring A have significantly increased activity in both of biochemical assay and cellular assay, compared to examples with other rings as ring A (i.e., examples A8a, G92-R, G94-R, G95-R and G96-R with phenyl rings as ring A, and C3, G30-a, G30b, G10b-a, G10b-b, G24b-a, G24b-b, G9-a, G9-b, G8-a, G8-b, G107-a, G107-b, G90-a, and G90-b with hexene rings as ring A, and D2b-S and G76-S, G77-S with hexane rings as ring A). Compounds in the current patent show unexpected SAR, which can be further explained by an additional sulfur-π interaction with Met115 in co-crystal of compound F22 having a spiro ring as ring A with bcl-2 protein compared to those of compounds G10b-a, G10b-b having hexene rings as ring A with bcl-2 protein.

Examples F21, F22, F23, F24, F25, F26, F34, F37, F38, F40, F41, F43-F48, F62-F64, F90, F91b, F92, F99, F104, F106, F109, F111, F120, F126, F130 and F132b with spiro rings as ring A are 3 to >10 fold more potent than ABT-199 and Example 8 from CN106749233A in biochemical assay using method B, and >1 to >8 fold more potent than ABT-199 in cellular assay. Moreover, the selectivity of examples with spiro ring as ring A against Bcl-xl is better than that of ABT-199 in biochemical assay or cellular assay. Further, the unexpected SAR also happened on the chiral center of pyrrolidine ring. The more potent isomer in example with phenyl ring as ring A has R configuration (i.e., examples G92-R, G94-R, G95-R, G96-R, G118, G122 and G124), while the more potent isomer in example with hexene, hexane or spiro ring as ring A has S configuration.

TABLE 3B

| Example | Biochemical activity (IC$_{50}$, nM) | | Celluclar activity (IC$_{50}$, nM) | |
|---|---|---|---|---|
| | Bcl-2 | Bcl-xl | RS 4; 11 | Molt-4 |
| A8[A] | 7.2 | 900 | 48 | 7584 |
| A8a (faster isomer)[A] | 1.9 | 162 | 19 | 1870 |
| G92-R[A] | 1.8 | 198 | 8.2 | 1266 |
| G92-R[B] | 1.1 | ND | ND | ND |
| G94-R[A] | 2.7 | 157 | 12 | 1423 |
| G94-R[B] | 1.5 | ND | ND | ND |
| G95-R[A] | 3.5 | 110 | 16 | 1439 |
| G95-R[B] | 1.6 | ND | ND | ND |
| G96-R[A] | 4.9 | 227 | 29 | 2065 |
| G118 | 0.068 | 17 | 2.8 | >10000 |
| G122 | 0.053 | 19 | 1.6 | >10000 |
| G124 | 0.063 | 22 | 3.8 | >10000 |
| C3[A] | 7.3 | 1816 | 56 | 7722 |
| G30-a[A] | 4.5 | 1362 | 22 | 4607 |
| G30-b[A] | 3.4 | 1362 | 13 | 4157 |
| G10b-a[A] | 4.6 | 5372 | 14 | 4112 |
| G10b-b[A] | 3.0 | 5125 | 10 | 4086 |
| G24b-a[A] | 3.6 | 1508 | 10 | 4583 |
| G24b-b[A] | 2.6 | 1052 | 4.9 | 4045 |
| G9-a[A] | 7.1 | 1491 | 42 | >10000 |
| G9-b[A] | 5.9 | 1727 | 28 | 6450 |
| G8-a[A] | 5.3 | 884 | 15 | 5645 |
| G8-b[A] | 4.3 | 868 | 10 | 4754 |
| G107-a[A] | 1.6 | 1646 | 18 | 7251 |
| G107-b[A] | 1.2 | 1944 | 11 | >10000 |
| G90-a[A] | 3.3 | 1344 | 25 | 3218 |
| G90-b[A] | 2.3 | 1135 | 16 | 4655 |
| D2b-S[A] | 4.0 | 949 | 19 | 5745 |
| G76-S[A] | 4.2 | 1099 | 38 | 8091 |
| G77-S[A] | 3.1 | 720 | 35 | 7397 |
| F21[A] | 1.6 | ND | ND | ND |
| F21[B] | 0.022 | 24 | 1.1 | 2035 |
| F22[A] | 1.7 | ND | ND | ND |
| F22[B] | 0.032 | 26 | 1.3 | 2825 |
| F23[A] | 1.7 | ND | ND | ND |
| F23[B] | 0.039 | 35 | 2.2 | 3736 |
| F24[B] | 0.078 | 58 | 5.9 | 2848 |
| F25[B] | 0.042 | 36 | 2.0 | 4411 |
| F26[B] | 0.034 | 43 | 1.9 | >10000 |
| F34[B] | 0.042 | 74 | 6.7 | 7417 |
| F37[B] | 0.041 | 20 | 2.8 | 1442 |
| F38[B] | 0.07 | 38 | 3.8 | 1745 |
| F40[B] | 0.045 | 18 | 2.7 | 2702 |
| F41[B] | 0.059 | 22 | 4.5 | 4302 |
| F43[B] | 0.015 | 18 | 0.41 | 2520 |
| F44[B] | 0.048 | 61 | 1.1 | 1378 |
| F45[B] | 0.036 | 46 | 1.0 | 5979 |
| F46[B] | 0.052 | 28 | 0.4 | 2847 |
| F47[B] | 0.038 | 34 | 0.7 | 1468 |
| F48[B] | 0.074 | 132 | 1.8 | 3753 |
| F62[B] | 0.023 | 29 | 1.4 | 991 |
| F63[B] | 0.021 | 17 | 0.8 | 6819 |
| F64[B] | 0.02 | 28 | 0.8 | 2442 |
| F90[B] | 0.094 | 99 | 3.6 | >10000 |
| F91b[B] | 0.063 | 27 | 0.38 | 957 |
| F92[B] | 0.025 | 22 | 1.2 | 1370 |
| F99[B] | 0.024 | 52 | 2.6 | 3080 |
| F104[B] | 0.055 | 86 | 0.4 | 1490 |
| F106[B] | 0.021 | 67 | 0.7 | 1206 |
| F109[B] | 0.039 | 167 | 1.2 | 3847 |
| F111[B] | 0.03 | 61 | 0.4 | 1663 |
| F120[B] | 0.025 | 37 | 2.7 | 2520 |
| F126[B] | 0.076 | 50 | 7.5 | >10000 |
| F130[B] | 0.021 | 23 | 0.5 | 7350 |
| F132b[B] | 0.015 | 7.1 | 0.49 | 4260 |

TABLE 3B-continued

| Example | | Biochemical activity (IC$_{50}$, nM) | | Celluclar activity (IC$_{50}$, nM) | |
|---|---|---|---|---|---|
| | | Bcl-2 | Bcl-xl | RS 4; 11 | Molt-4 |
| ABT-199[A] | | 2.3 | ND | ND | ND |
| ABT-199[B] | 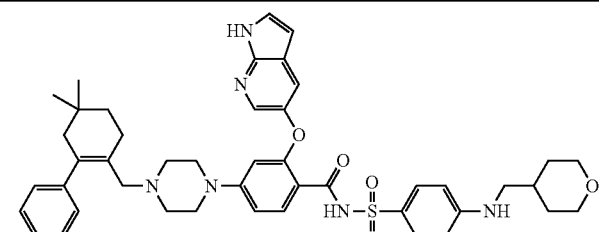 Venetoclax (ABT-199, GDC-0199) | 0.34 | 190 | 9.5 | 3166 |
| F133 | | 49 | >10000 | ND | ND |
| Example 8 from CN106749233 A[B] | 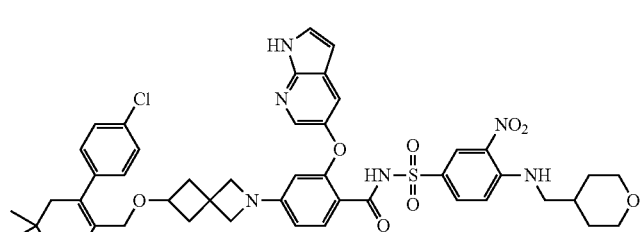 | 84 | >10000 | ND | ND |

[A]Biochemical data using method A; [B]Biochemical data using method B.

Table 3C describes compounds with spiro ring as ring A and their activity in both of biochemical assay (using method B) and cellular assay. As can be seen from the table, inserting CH$_2$— between ring A (spiro ring) and ring B (pyrrolidine ring) dramatically reduced the potency, which is consistent with the unexpected structure-activity relationship (SAR). For example, the 1115 shows >100 folds and 50 folds less potent than its analog F23 in biochemical assay and cellular assay, respectively. FI 13 and FI 14 show 28 to 80 folds and 15 to 22 folds less potent than their analog F34 in biochemical assay and cellular assay, respectively.

Moreover, all these compounds are much more potent than Example 8 from CN106749233A and F133 in biochemical assay, which may be attributed to the optimum combination of the spiro moiety and the 2-(2-substituted phenyl)pyrrolidin-1-yl moiety or 2-(2-substituted phenyl)-4-alkylpiperazin-1-yl moiety of the compounds disclosed herein.

TABLE 3C#

| Example | | Biochemical activity# (IC50, nM) Bcl-2 | Celluclar activity (IC50, nM) RS4;11 |
|---|---|---|---|
| F23 | | 0.039 | 2.2 |
| F90 | | 0.094 | 3.6 |
| F115 | | 6.4 | 123 |
| F34 | | 0.042 | 6.7 |
| F113 | | 7.8 | 103 |
| F114 | | 2.6 | 152 |
| F133 | | 49 | ND |
| Example 8 from CN106749 233A | | 84 | ND |

Protein Purification and Co-Crystallization of Bcl2 with A4a

Recombinant Bcl-2 protein with GST tag was expressed in E. coli BL21 (DE3), induced with 0.1 mM IPTG for 16 h at 16° C., The cells were harvested by centrifugation at 5.000 g for 15 min, re-suspended in lysis buffer containing 20 mM Tris, pH 8.0 and 300 mM NaCl, and lysed by sonication. After centrifugation at 20,000 g for 40 min, the supernatant was incubated with Glutathione S-transferase resin at 4° C. for 30 min. The resin was rinsed three times with the lysis buffer, followed by treatment with PreScission protease at 4° C. overnight. The flow through was concentrated and sequentially applied to a size-exclusion chromatography column (Superdex-75, GE Healthcare) in a buffer containing 20 mM Tris, pH 8.0 and 150 mM NaCl. The peak was collected and concentrated to approximately 10 mg/ml. Protein solution was incubated with A4a for 30 min at 4° C., and then mixed with a reservoir solution containing 0.1 M Bis-Tris, pH 6.6 and 25% PEG 3,350. Co-crystals of Bcl-2 with A4a were obtained by vapor diffusion from hanging drops cultured at 20° C.

X-Ray Data Collection and Structural Determination

Nylon loops were used to harvest the co-crystals and then immersed the crystals in the reservoir solution supplemented with 20% glycerol for 10 sec. Diffraction data were collected on Eiger 16M detector at BL17U1, Shanghai Synchrotron Radiation Facility, and were processed with XDS program. The phase was solved with program PHASER using the Bcl-2 crystal structure (PDB code 4MAN) as the molecular replacement searching model. Phenix.refine was used to perform rigid body, TLS, restrained refinement against X-ray data, followed by manually adjustment in COOT program and further refinement in Phenix.refine program.

| Data collection and refinement statistics | |
|---|---|
| Data collection | |
| Beamline | BL17U1 |
| Space group | P 1 21 1 |
| Cell dimensions (Å) | a = 31.90 b = 40.60 c = 53.81 |
| Angles (°) | α = 90.00 β = 103.66 γ = 90.00 |
| Resolution (Å) | 32.07-1.60 (1.63-1.60) |
| Total number of reflections | 111450 (3130) |
| Number of unique reflections | 17216 (709) |
| Completeness (%) | 96.7 (82.3) |
| Average redundancy | 6.5 (4.4) |
| Rmerge$^a$ | 0.074 (0.619) |
| I/sigma (I) | 12.5 (1.9) |
| Wilson B factor (Å) | 22.8 |
| Refinement | |
| Resolution (Å) | 31.00-1.60 |
| Number of reflections | 17200 |
| rmsd bond lengths (Å) | 0.006 |
| rmsd bond angles (°) | 0.991 |
| $R_{work}^b$ (%) | 18.19 |
| $R_{free}^c$ (%) | 22.27 |
| Average B-factors of protein | 33.360 |
| Ramachandran plot (%) | |
| Favored | 99.26 |
| Allowed | 0.74 |
| Outliers | 0.00 |

Values in parentheses refer to the highest resolution shell.
$^a$Rmerge = $\Sigma\Sigma_i|I(h)_i - \langle I(h)\rangle|/\Sigma\Sigma_i|I(h)_i|$, where $\langle I(h)\rangle$ is the mean intensity of equivalent.
$^b R_{work} = \Sigma|Fo - Fc|/\Sigma|Fo|$, where Fo and Fc are the observed and calculated structure factor amplitudes, respectively.
$^c R_{free} = \Sigma|Fo - Fc|/\Sigma|Fo|$, calculated using a test data set, 5% of total data randomly selected from the observed reflections.

The absolute stereochemistry of the more potent compound A4a in enzymatic and cellular assays is assigned as (S)-configuration on the chiral carbon atom based on its co-crystal structure with Bcl-2 protein. The binding pose of A4a is distinct from that of ABT-199 analog (compound structure see table 3, PDB code: 4MAN) to Bcl2 protein. Compared to ABT-199 analog, 2-(2-chlorophenyl)-pyrrolidinyl moiety of A4a induces a different conformation of the residues around p2 pocket of Bcl-2, such as Phe112, Met115, Glu136 and Phe153, which results in a larger and flatter pocket on the surface of the protein.

Co-Crystal Structure of Bcl-2 with F22

As shown in FIGS. 4, and 5, binding pose of F22 is distinct from that of ABT-199 analog (PDB code: 4MAN). Compared to ABT-199 analog, 2-(2-cyclopropylphenyl)-pyrrolidinyl moiety of F22 induces a different conformation of the residues around p2 pocket of Bcl-2, such as Asp111, Phe112 and Met115, which create an extra sub-pocket. Hydrophobic interaction between 2-cyclopropylphenyl with the surrounding residues contributes to the better potency of F22.

As shown in FIG. 6, water bridge is observed between nitrogen atom of F22 pyrrolidinyl ring and backbone carbonyl of Val133 through 2 water molecules in the crystal structure. This water bridge contributes to a more stable interaction between F22 and Bcl-2 protein, while no such water bridge can be observed between ABT-199 analog and Bcl-2. As shown in FIG. 7, optimal sulfur-π interaction between Met115 and 2-cyclopropylphenyl of F22 is observed in the crystal structure. Similar interaction can also be observed in the crystal structure of ABT-199 analog (PDB code: 4MAN), but the interaction is not optimal in that crystal structure.

In summary, based on the crystal structure of F22, hydrophobic interaction between the cyclopropyl group and induced sub-pocket, water bridge with Val133 and sulfur-π interaction with Met115 all contribute to the better potency of F22.

Protein Purification and Co-Crystallization of Bcl-2 with F22

Protein was purified as described previously. Protein solution was incubated with F22 by a molar ratio 1:2 for 30 min at 4° C., and then mixed with a reservoir solution containing 0.2 M ammonium acetate, 0.1 M Bis-Tris, pH 5.5 and 25% PEG 3,350. Co-crystals were obtained by vapor diffusion from hanging drops cultured at 20° C.

X-Ray Data Collection and Structural Determination

Nylon loops were used to harvest the co-crystals and then immersed the crystals in the reservoir solution supplemented with 20% glycerol for 10 sec. Diffraction data were collected at home lab diffractometer, and were processed with XDS program. The phase was solved with program PHASER using the Bcl-2_G10B-a in house crystal structure as the molecular replacement searching model. Phenix.refine was used to perform rigid body, TLS, restrained refinement against X-ray data, followed by manually adjustment in COOT program and further refinement in Phenix.refine program.

Data Collection and Refinement Statistics

| Data collection | |
|---|---|
| Beamline | Home lab diffractometer |
| Space group | P 21 21 21 |
| Cell dimensions (Å) | a = 32.91 b = 45.73 c = 98.95 |
| Angles (°) | α = 90.00 β = 90.00 γ = 90.00 |
| Resolution (Å) | 41.51-2.60 (2.72-2.60) |
| Total number of reflections | 46305 (5642) |
| Number of unique reflections | 4831 (561) |
| Completeness (%) | 97.5 (95.4) |

-continued

| | |
|---|---|
| Average redundancy | 9.6 (10.1) |
| Rmerge$^a$ | 0.065 (0.478) |
| I/sigma (I) | 28.1 (4.7) |
| Wilson B factor (Å) | 16.14 |
| Refinement | |
| Resolution (Å) | 33.58-2.60 |
| Number of reflections | 4805 |
| rmsd bond lengths (Å) | 0.003 |
| rmsd bond angles (°) | 0.612 |
| R$_{work}^b$ (%) | 18.90 |
| R$_{free}^c$ (%) | 23.20 |
| Average B-factors of protein | 20.74 |
| Ramachandran plot (%) | |
| Favored | 96.75 |
| Allowed | 3.25 |
| Outliers | 0.00 |

Values in parentheses refer to the highest resolution shell.

$^a$Rmerge = $\Sigma\Sigma_i|I(h)_i - \langle I(h)\rangle|/\Sigma\Sigma_i|I(h)_i|$, where $\langle I(h)\rangle$ is the mean intensity of equivalent.
$^b$R$_{work}$ = $\Sigma|Fo - Fc|/\Sigma|Fo|$, where Fo and Fc are the observed and calculated structure factor amplitudes, respectively.
$^c$ R$_{free}$ = $\Sigma|Fo - Fc|/\Sigma|Fo|$, calculated using a test data set, 5% of total data randomly selected from the observed reflections.

Cytochrome P450 Inhibition Assay in Human Liver Microsomes

Method: The five isoform-selective probe substrate (in a cocktail manner) was used as a measure of activity for the individual cytochrome P450 (CYPs) in a pool of human liver microsomes, i.e., phenacetin for CYP1A2, diclofenac for CYP2C9, S-Mephenyloin for CYP2C19, dextromethorphan for CYP2D6, midazolam for CYP3A. Test compounds, at 7 concentration levels including zero, were incubated in human liver microsomes (HLM) together with the 5 probe substrate (in a cocktail manner). IC$_{50}$ was determined by monitoring the reduction of the CYP activity as a function of test compound concentration and quantified by product formation using LC-MS/MS. Ketoconazole for CYP3A was included as quality control. All incubations were performed in singlet. The final incubation conditions are listed below.

| Reaction Component | Final Concentration |
|---|---|
| HLM | 0.1 mg · mL$^{-1}$ |
| Buffer | Phosphate Buffer (100 mM, pH 7.4) |
| Test Compound | 7 Concentration Points Including Zero (0~30 µM or 0~10 µM, as requested) |
| Positive Control | Ketoconazole for CYP3A (7 Concentration Points Containing Zero, 0~0.3 µM) |
| Probe Substrate | Phenacetin for CYP1A2 (10 µM) |
| (in a cocktail manner) | Diclofenac for CYP2C9 (5 µM) |
| | S-Mephenytoin for CYP2C19 (30 µM) |
| | Dextromethorphan for CYP2D6 (5 µM) |
| | Midazolam for CYP3A (2 µM) |
| NADPH | 1 mM |
| Incubation Time | 15 min |
| MgCl$_2$ | 3 mM |

Data Analysis: The uninhibited fraction of CYP activity (remaining activity fraction) will be calculated as $$\frac{(A_M/A_{IS})_I}{(A_M/A_{IS})_0},$$

where $A_M$ and $A_{IS}$ denote the peak areas of the probe metabolites and IS, respectively, and "1" and "0" represent the incubations in the presence and absence of the test compound, respectively. The IC$_{50}$ value of test compound will be determined as appropriate by fitting a curve of uninhibited fraction versus concentration of the test compound, using the following four-parameter model (Hill equation):

$$y = \text{Botttom} + \frac{\text{Top} - \text{Bottom}}{1 + \left(\frac{IC50}{x}\right)^S}$$

where Top, Bottom, S, x and y donate the experimentally maximum remaining enzyme activity (%), the experimentally minimum remaining enzyme activity (%), the slope factor, the test compound concentration, and the uninhibited fraction (%), respectively.

In the case that no significant inhibition is observed over the concentration range (the uninhibited fraction does not reach 50% even at the highest test compound concentration), the IC$_{50}$ will not be calculated.

The general criteria to e valuate the potential risk of drug-drug interaction (DDI) is as followed IC50>10 µM: low CYP inhibition;

µM<IC50<10 11M: moderate CYP inhibition;

IC50<3 µM: high CYP inhibition.

| Compound/Example | CYP 2C9 (IC$_{50}$ µM) |
|---|---|
| ABT-199 | 1.77 |
| ABT-263 | 1.50 |
| G2 | 16.8 |
| G12 | 6.25 |
| G10b-b | 6.85 |
| G24b-b | 8.21 |
| G35b | 8.86 |
| G77-S | 17.5 |
| F21 | >30 |
| F26 | >30 |
| F37 | 15.9 |
| F43 | >30 |
| F44 | >10 |
| F45 | 8.9 |
| F106 | 6.3 |
| F107 | 7.4 |
| G122 | >10 |
| G124 | >10 |

Compared with Compound ABT-199 (Venetoclax) and ABT-263 (Navitoclax) showing high CYP 2C9 inhibition, representative compounds disclosed herein, for example. Compounds G2, G12, G10b-b, G24 h-b, G35b, G77-S, F21, F26, F37, F43, F44, F45, F106, F107, G122 and G124 showed much lower CYP 2C9 inhibition, indicating the compounds disclosed herein have lower potential risk of drug-drug interaction (DD1).

It is to be understood that, if any prior art publication is referred to herein; such reference does not constitute an admission that the publication forms a part of the common general knowledge in the art in any country.

The disclosures of all publications, patents, patent applications and published patent applications referred to herein by an identifying citation are hereby incorporated herein by reference in their entirety.

Although the foregoing invention has been described in some detail by way of illustration and example for purposes of clarity of understanding, it is apparent to those skilled in the art that certain minor changes and modifications will be practiced. Therefore, the description and Examples should not be construed as limiting the scope of the invention.

What is claimed is:
1. A compound of Formula (II)

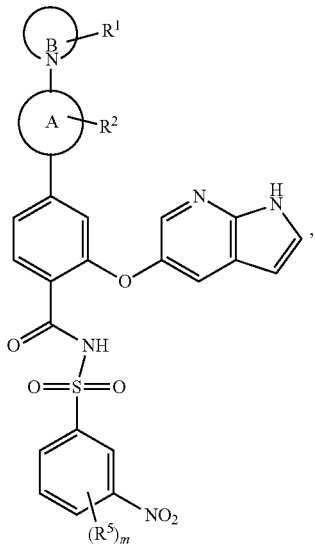

(II)

or a pharmaceutically acceptable salt thereof, or a stereoisomer thereof,
wherein
ring A is a phenyl ring, which is 1,4-phenylene; or a 5 to 12-membered spiro heterocyclyl comprising one or two heteroatoms selected from nitrogen, sulfur, and oxygen as ring members, each of which is optionally substituted with 1 to 4 substituents $R^2$;
$R^2$, at each occurrence, is independently selected from the group consisting of hydrogen, halogen, and —$C_{1-8}$alkyl optionally substituted with halogen;
ring B is a monocyclic 4 to 9-membered heterocyclyl comprising one nitrogen atom as the ring member or a monocyclic 4 to 9-membered heterocyclyl comprising one nitrogen atom and one additional heteroatom selected from the group consisting of NH, O, S, SO and $SO_2$ heteroatoms as ring members, wherein ring B is N-linked to ring A;
$R^1$, at each occurrence, is independently hydrogen, halogen, —$C_{1-8}$alkyl, —$C_{2-8}$alkenyl, —$C_{2-8}$ alkynyl, cycloalkyl, heterocyclyl, aryl, heteroaryl, oxo, —CN, —$NO_2$, —$OR^{1a}$, —$SO_2R^{1a}$, —$COR^{1a}$, —$CO_2R^{1a}$, —$CONR^{1a}R^{1b}$, —$C(=NR^{1a})NR^{1b}R^{1c}$, —$NR^{1a}R^{1b}$, —$NR^{1a}COR^{1b}$, —$NR^{1a}CONR^{1b}R^{1c}$, —$NR^{1a}CO_2R^{1b}$, —$NR^{1a}SONR^{1b}R^{1c}$, —$NR^{1a}SO_2NR^{1b}R^{1c}$, or —$NR^{1a}SO_2R^{1b}$; wherein said —$C_{1-8}$alkyl, —$C_{2-8}$alkenyl, —$C_{2-8}$alkynyl, cycloalkyl, heterocyclyl, aryl or heteroaryl are each independently optionally substituted with 1 to 4 substituents $R^{1d}$,
$R^{1a}$, $R^{1b}$, and $R^{1c}$, are each independently hydrogen, —$C_{1-8}$alkyl, —$C_{2-8}$alkenyl, —$C_{2-8}$alkynyl, cycloalkyl, heterocyclyl, aryl, or heteroaryl, each of-said —$C_{1-8}$alkyl, —$C_{2-8}$alkenyl, —$C_{2-8}$alkynyl, cycloalkyl, heterocyclyl, aryl, or heteroaryl is optionally substituted with halogen, hydroxy or —$C_{1-8}$alkyoxy;
$R^{1d}$, at each occurrence is independently halogen, —$C_{1-8}$alkyl, —$C_{2-8}$alkenyl, —$C_{2-8}$alkynyl, cycloalkyl, heterocyclyl, aryl, or heteroaryl, oxo, —CN, —$NO_2$, —$OR^{Ba}$, —$SO_2R^{Ba}$, —$COR^{Ba}$, —$CO_2R^{Ba}$, —$CONR^{Ba}R^{Bb}$, —$C(=NR^{Ba})NR^{Bb}R^{Bc}$, —$NR^{Ba}R^{Bb}$, —$NR^{Ba}COR^{Bb}$, —$NR^{Ba}CONR^{Bb}R^{Bc}$, —$NR^{Ba}CO_2R^{Bb}$, —$NR^{Ba}SONR^{Bb}R^{Bc}$, —$NR^{Ba}SO_2NR^{Bb}R^{Bc}$, or —$NR^{Ba}SO_2R^{Bb}$; wherein said —$C_{1-8}$alkyl, —$C_{2-8}$alkenyl, —$C_{2-8}$alkynyl, cycloalkyl, heterocyclyl, aryl or heteroaryl are each independently optionally substituted with 1 to 4 substituents $R^{Bd}$;
$R^{Ba}$, $R^{Bb}$, and $R^{Bc}$, are each independently hydrogen, —$C_{1-8}$alkyl, —$C_{2-8}$alkenyl, —$C_{2-8}$alkynyl, cycloalkyl, heterocyclyl, aryl, or heteroaryl, each of said —$C_{1-8}$alkyl, —$C_{2-8}$alkenyl, —$C_{2-8}$alkynyl, cycloalkyl, heterocyclyl, aryl, or heteroaryl is optionally substituted with halogen, hydroxy, —$NH_2$ or —$N(C_{1-6}$alkyl$)_2$, —$C_{1-8}$alkyoxy, cycloalkyl, heterocyclyl, aryl, or heteroaryl;
$R^{Bd}$, at each occurrence, is independently hydrogen, halogen, oxo, —CN, —$NO_2$, —$C_{1-8}$alkyl, —$C_{2-8}$alkenyl, —$C_{2-8}$alkynyl, cycloalkyl, heterocyclyl, aryl, or heteroaryl, each of-said —$C_{1-8}$alkyl, —$C_{2-8}$alkenyl, —$C_{2-8}$alkynyl, cycloalkyl, heterocyclyl, aryl, or heteroaryl is optionally substituted with halogen, hydroxy, —$C_{1-8}$alkyoxy, cycloalkyl, heterocyclyl, aryl, or heteroaryl;
$R^5$ is -$L^5$-CyC,
wherein $L^5$ is a direct bond, —$(CR^aR^b)_t$—, —$(CR^aR^b)_{t-1}$—$(CR^c=CR^d)$—$(CR^aR^b)_{v-1}$—, —$(CR^aR^b)_{t-1}$—$(C\equiv C)$—$(CR^aR^b)_{v-1}$, —O—, —S—, —S(O)—, —$SO_2$—, —C(O)—, C(O)O—, —OC(O)—, —$NR^a$—, —$C(O)NR^a$—, —$NR^aC(O)$—, —$NR^aC(O)O$—, —$NR^aC(O)NR^b$—, —$SO_2NR^a$—, —$NR^aSO_2$—, —$NR^aS(O)_2NR^b$—, —$N^aS(O)NR^b$—, —$C(O)NR^aSO_2$—, —$C(O)NR^aSO$—, or —$C(=NR^a)NR^b$—,
wherein t and v, at each occurrence, are independently a number of 1 to 7, and one or two $CR^aR^b$ moieties in —$(CR^aR^b)_t$—, —$(CR^aR^b)_{t-1}$—$(CR^c=CR^d)$—$(CR^aR^b)_{v-1}$—, or —$(CR^aR^b)_{t-1}$—$(C\equiv C)$—$(CR^aR^b)_{v-1}$— are un-replaced or replaced with one or more moieties selected from the group consisting of O, S, SO, $SO_2$, C(O) and $NR^a$;
CyC is cycloalkyl, heterocyclyl, aryl, or heteroaryl, each of which is optionally substituted with one or two substituents $R^{5a}$;
$R^{5a}$, at each occurrence, is independently selected from hydrogen, halogen, cyano, oxo, —$NO_2$, —$OR^{5b}$, —$SR^{5b}$, —$NR^{5b}R^{5c}$, —$COR^{5b}$, —$SO_2R^{5b}$, —$C(=O)OR^{5b}$, —$C(=O)NR^{5b}R^{5c}$, —$C(=NR^{5b})NR^{5c}R^{5d}$, —$N(R^{5b})C(=O)R^{5c}$, —$N(R^{5b})C(=O)OR^{5c}$, —$N(R^{5b})C(O)NR^{5c}R^{5d}$, —$N(R^{5b})S(O)NR^{5c}R^{5d}$, —$N(R^{5b})S(O)_2NR^{5c}R^{5d}$, —$NR^{5b}SO_2R^{5c}$, —$C_{1-8}$alkyl, —$C_{2-8}$alkenyl, —$C_{2-8}$alkynyl, -cycloalkyl, heterocyclyl, aryl, or heteroaryl, each of said —$C_{1-8}$alkyl, —$C_{2-8}$alkenyl, —$C_{2-8}$alkynyl, -cycloalkyl, heterocyclyl, aryl, or heteroaryl is optionally substituted with one or two substituents $R^{5e}$;
wherein $R^{5b}$, $R^{5c}$, and $R^{5d}$ are each independently hydrogen, —$C_{1-8}$alkyl, —$C_{2-8}$alkenyl, —$C_{2-8}$alkynyl, cycloalkyl, heterocyclyl, aryl, or heteroaryl, each of said —$C_{1-8}$alkyl, —$C_{2-8}$alkenyl, $C_{2-8}$alkynyl, -cycloalkyl, heterocyclyl, aryl, or heteroaryl is optionally substituted with one or two substituents $R^{5e}$;
$R^{5e}$, at each occurrence, is independently selected from hydrogen, halogen, cyano, oxo, —$NO_2$, —$OR^{5f}$, —$SR^{5f}$, —$NR^{5f}R^{5g}$, —$COR^{5f}$, —$SO_2R^{5f}$, —$C(=O)OR^{5f}$, —$C(=O)NR^{5f}R^{5g}$, —$C(=NR^{5f})NR^{5g}R^{5h}$, —N(R$^{5f}$)C(=O)R$^{5g}$, —N(R$^{5f}$)C(=O)OR$^{5g}$, —N(R$^{5f}$)C(O)NR$^{5g}$R$^{5h}$, —N(R$^{5f}$)S(O)NR$^{5g}$R$^{5h}$, —N(R$^{5f}$)S(O)$_2$NR$^{5g}$R$^{5h}$, —NR$^5$SO$_2$R$^{5g}$, —C$_{1-8}$alkyl, —C$_{2-8}$alkenyl, —C$_{2-8}$alkynyl, -cycloalkyl, heterocyclyl, aryl, or heteroaryl;

R$^{5f}$, R$^{5g}$, and R$^{5h}$ are each independently hydrogen, —C$_{1-8}$alkyl, —C$_{2-8}$alkenyl, —C$_{2-8}$alkynyl, cycloalkyl, heterocyclyl, aryl, or heteroaryl;

or, two adjacent R$^5$ on the phenyl ring together with the phenyl ring form a benzo ring, said ring is optionally substituted with halogen, oxo, cyano, —NO$_2$, —OR$^{5i}$, —SR$^{5i}$, —NR$^{5i}$R$^{5j}$, —COR$^{5i}$, —SO$_2$R$^{5i}$, —C(=O)OR$^{5i}$, —C(=O)NR$^{5i}$R$^{5j}$, —C(=NR$^{5i}$)NR$^{5j}$R$^{5k}$, —N(R$^{5i}$)C(=O)R$^{5j}$, —N(R$^{5i}$)C(=O)OR$^{5j}$, —N(R$^{5i}$)C(O)NR$^{5j}$R$^{5k}$, —N(R$^{5i}$)S(O)NR$^{5j}$R$^{5k}$, —N(R$^{5i}$)S(O)$_2$NR$^{5j}$R$^{5k}$, —NR$^{5i}$SO$_2$R$^{5k}$, —C$_{1-8}$alkyl, —C$_{2-8}$alkenyl, —C$_{2-8}$alkynyl, -cycloalkyl, heterocyclyl, aryl, or heteroaryl;

R$^{5i}$, R$^{5j}$, and R$^{5k}$ are independently hydrogen, —C$_{1-8}$alkyl, —C$_{2-8}$alkenyl, —C$_{2-8}$alkynyl, cycloalkyl, heterocyclyl, aryl, or heteroaryl, each of said —C$_{1-8}$alkyl, —C$_{2-8}$alkenyl, —C$_{2-8}$alkynyl, cycloalkyl, heterocyclyl, aryl, or heteroaryl is optionally substituted with halogen, hydroxy or —C$_{1-8}$alkyoxy;

m is an integer of 1-4; and

R$^a$, R$^b$, R$^c$, and R$^d$ at each occurrence, are independently hydrogen, —C$_{1-8}$alkyl, —C$_{2-8}$alkenyl, —C$_{2-8}$alkynyl, cycloalkyl, heterocyclyl, aryl, or heteroaryl, said —C$_{1-8}$alkyl, —C$_{2-8}$alkenyl, —C$_{2-8}$alkynyl, cycloalkyl, heterocyclyl, aryl, or heteroaryl are each independently substituted with —CN, halogen, —NO$_2$, —NR$^e$R$^f$, oxo, —OR$^e$, or —SR$^e$;

wherein R$^e$ and R$^f$ are each independently hydrogen, C$_{1-8}$alkyl, C$_{1-8}$alkoxy-C$_{1-8}$alkyl-, C$_{2-8}$alkenyl, C$_{2-8}$alkynyl, cycloalkyl, aryl, heterocyclyl, or heteroaryl.

2. The compound of claim 1, wherein ring A is 1,4-phenylene.

3. The compound of claim 1, wherein ring A is 4-membered/4-membered, 3-membered/5-membered, 4-membered/5-membered, 4-membered/6-membered, 5-membered/5-membered, or 5-membered/6-membered monospiro heterocyclyl comprising one or two nitrogen or oxygen as ring members.

4. The compound of claim 3, wherein ring A is

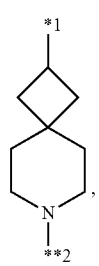

(7-azaspiro[3.5]nonan-2,7-diyl)

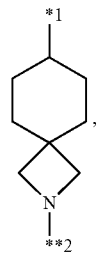

(2-azaspiro[3.5]nonan-2,7-diyl)

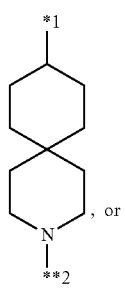

, or (3-azaspiro[5.5]undecan-3,9-diyl)

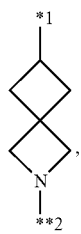

(2-azaspiro[3.3]heptan-2,6-diyl)

wherein *1 refers to the position attached to ring B, and **2 refers to the position attached to the phenyl ring.

5. The compound of claim 1, wherein ring B is aziridin-1-yl, azetidin-1-yl, pyrrolidin-1-yl, pyrrolidin-2-yl, piperidin-1-yl, azepan-1-yl, or azocan-1-yl, which is substituted with a phenyl group at position 2 and ring B is further optionally substituted with R$^1$, and said phenyl group at position 2 (i.e., ortho position) is optionally substituted with R$^{1d}$.

6. The compound of claim 1, wherein the compound has the following formula (III)

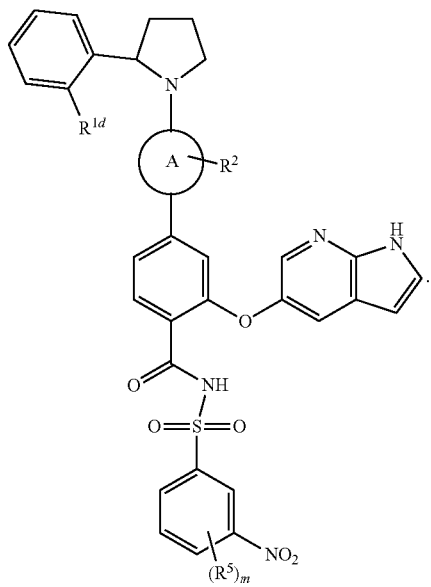
(III)

or a pharmaceutically acceptable salt thereof, or a stereoisomer thereof.

7. The compound of claim 6, wherein ring A is

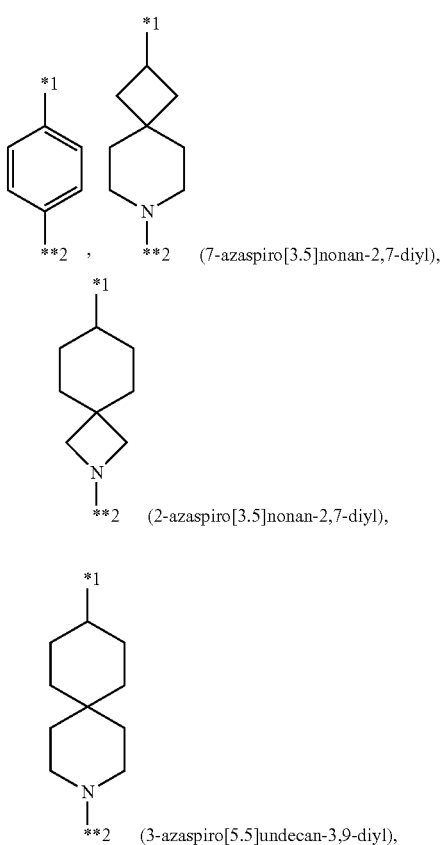

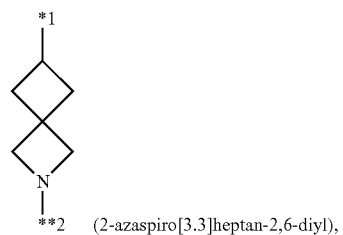
(2-azaspiro[3.3]heptan-2,6-diyl), wherein *1 refers to the position attached to the pyrrolidinyl ring, and **2 refers to the position attached to the phenyl ring.

8. The compound of claim 7, wherein the compound is represented by the following subgenus formulas (III-A), (III-B), (III-C), (III-D) or (III-E)

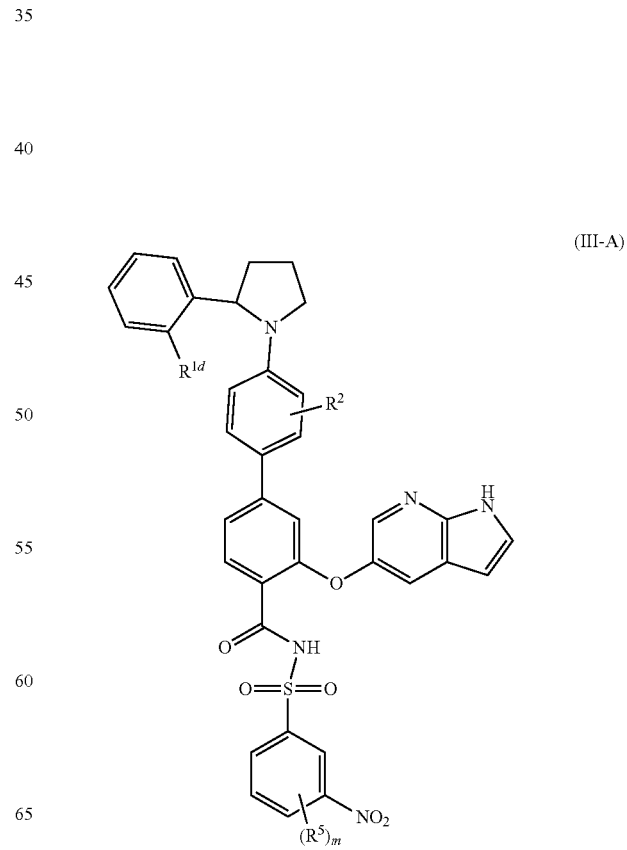
(III-A)

-continued (III-B)

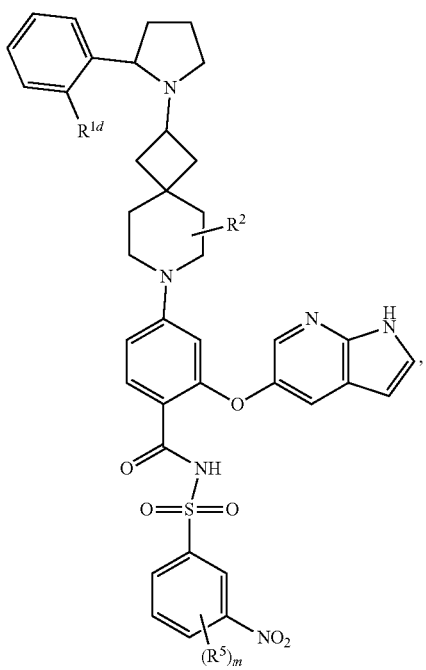

(III-C)

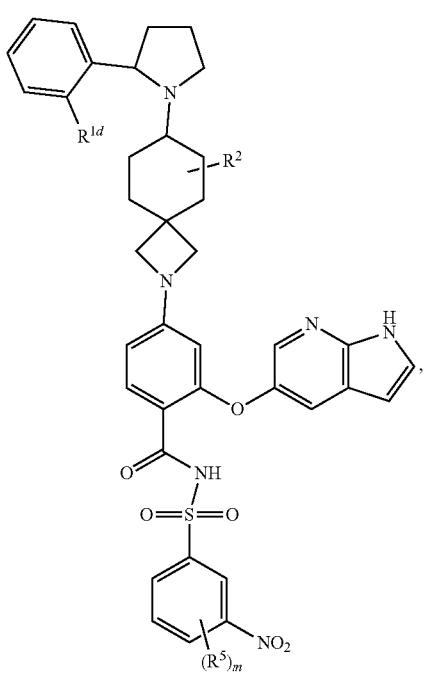

-continued (III-D)

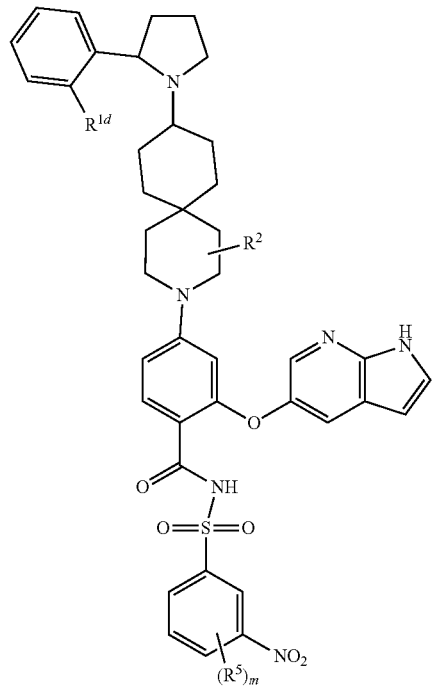

(III-E)

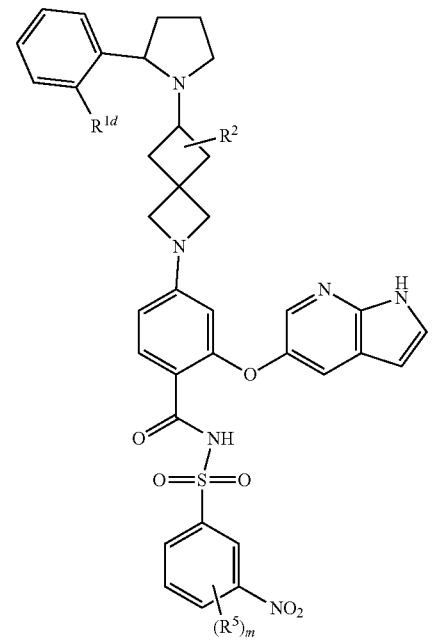

or a pharmaceutically acceptable salt thereof, or a stereoisomer thereof.

9. The compound of claim 1, wherein $R^2$ is hydrogen.

10. The compound of claim 1, wherein $R^{1d}$ is independently halogen, —$C_{1-8}$alkyl, —$C_{2-8}$alkenyl, —$C_{2-8}$alkynyl, cycloalkyl, heterocyclyl, aryl, heteroaryl, —CN, —$OR^{Ba}$, —$SO_2R^{Ba}$, —$CONR^{Ba}R^{Bb}$, —$NO_2$, —$NR^{Ba}R^{Bb}$, —$NR^{Ba}COR^{Bb}$, or —$NR^{Ba}SO_2R^{Bb}$; wherein said —$C_{1-8}$alkyl, —$C_{2-8}$alkenyl, —$C_{2-8}$alkynyl, cycloalkyl, heterocyclyl, aryl or heteroaryl are each independently optionally substituted with 1 to 4 $R^{Bd}$ substituents.

11. The compound of claim 10, wherein $R^{1d}$ is methyl, ethyl, isopropyl, propyl, methoxymethyl, propenyl, cyclopropyl, cyclobutyl, cyclopentyl, cyclohexyl, ethoxy, isopropoxy, amino or dimethylamino.
12. The compound of claim 1, wherein ring B with R¹ substituent is selected from the group consisting of:
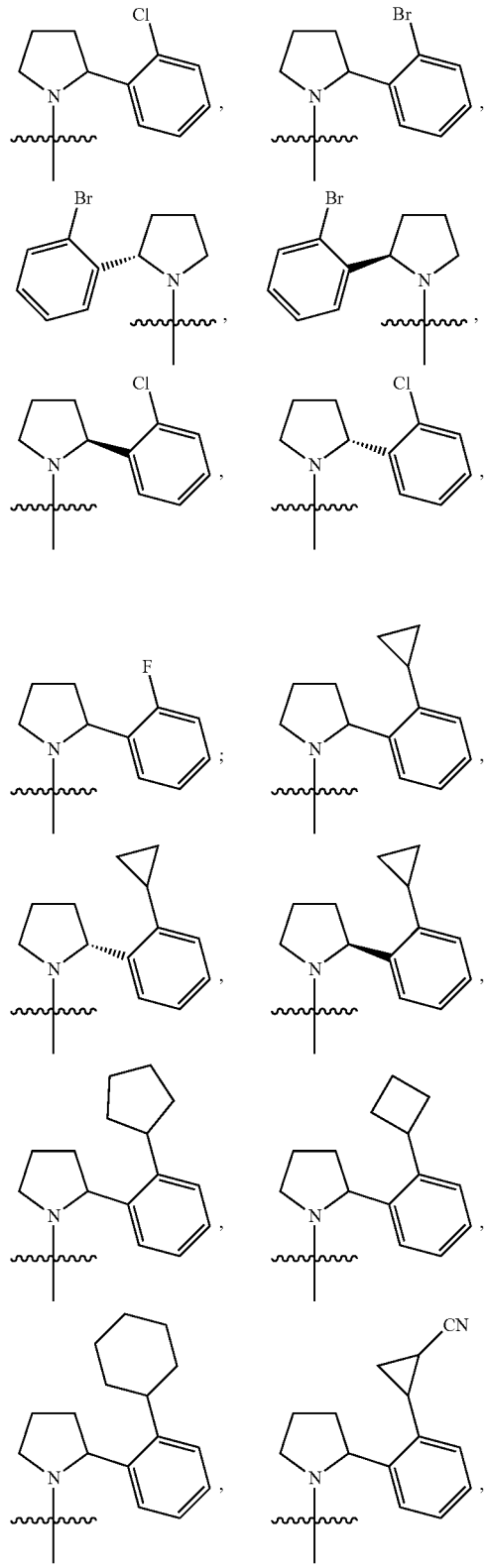
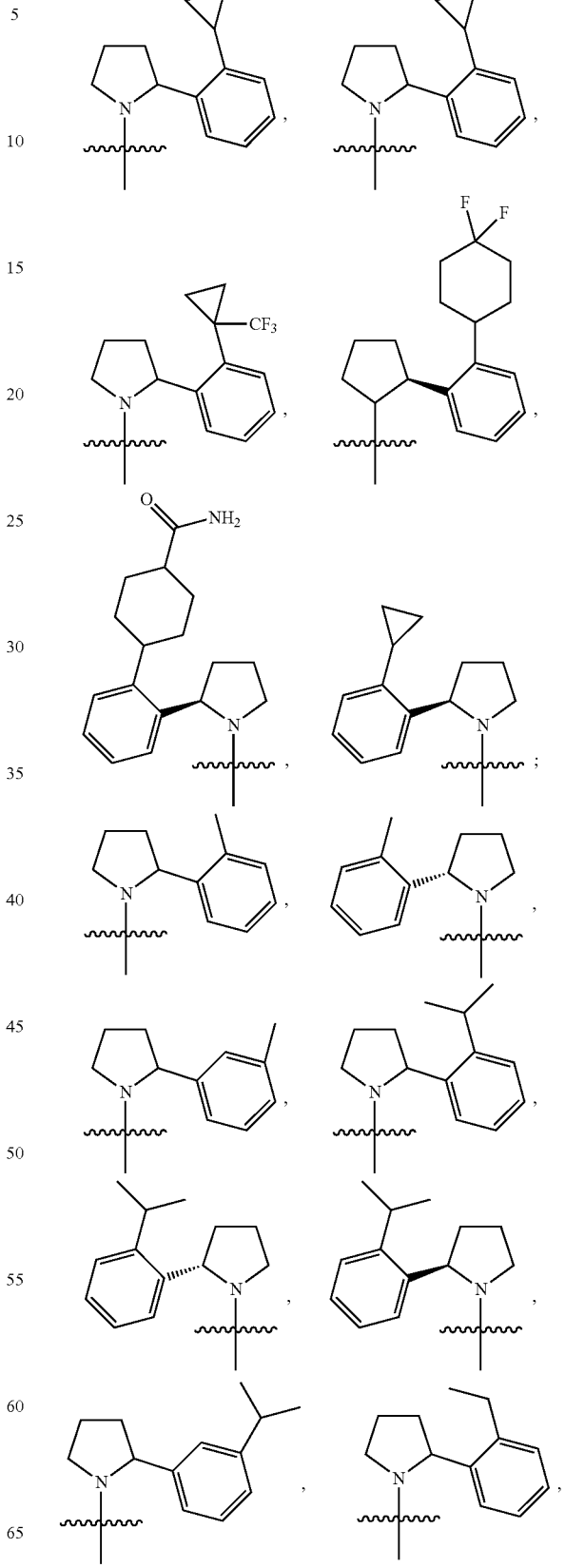

949 -continued
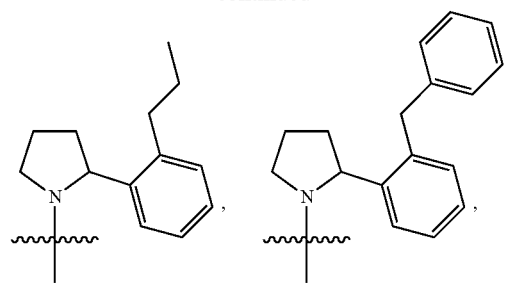
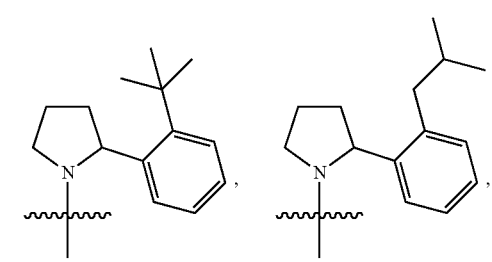
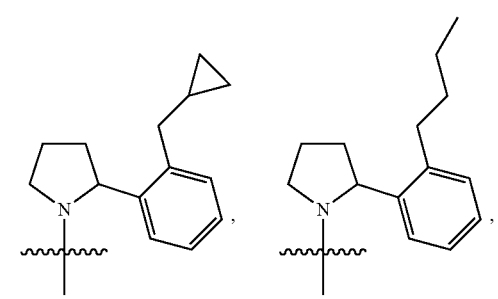
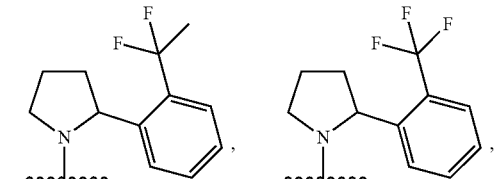
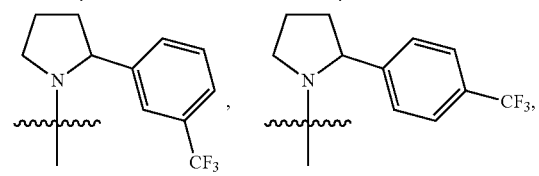
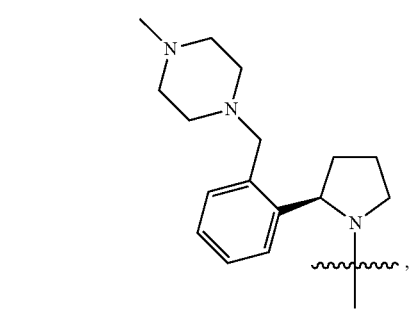
950 -continued
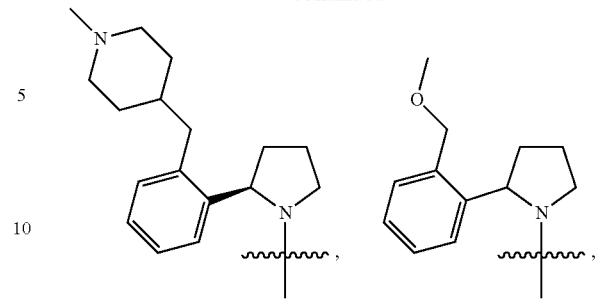
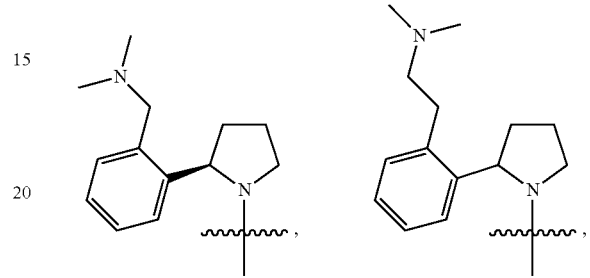
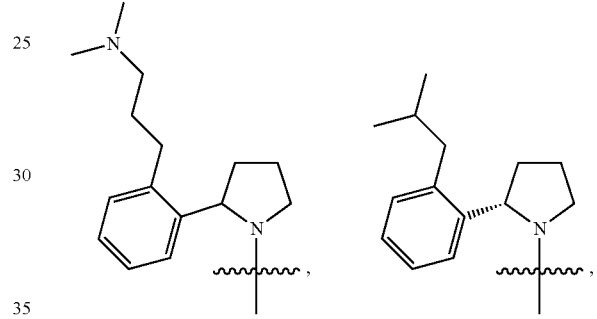
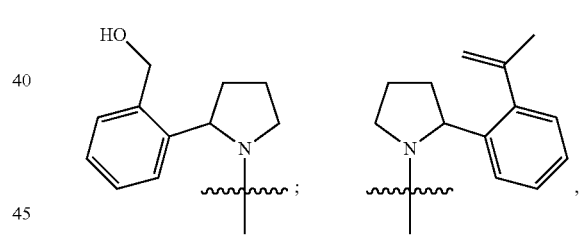
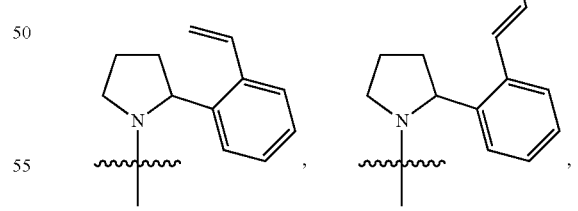
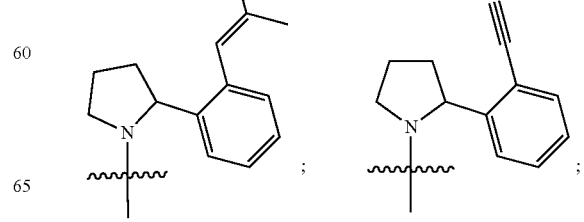

951
-continued
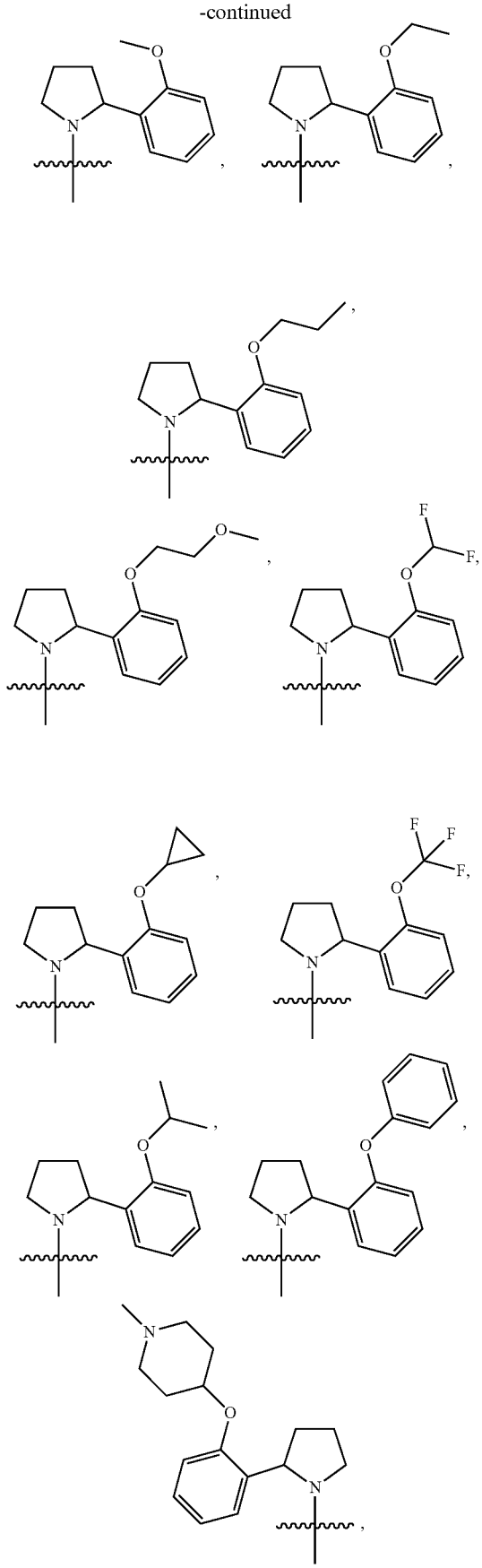
952
-continued
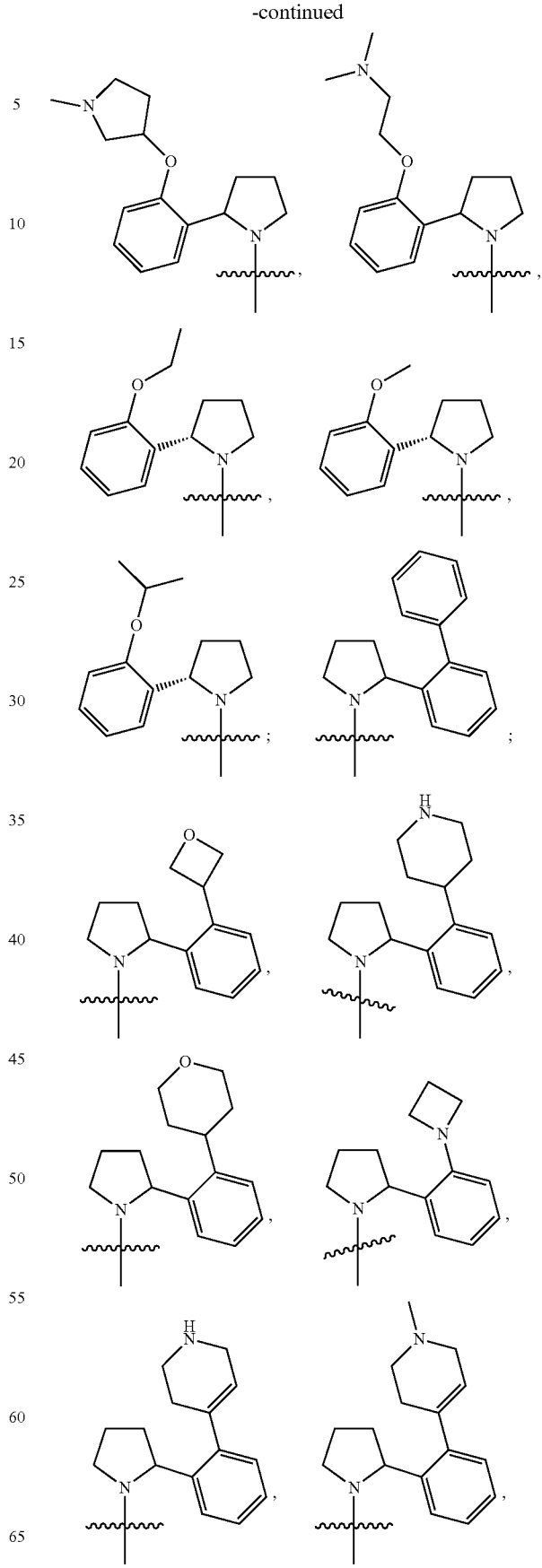

953
-continued
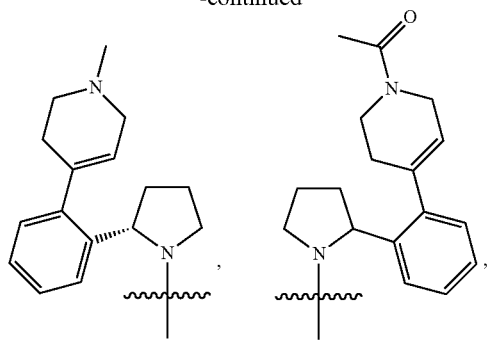
954
-continued
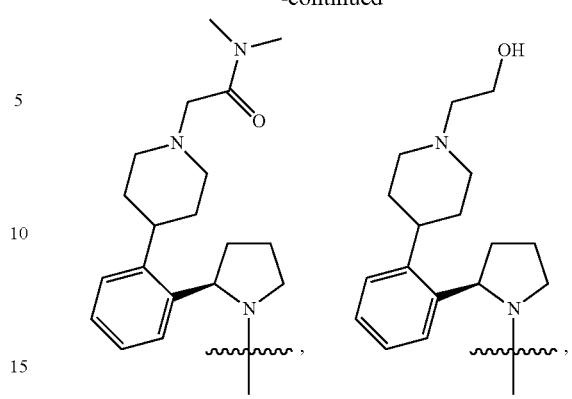
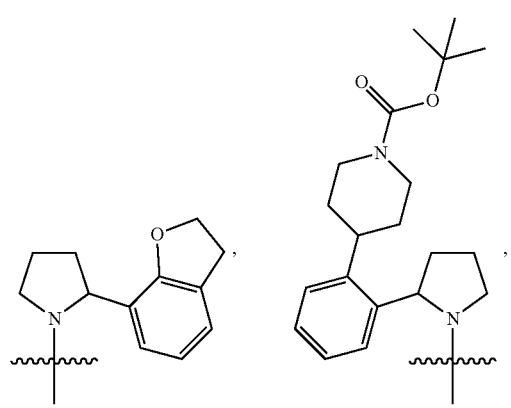
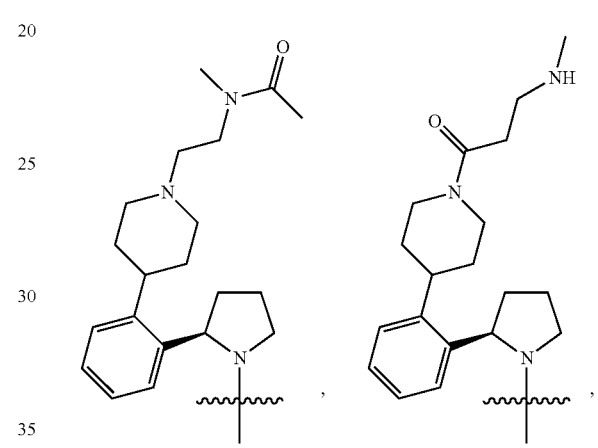
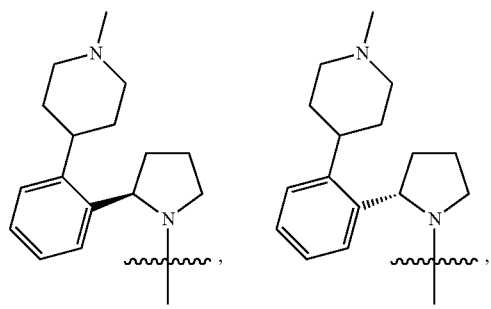
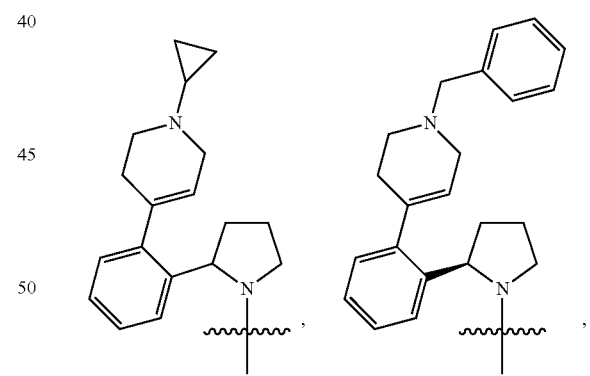
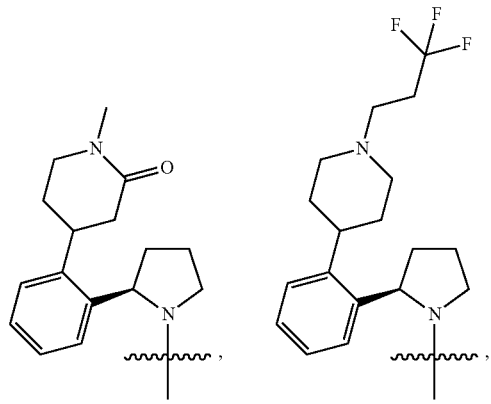
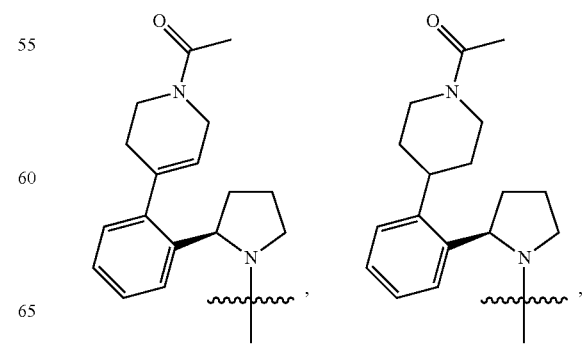

955
-continued
956
-continued
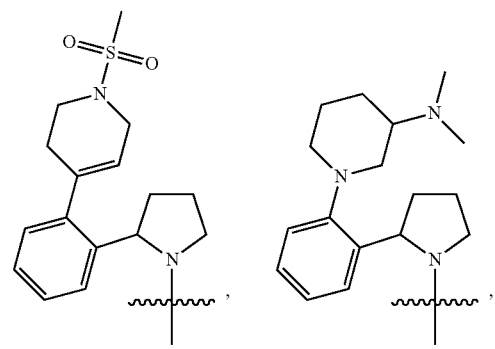
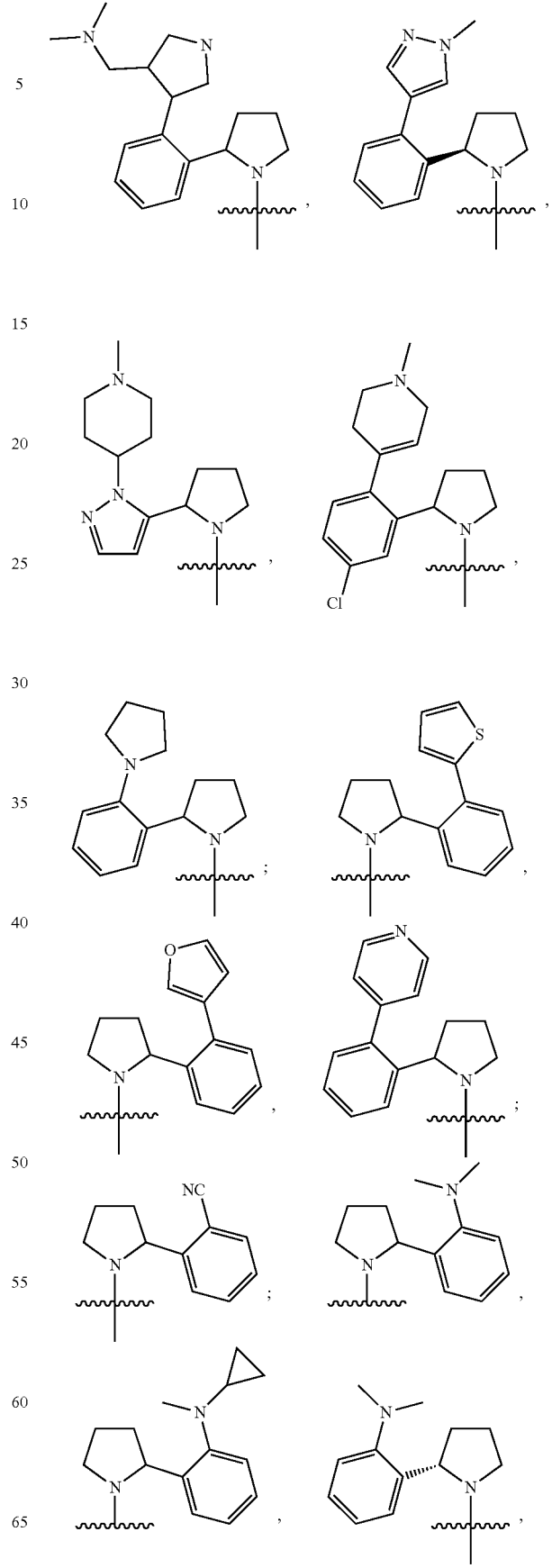

-continued

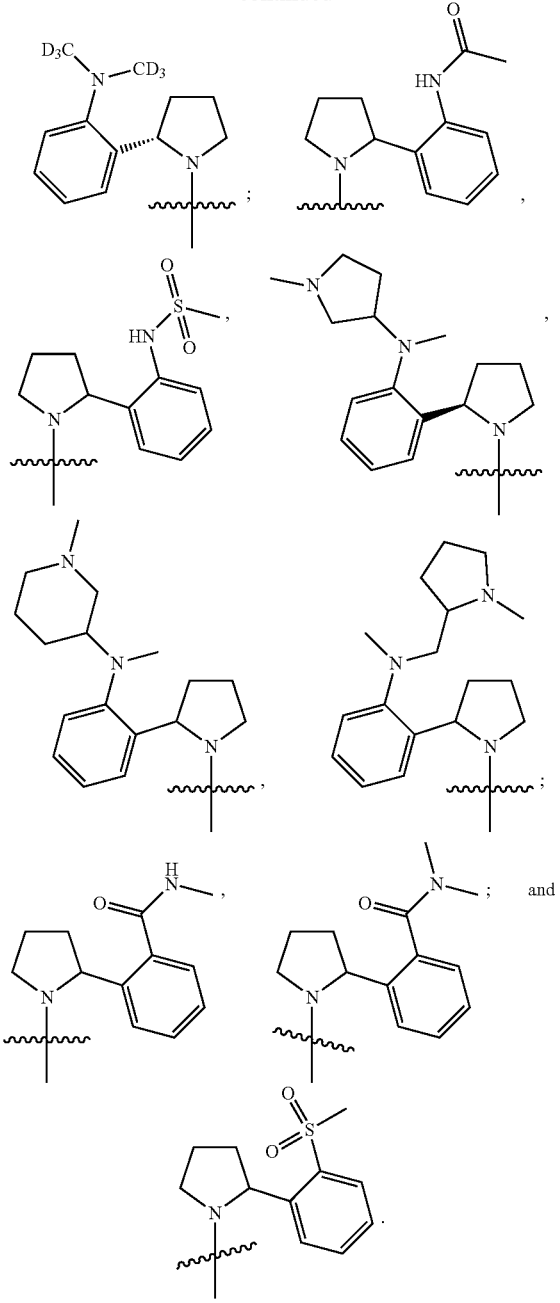

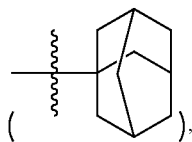

13. The compound of claim 1, wherein m is 1; and $L^5$ is a direct bond, —$(CR^aR^b)_t$— or —$NR^a$—, wherein t is a number of 1 to 7, and one or two $CR^aR^b$ moieties in —$(CR^aR^b)_t$— are un-replaced or replaced with one or more moieties selected from O and $NR^a$.

14. The compound of claim 1, wherein:
(i) $L^5$ is a direct bond, —$(CH_2)_{1-4}$—, —O—$(CH_2)_{1-3}$—, —NH—$(CH_2)_{1-3}$—, or —NH—; or
(ii) $L^5$ is —NH—$(CR^aR^b)$—$(CH_2)_2$—, wherein $R^a$ is hydrogen; and $R^b$ is $C_{1-8}$alkyl optionally substituted with phenyl-S—.

15. The compound of claim 1, wherein CyC is cycloalkyl, or heterocyclyl, each of which is optionally substituted with one or two substituents $R^{5a}$;
$R^{5a}$ is independently selected from hydrogen, halogen, cyano, oxo, —$OR^{5b}$, —$NR^{5b}R^{5c}$, —$COR^{5b}$, —$SO_2R^{5b}$, —$C_{1-8}$alkyl, —$C_{2-8}$alkynyl, -cycloalkyl, or heterocyclyl, each of said —$C_{1-8}$ alkyl, and heterocyclyl is optionally substituted with one or two substituents $R^{5e}$ which is selected from hydrogen, halogen, cyano, —$OR^{5f}$, —$C_{1-8}$alkyl, -cycloalkyl, or heterocyclyl;
wherein $R^{5b}$, and $R^{5c}$ are each independently hydrogen, —$C_{1-8}$alkyl or heterocyclyl, said —$C_{1-8}$alkyl is optionally substituted with one or two substituents $R^{5e}$ which is hydrogen, —$NR^{5f}R^{5g}$, or -cycloalkyl; $R^{5f}$ and $R^{5g}$ are each independently hydrogen or —$C_{1-8}$alkyl;
or, two adjacent $R^5$ on the phenyl ring together with the phenyl ring form a benzo ring, said ring is optionally substituted with heteroaryl.

16. The compound of claim 15, wherein CyC is cycloalkyl selected from monocyclic $C_{3-8}$cycloalkyl or bridged cycloalkyl each of which is optionally substituted with one or two substituents $R^{5a}$.

17. The compound of claim 15, wherein CyC is heterocyclyl selected from:
a) monocyclic 4 to 9-membered heterocyclyl groups containing one nitrogen or oxygen or sulfur heteroatom as ring member;
b) monocyclic 4 to 9-membered heterocyclyl groups containing two heteroatoms selected from oxygen, sulfur and nitrogen as ring members; and
c) 5 to 20-membered spiro heterocyclyl comprising one or two heteroatoms selected from nitrogen, sulfur and oxygen as ring members,
each of which is optionally substituted with one or two $R^{5a}$.

18. The compound of claim 17, wherein CyC is monocyclic 4 to 6-membered heterocyclyl groups containing one nitrogen or oxygen or sulfur heteroatom as ring member.

19. The compound of claim 17, wherein CyC is monocyclic 6-membered heterocyclyl group containing two heteroatoms selected from oxygen and nitrogen as ring members.

20. The compound of claim 15, wherein $R^{5a}$ is independently selected from hydrogen, halogen, cyano, oxo, —$OR^{5b}$, —$NR^{5b}R^{5c}$, —$COR^{5b}$, —$SO_2R^{5b}$, —$C_{1-8}$alkyl, —$C_{2-8}$alkynyl, monocyclic $C_{3-8}$cycloalkyl, or monocyclic 4 to 9-membered heterocyclyl group containing one or two heteroatoms selected from nitrogen or oxygen or sulfur heteroatom as ring members, each of said —$C_{1-8}$alkyl and monocyclic 4 to 9-membered heterocyclyl group is optionally substituted with one or two substituents $R^{5e}$.

21. The compound of claim 15, wherein $R^{5e}$ is monocyclic 4 to 9-membered heterocyclyl group containing one or two heteroatoms selected from nitrogen or oxygen or sulfur heteroatom as ring members.

22. The compound of claim 21, wherein $R^{5e}$ is tetrahydropyran-4-yl.

23. The compound of claim 15, wherein two adjacent $R^5$ on the phenyl ring together with the phenyl ring form indazolyl which is substituted with tetrahydropyranyl.

24. The compound of claim 15, wherein m is 1, and $R^5$ is -$L^5$-CyC selected from the group consisting of:
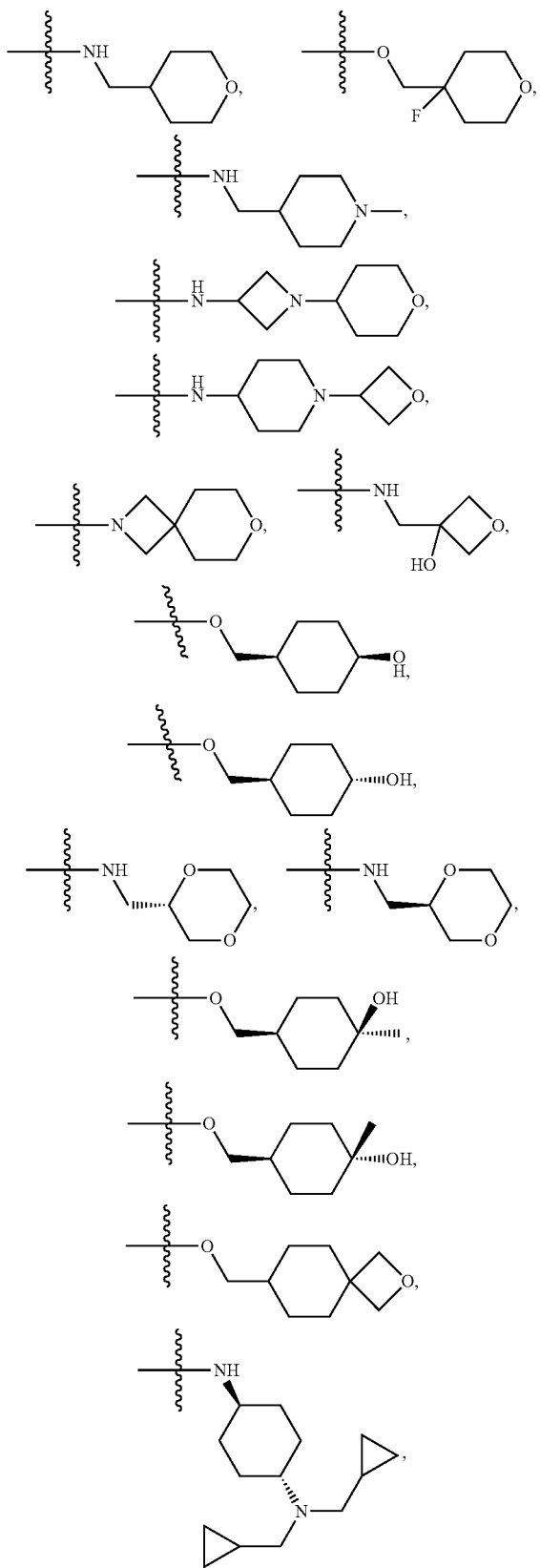
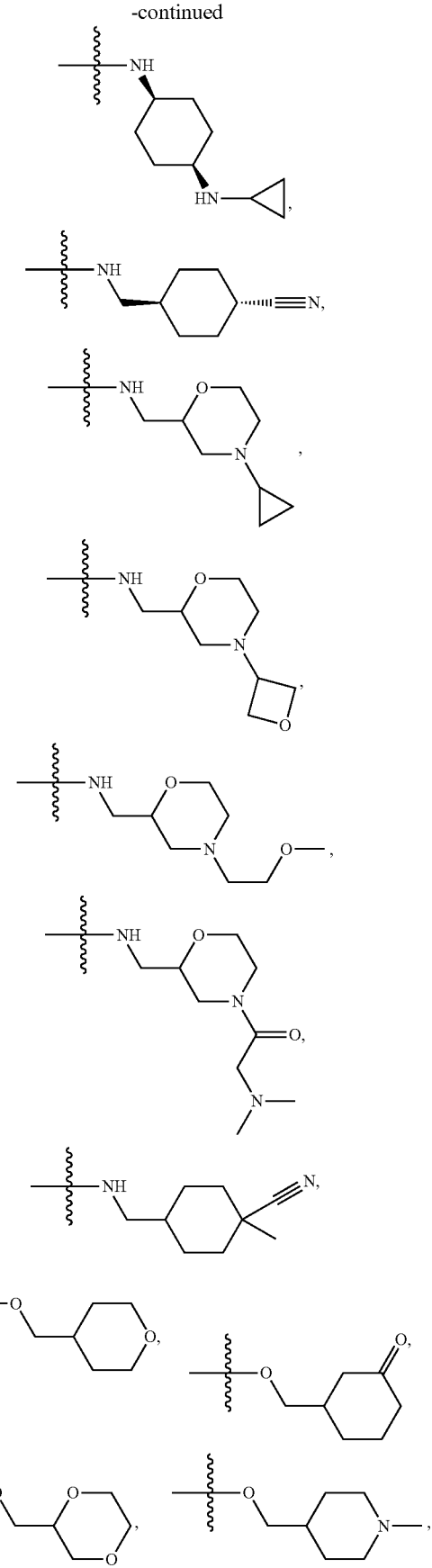

961
-continued
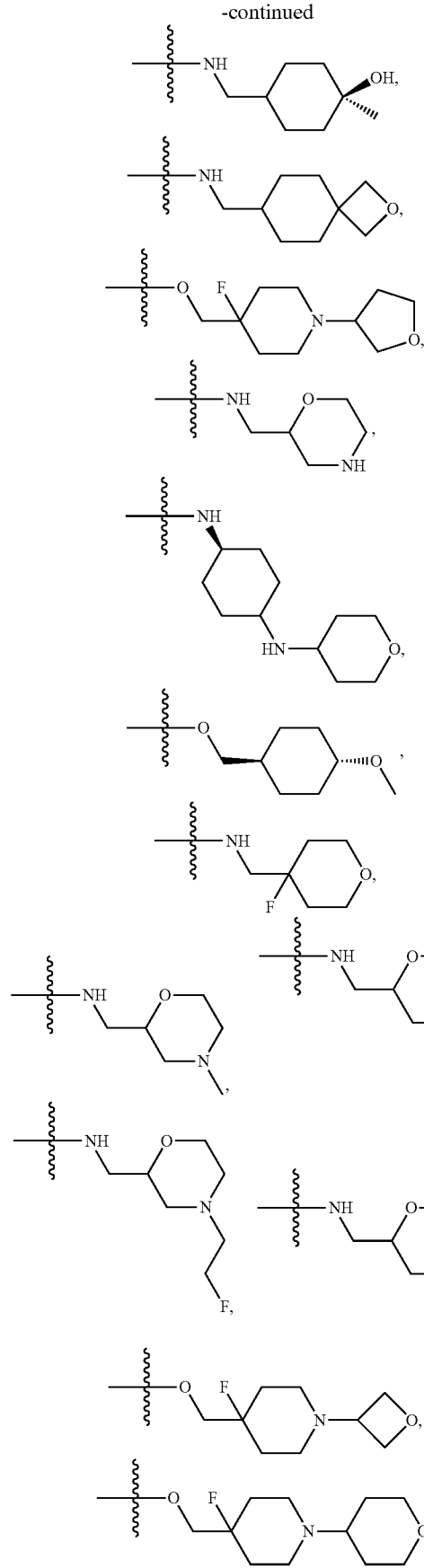
962
-continued
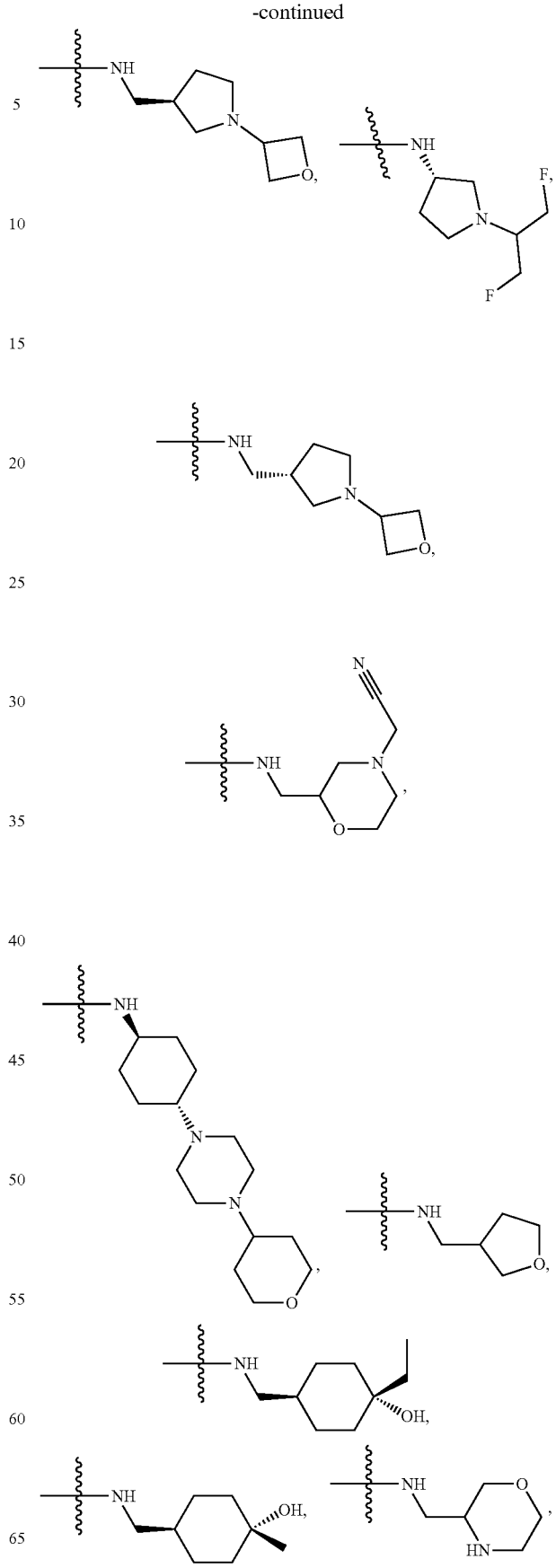

963
-continued
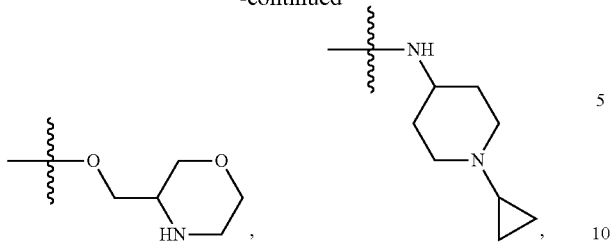
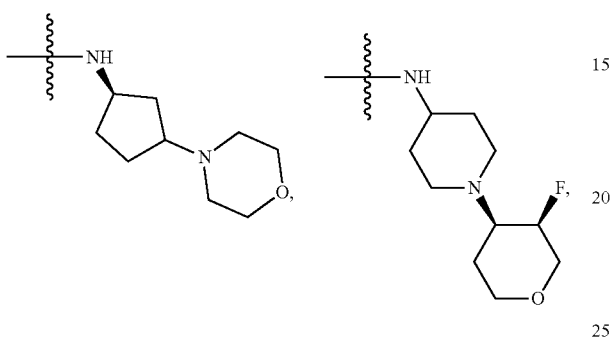
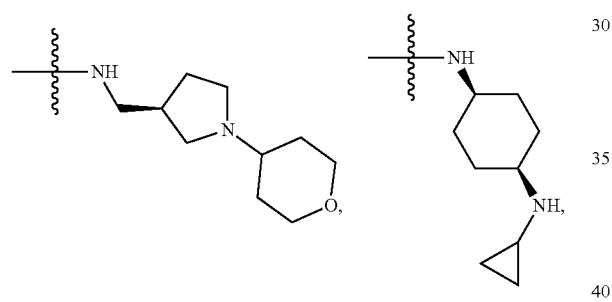
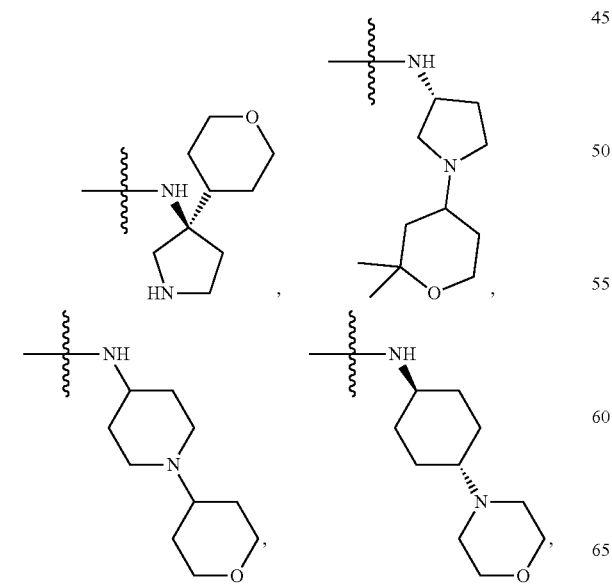
964
-continued
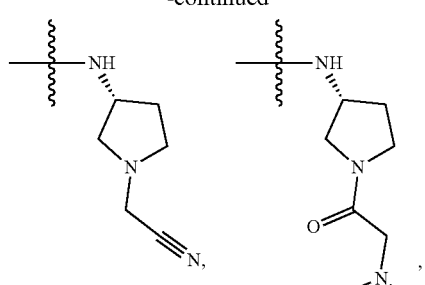
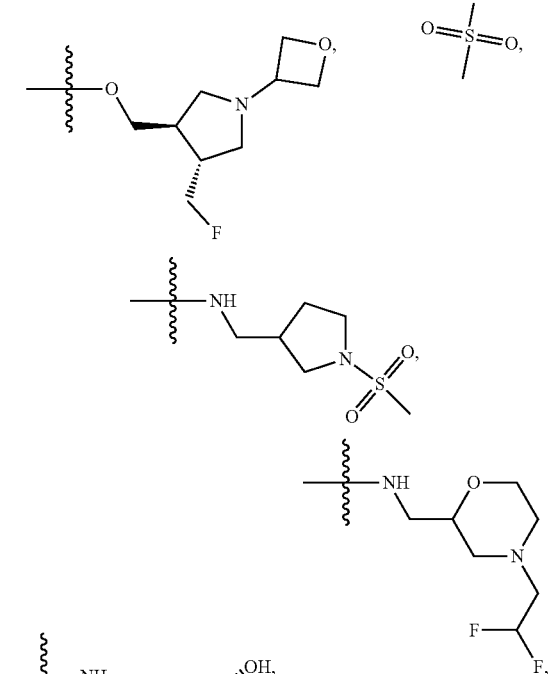
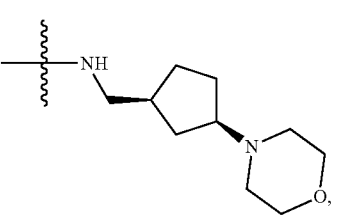

965
-continued
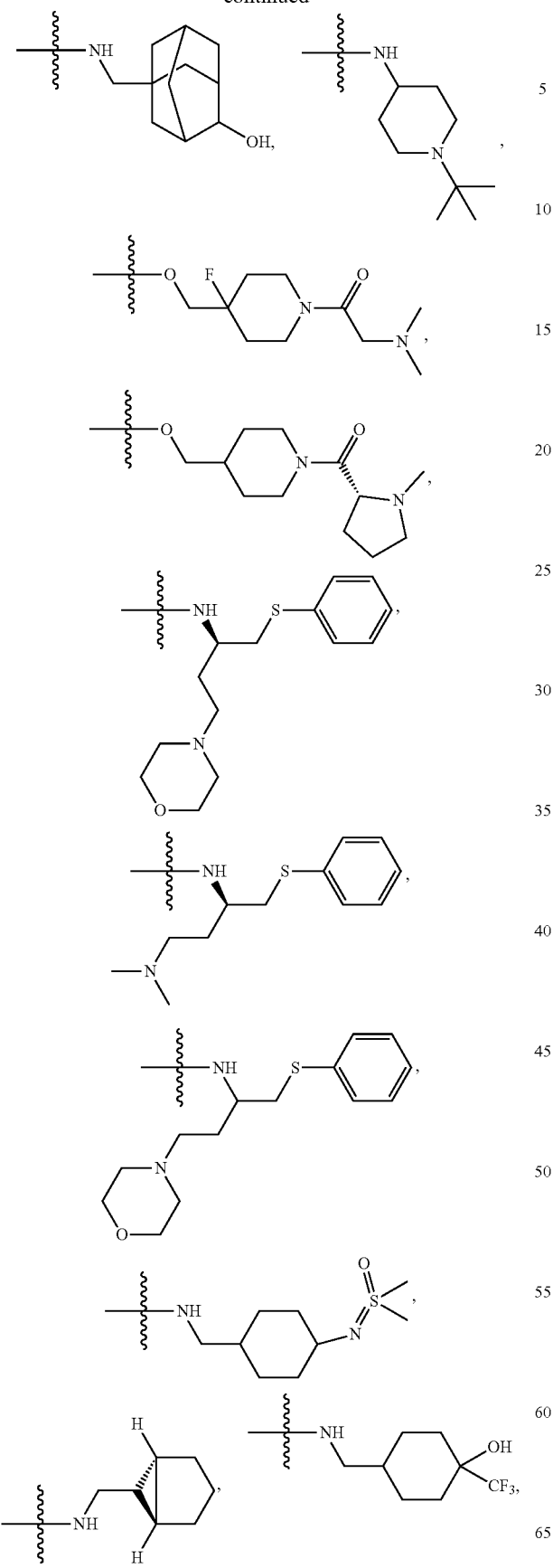
966
-continued
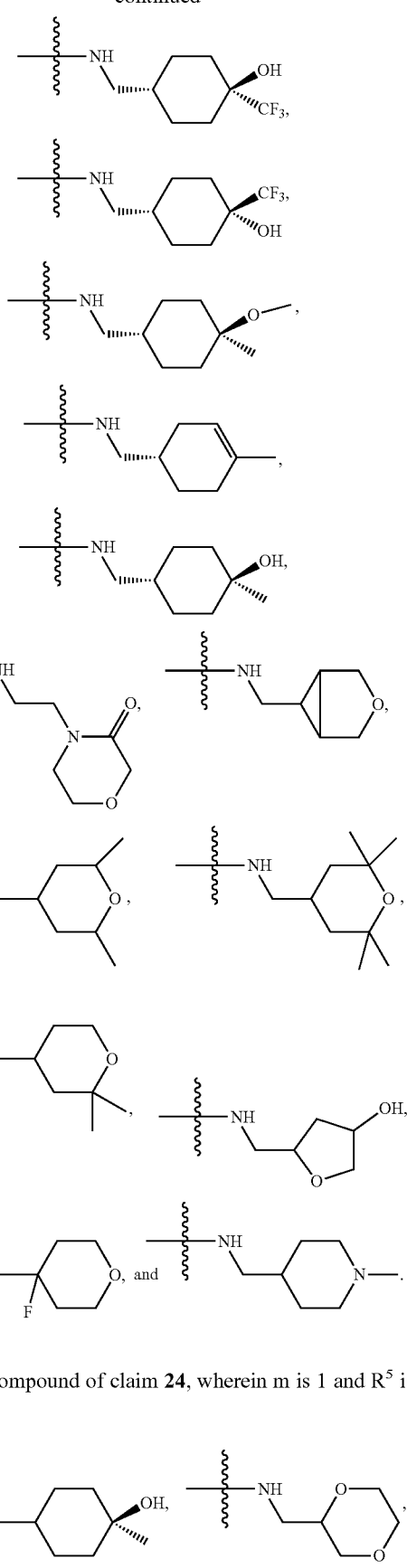
25. The compound of claim 24, wherein m is 1 and $R^5$ is -continued

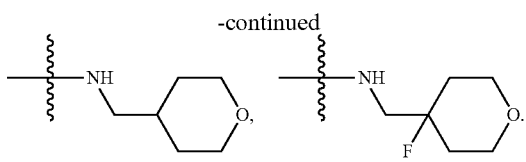

26. A compound of formula (IV)

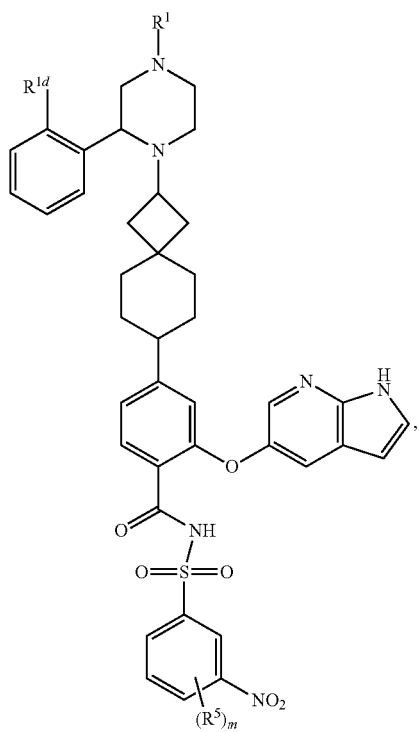

(IV)

or a pharmaceutically acceptable salt thereof, or a stereoisomer thereof,
wherein
R$^1$, at each occurrence, is independently hydrogen, halogen, —C$_{1-8}$alkyl, —C$_{2-8}$alkenyl, —C$_{2-8}$ alkynyl, cycloalkyl, heterocyclyl, aryl, heteroaryl, oxo, —CN, —NO$_2$, —OR$^{1a}$, —SO$_2$R$^{1a}$, —COR$^{1a}$, —CO$_2$R$^{1a}$, —CONR$^{1a}$R$^{1b}$, —C(=NR$^{1a}$)NR$^{1b}$R$^{1c}$, —NR$^{1a}$R$^{1b}$, —NR$^{1a}$COR$^{1b}$, —NR$^{1a}$CONR$^{1b}$R$^{1c}$, —NR$^{1a}$CO$_2$R$^{1b}$, —NR$^{1a}$SONR$^{1b}$R$^{1c}$, —NR$^{1a}$SO$_2$NR$^{1b}$R$^{1c}$, or —NR$^{1a}$SO$_2$R$^{1b}$; wherein said —C$_{1-8}$alkyl, —C$_{2-8}$alkenyl, —C$_{2-8}$alkynyl, cycloalkyl, heterocyclyl, aryl or heteroaryl are each independently optionally substituted with 1 to 4 substituents R$^{1d}$, R$^{1a}$, R$^{1b}$, and R$^{1c}$, are each independently hydrogen, —C$_{1-8}$alkyl, —C$_{2-8}$alkenyl, —C$_{2-8}$alkynyl, cycloalkyl, heterocyclyl, aryl, or heteroaryl, each of-said —C$_{1-8}$alkyl, —C$_{2-8}$alkenyl, —C$_{2-8}$alkynyl, cycloalkyl, heterocyclyl, aryl, or heteroaryl is optionally substituted with halogen, hydroxy or —C$_{1-8}$alkyoxy;

R$^{1d}$, at each occurrence, is independently halogen, —C$_{1-8}$alkyl, —C$_{2-8}$alkenyl, —C$_{2-8}$alkynyl, cycloalkyl, heterocyclyl, aryl, heteroaryl, oxo, —CN, —NO$_2$, —OR$^{Ba}$, —SO$_2$R$^{Ba}$, —COR$^{Ba}$, —CO$_2$R$^{Ba}$, —CONR$^{Ba}$R$^{Bb}$, —C(=NR$^{Ba}$)NR$^{Bb}$R$^{Bc}$, —NR$^{Ba}$R$^{Bb}$, —NR$^{Ba}$COR$^{Bb}$, —NR$^{Ba}$CONR$^{Bb}$R$^{Bc}$, —NR$^{Ba}$CO$_2$R$^{Bb}$, —NR$^{Ba}$SONR$^{Bb}$R$^{Bc}$, —NR$^{Ba}$SO$_2$NR$^{Bb}$R$^{Bc}$, or —NR$^{Ba}$SO$_2$R$^{Bb}$; wherein said —C$_{1-8}$alkyl, —C$_{2-8}$alkenyl, —C$_{2-8}$alkynyl, cycloalkyl, heterocyclyl, aryl or heteroaryl are each independently optionally substituted with 1 to 4 substituents R$^{Bd}$;

R$^{Ba}$, R$^{Bb}$, and R$^{Bc}$, are each independently hydrogen, —C$_{1-8}$alkyl, —C$_{2-8}$alkenyl, —C$_{2-8}$alkynyl, cycloalkyl, heterocyclyl, aryl, or heteroaryl, each of said —C$_{1-8}$alkyl, —C$_{2-8}$alkenyl, —C$_{2-8}$alkynyl, cycloalkyl, heterocyclyl, aryl, or heteroaryl is optionally substituted with halogen, hydroxy, —NH$_2$ or —N(C$_{1-6}$alkyl)$_2$, —C$_{1-8}$alkyoxy, cycloalkyl, heterocyclyl, aryl, or heteroaryl;

R$^{Bd}$, at each occurrence, is independently hydrogen, halogen, oxo, —CN, —NO$_2$, —C$_{1-8}$alkyl, —C$_{2-8}$alkenyl, —C$_{2-8}$alkynyl, cycloalkyl, heterocyclyl, aryl, or heteroaryl, each of-said —C$_{1-8}$alkyl, —C$_{2-8}$alkenyl, —C$_{2-8}$alkynyl, cycloalkyl, heterocyclyl, aryl, or heteroaryl is optionally substituted with halogen, hydroxy, —C$_{1-8}$alkyoxy, cycloalkyl, heterocyclyl, aryl, or heteroaryl;

R$^5$ is -L$^5$-CyC,
wherein L$^5$ is a direct bond, —(CR$^a$R$^b$)$_t$—, —(CR$^a$R$^b$)$_{t-1}$—(CR$^c$=CR$^d$)—(CR$^a$R$^b$)$_{v-1}$—, —(CR$^a$R$^b$)$_{t-1}$—(C≡C)—(CR$^a$R$^b$)$_{v-1}$, —O—, —S—, —S(O)—, —SO$_2$—, —C(O)—, C(O)O—, —OC(O)—, —NR$^a$—, —C(O)NR$^a$, —NR$^a$C(O)—, —NR$^a$C(O)O—, —NR$^a$C(O)NR$^b$—, —SO$_2$NR$^a$—, —NR$^a$SO$_2$—, —NR$^a$S(O)$_2$NR$^b$—, —N$^a$S(O)NR$^b$—, —C(O)NR$^a$SO$_2$—, —C(O)NR$^a$SO—, or —C(=NR$^a$)NR$^b$—, wherein t and v, at each occurrence, are independently a number of 1 to 7, and one or two CR$^a$R$^b$ moieties in —(CR$^a$R$^b$)$_t$—, —(CR$^a$R$^b$)$_{t-1}$—(CR$^c$=CR$^d$)—(CR$^a$R$^b$)$_{v-1}$—, or —(CR$^a$R$^b$)$_{t-1}$—(C≡C)—(CR$^a$R$^b$)$_{v-1}$— are un-replaced or replaced with one or more moieties selected from the group consisting of O, S, SO, SO$_2$, C(O) and NR$^a$;

CyC is cycloalkyl, heterocyclyl, aryl, or heteroaryl, each of which is optionally substituted with one or two substituents R$^{5a}$;

R$^{5a}$, at each occurrence, is independently selected from hydrogen, halogen, cyano, oxo, —NO$_2$, —OR$^{5b}$, —SR$^{5b}$, —NR$^{5b}$R$^{5c}$, —COR$^{5b}$, —SO$_2$R$^{5b}$, —C(=O)OR$^{5b}$, —C(=O)NR$^{5b}$R$^{5c}$, —C(=NR$^{5b}$)NR$^{5c}$R$^{5d}$, —N(R$^{5b}$)C(=O)R$^{5c}$, —N(R$^{5b}$)C(=O)OR$^{5c}$, —N(R$^{5b}$)C(O)NR$^{5c}$R$^{5d}$, —N(R$^{5b}$)S(O)NR$^{5c}$R$^{5d}$, —N(R$^{5b}$)S(O)$_2$NR$^{5c}$R$^{5d}$, —NR$^{5b}$SO$_2$R$^{5c}$, —C$_{1-8}$alkyl, —C$_{2-8}$alkenyl, —C$_{2-8}$alkynyl, -cycloalkyl, heterocyclyl, aryl, or heteroaryl, each of said —C$_{1-8}$alkyl, —C$_{2-8}$alkenyl, —C$_{2-8}$alkynyl, -cycloalkyl, heterocyclyl, aryl, or heteroaryl is optionally substituted with one or two substituents R$^{5e}$;

wherein R$^{5b}$, R$^{5c}$, and R$^{5d}$ are each independently hydrogen, —C$_{1-8}$alkyl, —C$_{2-8}$alkenyl, —C$_{2-8}$alkynyl, cycloalkyl, heterocyclyl, aryl, or heteroaryl, each of said —C$_{1-8}$alkyl, —C$_{2-8}$alkenyl, C$_{2-8}$alkynyl, -cycloalkyl, heterocyclyl, aryl, or heteroaryl is optionally substituted with one or two substituents R$^{5e}$;

R$^{5e}$, at each occurrence, is independently selected from hydrogen, halogen, cyano, oxo, —NO$_2$, —OR$^{5f}$, —SR$^{5f}$, —NR$^{5f}$R$^{5g}$, —COR$^{5f}$, —SO$_2$R$^{5f}$, —C(=O)OR$^{5f}$, —C(=O)NR$^{5f}$R$^{5g}$, —C(=NR$^{5f}$)NR$^{5g}$R$^{5h}$, —N(R$^{5f}$)C(=O)R$^{5g}$, —N(R$^{5f}$)C(=O)OR$^{5g}$, —N(R$^{5f}$)C(O)NR$^{5g}$R$^{5h}$, —N(R$^{5f}$)S(O)NR$^{5g}$R$^{5h}$, —N($R^{5f}$)S(O)$_2$NR$^{5g}$R$^{5h}$, —NR$^5$SO$_2$R$^{5g}$, —C$_{1-8}$alkyl, —C$_{2-8}$alkenyl, —C$_{2-8}$alkynyl, -cycloalkyl, heterocyclyl, aryl, or heteroaryl;

R$^{5f}$, R$^{5g}$, and R$^{5h}$ are each independently hydrogen, —C$_{1-8}$alkyl, —C$_{2-8}$alkenyl, —C$_{2-8}$alkynyl, cycloalkyl, heterocyclyl, aryl, or heteroaryl;

or, two adjacent R$^5$ on the phenyl ring together with the phenyl ring form a benzo ring, said ring is optionally substituted with halogen, oxo, cyano, —NO$_2$, —OR$^{5i}$, —SR$^{5i}$, —NR$^{5i}$R$^{5j}$, —COR$^{5i}$, —SO$_2$R$^{5i}$, —C(=O)OR$^{5i}$, —C(=O)NR$^{5i}$R$^{5j}$, —C(=NR$^{5i}$)NR$^{5j}$R$^{5k}$, —N(R$^{5i}$)C(=O)R$^{5j}$, —N(R$^{5i}$)C(=O)OR$^{5j}$, —N(R$^{5i}$)C(O)NR$^{5j}$R$^{5k}$, —N(R$^{5i}$)S(O)NR$^{5j}$R$^{5k}$, —N(R$^{5i}$)S(O)$_2$NR$^{5j}$R$^{5k}$, —NR$^{5i}$SO$_2$R$^{5k}$, —C$_{1-8}$alkyl, —C$_{2-8}$alkenyl, —C$_{2-8}$alkynyl, -cycloalkyl, heterocyclyl, aryl, or heteroaryl;

R$^{5i}$, R$^{5j}$, and R$^{5k}$ are independently hydrogen, —C$_{1-8}$alkyl, —C$_{2-8}$alkenyl, —C$_{2-8}$alkynyl, cycloalkyl, heterocyclyl, aryl, or heteroaryl, each of said —C$_{1-8}$alkyl, —C$_{2-8}$alkenyl, —C$_{2-8}$alkynyl, cycloalkyl, heterocyclyl, aryl, or heteroaryl is optionally substituted with halogen, hydroxy or —C$_{1-8}$alkyoxy;

R$^a$, R$^b$, R$^c$, and R$^d$ at each occurrence, are independently hydrogen, —C$_{1-8}$alkyl, —C$_{2-8}$alkenyl, —C$_{2-8}$alkynyl, cycloalkyl, heterocyclyl, aryl, or heteroaryl, said —C$_{1-8}$alkyl, —C$_{2-8}$alkenyl, —C$_{2-8}$alkynyl, cycloalkyl, heterocyclyl, aryl, or heteroaryl are each independently substituted with —CN, halogen, —NO$_2$, —NR$^e$R$^f$, oxo, —OR$^e$, or —SR$^e$;

wherein R$^e$ and R$^f$ are each independently hydrogen, C$_{1-8}$alkyl, C$_{1-8}$alkoxy-C$_{1-8}$alkyl-, C$_{2-8}$ alkenyl, C$_{2-8}$alkynyl, cycloalkyl, aryl, heterocyclyl, or heteroaryl; and m is an integer of 1-4.

27. The compound of claim 5, wherein ring B is pyrrolidine-1-yl.

28. The compound of claim 1, wherein L$^5$ is a direct bond, —CH$_2$—, —O—CH$_2$—, —NH—CH$_2$—, or —NH—.

29. The compound of claim 17, wherein Cyc is oxetan-2-yl, oxetan-3-yl, tetrahydrofuran-4-yl, tetrahydrofuran-2-yl, tetrahydrofuran-3-yl, tetrahydropyran-2-yl, tetrahydropyran-3-yl, tetrahydropyran-4-yl, azetidin-3-yl, azetidin-2-yl, pyrrolidin-2-yl, pyrrolidin-3-yl, piperidin-4-yl, piperidin-2-yl, or piperidin-3-yl.

30. The compound of claim 17, wherein CyC is 1,3-dioxan-2-yl, 1,3-dioxan-4-yl, 1,4-dioxan-2-yl, morpholin-1-yl, morpholin-2-yl, or morpholin-3-yl.

31. The compound of 15, wherein R$^{5a}$ is oxetan-3-yl, tetrahydrofuran-3-yl, tetrahydro-2H-pyran-4-yl, morphin-4-yl, —NR$^{5b}$R$^{5c}$, —OR$^{5b}$, —SO$_2$R$^{5b}$, or —COR$^{5b}$;

wherein when R$^{5a}$ is —NR$^{5b}$R$^{5c}$, R$^{5b}$ is hydrogen and R$^{5c}$ is heterocyclyl; or R$^{5b}$ and R$^{5c}$ are each independently hydrogen or —C$_{1-6}$alkyl substituted with cycloalkyl;

wherein when R$^{5a}$ is —OR$^{5b}$ or —SO$_2$R$^{5b}$, R$^{5b}$ is hydrogen or C$_{1-8}$alkyl; and wherein when R$^{5a}$ is —COR$^{5b}$, R$^{5b}$ is hydrogen or C$_{1-8}$alkyl optionally substituted with —NR$^{5f}$R$_{5g}$, wherein R$^{5f}$ and R$^{5g}$ are each independently hydrogen or C$_{1-8}$alkyl.

32. The compound of claim 1, wherein the compound is selected from:

3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-phenylpyrrolidin-1-yl)-[1,1'-biphenyl]-4-carboxamide;

3-((1H-pyrrolo[2,3-b]pyridin-5-yl)oxy)-4'-(2-(4-chlorophenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(2-(3-chlorophenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(2-(2-chlorophenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

(S)-3-((1H-pyrrolo[2,3-b]pyridin-5-yl)oxy)-4'-(2-(2-chlorophenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

(R)-3-((1H-pyrrolo[2,3-b]pyridin-5-yl)oxy)-4'-(2-(2-chlorophenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-3'-chloro-4'-(2-(2-chlorophenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-phenylpyrrolidin-1-yl)-3'-(trifluoromethyl)-[1,1'-biphenyl]-4-carboxamide;

3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(3-(trifluoromethyl)phenyl)pyrrolidin-1-yl)-[1,1'-biphenyl]-4-carboxamide;

3-((1H-pyrrolo[2,3-b]pyridin-5-yl)oxy)-4'-(2-(2-cyclopropylphenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

(S)-3-((1H-pyrrolo[2,3-b]pyridin-5-yl)oxy)-4'-(2-(2-cyclopropylphenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

(R)-3-((1H-pyrrolo[2,3-b]pyridin-5-yl)oxy)-4'-(2-(2-cyclopropylphenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(4-(trifluoromethyl)phenyl)pyrrolidin-1-yl)-[1,1'-biphenyl]-4-carboxamide;

3-((1H-pyrrolo[2,3-b]pyridin-5-yl)oxy)-4'-(2-(3-cyclopropylphenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(o-tolyl)pyrrolidin-1-yl)-[1,1'-biphenyl]-4-carboxamide;

3-((1H-pyrrolo[2,3-b]pyridin-5-yl)oxy)-4'-(2-(2-isopropylphenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(2-([1,1'-biphenyl]-2-yl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(2-(4-cyclopropylphenyl)pyrrolidin -1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-phenylazepan-1-yl)-[1,1'-biphenyl]-4-carboxamide;

3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-phenylpiperidin-1-yl)-[1,1'-biphenyl]-4-carboxamide;

3-((1H-pyrrolo[2,3-b]pyridin-5-yl)oxy)-4'-(2-(3,4-dichlorophenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(2-(2-methoxyphenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(2-(4-methoxyphenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(3,3-dimethyl-2-oxo-5-phenylpyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-oxo-4-phenylazetidin-1-yl)-[1,1'-biphenyl]-4-carboxamide;

3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(1-phenylpyrrolidin-2-yl)-[1,1'-biphenyl]-4-carboxamide;

3-((1H-pyrrolo[2,3-b]pyridin-5-yl)oxy)-4'-(1-benzylpyrrolidin-2-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(2-(2-ethylphenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(2-(2-cyclopentylphenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(2-(2-fluorophenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(2-methyl-2-phenylpyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(3-phenylpyrrolidin-1-yl)-[1,1'-biphenyl]-4-carboxamide;

3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(pyridin-3-yl)pyrrolidin-1-yl)-[1,1'-biphenyl]-4-carboxamide;

3-((1H-pyrrolo[2,3-b]pyridin-5-yl)oxy)-4'-(2-cyclohexylpyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(1-(o-tolyl)pyrrolidin-2-yl)-[1,1'-biphenyl]-4-carboxamide;

3-((1H-pyrrolo[2,3-b]pyridin-5-yl)oxy)-4'-(2-(2-chloro-6-fluorophenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-3'-fluoro-N-((3-nitro-4-(((tetrahydro-2H-pyran-4-yl)methyl)amino)phenyl)sulfonyl)-4'-(2-phenylpyrrolidin-1-yl)-[1,1'-biphenyl]-4-carboxamide;

3-((1H-pyrrolo[2,3-b]pyridin-5-yl)oxy)-4'-(2-(2-cyclobutylphenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(2-(2-cyclohexylphenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(4,4-dimethyl-2-phenylpyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-phenylazetidin-1-yl)-[1,1'-biphenyl]-4-carboxamide;

3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-phenyl-2-(trifluoromethyl)pyrrolidin-1-yl)-[1,1'-biphenyl]-4-carboxamide;

3-((1H-pyrrolo[2,3-b]pyridin-5-yl)oxy)-4'-(2-ethyl-2-phenylpyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(4-methyl-2-phenylpiperazin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(2-(2-isopropylphenyl)piperidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(1-(2-cyclopropylphenyl)-5-oxopyrrolidin-2-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(1-(2-cyclopropylphenyl)pyrrolidin-2-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(1-(2-nitrophenyl)pyrrolidin-2-yl)-[1,1'-biphenyl]-4-carboxamide;

3-((1H-pyrrolo[2,3-b]pyridin-5-yl)oxy)-4'-(2-(2-(tert-butyl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(2-(2-(dimethylamino)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(2-(2-(azetidin-1-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;
3-((1H-pyrrolo[2,3-b]pyridin-5-yl)oxy)-4'-(2-(2-(methylsulfonamido)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;
3-((1H-pyrrolo[2,3-b]pyridin-5-yl)oxy)-4'-(2-(2-(1-methyl-1,2,3,6-tetrahydropyridin-4-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;
(R)-3-((1H-pyrrolo[2,3-b]pyridin-5-yl)oxy)-4'-(2-(2-(1-methyl-1,2,3,6-tetrahydropyridin-4-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;
(S)-3-((1H-pyrrolo[2,3-b]pyridin-5-yl)oxy)-4'-(2-(2-(1-methyl-1,2,3,6-tetrahydropyridin-4-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;
3-((1H-pyrrolo[2,3-b]pyridin-5-yl)oxy)-4'-(2-(2-cyclopropylphenyl)pyrrolidin-1-yl)-3'-fluoro-N-((3-nitro-4-(((tetrahydro-2H-pyran-4-yl)methyl)amino)phenyl)sulfonyl)-[1,1'-biphenyl]-4-carboxamide;
3-((1H-pyrrolo[2,3-b]pyridin-5-yl)oxy)-4'-(2-(2-cyclopropylphenyl)pyrrolidin-1-yl)-2'-fluoro-N-((3-nitro-4-(((tetrahydro-2H-pyran-4-yl)methyl)amino)phenyl)sulfonyl)-[1,1'-biphenyl]-4-carboxamide;
3-((1H-pyrrolo[2,3-b]pyridin-5-yl)oxy)-4'-(2-(2-cyclopropylphenyl)-2-(trifluoromethyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;
3-((1H-pyrrolo[2,3-b]pyridin-5-yl)oxy)-4'-(2-(2-cyclopropylphenyl)piperidin-1-yl)-N-((3-nitro-4-(((tetrahydro-2H-pyran-4-yl)methyl)amino)phenyl)sulfonyl)-[1,1'-biphenyl]-4-carboxamide;
3-((1H-pyrrolo[2,3-b]pyridin-5-yl)oxy)-4'-(2-(2-cyclopropylphenyl)-4-fluoropyrrolidin-1-yl)-N-((3-nitro-4-(((tetrahydro-2H-pyran-4-yl)methyl)amino)phenyl)sulfonyl)-[1,1'-biphenyl]-4-carboxamide;
3-((1H-pyrrolo[2,3-b]pyridin-5-yl)oxy)-4'-(4-chloro-2-(2-cyclopropylphenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;
3-((1H-pyrrolo[2,3-b]pyridin-5-yl)oxy)-4'-(2-(2-cyclopropylphenyl)-4-methoxypyrrolidin-1-yl)-N-((3-nitro-4-(((tetrahydro-2H-pyran-4-yl)methyl)amino)phenyl)sulfonyl)-[1,1'-biphenyl]-4-carboxamide;
3-((1H-pyrrolo[2,3-b]pyridin-5-yl)oxy)-4'-(2-(2-cyclopropylphenyl)-3-methylpyrrolidin-1-yl)-N-((3-nitro-4-(((tetrahydro-2H-pyran-4-yl)methyl)amino)phenyl)sulfonyl)-[1,1'-biphenyl]-4-carboxamide;
3-((1H-pyrrolo[2,3-b]pyridin-5-yl)oxy)-4'-(2-(2-cyclopropylphenyl)-3,3-dimethylpyrrolidin-1-yl)-N-((3-nitro-4-(((tetrahydro-2H-pyran-4-yl)methyl)amino)phenyl)sulfonyl)-[1,1'-biphenyl]-4-carboxamide;
3-((1H-pyrrolo[2,3-b]pyridin-5-yl)oxy)-4'-(1-(2-cyclopropylphenyl)hexahydrocyclopenta[c]pyrrol-2(1H)-yl)-N-((3-nitro-4-(((tetrahydro-2H-pyran-4-yl)methyl)amino)phenyl)sulfonyl)-[1,1'-biphenyl]-4-carboxamide;
3-((1H-pyrrolo[2,3-b]pyridin-5-yl)oxy)-4'-(2-cyclopropylpyrrolidine-1-yl)-N-((3-nitro-4-(((tetrahydro-2H-pyran-4-yl)methyl)amino)phenyl)sulfonyl)-[1,1'-biphenyl]-4-carboxamide;
3-((1H-pyrrolo[2,3-b]pyridin-5-yl)oxy)-4'-(2-(2-ethylcyclohexyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;
3-((1H-pyrrolo[2,3-b]pyridin-5-yl)oxy)-4'-(2-(2-cyclopropylbenzyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;
3-((1H-pyrrolo[2,3-b]pyridin-5-yl)oxy)-4'-(2-(4-cyclopropylpyridin-3-yl)pyrrolidin-1-yl)-N-((3-nitro-4-(((tetrahydro-2H-pyran-4-yl)methyl)amino)phenyl)sulfonyl)-[1,1'-biphenyl]-4-carboxamide;
3-((1H-pyrrolo[2,3-b]pyridin-5-yl)oxy)-4'-(2-(1-cyclopropyl-1H-pyrazol-5-yl)pyrrolidin-1-yl)-N-((3-nitro-4-(((tetrahydro-2H-pyran-4-yl)methyl)amino)phenyl)sulfonyl)-[1,1'-biphenyl]-4-carboxamide;
3-((1H-pyrrolo[2,3-b]pyridin-5-yl)oxy)-4'-(2-(3-chloro-2-cyclopropylphenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;
3-((1H-pyrrolo[2,3-b]pyridin-5-yl)oxy)-4'-(2-(2-cyclopropyl-5-methylphenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;
3-((1H-pyrrolo[2,3-b]pyridin-5-yl)oxy)-4'-(2-(2,3-dihydrobenzofuran-7-yl)pyrrolidin-1-yl)-N-((3-nitro-4-(((tetrahydro-2H-pyran-4-yl)methyl)amino)phenyl)sulfonyl)-[1,1'-biphenyl]-4-carboxamide;
3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(1-phenylhexahydrocyclopenta[c]pyrrol-2(1H)-yl)-[1,1'-biphenyl]-4-carboxamide;
3-((1H-pyrrolo[2,3-b]pyridin-5-yl)oxy)-3'-(2-(2-cyclopropylphenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;
3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(2-phenoxyphenyl)pyrrolidin-1-yl)-[1,1'-biphenyl]-4-carboxamide;
3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(2-(tetrahydro-2H-pyran-4-yl)phenyl)pyrrolidin-1-yl)-[1,1'-biphenyl]-4-carboxamide;
3-((1H-pyrrolo[2,3-b]pyridin-5-yl)oxy)-4'-(2-(2-cyclopropylcyclohex-1-en-1-yl)pyrrolidin-1-yl)-N-((3-nitro-4-(((tetrahydro-2H-pyran-4-yl)methyl)amino)phenyl)sulfonyl)-[1,1'-biphenyl]-4-carboxamide;
3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-phenylcyclopentyl)-[1,1'-biphenyl]-4-carboxamide;
3-((1H-pyrrolo[2,3-b]pyridin-5-yl)oxy)-4'-(2-(2-cyclopropylphenyl)pyrrolidin-1-yl)-N-(methyl(3-nitro-4-(((tetrahydro-2H-pyran-4-yl)methyl)amino)phenyl)(oxo)-16-sulfaneylidene)-[1,1'-biphenyl]-4-carboxamide;
3-((1H-pyrrolo[2,3-b]pyridin-5-yl)oxy)-4'-(2-(2-(cyclopropylmethyl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;
3-((1H-pyrrolo[2,3-b]pyridin-5-yl)oxy)-2'-chloro-4'-(2-(2-cyclopropylphenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;
(R)-3-((1H-pyrrolo[2,3-b]pyridin-5-yl)oxy)-4'-(2-(2-(4,4-difluorocyclohexyl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;
3-((1H-pyrrolo[2,3-b]pyridin-5-yl)oxy)-4'-((2R)-2-(2-(2-(dimethylamino)cyclopropyl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;
tert-butyl 4-(2-(1-(3'-((1H-pyrrolo[2,3-b]pyridin-5-yl)oxy)-4'-(((3-nitro-4-(((tetrahydro-2H-pyran-4-yl)methyl)amino)phenyl)sulfonyl)carbamoyl)-[1,1'-biphenyl]-4-yl)pyrrolidin-2-yl)phenyl)piperidine-1-carboxylate;
3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(2-(piperidin-4-yl)phenyl)pyrrolidin-1-yl)-[1,1'-biphenyl]-4-carboxamide;
(R)-3-((1H-pyrrolo[2,3-b]pyridin-5-yl)oxy)-4'-(2-(2-(1-methylpiperidin-4-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;
3-((1H-pyrrolo[2,3-b]pyridin-5-yl)oxy)-4'-((2R)-2-(2-(1-methyl-2-oxopiperidin-4-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;
(R)-3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(2-(1-(3,3,3-trifluoropropyl)piperidin-4-yl)phenyl)pyrrolidin-1-yl)-[1,1'-biphenyl]-4-carboxamide;
(R)-3-((1H-pyrrolo[2,3-b]pyridin-5-yl)oxy)-4'-(2-(2-(1-(2-hydroxyethyl)piperidin-4-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;
(R)-3-((1H-pyrrolo[2,3-b]pyridin-5-yl)oxy)-4'-(2-(2-(1-(2-(dimethylamino)-2-oxoethyl)piperidin-4-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;
(R)-3-((1H-pyrrolo[2,3-b]pyridin-5-yl)oxy)-4'-(2-(2-(1-(2-(N-methylacetamido)ethyl)piperidin-4-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;
(R)-3-((1H-pyrrolo[2,3-b]pyridin-5-yl)oxy)-4'-(2-(2-(1-(3-(methylamino)propanoyl)piperidin-4-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;
3-((1H-pyrrolo[2,3-b]pyridin-5-yl)oxy)-4'-(2-(2-(1-cyclopropyl-1,2,3,6-tetrahydropyridin-4-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;
(R)-3-((1H-pyrrolo[2,3-b]pyridin-5-yl)oxy)-4'-(2-(2-(1-benzyl-1,2,3,6-tetrahydropyridin-4-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;
(R)-3-((1H-pyrrolo[2,3-b]pyridin-5-yl)oxy)-4'-(2-(2-(1-acetyl-1,2,3,6-tetrahydropyridin-4-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;
(R)-3-((1H-pyrrolo[2,3-b]pyridin-5-yl)oxy)-4'-(2-(2-(1-acetylpiperidin-4-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;
3-((1H-pyrrolo[2,3-b]pyridin-5-yl)oxy)-4'-(2-(2-(1-(methylsulfonyl)-1,2,3,6-tetrahydropyridin-4-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;
(R)-3-((1H-pyrrolo[2,3-b]pyridin-5-yl)oxy)-4'-(2-(2-((1-methylpiperidin-4-yl)methyl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;
3-((1H-pyrrolo[2,3-b]pyridin-5-yl)oxy)-4'-(2-(2-((1-methylpiperidin-4-yl)oxy)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;
(R)-3-((1H-pyrrolo[2,3-b]pyridin-5-yl)oxy)-4'-(2-(2-((4-methylpiperazin-1-yl)methyl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;
(R)-3-((1H-pyrrolo[2,3-b]pyridin-5-yl)oxy)-4'-(2-(2-(4-carbamoylcyclohexyl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;
3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(2-(pyridin-4-yl)phenyl)pyrrolidin-1-yl)-[1,1'-biphenyl]-4-carboxamide;
3-((1H-pyrrolo[2,3-b]pyridin-5-yl)oxy)-4'-(2-(2-(1-methylpiperidin-3-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide (isomer 1, first eluting isomer);
3-((1H-pyrrolo[2,3-b]pyridin-5-yl)oxy)-4'-(2-(2-(1-methylpiperidin-3-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide (isomer 2, second eluting isomer);
3-((1H-pyrrolo[2,3-b]pyridin-5-yl)oxy)-4'-(2-(2-(3-(dimethylamino)piperidin-1-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide (isomer 1, first eluting isomer);
3-((1H-pyrrolo[2,3-b]pyridin-5-yl)oxy)-4'-(2-(2-(3-(dimethylamino)piperidin-1-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide (isomer 2, second eluting isomer);
3-((1H-pyrrolo[2,3-b]pyridin-5-yl)oxy)-4'-(2-(2-(8-methyl-3,8-diazabicyclo[3.2.1]octan-3-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;
3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(2-(piperazin-1-yl)phenyl)pyrrolidin-1-yl)-[1,1'-biphenyl]-4-carboxamide;
3-((1H-pyrrolo[2,3-b]pyridin-5-yl)oxy)-4'-(2-(2-(4-methylpiperazin-1-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;
3-((1H-pyrrolo[2,3-b]pyridin-5-yl)oxy)-4'-(2-(2-morpholinophenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

(R)-3-((1H-pyrrolo[2,3-b]pyridin-5-yl)oxy)-4'-(2-(2-(1,1-dioxidotetrahydro-2H-thiopyran-4-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(2-(2-(4-hydroxypiperidin-1-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(2-(2-(4-(dimethylamino)piperidin-1-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(2-(2-(1-methylpyrrolidin-3-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(2-(2-(2-(dimethylamino)ethoxy)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(2-(2-(methoxymethyl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

(R)-3-((1H-pyrrolo[2,3-b]pyridin-5-yl)oxy)-4'-(2-(2-((dimethylamino)methyl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(2-(2-(2-(dimethylamino)ethyl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(2-(2-(3-(dimethylamino)propyl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(2-(2-((1-methylpyrrolidin-3-yl)oxy)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-((2R)-2-(2-(methyl(1-methylpyrrolidin-3-yl)amino)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(2-(2-(methyl(1-methylpiperidin-3-yl)amino)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(2-(2-(methyl((1-methylpyrrolidin-2-yl)methyl)amino)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

(R)-3-((1H-pyrrolo[2,3-b]pyridin-5-yl)oxy)-4'-(2-(2-(7-methyl-2,7-diazaspiro[3.5]nonan-2-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(2-(2-(2-((dimethylamino)methyl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

(R)-3-((1H-pyrrolo[2,3-b]pyridin-5-yl)oxy)-4'-(2-(2-(1-methyl-1H-pyrazol-4-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(2-(1-(1-methylpiperidin-4-yl)-1H-pyrazol-5-yl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(2-(5-chloro-2-(1-methyl-1,2,3,6-tetrahydropyridin-4-yl)phenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(2-(isoquinolin-8-yl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(2-(2-methyl-2H-indazol-7-yl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(2-(2-methyl-1,2,3,4-tetrahydroisoquinolin-8-yl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(2-(2-(2-cyclopropylphenyl)propan-2-yl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-((2R,4S) or (2S,4R)-2-(2-cyclopropylphenyl)-4-fluoropyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-((2S,4R) or (2R,4S)-2-(2-cyclopropylphenyl)-4-fluoropyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-((2R,4R) or (2S,4S)-2-(2-cyclopropylphenyl)-4-fluoropyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-((2S,4S) or (2R,4R)-2-(2-cyclopropylphenyl)-4-fluoropyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(2-(2-cyclopropylphenyl)-4-fluoro-2,5-dihydro-1H-pyrrol-1-yl)-N-((3-nitro-4-(((tetrahydro-2H-pyran-4-yl)methyl)amino)phenyl)sulfonyl)-[1,1'-biphenyl]-4-carboxamide;

(S)-3-((1H-pyrrolo[2,3-b]pyridin-5-yl)oxy)-4'-(2-(2-cyclopropylphenyl)-4,4-difluoropyrrolidin-1-yl)-N-((3-nitro-4-(((tetrahydro-2H-pyran-4-yl)methyl)amino)phenyl)sulfonyl)-[1,1'-biphenyl]-4-carboxamide;

(R)-3-((1H-pyrrolo[2,3-b]pyridin-5-yl)oxy)-4'-(2-(2-cyclopropylphenyl)-4,4-difluoropyrrolidin-1-yl)-N-((3- nitro-4-(((tetrahydro-2H-pyran-4-yl)methyl)amino)
phenyl)sulfonyl)-[1,1'-biphenyl]-4-carboxamide;

3-((1H-pyrrolo[2,3-b]pyridin-5-yl)oxy)-4'-(4-cyclopropyl-2-(2-cyclopropylphenyl)pyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(2-(2-cyclopropylphenyl)-4-phenylpyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(2-(2-cyclopropylphenyl)-4-methylenepyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(2-(2-cyclopropylphenyl)-4-(dimethylamino)pyrrolidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(2-(2-cyclopropylphenyl)piperidin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(3-(2-cyclopropylphenyl)-5-oxomorpholino)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(3-(2-cyclopropylphenyl)morpholino)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(2-(2-cyclopropylphenyl)-4-methylpiperazin-1-yl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(2-(2-cyclopropylphenyl)pyrazolidin-1-yl)-N-((3-nitro-4-(((tetrahydro-2H-pyran-4-yl)methyl)amino)phenyl)sulfonyl)-[1,1'-biphenyl]-4-carboxamide;

(R)-4'-(2-(2-cyclopropylphenyl)pyrrolidin-1-yl)-N-((3-nitro-4-(((tetrahydro-2H-pyran-4-yl)methyl)amino)phenyl)sulfonyl)-3-(3-(pyrimidin-2-ylamino)phenoxy)-[1,1'-biphenyl]-4-carboxamide;

(R)-5-((4'-(2-(2-cyclopropylphenyl)pyrrolidin-1-yl)-4-(((3-nitro-4-(((tetrahydro-2H-pyran-4-yl)methyl)amino)phenyl)sulfonyl)carbamoyl)-[1,1'-biphenyl]-3-yl)oxy)-N-methylpicolinamide;

3-((1H-pyrrolo[2,3-b]pyridin-5-yl)oxy)-N-((3-nitro-4-(((tetrahydro-2H-pyran-4-yl)methyl)amino)phenyl)sulfonyl)-4'-((2-phenylpyrrolidin-1-yl)methyl)-[1,1'-biphenyl]-4-carboxamide;

3-((1H-pyrrolo[2,3-b]pyridin-5-yl)oxy)-4'-((2-(2-chlorophenyl)pyrrolidin-1-yl)methyl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-((2-(2-cyclopropylphenyl)pyrrolidin-1-yl)methyl)-N-((3-nitro-4-(((tetrahydro-2H-pyran-4-yl)methyl)amino)phenyl)sulfonyl)-[1,1'-biphenyl]-4-carboxamide;

2-((1H-pyrrolo[2,3-b]pyridin-5-yl)oxy)-N-((3-nitro-4-(((tetrahydro-2H-pyran-4-yl)methyl)amino)phenyl)sulfonyl)-4-(1-((1-phenylpyrrolidin-2-yl)methyl)-1,2,3,6-tetrahydropyridin-4-yl)benzamide;

3-((1H-pyrrolo[2,3-b]pyridin-5-yl)oxy)-4'-((2-(4-chlorophenyl)pyrrolidin-1-yl)methyl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-((4'-chloro-5,5-dimethyl-3,4,5,6-tetrahydro-[1,1'-biphenyl]-2-yl)methyl)-N-((3-nitro-4-(((tetrahydro-2H-pyran-4-yl)methyl)amino)phenyl)sulfonyl)-[1,1'-biphenyl]-4-carboxamide;

2-((1H-pyrrolo[2,3-b]pyridin-5-yl)oxy)-N-((3-nitro-4-(((tetrahydro-2H-pyran-4-yl)methyl)amino)phenyl)sulfonyl)-4-(1-(phenylpropyl)-1,2,3,6-tetrahydropyridin-4-yl)benzamide;

2-((1H-pyrrolo[2,3-b]pyridin-5-yl)oxy)-4-(3-((2-(2-cyclopropylphenyl)pyrrolidin-1-yl)methyl)azetidin-1-yl)-N-((3-nitro-4-(((tetrahydro-2H-pyran-4-yl)methyl)amino)phenyl)sulfonyl)benzamide;

3-((1H-pyrrolo[2,3-b]pyridin-5-yl)oxy)-3'-((2-(2-cyclopropylphenyl)pyrrolidin-1-yl)methyl)-N-((3-nitro-4-(((tetrahydro-2H-pyran-4-yl)methyl)amino)phenyl)sulfonyl)-[1,1'-biphenyl]-4-carboxamide;

(R)-3-((1H-pyrrolo[2,3-b]pyridin-5-yl)oxy)-4'-(2-(2-(2-cyclopropylphenyl)pyrrolidin-1-yl)ethyl)-N-((3-nitro-4-(((tetrahydro-2H-pyran-4-yl)methyl)amino)phenyl)sulfonyl)-[1,1'-biphenyl]-4-carboxamide;

(S)-3-((1H-pyrrolo[2,3-b]pyridin-5-yl)oxy)-4'-(2-(2-(2-cyclopropylphenyl)pyrrolidin-1-yl)ethyl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(((S)-2-(2-cyclopropylphenyl)pyrrolidin-1-yl)methyl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

2-((1H-pyrrolo[2,3-b]pyridin-5-yl)oxy)-4-(4-((2-(2-cyclopropylphenyl)pyrrolidin-1-yl)methyl)piperidin-1-yl)-N-((3-nitro-4-(((tetrahydro-2H-pyran-4-yl)methyl)amino)phenyl)sulfonyl)benzamide;

(S)-2-((1H-pyrrolo[2,3-b]pyridin-5-yl)oxy)-4-(4-((2-(2-cyclopropylphenyl)pyrrolidin-1-yl)methyl)piperidin-1-yl)-N-((3-nitro-4-(((tetrahydro-2H-pyran-4-yl)methyl)amino)phenyl)sulfonyl)benzamide;

(S) 2-((1H-pyrrolo[2,3-b]pyridin-5-yl)oxy)-4-(3-(((S)-2-(2-cyclopropylphenyl)pyrrolidin-1-yl)methyl)piperidin-1-yl)-N-((3-nitro-4-(((tetrahydro-2H-pyran-4-yl)methyl)amino)phenyl)sulfonyl)benzamide;

(R) 2-((1H-pyrrolo[2,3-b]pyridin-5-yl)oxy)-4-(3-(((S)-2-(2-cyclopropylphenyl)pyrrolidin-1-yl)methyl)piperidin-1-yl)-N-((3-nitro-4-(((tetrahydro-2H-pyran-4-yl)methyl)amino)phenyl)sulfonyl)benzamide;

(S) 2-((1H-pyrrolo[2,3-b]pyridin-5-yl)oxy)-4-(3-(((R)-2-(2-cyclopropylphenyl)pyrrolidin-1-yl)methyl)piperidin-1-yl)-N-((3-nitro-4-(((tetrahydro-2H-pyran-4-yl)methyl)amino)phenyl)sulfonyl)benzamide;

(R) 2-((1H-pyrrolo[2,3-b]pyridin-5-yl)oxy)-4-(3-(((R)-2-(2-cyclopropylphenyl)pyrrolidin-1-yl)methyl)piperidin-1-yl)-N-((3-nitro-4-(((tetrahydro-2H-pyran-4-yl)methyl)amino)phenyl)sulfonyl)benzamide;

(S)-3-((1H-pyrrolo[2,3-b]pyridin-5-yl)oxy)-4'-((2-(3-cyclopropylphenyl)pyrrolidin-1-yl)methyl)-N-((3-nitro-4-(((tetrahydro-2H-pyran-4-yl)methyl)amino)phenyl)sulfonyl)-[1,1'-biphenyl]-4-carboxamide;

(R)-3-((1H-pyrrolo[2,3-b]pyridin-5-yl)oxy)-4'-((2-(3-cyclopropylphenyl)pyrrolidin-1-yl)methyl)-N-((3-nitro-4-(((tetrahydro-2H-pyran-4-yl)methyl)amino)phenyl)sulfonyl)-[1,1'-biphenyl]-4-carboxamide;

3-((1H-pyrrolo[2,3-b]pyridin-5-yl)oxy)-4'-(2-(2-(2-cyclopropylphenyl)pyrrolidin-1-yl)propan-2-yl)-N-((3-nitro-4-(((tetrahydro-2H-pyran-4-yl)methyl)amino)phenyl)sulfonyl)-[1,1'-biphenyl]-4-carboxamide;

2-((1H-pyrrolo[2,3-b]pyridin-5-yl)oxy)-4-(5-((2-(2-cyclopropylphenyl)pyrrolidin-1-yl)methyl)furan-2-yl)-N-((3-nitro-4-((((tetrahydro-2H-pyran-4-yl)methyl)amino)phenyl)sulfonyl)benzamide;

3-((1H-pyrrolo[2,3-b]pyridin-5-yl)oxy)-4'-(3-(2-(2-cyclopropylphenyl)pyrrolidin-1-yl)azetidin-1-yl)-N-((3-nitro-4-((((tetrahydro-2H-pyran-4-yl)methyl)amino)phenyl)sulfonyl)-[1,1'-biphenyl]-4-carboxamide;

2-((1H-pyrrolo[2,3-b]pyridin-5-yl)oxy)-4-(3-(2-(2-cyclopropylphenyl)pyrrolidin-1-yl)-[1,3'-biazetidin]-1'-yl)-N-((3-nitro-4-((((tetrahydro-2H-pyran-4-yl)methyl)amino)phenyl)sulfonyl)benzamide;

(S)-2-((1H-pyrrolo[2,3-b]pyridin-5-yl)oxy)-4-(4-(3-(2-(2-cyclopropylphenyl)pyrrolidin-1-yl)cyclobutyl)piperidin-1-yl)-N-((3-nitro-4-((((tetrahydro-2H-pyran-4-yl)methyl)amino)phenyl)sulfonyl)benzamide;

(R)-2-((1H-pyrrolo[2,3-b]pyridin-5-yl)oxy)-4-(4-(2-(2-cyclopropylphenyl)pyrrolidin-1-yl)benzyl)-N-((3-nitro-4-((((tetrahydro-2H-pyran-4-yl)methyl)amino)phenyl)sulfonyl)benzamide;

2-((1H-pyrrolo[2,3-b]pyridin-5-yl)oxy)-4-((4-(2-(2-cyclopropylphenyl)pyrrolidin-1-yl)cyclohexyl)methyl)-N-((3-nitro-4-((((tetrahydro-2H-pyran-4-yl)methyl)amino)phenyl)sulfonyl)benzamide;

2-((1H-pyrrolo[2,3-b]pyridin-5-yl)oxy)-4-(4-((2-(2-cyclopropylphenyl)pyrrolidin-1-yl)methyl)benzyl)-N-((3-nitro-4-((((tetrahydro-2H-pyran-4-yl)methyl)amino)phenyl)sulfonyl)benzamide;

(S)-2-((1H-pyrrolo[2,3-b]pyridin-5-yl)oxy)-4-((4-(2-(2-cyclopropylphenyl)pyrrolidin-1-yl)phenyl)amino)-N-((3-nitro-4-((((tetrahydro-2H-pyran-4-yl)methyl)amino)phenyl)sulfonyl)benzamide;

2-((1H-pyrrolo[2,3-b]pyridin-5-yl)oxy)-4-(1-(2-cyclopropylphenyl)-1,8-diazaspiro[4.5]decan-8-yl)-N-((3-nitro-4-((((tetrahydro-2H-pyran-4-yl)methyl)amino)phenyl)sulfonyl)benzamide;

3-((1H-pyrrolo[2,3-b]pyridin-5-yl)oxy)-4'-(1-(2-cyclopropylphenyl)-1,8-diazaspiro[4.5]decan-8-yl)-N-((4-(((((1r,4r)-4-hydroxy-4-methylcyclohexyl)methyl)amino)-3-nitrophenyl)sulfonyl)-[1,1'-biphenyl]-4-carboxamide;

2-((1H-pyrrolo[2,3-b]pyridin-5-yl)oxy)-4-(1-(2-bromophenyl)-1,8-diazaspiro[4.5]decan-8-yl)-N-((3-nitro-4-((((tetrahydro-2H-pyran-4-yl)methyl)amino)phenyl)sulfonyl)benzamide;

2-((1H-pyrrolo[2,3-b]pyridin-5-yl)oxy)-4-(6-((S)-2-(2-cyclopropylphenyl)pyrrolidin-1-yl)-5,6,7,8-tetrahydronaphthalen-2-yl)-N-((4-(((((1r,4r)-4-hydroxy-4-methylcyclohexyl)methyl)amino)-3-nitrophenyl)sulfonyl)benzamide;

2-((1H-pyrrolo[2,3-b]pyridin-5-yl)oxy)-4-(2-(2-(2-cyclopropylphenyl)pyrrolidin-1-yl)-1H-benzo[d]imidazol-5-yl)-N-((3-nitro-4-((((tetrahydro-2H-pyran-4-yl)methyl)amino)phenyl)sulfonyl)benzamide;

3-((1H-pyrrolo[2,3-b]pyridin-5-yl)oxy)-4'-(1-(2-(2-cyclopropylphenyl)pyrrolidin-1-yl)ethyl)-N-((3-nitro-4-((((tetrahydro-2H-pyran-4-yl)methyl)amino)phenyl)sulfonyl)-[1,1'-biphenyl]-4-carboxamide;

(S)-2-((1H-pyrrolo[2,3-b]pyridin-5-yl)oxy)-4-(1-(3-(2-(2-cyclopropylphenyl)pyrrolidin-1-yl)cyclobutyl)-1H-pyrazol-4-yl)-N-((3-nitro-4-((((tetrahydro-2H-pyran-4-yl)methyl)amino)phenyl)sulfonyl)benzamide;

3-((1H-pyrrolo[2,3-b]pyridin-5-yl)oxy)-N-((3-nitro-4-((((tetrahydro-2H-pyran-4-yl)methyl)amino)phenyl)sulfonyl)-4'-(3-phenyl-6,7-dihydrothieno[3,2-c]pyridin-5(4H)-yl)-[1,1'-biphenyl]-4-carboxamide;

2-((1H-pyrrolo[2,3-b]pyridin-5-yl)oxy)-4-(2-(2-cyclopropylphenyl)-2,9-diazaspiro[5.5]undecan-9-yl)-N-((3-nitro-4-((((tetrahydro-2H-pyran-4-yl)methyl)amino)phenyl)sulfonyl)benzamide;

3-((1H-pyrrolo[2,3-b]pyridin-5-yl)oxy)-N-((3-nitro-4-((((tetrahydro-2H-pyran-4-yl)methyl)amino)phenyl)sulfonyl)-4'-(2-phenylpyrrolidin-1-yl)-2',3',4',5'-tetrahydro-[1,1'-biphenyl]-4-carboxamide;

3-((1H-pyrrolo[2,3-b]pyridin-5-yl)oxy)-4'-(2-(2-bromophenyl)pyrrolidin-1-yl)-N-((3-nitro-4-((((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2-cyclopropylphenyl)pyrrolidin-1-yl)-N-((3-nitro-4-((((tetrahydro-2H-pyran-4-yl)methyl)amino)phenyl)sulfonyl)-2',3',4',5'-tetrahydro-[1,1'-biphenyl]-4-carboxamide;

(S)-3-((1H-pyrrolo[2,3-b]pyridin-5-yl)oxy)-4'-((S)-2-(2-cyclopropylphenyl)pyrrolidin-1-yl)-N-((3-nitro-4-((((tetrahydro-2H-pyran-4-yl)methyl)amino)phenyl)sulfonyl)-2',3',4',5'-tetrahydro-[1,1'-biphenyl]-4-carboxamide;

(R)-3-((1H-pyrrolo[2,3-b]pyridin-5-yl)oxy)-4'-((S)-2-(2-cyclopropylphenyl)pyrrolidin-1-yl)-N-((3-nitro-4-((((tetrahydro-2H-pyran-4-yl)methyl)amino)phenyl)sulfonyl)-2',3',4',5'-tetrahydro-[1,1'-biphenyl]-4-carboxamide;

(S)-3-((1H-pyrrolo[2,3-b]pyridin-5-yl)oxy)-4'-((R)-2-(2-cyclopropylphenyl)pyrrolidin-1-yl)-N-((3-nitro-4-((((tetrahydro-2H-pyran-4-yl)methyl)amino)phenyl)sulfonyl)-2',3',4',5'-tetrahydro-[1,1'-biphenyl]-4-carboxamide;

(R)-3-((1H-pyrrolo[2,3-b]pyridin-5-yl)oxy)-4'-((R)-2-(2-cyclopropylphenyl)pyrrolidin-1-yl)-N-((3-nitro-4-((((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(3-cyclopropylphenyl)pyrrolidin-1-yl)-N-((3-nitro-4-((((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-N-((3-nitro-4-((((tetrahydro-2H-pyran-4-yl)methyl)amino)phenyl)sulfonyl)-4'-(2-(pyridin-3-yl)pyrrolidin-1-yl)-2',3',4',5'-tetrahydro-[1,1'-biphenyl]-4-carboxamide;

3-((1H-pyrrolo[2,3-b]pyridin-5-yl)oxy)-4'-(2-benzylpyrrolidin-1-yl)-N-((3-nitro-4-((((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-N-((3-nitro-4-((((tetrahydro-2H-pyran-4-yl)methyl)amino)phenyl)sulfonyl)-4'-(2-(pyridin-2-yl)pyrrolidin-1-yl)-2',3',4',5'-tetrahydro-[1,1'-biphenyl]-4-carboxamide;

3-((1H-pyrrolo[2,3-b]pyridin-5-yl)oxy)-4'-(2-(2-(furan-3-yl)phenyl)pyrrolidin-1-yl)-N-((3-nitro-4-((((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2-chlorophenyl)pyrrolidin-1-yl)-N-((3-nitro-4-((((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-N-((3-nitro-4-((((tetrahydro-2H-pyran-4-yl)methyl)amino)phenyl)sulfonyl)-4'-(2-(2-(trifluoromethyl)phenyl)pyrrolidin-1-yl)-2',3',4',5'-tetrahydro-[1,1'-biphenyl]-4-carboxamide;

3-((1H-pyrrolo[2,3-b]pyridin-5-yl)oxy)-4'-(2-(naphthalen-1-yl)pyrrolidin-1-yl)-N-((3-nitro-4-((((tetrahydro- 2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(4,4-dimethyl-2-phenylpyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2,6-dichlorophenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(2-propylphenyl)pyrrolidin-1-yl)-2',3',4',5'-tetrahydro-[1,1'-biphenyl]-4-carboxamide;

3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(2-(thiophen-2-yl)phenyl)pyrrolidin-1-yl)-2',3',4',5'-tetrahydro-[1,1'-biphenyl]-4-carboxamide;

3-((1H-pyrrolo[2,3-b]pyridin-5-yl)oxy)-4'-(2-(2-benzylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(pyridin-4-yl)pyrrolidin-1-yl)-2',3',4',5'-tetrahydro-[1,1'-biphenyl]-4-carboxamide;

3-((1H-pyrrolo[2,3-b]pyridin-5-yl)oxy)-4'-(2-(2-isopropylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(2-(prop-1-en-2-yl)phenyl)pyrrolidin-1-yl)-2',3',4',5'-tetrahydro-[1,1'-biphenyl]-4-carboxamide;

3-((1H-pyrrolo[2,3-b]pyridin-5-yl)oxy)-4'-(2-(2-isobutylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2-(cyclopropylmethyl)phenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

cis-3-((1H-pyrrolo[2,3-b]pyridin-5-yl)oxy)-4'-(2-(2-(2-cyanocyclopropyl)phenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

trans-3-((1H-pyrrolo[2,3-b]pyridin-5-yl)oxy)-4'-(2-(2-(2-cyanocyclopropyl)phenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide 3-((1H-pyrrolo[2,3-b]pyridin-5-yl)oxy)-4'-(2-(2-((S)-2,2-difluorocyclopropyl)phenyl)pyrrolidin-1-yl)-N-((3-nitro-4-(((tetrahydro-2H-pyran-4-yl)methyl)amino)phenyl)sulfonyl)-2',3a',4',5'-tetrahydro-[1,1'-biphenyl]-4-carboxamide;

3-((1H-pyrrolo[2,3-b]pyridin-5-yl)oxy)-4'-(2-(2-((R)-2,2-difluorocyclopropyl)phenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide 3-((1H-pyrrolo[2,3-b]pyridin-5-yl)oxy)-4'-(2-(2-cyclobutylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2-(dimethylamino)phenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2-(difluoromethoxy)phenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(2-(trifluoromethoxy)phenyl)pyrrolidin-1-yl)-2',3',4',5'-tetrahydro-[1,1'-biphenyl]-4-carboxamide;

3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(2-propoxyphenyl)pyrrolidin-1-yl)-2',3',4',5'-tetrahydro-[1,1'-biphenyl]-4-carboxamide;

3-((1H-pyrrolo[2,3-b]pyridin-5-yl)oxy)-4'-(2-(2-(2-methoxyethoxy)phenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2-isopropoxyphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2-cyclopropoxyphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2-chloro-6-cyclopropylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2,6-dimethylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2-chloro-3-fluorophenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2,3-dichlorophenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(3-chloro-2-cyclopropylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2-cyclopropyl-3-fluorophenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2-cyclopropyl-4-fluorophenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2-cyclopropyl-5-fluorophenyl)pyrrolidin-1-yl)-N-((3-nitro-4-

(((tetrahydro-2H-pyran-4-yl)methyl)amino)phenyl) sulfonyl)-2',3',4',5'-tetrahydro-[1,1'-biphenyl]-4-carboxamide;

3-((1H-pyrrolo[2,3-b]pyridin-5-yl)oxy)-4'-(2-(2-cyclopropyl-6-fluorophenyl)pyrrolidin-1-yl)-N-((3-nitro-4-(((tetrahydro-2H-pyran-4-yl)methyl)amino)phenyl) sulfonyl)-2',3',4',5'-tetrahydro-[1,1'-biphenyl]-4-carboxamide;

3-((1H-pyrrolo[2,3-b]pyridin-5-yl)oxy)-4'-(2-(3-cyclopropylthiophen-2-yl)pyrrolidin-1-yl)-N-((3-nitro-4-(((tetrahydro-2H-pyran-4-yl)methyl)amino)phenyl) sulfonyl)-2',3',4',5'-tetrahydro-[1,1'-biphenyl]-4-carboxamide;

3-((1H-pyrrolo[2,3-b]pyridin-5-yl)oxy)-4'-(2-cyclohexylpyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(benzo[b]thiophen-7-yl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-N-((3-nitro-4-(((tetrahydro-2H-pyran-4-yl)methyl)amino)phenyl) sulfonyl)-4'-(2-(phenylethynyl)pyrrolidin-1-yl)-2',3',4',5'-tetrahydro-[1,1'-biphenyl]-4-carboxamide;

3-((1H-pyrrolo[2,3-b]pyridin-5-yl)oxy)-N-((3-nitro-4-(((tetrahydro-2H-pyran-4-yl)methyl)amino)phenyl) sulfonyl)-4'-(2-(2-(piperidin-4-yl)phenyl)pyrrolidin-1-yl)-2',3',4',5'-tetrahydro-[1,1'-biphenyl]-4-carboxamide;

3-((1H-pyrrolo[2,3-b]pyridin-5-yl)oxy)-N-((3-nitro-4-(((tetrahydro-2H-pyran-4-yl)methyl)amino)phenyl) sulfonyl)-4'-(2-(2-phenoxyphenyl)pyrrolidin-1-yl)-2',3',4',5'-tetrahydro-[1,1'-biphenyl]-4-carboxamide;

3-((1H-pyrrolo[2,3-b]pyridin-5-yl)oxy)-4'-(2-(2-cyclopropyl-5-methoxyphenyl)pyrrolidin-1-yl)-N-((3-nitro-4-(((tetrahydro-2H-pyran-4-yl)methyl)amino)phenyl) sulfonyl)-2',3',4',5'-tetrahydro-[1,1'-biphenyl]-4-carboxamide;

3-((1H-pyrrolo[2,3-b]pyridin-5-yl)oxy)-4'-(2-(2-cyclopropylphenyl)-2,5-dihydro-1H-pyrrol-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(1-(2-cyclopropylphenyl)isoindolin-2-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(4-hydroxy-2-phenylpyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-((4S)-2-(2-cyclopropylphenyl)-4-methoxypyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-((4R)-2-(2-cyclopropylphenyl)-4-methoxypyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2-cyclopropylphenyl)-4-fluoropyrrolidin-1-yl)-N-((3-nitro-4-(((tetrahydro-2H-pyran-4-yl)methyl)amino)phenyl) sulfonyl)-2',3',4',5'-tetrahydro-[1,1'-biphenyl]-4-carboxamide;

3-((1H-pyrrolo[2,3-b]pyridin-5-yl)oxy)-4'-(2-(2-cyclopropylphenyl)-4,4-difluoropyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-N-((3-nitro-4-(((tetrahydro-2H-pyran-4-yl)methyl)amino)phenyl) sulfonyl)-4'-(2-phenylazetidin-1-yl)-2',3',4',5'-tetrahydro-[1,1'-biphenyl]-4-carboxamide;

3-((1H-pyrrolo[2,3-b]pyridin-5-yl)oxy)-4'-(2-(2-cyclopropylbenzyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-N-((3-nitro-4-(((tetrahydro-2H-pyran-4-yl)methyl)amino)phenyl) sulfonyl)-4'-(2-(o-tolyl)pyrrolidin-1-yl)-2',3',4',5'-tetrahydro-[1,1'-biphenyl]-4-carboxamide;

3-((1H-pyrrolo[2,3-b]pyridin-5-yl)oxy)-4'-(2-(2-ethylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide 3-((1H-pyrrolo[2,3-b]pyridin-5-yl)oxy)-N-((3-nitro-4-(((tetrahydro-2H-pyran-4-yl)methyl)amino)phenyl) sulfonyl)-4'-(2-(2-vinylphenyl)pyrrolidin-1-yl)-2',3',4',5'-tetrahydro-[1,1'-biphenyl]-4-carboxamide;

3-((1H-pyrrolo[2,3-b]pyridin-5-yl)oxy)-4'-(2-(2-chloro-4-fluorophenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2-bromo-6-chlorophenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-cyclopentylpyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide 3-((1H-pyrrolo[2,3-b]pyridin-5-yl)oxy)-4'-(2-(2-butylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(5-bromo-2-isopropoxyphenyl)pyrrolidin-1-yl)-N-((3-nitro-4-(((tetrahydro-2H-pyran-4-yl)methyl)amino)phenyl) sulfonyl)-2',3',4',5'-tetrahydro-[1,1'-biphenyl]-4-carboxamide;

3-((1H-pyrrolo[2,3-b]pyridin-5-yl)oxy)-N-((3-nitro-4-(((tetrahydro-2H-pyran-4-yl)methyl)amino)phenyl) sulfonyl)-4'-(2-(m-tolyl)pyrrolidin-1-yl)-2',3',4',5'-tetrahydro-[1,1'-biphenyl]-4-carboxamide;

3-((1H-pyrrolo[2,3-b]pyridin-5-yl)oxy)-4'-(2-(3-isopropylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(3-methoxyphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(3-cyanophenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-N-((3-nitro-4-(((tetrahydro-2H-pyran-4-yl)methyl)amino)phenyl) sulfonyl)-4'-(2-(3-vinylphenyl)pyrrolidin-1-yl)-2',3',4',5'-tetrahydro-[1,1'-biphenyl]-4-carboxamide;

3-((1H-pyrrolo[2,3-b]pyridin-5-yl)oxy)-4'-(2-(benzo[d] [1,3]dioxol-4-yl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2,2-difluorobenzo[d][1,3]dioxol-4-yl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2-cyclopropylphenyl)-3-methylpyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2-cyclopropylphenyl)-3,3-dimethylpyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(4-chloro-2-cyclopropylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(5-chloro-2-cyclopropylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2-(1,1-difluoroethyl)phenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(2-(2,2,2-trifluoroethyl)phenyl)pyrrolidin-1-yl)-2',3',4',5'-tetrahydro-[1,1'-biphenyl]-4-carboxamide;

3-((1H-pyrrolo[2,3-b]pyridin-5-yl)oxy)-4'-(2-(2-cyclopentylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2,2-dimethylbenzo[d][1,3]dioxol-4-yl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(3-ethynylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(3-cyano-2-(2-cyclopropylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2-cyclopropylphenyl)-3-ethynylpyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2-methoxyphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(benzo[b]thiophen-3-yl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(3-(2-chlorophenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(5-cyclopropyl-2-fluorophenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2-chloro-5-cyclopropylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2-cyclopropyl-5-methylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2-cyclopropyl-5-((2-(dimethylamino)ethyl)(methyl)amino)phenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2-cyclopropyl-5-((2-(dimethylamino)ethyl)amino)phenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2-(but-1-en-1-yl)phenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2-(cyclopropyl(methyl)amino)phenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2-(1-methyl-1,2,3,6-tetrahydropyridin-4-yl)phenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2-(1-acetyl-1,2,3,6-tetrahydropyridin-4-yl)phenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(4-cyclopropylthiophen-2-yl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(1-cyclopropyl-1H-pyrazol-3-yl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(4-chloro-2-(2-cyclopropylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide 3-((1H-pyrrolo[2,3-b]pyridin-5-yl)oxy)-4'-(2-(2-cyclopropylphenyl)-4-methylenepyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(1-(2-cyclopropylphenyl)hexahydrocyclopenta[c]pyrrol-2(1H)-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(1-phenylisoindolin-2-yl)-2',3',4',5'-tetrahydro-[1,1'-biphenyl]-4-carboxamide;

3-((1H-pyrrolo[2,3-b]pyridin-5-yl)oxy)-4'-(2-((2-cyclopropylphenyl)(methoxy)methyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2-isopropylbenzyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(3-(2-cyclopropylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(3-(2-isopropylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(3-fluoro-2-methylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2-(2-methylprop-1-en-1-yl)phenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(benzo[b]thiophen-2-yl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide 3-((1H-pyrrolo[2,3-b]pyridin-5-yl)oxy)-4'-(2-(4-cyclopropylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(1-butylhexahydrocyclopenta[c]pyrrol-2(1H)-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(3-chloro-2-methylphenyl)pyrrolidin-1-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-N-((3-nitro-4-(((tetrahydro-2H-pyran-4-yl)methyl)amino)phenyl)sulfonyl)-4'-(2-(2-(1,2,3,6-tetrahydropyridin-4-yl)phenyl)pyrrolidin-1-yl)-2',3',4',5'-tetrahydro-[1,1'-biphenyl]-4-carboxamide;

cis-2-((1H-pyrrolo[2,3-b]pyridin-5-yl)oxy)-4-(4-(2-(2-chlorophenyl)pyrrolidin-1-yl)cyclohexyl)-N-((3-nitro-4-(((tetrahydro-2H-pyran-4-yl)methyl)amino)phenyl)sulfonyl)benzamide;

trans-2-((1H-pyrrolo[2,3-b]pyridin-5-yl)oxy)-4-(4-(2-(2-chlorophenyl)pyrrolidin-1-yl)cyclohexyl)-N-((3-nitro-4-(((tetrahydro-2H-pyran-4-yl)methyl)amino)phenyl)sulfonyl)benzamide;

cis-2-((1H-pyrrolo[2,3-b]pyridin-5-yl)oxy)-4-(4-(2-(2-cyclopropylphenyl)pyrrolidin-1-yl)cyclohexyl)-N-((3-nitro-4-(((tetrahydro-2H-pyran-4-yl)methyl)amino)phenyl)sulfonyl)benzamide;

trans-2-((1H-pyrrolo[2,3-b]pyridin-5-yl)oxy)-4-(4-(2-(2-cyclopropylphenyl)pyrrolidin-1-yl)cyclohexyl)-N-((3-nitro-4-(((tetrahydro-2H-pyran-4-yl)methyl)amino)phenyl)sulfonyl)benzamide;

cis-(S)-2-((1H-pyrrolo[2,3-b]pyridin-5-yl)oxy)-4-(4-(2-(2-cyclopropylphenyl)pyrrolidin-1-yl)cyclohexyl)-N-((3-nitro-4-(((tetrahydro-2H-pyran-4-yl)methyl)amino)phenyl)sulfonyl)benzamide;

trans-(S)-2-((1H-pyrrolo[2,3-b]pyridin-5-yl)oxy)-4-(4-(2-(2-cyclopropylphenyl)pyrrolidin-1-yl)cyclohexyl)-N-((3-nitro-4-(((tetrahydro-2H-pyran-4-yl)methyl)amino)phenyl)sulfonyl)benzamide;

cis-(R)-2-((1H-pyrrolo[2,3-b]pyridin-5-yl)oxy)-4-(4-(2-(2-cyclopropylphenyl)pyrrolidin-1-yl)cyclohexyl)-N-((3-nitro-4-(((tetrahydro-2H-pyran-4-yl)methyl)amino)phenyl)sulfonyl)benzamide;

trans-(R)-2-((1H-pyrrolo[2,3-b]pyridin-5-yl)oxy)-4-(4-(2-(2-cyclopropylphenyl)pyrrolidin-1-yl)cyclohexyl)-N-((3-nitro-4-(((tetrahydro-2H-pyran-4-yl)methyl)amino)phenyl)sulfonyl)benzamide;

cis-2-((1H-pyrrolo[2,3-b]pyridin-5-yl)oxy)-4-(4-(2-(3-cyclopropylphenyl)pyrrolidin-1-yl)cyclohexyl)-N-((3-nitro-4-(((tetrahydro-2H-pyran-4-yl)methyl)amino)phenyl)sulfonyl)benzamide;

trans-2-((1H-pyrrolo[2,3-b]pyridin-5-yl)oxy)-4-(4-(2-(3-cyclopropylphenyl)pyrrolidin-1-yl)cyclohexyl)-N-((3-nitro-4-(((tetrahydro-2H-pyran-4-yl)methyl)amino)phenyl)sulfonyl)benzamide;

cis-2-((1H-pyrrolo[2,3-b]pyridin-5-yl)oxy)-4-(4-(2-(4-cyclopropylphenyl)pyrrolidin-1-yl)cyclohexyl)-N-((3-nitro-4-(((tetrahydro-2H-pyran-4-yl)methyl)amino)phenyl)sulfonyl)benzamide;

trans-2-((1H-pyrrolo[2,3-b]pyridin-5-yl)oxy)-4-(4-(2-(4-cyclopropylphenyl)pyrrolidin-1-yl)cyclohexyl)-N-((3-nitro-4-(((tetrahydro-2H-pyran-4-yl)methyl)amino)phenyl)sulfonyl)benzamide;

cis-2-((1H-pyrrolo[2,3-b]pyridin-5-yl)oxy)-4-(4-(2-(2-isopropylphenyl)pyrrolidin-1-yl)cyclohexyl)-N-((3-nitro-4-(((tetrahydro-2H-pyran-4-yl)methyl)amino)phenyl)sulfonyl)benzamide;

trans-2-((1H-pyrrolo[2,3-b]pyridin-5-yl)oxy)-4-(4-(2-(2-isopropylphenyl)pyrrolidin-1-yl)cyclohexyl)-N-((3-nitro-4-(((tetrahydro-2H-pyran-4-yl)methyl)amino)phenyl)sulfonyl)benzamide;

cis-2-((1H-pyrrolo[2,3-b]pyridin-5-yl)oxy)-N-((3-nitro-4-(((tetrahydro-2H-pyran-4-yl)methyl)amino)phenyl)sulfonyl)-4-(4-(2-(2-(prop-1-en-2-yl)phenyl)pyrrolidin-1-yl)cyclohexyl)benzamide;

trans-2-((1H-pyrrolo[2,3-b]pyridin-5-yl)oxy)-N-((3-nitro-4-(((tetrahydro-2H-pyran-4-yl)methyl)amino)phenyl)sulfonyl)-4-(4-(2-(2-(prop-1-en-2-yl)phenyl)pyrrolidin-1-yl)cyclohexyl)benzamide;

cis-2-((1H-pyrrolo[2,3-b]pyridin-5-yl)oxy)-4-(4-(2-(3-chlorophenyl)pyrrolidin-1-yl)cyclohexyl)-N-((3-nitro-4-(((tetrahydro-2H-pyran-4-yl)methyl)amino)phenyl)sulfonyl)benzamide;

trans-2-((1H-pyrrolo[2,3-b]pyridin-5-yl)oxy)-4-(4-(2-(3-chlorophenyl)pyrrolidin-1-yl)cyclohexyl)-N-((3-nitro-4-(((tetrahydro-2H-pyran-4-yl)methyl)amino)phenyl)sulfonyl)benzamide;

cis-2-((1H-pyrrolo[2,3-b]pyridin-5-yl)oxy)-4-(4-(2-(4-chlorophenyl)pyrrolidin-1-yl)cyclohexyl)-N-((3-nitro-4-(((tetrahydro-2H-pyran-4-yl)methyl)amino)phenyl)sulfonyl)benzamide;

trans-2-((1H-pyrrolo[2,3-b]pyridin-5-yl)oxy)-4-(4-(2-(4-chlorophenyl)pyrrolidin-1-yl)cyclohexyl)-N-((3-nitro-4-(((tetrahydro-2H-pyran-4-yl)methyl)amino)phenyl)sulfonyl)benzamide;

cis-2-((1H-pyrrolo[2,3-b]pyridin-5-yl)oxy)-N-((3-nitro-4-(((tetrahydro-2H-pyran-4-yl)methyl)amino)phenyl)sulfonyl)-4-(4-(2-phenylpyrrolidin-1-yl)cyclohexyl)benzamide;

trans-2-((1H-pyrrolo[2,3-b]pyridin-5-yl)oxy)-N-((3-nitro-4-(((tetrahydro-2H-pyran-4-yl)methyl)amino)phenyl)sulfonyl)-4-(4-(2-phenylpyrrolidin-1-yl)cyclohexyl)benzamide;

cis-2-((1H-pyrrolo[2,3-b]pyridin-5-yl)oxy)-N-((3-nitro-4-(((tetrahydro-2H-pyran-4-yl)methyl)amino)phenyl)sulfonyl)-4-(4-(2-(o-tolyl)pyrrolidin-1-yl)cyclohexyl)benzamide;

trans-2-((1H-pyrrolo[2,3-b]pyridin-5-yl)oxy)-N-((3-nitro-4-(((tetrahydro-2H-pyran-4-yl)methyl)amino)phenyl)sulfonyl)-4-(4-(2-(o-tolyl)pyrrolidin-1-yl)cyclohexyl)benzamide;

cis-2-((1H-pyrrolo[2,3-b]pyridin-5-yl)oxy)-4-(4-(2-(2-ethylphenyl)pyrrolidin-1-yl)cyclohexyl)-N-((3-nitro-4-(((tetrahydro-2H-pyran-4-yl)methyl)amino)phenyl)sulfonyl)benzamide;

trans-2-((1H-pyrrolo[2,3-b]pyridin-5-yl)oxy)-4-(4-(2-(2-ethylphenyl)pyrrolidin-1-yl)cyclohexyl)-N-((3-nitro-4-(((tetrahydro-2H-pyran-4-yl)methyl)amino)phenyl)sulfonyl)benzamide;

cis-2-((1H-pyrrolo[2,3-b]pyridin-5-yl)oxy)-4-(4-(3-(3-chlorophenyl)pyrrolidin-1-yl)cyclohexyl)-N-((3-nitro-4-(((tetrahydro-2H-pyran-4-yl)methyl)amino)phenyl)sulfonyl)benzamide;

trans-2-((1H-pyrrolo[2,3-b]pyridin-5-yl)oxy)-4-(4-(3-(3-chlorophenyl)pyrrolidin-1-yl)cyclohexyl)-N-((3-nitro-4-(((tetrahydro-2H-pyran-4-yl)methyl)amino)phenyl)sulfonyl)benzamide;

cis-2-((1H-pyrrolo[2,3-b]pyridin-5-yl)oxy)-N-((3-nitro-4-(((tetrahydro-2H-pyran-4-yl)methyl)amino)phenyl)sulfonyl)-4-(4-(2-(2-phenoxyphenyl)pyrrolidin-1-yl)cyclohexyl)benzamide;

trans-2-((1H-pyrrolo[2,3-b]pyridin-5-yl)oxy)-N-((3-nitro-4-(((tetrahydro-2H-pyran-4-yl)methyl)amino)phenyl)sulfonyl)-4-(4-(2-(2-phenoxyphenyl)pyrrolidin-1-yl)cyclohexyl)benzamide;

cis-2-((1H-pyrrolo[2,3-b]pyridin-5-yl)oxy)-4-(4-(2-(2-cyclopropylstyryl)pyrrolidin-1-yl)cyclohexyl)-N-((3-nitro-4-(((tetrahydro-2H-pyran-4-yl)methyl)amino)phenyl)sulfonyl)benzamide;

trans-2-((1H-pyrrolo[2,3-b]pyridin-5-yl)oxy)-4-(4-(2-(2-cyclopropylstyryl)pyrrolidin-1-yl)cyclohexyl)-N-((3-nitro-4-(((tetrahydro-2H-pyran-4-yl)methyl)amino)phenyl)sulfonyl)benzamide;

2-((1H-pyrrolo[2,3-b]pyridin-5-yl)oxy)-N-((3-nitro-4-(((tetrahydro-2H-pyran-4-yl)methyl)amino)phenyl)sulfonyl)-4-(4-(2-styrylpyrrolidin-1-yl)cyclohexyl)benzamide;

2-((1H-pyrrolo[2,3-b]pyridin-5-yl)oxy)-4-(4-(2-(2-methoxyphenyl)pyrrolidin-1-yl)cyclohexyl)-N-((3-nitro-4-(((tetrahydro-2H-pyran-4-yl)methyl)amino)phenyl)sulfonyl)benzamide;

2-((1H-pyrrolo[2,3-b]pyridin-5-yl)oxy)-4-(4-(dibenzylamino)cyclohexyl)-N-((3-nitro-4-(((tetrahydro-2H-pyran-4-yl)methyl)amino)phenyl)sulfonyl)benzamide;

2-((1H-pyrrolo[2,3-b]pyridin-5-yl)oxy)-4-(4-(benzhydrylamino)cyclohexyl)-N-((3-nitro-4-(((tetrahydro-2H-pyran-4-yl)methyl)amino)phenyl)sulfonyl)benzamide;

(R)-2-((1H-pyrrolo[2,3-b]pyridin-5-yl)oxy)-4-(4-(methyl(1-phenylethyl)amino)cyclohexyl)-N-((3-nitro-4-(((tetrahydro-2H-pyran-4-yl)methyl)amino)phenyl)sulfonyl)benzamide;

2-((1H-pyrrolo[2,3-b]pyridin-5-yl)oxy)-4-(cis-4-(3-(2-(2-cyclopropylphenyl)pyrrolidin-1-yl)azetidin-1-yl)cyclohexyl)-N-((3-nitro-4-(((tetrahydro-2H-pyran-4-yl)methyl)amino)phenyl)sulfonyl)benzamide;

2-((1H-pyrrolo[2,3-b]pyridin-5-yl)oxy)-4-(trans-4-(3-(2-(2-cyclopropylphenyl)pyrrolidin-1-yl)azetidin-1-yl)cyclohexyl)-N-((3-nitro-4-(((tetrahydro-2H-pyran-4-yl)methyl)amino)phenyl)sulfonyl)benzamide;

2-((1H-pyrrolo[2,3-b]pyridin-5-yl)oxy)-N-((3-nitro-4-(((tetrahydro-2H-pyran-4-yl)methyl)amino)phenyl)sulfonyl)-4-(6-(2-phenylpyrrolidin-1-yl)pyridin-3-yl)benzamide;

2-((1H-pyrrolo[2,3-b]pyridin-5-yl)oxy)-N-((3-nitro-4-(((tetrahydro-2H-pyran-4-yl)methyl)amino)phenyl)sulfonyl)-4-(4-(2-phenylpyrrolidin-1-yl)piperidin-1-yl)benzamide;

2-((1H-pyrrolo[2,3-b]pyridin-5-yl)oxy)-4-(4-(2-(2-chlorophenyl)pyrrolidin-1-yl)piperidin-1-yl)-N-((3-nitro-4-(((tetrahydro-2H-pyran-4-yl)methyl)amino)phenyl)sulfonyl)benzamide;

2-((1H-pyrrolo[2,3-b]pyridin-5-yl)oxy)-4-(4-(2-(3-chlorophenyl)pyrrolidin-1-yl)piperidin-1-yl)-N-((3-nitro-4-(((tetrahydro-2H-pyran-4-yl)methyl)amino)phenyl)sulfonyl)benzamide;

2-((1H-pyrrolo[2,3-b]pyridin-5-yl)oxy)-4-(4-(2-(2-cyclopropylphenyl)pyrrolidin-1-yl)piperidin-1-yl)-N-((3-nitro-4-(((tetrahydro-2H-pyran-4-yl)methyl)amino)phenyl)sulfonyl)benzamide;

2-((1H-pyrrolo[2,3-b]pyridin-5-yl)oxy)-4-(5-(2-(2-cyclopropylphenyl)pyrrolidin-1-yl)pyridin-2-yl)-N-((3-nitro-4-(((tetrahydro-2H-pyran-4-yl)methyl)amino)phenyl)sulfonyl)benzamide;

2-((1H-pyrrolo[2,3-b]pyridin-5-yl)oxy)-N-((3-nitro-4-(((tetrahydro-2H-pyran-4-yl)methyl)amino)phenyl)sulfonyl)-4-(5-(2-phenylpyrrolidin-1-yl)pyrazolo[1,5-a]pyrimidin-2-yl)benzamide;

2-((1H-pyrrolo[2,3-b]pyridin-5-yl)oxy)-N-((3-nitro-4-(((tetrahydro-2H-pyran-4-yl)methyl)amino)phenyl)sulfonyl)-4-(5-(2-phenylpyrrolidin-1-yl)benzo[b]thiophen-2-yl)benzamide;

cis-2-((1H-pyrrolo[2,3-b]pyridin-5-yl)oxy)-4-((4-(2-(2-cyclopropylphenyl)pyrrolidin-1-yl)cyclohexyl)oxy)-N-((3-nitro-4-(((tetrahydro-2H-pyran-4-yl)methyl)amino)phenyl)sulfonyl)benzamide;

trans-2-((H-pyrrolo[2,3-b]pyridin-5-yl)oxy)-4-((4-(2-(2-cyclopropylphenyl)pyrrolidin-1-yl)cyclohexyl)oxy)-N-((3-nitro-4-(((tetrahydro-2H-pyran-4-yl)methyl)amino)phenyl)sulfonyl)benzamide;

cis-2-((1H-pyrrolo[2,3-b]pyridin-5-yl)oxy)-4-((4-(2-(2-cyclopropylphenyl)pyrrolidin-1-yl)cyclohexyl)(methyl)amino)-N-((3-nitro-4-(((tetrahydro-2H-pyran-4-yl)methyl)amino)phenyl)sulfonyl)benzamide;

trans-2-((H-pyrrolo[2,3-b]pyridin-5-yl)oxy)-4-((4-(2-(2-cyclopropylphenyl)pyrrolidin-1-yl)cyclohexyl)(methyl)amino)-N-((3-nitro-4-(((tetrahydro-2H-pyran-4-yl)methyl)amino)phenyl)sulfonyl)benzamide;

2-((H-pyrrolo[2,3-b]pyridin-5-yl)oxy)-4-(2-((S)-2-(2-cyclopropylphenyl)pyrrolidin-1-yl)-7-azaspiro[3.5]nonan-7-yl)-N-((4-((((1r,4r)-4-hydroxy-4-methylcyclohexyl)methyl)amino)-3-nitrophenyl)sulfonyl)benzamide;

(S)-2-((1H-pyrrolo[2,3-b]pyridin-5-yl)oxy)-4-(2-(2-(2-cyclopropylphenyl)pyrrolidin-1-yl)-7-azaspiro[3.5]nonan-7-yl)-N-((4-(((4-fluorotetrahydro-2H-pyran-4-yl)methyl)amino)-3-nitrophenyl)sulfonyl)benzamide;

(S)-2-((1H-pyrrolo[2,3-b]pyridin-5-yl)oxy)-4-(2-(2-(2-cyclopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide;

(S)-2-((1H-pyrrolo[2,3-b]pyridin-5-yl)oxy)-4-(2-(2-(2-ethylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide;

(S)-2-((H-pyrrolo[2,3-b]pyridin-5-yl)oxy)-4-(2-(2-ethylphenyl)pyrrolidin-1-yl)-7-azaspiro[3.5]nonan-7-yl)-N-((4-(((4-fluorotetrahydro-2H-pyran-4-yl)methyl)amino)-3-nitrophenyl)sulfonyl)benzamide;

2-((1H-pyrrolo[2,3-b]pyridin-5-yl)oxy)-4-(2-((S)-2-(2-ethylphenyl)pyrrolidin-1-yl)-7-azaspiro[3.5]nonan-7-yl)-N-((4-((((1r,4r)-4-hydroxy-4-methylcyclohexyl)methyl)amino)-3-nitrophenyl)sulfonyl)benzamide;

(R)-2-((1H-pyrrolo[2,3-b]pyridin-5-yl)oxy)-4-(2-(2-(2-cyclopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide;

(R)-2-((1H-pyrrolo[2,3-b]pyridin-5-yl)oxy)-4-(2-(2-(2-cyclopropylphenyl)pyrrolidin-1-yl)-7-azaspiro[3.5]nonan-7-yl)-N-((4-(((4-fluorotetrahydro-2H-pyran-4-yl)methyl)amino)-3-nitrophenyl)sulfonyl)benzamide;

2-((1H-pyrrolo[2,3-b]pyridin-5-yl)oxy)-4-(2-((R)-2-(2-cyclopropylphenyl)pyrrolidin-1-yl)-7-azaspiro[3.5]nonan-7-yl)-N-((4-((((1r,4r)-4-hydroxy-4-methylcyclohexyl)methyl)amino)-3-nitrophenyl)sulfonyl)benzamide;

(S)-2-((1H-pyrrolo[2,3-b]pyridin-5-yl)oxy)-4-(7-(2-(2-cyclopropylphenyl)pyrrolidin-1-yl)-2-azaspiro[3.5]nonan-2-yl)-N-((3-nitro-4-(((tetrahydro-2H-pyran-4-yl)methyl)amino)phenyl)sulfonyl)benzamide;

(R)-2-((1H-pyrrolo[2,3-b]pyridin-5-yl)oxy)-4-(7-(2-(2-cyclopropylphenyl)pyrrolidin-1-yl)-2-azaspiro[3.5]nonan-2-yl)-N-((3-nitro-4-(((tetrahydro-2H-pyran-4-yl)methyl)amino)phenyl)sulfonyl)benzamide;

(S)-2-((1H-pyrrolo[2,3-b]pyridin-5-yl)oxy)-4-(9-(2-(2-cyclopropylphenyl)pyrrolidin-1-yl)-3-azaspiro[5.5]undecan-3-yl)-N-((3-nitro-4-(((tetrahydro-2H-pyran-4-yl)methyl)amino)phenyl)sulfonyl)benzamide;

(R)-2-((1H-pyrrolo[2,3-b]pyridin-5-yl)oxy)-4-(9-(2-(2-cyclopropylphenyl)pyrrolidin-1-yl)-3-azaspiro[5.5]undecan-3-yl)-N-((3-nitro-4-(((tetrahydro-2H-pyran-4-yl)methyl)amino)phenyl)sulfonyl)benzamide;

(S)-2-((1H-pyrrolo[2,3-b]pyridin-5-yl)oxy)-4-(6-(2-(2-cyclopropylphenyl)pyrrolidin-1-yl)-2-azaspiro[3.3]heptan-2-yl)-N-((3-nitro-4-(((tetrahydro-2H-pyran-4-yl)methyl)amino)phenyl)sulfonyl)benzamide;

(R)-2-((1H-pyrrolo[2,3-b]pyridin-5-yl)oxy)-4-(6-(2-(2-cyclopropylphenyl)pyrrolidin-1-yl)-2-azaspiro[3.3]heptan-2-yl)-N-((3-nitro-4-(((tetrahydro-2H-pyran-4-yl)methyl)amino)phenyl)sulfonyl)benzamide;

2-((1H-pyrrolo[2,3-b]pyridin-5-yl)oxy)-4-(2-(2-(3-chloro-2-(dimethylamino)phenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide;

N-((4-((((S)-1,4-dioxan-2-yl)methyl)amino)-3-nitrophenyl)sulfonyl)-2-((1H-pyrrolo[2,3-b]pyridin-5-yl)oxy)-4-(2-((S)-2-(2-cyclopropylphenyl)pyrrolidin-1-yl)-7-azaspiro[3.5]nonan-7-yl)benzamide;

N-((4-((((R)-1,4-dioxan-2-yl)methyl)amino)-3-nitrophenyl)sulfonyl)-2-((1H-pyrrolo[2,3-b]pyridin-5-yl)oxy)-4-(2-((S)-2-(2-cyclopropylphenyl)pyrrolidin-1-yl)-7-azaspiro[3.5]nonan-7-yl)benzamide;

(S) 2-((1H-pyrrolo[2,3-b]pyridin-5-yl)oxy)-4-(2-((S)-2-(2-cyclopropylphenyl)pyrrolidin-1-yl)-8-azaspiro[4.5]decan-8-yl)-N-((3-nitro-4-(((tetrahydro-2H-pyran-4-yl)methyl)amino)phenyl)sulfonyl)benzamide;

(R) 2-((1H-pyrrolo[2,3-b]pyridin-5-yl)oxy)-4-(2-((S)-2-(2-cyclopropylphenyl)pyrrolidin-1-yl)-8-azaspiro[4.5]decan-8-yl)-N-((3-nitro-4-(((tetrahydro-2H-pyran-4-yl)methyl)amino)phenyl)sulfonyl)benzamide;

N-((4-((((S)-1,4-dioxan-2-yl)methyl)amino)-3-nitrophenyl)sulfonyl)-2-((1H-pyrrolo[2,3-b]pyridin-5-yl)oxy)-4-(2-((S)-2-(2-ethylphenyl)pyrrolidin-1-yl)-7-azaspiro[3.5]nonan-7-yl)benzamide;

N-((4-((((R)-1,4-dioxan-2-yl)methyl)amino)-3-nitrophenyl)sulfonyl)-2-((1H-pyrrolo[2,3-b]pyridin-5-yl)oxy)-4-(2-((S)-2-(2-ethylphenyl)pyrrolidin-1-yl)-7-azaspiro[3.5]nonan-7-yl)benzamide;

(S)-2-((1H-pyrrolo[2,3-b]pyridin-5-yl)oxy)-4-(8-(2-(2-cyclopropylphenyl)pyrrolidin-1-yl)-2-azaspiro[4.5]decan-2-yl)-N-((3-nitro-4-(((tetrahydro-2H-pyran-4-yl)methyl)amino)phenyl)sulfonyl)benzamide;

2-((1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)benzamide;

N-((4-((((S)-1,4-dioxan-2-yl)methyl)amino)-3-nitrophenyl)sulfonyl)-2-((1H-pyrrolo[2,3-b]pyridin-5-yl)oxy)-4-(2-((S)-2-(2-isopropylphenyl)pyrrolidin-1-yl)-7-azaspiro[3.5]nonan-7-yl)benzamide;

(S)-2-((1H-pyrrolo[2,3-b]pyridin-5-yl)oxy)-4-(2-(2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide;

(S)-2-((1H-pyrrolo[2,3-b]pyridin-5-yl)oxy)-N-((4-(((4-fluorotetrahydro-2H-pyran-4-yl)methyl)amino)-3-nitrophenyl)sulfonyl)-4-(2-(2-(2-isopropylphenyl)pyrrolidin-1-yl)-7-azaspiro[3.5]nonan-7-yl)benzamide;

N-((4-((((R)-1,4-dioxan-2-yl)methyl)amino)-3-nitrophenyl)sulfonyl)-2-((1H-pyrrolo[2,3-b]pyridin-5-yl)oxy)-4-(2-((S)-2-(2-isopropylphenyl)pyrrolidin-1-yl)-7-azaspiro[3.5]nonan-7-yl)benzamide;

2-((1H-pyrrolo[2,3-b]pyridin-5-yl)oxy)-N-((4-((((1s,4s)-4-hydroxy-4-methylcyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)benzamide;

2-((1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(2-((R)-2-(2-isopropylphenyl)pyrrolidin-1-yl)-7-azaspiro[3.5]nonan-7-yl)benzamide;

2-((1H-pyrrolo[2,3-b]pyridin-5-yl)oxy)-N-((4-((((1s,4s)-4-hydroxy-4-methylcyclohexyl)methyl)amino)-3-nitrophenyl)sulfonyl)-4-(2-((R)-2-(2-isopropylphenyl)pyrrolidin-1-yl)-7-azaspiro[3.5]nonan-7-yl)benzamide;

2-((1H-pyrrolo[2,3-b]pyridin-5-yl)oxy)-4-(2-(2-(2-cyclobutylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide;

(S)-2-((1H-pyrrolo[2,3-b]pyridin-5-yl)oxy)-4-(2-(2-(2-isobutylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide;

2-((1H-pyrrolo[2,3-b]pyridin-5-yl)oxy)-4-(2-(2-(3-cyclopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide;

(S)-2-((1H-pyrrolo[2,3-b]pyridin-5-yl)oxy)-N-((3-nitro-4-(((tetrahydro-2H-pyran-4-yl)methyl)amino)phenyl)sulfonyl)-4-(2-(2-(o-tolyl)pyrrolidin-1-yl)-7-azaspiro[3.5]nonan-7-yl)benzamide;

(S)-2-((1H-pyrrolo[2,3-b]pyridin-5-yl)oxy)-4-(2-(2-(2-chlorophenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide;

(S)-2-((1H-pyrrolo[2,3-b]pyridin-5-yl)oxy)-4-(2-(2-(2-bromophenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide;

(R)-2-((1H-pyrrolo[2,3-b]pyridin-5-yl)oxy)-4-(2-(2-(2-chlorophenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide;

(S)-2-((1H-pyrrolo[2,3-b]pyridin-5-yl)oxy)-4-(2-(2-(3-chlorophenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide;

(R)-2-((1H-pyrrolo[2,3-b]pyridin-5-yl)oxy)-4-(2-(2-(3-chlorophenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide;

(S)-2-((1H-pyrrolo[2,3-b]pyridin-5-yl)oxy)-4-(2-(2-(4-chlorophenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide;

(S)-2-((1H-pyrrolo[2,3-b]pyridin-5-yl)oxy)-4-(2-(2-(2-ethoxyphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide;

(S)-2-((1H-pyrrolo[2,3-b]pyridin-5-yl)oxy)-4-(2-(2-(2-(dimethylamino)phenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide;

2-((1H-pyrrolo[2,3-b]pyridin-5-yl)oxy)-4-(2-((S)-2-(2-(dimethylamino)phenyl)pyrrolidin-1-yl)-7-azaspiro[3.5]nonan-7-yl)-N-((4-((((1r,4r)-4-hydroxy-4-methylcyclohexyl)methyl)amino)-3-nitrophenyl)sulfonyl)benzamide;

2-((1H-pyrrolo[2,3-b]pyridin-5-yl)oxy)-4-(2-((S)-2-(2-(bis(methyl-d3)amino)phenyl)pyrrolidin-1-yl)-7-azaspiro[3.5]nonan-7-yl)-N-((4-((((1r,4r)-4-hydroxy-4-methylcyclohexyl)methyl)amino)-3-nitrophenyl)sulfonyl)benzamide;

2-((1H-pyrrolo[2,3-b]pyridin-5-yl)oxy)-N-((3-nitro-4-(((tetrahydro-2H-pyran-4-yl)methyl)amino)phenyl)sulfonyl)-4-(2-(2-(2-(pyrrolidin-1-yl)phenyl)pyrrolidin-1-yl)-7-azaspiro[3.5]nonan-7-yl)benzamide;

(S)-2-((1H-pyrrolo[2,3-b]pyridin-5-yl)oxy)-4-(2-(2-(2-(1-methyl-1,2,3,6-tetrahydropyridin-4-yl)phenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide;

(S)-2-((1H-pyrrolo[2,3-b]pyridin-5-yl)oxy)-4-(2-(2-(2-(1-methylpiperidin-4-yl)phenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide;

(S)-2-((1H-pyrrolo[2,3-b]pyridin-5-yl)oxy)-4-(2-(2-(2-methoxyphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide;

(S)-2-((1H-pyrrolo[2,3-b]pyridin-5-yl)oxy)-4-(2-(2-(2-isopropoxyphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide;

2-((1H-pyrrolo[2,3-b]pyridin-5-yl)oxy)-4-(2-(2-(2-(methoxymethyl)phenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide;

2-((1H-pyrrolo[2,3-b]pyridin-5-yl)oxy)-4-(2-(2-(2-(hydroxymethyl)phenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide;

(S)-2-((1H-pyrrolo[2,3-b]pyridin-5-yl)oxy)-4-(2-(2-(3-chloro-2-cyclopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide;

(R)-2-((1H-pyrrolo[2,3-b]pyridin-5-yl)oxy)-4-(2-(2-(3-chloro-2-cyclopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide;

2-((1H-pyrrolo[2,3-b]pyridin-5-yl)oxy)-4-(2-(2-(5-chloro-2-cyclopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide;

(S)-2-((1H-pyrrolo[2,3-b]pyridin-5-yl)oxy)-4-(2-(2-(3-chloro-2-ethylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide;

(R)-2-((1H-pyrrolo[2,3-b]pyridin-5-yl)oxy)-4-(2-(2-(3-chloro-2-ethylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide;

2-((1H-pyrrolo[2,3-b]pyridin-5-yl)oxy)-4-(2-(2-(2,4-dicyclopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide;

2-((1H-pyrrolo[2,3-b]pyridin-5-yl)oxy)-4-(2-(2-(2,5-dicyclopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide;

2-((1H-pyrrolo[2,3-b]pyridin-5-yl)oxy)-4-(2-(2-(3-(2-chlorophenyl)thiophen-2-yl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide;

2-((1H-pyrrolo[2,3-b]pyridin-5-yl)oxy)-4-(2-(2-(2-cyclopropylphenyl)-4-methylpyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide;

2-((1H-pyrrolo[2,3-b]pyridin-5-yl)oxy)-4-(2-(4-cyclopropyl-2-(2-cyclopropylphenyl)pyrrolidin-1-yl)-7- azaspiro[3.5]nonan-7-yl)-N-((3-nitro-4-(((tetrahydro-2H-pyran-4-yl)methyl)amino)phenyl)sulfonyl)benzamide;

2-((1H-pyrrolo[2,3-b]pyridin-5-yl)oxy)-4-(2-(2-(2-cyclopropylphenyl)-4-phenyl-2,5-dihydro-1H-pyrrol-1-yl)-7-azaspiro[3.5]nonan-7-yl)-N-((3-nitro-4-(((tetrahydro-2H-pyran-4-yl)methyl)amino)phenyl)sulfonyl)benzamide;

2-((1H-pyrrolo[2,3-b]pyridin-5-yl)oxy)-4-(2-(6-(2-cyclopropylphenyl)-5-azaspiro[2.4]heptan-5-yl)-7-azaspiro[3.5]nonan-7-yl)-N-((3-nitro-4-(((tetrahydro-2H-pyran-4-yl)methyl)amino)phenyl)sulfonyl)benzamide;

2-((1H-pyrrolo[2,3-b]pyridin-5-yl)oxy)-4-(2-(2-(2-cyclopropylphenyl)-4,4-dimethylpyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide;

2-((1H-pyrrolo[2,3-b]pyridin-5-yl)oxy)-4-(2-(2-(2-cyclopropylphenyl)-4,4-difluoropyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide;

2-((1H-pyrrolo[2,3-b]pyridin-5-yl)oxy)-4-(2-(2-(2-cyclopropylphenyl)-4-(trifluoromethyl)pyrrolidin-1-yl)-7-azaspiro[3.5]nonan-7-yl)-N-((4-((((1r,4r)-4-hydroxy-4-methylcyclohexyl)methyl)amino)-3-nitrophenyl)sulfonyl)benzamide;

2-((1H-pyrrolo[2,3-b]pyridin-5-yl)oxy)-4-(2-(2-(2-cyclopropylphenyl)-4-(dimethylamino)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide;

2-((1H-pyrrolo[2,3-b]pyridin-5-yl)oxy)-4-(2-(2-(2-cyclopropylphenyl)-4-(2-(dimethylamino)ethoxy)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide;

2-((1H-pyrrolo[2,3-b]pyridin-5-yl)oxy)-4-(2-(3-(2-cyclopropylphenyl)-2-azabicyclo[3.1.0]hexan-2-yl)-7-azaspiro[3.5]nonan-7-yl)-N-((3-nitro-4-(((tetrahydro-2H-pyran-4-yl)methyl)amino)phenyl)sulfonyl)benzamide;

2-((1H-pyrrolo[2,3-b]pyridin-5-yl)oxy)-4-(2-(1-(2-cyclopropylphenyl)hexahydrocyclopenta[c]pyrrol-2(1H)-yl)-7-azaspiro[3.5]nonan-7-yl)-N-((3-nitro-4-(((tetrahydro-2H-pyran-4-yl)methyl)amino)phenyl)sulfonyl)benzamide;

2-((1H-pyrrolo[2,3-b]pyridin-5-yl)oxy)-4-(2-(2-(2-cyclopropylphenyl)-3,3-dimethylpyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide;

2-((1H-pyrrolo[2,3-b]pyridin-5-yl)oxy)-4-(2-(2-(2-cyclopropylphenyl)-4-methylpiperazin-1-yl)-7-azaspiro[3.5]nonan-7-yl)-N-((3-nitro-4-(((tetrahydro-2H-pyran-4-yl)methyl)amino)phenyl)sulfonyl)benzamide;

2-((1H-pyrrolo[2,3-b]pyridin-5-yl)oxy)-4-(2-((S)-2-(2-cyclopropylphenyl)-4-methylpiperazin-1-yl)-7-azaspiro[3.5]nonan-7-yl)-N-((4-((((1r,4r)-4-hydroxy-4-methylcyclohexyl)methyl)amino)-3-nitrophenyl)sulfonyl)benzamide;

2-((1H-pyrrolo[2,3-b]pyridin-5-yl)oxy)-4-(2-((R)-2-(2-cyclopropylphenyl)-4-methylpiperazin-1-yl)-7-azaspiro[3.5]nonan-7-yl)-N-((4-((((1r,4r)-4-hydroxy-4-methylcyclohexyl)methyl)amino)-3-nitrophenyl)sulfonyl)benzamide;

2-((1H-pyrrolo[2,3-b]pyridin-5-yl)oxy)-4-(2-(2-(2-cyclopropylphenyl)-4-isopropylpiperazin-1-yl)-7-azaspiro[3.5]nonan-7-yl)-N-((3-nitro-4-(((tetrahydro-2H-pyran-4-yl)methyl)amino)phenyl)sulfonyl)benzamide;

2-((1H-pyrrolo[2,3-b]pyridin-5-yl)oxy)-4-(2-(2'-cyclopropyl-[1,1'-biphenyl]-2-yl)-7-azaspiro[3.5]nonan-7-yl)-N-((3-nitro-4-(((tetrahydro-2H-pyran-4-yl)methyl)amino)phenyl)sulfonyl)benzamide;

2-((1H-pyrrolo[2,3-b]pyridin-5-yl)oxy)-N-((3-nitro-4-(((tetrahydro-2H-pyran-4-yl)methyl)amino)phenyl)sulfonyl)-4-(2-(2-(o-tolyl)azepan-1-yl)-7-azaspiro[3.5]nonan-7-yl)benzamide;

2-((1H-pyrrolo[2,3-b]pyridin-5-yl)oxy)-4-(2-(2-(2-cyclopropylphenyl)azepan-1-yl)-7-azaspiro[3.5]nonan-7-yl)-N-((3-nitro-4-(((tetrahydro-2H-pyran-4-yl)methyl)amino)phenyl)sulfonyl)benzamide;

2-((1H-pyrrolo[2,3-b]pyridin-5-yl)oxy)-4-(2-(2-(2-cyclopropylphenyl)pyrazolidin-1-yl)-7-azaspiro[3.5]nonan-7-yl)-N-((3-nitro-4-(((tetrahydro-2H-pyran-4-yl)methyl)amino)phenyl)sulfonyl)benzamide;

2-((1H-pyrrolo[2,3-b]pyridin-5-yl)oxy)-4-(2-((S)-2-(2-cyclopropylphenyl)pyrrolidin-1-yl)-7-azaspiro[3.5]nonan-7-yl)-N-((4-(((((1s,4s) or (1r,4r))-4-((dimethyl(oxo)-16-sulfaneylidene)amino)cyclohexyl)methyl)amino)-3-nitrophenyl)sulfonyl)benzamide;

2-((1H-pyrrolo[2,3-b]pyridin-5-yl)oxy)-4-(2-((S)-2-(2-cyclopropylphenyl)pyrrolidin-1-yl)-7-azaspiro[3.5]nonan-7-yl)-N-(methyl(3-nitro-4-(((tetrahydro-2H-pyran-4-yl)methyl)amino)phenyl)(oxo)-16-sulfaneylidene)benzamide;

2-((1H-pyrrolo[2,3-b]pyridin-5-yl)oxy)-N-((4-(((−3-oxabicyclo[3.1.0]hexan-6-yl)methyl)amino)-3-nitrophenyl)sulfonyl)-4-(2-((S)-2-(2-isopropylphenyl)pyrrolidin-1-yl)-7-azaspiro[3.5]nonan-7-yl)benzamide;

(S)-2-((1H-pyrrolo[2,3-b]pyridin-5-yl)oxy)-4-(2-(2-(2-cyclopropylphenyl)pyrrolidin-1-yl)-7-azaspiro[3.5]nonan-7-yl)-N-((4-(((4-hydroxy-4-(trifluoromethyl)cyclohexyl)methyl)amino)-3-nitrophenyl)sulfonyl)benzamide;

2-((1H-pyrrolo[2,3-b]pyridin-5-yl)oxy)-N-((4-((((1r,4r)-4-hydroxy-4-(trifluoromethyl)cyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)benzamide;

2-((1H-pyrrolo[2,3-b]pyridin-5-yl)oxy)-N-((4-((((1s,4s)-4-hydroxy-4-(trifluoromethyl)cyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)benzamide;

2-((1H-pyrrolo[2,3-b]pyridin-5-yl)oxy)-4-(2-((S)-2-(2-isopropylphenyl)pyrrolidin-1-yl)-7-azaspiro[3.5]nonan-7-yl)-N-((4-((((1r,4r)-4-methoxy-4-methylcyclohexyl)methyl)amino)-3-nitrophenyl)sulfonyl)benzamide;

2-((1H-pyrrolo[2,3-b]pyridin-5-yl)oxy)-4-(2-((S)-2-(2-isopropylphenyl)pyrrolidin-1-yl)-7-azaspiro[3.5]nonan-7-yl)-N-((4-((((S)-4-methylcyclohex-3-en-1-yl)methyl)amino)-3-nitrophenyl)sulfonyl)benzamide;

2-((1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(2-((S)-2-(2-(prop-1-en-2-yl)phenyl)pyrrolidin-1-yl)-7-azaspiro[3.5]nonan-7-yl)benzamide;

2-((1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(2-((S)-2-(2-propylphenyl)pyrrolidin-1-yl)-7-azaspiro[3.5]nonan-7-yl)benzamide;

2-((1H-pyrrolo[2,3-b]pyridin-5-yl)oxy)-4-(6-((S)-2-(2-cyclopropylphenyl)pyrrolidin-1-yl)-2-azaspiro[3.3]

heptan-2-yl)-N-((4-(((((1r,4r)-4-hydroxy-4-methylcyclohexyl)methyl)amino)-3-nitrophenyl)sulfonyl)benzamide;

N-((4-(((((S)-1,4-dioxan-2-yl)methyl)amino)-3-nitrophenyl)sulfonyl)-2-((1H-pyrrolo[2,3-b]pyridin-5-yl)oxy)-4-(6-((S)-2-(2-cyclopropylphenyl)pyrrolidin-1-yl)-2-azaspiro[3.3]heptan-2-yl)benzamide;

N-((4-(((((R)-1,4-dioxan-2-yl)methyl)amino)-3-nitrophenyl)sulfonyl)-2-((1H-pyrrolo[2,3-b]pyridin-5-yl)oxy)-4-(6-((S)-2-(2-cyclopropylphenyl)pyrrolidin-1-yl)-2-azaspiro[3.3]heptan-2-yl)benzamide;

2-((1H-pyrrolo[2,3-b]pyridin-5-yl)oxy)-N-((4-(((((1r,4r)-4-hydroxy-4-methylcyclohexyl)methyl)amino)-3-nitrophenyl)sulfonyl)-4-(6-((S)-2-(2-isopropylphenyl)pyrrolidin-1-yl)-2-azaspiro[3.3]heptan-2-yl)benzamide;

N-((4-(((((S)-1,4-dioxan-2-yl)methyl)amino)-3-nitrophenyl)sulfonyl)-2-((1H-pyrrolo[2,3-b]pyridin-5-yl)oxy)-4-(6-((S)-2-(2-isopropylphenyl)pyrrolidin-1-yl)-2-azaspiro[3.3]heptan-2-yl)benzamide;

2-((1H-pyrrolo[2,3-b]pyridin-5-yl)oxy)-4-(6-((S)-2-(2-ethylphenyl)pyrrolidin-1-yl)-2-azaspiro[3.3]heptan-2-yl)-N-((4-(((((1r,4r)-4-hydroxy-4-methylcyclohexyl)methyl)amino)-3-nitrophenyl)sulfonyl)benzamide;

N-((4-(((((S)-1,4-dioxan-2-yl)methyl)amino)-3-nitrophenyl)sulfonyl)-2-((1H-pyrrolo[2,3-b]pyridin-5-yl)oxy)-4-(6-((S)-2-(2-ethylphenyl)pyrrolidin-1-yl)-2-azaspiro[3.3]heptan-2-yl)benzamide;

2-((1H-pyrrolo[2,3-b]pyridin-5-yl)oxy)-4-(6-((2-(2-cyclopropylphenyl)pyrrolidin-1-yl)methyl)-2-azaspiro[3.3]heptan-2-yl)-N-((3-nitro-4-(((tetrahydro-2H-pyran-4-yl)methyl)amino)phenyl)sulfonyl)benzamide;

2-((1H-pyrrolo[2,3-b]pyridin-5-yl)oxy)-4-(6-((1-(2-cyclopropylphenyl)pyrrolidin-2-yl)methyl)-2,6-diazaspiro[3.3]heptan-2-yl)-N-((3-nitro-4-(((tetrahydro-2H-pyran-4-yl)methyl)amino)phenyl)sulfonyl)benzamide;

(S)-2-((1H-pyrrolo[2,3-b]pyridin-5-yl)oxy)-4-(2-((2-(2-cyclopropylphenyl)pyrrolidin-1-yl)methyl)-7-azaspiro[3.5]nonan-7-yl)-N-((3-nitro-4-(((tetrahydro-2H-pyran-4-yl)methyl)amino)phenyl)sulfonyl)benzamide;

(S)-2-((1H-pyrrolo[2,3-b]pyridin-5-yl)oxy)-4-(2-(2-(2-cyclopropylphenyl)pyrrolidin-1-yl)-7-azaspiro[3.5]nonan-7-yl)-N-((3-nitro-4-((2-(tetrahydro-2H-pyran-4-yl)ethyl)amino)phenyl)sulfonyl)benzamide;

(S)-2-((1H-pyrrolo[2,3-b]pyridin-5-yl)oxy)-4-(2-(2-(2-cyclopropylphenyl)pyrrolidin-1-yl)-7-azaspiro[3.5]nonan-7-yl)-N-((4-((2-morpholinoethyl)amino)-3-nitrophenyl)sulfonyl)benzamide;

(S)-2-((1H-pyrrolo[2,3-b]pyridin-5-yl)oxy)-4-(2-(2-(2-cyclopropylphenyl)pyrrolidin-1-yl)-7-azaspiro[3.5]nonan-7-yl)-N-((3-nitro-4-((2-(3-oxomorpholino)ethyl)amino)phenyl)sulfonyl)benzamide;

2-((1H-pyrrolo[2,3-b]pyridin-5-yl)oxy)-N-((4-(((3-oxabicyclo[3.1.0]hexan-6-yl)methyl)amino)-3-nitrophenyl)sulfonyl)-4-(2-((S)-2-(2-cyclopropylphenyl)pyrrolidin-1-yl)-7-azaspiro[3.5]nonan-7-yl)benzamide;

2-((1H-pyrrolo[2,3-b]pyridin-5-yl)oxy)-4-(2-((S)-2-(2-cyclopropylphenyl)pyrrolidin-1-yl)-7-azaspiro[3.5]nonan-7-yl)-N-((4-(((2,6-dimethyltetrahydro-2H-pyran-4-yl)methyl)amino)-3-nitrophenyl)sulfonyl)benzamide;

(S)-2-((1H-pyrrolo[2,3-b]pyridin-5-yl)oxy)-4-(2-(2-(2-cyclopropylphenyl)pyrrolidin-1-yl)-7-azaspiro[3.5]nonan-7-yl)-N-((3-nitro-4-(((2,2,6,6-tetramethyltetrahydro-2H-pyran-4-yl)methyl)amino)phenyl)sulfonyl)benzamide;

2-((1H-pyrrolo[2,3-b]pyridin-5-yl)oxy)-4-(2-((S)-2-(2-cyclopropylphenyl)pyrrolidin-1-yl)-6-azaspiro[3.4]octan-6-yl)-N-((4-(((((1r,4r)-4-hydroxy-4-methylcyclohexyl)methyl)amino)-3-nitrophenyl)sulfonyl)benzamide;

2-((1H-pyrrolo[2,3-b]pyridin-5-yl)oxy)-4-(6-((S)-2-(2-cyclopropylphenyl)pyrrolidin-1-yl)-2-azaspiro[3.4]octan-2-yl)-N-((4-(((((1r,4r)-4-hydroxy-4-methylcyclohexyl)methyl)amino)-3-nitrophenyl)sulfonyl)benzamide;

2-((1H-pyrrolo[2,3-b]pyridin-5-yl)oxy)-4-((7S)-7-((S)-2-(2-cyclopropylphenyl)pyrrolidin-1-yl)-2-azaspiro[4.4]nonan-2-yl)-N-((4-(((((1r,4r)-4-hydroxy-4-methylcyclohexyl)methyl)amino)-3-nitrophenyl)sulfonyl)benzamide;

2-((1H-pyrrolo[2,3-b]pyridin-5-yl)oxy)-4-((7R)-7-((S)-2-(2-cyclopropylphenyl)pyrrolidin-1-yl)-2-azaspiro[4.4]nonan-2-yl)-N-((4-(((((1r,4r)-4-hydroxy-4-methylcyclohexyl)methyl)amino)-3-nitrophenyl)sulfonyl)benzamide;

2-((1H-pyrrolo[2,3-b]pyridin-5-yl)oxy)-4-(2-((S)-2-(2-cyclopropylphenyl)pyrrolidin-1-yl)spiro[3.5]non-6-en-7-yl)-N-((4-(((((1r,4r)-4-hydroxy-4-methylcyclohexyl)methyl)amino)-3-nitrophenyl)sulfonyl)benzamide;

(S)-2-((6-amino-5-chloropyridin-3-yl)oxy)-4-(2-(2-cyclopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide;

2-((1H-pyrrolo[2,3-b]pyridin-5-yl)oxy)-4-(2-((S)-2-(2-cyclopropylphenyl)pyrrolidin-1-yl)-7-azaspiro[3.5]nonan-7-yl)-N-((4-(((2,2-dimethyltetrahydro-2H-pyran-4-yl)methyl)amino)-3-nitrophenyl)sulfonyl)benzamide;

(S)-2-((1H-pyrrolo[2,3-b]pyridin-5-yl)oxy)-4-(2-(2-(2-cyclopropylphenyl)pyrrolidin-1-yl)-7-azaspiro[3.5]nonan-7-yl)-N-((4-(3-methyl-3-((tetrahydro-2H-pyran-4-yl)methyl)ureido)-3-nitrophenyl)sulfonyl)benzamide;

2-((1H-pyrrolo[2,3-b]pyridin-5-yl)oxy)-N-((4-(((((1r,4r)-4-hydroxy-4-methylcyclohexyl)methyl)amino)-3-nitrophenyl)sulfonyl)-4-(2-((S)-2-phenylpyrrolidin-1-yl)-7-azaspiro[3.5]nonan-7-yl)benzamide;

2-((1H-pyrrolo[2,3-b]pyridin-5-yl)oxy)-4-(2-(2-(2-cyclopropylphenyl)-4-ethylpiperazin-1-yl)-7-azaspiro[3.5]nonan-7-yl)-N-((3-nitro-4-(((tetrahydro-2H-pyran-4-yl)methyl)amino)phenyl)sulfonyl)benzamide;

2-((1H-pyrrolo[2,3-b]pyridin-5-yl)oxy)-4-(2-((S)-2-(2-cyclopropylphenyl)pyrrolidin-1-yl)-7-azaspiro[3.5]nonan-7-yl)-N-((4-(((((cis)-4-hydroxytetrahydrofuran-2-yl)methyl)amino)-3-nitrophenyl)sulfonyl)benzamide;

2-((1H-pyrrolo[2,3-b]pyridin-5-yl)oxy)-4-(2-((S)-2-(2-cyclopropylphenyl)pyrrolidin-1-yl)-7-azaspiro[3.5]nonan-7-yl)-N-((4-(((((trans)-4-hydroxytetrahydrofuran-2-yl)methyl)amino)-3-nitrophenyl)sulfonyl)benzamide;

2-((1H-pyrrolo[2,3-b]pyridin-5-yl)oxy)-4-(2-((S)-2-(2-isopropylphenyl)-4-methylpiperazin-1-yl)-7-azaspiro[3.5]nonan-7-yl)-N-((4-(((((1r,4r)-4-hydroxy-4-methylcyclohexyl)methyl)amino)-3-nitrophenyl)sulfonyl)benzamide;

2-((1H-pyrrolo[2,3-b]pyridin-5-yl)oxy)-4-(2-((R)-2-(2-isopropylphenyl)-4-methylpiperazin-1-yl)-7-azaspiro[3.5]nonan-7-yl)-N-((4-(((((1r,4r)-4-hydroxy-4-methylcyclohexyl)methyl)amino)-3-nitrophenyl)sulfonyl)benzamide;

2-((1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(2-oxo-7-azaspiro[3.5]nonan-7-yl)benzamide;

3-((1H-pyrrolo[2,3-b]pyridin-5-yl)oxy)-4'-(2-(2-chlorophenyl)pyrrolidin-1-yl)-N-((4-((4-fluorotetrahydro-2H-pyran-4-yl)methoxy)-3-nitrophenyl)sulfonyl)-[1,1'-biphenyl]-4-carboxamide;

3-((1H-pyrrolo[2,3-b]pyridin-5-yl)oxy)-4'-(2-(2-cyclopropylphenyl)pyrrolidin-1-yl)-N-((4-((4-fluorotetrahydro-2H-pyran-4-yl)methoxy)-3-nitrophenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2-chlorophenyl)pyrrolidin-1-yl)-N-((4-(((1-methylpiperidin-4-yl)methyl)amino)-3-nitrophenyl)sulfonyl)-[1,1'-biphenyl]-4-carboxamide;

3-((1H-pyrrolo[2,3-b]pyridin-5-yl)oxy)-4'-(2-(2-cyclopropylphenyl)pyrrolidin-1-yl)-N-((4-(((1-methylpiperidin-4-yl)methyl)amino)-3-nitrophenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2-chlorophenyl)pyrrolidin-1-yl)-N-((3-nitro-4-((1-(tetrahydro-2H-pyran-4-yl)azetidin-3-yl)amino)phenyl)sulfonyl)-[1,1'-biphenyl]-4-carboxamide;

3-((1H-pyrrolo[2,3-b]pyridin-5-yl)oxy)-4'-(2-(2-chlorophenyl)pyrrolidin-1-yl)-N-((3-nitro-4-((1-(oxetan-3-yl)piperidin-4-yl)amino)phenyl)sulfonyl)-[1,1'-biphenyl]-4-carboxamide;

3-((1H-pyrrolo[2,3-b]pyridin-5-yl)oxy)-4'-(2-(2-chlorophenyl)pyrrolidin-1-yl)-N-((4-(((3-hydroxyoxetan-3-yl)methyl)amino)-3-nitrophenyl)sulfonyl)-[1,1'-biphenyl]-4-carboxamide;

3-((1H-pyrrolo[2,3-b]pyridin-5-yl)oxy)-4'-(2-(2-chlorophenyl)pyrrolidin-1-yl)-N-((4-((4-hydroxycyclohexyl)methoxy)-3-nitrophenyl)sulfonyl)-[1,1'-biphenyl]-4-carboxamide;

3-((1H-pyrrolo[2,3-b]pyridin-5-yl)oxy)-4'-(2-(2-chlorophenyl)pyrrolidin-1-yl)-N-((3-nitro-4-(7-oxa-2-azaspiro[3.5]nonan-2-yl)phenyl)sulfonyl)-[1,1'-biphenyl]-4-carboxamide;

N-((4-((((S)-1,4-dioxan-2-yl)methyl)amino)-3-nitrophenyl)sulfonyl)-3-((1H-pyrrolo[2,3-b]pyridin-5-yl)oxy)-4'-(2-(2-cyclopropylphenyl)pyrrolidin-1-yl)-2',3',4',5'-tetrahydro-[1,1'-biphenyl]-4-carboxamide;

N-((4-((((S)-1,4-dioxan-2-yl)methyl)amino)-3-nitrophenyl)sulfonyl)-3-((1H-pyrrolo[2,3-b]pyridin-5-yl)oxy)-4'-((S)-2-(2-cyclopropylphenyl)pyrrolidin-1-yl)-2',3',4',5'-tetrahydro-[1,1'-biphenyl]-4-carboxamide;

N-((4-((((S)-1,4-dioxan-2-yl)methyl)amino)-3-nitrophenyl)sulfonyl)-3-((1H-pyrrolo[2,3-b]pyridin-5-yl)oxy)-4'-((S)-2-(2-cyclopropylphenyl)pyrrolidin-1-yl)-2',3',4',5'-tetrahydro-[1,1'-biphenyl]-4-carboxamide (isomer 1, faster eluting isomer);

N-((4-((((S)-1,4-dioxan-2-yl)methyl)amino)-3-nitrophenyl)sulfonyl)-3-((1H-pyrrolo[2,3-b]pyridin-5-yl)oxy)-4'-((S)-2-(2-cyclopropylphenyl)pyrrolidin-1-yl)-2',3',4',5'-tetrahydro-[1,1'-biphenyl]-4-carboxamide (isomer 2, slower eluting isomer);

N-((4-((((R)-1,4-dioxan-2-yl)methyl)amino)-3-nitrophenyl)sulfonyl)-3-((1H-pyrrolo[2,3-b]pyridin-5-yl)oxy)-4'-(2-(2-cyclopropylphenyl)pyrrolidin-1-yl)-2',3',4',5'-tetrahydro-[1,1'-biphenyl]-4-carboxamide;

(S)—N-((4-((((R)-1,4-dioxan-2-yl)methyl)amino)-3-nitrophenyl)sulfonyl)-3-((1H-pyrrolo[2,3-b]pyridin-5-yl)oxy)-4'-((S)-2-(2-cyclopropylphenyl)pyrrolidin-1-yl)-2',3',4',5'-tetrahydro-[1,1'-biphenyl]-4-carboxamide;

(R)—N-((4-((((R)-1,4-dioxan-2-yl)methyl)amino)-3-nitrophenyl)sulfonyl)-3-((1H-pyrrolo[2,3-b]pyridin-5-yl)oxy)-4'-((S)-2-(2-cyclopropylphenyl)pyrrolidin-1-yl)-2',3',4',5'-tetrahydro-[1,1'-biphenyl]-4-carboxamide;

cis-3-((1H-pyrrolo[2,3-b]pyridin-5-yl)oxy)-4'-(2-(2-cyclopropylphenyl)pyrrolidin-1-yl)-N-((4-((4-hydroxy-4-methylcyclohexyl)methoxy)-3-nitrophenyl)sulfonyl)-2',3',4',5'-tetrahydro-[1,1'-biphenyl]-4-carboxamide;

trans-3-((1H-pyrrolo[2,3-b]pyridin-5-yl)oxy)-4'-(2-(2-cyclopropylphenyl)pyrrolidin-1-yl)-N-((4-((4-hydroxy-4-methylcyclohexyl)methoxy)-3-nitrophenyl)sulfonyl)-2',3',4',5'-tetrahydro-[1,1'-biphenyl]-4-carboxamide;

(trans- or cis-)3-((1H-pyrrolo[2,3-b]pyridin-5-yl)oxy)-4'-((S)-2-(2-cyclopropylphenyl)pyrrolidin-1-yl)-N-((4-((4-hydroxy-4-methylcyclohexyl)methoxy)-3-nitrophenyl)sulfonyl)-2',3',4',5'-tetrahydro-[1,1'-biphenyl]-4-carboxamide;

(trans- or cis-)3-((1H-pyrrolo[2,3-b]pyridin-5-yl)oxy)-4'-((S)-2-(2-cyclopropylphenyl)pyrrolidin-1-yl)-N-((4-((4-hydroxy-4-methylcyclohexyl)methoxy)-3-nitrophenyl)sulfonyl)-2',3',4',5'-tetrahydro-[1,1'-biphenyl]-4-carboxamide (isomer 1, faster eluting isomer);

(trans- or cis-)3-((1H-pyrrolo[2,3-b]pyridin-5-yl)oxy)-4'-((S)-2-(2-cyclopropylphenyl)pyrrolidin-1-yl)-N-((4-((4-hydroxy-4-methylcyclohexyl)methoxy)-3-nitrophenyl)sulfonyl)-2',3',4',5'-tetrahydro-[1,1'-biphenyl]-4-carboxamide (isomer 2, slower eluting isomer);

3-((1H-pyrrolo[2,3-b]pyridin-5-yl)oxy)-4'-(2-(2-cyclopropylphenyl)pyrrolidin-1-yl)-N-((3-nitro-4-(((4-(oxetan-3-yl)morpholin-2-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-N-((4-((2-oxaspiro[3.5]nonan-7-yl)methoxy)-3-nitrophenyl)sulfonyl)-4'-(2-(2-cyclopropylphenyl)pyrrolidin-1-yl)-2',3',4',5'-tetrahydro-[1,1'-biphenyl]-4-carboxamide;

3-((1H-pyrrolo[2,3-b]pyridin-5-yl)oxy)-N-((4-(((1r,4r)-4-(bis(cyclopropylmethyl)amino)cyclohexyl)amino)-3-nitrophenyl)sulfonyl)-4'-(2-(2-cyclopropylphenyl)pyrrolidin-1-yl)-2',3',4',5'-tetrahydro-[1,1'-biphenyl]-4-carboxamide;

3-((1H-pyrrolo[2,3-b]pyridin-5-yl)oxy)-N-((4-(((4-cyclopropylmorpholin-2-yl)methyl)amino)-3-nitrophenyl)sulfonyl)-4'-(2-(2-cyclopropylphenyl)pyrrolidin-1-yl)-2',3',4',5'-tetrahydro-[1,1'-biphenyl]-4-carboxamide;

3-((1H-pyrrolo[2,3-b]pyridin-5-yl)oxy)-4'-(2-(2-cyclopropylphenyl)pyrrolidin-1-yl)-N-((4-(((4-(dimethylglycyl)morpholin-2-yl)methyl)amino)-3-nitrophenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2-cyclopropylphenyl)pyrrolidin-1-yl)-N-((3-nitro-4-((tetrahydro-2H-pyran-4-yl)methoxy)phenyl)sulfonyl)-2',3',4',5'-tetrahydro-[1,1'-biphenyl]-4-carboxamide;

(trans- or cis-) 3-((1H-pyrrolo[2,3-b]pyridin-5-yl)oxy)-4'-(2-(2-cyclopropylphenyl)pyrrolidin-1-yl)-N-((4-(((4-hydroxy-4-methylcyclohexyl)methyl)amino)-3-nitrophenyl)sulfonyl)-2',3',4',5'-tetrahydro-[1,1'-biphenyl]-4-carboxamide;

(trans- or cis-) 3-((1H-pyrrolo[2,3-b]pyridin-5-yl)oxy)-4'-(2-(S)-(2-cyclopropylphenyl)pyrrolidin-1-yl)-N-((4-

(((4-hydroxy-4-methylcyclohexyl)methyl)amino)-3-nitrophenyl)sulfonyl)-2',3',4',5'-tetrahydro-[1,1'-biphenyl]-4-carboxamide (isomer 1, faster eluting isomer);

(trans- or cis-) 3-((1H-pyrrolo[2,3-b]pyridin-5-yl)oxy)-4'-(2-(S)-(2-cyclopropylphenyl)pyrrolidin-1-yl)-N-((4-(((4-hydroxy-4-methylcyclohexyl)methyl)amino)-3-nitrophenyl)sulfonyl)-2',3',4',5'-tetrahydro-[1,1'-biphenyl]-4-carboxamide (isomer 2, slower eluting isomer);

3-((1H-pyrrolo[2,3-b]pyridin-5-yl)oxy)-4'-(2-(2-cyclopropylphenyl)pyrrolidin-1-yl)-N-((4-((morpholin-2-ylmethyl)amino)-3-nitrophenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2-cyclopropylphenyl)pyrrolidin-1-yl)-N-((4-(((4-fluorotetrahydro-2H-pyran-4-yl)methyl)amino)-3-nitrophenyl)sulfonyl)-2',3',4',5'-tetrahydro-[1,1'-biphenyl]-4-carboxamide;

3-((1H-pyrrolo[2,3-b]pyridin-5-yl)oxy)-4'-((S)-2-(2-cyclopropylphenyl)pyrrolidin-1-yl)-N-((4-(((4-fluorotetrahydro-2H-pyran-4-yl)methyl)amino)-3-nitrophenyl)sulfonyl)-2',3',4',5'-tetrahydro-[1,1'-biphenyl]-4-carboxamide;

3-((1H-pyrrolo[2,3-b]pyridin-5-yl)oxy)-4'-((S)-2-(2-cyclopropylphenyl)pyrrolidin-1-yl)-N-((4-(((4-fluorotetrahydro-2H-pyran-4-yl)methyl)amino)-3-nitrophenyl)sulfonyl)-2',3',4',5'-tetrahydro-[1,1'-biphenyl]-4-carboxamide (isomer 1, faster eluting isomer);

3-((1H-pyrrolo[2,3-b]pyridin-5-yl)oxy)-4'-((S)-2-(2-cyclopropylphenyl)pyrrolidin-1-yl)-N-((4-(((4-fluorotetrahydro-2H-pyran-4-yl)methyl)amino)-3-nitrophenyl)sulfonyl)-2',3',4',5'-tetrahydro-[1,1'-biphenyl]-4-carboxamide (isomer 2, slower eluting isomer);

3-((1H-pyrrolo[2,3-b]pyridin-5-yl)oxy)-4'-((R)-2-(2-cyclopropylphenyl)pyrrolidin-1-yl)-N-((4-(((4-fluorotetrahydro-2H-pyran-4-yl)methyl)amino)-3-nitrophenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2-cyclopropylphenyl)pyrrolidin-1-yl)-N-((4-(((4-methylmorpholin-2-yl)methyl)amino)-3-nitrophenyl)sulfonyl)-2',3',4',5'-tetrahydro-[1,1'-biphenyl]-4-carboxamide;

3-((1H-pyrrolo[2,3-b]pyridin-5-yl)oxy)-N-((4-(((4-acetylmorpholine-2-yl)methyl)amino)-3-nitrophenyl)sulfonyl)-4'-(2-(2-cyclopropylphenyl)pyrrolidin-1-yl)-2',3',4',5'-tetrahydro-[1,1'-biphenyl]-4-carboxamide;

3-((1H-pyrrolo[2,3-b]pyridin-5-yl)oxy)-4'-((S)-2-(2-cyclopropylphenyl)pyrrolidin-1-yl)-N-((4-((4-fluoro-1-(oxetan-3-yl)piperidin-4-yl)methoxy)-3-nitrophenyl)sulfonyl)-2',3',4',5'-tetrahydro-[1,1'-biphenyl]-4-carboxamide;

3-((1H-pyrrolo[2,3-b]pyridin-5-yl)oxy)-4'-((S)-2-(2-cyclopropylphenyl)pyrrolidin-1-yl)-N-((4-((4-fluoro-1-(oxetan-3-yl)piperidin-4-yl)methoxy)-3-nitrophenyl)sulfonyl)-2',3',4',5'-tetrahydro-[1,1'-biphenyl]-4-carboxamide (isomer 1, faster eluting isomer);

3-((1H-pyrrolo[2,3-b]pyridin-5-yl)oxy)-4'-((S)-2-(2-cyclopropylphenyl)pyrrolidin-1-yl)-N-((4-((4-fluoro-1-(oxetan-3-yl)piperidin-4-yl)methoxy)-3-nitrophenyl)sulfonyl)-2',3',4',5'-tetrahydro-[1,1'-biphenyl]-4-carboxamide (isomer 2, slower eluting isomer);

3-((1H-pyrrolo[2,3-b]pyridin-5-yl)oxy)-4'-(2-(2-cyclopropylphenyl)pyrrolidin-1-yl)-N-((4-((4-fluoro-1-(tetrahydro-2H-pyran-4-yl)piperidin-4-yl)methoxy)-3-nitrophenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2-cyclopropylphenyl)pyrrolidin-1-yl)-N-((3-nitro-4-((((R)-1-(oxetan-3-yl)pyrrolidin-3-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2-cyclopropylphenyl)pyrrolidin-1-yl)-N-((3-nitro-4-((((S)-1-(oxetan-3-yl)pyrrolidin-3-yl)methyl)amino)phenyl)sulfonyl)-2',3',4',5'-tetrahydro-[1,1'-biphenyl]-4-carboxamide;

cis-3-((1H-pyrrolo[2,3-b]pyridin-5-yl)oxy)-4'-((S)-2-(2-cyclopropylphenyl)pyrrolidin-1-yl)-N-((4-(((4-ethyl-4-hydroxycyclohexyl)methyl)amino)-3-nitrophenyl)sulfonyl)-2',3',4',5'-tetrahydro-[1,1'-biphenyl]-4-carboxamide;

trans-3-((1H-pyrrolo[2,3-b]pyridin-5-yl)oxy)-4'-((S)-2-(2-cyclopropylphenyl)pyrrolidin-1-yl)-N-((4-(((4-ethyl-4-hydroxycyclohexyl)methyl)amino)-3-nitrophenyl)sulfonyl)-2',3',4',5'-tetrahydro-[1,1'-biphenyl]-4-carboxamide;

3-((1H-pyrrolo[2,3-b]pyridin-5-yl)oxy)-N-((4-((1-cyclopropyl-4-fluoropiperidin-4-yl)methoxy)-3-nitrophenyl)sulfonyl)-4'-(2-(2-cyclopropylphenyl)pyrrolidin-1-yl)-2',3',4',5'-tetrahydro-[1,1'-biphenyl]-4-carboxamide;

3-((1H-pyrrolo[2,3-b]pyridin-5-yl)oxy)-4'-(2-(2-cyclopropylphenyl)pyrrolidin-1-yl)-N-((4-(((R)-1-(1,3-difluoropropan-2-yl)pyrrolidin-3-yl)amino)-3-nitrophenyl)sulfonyl)-2',3',4',5'-tetrahydro-[1,1'-biphenyl]-4-carboxamide;

3-((1H-pyrrolo[2,3-b]pyridin-5-yl)oxy)-N-((3-chloro-4-(((tetrahydro-2H-pyran-4-yl)methyl)amino)phenyl)sulfonyl)-4'-(2-(2-cyclopropylphenyl)pyrrolidin-1-yl)-2',3',4',5'-tetrahydro-[1,1'-biphenyl]-4-carboxamide;

3-((1H-pyrrolo[2,3-b]pyridin-5-yl)oxy)-N-((3-cyano-4-(((tetrahydro-2H-pyran-4-yl)methyl)amino)phenyl)sulfonyl)-4'-(2-(2-cyclopropylphenyl)pyrrolidin-1-yl)-2',3',4',5'-tetrahydro-[1,1'-biphenyl]-4-carboxamide;

3-((1H-pyrrolo[2,3-b]pyridin-5-yl)oxy)-4'-(2-(2-cyclopropylphenyl)pyrrolidin-1-yl)-N-((4-(((tetrahydro-2H-pyran-4-yl)methyl)amino)-3-((trifluoromethyl)sulfonyl)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2-cyclopropylphenyl)pyrrolidin-1-yl)-N-((3-nitro-4-(((1-(oxetan-3-yl)piperidin-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2-cyclopropylphenyl)pyrrolidin-1-yl)-N-((3-nitro-4-(((1-(oxetan-3-yl)piperidin-4-yl)methyl)amino)phenyl)sulfonyl)-2',3',4',5'-tetrahydro-[1,1'-biphenyl]-4-carboxamide (isomer 1, faster eluting isomer);

3-((1H-pyrrolo[2,3-b]pyridin-5-yl)oxy)-4'-(2-(2-cyclopropylphenyl)pyrrolidin-1-yl)-N-((3-nitro-4-(((1-(oxetan-3-yl)piperidin-4-yl)methyl)amino)phenyl)sulfonyl)-2',3',4',5'-tetrahydro-[1,1'-biphenyl]-4-carboxamide (isomer 2, slower eluting isomer);

cis-N-((4-(((((R)-1,4-dioxan-2-yl)methyl)amino)-3-nitrophenyl)sulfonyl)-2-((1H-pyrrolo[2,3-b]pyridin-5-yl)oxy)-4-(4-(2-(2-cyclopropylphenyl)pyrrolidin-1-yl)cyclohexyl)benzamide;

trans-N-((4-((((R)-1,4-dioxan-2-yl)methyl)amino)-3-nitrophenyl)sulfonyl)-2-((1H-pyrrolo[2,3-b]pyridin-5-yl)oxy)-4-(4-(2-(2-cyclopropylphenyl)pyrrolidin-1-yl)cyclohexyl)benzamide;

cis-N-((4-((((R)-1,4-dioxan-2-yl)methyl)amino)-3-nitrophenyl)sulfonyl)-2-((1H-pyrrolo[2,3-b]pyridin-5-yl)oxy)-4-(4-((S)-2-(2-cyclopropylphenyl)pyrrolidin-1-yl)cyclohexyl)benzamide;

trans-N-((4-((((R)-1,4-dioxan-2-yl)methyl)amino)-3-nitrophenyl)sulfonyl)-2-((1H-pyrrolo[2,3-b]pyridin-5-yl)oxy)-4-(4-((S)-2-(2-cyclopropylphenyl)pyrrolidin-1-yl)cyclohexyl)benzamide;

cis-N-((4-((((S)-1,4-dioxan-2-yl)methyl)amino)-3-nitrophenyl)sulfonyl)-2-((1H-pyrrolo[2,3-b]pyridin-5-yl)oxy)-4-(4-(2-(2-cyclopropylphenyl)pyrrolidin-1-yl)cyclohexyl)benzamide;

trans-N-((4-((((S)-1,4-dioxan-2-yl)methyl)amino)-3-nitrophenyl)sulfonyl)-2-((1H-pyrrolo[2,3-b]pyridin-5-yl)oxy)-4-(4-(2-(2-cyclopropylphenyl)pyrrolidin-1-yl)cyclohexyl)benzamide;

cis-N-((4-((((S)-1,4-dioxan-2-yl)methyl)amino)-3-nitrophenyl)sulfonyl)-2-((1H-pyrrolo[2,3-b]pyridin-5-yl)oxy)-4-(4-((S)-2-(2-cyclopropylphenyl)pyrrolidin-1-yl)cyclohexyl)benzamide;

trans-N-((4-((((S)-1,4-dioxan-2-yl)methyl)amino)-3-nitrophenyl)sulfonyl)-2-((1H-pyrrolo[2,3-b]pyridin-5-yl)oxy)-4-(4-((S)-2-(2-cyclopropylphenyl)pyrrolidin-1-yl)cyclohexyl)benzamide;

cis-3-((1H-pyrrolo[2,3-b]pyridin-5-yl)oxy)-N-((4-((4-((tert-butyldimethylsilyl)oxy)cyclohexyl)methoxy)-3-nitrophenyl)sulfonyl)-4'-((S)-2-(2-cyclopropylphenyl)pyrrolidin-1-yl)-2',3',4',5'-tetrahydro-[1,1'-biphenyl]-4-carboxamide;

trans-3-((1H-pyrrolo[2,3-b]pyridin-5-yl)oxy)-N-((4-((4-((tert-butyldimethylsilyl)oxy)cyclohexyl)methoxy)-3-nitrophenyl)sulfonyl)-4'-((S)-2-(2-cyclopropylphenyl)pyrrolidin-1-yl)-2',3',4',5'-tetrahydro-[1,1'-biphenyl]-4-carboxamide;

cis-3-((1H-pyrrolo[2,3-b]pyridin-5-yl)oxy)-4'-((S)-2-(2-cyclopropylphenyl)pyrrolidin-1-yl)-N-((4-((4-hydroxycyclohexyl)methoxy)-3-nitrophenyl)sulfonyl)-2',3',4',5'-tetrahydro-[1,1'-biphenyl]-4-carboxamide;

trans-3-((1H-pyrrolo[2,3-b]pyridin-5-yl)oxy)-4'-((S)-2-(2-cyclopropylphenyl)pyrrolidin-1-yl)-N-((4-((4-hydroxycyclohexyl)methoxy)-3-nitrophenyl)sulfonyl)-2',3',4',5'-tetrahydro-[1,1'-biphenyl]-4-carboxamide;

N-(4-(N-(3-((1H-pyrrolo[2,3-b]pyridin-5-yl)oxy)-4'-(2-(2-cyclopropylphenyl)pyrrolidin-1-yl)-2',3',4',5'-tetrahydro-[1,1'-biphenyl]-4-carbonyl)sulfamoyl)-2-nitrophenyl)morpholine-4-carboxamide;

(S)-3-((1H-pyrrolo[2,3-b]pyridin-5-yl)oxy)-N-((4-(((4-fluorotetrahydro-2H-pyran-4-yl)methyl)amino)-3-nitrophenyl)sulfonyl)-4'-(2-(2-isopropylphenyl)pyrrolidin-1-yl)-[1,1'-biphenyl]-4-carboxamide;

(R)-3-((1H-pyrrolo[2,3-b]pyridin-5-yl)oxy)-N-((4-(((4-fluorotetrahydro-2H-pyran-4-yl)methyl)amino)-3-nitrophenyl)sulfonyl)-4'-(2-(2-isopropylphenyl)pyrrolidin-1-yl)-[1,1'-biphenyl]-4-carboxamide;

3-((1H-pyrrolo[2,3-b]pyridin-5-yl)oxy)-4'-(2-(2-cyclopropylphenyl)pyrrolidin-1-yl)-N-((4-(((4-(methoxymethyl)cyclohexyl)methyl)amino)-3-nitrophenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2-cyclopropylphenyl)pyrrolidin-1-yl)-N-((3-nitro-4-((((S)-1-(tetrahydro-2H-pyran-4-yl)pyrrolidin-3-yl)methyl)amino)phenyl)sulfonyl)-2',3',4',5'-tetrahydro-[1,1'-biphenyl]-4-carboxamide;

N-((4-((((S)-1,4-dioxan-2-yl)methyl)amino)-3-nitrophenyl)sulfonyl)-3-((1H-pyrrolo[2,3-b]pyridin-5-yl)oxy)-4'-((S)-2-(2-isopropylphenyl)pyrrolidin-1-yl)-[1,1'-biphenyl]-4-carboxamide;

N-((4-((((R)-1,4-dioxan-2-yl)methyl)amino)-3-nitrophenyl)sulfonyl)-3-((1H-pyrrolo[2,3-b]pyridin-5-yl)oxy)-4'-((S)-2-(2-isopropylphenyl)pyrrolidin-1-yl)-[1,1'-biphenyl]-4-carboxamide;

3-((1H-pyrrolo[2,3-b]pyridin-5-yl)oxy)-4'-((S)-2-(2-ethylphenyl)pyrrolidin-1-yl)-N-((4-(((4-fluorotetrahydro-2H-pyran-4-yl)methyl)amino)-3-nitrophenyl)sulfonyl)-2',3',4',5'-tetrahydro-[1,1'-biphenyl]-4-carboxamide;

3-((1H-pyrrolo[2,3-b]pyridin-5-yl)oxy)-4'-((S)-2-(2-ethylphenyl)pyrrolidin-1-yl)-N-((4-(((4-fluorotetrahydro-2H-pyran-4-yl)methyl)amino)-3-nitrophenyl)sulfonyl)-2',3',4',5'-tetrahydro-[1,1'-biphenyl]-4-carboxamide (isomer 1, faster eluting isomer);

3-((1H-pyrrolo[2,3-b]pyridin-5-yl)oxy)-4'-((S)-2-(2-ethylphenyl)pyrrolidin-1-yl)-N-((4-(((4-fluorotetrahydro-2H-pyran-4-yl)methyl)amino)-3-nitrophenyl)sulfonyl)-2',3',4',5'-tetrahydro-[1,1'-biphenyl]-4-carboxamide (isomer 2, slower eluting isomer);

3-((1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4'-((R)-2-(2-isopropylphenyl)pyrrolidin-1-yl)-[1,1'-biphenyl]-4-carboxamide;

3-((1H-pyrrolo[2,3-b]pyridin-5-yl)oxy)-4'-((R)-2-(2-cyclopropylphenyl)pyrrolidin-1-yl)-N-((4-((((1r,4r)-4-hydroxy-4-methylcyclohexyl)methyl)amino)-3-nitrophenyl)sulfonyl)-[1,1'-biphenyl]-4-carboxamide;

3-((1H-pyrrolo[2,3-b]pyridin-5-yl)oxy)-4'-((S)-2-(2-cyclopropylphenyl)pyrrolidin-1-yl)-N-((4-((((1r,4r)-4-hydroxy-4-methylcyclohexyl)methyl)amino)-3-nitrophenyl)sulfonyl)-[1,1'-biphenyl]-4-carboxamide;

3-((1H-pyrrolo[2,3-b]pyridin-5-yl)oxy)-4'-((R)-2-(2-cyclopropylphenyl)pyrrolidin-1-yl)-N-((4-((((1s,4s)-4-hydroxy-4-methylcyclohexyl)methyl)amino)-3-nitrophenyl)sulfonyl)-[1,1'-biphenyl]-4-carboxamide;

3-((1H-pyrrolo[2,3-b]pyridin-5-yl)oxy)-4'-((S)-2-(2-cyclopropylphenyl)pyrrolidin-1-yl)-N-((4-((((1s,4s)-4-hydroxy-4-methylcyclohexyl)methyl)amino)-3-nitrophenyl)sulfonyl)-[1,1'-biphenyl]-4-carboxamide;

(R)-3-((1H-pyrrolo[2,3-b]pyridin-5-yl)oxy)-4'-(2-(2-cyclopropylphenyl)pyrrolidin-1-yl)-N-((4-(((4-fluorotetrahydro-2H-pyran-4-yl)methyl)amino)-3-nitrophenyl)sulfonyl)-[1,1'-biphenyl]-4-carboxamide;

(S)-3-((1H-pyrrolo[2,3-b]pyridin-5-yl)oxy)-4'-(2-(2-cyclopropylphenyl)pyrrolidin-1-yl)-N-((4-(((4-fluorotetrahydro-2H-pyran-4-yl)methyl)amino)-3-nitrophenyl)sulfonyl)-[1,1'-biphenyl]-4-carboxamide;

N-((4-((((S)-1,4-dioxan-2-yl)methyl)amino)-3-nitrophenyl)sulfonyl)-3-((1H-pyrrolo[2,3-b]pyridin-5-yl)oxy)-4'-((R)-2-(2-cyclopropylphenyl)pyrrolidin-1-yl)-[1,1'-biphenyl]-4-carboxamide;

N-((4-((((S)-1,4-dioxan-2-yl)methyl)amino)-3-nitrophenyl)sulfonyl)-3-((1H-pyrrolo[2,3-b]pyridin-5-yl)oxy)-4'-((S)-2-(2-cyclopropylphenyl)pyrrolidin-1-yl)-[1,1'-biphenyl]-4-carboxamide;

N-((4-((((R)-1,4-dioxan-2-yl)methyl)amino)-3-nitrophenyl)sulfonyl)-3-((1H-pyrrolo[2,3-b]pyridin-5-yl)oxy)-4'-((R)-2-(2-cyclopropylphenyl)pyrrolidin-1-yl)-[1,1'-biphenyl]-4-carboxamide;

N-((4-((((R)-1,4-dioxan-2-yl)methyl)amino)-3-nitrophenyl)sulfonyl)-3-((1H-pyrrolo[2,3-b]pyridin-5-yl)oxy)-4'-((S)-2-(2-cyclopropylphenyl)pyrrolidin-1-yl)-[1,1'-biphenyl]-4-carboxamide;

(R)-3-((1H-pyrrolo[2,3-b]pyridin-5-yl)oxy)-4'-(2-(2-cyclopropylphenyl)pyrrolidin-1-yl)-N-((4-((4-fluoro-1-(oxetan-3-yl)piperidin-4-yl)methoxy)-3-nitrophenyl)sulfonyl)-[1,1'-biphenyl]-4-carboxamide;

(S)-3-((1H-pyrrolo[2,3-b]pyridin-5-yl)oxy)-4'-(2-(2-cyclopropylphenyl)pyrrolidin-1-yl)-N-((4-((4-fluoro-1-(oxetan-3-yl)piperidin-4-yl)methoxy)-3-nitrophenyl)sulfonyl)-[1,1'-biphenyl]-4-carboxamide;

(R)-3-((1H-pyrrolo[2,3-b]pyridin-5-yl)oxy)-4'-(2-(2-cyclopropylphenyl)pyrrolidin-1-yl)-N-((4-(((4-fluoro-1-(oxetan-3-yl)piperidin-4-yl)methyl)amino)-3-nitrophenyl)sulfonyl)-[1,1'-biphenyl]-4-carboxamide;

(R)-3-((1H-pyrrolo[2,3-b]pyridin-5-yl)oxy)-N-((4-((2-oxaspiro[3.5]nonan-7-yl)methoxy)-3-nitrophenyl)sulfonyl)-4'-(2-(2-cyclopropylphenyl)pyrrolidin-1-yl)-[1,1'-biphenyl]-4-carboxamide;

cis-(R)-3-((1H-pyrrolo[2,3-b]pyridin-5-yl)oxy)-4'-(2-(2-cyclopropylphenyl)pyrrolidin-1-yl)-N-((4-(((1-fluoro-4-hydroxy-4-methylcyclohexyl)methyl)amino)-3-nitrophenyl)sulfonyl)-[1,1'-biphenyl]-4-carboxamide;

trans-(R)-3-((1H-pyrrolo[2,3-b]pyridin-5-yl)oxy)-4'-(2-(2-cyclopropylphenyl)pyrrolidin-1-yl)-N-((4-(((1-fluoro-4-hydroxy-4-methylcyclohexyl)methyl)amino)-3-nitrophenyl)sulfonyl)-[1,1'-biphenyl]-4-carboxamide;

cis-(R)-3-((1H-pyrrolo[2,3-b]pyridin-5-yl)oxy)-4'-(2-(2-cyclopropylphenyl)pyrrolidin-1-yl)-N-((4-(((4-methoxy-4-methylcyclohexyl)methyl)amino)-3-nitrophenyl)sulfonyl)-[1,1'-biphenyl]-4-carboxamide;

trans-(R)-3-((1H-pyrrolo[2,3-b]pyridin-5-yl)oxy)-4'-(2-(2-cyclopropylphenyl)pyrrolidin-1-yl)-N-((4-(((4-methoxy-4-methylcyclohexyl)methyl)amino)-3-nitrophenyl)sulfonyl)-[1,1'-biphenyl]-4-carboxamide;

3-((1H-pyrrolo[2,3-b]pyridin-5-yl)oxy)-4'-((R)-2-(2-cyclopropylphenyl)pyrrolidin-1-yl)-N-((4-(((4-methylcyclohex-3-en-1-yl)methyl)amino)-3-nitrophenyl)sulfonyl)-[1,1'-biphenyl]-4-carboxamide;

3-((1H-pyrrolo[2,3-b]pyridin-5-yl)oxy)-4'-((R)-2-(2-ethylphenyl)pyrrolidin-1-yl)-N-((4-((((1r,4r)-4-hydroxy-4-methylcyclohexyl)methyl)amino)-3-nitrophenyl)sulfonyl)-[1,1'-biphenyl]-4-carboxamide;

(R)-3-((1H-pyrrolo[2,3-b]pyridin-5-yl)oxy)-4'-(2-(2-ethylphenyl)pyrrolidin-1-yl)-N-((4-((4-fluoro-1-(oxetan-3-yl)piperidin-4-yl)methoxy)-3-nitrophenyl)sulfonyl)-[1,1'-biphenyl]-4-carboxamide;

(S)-3-((1H-pyrrolo[2,3-b]pyridin-5-yl)oxy)-N-((4-((4-fluoro-1-(oxetan-3-yl)piperidin-4-yl)methoxy)-3-nitrophenyl)sulfonyl)-4'-(2-(2-isopropylphenyl)pyrrolidin-1-yl)-[1,1'-biphenyl]-4-carboxamide;

3-((1H-pyrrolo[2,3-b]pyridin-5-yl)oxy)-4'-(2-(3-chloro-2-cyclopropylphenyl)pyrrolidin-1-yl)-N-((4-((((1r,4r)-4-hydroxy-4-methylcyclohexyl)methyl)amino)-3-nitrophenyl)sulfonyl)-2',3',4',5'-tetrahydro-[1,1'-biphenyl]-4-carboxamide;

(S)-3-((1H-pyrrolo[2,3-b]pyridin-5-yl)oxy)-4'-((S)-2-(2-ethylphenyl)pyrrolidin-1-yl)-N-((4-((((1r,4r)-4-hydroxy-4-methylcyclohexyl)methyl)amino)-3-nitrophenyl)sulfonyl)-2',3',4',5'-tetrahydro-[1,1'-biphenyl]-4-carboxamide;

(R)-3-((1H-pyrrolo[2,3-b]pyridin-5-yl)oxy)-4'-((S)-2-(2-ethylphenyl)pyrrolidin-1-yl)-N-((4-((((1r,4r)-4-hydroxy-4-methylcyclohexyl)methyl)amino)-3-nitrophenyl)sulfonyl)-2',3',4',5'-tetrahydro-[1,1'-biphenyl]-4-carboxamide;

cis-3-((1H-pyrrolo[2,3-b]pyridin-5-yl)oxy)-4'-(2-(2-cyclopropylphenyl)pyrrolidin-1-yl)-N-((4-(((1-fluoro-4-hydroxycyclohexyl)methyl)amino)-3-nitrophenyl)sulfonyl)-2',3',4',5'-tetrahydro-[1,1'-biphenyl]-4-carboxamide;

trans-3-((1H-pyrrolo[2,3-b]pyridin-5-yl)oxy)-4'-(2-(2-cyclopropylphenyl)pyrrolidin-1-yl)-N-((4-(((1-fluoro-4-hydroxycyclohexyl)methyl)amino)-3-nitrophenyl)sulfonyl)-2',3',4',5'-tetrahydro-[1,1'-biphenyl]-4-carboxamide;

3-((1H-pyrrolo[2,3-b]pyridin-5-yl)oxy)-4'-((S)-2-(2-cyclopropylphenyl)pyrrolidin-1-yl)-N-((4-(((1-fluoro-4-hydroxycyclohexyl)methyl)amino)-3-nitrophenyl)sulfonyl)-2',3',4',5'-tetrahydro-[1,1'-biphenyl]-4-carboxamide;

cis-3-((1H-pyrrolo[2,3-b]pyridin-5-yl)oxy)-4'-((S)-2-(2-cyclopropylphenyl)pyrrolidin-1-yl)-N-((4-(((4-hydroxycyclohexyl)methyl)amino)-3-nitrophenyl)sulfonyl)-2',3',4',5'-tetrahydro-[1,1'-biphenyl]-4-carboxamide;

trans-3-((1H-pyrrolo[2,3-b]pyridin-5-yl)oxy)-4'-((S)-2-(2-cyclopropylphenyl)pyrrolidin-1-yl)-N-((4-(((4-hydroxycyclohexyl)methyl)amino)-3-nitrophenyl)sulfonyl)-2',3',4',5'-tetrahydro-[1,1'-biphenyl]-4-carboxamide;

(trans- or cis-)3-((1H-pyrrolo[2,3-b]pyridin-5-yl)oxy)-4'-((S)-2-(2-cyclopropylphenyl)pyrrolidin-1-yl)-N-((4-(((4-hydroxycyclohexyl)methyl)amino)-3-nitrophenyl)sulfonyl)-2',3',4',5'-tetrahydro-[1,1'-biphenyl]-4-carboxamide (isomer 1, faster eluting isomer);

(trans- or cis-)3-((1H-pyrrolo[2,3-b]pyridin-5-yl)oxy)-4'-((S)-2-(2-cyclopropylphenyl)pyrrolidin-1-yl)-N-((4-(((4-hydroxycyclohexyl)methyl)amino)-3-nitrophenyl)sulfonyl)-2',3',4',5'-tetrahydro-[1,1'-biphenyl]-4-carboxamide (isomer 2, slow eluting isomer);

3-((1H-pyrrolo[2,3-b]pyridin-5-yl)oxy)-4'-(2-(2-cyclopropylphenyl)pyrrolidin-1-yl)-N-((3-nitro-4-((((S)-4-(oxetan-3-yl)morpholin-2-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-((S)-2-(2-cyclopropylphenyl)pyrrolidin-1-yl)-N-((3-nitro-4-((((R)-4-(oxetan-3-yl)morpholin-2-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2-cyclopropylphenyl)pyrrolidin-1-yl)-N-((4-(((4-(methylsulfonyl)morpholin-2-yl)methyl)amino)-3-nitrophenyl)sulfonyl)-2',3',4',5'-tetrahydro-[1,1'-biphenyl]-4-carboxamide;

3-((1H-pyrrolo[2,3-b]pyridin-5-yl)oxy)-4'-((S)-2-(2-cyclopropylphenyl)pyrrolidin-1-yl)-N-((4-(((4-fluoro-1-(oxetan-3-yl)piperidin-4-yl)methyl)amino)-3-nitrophenyl)sulfonyl)-2',3',4',5'-tetrahydro-[1,1'-biphenyl]-4-carboxamide;

3-((1H-pyrrolo[2,3-b]pyridin-5-yl)oxy)-N-((5-chloro-6-((1-(dimethylglycyl)-4-fluoropiperidin-4-yl)methoxy)pyridin-3-yl)sulfonyl)-4'-(2-(2-cyclopropylphenyl)pyrrolidin-1-yl)-2',3',4',5'-tetrahydro-[1,1'-biphenyl]-4-carboxamide;

3-((1H-pyrrolo[2,3-b]pyridin-5-yl)oxy)-4'-(2-(3-chloro-2-cyclopropylphenyl)pyrrolidin-1-yl)-N-((4-((4-hydroxycyclohexyl)methoxy)-3-nitrophenyl)sulfonyl)-2',3',4',5'-tetrahydro-[1,1'-biphenyl]-4-carboxamide;

cis-2-((1H-pyrrolo[2,3-b]pyridin-5-yl)oxy)-4-(2-(2-cyclopropylphenyl)pyrrolidin-1-yl)cyclohexyl)-N-((3-nitro-4-(((4-(oxetan-3-yl)morpholin-2-yl)methyl)amino)phenyl)sulfonyl)benzamide;

trans-2-((1H-pyrrolo[2,3-b]pyridin-5-yl)oxy)-4-(4-(2-(2-cyclopropylphenyl)pyrrolidin-1-yl)cyclohexyl)-N-((3-nitro-4-(((4-(oxetan-3-yl)morpholin-2-yl)methyl)amino)phenyl)sulfonyl)benzamide;

3-((1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4'-((R)-2-(2-(1-methyl-1,2,3,6-tetrahydropyridin-4-yl)phenyl)pyrrolidin-1-yl)-[1,1'-biphenyl]-4-carboxamide;

(R)-3-((1H-pyrrolo[2,3-b]pyridin-5-yl)oxy)-N-((4-(((4-fluorotetrahydro-2H-pyran-4-yl)methyl)amino)-3-nitrophenyl)sulfonyl)-4'-(2-(2-(1-methyl-1,2,3,6-tetrahydropyridin-4-yl)phenyl)pyrrolidin-1-yl)-[1,1'-biphenyl]-4-carboxamide;

N-((4-(((((R)-1,4-dioxan-2-yl)methyl)amino)-3-nitrophenyl)sulfonyl)-3-((1H-pyrrolo[2,3-b]pyridin-5-yl)oxy)-4'-((R)-2-(2-(1-methyl-1,2,3,6-tetrahydropyridin-4-yl)phenyl)pyrrolidin-1-yl)-[1,1'-biphenyl]-4-carboxamide;

(R)-3-((1H-pyrrolo[2,3-b]pyridin-5-yl)oxy)-N-((4-(((4-fluoro-1-(oxetan-3-yl)piperidin-4-yl)methyl)amino)-3-nitrophenyl)sulfonyl)-4'-(2-(2-(1-methyl-1,2,3,6-tetrahydropyridin-4-yl)phenyl)pyrrolidin-1-yl)-[1,1'-biphenyl]-4-carboxamide;

3-((1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4'-((R)-2-(2-(1-methylpiperidin-4-yl)phenyl)pyrrolidin-1-yl)-[1,1'-biphenyl]-4-carboxamide;

3-((1H-pyrrolo[2,3-b]pyridin-5-yl)oxy)-4'-((R)-2-(2-(1-acetylpiperidin-4-yl)phenyl)pyrrolidin-1-yl)-N-((4-((((1r,4r)-4-hydroxy-4-methylcyclohexyl)methyl)amino)-3-nitrophenyl)sulfonyl)-[1,1'-biphenyl]-4-carboxamide;

3-((1H-pyrrolo[2,3-b]pyridin-5-yl)oxy)-4'-((R)-2-(2-(1-(dimethylglycyl)piperidin-4-yl)phenyl)pyrrolidin-1-yl)-N-((4-((((1r,4r)-4-hydroxy-4-methylcyclohexyl)methyl)amino)-3-nitrophenyl)sulfonyl)-[1,1'-biphenyl]-4-carboxamide;

3-((1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4'-((R)-2-(2-(1-(methylglycyl)piperidin-4-yl)phenyl)pyrrolidin-1-yl)-[1,1'-biphenyl]-4-carboxamide;

3-((1H-pyrrolo[2,3-b]pyridin-5-yl)oxy)-4'-((R)-2-(2-(1-(3-(dimethylamino)propanoyl)piperidin-4-yl)phenyl)pyrrolidin-1-yl)-N-((4-((((1r,4r)-4-hydroxy-4-methylcyclohexyl)methyl)amino)-3-nitrophenyl)sulfonyl)-[1,1'-biphenyl]-4-carboxamide;

3-((1H-pyrrolo[2,3-b]pyridin-5-yl)oxy)-4'-((R)-2-(2-(1-(2-amino-2-methylpropanoyl)piperidin-4-yl)phenyl)pyrrolidin-1-yl)-N-((4-((((1r,4r)-4-hydroxy-4-methylcyclohexyl)methyl)amino)-3-nitrophenyl)sulfonyl)-[1,1'-biphenyl]-4-carboxamide;

(R)-3-((1H-pyrrolo[2,3-b]pyridin-5-yl)oxy)-N-((4-(((1-acetylpiperidin-4-yl)methyl)amino)-3-nitrophenyl)sulfonyl)-4'-(2-(2-cyclopropylphenyl)pyrrolidin-1-yl)-[1,1'-biphenyl]-4-carboxamide;

(R)-3-((1H-pyrrolo[2,3-b]pyridin-5-yl)oxy)-4'-(2-(2-cyclopropylphenyl)pyrrolidin-1-yl)-N-((4-(((1-(methylsulfonyl)piperidin-4-yl)methyl)amino)-3-nitrophenyl)sulfonyl)-[1,1'-biphenyl]-4-carboxamide;

(R)-3-((1H-pyrrolo[2,3-b]pyridin-5-yl)oxy)-4'-(2-(2-cyclopropylphenyl)pyrrolidin-1-yl)-N-((4-((2-morpholinoethyl)amino)-3-nitrophenyl)sulfonyl)-[1,1'-biphenyl]-4-carboxamide;

(R)-3-((1H-pyrrolo[2,3-b]pyridin-5-yl)oxy)-4'-(2-(2-cyclopropylphenyl)pyrrolidin-1-yl)-N-((3-nitro-4-((2-(tetrahydro-2H-pyran-4-yl)-2-azaspiro[3.3]heptan-6-yl)amino)phenyl)sulfonyl)-[1,1'-biphenyl]-4-carboxamide;

(R)-3-((1H-pyrrolo[2,3-b]pyridin-5-yl)oxy)-4'-(2-(2-cyclopropylphenyl)pyrrolidin-1-yl)-N-((4-(((4-(cis)-((dimethyl(oxo)-16-sulfaneylidene)amino)cyclohexyl)methyl)amino)-3-nitrophenyl)sulfonyl)-[1,1'-biphenyl]-4-carboxamide;

(R)-3-((1H-pyrrolo[2,3-b]pyridin-5-yl)oxy)-4'-(2-(2-cyclopropylphenyl)pyrrolidin-1-yl)-N-((4-(((4-(trans)-((dimethyl(oxo)-16-sulfaneylidene)amino)cyclohexyl)methyl)amino)-3-nitrophenyl)sulfonyl)-[1,1'-biphenyl]-4-carboxamide;

(S)-3-((1H-pyrrolo[2,3-b]pyridin-5-yl)oxy)-4'-(2-(2-cyclopropylphenyl)-4,4-difluoropyrrolidin-1-yl)-N-((4-((((1r,4r)-4-hydroxy-4-methylcyclohexyl)methyl)amino)-3-nitrophenyl)sulfonyl)-[1,1'-biphenyl]-4-carboxamide;

(R)-3-((1H-pyrrolo[2,3-b]pyridin-5-yl)oxy)-4'-(2-(2-cyclopropylphenyl)-4,4-difluoropyrrolidin-1-yl)-N-((4-((((1r,4r)-4-hydroxy-4-methylcyclohexyl)methyl)amino)-3-nitrophenyl)sulfonyl)-[1,1'-biphenyl]-4-carboxamide;

3-((1H-pyrrolo[2,3-b]pyridin-5-yl)oxy)-4'-(2-(2-cyclopropylphenyl)-4-(trifluoromethyl)pyrrolidin-1-yl)-N-((4-((((1r,4r)-4-hydroxy-4-methylcyclohexyl)methyl)amino)-3-nitrophenyl)sulfonyl)-[1,1'-biphenyl]-4-carboxamide;

4'-((R)-2-(2-cyclopropylphenyl)pyrrolidin-1-yl)-3-((6-fluoro-1H-indol-4-yl)oxy)-N-((4-((((1r,4r)-4-hydroxy-4-methylcyclohexyl)methyl)amino)-3-nitrophenyl)sulfonyl)-[1,1'-biphenyl]-4-carboxamide;

4'-(2-(2-cyclopropylphenyl)pyrrolidin-1-yl)-N-((3-nitro-4-(((tetrahydro-2H-pyran-4-yl)methyl)amino)phenyl)sulfonyl)-3-(pyrazolo[4,3-b]pyrrolo[3,2-e]pyridin-1(5H)-yl)-2',3',4',5'-tetrahydro-[1,1'-biphenyl]-4-carboxamide;

4'-(2-(2-cyclopropylphenyl)pyrrolidin-1-yl)-3-(5-(hydroxymethyl)pyrazolo[4,3-b]pyrrolo[3,2-e]pyridin-1(5H)-yl)-N-((3-nitro-4-(((tetrahydro-2H-pyran-4-yl)methyl)amino)phenyl)sulfonyl)-2',3',4',5'-tetrahydro-[1,1'-biphenyl]-4-carboxamide;

3-((1H-pyrrolo[2,3-b]pyridin-5-yl)oxy)-4'-(2-(2-cyclopropylphenyl)pyrrolidin-1-yl)-N-((4-((4-morpholino-1-(phenylthio)butan-2-yl)amino)-3-nitrophenyl)sulfonyl)-2',3',4',5'-tetrahydro-[1,1'-biphenyl]-4-carboxamide;

4'-(2-(2-cyclopropylphenyl)pyrrolidin-1-yl)-N-((4-((4-morpholino-1-(phenylthio)butan-2-yl)amino)-3-nitrophenyl)sulfonyl)-2',3',4',5'-tetrahydro-[1,1'-biphenyl]-4-carboxamide 3-((1H-pyrrolo[2,3-b]pyridin-5-yl)oxy)-4'-(2-(2-cyclopropylphenyl)pyrrolidin-1-yl)-N-((4-((4-morpholino-1-(phenylthio)butan-2-yl)amino)-3-((trifluoromethyl)sulfonyl)phenyl)sulfonyl)-2',3',4',5'-tetrahydro-[1,1'-biphenyl]-4-carboxamide; or 4'-(2-(2-cyclopropylphenyl)pyrrolidin-1-yl)-N-((4-((4-morpholino-1-(phenylthio)butan-2-yl)amino)-3-((trifluoromethyl)sulfonyl)phenyl)sulfonyl)-2',3',4',5'-tetrahydro-[1,1'-biphenyl]-4-carboxamide;

or a pharmaceutically acceptable salt thereof.

33. The compound of claim 1, wherein the compound is 2-((1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)benzamide, or a pharmaceutically acceptable salt thereof.

34. A compound selected from:

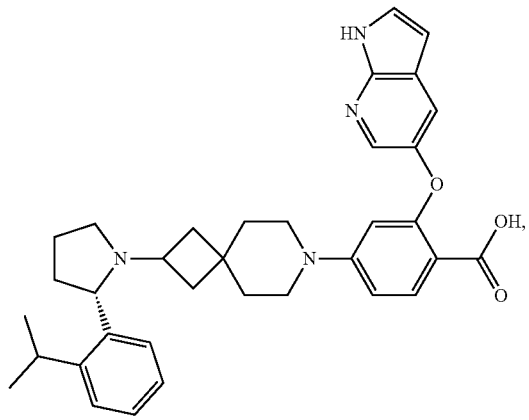

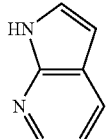

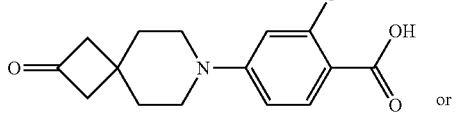

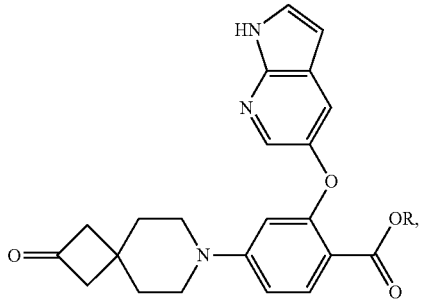

or a pharmaceutically acceptable salt thereof, or a stereoisomer thereof, wherein R is $C_{1-12}$ alkyl.

35. A pharmaceutical composition comprising the compound of claim 1, or a pharmaceutically acceptable salt thereof, or a stereoisomer thereof, and a pharmaceutically acceptable carrier.

36. A pharmaceutical composition comprising the compound of claim 26, or a pharmaceutically acceptable salt thereof, or a stereoisomer thereof, and a pharmaceutically acceptable carrier.

37. A method for inhibiting Bcl-2 activity in a subject in need thereof, comprising administering a therapeutically effective amount of the compound of claim 1, or a pharmaceutically acceptable salt thereof, or a stereoisomer thereof.

38. A method for inhibiting Bcl-2 activity in a subject in need thereof, comprising administering a therapeutically effective amount of the compound of claim 26, or a pharmaceutically acceptable salt thereof, or a stereoisomer thereof.

39. The compound of claim 31, wherein $R^{5a}$ is $-NR^{5b}R^{5c}$ and $R^{5b}$ and $R^{5c}$ are each independently hydrogen or $-C_{1-6}$ alkyl substituted with a monocyclic $C_{3-8}$cycloalkyl.

* * * * *